(12) United States Patent
Kazmierski et al.

(10) Patent No.: US 7,645,771 B2
(45) Date of Patent: Jan. 12, 2010

(54) CCR5 ANTAGONISTS AS THERAPEUTIC AGENTS

(75) Inventors: Wieslaw Mieczyslaw Kazmierski, Durham, NC (US); Chrisopher Joseph Aquino, Durham, NC (US); Neil Bifulco, Durham, NC (US); Eric Eugene Boros, Durham, NC (US); Brian Andrew Chauder, Durham, NC (US); Pek Yoke Chong, Durham, NC (US); Maosheng Duan, Durham, NC (US); Felix Deanda, Jr., Durham, NC (US); Cecilia Suarez Koble, Durham, NC (US); Ed Williams McLean, Durham, NC (US); Jennifer Poole Peckham, Durham, NC (US); Angilique C Perkins, Durham, NC (US); James Benjamin Thompson, Durham, NC (US); Dana Vanderwall, Durham, NC (US)

(73) Assignee: SmithKline Beecham Corp., Philadelphia, PA (US)

( * ) Notice: Subject to any disclaimer, the term of this patent is extended or adjusted under 35 U.S.C. 154(b) by 705 days.

(21) Appl. No.: 10/538,144

(22) PCT Filed: Dec. 12, 2003

(86) PCT No.: PCT/US03/39644

§ 371 (c)(1),
(2), (4) Date: Jun. 9, 2005

(87) PCT Pub. No.: WO2004/054974

PCT Pub. Date: Jul. 1, 2004

(65) Prior Publication Data

US 2006/0229336 A1    Oct. 12, 2006

Related U.S. Application Data

(60) Provisional application No. 60/433,634, filed on Dec. 13, 2002.

(51) Int. Cl.
*A61K 31/46* (2006.01)

(52) U.S. Cl. .................. 514/304; 514/319; 546/125; 548/310.1

(58) Field of Classification Search .................. 514/318, 514/319, 320, 322, 323, 304, 396; 546/233, 546/237, 126, 226, 125; 548/304.4, 310.1
See application file for complete search history.

(56) References Cited

U.S. PATENT DOCUMENTS

| 2,248,018 | A | | 7/1941 | Eisleb |
| 2,773,870 | A | | 12/1956 | Elpern |
| 3,334,106 | A | | 8/1967 | Biel |
| 3,539,580 | A | | 11/1970 | Hermans et al. |
| 5,340,822 | A | | 8/1994 | Emonds-Alt et al. |
| 5,360,805 | A | * | 11/1994 | Ask et al. .................. 514/316 |
| 5,968,953 | A | * | 10/1999 | Ask et al. .................. 514/316 |

FOREIGN PATENT DOCUMENTS

| WO | WO98/25604 | | 6/1998 |
| WO | WO98/25605 | | 6/1998 |
| WO | WO98/57962 | * | 12/1998 |
| WO | WO99/04794 | | 2/1999 |
| WO | WO00/06545 | * | 2/2000 |
| WO | WO0038680 | | 7/2000 |
| WO | WO02.079190 | | 10/2002 |

OTHER PUBLICATIONS

Burkholder et al., Bioog. Med. Chem. Lett., 1997, 7(19), 2531-2536.*
Whittenberger et al., Dialkyltin Oxide Mediated Addition of Trimethylsilyl Azide to Nitriles. A Novel Preparation of 5-Substituted Tetrazoles, J. Org. Chem 58:4139-4141 (1993).
Kohara et al., Synthesis and Angiotensin II Receptor Antagonistic Activities of Benzimidazole Derivatives Bearing Acidic Heterocycles as Novel Tetrazole Bioisosteres, J. Med. Chem 39:5228-5235 (1996).
Tyle, Iontophoretic Devices for Drug Delivery, Pharmaceutical Research 3(6):318-326 (1986).

* cited by examiner

*Primary Examiner*—Janet L Andres
*Assistant Examiner*—David E Gallis
(74) *Attorney, Agent, or Firm*—Bonnie L. Deppenbrock

(57) ABSTRACT

The present invention relates to compounds of formula (I) or a pharmaceutically acceptable derivatives thereof, useful in the treatment of prophylazis of CCR5-related diseases and disorders, for example, in the inhibition of HIV replication, the prevention or treatment of HIV infection, and in the treatment of the resulting acquired immune deficiency syndrome (AIDS).

4 Claims, No Drawings

CCR5 ANTAGONISTS AS THERAPEUTIC AGENTS

CROSS-REFERENCE TO RELATED APPLICATIONS

This application is filed pursuant to 35 USC 371 as a United States National Phase Application of International Patent Application Serial No. PCT/US03/39644 filed on Dec. 12, 2003, which claims priority from U.S. Provisional Application No. 60/433,634 filed on Dec. 13, 2002.

FIELD OF THE INVENTION

The present invention relates to a novel class of piperidine derivatives useful as antagonists of the chemokine receptor CCR5, compositions containing such compounds and methods of treating HIV infection and associated conditions. The invention also relates to methods of treatment or prophylaxis of other CCR5 mediated diseases and disorders.

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss.

In addition to CD4, HIV requires a co-receptor for entry into target cells. The chemokine receptors function together with CD4 as co-receptors for HIV. The chemokine receptors CXCR4 and CCR5 have been identified as the main co-receptors for HIV-1. CCR5 acts as a major co-receptor for fusion and entry of macrophage-tropic HIV into host cells. These chemokine receptors are thought to play an essential role in the establishment and dissemination of an HIV infection. Therefore, CCR5 antagonists are useful as therapeutic agents active against HIV.

CCR5 receptors have also been reported to mediate cell transfer in inflammatory and immunoregulatory diseases and disorders such as multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, human papilloma virus infection, prostate cancer, wound healing, amyotrophic lateral sclerosis, and immune mediated disorders.

There is a continued need to find new therapeutic agents to treat human diseases. CCR5 is an attractive target for the discovery of new therapeutics due to its important role in viral infections, particularly HIV infections, and other inflammatory and immune diseases and disorders.

SUMMARY OF THE INVENTION

The present invention features compounds that are CCR5 antagonists and therefore are useful in the inhibition of HIV replication, the prevention and/or treatment of infection by HIV, and in the treatment of AIDS and/or ARC. These compounds having the general formula I:

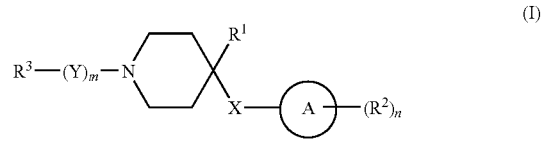

wherein $R^1$, $R^2$, $R^3$, X, Y, m, n and Ring A are as defined herein. The compounds of this invention may also be either pharmaceutically acceptable salts or pharmaceutical composition ingredients.

The present invention also features pharmaceutical compositions, comprising the above-mentioned compounds that are suitable for the prevention or treatment of CCR5-related diseases and conditions.

The present invention also features methods of antagonizing CCR5 chemokine receptor activity in a biological sample comprising contacting the biological sample with an effective amount of compounds of formula I or pharmaceutically acceptable derivatives or compositions thereof. The present invention also features methods of antagonizing CCR5 chemokine receptor activity in a patient comprising administering to the patient a therapeutically effective amount of compounds of formula I or pharmaceutically acceptable derivatives or compositions thereof.

The present invention further features methods of treating AIDS, methods of preventing infection by HIV, and methods of treating infection by HIV as monotherapy or in combination with other antivirals, anti-infectives, immunomodulators, antibiotics or vaccines.

The present invention further features methods of synthesizing compounds of formula I and preparing pharmaceutical compositions comprising these above-mentioned compounds.

DETAILED DESCRIPTION OF THE INVENTION

The present invention features a compound of formula (I):

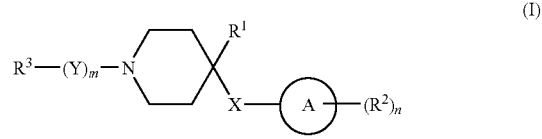

or a pharmaceutically acceptable derivative thereof, wherein:
$R^1$ is alkyl, carbocyclyl, aryl, heterocyclyl, or heteroaryl, wherein said alkyl is optionally substituted by one or more $R^7$, said carbocyclyl or heterocyclyl is optionally substituted by one or more $R^8$ and said aryl or heteroaryl is optionally substituted by one or more $R^6$; or $R^1$ and X taken together form a saturated, partially saturated or aromatic 5-7 membered ring having 0-3 heteroatoms chosen from oxygen, sulfur, nitrogen and phosphorus that is fused to Ring A;

X is a $C_{1-5}$ alkylene chain, wherein said $C_{1-5}$ alkylene chain is optionally substituted by one or more groups chosen from =O, =S and halo, and wherein said $C_{1-5}$ alkylene chain optionally contains 1-3 heteroatoms chosen from oxygen, sulfur, nitrogen and phosphorus;

each $R^2$ is independently chosen from —$OR^o$, —$C(O)R^o$, —$C(O)N(R^o)_2$, —$N(R^o)(-V_m-R^+)$, —$S(O)_2-R^o$, —$S(O)_2-N(R^o)_2$, —$(CH_2)_a-N(R^o)(-V_b-R^+)$, —$(CH_2)_a-(-V_b-R^+)$, halo, alkyl, aryl, carbocyclyl, heteroaryl and heterocyclyl, wherein said alkyl is optionally substituted by one or more $R^7$, said aryl or heteroaryl is optionally substituted by one or more $R^6$, and said carbocyclyl or heterocyclyl is optionally substituted by one or more $R^8$; or two adjacent $R^2$s on Ring A are optionally taken together to form a fused, saturated, partially saturated or aromatic 4-7 membered ring having 0-3 heteroatoms chosen from oxygen, sulfur, nitrogen and phosphorus; or two geminal $R^2$s are optionally taken together to form a spiro, saturated, partially saturated or aromatic 5-6 membered ring having 0-3 heteroatoms chosen from oxygen, sulfur and nitrogen, said fused or spiro ring being optionally substituted by one or more groups chosen from oxo, alkyl optionally substituted by one or more $R^7$, and aryl optionally substituted by one or more $R^6$;

each a is independently 0-3;

each b is independently 0 or 1;

V is alkyl, —$C(O)-$, —$S(O)_2-$, —$C(O)O-$, or —$C(O)-N(R^o)-$ (where V is attached to $R^+$ through the right hand side of the radical as shown hereinafter);

$R^+$ is alkyl, aralkyl, aryl, heteroaryl, heteroaralkyl, wherein said alkyl is optionally substituted by one or more $R^7$ and said aralkyl or aryl is optionally substituted by one or more $R^6$;

m is 0 or 1;

n is 0-5;

$R^3$ is H, halo, —$N(R^o)_2$, —$N(R^o)C(O)R^o$, —CN, —$CF_3$, alkyl optionally substituted by one or more groups chosen from $R^7$, and —S-aryl optionally substituted by —$(CH_2)_{1-6}-N(R^o)SO_2(R^o)$, carbocyclyl, aryl, heteroaryl or heterocyclyl, wherein said carbocyclyl or heterocyclyl is optionally substituted by one or more $R^8$, and said aryl or heteroaryl is optionally substituted by one or more $R^6$;

Y is —$(CR^4R^5)_p-$, —$C(O)-$, —$C(O)C(O)-$, —$C(S)-$, —$O-(CH_2)_{0-4}-C(O)-$, —$N(R^o)-C(O)-$, —$C(O)-N(R^o)-$, —$N(R^o)-C(S)-$, —$S(O)_t-$, —$O-C(=N-CN)-$, —$O-C(=N-R^o)-$, —$S-C(=N-CN)-$, —$N(R^o)-C(=N-CN)-$, —$C(=N-CN)-$, —$N(R^o)-C[=N-C(O)-R^o]-$, —$N(R^o)-C[=N-S(O)_t-R^o]-$, —$N(R^o)-C(=N-OR^o)-$, —$N(R^o)-C(=N-R^o)-$, —$C(=N-R^o)-$, —$(CH_2)_{0-4}-C(O)-O-$, —$C(=N-CN)-O-$, —$C(=N-R^o)-O-$, or —$C(=N-CN)-S-$ (where Y is attached to $R^3$ through the left hand side of the radical as shown hereinafter);

each $R^4$ is independently H or alkyl optionally substituted by $R^7$;

each $R^5$ is independently chosen from H, —$C(O)-OR^o$, aryl optionally substituted by $R^6$, —$C(O)-OR^6$, —$C(O)-N(R^o)_2$, —$S(O)_2-N(R^o)_2$, —$S(O)_2-R^o$, and heteroaryl optionally substituted by $R^6$;

p is 1-5;

t is 1 or 2;

each $R^6$ is independently chosen from halo, —$CF_3$, —$OCF_3$, —$OR^o$, —$SR^o$, —$SCF_3$, —$R^o$, methylenedioxy, ethylenedioxy, —$NO_2$, —CN, —$N(R^o)_2$, —$NR^oC(O)R^o$, —$NR^oC(O)N(R^o)_2$, —$NR^oC(S)N(R^o)_2$, —$NR^oCO_2R^o$, —$NR^oNR^oC(O)R^o$, —$NR^oNR^oC(O)N(R^o)_2$, —$NR^oNR^oCO_2R^o$, —$C(O)C(O)R^o$, —$C(O)CH_2C(O)R^o$, —$CO_2R^o$, —$O-C(O)R^o$, —$C(O)$ $R^o$, —$C(O)N(R^o)_2$, —$OC(O)N(R^o)_2$, —$S(O)_tR^o$, —$S(O)_t-OR^o$, —$SO_2N(R^o)C(O)R^o$, —$NR^oSO_2N(R^o)_2$, —$NR^oSO_2R^o$, —$C(=S)N(R^o)_2$, —$C(=NH)-N(R^o)_2$, —$C(=N-OR^o)-N(R^o)_2$, —$O-(CH_2)_{0-6}-SO_2N(R^o)_2$, —$(CH_2)_{1-6}NHC(O)R^o$, —$SO_2N(R^o)_2$, —$(CH_2)_{1-6}-OR^o$, —$(CH_2)_{1-6}-SR^o$, —$(CH_2)_{1-6}-CN$, —$(CH_2)_{1-6}-N(R^o)_2$, —$(CH_2)_{1-6}CO_2R^o$, —$C(O)N(R^o)N(R^o)_2$, —$C(O)N(R^o)OH$, —$C(O)N(R^o)SO_2R^o$, —$S(O)_tN(R^o)OR$, and —$(CH_2)_{1-6}-C(O)R^o$, wherein the two $R^o$s on the same nitrogen optionally taken together forming a 5-8 membered saturated, partially saturated or aromatic ring having additional 0-4 ring heteroatoms chosen from oxygen, nitrogen, sulfur and phosphorus;

each $R^7$ is independently chosen from halogen, —$CF_3$, —$R^o$, —$OR^o$, —$SR^o$, aryl optionally substituted by $R^6$, —$NO_2$, —CN, —$N(R^o)_2$, —$NR^oC(O)R^o$, —$NR^oC(O)N(R^o)_2$, —$N(R^o)C(S)N(R^o)_2$, —$NR^oCO_2R^o$, —$NR^oNR^oC(O)R^o$, —$NR^oNR^oC(O)N(R^o)_2$, —$NR^oNR^oCO_2R^o$, —$C(O)C(O)R^o$, —$C(O)CH_2C(O)R^o$, —$CO_2R^o$, —$C(O)R^o$, —$C(O)N(R^o)-N(R^o)_2$, —$C(O)N(R^o)_2$, —$C(O)NR^oSO_2R^o$, —$OC(O)N(R^o)_2$, —$S(O)_tR^o$, —$NR^oSO_2N(R^o)_2$, —$NR^oSO_2R^o$, —$C(=S)N(R^o)_2$, —$C(=NH)-N(R^o)_2$, —$(CH_2)_{1-6}-C(O)R^o$, —$SO_2N(R^o)_2$, —$OCF_3$, —$SCF_3$, —$(CH_2)_{1-6}SR^o$, methylenedioxy, ethylenedioxy, —$(CH_2)_{1-6}-CN$, —$(CH_2)_{1-6}-N(R^o)_2$, —$S(O)_tN(R^o)OR^o$, —$(CH_2)_{1-6}-C(O)R^o$, —$C(=N-OR^o)-N(R^o)_2$, —$O-(CH_2)_{0-6}-SO_2N(R^o)_2$, and —$(CH_2)_{1-6}-NHC(O)R^o$, wherein the two $R^o$s on the same nitrogen optionally taken together form a 5-8 membered saturated, partially saturated or aromatic ring having additional 0-4 ring heteroatoms chosen from oxygen, nitrogen, sulfur and phosphorous;

each $R^8$ is independently chosen from $R^7$, =O, =S, =$N(R^o)$, and =N(CN);

each $R^o$ is independently chosen from $R^*$, —C(O)-aralkyl, —$S(O)_t$-heteroaryl, carbocyclylalkyl, aralkyl, heteroaralkyl, and heterocyclylalkyl, wherein each member of $R^o$ except H is optionally substituted by one or more groups chosen from $R^*$, —$OR^*$, $N(R^*)_2$, =O, =S, halo, —$CF_3$, —$NO_2$, —CN, —$C(O)R^*$, —$CO_2R^*$, —C(O)-aryl, —C(O)-heteroaryl, —O-aryl, aralkyl, —$S(O)_t$-aryl, —$NR^*SO_2R^*$, —$NR^*C(O)R^*$, —$NR^*C(O)N(R^*)_2$, —$N(R^*)C(S)N(R^*)_2$, —$NR^*CO_2R^*$, —$NR^*NR^*C(O)R^*$, —$NR^*NR^*C(O)N(R^*)_2$, —$NR^*NR^*CO_2R^*$, —$C(O)C(O)R^*$, —$C(O)CH_2C(O)R^*$, —$C(O)N(R^*)N(R^*)_2$, —$C(O)N(R^*)_2$, —$C(O)NR^*SO_2R^*$, —$OC(O)N(R^*)_2$, —$S(O)_tR^*$, —$NR^*SO_2N(R^*)_2$, and —$SO_2N(R^*)_2$ wherein the two $R^*$s on the same nitrogen optionally taken together form a 5-8 membered saturated, partially saturated or aromatic ring having additional 0-4 ring heteroatoms chosen from oxygen, nitrogen, sulfur and phosphorus; and each $R^*$ is independently H, alkyl, cycloalkyl, aryl, heteroaryl, or heterocyclyl;

provided that when $R^1$ is m-methylphenyl, X is a $C_2$ unsubstituted saturated alkylene chain, and $R^2$ substituted Ring A is 4-benzyl or 4-phenyl-4'-hydroxy substituted N-piperinyl, $R^3-(Y)_m-$ is other than H, triphenylmethyl, benzoyl, 2,4-dimethoxybenzoyl, (3,5-dimethoxyphenyl)acetyl, or (3-chlorophenyl)acetyl.

As used herein, the following definitions shall apply unless otherwise indicated. The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "alkyl", alone or in combination with any other term, refers to a $C_{1-20}$ straight or branched acyclic hydrocarbon radical that is either completely saturated or contains one or more units of unsaturation.

Preferably, an alkyl radical contains from one to twelve carbon atoms. More preferably, an alkyl radical contains from one to eight carbon atoms. A $C_{2-20}$ linear or branched alkyl radical having at least one carbon-carbon double bond is also referred to as "alkenyl". The double bond(s) of the unsaturated hydrocarbon chain may be in either the cis or trans configuration and may occur in any stable point along the chain. A $C_{2-20}$ linear or branched alkyl having at least one carbon-carbon triple bond is also referred to as "alkynyl". The tripe bond(s) in an alkynyl radical may occur in any stable point along the chain. The terms "alkoxy", "hydroxyalkyl", "alkoxyalkyl", and "alkoxycarbonyl", alone or in combination with any other term, include both straight and branched hydrocarbon chains.

Examples of alkyl radicals include, but are not limited to, methyl, ethyl, n-propyl, isopropyl, n-butyl, isobutyl, sec-butyl, tert-butyl, pentyl, isoamyl, n-hexyl, ethenyl, propenyl, isopropenyl, butenyl, isobutenyl, pentenyl, hexenyl, hexadienyl, ethynyl, propynyl, butynyl, pentynyl and the like.

The term "alkoxy" refers to an alkyl ether radical (—O-alkyl). Examples of alkoxy radicals include, but are not limited to, methoxy, ethoxy, n-propoxy, isopropoxy, n-butoxy, isobutoxy, sec-butoxy, tert-butoxy and the like.

The term "cycloalkyl", "carbocyclyl", "carbocyclic", "carbocycle", or "carbocyclo", alone or in combination with any other term, refers to a monocyclic or polycyclic non-aromatic hydrocarbon ring radical having three to twenty carbon atoms, preferably from three to twelve carbon atoms, and more preferably from three to ten carbon atoms. If polycyclic, each ring in a carbocyclyl radical is non-aromatic unless otherwise indicated. A carbocylyl radical is either completely saturated or contains one or more units of unsaturation but is not aromatic. The unsaturation, if present, may occur in any point in the ring that may result in any chemically stable configuration. The term "cycloalkyl", "carbocyclyl", "carbocyclic", "carbocycle", or "carbocyclo" also includes hydrocarbon rings that are fused to one or more aromatic rings, such as in tetrahydronaphthyl, where the radical or point of attachment is on the non-aromatic ring.

Unless otherwise indicated, the term "cycloalkyl", "carbocyclyl", "carbocyclic", "carbocycle", or "carbocyclo" also includes each possible positional isomer of a non-aromatic hydrocarbon radical, such as in 1-decahydronaphthyl, 2-decahydronaphthyl, 1-tetrahydronaphthyl and 2-tetrahydronaphthyl. Examples of suitable cycloalkyl groups include, but are not limited to, cyclopropyl, cyclobutyl, cyclopentyl, cyclohexyl, cyclohexenyl, decahydronaphthyl, tetrahydronaphthyl and the like.

The term "halogen" refers fluorine (F), chlorine (Cl), bromine (Br), or iodine (I).

The term "aryl", alone or in combination with any other term, refers to an aromatic monocyclic or polycyclic hydrocarbon ring radical containing five to twenty carbon atoms, preferably from six to fourteen carbon atoms, and more preferably from six to ten carbon atoms. Also included within the scope of the term "aryl", as it is used herein, is a group in which an aromatic hydrocarbon ring is fused to one or more non-aromatic carbocyclic or heteroatom-containing rings, such as in an indanyl, phenanthridinyl or tetrahydronaphthyl, where the radical or point of attachment is on the aromatic hydrocarbon ring.

Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. The term "aralkyl" refers to an alkyl group substituted by an aryl. Examples of aralkyl groups include, but are not limited to, benzyl and phenethyl.

The term "heterocycle", "heterocyclic", or "heterocyclyl", alone or in combination with any other term, refers to a non-aromatic monocyclic or polycyclic ring radical containing three to twenty carbon atoms, preferably three to seven carbon atoms if monocyclic and eight to eleven carbon atoms if bicyclic, and in which one or more ring carbons, preferably one to four, are each replaced by a heteroatom such as N, O, and S. If polycyclic, each ring in a heterocyclyl radical is non-aromatic unless otherwise indicated. A heterocyclic ring may be fully saturated or may contain one or more units of unsaturation but is not aromatic. The unsaturation, if present, may occur in any point in the ring that may result in any chemically stable configuration. The heterocyclic ring may be attached at a carbon or heteroatom that results in the creation of a stable structure. Preferred heterocycles include 5-7 membered monocyclic heterocycles and 8-10 membered bicyclic heterocycles.

Also included within the scope of the term "heterocycle", "heterocyclic", or "heterocyclyl" is a group in which a non-aromatic heteroatom-containing ring is fused to one or more aromatic rings, such as in an indolinyl, chromanyl, phenanthridinyl or tetrahydro-quinolinyl, where the radical or point of attachment is on the non-aromatic heteroatom-containing ring. Unless otherwise indicated, the term "heterocycle", "heterocyclic", or "heterocyclyl" also includes each possible positional isomer of a heterocyclic radical, such as in 1-decahydroquinoline, 2-decahydroquinoline, 3-decahydroquinoline, 4-decahydroquinoline, 5-decahydroquinoline, 6-decahydroquinoline, 7-decahydroquinoline, 7-decahydroquinoline, 8-decahydroquinoline, 4a-decahydroquinoline, 8a-decahydroquinoline, 1-indolinyl, 2-indolinyl, 3-indolinyl, 1-tetrahydroquinoline, 2-tetrahydro-quinoline, 3-tetrahydro-quinoline and 4-tetrahydro-quinoline. The term "heterocylylalkyl" refers to an alkyl group substituted by a heterocyclyl.

Examples of heterocyclic groups include, but are not limited to, imidazolinyl, 2,3-dihydro-1H-imidazolyl, imidazolidinyl, indazolinolyl, perhydropyridazyl, pyrrolinyl, pyrrolidinyl, 4H-pyrazolyl, piperidinyl, pyranyl, pyrazolinyl, piperazinyl, morpholinyl, thiamorpholinyl, thiazolidinyl, thiamorpholinyl, oxopiperidinyl, oxopyrrolidinyl, azepinyl, tetrahydrofuranyl, oxoazepinyl, tetrahydropyranyl, thiazolyl, dioxolyl, dioxinyl, oxathiolyl, benzodioxolyl, dithiolyl, dithiolanyl, tetrahydrothiophenyl, sulfolanyl, dioxanyl, dioxolanyl, tetrahydrofurodihydrofuranyl, dihydropyranyl, tetrahydropyranodihydrofuranyl, tetradyrofurofuranyl, tetrahydropyranofuranyl, diazolonyl, phthalimidinyl, benzoxanyl, benzopyrrolidinyl, benzopiperidinyl, benzoxolanyl, benzothiolanyl and benzothianyl.

The term "heteroaryl", alone or in combination with any other term, refers to an aromatic monocyclic or polycyclic ring radical containing five to twenty carbon atoms, preferably five to ten carbon atoms, in which one or more ring carbons, preferably one to four, are each replaced by a heteroatom such as N, O, S and P. Preferred heteroaryl groups include 5-6 membered monocyclic heteroaryls and 8-10 membered bicyclic heteroaryls.

Also included within the scope of the term "heteroaryl" is a group in which a heteroaromatic ring is fused to one or more aromatic or non-aromatic rings where the radical or point of attachment is on the heteroaromatic ring. Examples include, but are not limited to, pyrido[3,4-d]pyrimidinyl, 7,8-dihydro-pyrido[3,4-d]pyrimidine and 5,6,7,8-tetrahydro-pyrido[3,4-d]pyrimidine. Unless otherwise indicated, the term "heteroaryl" also includes each possible positional isomer of a heteroaryl radical, such as in 2-pyrido[3,4-d]pyrimidinyl and 4-pyrido[3,4-d]pyrimidinyl. The term "heteroaralkyl" refers to an alkyl group substituted by a heteroaryl.

Examples of heteroaryl groups include, but are not limited to, imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, carbazolyl, carbolinyl, tetrazolyl, benzofuranyl, oxazolyl, benzoxazolyl, isoxozolyl, isothiazolyl, thiadiazolyl, furazanyl, oxadiazolyl, benzimidazolyl, benzothienyl, quinolinyl, benzotriazolyl, benzothiazolyl, isoquinolinyl, isoindolyl, acridinyl and benzoisoxazolyl.

The term "heteroatom" means nitrogen, oxygen, sulfur, or phosphorus and includes any oxidized form of nitrogen, such as $N(O)$ [$N^+$—$O^-$], sulfur such as $S(O)$ and $S(O)_2$, phosphorus such as $PO_3$ and $PO_4$ and the quaternized form of any basic nitrogen. Suitable substituents on a substitutable ring nitrogen include alkyl, —$N(R')_2$, —C(O)R', —$CO_2R'$, —C(O)C(O)R', —C(O)CH$_2$C(O)R', —SO$_2$R', —SO$_2$N(R')$_2$, —C(=S)N(R')$_2$, —C(=NH)—N(R')$_2$, and —NR'SO$_2$R'; wherein R' is hydrogen, alkyl, phenyl (Ph), —OPh, —CH$_2$Ph, wherein said alkyl or phenyl is optionally substituted by one or more groups independently chosen from alkyl, amino, alkylamino, dialkylamino, aminocarbonyl, halo, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

The term "alkylene chain" refers to a straight or branched hydrocarbon chain that may be fully saturated or have one or more units of unsaturation. The unsaturation may occur in any stable point along the chain. The double bond(s) in the unsaturated alkylidene chain may be in either the cis or trans configuration.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all endo or exo, cis or trans isomers as well as all stereochemical forms of the structure, i.e., the R and S configurations for each asymmetric center. Therefore, racemates and racemic mixtures, single enantiomers, diastereomeric mixtures and individual diastereoisomers of the present compounds are expressly included within the scope of the invention. Although the specific compounds exemplified herein may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are also within the scope of this invention.

It will be apparent to one skilled in the art that certain compounds of this invention may exist in alternative tautomeric forms. All such tautomeric forms of the present compounds are within the scope of the invention. Unless otherwise indicated, the representation of either tautomer is meant to include the other.

Certain preferred compounds of the present invention are those represented by formula II:

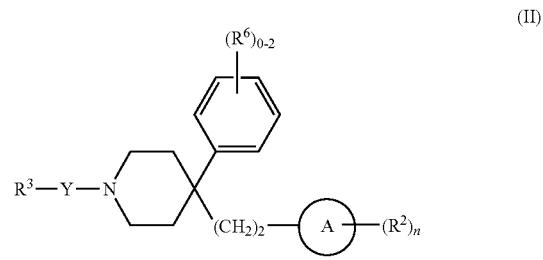

(II)

or a pharmaceutically acceptable derivative thereof, wherein $R^2$, $R^3$, $R^6$, n, Y and Ring A are as defined for formula I.

Preferred compounds of formula II are those wherein Ring A is a heterocycle having one ring nitrogen and 0-1 additional ring oxygen or ring nitrogen. Other preferred compounds of formula If are those wherein Ring A is piperidinyl, piperazinyl, pyrrolidinyl, azabicyclo[3.2.1]octanyl, aza-bicyclo[3.2.1]octenyl or oxa-aza-bicyclo[4.3.1]decanyl. In some embodiments of the invention, Ring A is connected to the alkylene chain X through an endocyclic nitrogen.

Also preferred are compounds of formula II, wherein $R^2$ is aryl, aralkyl, heteroaryl, heterocyclyl, —N(H)(—V$_m$—R$^+$), or —N(alkyl)(—V$_m$—R$^+$), wherein V is —C(O)—, —S(O)$_2$—, —C(O)O— or —C(O)—N(H)—, m is 0 or 1, R$^+$ is phenyl or benzyl, and said aryl, aralkyl, heteroaryl or heterocyclyl is optionally substituted. More preferably, $R^2$ of compounds of formula II is phenyl, naphthyl, benzyl, —NH-phenyl, —NH-benzyl, —NHC(O)-phenyl, —NHSO$_2$-phenyl, —NHC(O)NH-phenyl, benzoimidazolyl, dihydrobenzo-imidazolyl, oxodihydrobenzoimidazolyl, 3H-indolyl, quinolinyl, dihydro-1H-isoindolyl, dioxodihydro-1H-isoindolyl, tetrahydroquinoxalinyl, dioxotetrahydroquinoxalinyl, 3H-imidazo[4,5-b]pyridinyl, dihydro-1H-imidazo[4,5-b]pyridinyl, benzotriazolyl, oxadiazolyl or triazolyl, wherein each member of $R^2$ is optionally substituted. Preferred substituents of $R^2$ include alkyl, halo, —SO$_2$R$^0$, —CF$_3$, alkoxy, —NR$^0$, —N(R$^0$)C(O)R$^0$, —N(R$^0$)C(O)OR$^0$, —N(R$^0$)C(S)N(R$^0$)$_2$, =O, —(CH$_2$)$_{1-6}$—C(O)R$^0$, optionally substituted alkyl, and optionally substituted aralkyl. More preferred substituents of $R^2$ include methyl, ethyl, n-propyl, i-propyl, n-butyl, i-butyl, t-butyl, F, Cl, —SO$_2$CH$_3$, —CF$_3$, —OMe, —OEt, —NH$_2$, —NHMe, —N(H)C(O)Me, —N(H)C(O)OMe, —N(H)C(O)OEt, —N(H)C(S)N(H)(Me), =O, —(CH$_2$)$_2$SO$_2$Ph, =O, —CH$_2$—C(O)-cyclopropyl, and methoxy substituted benzyl. Preferably, n is 1-3, and more preferably, n is 1-2. In certain embodiments of the invention, $R^2$ is attached to Ring A through a $R^2$ nitrogen.

Preferred Y of formula II includes —C(O)—, —O—C(O)—, —N(R$^0$)—C(O)—, —S(O)$_2$—, —O—C(=N—CN)—, —S—C(=N—CN)—, —N(R$^0$)—C(=N—CN)—, —C(=N—CN)—, —N(R$^0$)—C(S)—, —N(R$^0$)—C(=N—

OR⁰)—, —N(R⁰)—C[=N—S(O)ₜ—R⁰], —O—C(=N—
R⁰)—, —N(R⁰)—C[=N—C(O)—R⁰], —N(R⁰)—C(=N—
R⁰)—, and —C(=N—R⁰)—. More preferably, each R° in Y
is independently R* and m is 1.

Preferred R³ of formula II includes optionally substituted
alkyl, aryl, heteroaryl, heterocyclyl and carbocyclyl. More
preferred R³ of formula II includes optionally substituted
fully saturated alkyl, 3-7 membered carbocyclyl, 5-7 membered aryl, 6-10 membered heteroaryl and 4-10 membered
heterocyclyl. Even more preferred R³ of formula II includes
cyclopropyl, cyclobutyl, cyclopentyl, cyclohexyl, cycloheptyl, cyclohexenyl, tetrahydrofuranyl, azetidinyl, piperidinyl,
hexahydrofuro[2,3-b]furanyl, oxopyrrolidinyl, dihydro-2H-
[1,3]thiazinyl, tetrahydro-pyrimidinyl, dihydrobenzo[1,4]dioxinyl, dihydro-2H-benzo[1,2,4]thiadiazinyl, dihydrobenzo
[d]isothiazolyl, morpholinyl, dihydro-1H-imidazolyl,
dihydrobenzooxazolyl, chromenyl, dihydroquinolinyl, pyrrolyl, benzotriazolyl, benzothiazolyl, benzofuranyl, furanyl,
pyridyl, thienyl, thiadiazolyl, isoxazolyl, triazolyl, thiazolyl,
benzoyl, isothiazolyl, imidazolyl, indolyl, pyrazolo[3,4-b]
pyridinyl, quinoxalinyl, and phenyl. Preferred substituents of
R³ includes halo, methylenedioxy, —OR⁰, R⁰, —C(O)OR⁰,
—SO₂R⁰, —SO₂(OR⁰), —SO₂N(R⁰)₂, —SO₂N(R⁰)OR⁰,
and —SO₂N(R⁰)C(O)R⁰. More preferred substituents of R³
includes Cl, Br, F, CF₃, Me, tetrazolyl, methylenedioxy,
—OMe, —C(O)OH, —SO₂R⁰, —SO₂(OH), —SO₂NH₂,
—SO₂NHMe, —SO₂N(H)C(O)Me, and —SO₂N(H)OMe.

In certain embodiments of the invention, —(Y)ₘ—R³ is
selected from the following:

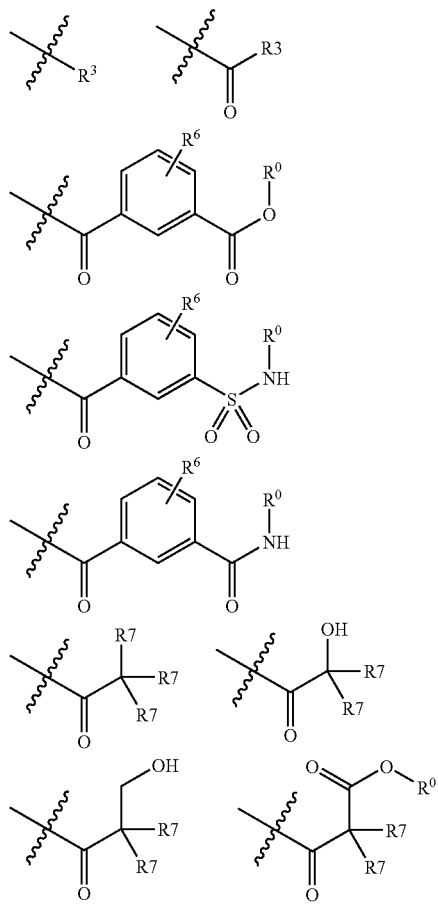

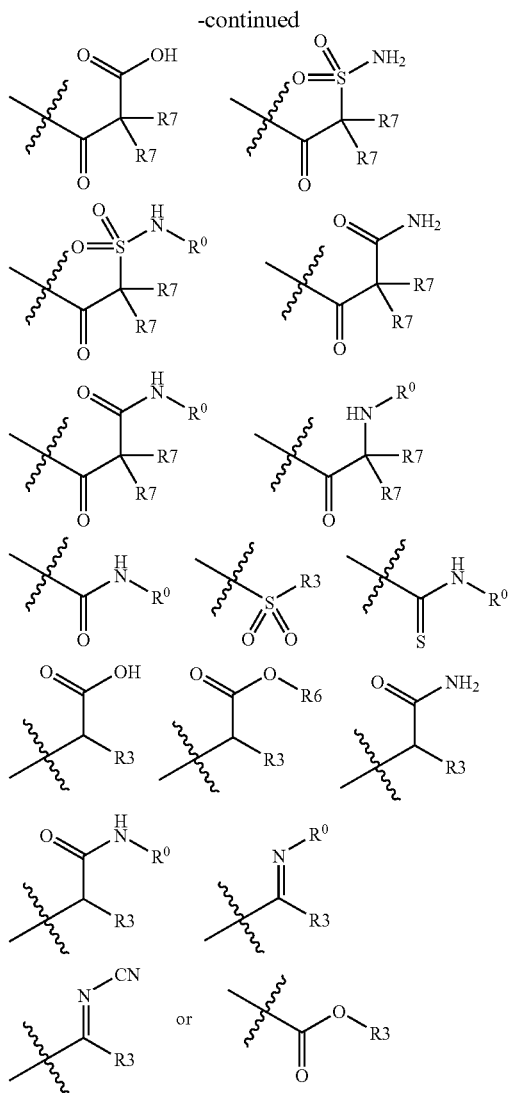

More preferably, —(Y)ₘ—R³ is selected from the following:

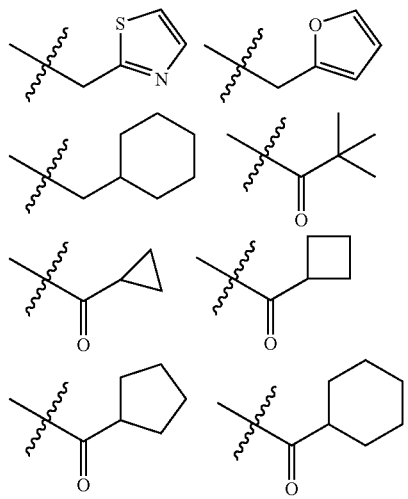

-continued
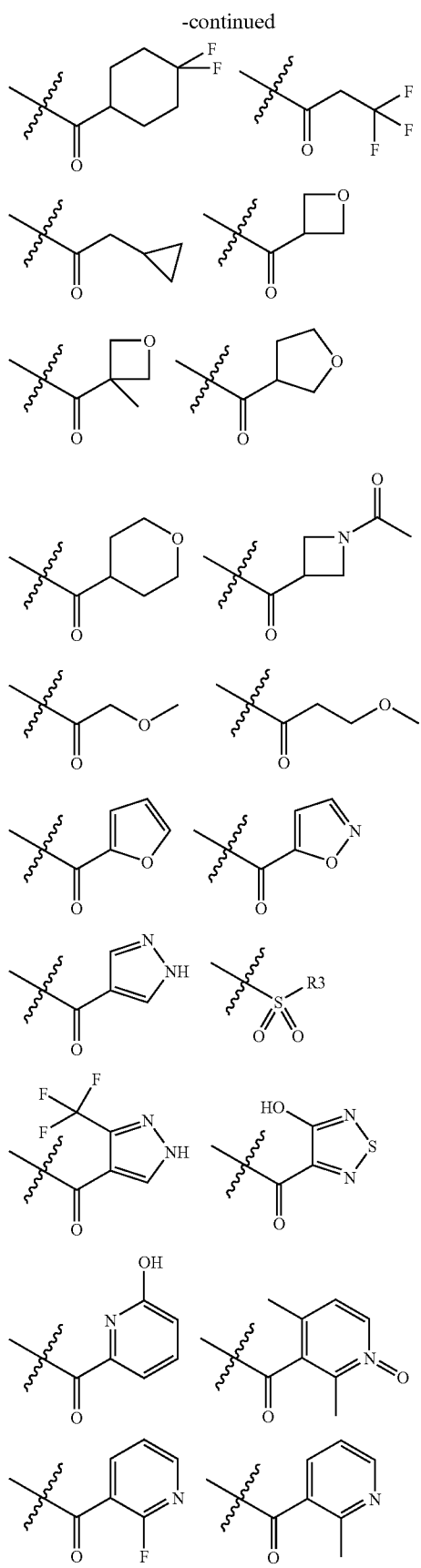
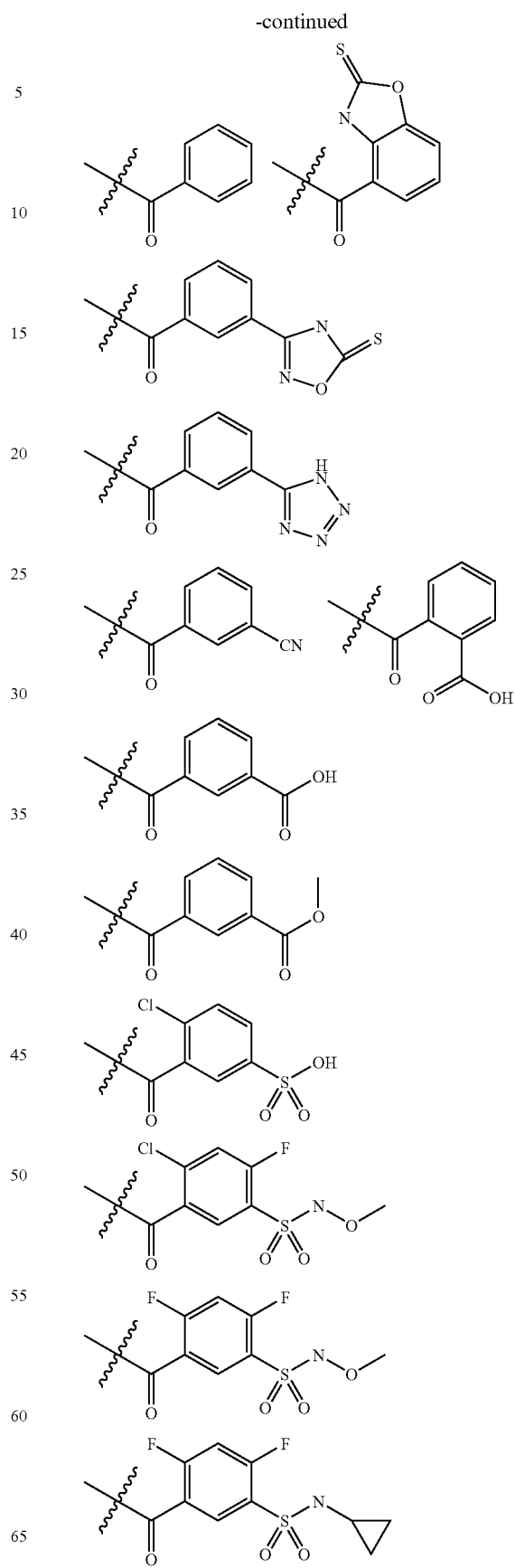

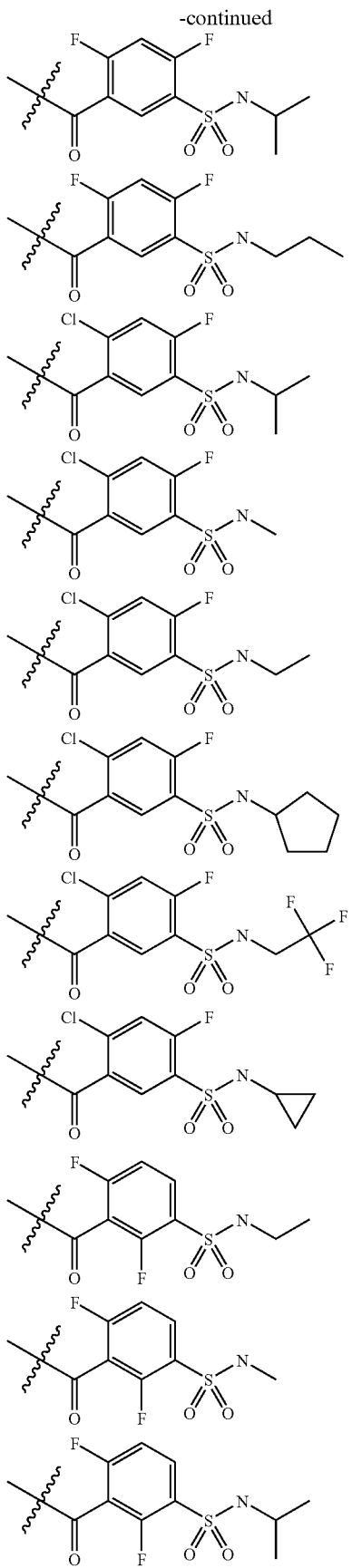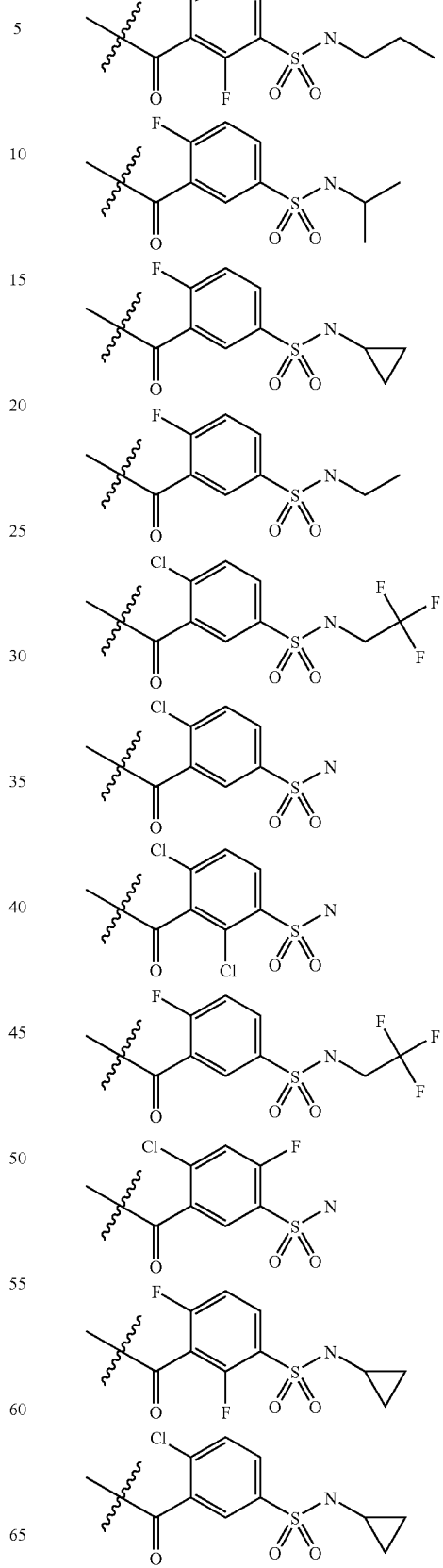

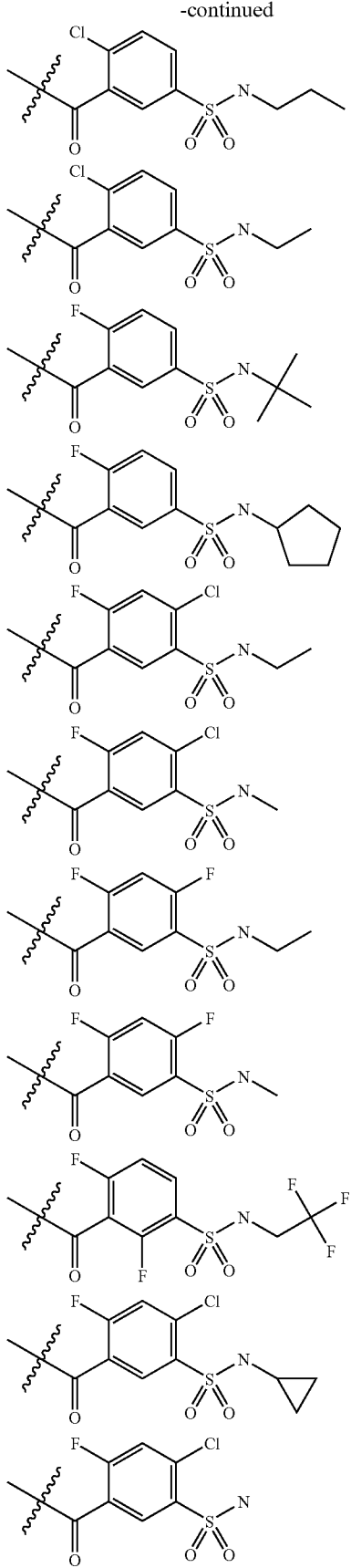
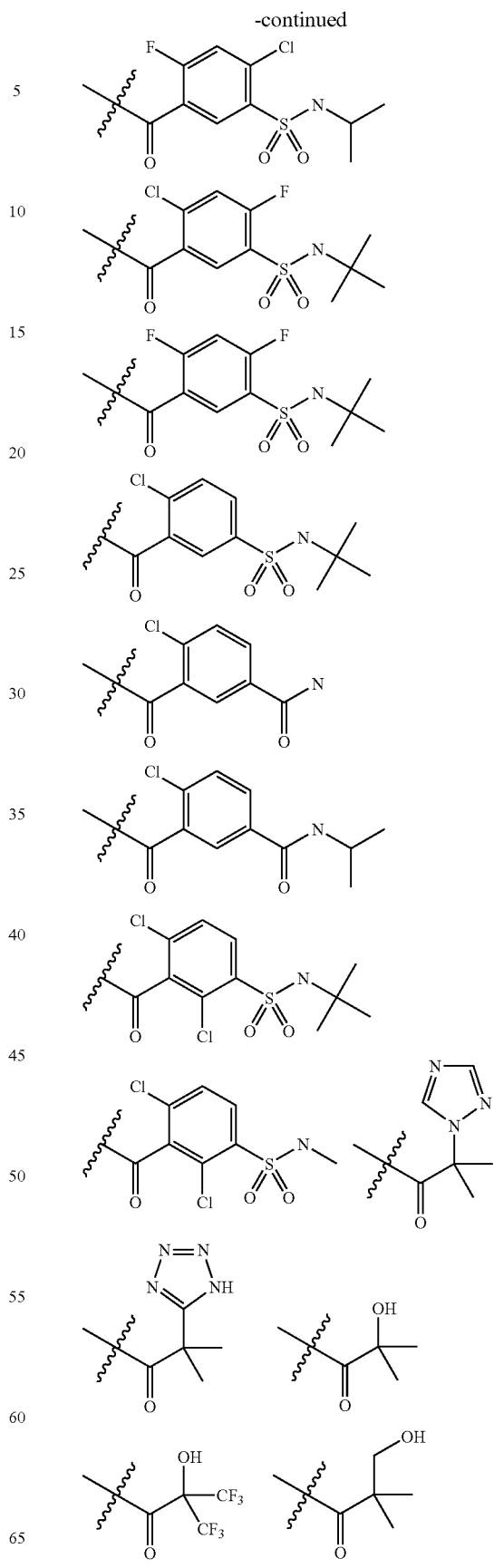

-continued
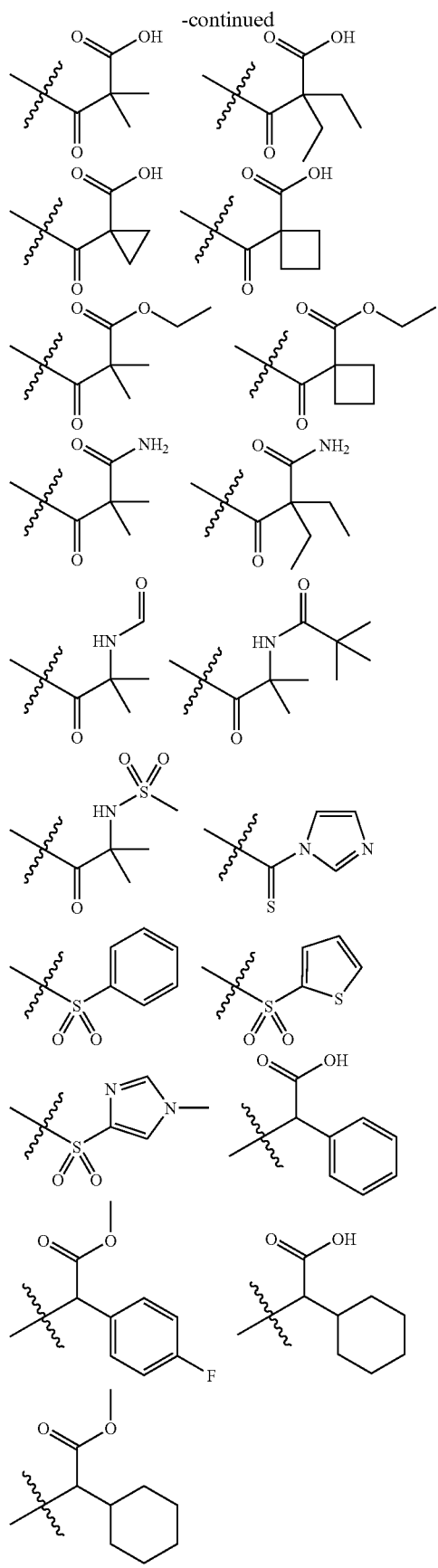
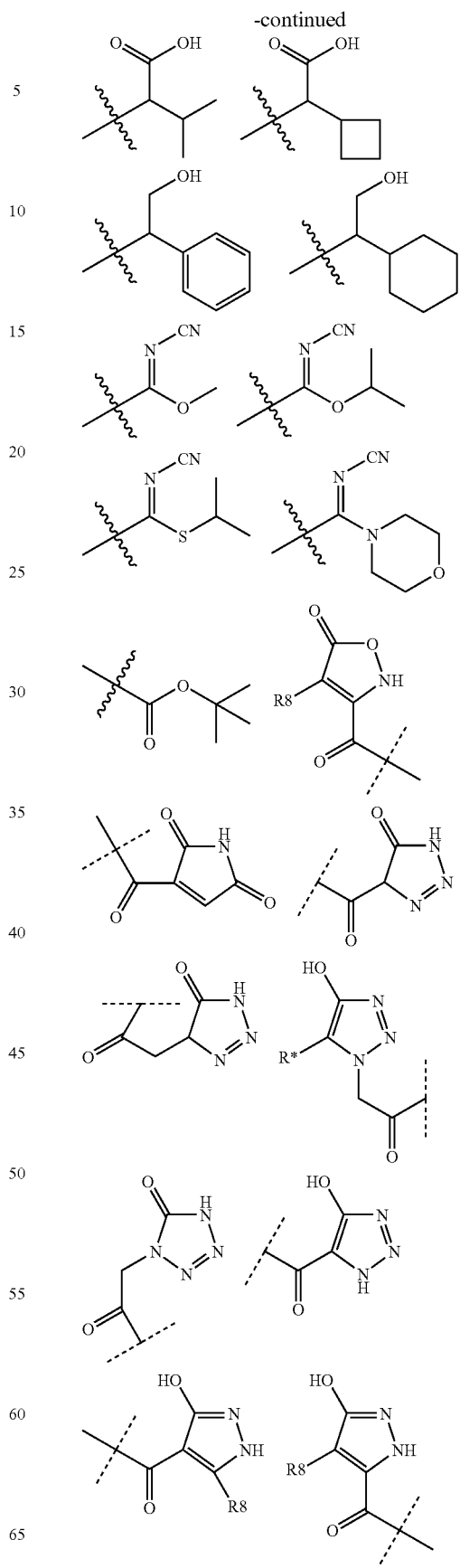

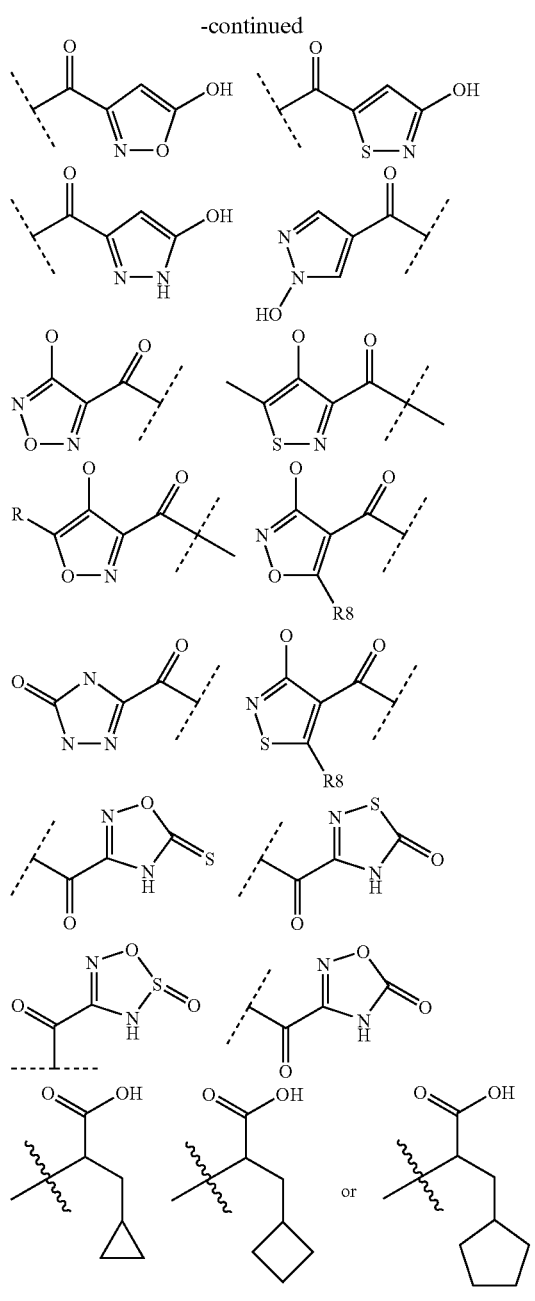

Specifically X may be —(CF$_2$—CH$_2$)—. Further X optionally has 1-3 heteroatoms selected from oxygen, phosphorus, sulfur, or nitrogen.

In one embodiment the A ring is selected from the following, where the asterisk (*) indicates the preferred, but not limiting, point(s) of substitution:

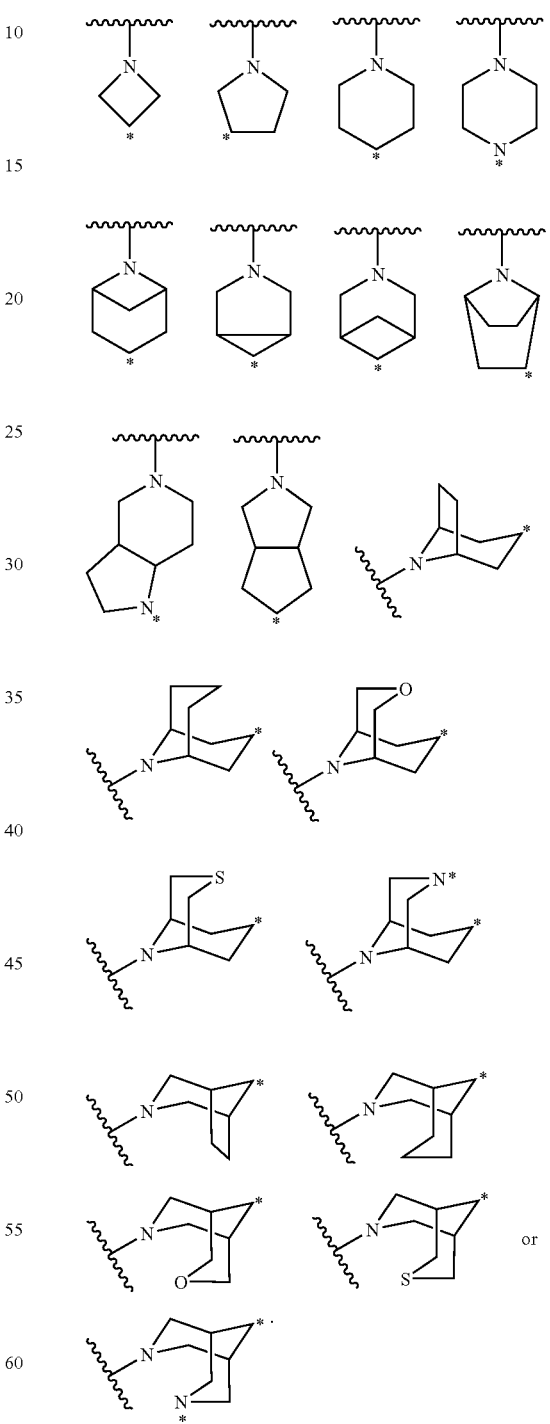

In one embodiment m is 1, Y is —C(O)—, and R$^3$ is aryl, heteroaryl, alkyl, or cycloalkyl, each optionally substituted.

In one embodiment m is 1, Y is —(C=N—CN)—O—, and R$^3$ is optionally substituted aryl, optionally substituted alkyl, optionally substituted cycloalkyl, optionally substituted heteroaryl, or optionally substituted heterocyclyl.

In one embodiment m is 1, Y is —(CH$_2$)—, and R$^3$ is optionally substituted aryl.

In one embodiment m is 1, Y is —C(O)O—, and R$^3$ is optionally substituted alkyl or optionally substituted aryl.

In one embodiment m is 0 and R$^3$ is optionally substituted heteroaryl or optionally substituted heterocyclyl.

In one embodiment X is —(CH$_2$)—, —(CH$_2$—CH$_2$)—, or —(CH$_2$—CH$_2$—CH$_2$)—. Further X is optionally substituted by one or more halogen or oxo. Still further X is disubstituted with halogen. Still further X is disubstituted with fluoro.

Suitably each R$^2$, with the asterisk (*) indicating a preferred, but not limiting, point of substitution from Ring A, independently is selected from

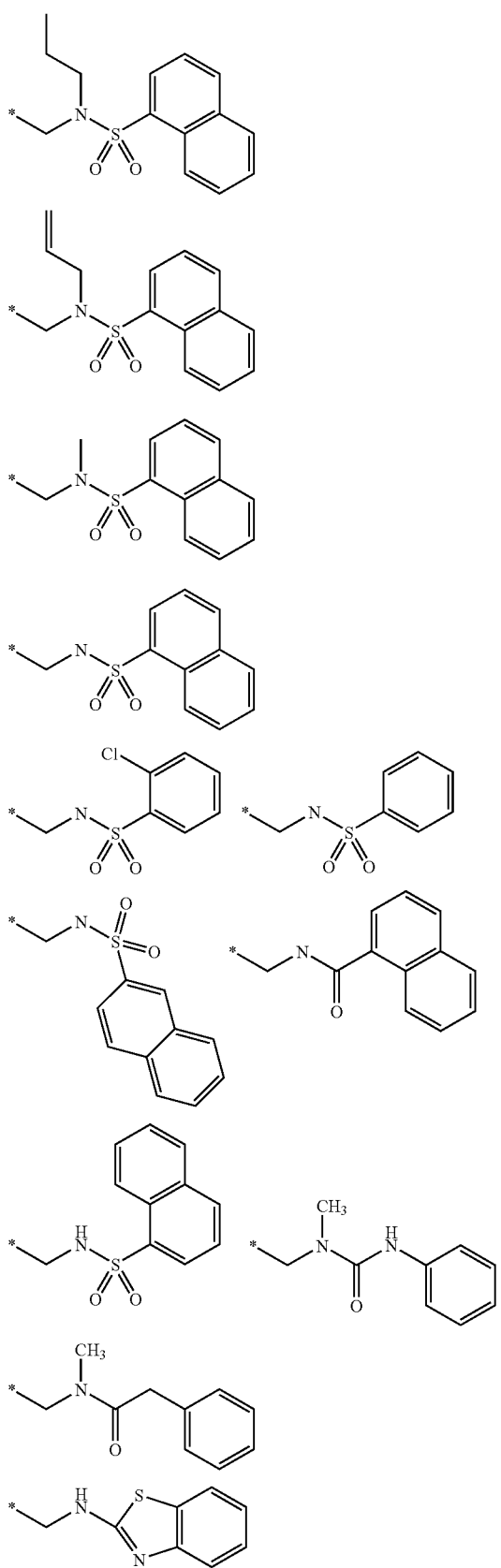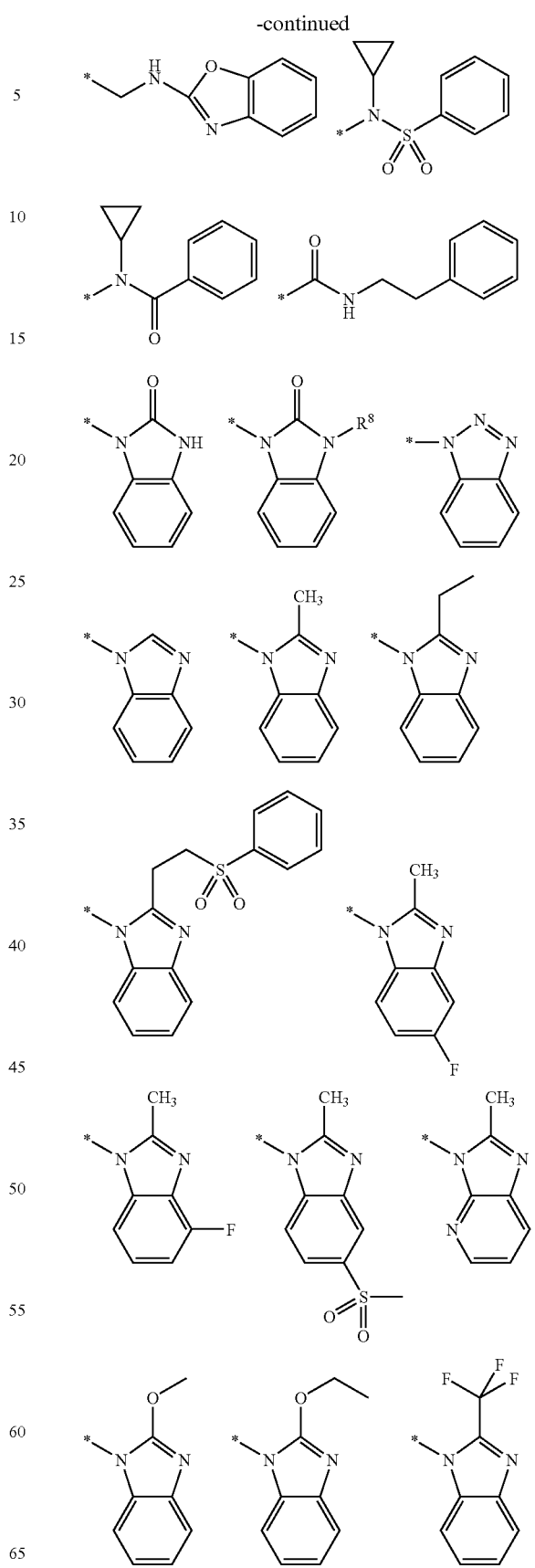
-continued

-continued
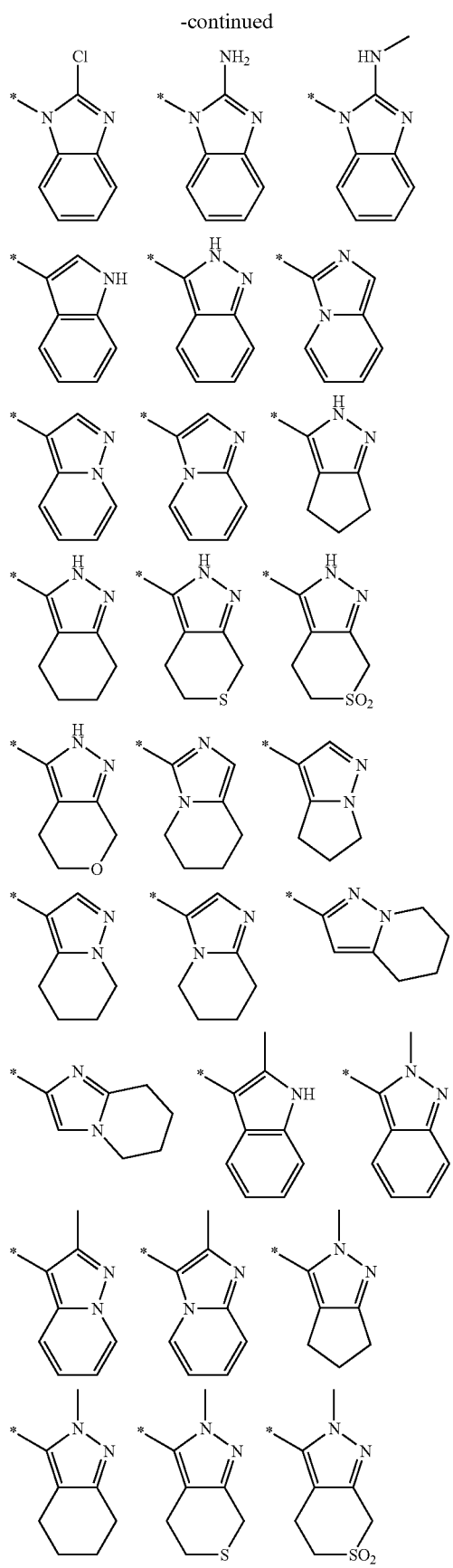
-continued
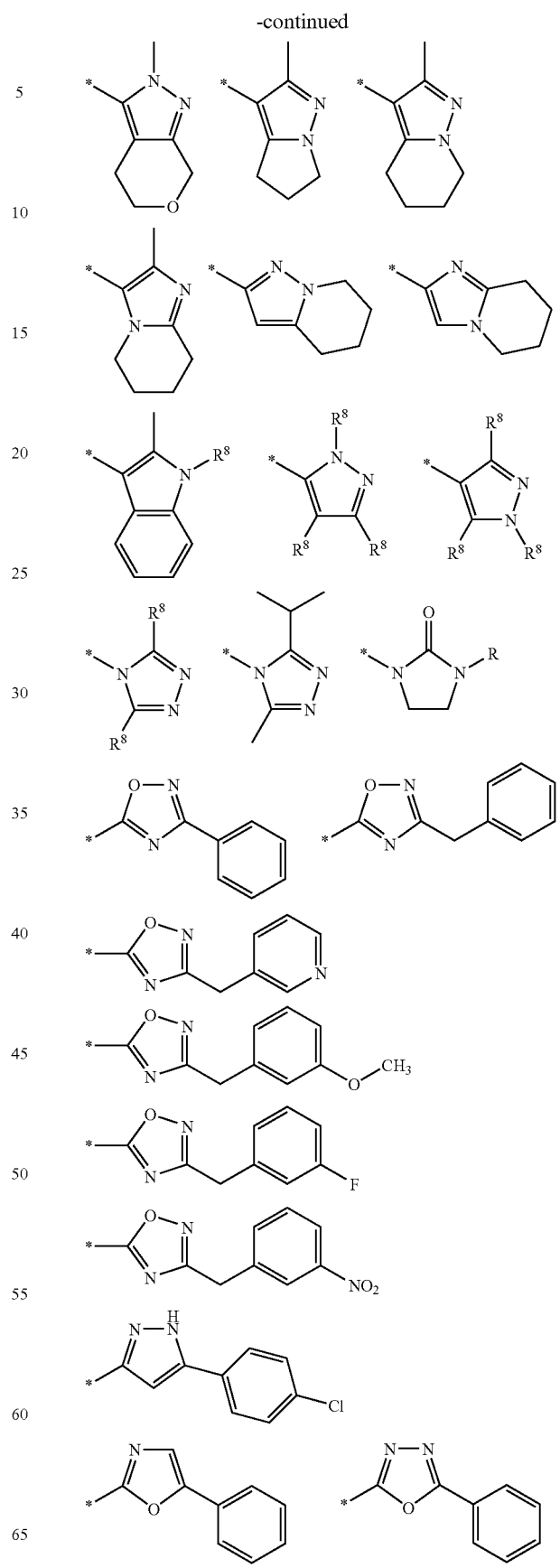

-continued
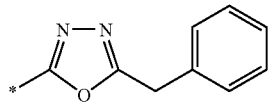
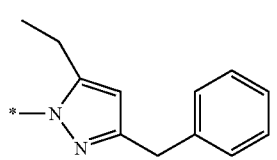
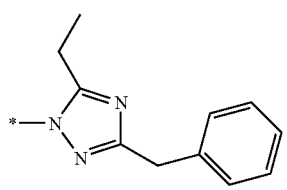
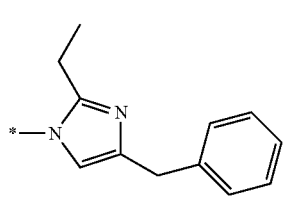
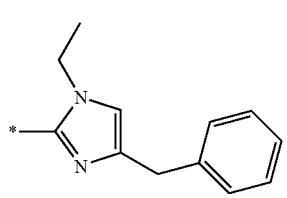
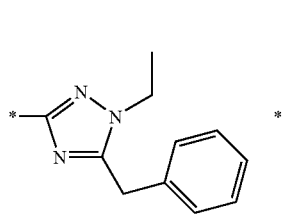
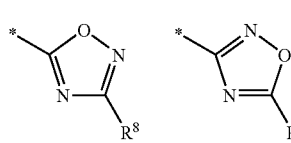

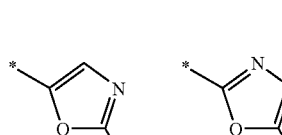
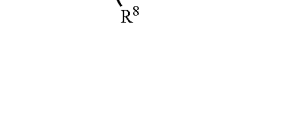
-continued
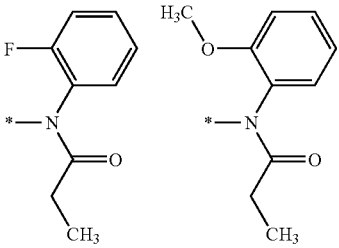
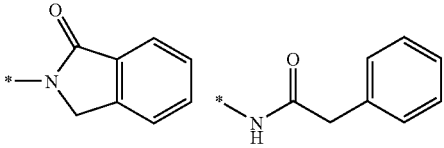
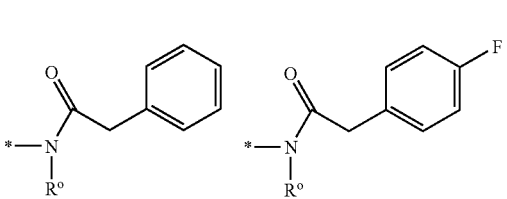
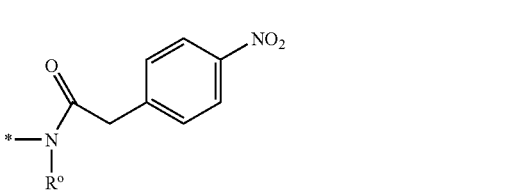
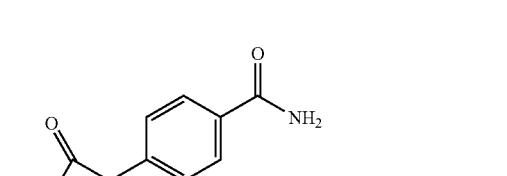
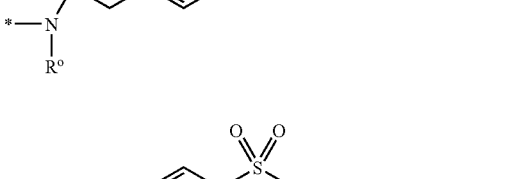
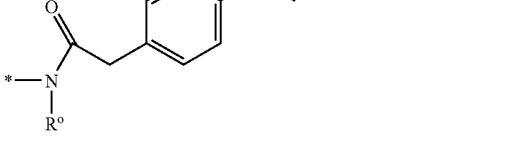
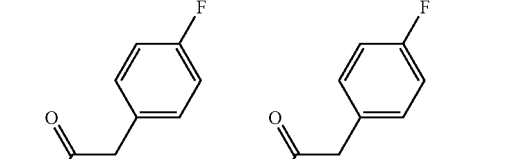
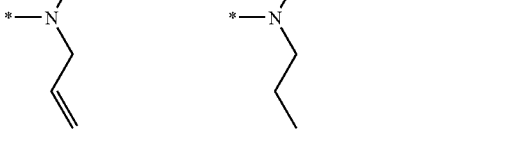

-continued
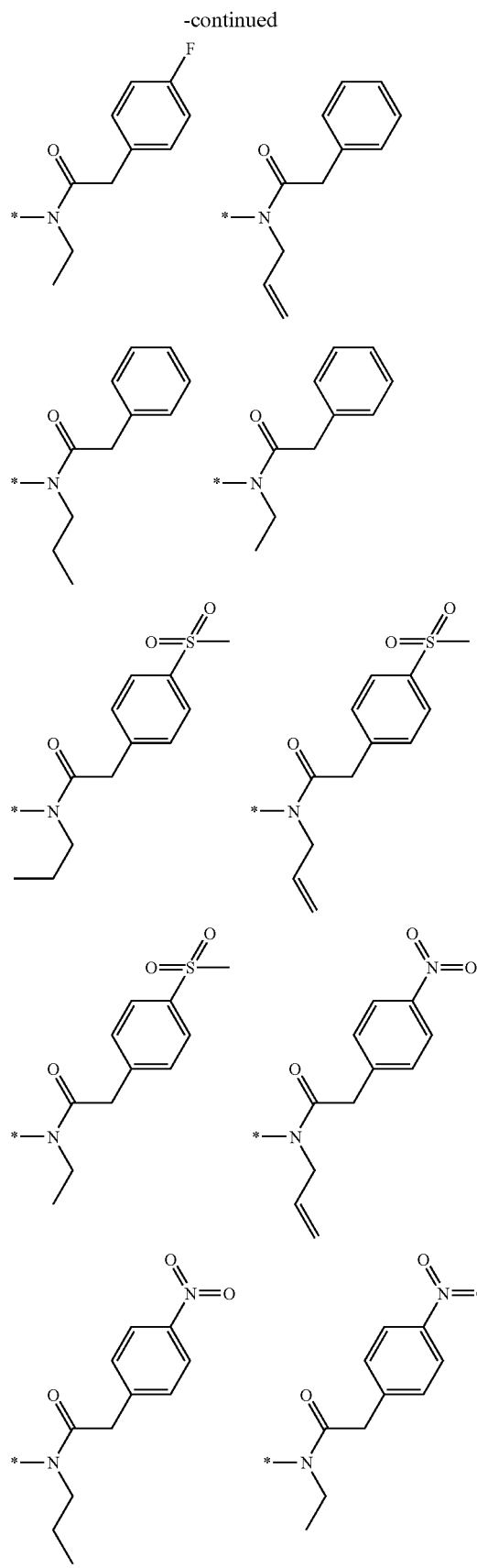
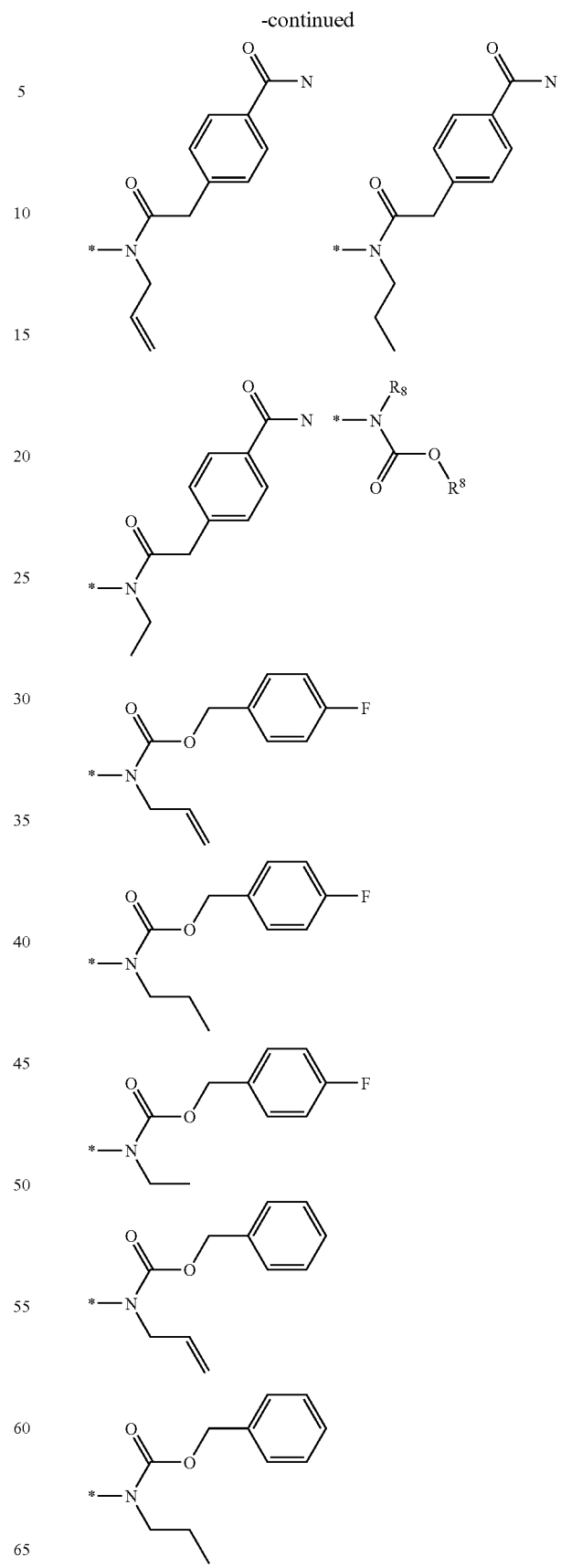

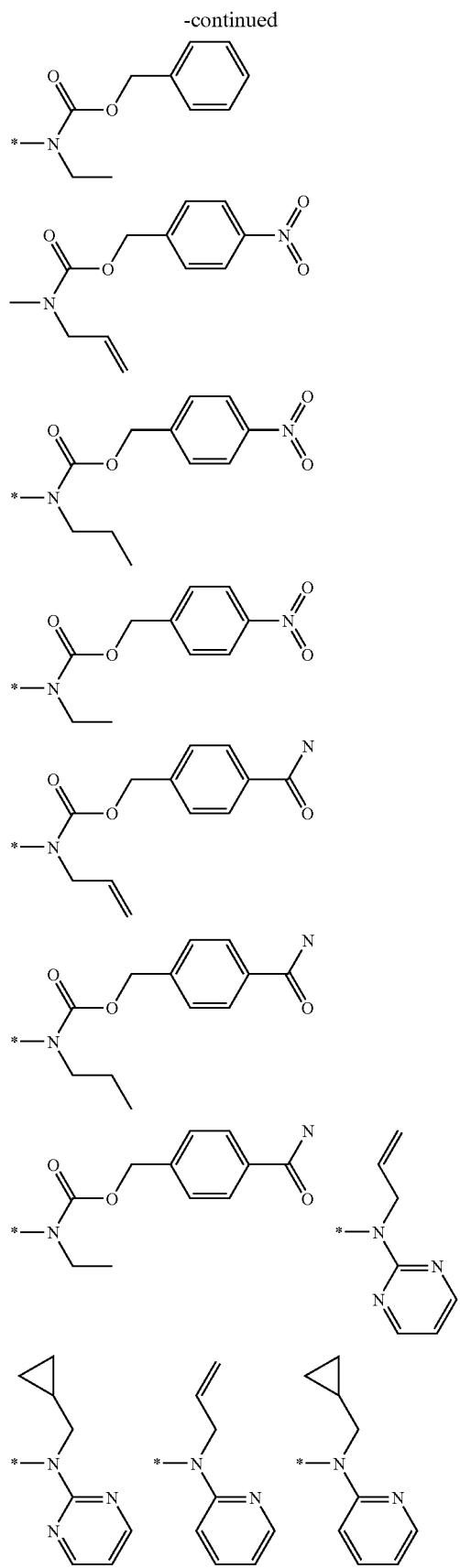
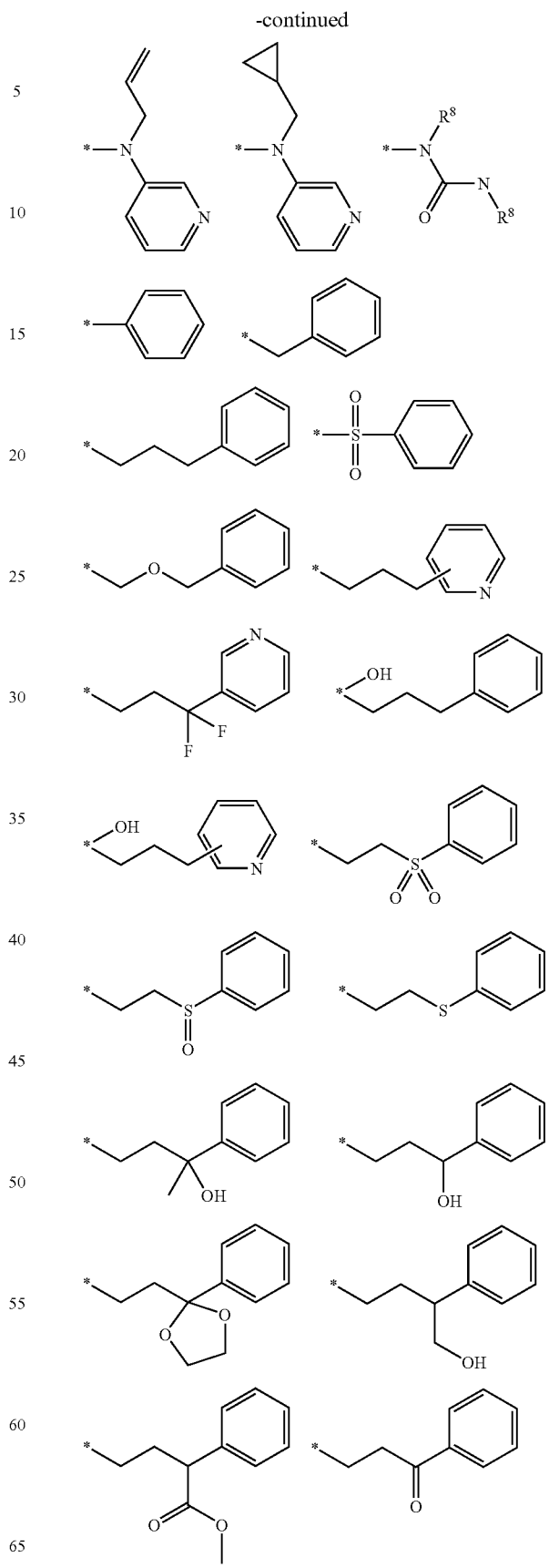

-continued

In one embodiment the ring A, with two geminal R²s, is selected from:

Suitably the A ring is tropane or piperidine, either optionally substituted with one or more R². Preferably, A—R² is comprised of one of the following:

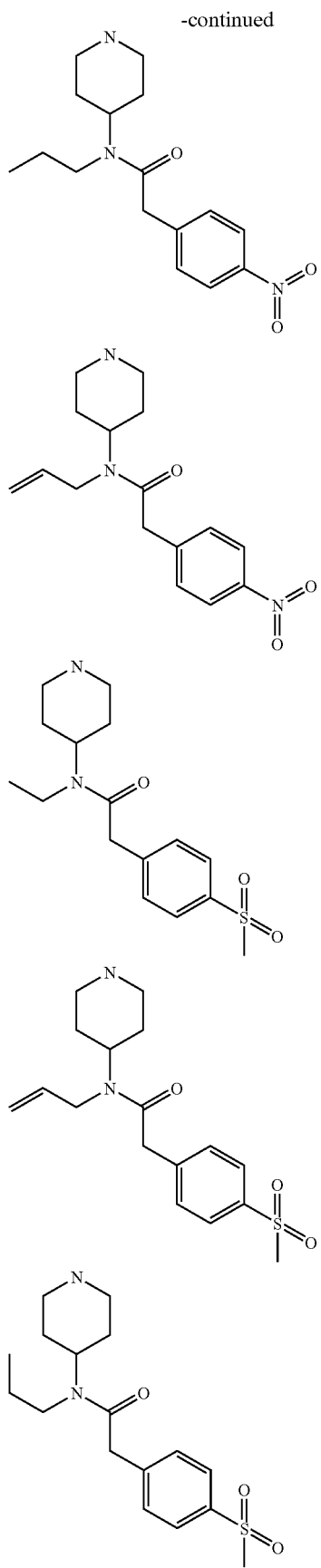
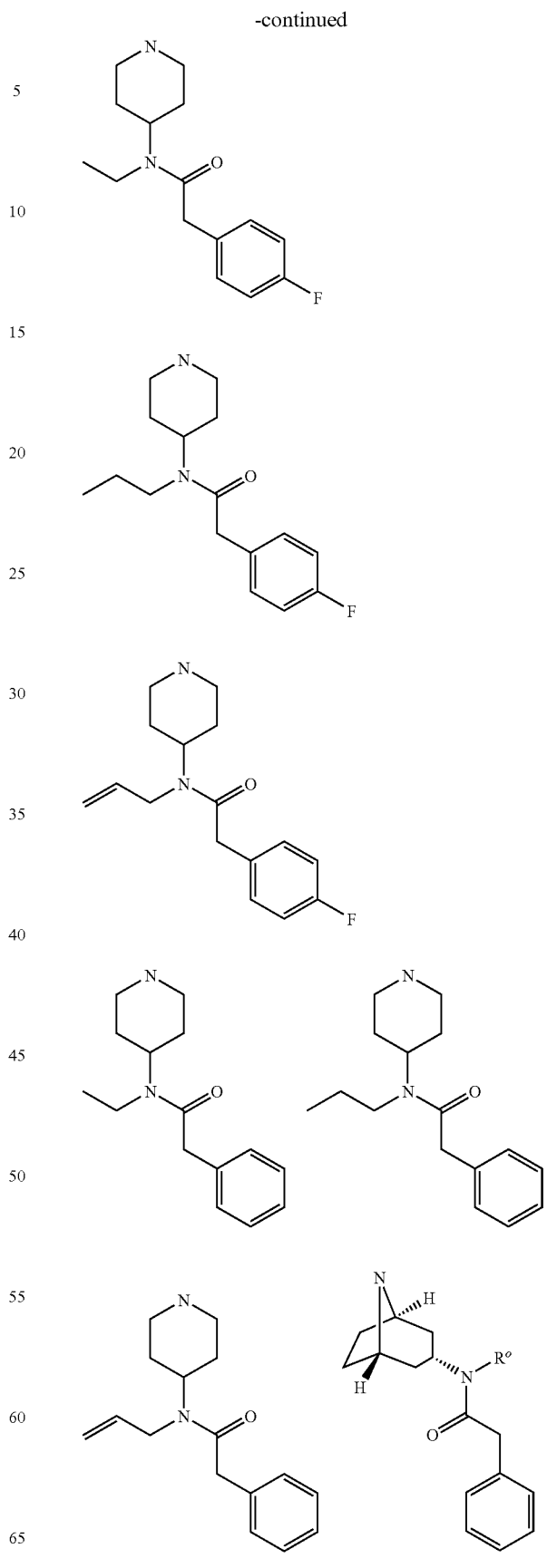

-continued
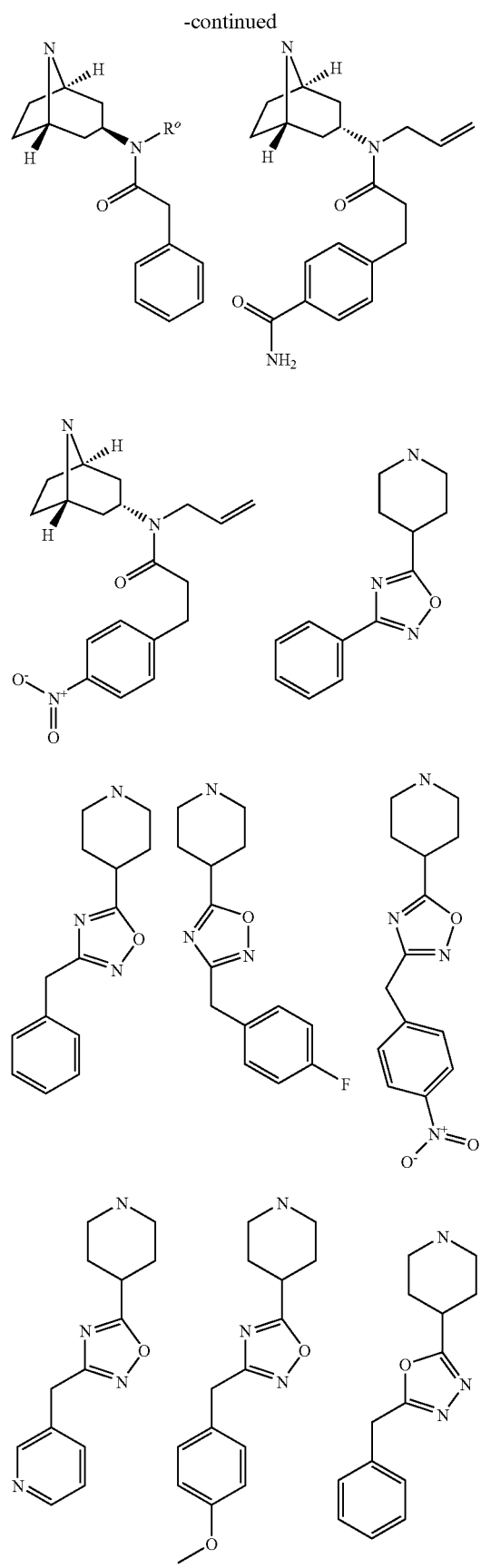
-continued
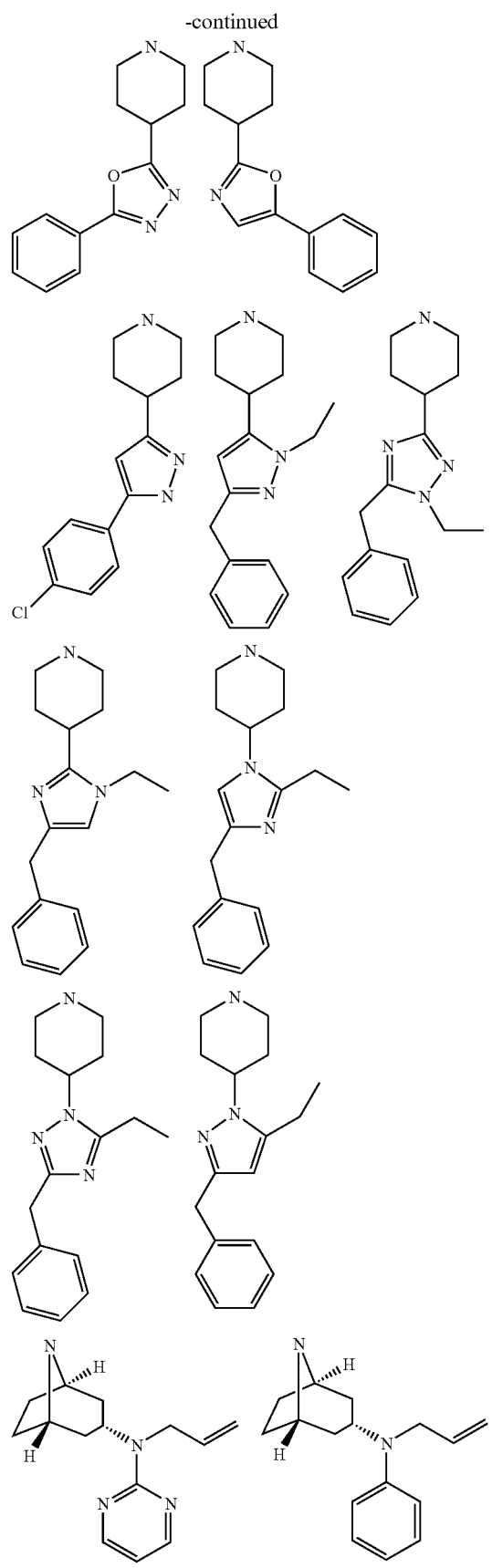

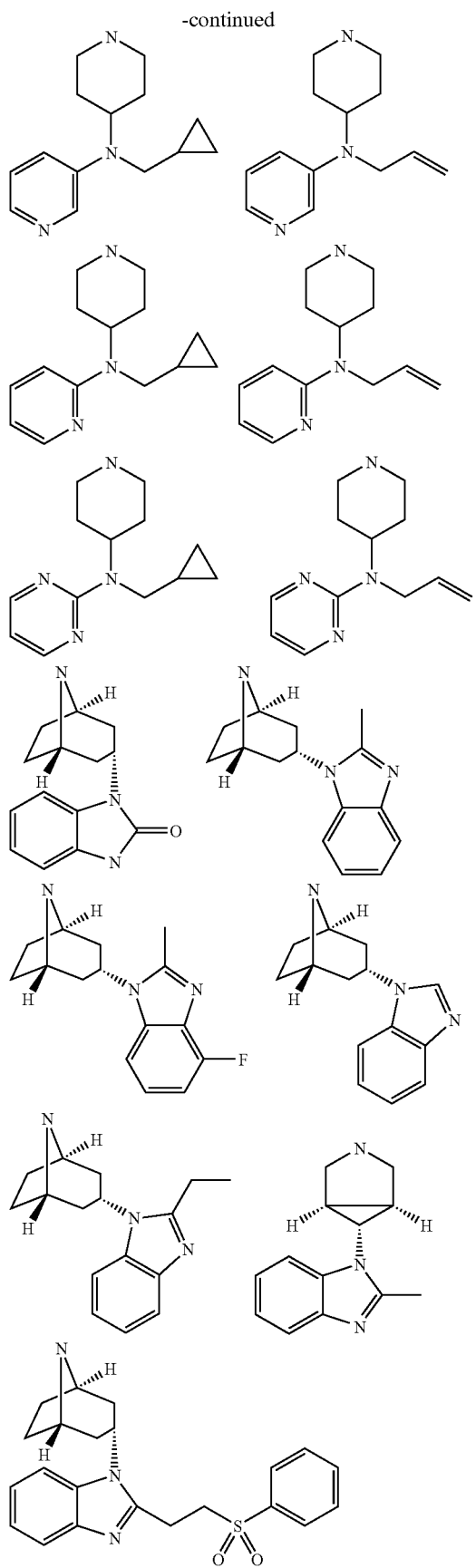
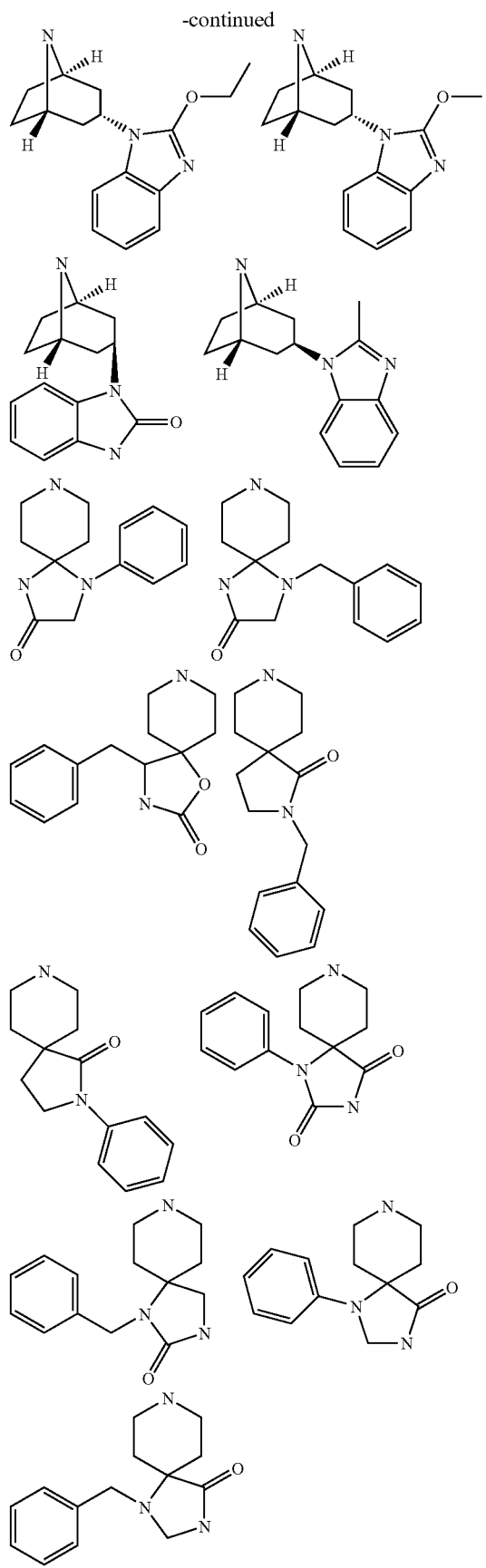

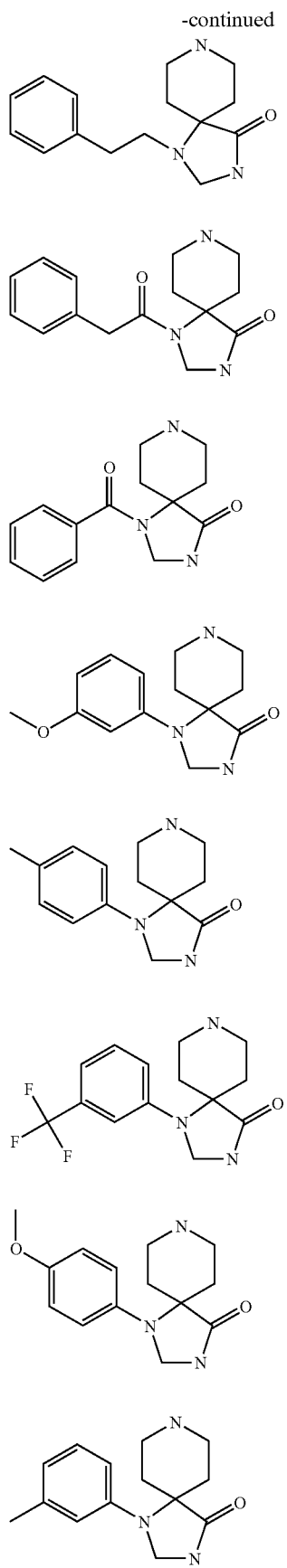
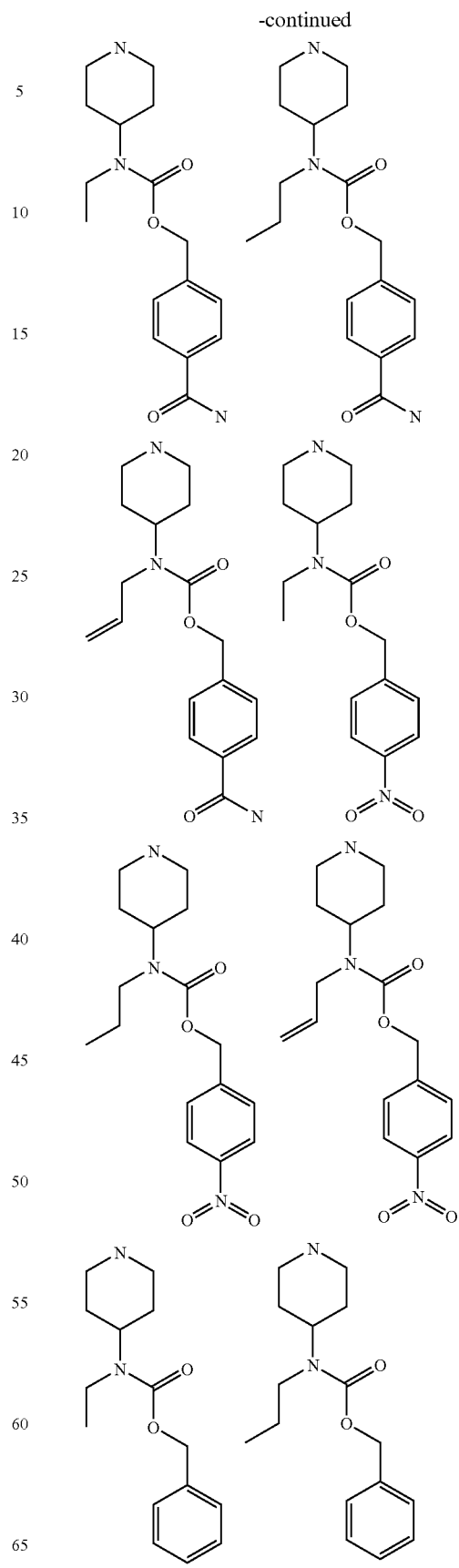

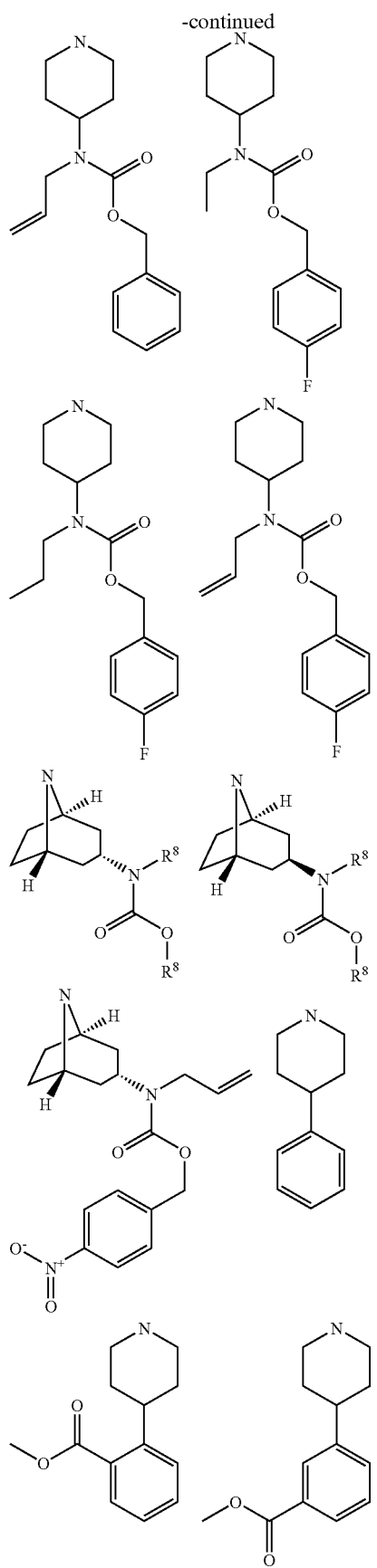
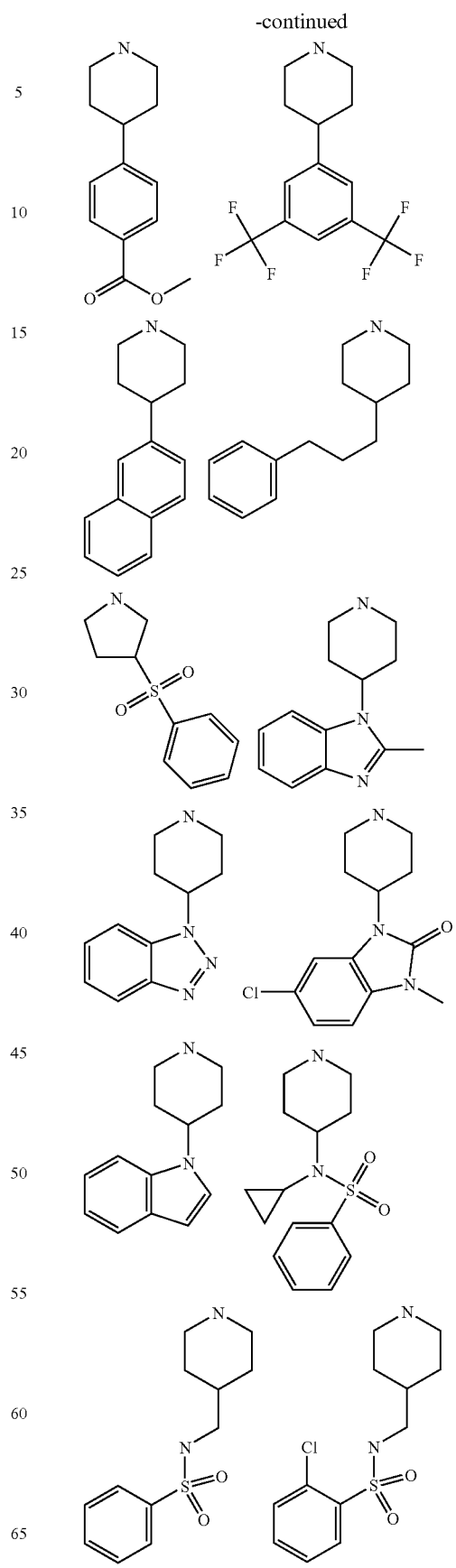

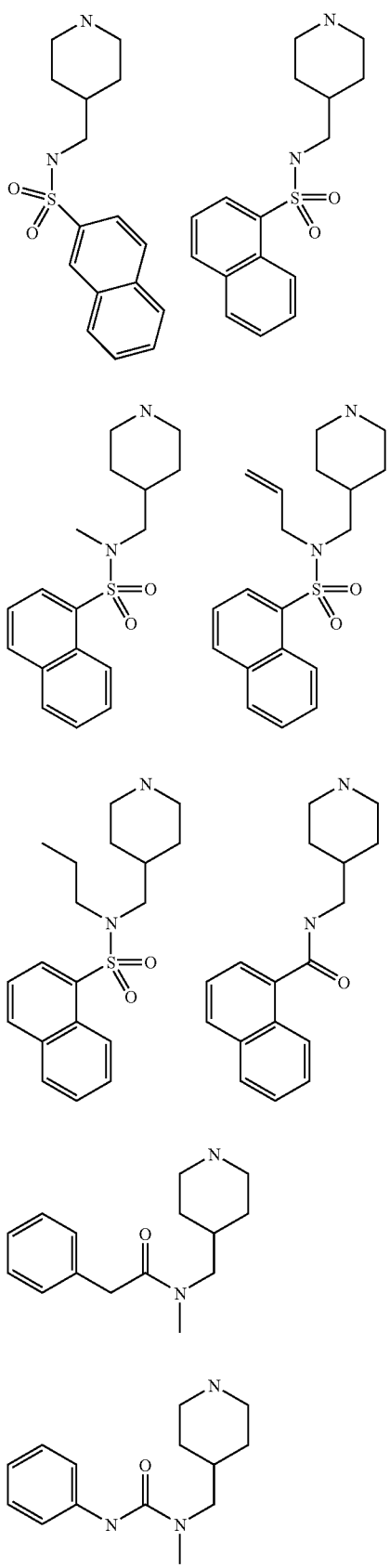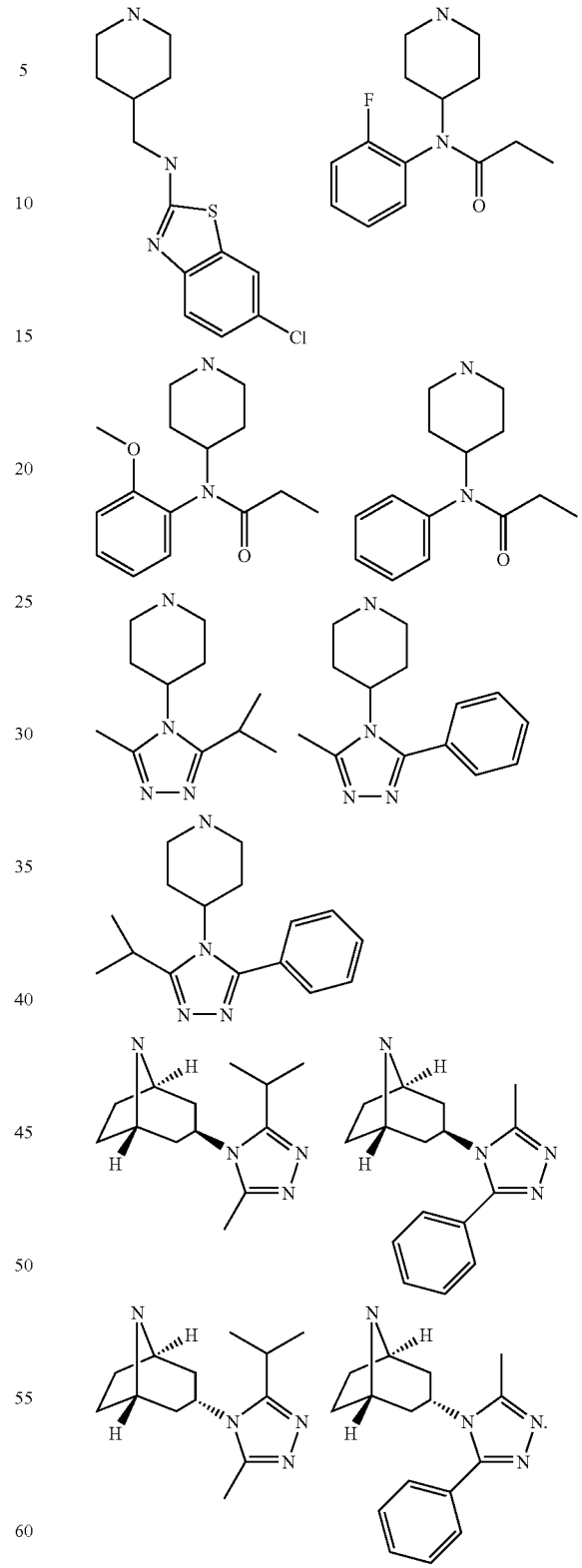
In one embodiment the A ring contains at least one additional nitrogen atom and said A ring optionally is N-substituted. Suitably the A ring is N-substituted with —(CH$_2$)$_a$—(V$_b$—R+).

Preferred $R^6$ of formula II includes alkyl, halo, $SO_2R^0$ and $SO_2N(R^0)_2$. More preferred $R^6$ of formula II includes Me, F, Cl, $SO_2NH_2$, $SO_2Me$, and methylenedioxy.

Other preferred compounds of the present invention are those represented by formula III:

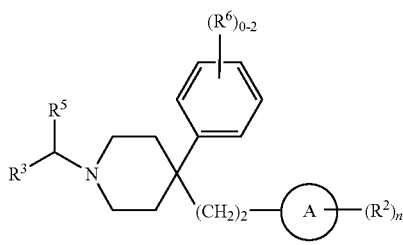

(III)

or a pharmaceutically acceptable derivative thereof, wherein $R^2$, $R^3$, $R^5$, $R^6$, n and Ring A are as defined for formula I. Preferred compounds of formula III are those wherein $R^3$ is optionally substituted aryl. More preferably, $R^3$ is phenyl optionally substituted by one or more alkyl (such as Me) or halo (such as F and Cl).

Other preferred compounds of the present invention are those represented by formulae IV-IX:

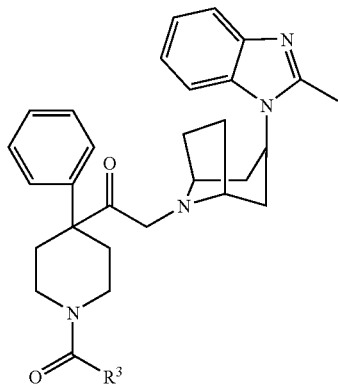

IV

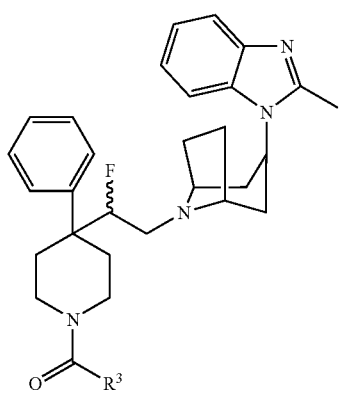

V

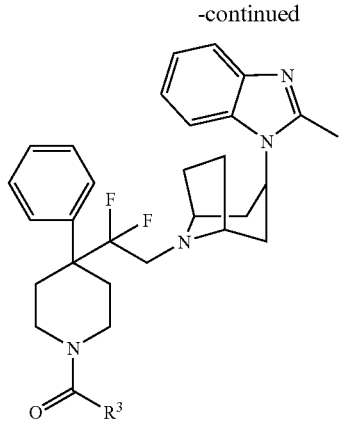

VI

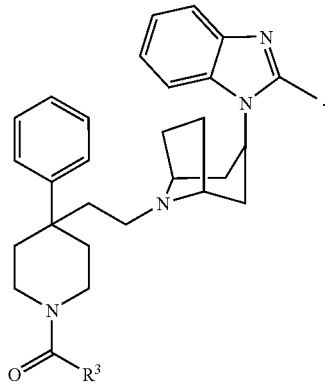

VII $R^3$ in formulae IV-VII is as defined for formula I.

Preferred compounds of formula I have one or more, and more preferably all, of the features selected from the group consisting of:

(a) $R^1$ is alkyl, aryl, heteroaryl or heterocyclyl, wherein said alkyl is optionally substituted by one or more $R^7$, said aryl or heteroaryl is optionally substituted by one or more $R^6$, and said heterocyclyl is optionally substituted by one or more $R^8$;

(b) X is a $C_{1-5}$ alkylene chain optionally substituted by one or more groups chosen from =O and halo;

(c) Ring A is an 8-10 membered bicyclic ring having 0-5 ring heteroatoms chosen from oxygen, sulfur and nitrogen;

(d) $R^2$ is aryl, heteroaryl or heterocyclyl, wherein said aryl or heteroaryl is optionally substituted by one or more $R^6$ and said heterocyclyl is optionally substituted by one or more $R^8$;

(e) Y is —C($R^0$)[C(O)O$R^0$]—, —C(O)—, —O—C(O)—, —N($R^0$)—C(O)—, —S(O)$_2$—, —O—C(=N—CN)—, —S—C(=N—CN)—, —N($R^0$)—C(=N—CN)—, —C(=N—CN)—, —N($R^0$)—C(S)—, —N($R^0$)—C(=N—O$R^0$)—, —N($R^0$)—C[=N—S(O)$_r$$R^0$], —O—C(=N—$R^0$)—, —N($R^0$)—C[=N—C(O)—$R^0$], —N($R^0$)—C(=N—$R^0$)—, or —C(=N—$R^0$)—; wherein each $R^0$ is independently R* and m is 1; and (f) $R^3$ is alkyl, aryl, heteroaryl, heterocyclyl or carbocyclyl, wherein said alkyl is optionally substituted by one or more $R^7$, said aryl or heteroaryl is optionally substituted by one or more $R^6$, and said heterocyclyl or carbocyclyl is optionally substituted by one or more $R^8$.

More preferred compounds of the present invention have one or more, and more preferably all, of the features selected from the group consisting of:
(a) $R^1$ is aryl optionally substituted by one or more $R^6$;
(b) X is a $C_2$ alkylene chain optionally substituted by one or more groups chosen from =O and halo;
(c) Ring A is an 8-9 membered bicyclic ring having one ring nitrogen and 0-4 additional ring heteroatoms chosen from oxygen, sulfur and nitrogen;
(d) $R^2$ is heteroaryl optionally substituted by one or more $R^6$, or heterocyclyl optionally substituted by one or more $R^8$;
(e) Y is —C($R^o$)[C(O)O$R^o$]—, —CH(COOH)—, —C(O)—, —O—C(O)—, —N($R^o$)—C(O)—, —O—C(=N—CN)—, or —N($R^o$)—C(S)—; wherein each $R^o$ is independently R* and m is 1; and
(f) $R^3$ is alkyl optionally substituted by one or more $R^7$, aryl or heteroaryl wherein said aryl or heteroaryl is optionally substituted by one or more $R^8$.

Other more preferred compounds of the present invention have one or more, and more preferably all, of the features selected from the group consisting of:
(a) $R^1$ is phenyl optionally substituted by one or more groups chosen from alkyl, halo, —O$R^o$, —CF$_3$, $R^o$, —SO$_2R^o$, methylenedioxy and —SO$_2$N($R^o$)$_2$; wherein each $R^o$ is independently R*;
(b) X is a saturated $C_2$ alkylene chain optionally substituted by one or more groups chosen from =O and halo;
(c) Ring A is an 8-9 membered non-aromatic bicyclic ring having one ring nitrogen and 0-1 additional ring heteroatoms chosen from oxygen, sulfur and nitrogen;
(d) $R^2$ is a 9-10 membered bicyclic heteroaryl or heterocyclyl each having one to three ring nitrogens, wherein said heteroaryl is optionally substituted by one or more groups chosen from alkyl, halo, —SO$_2R^o$, —CF$_3$, alkoxy, —N$R^o$, —N($R^o$)C(O)$R^o$, —N($R^o$)C(O)O$R^o$, and —N($R^o$)C(S)N($R^o$)$_2$ and said heterocyclyl is optionally substituted by one or more groups chosen from alkyl, halo, —SO$_2R^o$, —CF$_3$, alkoxy, —N$R^o$, —N($R^o$)C(O)$R^o$, —N($R^o$)C(O)O$R^o$, —N($R^o$)C(S)N($R^o$)$_2$ and =O;
(e) Y is —CH(COOH)—, —CH(COOMe)—, —C(O)—, —O—C(O)—, —N($R^o$)—C(O)—, —O—C(=N—CN)—, or —N($R^o$)—C(S)—; wherein each $R^o$ is independently H and m is 1; and
(f) $R^3$ is methyl, butyl, pentyl, cyclobutyl optionally substituted by one or more $R^8$, phenyl, pyrazolyl, thiadiazolyl, benzotriazolyl, pyrrolyl, benzothiazolyl, benzofuranyl, furanyl, pyridyl, thienyl, isoxazolyl, triazolyl, thiazolyl, isothiazolyl, imidazolyl, indolyl, pyrazolo[3, 4-b]pyridinyl, or quinoxalinyl, wherein each member of $R^3$ except methyl, butyl, pentyl and cyclobutyl is optionally substituted by one or more $R^6$ and said methyl, butyl and pentyl are optionally substituted by one or more $R^7$.

Even more preferred compounds of the present invention have one or more, and more preferably all, of the features selected from the group consisting of:
(a) $R^1$ is phenyl optionally substituted by one or more groups chosen from halo, —CF$_3$, methyleneoxy, alkyl, alkoxy and sulfonamide;
(b) X is a saturated $C_2$ alkylene chain;
(c) Ring A is azabicyclo[3.2.1]octanyl or piperidinyl;
(d) $R^2$ is benzoimidazolyl, imidazo[4,5-b]pyridinyl, benzotriazolyl, or oxadiazolyl, wherein each member of $R^2$ is optionally substituted by one or more groups chosen from alkyl, halo, $R^o$, —SO$_2R^o$, —CF$_3$, alkoxy, benzyl, —CH$_2$-pyridyl and —N$R^o$;
(e) Y is —C(O)—, —C(S)—, —C(O)C(O)—, —O—C(O)—, —CH(COOH)—, —CH(COOMe)—, —NH—C(O)—, —NH—C(S)—, —SO$_2$—, —CH$_2$—, or —O—C(=N—CN)— and m is 0 or 1; and
(f) $R^3$ is methyl, butyl, pentyl, cyclopropyl, cyclobutyl, cyclopentyl, cyclohexyl, cyclohexenyl, cycloheptanyl, phenyl, naphthyl, thienyl, furanyl, benzofuranyl, thiazolyl, isothiazolyl, isoxazolyl, pyrazolyl, pyrrolyl, piperidinyl, pyrimidinyl, benzooxazole-2-thionyl, imidazolyl, oxiranyl, pyrazolo[3,4-b]pyridinyl, pyrazolo[1,5-a]pyrimidinyl, thioxodihydrotriazinonyl, dihydrotetrazolethionyl, benzotriazolyl, pyrrolidinonyl, pyrrolidine-2,5-dionyl, imidazolidin-2-onyl, indolyl, dihydrofuran-2-onyl, pyrimidine-2,4-dionyl, quinolinyl, pyran-2-onyl, benzothiazolyl, dihydrobenzo[1,4]dioxinyl, quinoxalinyl, chromen-4-onyl, tetrazolyl, pyridyl, thiadiazolyl or thiazinedionyl, wherein said $R^3$ is optionally substituted by one or more groups chosen from —C(O)O$R^o$, —C(O)N($R^o$)SO$_2R^o$, —N($R^o$)C(O)$R^o$, —N($R^o$)C(O)O$R^o$, NO$_2$, CN, CF$_3$, halo, methylenedioxy, —O$R^o$, —N($R^o$)$_2$, $R^o$, tetrazolyl, —SO$_2R^o$, —SO$_2$(O$R^o$), —SO$_2$N($R^o$)$_2$, —SO$_2$N($R^o$)O$R^o$, —SO$_2$N(CH$_2$CH$_2$O$R^o$)$_2$, —O—SO$_2$N($R^o$)$_2$, —N$R^o$SO$_2R^o$, —N($R^o$)C(O)N($R^o$)$_2$, —SO$_2$N($R^o$)(CH$_2$CF$_3$), —SO$_2$NH(cyclopropyl), and —SO$_2$N($R^o$)—C(O)$R^o$.

The compounds of this invention generally may be prepared from known or readily prepared starting materials, following methods known to those skilled in the art, such as those illustrated by general Scheme I below, wherein R corresponds to $R_3$—(Y)$_m$— in formula I, and by the examples described herein.

Scheme I

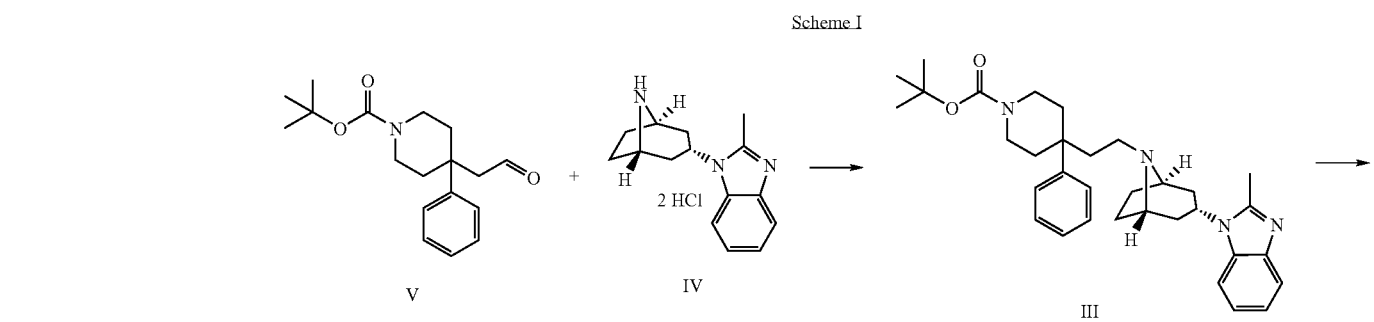

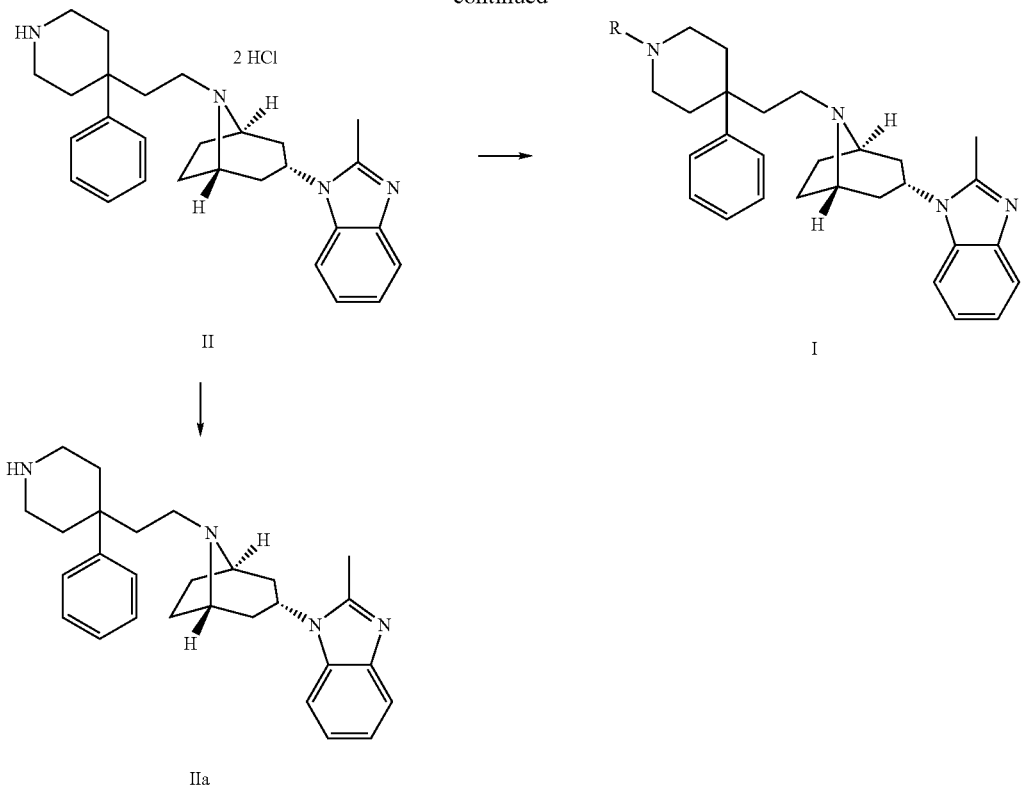

Other compounds of this invention may be prepared by one skilled in the art following the teachings of the specification coupled with knowledge in the art using reagents that are readily synthesized or commercially available.

Compounds of the present invention are useful as CCR5 antagonists. One aspect of the instant invention relates to methods of antagonizing CCR5 chemokine receptor activity in a biological sample comprising contacting the biological sample with compounds of formula I or pharmaceutically acceptable derivatives thereof. Another aspect of the instant invention relates to methods of antagonizing CCR5 chemokine receptor activity in a patient comprising administering to the patient with a therapeutically effective amount of compounds of formula I or pharmaceutically acceptable derivatives thereof. The antagonistic activity of the present compounds towards the chemokine receptor CCR5 may be assayed by methods known in the art, for example, by using the methods as described in example 801.

According to one embodiment of the invention, compounds of formulae I-VII or salts thereof may be formulated into compositions. In a preferred embodiment, the composition is a pharmaceutical composition, which comprises a compound of formula I and pharmaceutically acceptable carrier, adjuvant or vehicle. In one embodiment, the composition comprises an amount of a CCR5 antagonist of the present invention effective to antagonize CCR5 chemokine receptor activity in a biological sample or in a patient. In another embodiment, compounds of this invention and pharmaceutical compositions thereof, which comprise an amount of a CCR5 antagonist of the present invention effective to antagonize CCR5 chemokine receptor activity to treat or prevent a CCR5-mediated disease or disorder and a pharmaceutically acceptable carrier, adjuvant or vehicle, may be formulated for administration to a patient, for example, for oral administration.

The term "pharmaceutically effective amount" or "therapeutically effective amount" refers to an amount of a compound of this invention that is effective in treating a CCR5-related disease, for example a virus infection, for example an HIV infection, in a patient either as monotherapy or in combination with other agents.

The term "antagonist of CCR5 chemokine receptor" refers to a compound that binds to the chemokine receptor CCR5 but fails to elicit a response thereby blocking agonist action. The term "antagonizing CCR5 chemokine receptor" refers to binding to the receptor but failing to elicit a response thereby blocking agonist action, i.e, inhibiting a function of CCR5. For example, an antagonist of CCR5 chemokine receptor may inhibit the binding of one or more ligands (e.g., MIP-1α, RANTES, MIP-1β, and gp120) to CCR5 and/or inhibit signal transduction mediated through CCR5 (e.g., GDP/GTP exchange by CCR5-associated G proteins, intracellular calcium flux). Accordingly, CCR5-mediated processes and cellular responses (e.g., proliferation, migration, chemotactic responses, secretion or degranulation) can be inhibited with an antagonist of CCR5.

The term "CCR5 mediated disease or disorder" or "CCR5 related disease or disorder" is used herein at all occurrences to mean any disease, disorder or other deleterious condition or state in which CCR5 is known to play a role.

The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylaxis" refers to preventing a disease or condition or preventing the occurrence of symptoms of such a disease or condition, in a patient. As used herein, the term "patient" refers to a mammal, including a human.

As used herein, the term "subject" refers to a patient or a biological sample. The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

The term "pharmaceutically acceptable carrier, adjuvant or vehicle" refers to a carrier, adjuvant or vehicle that may be administered to a patient, together with a compound of this invention, and which does not destroy the pharmacological activity thereof and is nontoxic when administered in doses sufficient to deliver a therapeutic amount of the therapeutic agent.

The term "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Throughout this specification, the word "comprise" or variations such as "comprises" or "comprising" will be understood to imply the inclusion of a stated integer or groups of integers but not the exclusion of any other integer or group of integers.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physio-logically acceptable salts of a compound with a hydroxy group include the anion of said compound in combination with a suitable cation such as $Na^+$, $NH_4^+$, and $NW_4^+$ (wherein W is a $C_{1-4}$ alkyl group).

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

The present invention features compounds according to the invention for use in medical therapy, for example for the treatment including prophylaxis of CCR5-related diseases and disorders, including but not limited to, viral infections such as an HIV infection and associated conditions.

As discussed above, the compounds of the present invention are CCR5 antagonists. Accordingly, these compounds are capable of targeting and inhibiting the entry of a virus, e.g, HIV, into its target cell. The compounds according to the invention are especially useful for the treatment of AIDS and related clinical conditions such as AIDS related complex (ARC), progressive generalized lymphadenopathy (PGL), Kaposi's sarcoma, thrombocytopenic purpura, AIDS-related neurological conditions such as AIDS dementia complex, multiple sclerosis or tropical paraperesis, anti-HIV antibody-positive and HIV-positive conditions, including such conditions in asymptomatic patients.

According to another aspect, the present invention provides a method for the treatment including prevention of the symptoms or effects of a viral infection in an infected patient, for example, a mammal including a human, which comprises treating said patient with a pharmaceutically effective amount of a compound according to the invention. According to one aspect of the invention, the viral infection is a retroviral infection, in particular an HIV infection. A further aspect of the invention includes a method for the treatment including prevention of the symptoms or effects of an HBV infection.

The compounds according to the invention may also be used in adjuvant therapy in the treatment of HIV infections or HIV-associated symptoms or effects, for example Kaposi's sarcoma.

The compounds of the present invention may also be used in the treatment (including prevention) of other CCR5-related diseases and conditions, including multiple sclerosis, rheumatoid arthritis, autoimmune diabetes, chronic implant rejection, asthma and topic disorders (for example, atopic dermatitis and allergies), rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, human papilloma virus infection, prostate cancer, wound healing, amyotrophic lateral sclerosis, psoriasis, multiple sclerosis, chronic obstructive pulmonary disease (COPD), sarcoidosis, immune-mediated disorders, and bacterial infections, including bubonic and pneumonic plague, particularly infections of *Yersinia pestis.*

The present invention further provides a method for the treatment of a clinical condition in a patient, for example, a mammal including a human which clinical condition includes those which have been discussed hereinbefore, which comprises treating said patient with a pharmaceutically effective amount of a compound according to the invention. The present invention also includes a method for the treatment including prophylaxis of any of the aforementioned diseases or conditions.

In yet a further aspect, the present invention provides the use of a compound according to the invention in the manufacture of a medicament for the treatment including prophylaxis of any of the above mentioned CCR5-related diseases or conditions including viral infections (e.g., HIV infection) and associated conditions.

Reference herein to treatment extends to prophylaxis as well as the treatment of established conditions, disorders and infections, symptoms thereof, and associated clinical conditions.

The above compounds according to the invention and their pharmaceutically acceptable derivatives may be employed in combination with other therapeutic agents for the treatment of the above infections or conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously (i.e., concurrently) in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of such therapeutic agents include, but are not limited to, agents that are effective for the treatment of viral infections or associated conditions. Among these agents are (1-alpha, 2-beta, 3-alpha)-9-[2,3-bis(hydroxymethyl)cyclobutyl]guanine[(−)BHCG, SQ-34514, lobucavir]; 9-[(2R, 3R,4S)-3,4-bis(hydroxy methyl)2-oxetanosyl]adenine (oxetanocin-G); acyclic nucleosides, for example acyclovir, valaciclovir, famciclovir, ganciclovir, and penciclovir; acyclic nucleoside phosphonates, for example (S)-1-(3-hydroxy-2-phosphonyl-methoxypropyl) cytosine (HPMPC), [[[2-(6-amino-9H-purin-9-yl)ethoxy]methyl]phosphinylidene]bis (oxymethylene)-2,2-dimethyl propanoic acid (bis-POM PMEA, adefovir dipivoxil), [[(1R)-2-(6-amino-9H-purin-9-yl)-1-methylethoxy]methyl]phosphonic acid (tenofovir), and (R)-[[2-(6-Amino-9H-purin-9-yl)-1-methylethoxy]methyl] phosphonic acid bis-(isopropoxycarbonyloxymethyl)ester (bis-POC-PMPA); ribonucleotide reductase inhibitors, for example 2-acetylpyridine 5-[(2-chloroanilino)thiocarbonyl) thiocarbonohydrazone and hydroxyurea; nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclo-propylamino)-9H-purin-9-yl]-2-cyclopentene-1-methanol (abacavir), 9-[4-hydroxy-2-(hydroxymethyl)but-1-yl]-guanine (H2G), ABT-606 (2HM-H2G) and ribavirin; protease inhibitors, for example indinavir, ritonavir, nelfinavir, amprenavir, saquinavir, fosamprenavir, (R)—N-tert-butyl-3 [(2S,3S)-2-hydroxy-3-N—[(R)-2-N-(isoquinolin-5-yloxy-acetyl)amino-3-methylthio-propanoyl]amino-4-phenylbutanoyl]-5,5-dimethyl-1,3-thiazolidine-4-carboxamide (KNI-272), 4R-(4alpha, 5alpha, 6beta)]-1,3-bis[(3-aminophenyl) methyl]hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-l-tert-leucylamino]4-phenylbutyl-$N^{alpha}$-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-hydroxy-1(S)-indanyl)-2 (R)-phenyl-methyl-4(S)-hydroxy-5-(1-(1-(4-benzo[b] furanylmethyl)-2(S)—N'-(tert-butyl carboxamido) piperazinyl)pentanamide (MK-944A); interferons such as α-interferon; renal excretion inhibitors such as probenecid; nucleoside transport inhibitors such as dipyridamole, pentoxifylline, N-acetylcysteine (NAC), Procysteine, α-trichosanthin, phosphonoformic acid; as well as immunomodulators such as interleukin II or thymosin, granulocyte macrophage colony stimulating factors, erythropoetin, soluble $CD_4$ and genetically engineered derivatives thereof; non-nucleoside reverse transcriptase inhibitors (NNRTIs), for example nevirapine (BI-RG-587), alpha-((2-acetyl-5-methylphenyl)amino)-2,6-dichloro-benzeneacetamide (loviride), 1-[3-(isopropyl amino)-2-pyridyl]-4-[5-(methanesulfonamido)-1H-indol-2-ylcarbonyl]piperazine monomethanesulfonate (delavirdine), (10R,11S,12S)-12-Hydroxy-6,6,10,11-tetramethyl-4-propyl-11,12-dihydro-2H, 6H, 10H-benzo(1,2-b:3,4-b':5,6-b")tripyran-2-one ((+) calanolide A), (4S)-6-Chloro-4-[1E)-cyclopropyl ethenyl)-3, 4-dihydro-4-(trifluoromethyl)-2(1H)-quinazolinone (DPC-083), (S)-6-chloro-4-(cyclopropyl ethynyl)-1,4-dihydro-4-(trifluoromethyl)-2H-3,1-benzoxazin-2-one (efavirenz, DMP 266), 1-(ethoxy methyl)-5-(1-methylethyl)-6-(phenyl-methyl)-2,4(1H,3H)-pyrimidinedione (MKC-442), and 5-(3, 5-dichloro phenyl)thio-4-isopropyl-1-(4-pyridyl)methyl-1H-imidazol-2-ylmethyl carbamate (capravirine); glycoprotein 120 antagonists, for example PRO-2000, PRO-542 and 1,4-bis[3-[(2,4-dichlorophenyl)carbonyl amino]-2-oxo-5,8-disodiumsulfanyl]naphthalyl-2,5-dimethoxyphenyl-1,4-dihydrazone (FP-21399); cytokine antagonists, for example reticulose (Product-R), 1,1'-azobis-formamide (ADA), 1,11-(1,4-phenylenebis (methylene))bis-1,4,8,11-tetraazacyclotetradecane octahydrochloride (AMD-3100); integrase inhibitors; and fusion inhibitors, for example T-20 and T-1249.

The present invention further includes the use of a compound according to the invention in the manufacture of a medicament for simultaneous or sequential administration with at least another therapeutic agent, such as those defined hereinbefore.

Compounds of the present invention may be administered with an agent known to inhibit or reduce the metabolism of compounds, for example ritonavir. Accordingly, the present invention features a method for the treatment including prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 50 to 400 mg of active ingredient per unit dosage form.

While it is possible for the active ingredient to be administered alone, it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3(6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray Pharmaceutical compositions containing in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

In order that the invention described herein may be more fully understood, the following examples are set forth. It should be understood that these examples are for illustrative purposes only and are not to be construed as limiting this invention in any manner.

EXAMPLES

General Procedures

Plate Purification Chromatographic Conditions:

Prep. HPLC Conditions A

Approximately 100 milligrams of the impure compound was dissolved in 500 microliters of methanol. This 500 microliter solution was injected by a Waters 2767 autosampler into a Phenomenex Luna C18 5 micron particle HPLC column (21.20 mm×150 mm). Initial solvent flow was 20 ml/min with 30% methanol and 70% water at a pH of 2.5 using formic acid as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. About 35 mg of purified compound was isolated.

Prep. HPLC Conditions B

Approximately 100 milligrams of the impure compound was dissolved in 300 microliters of DMSO and brought up to a final volume of 500 microliters using methanol. This 500 microliter solution was injected by a Waters 2767 autosampler into an XTerra C18 5 micron particle HPLC column (19 mm×50 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. About 35 mg of purified compound was isolated.

Analytical and Preparative C18 HPLC Chromatography

Method W

Analytical High Pressure Liquid Chromotography data was acquired using a Waters LC-UV system. The system operated using a Waters Symmetry Shield RP18 3.9×150 mm, 5 μm column at 1.5 mL/minute. The mobile phase consisted of Water (0.1% DEA) and Acetonitrile (0.1% DEA). The gradient used started with a 10% ACN (0.1% DEA): 90% H2O (0.1% DEA) and moved to 90% ACN (0.1% DEA):10% H2O (0.1% DEA) over 7 minutes. There was a one minute wash of the column using 100% ACN (0.1% DEA) for one minute, until eight minutes and then original conditions returned at 8.1 minutes to 8.5 minutes.

Method Y

Preparative High Pressure Liquid Chromatography data was acquired using a Waters LC-UV system. The system operated using a Waters Symmetry Shield RP18 3.9×150 mm, 5 μm column at 35 mL/minute. The mobile phase consisted of Water (0.1% DEA) and Acetonitrile (0.1% DEA). The gradient used started with a 10% ACN (0.1% DEA):90% $H_2O$ (0.1% DEA) and moved to 90% ACN (0.1% DEA):10% $H_2O$ (0.1% DEA) over 7 minutes. There was a one minute wash of the column using 100% ACN (0.1% DEA) for one minute, until eight minutes and then original conditions returned at 8.1 minutes to 8.5 minutes.

Low resolution, open-access LC-MS data were acquired in either ESI pos/neg or APCI pos/neg mode with scanning from 100-1100 amu @ 0.5 sec/scan.

LC conditions: flowrate 0.8 mL/min. 85% H2O (0.1% formic acid) to 100% MeOH (0.075% formic acid) in 6 minutes. Phenomenex Max-RP column, 2.0×50 mm.

High Resolution Mass Spectra were acquired using Micromass LCT mass spectrometer (time-of-flight) with flow injection (FIA-MS) at 0.3 mL/min with 100% MeOH (0.1% formic acid), run time of 2 minutes, in ESI+ mode, scanning from 100-1100 amu @ 0.5 sec/scan.

Reserpine was used as the lock mass (m/z 609.2812) and to adjust mass scale.

Example 1

Compound IV of Scheme I was synthesized according to the procedure outlined in Scheme II below.

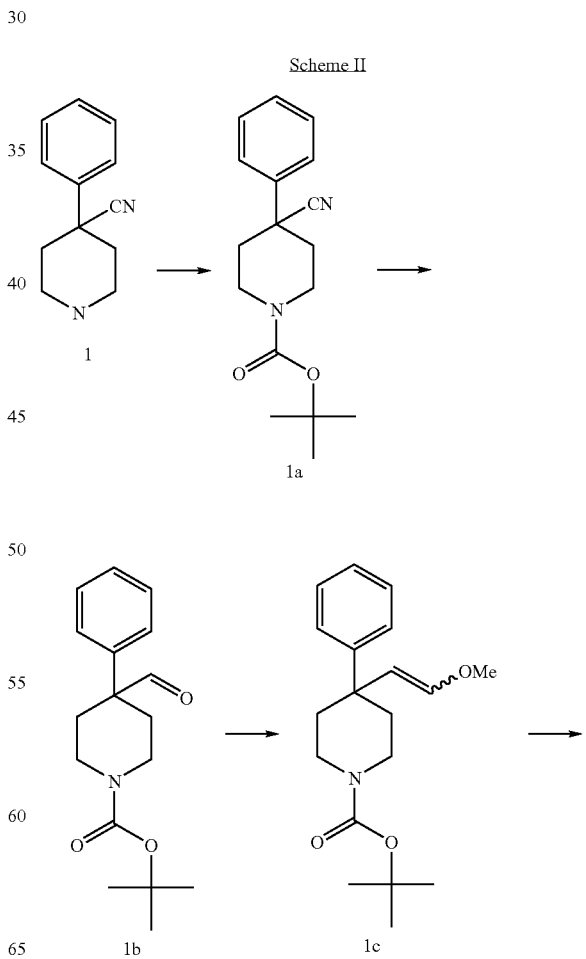

Scheme II

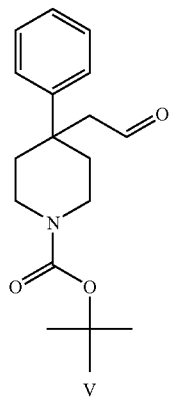

Tert-Butyl 4-cyano-4-phenylpiperidine-1-carboxylate (1a)

To a suspension of 4-cyano-4-phenylpiperidine hydrochloride (50.4 g, 0.266 mol) in tetrahydrofuran (440 ml) was added triethylamine (95 ml), followed by addition of a solution of di-tert-butyl dicarbonate (47.95 g, 0.22 mol) in tetrahydrofuran (150 ml) dropwise. The reaction mixture was stirred at room temperature for 2 hours. The solids were filtered and the filtrate was diluted with 200 ml of ethyl acetate, washed once with 200 ml of 1N citric acid, once with 200 ml of saturated aqueous sodium bicarbonate and once with 200 ml of brine. After drying over sodium sulfate, the solution was concentrated to a colorless thick oil (64.40 g, 99%). $^1$H-NMR (300 MHz, CDCl$_3$): δ 7.51-7.34 (m, 5H), 4.33-4.18 (m, 2H), 3.27-3.19 (m, 2H), 2.14-1.92 (m, 4H), and 1.51 (s, 9H). ES-LCMS m/z 308 (M+H).

Tert-Butyl 4-formyl-4-phenylpiperidine-1-carboxylate (1b)

To a solution of tert-butyl 4-cyano-4-phenylpiperidine-1-carboxylate (33.32 g, 0.116 mol) in toluene (600 ml), cooled to −78° C. was added a 1M solution of diisobutylaluminum hydride in toluene (248 ml) over a period of 3 h. The reaction mixture was allowed to warm up to −35° C. over a period of 2 h and stirred at −35° C. for 1 hour. The reaction mixture was quenched by dropwise addition of 150 ml of methanol, followed by addition of 150 ml of saturated aqueous ammonium chloride and filteration through Celite. The organic layer was washed once with 200 ml of water, once with 200 ml of brine and after drying over sodium sulfate, the solution was concentrated to a light yellow oil (29.71 g, 88%). $^1$H-NMR (300 MHz, CDCl$_3$): δ 9.43 (s, 1H), 7.55-7.18 (m, 5H), 3.92-3.82 (m, 2H), 3.31-3.18 (m, 2H), 2.40-1.92 (m, 4H), and 1.38 (s, 9H). ES-LCMS m/z 290 (M+H).

Tert-Butyl 4-[(E/Z)-2-methoxyethenyl]-4-phenylpiperidine-1-carboxylate (1c)

To a slurry of (methoxymethyl)triphenyl-phosphonium chloride (7.39 g, 21.56 mmol) in tetrahydrofuran (90 ml) was added a 1M solution of potassium tert-butoxide in tetrahydrofuran (22 ml) dropwise. The reaction mixture was stirred at room temperature for 30 minutes and a solution of tert-butyl 4-formyl-4-phenylpiperidine-1-carboxylate (6.24 g, 21.56 mmol) in tetrahydrofuran (18 ml) was added dropwise. The mixture was stirred at room temperature for 16 hours and then heated to reflux for 2 hours. The mixture was allowed to cool to room temperature, diluted with 100 ml of water and 100 ml of ethyl acetate. The aqueous layer was extracted twice with 100 ml portions of ethyl acetate and washed once with 100 ml of brine. After drying over sodium sulfate, the solution was concentrated to a brown oil, which was further purified by column chromatography on silica gel. Elution with a gradient of 10-40% ethyl acetate in hexanes afforded a 1:1 mixture of E/Z isomers as a light yellow oil (4.64 g, 68%). $^1$H-NMR (300 MHz, CDCl$_3$): δ 7.51-7.19 (m, 5H), 6.07 and 4.84 (d, J=13.0 Hz, 1H), 5.95 and 4.23 (d, J=7.1 Hz, 1H), 3.95-3.78 (m, 2H), 3.54 and 3.51 (s, 3H), 3.30-3.06 (m, 2H), 2.20-2.09 (m, 2H), 1.98-1.76 (m, 2H), and 1.52 and 1.49 (s, 9H). ES-LCMS m/z 318 (M+H).

Tert-Butyl 4-(2-oxoethyl)-4-phenylpiperidine-1-carboxylate (Compound V)

To a solution of tert-butyl 4-[(E/Z)-2-methoxyethenyl]-4-phenylpiperidine-1-carboxylate (4.64 g, 14.61 mmol) in acetone (48 ml) was added dropwise a solution of p-toluenesulfonic acid monohydrate (1.95 g, 10.28 mmol) in water (24 ml). The reaction mixture was stirred at room temperature for 48 hours. Acetone was evaporated without using any heat, and the reaction mixture was made basic with solid sodium bicarbonate to pH 9, extracted with three 30 ml portions of dichloromethane and washed once with 30 ml of brine. After drying over sodium sulfate, the solution was concentrated to a colorless oil, which was further purified by column chromatography on silica gel. Elution with 25% ethyl acetate in hexanes afforded the product (2.23 g, 50%). $^1$H-NMR (300 MHz, CDCl$_3$): δ 9.39 (s, 1H), 7.43-7.25 (m, 5H), 3.69-3.61 (m, 2H), 3.31-3.22 (m, 2H), 2.65 (s, 2H), 2.28-2.23 (m, 2H), 1.92-1.83 (m, 2H), and 1.46 (s, 9H). ES-LCMS m/z 304 (M+H).

(1-Benzoyl-4-phenylpiperidine-4-yl)acetaldehyde (2)

(1-Benzoyl-4-phenylpiperidine-4-yl)acetaldehyde (2) was synthesized according to the procedure outlined below.

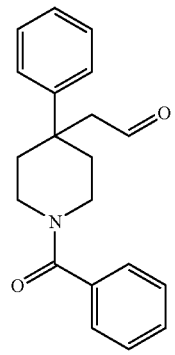

To a solution of tert-butyl 4-[(E/Z)-2-methoxyethenyl]-4-phenylpiperidine-1-carboxylate (8.75 g, 27.57 mmol) obtained by following the procedure outlined in example 1c above in tetrahydrofuran (27 ml) was added a 4M solution of hydrochloric acid in dioxane (9 ml). The reaction mixture was stirred at room temperature for 1 hour and concentrated to an oil. The mixture was dissolved in dichloromethane (40 ml) and cooled to 0° C. A solution of benzoyl chloride (4.65 g, 33.08 mmol) in dichloromethane (5 ml) was added dropwise, followed by the addition of triethylamine 8.37 g, 82.71 mmol)

in dichloromethane (5 ml). The mixture was stirred at room temperature for 1 hour, quenched by addition of 5 ml water, and washed once with 150 ml of saturated aqueous sodium bicarbonate and once with 150 ml of brine. After drying over sodium sulfate, the solution was concentrated to an oil, which was further purified by column chromatography on silica gel. Elution with a gradient of 25-50% ethyl acetate in hexanes afforded a light yellow oil (3.47 g, 41%). $^1$H-NMR (300 MHz, CDCl$_3$): δ 9.37 (s, 1H), 7.42-7.25 (m, 10H), 4.14-4.09 (m, 1H), 3.54-3.30 (m, 3H), 2.67 (s, 2H), 2.38-2.24 (m, 2H), and 1.97-1.85 (m, 2H). ES-LCMS m/z 308 (M+H).

The synthesis of endo 1-(8-azabicyclo[3.2.1]oct-3-yl)-2-methyl-1H-benzimidazole dihydrochloride (compound IV of Scheme I)

a) endo tert-Butyl 3-Anilino-8-azabicyclo[3.2.1]octane-8-carboxylate

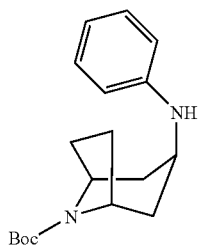

Sodium triacetoxyborohydride (125 g, 0.59 mol) was added portionwise during 45 min to a mechanically stirred mixture of tert-butyl 3-oxo-8-azabicyclo[3.2.1]octane-8-carboxylate (88.3 g, 0.39 mol), pulverized 4A molecular sieves (88 g) and benzylamine (44.1 g, 0.41 mol) in dichloromethane (1 L) at rt under Nitrogen. The mixture was stirred at rt for 2 days. Saturated sodium carbonate solution (1 L) was added. The mixture was stirred for 1 h at room temperature, filtered and the aqueous was further extracted with dichloromethane (3×500 mL). The combined organic layers were dried and concentrated to a white solid (123 g, 99%). $^1$H NMR (400 MHz; CDCl$_3$) δ 7.24-7.33 (m, 5H), 4.19 (m, 1H), 4.10 (m, 1H), 3.76 (s, 2H), 3.00 (t, 1H), 2.15 (m, 3H), 1.91 (m, 2H), 1.60 (m, 1H), 1.57 (m, 1H), 1.49 (m, 1H), 1.48 (m, 1H), 1.45 (s, 9H). AP-LCMS m/z 317 (M+1).

b) endo tert-Butyl 3-Amino-8-azabicyclo[3.2.1]octane-8-carboxylate

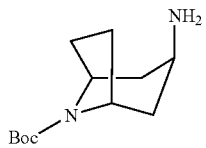

A stirred mixture of tert-butyl 3-anilino-8-azabicyclo[3.2.1]octane-8-carboxylate (123 g, 0.39 mol), ammonium formate (175 g, 2.78 mol) and 20% palladium hydroxide on carbon (12.3 g) in absolute ethanol (1.5 L) was heated to 50° C. under nitrogen for 7 h. The mixture was filtered and the filtrate was concentrated. The residue in ethyl acetate was washed with water, dried and concentrated to give the product (65.4 g, 74%). $^1$H NMR (400 MHz; CDCl$_3$) δ 4.19 (m, 1H), 4.10 (m, 1H), 3.30 (t, 1H), 3.03-2.19 (m, 4H), 1.94 (m, 2H), 1.58 (m, 2H), 1.44 (s, 9H). AP-LCMS m/z 127 (M–99).

c) endo tert-Butyl 3-[(2-Nitrophenyl)amino]-8-azabicyclo[3.2.1]octane-8-carboxylate)

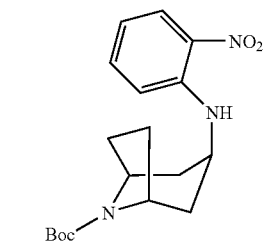

A mixture of tert-butyl 3-amino-8-azabicyclo[3.2.1]octane-8-carboxylate (65.4 g, 0.29 mol), N,N-diisopropylethylamine (56 mL, 0.32 mol) and 1-fluoro-2-nitrobenzene (40.9 g, 0.29 mol) in 1-methyl-2-pyrrolidinone (200 mL) was heated at 70° C. under nitrogen for 16 h. The reaction mixture was diluted with water (500 mL) and extracted with ethyl acetate (3×300 mL). The combined organic layers were dried and concentrated to an orange oil. urification was accomplished by chromatography on silica gel eluting with dichloromethane and ethyl acetate:hexane 1:1 in succession to give an orange solid (98.2 g, 98%). $^1$H NMR (400 MHz; CDCl$_3$) δ 8.74 (m, 1H), 8.18 (m, 1H), 7.43 (m, 1H), 6.61-6.73 (m, 2H), 4.26 (m, 2H), 3.90 (t, 1H), 2.26-2.32 (m, 2H), 2.03 (m, 4H), 1.83 (m, 2H), 1.44 (s, 9H).

d) endo tert-Butyl 3-[(2-Aminophenyl)amino]-8-azabicyclo[3.2.1]octane-8-carboxylate

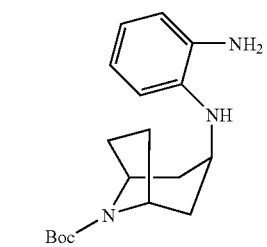

A mixture of tert-butyl 3-[(2-nitrophenyl)amino]-8-azabicyclo[3.2.1]octane-8-carboxylate (98.2 g, 0.28 mol) and 10% palladium on carbon (10 g) in ethanol:ethyl acetate 1:1 (1 L) was hydrogenated for 24 h at atmospheric pressure. Uptake of hydrogen was 17.4 L. The mixture was filtered through celite and concentrated to give the product (76.2 g, 86%). $^1$H NMR (400 MHz; CDCl$_3$) δ 6.67-6.83 (m, 3H), 6.57 (m, 1H), 4.25 (m, 1H), 4.17 (m, 1H), 3.70 (m, 2H), 3.32 (br s, 2H), 2.28 (m, 2H), 1.98-2.07 (m, 4H), 1.76 (m, 2H), 1.47 (s, 9H). AP-LCMS m/z 318 (M+1).

e) endo 1-(8-Azabicyclo[3.2.1]oct-3-yl)-2-methyl-1H-benzimidazole Hydrochloride

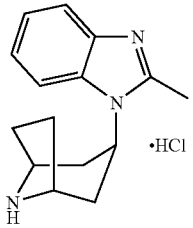

A solution of tert-butyl 3-[(2-aminophenyl) amino]-8-azabicyclo[3.2.1]octane-8-carboxylate (76.2 g, 0.24 mol) in triethylorthoacetate (250 mL) was refluxed under nitrogen for 2.5 h. The mixture was concentrated, redissolved in ethyl acetate (500 mL), washed with water (2×200 mL), washed with brine, dried and concentrated to a dark oil. The oil was dissolved in ethanol (250 mL), treated with 6 N hydrochloric acid (200 mL) and refluxed for 2 h. The reaction mixture was cooled to room temperature, concentrated to 300 mL and the resulting pale pink precipitate was collected by filtering, washed with ethanol (50 mL) and dried (61.5 g, 92%). $^1$H NMR (400 MHz; DMSO-$d_6$) δ 10.16 (d, J=10 Hz, 1H), 9.47 (d, J=10 Hz, 1H), 7.95 (d of d, J=3.6 Hz, 1H), 7.79 (d of d, J=4.8 Hz, 1H), 7.54 (m, 2H), 5.63 (m, 1H), 4.13 (d, J=9 Hz, 2H), 2.88 (s, 3H), 2.71 (m, 2H), 2.17 (m, 6H). ES-LCMS m/z 242 (M+1).

The synthesis of exo-amine: exo1-(8-azabicyclo[3.2.1]oct-3-yl)-2-methyl-1H-benzimidazole 8-Benzyl-8-azabicyclo[3.2.1]octan-3-one

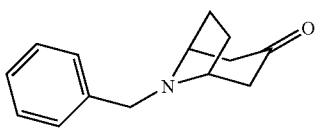

To cooled 192 ml of 0.025M HCl at 0° C. was added 60 g (454 mmol) of 2,5-dimethoxytetrahydrofuran and the mixture was stirred at 0° C. for 17 hrs. Then sequentially 78 g (543.6 mmol) of benzyl amine, 66 g (452.0 mmol) of 3-oxopentanedioic acid, and 20.4 g (248.4 mmol) of sodium acetate in 360 ml of water was added all at 0° C. The mixture was allowed to warm to room temperature and was stirred at room temperature for 1 hr. The mixture was clear, golden yellow in color. The mixture was heated to 50° C. for 2 hrs. The mixture turned cloudy. The mixture was then cooled to ambient temperature and adjusted to pH~12 using 50% NaOH in water. The mixture was extracted with ethyl acetate (×3), dried over sodium sulfate and removed solvent to yield a brown oil. The mixture was further purified by distillation, desired product collected ~120° C. 25 g crude product was recovered as a yellow oil to be carried on to next step.

8-Benzyl-8-azabicyclo[3.2.1]octan-3-one oxime

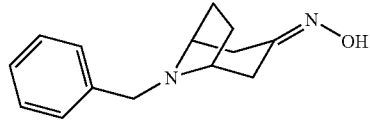

4.85 g (22.56 mmol) of 8-benzyl-8-azabicyclo[3.2.1]octan-3-one was dissolved in 60 ml of ethanol. 3.13 g (45 mmol) hydroxylamine hydrochloride was then added followed by 1.8 g (45 mmol) of NaOH in 15 ml of water. The mixture was refluxed for 20 hrs and was cooled to ambient temperature. The solvent was removed in vaccuo. The residue was diluted with ethyl acetate and washed with water and the organic layer was dried over sodium sulfate. The solvent was removed to give 4.28 g of product as a light yellow solid.

8-Benzyl-8-azabicyclo[3.2.1]octan-3-amine

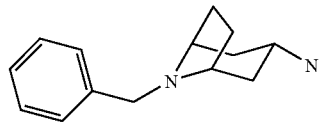

To 3.9 g (16.9 mmol) 8-benzyl-8-azabicyclo[3.2.1]octan-3-one oxime was added 3.5 g of sodium in 200 ml of pentanol by portion over 1 hr. The mixture was refluxed for 3 hrs and cooled to ambient temperature. The reaction mixture was quenched with water and extracted with 6 N HCl. The aqueous layer was basified using NaOH pellets and extracted with EtOAc. The organic layer was dried over magnesium sulfate and the solvent was removed to afford 2.9 g (80%) of crude product as a brown oil.

8-Benzyl-N-(2-nitrophenyl)-8-azabicyclo[3.2.1]octan-3-amine

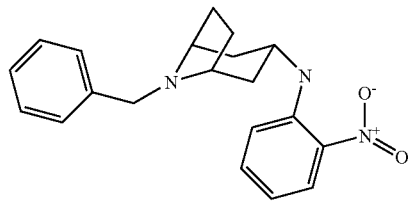

5.62 g (27.82 mmol) 8-benzyl-8-azabicyclo[3.2.1]octan-3-amine (u17094-94) and 9.7 ml (55.46 mmoml) of Hunig's base were dissolved in 200 ml NMP. 4.32 g (30.60 mmol) 1-fluoro-2-nitrobenzene was then added and the mixture was stirred at RT for 3 hrs. The reaction mixture was diluted with EtOAc and washed with water and dried over sodium sulfate. The solvent was removed partially under reduced pressure and was left in refrigerator overnight. The solid was filtered off to afford 2.92 g of product as a yellow powder. The solvent was removed from filtration to give additional 5.7 g of product as an orange-yellow residue.

N-(8-Benzyl-8-azabicyclo[3.2.1]oct-3-yl)benzene-1, 2-diamine

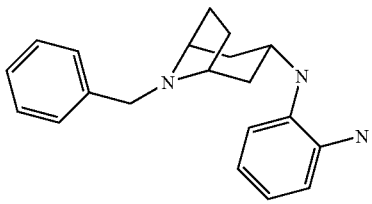

2.92 g (9.04 mmol) 8-benzyl-N-(2-nitrophenyl)-8-azabicyclo[3.2.1]octan-3-amine was dissolved in 150 ml EtOAc and 25 ml Methanol. 1 g Pd/C was then added and the mixture was stirred at 1 atm H₂ for 3.5 hrs. Yellow color disappeared and the reaction mixture was filtered through celite. The solvent was removed to afford 2.2 g of desired solid.

1-(8-Benzyl-8-azabicyclo[3.2.1]oct-3-yl)-2-methyl-1H-benzimidazole

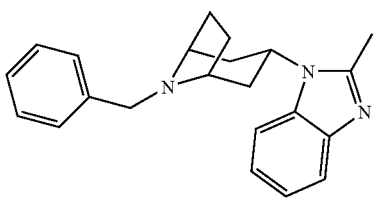

7.7 g (25.08 mmol) N-(8-benzyl-8-azabicyclo[3.2.1]oct-3-yl)benzene-1,2-diamine was refluxed in 200 ml of 1,1,1-triethoxyethane for 18 hrs. The mixture was cooled to ambient temperature and the solvent was then removed. The residue was dissolved in toluene and 1.8 g (9.47 mmol) of p-toluenesulfonic acid was added and the reaction mixture was heated to reflux while stirring for 18 hrs. The mixture was cooled to ambient temperature and filtered off solid and removed toluene under reduced pressure. The crude product was purified by flash column chromatography with 5% methanol and 0.5% ammonium hydroxide in dichloromethane on silica gel. 2.2 g of the product was recovered as a yellow residue.

1-(8-Azabicyclo[3.2.1]oct-3-yl)-2-methyl-1H-benzimidazole

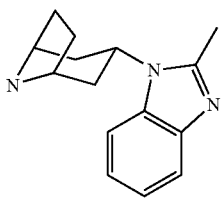

2.2 g (6.65 mmol) 1-(8-benzyl-8-azabicyclo[3.2.1]oct-3-yl)-2-methyl-1H-benzimidazole was dissolved in 150 ml ethanol and 2.09 g (33.23 mmol) ammonium formate and 0.4 g palladium hydroxide (20% on carbon) were added. The mixture was refluxed for 2.5 hrs. The mixture was cooled to ambient temperature and filtered through celite. The solvent was removed under reduced pressure and the crude product was purified by column chromatography CH₂Cl:CH₃OH:NH₄OH (95:5:0.5) to afford 1.06 g of the desired product as a solid.

Example 2

Endo 2-methyl-1-{8-[2-(4-phenylpiperidin-4-yl)ethyl]-8-azabicyclo[3.2.1]oct-3-yl}-1H-benzimidazole dihydrochloride (compound II in Scheme I) was prepared by following the procedure depicted in Scheme III below.

Scheme III

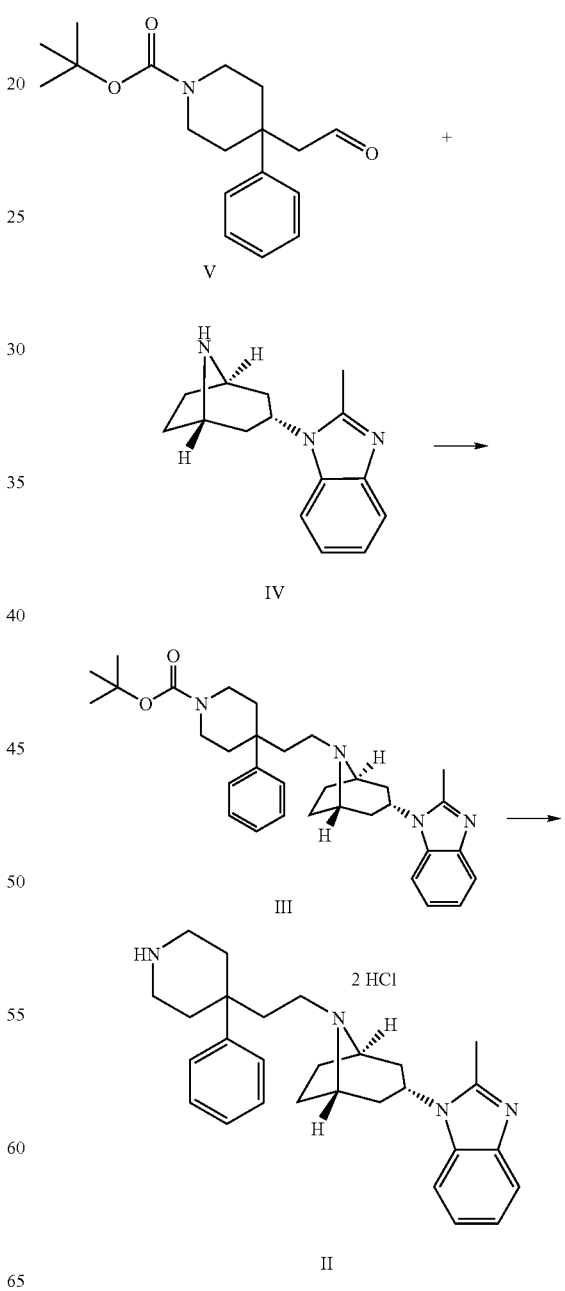

tert-butyl 4-{2-[(1R,5S)-3-(2-methyl-1H-benzimidazol-1-yl)-8-endo-azabicyclo[3.2.1]oct-8-yl)ethyl}-4-phenylpiperidine-1-carboxylate (III)

To a solution of 483 mg (2.0 mmol) of endo 1-(8-Azabicyclo[3.2.1]oct-3-yl)-2-methyl-1H-benzimidazole dihydrochloride (IV) and of 606 mg (2.0 mmol) tert-butyl 4-(2-oxoethyl)-4-phenylpiperidine-1-carboxylate (V) in 25 mL dichloroethylene was added 847 mg (4.0 mmol) of sodium triacetoxyborohydride at room temperature and stirred for 30 minutes. The reaction was quenched with 10% aqueous sodium bicarbonate, solvents were removed and the residue partitioned between ethyl acetate and water, resulting in 925 mg of tert-butyl 4-{2-[(1R,5S)-3-(2-methyl-1H-benzimidazol-1-yl)-8-endo-azabicyclo[3.2.1]oct-8-yl)ethyl}-4-phenylpiperidine-1-carboxylate III (87.6% yield). $^1$H NMR (400 MHz, CDCl$_3$): δ 7.21 (1H, d, J=8.3 Hz), 6.63-6.97 (8H, m), 4.15 (1H, m), 3.20 (2H, m), 2.78m (4H, m), 2.12 (3H, s), 1.92 (2H, m), 1.70 (2H, m), 1.45 (6H, m), 1.33 (4H, m), 1.18 (2H, m), and 1.02 (OH, s). $^{13}$C NMR (400 MHz, CDCl$_3$): δ 155.2, 152.0, 144.9, 143.6, 133.8, 128.7, 126.8, 126.3, 121.6, 119.7, 111.0, 79.6, 57.4, 48.1, 46.3, 42.0, 41.0 (broad), 40.2 (broad), 39.4 (quat), 36.6, 35.8 (broad), 30.0, 28.7, and 14.9. MS ES+ (m/z) M+1=529.61.

endo 2-methyl-1-{8-[2-(4-phenylpiperidin-4-yl)ethyl]-8-azabicyclo[3.2.1]oct-3-yl}-1H-benzimidazole dihydrochloride (Compound II)

0.67 g (1.27 mmol) of tert-butyl 4-{2-[(1R,5S)-3-(2-methyl-1H-benzimidazol-1-yl)-8-endo-azabicyclo[3.2.1]oct-8-yl)ethyl}-4-phenylpiperidine-1-carboxylate III was dissolved in 5 mL dichloromethane and added 14 mL of 4N hydrochloric acid in dioxane. The mixture was stirred at room temperature for 30 minutes, resulting in a gummy precipitate. Solvents were decanted and the gum dried in vacuo, resulting in 0.63 g (quantitative) of endo 2-methyl-1-{8-[2-(4-phenylpiperidin-4-yl)ethyl]-8-azabicyclo[3.2.1]oct-3-yl}-1H-benzimidazole dihydrochloride II, which was subsequently used without additional work-up. MS ES+ (m/z) M+1=429.30.

Neutralization of Dihydrochloride II to Free Base IIa: endo 2-Methyl-1-{8-[2-(4-phenylpiperidin-4-yl)ethyl]-8-azabicyclo[3.2.1]oct-3-yl}-1H-benzimidazole (Compound IIa)

2-methyl-1-{8-[2-(4-phenylpiperidin-4-yl)ethyl]-8-azabicyclo[3.2.1]oct-3-yl}-1H-benzimidazole dihydrochloride was partitioned between saturated sodium bicarbonate solution (300 mL) and dichloromethane (600 mL). The organic layer was dried over anhydrous sodium sulfate. After evaporation of solvents, 2-methyl-1-{8-[2-(4-phenylpiperidin-4-yl)ethyl]-8-azabicyclo[3.2.1]oct-3-yl}-1H-benzimidazole IIa was obtained as foam, which was used for the next step without further purification.

Example 3

1-(8-{2-[1-(2,2-Dimethylpropanoyl)-4-phenylpiperidin-4-yl]ethyl}-8-azabicyclo[3.2.1]oct-3-yl)-2-methyl-1H-benzimidazole (3)

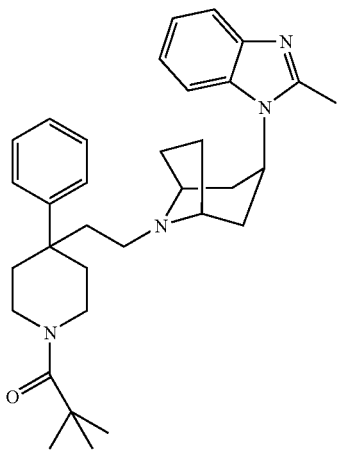

3

To a solution of endo 2-methyl-1-{8-[2-(4-phenylpiperidin-4-yl)ethyl]-8-azabicyclo[3.2.1]oct-3-yl}-1H-benzimidazole dihydrochloride II (0.18 g, 0.42 mmol) in dichloromethane (5 ml) was added triethylamine (0.117 ml), followed by addition of trimethylacetyl chloride (0.056 g, 0.462 mmol). The mixture was stirred at room temperature for 1 h and 0.5 ml water and 1 ml saturated aqueous sodium bicarbonate were added. The mixture was extracted three times with 5 ml of ethyl acetate and washed once with 5 ml brine. After drying over sodium sulfate, the solution was concentrated to a tan oil, which was further purified by column chromatography on silica gel. Elution with a gradient of 2.5-5% methanol in dichloromethane afforded a colorless oil (0.142 g, 66%). $^1$H-NMR (300 MHz, DMSO-d$_6$) δ 7.49 (d, J=7.2 Hz, 1H), 7.40-7.35 (m, 5H), 7.23-7.20 (m, 1H), 7.14-7.08 (m, 2H), 4.54-4.50 (m, 1H), 3.80-3.76 (m, 2H), 3.34-3.23 (m, 4H), 2.49 (s, 3H), 2.38-2.32 (m, 2H), 2.09-2.05 (m, 2H), 1.87-1.74 (m, 10H), 1.59-1.57 (m, 2H), 1.18 (s, 6H), 1.11 (s, 3H). ES-LCMS m/z 513 (M+H). HRMS m/z (M+H)$^+$ calcd 513.3593, (M+H)$^+$ obsvd 513.3586.

Example 4

4-[(4-{2-[3-(2-Methyl-1H-benzimidazol-1-yl)-8-azabicyclo[3.2.1]oct-8-yl]ethyl}-4-phenylpiperidin-1-yl)carbonyl]benzene-sulfonamide (4)

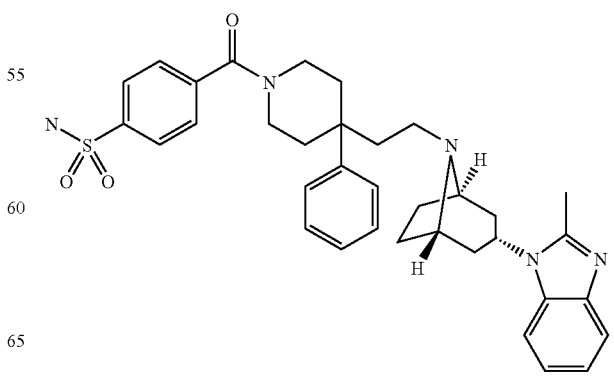

4

4-[(4-{2-[3-(2-Methyl-1H-benzimidazol-1-yl)-8-azabicyclo[3.2.1]oct-8-yl]ethyl}-4-phenylpiperidin-1-yl)carbonyl]benzenesulfonamide (25.8 mg, 83%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride II (25.3 mg, 0.05 mmol) and p-carboxybenzenesulfonamide (10 mg, 0.05 mmol) by the similar procedure outlined for example 5. $^1$H NMR (300 MHz, DMSO-d$_6$) δ 7.86 (d, J=8.2 Hz, 2H), 7.57 (d, J=8.4 Hz, 2H), 7.49-7.47 (m, 2H), 7.39-7.34 (m, 4H), 7.24-7.20 (m, 1H), 7.14-7.06 (m, 2H), 4.52-4.47 (m, 1H), 3.89 (br, 1H), 3.22-3.15 (m, 6H), 2.44 (s, 3H), 2.42-2.30 (m, 2H), 2.14-2.08 (br, 2H), 1.87-1.72 (m, 10H), 1.58 (d, J=7.6 Hz, 2H). HRMS m/z (M+H)$^+$ calcd 612.3008; obsd 612.2993.

Example 5

2-chloro-5-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide Example 5 Via Carbodiimide Coupling To a stirred solution of 2-methyl-1-{8-[2-(4-phenylpiperidin-4-yl)ethyl]-8-azabicyclo[3.2.1]oct-3-yl}-1H-benzimidazole dihydrochloride II (102 mg, 0.2 mmol) in dichloromethane (15 mL) was added 3-chloro-4-sulfamoylbenzoic acid (48 mg, 0.2 mmol) and triethylamine (60 μL, 0.4 mmol). The resulting mixture was then cooled down on an ice-water bath before the addition of 1-[3-(dimethylamino)propyl]-3-ethylcarbodiimide hydrochloride (38 mg, 0.2 mmol) and 4-dimethylaminopyridine (4.8 mg, 0.04 mmol). After being stirred overnight at ambient temperature, the reaction mixture was diluted with dichloromethane (40 mL) and washed with saturated sodium bicarbonate solution. The organic phase was dried over anhydrous sodium sulfate. After evaporation of the solvent, the crude product was purified by flash chromatography on silical gel, eluting with a gradient of 0-10% methanol in ethyl acetate to afford 2-chloro-5-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide as amorphous solid (69 mg, 53%). $^1$H NMR (300 MHz, DMSO-d$_6$) δ 7.87-7.71 (m, 3H), 7.57 (s, 1H), 7.50-7.47 (m, 2H), 7.38-7.33 (m, 4H), 7.24 (s, 1H), 7.14-7.06 (m, 2H), 4.49 (m, 1H), 3.98 (m, 1H), 3.42-3.23 (m, 5H), 3.06-3.00 (m, 1H), 2.43 (s, 3H), 2.39-2.22 (m, 2H), 2.17-2.08 (m, 2H), 1.92-1.76 (m, 10H), 1.58-1.56 (br, 2H). HRMS m/z (M+H)$^+$ calcd 646.2619; obsd 646.2610.

Example 5 Via HATU Coupling

To a stirred solution of 2-methyl-1-{8-[2-(4-phenylpiperidin-4-yl)ethyl]-8-azabicyclo[3.2.1]oct-3-yl}-1H-benzimidazole dihydrochloride (200 mg, 0.4 mmol) in DMF (8 mL) was added 3-chloro-4-sulfamoylbenzoic acid (94 mg, 0.4 mmol), triethylamine (166 μL, 1.2 mmol) and HATU (152 mg, 0.4 mmol). The resulting mixture was stirred at ambient temperature for 3 hours before being diluted with methylene chloride (50 mL). The reaction was then washed with saturated sodium bicarbonate solution. The organic phase was dried over anhydrous sodium sulfate. After evaporation of the solvent, the crude product was purified by flash chromatography on silical gel, eluting with a gradient of 0-10% methanol in ethyl acetate to afford 2-chloro-5-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide as amorphous solid (120 mg, 47%). $^1$H NMR (300 MHz, DMSO-d$_6$) δ 7.87-7.71 (m, 3H), 7.57 (s, 1H), 7.50-7.47 (m, 2H), 7.38-7.33 (m, 4H), 7.24 (s, 1H), 7.14-7.06 (m, 2H), 4.49 (m, 1H), 3.98 (m, 1H), 3.42-3.23 (m, 5H), 3.06-3.00 (m, 1H), 2.43 (s, 3H), 2.39-2.22 (m, 2H), 2.17-2.08 (m, 2H), 1.92-1.76 (m, 10H), 1.58-1.56 (br, 2H). HRMS m/z (M+H)$^+$ calcd: 646.2619; obsd: 646.2610.

Example 6

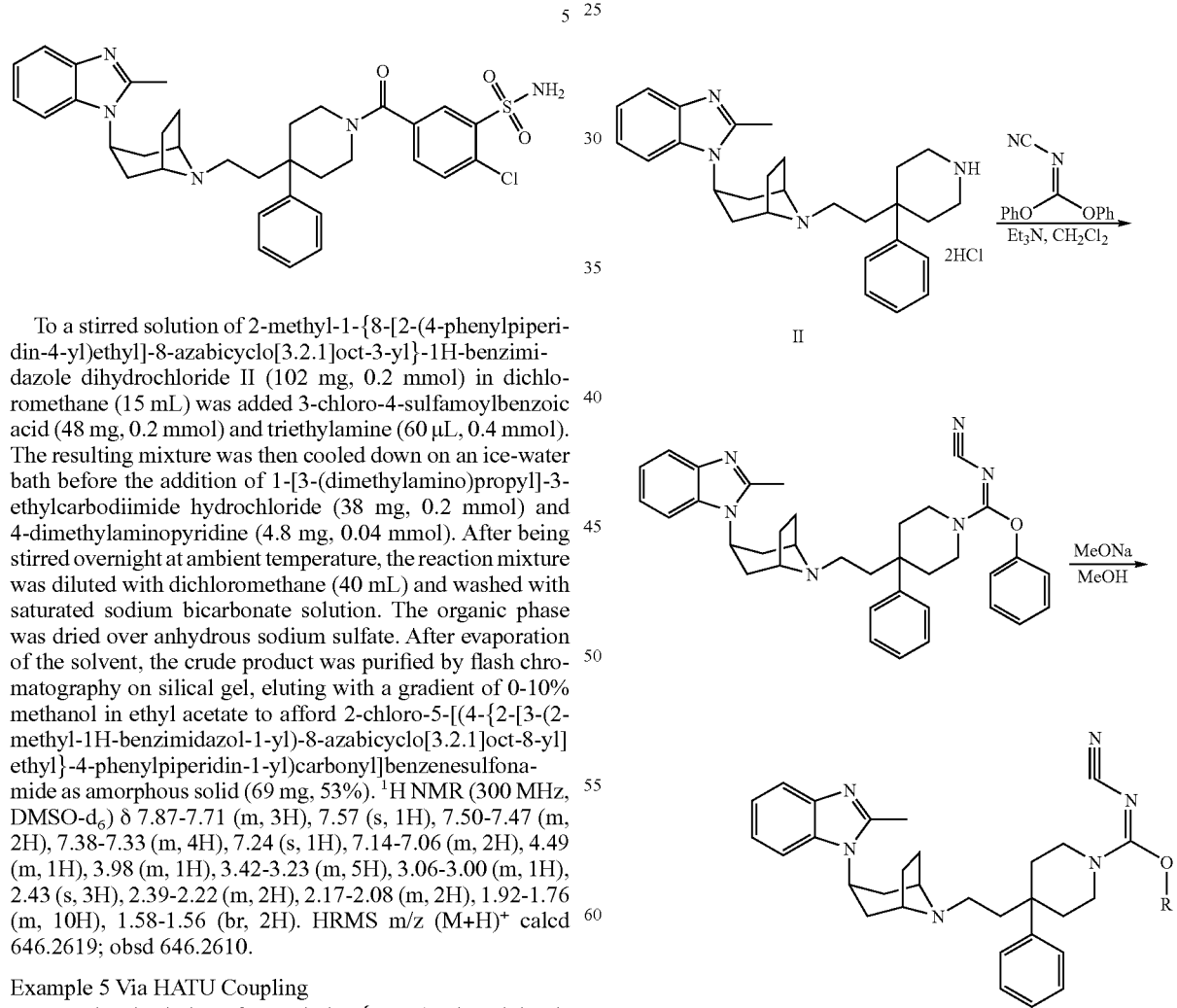

Phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (6)

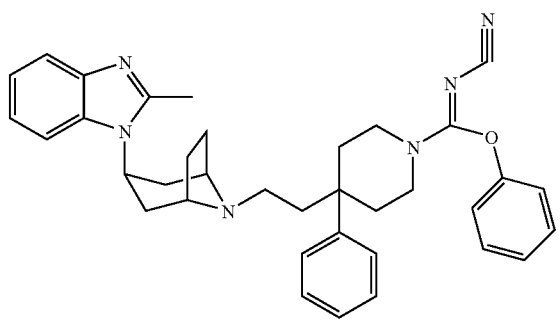

6

To a stirred solution of 2-methyl-1-{8-[2-(4-phenylpiperidin-4-yl)ethyl]-8-azabicyclo[3.2.1]oct-3-yl}-1H-benzimidazole dihydrochloride II (253 mg, 0.5 mmol) in dichloromethane (20 mL) was added triethyl-amine (140 μL, 1 mmol) and diphenylcyanocarbonimide (143 mg, 0.6 mmol). The resulting mixture was stirred at ambient temperature for 4 hours before it was quenched with saturated sodium bicarbonate solution. The layers were separated and the aqueous layer was extracted with dichloromethane (2×20 mL). The combined organic layers were dried over anhydrous sodium sulfate. After evaporation of the solvent, the residue was purified by flash chromatography on silical gel, eluting with a gradient of 0-10% methanol in ethyl acetate to afford phenyl N-cyano-4-{2-[3-(2-methyl-1H-benzimidazol-1-yl)-8-azabicyclo[3.2.1]oct-8-yl]ethyl}-4-phenylpiperidine-1-carboximidoate as amorphous solid (270 mg, 94%). $^1$H NMR (300 MHz, CDCl$_3$) δ 7.69-7.66 (m, 1H), 7.41-7.36 (m, 4H), 7.30-7.21 (m, 5H), 7.19-7.12 (m, 2H), 7.06-7.03 (m, 2H), 4.65-4.58 (m, 1H), 4.07 (br, 1H), 3.37 (br, 2H), 3.23 (br, 2H), 2.56 (s, 3H), 2.40-2.32 (m, 4H), 1.93-1.82 (m, 11H), 1.62 (d, J=7.9, 2H). HRMS m/z (M+H)$^+$ calcd 573.3344; obsd 573.3348.

Example 7

Methyl N-cyano-4-{2-[3-(2-methyl-1H-benzimidazol-1-yl)-8-azabicyclo[3.2.1]oct-8-yl]ethyl}-4-phenylpiperidine-1-carboximidoate (7)

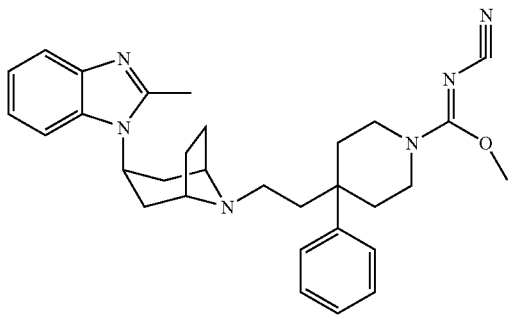

7

To a stirred solution of phenyl N-cyano-4-{2-[3-(2-methyl-1H-benzimidazol-1-yl)-8-azabicyclo[3.2.1]oct-8-yl]ethyl}-4-phenylpiperidine-1-carboximidoate 6 (35 mg, 0.06 mmol) in THF (1 mL) was added sodium methoxide in methanol (100 μL, ~0.8 M, freshly made from methanol and sodium). The resulting mixture was stirred at ambient temperature for 30 minutes before evaporation of the solvent. The crude product was then purified by flash chromatography on silical gel, eluting with a gradient of 0-15% methanol in ethyl acetate to afford methyl N-cyano-4-{2-[3-(2-methyl-1H-benzimidazol-1-yl)-8-azabicyclo[3.2.1]oct-8-yl]ethyl}-4-phenylpiperidine-1-carboximidoate as amorphous solid (21.8 mg, 72%). $^1$H NMR (300 MHz, CDCl$_3$) δ 7.69-7.66 (m, 1H), 7.42-7.37 (m, 2H), 7.32-7.24 (m, 4H), 7.21-7.13 (m, 2H), 4.64 (br, 1H), 4.19-4.07 (br, 2H), 3.92 (s, 3H), 3.40-3.27 (m, 4H), 2.59 (s, 3H), 2.35-2.30 (m, 4H), 1.97-1.83 (m, 10H), 1.66-1.63 (m, 2H). HRMS m/z (M+H)$^+$ calcd 511.3185; obsd 511.3211.

Example 8

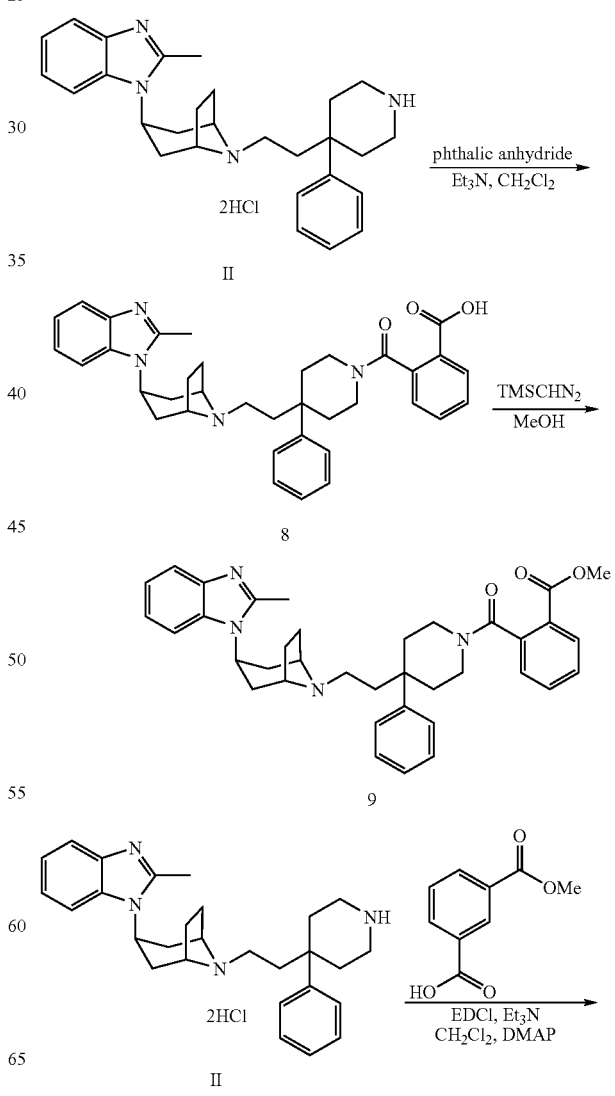

-continued

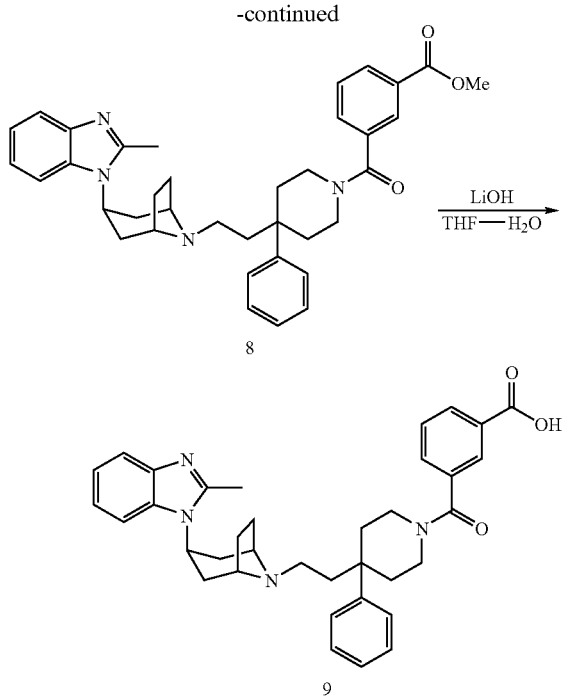

8

2-[(4-{2-[3-(2-methyl-1H-benzimidazol-1-yl)-8-azabicyclo-[3.2.1]oct-8-yl]ethyl}-4-phenylpiperidin-1-yl)carbonyl]benzoic acid (8)

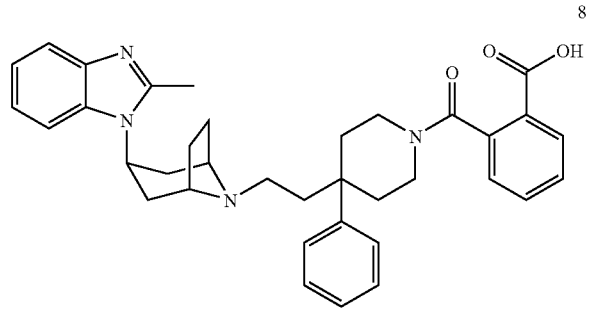

8

To a stirred solution of 2-methyl-1-{8-[2-(4-phenylpiperidin-4-yl)ethyl]-8-azabicyclo[3.2.1]oct-3-yl}-1H-benzimidazole dihydrochloride II (25.3 mg, 0.05 mmol) in 1,2-dichloroethane (3 mL) was added triethyl amine (14 µL, 0.1 mmol) and phthalic anhydride (7.4 mg, 0.05 mmol). The resulting mixture was stirred at ambient temperature for 4 hours. After evaporation of the solvents, the residue was purified by flash chromatography on silical gel, eluting with a gradient of 10-30% methanol in ethyl acetate to afford 2-[(4-{2-[3-(2-methyl-1H-benzimidazol-1-yl)-8-azabicyclo[3.2.1]oct-8-yl]ethyl}-4-phenylpiperidin-1-yl)carbonyl]benzoic acid as amorphous solid (29 mg, quant.). $^1$H NMR (300 MHz, DMSO-d$_6$) δ 7.94 (d, J=6.6 Hz, 1H), 7.53-7.50 (m, 1H), 7.48-7.36 (m, 7H), 7.25-7.21 (m, 1H), 7.17-7.09 (m, 3H), 4.61-4.54 (m, 1H), 3.26 (br, 4H), 3.95 (br, 1H), 3.09 (br, 1H), 2.46 (s, 3H), 2.42-2.32 (m, 3H), 2.24-2.06 (m, 1H), 2.00-1.86 (m, 5H), 1.86-1.76 (m, 5H), 1.61 (d, J=7.7 Hz, 2H). HRMS m/z (M+H)$^+$ calcd 577.3179; obsd 577.3176.

Example 9 methyl 2-[(4-{2-[3-(2-methyl-1H-benzimidazol-1-yl)-8-azabicyclo[3.2.1]oct-8-yl]ethyl}-4-phenylpiperidin-1-yl)carbonyl]benzoate (9)

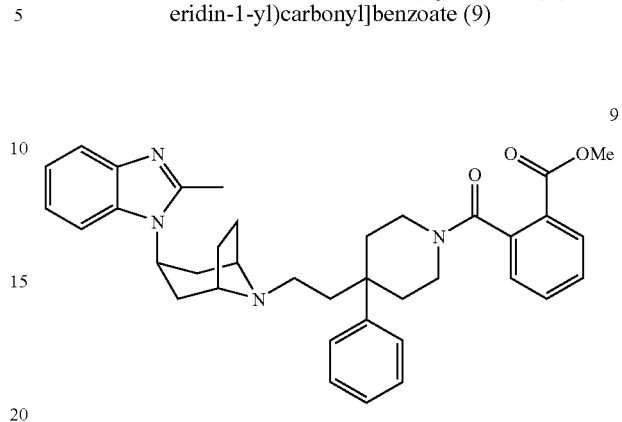

9

To a stirred solution of 2-[(4-{2-[3-(2-methyl-1H-benzimidazol-1-yl)-8-azabicyclo[3.2.1]oct-8-yl]ethyl}-4-phenylpiperidin-1-yl)carbonyl]benzoic acid 8 (40 mg, 0.07 mmol) in methanol (2 mL) was added (trimethylsilyl)diazomethane (0.35 mL, 2.0 M in hexanes). The resulting mixture was further stirred for 30 minutes. After evaporation of solvents, the residue was purified by flash chromatography on silical gel, eluting with a gradient of 0-10% methanol in ethyl acetate to afford methyl 2-[(4-{2-[3-(2-methyl-1H-benzimidazol-1-yl)-8-azabicyclo[3.2.1]oct-8-yl]ethyl}-4-phenylpiperidin-1-yl)carbonyl]benzoate 9 as an oil (40 mg, quant.). $^1$H NMR (400 MHz, CDCl$_3$) δ 8.01 (d, J=7.6 Hz, 1H), 7.64 (d, J=7.7 Hz, 1H), 7.54 (s, 1H), 7.45-7.41 (m, 1H), 7.37-7.34 (m, 2H), 7.29-7.21 (m, 5H), 7.18-7.10 (m, 2H), 4.63-4.53 (m, 1H), 4.21-4.18 (m, 1H), 3.86 (br, 3H), 3.44 (br, 1H), 3.24 (br, 3H), 3.08 (br, 1H), 2.53 (s, 3H), 2.36-2.34 (m, 3H), 1.91-1.71 (m, 11H), 1.59 (d, J=7.0 Hz, 2H). HRMS m/z (M+H)$^+$ calcd 591.3335; obsd 591.3353.

Example 10 methyl 3-[(4-{2-[3-(2-methyl-1H-benzimidazol-1-yl)-8-azabicyclo[3.2.1]oct-8-yl]ethyl}-4-phenylpiperidin-1-yl)carbonyl]benzoate (10)

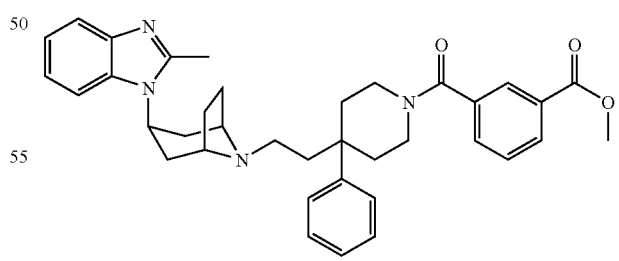

10

To a stirred solution of 2-methyl-1-{8-[2-(4-phenylpiperidin-4-yl)ethyl]-8-azabicyclo[3.2.1]oct-3-yl}-1H-benzimidazole IIa (300 mg, 0.7 mmol) in dichloromethane (10 mL) was added isophthalic acid monomethyl ester (138.9 mg, 0.77 mmol) and triethyl amine (107 µL, 0.77 mmol). The resulting mixture was then cooled down on an ice-water bath before the addition of 1-[3-(dimethylamino)propyl]-3-ethyl carbodiimide hydrochloride (146.7 mg, 0.77 mmol) and 4-dimethylaminopyridine (8.5 mg. 0.07 mmole). After being stirred for 4 hours at ambient temperature, the reaction mixture was quenched with saturated sodium bicarbonate solution and extracted with dichloromethane (3×40 mL). The combined organic phase was dried over anhydrous sodium sulfate. After evaporation of the solvent, the crude product was purified by flash chromatography on silica gel, eluting with a gradient of 0-10% methanol in ethyl acetate to afford methyl 2-[(4-{2-[3-(2-methyl-1H-benzimidazol-1-yl)-8-azabicyclo[3.2.1]oct-8-yl]ethyl}-4-phenylpiperidin-1-yl)carbonyl]benzoate 10 as amorphous solid (297 mg, 72%). $^1$H NMR (300 MHz, CDCl$_3$) δ 8.13-8.08 (m, 2H), 7.70 (d, J=8.3 Hz, 1H), 7.63 (d, J=7.5 Hz, 1H), 7.53 (t, J=7.7 Hz, 1H), 7.45-7.40 (m, 2H), 7.35-7.30 (m, 4H), 7.20-7.15 (m, 2H), 4.68 (br, 1H), 4.2 (br, 1H), 3.96 (s, 3H), 3.57 (br, 1H), 3.43-4.31 (m, 4H), 2.60 (s, 3H), 2.42 (br, 3H), 2.19 (br, 1H), 1.99-1.92 (m, 10H), 1.69 (br, 2H). HRMS m/z (M+H)$^+$ calcd 591.33335; obsd 591.3325.

Example 11

3-[(4-{2-[3-(2-methyl-1H-benzimidazol-1-yl)-8-azabicyclo-[3.2.1]oct-8-yl]ethyl}-4-phenylpiperidin-1-yl)carbonyl]benzoic acid (11)

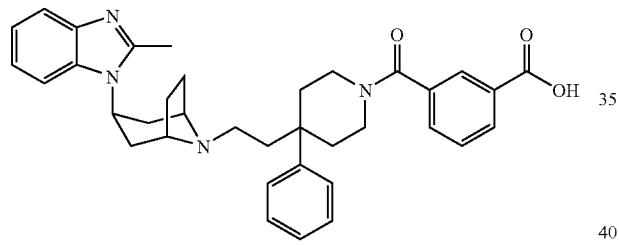

11

To a precooled (0° C.) stirred solution of methyl 3-[(4-{2-[3-(2-methyl-1H-benzimidazol-1-yl)-8-azabicyclo[3.2.1]oct-8-yl]ethyl}-4-phenylpiperidin-1-yl)carbonyl]benzoate 10 (20 mg, 0.034 mmol) in a 2 mL-mixed solvent of THF-H$_2$O (3:1) was added lithium hydroxide monohydrate (4.3 mg, 0.1 mmol). The resulting mixture was stirred for 2 hours at 0° C. before being buffered with saturated sodium bicarbonate solution. The reaction mixture was then extracted with dichloromethane (3×20 mL). The combined extracts were washed with brine and dried over anhydrous sodium sulfate. After evaporation of the solvent, the crude product was purified by flash chromatography on silical gel, eluting with a gradient of 10-30% methanol in ethyl acetate to afford 3-[(4-{2-[3-(2-methyl-1H-benzimidazol-1-yl)-8-azabicyclo[3.2.1]oct-8-yl]ethyl}-4-phenylpiperidin-1-yl)carbonyl]benzoic acid 11 as white powder solid (18 mg, 95%). $^1$H NMR (300 MHz, DMSO-d$_6$) δ 7.98 (s, 1H), 7.91 (s, 1H), 7.51 (d, J=6.9 Hz, 1H), 7.40-7.36 (m, 7H), 7.26-7.24 (m, 2H), 7.14-7.08 (m, 2H), 4.55-4.49 (m, 1H), 3.92 (br, 1H), 3.34 (br, 1H), 4.24 (br, 2H), 2.45 (s, 3H), 2.39-2.32 (m, 3H), 2.14 (br, 3H), 1.86-1.73 (m, 10H), 1.59 (d, J=7.3 Hz, 2H). HRMS m/z (M+H)$^+$ calcd 577.3179; obsd 577.3192.

Example 12 ethyl 2-ethyl-2-[(4-{2-[(1R,5S)-3-(2-methyl-1H-benzimidazol-1-yl)-8-azabicyclo[3.2.1]oct-8-yl]ethyl}-4-phenylpiperdin-1-yl)carbonyl]butonate (12)

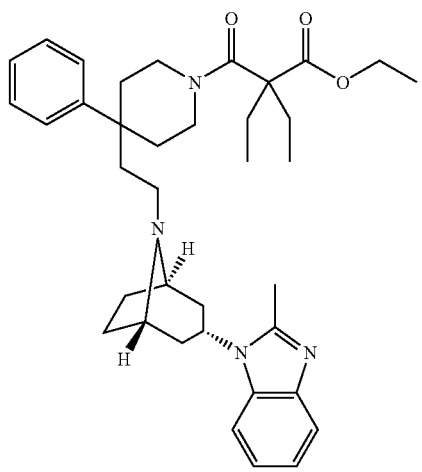

2-(ethoxycarbonyl)-2-ethylbutanoic acid

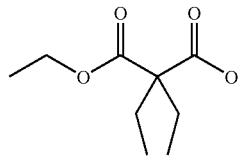

12a

A solution of diethyl-malonic acid diethyl ester (3.0 g, 13.89 mmol) and potassium hydroxide (0.778 g, 13.89 mmol) in ethanol (50 ml) was stirred at room temperature for 18 hrs. The solvent was evaporated off and the residue was dissolved in water (20 ml) and extracted with dichloromethane (20 ml). This organic layer was discarded. The aqueous layer was then acidified with concentrated HCl and extracted with dichloromethane (3×20 ml). The combined organic layers were dried over magnesium sulfate and concentrated to give a colorless oil 12a (1.9 g, 72%). $^1$H NMR (300 MHz, Methanol-d$_4$) δ 4.17 (m, 2H), 1.89 (m, 4H), 1.25 (m, 3H), 0.83 (m, 6H). ES-LCMS m/z 188 (M+H)

A solution of 2-(ethoxycarbonyl)-2-ethylbutanoic acid 12a (0.043 g, 0.25 mmol), 1-1'-Carbonyldiimdazole (0.048 g, 0.25 mmol) and 1-Hydroxybenzotriazole hydrate (0.034 g, 0.25 mmol) in dichloromethane (8 ml) was stirred for 10 min at RT. Then 2-methyl-1-{8-[2-(4-phenylpiperidin-4-yl)ethyl]-8-azabicyclo[3.2.1]oct-3-yl}-1H-benzimidazole IIa (0.090 g, 0.21 mmol) and triethylamine (0.64 g, 0.088 ml, 0.63 mmol) were added and stirred for 18 hrs at room temperature. The reaction was diluted with dichloromethane (10 ml) and extracted 1M citric acid (3×10 ml). The aqueous layer was neutralized with 1M sodium carbonate and extracted with dichloromethane (3×10 ml). Organic layer was dried using magnesium sulfate and solvent evaporated to white oil. The desired product was further purified column chromatography on silica gel using an elution gradient of dichloromethane:methanol (100:0 to 90:10) to afford the product as a colorless oil (0.115 g, 91%). $^1$H NMR (300 MHz, CDCl$_3$) δ 7.88 (d, 1H), 7.67 (t, 1H), 7.40-7.15 (m, 7H), 5.20-4.50 (m, 3H), 4.15 (m, 3H), 3.41 (m, 3H), 3.12 (m, 2H), 2.55 (s, 3H), 2.45 (m, 1H), 2.20-1.60 (m, 16H), 1.44 (s, 1H), 1.21 (m, 3H) 0.87 (m, 6H). HRMS C$_{37}$H$_{50}$N$_4$O$_3$ m/z (M+H)$_{Cal.}$ 599.3961; (M+H)$_{Obs.}$ 599.3981.

Example 13

2-ethyl-2-[(4-{2-[(1R,5S)-3-(2-methyl-1H-benzimidazol-1-yl)-8-azabicyclo[3.2.1]oct-8-yl]ethyl}-4-phenylpiperdin-1-yl)carbonyl]butonic acid

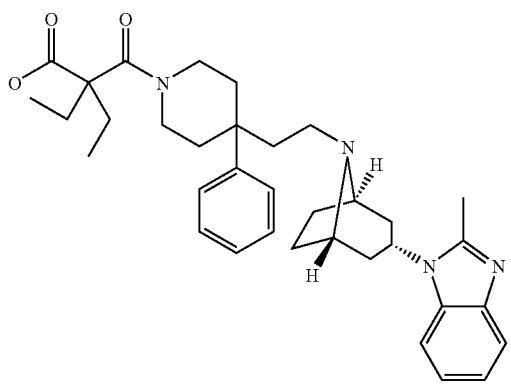

13

A solution of ethyl 2-ethyl-2-[(4-{2-[(1R,5S)-3-(2-methyl-1H-benzimidazol-1-yl)-8-azabicyclo[3.2.1]oct-8-yl]ethyl}-4-phenylpiperdin-1-yl)carbonyl]butonate 12 (0.100 g, 0.17 mmol), 5 N NaOH (10 ml) and ethanol (4 ml) was stirred at 90° C. for 3 hrs. The reaction was evaporated to dryness and residue was suspend in water (10 ml) and neutralized with 1 N HCl. The aqueous layer was extracted with ethyl acetate (3×10 ml). The organic layer was dried using magnesium sulfate and concentrated down to form a white oil 13 (0.060 g, 62%). $^1$H NMR (300 MHz, CDCl$_3$) δ 7.80 (d, 1H), 7.38-7.23 (m, 8H), 4.73 (m, 1H), 4.12 (m, 1H), 3.20 (m, 3H), 2.66 (s, 3H), 2.24 (m, 2H), 2.05-1.70 (m, 9H), 1.60 (m, 2H), 1.35-1.05 (m, 15H). HRMS C$_{35}$H$_{46}$N$_4$O$_3$ m/z (M+H)$_{Cal.}$ 571.3648; (M+H)$_{Obs.}$ 571.3650.

Example 14

Ethyl 1-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]cyclobutanecaboxylate

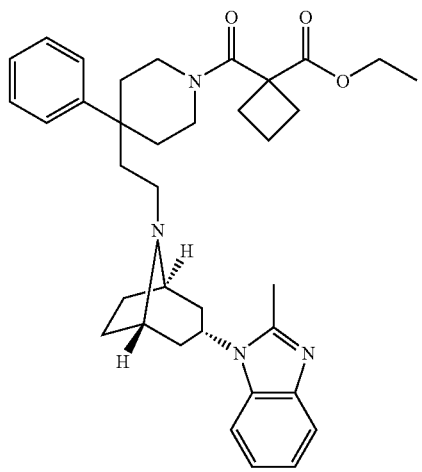

1-(ethoxycarbonyl)cyclobutanecarboxylic acid

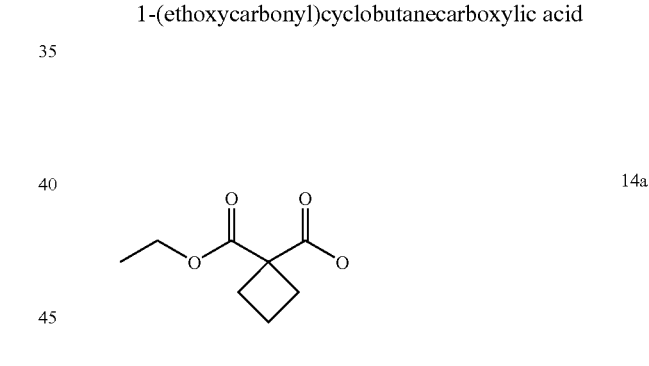

14a

A solution of diethyl ester (1.6 g, 8.20 mmol) and potassium hydroxide (0.459 g, 8.20 mmol) in ethanol (50 ml) was stirred at room temperature for 18 hrs. The solvent was evaporated off and the residue was dissolved in water (20 ml) and extracted with dichloromethane (20 ml). This organic layer was discarded. The aqueous layer was then acidified with concentrated HCl and extracted with dichloromethane (3×20 ml). The combined organic layers were dried over magnesium sulfate and concentrated to give a colorless oil (0.900 g, 63%). $^1$H NMR (300 MHz, CDCl$_3$) δ 4.25 (m, 2H), 2.60 (m, 4H), 2.00 (m, 2H), 1.30 (m, 3H). ES-LCMS m/z 172 (M+H).

A solution of 1-(ethoxycarbonyl)cyclobutane carboxylic acid (0.043 g, 0.25 mmol), 1-1'-carbonyl-diimdazole (0.048 g, 0.25 mmol) and 1-Hydroxybenzo-triazole hydrate (0.034 g, 0.25 mmol) in dichloro-methane (8 ml) was stirred for 10 min at RT. Then 2-methyl-1-{8-[2-(4-phenylpiperidin-4-yl)ethyl]-8-azabicyclo[3.2.1]oct-3-yl}-1H-benzimidazole IIa (0.090 g, 0.21 mmol) and triethylamine (0.64 g, 0.088 ml, 0.63 mmol) were added and stirred for 18 hrs at room temperature. The reaction was diluted with dichloromethane (10 ml) and extracted 1 M citric acid (3×10 ml). The aqueous layer was neutralized with 1M sodium carbonate and extracted with dichloromethane (3×10 ml). The organic layer was dried using magnesium sulfate and the solvent evaporated to white oil. The desired product was further purified column chromatography on silica gel using an elution gradient of dichloromethane:methanol (100:0 to 90:10) to afford the product as a colorless oil 14 (0.085 g, 70%). $^1$H NMR (300 MHz, CDCl$_3$) δ 7.89 (m, 1H), 7.67 (m, 1H), 7.26 (m, 7H), 4.86 (m, 1H), 4.25-3.90 (m, 3H), 3.89 (s, 2H), 3.21 (m, 2H), 2.96 (m, 1H), 2.70-2.35 (m, 9H), 2.55-1.55 (m, 16H), 1.22 (m, 3H). HRMS C$_{36}$H$_{46}$N$_4$O$_3$ m/z 583.3648 (M+H)$_{Cal.}$; 583.3623 (M+H)$_{Obs.}$.

Example 15

1-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]cyclobutanecarboxylic acid

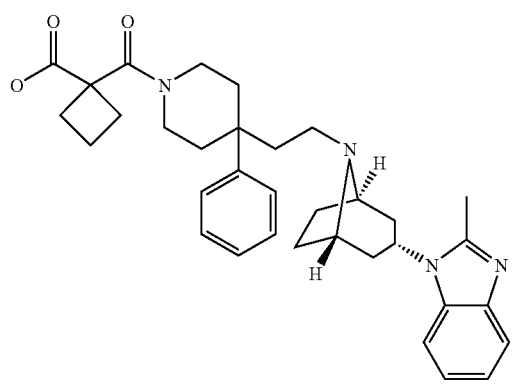

15

A solution of ethyl 1-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]cyclobutane-carboxylate from example 14 (0.050 g, 0.086 mmol), 5 N NaOH (10 ml) and ethanol (4 ml) was stirred at 90° C. for 3 hrs. The reaction was evaporated to dryness and residue was suspend in water (10 ml) and neutralized with 1N HCl. The aqueous layer was extracted with ethyl acetate (3×10 ml). The organic layer was dried using magnesium sulfate and concentrated down to form a white oil (0.032 g, 67%). $^1$H NMR (300 MHz, CDCl$_3$) δ 7.68 (d, 1H), 7.27 (m, 8H), 4.63 (m, 1H), 3.84 (m, 1H), 3.41 (m, 1H), 3.25-2.95 (m, 4H), 2.87 (m, 1H), 2.58 (s, 3H), 2.45-2.20 (m, 4H), 2.05 (m, 2H), 1.89 (m, 8H), 1.63 (m, 5H), 1.61 (s, 2H). HRMS C$_{34}$H$_{42}$N$_4$O$_3$ m/z 555.3335 (M+H)$_{Cal.}$; 555.3320 (M+H)$_{Obs.}$.

Example 16

Endo-1-(8-{2-[4-(3-chlorophenyl)-1-(2,2-dimethylpropanoyl)piperidin-4-yl]ethyl}-8-azabicyclo[3.2.1]oct-3-yl)-2-methyl-1H-benzimidazole (16) was synthesized according to the method outlined below.

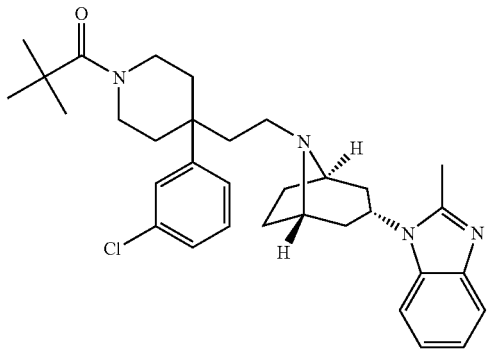

16

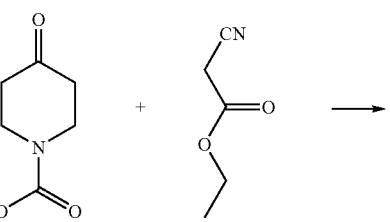

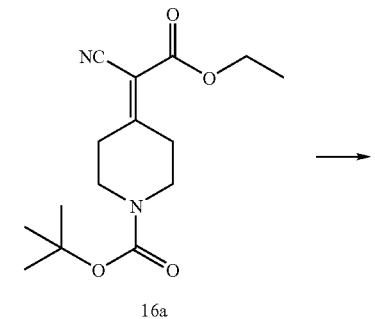

16a

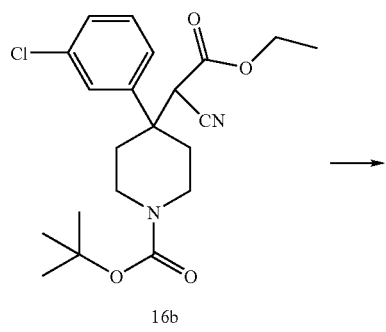

16b

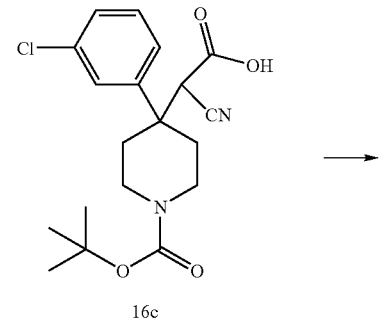

16c

-continued

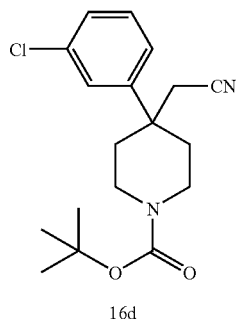

16d

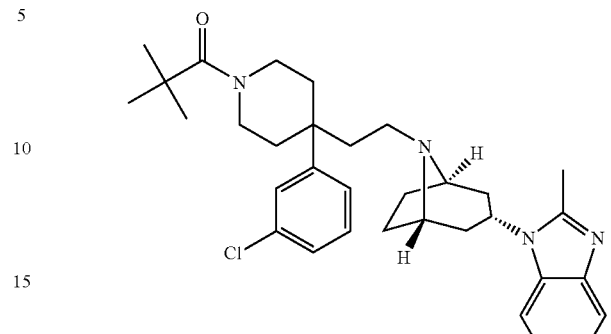

16

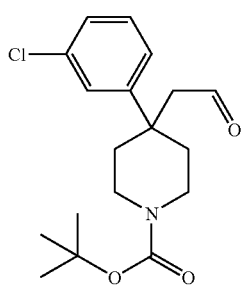

16e tert-butyl 4-(1-cyano-2-ethoxy-2-oxoethylidene)piperidine-1-carboxylate (16a)

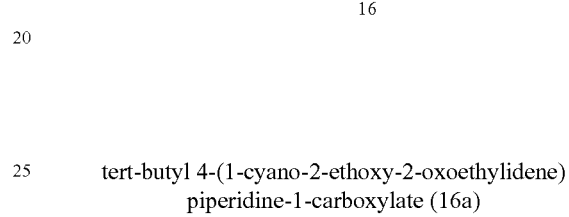

16a

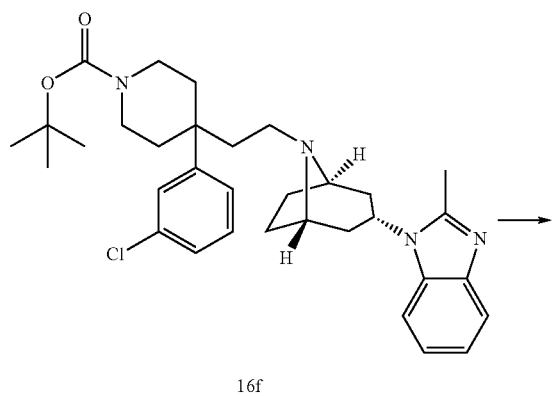

16f

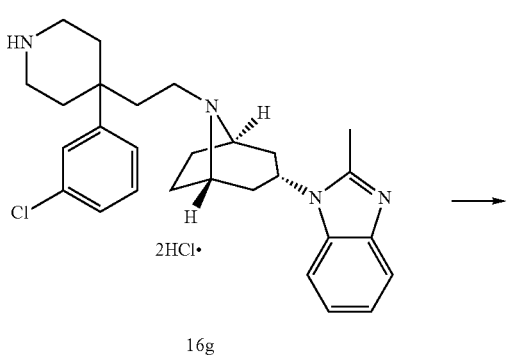

16g

A mixture of tert-butyl 4-oxo-1-piperidinecarboxylate (25.25 g, 127 mmol), ethyl cyanoacetate (13.8 ml, 130 mmol), ammonium acetate (2.73 g, 35.4 mmol), glacial acetic acid (6.3 ml) and benzene (250 ml) was heated for 4 hours at reflux under Dean Stark conditions. The reaction mixture was cooled to room temperature and washed successively with water, sodium bicarbonate solution and brine. Drying, filtration and evaporation of the organic phase provided tert-butyl 4-(1-cyano-2-ethoxy-2-oxoethylidene)piperidine-1-carboxylate as an oil that crystallized on standing (37 g, 99%). $^1$H NMR (400 MHz, CDCl$_3$): δ 4.28 (q, 2H, J=7 Hz), 3.60 (br t, 2H, J=6 Hz), 3.54 (br t, 2H, J=6 Hz), 3.12 (t, 2H, J=6 Hz), 2.76 (t, 2H, J=6 Hz), 1.47 (s, 9H), and 1.35 (t, 3H, J=7 Hz). ES-LCMS m/z 293 (M−1).

tert-butyl 4-(3-chlorophenyl)-4-(1-cyano-2-ethoxy-2-oxoethyl)piperidine-1-carboxylate (16b)

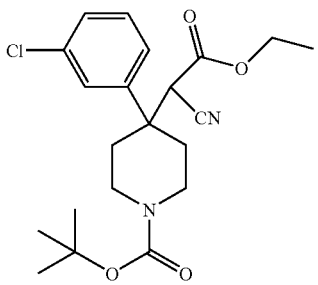

16b

A solution of 1-chloro-3-iodobenzene (14.1 g, 59.28 mmol) in diethyl ether (12 ml) was added dropwise to a mixture of magnesium turnings (1.59 g, 65.4 mmol) in diethyl ether (50 ml) at room temperature. When the Grignard reaction was complete, the resulting organomagnesium reagent was added dropwise to a stirred mixture of compound 16a (5.0 g, 17 mmol) and cuprous iodide (800 mg, 4.2 mmol) in tetrahydrofuran (30 mL) cooled to 0° C. The reaction mixture was stirred 1 hour at 0° C. and then quenched with saturated ammonium chloride solution. Ethyl acetate (500 ml) was added and the mixture was washed successively with saturated ammonium chloride, water and brine. The organic layer was dried and concentrated and the resulting crude material was purified by column chromatography on silica gel eluting with 4:1 hexane:ethyl acetate. This afforded tert-butyl 4-(3-chlorophenyl)-4-(1-cyano-2-ethoxy-2-oxoethyl)piperidine-1-carboxylate (16b) as an oil (5.2 g, 75%). $^1$H NMR (400 MHz, CDCl$_3$): δ 7.37-7.26 (m, 4H), 3.99 (br.q, 2H, J=6 Hz), 3.91 (br m, 2H), 3.58 (s, 1H), 2.88 (br.m, 2H), 2.52 (ddd, 2H, J=6, 4, 3 Hz), 2.04 (m, 2H), 1.43 (s, 9H), and 1.06 (t, 3H, J=6 Hz). ES-LCMS m/z 429 (M+Na$^+$).

[1-(tert-butoxycarbonyl)-4-(3-chlorophenyl)piperidin-4-yl](cyano)acetic acid (16c)

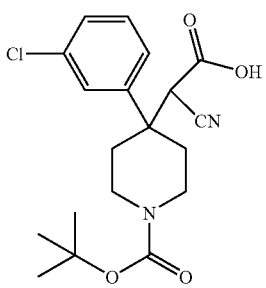

16c

A solution of 16b (5.2 g, 12.8 mmol) was dissolved in ethanol (30 ml) and 4 M aqueous sodium hydroxide (30 ml, 120 mmol) was added. The resulting solution was stirred at room temperature for 6.5 hours and then stored at 0° C. overnight. Concentrated hydrochloric acid (10 ml) was added dropwise at 0° C. and the mixture was then adjusted to pH~4 with 1 M hydrochloric acid. The solution was extracted with ethyl acetate (500 ml) and the aqueous phase was acidified to pH~3 and re-extracted with ethyl acetate. Both ethyl acetate layers were combined and washed with water and brine and then dried and concentrated to afford [1-(tert-butoxycarbonyl)-4-(3-chlorophenyl) piperidin-4-yl](cyano)acetic acid (16c) as a rigid foam (3.75 g, 77%). This material was used without further purification.

tert-butyl 4-(3-chlorophenyl)-4-(cyanomethyl)piperidine-1-carboxylate (16d)

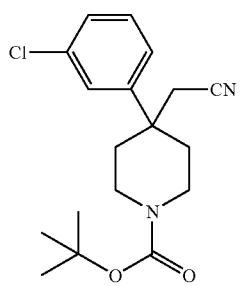

16d 16d (3.75 g, 9.90 mmol) was dissolved in acetonitrile (30 ml) and cupric oxide (355 mg, 0.025 mmol) was added. This mixture was heated at reflux with stirring for 30 minutes and then cooled to room temperature and filtered through celite. Evaporation of the filtrate gave tert-butyl 4-(3-chlorophenyl)-4-(cyanomethyl)piperidine-1-carboxylate 16d as an oil that crystallized on standing (3.0 g, 91%). $^1$H NMR (400 MHz, CDCl$_3$): δ 7.37-7.27 (m, 4H), 3.74 (br.m, 2H), 3.08 (br.t, 2H, J=11 Hz), 2.55 (s, 2H), 2.27 (br.dd, 2H, J=11, 3 Hz), 1.86 (ddd, 2H, J=14, 11, 4 Hz), and 1.44 (s, 9H).

tert-butyl 4-(3-chlorophenyl)-4-(2-oxoethyl)piperidine-1-carboxylate (16e)

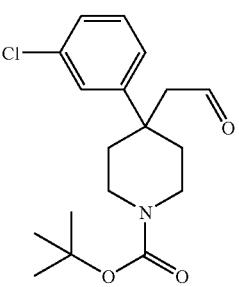

16e

A solution of 16d (1.96 g, 5.85 mmol) in dichloromethane (25 mL) was cooled to −30° C. and a 1M solution of diisobutyl aluminum hydride in dichloromethane (15.5 ml, 17.5 mmol) was added dropwise. During this addition the internal temperature was maintained at or below −35° C. When the addition was complete, the reaction mixture was stirred 30 min and then quenched at −35° C. with methanol (0.7 ml) followed by saturated citric acid solution (50 ml). The mixture was allowed to warm to room temperature and then extracted with dichloromethane. Combined dichloromethane layers were dried, filtered and evaporated to provide tert-butyl 4-(3-chlorophenyl)-4-(2-oxoethyl)piperidine-1-carboxylate (16e) as an oil (1.3 g, 66%). $^1$H NMR (400 MHz, CDCl$_3$): δ 9.40 (t, 1H, J=3 Hz), 7.34-7.22 (m, 4H), 3.61 (m, 2H), 3.26 (ddd, 2H, J=13, 9, 3 Hz), 2.66 (d, 2H, J=3 Hz), 2.19 (m, 2H), 1.86 (ddd, 2H, J=13, 9, 3 Hz), and 1.44 (s, 9H). $^{13}$C NMR (100 MHz, CDCl$_3$): δ 201.4 (CH), 154.97 (C), 145.8 (C), 135.2 (C), 130.4 (CH), 127.3 (CH), 127.0 (CH), 124.9 (CH), 79.9 (C), 54.6 (2CH$_2$), 53.3 (C), 39.2 (CH$_2$), 35.5 (2CH$_2$), and 28.6 (3CH$_3$).

tert-butyl endo-4-(3-chlorophenyl)-4-{2-[3-(2-methyl-1H-benzimidazol-1-yl)-8-azabicyclo[3.2.1]oct-8-yl]ethyl}piperidine-1-carboxylate (16f)

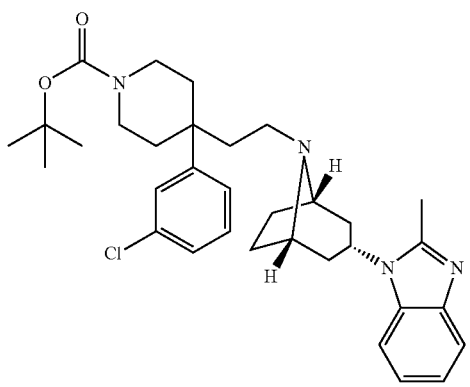

16f

Sodium triacetoxyborohydride (286 mg, 1.35 mmol) was added in one portion to a stirred mixture of 3-endo-1-(8-azabicyclo[3.2.1]oct-3-yl)-2-methyl-1H-benzimidazole dihydrochloride (compound IV, 250 mg, 0.90 mmol), 16e (304 mg, 0.90 mmol), triethylamine (0.25 ml, 1.79 mmol) and powdered molecular sieves (250 mg) in dichloromethane (3 ml). After stirring 1 hour at room temperature, the reaction was quenched with saturated sodium bicarbonate solution and the dichloromethane layer was removed. The aqueous layer was extracted with dichloromethane and the combined organic layers were dried, filtered and concentrated to afford tert-butyl endo-4-(3-chlorophenyl)-4-{2-[3-(2-methyl-1H-benzimidazol-1-yl)-8-azabicyclo[3.2.1]oct-8-yl]ethyl}piperidine-1-carboxylate as a rigid foam (500 mg, 99%). $^1$H NMR (400 MHz, DMSO-d$_6$): δ 7.47 (dd, 1H, J=7, 2 Hz), 7.40 (br s, 1H), 7.39-7.35 (m, 3H), 7.27 (d, 1H, J=7 Hz), 7.11 (dd, 1H, J=7, 6 Hz), 7.08 (dd, 1H, J=7, 6 Hz), 4.50 (m, 1H, J=8 Hz), 3.48 (m, 2H); 3.24 (m, 2H), 3.11 (m, 2H), 2.48 (s, 3H), 2.35 (br dd, 2H, J=15, 9 Hz), 1.98 (m, 2H), 1.90-1.70 (m, 10H), 1.59 (d, 2H, J=8 Hz), and 1.36 (s, 9H). ES-LCMS m/z 585 (M+Na$^+$).

endo-1-(8-{2-[4-(3-chlorophenyl) piperidin-4-yl] ethyl}-8-azabicyclo[3.2.1]oct-3-yl)-2-methyl-1H-benzimidazole dihydrochloride (16g)

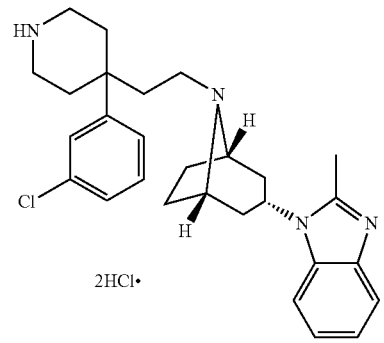

16g

2HCl•

To a stirring solution of the product from example 16f (500 mg, 0.888 mmol) in dichloromethane (6 ml) was added a 4 M solution of hydrogen chloride in 1,4-dioxane (7 ml, 28 mmol). After stirring 15 minutes at room temperature, the supernatant was decanted. The remaining precipitate was triturated with ethyl acetate and dried under high vacuum to afford endo-1-(8-{2-[4-(3-chlorophenyl)piperidin-4-yl]ethyl}-8-azabicyclo[3.2.1]oct-3-yl)-2-methyl-1H-benzimidazole dihydrochloride (16g) as a pink solid (548 mg, 100%). This material was used without further purification. ES-LCMS m/z 463 (M+H).

endo-1-(8-{2-[4-(3-chlorophenyl)-1-(2,2-dimethylpropanoyl)piperidin-4-yl]ethyl}-8-azabicyclo[3.2.1] oct-3-yl)-2-methyl-1H-benzimidazole (16)

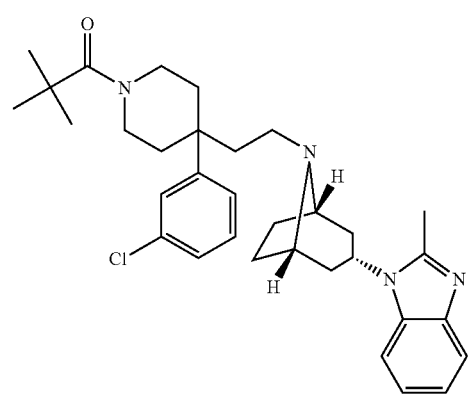

16

To a solution of 169 (165 mg, 0.308 mmol) and triethylamine (0.086 ml, 0.616 mmol) in dichloromethane (3 ml) was added pivaloyl chloride (0.040 ml, 0.325 mmol). After stirring 1 hour at room temperature the reaction mixture was quenched with saturated sodium bicarbonate solution. The organic layer was separated, dried and concentrated. Purification of the resulting material by chromatography on silica gel eluting with 24:1 dichloromethane:methanol gave endo-1-(8-{2-[4-(3-chlorophenyl)-1-(2,2-dimethylpropanoyl)piperidin-4-yl]ethyl}-8-azabicyclo[3.2.1]oct-3-yl)-2-methyl-1H-benzimidazole (16) as a rigid white foam (100 mg, 59%). $^1$H NMR (400 MHz, DMSO-d$_6$): 37.48 (d, 1H, J=7 Hz), 7.42

(s, 1H), 7.41-7.34 (m, 3H), 7.28 (d, 1H, J=7 Hz), 7.11 (br.t, 1H, J=7 Hz), 7.08 (br.t, 1H, J=7), 4.50 (m, 1H, J=8 Hz), 3.73 (m, 2H), 3.29 (s, 3H), 3.25 (m, 4H), 2.35 (br.dd, 2H, J=22, 9 Hz), 2.02 (m 2H), 1.84-1.73 (m, 10H), 1.59 (d, 2H, J=8 Hz), and 1.16 (s, 9H). ES-LCMS m/z 547 (M+H). HRMS $C_{33}H_{43}ClN_4O$ m/z 547.3186 (M+H)$_{Cal.}$ 547.3204 (M+H)$_{Obs.}$

Example 17

1-{(1R,5S)-8-[2-(1-benzoyl-4-phenylpiperidin-4-yl)ethyl]-8-azabicyclo[3.2.1]oct-3-yl}-2-ethyl-1H-benzimidazole

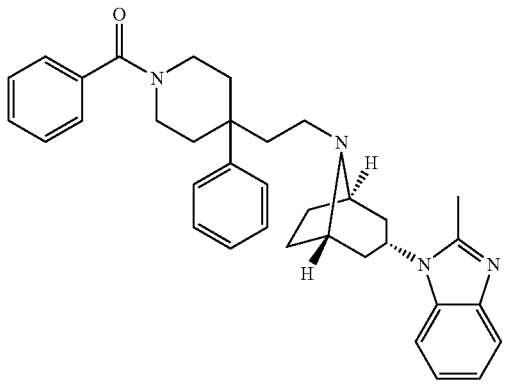

17

To a stirred solution of endo 2-methyl-1-{8-[2-(4-phenylpiperidin-4-yl)ethyl]-8-azabicyclo[3.2.1]oct-3-yl}-1H-benzimidazole dihydrochloride II (0.53 g, 1.06 mmol) in dichloromethane (10 mL) and triethylamine (0.32 g, 3.18 mmol) was added benzoyl chloride (0.156 g, 1.11 mmol) at 0° C. The ice bath was then removed and the mixture allowed to stir for 30 min. The solvents were then removed in vacuo and the resulting solid was partitioned between ethyl acetate and water (3×). The organic layer was dried with magnesium sulfate and the solvent removed in vacuo, yielding crude 17, which was them purified using the supercritical fluid chromatography, resulting in 525 mg of pure 1-{(1R,5S)-8-[2-(1-benzoyl-4-phenylpiperidin-4-yl)ethyl]-8-azabicyclo[3.2.1]oct-3-yl}-2-methyl-1H-benzimidazole 17 (yield 93%). $^1$H NMR (400 MHz, CDCl$_3$) δ 7.20 (1H, m), 6.94 (7H, m), 6.82 (4H, m), 6.70 (2H, m), 4.15 (1H, m), 3.75 (1H, m), 3.11 (1H, m), 2.98 (4H, m), 2.93 (1H, m), 2.78 (3H, m), 2.05 (3H, s), 2.04 (2H, m), 1.88 (3H, m), 1.70 (1H, m), 1.59-1.24 (4H, m), 1.14 (2H, m). HRMS m/z (M+H)$^+_{Calc}$ 533.3280; (M+H)+$_{Obs}$ 533.3300.

Example 18

1-((1R,5S)-8-{2-[1-(cyclopentylcarbonyl)-4-phenylpiperidin-4-yl]ethyl}-8-azabicyclo[3.2.1]oct-3-yl)-2-methyl-1H-benzimidazole

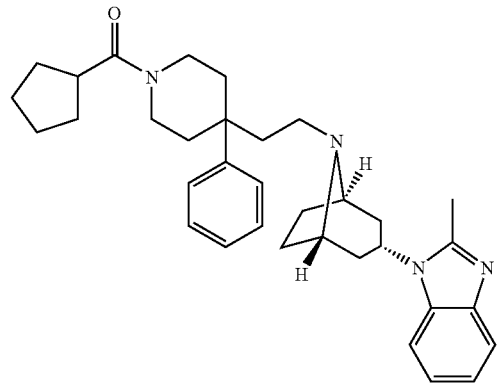

18

To a stirred solution of endo 2-methyl-1-{8-[2-(4-phenylpiperidin-4-yl)ethyl]-8-azabicyclo[3.2.1]oct-3-yl}-1H-benzimidazole dihydrochloride II (0.38 g, 0.75 mmol) in dichloromethane (7 mL) and triethylamine (0.227 g, 2.25 mmol) was added cyclopentantane carbonyl chloride (0.104 g, 0.79 mmol) at 0° C. The ice bath was then removed and the mixture allowed to stir for 20 min. The solvents were then removed in vacuo and the solid partitioned between dichloroethane and water (3×), and the organic layer evaporated in vacuo resulting in 0.270 g of crude product. Following SFC purification, 156 mg of the desired product 1-((1R,5S)-8-{2-[1-(cyclopentylcarbonyl)-4-phenylpiperidin-4-yl]ethyl}-8-azabicyclo[3.2.1]oct-3-yl)-2-methyl-1H-benzimidazole (18). $^1$H NMR (400 MHz, CD$_3$OD) δ 7.40 (1H, m), 7.25 (5H, m), 7.10 (3H, m), 4.52 (1H, m), 3.84 (1H, m), 3.63 (1H, m), 3.20-2.94 (4H, m), 2.86 (1H, m), 2.39 (3H, s), 2.10 (4H, m), 1.92-1.36 (20H, m). HRMS m/z (M+H)$^+_{Calc}$ 525.3606; (M+H)$^+_{Obs}$ 525.3593.

Example 19

1-((1R,5S)-8-{2-[1-(2-furoyl)-4-phenylpiperidin-4-yl]ethyl}-8-azabicyclo[3.2.1]oct-3-yl)-2-methyl-1H-benzimidazole

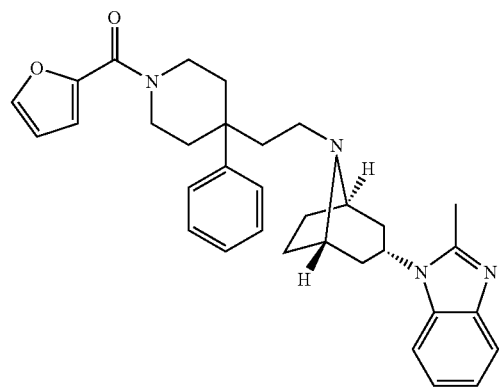

19

To a stirred solution of endo 2-methyl-1-{8-[2-(4-phenylpiperidin-4-yl)ethyl]-8-azabicyclo[3.2.1]oct-3-yl}-1H-benzimidazole dihydrochloride II (0.35 g, 0.69 mmol) in dichloromethane (7 mL) and triethylamine (0.209 g, 2.07 mmol) was added 2-furoyl chloride (0.094 g, 0.72 mmol) at 0° C. The ice bath was then removed and the mixture allowed to stir for 30 min. The solvents were then removed in vacuo and the solid was added ethyl acetate and water. The insoluble precipitate was then filtered off and subsequently characterized as the desired product 19. Additional 0.18 g of the desired product 19 was obtained by extracting the organic layer with water (3×), drying with magnesium sulfate and evaporating solvents in vacuo. Following the SFC purification, on a portion of crude 19, 60 mg of the desired product 1-((1R,5S)-8-{2-[1-(2-furoyl)-4-phenylpiperidin-4-yl]ethyl}-8-azabicyclo[3.2.1]oct-3-yl)-2-methyl-1H-benzimidazole 19 was obtained (calculated yield 86%). $^1$H NMR (400 MHz, CD$_3$OD) δ 7.57 (1H, dist. d, J=1.1 Hz), 7.47 (1H, d, J=7.1 Hz), 7.43-7.29 (5H, m), 7.26-7.09 (3H, m), 6.89 (1H, d, J=3.6 Hz), 6.48 (1H, dd, J=1.8, 3.6 Hz), 4.08 (2H, m), 3.84 (2H, m), 2.60 (5H, m), 2.42 (3H, s), 2.30 (2H, m), 2.20 (2H, m), 2.05 (7H, m), 1.83 (2H, m). HRMS m/z (M+H)$^+_{Calc}$ 523.3062; (M+H)+$_{Obs}$ 523.3073.

Example 20

2-methyl-1-(4-{2-[3-(2-methyl-1H-benzimidazol-1-yl)-8-azabicyclo[3.2.1]oct-8-yl]ethyl}-4-phenyl-1-piperidinyl)-1-oxo-2-propanol

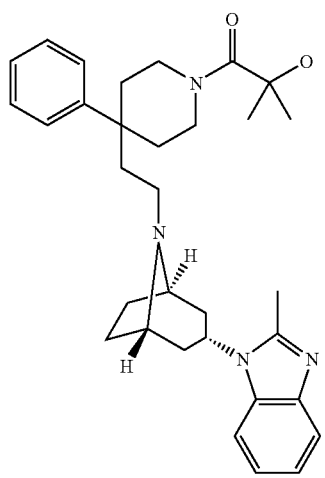

2-hydroxy-2-methylpropanoic acid (36 mg, 0.35 mmole) was dissolved in 0.92 ml of 1,2-dichloroethane. To this was added 1,1'-carbonyldiimidazole (37 mg, 0.23 mmole) and shaken for 30 min. 2-Methyl-1-{8-[2-(4-phenyl-4-piperidinyl)ethyl]-8-azabicyclo[3.2.1]oct-3-yl}-1H-benzimidazole (50 mg, 0.12 mmole) was added as a dry powder and shaking was resumed overnight. 1 ml of NaHCO$_3$ sat. was added to the reaction mixture and shaken, followed by filtration through a hydrophobic frit and concentrated to an oil. The oil was separated on silica using gradient flash chromatography (0-8% MeOH in CHCl$_3$) to afford 2-methyl-1-(4-{2-[3-(2-methyl-1H-benzimidazol-1-yl)-8-azabicyclo[3.2.1]oct-8-yl]ethyl}-4-phenyl-1-piperidinyl)-1-oxo-2-propanol 20 23.7 mg (38%) as a white glassy solid. $^1$H NMR (300 MHz, CDCl$_3$) δ 7.7-7.6 (m, 1H), 7.1-7.4 (m, 8H), 4.7 (s, 1H), 4.0 (s, 2H), 3.2-3.4 (m, 4H), 2.6 (s, 3H), 2.2-2.5 (m, 5H), 2.1-1.7 (m, 11H), 1.7-1.5 (m, 2H).

Selected Coupling Methods Used in the Synthesis Of Compounds of Formula I from II or IIa (Scheme I)

Method A (HATU)

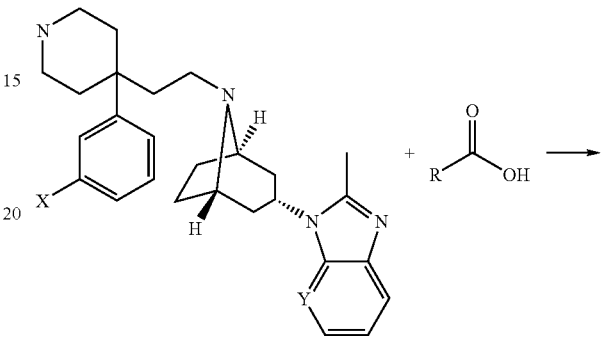

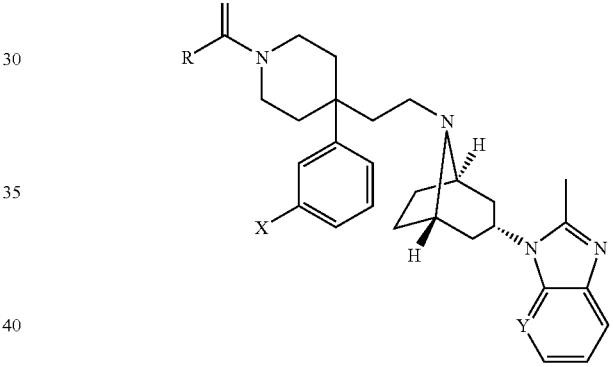

To 117 µmoles of each acid was added 117 µmoles (1 eq.) of amine-scaffold dissolved in 1 mL DMF and 351 µmoles (3 eq.) of DIPEA in 1 mL DMF at ambient temperature. After shaking 5 min to affect dissolution of materials, 117 µmoles (1 eq.) of HATU in 1 mL DMF was added and the reaction mixture and shaken at ambient temperature for 16 h. 351 µmoles of solid supported MP-Carbonate (Argonaut Technologies, Inc.) was added to the reaction mixture and shaken an additional 20 h. The resin-bound carbonate was filtered off and the reaction mixture concentrated to dryness. The approximately 100 milligrams of impure compound was dissolved in 300 microliters of DMSO and brought up to a final volume of 500 microliters using methanol. This 500 microliter solution was injected by a Waters 2767 autosampler into an XTerra C18 5 micron particle HPLC column (19 mm×50 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor and split off the eluate for desired mass, and the purified fractions were collected using Micromass Fractionlynx software. Isolated compounds were characterized by LC-MS and ¹H NMR. Yields and representative data were included in the accompanying tables.

Method B (Anhydride)

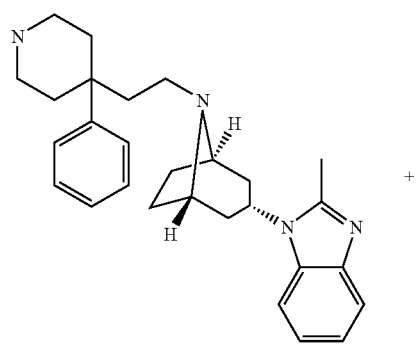

+

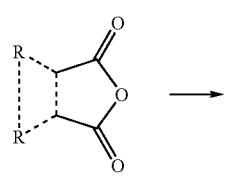

To 117 μmoles of the anhydride in 1 mL DCM was added 117 μmoles (1 eq.) of amine-scaffold dissolved in 1 mL DCM and stirred at ambient temperature for 1 h. In some cases, product crystallized from the reaction mixture and was isolated by filtration. Otherwise, the reaction mixture was concentrated and purified either by normal phase flash chromatography (SiO₂, CHCl₃/CH₃OH) or by reverse phase mass-directed HPLC as described in the Preparative HPLC Conditions A. Yields and representative data were included in the accompanying tables.

Method C—Example of TFA-Mediated Boc-Deprotection

Example 21

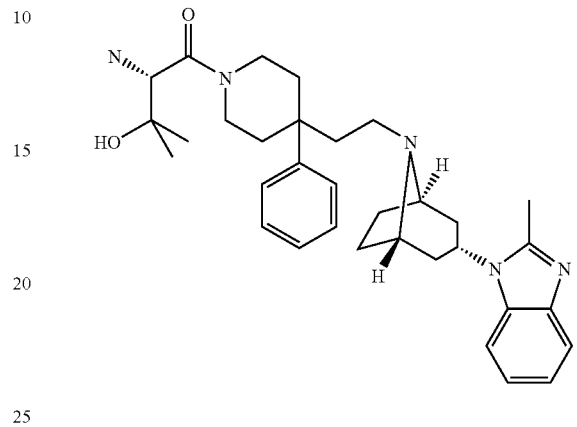

Boc-derivative (248 μmoles) was dissolved in 3 mL DCM and treated with 3 mL TFA for 40 min at ambient temperature. The reaction mixture was concentrated and pumped dry to give the TFA salt (example 21, mass 224 mg, Exact Mass=543.3573) as a clear oil. Yield and representative data were included in the accompanying tables.

Method D—Sulfonamide Via Sulfonyl Chloride or Amide Via Acyl Chloride

Example 22 and Example 23

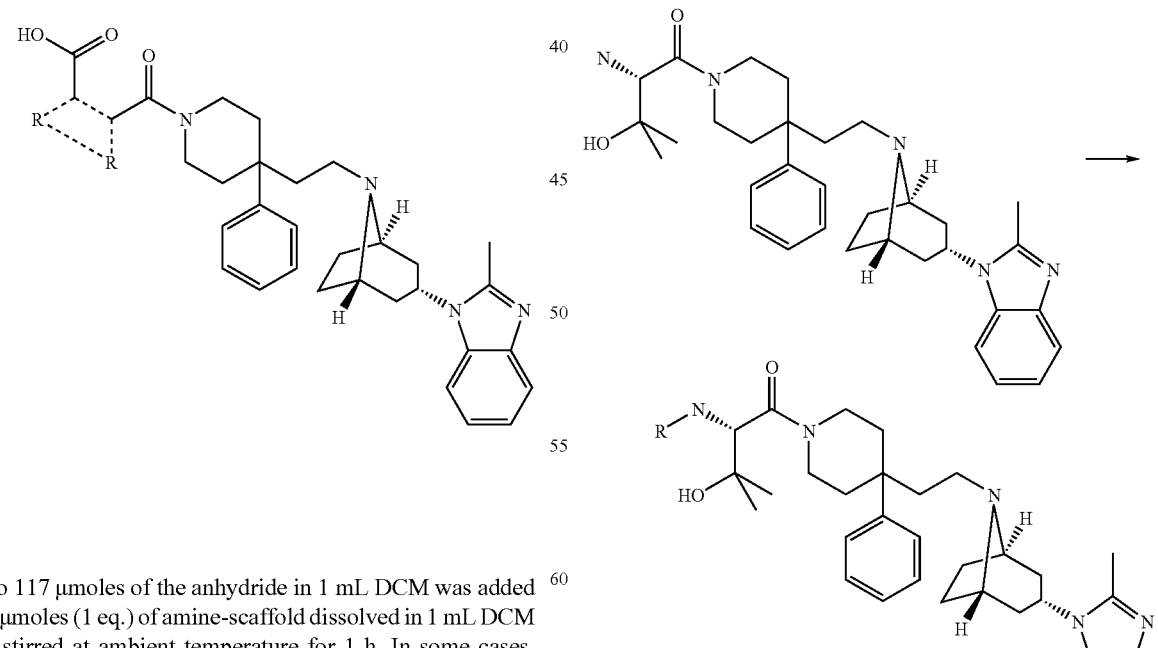

Product from example 21 (91 µmoles) was dissolved in 2 mL DCM and cooled to 0° C. was treated with TEA (273 µmoles, 3 eq.) followed by either acetyl chloride or methanesulfonyl chloride (91 µmoles, 1 eq.). The reaction mixture was stirred 5 min at 0° C. and then allowed to warm to ambient temperature and stirred an additional 30 min. The reaction mixture was diluted with 10 mL DCM, washed successively with saturated NaHCO₃ and brine, dried over MgSO₄, filtered, and concentrated to give the acetyl derivative (example 22) or methylsulfonyl (example 23), respectively. Products were purified by reverse phase mass-directed HPLC as described in Preparative HPLC Conditions A. Yields and representative data were included in the accompanying tables.

Method E—Example of TFA-Mediated Boc-Deprotection

Method F—HATU Mediated Formation of Amides

Example 24

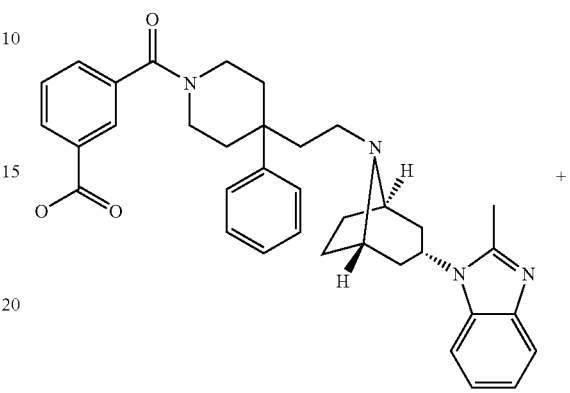

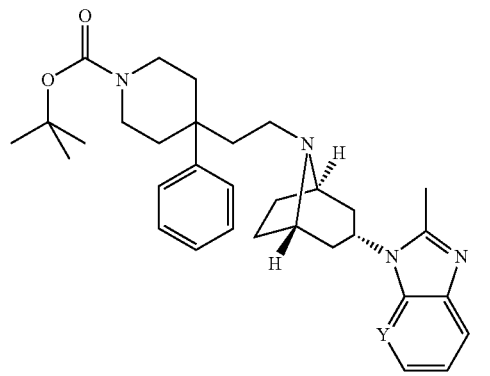

The Boc-protected amine (1.02 mmoles) was dissolved in 5 mL DCM and treated with 5 mL TFA at ambient temperature for 1 h. The reaction mixture was concentrated and treated with a biphasic mixture of EtOAc and saturated aqueous NaHCO₃. The mixture was stirred vigorously, and the solid filtered off and washed successively with water and EtOAc to give the TFA salt of the amine. Yields and representative data were included in the accompanying tables.

3-[(4-{2-[(1R,5S)-3-(2-methyl-1H-benzimidazol-1-yl)-8-azabicyclo[3.2.1]oct-8-yl]ethyl}-4-phenylpiperidin-1-yl) carbonyl]benzoic acid (259 mg, 449 µmoles) was combined with 2,4-dimethoxybenzylamine (449 µmoles, 1 eq.) in 3 mL DMF with DIPEA (449 µmoles, 1 eq.) and treated with HATU (449 μmoles, 1 eq.) at ambient temperature for 16 h. The reaction mixture was concentrated, dissolved in EtOAc, washed successively with saturated NaHCO₃ and brine, dried over MgSO₄, filtered, and concentrated. Products were purified by reverse phase HPLC as described in Preparative HPLC Conditions A to give the desired product. Yields and representative data were included in the accompanying tables.

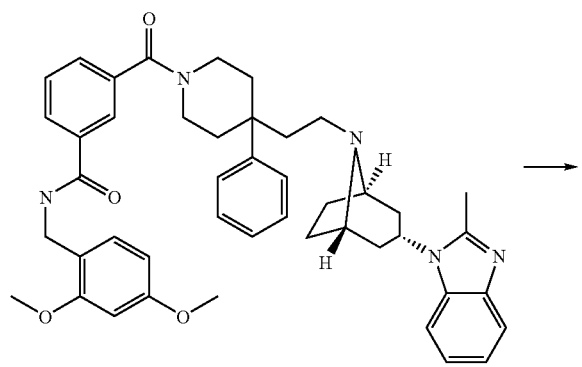

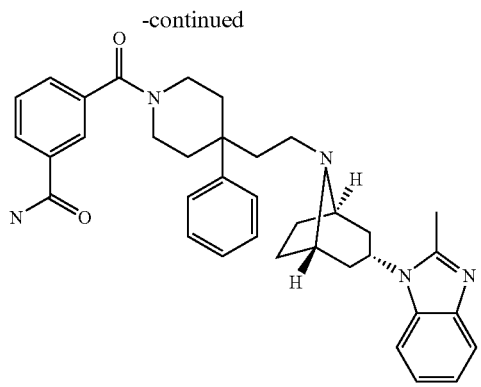

The product (73 mg, 101 μmoles) was dissolved in 3 mL DCM and treated with 3 mL TFA at ambient temperature for 24 h. The reaction mixture was concentrated, dissolved in DCM, washed with saturated aqueous NaHCO₃, dried over MgSO₄, filtered and concentrated. The crude product was purified by normal phase flash chromatography (SiO₂, DCM/CH₃OH) to give the desired product.

The accompanying tables list yields and representative data for pounds of the present invention.

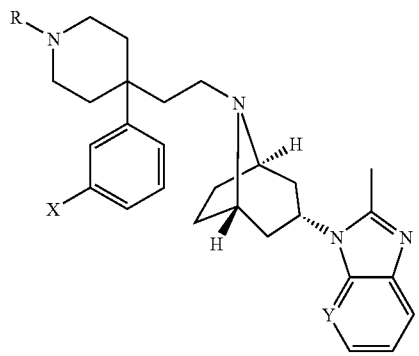

| Example # | Acid # (for non-commercial compounds) | R | X | Y | % yield | LCMS result | Ion | Acylation/coupling Method |
|---|---|---|---|---|---|---|---|---|
| 25 | | 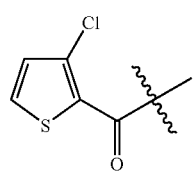 | H | C | 53 | 573 | (M + H) | Acid cloride |
| 26 | | 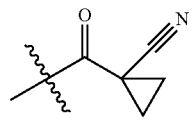 | H | C | | 522 | (M + H) | CDI |

-continued
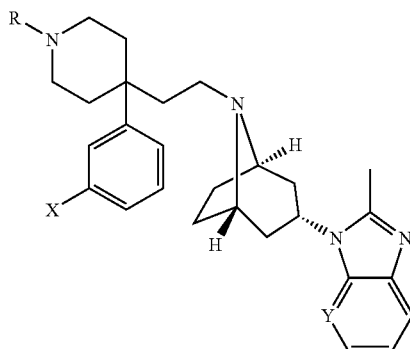
| Example # | Acid # (for non-commercial compounds) | R | X | Y | % yield | LCMS result | Ion | Acylation/ coupling Method |
|---|---|---|---|---|---|---|---|---|
| 27 | | HO-CH2-C(CH3)2-C(O)- | H | C | | 529 | (M + H) | A |
| 28 | | CH3CH2-C(CH3)2-C(O)- | H | C | | 527 | (M + H) | A |
| 29 | | HO-cyclopropyl-C(O)- | H | C | | 513 | (M + H) | A |
| 30 | | Cbz-NH-C(CH3)2-C(O)- | H | C | | 648 | (M + H) | A |
| 31 | | iPr-C(O)-C(CH3)- | H | C | | 499 | (M + H) | A |
| 33 | | triazolyl-C(CH3)2-C(O)- | H | C | | 566 | (M + H) | A |
| 34 | | 2-(Me2NSO2O)-phenyl-C(O)-C(CH3)- | H | C | 13 | 656 | (M + H) | A |

-continued
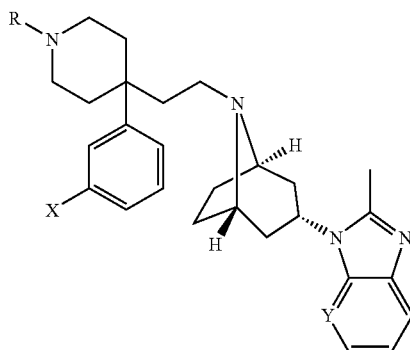
| Example # | Acid # (for non-commercial compounds) | R | X | Y | % yield | LCMS result | Ion | Acylation/ coupling Method |
|---|---|---|---|---|---|---|---|---|
| 35 | | (2,5-dimethyl-furan with SO2N(CH3)2 and C(O)) | H | C | 17 | 658 | (M + H) | A |
| 36 | | (4-(methylsulfonamido)phenyl C(O)) | H | C | 34 | 626 | (M + H) | A |
| 37 | | (formamido dimethyl C(O)) | H | C | 8 | 542 | (M + H) | A |
| 37 | | (4-hydroxy-5-methyl-isothiazole C(O)) | H | C | 8 | 570 | (M + H) | A |
| 38 | | (2-acetamido-thiazol-5-yl C(O)) | H | C | 41 | 597 | (M + H) | A |
| 39 | | (4-hydroxy-1,2,5-thiadiazol-3-yl C(O)) | H | C | 17 | 557 | (M + H) | A |
| 40 | | (2,4-dioxo-thiazine C(O)) | H | C | 39 | 584 | (M + H) | A |

-continued

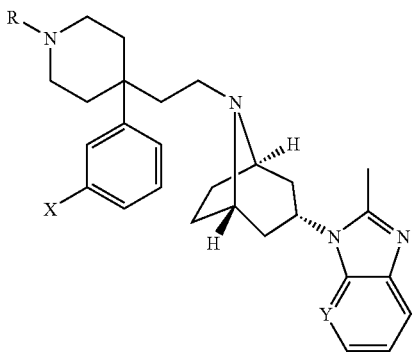

| Example # | Acid # (for non-commercial compounds) | R | X | Y | % yield | LCMS result | Ion | Acylation/coupling Method |
|---|---|---|---|---|---|---|---|---|
| 41 | | (3-(1H-tetrazol-5-yl)phenyl ketone) | H | C | 39 | 601 | (M + H) | A |
| 42 | | (2-acetamidopyridin-4-yl ketone) | H | C | 12 | 591 | (M + H) | A |
| 43 | | (N-methylsulfonyl dimethylmalonamide) | H | C | | 620 | (M + H) | A |
| 43 | | (2-(isopropylamino)-4-hydroxypyrimidin-5-yl ketone) | H | C | 44 | 608 | (M + H) | A |
| 44 | | (2-thioxo-2,3-dihydrobenzoxazol-4-yl ketone) | H | C | 26 | 606 | (M + H) | A |
| 45 | | (3,3,5-trimethyl-2-oxopyrrolidin-5-yl ketone) | H | C | 41 | 582 | (M + H) | A |

-continued
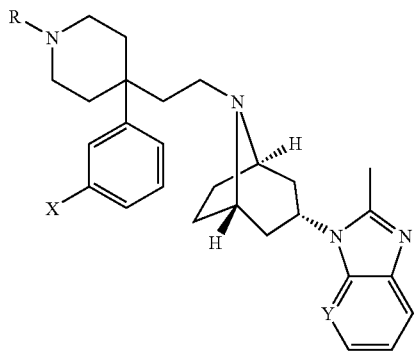
| Example # | Acid # (for non-commercial compounds) | R | X | Y | % yield | LCMS result | Ion | Acylation/coupling Method |
|---|---|---|---|---|---|---|---|---|
| 46 | | (3-acetamido-pyridin-2-yl)carbonyl | H | C | 32 | 591 | (M + H) | A |
| 47 | | (2-hydroxy-5-methylpyrazolo[1,5-a]pyrimidin-7-yl)carbonyl | H | C | 6 | 604 | (M + H) | A |
| 48 | | (2-methyl-3-thioxo-5-oxo-2,3,4,5-tetrahydro-1,2,4-triazin-6-yl)carbonyl | H | C | 36 | 598 | (M + H) | A |
| 49 | | (5-thioxo-tetrazol-1-yl)acetyl | H | C | 15 | 571 | (M + H) | A |
| 50 | | (6-hydroxybenzofuran-3-yl)carbonyl | H | C | 19 | 589 | (M + H) | A |

-continued

| Example # | Acid # (for non-commercial compounds) | R | X | Y | % yield | LCMS result | Ion | Acylation/ coupling Method |
|---|---|---|---|---|---|---|---|---|
| 51 | | H2N-SO2-furan-C(O)- | H | C | 27 | 602 | (M + H) | A |
| 52 | | AcNH-CH(Ph)-C(O)-C(CH3)2- | H | C | 40 | 604 | (M + H) | A |
| 53 | | 1-hydroxycyclopentyl-C(O)-C(CH3)2- | H | C | 33 | 541 | (M + H) | A |
| 54 | | 6-hydroxypyridin-2-yl-C(O)-C(CH3)2- | H | C | 46 | 550 | (M + H) | A |
| 55 | | 2-hydroxy-5-methoxyphenyl-C(O)-C(CH3)2- | H | C | 43 | 579 | (M + H) | A |
| 56 | | 2-hydroxy-4-methoxyphenyl-C(O)-C(CH3)2- | H | C | 48 | 579 | (M + H) | A |

-continued
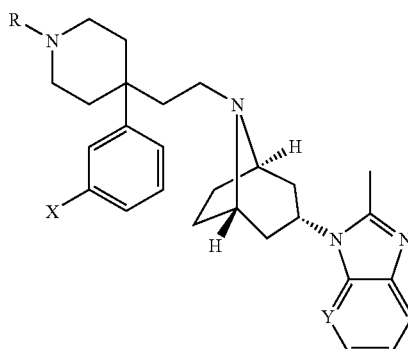
| Example # | Acid # (for non-commercial compounds) | R | X | Y | % yield | LCMS result | Ion | Acylation/coupling Method |
|---|---|---|---|---|---|---|---|---|
| 57 | | 3-(trifluoromethyl)phenylsulfonyl-NH-CH(CH₃)-C(=O)- | H | C | 49 | 708 | (M + H) | A |
| 58 | | 2-hydroxypyridin-3-yl-C(=O)-C(CH₃)₂- | H | C | 49 | 550 | (M + H) | A |
| 59 | | 2-chloro-5-sulfamoylpyridin-3-yl-C(=O)-C(CH₃)₂- | H | C | | 647 | (M + H) | A |
| 60 | | 6-chloropyridin-3-yl-C(=O)-C(CH₃)₂- | H | C | 66 | 568 | (M + H) | A |
| 61 | | 2-methylphenyl-CH₂-C(=O)-C(CH₃)₂- | H | C | 25 | 561 | (M + H) | A |
| 62 | | benzo[1,3]dioxol-5-yl-C(=O)-C(CH₃)₂- | H | C | 33 | 577 | (M + H) | A |

-continued
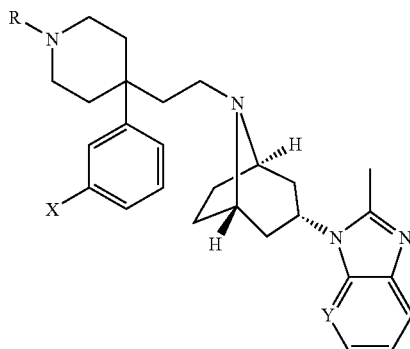
| Example # | Acid # (for non-commercial compounds) | R | X | Y | % yield | LCMS result | Ion | Acylation/ coupling Method |
|---|---|---|---|---|---|---|---|---|
| 63 | | phenyl-CHF-C(O)-C(CH3)2- | H | C | 69 | 565 | (M + H) | A |
| 64 | | 2-amino-pyridin-3-yl-C(O)-C(CH3)2- | H | C | 60 | 549 | (M + H) | A |
| 65 | | 3,4-difluorophenyl-C(O)-C(CH3)2- | H | C | 69 | 569 | (M + H) | A |
| 66 | | 4-oxo-4H-chromen-2-yl-C(O)-C(CH3)2- | H | C | 46 | 601 | (M + H) | A |
| 67 | | 3-(trifluoromethyl)phenyl-C(O)-C(CH3)2- | H | C | 65 | 601 | (M + H) | A |
| 68 | | 4-tert-butylphenyl-C(O)-C(CH3)2- | H | C | 34 | 561 | (M + H) | A |

-continued
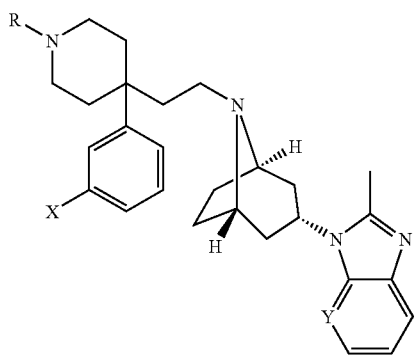
| Example # | Acid # (for non-commercial compounds) | R | X | Y | % yield | LCMS result | Ion | Acylation/coupling Method |
|---|---|---|---|---|---|---|---|---|
| 69 | | 3,5-dimethylphenyl-C(=O)-C(CH3)2- | H | C | 46 | 561 | (M + H) | A |
| 70 | | 3-chlorobenzyl-C(=O)-C(CH3)2- | H | C | 10 | 581 | (M + H) | A |
| 71 | | 4-methylphenyl-CH2CH2-C(=O)-C(CH3)2- | H | C | 61 | 575 | (M + H) | A |
| 72 | | 3,4-dichlorophenyl-C(=O)-C(CH3)2- | H | C | 60 | 601 | (M + H) | A |
| 73 | | 3-chlorophenyl-C(=O)-C(CH3)2- | H | C | 59 | 567 | (M + H) | A |
| 74 | | 2,4,6-trimethylphenyl-C(=O)-C(CH3)2- | H | C | 56 | 575 | (M + H) | A |

-continued
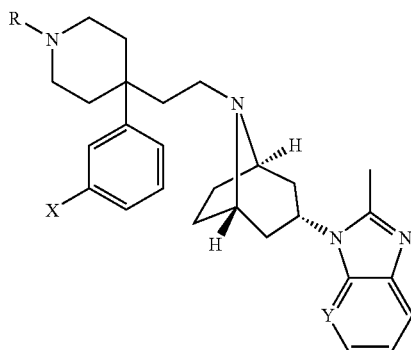
| Example # | Acid # (for non-commercial compounds) | R | X | Y | % yield | LCMS result | Ion | Acylation/coupling Method |
|---|---|---|---|---|---|---|---|---|
| 75 | | 4-tert-butylbenzoyl | H | C | 100 | 589 | (M + H) | A |
| 76 | | 2-naphthoyl | H | C | 97 | 583 | (M + H) | A |
| 77 | | 4-chlorobenzoyl | H | C | 77 | 567 | (M + H) | A |
| 78 | | 2-methylpentanoyl | H | C | 59 | 499 | (M + H) | A |
| 79 | | 3-fluorobenzoyl | H | C | 67 | 551 | (M + H) | A |
| 80 | | ureido-alanyl | H | C | 60 | 543 | (M + H) | A |
| 81 | | N-acetyl-threonyl | H | C | 66 | 572 | (M + H) | A |

-continued
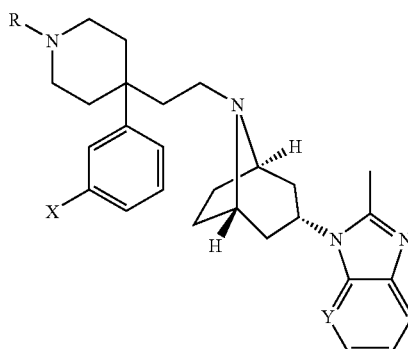
| Example # | Acid # (for non-commercial compounds) | R | X | Y | % yield | LCMS result | Ion | Acylation/ coupling Method |
|---|---|---|---|---|---|---|---|---|
| 82 | | 1,1,1-trifluoro-pentan-4-one group | H | C | 54 | 553 | (M + H) | A |
| 83 | | indol-3-yl-acetone group | H | C | 66 | 586 | (M + H) | A |
| 84 | | 2-chloropyridin-3-yl ketone group | H | C | 48 | 568 | (M + H) | A |
| 85 | | 3-nitrophenyl ketone group | H | C | 79 | 578 | (M + H) | A |
| 86 | | 5,5-dimethyl-dihydrofuran-2-one ketone group | H | C | 46 | 569 | (M + H) | A |
| 87 | | uracil-6-yl ketone group | H | C | 87 | 567 | (M + H) | A |

-continued

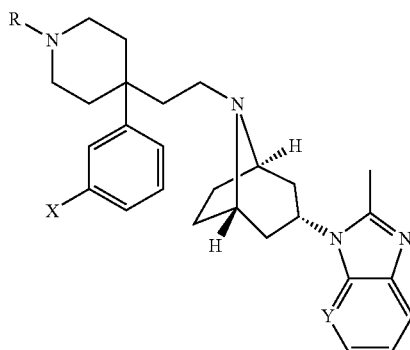

| Example # | Acid # (for non-commercial compounds) | R | X | Y | % yield | LCMS result | Ion | Acylation/coupling Method |
|---|---|---|---|---|---|---|---|---|
| 88 | | 2-nitrobenzoyl (with gem-dimethyl) | H | C | 73 | 578 | (M + H) | A |
| 89 | | phenylacetyl (with gem-dimethyl) | H | C | 49 | 547 | (M + H) | A |
| 90 | | 1-naphthoyl (with gem-dimethyl) | H | C | 100 | 583 | (M + H) | A |
| 91 | | 2,3-dichlorobenzoyl (with gem-dimethyl) | H | C | 69 | 601 | (M + H) | A |
| 92 | | 2-phenoxypropanoyl (with gem-dimethyl) | H | C | 69 | 577 | (M + H) | A |
| 93 | | 4-oxo-4H-chromen-3-ylcarbonyl (with gem-dimethyl) | H | C | 19 | 601 | (M + H) | A |
| 94 | | 2,3-dihydrobenzo[1,4]dioxin-2-ylcarbonyl (with gem-dimethyl) | H | C | 72 | 591 | (M + H) | A |

-continued
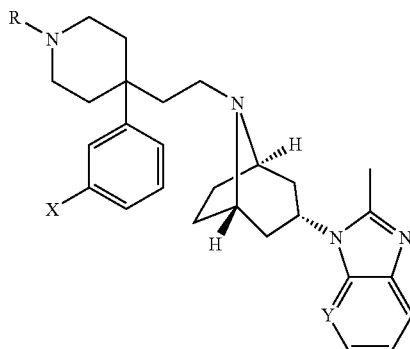
| Example # | Acid # (for non-commercial compounds) | R | X | Y | % yield | LCMS result | Ion | Acylation/coupling Method |
|---|---|---|---|---|---|---|---|---|
| 95 | | pyridin-2-yl CH=CH-C(O)- | H | C | 73 | 560 | (M + H) | A |
| 96 | | pyridin-3-yl-CH2-C(O)- | H | C | 77 | 547 | (M + H) | A |
| 97 | | 4-ethoxyphenyl-C(O)- | H | C | 81 | 577 | (M + H) | A |
| 98 | | pyridin-3-yl-CH2-C(O)- | H | C | 44 | 548 | (M + H) | A |
| 99 | | 2-ethoxyphenyl-C(O)- | H | C | 64 | 577 | (M + H) | A |
| 100 | | 2,4-dimethylphenyl-C(O)- | H | C | 54 | 561 | (M + H) | A |
| 101 | | 2,6-dichlorophenyl-C(O)- | H | C | 57 | 601 | (M + H) | A |

-continued

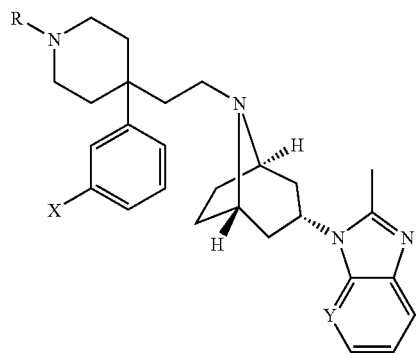

| Example # | Acid # (for non-commercial compounds) | R | X | Y | % yield | LCMS result | Ion | Acylation/coupling Method |
|---|---|---|---|---|---|---|---|---|
| 102 | | 3,4-dimethylbenzoyl | H | C | 50 | 561 | (M + H) | A |
| 103 | | quinoxaline-2-carbonyl | H | C | 84 | 585 | (M + H) | A |
| 104 | | 4-(trifluoromethyl)pyridine-3-carbonyl | H | C | 71 | 602 | (M + H) | A |
| 105 | | 2,2-dimethylpent-4-enoyl | H | C | 64 | 539 | (M + H) | A |
| 108 | | 2,2-dimethyl-3-(2-methylprop-1-enyl)cyclopropanecarbonyl | H | C | 63 | 579 | (M + H) | A |
| 107 | | 4-(trifluoromethyl)pyridine-3-carbonyl | H | C | 50 | 602 | (M + H) | A |
| 106 | | 1-carbamoylcyclopropanecarbonyl | H | C | 16 | 540 | (M + H) | A |

-continued
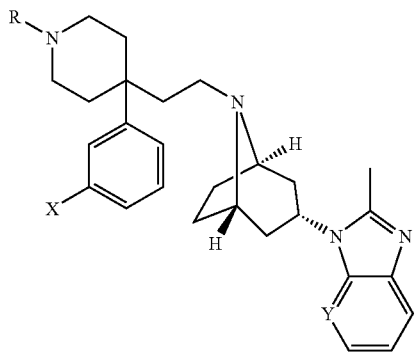
| Example # | Acid # (for non-commercial compounds) | R | X | Y | % yield | LCMS result | Ion | Acylation/coupling Method |
|---|---|---|---|---|---|---|---|---|
| 108 | | (2-methylcyclopropyl ketone) | H | C | 38 | 511 | (M + H) | A |
| 110 | | (1-methyl-3-tert-butylpyrazole-5-carbonyl) | H | C | 50 | 593 | (M + H) | A |
| 111 | | (1-phenylcyclopentanecarbonyl) | H | C | 78 | 601 | (M + H) | A |
| 112 | | (6-hydroxypyridine-3-carbonyl) | H | C | 65 | 550 | (M + H) | A |
| 113 | | (2,4-dichlorobenzoyl) | H | C | 67 | 601 | (M + H) | A |
| 114 | | (6-methylpyridine-3-carbonyl) | H | C | 60 | 548 | (M + H) | A |
| 115 | | (furan-2-carboxamidoacetyl) | H | C | 12 | 580 | (M + H) | A |

-continued
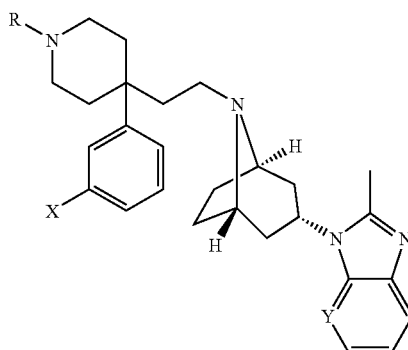
| Example # | Acid # (for non-commercial compounds) | R | X | Y | % yield | LCMS result | Ion | Acylation/coupling Method |
|---|---|---|---|---|---|---|---|---|
| 116 | | dimethylaminoacetyl | H | C | 67 | 514 | (M + H) | A |
| 117 | | 4-vinylbenzoyl | H | C | 48 | 559 | (M + H) | A |
| 118 | | 1-methylindole-3-carbonyl | H | C | 56 | 586 | (M + H) | A |
| 119 | | 4-fluoromandeloyl | H | C | 58 | 581 | (M + H) | A |
| 120 | | 3,5-dimethoxyphenylacetyl | H | C | 59 | 607 | (M + H) | A |
| 121 | | 2,5-dimethylbenzoyl | H | C | 68 | 561 | (M + H) | A |

-continued
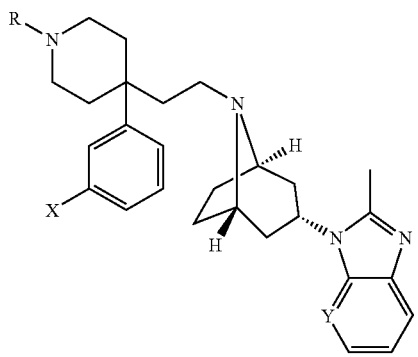
| Example # | Acid # (for non-commercial compounds) R | X | Y | % yield | LCMS result | Ion | Acylation/coupling Method |
|---|---|---|---|---|---|---|---|
| 122 | phenyl-C(O)-CH2CH2-C(O)-C(CH3)- | H | C | 15 | 589 | (M + H) | A |
| 123 | 4-methoxyphenyl-cyclopropyl-C(O)-C(CH3)- | H | C | 52 | 603 | (M + H) | A |
| 124 | 3-fluoro-4-methoxyphenyl-C(O)-C(CH3)2- | H | C | 17 | 561 | (M + H) | A |
| 125 | 4-propoxyphenyl-C(O)-C(CH3)2- | H | C | 61 | 591 | (M + H) | A |
| 126 | 2,3-difluorophenyl-C(O)-C(CH3)2- | H | C | 58 | 569 | (M + H) | A |
| 127 | 2,4-difluorophenyl-C(O)-C(CH3)2- | H | C | 52 | 569 | (M + H) | A |

-continued
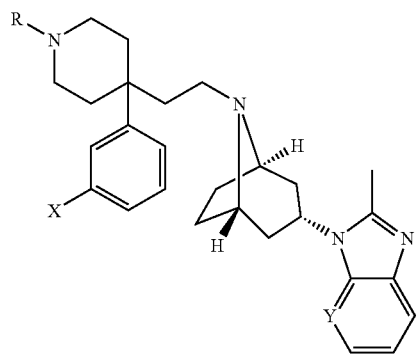
| Example # | Acid # (for non-commercial compounds) | R | X | Y | % yield | LCMS result | Ion | Acylation/coupling Method |
|---|---|---|---|---|---|---|---|---|
| 128 | | biphenyl-2-yl ketone | H | C | 59 | 609 | (M + H) | A |
| 129 | | (2-oxocyclopentyl)methyl ketone | H | C | 59 | 553 | (M + H) | A |
| 130 | | 1-phenylcyclopropyl ketone | H | C | 58 | 573 | (M + H) | A |
| 131 | | 4-(1H-imidazol-1-yl)phenyl ketone | H | C | 69 | 599 | (M + H) | A |
| 132 | | 3,5-dichlorophenyl ketone | H | C | 48 | 601 | (M + H) | A |
| 133 | | 4-isopropylphenyl ketone | H | C | 58 | 575 | (M + H) | A |

-continued
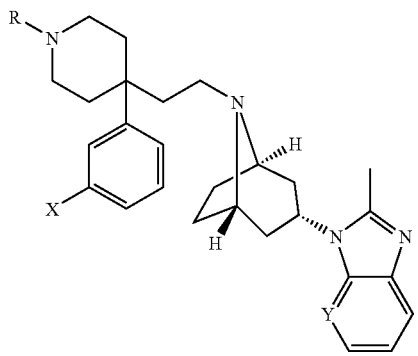
| Example # | Acid # (for non-commercial compounds) | R | X | Y | % yield | LCMS result | Ion | Acylation/coupling Method |
|---|---|---|---|---|---|---|---|---|
| 134 | | 2-methoxypyridin-3-yl carbonyl | H | C | 53 | 564 | (M + H) | A |
| 135 | | 2,4,6-trimethylphenylacetyl | H | C | 31 | 589 | (M + H) | A |
| 136 | | 2-propoxyphenyl carbonyl | H | C | 47 | 591 | (M + H) | A |
| 137 | | 3,5-difluorophenyl(hydroxy)acetyl | H | C | 60 | 599 | (M + H) | A |
| 138 | | 2-methoxyphenylpropanoyl | H | C | 49 | 591 | (M + H) | A |
| 139 | | cyclopentylacetyl | H | C | 36 | 539 | (M + H) | A |

-continued
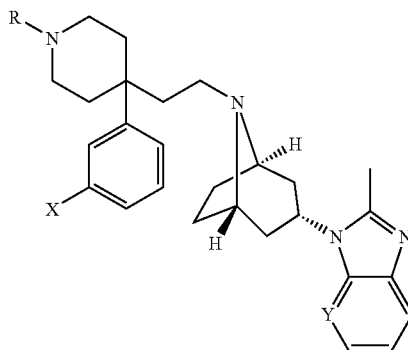
| Example # | Acid # (for non-commercial compounds) | R | X | Y | % yield | LCMS result | Ion | Acylation/coupling Method |
|---|---|---|---|---|---|---|---|---|
| 140 | | 1-acetylpiperidine-4-carbonyl | H | C | 53 | 582 | (M + H) | A |
| 141 | | 4-oxo-1H-quinoline-2-carbonyl | H | C | 48 | 600 | (M + H) | A |
| 142 | | 3-(benzo[d][1,3]dioxol-5-yl)propanoyl | H | C | 47 | 605 | (M + H) | A |
| 143 | | 5-(2,2-dimethylhydrazinyl)-5-oxopentanoyl | H | C | 48 | 571 | (M + H) | A |
| 144 | | 4-methyl-1,2,3-thiadiazole-5-carbonyl | H | C | 11 | 555 | (M + H) | A |
| 145 | | propanoyl | H | C | 27 | 485 | (M + H) | A |

-continued

| Example # | Acid # (for non-commercial compounds) | R | X | Y | % yield | LCMS result | Ion | Acylation/ coupling Method |
|---|---|---|---|---|---|---|---|---|
| 146 | | 2-F, 6-Cl phenyl ketone | H | C | 31 | 585 | (M + H) | A |
| 147 | | quinoline-2-yl ketone | H | C | 47 | 584 | (M + H) | A |
| 148 | | allyl ketone (pent-4-en-2-one type) | H | C | 41 | 497 | (M + H) | A |
| 149 | | 3-hydroxypyridin-2-yl ketone | H | C | 18 | 550 | (M + H) | A |
| 150 | | 4,6-dimethyl-2-oxo-2H-pyran-5-yl ketone | H | C | 94 | 579 | (M + H) | A |
| 151 | | ureido ethyl ketone | H | C | 89 | 557 | (M + H) | A |
| 152 | | nicotinamido methyl ketone | H | C | 81 | 591 | (M + H) | A |

-continued

| Example # | Acid # (for non-commercial compounds) R | X | Y | % yield | LCMS result | Ion | Acylation/coupling Method |
|---|---|---|---|---|---|---|---|
| 153 | 3,4,5-trifluorobenzoyl | H | C | 44 | 587 | (M + H) | A |
| 154 | 3,5-difluorophenylacetyl | H | C | 71 | 583 | (M + H) | A |
| 155 | 3,4-methylenedioxyphenylacetyl | H | C | 61 | 591 | (M + H) | A |
| 156 | indole-3-carbonyl | H | C | 29 | 572 | (M + H) | A |
| 157 | 2-fluoro-5-methylbenzoyl | H | C | 64 | 565 | (M + H) | A |
| 158 | coumarin-3-carbonyl | H | C | 73 | 601 | (M + H) | A |

-continued
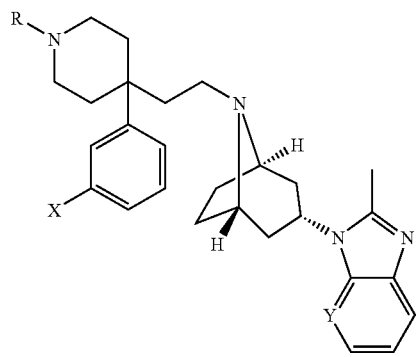
| Example # | Acid # (for non-commercial compounds) | R | X | Y | % yield | LCMS result | Ion | Acylation/coupling Method |
|---|---|---|---|---|---|---|---|---|
| 159 | | isobutyl-C(=O)-C(CH3)2- | H | C | 43 | 513 | (M+H) | A |
| 160 | | (indol-4-yl)-C(=O)-C(CH3)2- | H | C | 64 | 572 | (M+H) | A |
| 161 | | (4-methoxyphenyl)-CH(OH)-C(=O)-C(CH3)2- | H | C | 61 | 593 | (M+H) | A |
| 162 | | (3-ethoxythiophen-2-yl)-C(=O)-C(CH3)2- | H | C | 54 | 583 | (M+H) | A |
| 163 | | (1-methylcyclopropyl)-C(=O)-C(CH3)2- | H | C | 75 | 511 | (M+H) | A |
| 164 | | (3-methoxyphenyl)-CH2CH2-C(=O)-C(CH3)2- | H | C | 66 | 591 | (M+H) | A |
| 165 | | (4-isopropoxyphenyl)-C(=O)-C(CH3)2- | H | C | 61 | 591 | (M+H) | A |

-continued
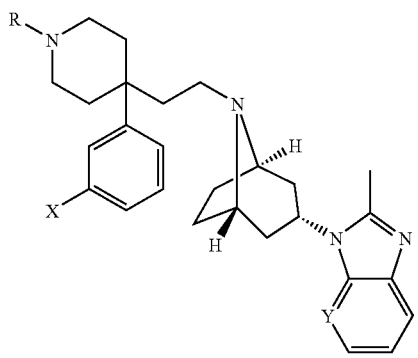
| Example # | Acid # (for non-commercial compounds) R | X | Y | % yield | LCMS result | Ion | Acylation/coupling Method |
|---|---|---|---|---|---|---|---|
| 166 | 1-hydroxy-1-phenyl-2,2-dimethyl-3-oxo (OH, phenyl, dimethyl, C=O) | H | C | 47 | 605 | (M + H) | A |
| 167 | 2,5-difluorobenzoyl | H | C | 60 | 569 | (M + H) | A |
| 168 | 6-amino-pyridin-3-yl carbonyl | H | C | 44 | 549 | (M + H) | A |
| 169 | 2,6-dimethoxy-pyridin-3-yl carbonyl | H | C | 62 | 594 | (M + H) | A |
| 170 | 3-cyclopentyl-propanoyl (dimethyl) | H | C | 37 | 553 | (M + H) | A |
| 171 | 4-(4-methoxyphenyl)-2,2-dimethyl-butanoyl | H | C | 55 | 591 | (M + H) | A |

-continued
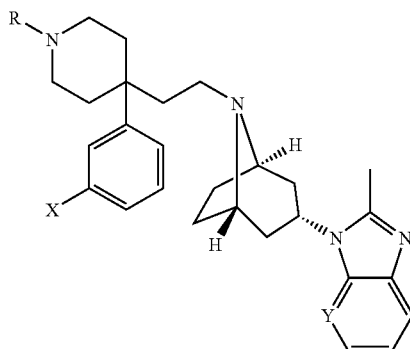
| Example # | Acid # (for non-commercial compounds) | R | X | Y | % yield | LCMS result | Ion | Acylation/ coupling Method |
|---|---|---|---|---|---|---|---|---|
| 172 | | 4-nitrobenzoyl isobutyryl | H | C | 8 | 578 | (M + H) | A |
| 173 | | 4-ethylbenzoyl isobutyryl | H | C | 56 | 561 | (M + H) | A |
| 174 | | 3,5-difluorobenzoyl isobutyryl | H | C | 12 | 569 | (M + H) | A |
| 175 | | 4-chloro-2-methoxybenzoyl isobutyryl | H | C | 62 | 597 | (M + H) | A |
| 176 | | 3-methylbenzoyl isobutyryl | H | C | 48 | 547 | (M + H) | A |
| 177 | | 4-propylbenzoyl isobutyryl | H | C | 53 | 575 | (M + H) | A |

-continued


| Example # | Acid # (for non-commercial compounds) | R | X | Y | % yield | LCMS result | Ion | Acylation/coupling Method |
|---|---|---|---|---|---|---|---|---|
| 178 | | benzyl methyl ketone group | H | C | 57 | 575 | (M + H) | A |
| 179 | | cinnamyl ketone group | H | C | 36 | 573 | (M + H) | A |
| 180 | | N-acetyl alanyl group | H | C | 58 | 542 | (M + H) | A |
| 181 | | 1-(4-chlorophenyl)cyclopropyl ketone group | H | C | 15 | 607 | (M + H) | A |
| 182 | | succinimidyl methyl ketone group | H | C | 43 | 568 | (M + H) | A |
| 183 | | 4-(trifluoromethyl)phenyl ketone group | H | C | 49 | 601 | (M + H) | A |
| 184 | | 2,4-difluorophenyl hydroxymethyl ketone group | H | C | 40 | 599 | (M + H) | A |

-continued

| Example # | Acid # (for non-commercial compounds) | R | X | Y | % yield | LCMS result | Ion | Acylation/coupling Method |
|---|---|---|---|---|---|---|---|---|
| 185 | | (imidazolidinone-carbonyl) | H | C | 47 | 541 | (M + H) | A |
| 186 | | 2-fluorobenzoyl | H | C | 43 | 551 | (M + H) | A |
| 187 | | N-methyl-N-benzoyl-glycyl | H | C | 51 | 604 | (M + H) | A |
| 188 | | (3-methylphenyl)acetyl | H | C | 17 | 561 | (M + H) | A |
| 189 | | (1H-tetrazol-5-yl)-dimethyl-acetyl | H | C | 90 | 565.31 | (M − H) | A |
| 190 | | 4-(benzylamino)-2-chloro-5-sulfamoyl-benzoyl | H | C | 20 | 751.18 | (M + H) | A |
| 191 | | 3-acetamidobenzoyl | H | C | 29 | 590.14 | (M + H) | A |

-continued
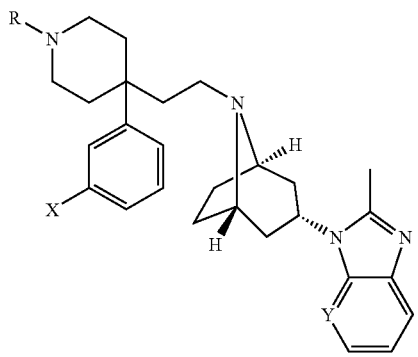
| Example # | Acid # (for non-commercial compounds) R | X | Y | % yield | LCMS result | Ion | Acylation/coupling Method |
|---|---|---|---|---|---|---|---|
| 192 | 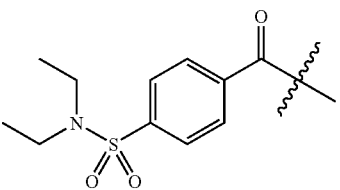 | H | C | 7 | 668.16 | (M + H) | A |
| 193 | 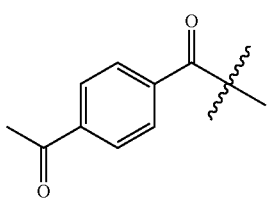 | H | C | 71 | 575.17 | (M + H) | A |
| 194 | 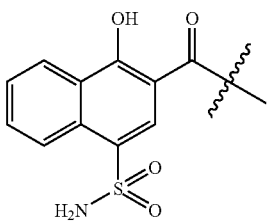 | H | C | 25 | 677.78 | (M + H) | A |
| 195 | 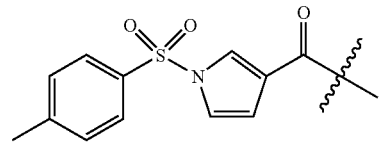 | H | C | 53 | 675.81 | (M + H) | A |
| 196 | 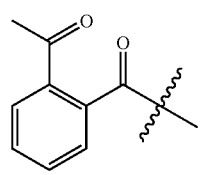 | H | C | 59 | 574.92 | (M + H) | A |

-continued
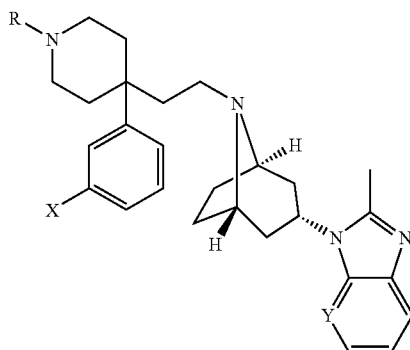
| Example # | Acid # (for non-commercial compounds) | R | X | Y | % yield | LCMS result | Ion | Acylation/coupling Method |
|---|---|---|---|---|---|---|---|---|
| 197 | | 4-(methylsulfonyl)benzoyl | H | C | 74 | 610.85 | (M + H) | A |
| 198 | | 4-chloro-3-hydroxybenzoyl | H | C | 44 | 582.92 | (M + H) | A |
| 199 | | 2-acetamidobenzoyl | H | C | 9 | 590.15 | (M + H) | A |
| 200 | | 4-acetamidobenzoyl | H | C | 84 | 589.97 | (M + H) | A |
| 201 | | 4-carbamoyl-2,6-dimethylbenzoyl | H | C | 31 | 604.03 | (M + H) | A |
| 202 | | phenylglyoxyloyl | H | C | 11 | 561.19 | (M + H) | A |

-continued

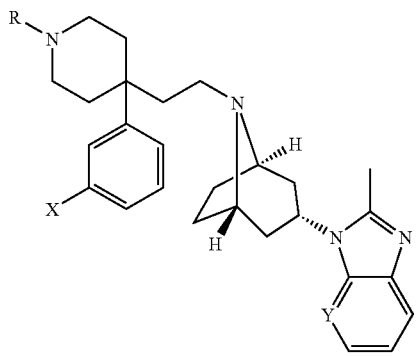

| Example # | Acid # (for non-commercial compounds) R | X | Y | % yield | LCMS result | Ion | Acylation/coupling Method |
|---|---|---|---|---|---|---|---|
| 203 | 4-sulfo-benzoyl | H | C | 11 | 613.09 | (M + H) | A |
| 204 | 5-methyl-4-(morpholinosulfonyl)furan-2-yl carbonyl | H | C | 21 | 685.72 | (M + H) | A |
| 205 | 5-methyl-4-(N,N-dimethylsulfamoyl)furan-2-yl carbonyl | H | C | 25 | 643.83 | (M + H) | A |
| 206 | 2,5-dimethyl-4-(N-(thiophen-2-ylmethyl)sulfamoyl)furan-3-yl carbonyl | H | C | 18 | 725.84 | (M + H) | A |
| 207 | 4-(hydroxymethyl)benzoyl | H | C | 26 | 562.89 | (M + H) | A |
| 208 | 2-methyl-4-(tosylamino)thiophen-3-yl carbonyl | H | C | 23 | 721.94 | (M + H) | A |

-continued

| Example # | Acid # (for non-commercial compounds) | R | X | Y | % yield | LCMS result | Ion | Acylation/coupling Method |
|---|---|---|---|---|---|---|---|---|
| 209 | | H₂N-SO₂-C₆H₄-C(O)-C(CH₃)₂- (3-sulfamoyl) | H | C | 16 | 612.04 | (M+H) | A |
| 210 | | MeNH-SO₂-C₆H₄-C(O)-C(CH₃)₂- (3-) | H | C | 13 | 626.03 | (M+H) | A |
| 211 | | Me₂N-SO₂-C₆H₄-C(O)-C(CH₃)₂- (3-) | H | C | 50 | 639.75 | (M+H) | A |
| 212 | | MeNH-SO₂-C₆H₄-C(O)-C(CH₃)₂- (4-) | H | C | 40 | 625.76 | (M+H) | A |
| 213 | | Me₂N-SO₂-C₆H₄-C(O)-C(CH₃)₂- (4-) | H | C | 39 | 639.75 | (M+H) | A |
| 214 | | H₂N-SO₂-(4-Me-C₆H₃)-C(O)-C(CH₃)₂- | H | C | 44 | 625.79 | (M+H) | A |
| 215 | | MeSO₂-C₆H₄-C(O)-C(CH₃)₂- (3-) | H | C | 42 | 610.79 | (M+H) | A |

-continued

| Example # | Acid # (for non-commercial compounds) | R | X | Y | % yield | LCMS result | Ion | Acylation/coupling Method |
|---|---|---|---|---|---|---|---|---|
| 216 | | 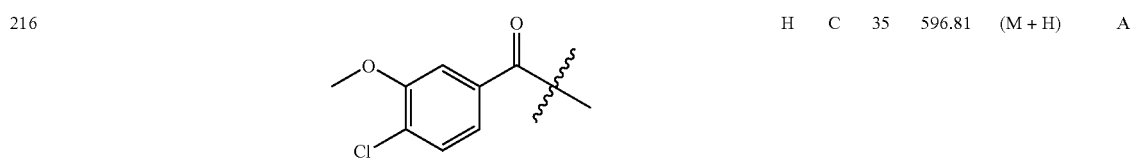 | H | C | 35 | 596.81 | (M + H) | A |
| 217 | | 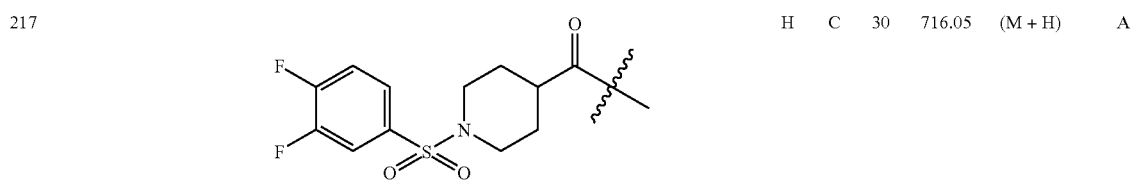 | H | C | 30 | 716.05 | (M + H) | A |
| 218 | | 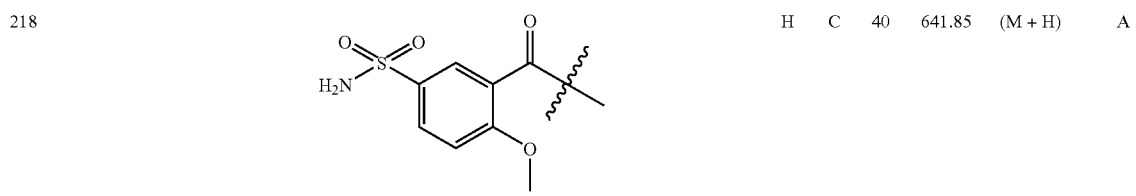 | H | C | 40 | 641.85 | (M + H) | A |
| 219 | | 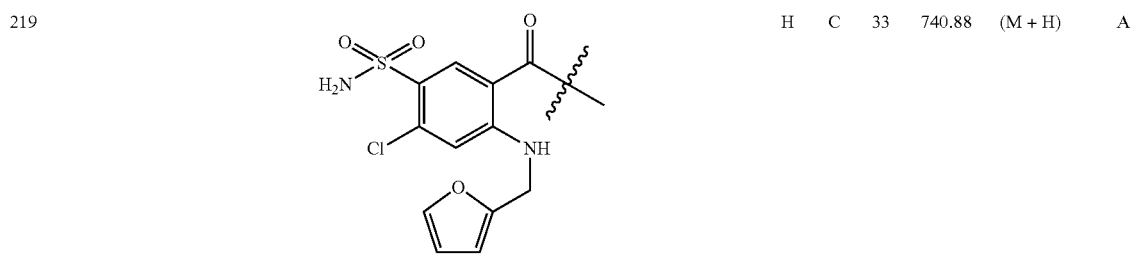 | H | C | 33 | 740.88 | (M + H) | A |
| 220 | | 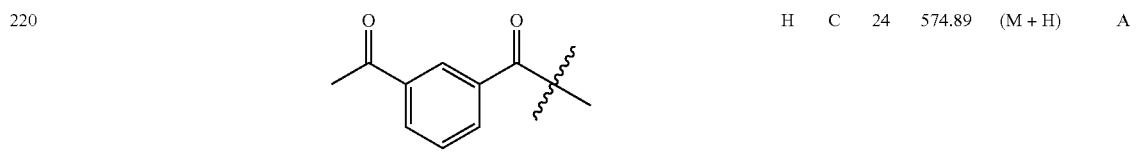 | H | C | 24 | 574.89 | (M + H) | A |
| 221 | | 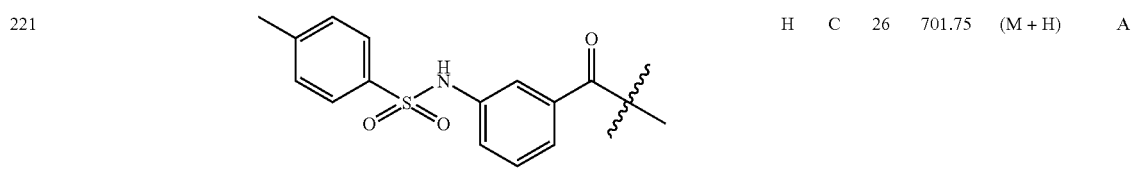 | H | C | 26 | 701.75 | (M + H) | A |

-continued
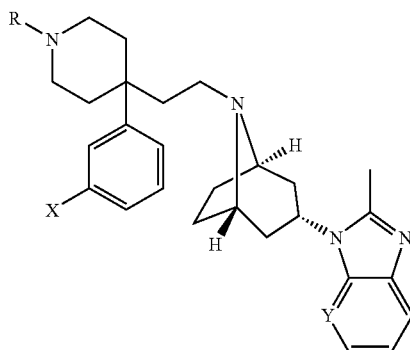
| Example # | Acid # (for non-commercial compounds) R | X | Y | % yield | LCMS result | Ion | Acylation/ coupling Method |
|---|---|---|---|---|---|---|---|
| 222 | 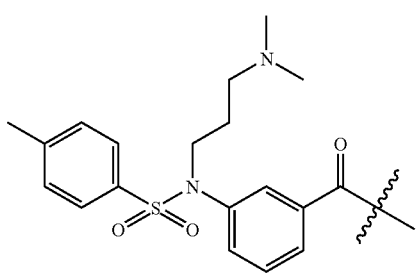 | H | C | 32 | 787.25 | (M + H) | A |
| 223 | 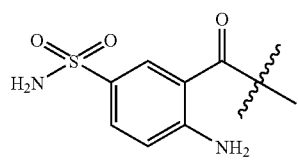 | H | C | 26 | 627.08 | (M + H) | A |
| 224 | 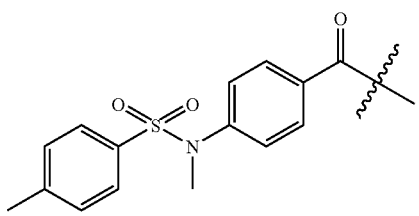 | H | C | 26 | 716.13 | (M + H) | A |
| 225 | 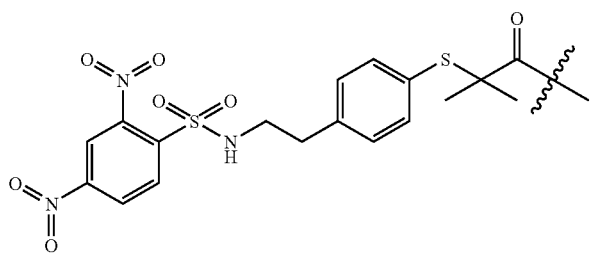 | H | C | 16 | 880.29 | (M + H) | A |
| 226 | 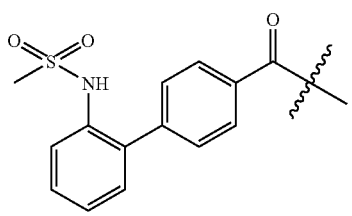 | H | C | 24 | 702.17 | (M + H) | A |

-continued
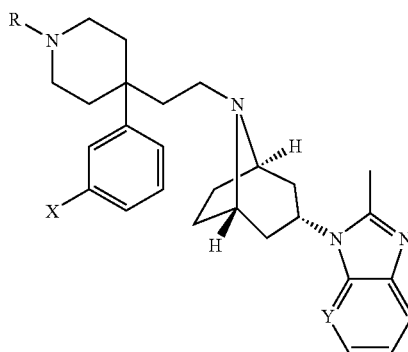
| Example # | Acid # (for non-commercial compounds) R | X | Y | % yield | LCMS result | Ion | Acylation/ coupling Method |
|---|---|---|---|---|---|---|---|
| 227 | benzylamino, Cl, sulfamoyl substituted benzoyl | H | C | 20 | 751.18 | (M + H) | A |
| 228 | 4-nitrophenylsulfonyl-NH-CH2CH2-C(O)- | H | C | 4 | 685.14 | (M + H) | A |
| 229 | 4-nitrophenylsulfonyl-NH-(CH2)3-C(O)- | H | C | 17 | 699.16 | (M + H) | A |
| 230 | 4-sulfamoylphenyl-CH2CH2-C(O)- | H | C | 27 | 640.17 | (M + H) | A |
| 231 | 4-(methylsulfonylamino)phenyl-CH2-C(O)- | H | C | 20 | 640.17 | (M + H) | A |

-continued
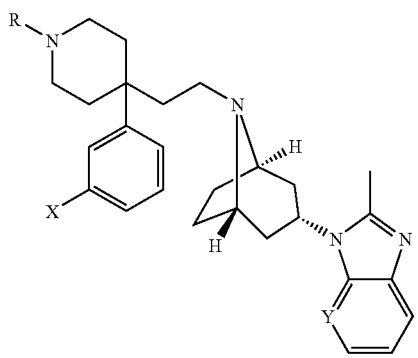
| Example # | Acid # (for non-commercial compounds) | R | X | Y | % yield | LCMS result | Ion | Acylation/ coupling Method |
|---|---|---|---|---|---|---|---|---|
| 232 | | 4-nitrophenyl-SO2-NH-(CH2)4-C(=O)- | H | C | 16 | 713.17 | (M + H) | A |
| 233 | | 4-methylphenyl-SO2-NH-CH(CH3)-C(=O)- | H | C | 64 | 654.17 | (M + H) | A |
| 234 | | 4-H2NSO2-phenyl-O-CH2-C(=O)- | H | C | 44 | 642.12 | (M + H) | A |
| 235 | Acid 3 | 2-Cl-5-(CH3NHSO2)-phenyl-C(=O)- | H | C | 47 | 660.01 | (M + H) | A |
| 236 | Acid 4 | 2-Cl-5-(iPrNHSO2)-phenyl-C(=O)- | H | C | 64 | 688.05 | (M + H) | A |

-continued
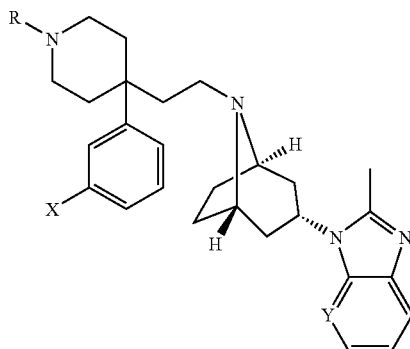
| Example # | Acid # (for non-commercial compounds) | R | X | Y | % yield | LCMS result | Ion | Acylation/ coupling Method |
|---|---|---|---|---|---|---|---|---|
| 237 | Acid 5 | 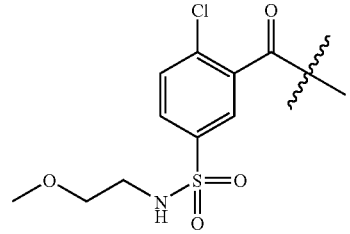 | H | C | 66 | 704.06 | (M + H) | A |
| 238 | Acid 6 | 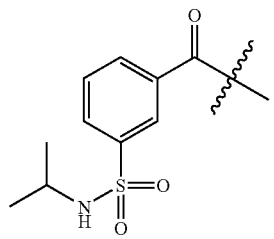 | H | C | 22 | 654.16 | (M + H) | A |
| 239 | Acid 7 | 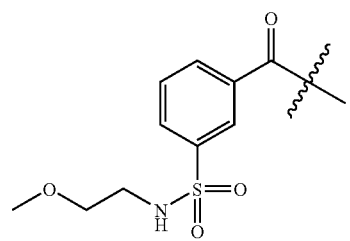 | H | C | 20 | 670.17 | (M + H) | A |
| 240 | Acid 8 | 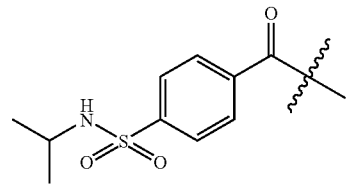 | H | C | 19 | 654.16 | (M + H) | A |
| 241 | Acid 9 | 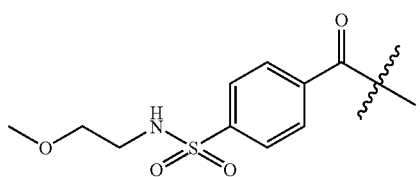 | H | C | 14 | 670.19 | (M + H) | A |

-continued
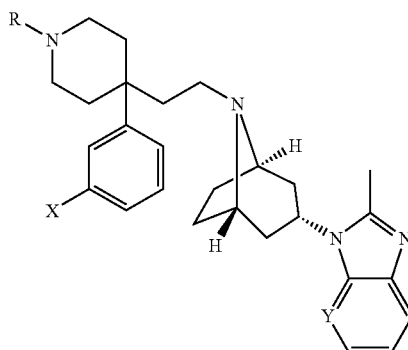
| Example # | Acid # (for non-commercial compounds) | R | X | Y | % yield | LCMS result | Ion | Acylation/coupling Method |
|---|---|---|---|---|---|---|---|---|
| 242 | Acid 10 | (4-(HOCH₂CH₂NHSO₂)phenyl-C(O)-) | H | C | 15 | 658.12 | (M + H) | A |
| 243 | Acid 11 | (4-methoxy-3-C(O)-, 5-MeNHSO₂-phenyl) | H | C | 19 | 656.12 | (M + H) | A |
| 244 | Acid 12 | (3-MeNHSO₂-4-Cl-phenyl-C(O)-) | H | C | 53 | 659.84 | (M + H) | A |
| 245 | Acid 13 | (3-(MeOCH₂CH₂NHSO₂)-4-Cl-phenyl-C(O)-) | H | C | 30 | 703.96 | (M + H) | A |
| 246 | Acid 14 | (3-(N,N-bis(MeOCH₂CH₂)NSO₂)-4-Cl-phenyl-C(O)-) | H | C | 35 | 762.11 | (M + H) | A |
| 247 |  | (CF₃)₂C(OH)C(O)- | H | C | 8 | 623.02 | (M + H) | A |

-continued


| Example # | Acid # (for non-commercial compounds) | R | X | Y | % yield | LCMS result | Ion | Acylation/coupling Method |
|---|---|---|---|---|---|---|---|---|
| 248 | Acid 15 | (dimethylsulfamoyl-chloro-phenyl ketone) | H | C | 44 | 673.86 | (M + H) | A |
| 249 | Acid 16 | (sulfamoyl-chloro-phenyl ketone) | H | C | 46 | 646.02 | (M + H) | A |
| 250 | Acid 2 | (Boc-amino-hydroxy-dimethyl ketone) | H | C | 36 | 644.14 | (M + H) | A |
| 251 |  | (acetyl-hydroxypyrrolidine ketone) | H | C | 72 | 584.13 | (M + H) | A |
| 252 |  | (hydroxy-dimethyl ketone) | H | C | 60 | 529.14 | (M + H) | A |
| 253 |  | (hydroxy-phenyl ketone) | H | C | 65 | 577.15 | (M + H) | A |
| 254 |  | (trifluoro-hydroxy-methyl ketone) | H | C | 51 | 569.17 | (M + H) | A |

-continued
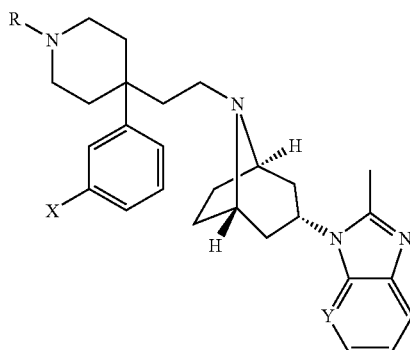
| Example # | Acid # (for non-commercial compounds) | R | X | Y | % yield | LCMS result | Ion | Acylation/coupling Method |
|---|---|---|---|---|---|---|---|---|
| 255 | | 1-hydroxycycloheptyl-C(CH3)- | H | C | 41 | 569.17 | (M+H) | A |
| 256 | | 1-hydroxycyclohexyl-C(CH3)- | H | C | 47 | 555.19 | (M+H) | A |
| 257 | | CH3-CH(OH)-CH2-C(CH3)- | H | C | 72 | 515.16 | (M+H) | A |
| 258 | | 3-hydroxy-3-ethylpentyl-C(CH3)- | H | C | 24 | 543.18 | (M+H) | A |
| 259 | | 4-(2-methanesulfonamidoethoxy)-3-methoxyphenyl-C(CH3)- | H | C | 70 | 700.05 | (M+H) | A |
| 260 | | phenyl-C(OH)(CH3)-C(CH3)- | H | C | 68 | 577.15 | (M+H) | A |
| 261 | | phenyl-CH(OH)-CH2-C(CH3)- | H | C | 63 | 577.15 | (M+H) | A |

-continued
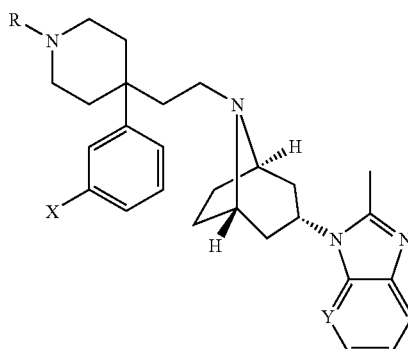
| Example # | Acid # (for non-commercial compounds) | R | X | Y | % yield | LCMS result | Ion | Acylation/ coupling Method |
|---|---|---|---|---|---|---|---|---|
| 262 | | | H | C | 52 | 702.03 | (M + H) | A |
| 263 | | | H | C | 68 | 577.15 | (M + H) | A |
| 264 | | | H | C | 33 | 664.08 | (M + H) | A |
| 265 | | | H | C | 72 | 700.05 | (M + H) | A |
| 266 | | | H | C | 62 | 702.02 | (M + H) | A |
| 267 | Acid 17 | | H | C | 48 | 694.05 | (M + H) | A |

-continued

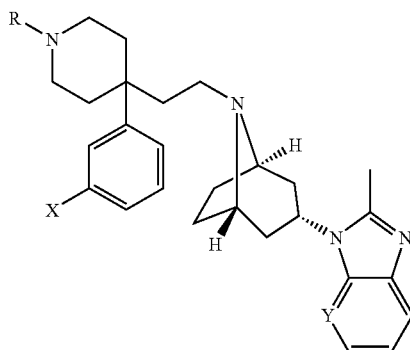

| Example # | Acid # (for non-commercial compounds) | R | X | Y | % yield | LCMS result | Ion | Acylation/coupling Method |
|---|---|---|---|---|---|---|---|---|
| 268 | | (5-trifluoromethyl-pyridin-2-ylsulfonyl dimethyl group) | H | C | 33 | 708.14 | (M + H) | A |
| 269 | | (methylsulfamoylamino propanoyl) | H | C | 54 | 593.15 | (M + H) | A |
| 270 | | (N-acetyl histidinyl) | H | C | 54 | 608.22 | (M + H) | A |
| 271 | | (N,N-dimethyl histidinyl) | H | C | 48 | 594.25 | (M + H) | A |
| 272 | | (3-sulfamoyl-4-chloro-5-nitrobenzoyl dimethyl) | H | C | 8 | 691.08 | (M + H) | A |
| 273 | Acid 18 | (3-ethylsulfamoyl-6-chlorobenzoyl dimethyl) | H | C | 40 | 674.06 | (M + H) | A |

-continued
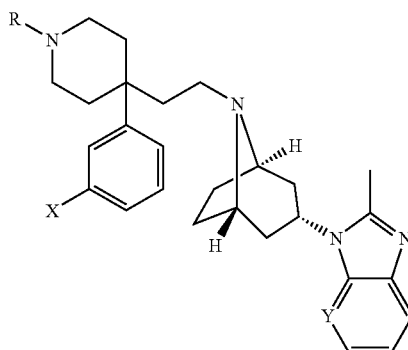
| Example # | Acid # (for non-commercial compounds) | R | X | Y | % yield | LCMS result | Ion | Acylation/coupling Method |
|---|---|---|---|---|---|---|---|---|
| 274 | Acid 19 | propyl-NH-SO2-C6H3(Cl)-C(O)- | H | C | 48 | 688.04 | (M + H) | A |
| 275 | Acid 20 | cyclopropyl-NH-SO2-C6H3(Cl)-C(O)- | H | C | 40 | 686.06 | (M + H) | A |
| 276 | Acid 21 | CF3CH2-NH-SO2-C6H3(F)-C(O)- | H | C | 39 | 711.97 | (M + H) | A |
| 277 | | H2N-SO2-C6H2(Cl)(Cl)-C(O)- | H | C | 41 | 679.93 | (M + H) | A |
| 278 | Acid 22 | H2N-SO2-C6H3(F)-C(O)- | H | C | 62 | 630.01 | (M + H) | A |
| 279 | Acid 23 | MeNH-SO2-C6H3(F)-C(O)- | H | C | 53 | 644.00 | (M + H) | A |
| 280 | Acid 24 | EtNH-SO2-C6H3(F)-C(O)- | H | C | 59 | 658.02 | (M + H) | A |

-continued
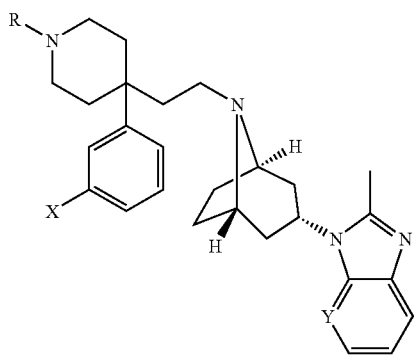
| Example # | Acid # (for non-commercial compounds) | R | X | Y | % yield | LCMS result | Ion | Acylation/ coupling Method |
|---|---|---|---|---|---|---|---|---|
| 281 | Acid 25 | propyl-NH-SO2-(4-F-phenyl)-C(O)- | H | C | 50 | 672.00 | (M + H) | A |
| 282 | Acid 26 | cyclopropyl-NH-SO2-(4-F-phenyl)-C(O)- | H | C | 53 | 670.01 | (M + H) | A |
| 283 | Acid 27 | isopropyl-NH-SO2-(4-F-phenyl)-C(O)- | H | C | 44 | 672.03 | (M + H) | A |
| 284 | Acid 28 | CF3CH2-NH-SO2-(4-F-phenyl)-C(O)- | H | C | 49 | 711.96 | (M + H) | A |
| 285 | Acid 29 | CF3CH2-NH-SO2-(4-Cl-phenyl)-C(O)- | H | C | 46 | 727.95 | (M + H) | A |
| 286 | Acid 30 | CF3CH2-NH-SO2-(4-Cl-phenyl)-C(O)- | H | C | 45 | 727.95 | (M + H) | A |
| 287 |  | HO-SO2-(4-Cl-phenyl)-C(O)- | F | C | 33 | 665.04 | (M + H) | A |

-continued
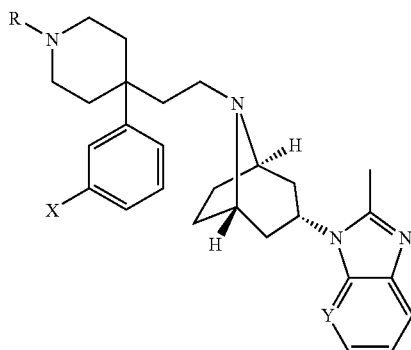
| Example # | Acid # (for non-commercial compounds) | R | X | Y | % yield | LCMS result | Ion | Acylation/coupling Method |
|---|---|---|---|---|---|---|---|---|
| 288 | Acid 3 | 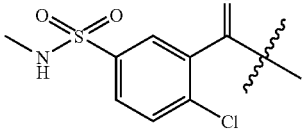 | F | C | 51 | 678.05 | (M + H) | A |
| 289 | Acid 18 | 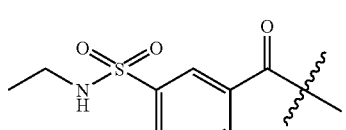 | F | C | 37 | 692.03 | (M + H) | A |
| 290 | Acid 19 | 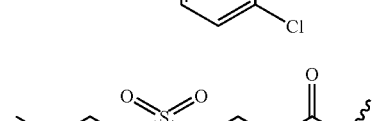 | F | C | 47 | 706.08 | (M + H) | A |
| 291 | Acid 20 | 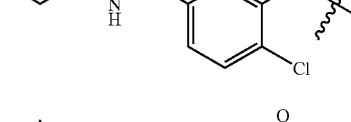 | F | C | 39 | 704.06 | (M + H) | A |
| 292 | Acid 4 | 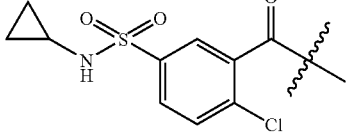 | F | C | 37 | 705.94 | (M + H) | A |
| 293 | Acid 12 | 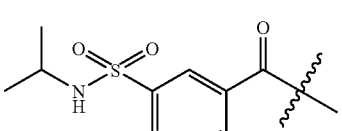 | F | C | 36 | 678.05 | (M + H) | A |
| 294 | | 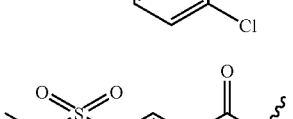 | F | C | 45 | 681.96 | (M + H) | A |

-continued
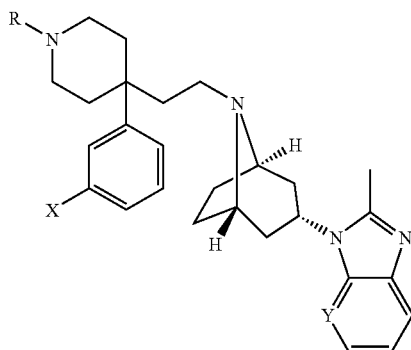
| Example # | Acid # (for non-commercial compounds) | R | X | Y | % yield | LCMS result | Ion | Acylation/ coupling Method |
|---|---|---|---|---|---|---|---|---|
| 295 | Acid 22 | 4-F, 3-(H2N-SO2-) benzoyl (sulfamoyl-fluoro benzoyl) | F | C | 57 | 647.99 | (M + H) | A |
| 296 | | 4-Cl, 3-(H2N-SO2-) benzoyl | F | C | 22 | 663.99 | (M + H) | A |
| 297 | Acid 28 | 4-F, 3-(CF3CH2-NH-SO2-) benzoyl | F | C | 54 | 729.95 | (M + H) | A |
| 298 | Acid 29 | 4-Cl, 3-(CF3CH2-NH-SO2-) benzoyl | F | C | 54 | 745.92 | (M + H) | A |
| 299 | Acid 30 | 4-Cl, 3-(CF3CH2-NH-SO2-) benzoyl (isomer) | F | C | 52 | 745.89 | (M + H) | A |
| 300 | Acid 21 | 4-F, 3-(CF3CH2-NH-SO2-) benzoyl (isomer) | F | C | 51 | 729.98 | (M + H) | A |
| 301 | | 2,4-diCl, 5-(H2N-SO2-) benzoyl | F | C | 45 | 697.90 | (M + H) | A |

-continued


| Example # | Acid # (for non-commercial compounds) | R | X | Y | % yield | LCMS result | Ion | Acylation/ coupling Method |
|---|---|---|---|---|---|---|---|---|
| 302 | Acid 23 | (methylsulfamoyl, fluoro benzoyl) | F | C | 50 | 661.97 | (M + H) | A |
| 303 | Acid 24 | (isopropylsulfamoyl, fluoro benzoyl) | F | C | 48 | 676.04 | (M + H) | A |
| 304 | Acid 25 | (propylsulfamoyl, fluoro benzoyl) | F | C | 52 | 690.00 | (M + H) | A |
| 305 | Acid 26 | (cyclopropylsulfamoyl, fluoro benzoyl) | F | C | 53 | 687.97 | (M + H) | A |
| 306 | Acid 27 | (isopropylsulfamoyl, fluoro benzoyl) | F | C | 41 | 690.00 | (M + H) | A |
| 307 |  | (hydroxysulfonyl, chloro benzoyl) | $CH_3$ | C | 28 | 661.06 | (M + H) | A |
| 308 | Acid 3 | (methylsulfamoyl, chloro benzoyl) | $CH_3$ | C | 35 | 674.06 | (M + H) | A |

-continued
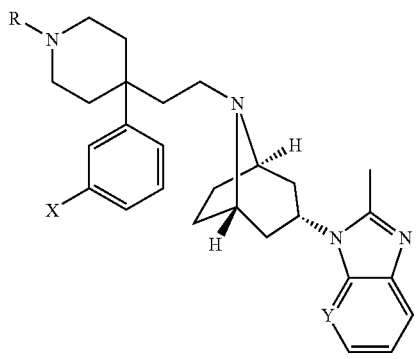
| Example # | Acid # (for non-commercial compounds) | R | X | Y | % yield | LCMS result | Ion | Acylation/coupling Method |
|---|---|---|---|---|---|---|---|---|
| 309 | Acid 18 | ethyl-NH-SO2-(4-Cl-phenyl)-C(O)- | CH3 | C | 46 | 688.04 | (M + H) | A |
| 310 | Acid 19 | propyl-NH-SO2-(4-Cl-phenyl)-C(O)- | CH3 | C | 44 | 702.05 | (M + H) | A |
| 311 | Acid 20 | cyclopropyl-NH-SO2-(4-Cl-phenyl)-C(O)- | CH3 | C | 42 | 700.07 | (M + H) | A |
| 312 | Acid 4 | isopropyl-NH-SO2-(4-Cl-phenyl)-C(O)- | CH3 | C | 35 | 702.10 | (M + H) | A |
| 313 | Acid 12 | methyl-NH-SO2-(2-Cl-phenyl)-C(O)- | CH3 | C | 45 | 674.06 | (M + H) | A |
| 314 | | H2N-SO2-(2,4-diCl-phenyl)-C(O)- | CH3 | C | 54 | 693.92 | (M + H) | A |
| 315 | | H2N-SO2-(4-Cl-phenyl)-C(O)- | CH3 | C | 47 | 659.97 | (M + H) | A |

-continued
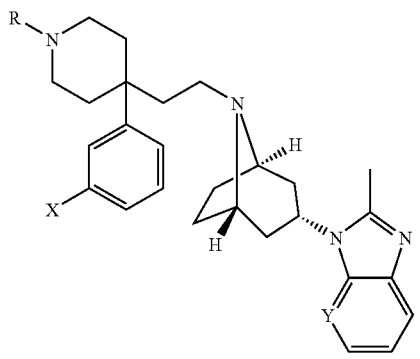
| Example # | Acid # (for non-commercial compounds) | R | X | Y | % yield | LCMS result | Ion | Acylation/coupling Method |
|---|---|---|---|---|---|---|---|---|
| 316 | Acid 1 | tetrazolyl-C(CH3)2-C(O)- | H | N | 44 | 567.92 | (M + H) | A |
| 317 |  | tBu-C(O)-C(CH3)2- | H | N | 37 | 513.93 | (M + H) | A |
| 318 |  | 1H-pyrazol-4-yl-C(O)-C(CH3)2- | H | N | 35 | 523.99 | (M + H) | A |
| 319 |  | CF3-C(O)-C(CH3)2- | H | C | 47 | 525.23 | (M + H) | B |
| 320 |  | HOOC-CH2CH2-C(O)-C(CH3)2- | H | C | 68 | 527.42 | (M − 1) | B |
| 321 |  | 2-(HOOC)-cyclohex-4-enyl-C(O)-C(CH3)2- | H | C | 90 | 579.46 | (M − 1) | B |
| 322 |  | 2-(HOOC)-cyclohexyl-C(O)-C(CH3)2- | H | C | 78 | 581.48 | (M − 1) | B |

-continued
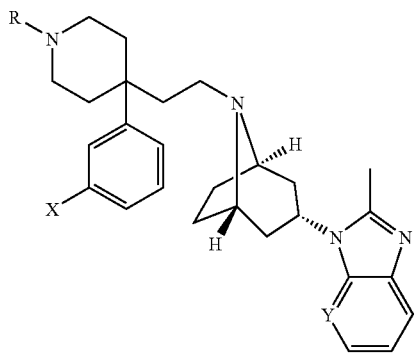
| Example # | Acid # (for non-commercial compounds) | R | X | Y | % yield | LCMS result | Ion | Acylation/ coupling Method |
|---|---|---|---|---|---|---|---|---|
| 323 | | HOOC-CH2CH2CH2-C(O)- | H | C | 92 | 541.42 | (M − 1) | B |
| 324 | | HOOC-CH2-C(CH3)2-CH2-C(O)- | H | C | 99 | 569.43 | (M − 1) | B |
| 325 | | HOOC-C(CH3)2-CH2-C(O)- | H | C | 94 | 555.46 | (M − 1) | B |
| 326 | | pyrazine-2,3-dicarbonyl | H | C | 24 | 577.29 | (M − 1) | B |
| 21 | | H2N-CH(C(CH3)2OH)-C(O)- | H | C | 100 | 544.21 | (M + H) | C |
| 328 | | AcNH-CH(C(CH3)2OH)-C(O)- | H | C | 88 | 586.12 | (M + H) | D |
| 329 | | MeSO2NH-CH(C(CH3)2OH)-C(O)- | H | C | 46 | 622.13 | (M + H) | D |

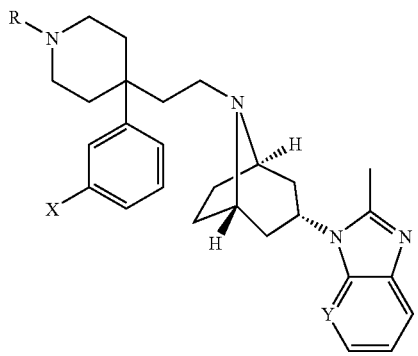
| Example # | Acid # (for non-commercial compounds) | R | X | Y | % yield | LCMS result | Ion | Acylation/coupling Method |
|---|---|---|---|---|---|---|---|---|
| 330 | | —H | H | C | 70 | 429.25 | (M + H) | E |
| 331 | | —H | H | N | 100 | 430.28 | (M + H) | E |
| 332 | |  | H | C | 31 | 726.12 | (M + H) | F |
| 333 | | 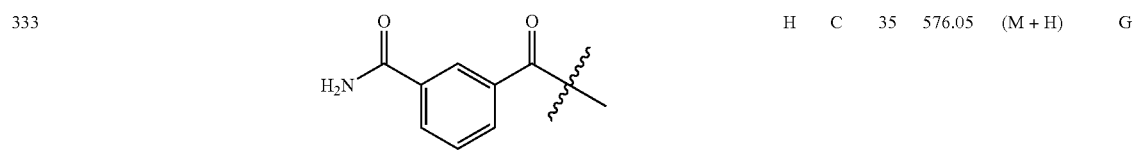 | H | C | 35 | 576.05 | (M + H) | G |

Proton NMR data for selected compounds from the above table:

Example 186

1-((1R,5S)-8-{2-[1-(2-fluorobenzoyl)-4-phenyl-4-piperidinyl]ethyl}-8-azabicyclo[3.2.1]oct-3-yl)-2-methyl-1H-benzimidazole

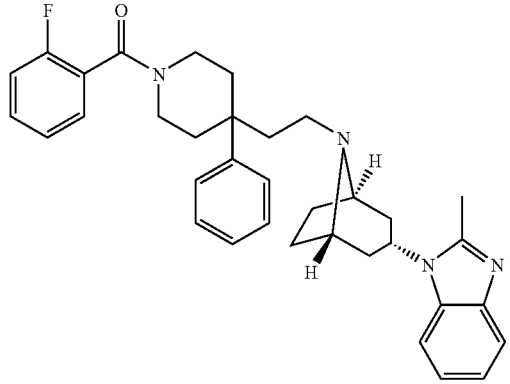

$^1$H NMR (400 MHz, Methanol-d4, ppm) δ 1.3 (m, 1H), 1.7 (m, 2H), 1.9 (m, 6H), 2.0 (m, 2H), 2.2 (m, 1H), 2.4 (m, 3H), 2.5 (s, 3H), 3.2 (m, 1H), 3.3 (m, 4H), 3.5 (m, 1H), 4.2 (m, 1H), 4.7 (m, 1H), 7.2 (m, 2H), 7.2 (m, 2H), 7.4 (m, 6H), 7.5 (m, 3H).

Example 147

2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]quinoline

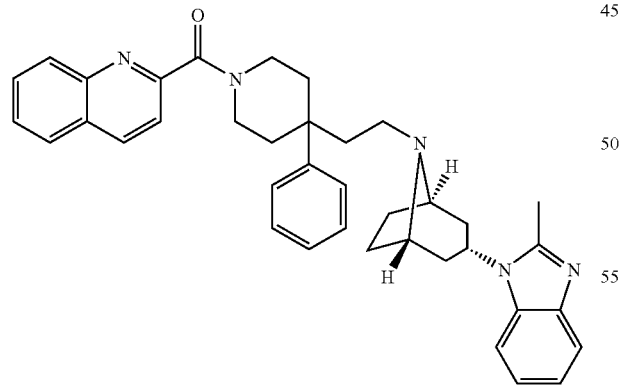

$^1$H NMR (400 MHz, Methanol-d4, ppm) δ 1.9 (s, 1H), 2.3 (m, 2H), 2.6 (m, 9H), 2.9 (m, 1H), 3.1 (m, 3H), 3.2 (m, 2H), 3.9 (m, 5H), 4.2 (m, J=3.6 Hz, 1H), 4.8 (m, 1H), 5.4 (m, 1H), 7.8 (m, 2H), 7.9 (m, 1H), 8.0 (m, 1H), 8.0 (m, J=8.2 Hz, 1H), 8.1 (s, 5H), 8.1 (m, 3H), 8.1 (m, J=4.3, 2.5 Hz, 1H), 8.2 (m, 1H).

Example 146

1-((1R,5S)-8-{2-[1-(2-chloro-6-fluorobenzoyl)-4-phenyl-4-piperidinyl]ethyl}-8-azabicyclo[3.2.1]oct-3-yl)-2-methyl-1H-benzimidazole

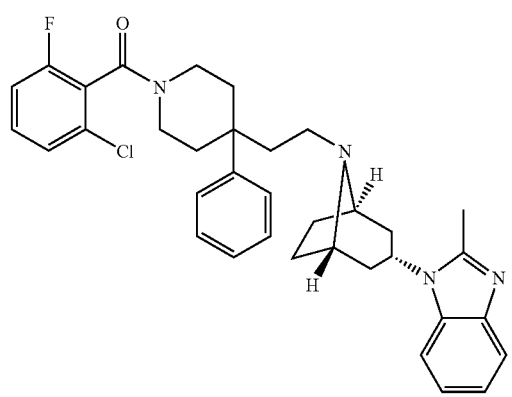

$^1$H NMR (400 MHz, Methanol-d4, ppm) δ 1.2 (m, 1H), 1.6 (m, 2H), 1.8 (m, 8H), 1.9 (m, 2H), 2.3 (m, 4H), 2.4 (m, 3H), 3.1 (m, 1H), 3.3 (m, 3H), 4.1 (m, 1H), 4.6 (m, 1H), 7.1 (m, 2H), 7.2 (m, 2H), 7.3 (m, 6H), 7.4 (m, 1H), 7.4 (m, 1H).

Example 166

2,2-dimethyl-3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxo-1-phenyl-1-propanol

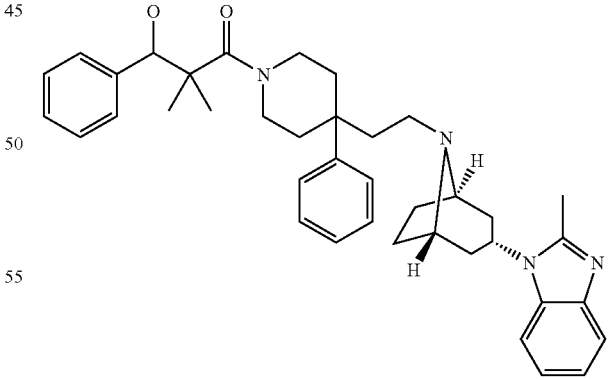

$^1$H NMR (400 MHz, Methanol-d4, ppm) δ 1.8 (m, 3H), 1.9 (s, 3H), 2.3 (m, 3H), 2.5 (m, 5H), 2.7 (m, 4H), 3.0 (m, 2H), 3.1 (m, 3H), 3.2 (m, 3H), 4.0 (m, 5H), 4.7 (m, 2H), 5.4 (m, 1H), 7.8 (m, 2H), 7.9 (m, 2H), 7.9 (m, 1H), 8.0 (m, 1H), 8.1 (m, 6H), 8.2 (m, 2H).

Example 105

1-((1R,5S)-8-{2-[1-(2,2-dimethyl-4-pentenoyl)-4-phenyl-4-piperidinyl]ethyl}-8-azabicyclo[3.2.1]oct-3-yl)-2-methyl-1H-benzimidazole

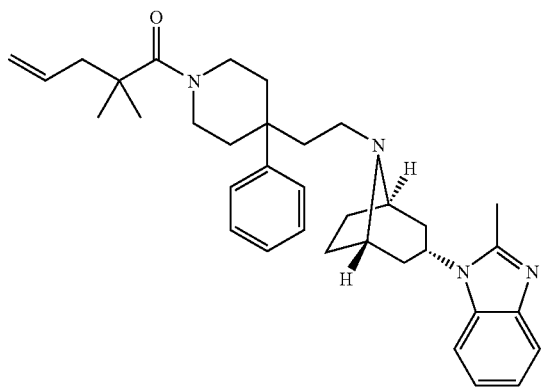

$^1$H NMR (400 MHz, Methanol-d4, ppm) δ 0.6 (m, 1H), 0.9 (m, 1H), 1.5 (m, 1H), 1.7 (m, 3H), 1.9 (m, 9H), 2.3 (m, 2H), 2.4 (m, 4H), 2.5 (d, J=6.1 Hz, 3H), 3.1 (m, 1H), 3.3 (m, 5H), 4.0 (m, 3H), 4.8 (m, 1H), 5.0 (m, 2H), 5.7 (m, 1H), 7.2 (m, 2H), 7.2 (m, 1H), 7.4 (m, 5H), 7.5 (m, 1H).

Example 101

1-((1R,5S)-8-{2-[1-(2,6-dichlorobenzoyl)-4-phenyl-4-piperidinyl]ethyl}-8-azabicyclo[3.2.1]oct-3-yl)-2-methyl-1H-benzimidazole

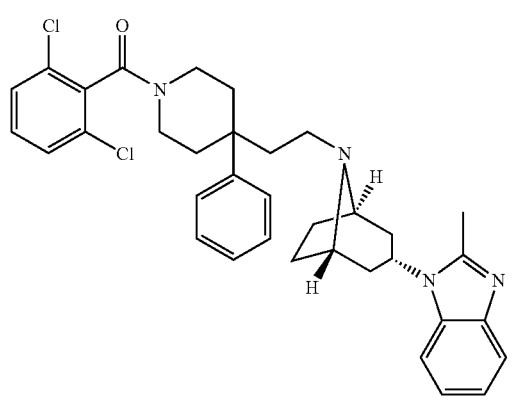

$^1$H NMR (400 MHz, Methanol-d4, ppm) δ 1.2 (m, 1H), 1.6 (m, 2H), 1.8 (m, 6H), 1.9 (m, 2H), 2.2 (m, 1H), 2.3 (m, 3H), 2.4 (m, 3H), 3.1 (m, 1H), 3.3 (m, 5H), 4.1 (m, 1H), 4.7 (m, 1H), 7.1 (m, 2H), 7.2 (m, 1H), 7.3 (m, 5H), 7.4 (m, 2H), 7.4 (m, 1H), 7.4 (m, 1H).

Example 84

1-[(1R,5S)-8-(2-{1-[(2-chloro-3-pyridinyl)carbonyl]-4-phenyl-4-piperidinyl}ethyl)-8-azabicyclo[3.2.1]oct-3-yl]-2-methyl-1H-benzimidazole

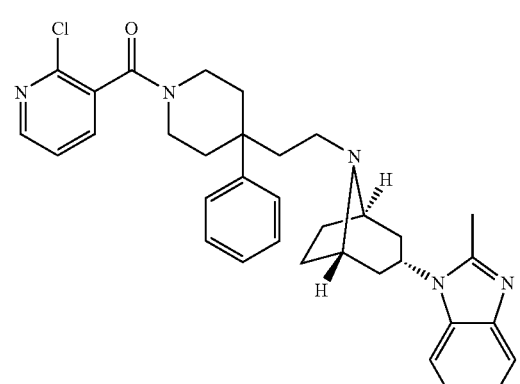

$^1$H NMR (400 MHz, Methanol-d4, ppm) δ 1.6 (d, J=7.5 Hz, 2H), 1.9 (m, 9H), 2.2 (d, J=15.7 Hz, 1H), 2.4 (m, 3H), 2.5 (m, 3H), 3.1 (m, 1H), 3.3 (m, 5H), 4.1 (dd, J=9.3, 4.3 Hz, 1H), 4.7 (m, 1H), 7.1 (m, 2H), 7.2 (m, 1H), 7.3 (m, 5H), 7.4 (m, 2H), 7.8 (m, 1H), 8.4 (m, 1H).

Example 334

1-((1R,5S)-8-{2-[1-(2-ethylbutanoyl)-4-phenyl-4-piperidinyl]ethyl}-8-azabicyclo[3.2.1]oct-3-yl)-2-methyl-1H-benzimidazole

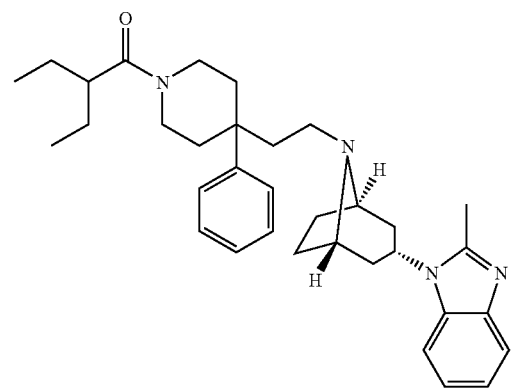

$^1$H NMR (400 MHz, Methanol-d4, ppm) 81.4 (t, J=7.5 Hz, 3H), 1.6 (t, J=7.5 Hz, 3H), 1.9 (m, 1H), 2.2 (m, 6H), 2.5 (m, 9H), 2.9 (m, 2H), 3.1 (m, 2H), 3.2 (d, J=6.4 Hz, 3H), 3.4 (m, 1H), 3.9 (m, 1H), 4.0 (none, 2H), 4.0 (m, 1H), 4.5 (m, 1H), 4.7 (m, 1H), 5.4 (m, 1H), 7.8 (m, 2H), 7.9 (m, 1H), 8.1 (m, 5H), 8.2 (m, 1H).

Example 335

1-((1R,5S)-8-{2-[1-(2-ethylbutanoyl)-4-phenyl-4-piperidinyl]ethyl}-8-azabicyclo[3.2.1]oct-3-yl)-2-methyl-1H-benzimidazole

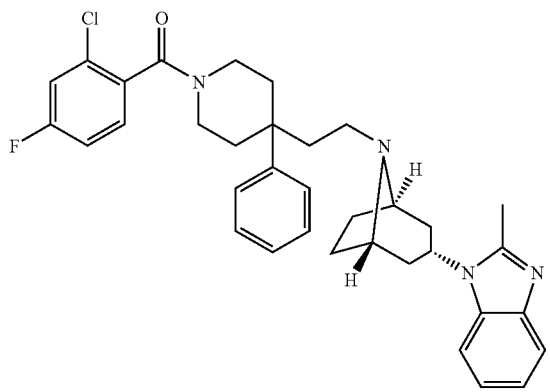

$^1$H NMR (400 MHz, Methanol-d4, ppm) δ 1.2 (s, 1H), 1.6 (m, 2H), 1.8 (m, 9H), 2.2 (m, 1H), 2.3 (m, 3H), 2.4 (m, 3H), 3.1 (m, 1H), 3.3 (m, 4H), 4.1 (m, 1H), 4.7 (m, 1H), 7.1 (m, 2H), 7.2 (m, 2H), 7.3 (m, 1H), 7.3 (m, 5H), 7.4 (dd, J=8.6, 6.1 Hz, 1H), 7.4 (m, 1H).

Example 336

2-methyl-1-((1R,5S)-8-{2-[1-(2-methylbenzoyl)-4-phenyl-4-piperidinyl]ethyl}-8-azabicyclo[3.2.1]oct-3-yl)-1H-benzimidazole

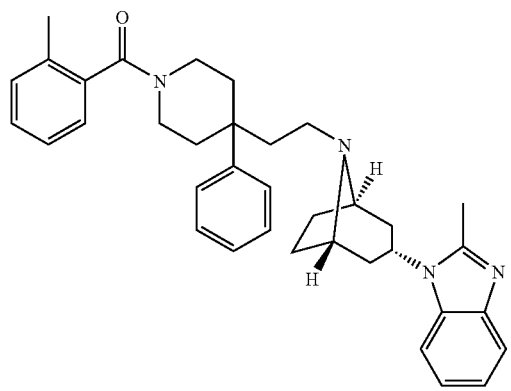

$^1$H NMR (400 MHz, Methanol-d4, ppm) δ 1.2 (m, 1H), 1.6 (m, 2H), 1.7 (m, 1H), 1.9 (m, 8H), 2.1 (m, 2H), 2.3 (m, 4H), 2.4 (m, 3H), 3.1 (m, 1H), 3.3 (m, 5H), 4.1 (m, 1H), 4.6 (m, 1H), 7.1 (m, 7H), 7.3 (m, 5H), 7.4 (m, 1H).

Example 337

3-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-pyridinol

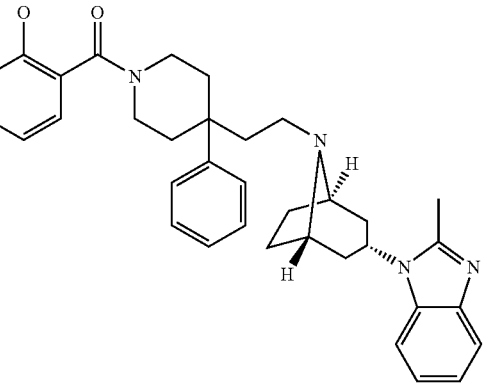

$^1$H NMR (400 MHz, DMSO-d6) δ ppm 1.5 (m, 2H), 1.8 (m, 9H), 2.0 (m, 2H), 2.3 (m, 3H), 2.4 (s, 3H), 3.2 (d, J=6.4 Hz, 4H), 3.7 (s, 2H), 4.5 (m, 1H), 6.4 (m, 2H), 7.0 (d, J=8.6 Hz, 1H), 7.1 (m, 2H), 7.2 (m, 1H), 7.3 (m, 5H), 7.4 (m, 1H), 9.8 (s, 1H).

Example 338

5-methoxy-2-[(4-{2-[(1R,5S)-3-(2-methyl-1H-benzimidazol-1-yl-8-azabicyclo[3.2.1]oct-8-yl]ethyl}-4-phenyl-1-piperidinyl)carbonyl]phenol

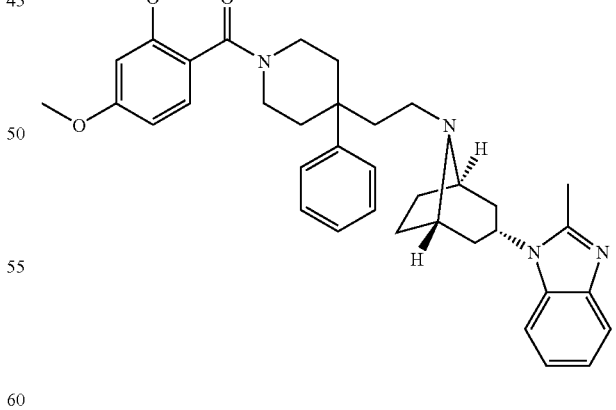

$^1$H NMR (400 MHz, DMSO-d6) δ ppm 1.5 (m, 2H), 1.8 (m, 8H), 2.1 (m, 2H), 2.3 (m, 2H), 2.4 (m, 3H), 2.4 (m, 1H), 3.2 (d, J=7.1 Hz, 3H), 3.3 (s, 3H), 3.6 (m, 2H), 3.7 (s, 2H), 4.5 (m, 1H), 6.4 (m, 2H), 7.0 (d, J=8.2 Hz, 1H), 7.1 (m, 2H), 7.2 (m, 1H), 7.3 (m, 5H), 7.4 (m, 1H), 9.8 (s, 1H).

Example 339

4-methoxy-2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]phenol

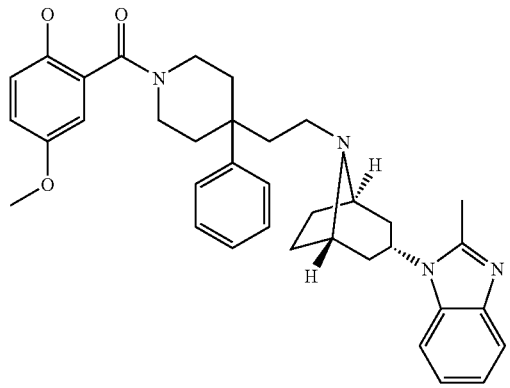

$^1$H NMR (400 MHz, DMSO-d6) δ ppm 1.5 (m, 2H), 1.8 (m, 9H), 2.0 (m, 2H), 2.3 (m, 2H), 2.4 (m, 3H), 2.5 (m, 1H), 3.2 (m, 6H), 3.6 (s, 2H), 3.8 (m, 1H), 4.4 (m, 1H), 6.6 (d, J=2.9 Hz, 1H), 6.7 (d, J=8.6 Hz, 1H), 6.8 (m, 1H), 7.1 (m, 2H), 7.2 (m, 1H), 7.3 (m, 5H), 7.4 (dd, J=8.2, 6.4 Hz, 1H), 9.2 (s, 1H).

Example 340

6-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-pyridinol

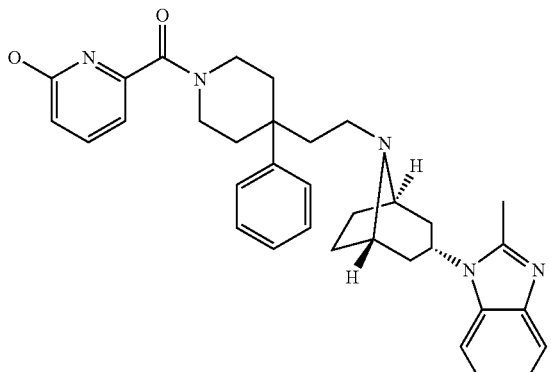

$^1$H NMR (400 MHz, DMSO-d6) δ ppm 1.5 (m, 2H), 1.8 (m, 8H), 2.1 (m, 2H), 2.3 (m, 2H), 2.4 (m, 3H), 2.5 (m, 1H), 3.3 (m, 7H), 3.8 (s, 1H), 4.5 (m, 1H), 6.3 (d, J=6.4 Hz, 1H), 6.4 (d, J=9.3 Hz, 1H), 7.1 (m, 2H), 7.2 (m, 1H), 7.3 (m, 5H), 7.4 (m, 2H).

Example 341

1-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]cyclopentanol

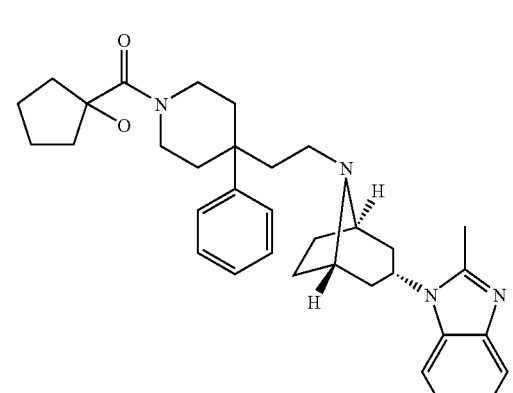

$^1$H NMR (400 MHz, DMSO-d6) δ ppm 1.7 (m, 15H), 2.0 (m, 3H), 2.3 (m, 2H), 2.4 (m, 4H), 2.5 (m, 1H), 2.7 (m, 1H), 3.2 (m, 7H), 3.8 (d, J=109.2 Hz, 1H), 4.5 (m, 1H), 7.1 (m, 2H), 7.1 (m, 1H), 7.3 (m, 5H), 7.4 (m, J=7.1 Hz, 1H).

Example 51

5-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-furansulfonamide

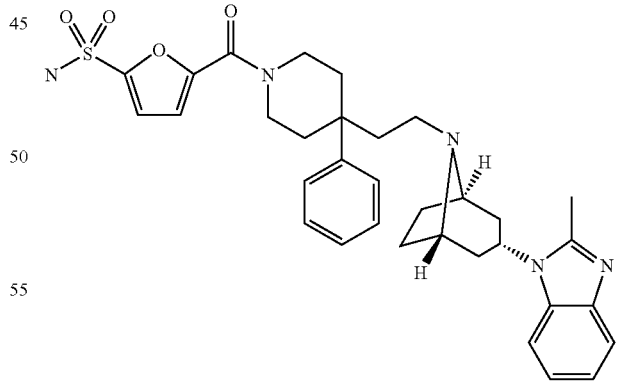

$^1$H NMR (400 MHz, DMSO-d$_6$) δ ppm 1.2 (s, 1H), 1.5 (m, 2H), 1.8 (m, 8H), 2.1 (m, 1H), 2.3 (m, 2H), 2.4 (s, 3H), 2.5 (m, 3H), 3.2 (m, 2H), 3.2 (m, 1H), 3.4 (m, 2H), 3.8 (m, 2H), 4.5 (m, 1H), 7.1 (m, 2H), 7.2 (t, J=7.0 Hz, 1H), 7.3 (m, 5H), 7.4 (m, 1H).

Example 50

3-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-1-benzofuran-6-ol

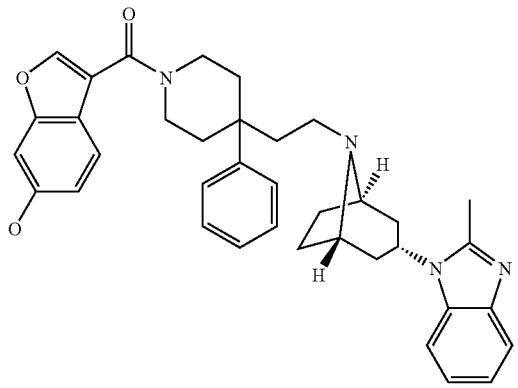

$^1$H NMR (400 MHz, DMSO-d6) δ ppm 1.5 (m, 2H), 1.7 (m, 9H), 2.1 (d, J=5.7 Hz, 2H), 2.3 (m, 2H), 2.4 (s, 3H), 2.5 (m, 2H), 2.5 (m, 1H), 3.2 (m, 2H), 3.3 (m, 1H), 3.7 (m, 2H), 4.5 (m, 1H), 6.8 (dd, J=8.6, 2.1 Hz, 1H), 6.9 (d, J=1.8 Hz, 1H), 7.1 (m, 2H), 7.2 (t, J=7.0 Hz, 1H), 7.3 (m, 6H), 7.4 (m, 1H), 8.0 (s, 1H).

Example 44

4-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-1,3-benzoxazole-2(3H)-thione

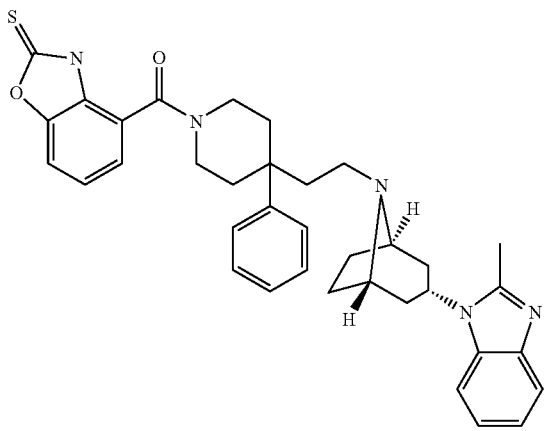

$^1$H NMR (400 MHz, DMSO-d6) δ ppm 1.7 (s, 3H), 1.9 (m, 7H), 2.0 (m, 3H), 2.2 (m, 1H), 2.4 (m, 5H), 2.5 (m, 2H), 3.1 (m, 2H), 3.4 (m, 2H), 3.9 (m, 1H), 4.6 (m, 1H), 7.1 (m, 4H), 7.2 (m, 1H), 7.3 (m, 6H), 7.4 (m, 1H).

Example 43

N-[2,2-dimethyl-3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxopropanoyl] methane sulfonamide

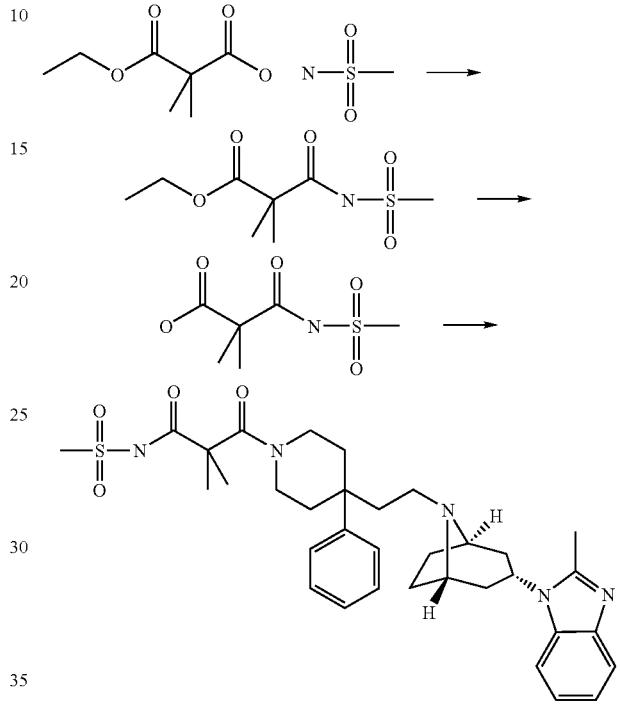

example 43

3-Ethoxy-2,2-dimethyl-3-oxopropanoic acid (100 mg, 0.624 mmole) was added to a stirring suspension of 2.5 equivalents of PS-DCC from Argonaut and 3 equivalents of dimethylaminopyridine in DCM. To this was added methanesulfonamide (41.6 mg, 0.437 mmole). The solution was filtered of and concentrated to give 69.3 mg of ethyl 2,2-dimethyl-3-[(methylsulfonyl)amino]-3-oxopropanoate (67% yield crude). MS ES− 236 (M−H). $^1$H NMR (300 MHz, Chloroform-d) δ ppm 1.4 (t, J=6.7 Hz, 3H), 1.6 (s, 6H), 3.3 (m, 3H), 4.3 (m, 2H).

Ethyl 2,2-dimethyl-3-[(methylsulfonyl)amino]-3-oxopropanoate was hydrolyzed without purification in 2 ml of 1,4-dioxane and 2 ml of 1M LiOH at 45° C. The solvent was removed under vacuum and the residue 2,2-dimethyl-N-(methylsulfonyl)-3-oxo-alanine was used in the next step without further purification. MS ES− 209 (M−H) $^1$H NMR (400 MHz, methanol-d4) δ ppm 1.4 (s, 6H) and 3.2 (s, 3H).

Example 43

N-[2,2-dimethyl-3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxopropanoyl]methanesulfonamide was made using the HATU coupling method A. MS ES+ 620 (M+H). $^1$H NMR (300 MHz, methanol-d4) δ ppm 1.4 (m, 4H), 1.9 (s, 2H), 2.2 (m, 2H), 2.3 (s, 4H), 2.4 (m, 2H), 2.8 (m, 2H), 2.8 (s, 3H), 2.9 (m, 2H), 3.2 (d, J=7.5 Hz, 2H), 3.3 (m, 2H), 3.5 (s, 1H), 4.1 (d, J=8.5 Hz, 2H), 4.9 (s, 6H), 5.3 (s, 1H), 7.3 (m, 1H), 7.5 (d, J=4.2 Hz, 4H), 7.6 (m, 2H), 7.8 (m, 2H).

Example 42

N-{4-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-pyridinyl}acetamide

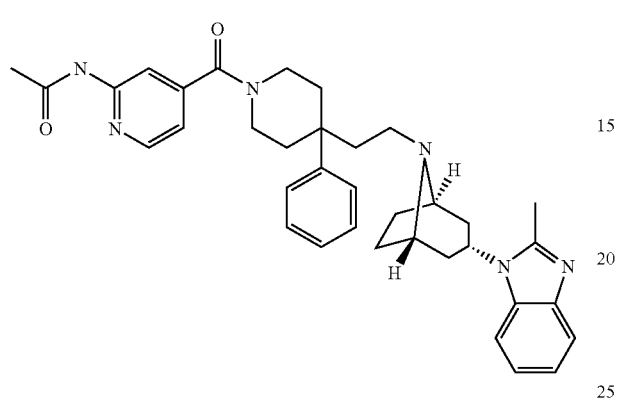

¹H NMR (400 MHz, methanol-d4) δ ppm 1.6 (m, 2H), 1.8 (m, 9H), 2.2 (m, 2H), 2.3 (m, 3H), 2.4 (m, 3H), 3.2 (m, 8H), 3.4 (m, 1H), 4.0 (m, 1H), 4.7 (m, 1H), 7.0 (dd, J=5.0, 1.4 Hz, 1H), 7.1 (m, 2H), 7.2 (m, 1H), 7.3 (m, 5H), 7.4 (m, 1H), 8.0 (s, 1H), 8.3 (d, J=5.0 Hz, 1H).

Example 39

4-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-1,2,5-thiadiazol-3-ol

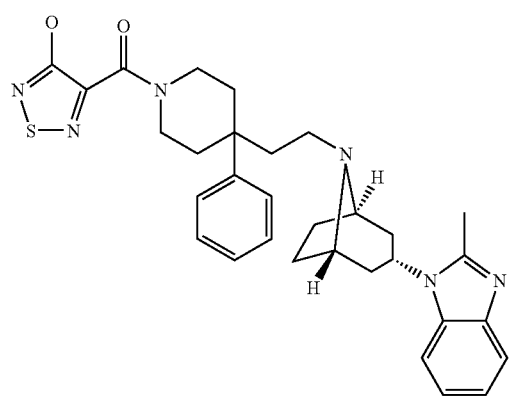

¹H NMR (300 MHz, DMSO-d6) δ ppm 1.6 (d, J=7.5 Hz, 2H), 1.8 (m, 7H), 2.1 (s, 2H), 2.3 (s, 2H), 2.5 (s, 3H), 2.5 (m, 2H), 3.1 (m, 1H), 3.4 (m, 6H), 3.8 (s, 1H), 4.5 (s, 1H), 7.1 (m, 2H), 7.2 (m, 1H), 7.4 (m, 5H), 7.5 (m, 1H).

Example 37

1,1-dimethyl-2-(4-{2-[(1R,5S)-3-(2-methyl-1H-benzimidazol-1-yl)-8-azabicyclo[3.2.1]oct-8-yl]ethyl}-4-phenyl-1-piperidinyl)-2-oxoethylformamide

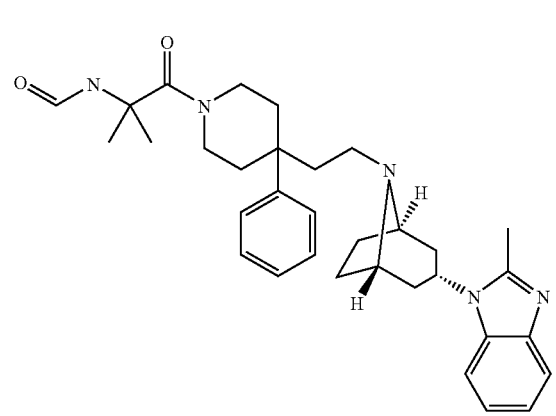

¹H NMR (400 MHz, methanol-d4) δ ppm 1.5 (m, 6H), 1.7 (m, 2H), 1.9 (m, 8H), 2.2 (s, 2H), 2.4 (m, 2H), 2.5 (s, 3H), 3.3 (m, 4H), 3.3 (m, 2H), 3.6 (m, 1H), 4.0 (s, 2H, 4.7 (m, 1H), 7.2 (m, 2H), 7.2 (m, 1H), 7.4 (m, 5H), 7.5 (m, 1H), 8.0 (s, 1H).

Example 36

N-{4-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]phenyl}methanesulfonamide formate salt

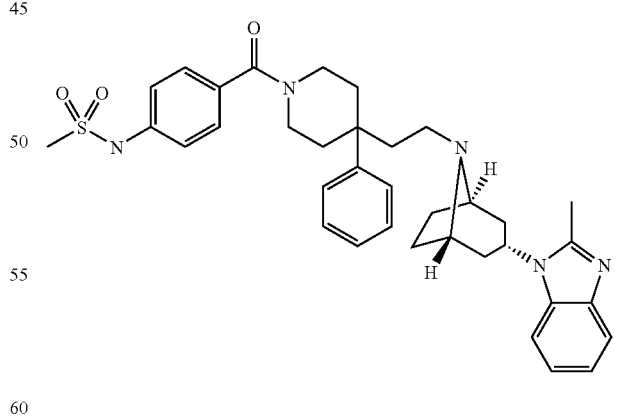

¹H NMR (400 MHz, methanol-d4) δ ppm 1.8 (m, 11H), 2.2 (m, 3H), 2.3 (m, 1H), 2.4 (m, 5H), 2.9 (m, 3H), 3.2 (m, 3H), 3.4 (m, 2H), 3.6 (m, 1H), 4.0 (m, J=4.3 Hz, 1H), 4.7 (m, 1H), 7.1 (m, 2H), 7.2 (m, 1H), 7.2 (m, 2H), 7.3 (m, 6H), 7.4 (m, 1H).

Example 35

N,N,2,5-tetramethyl-4-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-3-furansulfonamide formate salt

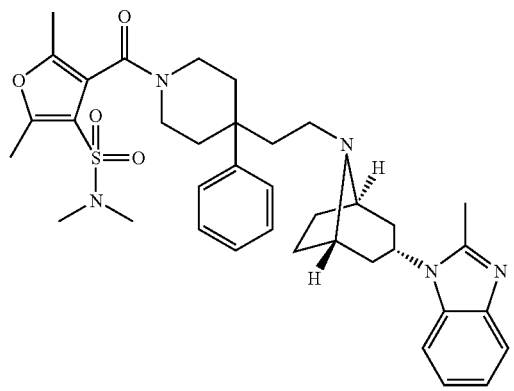

$^1$H NMR (400 MHz, chloroform-d) δ ppm 1.6 (m, 2H), 1.8 (m, 8H), 2.1 (m, 5H), 2.3 (m, 4H), 2.4 (m, 6H), 2.6 (m, 3H), 2.7 (m, 3H), 3.1 (m, 2H), 3.3 (m, 2H), 3.4 (m, 1H), 4.0 (m, 1H), 4.7 (m, 1H), 7.1 (m, 2H), 7.1 (m, 1H), 7.3 (m, 5H), 7.4 (m, 1H).

Example 33

2-methyl-1-[(1R,5S)-8-(2-{1-[2-methyl-2-(1H-1,2,4-triazol-1-yl)propanoyl]-4-phenyl-4-piperidinyl}ethyl)-8-azabicyclo[3.2.1]oct-3-yl]-1H-benzimidazole

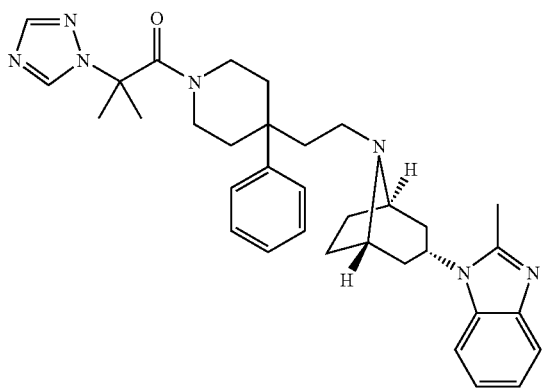

$^1$H NMR (300 MHz, chloroform-d) δ ppm 1.5 (m, 5H) 1.7 (d, J=15.1 Hz, 3H), 1.9 (m, 10H), 2.0 (s, 2H), 2.4 (m, 3H), 2.6 (s, 3H), 3.0 (m, 5H), 4.6 (m, 1H), 7.2 (m, 5H), 7.3 (m, 3H), 7.6 (m, 1H), 8.0 (s, 1H), 8.1 (s, 1H).

Example 31

1-{(1R,5S)-8-[2-(1-isobutyryl-4-phenyl-4-piperidinyl)ethyl]-8-azabicyclo[3.2.1]oct-3-yl}-2-methyl-1H-benzimidazole

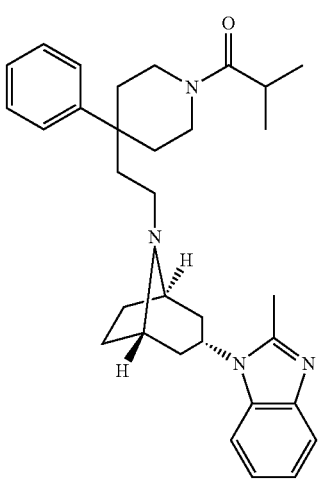

$^1$H NMR (300 MHz, chloroform-d) δ ppm 1.1 (d, J=6.7 Hz, 3H), 1.1 (d, J=6.7 Hz, 3H), 1.2 (m, 2H), 1.6 (m, J=7.3, 7.3 Hz, 2H), 1.8 (m, 8H), 2.2 (m, 2H) 2.4 (m, 2H), 2.5 (m, 3H), 2.8 (m, 1H), 3.2 (m, 4H), 3.7 (m, 1H), 4.0 (m, 1H), 4.7 (m, 1H), 7.2 (m, 3H), 7.3 (m, 5H), 7.7 (m, 1H).

Example 30 benzyl 1,1-dimethyl-2-(4-{2-[(1R,5S)-3-(2-methyl-1H-benzimidazol-1-yl)-8-azabicyclo[3.2.1]oct-8-yl]ethyl}-4-phenyl-1-piperidinyl)-2-oxoethylcarbamate

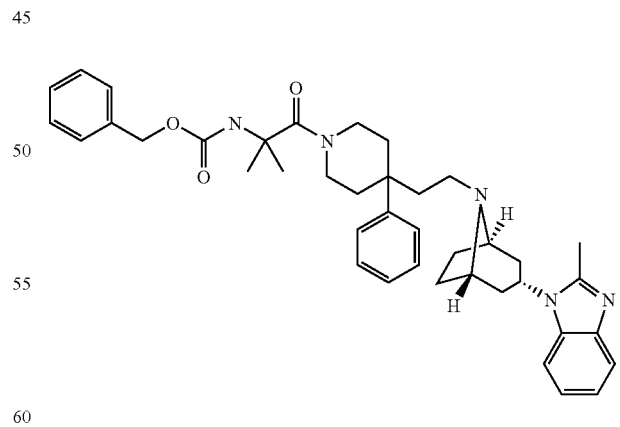

$^1$H NMR (400 MHz, chloroform-d) δ ppm 1.0 (m, J=7.1, 7.1 Hz, 1H), 1.5 (m, 8H), 1.8 (d, J=6.1 Hz, 4H), 1.9 (m, 7H), 2.1 (m, 3H), 2.3 (m, 2H), 2.5 (s, 3H), 3.3 (m, 4H), 4.6 (m, 1H), 5.0 (s, 2H), 7.1 (m, 3H), 7.3 (m, 8H), 7.4 (t, J=7.7 Hz, 2H), 7.6 (m, 1H).

Example 29

1-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]cyclopropanol

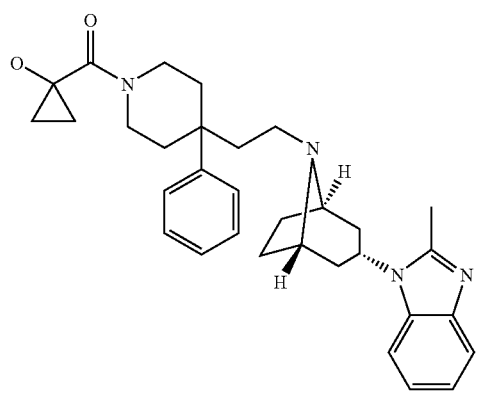

¹H NMR (400 MHz, chloroform-d) δ ppm 0.9 (m, J=20.3 Hz, 2H), 1.0 (m, 2H), 1.3 (m, 4H), 1.6 (m, 3H), 1.8 (m, 6H), 2.2 (m, 2H), 2.4 (m, 2H), 2.6 (s, 3H), 3.2 (d, J=3.2 Hz, 4H), 4.1 (m, 2H), 4.6 (m, 1H), 7.1 (m, 2H), 7.3 (m, 4H), 7.4 (t, J=7.7 Hz, 2H), 7.6 (d, J=7.1 Hz, 1H).

Example 28

1-((1R,5S)-8-{2-[1-(2,2-dimethylbutanoyl)-4-phenyl-4-piperidinyl]ethyl}-8-azabicyclo[3.2.1]oct-3-yl)-2-methyl-1H-benzimidazole

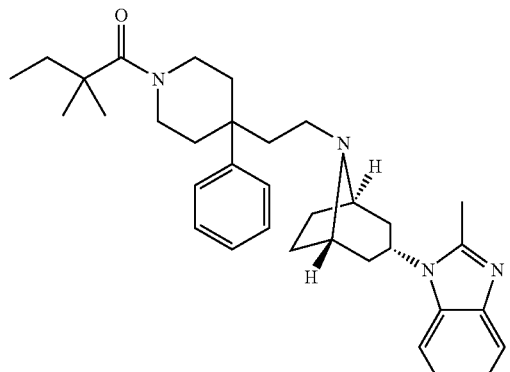

¹H NMR (400 MHz, chloroform-d) δ ppm 0.9 (t, J=7.5 Hz, 3H), 1.2 (s, 6H), 1.6 (m, 4H), 1.8 (m, 8H), 2.2 (dd, J=12.5, 3.2 Hz, 2H), 2.3 (m, 2H), 2.5 (m, 1H), 2.6 (s, 3H), 3.0 (m, 1H), 3.2 (m, 4H), 3.9 (m, 2H), 4.6 (m, 1H), 7.1 (m, 2H), 7.2 (m, 1H), 7.3 (m, 3H), 7.4 (m, 2H), 7.6 (m, 1H).

Example 27

2,2-dimethyl-3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxo-1-propanol

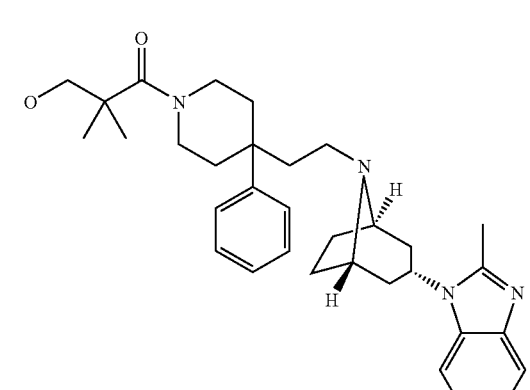

¹H NMR (400 MHz, chloroform-d) δ ppm 1.0 (d, J=6.8 Hz, 2H), 1.2 (s, 6H), 1.6 (m, 2H), 1.8 (m, 4H), 1.9 (m, 4H), 2.2 (dd, J=12.0, 2.7 Hz, 2H), 2.3 (m, 2H), 2.6 (s, 3H), 3.2 (m, J=11.1, 11.1 Hz, 4H), 3.5 (s, 2H), 3.8 (m, 1H), 3.9 (d, J=13.2 Hz, 2H), 4.6 (m, 1H), 7.1 (m, 2H), 7.3 (m, 4H), 7.4 (m, 2H), 7.6 (m, 1H).

Example 26

1-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]cyclopropanecarbonitrile

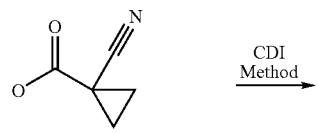

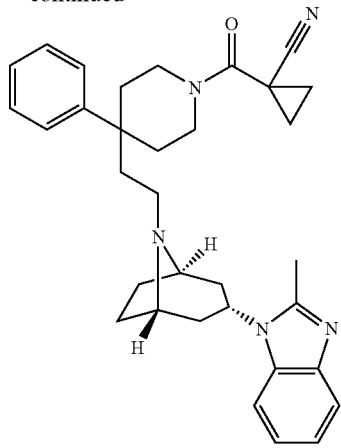

To a solution of 1-cyanocyclopropane-carboxylic acid (38.9 mg, 0.351 mmole) in 1 ml of DCE was added carbonyldiimidazole (38.0 mg, 0.234 mmole) and the mixture was stirred until gas evolution stopped. 2-Methyl-1-{(1R,5S)-8-[2-(4-phenyl-4-piperidinyl)ethyl]-8-azabicyclo[3.2.1]oct-3-yl}-1H-benzimidazole (50.0 mg, 0.117 mmole) was added and the resulting mixture was stirred overnight. The solvent was evaporated and the reaction mixture was flashed on silica using a gradient of 1-8% MeOH in CHCl₃ to afford 1-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]cyclopropanecarbonitrile. MS ES+ 522 (M+H). ¹H NMR (300 MHz, chloroform-d) δ ppm 1.6 (m, J=43.1 Hz, 6H), 1.9 (d, J=25.3 Hz, 10H), 2.4 (m, J=10.0 Hz, 4H), 2.6 (s, 3H), 3.3 (m, 3H), 3.5 (m, 1H), 4.1 (m, 2H), 4.7 (m, 1H), 7.3 (m, 8H), 7.7 (m, 1H).

Example 25

1-[(1R,5S)-8-(2-{1-[(3-chloro-2-thienyl)carbonyl]-4-phenyl-4-piperidinyl}ethyl)-8-azabicyclo[3.2.1]oct-3-yl]-2-methyl-1H-benzimidazole

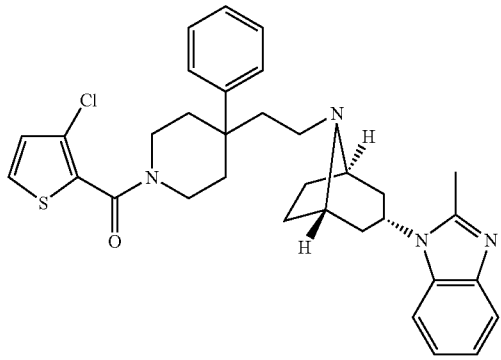

¹H NMR (300 MHz, methanol-d4) δ ppm 0.9 (m, 1H), 1.1 (m, 3H), 1.6 (d, J=12.2 Hz, 2H), 1.9 (m, 8H), 2.3 (m, 4H), 2.4 (s, 3H), 3.2 (m, 2H), 3.6 (m, 1H), 4.0 (m, J=7.1 Hz, 1H), 4.7 (m, 1H), 6.9 (d, J=5.2 Hz, 1H), 7.1 (m, 2H), 7.2 (d, J=6.2 Hz, 1H), 7.3 (m, 5H), 7.4 (m, J=1.5 Hz, 1H), 7.6 (d, J=5.2 Hz, 1H).

Example 342

1-[(1R,5S)-8-(2-{1-[(3-chlorophenyl)sulfonyl]-4-phenyl-4-piperidinyl}ethyl)-8-azabicyclo[3.2.1]oct-3-yl]-2-methyl-1H-benzimidazole

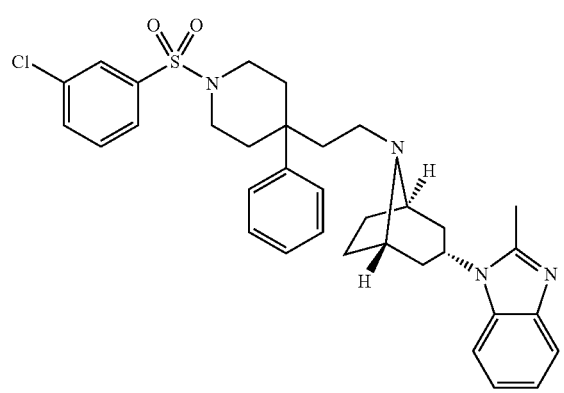

¹H NMR (300 MHz, chloroform-d) δ ppm 1.6 (m, 2H), 1.7 (m, 4H), 1.9 (m, 8H), 2.4 (m, 4H), 2.6 (s, 3H), 2.8 (m, 2H), 3.4 (m, 2H), 4.6 (m, 1H), 7.2 (m, 5H), 7.3 (m, 3H), 7.4 (t, J=7.9 Hz, 1H), 7.5 (m, 1H), 7.6 (d, J=7.8 Hz, 1H), 7.7 (m, 1H), 7.7 (m, J=1.8, 1.8 Hz, 1H).

Example 343

2-methyl-1-[(1R,5S)-8-(2-{1-[(3-methylphenyl)sulfonyl]-4-phenyl-4-piperidinyl}ethyl)-8-azabicyclo[3.2.1]oct-3-yl]-1H-benzimidazole

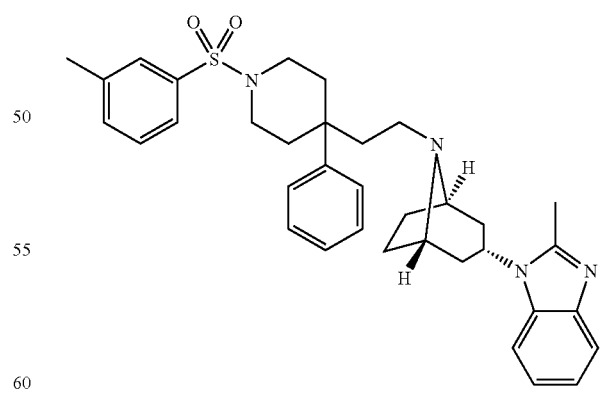

¹H NMR (300 MHz, chloroform-d) δ ppm 1.6 (m, 2H), 1.7 (dd, J=9.3, 5.6 Hz, 2H), 1.9 (m, 8H), 2.3 (m, 4H), 2.4 (s, 3H), 2.5 (d, J=13.9 Hz, 3H), 2.8 (m, 2H), 3.2 (m, 2H), 3.4 (m, 2H), 4.5 (m, 1H), 7.1 (m, 5H), 7.3 (m, 5H), 7.5 (m, 2H), 7.6 (m, 1H).

Example 344

4-chlorophenyl 1,1-dimethyl-2-(4-{2-[(1R,5S)-3-(2-methyl-1H-benzimidazol-1-yl)-8-azabicyclo[3.2.1]oct-8-yl]ethyl}-4-phenyl-1-piperidinyl)-2-oxoethyl ether

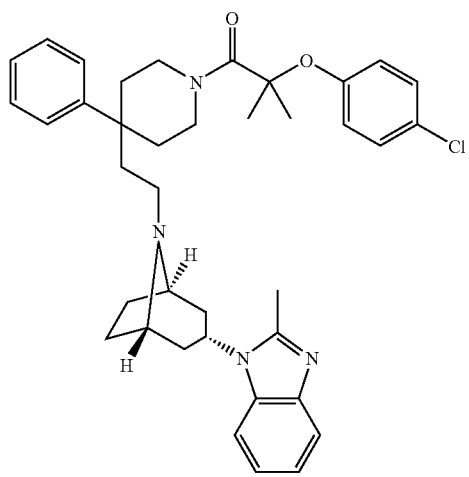

¹H NMR (300 MHz, chloroform-d) δ ppm 1.3 (m, 1H), 1.6 (m, 11H), 1.9 (m, 7H), 2.2 (m, J=10.7 Hz, 1H), 2.4 (m, J=23.3 Hz, 2H), 2.6 (s, 3H), 3.1 (m, 1H), 3.2 (m, 2H), 3.4 (m, 1H), 4.2 (m, 2H), 4.6 (m, 1H), 6.8 (m, 2H), 7.2 (m, 8H), 7.3 (m, 2H), 7.7 (m, 1H).

Example 34

2-[(4-{2-[(1R,5S)-3-(2-methyl-1H-benzimidazol-1-yl)-8-azabicyclo[3.2.1]oct-8-yl]ethyl}-4-phenyl-1-piperi-dinyl)carbonyl]phenyl dimethylsulfamate formate salt

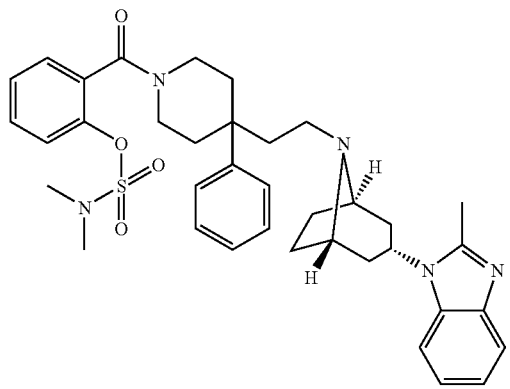

¹H NMR (400 MHz, chloroform-d) δ ppm 1.9 (m, 10H), 2.3 (m, 9H), 2.7 (s, 3H), 2.9 (s, 3H), 3.1 (m, 2H), 3.4 (m, 3H), 4.1 (m, J=13.6 Hz, 1H), 4.7 (m, 1H), 7.1 (m, 2H), 7.2 (m, 4H), 7.3 (m, 4H), 7.4 (m, 2H), 7.4 (m, 1H).

Example 37

5-methyl-3-[(4-{2-[(1R,5S)-3-(2-methyl-1H-benzimidazol-1-yl)-8-azabicyclo[3.2.1]oct-8-yl]ethyl}-phenyl-1-piperidinyl)carbonyl]-4-isothiazolol

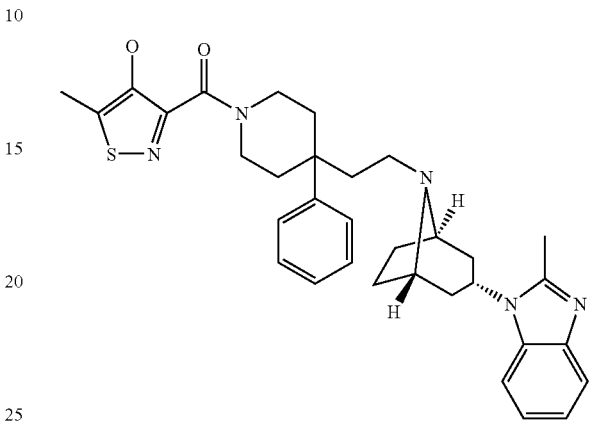

¹H NMR (300 MHz, DMSO-d6) δ ppm 2.7 (m, 3H), 3.1 (m, 4H), 3.3 (m, 10H), 3.6 (m, 2H), 3.8 (s, 6H), 4.0 (m, 3H), 4.2 (m, 1H), 4.7 (m, 1H), 8.6 (m, J=4.6, 4.6 Hz, 2H), 8.7 (d, J=6.6 Hz, 1H), 8.8 (d, J=14.8 Hz, 5H), 8.9 (m, 1H).

Example 38

N-{5-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-1,3-thiazol-2-yl}acetamide

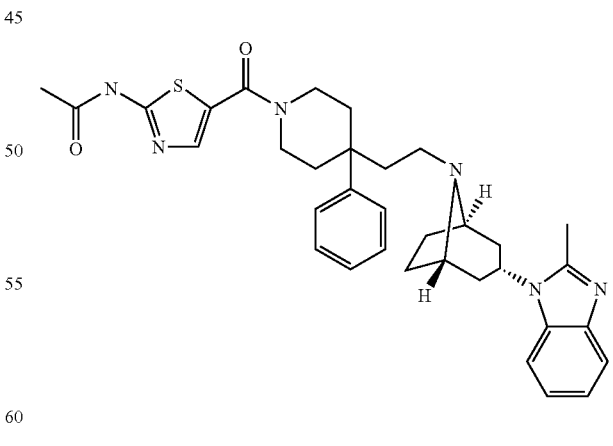

¹H NMR (400 MHz, methanol-d4) δ ppm 1.6 (s, 1H), 2.0 (m, 12H), 2.5 (m, 5H), 3.1 (s, 2H), 3.2 (m, 2H), 3.5 (m, 4H), 3.7 (m, 2H), 4.0 (m, 2H), 7.1 (m, 4H), 7.3 (m, 5H), 7.5 (m, 1H).

Example 43

2-(isopropylamino)-5-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-4-pyrimidinol

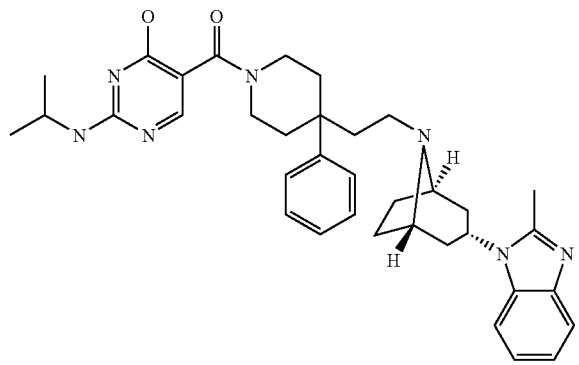

$^1$H NMR (400 MHz, DMSO-d6) δ ppm 1.1 (dd, J=20.0, 6.4 Hz, 5H), 1.6 (d, J=7.8 Hz, 2H), 1.8 (m, 8H), 2.1 (m, 2H), 2.4 (m, 2H), 2.5 (d, J=7.5 Hz, 3H), 2.5 (m, 1H), 3.3 (m, 8H), 3.8 (m, J=21.0 Hz, 1H), 4.0 (m, 1H), 4.5 (m, 1H), 6.7 (s, 1H), 7.1 (m, 2H), 7.2 (m, 1H), 7.4 (m, 5H), 7.5 (m, 1H), 7.8 (s, 1H).

Example 45

3,3,5-trimethyl-5-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-pyrrolidinone

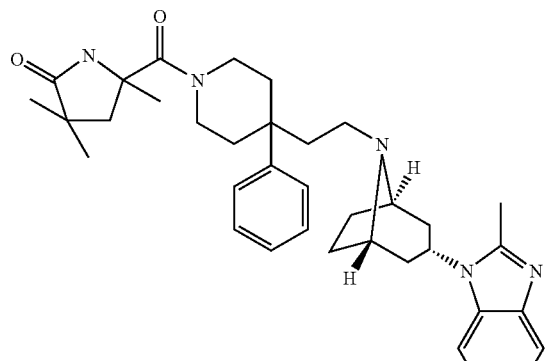

$^1$H NMR (400 MHz, DMSO-d6) δ ppm 0.9 (m, 3H), 1.1 (s, 3H), 1.4 (m, 2H), 1.6 (m, 2H), 1.8 (m, 8H), 2.0 (m, 3H), 2.3 (m, 3H), 2.5 (m, 1H), 3.3 (m, 4H), 3.3 (d, J=11.1 Hz, 5H), 3.7 (m, J=1.4 Hz, 2H), 4.5 (m, 1H), 7.1 (m, 2H), 7.2 (m, 1H), 7.4 (m, 5H), 7.5 (m, 1H), 7.8 (s, 1H).

Example 46

N-{2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-3-pyridinyl}acetamide

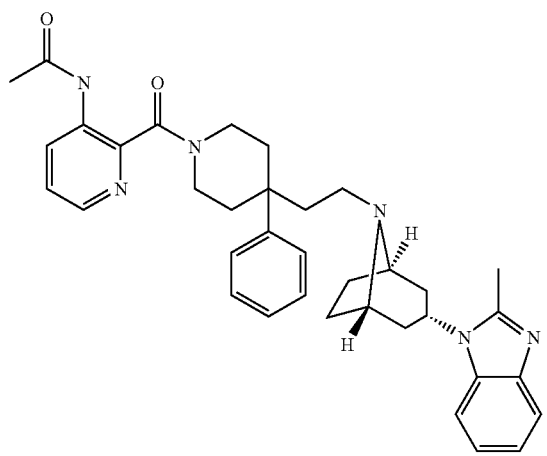

$^1$H NMR (400 MHz, DMSO-d6) δ ppm 1.6 (m, 2H), 1.8 (m, 8H), 2.0 (s, 3H), 2.2 (m, 2H), 2.4 (m, 2H), 2.4 (s, 3H), 2.5 (m, 2H), 3.1 (m, 1H), 3.3 (m, 3H), 3.4 (dd, J=7.0, 3.0 Hz, 1H), 3.9 (m, 1H), 4.5 (m, 1H), 7.1 (m, 2H), 7.2 (m, 1H), 7.4 (m, 5H), 7.4 (dd, J=8.2, 4.6 Hz, 1H), 7.5 (m, 1H), 8.0 (m, 1H), 8.3 (m, 1H), 9.7 (s, 1H).

Example 52

N-[2-(4-{2-[(1R,5S)-3-(2-methyl-1H-benzimidazol-1-yl)-8-azabicyclo[3.2.1]oct-8-yl]ethyl}-4-phenyl-1-piperidinyl)-2-oxo-1-phenylethyl]acetamide

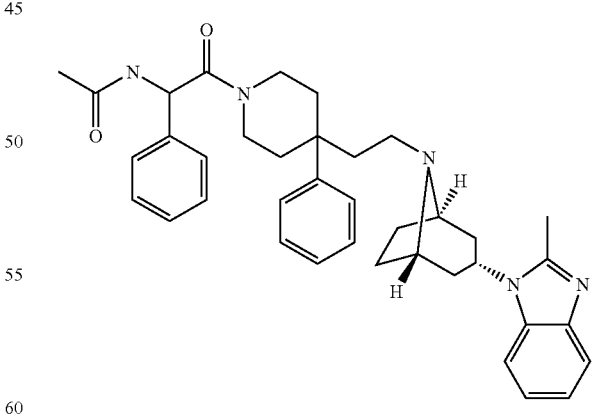

$^1$H NMR (400 MHz, DMSO-d6) δ ppm 1.6 (m, 3H), 1.8 (m, 9H), 2.0 (m, 2H), 2.4 (m, 2H), 2.5 (m, 3H), 3.2 (m, 4H), 3.4 (d, J=11.4 Hz, 3H), 3.6 (m, 2H), 3.8 (m, 1H), 4.5 (m, 1H), 5.9 (dd, J=24.6, 7.8 Hz, 1H), 7.1 (m, 2H), 7.3 (m, 10H), 7.5 (d, J=7.1 Hz, 1H), 8.5 (dd, J=7.8, 5.4 Hz, 1H).

Example 59

6-chloro-5-[(4-{2-[(1R,5S)-3-(2-methyl-1H-benz-imidazol-1-yl)-8-azabicyclo[3.2.1]oct-8-yl]ethyl}-4-phenyl-1-piperidinyl)carbonyl]-3-pyridinesulfona-mide

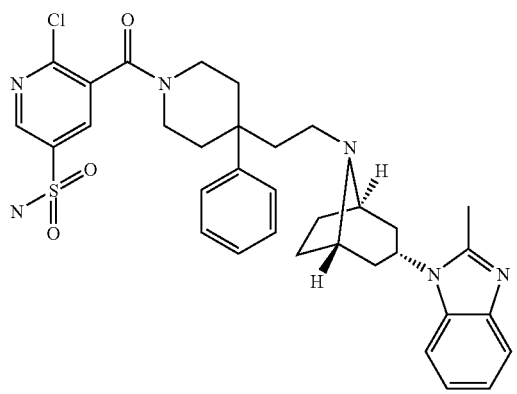

¹H NMR (400 MHz, methanol-d4) δ ppm 1.6 (m, 2H), 1.8 (m, 8H), 2.0 (d, J=6.6 Hz, 2H), 2.2 (d, J=7.7 Hz, 2H), 2.4 (m, 4H), 2.5 (s, 3H), 3.1 (m, 2H), 3.3 (m, 3H), 4.1 (m, 1H), 4.7 (s, 1H), 7.1 (m, 2H), 7.2 (m, 1H), 7.3 (m, 5H), 7.4 (m, 1H), 8.2 (m, J=61.5, 2.4 Hz, 1H), 8.8 (dd, J=2.4, 1.5 Hz, 1H).

Example 345

1-((1R,5S)-8-{2-[1-(3-cyclohexylpropanoyl)-4-phe-nyl-4-piperidinyl]ethyl}-8-azabicyclo[3.2.1]oct-3-yl)-2-methyl-1H-benzimidazole

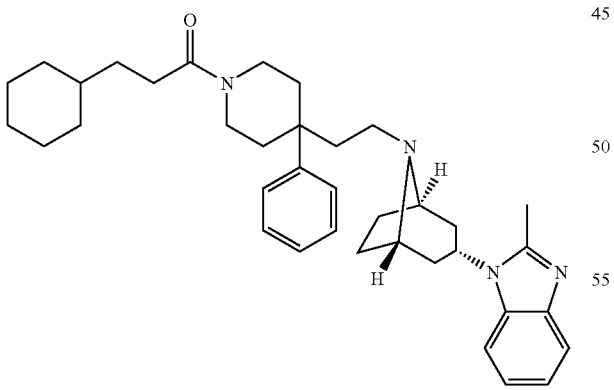

¹H NMR (400 MHz, methanol-d4) δ ppm 0.8 (m, 2H), 1.2 (m, 4H), 1.4 (q, J=7.4 Hz, 2H), 1.8 (m, 16H), 2.2 (m, 2H), 2.3 (m, 4H), 2.5 (s, 3H), 3.1 (m, 1H), 3.2 (m, 4H), 3.7 (dd, J=9.5, 4.8 Hz, 1H), 3.9 (m, 1H), 4.7 (m, 1H), 7.1 (m, 3H), 7.3 (m, 5H), 7.4 (m, 1H).

Example 346

N-[2-(4-{2-[(1R,5S)-3-(2-methyl-1H-benzimidazol-1-yl)-8-azabicyclo[3.2.1]oct-8-yl]ethyl}-4-phenyl-1-piperidinyl)-2-oxoethyl]benzamide

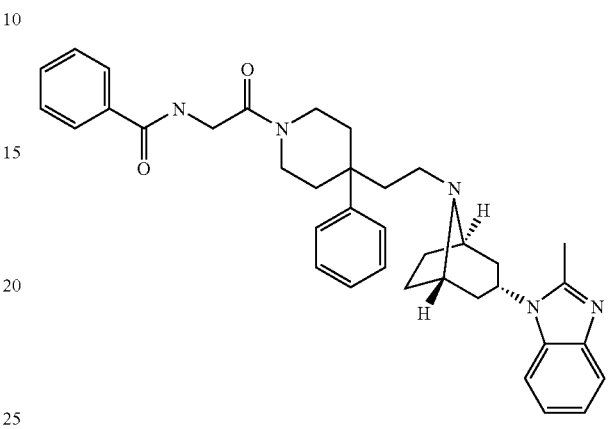

¹H NMR (400 MHz, methanol-d4) δ ppm 1.7 (m, 2H), 1.9 (m, 10H), 2.4 (m, 4H), 2.5 (m, J=3.6 Hz, 3H), 3.2 (m, 1H), 3.3 (m, 4H), 3.8 (m, 1H), 4.0 (m, 1H), 4.3 (m, 2H), 4.7 (m, 1H), 7.2 (m, 3H), 7.4 (m, 7H), 7.5 (m, 2H), 7.9 (m, 1H).

Example 347

2-methyl-1-((1R,5S)-8-{2-[4-phenyl-1-(3-pyridinyl carbonyl)-4-piperidinyl]ethyl}-8-azabicyclo[3.2.1] oct-3-yl)-1H-benzimidazole

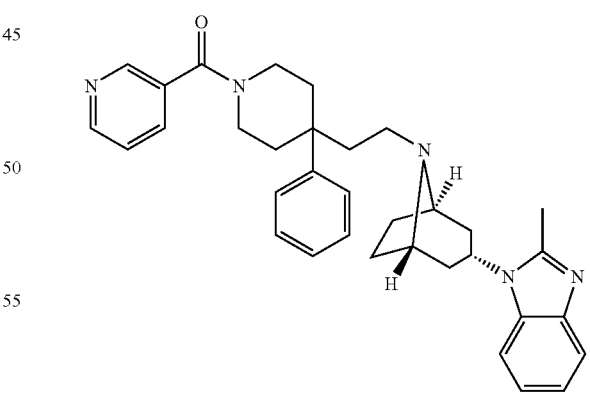

¹H NMR (400 MHz, methanol-d4) δ ppm 1.6 (m, 2H), 1.9 (m, 10H), 2.2 (m, 1H), 2.3 (m, 4H), 2.4 (s, 3H), 3.2 (m, 3H), 3.5 (m, 1H), 4.1 (m, J=13.2 Hz, 1H), 4.7 (m, 1H), 7.1 (m, 3H), 7.3 (m, 5H), 7.4 (m, 2H), 7.8 (m, 1H), 8.5 (d, J=1.4 Hz, 1H), 8.6 (dd, J=5.0, 1.8 Hz, 1H).

Example 348

3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxo-2-phenyl-1-propanol

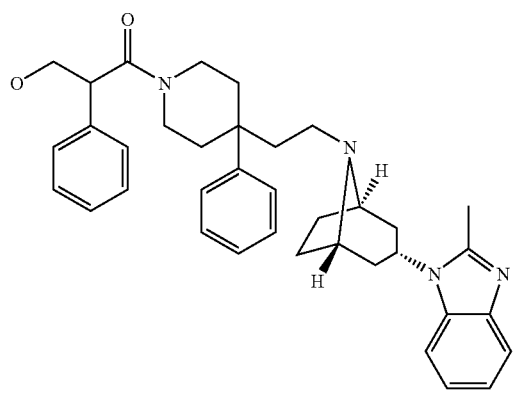

¹H NMR (400 MHz, methanol-d4) δ ppm 1.6 (m, 2H), 1.8 (m, 10H), 2.1 (m, 1H), 2.4 (m, 2H), 2.5 (s, 3H), 2.5 (s, 2H), 3.1 (m, 3H), 3.3 (m, 2H), 3.7 (m, 2H), 4.1 (m, 2H), 4.7 (m, 1H), 7.3 (m, 13H), 7.5 (m, 1H).

Example 349

4-[2-(4-{2-[(1R,5S)-3-(2-methyl-1H-benzimidazol-1-yl)-8-azabicyclo[3.2.1]oct-8-yl]ethyl}-4-phenyl-1-piperidinyl)-2-oxoethyl]phenol

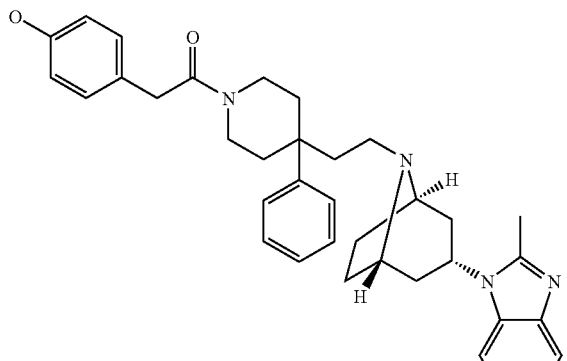

¹H NMR (400 MHz, methanol-d4) δ ppm 1.4 (m, 1H), 1.6 (m, 1H), 2.0 (m, 8H), 2.3 (m, 2H), 2.4 (s, 3H), 2.5 (m, 2H), 3.0 (m, 1H), 3.1 (m, 1H), 3.4 (s, 1H), 3.6 (m, 5H), 3.9 (m, 1H), 4.9 (m, 1H), 6.6 (m, 2H), 7.0 (m, 2H), 7.2 (m, 3H), 7.3 (m, 5H), 7.4 (m, 1H), 7.5 (m, 1H).

Example 350

2-methyl-1-[(1R,5S)-8-(2-{4-phenyl-1-[2-(trifluoromethyl)benzoyl]-4-piperidinyl}ethyl)-8-azabicyclo[3.2.1]oct-3-yl]-1H-benzimidazole

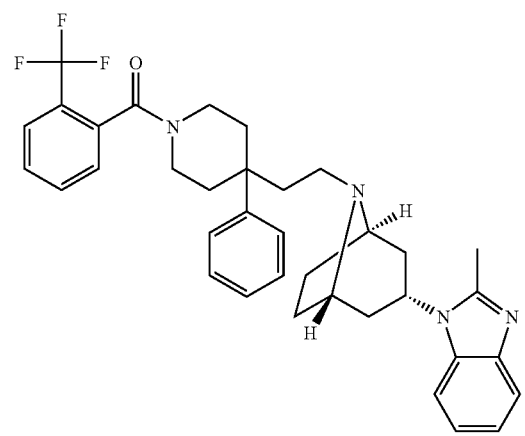

¹H NMR (400 MHz, methanol-d4) δ ppm 1.8 (m, 10H), 2.1 (m, 3H), 2.4 (m, 6H), 3.0 (m, 2H), 3.2 (m, 1H), 3.4 (m, 2H), 4.1 (m, 1H), 4.7 (m, 1H), 7.1 (m, 3H), 7.3 (m, 1H), 7.3 (m, 5H), 7.4 (m, 1H), 7.6 (m, 3H).

Example 351

1-((1R,5S)-8-{2-[1-(3-chloro-2-fluorobezoyl)-4-phenyl-4-piperidinyl]ethyl}-8-azabicyclo[3.2.1]oct-3-yl)-2-methyl-1H-benzimidazole

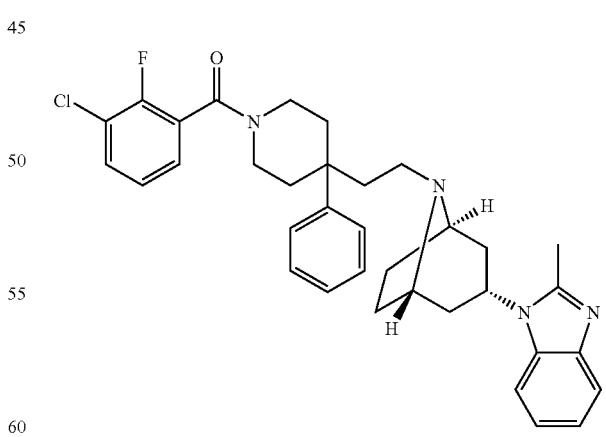

¹H NMR (400 MHz, methanol-d4) δ ppm 1.7 (m, 2H), 1.9 (m, 10H), 2.3 (m, 1H), 2.4 (m, 3H), 2.5 (s, 3H), 3.2 (m, 2H), 3.4 (m, 1H), 3.4 (m, 2H), 4.2 (m, 1H), 4.7 (m, 1H), 7.2 (m, 2H), 7.3 (m, 2H), 7.4 (m, 6H), 7.5 (m, 1H), 7.6 (m, 1H).

Example 352

1-[(1R,5S)-8-(2-{1-[(6-chloro-2-pyridinyl)carbonyl]-4-phenyl-4-piperidinyl}ethyl)-8-azabicyclo[3.2.1]oct-3-yl]-2-methyl-1H-benzimidazole

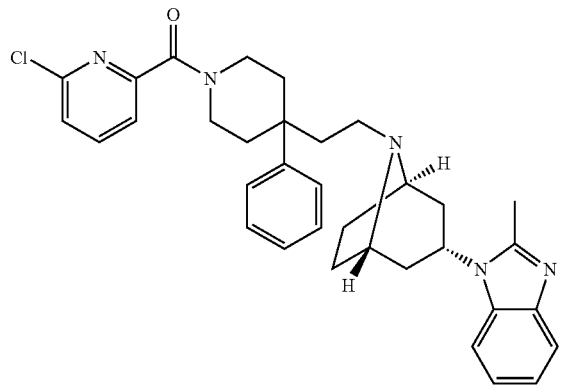

$^1$H NMR (400 MHz, methanol-d4) δ ppm 1.6 (m, 2H), 1.9 (m, 10H), 2.2 (m, 1H), 2.4 (m, 3H), 2.4 (s, 3H), 3.2 (m, 1H), 3.3 (m, 3H), 3.5 (m, 1H), 4.1 (m, 1H), 4.7 (m, 1H), 7.1 (m, 3H), 7.3 (m, 5H), 7.4 (m, 3H), 7.8 (t, J=7.7 Hz, 1H).

Example 353

1-((1R,5S)-8-{2-[1-(2-chloroisonicotinoyl)-4-phenyl-4-piperidinyl]ethyl}-8-azabicyclo[3.2.1]oct-3-yl)-2-methyl-1H-benzimidazole

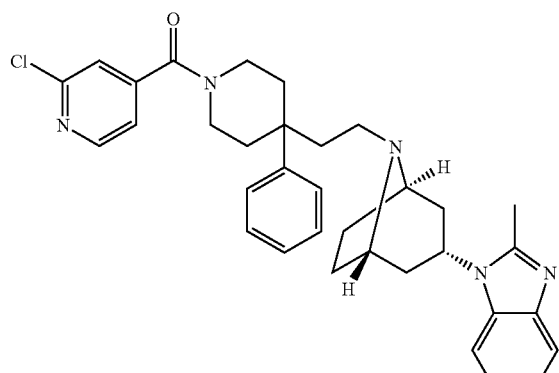

$^1$H NMR (400 MHz, methanol-d4) δ ppm 1.7 (m, 2H), 1.9 (m, 10H), 2.3 (m, 1H), 2.4 (m, 3H), 2.5 (s, 3H), 2.6 (m, 1H), 3.3 (m, 3H), 3.5 (m, 1H), 4.2 (m, 1H), 4.7 (m, 1H), 7.2 (m, 3H), 7.4 (m, 6H), 7.5 (m, 2H), 8.5 (d, J=5.0 Hz, 1H).

Example 354

1-((1R,5S)-8-{2-[1-(4-chloro-2-fluorobenzoyl)-4-phenyl-4-piperidinyl]ethyl}-8-azabicyclo[3.2.1]oct-3-yl)-2-methyl-1H-benzimidazole

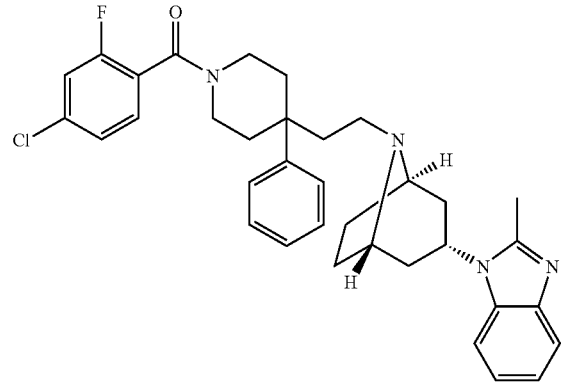

$^1$H NMR (400 MHz, methanol-d4) δ ppm 1.6 (m, 2H), 1.8 (m, 10H), 2.2 (m, 1H), 2.3 (m, 3H), 2.4 (s, 3H), 2.5 (m, 1H), 3.1 (m, 1H), 3.3 (m, 2H), 3.4 (m, 1H), 4.1 (m, 1H), 4.6 (m, 1H), 7.1 (m, 2H), 7.2 (m, 1H), 7.3 (m, 8H), 7.4 (m, 1H).

Example 355

1-((1R,5S)-8-{2-[1-(2,3-dimethylbenzoyl)-4-phenyl-4-piperidinyl]ethyl}-8-azabicyclo[3.2.1]oct-3-yl)-2-methyl-1H-benzimidazole

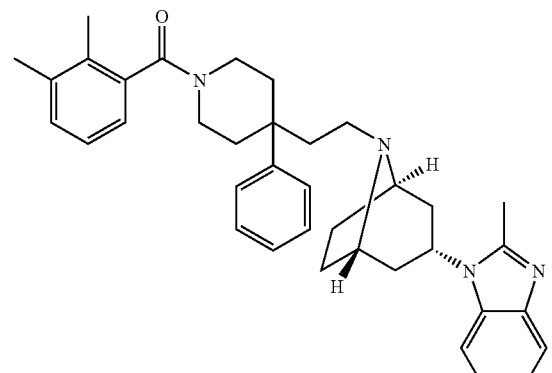

$^1$H NMR (400 MHz, methanol-d4) δ ppm 1.8 (m, 10H), 2.0 (s, 3H), 2.1 (m, 1H), 2.2 (m, 3H), 2.3 (m, 4H), 2.4 (m, 3H), 2.5 (m, 1H), 3.0 (m, 1H), 3.3 (m, 4H), 4.1 (m, 1H), 4.6 (m, 1H), 6.8 (d, J=7.1 Hz, 1H), 7.1 (m, 5H), 7.3 (m, 5H), 7.4 (m, 1H).

Example 356

1-((1R,5S)-8-{2-[1-(1H-indol-5-ylcarbonyl)-4-phenyl-4-piperidinyl]ethyl}-8-azabicyclo[3.2.1]oct-3-yl)-2-methyl-1H-benzimidazole

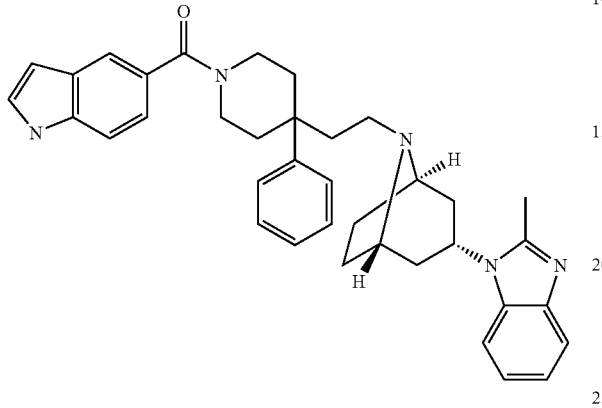

¹H NMR (400 MHz, methanol-d4) δ ppm 1.6 (m, 2H), 1.9 (m, 10H), 2.2 (m, 3H), 2.4 (m, 4H), 3.3 (m, 2H), 3.7 (m, 1H), 4.1 (m, 1H), 4.5 (m, 2H), 4.7 (m, 1H), 6.4 (d, J=2.5 Hz, 1H), 7.1 (m, 2H), 7.2 (m, 1H), 7.2 (d, J=3.2 Hz, 1H), 7.3 (m, 8H), 7.4 (m, 1H), 7.6 (s, 1H).

Example 357

1-((1R,5S)-8-{2-[1-(1H-indol-6-ylcarbonyl)-4-phenyl-4-piperidinyl]ethyl}-8-azabicyclo[3.2.1]oct-3-yl)-2-methyl-1H-benzimidazole

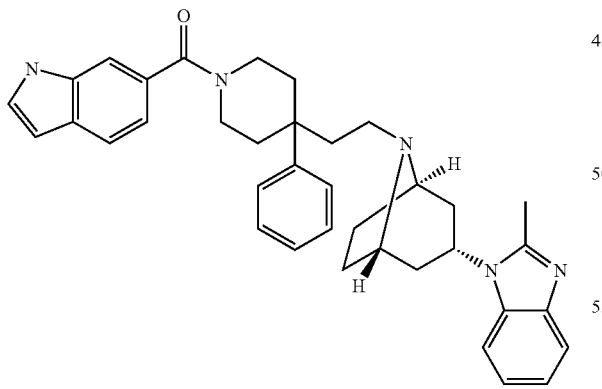

¹H NMR (400 MHz, methanol-d4) δ ppm 1.2 (m, 2H), 1.6 (m, 2H), 1.8 (m, 8H), 2.2 (m, 5H), 2.4 (m, 3H), 2.5 (m, 1H), 3.3 (m, 2H), 3.6 (m, 1H), 4.0 (m, 1H), 4.6 (m, 1H), 6.4 (d, J=2.1 Hz, 1H), 7.0 (dd, J=7.8, 1.4 Hz, 1H), 7.1 (m, 2H), 7.2 (m, 1H), 7.3 (d, J=3.2 Hz, 1H), 7.3 (m, 6H), 7.4 (s, 1H), 7.4 (m, 1H), 7.5 (m, 1H).

Example 358

2-chloro-6-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]phenol

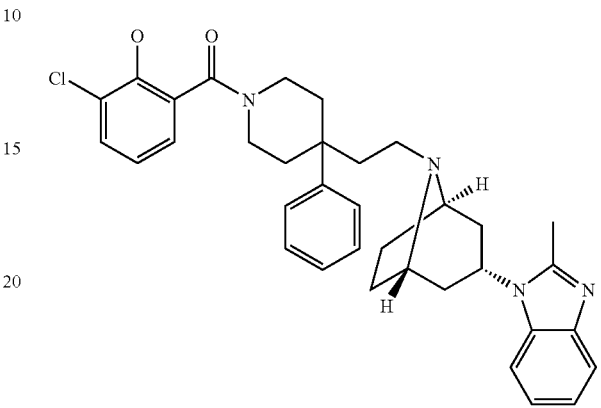

¹H NMR (400 MHz, methanol-d4) δ ppm 1.3 (m, 2H), 1.7 (m, 2H), 2.0 (m, 10H), 2.4 (m, 5H), 2.5 (m, 3H), 3.6 (m, 2H), 4.1 (m, 1H), 4.7 (m, 1H), 6.9 (t, J=7.7 Hz, 1H), 7.1 (d, J=7.5 Hz, 1H), 7.2 (m, 3H), 7.4 (m, 6H), 7.5 (m, 1H).

Example 359

2-methyl-1-[(1R,5S)-8-(2-{1-[3-(2-methylphenyl)propanoyl]-4-phenyl-4-piperidinyl}ethyl)-8-azabicyclo[3.2.1]oct-3-yl]-1H-benzimidazole

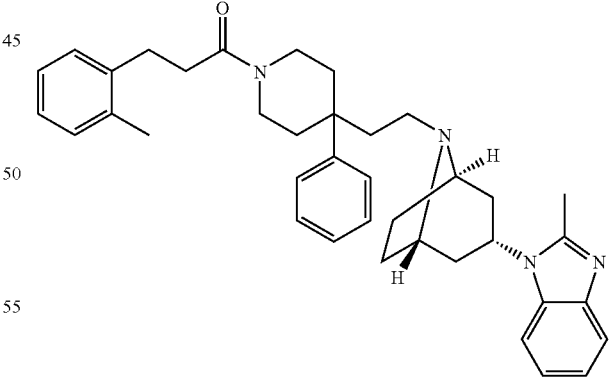

¹H NMR (400 MHz, methanol-d4) δ ppm 1.2 (m, 1H), 1.4 (m, 1H), 1.6 (m, 4H), 1.9 (m, 6H), 2.1 (m, 1H), 2.3 (m, 3H), 2.3 (m, 2H), 2.5 (m, 3H), 2.6 (m, 4H), 2.8 (m, 2H), 3.0 (m, 2H), 3.2 (d, J=5.7 Hz, 1H), 3.5 (m, 1H), 3.9 (m, 1H), 4.6 (m, 1H), 7.0 (m, 2H), 7.0 (m, 2H), 7.1 (m, 2H), 7.1 (m, 1H), 7.3 (m, 5H), 7.4 (m, 1H).

Example 360

2-methyl-1-[(1R,5S)-8-(2-{1-[(4-methylcyclohexyl)carbonyl]-4-phenyl-4-piperidinyl}ethyl)-8-azabicyclo[3.2.1]oct-3-yl]-1H-benzimidazole

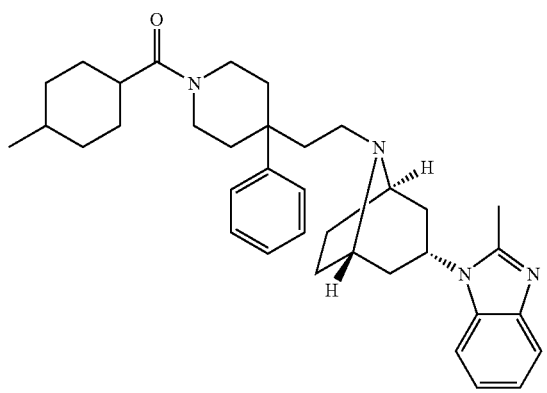

$^1$H NMR (400 MHz, methanol-d4) δ ppm 0.8 (m, 2H), 0.9 (m, 4H), 1.5 (m, 18H), 2.3 (m, 4H), 2.5 (m, 3H), 2.5 (m, 1H), 3.1 (m, 1H), 3.2 (m, 3H), 3.7 (m, 1H), 3.9 (m, 1H), 4.7 (m, 1H), 7.1 (m, 2H), 7.2 (m, 1H), 7.3 (m, 5H), 7.4 (m, 1H).

Example 361

2-methyl-1-((1R,5S)-8-{2-[4-phenyl-1-(3-phenylbutanoyl)-4-piperidinyl]ethyl}-8-azabicyclo[3.2.1]oct-3-yl)-1H-benzimidazole

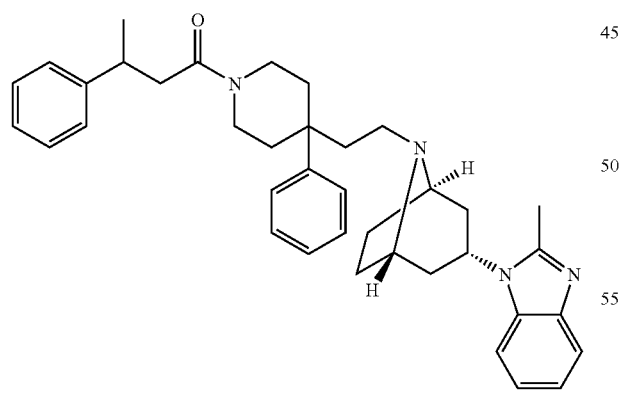

$^1$H NMR (400 MHz, methanol-d4) δ ppm 1.2 (m, 4H), 1.4 (m, 1H), 1.6 (m, 3H), 1.9 (m, 8H), 2.3 (m, 2H), 2.5 (m, 1H), 2.7 (m, 2H), 3.0 (m, 2H), 3.0 (m, 1H), 3.2 (m, 4H), 3.5 (m, 1H), 3.7 (m, 1H), 3.9 (m, 1H), 4.7 (m, 1H), 7.1 (m, 5H), 7.3 (m, 8H), 7.4 (m, 1H).

Example 362

3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxopropyl phenyl ether

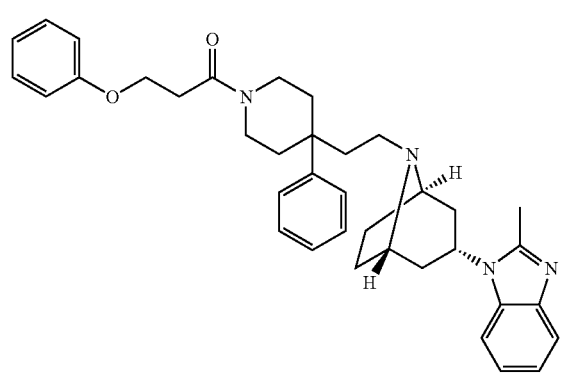

$^1$H NMR (400 MHz, methanol-d4) δ ppm 1.3 (m, 4H), 1.8 (m, 10H), 2.4 (m, 4H), 2.5 (s, 3H), 2.6 (m, 1H), 2.9 (m, 2H), 3.2 (m, 1H), 3.4 (m, 2H), 3.8 (m, 1H), 4.0 (m, 1H), 4.8 (m, 1H), 6.9 (m, 3H), 7.2 (m, 5H), 7.4 (m, 5H), 7.5 (m, 1H).

Example 363

1-((1R,5S)-8-{2-[1-(cyclohexylacetyl)-4-phenyl-4-piperidinyl]ethyl}-8-azabicyclo[3.2.1]oct-3-yl)-2-methyl-1H-benzimidazole

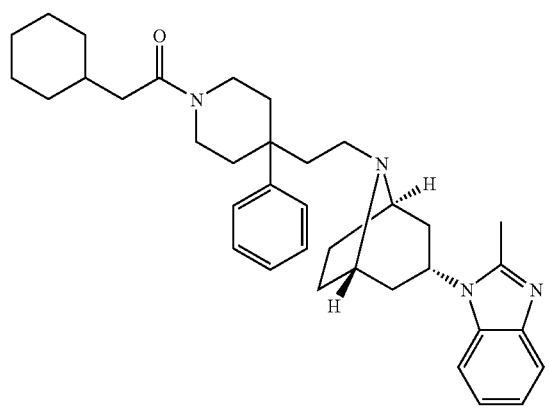

$^1$H NMR (400 MHz, methanol-d4) δ ppm 1.0 (m, 2H), 1.2 (m, 3H), 1.7 (m, 9H), 1.9 (m, 11H), 2.3 (m, 4H), 2.4 (m, 2H), 2.5 (s, 3H), 3.2 (m, 1H), 3.3 (m, 1H), 3.8 (m, 1H), 4.0 (m, 1H), 4.8 (m, 1H), 7.2 (m, 2H), 7.2 (m, 1H), 7.4 (m, 5H), 7.5 (m, 1H).

Example 62

1-((1R,5S)-8-{2-[1-(1,3-benzodioxol-5-ylcarbonyl)-4-phenyl-4-piperidinyl]ethyl}-8-azabicyclo[3.2.1]oct-3-yl)-2-methyl-1H-benzimidazole

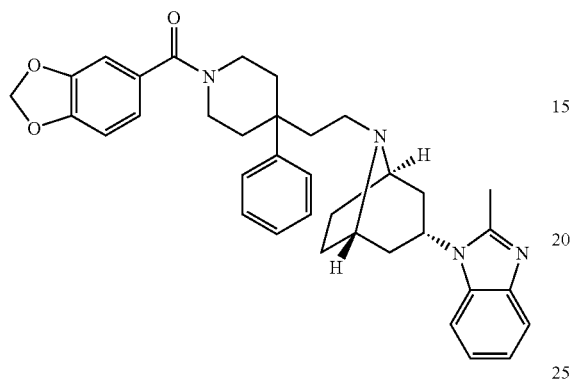

$^1$H NMR (400 MHz, methanol-d4) δ ppm 1.3 (m, 2H), 1.7 (m, 2H), 1.9 (m, 11H), 2.3 (m, 5H), 2.5 (d, J=6.4 Hz, 3H), 2.6 (m, 1H), 3.3 (m, 1H), 3.7 (m, 1H), 4.1 (m, 1H), 4.7 (m, 1H), 6.9 (m, 2H), 7.2 (m, 2H), 7.2 (m, 1H), 7.4 (m, 6H), 7.5 (m, 1H).

Example 63

1-[(1R,5S)-8-(2-{1-[fluoro(phenyl)acetyl]-4-phenyl-4-piperidinyl}ethyl)-8-azabicyclo[3.2.1]oct-3-yl]-2-methyl-1H-benzimidazole

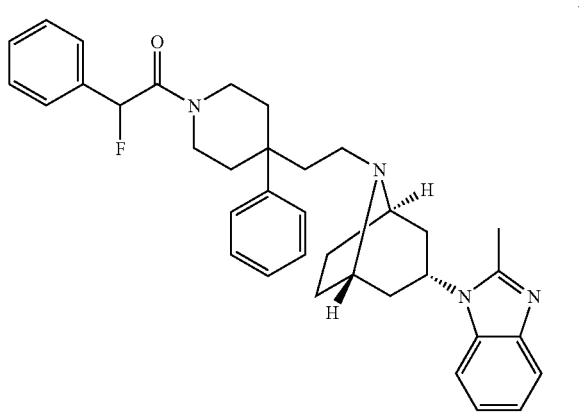

$^1$H NMR (400 MHz, methanol-d4) δ ppm 1.9 (m, 14H), 2.3 (m, 3H), 2.5 (m, 3H), 3.0 (m, 3H), 3.6 (m, 1H), 4.0 (m, 1H), 4.7 (m, 1H), 6.3 (dd, J=48.3, 20.9 Hz, 1H), 7.3 (m, 14H).

Example 64

3-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-pyridinylamine

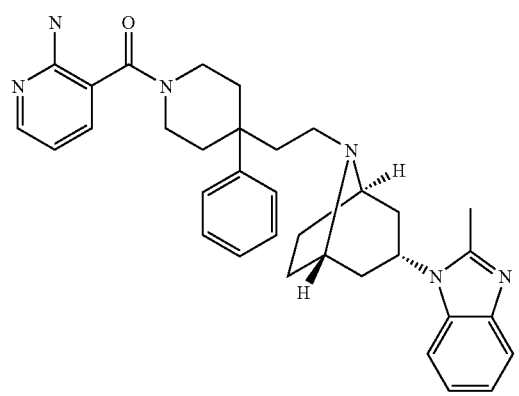

$^1$H NMR (400 MHz, methanol-d4) δ ppm 1.7 (m, 2H), 1.9 (m, 10H), 2.3 (m, 4H), 2.5 (s, 3H), 3.3 (m, 2H), 3.8 (m, 4H), 4.7 (m, 1H), 6.7 (dd, J=7.3, 5.2 Hz, 1H), 7.2 (m, 3H), 7.4 (m, 5H), 7.5 (m, 1H), 8.0 (dd, J=5.2, 2.0 Hz, 1H).

Example 66

2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-4H-chromen-4-one

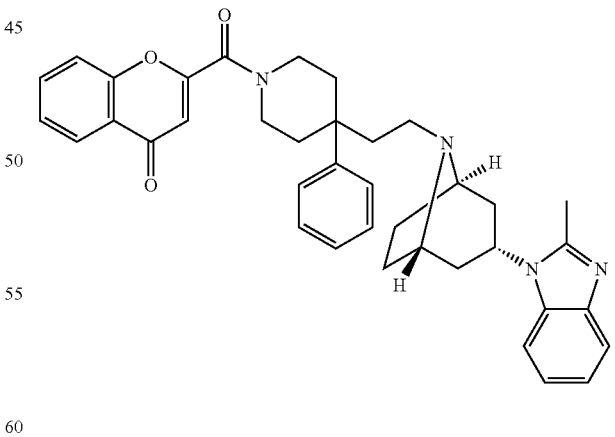

$^1$H NMR (400 MHz, methanol-d4) δ ppm 1.3 (m, 3H), 1.7 (m, 2H), 2.0 (m, 8H), 2.4 (m, 4H), 2.5 (m, 3H), 2.9 (m, 1H), 3.1 (m, 1H), 3.3 (m, 2H), 3.6 (m, 1H), 4.1 (m, 1H), 4.8 (m, 1H), 7.2 (m, 2H), 7.3 (m, 1H), 7.4 (m, 5H), 7.5 (m, 2H), 7.6 (d, J=7.8 Hz, 1H), 7.8 (m, 1H), 8.2 (dd, J=8.0, 1.6 Hz, 1H).

Example 67

2-methyl-1-[(1R,5S)-8-(2-{4-phenyl-1-[3-(trifluoromethyl)benzoyl]-4-piperidinyl}ethyl)-8-azabicyclo[3.2.1]oct-3-yl-1H-benzimidazole

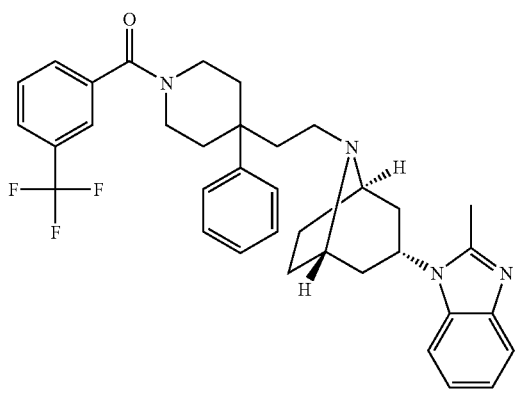

$^1$H NMR (400 MHz, methanol-d4) δ ppm 1.3 (m, 1H), 1.7 (m, 2H), 1.9 (m, 10H), 2.3 (m, 1H), 2.4 (m, 4H), 2.5 (s, 3H), 3.3 (m, 2H), 3.5 (m, 1H), 4.2 (m, 1H), 4.7 (m, 1H), 7.2 (m, 2H), 7.2 (m, 1H), 7.4 (m, 5H), 7.5 (m, 1H), 7.7 (m, 2H), 7.7 (s, 1H), 7.8 (m, 1H).

Example 71

2-methyl-1-[(1R,5S)-8-(2-{1-[3-(4-methylphenyl)propanoyl]-4-phenyl-4-piperidinyl}ethyl)-8-azabicyclo[3.2.1]oct-3-yl]-1H-benzimidazole

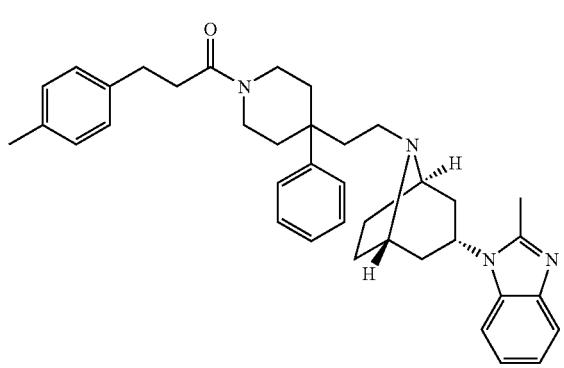

$^1$H NMR (400 MHz, methanol-d4) δ ppm 1.5 (m, 1H), 1.7 (m, 4H), 1.8 (m, 2H), 1.9 (m, 10H), 2.2 (m, 1H), 2.2 (s, 3H), 2.4 (m, 2H), 2.5 (m, 3H), 2.8 (m, 2H), 3.2 (m, 2H), 3.6 (m, 1H), 3.9 (m, 1H), 4.7 (m, 1H), 7.1 (m, 3H), 7.2 (m, 3H), 7.4 (m, 6H), 7.5 (m, 1H).

Example 72

1-((1R,5S)-8-{2-[1-(3,4-dichlorobenzoyl)-4-phenyl-4-piperidinyl]ethyl}-8-azabicyclo[3.2.1]oct-3-yl)-2-methyl-1H-benzimidazole

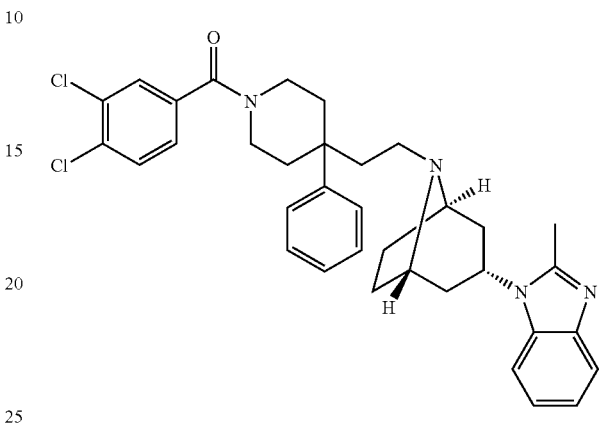

$^1$H NMR (400 MHz, methanol-d4) δ ppm 1.7 (m, 2H), 1.9 (m, 11H), 2.3 (m, 1H), 2.4 (m, 4H), 2.5 (m, 3H), 3.3 (m, 2H), 3.6 (m, 1H), 4.1 (m, 1H), 4.7 (m, 1H), 7.2 (m, 2H), 7.2 (m, 1H), 7.3 (dd, J=8.2, 1.8 Hz, 1H), 7.4 (m, 5H), 7.5 (m, 1H), 7.6 (m, 2H).

Example 73

1-((1R,5S)-8-{2-[1-(3-chlorobenzoyl)-4-phenyl-4-piperidinyl]ethyl}-8-azabicyclo[3.2.1]oct-3-yl)-2-methyl-1H-benzimidazole

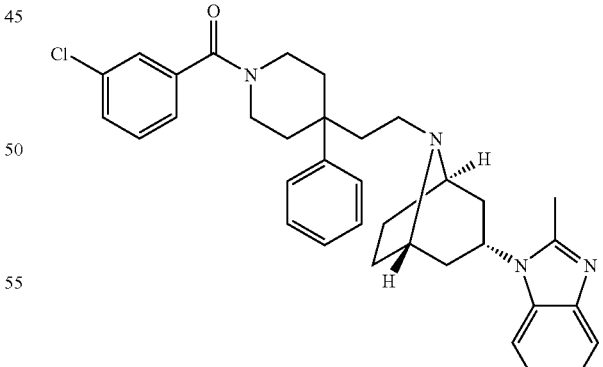

$^1$H NMR (400 MHz, methanol-d4) δ ppm 1.7 (m, 2H), 1.9 (m, 10H), 2.2 (m, 1H), 2.4 (m, 3H), 2.5 (s, 3H), 3.3 (m, 4H), 3.6 (m, 1H), 4.1 (m, J=11.1, 4.3 Hz, 1H), 4.7 (m, 1H), 7.2 (m, 2H), 7.2 (m, 1H), 7.3 (m, 1H), 7.4 (m, 5H), 7.4 (m, 2H), 7.5 (m, 1H).

Example 74

1-((1R,5S)-8-{2-[1-(mesitylcarbonyl)-4-phenyl-4-piperidinyl]ethyl}-8-azabicyclo[3.2.1]oct-3-yl)-2-methyl-1H-benzimidazole

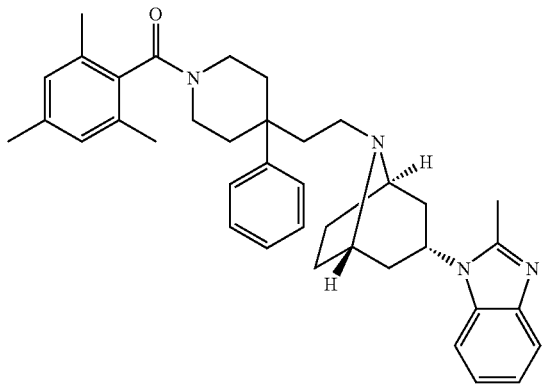

¹H NMR (400 MHz, methanol-d4) δ ppm 1.7 (m, 2H), 1.8 (m, 1H), 1.9 (m, 10H), 2.1 (s, 3H), 2.2 (m, 1H), 2.3 (m, 6H), 2.4 (m, 3H), 2.5 (m, 3H), 3.1 (m, 1H), 3.3 (m, 3H), 4.2 (m, 1H), 4.7 (m, 1H), 6.9 (s, 1H), 7.2 (m, 2H), 7.2 (m, 1H), 7.4 (m, 5H), 7.5 (m, 1H).

Example 78

1-{(1R,5S)-8-[2-(1-butyryl-4-phenyl-4-piperidinyl)ethyl]-8-azabicyclo[3.2.1]oct-3-yl}-2-methyl-1H-benzimidazole

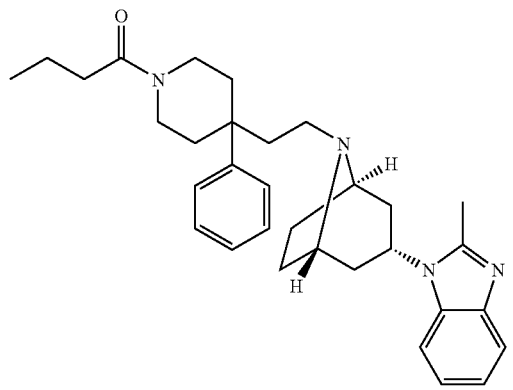

¹H NMR (400 MHz, methanol-d4) δ ppm 1.0 (t, J=7.4 Hz, 3H), 1.6 (m, 4H), 1.9 (m, 10H), 2.4 (m, 7H), 2.5 (s, 3H), 3.2 (m, 1H), 3.3 (m, 2H), 3.7 (m, 1H), 4.0 (d, J=3.7 Hz, 1H), 4.7 (m, 1H), 7.2 (m, 2H), 7.2 (m, 1H), 7.4 (m, 5H), 7.5 (m, 1H).

Example 79

1-((1R,5S)-8-{2-[1-(3-fluorobenzoyl)-4-phenyl-4-piperidinyl]ethyl}-8-azabicyclo[3.2.1]oct-3-yl)-2-methyl-1H-benzimidazole

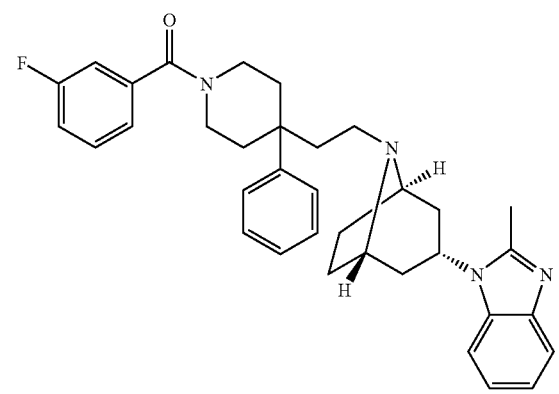

¹H NMR (400 MHz, methanol-d4) δ ppm 1.7 (m, 2H), 2.0 (m, 10H), 2.2 (m, 1H), 2.4 (m, 3H), 2.5 (m, 3H), 3.3 (m, 4H), 3.5 (m, J=5.6, 1.6 Hz, 1H), 4.1 (m, J=4.0 Hz, 1H), 4.7 (m, 1H), 7.2 (m, 6H), 7.4 (m, 5H), 7.5 (m, 1H), 7.5 (m, 1H).

Example 81

N-{(1S,2R)-2-hydroxy-1-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]propyl}acetamide

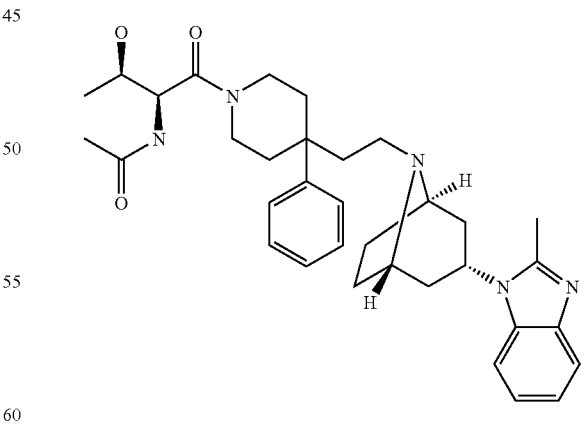

¹H NMR (400 MHz, methanol-d4) δ ppm 1.2 (m, 3H), 1.7 (m, 2H), 1.9 (m, 13H), 2.4 (m, 5H), 2.5 (s, 3H), 3.3 (m, 5H), 4.0 (m, 3H), 4.8 (m, 2H), 7.2 (m, 2H), 7.2 (m, 1H), 7.4 (m, 5H), 7.5 (m, 1H).

Example 82

2-methyl-1-((1R,5S)-8-{2-[4-phenyl-1-(4,4,4-trifluo-robutanoyl)-4-piperidinyl]ethyl}-8-azabicyclo[3.2.1]oct-3-yl)-1H-benzimidazole

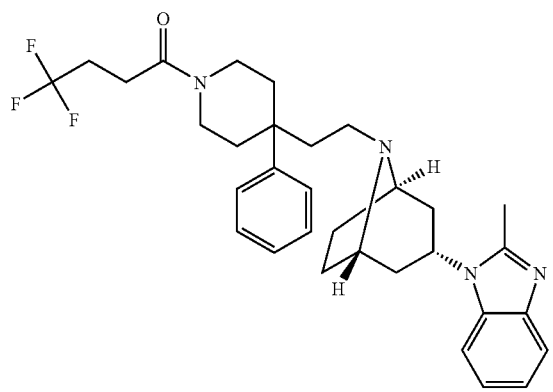

¹H NMR (400 MHz, methanol-d4) δ ppm 1.7 (m, 2H), 1.9 (m, 10H), 2.3 (m, 2H), 2.5 (m, 4H), 2.5 (s, 3H), 2.7 (m, 2H), 3.2 (m, 1H), 3.3 (m, 3H), 3.7 (m, 1H), 4.0 (m, 1H), 4.7 (m, 1H), 7.2 (m, 2H), 7.2 (m, 1H), 7.4 (m, 5H), 7.5 (m, 1H).

Example 83

1-((1R,5S)-8-{2-[1-(1H-indol-3-ylacetyl)-4-phenyl-4-piperidinyl]ethyl}-8-azabicyclo[3.2.1]oct-3-yl)-2-methyl-1H-benzimidazole

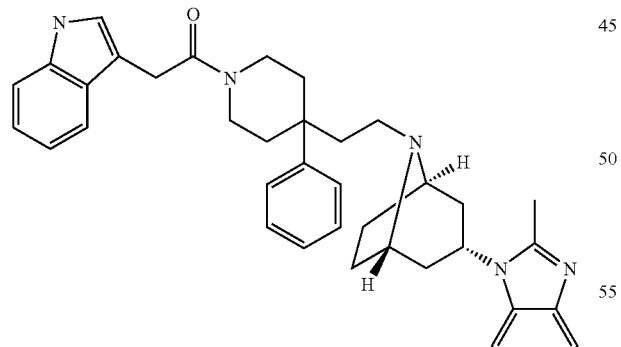

¹H NMR (400 MHz, methanol-d4) δ ppm 1.4 (m, 1H), 1.7 (m, 6H), 1.9 (m, 6H), 2.0 (m, 1H), 2.2 (m, 1H), 2.4 (m, 2H), 2.5 (s, 3H), 3.1 (m, 1H), 3.2 (m, 3H), 3.8 (m, 2H), 3.9 (m, 1H), 4.1 (m, 1H), 4.7 (m, 1H), 7.0 (t, J=7.0 Hz, 1H), 7.1 (m, 2H), 7.2 (m, 3H), 7.4 (m, 6H), 7.5 (m, 1H), 7.6 (d, J=7.8 Hz, 1H).

Example 85

2-methyl-1-((1R,5S)-8-{2-[1-(3-nitrobenzoyl)-4-phenyl-4-piperidinyl]ethyl}-8-azabicyclo[3.2.1]oct-3-yl)-1H-benzimidazole

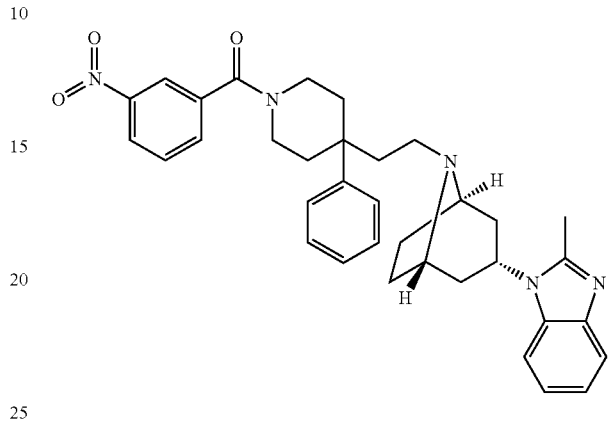

¹H NMR (400 MHz, methanol-d4) δ ppm 1.7 (m, 2H), 2.0 (m, 12H), 2.3 (m, 1H), 2.4 (m, 3H), 2.5 (s, 3H), 3.3 (m, 2H), 3.6 (m, 1H), 4.2 (m, J=113.6 Hz, 1H), 4.7 (m, 1H), 7.2 (m, 3H), 7.4 (m, 5H), 7.5 (m, 1H), 7.7 (t, J=7.8 Hz, 1H), 7.8 (d, J=7.8 Hz, 1H), 8.3 (s, 1H), 8.3 (d, J=8.2 Hz, 1H).

Example 86

5,5-dimethyl-4-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]dihydro-2(3H)-furanone

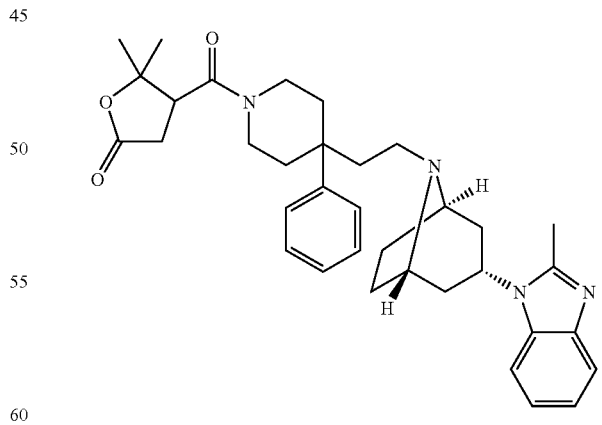

¹H NMR (400 MHz, methanol-d4) δ ppm 1.2 (m, 2H), 1.5 (m, 3H), 1.9 (m, 14H), 2.4 (m, 4H), 2.5 (s, 3H), 2.8 (m, 2H), 3.1 (m, 1H), 3.4 (m, 2H), 3.8 (m, 2H), 4.1 (m, 1H), 4.8 (m, 1H), 7.2 (m, 3H), 7.4 (m, 5H), 7.5 (m, 1H).

Example 88

2-methyl-1-((1R,5S)-8-{2-[1-(2-nitrobenzoyl)-4-phenyl-4-piperidinyl]ethyl}-8-azabicyclo[3.2.1]oct-3-yl)-1H-benzimidazole

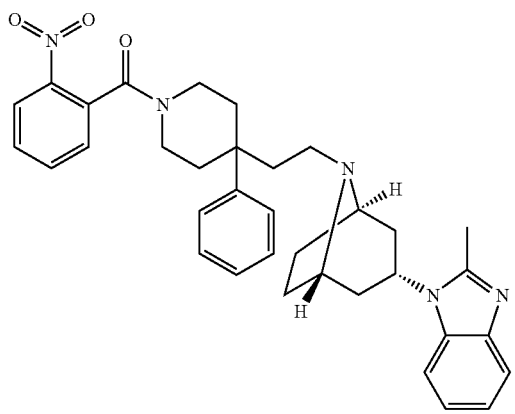

$^1$H NMR (400 MHz, methanol-d4) δ ppm 1.3 (m, 1H), 1.7 (m, 2H), 2.0 (m, 10H), 2.2 (m, 1H), 2.4 (m, 3H), 2.5 (m, J=1.4 Hz, 3H), 3.2 (m, 2H), 3.4 (m, 2H), 4.2 (m, 1H), 4.7 (m, 1H), 7.2 (m, 2H), 7.3 (m, 1H), 7.4 (m, 6H), 7.5 (m, 1H), 7.7 (m, 1H), 7.8 (m, 1H), 8.2 (m, 1H).

Example 90

2-methyl-1-((1R,5S)-8-{2-[1-(1-naphthoyl)-4-phenyl-4-piperidinyl]ethyl}-8-azabicyclo[3.2.1]oct-3-yl)-1H-benzimidazole

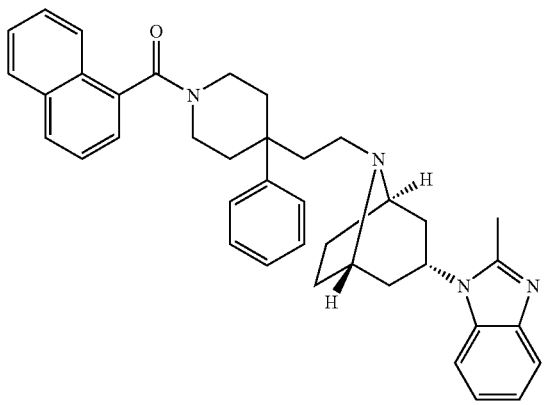

$^1$H NMR (400 MHz, methanol-d4) δ ppm 0.6 (m, 2H), 1.8 (m, 12H), 2.4 (m, 4H), 2.5 (m, 3H), 3.3 (m, 2H), 3.5 (m, 1H), 4.3 (m, 1H), 4.7 (m, 1H), 7.2 (m, 2H), 7.2 (m, 1H), 7.4 (m, 6H), 7.5 (m, 5H), 7.9 (m, 2H).

Example 91

1-((1R,5S)-8-{2-[1-(2,3-dichlorobenzoyl)-4-phenyl-4-piperidinyl]ethyl}-8-azabicyclo[3.2.1]oct-3-yl)-2-methyl-1H-benzimidazole

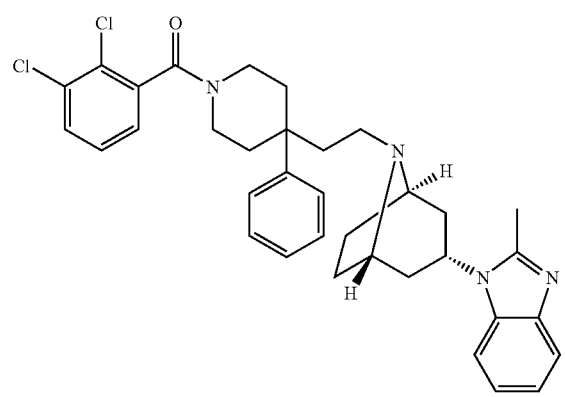

$^1$H NMR (400 MHz, methanol-d4) δ ppm 1.8 (m, 2H), 1.9 (m, 8H), 2.1 (m, 2H), 2.3 (m, 1H), 2.5 (m, 3H), 2.5 (m, 3H), 3.2 (m, 1H), 3.4 (m, 4H), 4.2 (m, 1H), 4.8 (m, 1H), 7.2 (m, 2H), 7.3 (m, 1H), 7.4 (m, 7H), 7.5 (m, 1H), 7.6 (m, 1H).

Example 92

1-methyl-2-(4-{2-[(1R,5S)-3-(2-methyl-1H-benzimidazol-1-yl)-8-azabicyclo[3.2.1]oct-8-yl]ethyl}-4-phenyl-1-piperidinyl)-2-oxoethyl phenyl ether

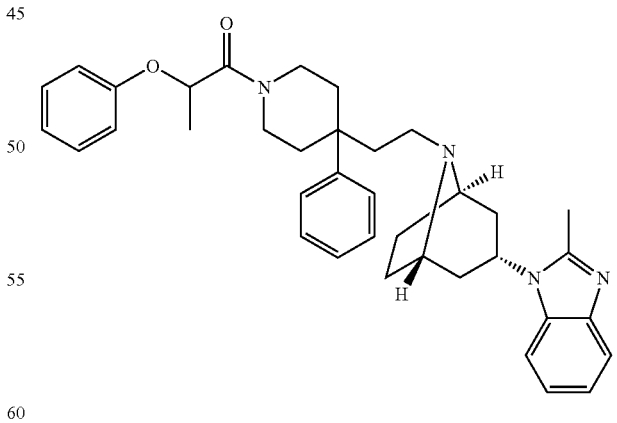

$^1$H NMR (400 MHz, methanol-d4) δ ppm 1.5 (dd, J=19.8, 6.6 Hz, 3H), 1.9 (m, 13H), 2.3 (m, 2H), 2.4 (m, 2H), 2.5 (m, 3H), 3.1 (m, 1H), 3.3 (m, 2H), 3.9 (m, 2H), 4.7 (m, 1H), 5.1 (m, 1H), 6.9 (m, 3H), 7.2 (m, 5H), 7.4 (m, 5H), 7.5 (m, 1H).

Example 93

3-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-4H-chromen-4-one

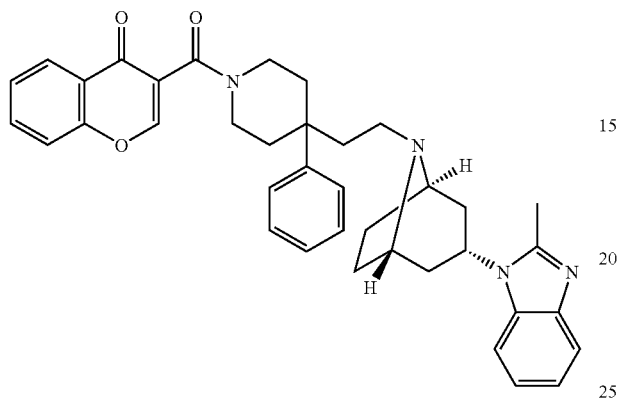

$^1$H NMR (400 MHz, methanol-d4) δ ppm 1.7 (m, 2H), 1.9 (m, 8H), 2.1 (m, 2H), 2.4 (m, 4H), 2.5 (m, J=1.4 Hz, 3H), 3.3 (m, 4H), 3.5 (m, 1H), 4.2 (s, 1H), 4.8 (m, 1H), 7.0 (m, 1H), 7.2 (m, 2H), 7.3 (m, 1H), 7.4 (m, 5H), 7.5 (m, 2H), 7.7 (d, J=7.8 Hz, 1H), 7.8 (m, 1H), 8.2 (dd, J=8.2, 1.4 Hz, 1H).

Example 94

1-((1R,5S)-8-{2-[1-(2,3-dihydro-1,4-benzodioxin-2-ylcarbonyl)-4-phenyl-4-piperidinyl]ethyl}-8-azabicyclo[3.2.1]oct-3-yl)-2-methyl-1H-benzimidazole

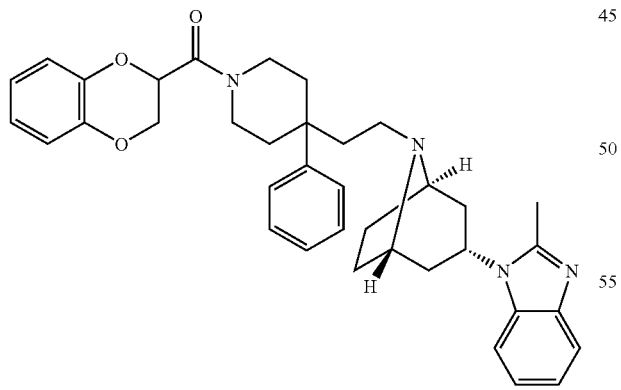

$^1$H NMR (400 MHz, methanol-d4) δ ppm 1.7 (m, 2H) 2.0 (m, 10H) 2.3 (m, 4H) 2.6 (m, 3H) 3.1 (m, 1H) 3.4 (m, 3H) 4.0 (m, 2H) 4.2 (m, 1H) 4.4 (m, 1H) 4.8 (m, 1H) 5.1 (m, 1H) 6.8 (m, 3H) 6.9 (m, 1H) 7.2 (m, 2H) 7.3 (t, J=7.0 Hz, 1H) 7.4 (m, 5H) 7.5 (m, 1H).

Example 96

2-methyl-1-((1R,5S)-8-{2-[1-(4-methylbenzoyl)-4-phenyl-4-piperidinyl]ethyl}-8-azabicyclo[3.2.1]oct-3-yl)-1H-benzimidazole

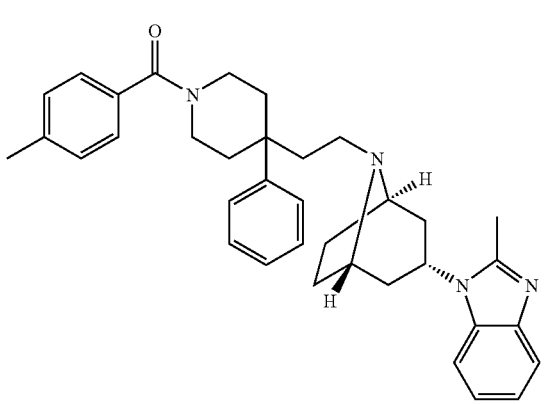

$^1$H NMR (400 MHz, methanol-d4) δ ppm 1.7 (m, 2H), 1.9 (m, 10H), 2.2 (m, 2H), 2.4 (m, 7H), 2.5 (s, 3H), 3.3 (m, 2H), 3.6 (m, 1H), 4.1 (m, 1H), 4.7 (m, 1H), 7.2 (m, 2H), 7.3 (m, 5H), 7.4 (m, 5H), 7.5 (m, 1H).

Example 97

1-((1R,5S)-8-{2-[1-(4-ethoxybenzoyl)-4-phenyl-4-piperidinyl]ethyl}-8-azabicyclo[3.2.1]oct-3-yl)-2-methyl-1H-benzimidazole

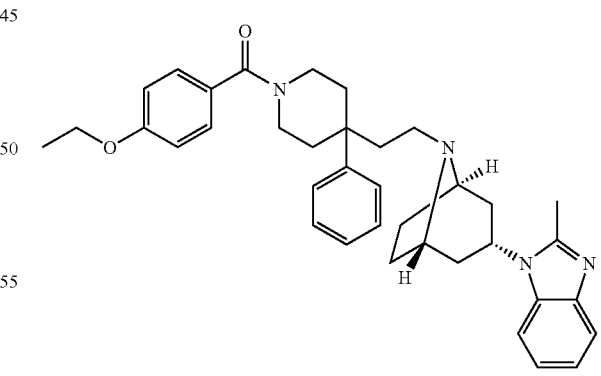

$^1$H NMR (400 MHz, methanol-d4) δ ppm 1.3 (m, 1H), 1.4 (t, J=7.1 Hz, 3H), 1.7 (m, 2H), 1.9 (m, 10H), 2.3 (m, 4H), 2.5 (m, 3H), 3.3 (m, 3H), 3.7 (m, 1H), 4.1 (m, 3H), 4.7 (m, 1H), 7.0 (m, 2H), 7.2 (m, 2H), 7.2 (m, 1H), 7.4 (m, 2H), 7.4 (m, 5H), 7.5 (m, 1H).

Example 99

1-((1R,5S)-8-{2-[1-(2-ethoxybenzoyl)-4-phenyl-4-piperidinyl]ethyl}-8-azabicyclo[3.2.1]oct-3-yl)-2-methyl-1H-benzimidazole

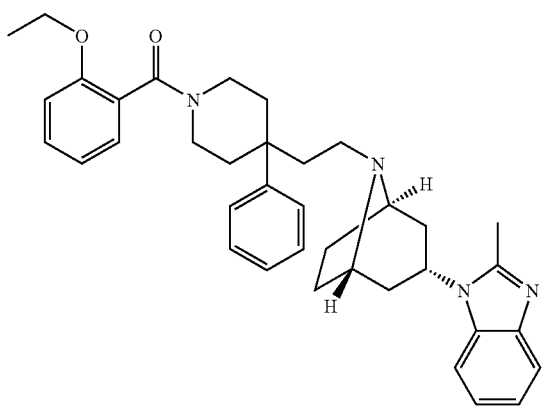

$^1$H NMR (400 MHz, methanol-d4) δ ppm 1.2 (t, J=7.1 Hz, 2H), 1.5 (t, J=7.0 Hz, 2H), 1.9 (m, 12H), 2.3 (m, 5H), 2.5 (m, 3H), 3.2 (m, 1H), 3.4 (m, 3H), 4.0 (q, J=7.1 Hz, 1H), 4.1 (m, 2H), 4.7 (m, 1H), 7.0 (m, 3H), 7.2 (m, 3H), 7.4 (m, 5H), 7.5 (d, J=7.1 Hz, 1H).

Example 100

1-((1R,5S)-8-{2-[1-(2,4-dimethylbenzoyl)-4-phenyl-4-piperidinyl]ethyl}-8-azabicyclo[3.2.1]oct-3-yl)-2-methyl-1H-benzimidazole

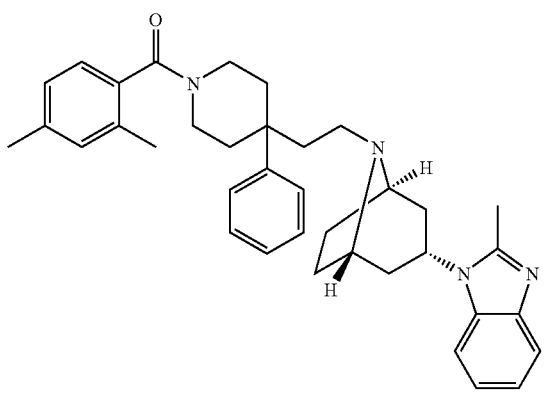

$^1$H NMR (400 MHz, methanol-d4) δ ppm 1.9 (m, 13H), 2.2 (m, 3H), 2.3 (m, 7H), 2.5 (s, 3H), 3.1 (m, 1H), 3.4 (m, 3H), 4.1 (m, J=111.1, 4.6 Hz, 1H), 4.7 (m, 1H), 7.1 (m, 3H), 7.2 (m, 2H), 7.2 (m, 1H), 7.4 (m, 5H), 7.5 (m, 1H).

Example 104

1-((1R,5S)-8-{2-[1-(2,4-dimethylbenzoyl)-4-phenyl-4-piperidinyl]ethyl}-8-azabicyclo[3.2.1]oct-3-yl)-2-methyl-1H-benzimidazole

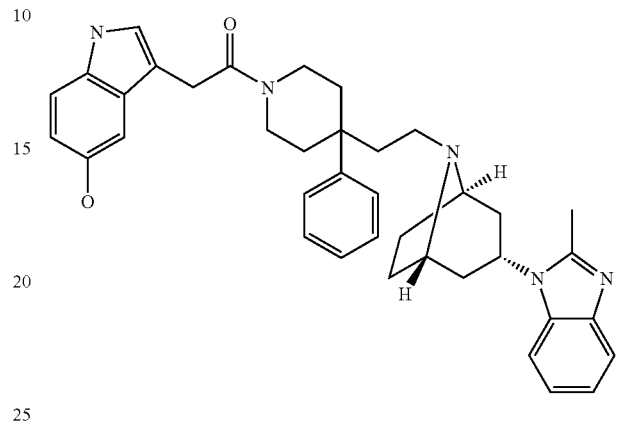

$^1$H NMR (400 MHz, methanol-d4) δ ppm 1.3 (m, 1H), 1.7 (m, 5H), 1.9 (m, 7H), 2.2 (m, 1H), 2.4 (m, 4H), 2.5 (s, 3H), 3.1 (m, 1H), 3.2 (m, 3H), 3.8 (m, 2H), 4.1 (t, J=5.5 Hz, 1H), 4.7 (d, J=8.6 Hz, 1H), 6.7 (dd, J=8.6, 2.1 Hz, 1H), 7.0 (d, J=2.5 Hz, 1H), 7.1 (s, 1H), 7.2 (m, 4H), 7.3 (m, 5H), 7.4 (dd, J=5.9, 2.7 Hz, 1H), 7.5 (m, 1H).

Example 106

1-{(1R,5S)-8-[2-(1-{[2,2-dimethyl-3-(2-methyl-1-propenyl)cyclopropyl]carbonyl}-4-phenyl-4-piperidinyl)ethyl]-8-azabicyclo[3.2.1]oct-3-yl}-2-methyl-1H-benzimidazole

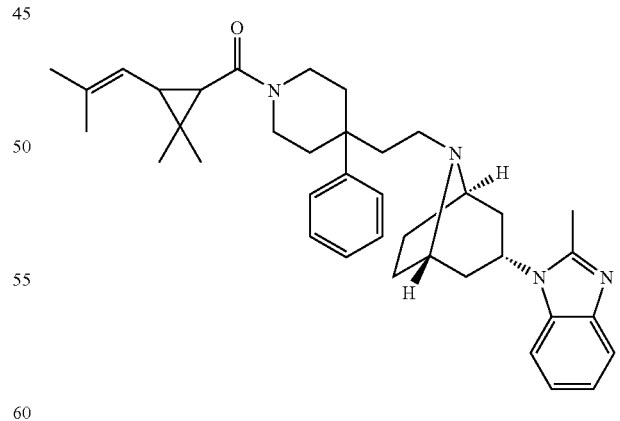

$^1$H NMR (400 MHz, methanol-d4) δ ppm 1.2 (m, 3H), 1.3 (m, 2H), 1.8 (m, 20H), 2.2 (m, 3H), 2.4 (m, 3H), 2.5 (s, 3H), 3.4 (m, 1H), 3.8 (m, 2H), 4.1 (m, 1H), 4.8 (m, 1H), 4.9 (m, 1H), 5.1 (dd, J=35.7, 8.9 Hz, 1H), 7.2 (m, 2H), 7.2 (m, 1H), 7.4 (m, 5H), 7.5 (m, 1H).

Example 107

2-methyl-1-{(1R,5S)-8-[2-(4-phenyl-1-{(4-(trifluoro-methyl)-3-pyridinyl]carbonyl}-4-piperidinyl)ethyl]-8-azabicyclo[3.2.1]oct-3-yl}-1H-benzimidazole

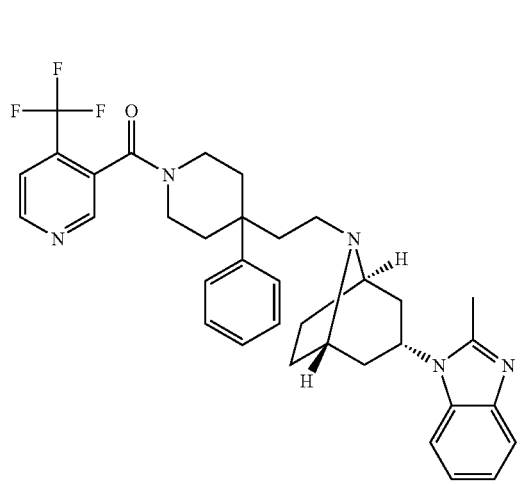

$^1$H NMR (400 MHz, methanol-d4) δ ppm 1.3 (m, 1H), 1.9 (m, 12H), 2.3 (m, 1H), 2.4 (m, 4H), 2.5 (m, 3H), 3.2 (m, 1H), 3.4 (m, 2H), 4.2 (m, 1H), 4.7 (m, 1H), 7.2 (m, 2H), 7.3 (m, 1H), 7.4 (m, 5H), 7.5 (m, 1H), 7.8 (dd, J=13.7, 5.2 Hz, 1H), 8.7 (m, J=72.4 Hz, 1H), 8.9 (t, J=5.7 Hz, 1H).

Example 108

1-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]cyclopropanecarboxamide

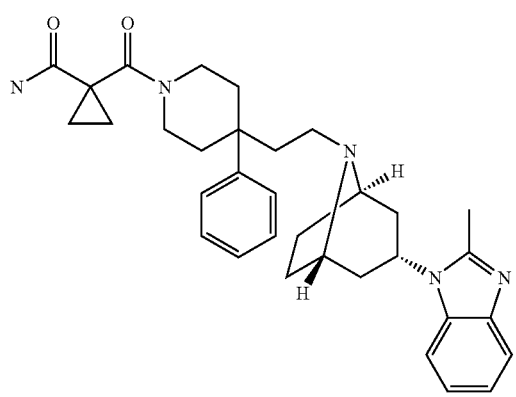

$^1$H NMR (400 MHz, methanol-d4) δ ppm 1.3 (m, 7H), 1.7 (m, 2H), 2.0 (m, 10H), 2.4 (m, 4H), 2.5 (s, 2H), 3.3 (m, 4H), 3.8 (m, 1H), 4.1 (m, J=11.4, 6.1 Hz, 1H), 4.7 (m, 1H), 7.2 (m, 2H), 7.2 (m, 1H), 7.4 (m, 5H), 7.5 (m, 1H).

Example 109

2-methyl-1-[(1R,5S)-8-(2-{1-[(2-methylcyclopropyl)carbonyl]-4-phenyl-4-piperidinyl}ethyl)-8-azabicyclo[3.2.1]oct-3-yl]-1H-benzimidazole

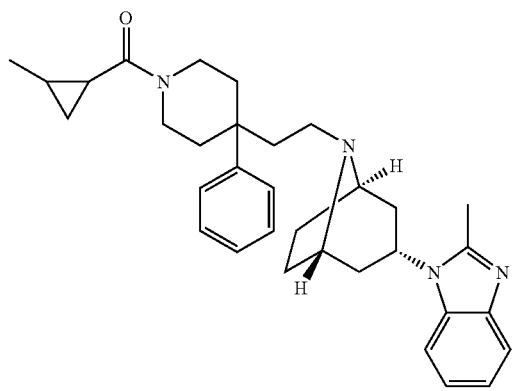

$^1$H NMR (400 MHz, methanol-d4) δ ppm 1.1 (m, 5H), 1.9 (m, 14H), 2.3 (m, 4H), 2.6 (m, 3H), 3.2 (m, 1H), 3.3 (m, 2H), 3.5 (m, 1H), 4.0 (m, 2H), 4.7 (m, 1H), 7.2 (m, 2H), 7.2 (m, 1H), 7.4 (m, 5H), 7.5 (m, 1H).

Example 111

2-methyl-1-[(1R,5S)-8-(2-{4-phenyl-1-[(1-phenylcyclopentyl)carbonyl]-4-piperidinyl}ethyl)-8-azabicyclo[3.2.1]oct-3-yl]-1H-benzimidazole

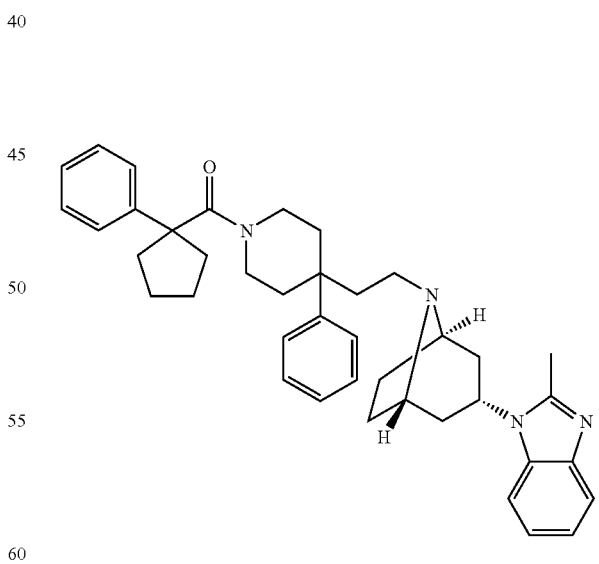

$^1$H NMR (400 MHz, methanol-d4) δ ppm 1.2 (m, 1H), 1.7 (m, 10H), 2.0 (m, 7H), 2.3 (m, 6H), 2.5 (m, 3H), 2.9 (m, 1H), 3.2 (m, 3H), 3.4 (m, 1H), 4.0 (m, 2H), 4.7 (m, 1H), 7.2 (m, 7H), 7.3 (m, 5H), 7.4 (m, 1H), 7.5 (m, 1H).

Example 113

1-((1R,5S)-8-{2-[1-(2,4-dichlorobenzoyl)-4-phenyl-4-piperidinyl]ethyl}-8-azabicyclo[3.2.1]oct-3-yl)-2-methyl-1H-benzimidazole

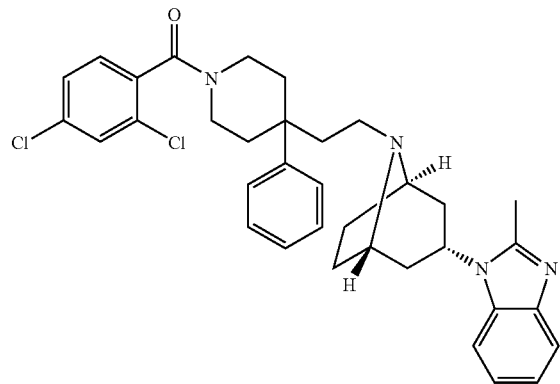

$^1$H NMR (400 MHz, methanol-d4) δ ppm 1.7 (m, 2H), 1.9 (m, 11H), 2.3 (m, 1H), 2.4 (m, 4H), 2.5 (m, J=2.5 Hz, 3H), 3.2 (m, 1H), 3.3 (m, 2H), 4.2 (m, 1H), 4.7 (m, J=10.9, 9.1 Hz, 1H), 7.2 (m, 2H), 7.2 (m, 1H), 7.4 (m, 6H), 7.5 (m, 3H).

Example 117

2-methyl-1-((1R,5S)-8-{2-[4-phenyl-1-(4-vinylbenzoyl)-4-piperidinyl]ethyl}-8-azabicyclo[3.2.1]oct-3-yl)-1H-benzimidazole

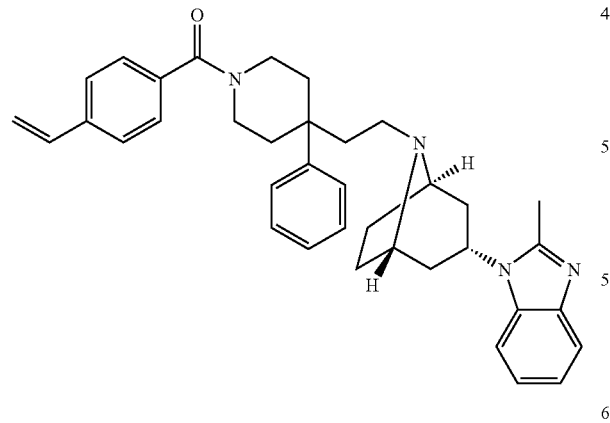

$^1$H NMR (400 MHz, methanol-d4) δ ppm 1.7 (m, 2H), 1.9 (m, 10H), 2.2 (m, 1H), 2.4 (m, 4H), 2.5 (m, 3H), 3.3 (m, 4H), 3.6 (m, 1H), 4.1 (m, J=11.1, 4.3 Hz, 1H), 4.7 (m, 1H), 5.3 (d, J=11.1 Hz, 1H), 5.9 (d, J=17.5 Hz, 1H), 6.8 (dd, J=17.7, 10.9 Hz, 1H), 7.2 (m, 2H), 7.2 (m, 1H), 7.4 (d, 7H), 7.5 (m, 2H).

Example 120

1-[(1R,5S)-8-(2-{1-[(3,5-dimethoxyphenyl)acetyl]-4-phenyl-4-piperidinyl}ethyl)-8-azabicyclo[3.2.1]oct-3-yl]-2-methyl-1H-benzimidazole

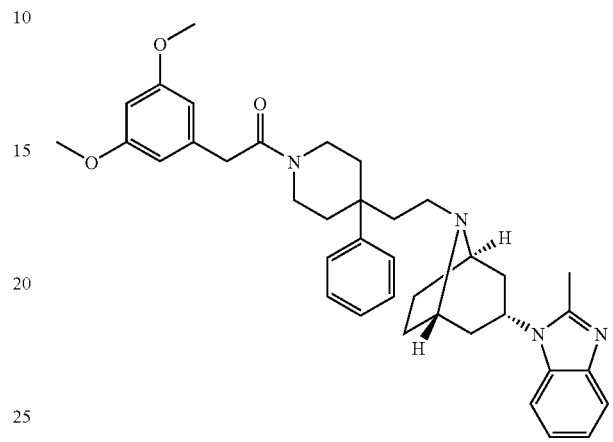

$^1$H NMR (400 MHz, methanol-d4) δ ppm 1.7 (m, 5H), 1.9 (m, 8H), 2.2 (m, 2H), 2.4 (m, 3H), 2.5 (m, 3H), 3.2 (m, 4H), 3.7 (m, 8H), 4.0 (m, 1H), 4.7 (t, 1H), 6.4 (t, J=2.1 Hz, 1H), 6.4 (d, J=2.1 Hz, 1H), 7.2 (m, 2H), 7.2 (m, 1H), 7.4 (m, 5H), 7.5 (m, 1H).

Example 123 methyl 4-{1-[(4-{2-[(1R,5S)-3-(2-methyl-1H-benzimi-dazol-1-yl)-8-azabicyclo[3.2.1]oct-8-yl]ethyl}-4-phenyl-1-piperidinyl)carbonyl]cyclopropyl}phenyl ether

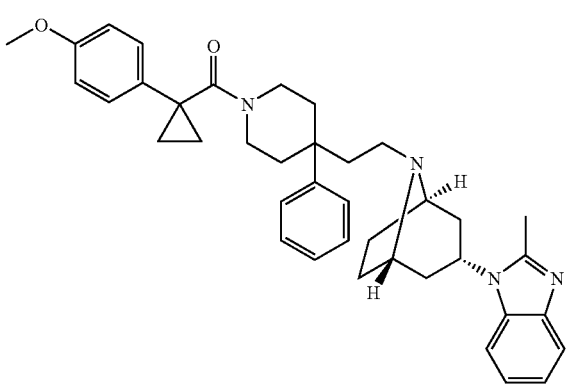

$^1$H NMR (400 MHz, methanol-d4) δ ppm 1.3 (m, 6H), 1.7 (m, 2H), 2.0 (m, 8H), 2.2 (m, 1H), 2.4 (m, 3H), 2.5 (s, 3H), 3.2 (m, 5H), 3.7 (s, 3H), 3.8 (m, 1H), 4.0 (m, 1H), 4.7 (m, 1H), 6.9 (m, 2H), 7.1 (m, 2H), 7.2 (m, 3H), 7.3 (m, 4H), 7.5 (m, 1H).

Example 127

1-((1R,5S)-8-{2-[1-(2,4-difluorobenzoyl)-4-phenyl-4-piperidinyl]ethyl}-8-azabicyclo[3.2.1]oct-3-yl)-2-methyl-1H-benzimidazole

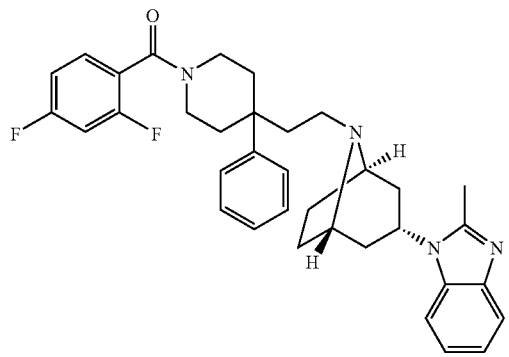

¹H NMR (400 MHz, methanol-d4) δ ppm 1.7 (m, 2H), 1.9 (m, 8H), 2.3 (m, 1H), 2.4 (m, 3H), 2.5 (m, 3H), 3.2 (m, 1H), 3.3 (m, 5H), 3.5 (m, 1H), 4.2 (m, 1H), 4.7 (m, 1H), 7.1 (m, J=9.6, 9.6 Hz, 2H), 7.2 (m, 2H), 7.2 (m, 1H), 7.4 (m, 6H), 7.5 (m, 1H).

Example 128

1-((1R,5S)-8-{2-[1-([1,1'-biphenyl]-2-ylcarbonyl)-4-phenyl-4-piperidinyl]ethyl}-8-azabicyclo[3.2.1]oct-3-yl)-2-methyl-1H-benzimidazole

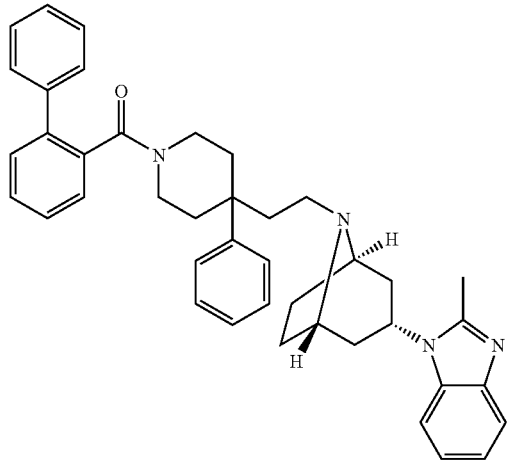

¹H NMR (400 MHz, methanol-d4) δ ppm 1.5 (m, 3H), 1.9 (m, 8H), 2.2 (m, 1H), 2.4 (m, 2H), 2.5 (m, 3H), 2.8 (m, 1H), 3.0 (m, 1H), 3.2 (m, 3H), 3.4 (m, 1H), 3.8 (m, 1H), 4.2 (m, 1H), 4.7 (m, 1H), 7.4 (m, 18H).

Example 130

2-methyl-1-[(1R,5S)-8-(2-{4-phenyl-1-[(1-phenylcyclopropyl)carbonyl]-4-piperidinyl}ethyl)-8-azabicyclo[3.2.1]oct-3-yl]-1H-benzimidazole

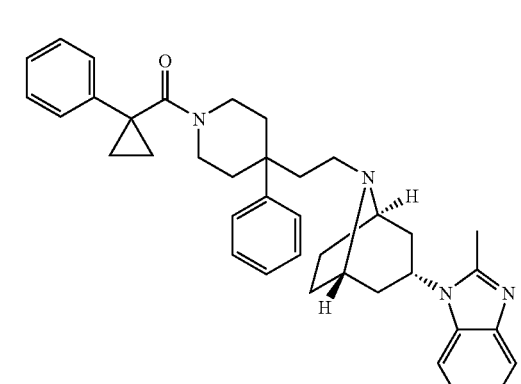

¹H NMR (400 MHz, methanol-d4) δ ppm 1.3 (m, 5H), 1.6 (m, 2H), 1.7 (m, 3H), 1.9 (m, 8H), 2.2 (m, 1H), 2.4 (m, 2H), 2.5 (m, 3H), 3.2 (m, 3H), 3.8 (m, 1H), 4.0 (m, J=112.1, 5.7 Hz, 1H), 4.7 (m, 1H), 7.2 (m, 6H), 7.3 (m, 6H), 7.4 (m, 1H), 7.5 (m, 1H).

Example 131

1-[(1R,5S)-8-(2-{1-[4-(1H-imidazol-1-yl)benzoyl]-4-phenyl-4-piperidinyl}ethyl)-8-azabicyclo[3.2.1]oct-3-yl]-2-methyl-1H-benzimidazole

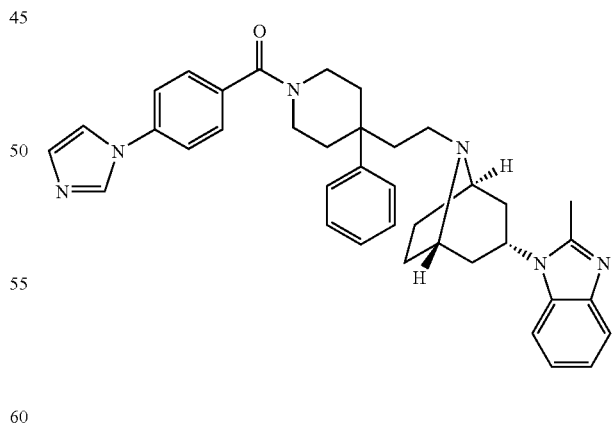

¹H NMR (400 MHz, methanol-d4) δ ppm 1.7 (m, 2H), 2.0 (m, 10H), 2.3 (m, 1H), 2.4 (m, 4H), 2.5 (m, 3H), 3.4 (m, 3H), 3.6 (m, 1H), 4.2 (m, 1H), 4.7 (m, 1H), 7.2 (m, 3H), 7.2 (m, 1H), 7.4 (m, 6H), 7.5 (m, 1H), 7.6 (m, 2H), 7.6 (d, J=1.4 Hz, 1H), 7.7 (m, 2H).

Example 133

1-((1R,5S)-8-{2-[1-(4-isopropylbenzoyl)-4-phenyl-4-piperidinyl]ethyl}-8-azabicyclo[3.2.1]oct-3-yl)-2-methyl-1H-benzimidazole

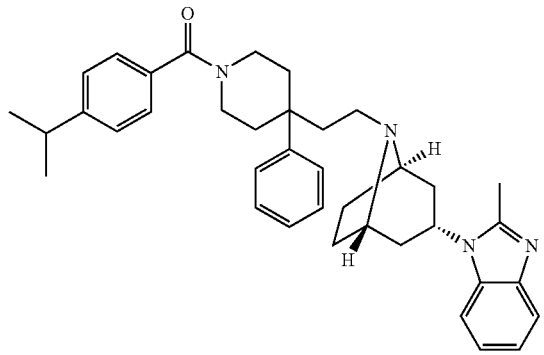

$^1$H NMR (400 MHz, methanol-d4) δ ppm 1.3 (m, 6H), 1.7 (m, 2H), 1.9 (m, 10H), 2.2 (m, 1H), 2.4 (m, 3H), 2.5 (s, 3H), 2.9 (m, 1H), 3.3 (m, 4H), 3.6 (m, 1H), 4.1 (m, 1H), 4.7 (m, 1H), 7.2 (m, 2H), 7.2 (m, 1H), 7.3 (m, 3H), 7.4 (m, 6H), 7.5 (m, 1H).

Example 134 methyl 3-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-pyridinyl ether

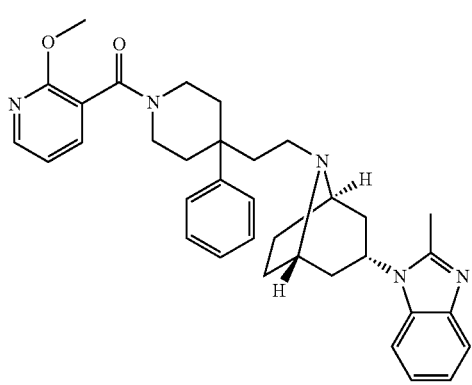

$^1$H NMR (400 MHz, methanol-d4) δ ppm 1.7 (m, J=7.5 Hz, 2H), 1.9 (m, 10H), 2.2 (m, 1H), 2.4 (m, 3H), 2.5 (m, 3H), 3.2 (m, 1H), 3.3 (m, 4H), 3.9 (d, J=54.6 Hz, 3H), 4.2 (m, 1H), 4.7 (m, 1H), 7.1 (m, 1H), 7.2 (m, 2H), 7.2 (d, J=4.6 Hz, 1H), 7.4 (m, 5H), 7.5 (m, 1H), 7.6 (dd, J=53.7, 7.3 Hz, 1H), 8.2 (dd, J=5.2, 2.0 Hz, 1H).

Example 136

2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]phenyl propyl ether

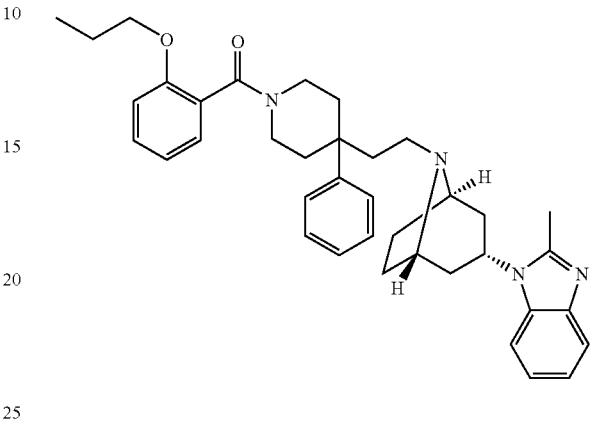

$^1$H NMR (400 MHz, methanol-d4) δ ppm 1.0 (m, 3H), 1.6 (m, 1H), 1.7 (m, 2H), 1.9 (m, 11H), 2.2 (m, 1H), 2.4 (m, 4H), 2.5 (d, J=7.1 Hz, 3H), 3.2 (m, 2H), 3.4 (m, 2H), 3.9 (t, J=6.4 Hz, 1H), 4.1 (m, 2H), 4.7 (m, 1H), 7.1 (m, 4H), 7.2 (m, 2H), 7.2 (m, 1H), 7.4 (m, 5H), 7.5 (m, 1H).

Example 138 methyl 2-[3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxopropyl]phenyl ether

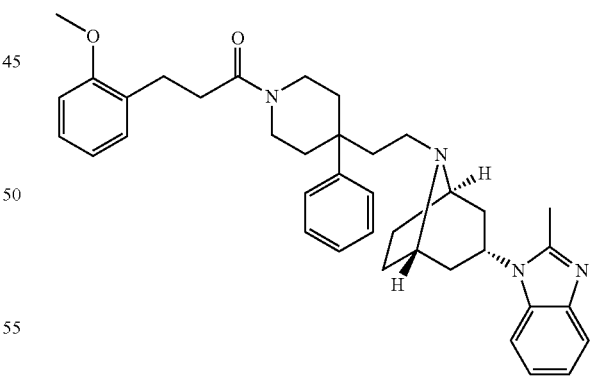

$^1$H NMR (400 MHz, methanol-d4) δ ppm 1.5 (m, 1H), 1.7 (m, 3H), 1.8 (m, 2H), 1.9 (m, 6H), 2.1 (m, 1H), 2.2 (m, 1H), 2.4 (m, 2H), 2.5 (m, J=5.7 Hz, 3H), 2.6 (m, 4H), 2.9 (m, 2H), 3.1 (m, 2H), 3.3 (m, 1H), 3.6 (m, 1H), 3.8 (s, 3H), 4.0 (m, 1H), 4.7 (m, 1H), 6.8 (t, J=7.0 Hz, 1H), 6.9 (d, J=8.2 Hz, 1H), 7.1 (dd, J=7.5, 1.8 Hz, 1H), 7.2 (m, 2H), 7.2 (m, 1H), 7.4 (m, 5H), 7.5 (m, 1H).

Example 139

1-((1R,5S)-8-{2-[1-(cyclopentylacetyl)-4-phenyl-4-piperidinyl]ethyl}-8-azabicyclo[3.2.1]oct-3-yl)-2-methyl-1H-benzimidazole

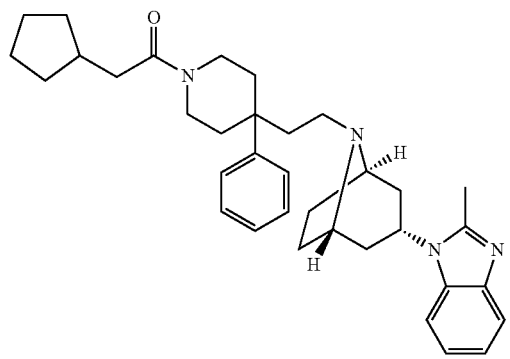

$^1$H NMR (400 MHz, methanol-d4) δ ppm 1.2 (m, 1H), 1.6 (m, 4H), 1.9 (m, 12H), 2.2 (m, 3H), 2.4 (m, 4H), 2.6 (m, 3H), 2.8 (t, J=5.7 Hz, 1H), 2.9 (d, J=2.1 Hz, 1H), 3.2 (m, 1H), 3.3 (m, 3H), 3.5 (m, 1H), 3.8 (m, 1H), 4.0 (m, 1H), 4.7 (m, 1H), 7.2 (m, 2H), 7.2 (m, 1H), 7.4 (m, 5H), 7.5 (m, 1H).

Example 141

2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-4(1H)-quinolinone

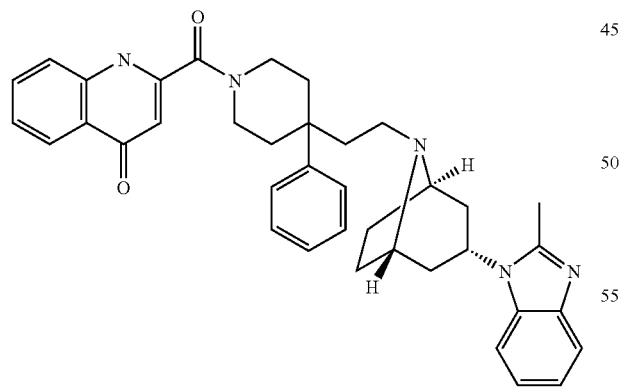

$^1$H NMR (400 MHz, methanol-d4) δ ppm 1.7 (m, 2H), 2.0 (m, 10H), 2.4 (m, 4H), 2.5 (m, 3H), 3.3 (m, 4H), 3.6 (m, 1H), 4.2 (m, 1H), 4.7 (m, 1H), 6.3 (s, 1H), 7.2 (m, 2H), 7.3 (m, 1H), 7.4 (m, 7H), 7.5 (m, 1H), 7.6 (d, J=8.2 Hz, 1H), 7.7 (m, 1H), 8.3 (d, J=7.1 Hz, 1H).

Example 142

1-[(1R,5S)-8-(2-{1-[3-(1,3-benzodioxol-5-yl)propanoyl]-4-phenyl-4-piperidinyl}ethyl)-8-azabicyclo[3.2.1]oct-3-yl]-2-methyl-1H-benzimidazole

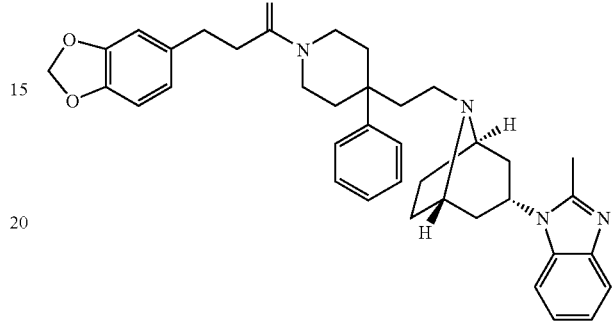

$^1$H NMR (400 MHz, methanol-d4) δ ppm 1.5 (m, 1H), 1.7 (m, 3H), 1.8 (m, 2H), 2.0 (m, 7H), 2.2 (m, 1H), 2.4 (m, 2H), 2.5 (s, 3H), 2.6 (m, 3H), 2.8 (m, 2H), 3.2 (m, 2H), 3.3 (m, J=3.9 Hz, 1H), 3.6 (m, 1H), 3.9 (m, 1H), 4.7 (m, 1H), 5.8 (d, J=1.4 Hz, 1H), 5.9 (s, 1H), 6.7 (m, 3H), 7.2 (m, 2H), 7.2 (m, 1H), 7.4 (m, 5H), 7.5 (m, 1H).

Example 144

2-methyl-1-[(1R,5S)-8-(2-{1-[(4-methyl-1,2,3-thiadiazol-5-yl)carbonyl]-4-phenyl-4-piperidinyl}ethyl)-8-azabicyclo[3.2.1]oct-3-yl]-1H-benzimidazole

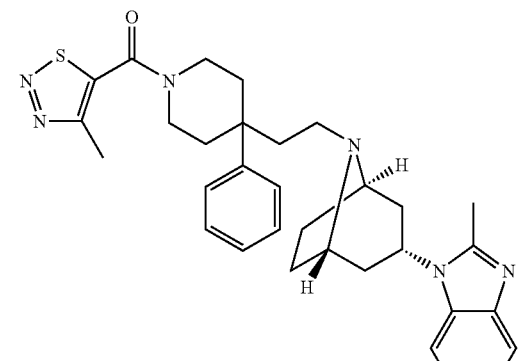

$^1$H NMR (400 MHz, methanol-d4) δ ppm 1.4 (m, 2H), 1.7 (m, 2H), 1.9 (m, 10H), 2.4 (m, 5H), 2.6 (m, 3H), 2.8 (m, 1H), 3.0 (m, 1H), 3.3 (m, 1H), 3.4 (m, 1H), 3.6 (m, 1H), 4.2 (m, 1H), 4.8 (m, 1H), 7.2 (m, 2H), 7.2 (m, 1H), 7.4 (m, 5H), 7.5 (m, 1H).

Example 145

2-methyl-1-{(1R,5S)-8-[2-(4-phenyl-1-propionyl-4-piperidinyl)ethyl]-8-azabicyclo[3.2.1]oct-3-yl}-1H-benzimidazole

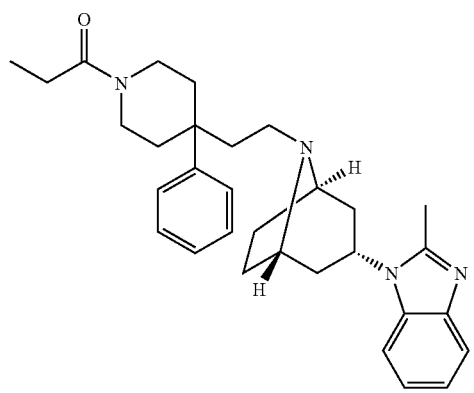

¹H NMR (400 MHz, methanol-d4) δ ppm 1.1 (t, J=7.5 Hz, 3H), 1.7 (m, 2H), 1.9 (m, 10H), 2.3 (s, 2H), 2.4 (m, 4H), 2.5 (d, J=6.6 Hz, 3H), 3.2 (m, 2H), 3.3 (m, 2H), 3.6 (m, 1H), 4.0 (m, 1H), 4.7 (m, 1H), 7.2 (m, 2H), 7.2 (m, 1H), 7.4 (m, 5H), 7.5 (m, 1H).

Example 149

2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-3-pyridinol

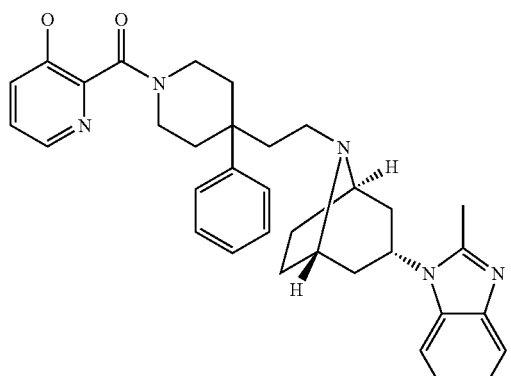

¹H NMR (400 MHz, methanol-d4) δ ppm 1.7 (m, 2H), 2.0 (m, 10H), 2.4 (m, 5H), 2.5 (m, 3H), 3.2 (m, 1H), 3.3 (m, 3H), 3.5 (m, 1H), 4.2 (m, J=4.6 Hz, 1H), 4.7 (m, 1H), 7.2 (m, 2H), 7.2 (m, 1H), 7.3 (m, 2H), 7.4 (m, 5H), 7.5 (m, 1H), 8.1 (dd, J=3.9, 2.1 Hz, 1H).

Example 150

4,6-dimethyl-5-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2H-pyran-2-one

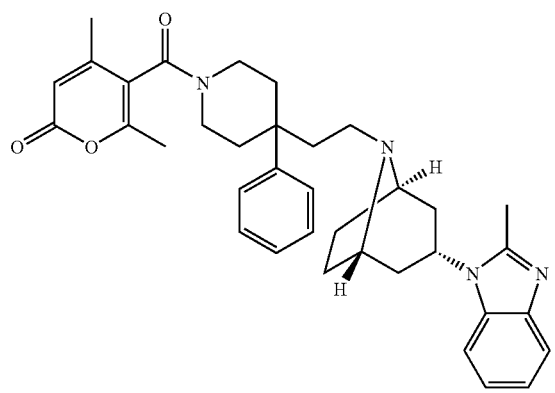

¹H NMR (400 MHz, methanol-d4) δ ppm 1.6 (m, 2H), 1.9 (m, 13H), 2.1 (m, 1H), 2.2 (m, J=6.4 Hz, 1H), 2.3 (m, 3H), 2.4 (m, 4H), 2.5 (m, J=1.4 Hz, 3H), 2.8 (m, 1H), 3.0 (m, 1H), 3.6 (m, 1H), 4.2 (m, 1H), 4.7 (m, 1H), 6.1 (d, J=21.8 Hz, 1H), 7.2 (m, 2H), 7.2 (m, 1H), 7.4 (m, 5H), 7.5 (m, 1H).

Example 151

N-{1-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]propyl}urea

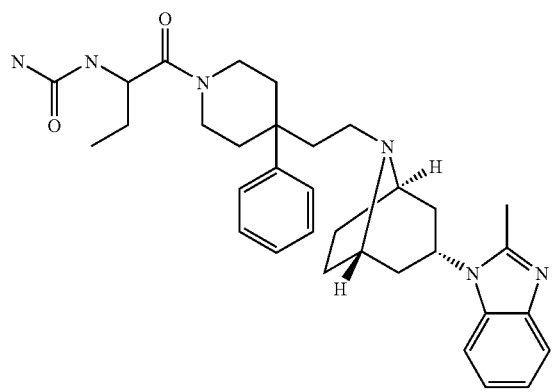

¹H NMR (400 MHz, methanol-d4) δ ppm 0.9 (m, 3H), 1.6 (m, 4H), 1.9 (m, 11H), 2.4 (m, 6), 2.5 (m, J=1.8 Hz, 3H), 2.8 (m, 1H), 3.0 (m, 2H), 3.4 (m, 1H), 3.8 (m, 1H), 4.1 (m, 1H), 4.7 (m, 1H), 4.8 (m, 1H), 7.2 (m, 2H), 7.2 (m, 1H), 7.4 (m, 5H), 7.5 (m, 1H).

Example 154

1-[(1R,5S)-8-(2-{1-[(3,5-difluorophenyl)acetyl]-4-phenyl-4-piperidinyl}ethyl)-8-azabicyclo[3.2.1]oct-3-yl]-2-methyl-1H-benzimidazole

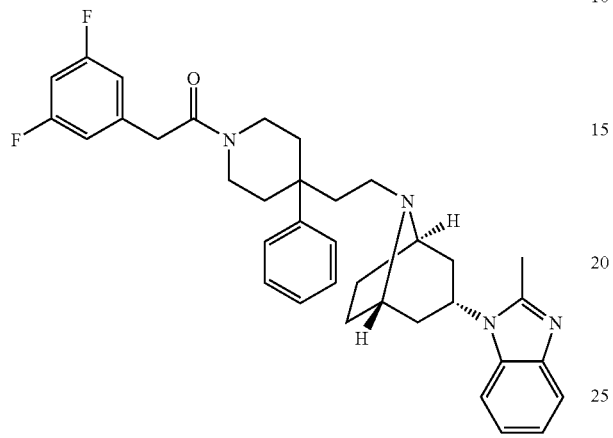

¹H NMR (400 MHz, methanol-d4) δ ppm 1.8 (m, 12H), 2.3 (m, 2H), 2.4 (m, 4H), 2.5 (s, 3H), 3.2 (m, 1H), 3.3 (m, 2H), 3.8 (m, 2H), 4.0 (m, 1H), 4.7 (m, 1H), 6.8 (m, 2H), 7.2 (m, 2H), 7.2 (m, 1H), 7.4 (m, 6H), 7.5 (m, 1H).

Example 156

1-((1R,5S)-8-{2-[1-(1H-indol-3-ylcarbonyl)-4-phenyl-4-piperidinyl]ethyl}-8-azabicyclo[3.2.1]oct-3-yl)-2-methyl-1H-benzimidazole

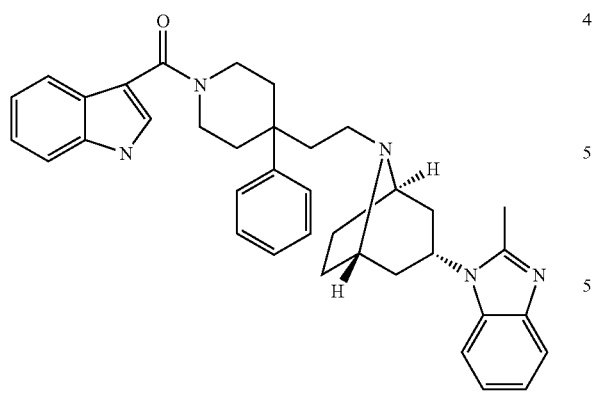

¹H NMR (400 MHz, methanol-d4) δ ppm 1.7 (m, 2H), 1.9 (m, 10H), 2.4 (m, 7H), 2.5 (s, 3H), 2.8 (m, 1H), 3.1 (m, 1H), 3.5 (m, J=10.3, 10.3 Hz, 1H), 4.1 (dd, J=11.6, 6.2 Hz, 1H), 4.7 (m, 1H), 7.2 (m, 4H), 7.2 (m, 1H), 7.4 (m, 7H), 7.5 (m, 1H), 7.6 (m, 1H).

Example 157

1-((1R,5S)-8-{2-[1-(2-fluoro-5-methylbenzoyl)-4-phenyl-4-piperidinyl]ethyl}-8-azabicyclo[3.2.1]oct-3-yl)-2-methyl-1H-benzimidazole

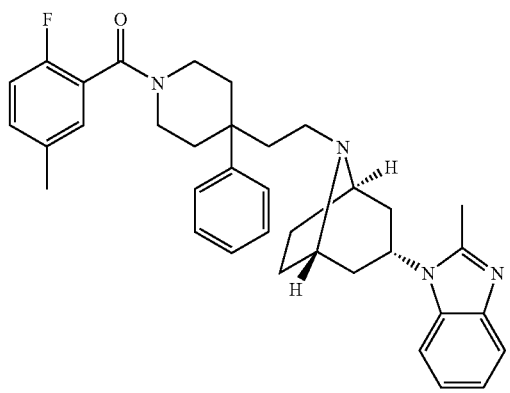

¹H NMR (400 MHz, methanol-d4) δ ppm 1.7 (m, 2H), 1.9 (m, 10H), 2.4 (m, 10H), 2.9 (m, 1H), 3.2 (m, 2H), 3.4 (m, 1H), 3.5 (m, 1H), 4.2 (m, 1H), 4.7 (m, 1H), 7.1 (m, 1H), 7.2 (m, 2H), 7.3 (m, 1H), 7.4 (m, 7H), 7.5 (m, 1H).

Example 158

3-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2H-chromen-2-one

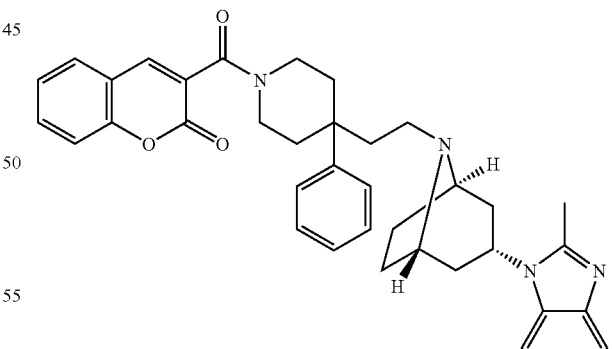

¹H NMR (400 MHz, methanol-d4) δ ppm 1.7 (m, 2H), 1.9 (m, 10H), 2.4 (m, 5H), 2.5 (m, 3H), 2.9 (m, 1H), 3.2 (m, 2H), 3.6 (m, 1H), 4.1 (m, 1H), 4.7 (m, 1H), 7.0 (m, 1H), 7.2 (m, 4H), 7.4 (m, 6H), 7.5 (m, J=6.8 Hz, 1H), 7.7 (m, 1H), 8.1 (s, 1H).

Example 159

2-methyl-1-((1R,5S)-8-{2-[1-(3-methylbutanoyl)-4-phenyl-4-piperidinyl]ethyl}-8-azabicyclo[3.2.1]oct-3-yl)-1H-benzimidazole

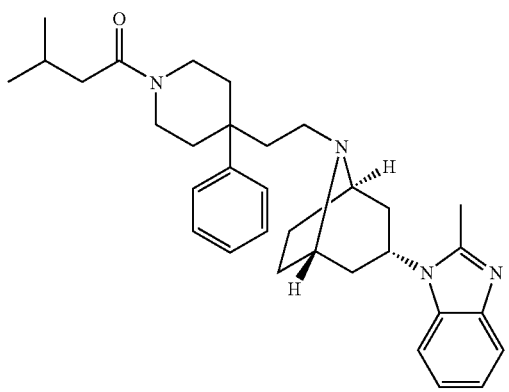

$^1$H NMR (400 MHz, methanol-d4) δ ppm 1.0 (m, 6H), 1.7 (m, 2H), 1.9 (m, 12H), 2.3 (m, 4H), 2.4 (m, 2H), 2.5 (m, J=6.4 Hz, 3H), 3.2 (m, 1H), 3.3 (m, 2H), 3.8 (m, 1H), 4.0 (m, 1H), 4.7 (m, 1H), 7.2 (m, 2H), 7.2 (m, 1H), 7.4 (m, 5H), 7.5 (m, 1H).

Example 160

1-((1R,5S)-8-{2-[1-(1H-indol-4-ylcarbonyl)-4-phenyl-4-piperidinyl]ethyl}-8-azabicyclo[3.2.1]oct-3-yl)-2-methyl-1H-benzimidazole

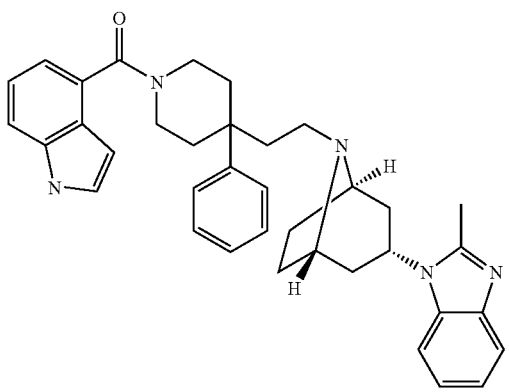

$^1$H NMR (400 MHz, methanol-d4) δ ppm 1.6 (m, 2H), 1.9 (m, 13H), 2.2 (m, 1H), 2.4 (m, 5H), 3.3 (m, 2H), 3.5 (m, 2H), 4.2 (m, 1H), 4.7 (m, 1H), 6.4 (d, J=2.9 Hz, 1H), 7.0 (d, J=7.1 Hz, 1H), 7.2 (m, 2H), 7.2 (m, 1H), 7.3 (m, J=3.4, 3.4 Hz, 1H), 7.4 (m, 6H), 7.5 (d, J=8.2 Hz, 1H), 7.5 (m, 1H).

Example 162

1-[(1R,5S)-8-(2-{1-[(3-ethoxy-2-thienyl)carbonyl]-4-phenyl-4-piperidinyl}ethyl)-8-azabicyclo[3.2.1]oct-3-yl]-2-methyl-1H-benzimidazole

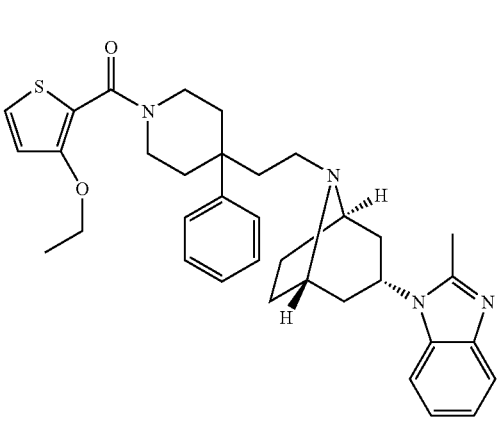

$^1$H NMR (400 MHz, methanol-d4) δ ppm 1.4 (t, J=7.1 Hz, 3H), 1.7 (m, 2H), 2.0 (m, 11H), 2.4 (m, 4H), 2.5 (m, 3H), 3.3 (m, 4H), 3.9 (m, 2H), 4.2 (m, 2H), 4.7 (m, 1H), 6.9 (d, J=5.7 Hz, 1H), 7.2 (m, 2H), 7.2 (m, 1H), 7.4 (m, 5H), 7.5 (m, 1H).

Example 163

2-methyl-1-[(1R,5S)-8-(2-{1-[(1-methylcyclopropyl)carbonyl]-4-phenyl-4-piperidinyl}ethyl)-8-azabicyclo[3.2.1]oct-3-yl]-1H-benzimidazole

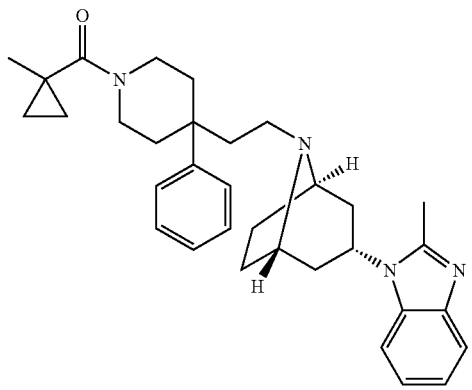

$^1$H NMR (400 MHz, methanol-d4) δ ppm 0.6 (d, J=1.4 Hz, 2H), 0.9 (m, 2H), 1.3 (d, J=20.0 Hz, 3H), 1.7 (m, 2H), 1.9 (m, 10H), 2.3 (m, 4H), 2.5 (s, 3H), 2.8 (m, 1H), 3.0 (m, 1H), 3.3 (m, 2H), 4.0 (m, 2H), 4.7 (m, 1H), 7.2 (m, 2H), 7.2 (m, 1H), 7.4 (m, 5H), 7.5 (m, 1H).

Example 164 methyl 3-[3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxopropyl]phenyl ether

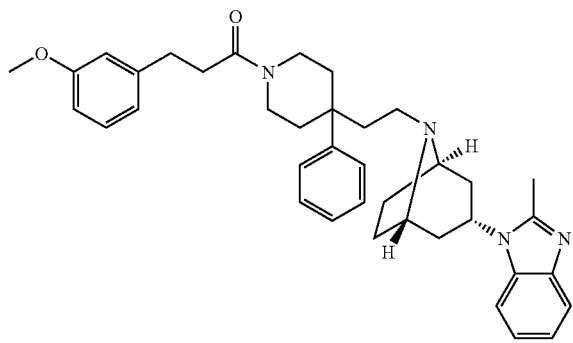

¹H NMR (400 MHz, methanol-d4) δ ppm 1.4 (m, 1H), 1.7 (m, 2H), 1.8 (m, 1H), 2.0 (m, 11H), 2.2 (m, 1H), 2.4 (m, 2H), 2.5 (m, 3H), 2.7 (m, 2H), 2.9 (m, 2H), 3.1 (m, 2H), 3.6 (m, 1H), 3.7 (s, 3H), 4.0 (m, 1H), 4.7 (m, 1H), 6.7 (dd, J=7.8, 2.1 Hz, 1H), 6.8 (m, 2H), 7.2 (m, 2H), 7.2 (m, 1H), 7.4 (m, 6H), 7.5 (m, 1H).

Example 167 methyl 3-[3-(4-{2-[(1R,5S)-3-(2-methyl-1H-benzimidazol-1-yl)-8-azabicyclo[3.2.1]oct-8-yl]ethyl}-4-phenyl-1-piperidinyl)-3-oxopropyl]phenyl ether

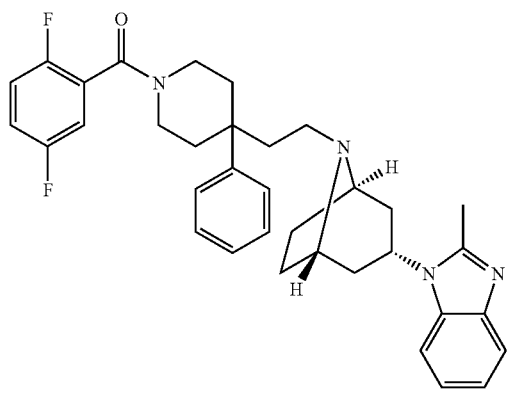

¹H NMR (400 MHz, methanol-d4) δ ppm 1.7 (m, 2H), 1.9 (m, 10H), 2.3 (m, 1H), 2.4 (m, 3H), 2.5 (s, 3H), 3.2 (m, 1H), 3.3 (m, 3H), 3.5 (m, 1H), 4.2 (m, J=8.9, 4.6 Hz, 1H), 4.7 (m, 1H), 7.2 (m, 2H), 7.2 (m, 4H), 7.4 (m, 5H), 7.5 (m, 1H).

Example 168

5-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-pyridinylamine

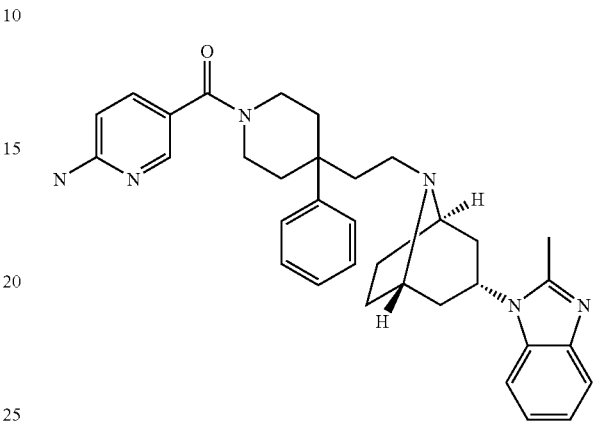

¹H NMR (400 MHz, methanol-d4) δ ppm 1.7 (m, 2H), 2.0 (m, 10H), 2.3 (m, 5H), 2.5 (m, 3H), 2.9 (m, 2H), 3.3 (m, 3H), 3.9 (m, 2H), 4.7 (m, 1H), 6.6 (d, J=8.6 Hz, 1H), 7.2 (m, 2H), 7.2 (m, 1H), 7.4 (m, 5H), 7.5 (m, 2H), 8.0 (d, J=2.1 Hz, 1H).

Example 169

1-[(1R,5S)-8-(2-{1-[(2,6-dimethoxy-3-pyridinyl)carbonyl]-4-phenyl-4-piperidinyl}ethyl)-8-azabicyclo[3.2.1]oct-3-yl]-2-methyl-1H-benzimidazole

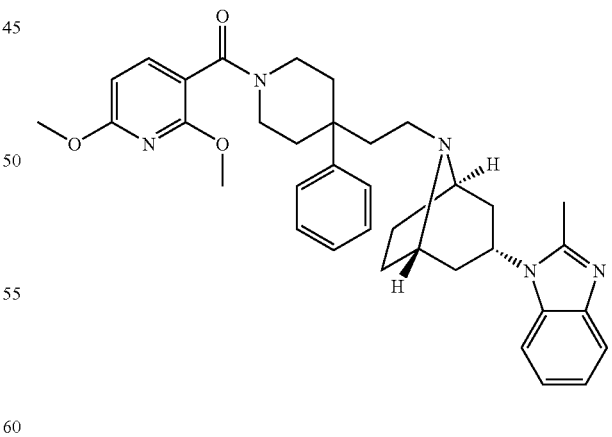

¹H NMR (400 MHz, methanol-d4) δ ppm 1.7 (m, 2H), 1.9 (m, 10H), 2.2 (m, 1H), 2.4 (m, 4H), 2.5 (m, 3H), 3.2 (m, 1H), 3.3 (m, 2H), 3.4 (m, 1H), 4.0 (m, 6H), 4.1 (m, 1H), 4.7 (m, 1H), 6.4 (d, J=7.8 Hz, 1H), 7.2 (m, 2H), 7.2 (t, J=6.4 Hz, 1H), 7.4 (m, 5H), 7.5 (m, 2H).

Example 171 methyl 4-[3-(4-{2-[(1R,5S)-3-(2-methyl-1H-benz-imidazol-1-yl)-8-azabicyclo[3.2.1]oct-8-yl]ethyl}-4-phenyl-1-piperidinyl)-3-oxopropyl]phenyl ether

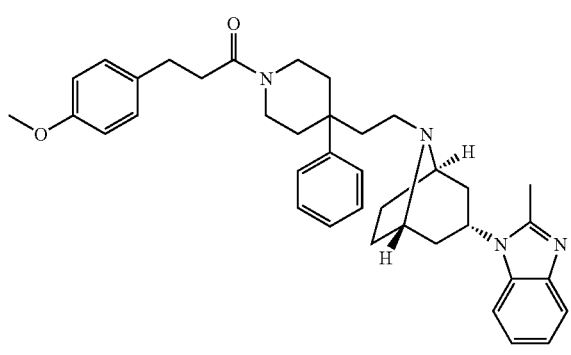

$^1$H NMR (400 MHz, methanol-d4) δ ppm 1.4 (m, 1H), 1.7 (m, 3H), 1.9 (m, 8H), 2.1 (m, 1H), 2.4 (m, 3H), 2.5 (s, 3H), 2.8 (m, 3H), 3.1 (m, 2H), 3.3 (m, 2H), 3.6 (m, 2H), 3.7 (d, J=12.8 Hz, 3H), 3.9 (m, 1H), 4.7 (m, 1H), 6.8 (m, 2H), 7.1 (m, 2H), 7.2 (m, 2H), 7.4 (m, 6H), 7.5 (m, 1H).

Example 172

2-methyl-1-((1R,5S)-8-{2-[1-(4-nitrobenzoyl)-4-phenyl-4-piperidinyl]ethyl}-8-azabicyclo[3.2.1]oct-3-yl)-1H-benzimidazole

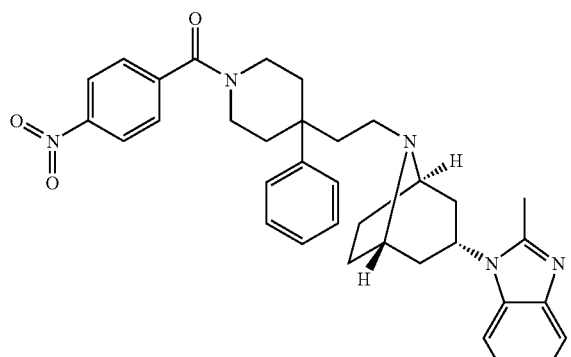

$^1$H NMR (400 MHz, methanol-d4) δ ppm 1.7 (d, J=7.8 Hz, 2H), 2.0 (d, J=12.5 Hz, 8H), 2.5 (d, J=7.1 Hz, 3H), 2.7 (s, 3H), 2.8 (m, J=13.6 Hz, 2H), 3.1 (s, 1H), 3.3 (m, 3H), 3.5 (s, 2H), 4.2 (m, 1H), 4.8 (d, J=31.8 Hz, 1H), 7.2 (m, 3H), 7.4 (m, 8H), 7.7 (m, 1H), 8.3 (d, J=8.9 Hz, 1H).

Example 173

1-((1R,5S)-8-{2-[1-(4-ethylbenzoyl)-4-phenyl-4-piperidinyl]ethyl}-8-azabicyclo[3.2.1]oct-3-yl)-2-methyl-1H-benzimidazole

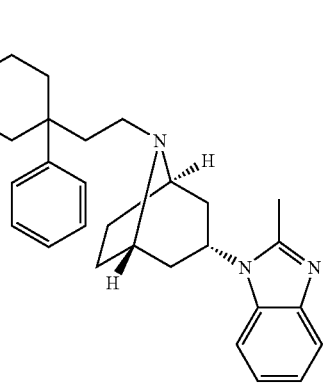

$^1$H NMR (400 MHz, methanol-d4) δ ppm 1.3 (m, 3H), 1.7 (m, 2H), 1.9 (m, 8H), 2.2 (m, 1H), 2.4 (m, 4H), 2.5 (s, 3H), 2.7 (m, 4H), 3.3 (m, 3H), 3.6 (m, 1H), 4.1 (m, 1H), 4.7 (m, 1H), 7.2 (m, 2H), 7.2 (m, 1H), 7.3 (m, 3H), 7.4 (m, 6H), 7.5 (m, 1H).

Example 175

1-((1R,5S)-8-{2-[1-(4-chloro-2-methoxybenzoyl)-4-phenyl-4-piperidinyl]ethyl}-8-azabicyclo[3.2.1]oct-3-yl)-2-methyl-1H-benzimidazole

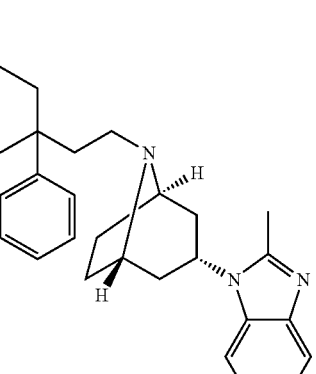

$^1$H NMR (400 MHz, methanol-d4) δ ppm 1.7 (m, 2H), 1.9 (m, 10H), 2.2 (m, 1H), 2.4 (m, 3H), 2.5 (m, 3H), 3.1 (m, 2H), 3.3 (m, 3H), 3.8 (m, J=57.4 Hz, 3H), 4.1 (m, 1H), 4.7 (m, 1H), 7.0 (m, 1H), 7.1 (m, 2H), 7.2 (m, 2H), 7.3 (m, 1H), 7.4 (m, 5H), 7.5 (m, 1H).

Example 178

2-methyl-1-((1R,5S)-8-{2-[1-(2-methyl-3-phenyl-propanoyl)-4-phenyl-4-piperidinyl]ethyl}-8-azabicyclo[3.2.1]oct-3-yl)-1H-benzimidazole

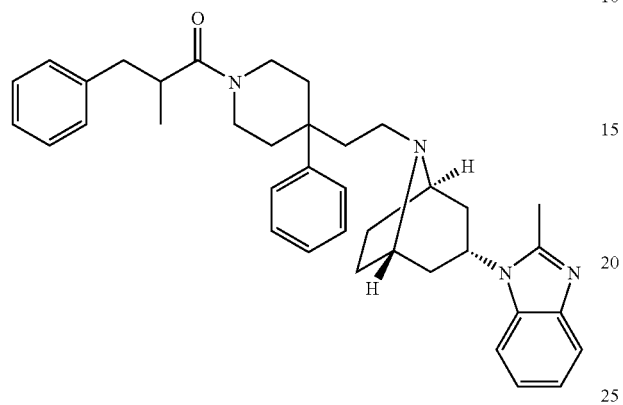

$^1$H NMR (400 MHz, methanol-d4) δ ppm 1.1 (m, J=16.8, 6.8 Hz, 3H), 1.4 (m, 1H), 1.6 (m, 4H), 1.9 (m, 8H), 2.1 (m, J=69.7, 13.7 Hz, 2H), 2.4 (m, 3H), 2.8 (m, 3H), 3.1 (m, 1H), 3.2 (m, 2H), 3.4 (m, 1H), 3.7 (m, 2H), 4.1 (m, J=13.6 Hz, 1H), 4.7 (m, 1H), 7.0 (m, 1H), 7.1 (m, 1H), 7.2 (m, 5H), 7.4 (m, 6H), 7.5 (m, 1H).

Example 179

2-methyl-1-[(1R,5S)-8-(2-{4-phenyl-1-[(3E)-4-phenyl-3-butenoyl]-4-piperidinyl}ethyl)-8-azabicyclo[3.2.1]oct-3-yl]-1H-benzimidazole

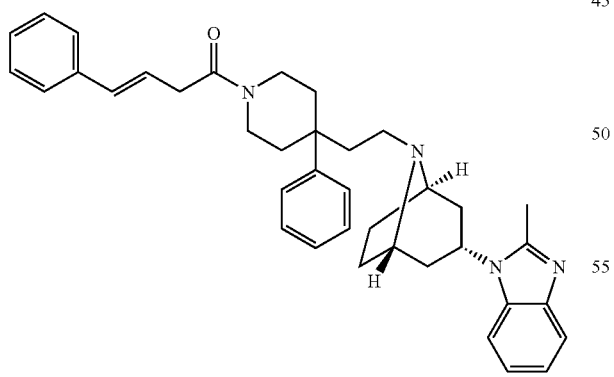

$^1$H NMR (400 MHz, methanol-d4) δ ppm 1.7 (m, 2H), 1.9 (m, 11H), 2.4 (m, 5H), 2.5 (s, 3H), 3.2 (m, 1H), 3.4 (m, 3H), 3.8 (m, 1H), 4.0 (m, 1H), 4.7 (m, 1H), 6.3 (m, 1H), 6.5 (d, J=16.1 Hz, 1H), 7.2 (m, 2H), 7.3 (m, 3H), 7.4 (m, 8H), 7.5 (m, 1H).

Example 181

1-{(1R,5S)-8-[2-(1-{[1-(4-chlorophenyl)cyclopropyl]carbonyl}-4-phenyl-4-piperidinyl)ethyl]-8-azabicyclo[3.2.1]oct-3-yl}-2-methyl-1H-benzimidazole

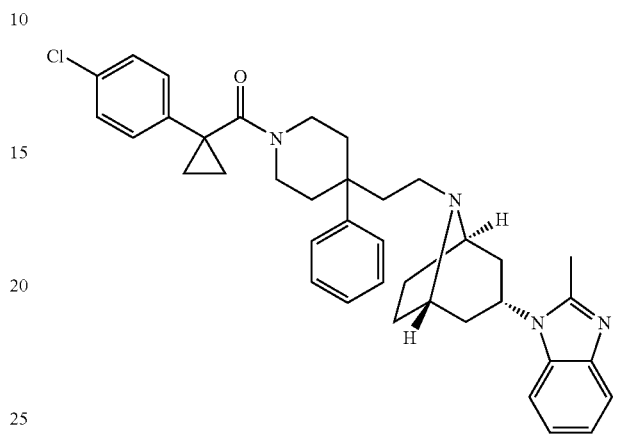

$^1$H NMR (400 MHz, methanol-d4) δ ppm 1.4 (m, 4H), 1.7 (m, 4H), 1.9 (m, 8H), 2.1 (s, 1H), 2.3 (m, 1H), 2.4 (m, 3H), 2.5 (s, 3H), 3.2 (m, 3H), 3.8 (m, 1H), 4.0 (m, 1H), 4.7 (m, 1H), 7.2 (m, 4H), 7.4 (m, 8H), 7.5 (m, 1H).

Example 183

2-methyl-1-[(1R,5S)-8-(2-{4-phenyl-1-[4-(trifluoromethyl)benzoyl]-4-piperidinyl}ethyl)-8-azabicyclo[3.2.1]oct-3-yl]-1H-benzimidazole

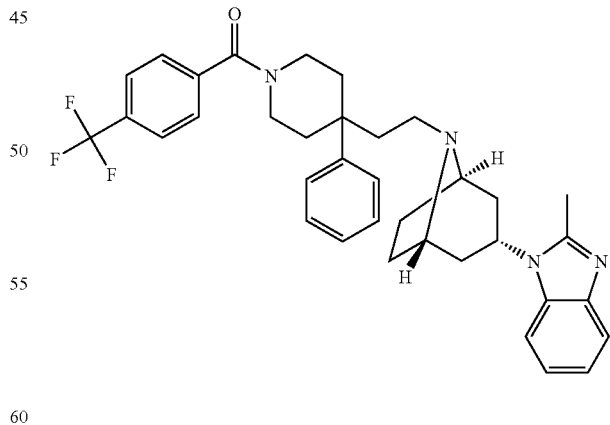

$^1$H NMR (400 MHz, methanol-d4) δ ppm 1.7 (m, 2H), 1.9 (m, 10H), 2.2 (m, 1H), 2.4 (m, 4H), 2.5 (m, 3H), 3.3 (m, 4H), 4.2 (m, J=8.9, 4.6 Hz, 1H), 4.7 (m, 1H), 7.2 (m, 2H), 7.2 (m, 1H), 7.4 (m, 5H), 7.5 (m, 1H), 7.6 (d, J=7.8 Hz, 2H), 7.8 (d, J=7.8 Hz, 2H).

Example 326A

4-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-2-imidazolidinone

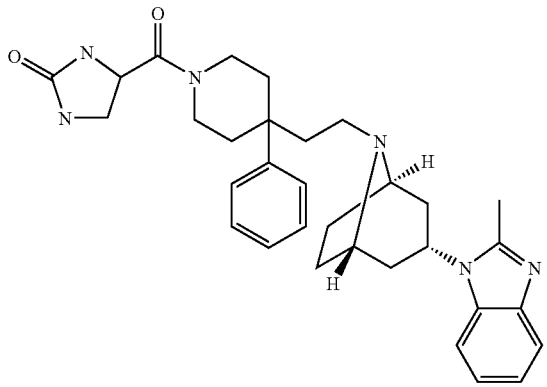

$^1$H NMR (400 MHz, methanol-d4) δ ppm 1.7 (m, 2H), 1.9 (m, 12H), 2.3 (m, 3H), 2.4 (m, 2H), 2.5 (s, 3H), 3.2 (m, 4H), 3.5 (m, 1H), 3.6 (m, 1H), 3.8 (m, 1H), 4.0 (m, 1H), 4.7 (m, 1H), 7.2 (m, 2H), 7.2 (m, 1H), 7.4 (m, 5H), 7.5 (m, 1H).

Example 326B $^1$H NMR (300 MHz, CD$_3$OD) δ ppm 1.97-2.45 (m, 12H), 2.62 (s, 3H), 2.70-2.93 (m, 5H), 3.12 (m, 1H), 3.42 (m, 1H), 4.02-4.20 (m, 3H), 5.35 (m, 1H), 7.23 (m, 1H), 7.33-7.44 (m, 5H), 7.62 (m, 2H), 8.73 (m, 3H).

Example 249

$^1$H NMR (300 MHz, CD$_3$OD) δ 7.63-8.00 (m, 3H), 7.49-7.59 (m, 1H), 7.36-7.49 (m, 5H), 7.14-7.33 (m, 3H), 4.68-4.83 (m, 1H), 4.16-4.30 (m, 1H), 3.36-3.51 (m, 2H, under methanol), 3.11-3.28 (m, 1H), 2.56 (s, 3H), 2.34-2.51 (m, 3H), 2.23-2.34 (m, 1H), 1.85-2.01 (m, 10H), 1.59-1.77 (m, 2H), 1.18-1.38 (m, 4H).

Example 236

$^1$H NMR (300 MHz, CD$_3$OD) δ 7.64-7.98 (m, 3H), 7.48-7.59 (m, 1H), 7.35-7.47 (m, 5H), 7.16-7.31 (m, 3H), 4.67-4.82 (m, 1H), 4.13-4.30 (m, 1H), 3.35-3.50 (m, 4H, under methanol), 3.11-3.27 (m, 1H), 2.55 (s, 3H), 2.36-2.52 (m, 3H), 2.23-2.36 (m, 1H), 1.83-2.11 (m, 10H), 1.64-1.75 (m, 2H), 1.31 (s, 1H), 0.98-1.15 (m, 7H).

Example 21

$^1$H NMR (300 MHz, CD$_3$OD) δ 7.71-7.86 (m, 2H), 7.55-7.68 (m, 2H), 7.40-7.55 (m, 4H), 7.27-7.40 (m, 1H), 5.22-5.46 (m, 1H), 4.31-4.46 (d, J=12.25 Hz, 1H), 4.03-4.28 (m, 2H), 3.99 (s, 2H), 3.77-3.97 (m, 2H), 3.42-3.61 (m, 1H), 3.35 (s, 3H), 2.87-3.02 (m, 2H), 2.83 (s, 3H), 2.66-2.79 (m, 2H), 2.33-2.52 (m, 3H), 2.10-2.33 (m, 7H), 1.72-2.08 (m, 2H), 1.40 (s, 1H), 1.19-1.36 (m, 5H).

Example 252

$^1$H NMR (300 MHz, CD$_3$OD) δ 7.49-7.59 (m, 1H), 7.33-7.49 (m, 5H), 7.12-7.31 (m, 3H), 4.67-4.84 (m, 1H), 3.97-4.12 (m, 1H), 3.76-3.89 (m, 1H), 3.34-3.40 (m, 1H, under methanol), 3.12-3.26 (m, 1H), 2.65 (s, 3H), 2.51-2.61 (m, 5H), 2.36-2.51 (m, 2H), 2.22-2.36 (m, 2H), 1.74-2.12 (m, 10H), 1.61-1.74 (m, 2H), 1.21-1.32 (d, J=1.69 Hz, 6H).

Example 253

$^1$H NMR (300 MHz, CD$_3$OD) δ 7.48-7.61 (m, 1H), 7.14-7.48 (m, 13H), 5.03-5.15 (m, 1H), 4.66-4.82 (m, 1H), 3.91-4.09 (m, 1H), 3.57-3.77 (m, 1H), 3.00-3.29 (m, 2H), 2.71-2.95 (m, 2H), 2.62-2.71 (m, 6H), 2.57 (s, 3H), 2.32-2.51 (m, 2H), 2.08-2.30 (m, 1H), 1.60-2.08 (m, 10H).

Example 254

$^1$H NMR (300 MHz, CD$_3$OD) δ 7.50-7.59 (m, 1H), 7.34-7.50 (m, 5H), 7.14-7.31 (m, 3H), 4.67-4.83 (m, 1H), 4.33-4.52 (bs, 1H), 3.92-4.15 (bs, 1H), 3.48-3.70 (bs, 1H), 3.08-3.27 (bs, 1H), 2.62-2.70 (m, 6H), 2.51-2.62 (m, 3H), 2.35 (s, 3H), 1.78-2.08 (m, 8H), 1.55-1.73 (m, 4H).

Example 255

$^1$H NMR (300 MHz, CD$_3$OD) δ 7.32-7.60 (m, 6H), 7.11-7.32 (m, 3H), 4.69-4.84 (m, 1H), 3.34-3.41 (m, 2H, under methanol), 2.66 (s, 1H), 2.56 (s, 3H), 2.36-2.52 (m, 2H), 2.21-2.35 (m, 2H), 1.49-2.21 (m, 18H).

Example 256

$^1$H NMR (300 MHz, CD$_3$OD) δ 7.33-7.59 (m, 6H), 7.12-7.31 (m, 3H), 4.71-4.85 (m, 1H), 3.84-4.15 (m, 1H), 3.34-3.50 (m, 2H, under methanol), 2.63-2.75 (m, 7H), 2.56 (s, 3H), 2.35-2.52 (m, 2H), 2.20-2.35 (m, 2H), 1.49-2.10 (m, 17H), 1.28 (s, 2H).

Example 257

$^1$H NMR (300 MHz, CD$_3$OD) δ 7.33-7.59 (m, 6H), 7.13-7.31 (m, 3H), 4.66-4.85 (m, 1H), 4.13-4.25 (m, 1H), 3.94-4.13 (m, 1H), 3.71-3.86 (m, 1H), 3.35-3.41 (m, 1H, under methanol), 3.09-3.27 (m, 1H), 2.64-2.71 (m, 5H), 2.53-2.64 (m, 4H), 2.20-2.53 (m, 5H), 1.74-2.12 (m, 8H), 1.63-1.74 (m, 2H), 1.18-1.27 (m, 3H).

Example 258

$^1$H NMR (300 MHz, CD$_3$OD) δ 7.35-7.59 (m, 6H), 7.13-7.32 (m, 3H), 4.67-4.85 (m, 1H), 3.98-4.32 (m, 1H), 3.35-3.63 (m, 1H, under methanol), 2.66 (s, 6H), 2.56 (s, 3H), 2.36-2.52 (m, 2H), 2.24-2.36 (m, 2H), 1.77-2.09 (m, 10H), 1.60-1.77 (m, 4H), 1.30 (s, 1H), 0.77-0.96 (t, J=7.26 Hz, 6H).

Example 260

$^1$H NMR (300 MHz, CD$_3$OD) δ 7.50-7.61 (m, 1H), 7.13-7.50 (m, 13H), 4.62-4.81 (m, 1H), 3.89-4.13 (m, 1H), 3.69-3.89 (m, 1H), 3.12-3.31 (m, 2H), 2.62-2.71 (m, 7H), 2.56 (s, 3H), 2.28-2.47 (m, 2H), 2.06-2.27 (m, 1H), 1.73-2.03 (m, 5H), 1.51-1.73 (m, 7H).

Example 262

$^1$H NMR (300 MHz, CD$_3$OD) δ 7.50-7.61 (m, 1H), 7.15-7.50 (m, 17H), 4.71-4.84 (m, 1H), 4.48 (s, 2H), 4.06-4.24 (m,

1H), 3.58-3.75 (m, 1H), 3.35-3.52 (m, 2H), 2.59-2.80 (m, 9H), 2.50 (s, 4H), 2.09-2.21 (m, 2H), 1.90-2.08 (m, 5H), 1.71-1.83 (m, 2H).

Example 263

$^{1}$H NMR (300 MHz, CD$_3$OD) δ 7.51-7.60 (m, 1H), 7.10-7.51 (m, 13H), 4.61-4.79 (m, 1H), 3.38-4.14 (m, 1H), 3.68-3.88 (m, 1H), 3.14-3.29 (m, 2H), 2.58-2.72 (m, 8H), 2.53 (s, 3H), 2.28-2.48 (m, 2H), 2.06-2.28 (m, 1H), 1.75-2.03 (m, 5H), 1.55-1.73 (m, 6H).

Example 264

$^{1}$H NMR (300 MHz, CD$_3$OD) δ 7.73-7.96 (dd, 1H, J=43.02, 7.44), 7.49-7.68 (m, 2H), 7.34-7.48 (m, 5H), 7.12-7.34 (m, 3H), 4.67-4.83 (m, 1H), 4.12-4.31 (m, 1H), 3.34-3.44 (m, 3H, under methanol), 3.12-3.28 (m, 1H), 2.56 (s, 3H), 2.35-2.52 (m, 3H), 2.23-2.35 (m, 1H), 1.83-2.12 (m, 11H), 1.62-1.78 (m, 2H), 1.10-1.21 (d, J=6.23 Hz, 2H).

Example 265

$^{1}$H NMR (300 MHz, CD$_3$OD) δ 7.985-8.04 (m, 2H), 7.62-7.77 (m, 2H), 7.49-7.61 (m, 1H), 7.33-7.48 (m, 5H), 7.12-7.33 (m, 3H), 4.66-4.84 (m, 1H), 4.09-4.27 (m, 1H), 3.64-3.80 (t, J=5.8 Hz, 4H), 3.46-3.64 (m, 1H), 2.61-2.73 (m, 7H), 2.51-2.60 (m, 3H), 2.35-2.50 (m, 3H), 2.19-2.35 (m, 1H), 1.79-2.15 (m, 9H), 1.57-1.79 (m, 3H), 1.19-1.41 (m, 3H).

Example 235

$^{1}$H NMR (300 MHz, CD$_3$OD) δ 7.67-7.94 (m, 3H), 7.48-7.60 (m, 1H), 7.34-7.48 (m, 5H), 7.13-7.33 (m, 3H), 4.66-4.83 (m, 1H), 4.16-4.29 (m, 1H), 3.33-3.49 (m, 4H, under methanol), 3.12-3.28 (m, 1H), 2.57-2.61 (m, 1H), 2.51-2.57 (m, 4H), 2.36-2.51 (m, 3H), 2.23-2.36 (m, 1H), 1.83-2.09 (m, 12H), 1.61-1.76 (m, 2H).

Example 237

$^{1}$H NMR (300 MHz, CD$_3$OD) δ 7.66-7.94 (m, 3H), 7.48-7.58 (m, 1H), 7.35-7.48 (m, 5H), 7.13-7.33 (m, 3H), 4.68-4.83 (m, 1H), 4.15-4.29 (m, 1H), 3.34-3.46 (m, 6H, under methanol), 3.16-3.28 (m, 4H), 3.02-3.14 (m, 2H), 2.55 (s, 3H), 2.35-2.50 (m, 3H), 2.24-2.35 (m, 1H), 1.83-2.13 (m, 11H), 1.63-1.77 (m, 2H).

Example 288

$^{1}$H NMR (300 MHz, CD$_3$OD) δ 7.67-7.94 (m, 3H), 7.51-7.59 (m, 1H), 7.38-7.51 (m, 2H), 7.16-7.30 (m, 4H), 6.97-7.08 (m, 1H), 4.68-4.82 (m, 1H), 4.13-4.29 (m, 1H), 3.35-3.54 (m, 3H, under methanol), 2.40-2.81 (m, 12H), 1.86-2.16 (m, 9H), 1.67-1.80 (m, 2H), 1.23-1.33 (m, 2H).

Example 364

$^{1}$H NMR (300 MHz, CD$_3$OD) δ 7.65-7.97 (m, 3H), 7.51-7.62 (m, 1H), 7.38-7.51 (m, 2H), 7.13-7.32 (m, 4H), 6.94-7.12 (m, 1H), 4.68-4.82 (m, 1H), 4.08-4.30 (m, 1H), 3.34-3.65 (m, 4H, under methanol), 2.84-3.06 (m, 2H), 2.67 (s, 3H), 2.44-2.61 (m, 4H), 2.32-2.44 (m, 1H), 2.16-2.32 (m, 2H), 1.77-2.16 (m, 9H), 1.27-1.39 (m, 2H), 1.00-1.17 (m, 3H).

Example 291

$^{1}$H NMR (300 MHz, CD$_3$OD) δ 7.68-7.96 (m, 3H), 7.50-7.59 (m, 1H), 7.38-7.50 (m, 2H), 7.14-7.33 (m, 4H), 6.95-7.11 (m, 1H), 4.68-4.83 (m, 1H), 4.08-4.32 (m, 1H), 3.34-3.61 (m, 5H, under methanol), 2.61-2.71 (m, 4H), 2.57 (s, 3H), 2.08-2.31 (m, 2H), 1.84-2.08 (m, 7H), 1.69-1.84 (m, 1H), 1.30 (s, 4H), 0.39-0.67 (m, 4H).

Example 292

$^{1}$H NMR (300 MHz, CD$_3$OD) δ 7.64-7.98 (m, 3H), 7.50-7.58 (m, 1H), 7.37-7.50 (m, 2H), 7.11-7.31 (m, 4H), 6.95-7.09 (m, 1H), 4.65-4.81 (m, 1H), 4.09-4.27 (m, 1H), 3.36-3.56 (m, 4H, under methanol), 3.08-3.26 (m, 1H), 2.57 (s, 3H), 2.31-2.51 (m, 4H), 2.16-2.31 (m, 1H), 1.78-2.13 (m, 11H), 1.64-1.78 (m, 2H), 0.96-1.11 (m, 6H).

Example 308

$^{1}$H NMR (300 MHz, CD$_3$OD) δ 7.63-7.93 (m, 3H), 7.49-7.59 (m, 1H), 7.38-7.48 (m, 1H), 7.13-7.35 (m, 5H), 7.03-7.13 (m, 1H), 4.67-4.83 (m, 1H), 4.15-4.29 (m, 1H), 3.34-3.41 (m, 5H, under methanol), 3.12-3.29 (m, 1H), 2.52-2.61 (m, 6H), 2.40-2.52 (m, 3H), 2.34-2.40 (m, 4H), 2.19-2.34 (m, 1H), 1.83-2.11 (m, 9H), 1.63-1.75 (m, 2H).

Example 309

$^{1}$H NMR (300 MHz, CD$_3$OD) δ 7.71-7.93 (m, 3H), 7.53-7.59 (m, 1H), 7.40-7.49 (m, 2H), 7.17-7.29 (m, 4H), 6.97-7.08 (m, 1H), 4.11-4.28 (m, 1H), 3.48-3.61 (m, 1H), 3.34-3.48 (m, 3H, under methanol), 3.12-3.30 (m, 1H), 2.84-3.03 (m, 2H), 2.67 (s, 3H), 2.49-2.62 (m, 3H), 2.31-2.46 (m, 1H), 2.16-2.31 (m, 2H), 1.80-2.15 (m, 9H), 1.27-1.41 (m, 3H), 1.01-1.13 (m, 3H).

Example 310

$^{1}$H NMR (300 MHz, CD$_3$OD) δ 7.67-7.93 (m, 3H), 7.51-7.57 (m, 1H), 7.40-7.45 (m, 1H), 7.17-7.33 (m, 5H), 7.05-7.12 (m, 1H), 4.69-4.84 (m, 1H), 4.11-4.31 (m, 1H), 3.35-3.48 (m, 2H, under methanol), 3.13-3.28 (m, 1H), 2.79-2.94 (m, 2H), 2.67 (s, 3H), 2.57 (s, 2H), 2.41-2.53 (m, 2H), 2.33-2.41 (m, 3H), 2.20-2.33 (m, 1H), 1.82-2.11 (m, 9H), 1.63-1.77 (m, 2H), 1.39-1.57 (m, 2H), 0.80-0.96 (m, 3H).

Example 311

$^{1}$H NMR (300 MHz, CD$_3$OD) δ 7.68-7.97 (m, 3H), 7.50-7.59 (m, 1H), 7.38-7.48 (m, 1H), 7.15-7.36 (m, 5H), 7.04-7.15 (m, 1H), 4.69-4.83 (m, 1H), 4.14-4.34 (m, 1H), 3.34-3.48 (m, 2H, under methanol), 3.13-3.26 (m, 1H), 2.67 (s, 2H), 2.57 (s, 3H), 2.42-2.51 (m, 2H), 2.33-2.42 (m, 3H), 2.13-2.33 (m, 2H), 1.81-2.13 (m, 9H), 1.66-1.79 (d, J=7.76 Hz, 2H), 1.31 (s, 3H), 0.44-0.65 (m, 4H).

Example 312

$^{1}$H NMR (300 MHz, CD$_3$OD) δ 7.66-7.94 (m, 3H), 7.51-7.56 (m, 1H), 7.39-7.45 (m, 1H), 7.16-7.33 (m, 5H), 7.05-7.13 (m, 1H), 4.72-4.83 (m, 1H), 4.13-4.31 (m, 1H), 3.35-3.49 (m, 3H, under methanol), 3.10-3.27 (m, 1H), 2.68 (s, 2H), 2.55 (s, 3H), 2.34-2.51 (m, 6H), 2.20-2.34 (m, 1H), 1.85-2.12 (m, 10H), 1.65-1.77 (m, 2H), 1.31 (s, 1H), 0.97-1.12 (m, 6H).

Example 293

$^{1}$H NMR (300 MHz, CD$_3$OD) δ 8.08 (s, 1H), 7.61-7.76 (m, 2H), 7.50-7.58 (m, 1H), 7.36-7.49 (m, 2H), 7.13-7.31 (m,

4H), 6.94-7.07 (m, 1H), 4.68-4.82 (m, 1H), 4.08-4.22 (m, 1H), 3.52-3.67 (m, 1H), 3.35-3.51 (m, 4H, under methanol), 2.52-2.62 (m, 6H), 2.34-2.52 (m, 3H), 2.17-2.30 (m, 1H), 1.81-2.14 (m, 11H), 1.64-1.77 (m, 2H).

Example 273

$^1$H NMR (300 MHz, CD$_3$OD) δ 7.66-7.94 (m, 3H), 7.49-7.57 (m, 1H), 7.35-7.49 (m, 5H), 7.23-7.33 (m, 1H), 7.14-7.23 (m, 2H), 4.67-4.83 (m, 1H), 4.16-4.30 (m, 1H), 3.34-3.43 (m, 4H, under methanol), 3.11-3.26 (m, 1H), 2.86-3.03 (m, 2H), 2.55 (s, 3H), 2.36-2.52 (m, 3H), 2.22-2.36 (m, 1H), 1.86-2.11 (m, 11H), 1.64-1.76 (m, 2H), 1.01-1.14 (dd, J=16.03, 7.5 Hz, 3H).

Example 274

$^1$H NMR (300 MHz, CD$_3$OD) δ 7.65-7.94 (m, 3H), 7.48-7.60 (m, 1H), 7.35-7.48 (m, 5H), 7.23-7.30 (m, 1H), 7.15-7.23 (m, 2H), 4.66-4.82 (m, 1H), 4.16-4.27 (m, 1H), 3.34-3.46 (m, 4H, under methanol), 3.10-3.27 (m, 1H), 2.77-2.92 (m, 2H), 2.55 (s, 3H), 2.35-2.51 (m, 3H), 2.21-2.35 (m, 1H), 1.84-2.09 (m, 11H), 1.61-1.75 (m, 2H), 1.37-1.56 (m, 2H), 0.81-0.94 (dd, J=16.10, 7.48 Hz, 3H).

Example 275

$^1$H NMR (300 MHz, CD$_3$OD) δ 7.68-7.98 (m, 3H), 7.48-7.60 (m, 1H), 7.35-7.48 (m, 5H), 7.24-7.35 (m, 1H), 7.14-7.24 (m, 2H), 4.66-4.82 (m, 1H), 4.16-4.30 (m, 1H), 3.34-3.43 (m, 6H, under methanol), 2.55 (s, 3H), 2.35-2.51 (m, 2H), 2.13-2.35 (m, 2H), 1.83-2.12 (m, 9H), 1.65-1.76 (m, 2H), 1.30 (s, 2H), 0.41-0.61 (m, 3H).

Example 210

$^1$H NMR (300 MHz, CD$_3$OD) δ 7.91-8.00 (m, 1H), 7.87 (s, 1H), 7.64-7.74 (m, 2H), 7.50-7.58 (m, 1H), 7.36-7.49 (m, 5H), 7.22-7.32 (m, 1H), 7.14-7.22 (m, 2H), 4.69-4.82 (m, 1H), 4.09-4.30 (m, 1H), 3.47-3.66 (m, 1H), 3.34-3.39 (m, 3H, under methanol), 2.50-2.59 (m, 6H), 2.36-2.50 (m, 3H), 2.22-2.35 (m, 1H), 1.83-2.11 (m, 10H), 1.65-1.76 (m, 2H), 1.30 (s, 2H).

Example 294

$^1$H NMR (300 MHz, CD$_3$OD) δ 7.74-7.96 (dd, J=38.00, 7.77 Hz, 1H), 7.49-7.68 (m, 2H), 7.35-7.49 (m, 2H), 7.12-7.32 (m, 4H), 6.94-7.09 (m, 1H), 4.66-4.83 (m, 1H), 4.12-4.25 (m, 1H), 3.34-3.54 (m, 3H, under methanol), 3.13-3.28 (m, 1H), 2.56 (s, 3H), 2.30-2.52 (m, 3H), 2.16-2.30 (m, 1H), 1.79-2.09 (m, 9H), 1.64-1.78 (m, 2H), 1.26-1.39 (m, 1H), 1.09-1.19 (d, J=6.13 Hz, 3H).

Example 295

$^1$H NMR (300 MHz, CD$_3$OD) δ 7.99-8.10 (m, 1H), 7.86-7.99 (m, 1H), 7.50-7.59 (m, 1H), 7.36-7.50 (m, 3H), 7.13-7.30 (m, 4H), 6.95-7.07 (m, 1H), 4.67-4.83 (m, 1H), 4.13-4.25 (m, 1H), 3.42-3.59 (m, 1H), 3.34-3.41 (m, 2H, under methanol), 2.56 (s, 3H), 2.30-2.50 (m, 3H), 2.18-2.30 (m, 1H), 1.80-2.12 (m, 10H), 1.65-1.80 (m, 2H), 1.22-1.42 (m, 1H), 1.09-1.19 (d, J=6.23 Hz, 3H).

Example 296

$^1$H NMR (300 MHz, CD$_3$OD) δ 7.89-8.00 (m, 1H), 7.61-7.88 (m, 2H), 7.50-7.60 (m, 1H), 7.34-7.50 (m, 2H), 7.12-7.34 (m, 4H), 6.94-7.07 (m, 1H), 4.64-4.83 (m, 1H), 4.10-4.27 (m, 1H), 3.34-3.54 (m, 3H, under methanol), 3.12-3.27 (m, 1H), 2.56 (s, 3H), 2.30-2.51 (m, 3H), 2.16-2.30 (m, 1H), 1.79-2.12 (m, 11H), 1.63-1.79 (m, 2H), 1.23-1.36 (m, 2H).

Example 297

$^1$H NMR (300 MHz, CD$_3$OD) δ 7.98-8.04 (m, 1H), 7.87-7.96 (m, 1H), 7.50-7.57 (m, 1H), 7.38-7.48 (m, 3H), 7.15-7.28 (m, 4H), 6.96-7.05 (m, 1H), 4.66-4.83 (m, 1H), 4.13-4.24 (m, 1H), 3.64-3.76 (m, 2H), 3.41-3.54 (m, 2H), 3.30-3.34 (m, 3H), 3.18-3.29 (m, 1H), 2.543 (s, 3H), 2.30-2.51 (m, 3H), 2.15-2.29 (m, 1H), 1.84-2.09 (m, 9H), 1.66-1.76 (m, 2H), 1.27-1.32 (m, 1H).

Example 298

$^1$H NMR (300 MHz, CD$_3$OD) δ 7.67-7.95 (m, 3H), 7.50-7.58 (m, 1H), 7.39-7.46 (m, 2H), 7.15-7.27 (m, 4H), 6.96-7.06 (m, 1H), 4.65-4.83 (m, 1H), 4.11-4.26 (m, 1H), 3.63-3.80 (m, 2H), 3.37-3.54 (m, 2H), 3.29-3.34 (m, 3H), 3.11-3.27 (m, 1H), 2.54 (s, 3H), 2.31-2.51 (m, 3H), 2.17-2.29 (m, 1H), 1.86-2.09 (m, 9H), 1.64-1.77 (m, 2H), 1.27-1.33 (m, 1H).

Example 315

$^1$H NMR (300 MHz, CD$_3$OD) δ 7.64-7.97 (m, 3H), 7.50-7.56 (m, 1H), 7.38-7.45 (m, 1H), 7.14-7.33 (m, 5H), 7.04-7.12 (m, 1H), 4.67-4.83 (m, 1H), 4.16-4.27 (m, 1H), 3.37-3.46 (m, 1H), 3.30-3.34 (m, 5H), 3.11-3.27 (m, 1H), 2.54 (s, 3H), 2.41-2.51 (m, 2H), 2.33-2.40 (m, 3H), 2.22-2.32 (m, 1H), 1.81-2.10 (m, 10H), 1.64-1.74 (m, 2H), 1.27-1.35 (m, 1H).

Example 278

$^1$H NMR (300 MHz, CD$_3$OD) δ 8.00-8.08 (m, 1H), 7.85-7.98 (br.s, 1H), 7.50-7.58 (m, 1H), 7.36-7.46 (m, 1H), 7.36-7.46 (m, 6H), 7.23-7.32 (m, 1H), 7.14-7.22 (m, 2H), 4.67-4.83 (m, 1H), 4.15-4.28 (m, 1H), 3.18-3.58 (m, 7H), 2.51-2.57 (m, 3H), 2.34-2.50 (m, 3H), 1.81-2.09 (m, 10H), 1.62-1.75 (m, 2H), 1.26-1.33 (m, 1H).

Example 279

$^1$H NMR (300 MHz, CD$_3$OD) δ 7.94-8.01 (m, 1H), 7.79-7.92 (m, 1H), 7.51-7.57 (m, 1H), 7.37-7.47 (m, 6H), 7.23-7.31 (m, 1H), 7.16-7.22 (m, 2H), 4.68-4.81 (m, 1H), 4.16-4.29 (m, 1H), 3.42-3.59 (m, 2H), 3.20-3.41 (m, 7H), 2.52-2.60 (m, 4H), 2.25-2.49 (m, 3H), 1.85-2.09 (m, 8H), 1.66-1.75 (m, 1H), 1.28-1.34 (s, 2H).

Example 280

$^1$H NMR (300 MHz, CD$_3$OD) δ 7.95-8.02 (m, 1H), 7.82-7.93 (m, 1H), 7.51-7.56 (m, 1H) 7.37-7.47 (m, 6H), 7.23-7.30 (m, 1H), 7.15-7.23 (m, 2H), 4.66-4.83 (m, 1H), 4.15-4.29 (m, 1H), 3.17-3.58 (m, 8H), 2.86-2.99 (q, 2H), 2.52-2.56 (s, 3H), 2.35-2.50 (m, 3H), 1.81-2.10 (m, 8H), 1.63-1.74 (q, 2H), 1.27-1.34 (s, 1H), 1.01-1.13 (t, 3H).

Example 281

$^1$H NMR (300 MHz, CD$_3$OD) δ 7.95-8.02 (m, 1H), 7.83-7.94 (br s, 1H), 7.50-7.57 (m, 1H), 7.37-7.48 (m, 6H), 7.23-7.30 (m, 1H), 7.15-7.23 (m, 2H), 4.67-4.83 (m, 1H), 4.16-

4.27 (m, 1H), 3.30-3.33 (m, 4H), 2.80-2.89 (m, 2H), 2.54 (s, 3H), 2.35-2.51 (m, 3H), 2.24-2.34 (m, 1H), 1.84-2.11 (m, 8H), 1.65-1.76 (m, 2H), 1.40-1.55 (m, 2H), 1.30 (s, 2H), 0.88 (t, J=7.4 Hz, 3H).

Example 282

¹H NMR (300 MHz, CD₃OD) δ 7.98-8.05 (m, 1H), 7.85-7.96 (m, 1H), 7.50-7.57 (m, 1H), 7.37-7.50 (m, 6H), 7.22-7.32 (m, 1H), 7.15-7.22 (m, 2H), 4.67-4.83 (m, 1H), 4.16-4.29 (m, 1H), 3.37-3.59 (m, 2H), 3.29-3.34 (m, 4H), 2.54 (s, 3H), 2.36-2.51 (m, 3H), 2.17-2.35 (m, 2H), 1.82-2.10 (m, 8H), 1.64-1.75 (m, 2H), 1.31 (s, 2H), 0.44-0.62 (m, 4H).

Example 283

¹H NMR (300 MHz, CD₃OD) δ 7.96-8.03 (m, 1H), 7.84-7.95 (m, 1H), 7.50-7.57 (m, 1H), 7.37-7.47 (m, 6H), 7.22-7.30 (m, 1H), 7.15-7.22 (m, 2H), 4.68-4.83 (m, 1H), 4.16-4.28 (m, 1H), 3.18-3.53 (m, 7H), 2.54 (s, 3H), 2.35-2.51 (m, 3H), 2.24-2.35 (m, 1H), 1.84-2.09 (m, 8H), 1.65-1.75 (m, 2H), 1.28-1.32 (m, 2H), 1.01-1.09 (d, J=6.4 Hz, 6H).

Example 303

¹H NMR (300 MHz, CD₃OD) δ 7.95-8.02 (m, 1H), 7.84-7.94 (m, 1H), 7.50-7.57 (m, 1H), 7.37-7.48 (m, 3H), 7.25-7.28 (m, 1H), 7.14-7.25 (m, 4H), 6.96-7.05 (m, 1H), 4.66-4.82 (m, 1H), 4.12-4.24 (m, 1H), 3.18-3.56 (m, 6H), 2.88-2.98 (q, J=7.3 Hz, 2H), 2.4 (s, 3H), 2.31-2.51 (m, 3H), 2.18-2.29 (m, 1H), 1.83-2.09 (m, 8H), 1.65-1.76 (m, 2H), 1.28-1.32 (m, 1H), 1.08 (t, J=7.3 Hz, 3H).

Example 304

¹H NMR (300 MHz, CD₃OD) δ 7.95-8.02 (m, 1H), 7.83-7.93 (m, 1H), 7.51-7.57 (m, 1H), 7.38-7.48 (m, 3H), 7.26-7.29 (m, 1H), 7.16-7.26 (m, 3H), 6.97-7.07 (m, 1H), 4.68-4.83 (m, 1H), 4.10-4.24 (m, 1H), 3.37-3.54 (m, 1H), 3.30-3.54 (m, 4H), 2.80-2.88 (t, J=7.0 Hz, 2H), 2.54 (s, 3H), 2.31-2.50 (m, 3H), 2.17-2.30 (m, 1H), 1.83-2.11 (m, 8H), 1.68-1.77 (m, 2H), 1.41-1.55 (m, 2H), 1.30 (m, 3H), 0.88 (t, J=7.0 Hz, 3H).

Example 305

¹H NMR (300 MHz, CD₃OD) δ 7.98-8.05 (m, 1H), 7.86-7.97 (m, 1H), 7.51-7.57 (m, 1H), 7.39-7.50 (m, 3H), 7.25-7.29 (m, 1H), 7.16-7.25 (m, 3H), 6.96-7.06 (m, 1H), 4.68-4.82 (m, 1H), 4.13-4.25 (m, 1H), 3.42-3.59 (m, 2H), 3.30-3.34 (m, 4H), 3.19-3.29 (m, 1H), 2.54 (s, 3H), 2.32-2.51 (m, 3H), 2.16-2.28 (m, 2H), 1.83-2.10 (m, 8H), 1.66-1.77 (m, 2H), 1.30 (s, 1H), 0.45-0.62 (m, 4H).

Example 306

¹H NMR (300 MHz, CD₃OD) δ 7.96-8.04 (m, 1H), 7.86-7.94 (m, 1H), 7.50-7.56 (m, 1H), 7.38-7.48 (m, 3H), 7.16-7.28 (m, 4H), 6.97-7.05 (m, 1H), 4.67-4.82 (m, 1H), 4.13-4.24 (m, 1H), 3.37-3.55 (m, 4H), 3.30-3.34 (m, 4H), 3.18-3.29 (m, 1H), 2.55 (s, 3H), 2.32-2.49 (m, 3H), 2.19-2.28 (m, 1H), 1.85-2.10 (m, 8H), 1.67-1.76 (m, 2H), 1.28-1.32 (m, 1H), 1.02-1.10 (d, J=6.6 Hz, 6H).

Example 284

¹H NMR (300 MHz, CD₃OD) δ 7.97-8.04 (m, 1H), 7.85-7.97 (m, 1H), 7.50-7.57 (m, 1H), 7.37-7.48 (m, 6H), 7.23-7.30 (m, 1H), 7.14-7.23 (m, 2H), 4.67-4.82 (m, 1H), 4.16-4.27 (m, 1H), 3.63-3.77 (m, 2H), 3.37-3.52 (m, 2H), 3.30-3.34 (m, 3H), 3.18-3.29 (m, 1H), 2.55 (s, 3H), 2.36-2.50 (m, 3H), 2.23-2.34 (m, 1H), 1.83-2.09 (m, 9H), 1.64-1.73 (m, 2H), 1.30 (s, 1H).

Example 285

¹H NMR (300 MHz, CD₃OD) δ 7.75-7.94 (m, 3H), 7.50-7.57 (m, 1H), 7.36-7.46 (m, 5H), 7.23-7.30 (m, 1H), 7.14-7.23 (m, 2H), 4.66-4.82 (m, 1H), 4.17-4.28 (m, 1H), 3.62-3.82 (m, 2H), 3.36-3.47 (m, 2H), 3.30-3.34 (m, 4H), 3.11-3.26 (m, 1H), 2.54 (s, 3H), 2.37-2.51 (m, 3H), 2.23-2.34 (m, 1H), 1.85-2.10 (m, 8H), 1.64-1.74 (m, 2H), 1.30 (s, 1H).

Example 365

¹H NMR (300 MHz, CD₃OD) δ 7.81-8.10 (m, 2H), 7.47-7.60 (m, 1H), 7.35-7.47 (m, 5H), 7.14-7.31 (m, 3H), 4.69-4.84 (m, 1H), 4.14-4.31 (m, 1H), 3.35-3.49 (m, 2H, under methanol), 3.11-3.27 (m, 1H), 2.50-2.64 (m, 6H), 2.36-2.50 (m, 3H), 2.22-2.36 (m, 1H), 1.82-2.10 (m, 11H), 1.62-1.75 (m, 2H), 1.11-1.20 (d, J=6.14 Hz, 2H).

Example 366

¹H NMR (300 MHz, CD₃OD) δ 7.64-7.95 (m, 3H), 7.49-7.59 (m, 1H), 7.34-7.48 (m, 2H), 7.10-7.30 (m, 4H), 6.95-7.06 (m, 1H), 4.72-4.83 (m, 1H), 4.11-4.25 (m, 1H), 3.34-3.53 (m, 5H, under methanol), 3.07-3.29 (m, 1H), 2.76-2.93 (m, 2H), 2.67 (s, 1H), 2.42-2.60 (m, 4H), 2.29-2.42 (m, 1H), 1.74-2.29 (m, 12H), 1.26-1.56 (m, 3H), 0.80-0.96 (m, 3H).

Example 367

¹H NMR (300 MHz, CD₃OD) δ 7.65-7.92 (m, 2H), 7.47-7.65 (m, 2H), 7.37-7.47 (m, 1H), 7.12-7.36 (m, 5H), 7.04-7.12 (m, 1H), 4.69-4.83 (m, 1H), 4.08-4.31 (m, 1H), 3.34-3.47 (m, 3H, under methanol), 3.13-3.28 (m, 3H), 2.32-2.64 (m, 8H), 2.20-2.32 (m, 1H), 1.79-2.13 (m, 9H), 1.64-1.78 (m, 2H), 1.24-1.43 (m, 5H).

Synthesis of Acids

Acid 1: 2-methyl-2-(1H-tetraazol-5-yl)propanoic acid

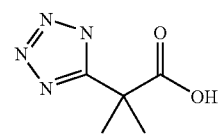

Ethyl 2-methyl-2-(1H-tetraazol-5-yl)propanoate

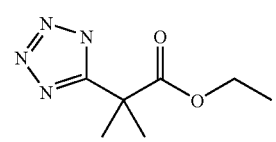

The title compound was prepared from ethyl 2-cyano-2-methylpropanoate (3.67 g, 26 mmoles) via the literature procedure [*J. Org. Chem.*, 58(15), 4139 (1993)] to give 3.83 g (80%) of pure product as an amber solid. $^{13}$C NMR (300 MHz, CDCl$_3$) δ 174.04, 159.73, 62.74, 42.30, 25.74, 14.12.

2-methyl-2-(1H-tetraazol-5-yl)propanoic acid

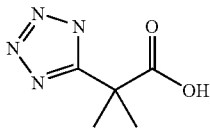

Ethyl 2-methyl-2-(1H-tetraazol-5-yl) propanoate (1.50 g, 8.14 mmoles) was dissolved in 8 mL EtOH and treated with 6.7 mL 6N NaOH at ambient temperature for 18 h. The reaction mixture was concentrated to dryness and the resultant solid was extracted with EtOH. Inorganics were filtered off and the filtrate were concentrated to give the title compound (1.24 g, 7.94 mmoles, 98%) as a tan solid. $^{13}$C NMR (300 MHz, D$_2$O) δ 176.88, 159.60, 41.69, 24.07.

Acid 2: N-(tert-butoxycarbonyl)-3-hydroxy-L-valine

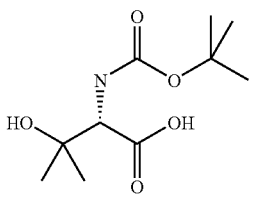

3-Hydroxy-L-valine (500 mg, 3.75 mmoles) in 10 mL DMF with TEA (1 eq.) was treated with di(tert-butyl)dicarbonate (3.75 mmoles, 1 eq.) for 18 h at ambient temperature. The reaction mixture was diluted with water, pH adjusted to 10 with 6 N NaOH, washed with EtOAc, and the aqueous phase was isolated. The aqueous phase was combined with fresh DCM, pH adjusted to 4 with 1N HCl. The organic phase was isolated, dried over MgSO$_4$, filtered and concentrated to give the title compound (68%) as a clear oil. $^1$H NMR (300 MHz, CD$_3$OD) δ 4.09 (s, 1H), 1.46 (s, 9H), 1.30 (s, 3H), 1.26 (s, 3H).

Synthesis of Sulfonamide Benzoid Acids Via Chlorosulfonylation/Amination Procedure Method G—Primary Sulfonamide, Lower Sulfonamides 4-chloro-3-(chlorosulfonyl)benzoic acid

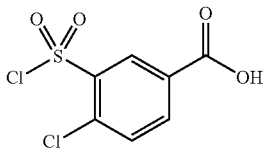

At 5-10° C., to stirred chlorosulfonic acid (200 mL) was added 4-chlorobenzoic acid (78 g, 0.5 mol). The reaction mixture was then brought up to 150~160° C. for 5 hours. After being cooled down to room temperature, the reaction mixture was slowly poured onto a large amount of ice and extracted with ether. The combined organic extracts were washed with ice water and dried over anhydrous magnesium sulfate. Evaporation of solvents afforded 4-chloro-3-(chlorosulfonyl) benzoic acid as a solid (76 g), which was directly used in the next steps.

4-Fluoro-3-(chlorosulfonyl)benzoic acid, 2,6-difluoro-3-(chlorosulfonyl)benzoic acid, 2,6-dichloro-3-(chlorosulfonyl)benzoic acid, 3,4-difluoro-5-(chloro-sulfonyl)benzoic acid, 2,6-methyl-3-(chlorosulfonyl) benzoic acid, 4-bromo-3-(chlorosulfonyl)benzoic acid, 2,6-difluoro-3-(chlorosulfonyl)benzoic acid, 4-methoxy-3-(chlorosulfonyl)benzoic acid, 5-chloro-3-(chloro-sulfonyl)-2-hydroxybenzoic acid, 2-chloro-5-(chloro-sulfonyl)benzoic acid, and 3-(chlorosulfonyl)-4-fluorobenzoic acid were prepared with the same procedure as above except for varying temperatures and heating time based on substrates. In some cases, the pure product was obtained as a precipitate from the ice quench in which case the product was filtered off and no extraction was necessary.

Synthesis of 3-(aminosulfonyl)-4-fluorobenzoic acid

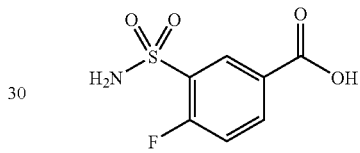

To ~50 mL of liquid ammonia at −78° C. was added 7.0 grams of freshly prepared 4-fluoro-3-(chloro-sulfonyl)benzoic acid. The excess ammonia was then naturally evaporated to dryness overnight at room temperature. The crude solid was dissolved in water (50 mL) and acidified to pH-6 with HCl (conc.). After removal of the precipitate by filtration, the filtrate was further acidified to pH ~1. The desired product was precipitated and collected by filtration (5.0 g). ES LC-MS m/z (M−1)− 218.

Acids 16, 22, 31, 37, 43, and 49 were prepared by this same method. Yields and representative data are included in the accompanying tables.

Method H—Secondary and Tertiary Sulfonamides

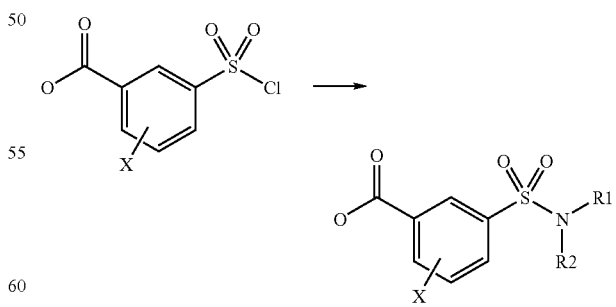

To the sulfonyl halide (8.00 mmoles) in 6 mL THF was added a 2N solution of the amine (24.0 mmoles, 3 eq.) in THF and the mixture was stirred overnight at ambient temperature. The reaction mixture was concentrated to dryness and partitioned between DCM and H$_2$O. The pH was adjusted to 10 with 6N NaOH and the aqueous phase was isolated. The aqueous phase was acidified to pH 2 with 6N HCl and the reaction mixture was stirred vigorously to give a white precipitate. The precipitate was filtered off, washed with water and air dried to give the desired product. In cases where precipitation did not occur, the aqueous phase was extracted with EtOAc, organic phases were combined, dried over MgSO$_4$, filtered, and concentrated to give the desired products. Yields and representative data are included in the accompanying tables.

Table of Carboxylic Acids

| Acid # | Structure | Yield | ES-LCMS | Ion | Method |
|---|---|---|---|---|---|
| Acid 3 | 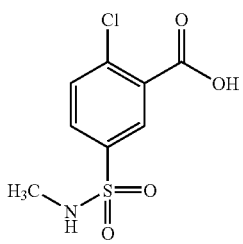 | 10 | 248.20 | (M + H) | H |
| Acid 4 | 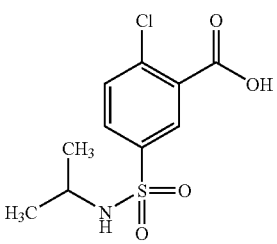 | 69 | 276.26 | (M − 1) | H |
| Acid 5 | 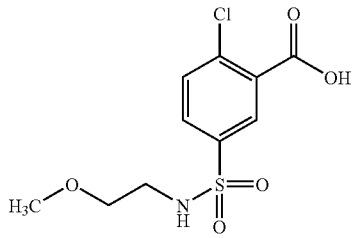 | 68 | 292.21 | (M − 1) | H |
| Acid 6 | 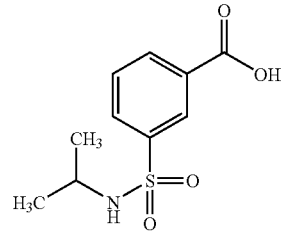 | 84 | 242.29 | (M − 1) | H |
| Acid 7 | 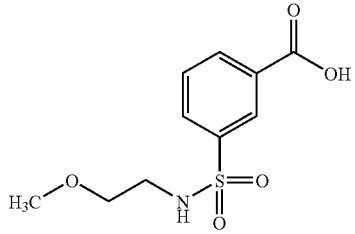 | 53 | 258.27 | (M − 1) | H |

-continued

Table of Carboxylic Acids

| Acid # | Structure | Yield | ES-LCMS | Ion | Method |
|---|---|---|---|---|---|
| Acid 8 | 4-(isopropylsulfamoyl)benzoic acid | 86 | 242.30 | (M − 1) | H |
| Acid 9 | 4-(2-methoxyethylsulfamoyl)benzoic acid | 66 | 258.27 | (M − 1) | H |
| Acid 10 | 4-(2-hydroxyethylsulfamoyl)benzoic acid | 74 | 244.26 | (M − 1) | H |
| Acid 11 | 2-methoxy-5-(methylsulfamoyl)benzoic acid | 70 | 244.22 | (M − 1) | H |
| Acid 12 | 4-chloro-3-(methylsulfamoyl)benzoic acid | 46 | 249.85, 251.83 | (M + H) | H |
| Acid 13 | 4-chloro-3-(2-methoxyethylsulfamoyl)benzoic acid | 10 | 294.10, 296.10 | (M + H) | H |
| Acid 14 | 4-chloro-3-(bis(2-methoxyethyl)sulfamoyl)benzoic acid | 10 | 352.12, 354.12 | (M + H) | H |
| Acid 15 | 4-chloro-3-(N,N-dimethylsulfamoyl)benzoic acid | 20 | 264.14 | (M + H) | H |

-continued

Table of Carboxylic Acids

| Acid # | Structure | Yield | ES-LCMS | Ion | Method |
|---|---|---|---|---|---|
| Acid 16 | 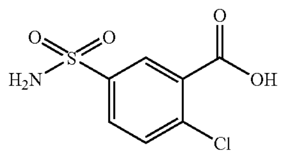 | 70 | 233.88 | (M − 1) | G |
| Acid 17 | 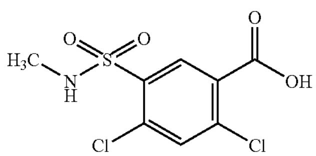 | 62 | 282.19 | (M − 1) | H |
| Acid 18 | 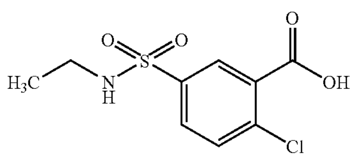 | 69 | 263.87, 265.92 | (M + H) | H |
| Acid 19 | 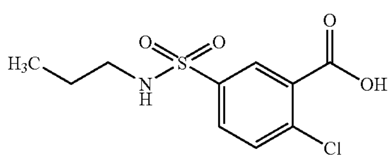 | 75 | 277.93, 279.88 | (M + H) | H |
| Acid 20 | 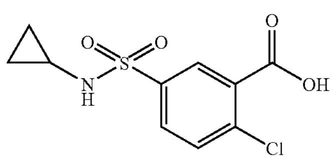 | 79 | 275.96, 277.85 | (M + H) | H |
| Acid 21 | 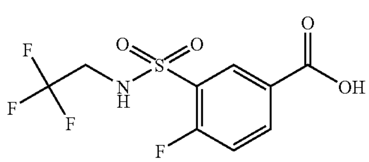 | 36 | 300.08 | (M − 1) | H |
| Acid 22 | 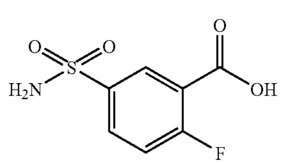 | 62 | 217.92 | (M − 1) | G |
| Acid 23 | 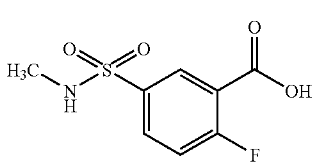 | 31 | 232.05 | (M − 1) | H |
| Acid 24 | 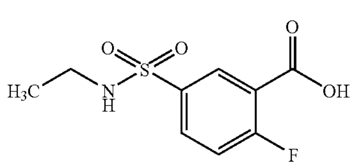 | 36 | 245.98 | (M − 1) | H |

-continued

Table of Carboxylic Acids

| Acid # | Structure | Yield | ES-LCMS | Ion | Method |
|---|---|---|---|---|---|
| Acid 25 | 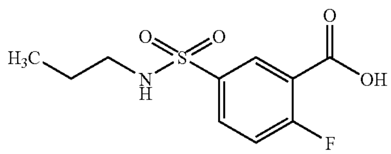 | 80 | 260.00 | (M − 1) | H |
| Acid 26 | 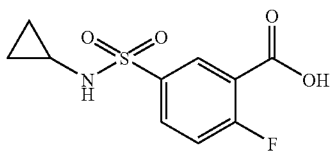 | 83 | 258.03 | (M − 1) | H |
| Acid 27 | 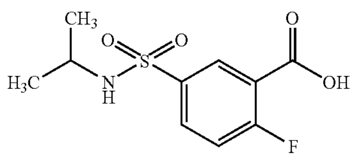 | 62 | 260.02 | (M − 1) | H |
| Acid 28 | 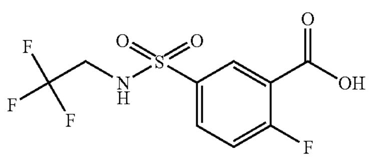 | 55 | 300.07 | (M − 1) | H |
| Acid 29 | 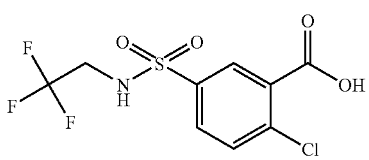 | 47 | 316.03 | (M − 1) | H |
| Acid 30 | 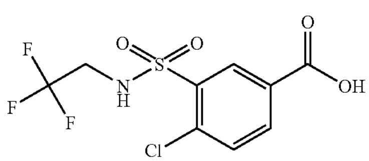 | 34 | 316.01 | (M − 1) | H |
| Acid 31 | 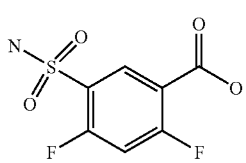 | 48 | 236 | (M − 1) | G |
| Acid 32 | 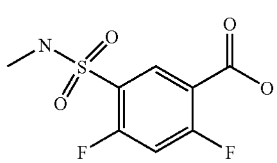 | 54 | 250 | (M − 1) | H |
| Acid 33 | 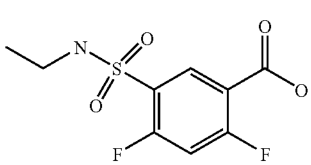 | 58 | 264 | (M − 1) | H |

Table of Carboxylic Acids

| Acid # | Structure | Yield | ES-LCMS | Ion | Method |
|---|---|---|---|---|---|
| Acid 34 | propyl-sulfamoyl-2,4-difluorobenzoic acid | 61 | 278 | (M − 1) | H |
| Acid 35 | isopropyl-sulfamoyl-2,4-difluorobenzoic acid | 66 | 278 | (M − 1) | H |
| Acid 36 | cyclopropyl-sulfamoyl-2,4-difluorobenzoic acid | 56 | 276 | (M − 1) | H |
| Acid 37 | sulfamoyl-4-bromobenzoic acid | 39 | 279 | (M − 1) | G |
| Acid 38 | methyl-sulfamoyl-4-bromobenzoic acid | 41 | 293 | (M − 1) | H |
| Acid 39 | ethyl-sulfamoyl-4-bromobenzoic acid | 33 | 307 | (M − 1) | H |
| Acid 40 | propyl-sulfamoyl-4-bromobenzoic acid | 42 | 321 | (M − 1) | H |
| Acid 41 | isopropyl-sulfamoyl-4-bromobenzoic acid | 38 | 321 | (M − 1) | H |
| Acid 42 | cyclopropyl-sulfamoyl-4-bromobenzoic acid | 29 | 319 | (M − 1) | H |

-continued

Table of Carboxylic Acids

| Acid # | Structure | Yield | ES-LCMS | Ion | Method |
|---|---|---|---|---|---|
| Acid 43 | 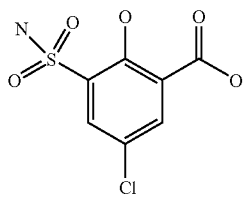 | 61 | 250 | (M − 1) | G |
| Acid 44 | 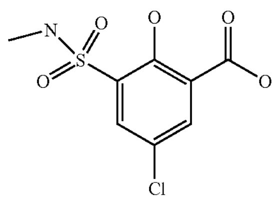 | 68 | 264 | (M − 1) | H |
| Acid 45 | 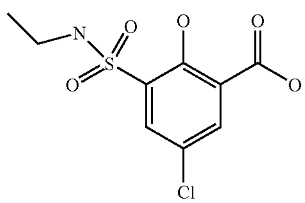 | 62 | 278 | (M − 1) | H |
| Acid 46 | 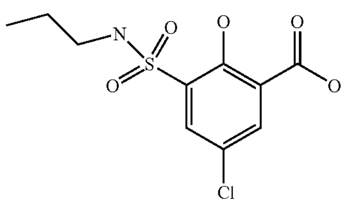 | 57 | 292 | (M − 1) | H |
| Acid 47 | 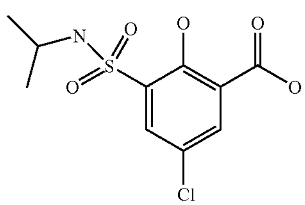 | 65 | 292 | (M − 1) | H |
| Acid 48 | 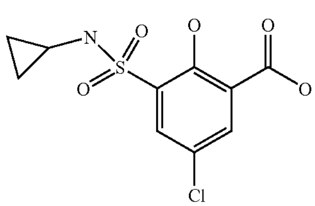 | 70 | 290 | (M − 1) | H |
| Acid 49 | 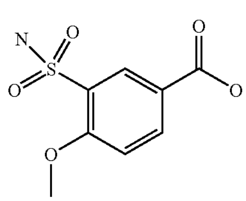 | 49 | 230 | (M − 1) | G |

| Acid # | Structure | Yield | ES-LCMS | Ion | Method |
|---|---|---|---|---|---|
| Acid 50 | 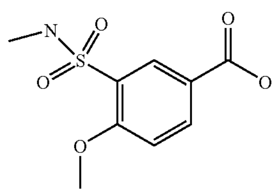 | 47 | 244 | (M − 1) | H |
| Acid 51 | 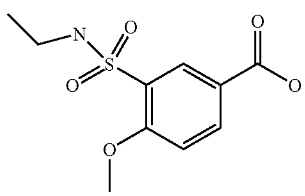 | 53 | 258 | (M − 1) | H |
| Acid 52 | 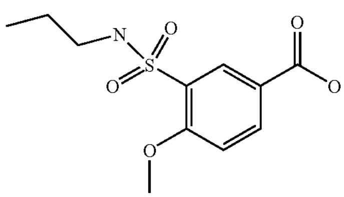 | 42 | 272 | (M − 1) | H |
| Acid 53 | 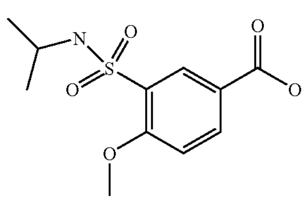 | 51 | 272 | (M − 1) | H |
| Acid 54 | 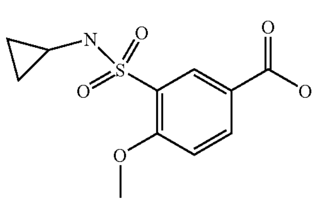 | 44 | 270 | (M − 1) | H |

Example 368

1-benzoyl-4-(2-{4-[3-(4-methoxybenzyl)-1,2,4-oxadiazol-5-yl]piperidin-1-yl}ethyl)-4-phenylpiperidine

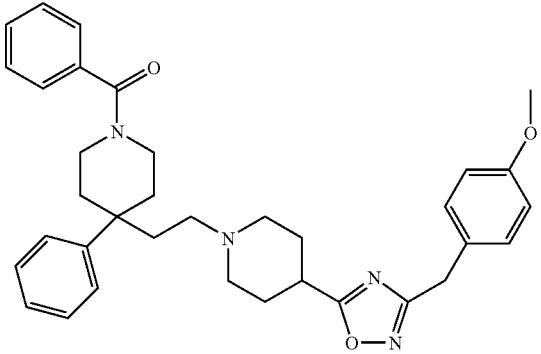

tert-butyl 4-[3-(4-methoxybenzyl)-1,2,4-oxadiazol-5-yl]piperidine-1-carboxylate

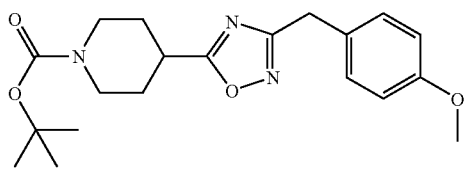

1-(tert-Butoxycarbonyl)piperidine-4-carboxylic acid (2.29 g, 10.0 mmoles) in 10 mL DMF was treated with 1,1'-carbonyldiimidazole (1.62 g, 10 mmoles, 1 eq.) at ambient temperature for 30 min until $CO_2$ evolution ceased. (1Z)-N'-hydroxy-2-(4-methoxyphenyl)ethanimidamide [*J. Med. Chem.*, 36(11), 1529 (1993)] (10.0 mmoles, 1 eq.) was dissolved in 5 mL DMF and added to the reaction mixture. The reaction mixture was heated at 70° C. for 6 h then at 120° C. for an additional 6 h. The reaction mixture was diluted with EtOAc and washed successively with water, 1N citric acid, saturated aqueous $NaHCO_3$, and brine. The organic phase was isolated, dried over $MgSO_4$, filtered and concentrated to give the title compound as an amber oil. $^1H$ NMR (300 MHz, $CDCl_3$) δ 7.26 (d, 2H, J=8.5 Hz), 6.88 (d, 2H, J=8.5 Hz), 4.10 (m, 2H), 4.00 (s, 2H), 3.80 (s, 3H), 3.08 (m, 1H), 2.97-2.90 (m, 2H), 2.04 (m, 2H), 1.87-1.73 (m, 2H), 1.47 (s, 9H). ES-LCMS m/z 395.99 (M+Na).

4-[3-(4-methoxybenzyl)-1,2,4-oxadiazol-5-yl]piperidine

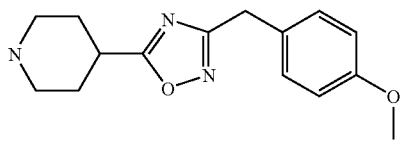

Tert-butyl 4-[3-(4-methoxybenzyl)-1,2,4-oxadiazol-5-yl]piperidine-1-carboxylate was treated with 10 mL TFA/DCM (1:1) for 30 min at ambient temperature. The reaction mixture was concentrated and the crude product was crystallized from EtOAc/$Et_2O$, filtered and dried to give the TFA salt of 4-[3-(4-methoxybenzyl)-1,2,4-oxadiazol-5-yl]piperidine as a tan solid (1.23 g, 3.17 mmol, 32%, 3 steps). $^1H$ NMR (300 MHz, DMSO-$d_6$) δ 7.22 (d, 2H, J=8.5 Hz), 6.88 (d, 2H, J=8.5 Hz), 4.00 (s, 2H), 3.72 (s, 3H), 3.43-3.29 (m, 2H), 3.02 (m, 2H), 2.17 (m, 2H), 1.92-1.80 (m, 2H). ES-LCMS m/z 274.30 (M+H).

1-benzoyl-4-(2-{4-[3-(4-methoxybenzyl)-1,2,4-oxadiazol-5-yl]piperidin-1-yl}ethyl)-4-phenylpiperidine

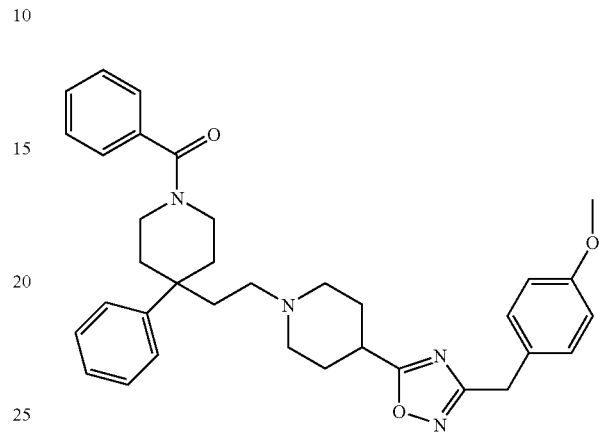

The TFA salt of 4-[3-(4-methoxybenzyl)-1,2,4-oxadiazol-5-yl]piperidine (29 mg, 0.076 mmol) was combined with (1-benzoyl-4-phenylpiperidin-4-yl)acetaldehyde (21 mg, 0.069 mmol) in 2 mL DCM and treated with $NaBH(OAc)_3$ (43 mg, 0.203 mmol) at ambient temperature with agitation for 18 h. 1 mL of saturated aqueous $NaHCO_3$ was added and agitated 1 h. The organic phase was separated and concentrated. The crude product was purified by HPLC to give 1-benzoyl-4-(2-{4-[3-(4-methoxybenzyl)-1,2,4-oxadiazol-5-yl]piperidin-1-yl}ethyl)-4-phenylpiperidine (16.1 mg, 0.026 mmol, 38%) as the formate salt. $^1H$ NMR (300 MHz, $CD_3OD$) δ 7.49-7.37 (m, 9H), 7.28 (m, 1H), 7.20 (d, 2H, J=8.8 Hz), 6.86 (d, 2H, J=8.8 Hz), 4.19 (m, 1H), 3.96 (s, 2H), 3.76 (s, 3H), 3.59 (m, 1H), 3.37-3.20 (m, 3H), 3.12-2.95 (m, 3H), 2.45-1.73 (m, 13H). ES-LCMS m/z 565.29 (M+H). HRMS $C_{35}H_{40}N_4O_3$ m/z 565.3179 (M+H)$_{Cal.}$ 565.3183 (M+H)$_{Obs.}$.

Example 369

3-[(5-{1-[2-(1-benzoyl-4-phenylpiperidin-4-yl)ethyl]piperidin-4-yl}-1,2,4-oxadiazol-3-yl)methyl]pyridine

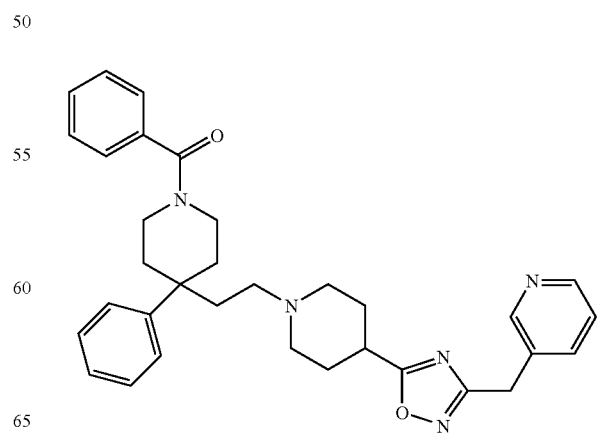

289

(1Z)-N'-hydroxy-2-pyridin-3-ylethanimidamide

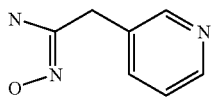

Hydroxylamine hydrochloride (0.87 g, 0.0125 mmol) was added to 0.5M NaOCH$_3$ (25 mL, 0.0125 mmol) and stirred at ambient temperature for 30 min. The reaction mixture was filtered and the filtrate was combined with pyridin-3-ylacetonitrile (1.18 g, 0.010 mmol). The resultant mixture was heated at reflux for 2 h, stirred at ambient temperature overnight and concentrated to give crude (1Z)-N'-hydroxy-2-pyridin-3-ylethanimidamide which was used immediately without purification. ES-LCMS m/z 152.18 (M+H).

tert-butyl 4-[3-(pyridin-3-ylmethyl)-1,2,4-oxadiazol-5-yl]piperidine-1-carboxylate

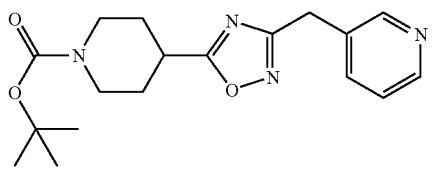

1-(Tert-butoxycarbonyl)piperidine-4-carboxylic acid (2.29 g, 0.010 mmol) was treated with 1,1'-carbonyldiimidazole (1.62 g, 0.010 mmol) in DMF (5 mL) at ambient temperature for 30 min. Following this activation period, the crude (1Z)-N'-hydroxy-2-pyridin-3-ylethanimidamide (0.010 mmol) was added and the reaction mixture heated at 70° C. for 6 h followed by 120° C. for an additional 6 h. The reaction mixture was cooled and partitioned between EtOAc and water. The organic phase was separated, washed successively with saturated NaHCO$_3$ and brine, dried over MgSO$_4$, filtered and concentrated to give tert-butyl 4-[3-(pyridin-3-ylmethyl)-1,2,4-oxadiazol-5-yl]piperidine-1-carboxylate.
$^1$H NMR (300 MHz, CDCl$_3$) δ 8.61 (s, 1H), 8.53 (m, 1H), 7.67 (d, 1H, J=7.7 Hz), 7.28 (m, 1H), 4.20-4.05 (m, 2H), 4.08 (s, 2H), 3.08 (m, 1H), 2.94 (m, 2H), 2.04 (m, 2H), 1.87-1.73 (m, 2H), 1.47 (s, 9H). ES-LCMS m/z 367.36 (M+Na).

290

3-[(5-piperidin-4-yl-1,2,4-oxadiazol-3-yl)methyl]pyridine

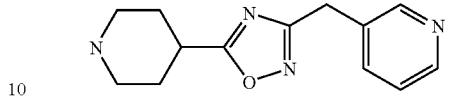

tert-Butyl 4-[3-(pyridin-3-ylmethyl)-1,2,4-oxadiazol-5-yl]piperidine-1-carboxylate was treated with 10 mL TFA/DCM (1:1) for 30 min at ambient temperature. The reaction mixture was concentrated to give the di-TFA salt of 3-[(5-piperidin-4-yl-1,2,4-oxadiazol-3-yl)methyl]pyridine as an amber oil (4.0 g, 8.47 mmol, 85%, 3 steps). $^1$H NMR (300 MHz, DMSO-d$_6$) δ 8.78 (s, 1H), 8.70 (d, 1H, J=5.0 Hz), 8.51 (br.s, 1H), 8.18 (d, 1H, J=7.9 Hz), 7.75 (m, 1H), 4.30 (s, 2H), 3.44-3.30 (m, 3H), 3.09-3.00 (m, 2H), 2.20-2.16 (m, 2H), 1.93-1.80 (m, 2H).

Example 370

3-[(5-{1-[2-(1-benzoyl-4-phenylpiperidin-4-yl)ethyl]piperidin-4-yl}-1,2,4-oxadiazol-3-yl)methyl]pyridine

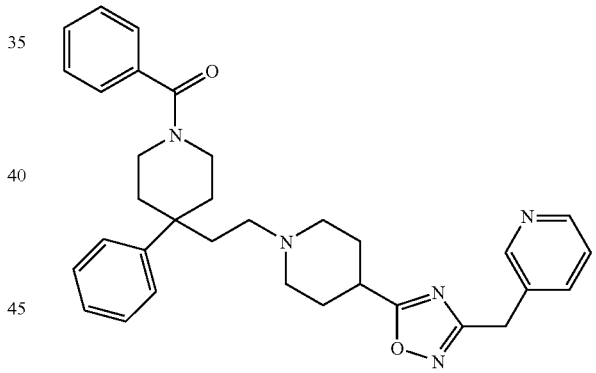

The TFA salt of 3-[(5-piperidin-4-yl-1,2,4-oxadiazol-3-yl)methyl]pyridine (27 mg, 0.076 mmol) was combined with (1-benzoyl-4-phenylpiperidin-4-yl)acetaldehyde (21 mg, 0.069 mmol) in 2 mL DCM and treated with NaBH(OAc)$_3$ (43 mg, 0.203 mmol) at ambient temperature with agitation for 18 h. 1 mL of saturated aqueous NaHCO$_3$ was added and agitated 1 h. The organic phase was separated and concentrated. The crude product was purified by HPLC (METHOD) to give 3-[(5-{1-[2-(1-benzoyl-4-phenylpiperidin-4-yl)ethyl]piperidin-4-yl}-1,2,4-oxadiazol-3-yl)methyl]pyridine (14.2 mg, 0.024 mmol, 34%) as the formate salt. $^1$H NMR (300 MHz, CD$_3$OD) δ 8.52-8.44 (m, 2H), 7.80 (d, 1H, J=7.9 Hz), 7.48-7.38 (m, 10H), 7.26 (m, 1H), 4.19 (m, 1H), 4.13 (s, 2H), 3.59 (m, 1H), 3.36-3.29 (m, 3H), 3.12-3.02 (m, 3H), 2.47-1.45 (m, 13H). ES-LCMS m/z 536.25 (M+H). HRMS C$_{33}$H$_{37}$N$_5$O$_2$ m/z 536.3026 (M+H)$_{Cal.}$ 536.3018 (M+H)$_{Obs.}$.

Reductive Amination Method I

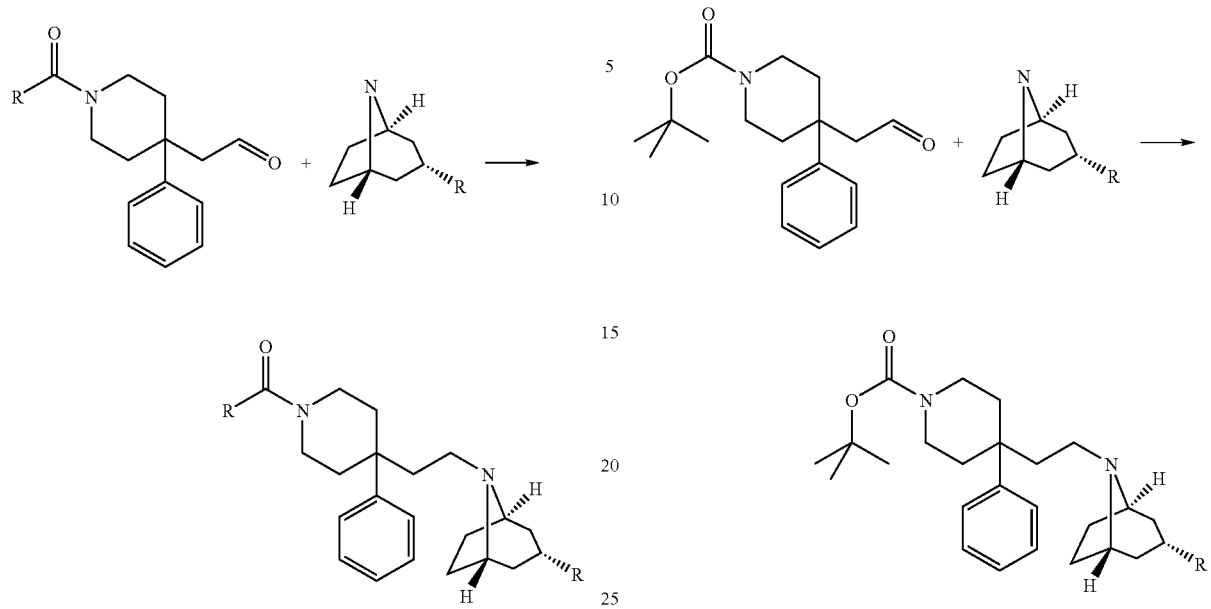

The TFA or HCl salt of the amine (390 μmoles) was combined with (1-benzoyl-4-phenylpiperidin-4-yl)acetaldehyde (120 mg, 390 μmoles, 1 eq.) in 4 mL DCE and/or 4 mL DMF and treated with NaBH(OAc)$_3$ (585 μmoles, 1.5 eq.) with or without TEA (780 μmoles, 2 eq.) at ambient temperature with agitation for 18 h. The reaction mixture was concentrated, dissolved in 5 mL DCM, and agitated 1 h with 5 mL of saturated aqueous NaHCO$_3$. The organic phase was separated and concentrated. The crude product was purified either by normal phase flash chromatography (SiO$_2$, CHCl$_3$/CH$_3$OH) or by reverse phase mass-directed HPLC as described in Preparative HPLC Conditions A. Yields and representative data are included in the accompanying tables.

The HCl salt of the amine (1.66 mmoles) was combined with tert-butyl 4-(2-oxoethyl)-4-phenyl piperidine-1-carboxylate (1.66 mmoles, 1 eq.) in 10 mL DCE and 10 mL DCM and treated with NaBH(OAc)$_3$ (2.49 mmoles, 1.5 eq.) with TEA (3.33 moles, 2 eq.) at ambient temperature with agitation for 18 h. The reaction mixture was washed with saturated aqueous NaHCO$_3$, the organic phase separated, dried over MgSO$_4$, filtered and concentrated. The crude product was purified by normal phase flash chromatography (SiO$_2$, CHCl$_3$/CH$_3$OH) to give the desired product. Yields and representative data are included in the accompanying tables.

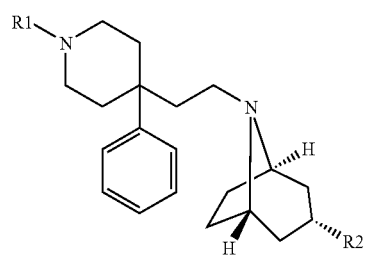

| Example # | Amine # | R1 | R2 | % yield | LCMS result | Ion | Method |
|---|---|---|---|---|---|---|---|
| 371 | Amine 1 | 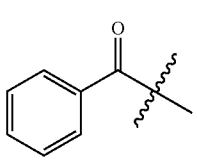 | | 55 | 519.32 | (M + H) | I |

-continued

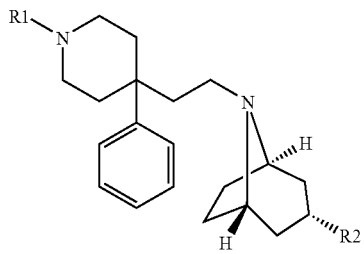

| Example # | Amine # | R1 | R2 | % yield | LCMS result | Ion | Method |
|---|---|---|---|---|---|---|---|
| 372 | Amine 2 | benzoyl-isopropyl | 2-ethyl-benzimidazol-1-yl | 17 | 547.35 | (M + H) | I |
| 373 | Amine 3 | benzoyl-isopropyl | 2-(2-(phenylsulfonyl)ethyl)benzimidazol-1-yl | 26 | 687.30 | (M + H) | I |
| 374 | Amine 4 | benzoyl-isopropyl | 2-methyl-5-(methylsulfonyl)benzimidazol-1-yl | 64 | 611.26 | (M + H) | I |
| 375 | Amine 5 | benzoyl-isopropyl | 2-methyl-6-fluoro-benzimidazol-1-yl | 53 | 551.18 | (M + H) | I |
| 376 | Amine 6 | benzoyl-isopropyl | 2-methyl-4-fluoro-benzimidazol-1-yl | 50 | 551.18 | (M + H) | I |

-continued
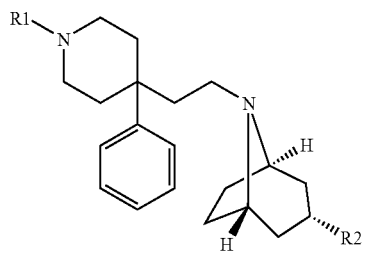
| Example # | Amine # | R1 | R2 | % yield | LCMS result | Ion | Method |
|---|---|---|---|---|---|---|---|
| 377 | Amine 7 | benzoyl-C(CH3) | 2-methyl-imidazo[4,5-b]pyridin-1-yl | 52 | 534.19 | (M + H) | I |
| 378 | Amine 8 | benzoyl-C(CH3) | 2-trifluoromethyl-benzimidazol-1-yl | 57 | 587.14 | (M + H) | I |
| 379 | Amine 9 | benzoyl-C(CH3) | 2-chloro-benzimidazol-1-yl | 7 | 553.12 | (M + H) | I |
| 380 | Amine 10 | benzoyl-C(CH3) | 2-methoxy-benzimidazol-1-yl | 37 | 549.38 | (M + H) | I |
| 381 | Amine 11 | benzoyl-C(CH3) | 2-ethoxy-benzimidazol-1-yl | 22 | 563.40 | (M + H) | I |

-continued

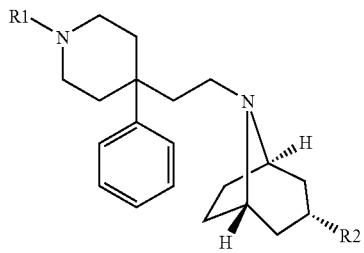

| Example # | Amine # | R1 | R2 | % yield | LCMS result | Ion | Method |
|---|---|---|---|---|---|---|---|
| 382 | Amine 12 | benzoyl | 2-amino-benzimidazol-1-yl | 11 | 534.43 | (M + H) | I |
| 383 | Amine 13 | benzoyl | 2-(methylamino)-benzimidazol-1-yl | 42 | 548.36 | (M + H) | I |
| 384 | Amine 14 | tert-butoxycarbonyl | 2-methyl-imidazo[4,5-b]pyridin-1-yl | 68 | 530.21 | (M + H) | J |

Additional analytical data of selected compounds from table above:

Example 371

Endo-1-{8-[2-(1-benzoyl-4-phenylpiperidin-4-yl)ethyl]-8-azabicyclo[3.2.1]oct-3-yl}-1H-benzimidazole $^1$H NMR (300 MHz, CD$_3$OD) δ 8.46 (s, 1H), 7.70 (m, 1H), 7.51-7.28 (m, 13H), 4.80 (m, 1H), 4.23 (m, 1H), 3.71 (m, 2H), 3.62 (m, 1H), 3.35-3.22 (m, 2H), 2.74-1.67 (m, 16H). HRMS C$_{34}$H$_{38}$N$_4$O m/z 519.3124 (M+H)$_{Cal.}$; 519.3110 (M+H)$_{Obs.}$.

Example 372

Endo-1-{8-[2-(1-benzoyl-4-phenylpiperidin-4-yl)ethyl]-8-azabicyclo[3.2.1]oct-3-yl}-2-ethyl-1H-benzimidazole $^1$H NMR (300 MHz, CD$_3$OD) δ ppm 1.35 (t, J=7.8 Hz, 3H), 1.76-2.53 (m, 16H), 2.89 (q, J=7.7 Hz, 2H), 3.31-3.46 (m, 4H), 3.62 (m, 1H), 4.19 (m, 1H), 4.80 (m, 1H), 7.17-7.29 (m, 3H), 7.39-7.49 (m, 10H), 7.57 (m, 1H).

Example 380

Endo-1-{8-[2-(1-benzoyl-4-phenylpiperidin-4-yl)ethyl]-8-azabicyclo[3.2.1]oct-3-yl}-2-methoxy-1H-benzimidazole $^1$H NMR (300 MHz, CD$_3$OD) δ 7.49-7.39 (m, 10H), 7.32 (m, 1H), 7.24 (m, 1H), 7.16 (m, 2H), 4.81 (pent, 1H), 4.25 (m, 1H), 4.17 (s, 3H), 3.75 (m, 2H), 3.63 (m, 1H), 3.35-3.27 (m, 2H), 2.65-1.79 (m, 16H). ES-LCMS M/z 549.38 (M+H). HRMS C$_{35}$H$_{40}$N$_4$O$_2$ m/z 549.3230 (M+H)$_{Cal.}$; 549.3217 (M+H)$_{Obs.}$.

Example 381

Endo-1-{8-[2-(1-benzoyl-4-phenylpiperidin-4-yl)ethyl]-8-azabicyclo[3.2.1]oct-3-yl}-2-ethoxy-1H-benzimidazole $^1$H NMR (300 MHz, CD$_3$OD) δ 7.51-7.39 (m, 10H), 7.32 (m, 1H), 7.24 (m, 1H), 7.16 (m, 2H), 4.85 (pent, 1H), 4.57 (q, 2H, J=7.0 Hz), 4.23 (m, 1H), 3.73 (m, 2H), 3.63 (m, 1H), 3.35-3.27 (m, 2H), 2.65-1.79 (m, 16H). ES-LCMS m/z 563.40 (M+H). HRMS $C_{36}H_{42}N_4O_2$ m/z 563.3386 (M+H)$_{Cal.}$; 563.3368 (M+H)$_{Obs.}$ Example 382

Endo-1-{8-[2-(1-benzoyl-4-phenylpiperidin-4-yl)ethyl]-8-azabicyclo[3.2.1]oct-3-yl}-1H-benzimidazol-2-amine $^1$H NMR (300 MHz, CD$_3$OD) δ 7.48-7.40 (m, 9H), 7.28 (m, 3H), 7.13 (m, 2H), 4.61 (pent, 1H), 4.19 (m, 1H), 3.59 (m, 1H), 3.39-3.27 (m, 4H), 2.48-1.65 (m, 16H). HRMS $C_{34}H_{39}N_5O$ m/z 534.3233 (M+H)$_{Cal.}$; 534.3241 (M+H)$_{Obs.}$ Preparation of Amines 1-14:

Amine 1: prepared by the literature procedure described in WO 00/38680

Amine 2: Endo-1-(8-azabicyclo[3.2.1]oct-3-yl)-2-ethyl-1H-benzimidazole

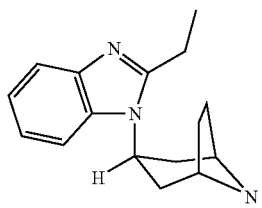

Endo-tert-butyl 3-[(2-aminophenyl)amino]-8-azabicyclo[3.2.1]octane-8-carboxylate (WO 00/38680) (2.5 g, 7.80 mmol) was treated with 20 mL 1,1,1-triethoxypropane at reflux for 3 h. The reaction mixture was concentrated to dryness, redissolved in CH$_3$OH (10 mL), and treated with 6 N HCl at reflux for 1 h. The reaction mixture was concentrated to dryness, chased with EtOH, and triturated with EtOH to give a solid that was filtered and dried to give the HCl salt of endo-1-(8-azabicyclo[3.2.1]oct-3-yl)-2-ethyl-1H-benzimidazole (1.35 g, 4.11 mmol, 53%) as a grey solid. $^1$H NMR (300 MHz, D$_2$O) δ 7.72-7.65 (m, 2H), 7.49-7.46 (m, 2H), 4.99 (m, 1H) 4.19 (m, 2H), 3.10 (q, 2H, J=7.6 Hz), 2.76-2.70 (m, 2H), 2.40-2.18 (m, 6H), 1.35 (t, 3H, J=7.6 Hz). ES-LCMS m/z 256.07 (M+H).

Amine 3: Endo-1-(8-azabicyclo[3.2.1]oct-3-yl)-2-[2-(phenylsulfonyl)ethyl]-1H-benzimidazole

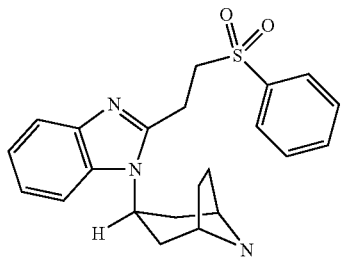

Endo-tert-butyl 3-[(2-aminophenyl)amino]-8-azabicyclo[3.2.1]octane-8-carboxylate (WO 00/38680) (1.8 g, 5.70 mmol) was treated with 20 mL [(3,3,3-triethoxypropyl)sulfonyl]benzene at 150° C. for 3 h. The reaction mixture was concentrated to dryness, redissolved in CH$_3$OH (10 mL), and treated with 6 N HCl at reflux for 1 h. The reaction mixture was concentrated to dryness, chased with EtOH, and triturated with EtOH to give a solid that was filtered and dried to give the di-HCl salt of endo-1-(8-azabicyclo[3.2.1]oct-3-yl)-2-[2-(phenylsulfonyl)ethyl]-1H-benzimidazole (1.68 g, 3.59 mmol, 63%) as a grey solid. $^1$H NMR (300 MHz, D$_2$O) δ 7.72-7.69 (m, 2H), 7.64 (m, 1H), 7.58 (m, 1H), 7.49-7.44 (m, 3H), 7.36 (m, 2H), 4.99 (m, 1H) 4.19 (m, 2H), 3.93 (t, 2H, J=7.0 Hz), 3.63 (t, 2H, J=7.0 Hz), 2.75-2.65 (m, 2H), 2.33-2.15 (m, 6H). ES-LCMS m/z 396.14 (M+H).

Amine 4: Endo-1-[(1R,5S)-8-azabicyclo[3.2.1]oct-3-yl]-2-methyl-5-(methylsulfonyl)-1H-benzimidazole

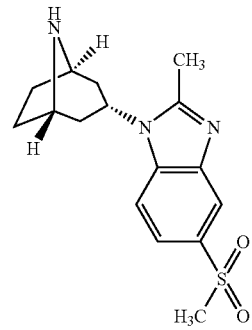

Endo-tert-butyl (1R,5S)-3-{[4-(methylsulfonyl)-2-nitrophenyl]amino}-8-azabicyclo[3.2.1]octane-8-carboxylate

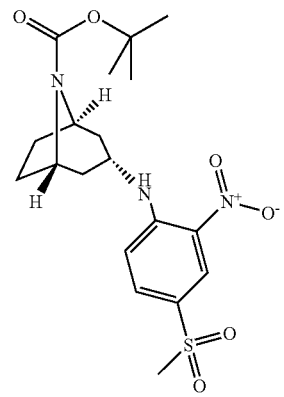

Endo-tert-butyl (1R,5S)-3-amino-8-azabicyclo[3.2.1]octane-8-carboxylate (WO 00/38680) (1.5 g, 6.66 mmoles) was treated with 1-fluoro-4-(methylsulfonyl)-2-nitrobenzene (1.46 g, 1 eq.) in 10 mL NMP with DIPEA (947 mg, 1.1 eq.) at 70° C. for 3 h. The reaction mixture was diluted with 5 mL NMP, cooled to ambient temperature, and water added to incipient cloudiness. The reaction mixture was stirred until a heavy precipitate formed. The precipitate was filtered off, washed successively with NMP/water (1:1) and water, and air dried to give endo-tert-butyl (1R,5S)-3-{[4-(methylsulfonyl)-2-nitrophenyl]amino}-8-azabicyclo[3.2.1]octane-8- carboxylate (2.21 g, 78%) as a yellow solid. $^1$H NMR (300 MHz, DMSO-$d_6$) δ 8.90 (d, 1H, J=7.0 Hz), 8.53 (d, 1H, J=2.0 Hz), 7.94 (dd, 1H, J=9.2, 2.0 Hz), 7.17 (d, 1H, J=9.3 Hz), 4.11 (m, 3H), 3.21 (s, 3H), 2.16 (m, 2H), 1.94 (m, 4H), 1.80 (m, 2H), 1.42 (s, 9H).

Endo-tert-butyl (1R,5S)-3-{[2-amino-4-(methylsulfonyl) phenyl]amino}-8-azabicyclo[3.2.1]octane-8-carboxylate

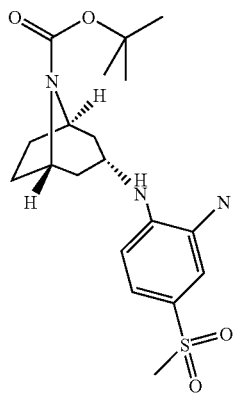

Endo-tert-butyl (1R,5S)-3-{[4-(methyl sulfonyl)-2-nitrophenyl]amino}-8-azabicyclo[3.2.1]octane-8-carboxylate (2.21 g, 5.19 mmoles) was subjected to catalytic hydrogenation with 10% Pd/C (260 mg) in EtOH/EtOAc (1:1, 100 mL) under 1 atm H$_2$(g) for 16 h. The catalyst was filtered off and the filtrate concentrated to a purple oil which was carried on to the next step without further characterization.

Endo-1-[(1R,5S)-8-azabicyclo[3.2.1]oct-3-yl]-2-methyl-5-(methylsulfonyl)-1H-benzimidazole

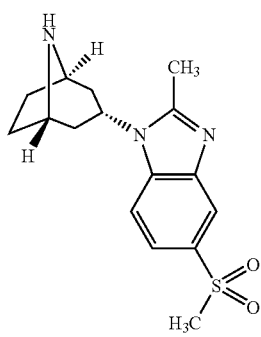

Endo-tert-butyl (1R,5S)-3-{[2-amino-4-(methylsulfonyl) phenyl]amino}-8-azabicyclo[3.2.1]octane-8-carboxylate was treated with 1,1,1-triethoxyethane at reflux for 2 h. The reaction mixture was concentrated to dryness, redissolved in CH$_3$OH (10 mL), and treated with 6 N HCl at reflux for 1 h. The reaction mixture was concentrated to dryness, chased with EtOH, and triturated with EtOH to give a solid that was filtered and dried to give the di-HCl salt of endo-tert-butyl (1R,5S)-3-{[2-amino-4-(methylsulfonyl) phenyl]amino}-8-azabicyclo[3.2.1]octane-8-carboxylate as a grey solid. $^1$H NMR (300 MHz, D$_2$O) δ 8.27 (m, 1H), 7.98-7.89 (m, 2H), 5.00 (m, 1H), 4.20 (m, 2H), 3.21 (s, 3H), 2.77 (s, 3H), 2.79-2.70 (m, 2H), 2.35-2.15 (6H).

Amine 5: Endo-1-[(1R,5S)-8-azabicyclo[3.2.1]oct-3-yl]-5-fluoro-2-methyl-1H-benzimidazole

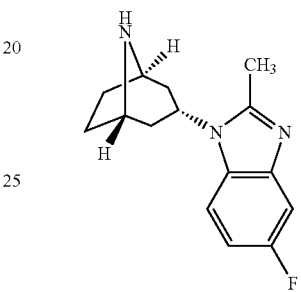

Endo-tert-butyl (1R,5S)-3-[(4-fluoro-2-nitrophenyl)amino]-8-azabicyclo[3.2.1]octane-8-carboxylate

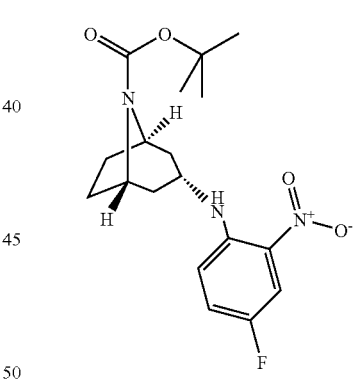

Endo-tert-butyl (1R,5S)-3-amino-8-azabicyclo[3.2.1]octane-8-carboxylate (WO 00/38680) (2.0 g, 8.88 mmoles) was treated with 1,4-difluoro-2-nitrobenzene (1.41 g, 1 eq.) in 10 mL NMP with DIPEA (1.26 g, 1.1 eq.) at 70° C. for 16 h. The reaction mixture was cooled to ambient temperature, and water (4 mL) added to incipient cloudiness. The reaction mixture was stirred until a heavy precipitate formed. The precipitate was filtered off, washed successively with NMP/water (1:1) and water, and air dried to give tert-butyl (1R,5S)-3-[(4-fluoro-2-nitrophenyl)amino]-8-azabicyclo[3.2.1]octane-8-carboxylate as an orange solid (2.74 g, 7.50 mmoles, 84%). $^1$H NMR (300 MHz, CDCl$_3$) δ 8.66 (d, 1H, J=5.7 Hz), 7.93 (m, 1H), 7.27 (m, 1H), 6.72 (m, 1H), 4.29 (m, 3H), 3.91 (m, 1H), 2.40-2.29 (m, 2H), 2.15-2.01 (m, 4H), 1.80 (m, 2H), 1.50 (s, 9H).

303

Endo-tert-butyl (1R,5S)-3-[(2-amino-4-fluorophenyl)amino]-8-azabicyclo[3.2.1]octane-8-carboxylate

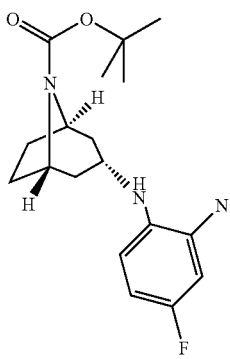

Endo-tert-butyl (1R,5S)-3-[(4-fluoro-2-nitrophenyl)amino]-8-azabicyclo[3.2.1]octane-8-carboxylate (2.74 g, 7.50 mmoles) was subjected to catalytic hydrogenation with 10% Pd/C (300 mg) in EtOH/EtOAc (1:1, 80 mL) under 1 atm H$_2$(g) for 16 h. The catalyst was filtered off and the filtrate concentrated to give the title compound (2.57 g, 100%) as a white foam. ES-LCMS m/z 336.26 (M+H).

Endo-1-[(1R,5S)-8-azabicyclo[3.2.1]oct-3-yl]-5-fluoro-2-methyl-1H-benzimidazole

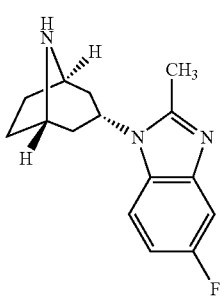

Endo-tert-butyl (1R,5S)-3-[(2-amino-4-fluorophenyl)amino]-8-azabicyclo[3.2.1]octane-8-carboxylate was treated with 1,1,1-triethoxyethane and a catalytic amount of camphor sulphonic acid at reflux for 3 h. The reaction mixture was concentrated to dryness, redissolved in CH$_3$OH (10 mL), and treated with 6N HCl at reflux for 1 h. The reaction mixture was concentrated to dryness, chased with EtOH, and triturated with EtOH to give a solid that was filtered and dried to give the di-HCl salt of endo-1-[(1R,5S)-8-azabicyclo[3.2.1] oct-3-yl]-5-fluoro-2-methyl-1H-benzimidazole as a grey solid. ES-LCMS m/z 260.27 (M+H).

304

Amine 6: Endo-1-[(1R,5S)-8-azabicyclo[3.2.1]oct-3-yl]-4-fluoro-2-methyl-1H-benzimidazole

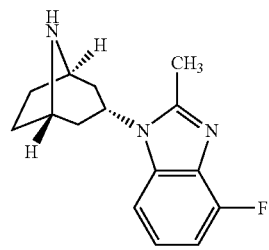

Prepared according to the method of Amine 5 from 1,3-difluoro-2-nitrobenzene. ES-LCMS m/z 260.24 (M+H).

Amine 7: Endo-3-[(1R,5S)-8-azabicyclo[3.2.1]oct-3-yl]-2-methyl-3H-imidazo[4,5-b]pyridine

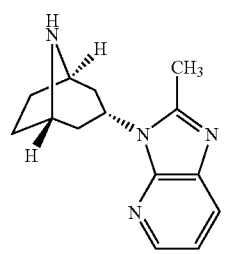

Prepared according to the method of Amine 5 from 2-chloro-3-nitropyridine. ES-LCMS m/z 243.22 (M+H).

Amine 8: Endo-1-[(1R,5S)-8-azabicyclo[3.2.1]oct-3-yl]-2-(trifluoromethyl)-1H-benzimidazole

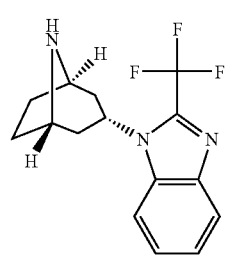

Endo-tert-butyl (1R,5S)-3-[2-(trifluoromethyl)-1H-benzimidazol-1-yl]-8-azabicyclo[3.2.1]octane-8-carboxylate

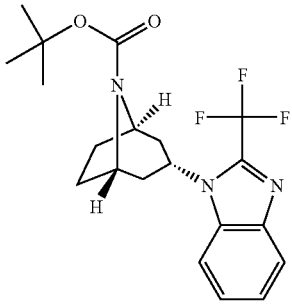

To a solution of trifluoroacetic acid (496 mg, 4.35 mmoles) in 5 mL DMF was added CDI (4.35 mmoles, 1 eq.) and stirred 30 min at ambient temperature until $CO_2$ evolution ceased. The reaction mixture was then cooled in an ice bath and Endo-tert-butyl 3-[(2-aminophenyl)amino]-8-azabicyclo[3.2.1]octane-8-carboxylate (WO 00/38680) (1.38 g, 4.35 mmoles, 1 eq.) dissolved in 10 mL DMF was added slowly. The reaction mixture was stirred 30 min at 0° C. and then warmed to ambient temperature and stirred for 30 min. The reaction mixture was then heated at 80° C. for 16 h. The reaction mixture was concentrated, dissolved in DCM, washed successively with saturated aqueous $NaHCO_3$ and water (3×). The organic phase was separated, dried over $MgSO_4$ and concentrated. A major impurity was removed by precipitation with $Et_2O$, filtered off, and the filtrate concentrated to dryness. The crude product was purified by normal phase flash chromatography ($SiO_2$, 10→40% EtOAc/Hexanes) to give Endo-tert-butyl (1R,5S)-3-[2-(trifluoromethyl)-1H-benzimidazol-1-yl]-8-azabicyclo[3.2.1]octane-8-carboxylate (0.36 g, 0.91 mmoles, 21%). ES-LCMS m/z 396.27 (M+H).

Endo-1-[(1R,5S)-8-azabicyclo[3.2.1]oct-3-yl]-2-(trifluoromethyl)-1H-benzimidazole

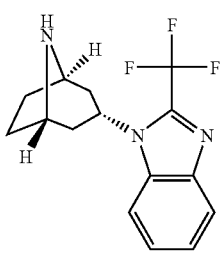

Endo-tert-butyl (1R,5S)-3-[2-(trifluoro-methyl)-1H-benzimidazol-1-yl]-8-azabicyclo[3.2.1]octane-8-carboxylate (330 mg, 0.84 mmoles) was dissolved in 6 mL DCM and treated with 4 mL 4N HCl in Dioxane at ambient temperature for 30 minutes. A solid precipitated from the reaction mixture and was filtered off to give the HCl salt of Endo-1-[(1R,5S)-8-azabicyclo[3.2.1]oct-3-yl]-2-(trifluoromethyl)-1H-benzimidazole (260 mg, 0.78 mmoles, 94%) as a pink solid. ES-LCMS m/z 295.67 (M+H).

Amine 9: Endo-1-[(1R,5S)-8-azabicyclo[3.2.1]oct-3-yl]-2-chloro-1H-benzimidazole

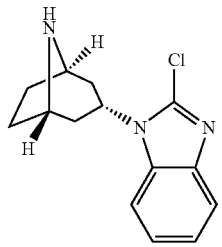

Endo-1-[(1R,5S)-8-azabicyclo[3.2.1]oct-3-yl]-1,3-dihydro-2H-benzimidazol-2-one

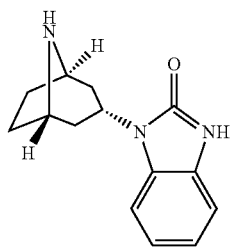

The title compound was obtained as a major by-product of the reaction of Endo-tert-butyl 3-[(2-aminophenyl)amino]-8-azabicyclo[3.2.1]octane-8-carboxylate (WO 00/38680) (1.7 g, 5.36 mmol) with 1-(triethoxymethoxy)ethane (5 mL) at 150° C. for 3 h, followed by concentration, dissolution in $CH_3OH$ (10 mL), and treatment with 6 N HCl at reflux for 1 h. The reaction mixture was concentrated to dryness, chased with EtOH, and triturated with EtOH to give a solid that was filtered and dried to give the HCl salt of Endo-1-[(1R,5S)-8-azabicyclo[3.2.1]oct-3-yl]-1,3-dihydro-2H-benzimidazol-2-one (0.73 g, 3.00 mmoles, 56%). ES-LCMS m/z 244.00 (M+H).

Endo-1-[(1R,5S)-8-azabicyclo[3.2.1]oct-3-yl]-2-chloro-1H-benzimidazole

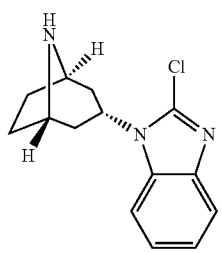

Endo-1-[(1R,5S)-8-azabicyclo[3.2.1]oct-3-yl]-1,3-dihydro-2H-benzimidazol-2-one (0.73 g, 3.00 mmoles) was treated with 5 mL $POCl_3$ with a catalytic amount of DMAP at reflux for 12 h. The reaction was cooled and quenched with slow addition of 6N NaOH until pH was basic. The reaction mixture was extracted with DCM, dried over $MgSO_4$, filtered and concentrated to give impure Endo-1-[(1R,5S)-8-azabicyclo[3.2.1]oct-3-yl]-2-chloro-1H-benzimidazole as a tan foam. The crude amine was used as is. ES-LCMS m/z 262.23 (M+H).

Amine 10: Endo-1-(8-azabicyclo[3.2.1]oct-3-yl)-2-methoxy-1H-benzimidazole

Endo-tert-butyl 3-(2-methoxy-1H-benzimidazol-1-yl)-8-azabicyclo[3.2.1]octane-8-carboxylate

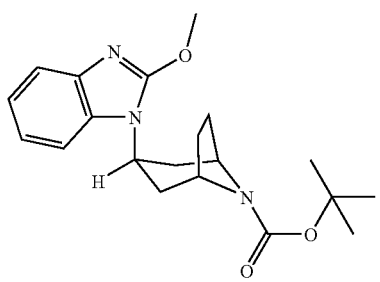

Endo-tert-butyl 3-[(2-aminophenyl)amino]-8-azabicyclo[3.2.1]octane-8-carboxylate (WO 00/38680) (1.0 g, 3.15 mmol) was treated with 5 mL tetramethyl orthocarbonate at reflux for 40 h. The reaction mixture was concentrated to dryness and purified by flash chromatography on silica gel eluted with 20% EtOAc in hexanes to give Endo-tert-butyl 3-(2-methoxy-1H-benzimidazol-1-yl)-8-azabicyclo[3.2.1] octane-8-carboxylate (0.50 g, 1.40 mmol, 44%) as an orange oil. ES-LCMS m/z 358.11 (M+H).

Endo-1-(8-azabicyclo[3.2.1]oct-3-yl)-2-methoxy-1H-benzimidazole

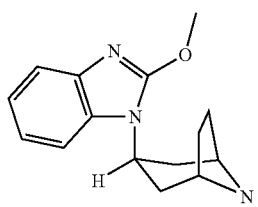

Tert-butyl 3-(2-methoxy-1H-benzimidazol-1-yl)-8-azabicyclo[3.2.1]octane-8-carboxylate (0.50 g, 1.40 mmol) suspended in DCM (2 mL) was treated with TFA (1 mL) at ambient temperature for 5 min. The reaction mixture was concentrated to dryness and the product was crystallized from EtOAc/Et$_2$O to give the di-TFA salt of Endo-1-(8-azabicyclo[3.2.1]oct-3-yl)-2-methoxy-1H-benzimidazole (340 mg, 0.722 mmol, 51%) as a tan solid. $^1$H NMR (300 MHz, D$_2$O) δ 7.35 (m, 1H), 7.26 (m, 1H), 7.12 (m, 2H), 4.65 (m, 1H), 4.08-4.00 (m, 2H), 4.03 (s, 3H), 2.55-2.45 (m, 2H), 2.17-2.02 (m, 6H). ES-LCMS m/z 258.02 (M+H).

Amine 11: Endo-1-(8-azabicyclo[3.2.1]oct-3-yl)-2-ethoxy-1H-benzimidazole

Endo-tert-butyl 3-(2-ethoxy-1H-benzimidazol-1-yl)-8-azabicyclo[3.2.1]octane-8-carboxylate

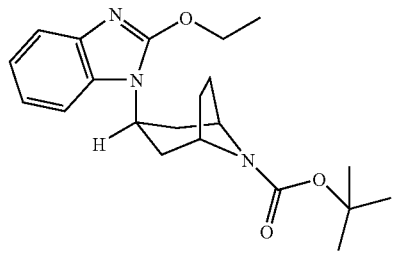

Endo-tert-butyl 3-[(2-aminophenyl)amino]-8-azabicyclo[3.2.1]octane-8-carboxylate (WO 00/38680) (1.7 g, 5.36 mmol) was treated with 10 mL tetraethyl orthocarbonate at reflux for 16 h. The reaction mixture was concentrated to dryness and purified by flash chromatography on silica gel eluted with DCM followed by 20% EtOAc in Hexanes to give Endo-tert-butyl 3-(2-ethoxy-1H-benzimidazol-1-yl)-8-azabicyclo[3.2.1]octane-8-carboxylate (1.15 g, 3.10 mmol, 58%) as an amber oil. ES-LCMS m/z 372.19 (M+H).

Endo-1-(8-azabicyclo[3.2.1]oct-3-yl)-2-ethoxy-1H-benzimidazole

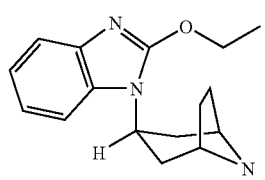

Endo-tert-butyl 3-(2-ethoxy-1H-benzimidazol-1-yl)-8-azabicyclo[3.2.1]octane-8-carboxylate (1.15 g, 3.10 mmol) suspended in DCM (4 mL) was treated with TFA (1 mL) at ambient temperature for 5 min. The reaction mixture was concentrated to dryness and the product crystallized from EtOAc/Et$_2$O to give the di-TFA salt of Endo-1-(8-azabicyclo[3.2.1]oct-3-yl)-2-ethoxy-1H-benzimidazole (715 mg, 1.43 mmol, 46%) as a white powder. $^1$H NMR (300 MHz, D$_2$O) δ 7.36 (m, 1H), 7.27 (m, 1H), 7.12 (m, 2H), 4.65 (m, 1H), 4.43 (q, 2H, J=7.1 Hz), 4.00 (m, 2H), 2.54-2.43 (m, 2H), 2.16-2.00 (m, 6H). ES-LCMS m/z 272.05 (M+H).

Amine 12: Endo-1-(8-azabicyclo[3.2.1]oct-3-yl)-1H-benzimidazol-2-amine

Endo-tert-butyl 3-(2-amino-1H-benzimidazol-1-yl)-8-azabicyclo[3.2.1]octane-8-carboxylate

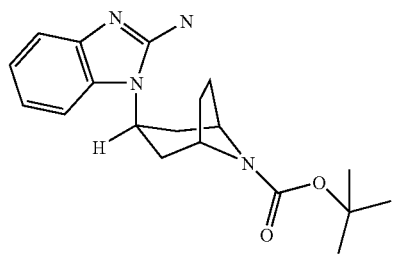

Endo-tert-butyl 3-[(2-aminophenyl)amino]-8-azabicyclo[3.2.1]octane-8-carboxylate (WO 00/38680) (2.5 g, 7.88 mmol) was treated with BrCN (0.92 g, 8.66 mmol) in CH$_3$OH (30 mL) at reflux for 3 h and concentrated to give endo-tert-butyl 3-(2-amino-1H-benzimidazol-1-yl)-8-azabicyclo[3.2.1]octane-8-carboxylate (2.30 g, 6.73 mmol, 85%). $^1$H NMR (300 MHz, DMSO-d$_6$) δ 7.15 (d, 2H, J=7.6 Hz), 6.97-6.86 (m, 2H), 6.21 (s, 2H), 4.34 (m, 2H), 4.22 (pent, 1H), 2.42-2.32 (m, 2H), 1.98-1.85 (m, 6H), 1.44 (s, 9H). ES-LCMS m/z 343.12 (M+H).

Endo-1-(8-azabicyclo[3.2.1]oct-3-yl)-1-benzimidazol-2-amine

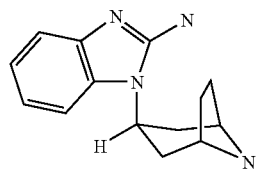

Endo-tert-butyl 3-(2-amino-1H-benzimidazol-1-yl)-8-azabicyclo[3.2.1]octane-8-carboxylate (0.244 g, 0.713 mmol) suspended in DCM (2 mL) was treated with TFA (2 mL) at ambient temperature for 30 min. The reaction mixture was concentrated to dryness and the product crystallized from EtOAc to give the di-TFA salt of Endo-1-(8-azabicyclo[3.2.1]oct-3-yl)-1H-benzimidazol-2-amine (320 mg, 0.681 mmol, 95%) as a white solid. $^1$H NMR (300 MHz, D$_2$O) δ 7.40-7.20 (m, 4H), 4.66-4.49 (m, 1H), 4.16 (m, 2H), 2.71-2.60 (m, 2H), 2.29-2.11 (m, 6H). ES-LCMS m/z 243.04 (M+H).

Amine 13: Endo-1-[(1R,5S)-8-azabicyclo[3.2.1]oct-3-yl]-N-methyl-1H-benzimidazol-2-amine

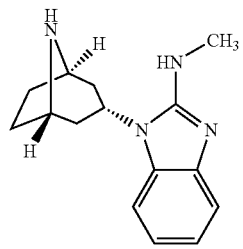

Endo-tert-butyl (1R,5S)-3-[2-(methylamino)-1H-benzimidazol-1-yl]-8-azabicyclo[3.2.1]octane-8-carboxylate

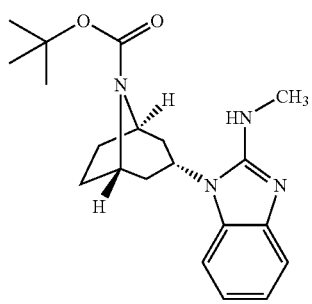

Endo-tert-butyl 3-[(2-aminophenyl)amino]-8-azabicyclo[3.2.1]octane-8-carboxylate (WO 00/38680) (900 mg, 2.83 mmol) in THF was treated with methyl isothiocyanate (230 mg, 3.15 mmoles, 1.1 eq.) at 0° C. for 1 h followed by 16 h at ambient temperature. The reaction mixture was concentrated, redissolved in 7 mL DMF and treated with 1-[3-(dimethylamino)propyl]-3-ethylcarbodiimide hydrochloride (815 mg, 1.5 eq.) at ambient temperature for 16 h. The reaction mixture was concentrated, dissolved in EtOAc, washed successively with saturated aqueous NaHCO$_3$, water (3×), and brine. The organic phase was separated, dried over MgSO$_4$ and concentrated to give the desired product, endo-tert-butyl (1R,5S)-3-[2-(methylamino)-1H-benzimidazol-1-yl]-8-azabicyclo[3.2.1]octane-8-carboxylate. ES-LCMS m/z 357.15 (M+H).

Endo-1-[(1R,5S)-8-azabicyclo[3.2.1]oct-3-yl]-N-methyl-1H-benzimidazol-2-amine

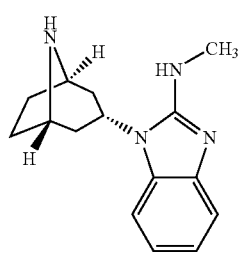

Endo-tert-butyl (1R,5S)-3-[2-(methylamino)-1H-benzimidazol-1-yl]-8-azabicyclo[3.2.1]octane-8-carboxylate was dissolved in 3 mL CH$_3$OH and treated with 3 mL 4N HCl in Dioxane at ambient temperature for 30 minutes. The reaction mixture was concentrated and triturated with EtOH, filtered, and dried to give the di-HCl salt of Endo-1-[(1R,5S)-8-azabicyclo[3.2.1]oct-3-yl]-N-methyl-1H-benzimidazol-2-amine (201 mg, 0.61 mmoles, 60%) as a pink solid. ES-LCMS m/z 257.04 (M+H).

Amine 14: Endo-3-[(1R,5S)-8-azabicyclo[3.2.1]oct-3-yl]-2-methyl-3H-imidazo[4,5-b]pyridine

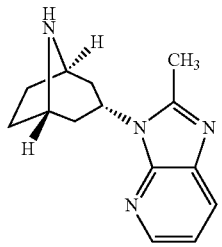

Endo-tert-butyl (1R,5S)-3-[(3-nitropyridin-2-yl)amino]-8-azabicyclo[3.2.1]octane-8-carboxylate

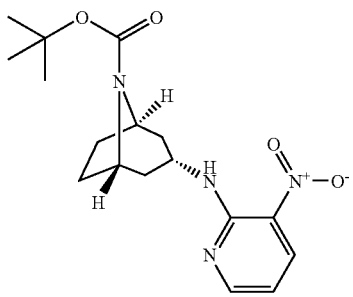

Endo-tert-butyl (1R,5S)-3-amino-8-azabicyclo[3.2.1]octane-8-carboxylate (WO 00/38680) (8.64 g, 38.3 mmoles) was treated with 2-chloro-3-nitropyridine (6.08 g, 1 eq.) in 50 mL NMP with DIPEA (10.9 g, 2.2 eq.) at 70° C. for 16 h. The reaction mixture was cooled to ambient temperature, and water (60 mL) added to incipient cloudiness. The reaction mixture was stirred until a heavy precipitate formed. The precipitate was filtered off, washed successively with NMP/water (1:1) and water, and air dried to give endo-tert-butyl (1R,5S)-3-[(3-nitropyridin-2-yl)amino]-8-azabicyclo[3.2.1]octane-8-carboxylate as an brown solid (11.5 g, 33.0 mmoles, 86%).

Endo-tert-butyl (1R,5S)-3-[(3-aminopyridin-2-yl)amino]-8-azabicyclo[3.2.1]octane-8-carboxylate

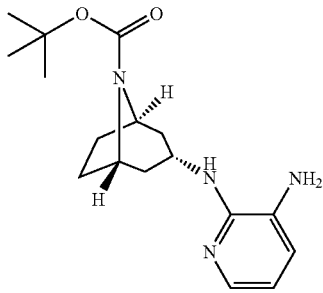

Endo-tert-butyl (1R,5S)-3-[(3-nitropyridin-2-yl)amino]-8-azabicyclo[3.2.1]octane-8-carboxylate (5.17 g, 14.8 mmoles) was subjected to catalytic hydrogenation with 10% Pd/C (500 mg) in EtOH/EtOAc (1:1, 200 mL) under 1 atm $H_2(g)$ for 16 h. The catalyst was filtered off and the filtrate was concentrated to give Endo-tert-butyl (1R,5S)-3-[(3-aminopyridin-2-yl)amino]-8-azabicyclo[3.2.1]octane-8-carboxylate as a brown foam and was used in the next step without further characterization.

Endo-tert-butyl (1R,5S)-3-(2-ethoxy-2-methyl-1,2-dihydro-3H-imidazo[4,5-b]pyridin-3-yl)-8-azabicyclo[3.2.1]octane-8-carboxylate

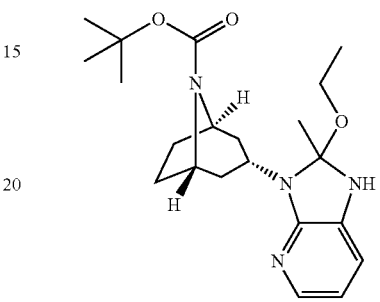

Endo-tert-butyl (1R,5S)-3-[(3-aminopyridin-2-yl)amino]-8-azabicyclo[3.2.1]octane-8-carboxylate (2.85 g, 8.52 mmoles) was treated with 1,1,1-triethoxyethane and a catalytic amount of camphor sulphonic acid at reflux for 3 h. The reaction mixture was concentrated to dryness, dissolved in EtOAc, washed with saturated aqueous $NaHCO_3$, the organic phase separated, dried over $MgSO_4$, filtered and concentrated. The crude product was purified by normal phase flash chromatography ($SiO_2$, 10→40% EtOAc/Hexanes) to give endo-tert-butyl (1R,5S)-3-(2-ethoxy-2-methyl-1,2-dihydro-3H-imidazo[4,5-b]pyridin-3-yl)-8-azabicyclo[3.2.1]octane-8-carboxylate (2.66 g, 6.84 mmoles, 80%). ES-LCMS m/z 411.08 (M+Na).

Endo-tert-butyl (1R,5S)-3-(2-methyl-3H-imidazo[4,5-b]pyridin-3-yl)-8-azabicyclo[3.2.1]octane-8-carboxylate

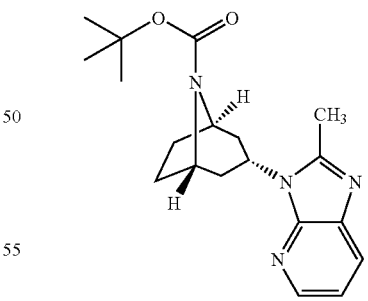

Endo-tert-butyl (1R,5S)-3-(2-ethoxy-2-methyl-1,2-dihydro-3H-imidazo[4,5-b]pyridin-3-yl)-8-azabicyclo[3.2.1]octane-8-carboxylate (2.66 g, 6.84 mmoles) and a catalytic amount of camphor sulphonic acid were combined in NMP at 150° C. for 12 h. The reaction mixture was cooled to ambient temperature, diluted with EtOAc, washed successively with saturated aqueous $NaHCO_3$ and brine (5×). The organic phase was separated, dried over $MgSO_4$, filtered and concentrated. The crude product was purified by normal phase flash chromatography (SiO$_2$, EtOAc) to give Endo-tert-butyl (1R,5S)-3-(2-methyl-3H-imidazo[4,5-b]pyridin-3-yl)-8-azabicyclo[3.2.1]octane-8-carboxylate (1.60 g, 4.67 mmoles, 68%). ES-LCMS m/z 343.24 (M+H).

Endo-3-[(1R,5S)-8-azabicyclo[3.2.1]oct-3-yl]-2-methyl-3H-imidazo[4,5-b]pyridine

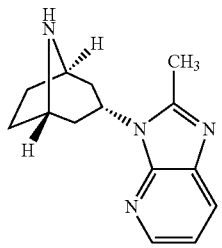

Endo-tert-butyl (1R,5S)-3-(2-methyl-3H-imidazo[4,5-b]pyridin-3-yl)-8-azabicyclo[3.2.1]octane-8-carboxylate (1.60 g, 4.67 mmoles) was dissolved in 15 mL DCM and treated with 4 N HCl in dioxane at ambient temperature for 30 min. A precipitate formed directly from the reaction mixture and was filtered and dried to give the HCl salt of Endo-3-[(1R,5S)-8-azabicyclo[3.2.1]oct-3-yl]-2-methyl-3H-imidazo[4,5-b]pyridine as a brown solid. ES-LCMS m/z 243.22 (M+H).

Synthesis of the 5-(aminosulfonyl)-2-chloronicotinic acid

2-Hydroxynicotinic acid (10.0 g, 71.8 mmol) was dissolved in 25 ml of chlorosulfonic acid and heated to 160° C. overnight. After cooling the reaction was slowly poured into ice and stirred in an ice bath until a white precipitate formed. The solid was filtered off and dried under vacuum to afford 7.55 g of 5-(chlorosulfonyl)-2-hydroxynicotinic acid (44% yield). 1H NMR (300 MHz, DMSO-d6) δ ppm 7.9 (dd, J=2.5, 0.7 Hz, 1H) 8.4 (dd, J=2.6, 0.7 Hz, 1H).

5-(Chlorosulfonyl)-2-hydroxynicotinic acid (500 mg, 2.10 mmol) vas suspended in 5 ml of POCl$_3$ in a sealed tube and heated to 130° C. until all solid had dissolved. The reaction was cooled to 0° C. and poured onto ice and stirred until a solid formed. The filtered white solid was dried to afford 2-chloro-5-(chlorosulfonyl)nicotinic acid. $^1$H NMR (400 MHz, Acetone-d6) δ ppm 8.9 (d, J=2.6 Hz, 10H), 9.3 (d, J=2.6 Hz, 10H).

2-Chloro-5-(chlorosulfonyl)nicotinic acid (400 mg, 1.56 mmol) was stirred in a slurry of ice and excess ammonium hydroxide was added at 0° C. and stirred until all of the ice had melted. The resulting solution was evaporated to afford a white solid 5-(aminosulfonyl)-2-chloronicotinic acid. MS ES+ 237 (M+H). $^1$H NMR (400 MHz, DMSO-D6) δ ppm 8.1 (dd, J=2.6, 0.9 Hz, 1H), 8.6 (m, 1H).

2-{[(dimethylamino)sulfonyl]oxy}benzoic acid

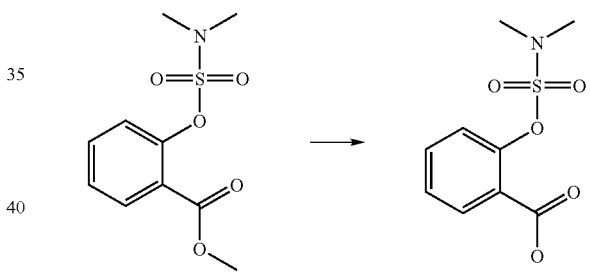

Methyl 2-{[(dimethylamino)sulfonyl]oxy}benzoate (325.0 mg, 1.253 mmol) was dissolved in 2 ml of 1,4-dioxane and 2 ml of 1M LiOH was added. The resulting solution was shaken overnight at 45° C. The reaction mixture was washed with DCE and separated using a hydrophobic frit. The aqueous layer was acidified to give a white solid which was filtered and dried to afford 244.4 mg (80% yield) of 2-{[(dimethylamino)sulfonyl]oxy}benzoic acid.

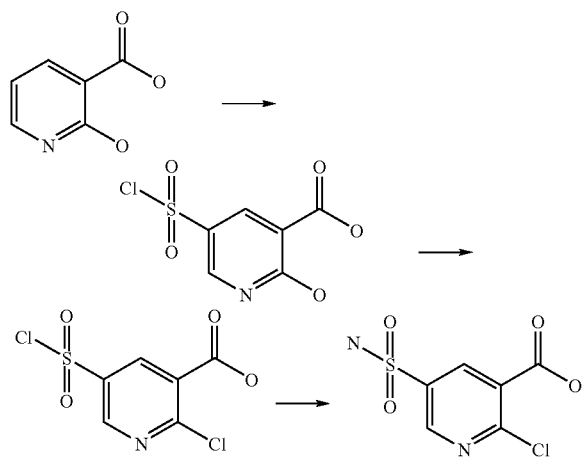

| Example | Acid source | R | X | Y | % yield | LCMS result | Ion | Method |
|---|---|---|---|---|---|---|---|---|
| Example 385 | Commercial | | H | C | 34 | 652 | (M + H) | sulfonyl |

-continued

| Example | Acid source | R | X | Y | % yield | LCMS result | Ion | Method |
|---|---|---|---|---|---|---|---|---|
| Example 386 | Commercial | 3-chlorophenyl sulfonyl | H | C | 21 | 603 | (M + H) | sulfonyl |
| Example 343 | Commercial | 3-methylphenyl sulfonyl | H | C | 41 | 583 | (M + H) | sulfonyl |
| Example 387 | Commercial | 3,5-dichlorophenyl sulfonyl | H | C | 74 | 637 | (M + H) | sulfonyl |

Example 386

1-[(1R,5S)-8-(2-{1-[3-chlorophenyl)sulfonyl]-4-phenyl-4-piperidinyl}ethyl)-8-azabicyclo[3.2.1]oct-3-yl]-2-methyl-1H-benzimidazole 3-Chlorobenzenesulfonyl chloride (31.6 mg, 0.122 mmol) was added to a solution of 2-methyl-1-{(1R,5S)-8-[2-(4-phenyl-4-piperidinyl)ethyl]-8-azabicyclo[3.2.1]oct-3-yl}-1H-benzimidazole (50.0 mg, 0.117 mmol) and diisopropylethylamine (44.9 mg, 0.348 mmol) in DCM. The reactions were quenched with sat. NaHCO$_3$ and separated with a hydrophobic frit. Flash chromatography on silica 0 to 10% MeOH in EtOAc afforded 1-[(1R,5S)-8-(2-{1-[(3-chlorophenyl)sulfonyl]-4-phenyl-4-piperidinyl}ethyl)-8-azabicyclo[3.2.1]oct-3-yl]-2-methyl-1H-benzimidazole 14.7 mg (20% yield). MS ES+ 603 (M+H). $^1$H NMR (300 MHz, chloroform-d) δ ppm 1.6 (m, 2H), 1.7 (m, 4H), 1.9 (m, 8H), 2.4 (m, 4H), 2.6 (s, 3H), 2.8 (m, 2H), 3.4 (m, 2H), 4.6 (m, 1H), 7.2 (m, 5H), 7.3 (m, 3H), 7.4 (t, J=7.9 Hz, 1H), 7.5 (m, 1H), 7.6 (d, J=7.8 Hz, 1H), 7.7 (m, 1H), 7.7 (m, J=1.8, 1.8 Hz, 1H).

General Scheme Towards Pyrimidinyl and Tetrahydro-biimidazolyl Derivatives of 2-Methyl-1-{8-[2-(4-Phenylpiperidin-4-yl)ethyl]-8-Azabicyclo[3.2.1]oct-3-yl}-1H-Benzimidazole

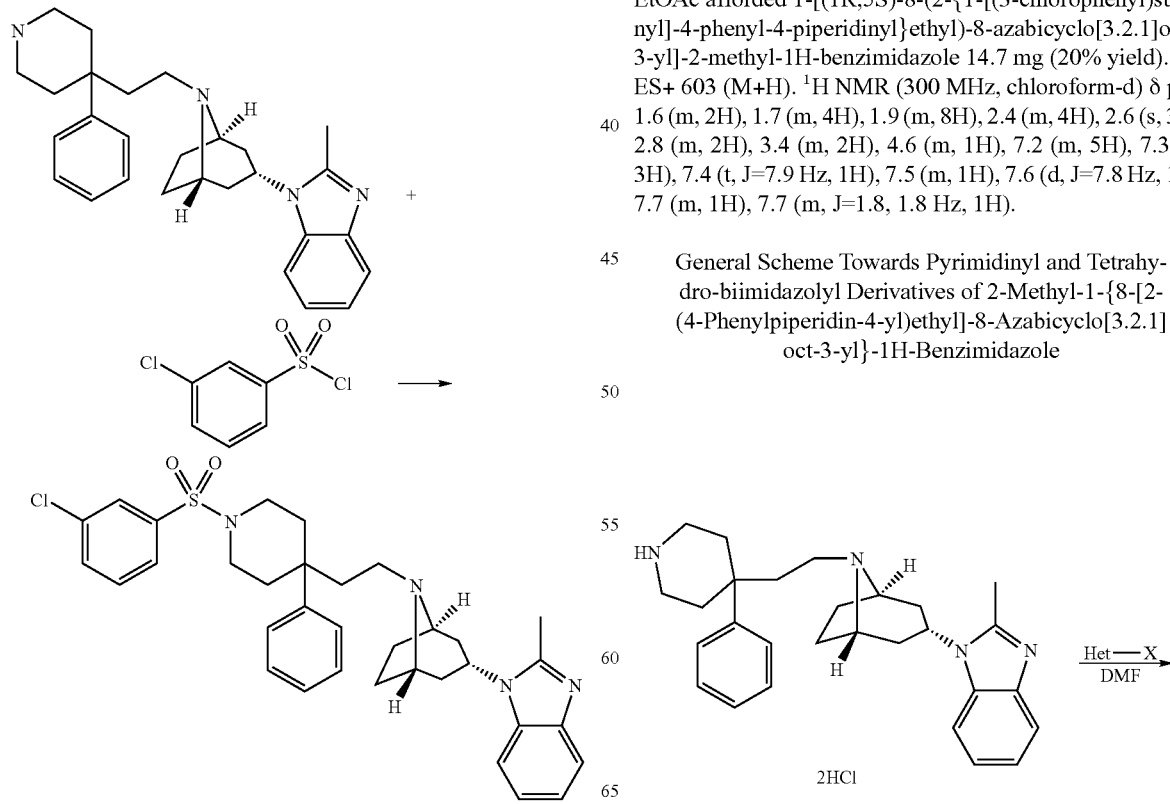

-continued

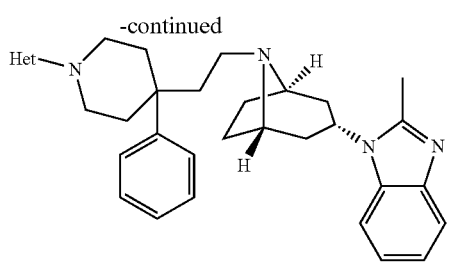

Example 388

Preparation of 2-methyl-1-{8-[2-(4-phenyl-1-pyrimidin-2-ylpiperidin-4-yl)ethyl]-8-azabicyclo[3.2.1]oct-3-yl}-1H-benzimidazole

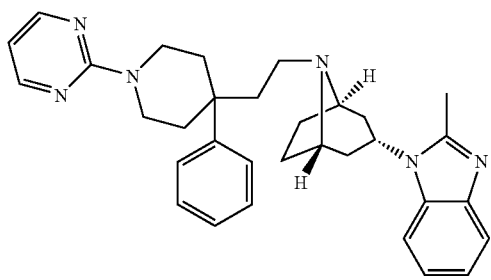

To a stirred solution of 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) in N,N-dimethylformade (2 mL) was added 2-chloropyrimidine (8.6 mg, 0.075 mmol) and triethylamine (21 µL, 0.15 mmol). The resulting mixture was stirred at 80° C. for 2.5 hours. After evaporation of the solvent, the crude product was directly purified by flash chromatography on silical gel, eluting with a gradient of 0-10% triethylamine in methanol to afford 2-methyl-1-{8-[2-(4-phenyl-1-pyrimidin-2-ylpiperidin-4-yl)ethyl]-8-azabicyclo[3.2.1]oct-3-yl}-1H-benzimidazole as amorphous solid (16.2 mg, 65%). $^1$H NMR (300 MHz, CDCl$_3$) δ 8.30 (d, J=6.0 Hz, 2H), 7.67 (dd, J=2.6, 7.0 Hz, 1H), 7.39-7.37 (m, 4H), 7.35-7.22 (m, 3H), 7.21-7.14 (m, 2H), 6.45 (t, J=4.7 Hz, 1H), 4.64 (m, 1H), 4.17-4.09 (m, 2H), 3.61-3.52 (m, 2H), 3.28-3.25 (m, 2H), 2.59 (s, 3H), 2.44-2.33 (m, 2H), 2.29-2.22 (m, 2H), 1.97-1.85 (m, 10H), 1.62 (d, J=7.7 Hz, 2H). HRMS m/z (M+H)$^+$ calcd: 507.3236; obsd: 507.3248.

Example 389

Preparation of 2-methyl-1-(8-{2-[4-phenyl-1-(4,4',5,5'-tetrahydro-1'H-1,2'-biimidazol-2-yl)piperidin-4-yl]ethyl}-8-azabicyclo[3.2.1]oct-3-yl)-1H-benzimidazole

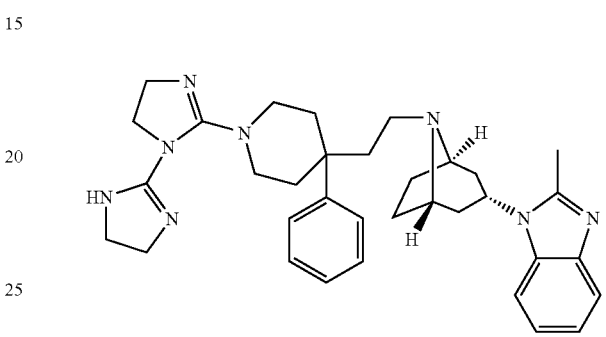

2-Methyl-1-(8-{2-[4-phenyl-1-(4,4',5,5'-tetrahydro-1'H-1,2'-biimidazol-2-yl)piperidin-4-yl]ethyl}-8-azabicyclo[3.2.1]oct-3-yl)-1H-benzimidazole (16 mg, 58%) was obtained as amorphous solid from 2-methyl-{8-[2-(4-phenylpiperidin-4-yl)ethyl]-8-azabicyclo[3.2.1]oct-3-yl}-1H-benzimidazole dihydrochloride (25.3 mg, 0.05 mmol) and 2-methylthio-2-imidazoline hydroiodide (24.4 mg, 0.1 mmol) by the similar procedure outlined in example 388. $^1$H NMR (300 MHz, CDCl$_3$) δ 7.68-7.65 (m, 1H), 7.40-7.35 (m, 2H), 7.31-7.25 (m, 4H), 7.21-7.12 (m, 2H), 5.87 (br, 1H), 4.65-4.58 (m, 1H), 4.06-3.97 (m, 2H), 3.17-3.65 (m, 6H), 3.32-3.26 (m, 4H), 3.12-3.06 (m, 2H), 2.58 (s, 3H), 2.42-2.32 (m, 2H), 2.25-2.19 (m, 2H), 1.97-1.86 (m, 10H), 1.62 (d, J=7.9 Hz, 2H). HRMS m/z (M+H)$^+$ calcd: 565.3767, obsd: 565.3755.

Preparation of Carboximidoate, Carboximidamide and Carbimdo-thioate Derivatives of 2-Methyl-1-{8-[2-(4-Phenylpiperidin-4-yl)ethyl]-8-Azabicyclo-[3.2.1]oct-3-yl}-1H-Benzimidazole

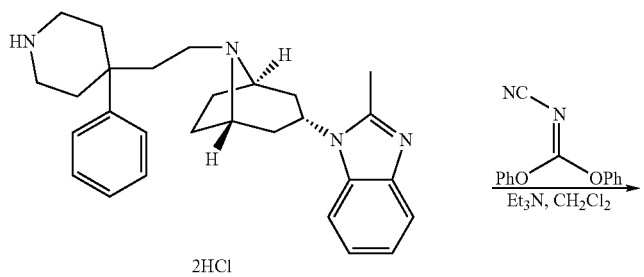 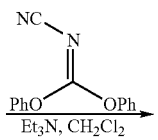 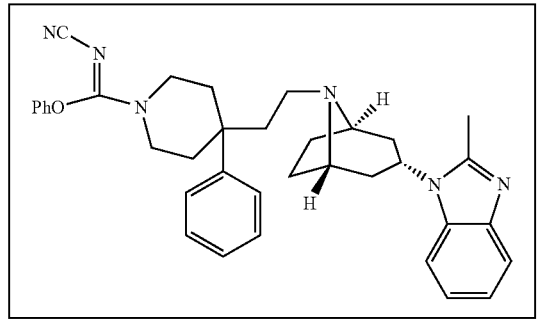

-continued

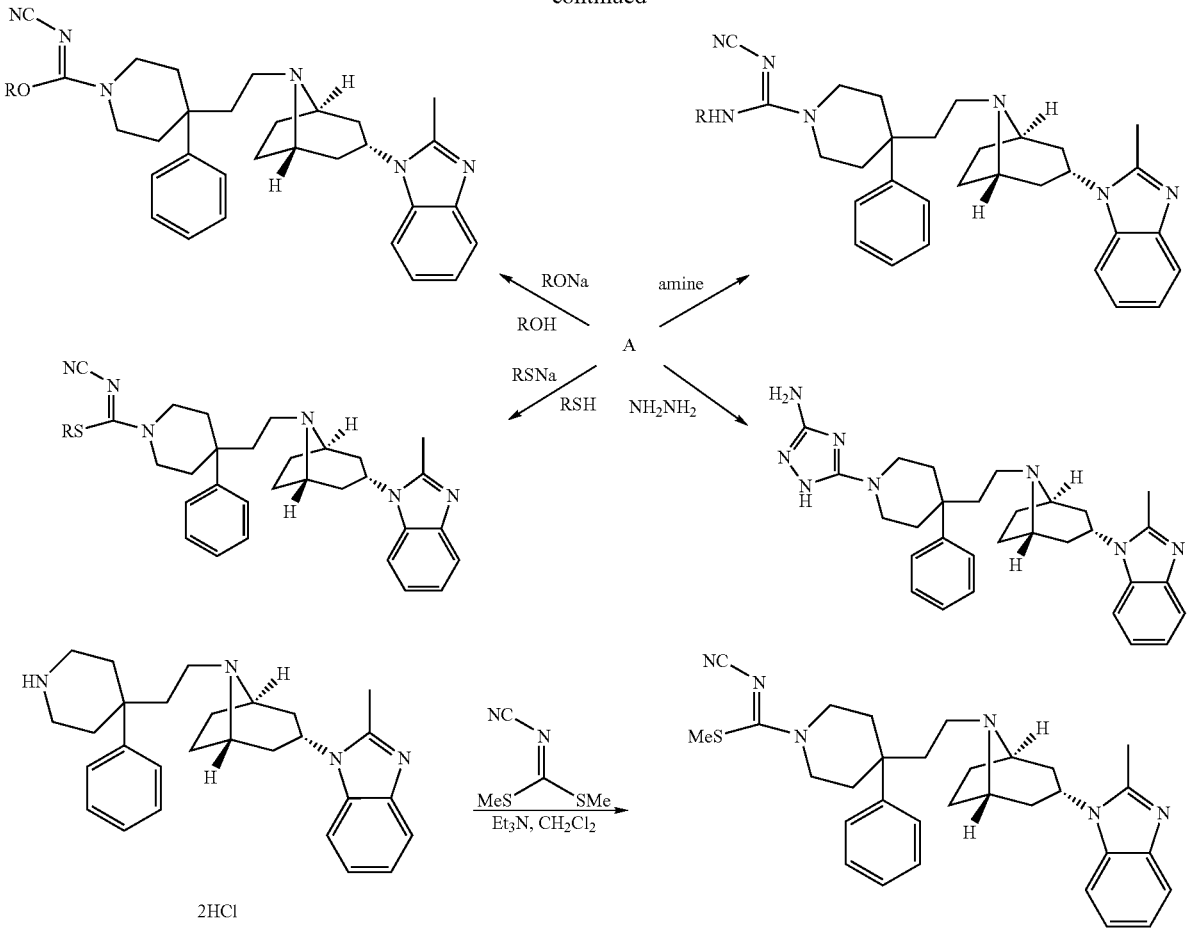

Example 390

Preparation of 5-(4-{2-[3-(2-methyl-1H-benzimidazol-1-yl)-8-azabicyclo[3.2.1]oct-8-yl]ethyl}-4-phenylpiperidin-1-yl)-1H-1,2,4-triazol-3-amine

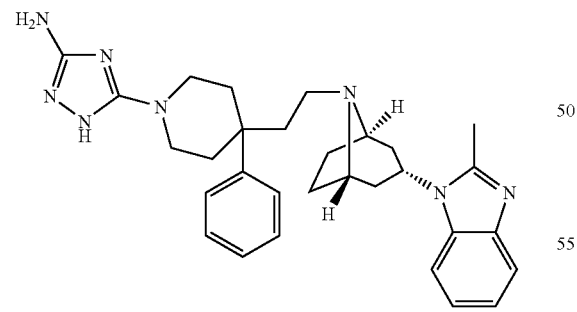

To a stirred solution of phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (18 mg, 0.031 mmol) in isopropyl alcohol (1 mL) was added hydrazine (3.6 μL, 0.11 mmol). The resulting mixture was then stirred at 80° C. for 4 hours. After evaporation of the solvents, the residue was purified by flash chromatography to afford 5-(4-{2-[3-(2-methyl-1H-benzimidazol-1-yl)-8-azabicyclo[3.2.1]oct-8-yl]ethyl}-4-phenylpiperidin-1-yl)-1H-1,2,4-triazol-3-amine as white solid (12.5 mg, 79%). $^1$H NMR (300 MHz, CDCl$_3$) δ 7.67-7.64 (m, 2H), 7.39-7.29 (m, 5H), 7.25-7.13 (m, 3H), 4.66-4.55 (m, 2H), 4.28 (br, 2H), 3.56-3.49 (m, 3H), 3.27-3.21 (m, 4H), 2.57 (s, 3H), 2.42-2.22 (m, 4H), 1.96-1.82 (m, 9H), 1.64-1.62 (m, 2H). HRMS m/z (M+H)$^+$ calcd: 511.3298, obsd: 511.3289.

Example 391

Preparation of isopropyl N-cyano-4-{2-[3-(2-methyl-1H-benzimidazol-1-yl)-8-azabicyclo[3.2.1]oct-8-yl]ethyl}-4-phenylpiperidine-1-carboximidoate

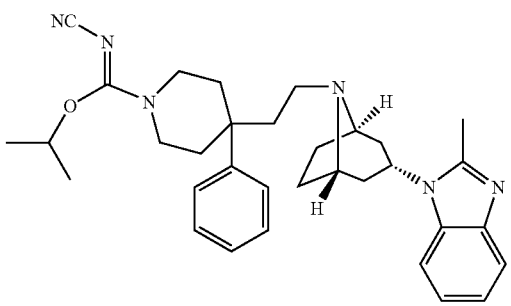

Isopropyl N-cyano-4-{2-[3-(2-methyl-1H-benzimidazol-1-yl)-8-azabicyclo[3.2.1]oct-8-yl]ethyl}-4-phenylpiperidine-1-carboximidoate (13 mg, 92%) was obtained as amorphous solid from phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (15 mg, 0.026 mmol) and sodium isopropoxide by the similar procedure outlined in example 7. $^1$H NMR (300 MHz, CDCl$_3$) δ 7.67 (d, J=7.0 Hz, 1H), 7.42-7.35 (m, 2H), 7.29-7.21 (m, 4H), 7.19-7.13 (m, 2H), 5.30-5.22 (m, 1H), 4.69 (br, 1H), 4.14-4.02 (m, 2H), 3.38-3.20 (m, 4H), 2.59 (s, 3H), 2.41-2.14 (m, 4H), 1.94-1.68 (m, 12H), 1.32 (d, J=6.2 Hz, 6H). HRMS m/z (M+H)$^+$ calcd: 539.3498, obsd: 539.3503.

Example 392

Preparation of cyclopentyl N-cyano-4-{2-[3-(2-methyl-1H-benzimidazol-1-yl)-8-azabicyclo[3.2.1]oct-8-yl]ethyl}-4-phenylpiperidine-1-carboximidoate

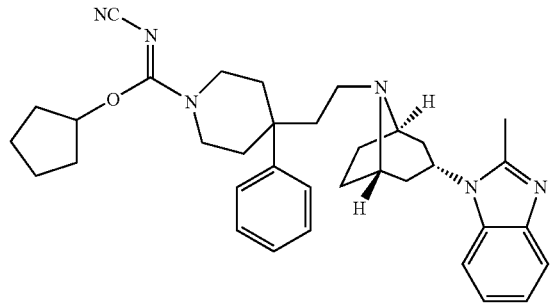

Cyclopentyl N-cyano-4-{2-[3-(2-methyl-1H-benzimidazol-1-yl)-8-azabicyclo[3.2.1]oct-8-yl]ethyl}-4-phenylpiperidine-1-carboximidoate (15 mg, 81%) was obtained from phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (19 mg, 0.033 mmol) and sodium cyclopentoxide by the similar procedure outlined in example 7. $^1$H NMR (CDCl$_3$, 300 MHz): δ 7.67 (d, J=6.9 Hz, 1H), 7.42-7.31 (m, 2H), 7.29-7.24 (m, 4H), 7.19-7.12 (m, 2H), 5.51-5.47 (m, 1H), 4.68 (br, 1H), 3.99 (br, 2H), 3.35-3.28 (m, 4H), 2.59 (s, 3H), 2.42-2.28 (m, 4H), 1.97-1.81 (m, 14H), 1.75-1.62 (m, 6H). HRMS m/z (M+H)$^+$ calcd: 565.3655, obsd: 565.3663.

Example 393A

Preparation of N'-cyano-4-{2-[3-(2-methyl-1H-benzimidazol-1-yl)-8-azabicyclo-[3.2.1]oct-8-yl]ethyl}-4-phenylpiperidine-1-carboximidamide

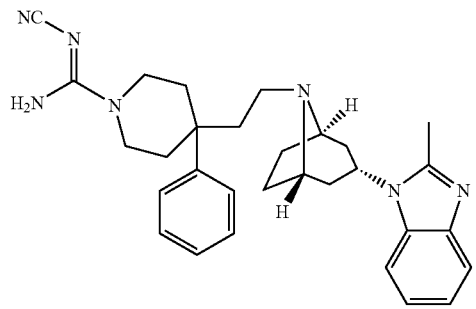

Phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (100 mg, 0.175 mmol) and a solution of ammonia in methanol (2 mL, 1.4 M) was stirred at ambient temperature for 20 hours. After evaporation of the excess ammonia and the solvent, the residue was subject to flash chromatography (Mega Bond Elut Si, MeOH/EtOAc, 10% to 40%) to afford N'-cyano-4-{2-[3-(2-methyl-1H-benzimidazol-1-yl)-8-azabicyclo[3.2.1]oct-8-yl]ethyl}-4-phenylpiperidine-1-carboximidamide as amorphous solid (79 mg, 91%). $^1$H NMR (CDCl$_3$, 300 MHz): δ 7.68-7.65 (m, 1H), 7.42-7.34 (m, 2H), 7.30-7.24 (m, 4H), 7.20-7.18 (m, 2H), 6.11 (s, 2H), 4.65 (t, J=8.5 Hz, 1H), 3.82-3.78 (m, 2H), 3.27-3.20 (m, 4H), 2.53 (s, 3H), 2.45-2.25 (m, 4H), 1.96-1.84 (m, 10H), 1.64 (d, J=7.5 Hz, 2H). HRMS m/z (M+H)$^+$ calcd: 496.3189, obsd: 496.3181.

Example 393B

Preparation of N'-cyano-N-methyl-4-{2-[3-(2-methyl-1H-benzimidazol-1-yl)-8-azabicyclo[3.2.1]oct-8-yl]ethyl}-4-phenylpiperidine-1-carboximidamide

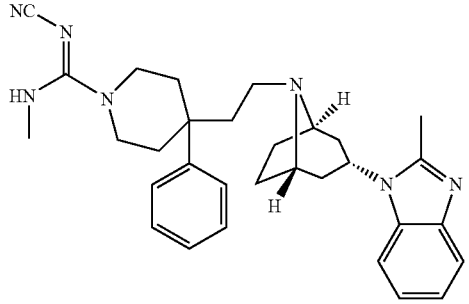

N'-cyano-N-methyl-4-{2-[3-(2-methyl-1H-benzimidazol-1-yl)-8-azabicyclo[3.2.1]oct-8-yl]ethyl}-4-phenylpiperidine-1-carboximidamide (18 mg, quant.) was obtained from phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (20 mg, 0.035 mmol) and methylamine (0.7 mL, 2 M in EtOH) by the similar procedure outlined in example 393. $^1$H NMR (CDCl$_3$, 300 MHz) δ 7.69 (d, J=7.3 Hz, 1H), 7.44-7.39 (m, 2H), 7.32-7.25 (m, 4H), 7.22-7.16 (m, 2H), 5.37 (s, 1H), 4.83 (br, 1H), 3.80-3.76 (m, 2H), 3.35-3.24 (m, 4H), 3.03 (d, J=4.6 Hz, 3H), 2.63 (s, 3H), 2.56-2.29 (m, 4H), 2.08-1.89 (m, 10H), 1.73-1.71 (m, 2H). HRMS m/z (M+H)$^+$ calcd: 510.3345, obsd: 510.3348.

Example 394

Preparation of (4-{2-[3-(2-methyl-1H-benzimidazol-1-yl)-8-azabicyclo[3.2.1]oct-8-yl]ethyl}-4-phenylpiperidin-1-yl)(morpholin-4-yl)methylidene-cyanamide

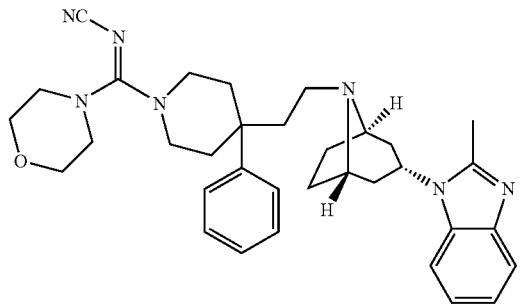

(4-{2-[3-(2-Methyl-1H-benzimidazol-1-yl)-8-azabicyclo[3.2.1]oct-8-yl]ethyl}-4-phenylpiperidin-1-yl)(morpholin-4-yl)methylidenecyanamide (5.1 mg, 26%) was obtained from phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (20 mg, 0.035 mmol) and morpholine (2 mL) by the similar procedure outlined in example 393. $^1$H NMR (CDCl$_3$, 300 MHz) δ 7.67 (d, J=7.5 Hz, 1H), 7.41-7.37 (m, 2H), 7.29-7.25 (m, 4H), 7.21-7.13 (m, 2H), 3.71-3.63 (m, 7H), 3.44-3.30 (m, 7H), 2.64 (s, 3H), 2.32-2.16 (m, 4H), 1.98 (br, 8H), 1.69 (br, 6H); HRMS m/z (M+H)$^+$ calcd: 566.3607, obsd: 566.3610.

Example 395

Preparation of methyl N-cyano-4-{2-[3-(2-methyl-1H-benzimidazol-1-yl)-8-azabicyclo[3.2.1]oct-8-yl]ethyl}-4-phenylpiperidine-1-carbimidothioate

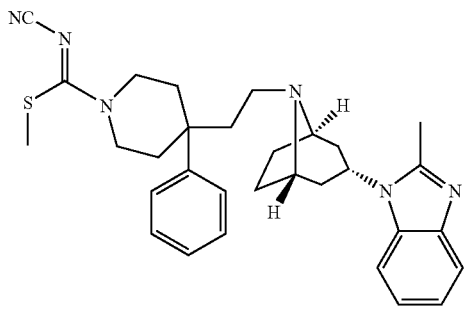

To a stirred solution of 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) in dichloromethane (2 mL) was added triethylamine (14 µL, 1 mmol) and dimethylcyanodithioiminocarbonate (8.8 mg, 0.06 mmol). The resulting mixture was stirred at ambient temperature for 3 hours before it was quenched with saturated sodium bicarbonate solution. The layers were separated and the aqueous layer was extracted with dichloromethane (2×10 mL). The combined organic extracts were dried over anhydrous sodium sulfate. After evaporation of the solvent, the crude product was purified by flash chromatography on silical gel, eluting with a gradient of 0-15% methanol in ethyl acetate to afford methyl N-cyano-4-{2-[3-(2-methyl-1H-benzimidazol-1-yl)-8-azabicyclo[3.2.1]oct-8-yl]ethyl}-4-phenylpiperidine-1-carbimidothioate as amorphous solid (18 mg, 68%). $^1$H NMR (300 MHz, CDCl$_3$) δ 7.70 (d, J=7.0 Hz, 1H), 7.46-7.37 (m, 2H), 7.33-7.28 (m, 4H), 7.24-7.16 (m, 2H), 4.72 (br, 1H), 4.29-4.24 (m, 2H), 3.46 (t, J=11.1 Hz, 2H), 3.31 (br, 2H), 2.78 (s, 3H), 2.62 (s, 3H), 2.54-2.35 (m, 4H), 2.08-1.86 (m, 10H), 1.69 (d, J=7.7 Hz, 2H). HRMS m/z (M+H)$^+$ calcd: 527.2957, obsd: 527.2933.

Example 396

Preparation of isopropyl N-cyano-4-{2-[3-(2-methyl-1H-benzimidazol-1-yl)-8-azabicyclo[3.2.1]oct-8-yl]ethyl}-4-phenylpiperidine-1-carbimidothioate

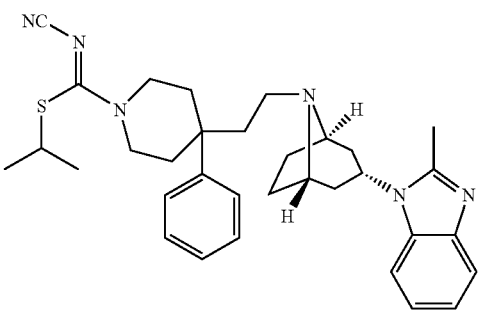

To a stirred solution of phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (20 mg, 0.035 mmol) in THF (1 mL) was added sodium 2-propanethiolate (6.8 mg, 0.07 mmol). The resulting mixture was stirred at ambient temperature for 30 minutes before evaporation of the solvent. The crude product was then purified by flash chromatography on silical gel, eluting with a gradient of 0-10% methanol in ethyl acetate to afford isopropyl N-cyano-4-{2-[3-(2-methyl-1H-benzimidazol-1-yl)-8-azabicyclo[3.2.1]oct-8-yl]ethyl}-4-phenylpiperidine-1-carbimidothioate as a white solid (14 mg, 72%). $^1$H NMR (300 MHz, CDCl$_3$) δ 7.69 (d, J=7.5 Hz, 1H), 7.45-7.40 (m, 2H), 7.32-7.24 (m, 4H), 7.21-7.14 (m, 2H), 4.39-4.26 (m, 3H), 3.53 (br, 4H), 2.65 (s, 3H), 2.33-2.05 (m, 4H), 1.99-1.85 (m, 13H), 1.38 (d, J=6.4 Hz, 6H). HRMS m/z (M+H)$^+$ calcd: 555.3270, obsd: 555.3274.

Example 397

Preparation of cyclopentyl N-cyano-{2-[3-(2-methyl-1H-benzimidazol-1-yl)-8-azabicyclo[3.2.1]oct-8-yl]ethyl}-4-phenylpiperidine-1-carbimidothioate

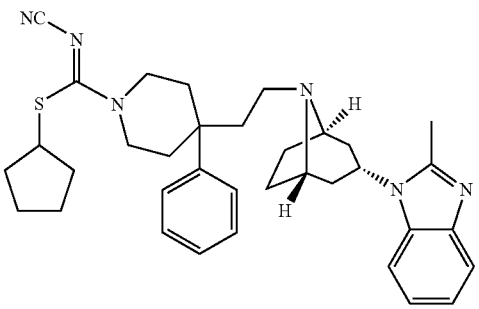

Cyclopentyl N-cyano-4-{2-[3-(2-methyl-1H-benzimidazol-1-yl)-8-azabicyclo[3.2.1]oct-8-yl]ethyl}-4-phenylpiperidine-1-carbimidothioate (20 mg, quant.) was obtained as amorphous solid from phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (20 mg, 0.035 mmol) and sodium cyclopentanethiolate by the similar procedure outlined in example 396. ¹H NMR (300 MHz, CDCl₃) δ 7.68 (d, J=7.2 Hz, 1H), 7.44-7.39 (m, 2H), 7.31-7.22 (m, 4H), 7.20-7.13 (m, 2H), 4.46-4.42 (m, 1H), 4.28-4.23 (m, 2H), 3.52-3.45 (m, 4H), 2.63 (s, 3H), 2.52 (br, 2H), 2.33-2.28 (m, 2H), 2.18-2.10 (m, 4H), 2.05-1.91 (m, 8H), 1.87-1.54 (m, 9H). HRMS m/z (M+H)⁺ calcd: 581.3426, obsd: 581.3438.

Preparation of Amide Derivatives Through HATU Promoted Amidation Method

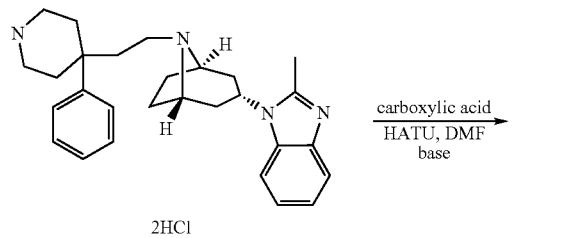

2HCl

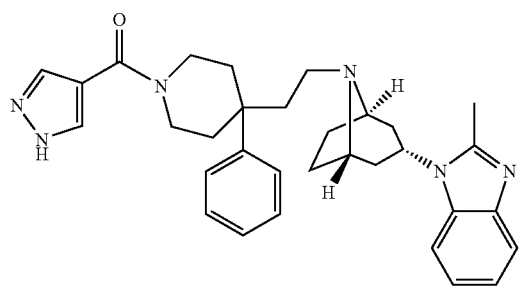

Example 398

Preparation of 2-methyl-1-(8-{2-[4-phenyl-1-(1H-pyrazol-4-ylcarbonyl) piperidin-4-yl]ethyl}-8-azabicyclo[3.2.1]oct-3-yl)-1H-benzimidazole 2-Methyl-1-(8-{2-[4-phenyl-1-(1H-pyrazol-4-ylcarbonyl)piperidin-4-yl]ethyl}-8-azabicyclo[3.2.1]oct-3-yl)-1H-benzimidazole (27 mg, quant.) was obtained as amorphous solid from 2-methyl-1-{8-[2-(4-phenyl piperidin-4-yl) ethyl]-8-azabicyclo[3.2.1]oct-3-yl}-1H-benzimidazole dihydrochloride (25.3 mg, 0.05 mmol) and 4-pyrazoolecarboxylic acid (6 mg, 0.05 mmol) by the similar procedure outlined in example 5. ¹H NMR (300 MHz, DMSO-d₆ 100° C.) δ 7.84 (s, 2H), 7.54-7.51 (m, 1H), 7.47-7.38 (m, 5H), 7.28-7.24 (m, 1H), 7.18-7.11 (m, 2H), 3.91-3.86 (m, 3H), 3.46-3.40 (m, 4H), 3.08 (br, 3H), 2.53 (s, 3H), 2.16 (m, 2H), 2.08-1.74 (m, 12H). HRMS m/z (M+H)⁺ calcd: 523.3185, obsd: 523.3195.

Example 399

Preparation of 2-methyl-1-[(1R,5S)-8-(2-{1-[(5-methyl-1H-pyrazol-3-yl)carbonyl]-4-phenylpiperidin-4-yl}ethyl)-8-azabicyclo[3.2.1]oct-3-yl]-1H-benzimidazole

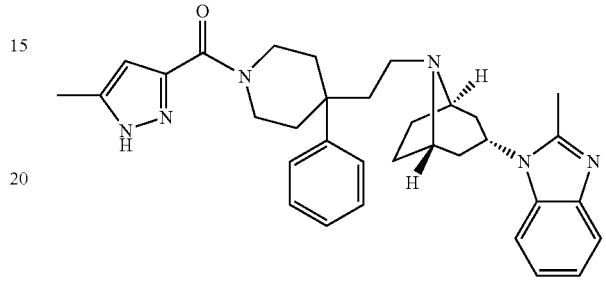

2-Methyl-1-[(1R,5S)-8-(2-{1-[(5-methyl-1H-pyrazol-3-yl)carbonyl]-4-phenylpiperidin-4-yl}ethyl)-8-azabicyclo[3.2.1]oct-3-yl]-1H-benzimidazole (34 mg, 53%) was obtained as amorphous solid from 2-methyl-1-{8-[2-(4-phenylpiperidin-4-yl)ethyl]-8-azabicyclo[3.2.1]oct-3-yl}-1H-benzimidazole (51 mg, 0.12 mmol), 5-methyl-1H-pyrazole-3-carboxylic acid (15 mg, 0.12 mmol) and HATU (47 mg, 0.12 mmol) by the similar procedure outlined in example 5. ¹H NMR (300 MHz, DMSO-d₆) δ 12.78 (s, 1H), 7.49-7.47 (m, 1H), 7.38-7.33 (m, 4H), 7.23-7.21 (m, 1H), 7.11-7.05 (m, 3H), 6.24 (s, 1H), 4.50 (br, 1H), 4.12 (br, 1H), 3.86 (br, 1H), 3.60 (br, 1H), 3.23 (br, 3H), 2.45 (s, 3H), 2.39-2.32 (m, 2H), 2.23 (s, 3H), 2.09 (br, 2H), 1.97-1.71 (m, 10H), 1.58-1.55 (m, 2H). HRMS m/z (M+H)⁺ calcd: 537.3342, obsd: 537.3367.

Example 400

Preparation of 6-methyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2(1H)-one

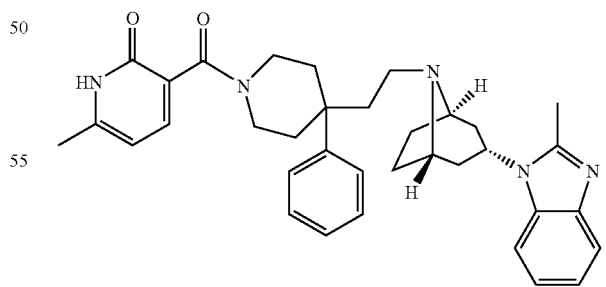

6-Methyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2(1H)-one (30 mg, 53%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (51 mg, 0.10 mmol), 2-hydroxyl-6-methylpyridine-3-carboxylic acid (15 mg, 0.10 mmol) and HATU (38 mg, 0.10 mmol) by the similar procedure outlined in example 5. ¹H NMR (400 MHz, CDCl₃) δ 8.15 (d, J=7.5 Hz, 1H), 7.65 (d, J=7.3 Hz, 1H), 7.50-7.34 (m, 2H), 7.30-7.21 (m, 5H), 7.19-7.12 (m, 2H), 6.18 (d, J=7.5 Hz, 1H), 4.66-4.56 (m, 1H), 4.14-4.07 (m, 1H), 3.88 (br, 2H), 3.25 (br, 3H), 2.56 (s, 3H), 2.40-2.08 (m, 8H), 1.93-1.84 (m, 10H), 1.61 (d, J=6.5 Hz, 2H). HRMS m/z (M+H)⁺ calcd: 564.3339, obsd: 564.3349.

Example 401

Preparation of 5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2(1H)-one

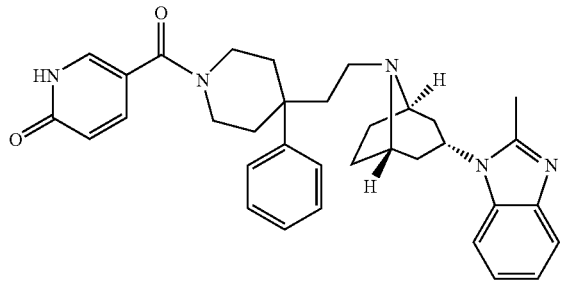

5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2(1H)-one (28 mg, 51%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (51 mg, 0.10 mmol), 6-hydroxynicotinic acid (14 mg, 0.10 mmol) and HATU (38 mg, 0.10 mmol) by the similar procedure outlined in example 5. ¹H NMR (400 MHz, CDCl₃) δ 7.66-7.62 (m, 2H), 7.54 (d, J=7.4 Hz, 1H), 7.40-7.36 (m, 2H), 7.35-7.23 (m, 4H), 7.19-7.12 (m, 2H), 6.57 (d, J=9.6 Hz, 1H), 4.64-4.59 (m, 1H), 3.88 (br, 2H), 3.34-3.25 (m, 4H), 2.56 (s, 3H), 2.41-2.20 (m, 4H), 1.93-1.82 (m, 10H), 1.62 (d, J=6.2 Hz, 2H). HRMS m/z (M+H)⁺ calcd: 550.3182, obsd: 550.3169.

Example 402

Preparation of 5-chloro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2(1H)-one

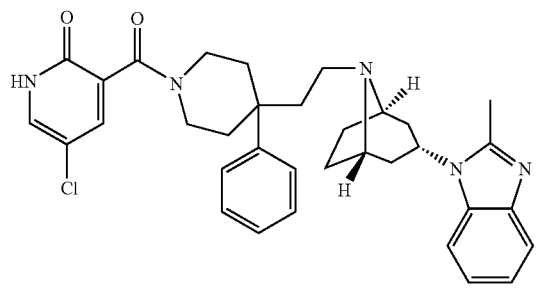

5-Chloro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2(1H) one (20 mg, 34%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (51 mg, 0.10 mmol), 5-chloro-2-hydroxylpyridine-3-carboxylic acid (18 mg, 0.10 mmol) and HATU (38 mg, 0.10 mmol) by the similar procedure outlined in example 5. ¹H NMR (400 MHz, CDCl₃) δ 7.65 (d, J=8.4 Hz, 1H), 7.51-7.45 (m, 2H), 7.40-7.35 (m, 2H), 7.31-7.24 (m, 4H), 7.22-7.12 (m, 2H), 4.64-4.58 (m, 1H), 4.15-4.08 (m, 2H), 3.45-3.23 (m, 6H), 2.57 (s, 3H), 2.42-2.26 (m, 5H), 1.94-1.85 (m, 10H), 1.60 (d, J=6.8 Hz, 2H). HRMS m/z (M+H)⁺ calcd: 584.2792, obsd: 584.2785.

Example 403

Preparation of 3-chloro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2-(1H)-one

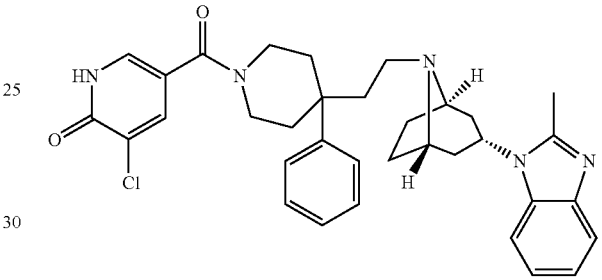

3-Chloro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2(1H)-one (25 mg, 42%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (51 mg, 0.10 mmol), 5-chloro-6-hydroxylnicotinic acid (18 mg, 0.10 mmol) and HATU (38 mg, 0.10 mmol) by the similar procedure outlined in example 5. ¹H NMR (400 MHz, CDCl₃) δ 7.76 (s, 1H), 7.66-7.63 (m, 2H), 7.41-7.38 (m, 2H), 7.35-7.24 (m, 4H), 7.19-7.12 (m, 2H), 4.64-4.59 (m, 1H), 3.89 (br, 2H), 3.35-3.26 (m, 4H), 2.57 (s, 3H), 2.41-2.28 (m, 4H), 1.94-1.83 (m, 11H), 1.62 (d, J=7.9 Hz, 2H). HRMS m/z (M+H)⁺ calcd: 584.2792, obsd: 584.2787.

Example 404

Preparation of (2S)—N¹,N¹-bis{4-{2-[(1R,5S)-3-(2-methyl-1H-benzimidazol-1-yl)-8-azabicyclo[3.2.1]oct-8-yl]ethyl}-1-[N-(methylsulfonyl)-L-seryl]-4-phenylpiperidin-2-yl}-N²-(methylsulfonyl)-L-serinamide

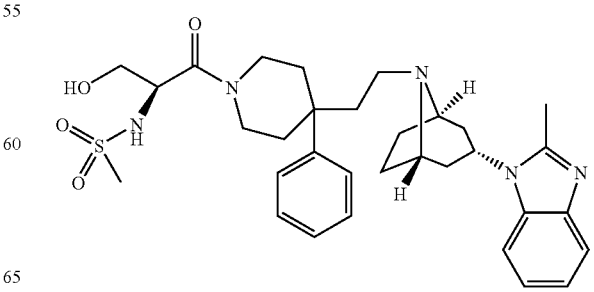

(2S)—N¹,N¹-Bis{4-{2-[(1R,5S)-3-(2-methyl-1H-benzimidazol-1-yl)-8-azabicyclo[3.2.1]oct-8-yl]ethyl}-1-[N-(methylsulfonyl)-L-seryl]-4-phenylpiperidin-2-yl}-N²-(methylsulfonyl)-L-serinamide (43 mg, 50%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (70 mg, 0.14 mmol), N-(methylsulfonyl)-L-serine (28 mg, 0.15 mmol, prepared from L-serine and methanesulfonyl chloride) and HATU (57 mg, 0.15 mmol) by the similar procedure outlined in example 5. ¹H NMR (400 MHz, CDCl₃) δ 7.65 (d, J=8.4 Hz, 1H), 7.40-7.36 (m, 2H), 7.29-7.23 (m, 4H), 7.19-7.12 (m, 2H), 5.78 (dd, J=8.6, 16.5 Hz, 1H), 4.63-4.58 (m, 1H), 4.56-4.45 (m, 1H), 4.09-4.04 (m, 1H), 3.85-3.65 (m, 3H), 3.40-3.09 (m, 4H), 3.02 (s, 3/2H), 2.90 (s, 3/2H), 2.57 (s, 3H), 2.41-2.20 (m, 5H), 1.99-1.74 (m, 10H), 1.64-1.59 (m, 2H). HRMS m/z (M+H)⁺ calcd: 594.3114, obsd: 594.3114.

Example 405

Preparation of (2S,3R)—N¹,N¹-bis{4-{2-[(1R,5S)-3-(2-methyl-1H-benzimidazol-1-yl)-8-azabicyclo[3.2.1]oct-8-yl]ethyl}-1-[N-(methylsulfonyl)-L-threonyl]-4-phenylpiperidin-2-yl}-N²-(methylsulfonyl)-L-threoninamide

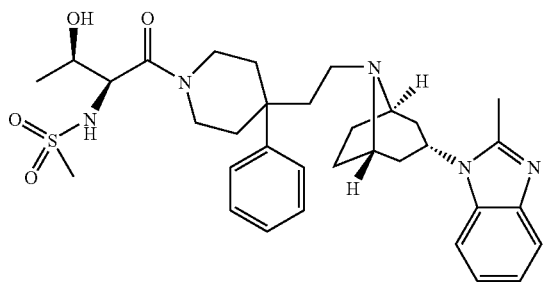

(2S,3R)—N¹,N¹-Bis{4-{2-[(1R,5S)-3-(2-methyl-1H-benzimidazol-1-yl)-8-azabicyclo[3.2.1]oct-8-yl]ethyl}-1-[N-(methylsulfonyl)-L-threonyl]-4-phenylpiperidin-2-yl}-N²-(methylsulfonyl)-L-threoninamide (54 mg, 63%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (70 mg, 0.14 mmol), N-(methylsulfonyl)-L-threonine (33 mg, 0.17 mmol, prepared from L-threonine and methanesulfonyl chloride) and HATU (57 mg, 0.15 mmol) by the similar procedure outlined in example 5. ¹H NMR (400 MHz, CDCl₃) δ 7.64 (d, J=8.6 Hz, 1H), 7.38-7.35 (m, 2H), 7.28-7.22 (m, 4H), 7.18-7.11 (m, 2H), 6.00 (br, 1H), 4.64-4.54 (m, 1H), 4.29 (d, J=9.7 Hz, 1H), 4.08-4.00 (m, 1H), 3.94-3.91 (m, 1H), 3.77-3.71 (m, 1H), 3.40-3.06 (m, 5H), 2.98 (s, 3/2H), 2.84 (s, 3/2H), 2.56 (s, 3H), 2.39-2.20 (m, 4H), 1.98-1.73 (m, 10H), 1.62-1.57 (m, 2H), 1.32 (d, J=6.2 Hz, 3/2H), 1.25 (d, J=6.2 Hz, 3/2H). HRMS m/z (M+H)⁺ calcd: 608.3271, obsd: 608.3283.

Example 406

Preparation of 1-(8-{2-[1-(isoxazol-3-ylcarbonyl)-4-phenylpiperidin-4-yl]ethyl}-8-azabicyclo[3.2.1]oct-3-yl)-2-methyl-1H-benzimidazole

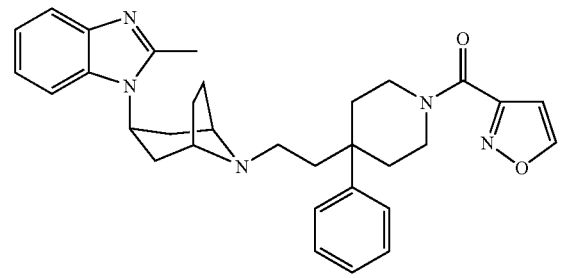

To a pre-cooled (0° C.) solution of 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) in dichloromethane (3 mL) was added isoxazole-5-carbonyl chloride (7.2 mg, 0.055 mmol) and triethylamine (15 μL, 0.11 mmol). The resulting mixture was stirred overnight at ambient temperature and was then diluted with ethyl acetate (20 mL). After being washed with saturated sodium bicarbonate solution, the organic phase was dried over anhydrous sodium sulfate and evaporated. The crude product was purified by flash chromatography on silical gel, eluting with a gradient of 0-10% methanol in ethyl acetate to afford 1-(8-{2-[1-(isoxazol-3-ylcarbonyl)-4-phenylpiperidin-4-yl]ethyl}-8-azabicyclo[3.2.1]oct-3-yl)-2-methyl-1H-benzimidazole as amorphous solid (18.4 mg, 68%). ¹H NMR (300 MHz, CDCl₃) δ 8.32 (d, J=1.8 Hz), 7.67 (dd, J=2.6, 7.0 Hz, 1H), 7.43-7.38 (m, 2H), 7.34-7.24 (m, 4H), 7.21-7.13 (m, 2H), 6.74 (d, J=1.8 Hz), 4.64 (br, 1H), 4.23-4.18 (m, 1H), 3.93-3.89 (m, 1H), 3.45-3.27 (m, 4H), 2.58 (s, 3H), 2.44-2.31 (m, 4H), 1.96-1.86 (m, 10H), 1.67-1.60 (m, 2H). HRMS m/z (M+H)⁺ calcd: 524.3026, obsd: 524.3024.

Preparation of the Derivatives of 2-Methyl-1-{8-[2-(4-Phenylpiperidin-4-yl)ethyl]-8-Azabicyclo[3.2.1]oct-3-yl}-1H-benzimidazole with Heterocycle-Methylene-Piperidine Linkages by Reductive Amination

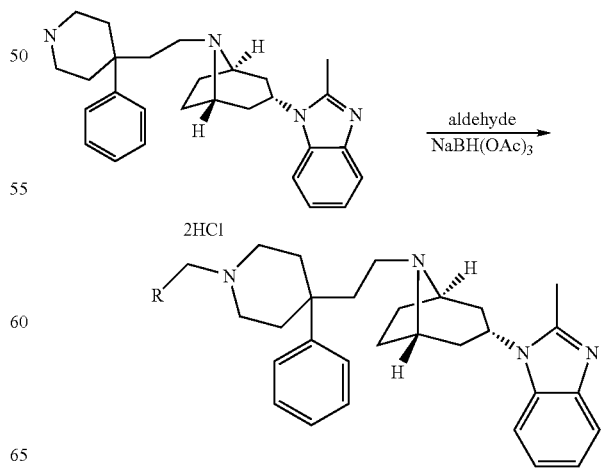

Example 407

Preparation of 2-methyl-1-(8-{2-[4-phenyl-1-(1,3-thiazol-2-ylmethyl)-piperidin-4-yl]ethyl}-8-azabicyclo[3.2.1]oct-3-yl)-1H-benzimidazole

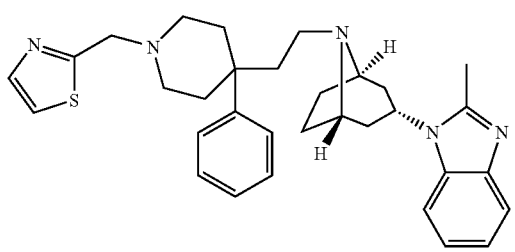

To a stirred solution of 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) in 1,2-dichloroethane (1 mL) was added triethylamine (14 μL, 0.1 mmol), 2-thiazole-carboxaldehyde (6.6 mg, 0.05 mmol) and sodium triacetoxylborohydride (10.6 mg, 0.05 mmol). The resulting mixture was stirred for 4 hours at ambient temperature before it was quenched with saturated sodium bicarbonate solution. The aqueous phase was extracted with ethyl acetate (2×10 mL). The combined extracts was washed with brine and dried over anhydrous sodium sulfate. After evaporation of the solvents, the residue was brought to a flash chromatography on silical gel, eluting with a gradient of 0-10% methanol in ethyl acetate to afford 2-methyl-1-(8-{2-[4-phenyl-1-(1,3-thiazol-2-ylmethyl)piperidin-4-yl]ethyl}-8-azabicyclo-[3.2.1]oct-3-yl)-1H-benzimidazole (23 mg, 87%). $^1$H NMR (300 MHz, CDCl$_3$) δ 7.79-7.65 (m, 2H), 7.46-7.37 (m, 2H), 7.34-7.15 (m, 7H), 5.32 (br, 1H), 3.68 (s, 2H), 3.54 (br, 2H), 2.82-2.80 (m, 2H), 2.67 (s, 3H), 2.63-2.47 (m, 4H), 2.25 (br, 4H), 2.08-1.96 (m, 8H), 1.86 (br, 2H). HRMS m/z (M+H)$^+$ calcd: 526.3004, obsd: 526.3008.

Example 408

Preparation of 1-(8-{2-[1-(1H-imidazol-2-ylmethyl)-4-phenylpiperidin-4-yl]ethyl}-8-azabicyclo[3.2.1]oct-3-yl)-2-methyl-1H-benzimidazole

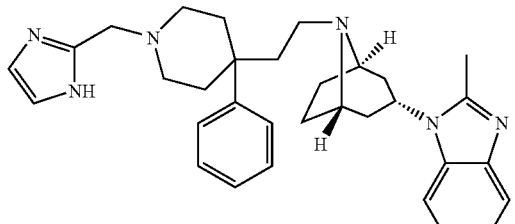

1-(8-(2-[1-(1H-imidazol-2-ylmethyl)-4-phenylpiperidin-4-yl]ethyl)-8-azabicyclo[3.2.1]oct-3-yl)-2-methyl-1H-benzimidazole (9.9 mg, 39%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) and imidazol-2-carboxaldehyde (14.4 mg, 0.15 mmol) following the procedure outlined in example 407. $^1$H NMR (300 MHz, CDCl$_3$) δ 9.78 (s, 10H), 7.69 (d, J=7.1 Hz, 2H), 7.41-7.27 (m, 5H), 7.25-7.17 (m, 3H), 7.03 (s, 2H), 4.68-4.63 (m, 1H), 3.63 (s, 2H), 3.26 (br, 2H), 2.66-2.64 (m, 2H), 2.60 (s, 3H), 2.45-2.35 (m, 4H), 2.20-2.10 (m, 4H), 1.96-1.71 (m, 8H), 1.63 (d, J=7.7 Hz, 2H). HRMS m/z (M+H)$^+$ calcd: 509.3393, obsd: 509.3393.

Example 409

Preparation of 1-(8-{2-[1-(2-furylmethyl)-4-phenylpiperidin-4-yl]ethyl}-8-azabicyclo[3.2.1]oct-3-yl)-2-methyl-1H-benzimidazole

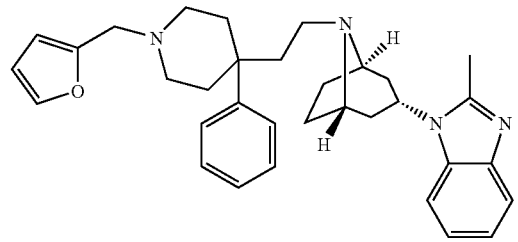

1-(8-{2-[1-(2-Furylmethyl)-4-phenylpiperidin-4-yl]ethyl}-8-azabicyclo[3.2.1]oct-3-yl)-2-methyl-1H-benzimidazole (18.4 mg, 72%) was obtained as oil from 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) and 2-furaldehyde (4.8 mg, 0.05 mmol) following the procedure outlined in example 407. $^1$H NMR (300 MHz, CDCl$_3$) δ 7.69 (d, J=7.0 Hz, 1H), 7.40-7.19 (m, 9H), 6.34 (s, 1H), 6.19 (s, 1H), 4.68-4.61 (m, 1H), 3.50 (s, 2H), 3.25 (br, 2H), 2.67 (br, 2H), 2.60 (s, 3H), 2.45-2.26 (m, 6H), 1.96-1.80 (m, 10H), 1.62 (d, J=7.8 Hz, 2H). HRMS m/z (M+H)$^+$ calcd: 509.3280, obsd: 509.3276.

Example 410

Preparation of (4-{2-[3-(2-methyl-1H-benzimidazol-1-yl)-8-azabicyclo[3.2.1]oct-8-yl]ethyl}-4-phenylpiperidin-1-yl)acetic acid

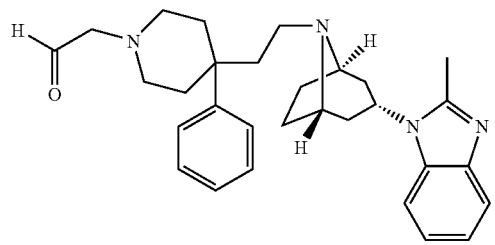

(4-{2-[3-(2-Methyl-1H-benzimidazol-1-yl)-8-azabicyclo[3.2.1]oct-8-yl]ethyl}-4-phenylpiperidin-1-yl)acetic acid (5.2 mg, 21%) was obtained as oil from 2-methyl-1-{8-[2-(4-phenylpiperidin-4-yl)ethyl]-8-azabicyclo[3.2.1]oct-3-yl}-1H-benzimidazole dihydro-chloride (25.3 mg, 0.05 mmol) and glyoxylic acid monohydrate (4.6 mg, 0.05 mmol) following the procedure outlined in example 407. $^1$H NMR (300 MHz, CDCl$_3$) δ 7.69 (s, 1H), 7.44 (d, J=7.3 Hz, 2H), 7.33-7.28 (m, 4H), 7.21 (br, 2H), 4.63 (m, 1H), 3.93-3.85 (m, 3H), 3.32 (br, 2H), 3.10-3.06 (m, 2H), 2.63 (s, 3H), 2.54-2.33 (m, 4H), 2.01-1.90 (m, 11H), 1.68 (d, J=7.7 Hz, 2H). HRMS m/z (M+H)$^+$ calcd: 487.3073, obsd: 487.3089.

Example 411

Preparation of 2,3-dimethoxy-6-[(4-{2-[3-(2-methyl-1H-benzimidazol-1-yl)-8-azabicyclo[3.2.1]oct-8-yl]ethyl}-4-phenylpiperidin-1-yl)methyl]benzoic acid

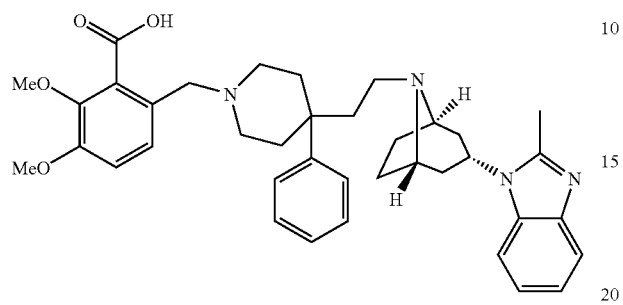

2,3-Dimethoxy-6-[(4-{2-[3-(2-methyl-1H-benzimidazol-1-yl)-8-azabicyclo-[3.2.1]oct-8-yl]ethyl}-4-phenylpiperidin-1-yl)methyl]benzoic acid (14.4 mg, 46%) was obtained as oil from 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) and 6-formyl-2,3-dimethoxybenzoic acid (10.5 mg, 0.05 mmol) following the procedure outlined in example 407. $^1$H NMR (300 MHz, CDCl$_3$) δ 7.69 (d, J=7.4 Hz, 1H), 7.41-7.39 (m, 2H), 7.30-7.23 (m, 4H), 7.23-7.14 (m, 2H), 6.81-6.77 (m, 2H), 4.63-4.58 (m, 1H), 3.95 (s, 3H), 3.86 (s, 3H), 3.65 (s, 2H), 3.23 (br, 2H), 2.95 (br, 2H), 2.57 (s, 3H), 2.42-2.38 (m, 6H), 1.94-1.81 (m, 10H), 1.62 (d, J=7.7 Hz, 2H). HRMS m/z (M+H)$^+$ calcd: 623.3597, obsd: 623.3585.

Preparation of Substituted Phenyl Acetic Acid Derivatives of 2-Methyl-1-{8-[2-(4-Phenylpiperidin-4-yl)ethyl]-8-Azabicyclo[3.2.1]oct-3-yl}-1H-benzimidazole by Petasis Coupling

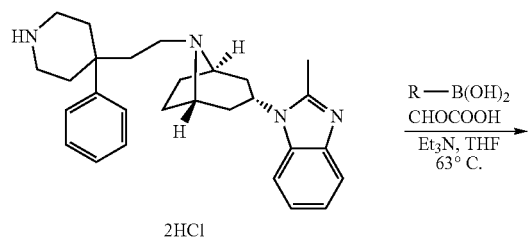

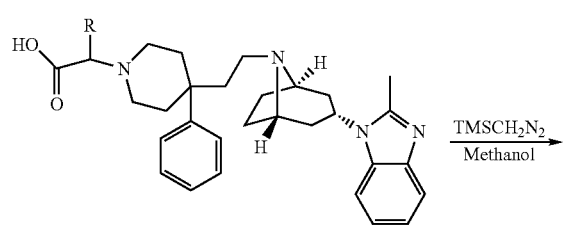

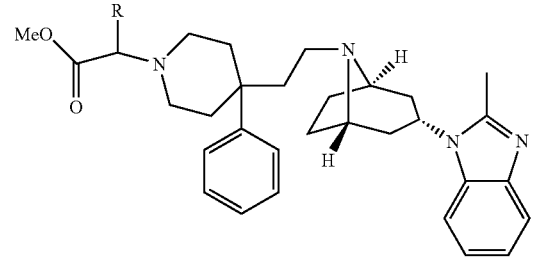

Example 412

Preparation of (4-{2-[3-(2-methyl-1H-benzimidazol-1-yl)-8-azabicyclo-[3.2.1]oct-8-yl]ethyl}-4-phenylpiperidin-1-yl)(phenyl)acetic acid

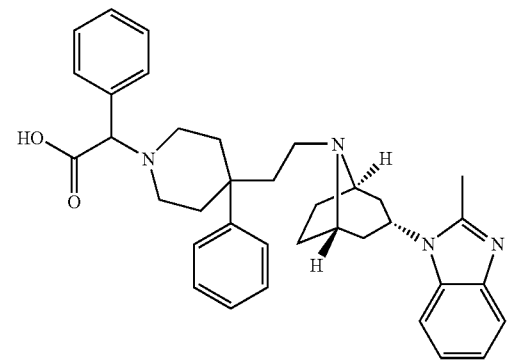

To a stirred solution of 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) in THF (3 mL) was added triethyl amine (14 μL), glyoxylic acid monohydrate (4.6 mg, 0.05 mmol) and phenyl boronic acid (6.1 mg, 0.05 mmol). The resulting mixture was then purged with nitrogen and sealed. After being heated to 60° C. for 3 hours, the solvent was evaporated and the residue was purified by flash chromatography on silical gel, eluting with a gradient of 10-80% methanol in ethyl acetate to afford (4-{2-[3-(2-methyl-1H-benzimidazol-1-yl)-8-azabicyclo[3.2.1]oct-8-yl]ethyl}-4-phenylpiperidin-1-yl)(phenyl)acetic acid (22 mg, 76%). $^1$H NMR (300 MHz, DMSO-d6) δ 9.41 (s, 1H), 7.53-7.48 (m, 3H), 7.36-7.34 (m, 8H), 7.24-7.23 (m, 1H), 7.17-7.09 (m, 2H), 4.58-4.45 (m, 1H), 4.20 (s, 1H), 3.24-3.21 (m, 2H), 3.08 (br, 1H), 2.82-2.65 (m, 2H), 2.82-2.65 (m, 2H), 2.44 (s, 3H), 2.39-2.05 (m, 7H), 1.83-1.68 (m, 8H), 1.59 (d, J=7.6 Hz, 2H). HRMS m/z (M+H)$^+$ calcd: 563.3386, obsd: 563.3390.

Example 413

Synthesis of methyl(4-{2-[3-(2-methyl-1H-benzimidazol-1-yl)-8-azabicyclo[3.2.1]oct-8-yl]ethyl}-4-phenylpiperidin-1-yl)(phenyl)acetate

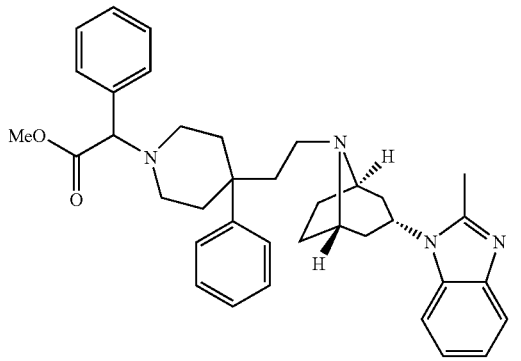

To a stirred solution of (4-{2-[3-(2-methyl-1H-benzimidazol-1-yl)-8-azabicyclo-[3.2.1]oct-8-yl]ethyl}-4-phenylpiperidin-1-yl)(phenyl)acetic acid (prepared above) (12 mg, 0.02 mmol) in methanol (2 mL) was added (trimethylsilyl) diazomethane (100 μL, 2.0 M in hexans). The reaction mixture was stirred for 30 minutes at room temperature. After evaporation of the solvents, the residue was purified by flash chromatography, eluting with a gradient of 0-10% methanol in ethyl acetate, to afford an oil (10 mg, 81%) as methyl(4-{2-[3-(2-methyl-1H-benzimidazol-1-yl)-8-azabicyclo[3.2.1]oct-8-yl]ethyl}-4-phenylpiperidin-1-yl)(phenyl)acetate. $^1$H NMR (300 MHz, CDCl$_3$) δ 7.67 (d, J=7.1 Hz, 1H), 7.45-7.42 (m, 2H), 7.37-7.27 (m, 8H), 7.23-7.15 (m, 3H), 4.61 (m, 1H), 3.89 (s, 1H), 3.67 (s, 3H), 3.25-3.24 (m, 2H), 2.72-2.70 (m, 1H), 2.55 (s, 4H), 2.42-2.16 (m, 6H), 2.03-1.85 (m, 7H), 1.81-1.76 (m, 3H), 1.61-1.58 (m, 2H). HRMS m/z (M+H)$^+$ calcd: 577.3543, obsd: 577.3557.

Example 414

Preparation of (5-chlorothien-2-yl)(4-{2-[3-(2-methyl-1H-benzimidazol-1-yl)-8-azabicyclo[3.2.1]oct-8-yl]ethyl}-4-phenylpiperidin-1-yl)acetic acid

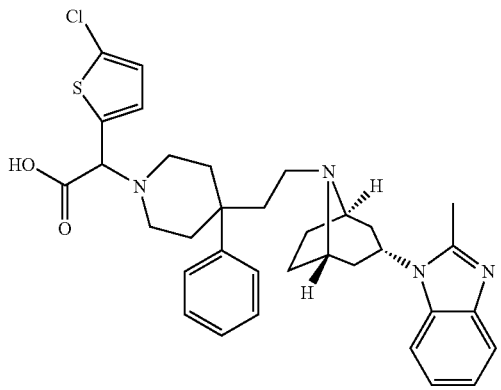

(5-Chlorothien-2-yl)(4-{2-[3-(2-methyl-1H-benzimidazol-1-yl)-8-azabicyclo[3.2.1]oct-8-yl]ethyl}-4-phenylpiperidin-1-yl)acetic acid (29 mg, 96%) was obtained as amorphous solid from 2-methyl-1 {8-[2-(4-phenylpiperidin-4-yl)ethyl]-8-azabicyclo[3.2.1]oct-3-yl}-1H-benzimidazole dihydrochloride (25.3 mg, 0.05 mmol) and 5-chlorothiophene-2-boronic acid (8.1 mg, 0.05 mmol) following the procedure outlined in example 412. $^1$H NMR (300 MHz, DMSO-d$_6$, 100° C.) δ 7.50-7.45 (m, 1H), 7.38-7.32 (m, 5H), 7.17-7.12 (m, 3H), 6.99-6.86 (m, 2H), 4.61-4.57 (m, 1H), 4.30-4.24 (m, 1H), 3.23 (br, 3H), 2.82-2.80 (m, 3H), 2.57-2.37 (m, 7H), 2.14 (br, 2H), 1.93-1.77 (m, 8H), 1.64-1.61 (m, 2H). HRMS m/z (M+H)$^+$ calcd: 603.2561, obsd: 603.2552.

Example 415

Preparation of (4-methoxyphenyl)(4-{2-[3-(2-methyl-1H-benzimidazol-1-yl)-8-azabicyclo[3.2.1]oct-8-yl]ethyl}-4-phenylpiperidin-1-yl)acetic acid

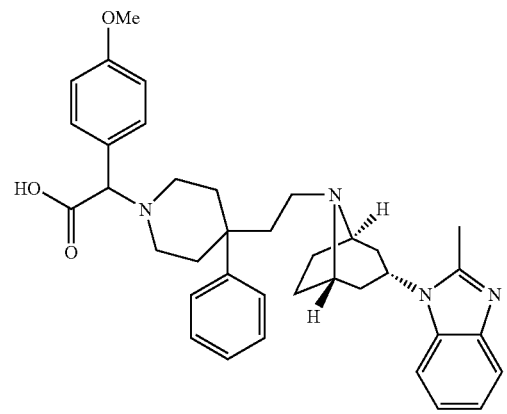

(4-Methoxyphenyl)(4-{2-[3-(2-methyl-1H-benzimidazol-1-yl)-8-azabicyclo[3.2.1]oct-8-yl]ethyl}-4-phenylpiperidin-1-yl)acetic acid (25.6 mg, 86%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) and 4-methoxyphenylboronic acid (7.6 mg, 0.05 mmol) following the procedure outlined in example 412. $^1$H NMR (300 MHz, DMSO-d$_6$, 80° C.) δ 9.44 (s, 1H), 7.52 (d, J=7.0 Hz, 1H), 7.38-7.36 (m, 7H), 7.24-7.21 (m, 1H), 7.17-7.12 (m, 2H), 6.92 (d, J=8.2 Hz, 2H), 4.60-4.51 (m, 1H), 4.04 (s, 1H), 3.78 (s, 3H), 3.26-3.22 (m, 3H), 2.97-2.90 (m, 2H), 2.75 (br, 1H), 2.47 (s, 3H), 2.40-1.81 (m, 9H), 1.63 (d, J=7.3 Hz, 2H). HRMS m/z (M+H)$^+$ calcd: 593.3492, obsd: 593.3496.

Example 416

Preparation of (4-fluorophenyl)(4-{2-[3-(2-methyl-1H-benzimidazol-1-yl)-8-azabicyclo[3.2.1]oct-8-yl]ethyl}-4-phenylpiperidin-1-yl)acetic acid

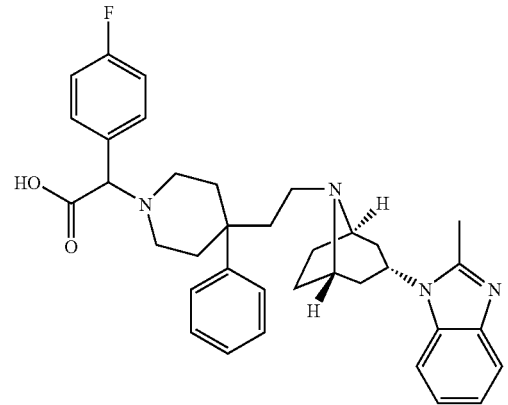

(4-Fluorophenyl)(4-{2-[3-(2-methyl-1H-benzimidazol-1-yl)-8-azabicyclo[3.2.1]oct-8-yl]ethyl}-4-phenylpiperidin-1-yl)acetic acid (24.5 mg, 84%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) and 4-fluorophenylboronic acid (7 mg, 0.05 mmol) following the procedure outlined in example 412. $^1$H NMR (300 MHz, DMSO-d$_6$) δ 7.52-7.48 (m, 3H), 7.37-7.35 (m, 4H), 7.24-7.05 (m, 6H), 4.54-4.48 (m, 1H), 4.07 (s, 1H), 3.23 (br, 2H), 2.98 (br, 1H), 2.69-2.63 (m, 2H), 2.45 (s, 3H), 2.42-2.31 (m, 3H), 2.18 (br, 2H), 2.00 (br, 2H), 1.87-1.74 (m, 8H), 1.59 (d, J=7.3 Hz, 2H). HRMS m/z (M+H)$^+$ calcd: 581.3293, obsd: 581.3287.

Example 417

Synthesis of methyl(4-fluorophenyl)(4-{2-[3-(2-methyl-1H-benzimidazol-1-yl)-8-azabicyclo[3.2.1]oct-8-yl]ethyl}-4-phenylpiperidin-1-yl)acetate

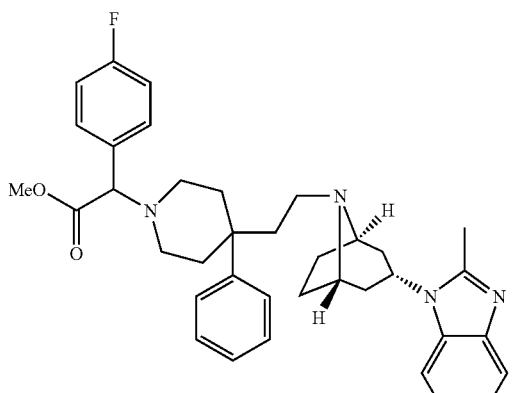

Methyl (4-fluorophenyl)(4-{2-[3-(2-methyl-1H-benzimidazol-1-yl)-8-azabicyclo[3.2.1]oct-8-yl]ethyl}-4-phenylpiperidin-1-yl)acetate (12 mg, 96%) was obtained as a solid from (4-fluorophenyl)(4-{2-[3-(2-methyl-1H-benzimidazol-1-yl)-8-azabicyclo[3.2.1]oct-8-yl]ethyl}-4-phenylpiperidin-1-yl)acetic acid (12 mg, 0.02 mmol) and (trimethylsilyl)diazomethane (100 μL 2.0 M in hexanes) following the procedure outlined for example 9. $^1$H NMR (300 MHz, CDCl$_3$) δ 7.67 (d, J=7.1 Hz, 1H), 7.47-7.45 (m, 1H), 7.41-7.38 (m, 2H), 7.32-7.29 (m, 5H), 7.17-7.11 (m, 3H), 7.09-7.06 (m, 2H), 4.60-4.40 (m, 1H), 4.00 (s, 1H), 3.54 (s, 3H), 3.17 (br, 2H), 2.60-2.43 (m, 1H), 2.43-2.41 (m, 4H), 2.33-2.25 (m, 2H), 2.24-2.20 (m, 1H), 2.19-2.00 (m, 3H), 1.78-1.69 (m, 10H), 1.54 (d, J=7.5 Hz, 2H). HRMS m/z (M+H)$^+$ calcd: 595.3448, obsd: 595.3467.

Example 418

Preparation of 1,3-benzodioxol-5-yl(4-{2-[3-(2-methyl-1H-benzimidazol-1-yl)-8-azabicyclo[3.2.1]oct-8-yl]ethyl}-4-phenylpiperidin-1-yl)acetic acid

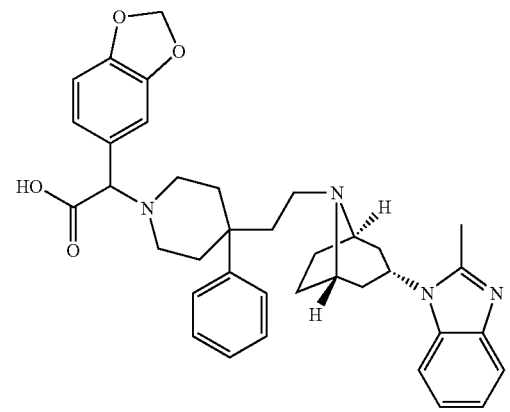

1,3-Benzodioxol-5-yl(4-{2-[3-(2-methyl-1H-benzimidazol-1-yl)-8-azabicyclo[3.2.1]oct-8-yl]ethyl}-4-phenylpiperidin-1-yl)acetic acid (25 mg, 81%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (25.3 mg, 0.05 mmol) and 3,4-dioxolmethylenephenyl boronic acid (9.3 mg, 0.05 mmol) following the procedure outlined in example 412. $^1$H NMR (300 MHz, DMSO-d$_6$) δ 9.40 (s, 1H), 7.52 (m, 1H), 7.38-7.37 (m, 5H), 7.24 (m, 1H), 7.17-7.08 (m, 3H), 6.96-6.87 (m, 2H), 6.03 (d, J=5.1 Hz, 2H), 4.45-4.48 (m, 1H), 4.16 (s, 1H), 3.23-3.08 (m, 5H), 2.82 (br, 2H), 2.45 (s, 3H), 2.40-2.01 (m, 6H), 1.82-1.79 (m, 7H), 1.60 (d, J=7.4 Hz, 2H). HRMS m/z (M+H)$^+$ calcd: 607.3284, obsd: 607.3270.

Example 419

Preparation of (2,6-dimethylphenyl)(4-{2-[3-(2-methyl-1H-benzimidazol-1-yl)-8-azabicyclo[3.2.1]oct-8-yl]ethyl}-4-phenylpiperidin-1-yl)acetic acid

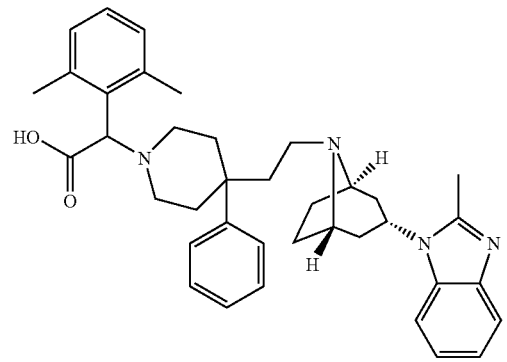

(2,6-Dimethylphenyl)(4-{2-[3-(2-methyl-1H-benzimidazol-1-yl)-8-azabicyclo[3.2.1]oct-8-yl]ethyl}-4-phenylpiperidin-1-yl)acetic acid (26 mg, 90%) was obtained as amorphous solid from 2-methyl-1-{8-[2-(4-phenylpiperidin-4-yl)

ethyl]-8-azabicyclo[3.2.1]oct-3-yl}-1H-benzimidazole dihydrochloride (25.3 mg, 0.05 mmol) and 2,6-dimethylphenyl boronic acid (9 mg, 0.06 mmol) following the procedure outlined in example 412. $^1$H NMR (300 MHz, DMSO-d$_6$) δ 9.31 (s, 1H), 7.48 (d, J=6.9 Hz, 1H), 7.33-7.32 (m, 5H), 7.19-7.17 (m, 1H), 7.13-6.96 (m, 5H), 4.5-4.49 (m, 1H), 4.29 (s, 1H), 3.24 (br, 2H), 2.83 (br, 1H), 2.41 (s, 3H), 2.37 (m, 7H), 2.29-2.07 (m, 5H), 1.97-1.72 (m, 10H), 1.58 (d, J=7.2 Hz, 2H). HRMS m/z (M+H)$^+$ calcd: 591.3699, obsd: 591.3690.

Example 420

Preparation of (2,3-dimethylphenyl)(4-{2-[3-(2-methyl-1H-benzimidazol-1-yl)-8-azabicyclo[3.2.1]oct-8-yl]ethyl}-4-phenylpiperidin-1-yl)acetic acid

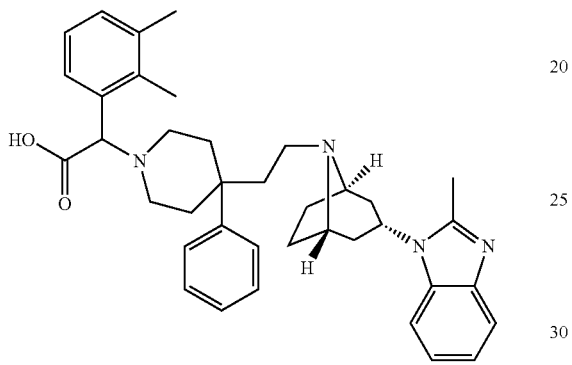

(2,3-Dimethylphenyl)(4-{2-[3-(2-methyl-1H-benzimidazol-1-yl)-8-azabicyclo[3.2.1]oct-8-yl]ethyl}-4-phenylpiperidin-1-yl)acetic acid (35 mg, 99%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (30 mg, 0.06 mmol) and 2,3-dimethylphenyl boronic acid (10.5 mg, 0.07 mmol) following the procedure outlined in example 412. $^1$H NMR (300 MHz, DMSO-d$_6$) δ 9.37 (s, 1H), 7.49-7.47 (m, 1H), 7.39-7.32 (m, 6H), 7.22-7.18 (m, 1H), 7.13-7.03 (m, 4H), 4.5-4.44 (m, 2H), 3.23 (br, 2H), 3.04-2.88 (m, 2H), 2.71 (br, 1H), 2.56-2.51 (m, 1H), 2.39 (s, 3H), 2.36-2.29 (m, 2H), 2.25 (s, 3H), 2.22 (s, 3H), 2.15-1.93 (m, 5H), 1.81 (br, 7H), 1.58 (d, J=7.2 Hz, 2H). HRMS m/z (M+H)$^+$ calcd: 591.3699, obsd: 591.3706.

Example 421

Synthesis of methyl(2,3-dimethylphenyl)(4-{2-[3-(2-methyl-1H-benzimidazol-1-yl)-8-azabicyclo[3.2.1]oct-8-yl]ethyl}-4-phenylpiperidin-1-yl)acetate

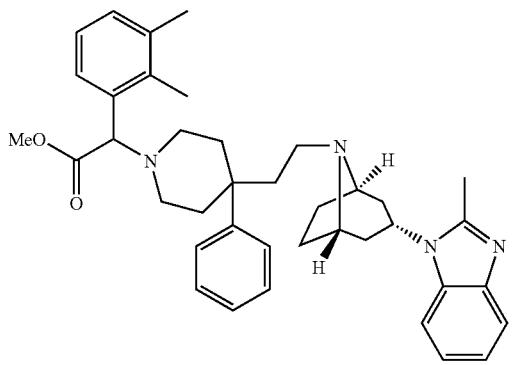

Methyl (2,3-dimethylphenyl)(4-{2-[3-(2-methyl-1H-benzimidazol-1-yl)-8-azabicyclo[3.2.1]oct-8-yl]ethyl}-4-phenylpiperidin-1-yl)acetate (40 mg, 66%) was obtained as a solid from (2,3-Dimethylphenyl)(4-{2-[3-(2-methyl-1H-benzimidazol-1-yl)-8-azabicyclo[3.2.1]oct-8-yl]ethyl}-4-phenylpiperidin-1-yl)acetic acid (40 mg, 0.067 mmol) and (trimethylsilyl)diazomethane (300 μL 2.0 M in hexanes) following the procedure outlined for example 9. $^1$H NMR (300 MHz, CDCl$_3$) δ 7.67 (d, J=7.8 Hz, 1H), 7.44-7.27 (m, 6H), 7.23-7.15 (m, 3H), 7.10-7.07 (m, 2H), 4.66-4.59 (m, 1H), 4.30 (s, 1H), 3.65 (s, 3H), 3.25 (br, 2H), 2.77 (br, 1H), 2.67 (br, 1H), 2.56 (s, 3H), 2.47-2.32 (m, 3H), 2.29 (s, 6H), 2.26-2.12 (m, 3H), 1.99-183 (m, 10H), 1.61-1.59 (m, 2H). HRMS m/z (M+H)$^+$ calcd: 605.3856, obsd: 605.3863.

Example 422

Preparation of (3,5-dimethylphenyl)(4-{2-[3-(2-methyl-1H-benzimidazol-1-yl)-8-azabicyclo[3.2.1]oct-8-yl]ethyl}-4-phenylpiperidin-1-yl)acetic acid

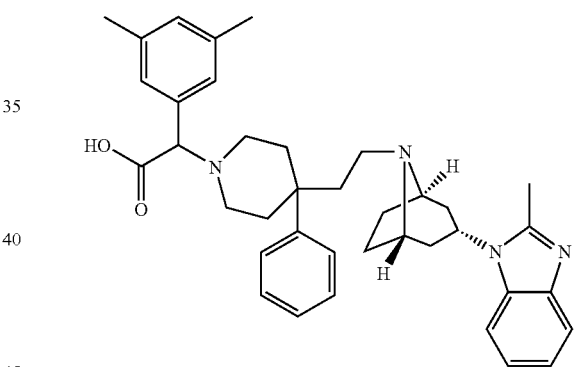

3,5-Dimethylphenyl)(4-{2-[3-(2-methyl-1H-benzimidazol-1-yl)-8-azabicyclo[3.2.1]oct-8-yl]ethyl}-4-phenylpiperidin-1-yl) acetic acid (28 mg, 94%) was obtained as amorphous solid from 2-methyl-1-{8-[2-(4-phenylpiperidin-4-yl)ethyl]-8-azabicyclo[3.2.1]oct-3-yl}-1H-benzimidazole dihydrochloride (25 mg, 0.05 mmol) and 3,5-dimethylphenyl boronic acid (9.0 mg, 0.06 mmol) following the procedure outlined in example 412. $^1$H NMR (300 MHz, DMSO-d$_6$) δ 9.37 (s, 1H), 7.48-7.47 (m, 1H), 7.35-7.33 (m, 5H), 7.23-7.19 (m, 1H), 7.11-7.07 (m, 4H), 6.94 (s, 1H), 4.53-4.47 (m, 1H), 4.13 (s, 1H), 3.23-3.15 (m, 4H), 2.83 (br, 2H), 2.39 (s, 3H), 2.36-2.25 (m, 3H), 2.21 (s, 6H), 2.14 (m, 4H), 1.81-1.70 (m, 8H), 1.58 (d, J=7.6 Hz, 2H). HRMS m/z (M+H)$^+$ calcd: 591.3699, obsd: 591.3707.

Preparation of ortho-, meta- and para-Carboxyl Benezamide Derivatives of 2-Methyl-1-{8-[2-(4-Phenylpiperidin-4-yl)ethyl]-8-Azabicyclo[3.2.1]oct-3-yl}-1H-Benzimidazole
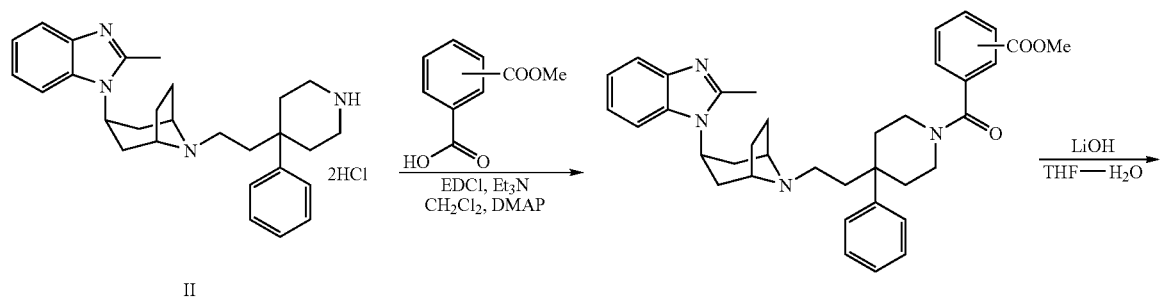
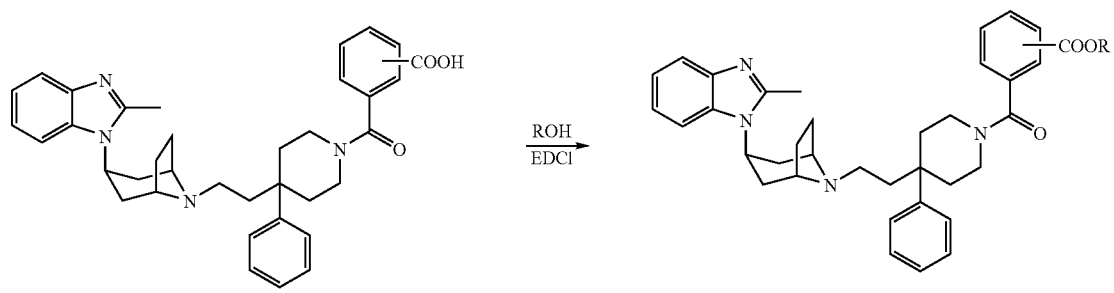
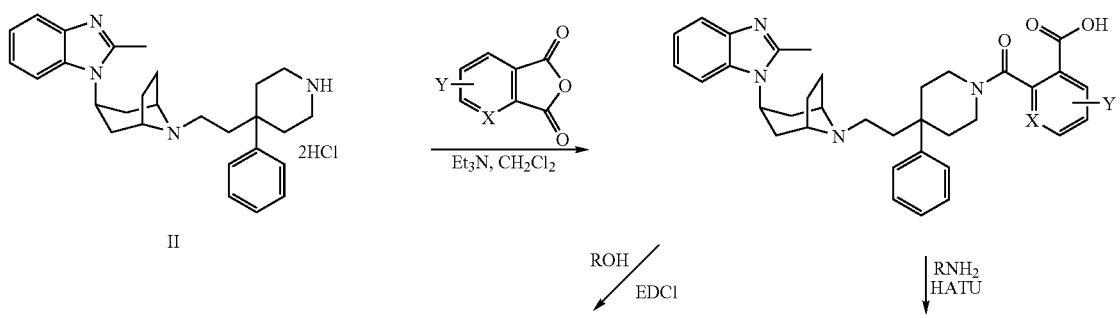
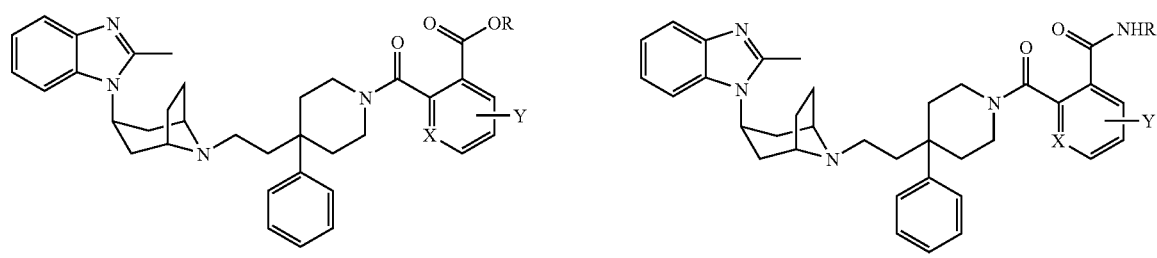

Example 423

Preparation of ethyl 2-[(4-{2-[3-(2-methyl-1H-benzimidazol-1-yl)-8-azabicyclo[3.2.1]oct-8-yl]ethyl}-4-phenylpiperidin-1-yl)carbonyl]benzoate

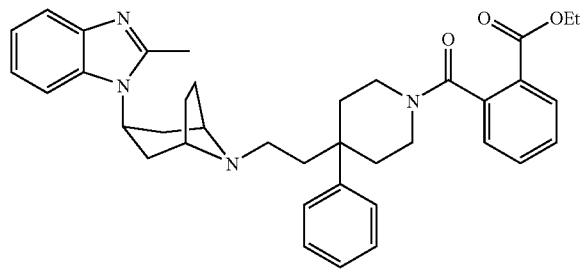

To a stirred solution of 2-[(4-{2-[3-(2-methyl-1H-benzimidazol-1-yl)-8-azabicyclo-[3.2.1]oct-8-yl]ethyl}-4-phenylpiperidin-1-yl)carbonyl]benzoic acid (58 mg, 0.1 mmol) in dichloromethane (5 mL) was added ethanol (8.6 JAL, 0.1 mmol) and triethyl amine (13 μL, 0.1 mmol). The resulting mixture was then cooled down on an ice-water bath before the addition of 1-[3-(dimethylamino)propyl]-3-ethylcarbodiimide hydrochloride (19 mg, 0.1 mmol) and 4-dimethylaminopyridine (catalytic amount). After being stirred overnight at ambient temperature, the reaction mixture was diluted with dichloromethane (40 mL) and washed with saturated sodium bicarbonate solution. The organic phase was dried over anhydrous sodium sulfate. After evaporation of the solvent, the crude product was purified by flash chromatography on silical gel, eluting with a gradient of 0-10% methanol in ethyl acetate to afford methyl 4-[(4-{2-[3-(2-methyl-1H-benzimidazol-1-yl)-8-azabicyclo[3.2.1]oct-8-yl]ethyl}-4-phenylpiperidin-1-yl)carbonyl]benzoate as amorphous solid (29 mg, 50%). $^1$H NMR (300 MHz, CDCl$_3$) δ 8.01 (d, J=7.9 Hz, 1H), 7.64 (d, J=7.6 Hz, 1H), 7.53 (br, 1H), 7.42 (t, J=7.6 Hz, 1H), 7.37-7.33 (m, 2H), 7.28-7.20 (m, 4H), 7.17-7.10 (m, 3H), 4.61-4.53 (m, 1H), 4.25 (br, 3H), 3.26-3.19 (m, 4H), 3.08 (br, 1H), 2.52 (s, 3H), 2.39-2.30 (m, 3H), 1.98-1.76 (m, 11H), 1.59 (d, J=7.8 Hz, 2H), 1.37-1.18 (br, 3H). HRMS m/z (M+H)$^+$ calcd: 605.3491, obsd: 605.3496.

Example 424

Preparation of isopropyl 2-[(4-{2-[3-(2-methyl-1H-benzimidazol-1-yl)-8-azabicyclo[3.2.1]oct-8-yl]ethyl}-4-phenylpiperidin-1-yl)carbonyl]benzoate

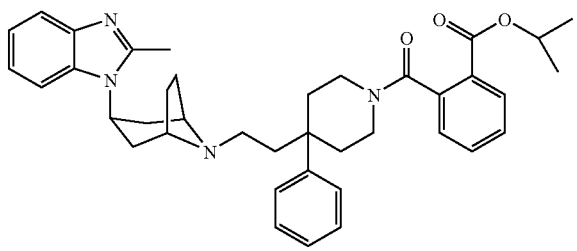

Isopropyl 2-[(4-{2-[3-(2-methyl-1H-benzimidazol-1-yl)-8-azabicyclo[3.2.1]oct-8-yl]ethyl}-4-phenylpiperidin-1-yl)carbonyl]benzoate (12 mg, 19%) was obtained as an oil from 2-[(4-{2-[3-(2-methyl-1H-benzimidazol-1-yl)-8-azabicyclo-[3.2.1]oct-8-yl]ethyl}-4-phenylpiperidin-1-yl)carbonyl]benzoic acid (58 mg, 0.1 mmol), isopropyl alcohol (10 μL, 0.15 mmol) and 1-[3-(dimethylamino)propyl]-3-ethylcarbodiimide hydrochloride (19 mg, 0.1 mmol) followed the procedure outlined in example 423. $^1$H NMR (400 MHz, CDCl$_3$) δ 8.00 (d, J=7.7 Hz, 1H), 7.64 (d, J=7.7 Hz, 1H), 7.52 (br, 1H), 7.42 (t, J=7.6 Hz, 1H), 7.37-7.33 (m, 2H), 7.28-7.20 (m, 4H), 7.18-7.10 (m, 3H), 5.22-5.08 (m, 1H), 4.63-4.53 (m, 1H), 4.34-3.67 (m, 2H), 3.26-3.00 (m, 4H), 2.53 (s, 3H), 2.48-2.30 (m, 2H), 2.17-2.07 (br, 2H), 1.96-1.62 (m, 10H), 1.59 (d, J=7.3 Hz, 2H), 1.35-1.09 (m, 6H). HRMS m/z (M+H)$^+$ calcd: 619.3648, obsd: 619.3637.

Example 425

Preparation of 2-[(4-{2-[3-(2-methyl-1H-benzimidazol-1-yl)-8-azabicyclo[3.2.1]oct-8-yl]ethyl}-4-phenylpiperidin-1-yl)carbonyl]benzamide

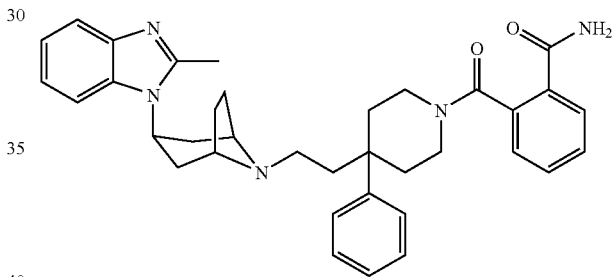

To a stirred solution of 2-[(4-{2-[3-(2-methyl-1H-benzimidazol-1-yl)-8-azabicyclo-[3.2.1]oct-8-yl]ethyl}-4-phenylpiperidin-1-yl)carbonyl]benzoic acid (69 mg, 0.12 mmol) in methylene chloride (4 mL) was added ammonia (1 mL, 0.5 M in dioxane), triethylamine (18 μL, 0.12 mmol) and HATU (46 mg, 0.12 mmol). The reaction mixture was stirred for 3 hours at ambient temperature before being diluted with methylene chloride and quenched with saturated sodium bicarbonate solution. The organic phase was dried over anhydrous sodium sulfate. After evaporation of the solvent, the crude product was purified by flash chromatography on silical gel, eluting with a gradient of 0-20% methanol in ethyl acetate to afford 2-[(4-{2-[3-(2-methyl-1H-benzimidazol-1-yl)-8-azabicyclo[3.2.1]oct-8-yl]ethyl}-4-phenylpiperidin-1-yl)carbonyl]benzamide (57 mg, 83%) $^1$H NMR (400 MHz, CDCl$_3$) δ 7.81 (d, J=8.6 Hz, 1H), 7.56 (d, J=7.3 Hz, 1H), 7.46-7.42 (m, 2H), 7.38-7.34 (m, 2H), 7.30-7.21 (m, 4H), 7.18-7.08 (m, 3H), 6.91 (br, 1H), 5.74 (br, 1H), 4.63-4.54 (m, 1H), 4.26 (br, 1H), 3.47-3.08 (m, 5H), 2.54 (s, 3H), 2.40-2.30 (m, 3H), 2.11-2.06 (m, 1H), 1.97-1.80 (m, 10H), 1.59 (d, J=7.9 Hz, 2H). HRMS m/z (M+H)$^+$ calcd: 576.3338, obsd: 576.3337.

Example 426

Preparation of 2-[(4-{2-[3-(2-methyl-1H-benzimidazol-1-yl)-8-azabicyclo[3.2.1]oct-8-yl]ethyl}-4-phenylpiperidin-1-yl)carbonyl]-N-propylbenzamide

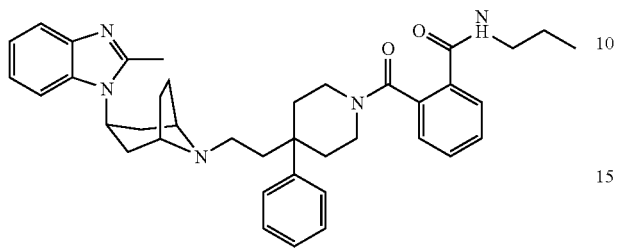

2-[(4-{2-[3-(2-Methyl-1H-benzimidazol-1-yl)-8-azabicyclo[3.2.1]oct-8-yl]ethyl}-4-phenylpiperidin-1-yl)carbonyl]-N-propylbenzamide (74 mg, quant.) was obtained as an oil from 2-[(4-{2-[3-(2-methyl-1H-benzimidazol-1-yl)-8-azabicyclo-[3.2.1]oct-8-yl]ethyl}-4-phenylpiperidin-1-yl)carbonyl]benzoic acid (69 mg, 0.12 mmol), propylamine (14 mg, 0.24 mmol) and HATU (46 mg, 0.12 mmol) following the procedure outlined in example 425. $^1$H NMR (400 MHz, CDCl$_3$) δ 7.76-7.74 (m, 1H), 7.65 (d, J=7.3 Hz, 1H), 7.43 (br, 2H), 7.37-7.34 (m, 2H), 7.30-7.23 (m, 4H), 7.18-7.11 (m, 3H), 6.88-6.73 (br, 1H), 4.63-4.54 (m, 1H), 4.19 (br, 1H), 3.36-3.06 (m, 7H), 2.54 (s, 3H), 2.40-2.29 (m, 3H), 2.11-2.08 (m, 1H), 1.97-1.79 (m, 9H), 1.72-1.53 (m, 5H), 1.25-0.83 (m, 3H). HRMS m/z (M+H)$^+$ calcd: 618.3808, obsd: 618.3811.

Example 427

Preparation of N-cyclopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzamide

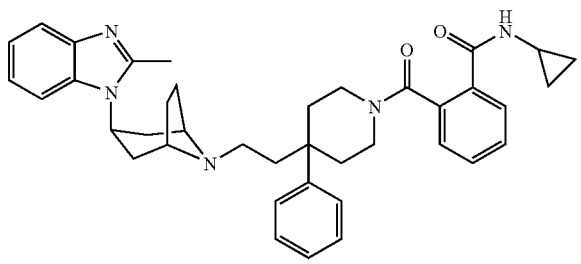

N-Cyclopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzamide (61 mg, 83%) was obtained as an oil from 2-[(4-{2-[3-(2-methyl-1H-benzimidazol-1-yl)-8-azabicyclo-[3.2.1]oct-8-yl]ethyl}-4-phenylpiperidin-1-yl) carbonyl]benzoic acid (69 mg, 0.12 mmol), cyclopropylamine (14 mg, 0.24 mmol) and HATU (46 mg, 0.12 mmol) following the procedure outlined in example 425. $^1$H NMR (400 MHz, CDCl$_3$) δ 7.71 (d, J=7.9 Hz, 1H), 7.65 (d, J=7.3 Hz), 7.41-7.33 (m, 4H), 7.29-7.23 (m, 4H), 7.21-7.09 (m, 3H), 7.03-6.84 (m, 1H), 4.63-4.54 (m, 1H), 4.20-4.17 (m, 1H), 3.37-3.22 (m, 4H), 3.10-3.05 (m, 1H), 2.92-2.70 (m, 1H), 2.54 (s, 3H), 2.36-2.29 (m, 3H), 2.11 (br, 1H), 1.98-1.61 (m, 10H), 1.59 (d, J=7.9 Hz, 2H), 0.86-0.47 (m, 4H). HRMS m/z (M+H)$^+$ calcd: 616.3651, obsd: 616.3649.

Example 428

Preparation of 2-[(4-{2-[3-(2-methyl-1H-benzimidazol-1-yl)-8-azabicyclo[3.2.1]oct-8-yl]ethyl}-4-phenylpiperidin-1-yl)carbonyl]nicotinamide

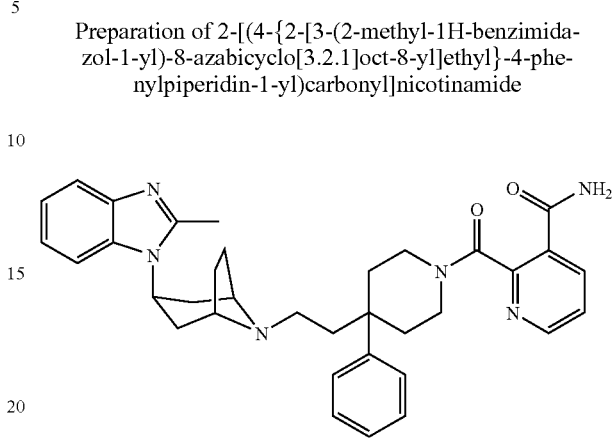

To a stirred solution of 2-methyl-1-{8-[2-(4-phenylpiperidin-4-yl)ethyl]-8-azabicyclo[3.2.1]oct-3-yl}-1H-benzimidazole (51 mg, 0.12 mmol) in dichloro-methane (4 mL) was added 2,3-pyridinedicarboxylic anhydride (18 mg, 0.12 mmol) and triethylamine (17 µL, 0.12 mmol). The resulting mixture was stirred for 2 hours at ambient temperature before addition of ammonia (1 mL, 0.5 M in dioxane) and 47 mg of HATU. The reaction mixture was then stirred for another 2 hours. After being diluted with methylene chloride and washed with saturated sodium bicarbonate solution, the organic phase was dried over anhydrous sodium sulfate. Evaporation of the solvent and purification by flash chromatography afforded 2-[(4-{2-[3-(2-methyl-1H-benzimidazol-1-yl)-8-azabicyclo[3.2.1]oct-8-yl]ethyl}-4-phenylpiperidin-1-yl)carbonyl]nicotinamide as a foam (51 mg, 69%). $^1$H NMR (300 MHz, CDCl$_3$) δ 8.63-8.61 (m, 1H), 8.17 (d, J=6.8 Hz, 1H), 7.66-7.64 (m, 2H), 7.38-7.33 (m, 3H), 7.30-7.22 (m, 4H), 7.20-7.10 (m, 2H), 5.79 (s, 1H), 4.61-4.55 (m, 1H), 4.27-4.22 (m, 1H), 3.40-3.08 (m, 5H), 2.54 (s, 3H), 2.47-2.33 (m, 3H), 2.19-2.15 (m, 1H), 1.97-1.80 (m, 10H), 1.63-1.61 (m, 2H). HRMS m/z (M+H)$^+$ calcd: 577.3291, obsd: 577.3286.

Example 429

Preparation of 2-[(4-{2-[3-(2-methyl-1H-benzimidazol-1-yl)-8-azabicyclo[3.2.1]oct-8-yl]ethyl}-4-phenylpiperidin-1-yl)carbonyl]-N-propylnicotinamide

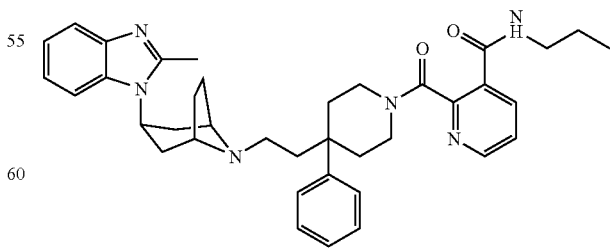

2-[(4-{2-[3-(2-Methyl-1H-benzimidazol-1-yl)-8-azabicyclo[3.2.1]oct-8-yl]ethyl}-4-phenylpiperidin-1-yl)carbonyl]-N-propylnicotinamide (68 mg, 99%) was obtained as a foam from 2-methyl-1-{8-[2-(4-phenylpiperidin-4-yl)ethyl]-8-azabicyclo[3.2.1]oct-3-yl}-1H-benzimidazole (51 mg, 0.12 mmol), 2,3-pyridinedicarboxylic anhydride (18 mg, 0.12 mmol), propylamine (14 mg, 0.24 mmol) and HATU (47 mg, 0.12 mmol), following the procedure outlined in example 428. $^1$H NMR (400 MHz, CDCl$_3$) δ 8.62-8.60 (m, 1H), 8.16 (d, J=7.9 Hz, 1H), 7.65 (d, J=8.6 Hz, 1H), 7.57 (t, J=5.7 Hz, 1H), 7.39-7.33 (m, 3H), 7.30-7.21 (m, 4H), 7.18-7.11 (m, 2H), 4.61-4.56 (m, 1H), 4.27-4.22 (dt, J=13.2, 4.3 Hz, 1H), 3.38-3.31 (m, 3H), 3.22-3.06 (m, 4H), 2.54 (s, 3H), 2.40-2.31 (m, 3H), 2.17-2.14 (m, 1H), 1.92-1.80 (m, 10H), 1.62-1.52 (m, 4H), 0.93 (t, J=7.3 Hz, 3H). HRMS m/z (M+H)$^+$ calcd: 619.3761, obsd: 619.3785.

Example 430

Preparation of N-cyclopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]nicotinamide

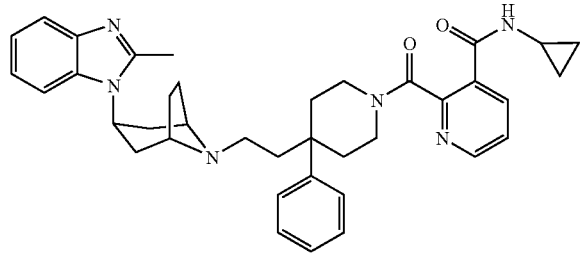

N-Cyclopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]nicotinamide (58 mg, 78%) was obtained as a foam from 2-methyl-1-{8-[2-(4-phenylpiperidin-4-yl)ethyl]-8-azabicyclo[3.2.1]oct-3-yl}-1H-benzimidazole (51 mg, 0.12 mmol), 2,3-pyridinedicarboxylic anhydride (18 mg, 0.12 mmol), cyclopropylamine (14 mg, 0.24 mmol) and HATU (47 mg, 0.12 mmol) following the procedure outlined in example 428. $^1$H NMR (400 MHz, CDCl$_3$) δ 8.56-8.54 (m, 1H), 8.03 (d, J=7.8 Hz, 1H), 7.80 (s, 1H), 7.65 (d, J=7.0 Hz, 1H), 7.37-7.22 (m, 5H), 7.20-7.12 (m, 2H), 4.62-4.55 (m, 1H), 4.23-4.19 (m, 1H), 3.35 (t, J=10.6 Hz, 1H), 3.22-3.06 (m, 4H), 2.89-2.87 (m, 1H), 2.54 (s, 3H), 2.47-2.33 (m, 3H), 2.18-2.09 (m, 1H), 1.88-1.83 (m, 10H), 1.61-1.58 (m, 2H), 0.84-0.62 (m, 2H), 0.59-0.56 (m, 2H). HRMS m/z (M+H)$^+$ calcd: 617.3604, obsd: 617.3627.

Example 431

Preparation of methyl 4-[(4-{2-[3-(2-methyl-1H-benzimidazol-1-yl)-8-azabicyclo[3.2.1]oct-8-yl]ethyl}-4-phenylpiperidin-1-yl)carbonyl]benzoate

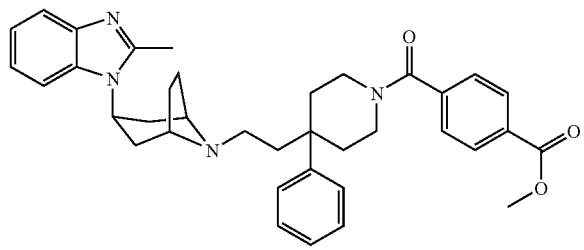

To a stirred solution of 2-methyl-1-{8-[2-(4-phenylpiperidin-4-yl)ethyl]-8-azabicyclo[3.2.1]oct-3-yl}-1H-benzimidazole dihydrochloride (50.5 mg, 0.1 mmol) in dichloromethane (5 mL) was added terephthalic acid monomethyl ester (18 mg, 0.1 mmol) and triethyl amine (30 μL, 0.2 mmol). The resulting mixture was then cooled down on an ice-water bath before the addition of 1-[3-(dimethylamino)propyl]-3-ethylcarbo-diimide hydrochloride (19 mg, 0.1 mmol) and 4-dimethylaminopyridine (catalytic amount). After being stirred overnight at ambient temperature, the reaction mixture was diluted with dichloromethane (40 mL) and washed with saturated sodium bicarbonate solution. The organic phase was dried over anhydrous sodium sulfate. After evaporation of the solvent, the crude product was purified by flash chromatography on silical gel, eluting with a gradient of 0-10% methanol in ethyl acetate to afford methyl 4-[(4-{2-[3-(2-methyl-1H-benzimidazol-1-yl)-8-azabicyclo[3.2.1]oct-8-yl]ethyl}-4-phenylpiperidin-1-yl)carbonyl]benzoate as amorphous solid (65 mg, quant.). $^1$H NMR (300 MHz, CDCl$_3$) δ 8.11 (d, J=8.2 Hz, 2H), 7.69 (d, J=7.2 Hz, 1H), 7.47 (d, J=8.2 Hz, 2H), 7.41 (d, J=7.3 Hz, 2H), 7.34-7.24 (m, 4H), 7.21-7.15 (m, 2H), 4.66 (br, 1H), 4.26-4.21 (m, 1H), 3.97 (s, 3H), 3.52-3.30 (m, 5H), 2.60 (s, 3H), 2.40 (br, 3H), 2.21-2.17 (br, 1H), 1.99-1.79 (m, 10H), 1.68-1.66 (m, 2H). HRMS m/z (M+H)$^+$ calcd: 591.3335, obsd: 591.3320.

Example 432

Preparation of isopropyl 3-[(4-{2-[3-(2-methyl-1H-benzimidazol-1-yl)-8-azabicyclo[3.2.1]oct-8-yl]ethyl}-4-phenylpiperidin-1-yl)carbonyl]benzoate

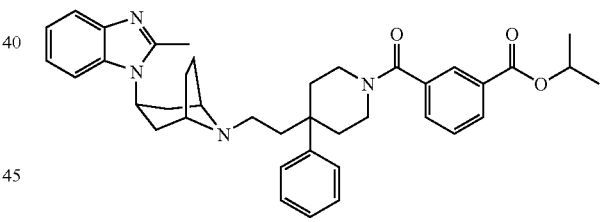

Isopropyl 3-[(4-{2-[3-(2-methyl-1H-benzimidazol-1-yl)$_8$-azabicyclo[3.2.1]oct-8-yl]ethyl}-4-phenylpiperidin-1-yl)carbonyl]benzoate (10 mg, 16%) was obtained as an oil from 3-[(4-{2-[3-(2-methyl-1H-benzimidazol-1-yl)-8-azabicyclo-[3.2.1]oct-8-yl]ethyl}-4-phenylpiperidin-1-yl)carbonyl]benzoic acid (70 mg, 0.12 mmol), isopropyl alcohol (10 μL, 0.12 mmol) and 1-[3-(dimethylamino)propyl]-3-ethylcarbodiimide hydrochloride (23 mg, 0.12 mmol) following the procedure outlined in example 423. $^1$H NMR (400 MHz, CDCl$_3$) δ 8.06 (d, J=7.9 Hz, 1H), 8.04 (s, 1H), 7.64 (d, J=7.2 Hz, 1H), 7.54 (d, J=7.7 Hz, 1H), 7.46 (t, J=7.7 Hz, 1H), 7.39-7.35 (m, 1H), 7.29-7.26 (m, 4H), 7.18-7.11 (m, 3H), 5.25-5.22 (m, 1H), 4.59 (br, 1H), 4.20 (br, 1H), 3.52 (br, 1H), 3.35 (br, 1H), 3.24 (br, 3H), 2.54 (s, 3H), 2.37-2.32 (m, 3H), 2.16 (br, 1H), 1.92-1.75 (m, 10H), 1.60 (d, J=7.7 Hz, 2H), 1.35 (d, J=6.2 Hz, 6H). HRMS m/z (M+H)$^+$ calcd: 619.3648, obsd: 619.3649.

Example 433

Preparation of 4-[(4-{2-[3-(2-methyl-1H-benzimidazol-1-yl)-8-azabicyclo-[3.2.1]oct-8-yl]ethyl}-4-phenylpiperidin-1-yl)carbonyl]benzoic acid

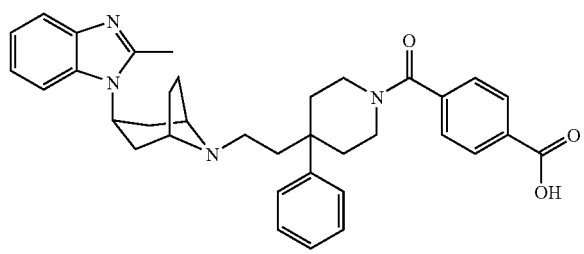

4-[(4-{2-[3-(2-Methyl-1H-benzimidazol-1-yl)-8-azabicyclo[3.2.1]oct-8-yl]ethyl}-4-phenylpiperidin-1-yl)carbonyl]benzoic acid (15 mg, 43%) was obtained as white powder from methyl 4-[(4-{2-[3-(2-methyl-1H-benzimidazol-1-yl)-8-azabicyclo[3.2.1]oct-8-yl]ethyl}-4-phenylpiperidin-1-yl)carbonyl]benzoate following the procedure outlined in the previous example. HRMS m/z (M+H)$^+$ calcd: 577.3179, obsd: 577.3189.

Preparation of Carboxamides and Carboxthioamides of 2-Methyl-1-{8-[2-(4-Phenylpiperidin-4-yl)ethyl]-8-Azabicyclo[3.2.1]oct-3-yl}-1H-Benzimidazole

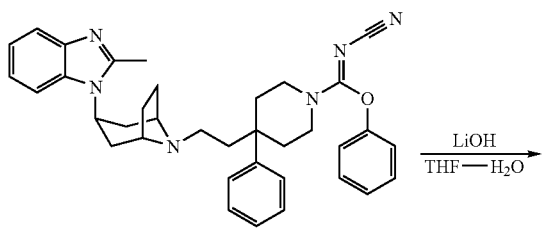

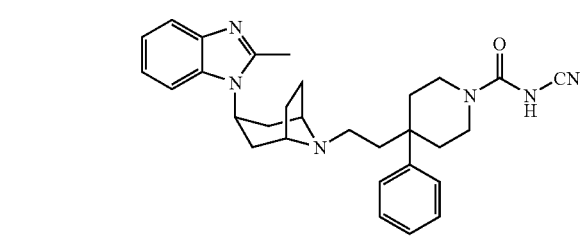

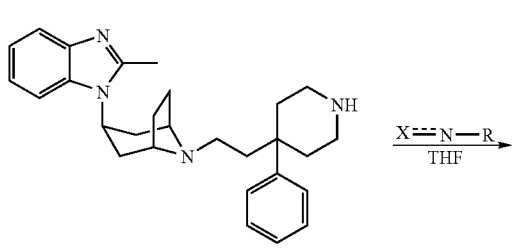

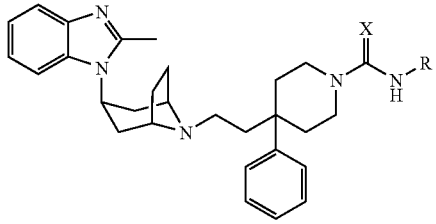

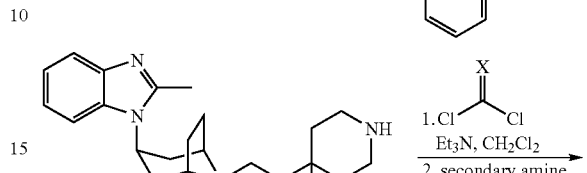

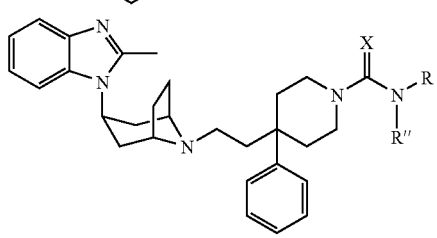

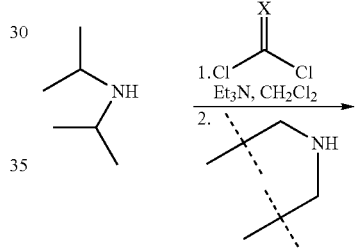

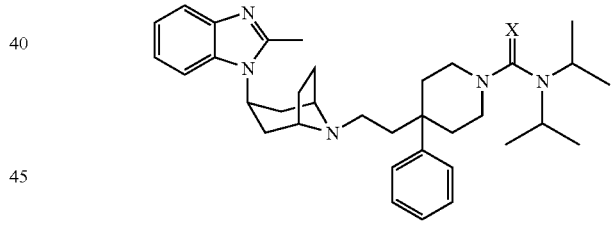

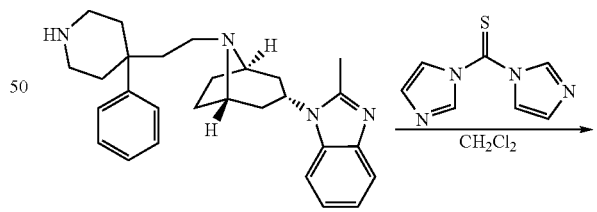

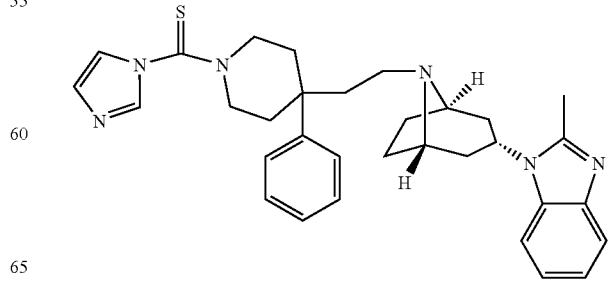

Example 434

Preparation of N-cyano-4-{2-[3-(2-methyl-1H-benzimidazol-1-yl)-8-azabicyclo[3.2.1]oct-8-yl]ethyl}-4-phenylpiperidine-1-carboxamide

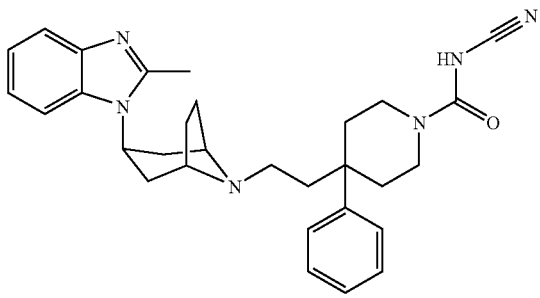

To a precooled (0° C.) solution of phenyl N-cyano-4-{2-[3-(2-methyl-1H-benzimidazol-1-yl)-8-azabicyclo[3.2.1]oct-8-yl]ethyl}-4-phenylpiperidine-1-carboximidoate (27 mg, 0.047 mmol) in a mixed solvent of THF-H$_2$O (2 mL, 3:1) was added lithium hydroxide monohydrate (7.7 mg, 0.18 mmol). After stirring for 3 hours on an ice-water bath, the reaction mixture was diluted with dichloromethane (20 mL) and buffered with saturated sodium bicarbonate solution (10 mL). The aqueous phase was extracted with dichloromethane (3×10 mL). The combined extracts were washed with brine and dried over anhydrous sodium sulfate. After evaporation of solvents, the residue was purified by flash chromatography on silical gel, eluting with a gradient of 10-30% methanol in ethyl acetate to afford N-cyano-4-{2-[3-(2-methyl-1H-benzimidazol-1-yl)-8-azabicyclo[3.2.1]oct-8-yl]ethyl}-4-phenylpiperidine-1-carboxamide as a white solid (20 mg, 83%). $^1$H NMR (400 MHz, DMSO-d$_6$) δ 7.46 (d, J=7.1 Hz, 1H), 7.33-7.29 (m, 5H), 7.17-7.14 (m, 1H), 7.11-7.04 (m, 2H), 4.53-4.48 (m, 1H), 4.09 (br, 1H), 3.55-3.51 (m, 2H), 3.21 (br, 2H), 3.06-3.03 (m, 2H), 2.45 (s, 3H), 2.37-2.29 (m, 2H), 1.87-1.64 (m, 10H), 1.59-1.55 (m, 4H). $^{13}$C NMR (125 MHz, DMSO-d$_6$) δ 165.0, 152.3, 146.7, 143.7, 134.0, 128.9, 127.3, 126.2, 125.0, 121.8, 121.4, 119.4, 111.6, 57.2, 55.6, 49.3, 48.0, 46.3, 36.3, 35.9, 30.0, 21.8, 14.9. HRMS m/z (M+H)$^+$ calcd: 497.3029, obsd: 497.3026.

Example 435

Preparation of N-isopropyl-4-{2-[3-(2-methyl-1H-benzimidazol-1-yl)-8-azabicyclo[3.2.1]oct-8-yl]ethyl}-4-phenylpiperidine-1-carboxamide

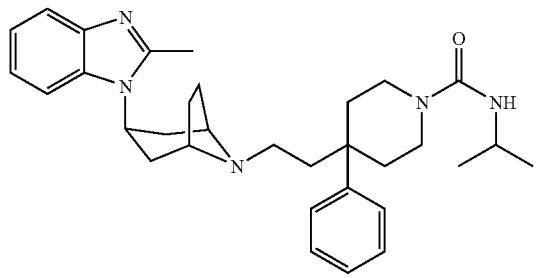

To a stirred solution of 2-methyl-1-{8-[2-(4-phenylpiperidin-4-yl)ethyl]-8-azabicyclo[3.2.1]oct-3-yl}-1H-benzimidazole (20 mg, 0.047 mmol) in THF (2 mL) was added isopropyl isocyanate (4.3 mg, 0.047 mmol). The resulting mixture was stirred at ambient temperature overnight. After evaporation of the solvent, the residue was purified on silical gel, eluting with a gradient of 10-30% methanol in ethyl acetate to afford N-isopropyl-4-{2-[3-(2-methyl-1H-benzimidazol-1-yl)-8-azabicyclo[3.2.1]oct-8-yl]ethyl}-4-phenylpiperidine-1-carboxamide as white solid (15 mg, 63%). $^1$H NMR (300 MHz, CDCl$_3$) δ 7.70 (d, J=7.2 Hz, 1H), 7.43-7.38 (m, 2H), 7.34-7.24 (m, 4H), 7.22-7.15 (m, 2H), 4.67 (br, 1H), 4.24 (d, J=7.3 Hz, 1H), 3.99 (m, 1H), 3.62-3.58 (m, 2H), 3.30 (br, 2H), 3.23-3.16 (m, 2H), 2.62 (s, 3H), 2.42 (br, 2H), 2.25-2.20 (m, 2H), 1.98-1.83 (m, 9H), 1.68 (br, 2H), 1.17 (d, J=6.4 Hz, 6H). HRMS m/z (M+H)$^+$ calcd: 514.3546, obsd: 514.3530.

Example 436

Preparation of N-(tert-butyl)-4-{2-[3-(2-methyl-1H-benzimidazol-1-yl)-8-azabicyclo[3.2.1]oct-8-yl]ethyl}-4-phenylpiperidine-1-carboxamide

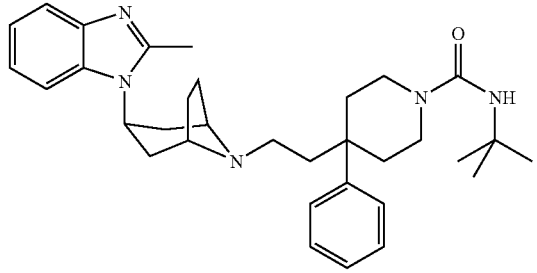

N-(tert-Butyl)-4-{2-[3-(2-methyl-1H-benzimidazol-1-yl)-8-azabicyclo-[3.2.1]oct-8-yl]ethyl}-4-phenylpiperidine-1-carboxamide (39 mg, quant.) was obtained as syrup from 2-methyl-1-{8-[2-(4-phenyl piperidin-4-yl)ethyl]-8-azabicyclo[3.2.1]oct-3-yl}-1H-benzimidazole (30 mg, 0.07 mmol) and t-butyl isocyanate (6.9 mg, 0.07 mmol) following the procedure outlined in example 435. $^1$H NMR (300 MHz, CDCl$_3$) δ 7.68 (d, J=7.5 Hz, 1H), 7.41-7.36 (m, 2H), 7.32-7.22 (m, 4H), 7.20-7.13 (m, 2H), 4.75 (br, 1H), 4.31 (s, 1H), 3.57-3.53 (m, 2H), 3.35 (br, 2H), 3.18-3.12 (m, 2H), 2.62 (s, 3H), 2.47 (br, 2H), 2.22-2.17 (m, 2H), 1.97-1.81 (m, 10H), 1.71 (br, 2H), 1.34 (s, 9H). HRMS m/z (M+H)$^+$ calcd: 528.3702, obsd: 528.3722.

Example 437

Preparation of ethyl N-[(4-{2-[3-(2-methyl-1H-benzimidazol-1-yl)-8-azabicyclo[3.2.1]oct-8-yl]ethyl}-4-phenylpiperidin-1-yl)carbonyl]glycinate

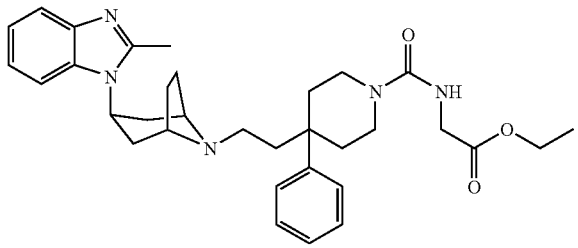

Ethyl N-[(4-{2-[3-(2-methyl-1H-benzimidazol-1-yl)-8-azabicyclo[3.2.1]oct-8-yl]ethyl}-4-phenyl piperidin-1-yl)carbonyl]glycinate (25 mg, 64%) was obtained as an oil from 2-methyl-1-{8-[2-(4-phenyl piperidin-4-yl)ethyl]-8-azabicyclo[3.2.1]oct-3-yl}-1H-benzimidazole (30 mg, 0.07 mmol) and ethyl isocyanatoacetate (9 mg, 0.07 mmol) following the procedure outlined in example 435. $^1$H NMR (400 MHz, DMSO-d$_6$) δ 7.46 (d, J=7.2 Hz, 1H), 7.37-7.32 (m, 5H), 7.20-7.17 (m, 1H), 7.11-7.04 (m, 2H), 6.88 (t, J=5.6 Hz, 1H), 4.51-4.47 (m, 1H), 4.02 (q, J=7.1 Hz, 2H), 3.66 (d, J=5.7 Hz, 2H), 3.51-3.47 (m, 2H), 3.20 (br, 2H), 3.05 (t, J=9.7 Hz, 2H), 2.46 (s, 3H), 2.36-2.29 (m, 2H), 1.99 (br, 2H), 1.84-1.70 (m, 10H), 1.55 (d, J=7.5 Hz, 2H), 1.13 (t, J=7.2 Hz, 3H). HRMS m/z (M+H)$^+$ calcd: 558.3444, obsd: 558.3445.

Example 438

Preparation of N-cyclohexyl-4-{2-[3-(2-methyl-1H-benzimidazol-1-yl)-8-azabicyclo[3.2.1]oct-8-yl]ethyl}-4-phenylpiperidine-1-carboxamide

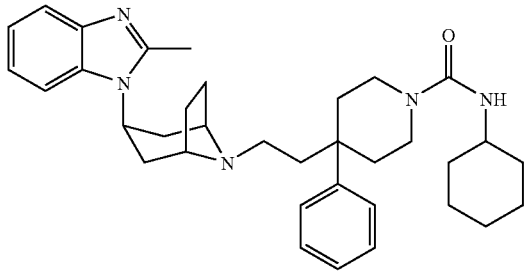

N-Cyclohexyl-4-{2-[3-(2-methyl-1H-benzimidazol-1-yl)-8-azabicyclo[3.2.1]oct-8-yl]ethyl}-4-phenylpiperidine-1-carboxamide (34 mg, 88%) was obtained as an oil from 2-methyl-1-{8-[2-(4-phenylpiperidin-4-yl)ethyl]-8-azabicyclo[3.2.1]oct-3-yl}-1H-benzimidazole (30 mg, 0.07 mmol) and cyclohexyl isocyanate (8.8 mg, 0.07 mmol) following the procedure outlined in example 435. $^1$H NMR (400 MHz, DMSO-d$_6$) δ 7.46 (d, J=7.1 Hz, 1H), 7.34-7.30 (m, 5H), 7.19-7.16 (m, 1H), 7.11-7.04 (m, 2H), 6.03 (d, J=7.7 Hz, 1H), 4.51-4.46 (m, 1H), 3.47-3.43 (m, 2H), 3.35-3.34 (m, 1H), 3.19 (br, 2H), 3.04-2.99 (m, 2H), 2.45 (s, 3H), 2.36-2.28 (m, 2H), 2.00-1.95 (m, 2H), 1.81-1.67 (m, 14H), 1.61-1.51 (m, 3H), 1.19-1.00 (m, 5H). HRMS m/z (M+H)$^+$ calcd: 554.3859, obsd: 554.3863.

Example 439

Preparation of 4-{2-[3-(2-methyl-1H-benzimidazol-1-yl)-8-azabicyclo[3.2.1]oct-8-yl]ethyl}-4-phenyl-N-[4-(trifluoromethyl)phenyl]piperidine-1-carboxamide

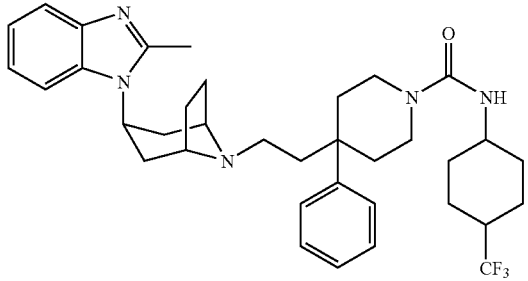

4-{2-[3-(2-M ethyl-1H-benzimidazol-1-yl)-8-azabicyclo[3.2.1]oct-8-yl]ethyl}-4-phenyl-N-[4-(trifluoromethyl)phenyl]piperidine-1-carboxamide (27 mg, 88%) was obtained as an oil from 2-methyl-1-{8-[2-(4-phenylpiperidin-4-yl)ethyl]-8-azabicyclo[3.2.1]oct-3-yl}-1H-benzimidazole (22 mg, 0.05 mmol) and p-trifluoromethylphenyl isocyanate (9 mg, 0.05 mmol) following the procedure outlined in example 435. $^1$H NMR (400 MHz, DMSO-d$_6$) δ 8.83 (s, 1H), 7.65 (d, J=8.2 Hz, 2H), 7.53 (d, J=8.2 Hz, 2H), 7.45 (d, J=6.9 Hz, 1H), 7.39-7.32 (m, 5H), 7.20 (t, J=7.0 Hz, 1H), 7.10-7.06 (m, 2H), 4.50 (m, 1H), 3.70-3.66 (m, 2H), 3.21 (br, 4H), 2.46 (s, 3H), 2.34-2.29 (m, 2H), 2.11-2.07 (m, 2H), 1.84-1.71 (m, 10H), 1.55 (d, J=7.5 Hz, 2H). HRMS m/z (M+H)$^+$ calcd: 616.3263, obsd: 616.3258.

Example 440

Preparation of N-isopropyl-4-{2-[3-(2-methyl-1H-benzimidazol-1-yl)-8-azabicyclo[3.2.1]oct-8-yl]ethyl}-4-phenylpiperidine-1-carbothioamide

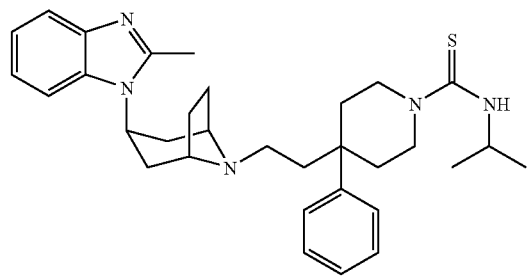

N-Isopropyl-4-{2-[3-(2-methyl-1H-benzimidazol-1-yl)-8-azabicyclo[3.2.1]oct-8-yl]ethyl}-4-phenylpiperidine-1-carbothioamide (28 mg, quant.) was obtained as an oil from 2-methyl-1-{8-[2-(4-phenylpiperidin-4-yl)ethyl]-8-azabicyclo[3.2.1]-oct-3-yl}-1H-benzimidazole (22 mg, 0.05 mmol) and isopropyl isothiocyanate (5.5 mg, 0.05 mmol) following the procedure outlined in example 435. $^1$H NMR (400 MHz, DMSO-d$_6$) δ 7.46 (d, J=7.1 Hz, I H), 7.37-7.32 (m, 5H), 7.20-7.15 (m, 2H), 7.11-7.05 (m, 2H), 4.53-4.45 (m, 1H), 4.00-3.97 (m, 2H), 3.48-3.43 (m, 2H), 3.20 (br, 2H), 2.46 (s, 3H), 2.36-2.28 (m, 2H), 2.06-2.01 (m, 2H), 1.82-1.70 (m, 10H), 1.55 (d, J=7.5 Hz, 2H). 1.09 (d, J=6.6 Hz, 6H). HRMS m/z (M+H)$^+$ calcd: 530.3317, obsd: 530.3310.

Example 441

Preparation of N-methyl-4-{2-[3-(2-methyl-1H-benzimidazol-1-yl)-8-azabicyclo3.2.1]oct-8-yl]ethyl}-4-phenylpiperidine-1-carbothioamide

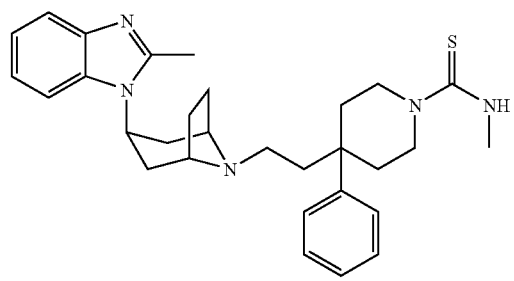

N-Methyl-4-{2-[3-(2-methyl-1H-benzimidazol-1-yl)-8-azabicyclo[3.2.1]oct-8-yl]ethyl}-4-phenyl piperidine-1-carbothioamide (23 mg, 92%) was obtained as an oil from 2-methyl-1-{8-[2-(4-phenylpiperidin-4-yl)ethyl]-8-azabicyclo[3.2.1]-oct-3-yl}-1H-benzimidazole (22 mg, 0.05 mmol) and methyl isothiocyanate (4 mg, 0.055 mmol) following the procedure outlined in example 435. $^1$H NMR (400 MHz, DMSO-$d_6$) δ 7.57 (d, J=4.1 Hz, 1H), 7.46 (d, J=7.1 Hz, 1H), 7.38-7.27 (m, 5H), 7.19 (t, J=6.8 Hz, 1H), 7.11-7.05 (m, 2H), 4.54-4.44 (m, 1H), 4.02-3.97 (m, 2H), 3.46-3.41 (m, 2H), 3.20 (br, 2H), 2.86 (d, J=3.9 Hz, 3H), 2.46 (s, 3H), 2.41-2.28 (m, 2H), 2.07-2.03 (m, 2H), 1.91-1.70 (m, 10H), 1.55 (d, J=7.5 Hz, 2H). HRMS m/z (M+H)$^+$ calcd: δ 502.3004, obsd: 502.2994.

Example 442

Preparation of N-cyclohexyl-4-{2-[3-(2-methyl-1H-benzimidazol-1-yl)-8-azabicyclo[3.2.1]oct-8-yl]ethyl}-4-phenylpiperidine-1-carbothioamide

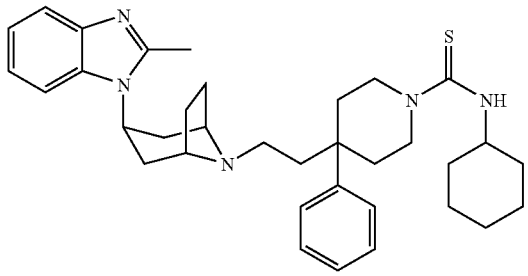

N-Cyclohexyl-4-{2-[3-(2-methyl-1H-benzimidazol-1-yl)-8-azabicyclo[3.2.1]oct-8-yl]ethyl}-4-phenylpiperidine-1-carbothioamide (26.9 mg, 94%) was obtained as an oil from 2-methyl-1-{8-[2-(4-phenylpiperidin-4-yl)ethyl]-8-azabicyclo[3.2.1]-oct-3-yl}-1H-benzimidazole (22 mg, 0.05 mmol) and cyclohexyl isothiocyanate (7.7 mg, 0.05 mmol) following the procedure outlined in example 435. $^1$H NMR (400 MHz, DMSO-$d_6$) δ 7.46 (d, J=7.2 Hz, 1H), 7.37-7.32 (m, 5H), 7.20-7.17 (m, 1H), 7.13-7.05 (m, 3H), 4.51-4.47 (m, 1H), 4.14 (br, 1H), 4.00-3.97 (m, 2H), 3.45 (t, J=9.7 Hz, 2H), 3.20 (br, 2H), 2.46 (s, 3H), 2.36-2.28 (m, 2H), 2.05-2.01 (m, 2H), 1.82-1.67 (m, 15H), 1.55 (d, J=7.8 Hz, 2H). 1.23-1.15 (m, 4H). HRMS m/z (M+H)$^+$ calcd: 570.3630, obsd: 570.3629.

Example 443

Preparation of N-(4-fluorobenzyl)-4-{2-[3-(2-methyl-1H-benzimidazol-1-yl)-8-azabicyclo[3.2.1]oct-8-yl]ethyl}-4-phenylpiperidine-1-carbothioamide

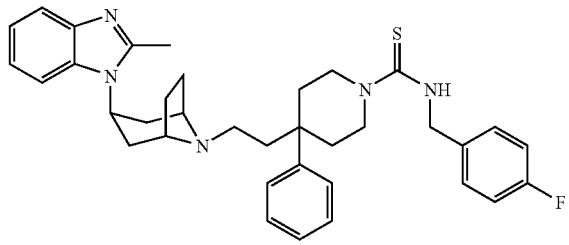

N-(4-Fluorobenzyl)-4-{2-[3-(2-methyl-1H-benzimidazol-1-yl)-8-azabicyclo[3.2.1]oct-8-yl]ethyl}-4-phenylpiperidine-1-carbothioamide (27.6 mg, 93%) was obtained as an oil from 2-methyl-1-{8-[2-(4-phenylpiperidin-4-yl)ethyl]-8-azabicyclo[3.2.1]-oct-3-yl}-1H-benzimidazole (22 mg, 0.05 mmol) and 4-fluorobenzyl isothiocyanate (9.0 mg, 0.054 mmol) following the procedure outlined in example 435. $^1$H NMR (400 MHz, DMSO-$d_6$) δ 8.13 (t, J=5.4 Hz, 1H), 7.46 (d, J=7.5 Hz, 1H), 7.39-7.30 (m, 5H), 7.29-7.26 (m, 2H), 7.20 (t, J=6.8 Hz, 1H), 7.11-7.05 (m, 4H), 4.73 (d, J=5.5 Hz, 2H), 4.51-4.47 (m, 1H), 4.07 (br, 2H), 3.51 (t, J=9.9 Hz, 2H), 3.21 (br, 2H), 2.46 (s, 3H), 2.41-2.29 (m, 2H), 2.09-2.05 (m, 2H), 1.83-1.71 (m, 10H), 1.56 (d, J=7.7 Hz, 2H). HRMS m/z (M+H)$^+$ calcd: 596.3223, obsd: 596.3232.

Example 444

Preparation of N,N-dimethyl-4-{2-[3-(2-methyl-1H-benzimidazol-1-yl)-8-azabicyclo[3.2.1]oct-8-yl]ethyl}-4-phenylpiperidine-1-carboxamide

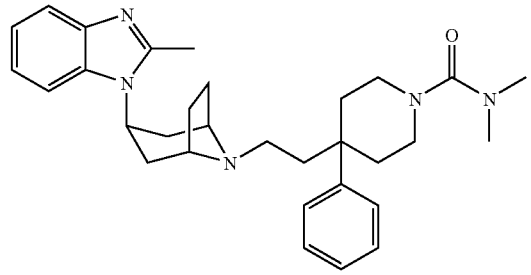

At 0° C., to a stirred solution of phosgen (0.25 mL, 2.0 in toluene) was added a solution of 2-methyl-1-{8-[2-(4-phenylpiperidin-4-yl)ethyl]-8-azabicyclo[3.2.1]-oct-3-yl}-1H-benzimidazole (71 mg, 0.17 mmol) in methylene chloride and triethylamine (excess). The mixture was stirred for 30 minutes at 0° C. and further one hour at room temperature. Nitrogene gas was then introduced to remove the excess phosgen. To this mixture was added excess dimethylamine and the resulting mixture was stirred overnight at ambient temperature. After being diluted with methylene chloride, the organic phase was washed with brine, dried over anhydrous sodium sulfate and purified by flash chromatography. N,N-dimethyl-4-{2-[3-(2-methyl-1H-benzimidazol-1-yl)-8-azabicyclo[3.2.1]oct-8-yl]ethyl}-4-phenylpiperidine-1-carboxamid was obtained as foam (52 mg, 63%). $^1$H NMR (400 MHz, CDCl$_3$) δ 7.66 (d, J=7.3 Hz, 1H), 7.37-7.34 (m, 2H), 7.31-7.29 (m, 3H), 7.23-7.12 (m, 3H), 4.61 (br, 1H), 3.44-3.38 (m, 2H), 3.25 (br, 2H), 3.12-3.06 (m, 2H), 2.80 (s, 6H), 2.58 (s, 3H), 2.38-2.36 (m, 2H), 2.19-2.15 (m, 2H), 1.93-1.81 (m, 10H), 1.61 (d, J=7.3 Hz, 2H). HRMS m/z (M+H)$^+$ calcd: 500.3389, obsd: 500.3386.

Example 445

Preparation of N,N-diethyl-4-{2-[3-(2-methyl-1H-benzimidazol-1-yl)-8-azabicyclo[3.2.1]oct-8-yl]ethyl}-4-phenylpiperidine-1-carboxamide

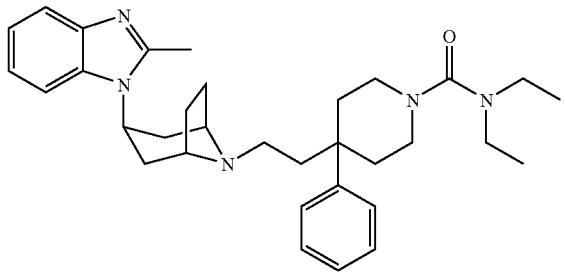

N,N-Diethyl-4-{2-[3-(2-methyl-1H-benzimidazol-1-yl)-8-azabicyclo[3.2.1]oct-8-yl]ethyl}-4-phenylpiperidine-1-carboxamide (50 mg, 57%) was obtained as an oil from 2-methyl-1-{8-[2-(4-phenyl piperidin-4-yl)ethyl]-8-azabicyclo[3.2.1]-oct-3-yl}-1H-benzimidazole (71 mg, 0.17 mmol), phosgen and diethylamine following the procedure outlined in example 444. $^1$H NMR (400 MHz, CDCl$_3$) δ 7.66 (d, J=7.3 Hz, 1H), 7.37-7.29 (m, 5H), 7.23-7.12 (m, 3H), 4.64-4.58 (m, 1H), 3.41-3.35 (m, 2H), 3.24-3.23 (m, 2H), 3.17 (q, J=7.2 Hz, 4H), 3.10-3.04 (m, 2H), 2.57 (s, 3H), 2.40-2.32 (m, 2H), 2.19-2.15 (m, 2H), 1.94-1.80 (m, 10H), 1.60 (d, J=7.7 Hz, 2H), 1.10 (t, J=7.0 Hz, 6H). HRMS m/z (M+H)$^+$ calcd: 528.3702, obsd: 528.3712.

Example 446

Preparation of N,N-diallyl-4-{2-[3-(2-methyl-1H-benzimidazol-1-yl)-8-azabicyclo[3.2.1]oct-8-yl]ethyl}-4-phenylpiperidine-1-carboxamide

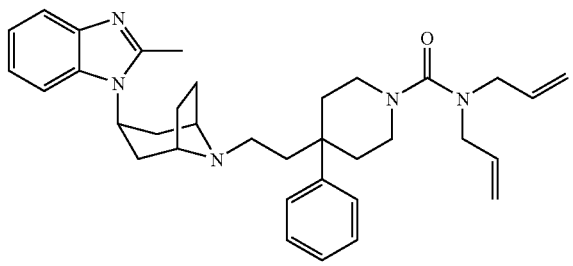

N,N-Diallyl-4-{2-[3-(2-methyl-1H-benzimidazol-1-yl)-8-azabicyclo[3.2.1]oct-8-yl]ethyl}-4-phenylpiperidine-1-carboxamide (42 mg, 46%) was obtained as an oil from 2-methyl-1-{8-[2-(4-phenylpiperidin-4-yl)ethyl]-8-azabicyclo[3.2.1]-oct-3-yl}-1H-benzimidazole (71 mg, 0.17 mmol), phosgen and diallylamine following the procedure outlined in example 444. $^1$H NMR (400 MHz, CDCl$_3$) δ 7.66 (d, J=7.1 Hz, 1H), 7.37-7.33 (m, 2H), 7.30-7.29 (m, 3H), 7.23-7.12 (m, 3H), 5.86-5.76 (m, 2H), 5.18-5.13 (m, 4H), 4.61 (br, 1H), 3.72 (d, J=5.5 Hz, 4H), 3.47-3.41 (m, 2H), 3.24 (br, 2H), 3.12-3.06 (m, 2H), 2.57 (s, 3H), 2.40-2.32 (m, 2H), 2.20-2.15 (m, 2H), 1.99-1.80 (m, 10H), 1.60 (d, J=7.7 Hz, 2H). HRMS m/z (M+H)$^+$ calcd: 552.3702, obsd: 552.3701.

Example 447

Preparation of N-ethyl-N-methyl-4-{2-[3-(2-methyl-1H-benzimidazol-1-yl)-8-azabicyclo[3.2.1]oct-8-yl]ethyl}-4-phenylpiperidine-1-carboxamide

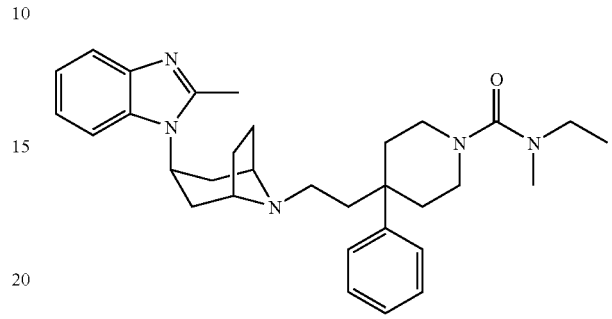

N-Ethyl-N-methyl-4-{2-[3-(2-methyl-1H-benzimidazol-1-yl)-8-azabicyclo[3.2.1]oct-8-yl]ethyl}-4-phenylpiperidine-1-carboxamide (53 mg, 62%) was obtained as an oil from 2-methyl-1-{8-[2-(4-phenylpiperidin-4-yl)ethyl]-8-azabicyclo[3.2.1]-oct-3-yl}-1H-benzimidazole (71 mg, 0.17 mmol), phosgen and N-ethyl-N-methylamine following the procedure outlined in example 444. $^1$H NMR (400 MHz, CDCl$_3$) δ 7.66 (d, J=7.1 Hz, 1H), 7.37-7.33 (m, 2H), 7.31-7.29 (m, 3H), 7.23-7.12 (m, 3H), 4.63-4.59 (m, 1H), 3.41-3.36 (m, 2H), 3.24 (br, 2H), 3.18 (q, J=7.1 Hz, 2H), 3.11-3.04 (m, 2H), 2.77 (s, 3H), 2.57 (s, 3H), 2.40-2.32 (m, 2H), 2.19-2.15 (m, 2H), 1.99-1.80 (m, 10H), 1.60 (d, J=7.9 Hz, 2H), 1.12 (t, J=7.1 Hz, 3H). HRMS m/z (M+H)$^+$ calcd: 514.3546, obsd: 514.3526.

Example 448

Preparation of N,N-diisopropyl-4-{2-[3-(2-methyl-1H-benzimidazol-1-yl)-8-azabicyclo[3.2.1]oct-8-yl]ethyl}-4-phenylpiperidine-1-carboxamide

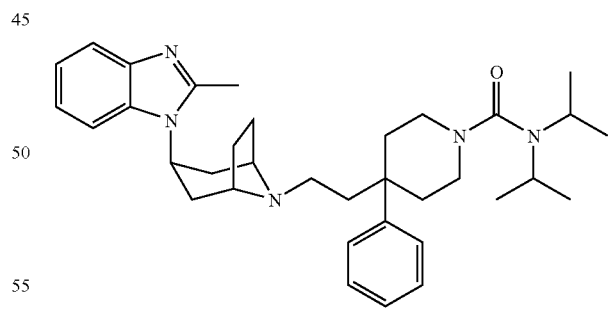

To a flask containing phosgen (2 mL, 2 M in toluene) in methylene chloride (10 mL) was added triethylamine (75 μL, 0.5 mmol) and diisopropylamine (76 μL, 0.5 mmol). The mixture was stirred at room temperature for 4 hours before nitrogen gas was introduced to remove excess phosgen. To this freshly prepared chlorodiisopropyl carbamate was added 2-methyl-1-{8-[2-(4-phenylpiperidin-4-yl)ethyl]-8-azabicyclo[3.2.1]-oct-3-yl}-1H-benzimidazole (85 mg, 0.2 mmol) and triethylamin (60 μL, 0.4 mmol). The resulting mixture was stirred overnight at ambient temperature. The excess chlorocarbamate was quenched with 1 mL of methanol. After evaporation of solvent, the residue was directly purified by flash chromatography, eluting with a gradient of 0-5% methanol in ethyl acetate, to afford an oil (81 mg, 73%). $^1$H NMR (400 MHz, CDCl$_3$) δ 7.66 (d, J=7.4 Hz, 1H), 7.37-7.33 (m, 2H), 7.31-7.30 (m, 3H), 7.22-7.12 (m, 3H), 4.63-4.59 (m, 1H), 3.62-3.55 (m, 2H), 3.29-3.23 (m, 4H), 3.03-2.97 (m, 2H), 2.57 (s, 3H), 2.40-2.32 (m, 2H), 2.18-2.14 (m, 2H), 1.95-1.80 (m, 10H), 1.60 (d, J=7.9 Hz, 2H), 1.26 (d, J=6.6 Hz, 6H). HRMS m/z (M+H)$^+$ calcd: 556.4015, obsd: 556.4008.

Example 449

Preparation of N,N-dimethyl-4-{2-[3-(2-methyl-1H-benzimidazol-1-yl)-8-azabicyclo[3.2.1]oct-8-yl]ethyl}-4-phenylpiperidine-1-carbothioamide

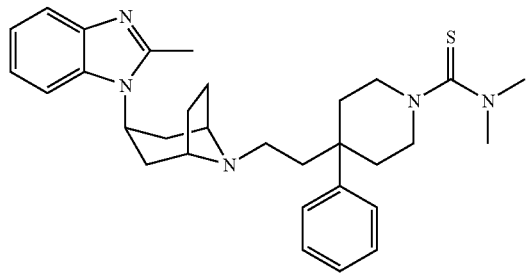

N,N-Dimethyl-4-{2-[3-(2-methyl-1H-benzimidazol-1-yl)-8-azabicyclo[3.2.1]oct-8-yl]ethyl}-4-phenylpiperidine-1-carbothioamide (58 mg, 75%) was obtained as a foam from 2-methyl-1-{8-[2-(4-phenylpiperidin-4-yl)ethyl]-8-azabicyclo[3.2.1]-oct-3-yl}H-benzimidazole dihydrochloride (75 mg, 0.15 mmol), thiophosgen and dimethylamine following the procedure outlined in example 444. $^1$H NMR (400 MHz, CDCl$_3$) δ 7.65 (d, J=7.1 Hz, 1H), 7.45-7.35 (m, 2H), 7.32-7.29 (m, 3H), 7.25-7.19 (m, 1H), 7.17-7.12 (m, 2H), 4.63-4.58 (m, 1H), 3.75-3.70 (m, 2H), 3.32-3.24 (m, 4H), 3.10 (s, 6H), 2.58 (s, 3H), 2.40-2.33 (m, 2H), 2.26-2.22 (m, 2H), 1.97-1.82 (m, 10H), 1.61 (d, J=7.9 Hz, 2H). HRMS m/z (M+H)$^+$ calcd: 516.3161, obsd: 516.3158.

Example 450

Preparation of N-ethyl-N-methyl-4-{2-[3-(2-methyl-1H-benzimidazol-1-yl)-8-azabicyclo[3.2.1]oct-8-yl]ethyl}-4-phenylpiperidine-1-carbothioamide

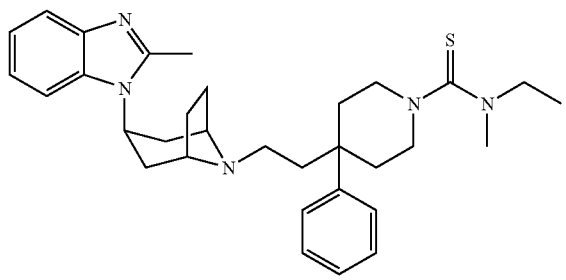

N-Ethyl-N-methyl-4-{2-[3-(2-methyl-1H-benzimidazol-1-yl)-8-azabicyclo[3.2.1]oct-8-yl]ethyl}-4-phenylpiperidine-1-carbothioamide (62 mg, 78%) was obtained as a foam from 2-methyl-1-{8-[2-(4-phenyl piperidin-4-yl)ethyl]-8-azabicyclo[3.2.1]-oct-3-yl}-1H-benzimidazole dihydrochloride (75 mg, 0.15 mmol), thiophosgen and N-ethyl-N-methylamine following the procedure outlined in example 444. $^1$H NMR (400 MHz, CDCl$_3$) δ 7.65 (d, J=7.2 Hz, 1H), 7.38-7.34 (m, 2H), 7.31-7.29 (m, 3H), 7.24-7.21 (m, 1H), 7.18-7.12 (m, 2H), 4.63-4.58 (m, 1H), 3.72-3.66 (m, 2H), 3.61 (q, J=7.0 Hz, 2H), 3.31-3.24 (m, 4H), 3.03 (s, 3H), 2.57 (s, 3H), 2.40-2.32 (m, 2H), 2.26-2.21 (m, 2H), 1.97-1.82 (m, 10H), 1.60 (d, J=7.8 Hz, 2H), 1.21 (t, J=7.1 Hz, 3H). HRMS m/z (M+H)$^+$ calcd: 530.3317, obsd: 530.3301.

Example 451

Preparation of N,N-diethyl-4-{2-[3-(2-methyl-1H-benzimidazol-1-yl)-8-azabicyclo[3.2.1]oct-8-yl]ethyl}-4-phenylpiperidine-1-carbothioamide

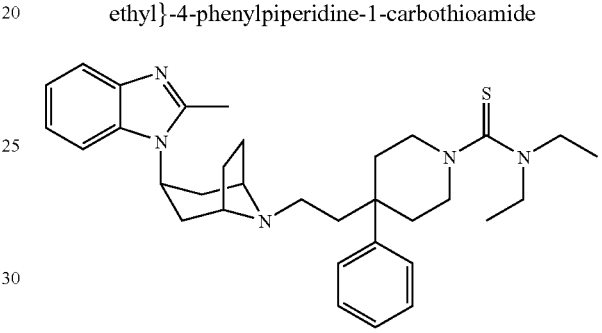

N,N-Diethyl-4-{2-[3-(2-methyl-1H-benzimidazol-1-yl)-8-azabicyclo[3.2.1]oct-8-yl]ethyl}-4-phenylpiperidine-1-carbothioamide (51 mg, 62%) was obtained as a foam from 2-methyl-1-{8-[2-(4-phenylpiperidin-4-yl)ethyl]-8-azabicyclo[3.2.1]-oct-3-yl}-1H-benzimidazole dihydrochloride (75 mg, 0.15 mmol), thiophosgen and diethylamine following the procedure outlined in example 444. $^1$H NMR (400 MHz, CDCl$_3$) δ 7.65 (d, J=7.4 Hz, 1H), 7.38-7.34 (m, 2H), 7.32-7.29 (m, 3H), 7.25-7.21 (m, 1H), 7.19-7.12 (m, 2H), 4.63-4.59 (m, 1H), 3.72-3.68 (m, 2H), 3.57 (q, J=7.1 Hz, 4H), 3.30-3.25 (m, 4H), 2.58 (s, 3H), 2.40-2.33 (m, 2H), 2.25-2.21 (m, 2H), 1.97-1.82 (m, 10H), 1.61 (d, J=7.7 Hz, 2H), 1.18 (t, J=7.1 Hz, 6H). HRMS m/z (M+H)$^+$ calcd: 544.3474, obsd: 544.3482.

Example 452

Preparation of N,N-diallyl-4-{2-[3-(2-methyl-1H-benzimidazol-1-yl)-8-azabicyclo[3.2.1]oct-8-yl]ethyl}-4-phenylpiperidine-1-carbothioamide

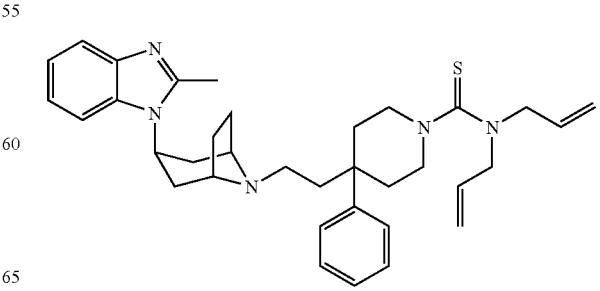

N,N-Diallyl-4-{2-[3-(2-methyl-1H-benzimidazol-1-yl)-8-azabicyclo[3.2.1]oct-8-yl]ethyl}-4-phenylpiperidine-1-carbothioamide (55 mg, 65%) was obtained as a foam from 2-methyl-1-{8-[2-(4-phenylpiperidin-4-yl)ethyl]-8-azabicyclo[3.2.1]-oct-3-yl}-1H-benzimidazole dihydrochloride (75 mg, 0.15 mmol), thiophosgen and diallylamine following the procedure outlined in example 444. $^1$H NMR (400 MHz, CDCl$_3$) δ 7.65 (d, J=7.1 Hz, 1H), 7.38-7.35 (m, 2H), 7.31-7.29 (m, 3H), 7.25-7.21 (m, 1H), 7.19-7.12 (m, 2H), 5.91-5.81 (m, 2H), 5.23-5.17 (m, 4H), 4.63-4.58 (m, 1H), 4.10 (d, J=5.6 Hz, 4H), 3.82-3.79 (m, 2H), 3.35-3.25 (m, 4H), 2.59 (s, 3H), 2.40-2.32 (m, 2H), 2.27-2.23 (m, 2H), 1.97-1.80 (m, 10H), 1.61 (d, J=7.9 Hz, 2H). HRMS m/z (M+H)$^+$ calcd: 568.3474, obsd: 568.3470.

Example 453

Preparation of 1-((1R,5S)-8-{2-[1-(1H-imidazol-1-ylcarbonothioyl)-4-phenylpiperidin-4-yl]ethyl}-8-azabicyclo[3.2.1]oct-3-yl)-2-methyl-1H-benzimidazole

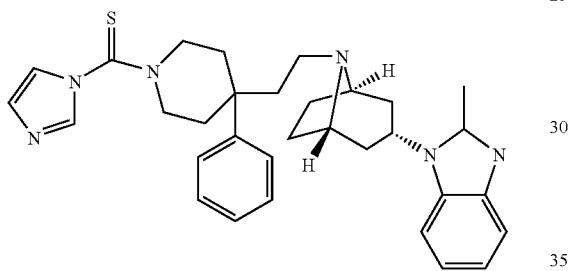

To a stirred solution of 2-methyl-1-{8-[2-(4-phenylpiperidin-4-yl)ethyl]-8-azabicyclo[3.2.1]-oct-3-yl}-1H-benzimidazole (214 mg, 0.5 mmol) in methylene chloride was added 1-(1H-imidazol-1-ylcarbonothioyl)-1H-imidazole (89 mg, 0.5 mmol). The resulting mixture was stirred overnight. After evaporation of the solvents, the crude product was purified by flash chromatography, eluting with a gradient of 0-5% methanol in ethyl acetate, to afford 1-((1R,5S)-8-{2-[1-(1H-imidazol-1-ylcarbonothioyl)-4-phenylpiperidin-4-yl]ethyl}-8-azabicyclo[3.2.1]oct-3-yl)-2-methyl-1H-benzimidazole as a foam (200 mg, 74%). $^1$H NMR (400 MHz, CDCl$_3$) δ 7.83 (s, 1H), 7.65 (d, J=7.1 Hz, 1H), 7.42-7.39 (m, 2H), 7.31-7.28 (m, 4H), 7.19-7.10 (m, 3H), 7.07 (s, 1H), 4.62-4.56 (m, 1H), 3.53 (br, 1H), 3.24-3.22 (m, 2H), 2.56 (s, 3H), 2.40-2.32 (m, 4H), 1.99-1.81 (m, 10, H), 1.62 (d, J=7.9 Hz, 2H). HRMS m/z (M+H)$^+$ calcd: 539.2957, obsd: 539.2958.

Preparation of N-acyl and N-sulfonyl guanidine Derivatives of 2-Methyl-1-{8-[2-(4-Phenylpiperidin-4-yl)ethyl]-8-Azabicyclo[3.2.1]-oct-3-yl}-1H-benzimidazole Synthesis of Acyl and Sulfonyl Derivatives

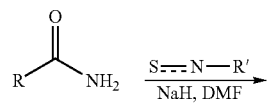

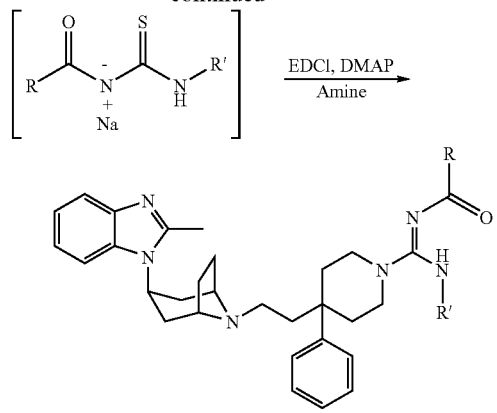

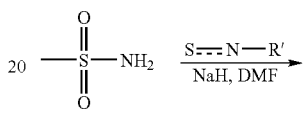

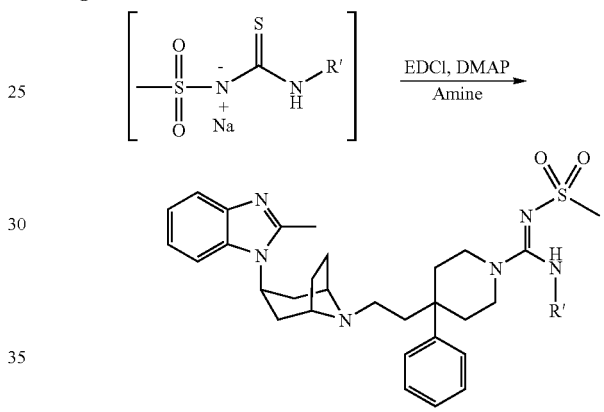

Example 454

Preparation of N-[(1E)-[(4-chlorophenyl)amino](4-{2-[3-(2-methyl-1H-benzimidazol-1-yl)-8-azabicyclo[3.2.1]oct-8-yl]ethyl}-4-phenylpiperidin-1-yl)methylidene]-2,2-dimethylpropanamide

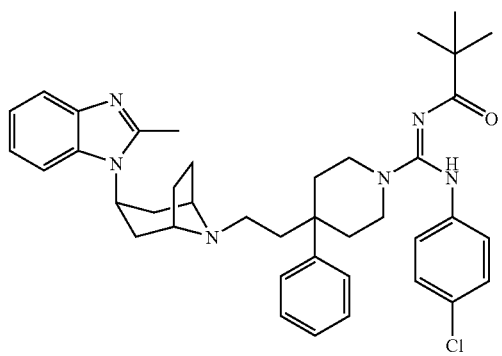

To a solution of trimethylacetamide (10 mg, 0.1 mmol) in DMF (0.5 mL) was added sodium hydride (60%, 5.2 mg, 0.13 mmol). After stirring for 5 minutes, 4-chlorophenylisothiocyanate (17 mg, 0.1 mmol) was added. The reaction mixture was stirred at 60° C. for one hour before being cooled down to room temperature. To this reaction mixture was then added 2-methyl-1-{8-[2-(4-phenylpiperidin-4-yl)ethyl]-8-azabicyclo[3.2.1]-oct-3-yl}-1H-benzimidazole (35 mg, 0.08 mmol), EDCI (19 mg, 0.1 mmol) and a catalytic amount of DMAP. After stirring at ambient temperature overnight, the reaction was quenched with water and extracted with dichloromethane (4×10 mL). The organic phase was washed with brine and dried over sodium sulfate. The solvent was removed and the residue was purified by flash chromatography on silical gel, eluting with a gradient of 0-15% methanol in ethyl acetate to afford N-[(1E)-[(4-chlorophenyl)amino](4-{2-[3-(2-methyl-1H-benzimidazol-1-yl)-8-azabicyclo[3.2.1]oct-8-yl]ethyl}-4-phenylpiperidin-1-yl) methylidene]-2,2-dimethylpropanamide as amorphous solid (20 mg, 38%). $^1$H NMR (400 MHz, DMSO-$d_6$) δ 8.9 (s, 1H), 7.46 (d, J=8.8 Hz, 1H), 7.39-7.33 (m, 6H), 7.22-7.19 (m, 1H), 7.13-7.05 (m, 3H), 6.61 (d, J=8.6 Hz, 2H), 4.51-4.47 (m, 1H), 3.80-3.40 (m, 2H), 3.26-3.13 (m, 4H), 2.46 (s, 3H), 2.37-2.30 (m, 2H), 2.14 (br, 2H), 1.85-1.71 (m, 10H), 1.56 (d, J=7.4 Hz, 2H), 0.88 (s, 9H). HRMS m/z (M+H)$^+$ calcd: 665.3735, obsd: 665.3741.

Example 455

Preparation of N-[(1E)-[(4-chlorophenyl)amino](4-{2-[3-(2-methyl-1H-benzimidazol-1-yl)-8-azabicyclo[3.2.1]oct-8-yl]ethyl}-4-phenylpiperidin-1-yl)methylidene]methane-sulfonamide

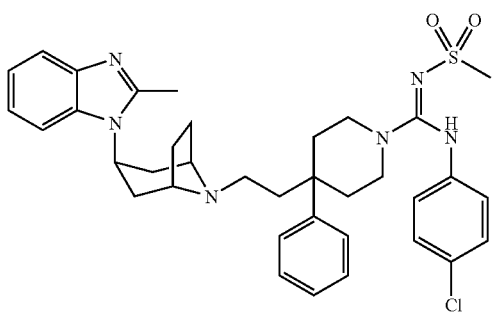

N-[(1E)-[(4-Chlorophenyl)amino](4-{2-[3-(2-methyl-1H-benzimidazol-1-yl)-8-azabicyclo[3.2.1]oct-8-yl]ethyl}-4-phenylpiperidin-1-yl)methylidene]methanesulfonamide (38 mg, 73%) was obtained as amorphous solid from methanesulfonamide (9.5 mg, 0.1 mmol), 4-chlorophenyl isothiocyanate (17 mg, 0.1 mmol) and 2-methyl-1-{8-[2-(4-phenylpiperidin-4-yl)ethyl]-8-azabicyclo[3.2.1]-oct-3-yl}-1H-benzimidazole (35 mg, 0.08 mmol) following the procedure outlined in example 454. $^1$H NMR (400 MHz, CDCl$_3$) δ 8.39 (s, 1H), 7.64 (d, J=7.1 Hz, 1H), 7.37-7.33 (m, 2H), 7.30-7.21 (m, 6H), 7.19-7.10 (m, 2H), 6.89 (d, J=8.6 Hz, 2H), 4.59-4.53 (m, 1H), 3.61 (d, J=13.5 Hz, 2H), 3.19 (br, 2H), 3.04 (t, J=11 Hz, 2H), 2.96 (s, 3H), 2.53 (s, 3H), 2.37-2.29 (m, 2H), 2.20-2.16 (m, 2H), 1.90-1.84 (m, 6H), 1.82-1.71 (m, 4H), 1.58 (d, J=7.4 Hz, 2H). HRMS m/z (M+H)$^+$ calcd: 659.2935, obsd: 659.2935.

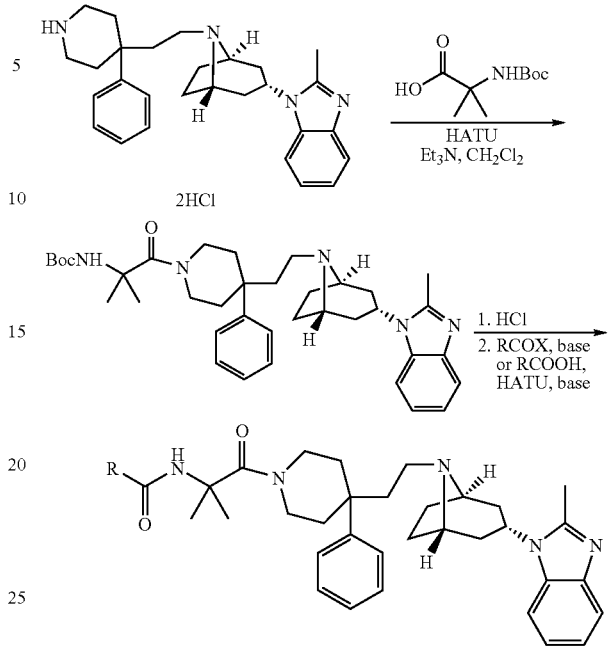

Example 456

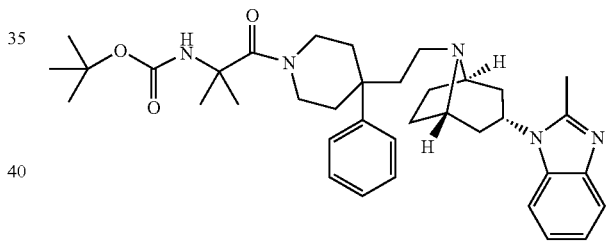

To a stirred solution of 2-methyl-1-{8-[2-(4-phenylpiperidin-4-yl)ethyl]-8-azabicyclo[3.2.1]oct-3-yl}-1H-benzimidazole dihydrochloride (505 mg, 1.0 mmol) in dichloromethane (20 mL) was added Boc-α-methyl alanine (203 mg, 1.0 mmol), triethylamine (470 μL, 3.0 mmol) and HATU (380 mg, 1.0 mmol). The resulting mixture was stirred at ambient temperature overnight before being quenched with saturated sodium bicarbonate. The layers were separated and the aqueous was extracted with dichloromethane. The combined organic phase was dried over anhydrous sodium sulfate. After evaporation of the solvent, the crude product was purified by flash chromatography on silical gel, eluting with a gradient of 0-8% methanol in ethyl acetate to afford compound 456 as amorphous solid (579 mg, 94%). $^1$H NMR (400 MHz, CDCl$_3$) δ 7.65 (d, J=7.1 Hz, 1H), 7.38-7.34 (m, 1H), 7.30-7.20 (m, 3H), 7.19-7.13 (m, 3H), 5.04 (s, 1H), 4.65-4.61 (m, 1H), 4.09-4.02 (m, 2H), 3.29-3.20 (m, 5H), 2.58 (s, 3H), 2.44-2.36 (m, 2H), 2.22-2.20 (m, 2H), 1.95-1.89 (m, 5H), 1.84-1.78 (m, 4H), 1.64 (d, J=7.8 Hz, 2H), 1.49 (s, 5H), 1.39-1.35 (m, 10H). HRMS m/z (M+H)$^+$ calcd: 614.4070, obsd: 614.4086.

Example 457

Preparation of 2-methyl-1-(4-{2-[(1R,5S)-3-(2-methyl-1H-benzimidazol-1-yl)-8-azabicyclo[3.2.1]oct-8-yl]ethyl}-4-phenylpiperidin-1-yl)-1-oxopropan-2-amine

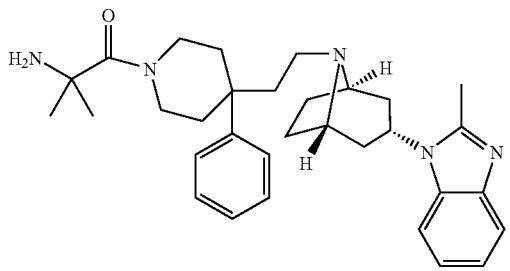

To a stirred solution of the product from example 456 (307 mg, 0.50 mmol) in methylene chloride was added HCl (2 mL, 4 M in dioxane). The reaction mixture was stirred for one hour at ambient temperature. Evaporation of solvents directly afforded 240 mg (99%) of white solid, which was then partitioned between ethyl acetate and saturated sodium bicarbonate solution. The organic phase was dried over anhydrous sodium sulfate. After removal of the solvent, the desired product was obtained as foam. $^1$H NMR (400 MHz, CDCl$_3$) δ 7.66 (d, J=7.1 Hz, 1H), 7.39-7.35 (m, 2H), 7.31-7.22 (m, 4H), 7.19-7.12 (m, 2H), 4.64 (m, 1H), 4.13-4.11 (m, 2H), 3.40 (br, 2H), 3.27 (br, 2H), 2.57 (s, 3H), 2.52-2.24 (m, 4H), 1.94-1.91 (m, 4H), 1.88-1.68 (m, 8H), 1.63 (d, J=7.9 Hz, 2H), 1.41 (s, 6H). HRMS m/z (M+H)$^+$ calcd: 514.3546, obsd: 514.3561.

Example 458

Preparation of (2S)—N,N-bis(4-{2-[(1R,5S)-3-(2-methyl-1H-benzimidazol-1-yl)-8-azabicyclo[3.2.1]oct-8-yl]ethyl}-4-phenyl-1-D-prolylpiperidin-2-yl)-D-prolinamide

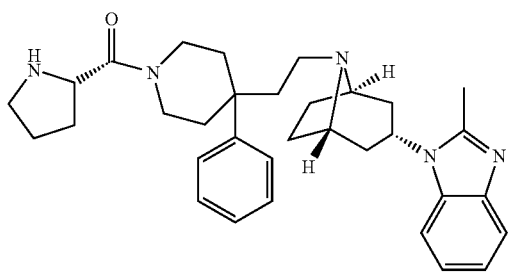

The Boc protected precursor was prepared from L-Boc-proline (47 mg, 0.15 mmol), 2-methyl-1-{8-[2-(4-phenylpiperidin-4-yl)ethyl]-8-azabicyclo[3.2.1]oct-3-yl}-1H-benzimidazole (64 mg, 0.15 mmol) and HATU (57 mg, 0.15 mmol), following the procedure outlined in example 456. After removal of Boc protecting group with a solution of 4N HCl in dioxane, (2S)—N,N-bis(4-{2-[(1R,5S)-3-(2-methyl-1H-benzimidazol-1-yl)-8-azabicyclo[3.2.1]oct-8-yl]ethyl}-4-phenyl-1-D-prolyl-piperidin-2-yl)-D-prolinamide was obtained as an oil (80 mg, quant.). $^1$H NMR (400 MHz, CDCl$_3$) δ 7.66 (d, J=7.4 Hz, 1H), 7.40-7.36 (m, 2H), 7.30-7.28 (m, 3H), 7.25-7.23 (m, 1H), 7.21-7.12 (m, 2H), 4.65-4.55 (m, 1H), 4.11-4.02 (m, 1H), 3.93-3.84 (m, 1H), 3.68-3.63 (m, 1H), 3.32-3.14 (m, 5H), 2.85-2.73 (m, 1H), 2.57 (s, 3H), 2.40-2.24 (m, 6H), 2.15-1.50 (m, 5H). HRMS m/z (M+H)$^+$ calcd: 526.3546, obsd: 526.3565.

Example 459

Preparation of N$^2$-acetyl-N$^1$,N$^1$-bis(1-(N-acetyl-2-methylalanyl)-4-{2-[(1R,5S)-3-(2-methyl-1H-benzimidazol-1-yl)-8-azabicyclo[3.2.1]oct-8-yl]ethyl}-4-phenylpiperidin-2-yl)-2-methylalaninamide

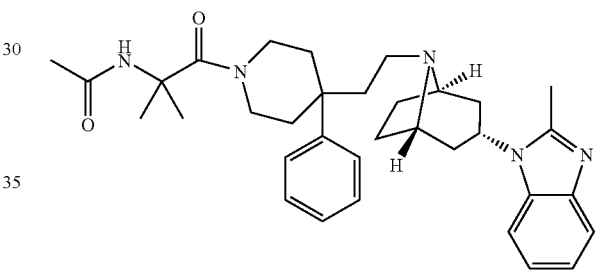

At 0° C., to a stirred solution of 2-methyl-1-(4-{2-[(1R,5S)-3-(2-methyl-1H-benzimidazol-1-yl)-8-azabicyclo[3.2.1]oct-8-yl]ethyl}-4-phenylpiperidin-1-yl)-1-oxopropan-2-amine dihydrochloride (40 mg, 0.068 mmol, obtained from compound 456 by removal of Boc protecting group with 4 M HCl in ether) in dichloromethane was added acetyl bromide (8.6 mg, 0.068 mmol), N,N-diethyl-isopropylamine (42 µL, 0.24 mmol) and DMAP (1 mg). The resulting mixture was stirred for 3 hours before being quenched with saturated sodium bicarbonate. The layers were separated and the aqueous layer was extracted with dichloromethane. The combined organic phase was dried over anhydrous sodium sulfate. After evaporation of the solvent, the crude product was purified by flash chromatography on silical gel, eluting with a gradient of 0-10% methanol in ethyl acetate to afford N$^2$-acetyl-N$^1$,N$^1$-bis(1-(N-acetyl-2-methylalanyl)-4-{2-[(1R,5S)-3-(2-methyl-1H-benzimidazol-1-yl)-8-azabicyclo[3.2.1]oct-8-yl]ethyl}-4-phenylpiperidin-2-yl)-2-methylalaninamide as amorphous solid (34 mg, 90%). $^1$H NMR (400 MHz, CDCl$_3$), δ 7.67 (d, J=6.5 Hz, 1H), 7.40-7.37 (m, 2H), 7.30-7.26 (m, 3H), 7.24-7.13 (m, 3H), 7.07 (s, 1H), 4.03-4.00 (m, 1H), 3.67-3.61 (m, 2H), 3.34 (t, J=7.8 Hz, 1H), 3.08 (q, J=7.3 Hz, 1H), 2.79-2.61 (m, 4H), 2.43-2.08 (m, 6H), 2.06-1.92 (m, 4H), 1.85-1.80 (m, 2H), 1.58 (s, 3H), 1.54 (s, 3H), 1.52-1.51 (m, 4H), 1.43 (d, J=6.6 Hz, 4H). HRMS m/z (M+H)$^+$ calcd: 556.3651, obsd: 556.3647.

Example 460

Preparation of N²-(2,2-dimethylpropanoyl)-N¹,N¹-bis(1-[N-(2,2-dimethylpropanoyl)-2-methylalanyl]-4-{2-[(1R,5S)-3-(2-methyl-1H-benzimidazol-1-yl)-8-azabicyclo[3.2.1]oct-8-yl]ethyl}-4-phenylpiperidin-2-yl)-2-methylalaninamide

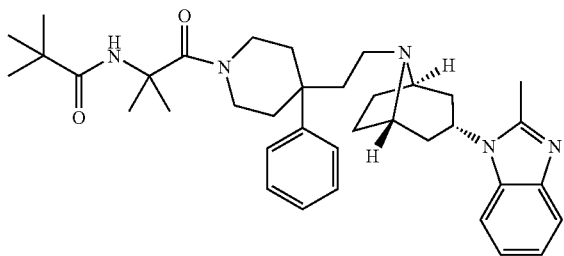

N²-(2,2-dimethylpropanoyl)-N¹,N¹-bis(1-[N-(2,2-dimethylpropanoyl)-2-methylalanyl]-4-{2-[(1R,5S)-3-(2-methyl-1H-benzimidazol-1-yl)-8-azabicyclo[3.2.1]oct-8-yl]ethyl}-4-phenylpiperidin-2-yl)-2-methyl alaninamide (17 mg, 42%) was obtained as an oil from 2-methyl-1-(4-{2-[(1R,5S)-3-(2-methyl-1H-benzimidazol-1-yl)-8-azabicyclo[3.2.1]oct-8-yl]ethyl}-4-phenyl piperidin-1-yl)-1-oxopropan-2-amine dihydrochloride (40 mg, 0.068 mmol) and pivaloyl chloride (8.4 µL, 0.068 mmol) following the procedure outlined in the example 459. $^1$H NMR (400 MHz, CDCl$_3$), δ 7.66 (d, J=7.1 Hz, 1H), 7.40-7.36 (m, 2H), 7.30-7.23 (m, 4H), 7.19-7.12 (m, 2H), 4.61 (br, 1H), 3.99 (br, 2H), 3.32-3.26 (m, 4H), 2.57 (s, 3H), 2.41-2.23 (m, 4H), 1.93-1.76 (m, 9H), 1.65 (s, 6H), 1.63-1.61 (m, 2H), 1.19 (s, 9H). HRMS m/z (M+H)⁺ calcd: 598.4121, obsd: 598.4116.

Example 461

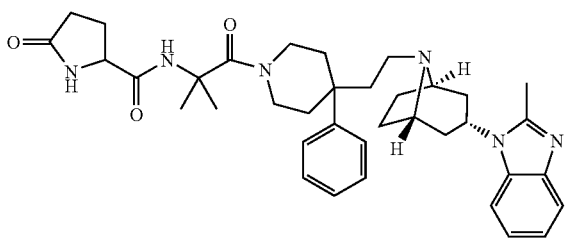

The product in example 461 (9 mg, 29%) was obtained from 2-methyl-1-(4-{2-[(1R,5S)-3-(2-methyl-1H-benzimidazol-1-yl)-8-azabicyclo[3.2.1]oct-8-yl]ethyl}-4-phenylpiperidin-1-yl)-1-oxopropan-2-amine dihydrochloride (26 mg, 0.05 mmol), 5-oxo-D-proline (6.5 mg, 0.05 mmol) and HATU (19 mg, 0.05 mmol) following the procedure outlined in example 5. $^1$H NMR (400 MHz, CDCl$_3$) δ 7.79 (s, 1H), 7.65 (d, J=7.2 Hz, 1H), 7.40-7.36 (m, 2H), 7.30-7.23 (m, 4H), 7.19-7.12 (m, 2H), 6.72 (s, 1H), 4.63-4.58 (m, 1H), 4.14-4.09 (m, 1H), 3.97 (br, 2H), 3.31-3.25 (m, 4H), 2.57 (s, 3H), 2.54-2.10 (m, 9H), 1.93-1.75 (m, 10H), 1.67-1.60 (m, 8H). HRMS m/z (M+H)⁺ calcd: 625.3866, obsd: 625.3863.

Example 462

Preparation of 2-Methyl-1-(8-{2-[4-phenyl-1-(1H-pyrrol-2-ylcarbonyl)piperidin-4-yl]ethyl}-8-azabicyclo[3.2.1]oct-3-yl)-1H-benzimidazole

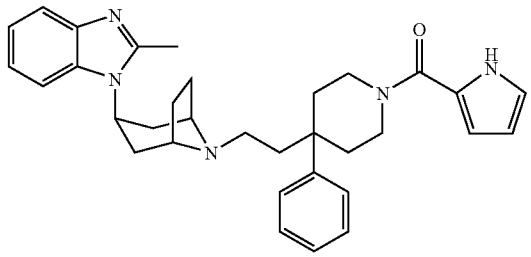

2-Methyl-1-(8-{2-[4-phenyl-1-(1H-pyrrol-2-ylcarbonyl)piperidin-4-yl]ethyl}-8-azabicyclo[3.2.1]oct-3-yl)-1H-benzimidazole (58.5 mg, 75%) was obtained as a white solid from 2-methyl-1-{8-[2-(4-phenyl piperidin-4-yl)ethyl]-8-azabicyclo[3.2.1]oct-3-yl}-1H-benzimidazole (64 mg, 0.15 mmol), 1H-pyrrole-2-carboxylic acid (16.6 mg, 0.15 mmol) and HATU (57 mg, 0.15 mmol), following the procedure outlined in example 5. $^1$H NMR (300 MHz, DMSO-d$_6$) δ 12.5 (br, 1H), 7.68 (s, 1H), 7.53-7.46 (m, 2H), 7.41-7.32 (m, 5H), 7.22-7.18 (m, 1H), 7.13-7.04 (m, 3H), 4.53-4.47 (m, 1H), 4.11 (br, 1H), 3.85 (br, 1H), 3.27-3.09 (m, 4H), 2.46 (s, 3H), 2.39-2.29 (m, 2H), 2.0 (br, 2H), 1.97-1.70 (m, 10H), 1.57-1.55 (m, 2H). HRMS m/z (M+H)⁺ calcd: 522.3233, obsd: 522.3226.

Example 463

Preparation of (5R)-5-[(4-{2-[3-(2-methyl-1H-benzimidazol-1-yl)-8-azabicyclo[3.2.1]oct-8-yl]ethyl}-4-phenylpiperidin-1-yl)carbonyl]pyrrolidin-2-one

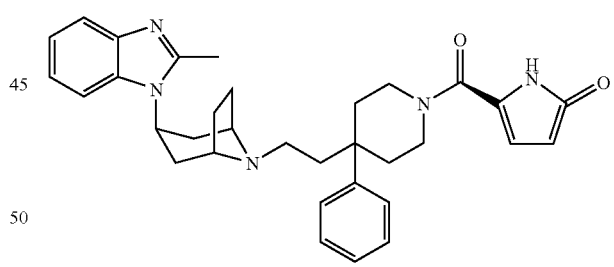

(5R)-5-[(4-{2-[3-(2-methyl-1H-benzimidazol-1-yl)-8-azabicyclo[3.2.1]oct-8-yl]ethyl}-4-phenyl piperidin-1-yl)carbonyl]pyrrolidin-2-one (59 mg, 85%) was obtained as white solid from 2-methyl-1-{8-[2-(4-phenylpiperidin-4-yl)ethyl]-8-azabicyclo[3.2.1]oct-3-yl}-1H-benzimidazole (64 mg, 0.15 mmol), 5-oxo-D-proline (19 mg, 0.15 mmol) and HATU (57 mg, 0.15 mmol), following the procedure outlined in example 5. $^1$H NMR (400 MHz, CDCl$_3$) δ 7.65 (d, J=8.8 Hz, 1H), 7.40-7.36 (m, 2H), 7.30-7.23 (m, 4H), 7.18-7.11 (m, 2H), 6.20 (s, A H), 6.09 (s, 2H), 4.62-4.56 (m, 1H), 4.50-4.42 (m, 1H), 4.07-4.02 (m, 1H), 3.58-3.55 (m, 1H), 3.25-3.16 (m, 4H), 2.56 (s, 3H), 2.46-2.14 (m, 47H), 2.03-1.73 (m, 11H), 1.63-1.58 (m, 2H). HRMS m/z (M+H)⁺ calcd: 540.3339, obsd: 540.3361.

Example 464

Preparation of 1-(8-{2-[1-(1H-imidazol-5-ylcarbonyl)-4-phenylpiperidin-4-yl]ethyl}-8-azabicyclo[3.2.1]oct-3-yl)-2-methyl-1H-benzimidazole

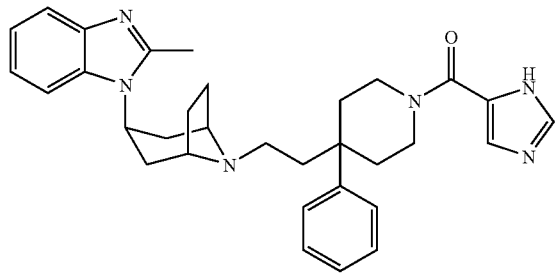

1-(8-{2-[1-(1H-Imidazol-5-ylcarbonyl)-4-phenylpiperidin-4-yl]ethyl}-8-azabicyclo[3.2.1]oct-3-yl)-2-methyl-1H-benzimidazole (18 mg, 23%) was obtained from 2-methyl-1-{8-[2-(4-phenylpiperidin-4-yl)ethyl]-8-azabicyclo[3.2.1]oct-3-yl}-1H-benzimidazole (64 mg, 0.15 mmol), 1H-imidazole-5-carboxylic acid (17 mg, 0.15 mmol) and HATU (57 mg, 0.15 mmol), following the procedure outlined in example 5. $^1$H NMR (400 MHz, CDCl$_3$) δ 9.68 (s, 1H), 7.66 (d, J=8.6 Hz, 1H), 7.41-7.23 (m, 6H), 7.19-7.12 (m, 2H), 6.90 (s, 1H), 6.51 (s, 1H), 6.24 (s, 1H), 4.64-4.58 (m, 1H), 4.20-4.14 (m, 2H), 3.48 (br, 1H), 3.25 (br, 2H), 2.56 (s, 3H), 2.41-2.28 (m, 4H), 2.01-1.81 (m, 10H), 1.64-1.58 (m, 2H). HRMS m/z (M+H)$^+$ calcd: 523.3185, obsd: 523.3204.

Example 465

Preparation of 3-[(4-{2-[(1R,5S)-3-(2-methyl-1H-benzimidazol-1-yl-8-azabicyclo[3.2.1]oct-8-yl]ethyl}-4-phenylpiperidin-1-yl)carbonyl]phenol

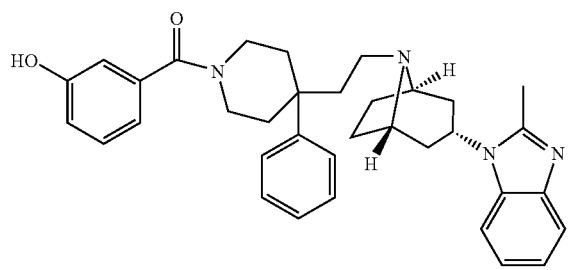

3-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]phenol (70 mg, 84%) was obtained from 2-methyl-1-{8-[2-(4-phenylpiperidin-4-yl)ethyl]-8-azabicyclo[3.2.1]oct-3-yl}-1H-benzimidazole (64 mg, 0.15 mmol), 3-hydroxybenzoic acid (21 mg, 0.15 mmol) and HATU (57 mg, 0.15 mmol), following the procedure outlined in example 5. $^1$H NMR (400 MHz, CDCl$_3$) δ 7.66 (d, J=6.9 Hz, 1H), 7.39-7.35 (m, 2H), 7.31-7.24 (m, 4H), 7.21-7.13 (m, 3H), 6.94 (s, 1H), 6.88-6.85 (m, 1H), 6.81 (d, J=7.5 Hz, 1H), 4.64-4.55 (m, 1H), 4.13 (br, 1H), 3.59-3.56 (m, 1H), 3.40-3.37 (m, 1H), 3.27-3.24 (m, 3H), 2.49 (s, 3H), 2.44-2.34 (m, 2H), 2.26 (br, 1H), 2.18-2.15 (m, 1H), 1.99-1.79 (m, 10H), 1.63-1.61 (m, 2H). HRMS m/z (M+H)$^+$ calcd: 549.3230, obsd: 549.3240.

Example 466

Preparation of 4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl acetate

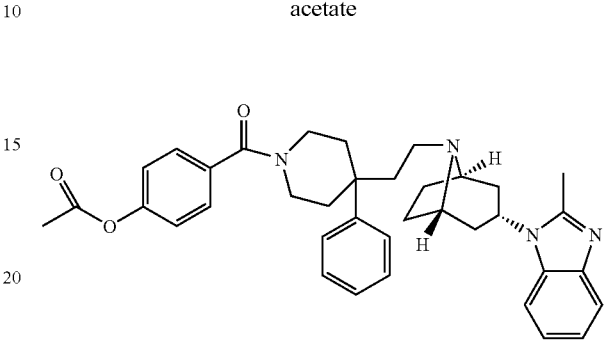

4-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]phenyl acetate (68 mg, 77%) was obtained as a foam from 2-methyl-1-{8-[2-(4-phenylpiperidin-4-yl)ethyl]-8-azabicyclo[3.2.1]oct-3-yl}-1H-benzimidazole (64 mg, 0.15 mmol), 4-(acetyloxy) benzoic acid (27 mg, 0.15 mmol) and HATU (57 mg, 0.15 mmol), following the procedure outlined in example 5. $^1$H NMR (400 MHz, CDCl$_3$) δ 7.65 (d, J=8.4 Hz, 1H), 7.41-7.33 (m, 4H), 7.30-7.22 (m, 4H), 7.21-7.08 (m, 4H), 4.64-4.54 (m, 1H), 4.10 (br, 1H), 3.58 (br, 1H), 3.36-3.24 (m, 4H), 2.54 (s, 3H), 2.39-2.34 (m, 3H), 2.30 (s, 3H), 2.14 (br, 21H), 1.98-1.82 (m, 10H), 1.60 (d, J=7.8 Hz, 2H). HRMS m/z (M+H)$^+$ calcd: 591.3335, obsd: 591.3348.

Example 467

Preparation of 4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenol

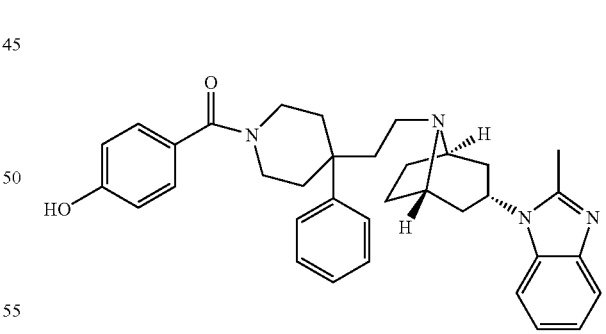

4-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]phenol (27 mg, 33%) was obtained as a foam from 2-methyl-1-{8-[2-(4-phenylpiperidin-4-yl)ethyl]-8-azabicyclo[3.2.1]oct-3-yl}-1H-benzimidazole (64 mg, 0.15 mmol), 4-hydroxybenzoic acid (21 mg, 0.15 mmol) and HATU (57 mg, 0.15 mmol), following the procedure outlined in example 5. $^1$H NMR (400 MHz, CDCl$_3$) δ 7.67-7.64 (m, 1H), 7.39-7.23 (m, 8H), 7.23-7.13 (m, 2H), 6.84 (d, J=8.4 Hz, 2H), 4.67-4.54 (m, 1H), 4.13 (br, 1H), 3.71 (br, 1H), 3.40-3.26 (m, 4H), 2.51 (s, 3H), 2.40-2.11 (m, 4H), 1.95-1.82 (m, 10H), 1.62 (d, J=8.0 Hz, 2H). HRMS m/z (M+H)+ calcd: 549.3230, obsd: 548.3233.

Example 468

Preparation of 2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenol

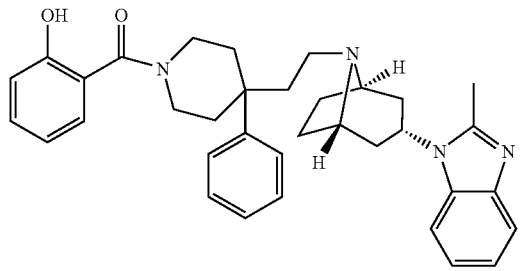

2-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]phenol (70 mg, 85%) was obtained as a syrupy from 2-methyl-1-{8-[2-(4-phenylpiperidin-4-yl)ethyl]-8-azabicyclo[3.2.1]oct-3-yl}-1H-benzimidazole (64 mg, 0.15 mmol), 2-hydroxybenzoic acid (21 mg, 0.15 mmol) and HATU (57 mg, 0.15 mmol), following the procedure outlined in example 5. $^1$H NMR (300 MHz, CDCl$_3$) δ 9.81 (s, 1H), 7.65 (d, J=7.8 Hz, 1H), 7.42-7.31 (m, 2H), 7.30-7.11 (m, 8H), 7.00 (d, J=8.1 Hz, 1H), 6.83 (t, J=7.4 Hz, 1H), 4.67-4.53 (m, 1H), 4.07-4.02 (m, 4H), 3.40 (t, J=10.7 Hz, 1H), 3.25 (br, 2H), 2.55 (s, 3H), 2.42-2.29 (m, 4H), 1.94-1.80 (m, 10H), 1.63-1.58 (m, 2H). HRMS m/z (M+H)+ calcd: 549.3230, obsd: 548.3223.

Example 469

Preparation of 2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl acetate

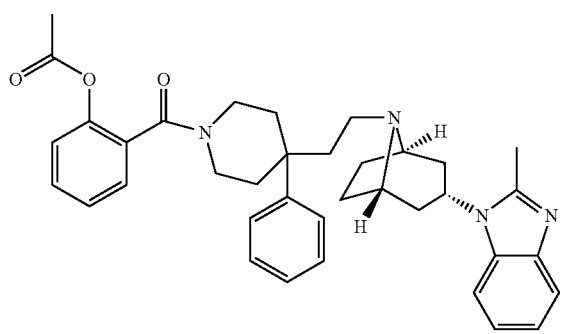

2-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]phenyl acetate (60 mg, 68%) was obtained as syrup from 2-methyl-1-{8-[2-(4-phenylpiperidin-4-yl)ethyl]-8-azabicyclo[3.2.1]oct-3-yl}-1H-benzimidazole (64 mg, 0.15 mmol), 2-(acetyloxy)benzoic acid (27 mg, 0.15 mmol) and HATU (57 mg, 0.15 mmol), following the procedure outlined in example 5. $^1$H NMR (400 MHz, CDCl$_3$) δ 7.66 (d, J=8.4 Hz, 1H), 7.43-7.32 (m, 3H), 7.30-7.23 (m, 6H), 7.21-7.12 (m, 3H), 4.62-4.56 (m, 1H), 4.16-4.11 (m, 1H), 3.46-3.34 (m, 2H), 3.23-3.20 (m, 3H), 2.53 (s, 3H), 2.41-2.27 (m, 4H), 2.16-2.13 (m, 2H), 1.92-1.79 (m, 11H), 1.62-1.57 (m, 2H). HRMS m/z (M+H)+ calcd: 591.3335, obsd: 591.3341.

Example 470

Preparation of 4-fluoro-2-[(4-{2-[(1R,5S)-3-(2-methyl-1H-benzimidazol-1-yl-8-azabicyclo[3.2.1]oct-8-yl]ethyl}-4-phenylpiperidin-1-yl)carbonyl]phenol

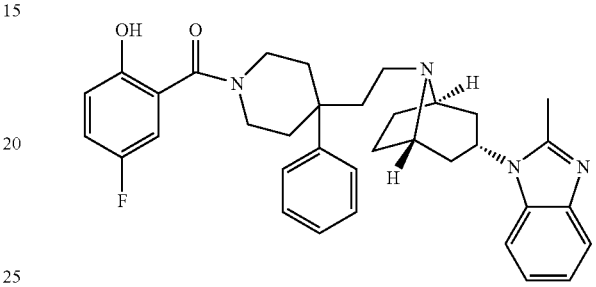

4-Fluoro-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenol (58 mg, 85%) was obtained as a foam from 2-methyl-1-{8-[2-(4-phenylpiperidin-4-yl)ethyl]-8-azabicyclo[3.2.1]oct-3-yl}-1H-benzimidazole (51 mg, 0.12 mmol), 5-fluoro-2-hydroxybenzoic acid (19 mg, 0.12 mmol) and HATU (47 mg, 0.12 mmol), following the procedure outlined in example 5. $^1$H NMR (400 MHz, CDCl$_3$) δ 9.67 (br, 1H), 7.65 (d, J=7.0 Hz, 1H), 7.41-7.37 (m, 2H), 7.32-7.24 (m, 4H), 7.21-7.12 (m, 2H), 7.05-7.01 (m, 1H), 7.00-6.86 (m, 2H), 4.61 (br, 1H), 4.04-4.00 (m, 2H), 3.38 (t, J=10.8 Hz, 2H), 3.25 (br, 2H), 2.55 (s, 3H), 2.40-2.20 (m, 4H), 1.94-1.83 (m, 10H), 1.63-1.61 (m, 2H). HRMS m/z (M+H)+ calcd: 567.3135, obsd: 567.3130.

Example 471

Preparation of 3-fluoro-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenol

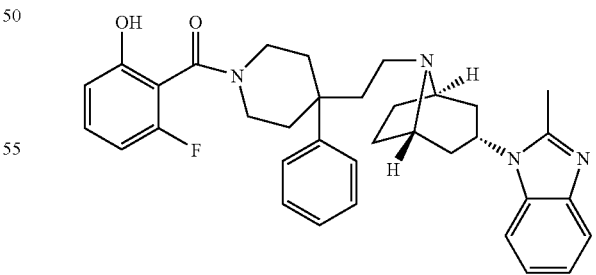

3-Fluoro-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenol (53 mg, 78%) was obtained as a foam from 2-methyl-1-{8-[2-(4-phenyl piperidin-4-yl)ethyl]-8-azabicyclo[3.2.1]oct-3-yl}-1H-benzimidazole (51 mg, 0.12 mmol), 6-fluoro-2-hydroxy-benzoic acid (19 mg, 0.12 mmol) and HATU (47 mg, 0.12 mmol), following the procedure outlined in example 5. $^1$H NMR (400 MHz, CDCl$_3$) δ 7.65 (d, J=8.6 Hz, 1H), 7.44-7.36 (m, 2H), 7.31-7.24 (m, 3H), 7.22-7.12 (m, 4H), 6.97 (d, J=8.4 Hz, 1H), 6.58 (t, J=9.0 Hz, 1H), 4.64-4.55 (m, 1H), 4.20 (br, 1H), 3.59 (br, 1H), 3.33 (br, 2H), 2.54 (s, 3H), 2.39-2.20 (m, 4H), 1.99-1.81 (m, 10H), 1.60 (d, J=7.1 Hz, 2H). HRMS m/z (M+H)$^+$ calcd: 567.3135, obsd: 567.3117.

Example 472

Preparation of 5-chloro-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenol

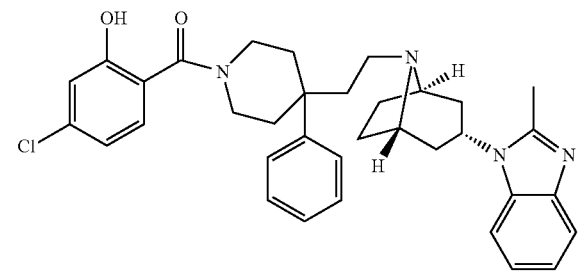

5-Chloro-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenol (46 mg, 66%) was obtained as a foam from 2-methyl-1-{8-[2-(4-phenylpiperidin-4-yl)ethyl]-8-azabicyclo[3.2.1]oct-3-yl}-1H-benzimidazole (51 mg, 0.12 mmol), 4-chloro-2-hydroxybenzoic acid (21 mg, 0.12 mmol) and HATU (47 mg, 0.12 mmol), following the procedure outlined in example 5. $^1$H NMR (400 MHz, CDCl$_3$) δ 7.66 (d, J=7.3 Hz, 1H), 7.41-7.37 (m, 2H), 7.32-7.24 (m, 4H), 7.21-7.12 (m, 3H), 7.02 (s, 1H), 6.82 (d, J=6.4 Hz, 1H), 4.60 (br, 1H), 4.02-3.99 (m, 2H), 3.41-3.35 (m, 2H), 3.25 (br, 2H), 2.56 (s, 3H), 2.36-2.29 (m, 4H), 1.94-1.84 (m, 10H), 1.63-1.62 (m, 2H). HRMS m/z (M+H)$^+$ calcd: 583.2840, obsd: 583.2839.

Preparation of Meta- and Para-N-Substituted Sulfonamides

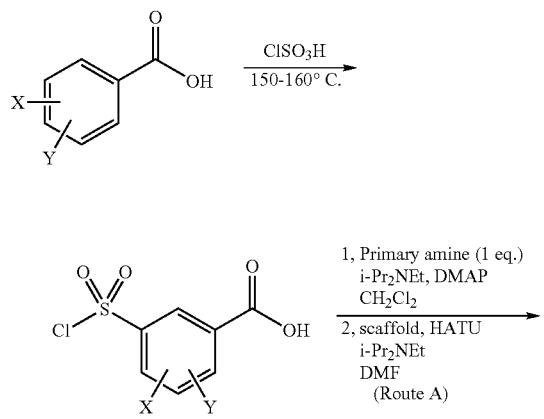

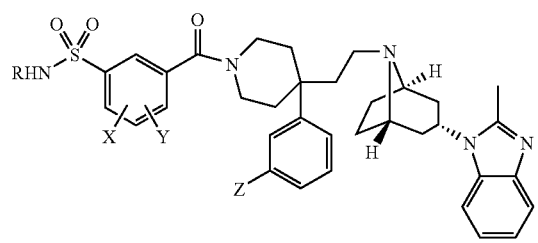

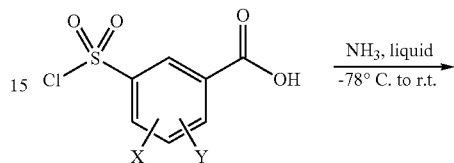

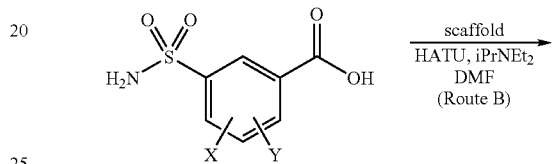

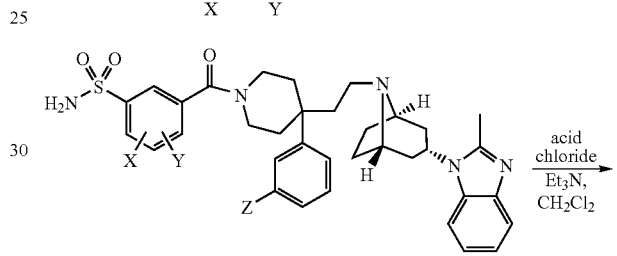

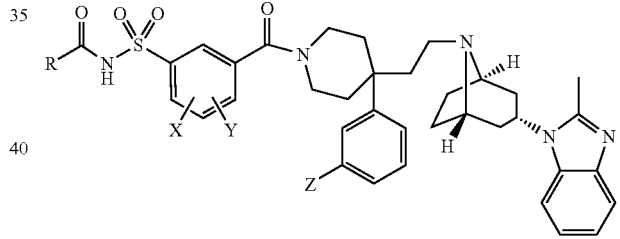

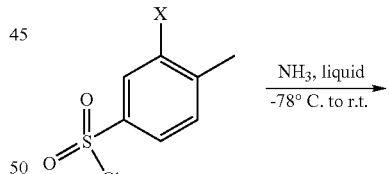

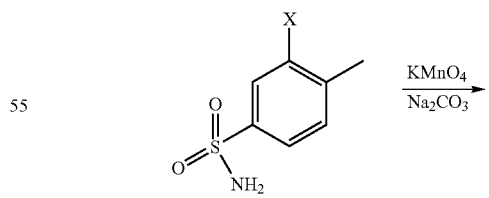

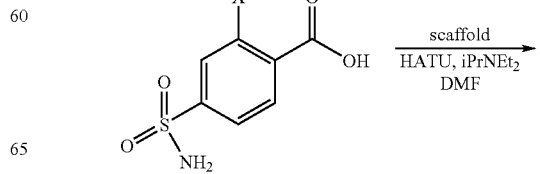

-continued

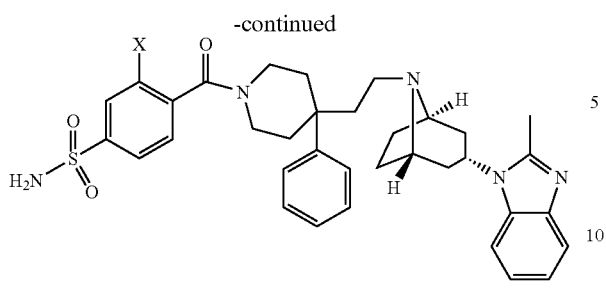

4-Chloro-3-(chlorosulfonyl)benzoic acid has been synthesized as described elsewhere in this application (Method G).

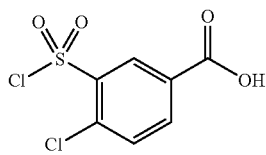

3-(Aminosulfonyl)-4-fluorobenzoic acid has been synthesized according to as Method G detailed elsewhere in this application.

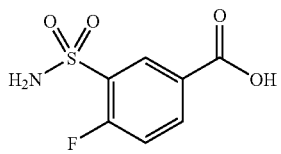

2,6-Difluoro-3-(aminosulfonyl)benzoic acid, 2,6-dichloro-3-(aminosulfonyl)benzoic acid, 3,4-difluoro-5-(aminosulfonyl)benzoic acid and 2,6-methyl-3-(aminosulfonyl)benzoic acid were prepared with the similar procedure as above.

Preparation of 3-fluoro-4-methylbenzenesulfonamide

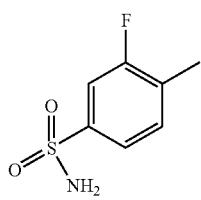

To ~20 mL of liquid ammonia at −78° C. was added 2.1 g (10 mmol) of 3-fluoro-4-methyl benzenesulfonyl chloride. The excess ammonia was then naturally evaporated to dryness overnight at room temperature. The crude sulfonamide was partitioned methylene chloride (100 mL) and water (100 mL). The aqueous phase was further extracted with methylene chloride. The combined organic extracts were dried over anhydrous sodium sulfate. Evaporation of the solvents afforded 1.9 g of 3-fluoro-4-methylbenzenesulfonamide as a solid.

Preparation of 4-(aminosulfonyl)-2-fluorobenzoic acid

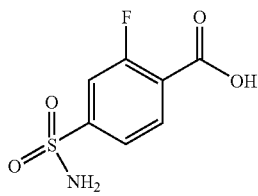

To a stirred solution of 3-fluoro-4-methyl-benzenesulfonamide (prepared above) in 50 mL of water was added sodium carbonate (0.53 g, 5 mmol) and potassium permanganate (3.16 g, 20 mmol) portionwise over three hours at 50~60° C. The resulting mixture was stirred for further 8 hours at this temperature before 0.2 mL of formic acid was added to quench the excess of potassium permanganate. The mixture was then filtered through celite while it was still hot and further washed with the hot water. The filtrate was concentrated to ~30 mL and adjusted to pH 9~10. The filtration was applied again to remove non-oxidized starting material. The final filtrate was acidified with HCl (conc.) to ~pH 1 and 4-(aminosulfonyl)-2-fluorobenzoic acid was precipitated and collected by filtration as white solid (1.10 g, 50%).

The corresponding 4-(aminosulfonyl)-2-chlorobenzoic acid was prepared by the similar procedures.

Example 473

Preparation of 2-chloro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide

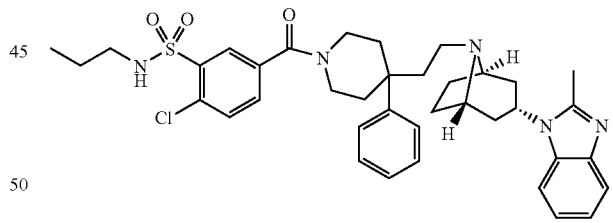

To a stirred solution of 4-chloro-3-(chlorosulfonyl)benzoic acid (25.4 mg, 0.1 mmol) in dichloromethane (3 mL) was added propylamine (9 μL, 0.11 mmol), N,N-diisopropylethylamine (39 mg, 0.3 mmol) and 4-N,N-dimethylaminopyridine (2 mg, 0.016 mmol). After the resultant mixture was stirred overnight, a solution of 2-methyl-1-{(1R,5S)-8-[2-(4-phenyl piperidin-4-yl)ethyl]-8-azabicyclo[3.2.1]oct-3-yl}-1H-benzimidazole dihydrochloride (50 mg, 0.1 mmol) in N,N-dimethylforamide (3 mL) was added and followed by addition of N,N-diisopropylethylamine (39 mg, 0.3 mmol) and HATU (38 mg. 0.1 mmol). The reaction mixture was stirred for further 4 hours before it was quenched with saturated sodium bicarbonate solution and extracted with dichloromethane. The combined organic extracts were dried over anhydrous sodium sulfate. After evaporation of solvents, the residue was purified by flash chromatography, eluting with a gradient of 0-8% methanol in ethyl acetate to afford 2-chloro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide as solid (30 mg, 43%). $^1$H NMR (400 MHz, CDCl$_3$) δ 8.09 (s, 1H), 7.65 (d, J=8.4 Hz, 1H), 7.65 (s, 2H), 7.38 (t, J=7.5 Hz, 2H), 7.30-7.23 (m, 4H), 7.19-7.12 (m, 2H), 5.10 (t, J=6.0 Hz, 1H), 4.64-4.59 (m, 1H), 4.19 (br, 1H), 3.48 (br, 1H), 3.34-3.35 (m, 4H), 2.90 (q, J=6.3 Hz, 2 H), 2.57 (s, 3H), 2.42-2.34 (m, 3H), 2.20 (br, 1H), 1.94-1.78 (m, 10H), 1.62 (d, J=6.4 Hz, 2H), 1.54-1.45 (m, 2H), 0.88 (t, J=7.5 Hz, 3H). HRMS m/z (M+H)$^+$ calcd: 688.3088, obsd: 688.3063.

Example 474

Preparation of 2-chloro-N-isopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

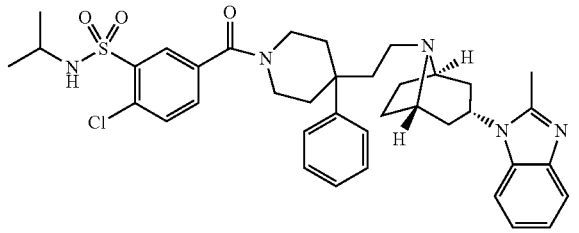

2-Chloro-N-isopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (10 mg, 15%) was obtained as solid from 4-chloro-3-(chlorosulfonyl)benzoic acid (25.4 mg, 0.1 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (50 mg, 0.1 mmol) and isopropylamine (9.4 μL, 0.11 mmol) following the procedure outlined in example 473. $^1$H NMR (300 MHz, CDCl$_3$) δ 8.11 (s, 1H), 7.67 (d, J=7.0 Hz, 1H), 7.57 (s, 2H), 7.42-7.37 (m, 2H), 7.30-7.20 (m, 4H), 7.18-7.12 (m, 2H), 4.89 (d, J=7.5 Hz, 1H), 4.64-4.59 (m, 1H), 4.18 (br, 1H), 3.49-3.29 (m, 6H), 2.58 (s, 3H), 2.38-2.16 (m, 4H), 1.95-1.88 (m, 10H), 1.65-1.63 (m, 2H), 1.10 (d, J=6.5 Hz, 6H). HRMS m/z (M+H)$^+$ calcd: 688.3088, obsd: 688.3093.

Example 475

Preparation of 2-chloro-N-cyclopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

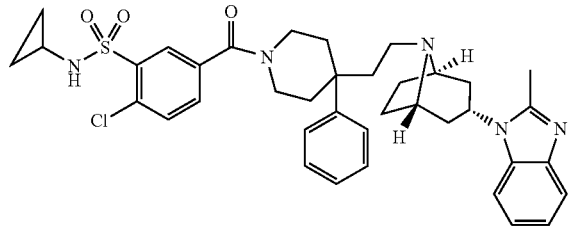

2-Chloro-N-cyclopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (15 mg, 22%) was obtained as solid from 4-chloro-3-(chlorosulfonyl)benzoic acid (25.4 mg, 0.1 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (50 mg, 0.1 mmole), cyclopropylamine (7.6 μL, 0.11 mmol) and HATU (38 mg, 0.1 mmol) following the procedure outlined in example 473. $^1$H NMR (400 MHz, CDCl$_3$) δ 8.14 (s, 1H), 7.66 (d, J=7.0 Hz, 1H), 7.59 (s, 2H), 7.41-7.37 (m, 2H), 7.30-7.20 (m, 4H), 7.18-7.13 (m, 2H), 5.46 (s, 1H), 4.65-4.60 (m, 1H), 4.19 (br, 1H), 3.50 (br, 1H), 3.35-3.26 (m, 4H), 2.57 (s, 3H), 2.43-2.35 (m, 3H), 2.19 (br, 2H), 1.94-1.78 (m, 10H), 1.63 (d, J=7.9 Hz, 2H), 0.68-0.58 (m, 4H). HRMS m/z (M+H)$^+$ calcd: 686.2932, obsd: 686.2935.

Example 476

Preparation of N-acetyl-4-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide

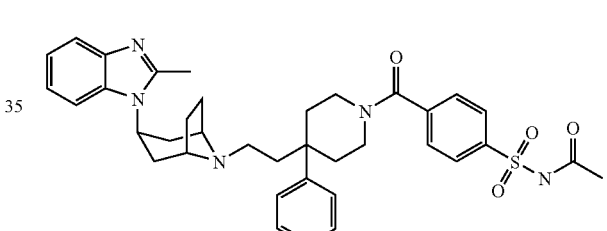

To a precooled (0° C.) solution of 4-[(4-{2-[3-(2-methyl-1H-benzimidazol-1-yl)-8-azabicyclo[3.2.1]oct-8-yl]ethyl}-4-phenylpiperidin-1-yl)carbonyl]-benzene-sulfonamide (20 mg, 0.033 mmol) in dichloromethane (2 mL) was added acetyl bromide (4.2 mg, 0.034 mmol) and N,N-diisopropylethyl amine (12 μL, 0.66 mmol). The resulting mixture was stirred overnight at ambient temperature. After evaporation of the solvent, the crude product was purified by flash chromatography on silical gel, eluting with a gradient of 15-30% methanol in ethyl acetate to afford N-acetyl-4-[(4-{2-[3-(2-methyl-1H-benzimidazol-1-yl)-8-azabicyclo[3.2.1]oct-8-yl]ethyl}-4-phenylpiperidin-1-yl)carbonyl]benzene-sulfonamide as amorphous solid (14 mg, 66%). $^1$H NMR (300 MHz, DMSO-d$_6$) δ 7.83 (d, J=8.1 Hz, 2H), 7.48-7.46 (m, 3H), 7.37-7.33 (m, 5H), 7.21 (br, 1H), 7.13-7.05 (m, 2H), 4.51 (t, J=8.1, 1H), 3.88 (br, 1H), 3.67-3.15 (m, 6H), 2.42 (s, 3H), 2.37-2.30 (m, 2H), 2.11-2.07 (br, 2H), 1.96-1.72 (m, 13H), 1.59 (d, J=7.4, 2H). HRMS m/z (M+H)$^+$ calcd: 654.3114, obsd: 654.3095.

Example 477

Preparation of 4-[(4-{2-[3-(2-methyl-1H-benzimidazol-1-yl)-8-azabicyclo-[3.2.1]oct-8-yl]ethyl}-4-phenylpiperidin-1-yl)carbonyl]-N-propionylbenzenesulfonamide

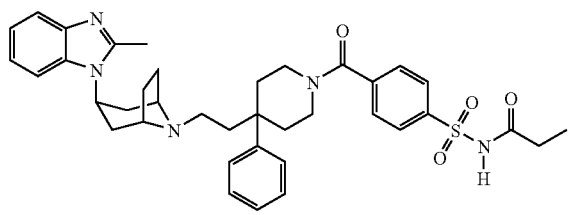

4-[(4-{2-[3-(2-Methyl-1H-benzimidazol-1-yl)-8-azabicyclo[3.2.1]oct-8-yl]ethyl}-4-phenylpiperidin-1-yl)carbonyl]-N-propionylbenzenesulfonamide (13 mg, 59%) was obtained from 4-[(4-{2-[3-(2-methyl-1H-benzimidazol-1-yl)-8-azabicyclo[3.2.1]oct-8-yl]ethyl}-4-phenylpiperidin-1-yl)carbonyl]-benzenesulfonamide (20 mg, 0.033 mmol) and propionyl chloride as amorphous solid by the similar procedure outlined in example 476. $^1$H NMR (300 MHz, DMSO-$d_6$) δ 7.87 (d, J=8.0 Hz, 2H), 7.53-7.42 (m, 3H), 7.39-7.35 (m, 5H), 7.25-7.21 (m, 1H), 7.15-7.07 (m, 2H), 4.66 (br, 1H), 3.90 (br, 1H), 3.19-3.16 (m, 5H), 2.45 (s, 3H), 2.42-2.35 (m, 2H), 2.22-2.09 (m, 5H), 1.98-1.78 (m, 10H), 1.66 (d, J=7.3 Hz, 2H), 1.17 (t, J=7.2 Hz, 3H). HRMS m/z (M+H)$^+$ calcd: 668.3271, obsd: 668.3256.

Example 478

Preparation of N-butyryl-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide

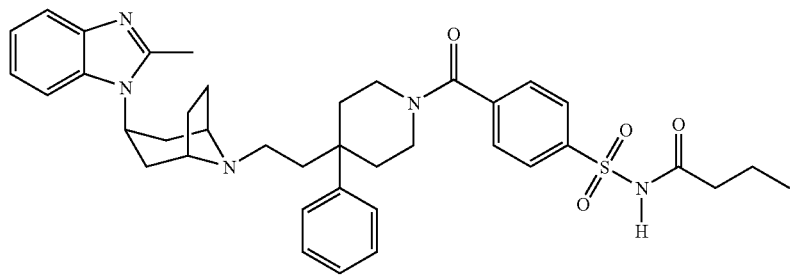

N-butyryl-4-[(4-{2-[3-(2-methyl-1H-benzimidazol-1-yl)-8-azabicyclo-[3.2.1]oct-8-yl]ethyl}-4-phenylpiperidin-1-yl)carbonyl]benzenesulfonamide (15 mg, 68%) was obtained from 4-[(4-{2-[3-(2-methyl-1H-benzimidazol-1-yl)-8-azabicyclo[3.2.1]oct-8-yl]ethyl}-4-phenylpiperidin-1-yl)carbonyl]-benzenesulfonamide (20 mg, 0.033 mmol) and butyryl chloride by the similar procedure outlined in example 476. $^1$H NMR (300 MHz, DMSO-$d_6$) δ 7.87 (d, J=8.1 Hz, 2H), 7.52-7.4 (m, 3H), 7.39-7.35 (m, 5H), 7.25-7.21 (m, 1H), 7.15-7.07 (m, 2H), 4.69 (br, 1H), 3.89 (br, 1H), 3.16 (m, 5H), 2.45 (s, 3H), 2.42-2.35 (m, 2H), 2.23-2.05 (m, 5H), 1.98-1.78 (m, 10H), 1.68-1.66 (m, 2H), 1.40 (q, J=7.3 Hz, 2H), 17 (t, J=7.3 Hz, 3H). HRMS m/z (M+H)$^+$ calcd: 682.3427, obsd: 682.3426.

Example 479

Preparation of N-isobutyryl-4-[(4-{2-[3-(2-methyl-1H-benzimidazol-1-yl)-8-azabicyclo[3.2.1]oct-8-yl]ethyl}-4-phenylpiperidin-1-yl)carbonyl]benzene sulfonamide

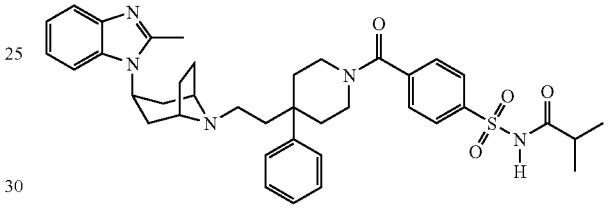

N-isobutyryl-4-[(4-{2-[3-(2-methyl-1H-benzimidazol-1-yl)-8-azabicyclo-[3.2.1]oct-8-yl]ethyl}-4-phenylpiperidin-1-yl)carbonyl]benzenesulfonamide (14 mg, 64%) was obtained from 4-[(4-{2-[3-(2-methyl-1H-benzimidazol-1-yl)-8-azabicyclo[3.2.1]oct-8-yl]ethyl}-4-phenylpiperidin-1-yl)carbonyl]-benzenesulfonamide (20 mg, 0.033 mmol) and isobutyryl chloride by the similar procedure outlined in example 476. $^1$H NMR (300 MHz, DMSO-$d_6$) δ 7.84 (d, J=8.2 Hz, 2H), 7.50-7.47 (m, 3H), 7.41-7.35 (m, 5H), 7.25-7.21 (m, 1H), 7.15-7.07 (m, 2H), 4.60 (br, 1H), 3.90 (br, 1H), 3.75-3.16 (m, 5H), 2.45 (s, 3H), 2.42-2.23 (m, 3H), 2.13-2.08 (m, 2H), 1.98-1.78 (m, 11H), 1.65-1.62 (m, 2H), 0.92 (d, J=6.8 Hz, 6H). HRMS m/z (M+H)$^+$ calcd: 682.3427, obsd: 682.3408.

Example 480

Preparation of N-acetyl-2-chloro-5-[(4-{2-[3-(2-methyl-1H-benzimidazol-1-yl)-8-azabicyclo[3.2.1]oct-8-yl]ethyl}-4-phenylpiperidin-1-yl)carbonyl]benzene-sulfonamide

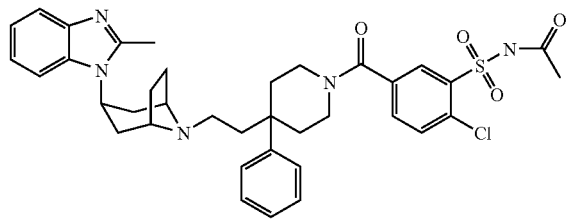

N-acetyl-2-chloro-5-[(4-{2-[3-(2-methyl-1H-benzimida-zol-1-yl)-8-azabicyclo[3.2.1]oct-8-yl]ethyl}-4-phenylpiperidin-1-yl)carbonyl]benzene-sulfonamide (21.8 mg, quant.) was obtained as amorphous solid from 2-chloro-5-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide and acetyl bromide following the procedure outlined in example 476. $^1$H NMR (300 MHz, DMSO-$d_6$) δ 7.85-7.50 (m, 3H), 7.49 (d, J=8.5 Hz, 1H), 7.41-7.35 (m, 5H), 7.25-7.21 (m, 1H), 7.15-7.09 (m, 2H), 4.54 (br, 1H), 3.96 (br, 1H), 3.42-3.29 (m, 5H), 3.06-3.03 (m, 1H), 2.45-2.36 (m, 5H), 2.17-2.07 (m, 2H), 1.98-1.75 (m, 10H), 1.71-1.70 (m, 3H), 1.63-1.61 (m, 2H). HRMS m/z (M+H)$^+$ calcd: 688.2724, obsd: 688.2745.

Example 481

Preparation of 2-chloro-5-[(4-{2-[3-(2-methyl-1H-benzimidazol-1-yl)-8-azabicyclo[3.2.1]oct-8-yl]ethyl}-4-phenylpiperidin-1-yl)carbonyl]-N-propionyl benzenesulfonamide

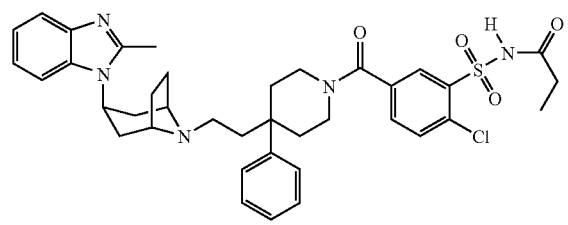

2-Chloro-5-[(4-{2-[3-(2-methyl-1H-benzimidazol-1-yl)-8-azabicyclo-[3.2.1]oct-8-yl]ethyl}-4-phenylpiperidin-1-yl)carbonyl]-N-propionylbenzene-sulfonamide (16 mg, 73%) was obtained as amorphous solid from 2-chloro-5-[(4-{2-[3-(2-methyl-1H-benzimidazol-1-yl)-8-azabicyclo[3.2.1]oct-8-yl]ethyl}-4-phenyl piperidin-1-yl)carbonyl]benzenesulfonamide and propionyl chloride following the procedure outlined in example 476. $^1$H NMR (300 MHz, DMSO-$d_6$) δ 7.81-7.56 (m, 3H), 7.49 (d, J=8.4 Hz, 1H), 7.39-7.26 (m, 5H), 7.24-7.08 (m, 3H), 4.80 (br, 1H), 3.99-3.93 (m, 1H), 3.58-3.38 (m, 5H), 3.11-2.99 (m, 1H), 2.47 (m, 4H), 2.22-1.72 (m, 17H), 0.89-0.81 (m, 3H). HRMS m/z (M+H)$^+$ calcd: 702.2881, obsd: 702.2885.

Example 482

Preparation of 2-chloro-N-isobutyryl-5-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide

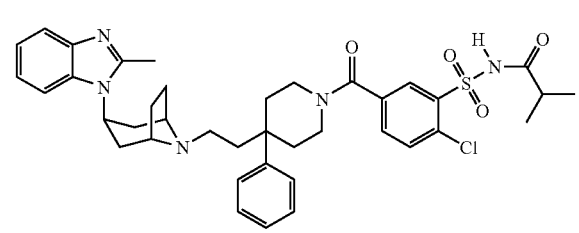

2-Chloro-N-isobutyryl-5-[(4-{2-[3-(2-methyl-1H-benzimidazol-1-yl)-8-azabicyclo[3.2.1]oct-8-yl]ethyl}-4-phenylpiperidin-1-yl)carbonyl]benzene-sulfonamide (19 mg, 80%) was obtained as amorphous solid from 2-chloro-5-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide and isobutyryl chloride following the procedure outlined in example 476. $^1$H NMR (300 MHz, DMSO-$d_6$, 100° C.) δ 7.85-7.76 (m, 2H), 7.60-7.50 (m, 2H), 7.42-7.28 (m, 5H), 7.26 (m, 1H), 7.18-7.12 (m, 2H), 4.76 (br, 1H), 3.36-3.08 (m, 7H), 2.53-2.27 (m, 7H), 2.04-1.82 (m, 10H), 1.69 (d, J=7.6 Hz, 2H), 0.95 (d, J=6.6 Hz, 6H). HRMS m/z (M+H)$^+$ calcd: 716.3037, obsd: 716.3013.

Example 483

Preparation of 2-fluoro-5-[(4-{2-[(1R,5S)-3-(2-methyl-1H-benzimidazol-1-yl-8-azabicyclo[3.2.1]oct-8-yl]ethyl}-4-phenylpiperidin-1-yl)carbonyl]benzene-sulfonamide

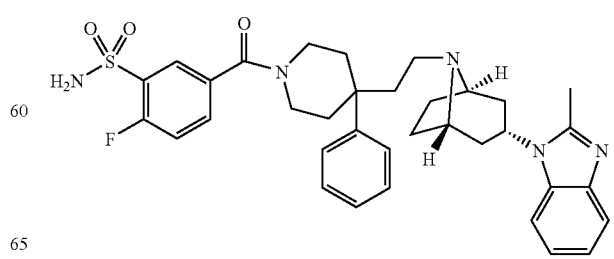

2-Fluoro-5-[(4-{2-[(1R,5S)-3-(2-methyl-1H-benzimidazol-1-yl)-8-azabicyclo[3.2.1]oct-8-yl]ethyl})-4-phenylpiperidin-1-yl)carbonyl]benzenesulfonamide (20 mg, 32%) was obtained as solid from 3-(aminosulfonyl)-4-fluorobenzoic acid (22 mg, 0.1 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (50 mg, 0.1 mmol) and HATU (38 mg, 0.1 mmol) following the procedure outlined in example 5. $^1$H NMR (400 MHz, CDCl$_3$) δ 7.93-7.91 (m, 1H), 7.64-7.58 (m, 2H), 7.40-7.36 (m, 2H), 7.30-7.21 (m, 5H), 7.19-7.12 (m, 2H), 5.61 (br, 1H), 4.66-4.56 (m, 1H), 4.20 (br, 1H), 3.56 (br, 1H), 3.26 (m, 4H), 2.57 (s, 3H), 2.42-2.34 (m, 4H), 2.20 (br, 2H), 1.99-1.83 (m, 9H), 1.62 (m, 2H). HRMS m/z (M+H)$^+$ calcd: 630.2914, obsd: 630.2925.

Example 484

Preparation of 2-fluoro-N-methyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene-sulfonamide

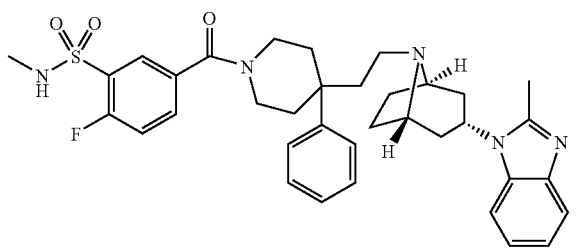

2-Fluoro-N-methyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (53.8 mg, 56%) was obtained as solid from 4-fluoro-3-(chlorosulfonyl)benzoic acid (48 mg, 0.2 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (76 mg, 0.15 mmol) and methylamine (0.10 mL, 2.0 M in THF) following the procedure outlined in example 473. $^1$H NMR (400 MHz, CDCl$_3$) δ 7.92-7.90 (m, 1H), 7.65-7.61 (m, 2H), 7.40-7.36 (m, 2H), 7.30-7.22 (m, 5H), 7.18-7.12 (m, 2H), 5.29 (d, J=4.9 Hz, 1H), 4.63-4.58 (m, 1H), 4.18 (br, 1H), 3.50 (br, 1H), 3.32-3.25 (m, 4H), 2.71 (d, J=4.1 Hz, 3H), 2.56 (s, 3H), 2.41-2.33 (m, 3H), 2.16 (br, 2H), 1.92-1.81 (m, 10H), 1.64-1.58 (m, 2H). HRMS m/z (M+H)$^+$ calcd: 644.3071, obsd: 644.3061.

Example 485

Preparation of N-ethyl-2-fluoro-5-[(4-{2-[(1R,5S)-3-(2-methyl-1H-benzimidazol-1-yl)-8-azabicyclo[3.2.1]oct-8-yl]ethyl}-phenylpiperidin-1-yl)carbonyl]benzene-sulfonamide

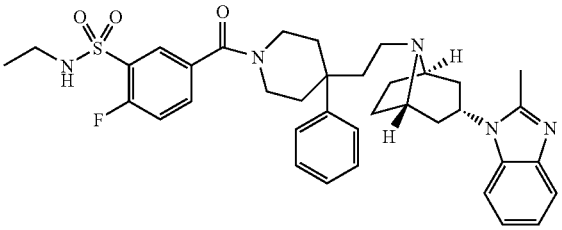

N-Ethyl-2-fluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (30.5 mg, 30%) was obtained as solid from 4-fluoro-3-(chlorosulfonyl)benzoic acid (48 mg, 0.2 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (76 mg, 0.15 mmol) and ethylamine (0.10 mL, 2.0 M in THF) following the procedure outlined in example 473. $^1$H NMR (400 MHz, CDCl$_3$) δ 7.93-7.90 (m, 1H), 7.66-7.61 (m, 2H), 7.40-7.36 (m, 2H), 7.30-7.22 (m, 5 H), 7.19-7.12 (m, 2H), 4.94 (t, J=6.1 Hz, 1H), 4.65-4.57 (m, 1H), 4.17 (br, 1H), 3.50 (br, 1H), 3.26 (br, 4H), 3.11-3.04 (m, 2H), 2.56 (s, 3H), 2.42-2.34 (m, 3H), 2.20-2.17 (m, 1H), 1.94-1.82 (m, 10H), 1.64 (d, J=6.4 Hz, 2H), 1.13 (t, J=7.1 Hz, 3H). HRMS m/z (M+H)$^+$ calcd: 658.3227, obsd: 658.3237.

Example 486

Preparation of 2-fluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide 2-Fluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzene sulfonamide (41.8 mg, 41%) was obtained as solid from 4-fluoro-3-(chlorosulfonyl)benzoic acid (48 mg, 0.2 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (76 mg, 0.15 mmol) and propylamine (16.5 μL, 0.2 mmol) following the procedure outlined in example 473. $^1$H NMR (400 MHz, CDCl$_3$) δ 7.92-7.90 (m, 1H), 7.66-7.61 (m, 2H), 7.40-7.36 (m, 2H), 7.30-7.22 (m, 5H), 7.19-7.12 (m, 2H), 5.03 (t, J=6.0 Hz, 1H), 4.64-4.56 (m, 1H), 4.18 (br, 1H), 3.50 (br, 1H), 3.33-3.25 (m, 4H), 2.97 (q, J=6.8 Hz, 2H), 2.56 (s, 3H), 2.42-2.34 (m, 3H), 2.19 (br, 1H), 2.10 (s, 1H), 1.93-1.82 (m, 10H), 1.62 (d, J=6.4 Hz, 2H), 1.55-1.46 (m, 2H), 0.88 (t, J=7.5 Hz, 3H). HRMS m/z (M+H)+ calcd: 672.3384, obsd: 672.3380.

Example 487

Preparation of 2-fluoro-N-isopropyl-5-[(4-{2-[(1R, 5S)-3-(2-methyl-1H-benzimidazol-1-yl)-8-azabicyclo[3.2.1]oct-8-yl]ethyl}-4-phenylpiperidin-1-yl) carbonyl]benzene sulfonamide

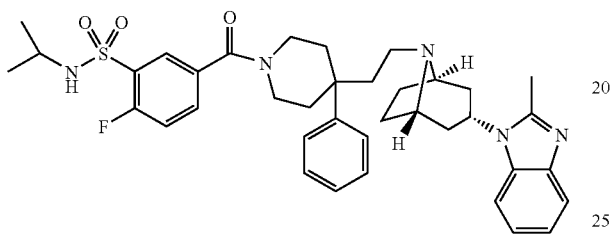

2-Fluoro-N-isopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (35.6 mg, 35%) was obtained as solid from 4-fluoro-3-(chlorosulfonyl)benzoic acid (48 mg, 0.2 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (76 mg, 0.15 mmol) and isopropylamine (17 μL, 0.2 mmol) following the procedure outlined in example 473. ¹H NMR (400 MHz, CDCl₃) δ 7.94-7.91 (m, 1H), 7.67-7.61 (m, 2H), 7.40-7.37 (m, 2H), 7.30-7.22 (m, 5H), 7.19-7.12 (m, 2H), 4.75 (d, J=7.5 Hz, 1H), 4.65-4.60 (m, 1H), 4.19 (br, 1H), 3.56-3.48 (m, 2H), 3.33-3.26 (br, 4H), 2.57 (s, 3H), 2.41-2.34 (m, 3H), 2.19-2.17 (br, 1H), 1.94-1.82 (m, 11H), 1.62 (d, J=7.9 Hz, 2H), 1.11 (d, J=6.4 Hz, 6H). HRMS m/z (M+H)+ calcd: 672.3384, obsd: 672.3398.

Example 488

Preparation of N-cyclopropyl-2-fluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

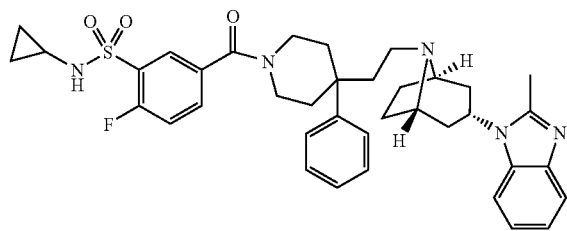

N-Cyclopropyl-2-fluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (43.0 mg, 43%) was obtained as solid from 4-fluoro-3-(chlorosulfonyl)benzoic acid (48 mg, 0.2 mmol), cyclopropyl amine (14 μL, 0.2 mmol) and 2-methyl-1-{(1R,5S)-8-[2-(4-phenylpiperidin-4-yl)ethyl]-8-azabicyclo[3.2.1]oct-3-yl}-1H-benzimidazole dihydrochloride (76 mg, 0.15 mmol) following the procedure outlined in example 473. ¹H NMR (400 MHz, CDCl₃) δ 7.97-7.95 (m, 1H), 7.69-7.64 (m, 2H), 7.40-7.36 (m, 2H), 7.30-7.23 (m, 5H), 7.19-7.12 (m, 2H), 5.47 (s, 1H), 4.64-4.56 (m, 1H), 4.19 (br, 1H), 3.51 (br, 1H), 3.33-3.26 (m, 4H), 2.56 (s, 3H), 2.41-2.28 (m, 3H), 2.27-2.17 (m, 2H), 1.99-1.82 (m, 12H), 1.62 (d, J=7.9 Hz, 2H), 0.68-0.60 (m, 4H). HRMS m/z (M+H)+ calcd: 670.3227, obsd: 670.3213.

Example 489

Preparation of 2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

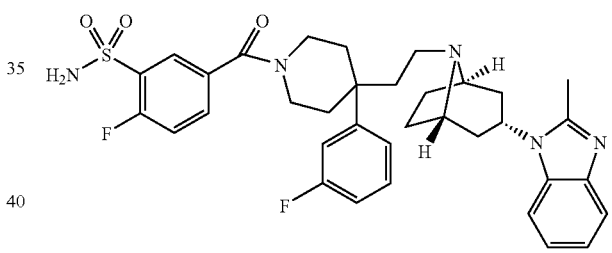

2-Fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (35 mg, 54%) was obtained as solid from 3-(aminosulfonyl)-4-fluorobenzoic acid (22 mg, 0.1 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.10 mmol) following the procedure outlined in example 473. ¹H NMR (400 MHz, CDCl₃), δ 7.96 (dd, J=6.8 Hz, 2.1 Hz, 1H), 7.63-7.61 (m, 1H), 7.59-7.55 (m, 1H), 7.37-7.32 (m, 1H), 7.29-7.20 (m, 2H), 7.18-7.10 (m, 2H), 7.06 (d, J=8.0 Hz, 1H), 6.99-6.90 (m, 2H), 6.04 (br, 2H), 4.66 (t, J=8.8 Hz, 1H), 4.14-4.08 (m, 1H), 3.50 (br, 1H), 3.9 (br, 4H), 2.52 (s, 3H), 2.44-2.36 (m, 2 H), 2.24 (br, 1H), 2.09 (br, 1H), 1.96-1.84 (m, 10H), 1.65 (d, J=7.8 Hz, 2H). HRMS m/z (M+H)+ calcd: 648.2820, obsd: 648.2822.

Example 490

Preparation of N-cyclopropyl-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

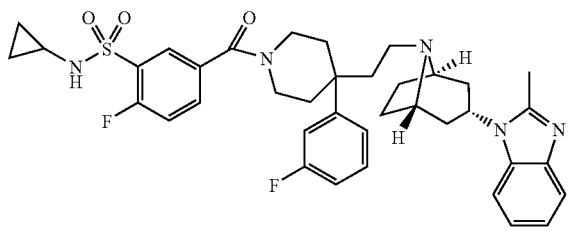

N-Cyclopropyl-2-fluoro-5-[(4-(3-fluoro phenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (22 mg, 32%) was obtained as solid from 4-fluoro-3-(chlorosulfonyl) benzoic acid (48 mg, 0.2 mmol), cyclopropyl amine (14 μL, 0.2 mmol) and 1-((1R,5S)-8-{2-[4-(3-fluorophenyl) piperidin-4-yl]ethyl}-8-azabicyclo[3.2.1]oct-3-yl)-2-methyl-1H-benzimidazole dihydrochloride (52 mg, 0.1 mmol) following the procedure outlined in example 473. $^1$H NMR (400 MHz, CDCl$_3$), δ 7.96 (dd, J=6.7 Hz, 2.2 Hz, 1H), 7.69-7.65 (m, 2H), 7.39-7.33 (m, 1H), 7.30-7.25 (m, 2H), 7.19-7.12 (m, 2H), 7.07 (d, J=8.0 Hz, 1H), 7.01-6.94 (m, 2H), 5.39 (s, 1H), 4.66 (br, 1H), 4.16 (br, 1H), 3.54 (br, 1H), 3.48-3.28 (m, 4H), 2.58 (s, 3H), 2.44-2.37 (m, 2H), 2.29-2.20 (m, 2H), 2.13 (br, 1H), 1.97-1.81 (m, 10H), 1.66 (d, J=7.9 Hz, 2H), 0.68-0.61 (m, 4H). HRMS m/z (M+H)$^+$ calcd: 688.3133, obsd: 688.3146.

Example 491

2,4-difluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide Preparation of 3-(chlorosulfonyl)-2,6-difluorobenzoic acid

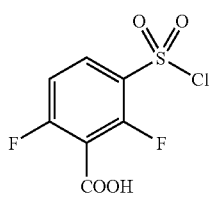

3-(Chlorosulfonyl)-2,6-difluorobenzoic acid (8.6 g, 67%) was obtained as solid from 2,6-difluorobenzic acid (8 g, 50 mmol), following the procedure outlined in the preparation of 4-chloro-3-(chlorosulfonyl)benzoic acid.

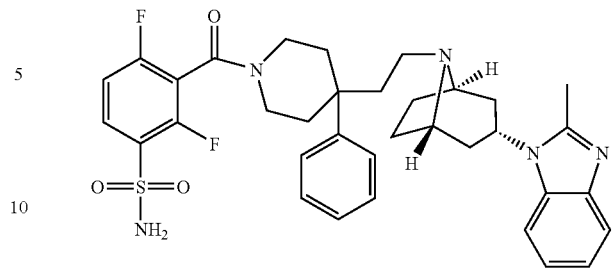

2,4-Difluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (22 mg, 34%) was obtained as solid from 3-(aminosulfonyl)-2,6-difluorobenzoic acid (24 mg, 0.1 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (50 mg, 0.10 mmol) and HATU (38 mg, 0.1 mmol) following the procedure outlined in example 473. $^1$H NMR (400 MHz, CDCl$_3$) δ 8.00-7.89 (m, 1H), 7.64 (d, J=7.7 Hz, 1H), 7.40-7.34 (m, 2H), 7.30-7.24 (m, 4H), 7.19-7.12 (m, 2H), 7.07-6.97 (m, 1H), 5.6 (br, 2H), 4.66-4.55 (m, 1H), 4.29-4.24 (m, 1H), 3.58-3.31 (m, 2H), 3.25-3.05 (m, 3H), 2.54 (s, 3H), 2.49-2.20 (m, 4H), 1.99-1.76 (m, 10H), 1.62 (d, J=7.7 Hz, 2H). HRMS m/z (M+H)$^+$ calcd: 648.2820, obsd: 648.2834.

Example 492

Preparation of 2,4-difluoro-N-methyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

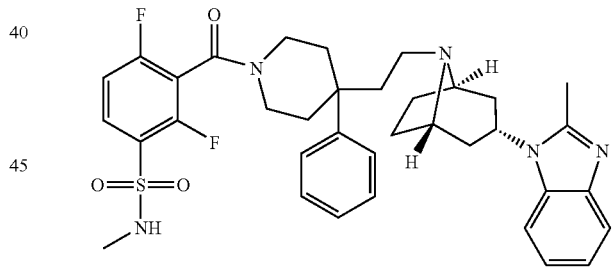

2,4-Difluoro-N-methyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (90 mg, 40%) was obtained as solid from 3-(chlorosulfonyl)-2,6-difluorobenzoic acid (105 mg, 0.4 mmol), 2-methyl-1-{(1R,5S)-8-[2-(4-phenyl piperidin-4-yl)ethyl]-8-azabicyclo[3.2.1]oct-3-yl}-1H-benzimidazole dihydrochloride (177 mg, 0.35 mmol) and methylamine (230 μL, 2.0 M in THF) following the procedure outlined in example 473. $^1$H NMR (400 MHz, CDCl$_3$) δ 7.98-7.92 (m, 1H), 7.67-7.65 (d, 1H), 7.41-7.37 (m, 2H), 7.30-7.28 (m, 4H), 7.21-7.03 (m, 3H), 4.84 (m, 1/2H, rotamer), 4.75-4.71 (m, 1/2H, rotamer), 4.66-4.58 (m, 1H), 3.41-3.20 (m, 5H), 2.74 (d, J=5.1 Hz, 3/2H, rotamer), 2.69 (d, J=5.1 Hz, 3/2H, rotamer), 2.57 (s, 3/2H, rotamer), 2.56 (s, 3/2H, rotamer), 2.41-2.37 (m, 3H), 2.26-2.23 (m, 2H), 1.99-1.77 (m, 9H), 1.69-1.62 (m, 4H). HRMS m/z (M+H)$^+$ calcd: 662.2976, obsd: 662.2982.

Example 493

Preparation of N-ethyl-2,4-difluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

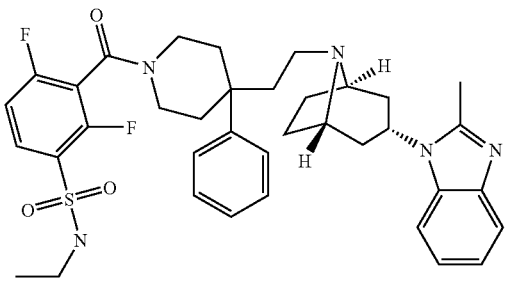

N-Ethyl-2,4-difluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (92 mg, 45%) was obtained as solid from 3-(chlorosulfonyl)-2,6-difluorobenzoic acid (105 mg, 0.4 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (150 mg, 0.30 mmol) and ethylamine (230 µL, 2.0 M in THF) following the procedure outlined in example 473. $^1$H NMR (400 MHz, CDCl$_3$) δ 8.01-7.92 (m, 1H), 7.70 (m, 1/2H, rotamer), 7.66 (d, J=7.1 Hz, 1H), 7.54-7.52 (m, 1/2H, rotamer), 7.41-7.32 (m, 2H), 7.30-7.25 (m, 4H), 7.20-7.13 (m, 2H), 7.11-7.02 (m, 1H), 4.90-4.59 (m, 2H), 4.35-4.27 (m, 2H), 3.42-3.20 (m, 5H), 3.18-2.96 (m, 2H), 2.57 (s, 3/2H, rotamer), 2.56 (s, 3/2H, rotamer), 2.42-2.35 (m, 3H), 2.26-2.23 (m, 1H), 1.99-1.76 (m, 9H), 1.68-1.62 (m, 2H), 0.89-0.82 (m, 3H). HRMS m/z (M+H)$^+$ calcd: 676.3133, obsd: 676.3154.

Example 494

Preparation of 2,4-difluoro-N-isopropyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

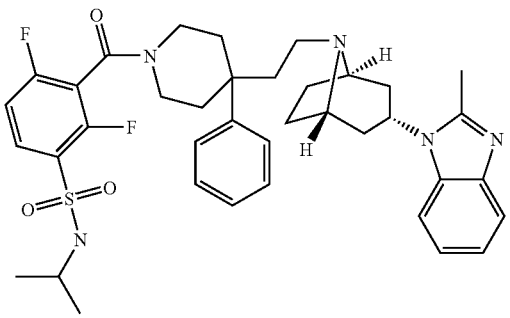

2,4-Difluoro-N-isopropyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (100 mg, 41%) was obtained as solid from 3-(chlorosulfonyl)-2,6-difluorobenzoic acid (105 mg, 0.4 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (177 mg, 0.35 mmol) and isopropylamine (40 µL, 0.45 mmol) following the procedure outlined in example 473. $^1$H NMR (400 MHz, CDCl$_3$) δ 8.01-7.93 (m, 1H), 7.66 (d, J=7.5 Hz, 1H), 7.41-7.37 (m, 2H), 7.30-7.25 (m, 5H), 7.20-7.14 (m, 2H), 7.12-7.01 (m, 1H), 4.80-4.65 (m, 2H), 4.29-4.23 (m, 1H), 3.55-3.49 (m, 1H), 3.40-3.18 (m, 5H), 2.58 (s, 3/2H, rotamer), 2.57 (s, 3/2H, rotamer), 2.40 (br, 3H), 2.24-2.23 (m, 1H), 1.96-1.73 (m, 10H), 1.67-1.65 (m, 2H), 1.21-1.16 (m, 3H), 1.10-1.04 (m, 3H). HRMS m/z (M+H)$^+$ calcd: 690.3289, obsd: 690.3276.

Example 495

Preparation of N-cyclopropyl-2,4-difluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

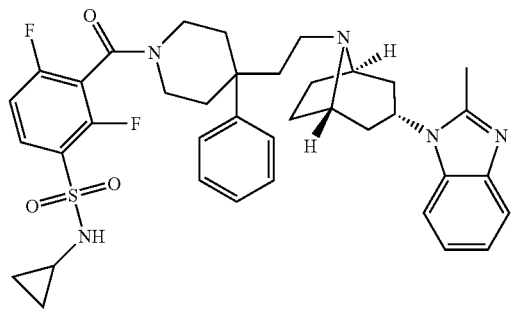

N-Cyclopropyl-2,4-difluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (110 mg, 48%) was obtained as solid from 3-(chlorosulfonyl)-2,6-difluorobenzoic acid (105 mg, 0.4 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (150 mg, 0.30 mmol) and cyclopropylamine (32 µL, 0.45 mmol) following the procedure outlined in example 473. $^1$H NMR (400 MHz, CDCl$_3$) δ 8.02-7.97 (m, 1H), 7.65 (d, J=7.2 Hz, 1H), 7.41-7.37 (m, 2H), 7.30-7.24 (m, 4H), 7.20-7.04 (m, 2H), 5.43 (s, 1/2H, rotamer), 5.31 (s, 1/2H, rotamer), 4.65-4.59 (m, 1H), 4.30-4.27 (m, 1H), 3.39-3.20 (m, 5H), 2.57 (s, 3/2H, rotamer), 2.56 (s, 3/2H, rotamer), 2.42-2.24 (m, 4H), 1.99-1.77 (m, 11H), 1.65-1.60 (m, 2H), 0.80-0.76 (m, 1H), 0.75-0.55 (m, 3H). HRMS m/z (M+H)$^+$ calcd: 688.3133, obsd: 688.3135.

Example 496

Preparation of 2,4-difluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide

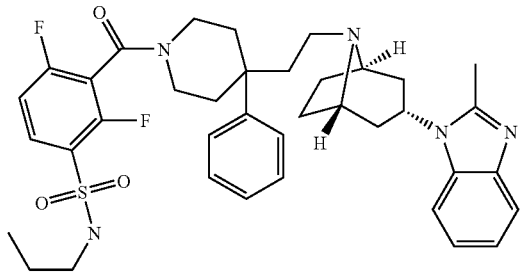

2,4-Difluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide (34.6 mg, 34%) was obtained as solid from 3-(chlorosulfonyl)-2,6-difluorobenzoic acid (52 mg, 0.2 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (76 mg, 0.15 mmol) and propylamine (16.5 µL, 0.2 mmol) following the procedure outlined in example 473. $^1$H NMR (400 MHz, CDCl$_3$), δ 8.01-7.91 (m, 1H), 7.65 (d, J=7.1 Hz, 1H), 7.41-7.37 (m, 2H), 7.30-7.28 (m, 4H), 7.19-7.01 (m, 3H), 4.96 (t, J=5.8 Hz, 1/2H, rotamer), 4.87 (t, J=6.2 Hz, 1/2H, rotamer), 4.65-4.58 (m, 1H), 4.31-4.25 (m, 1H), 3.40-3.23 (m, 5H), 2.57 (s, 3/2H, rotamer), 2.56 (s, 3/2H, rotamer), 2.39-2.37 (m, 3H), 2.25-2.22 (m, 1H), 1.97-1.76 (m, 10H), 1.65-1.63 (m, 2H), 1.56-1.47 (m, 2H), 0.92-0.85 (m, 3H). HRMS m/z (M+H)$^+$ calcd: 690.3289, obsd: 690.3301.

Example 497

Preparation of 2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

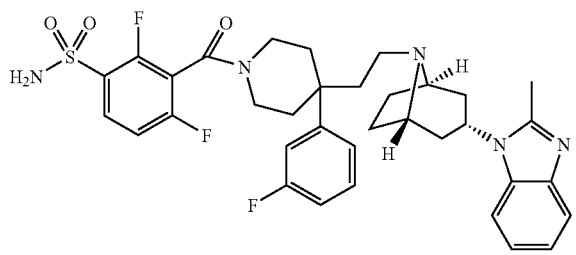

2,4-Difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (10 mg, 15%) was obtained as solid from 3-(aminosulfonyl)-2,6-difluorobenzoic acid (24 mg, 0.1 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.10 mmol) and HATU (38 mg, 0.1 mmol) following the procedure outlined in example 473. $^1$H NMR (400 MHz, CDCl$_3$) δ 8.01-7.92 (m, 1H), 7.65 (d, J=7.7 Hz, 1H), 7.39-7.34 (m, 1H), 7.30-7.26 (m, 1H), 7.21-7.13 (m, 2H), 7.08-6.95 (m, 4H), 5.35 (br, 2H), 4.64-4.60 (m, 1H), 4.26-4.23 (m, 1H), 3.48-3.20 (m, 5H), 2.56 (s, 3H), 2.46-2.17 (m, 4H), 1.99-1.64 (m, 12H). HRMS m/z (M+H)$^+$ calcd: 666.2725, obsd: 666.2746.

Example 498

Preparation of 2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methylbenzenesulfonamide

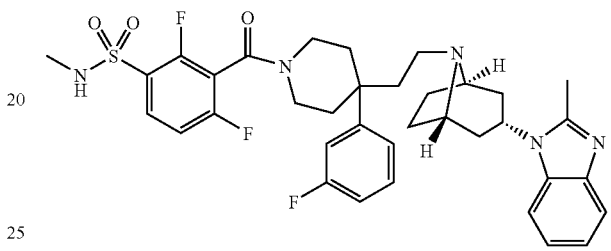

2,4-Difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methylbenzenesulfonamide (14 mg, 21%) was obtained as solid from 2,6-difluoro-3-(chlorosulfonyl)benzoic acid (52 mg, 0.2 mmol), methylamine (120 µL, 2.0 M in THF) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) following the procedure outlined in example 473. $^1$H NMR (400 MHz, CDCl$_3$), δ 7.94 (q, J=8.0 Hz, 1H), 7.65 (d, J=7.3 Hz, 1H), 7.35 (q, J=8.0 Hz, 1H), 7.29 (d, J=8.0 Hz, 1H), 7.19-7.12 (m, 2H), 7.09-7.02 (m, 2H), 6.98-6.94 (m, 2H), 4.99-4.86 (two sets of multiplets, 1H, rotamers), 4.63-4.61 (m, 1H), 4.27-4.23 (m, 1H), 3.41-3.34 (m, 2H), 3.25-3.18 (m, 3H), 2.73 (d, J=5.0 Hz, 3/2H, rotamer), 2.70 (d, J=4.9 Hz, 3/2H, rotamer), 2.57 (s, 3/2H, rotamer), 2.56 (s, 3/2H, rotamer), 2.43-2.28 (m, 3H), 2.22-2.17 (m, 1H), 1.94-1.77 (m, 10H), 1.66-1.63 (m, 2H). HRMS m/z (M+H)$^+$ calcd: 680.2882, obsd: 680.2881.

Example 499

Preparation of N-ethyl-2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

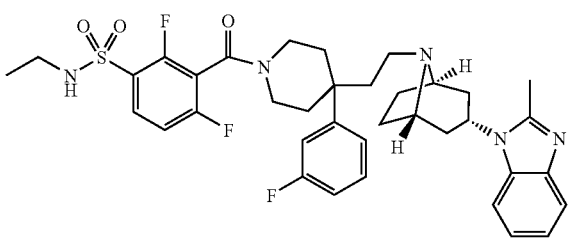

N-Ethyl-2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (16 mg, 23%) was obtained as solid from 2,6-difluoro-3-(chlorosulfonyl) benzoic acid (52 mg, 0.2 mmol), ethylamine (120 μL, 2.0 M in THF) and 1-((1R,5S)-8-{2-[4-(3-fluorophenyl) piperidin-4-yl]ethyl}-8-azabicyclo[3.2.1]oct-3-yl)-2-methyl-1H-benzimidazole dihydrochloride (52 mg, 0.1 mmol) following the procedure outlined in example 473. $^1$H NMR (400 MHz, CDCl$_3$) δ 7.95 (q, J=8.0 Hz, 1H), 7.66 (d, J=8.0 Hz, 1H), 7.36 (q, J=8.0 Hz, 1H), 7.30-7.28 (m, 1H), 7.19-7.12 (m, 2H), 7.09-7.04 (m, 2H), 7.01-6.95 (m, 2H), 4.93-4.84 (two sets of multiplets, 1H, rotamers), 4.64 (br, 1H), 4.27-4.24 (m, 1H), 3.41-3.37 (m, 2H), 3.26-3.25 (m, 3H), 3.22-2.95 (m, 2H), 2.58 (s, 3/2H, rotamer), 2.56 (s, 3/2H, rotamer), 2.43-2.30 (m, 3H), 2.20-2.10 (m, 1H), 1.95-1.78 (m, 10H), 1.66-1.64 (m, 2H), 1.16-1.10 (m, 3H). HRMS m/z (M+H)$^+$ calcd: 694.3039, obsd: 694.3051.

Example 500

Preparation of 2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-propylbenzenesulfonamide

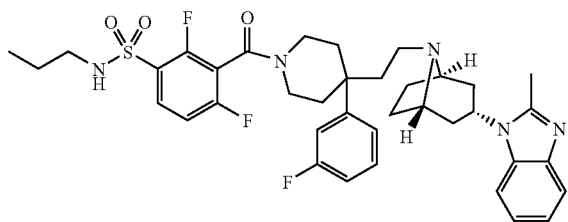

2,4-Difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-propylbenzenesulfonamide (42 mg, 59%) was obtained as solid from 2,6-difluoro-3-(chlorosulfonyl) benzoic acid (52 mg, 0.2 mmol), propylamine (18 μL, 0.22 mmol) and 1-((1R,5S)-8-{2-[4-(3-fluorophenyl) piperidin-4-yl]ethyl}-8-azabicyclo[3.2.1]oct-3-yl)-2-methyl-1H-benzimidazole dihydrochloride (52 mg, 0.1 mmol) following the procedure outlined in example 473. $^1$H NMR (400 MHz, CDCl$_3$) δ 7.95-7.91 (m, 1H), 7.65 (d, J=8.0 Hz, 1H), 7.39-7.35 (m, 1H), 7.30-7.29 (m, 1H), 7.16-7.14 (m, 2H), 7.12-7.04 (m, 2H), 6.96-6.95 (m, 2H), 5.05-4.97 (two sets of multiplets, 1H, rotamers), 4.63-4.57 (m, 1H), 4.26-4.23 (m, 1H), 3.41-3.35 (m, 2H), 3.25-3.21 (m, 4H), 3.04-2.90 (m, 2H), 2.57 (s, 3/2H, rotamer), 2.56 (s, 3/2H, rotamer), 2.39-2.34 (m, 3H), 2.20-2.10 (m, 1H), 1.97-1.80 (m, 10H), 1.65-1.63 (m, 2H), 1.54-1.49 (m, 2H), 0.90-0.85 (m, 3H). HRMS m/z (M+H)$^+$ calcd: 708.3195, obsd: 708.3189.

Example 501

Preparation of 2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-isopropylbenzenesulfonamide

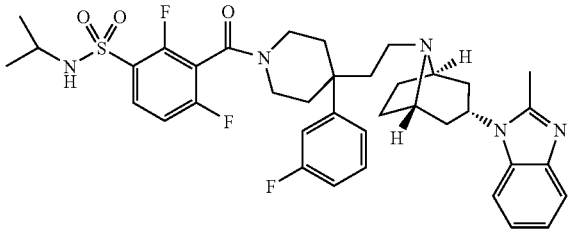

2,4-Difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-isopropylbenzenesulfonamide (40 mg, 56%) was obtained as solid from 2,6-difluoro-3-(chloro sulfonyl)benzoic acid (52 mg, 0.2 mmol), isopropylamine (19 μL, 0.22 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) following the procedure outlined in example 473. $^1$H NMR (400 MHz, CDCl$_3$) δ 7.95 (q, J=7.3 Hz, 1H), 7.65 (d, J=7.1 Hz, 1H), 7.36 (q, J=7.7 Hz, 1H), 7.29 (d, J=7.7 Hz, 1H), 7.19-7.12 (m, 2H), 7.10-7.04 (m, 2H), 7.00-6.94 (m, 2H), 4.91 (d, J=7.7 Hz, 1/2H, rotamer), 4.86 (d, J=7.7 Hz, 1/2H, rotamers), 4.62-4.59 (m, 1H), 4.26-4.22 (m, 1H), 3.55-3.50 (m, 1H), 3.41-3.37 (m, 2H), 3.24-3.19 (m, 3H), 2.57 (s, 3/2H, rotamer), 2.56 (s, 3/2H, rotamer), 2.42-2.29 (m, 3H), 2.17-2.14 (m, 1H), 1.96-1.77 (m, 10H), 1.66-1.65 (m, 2H), 1.18 (dd, J=15, 6.6 Hz, 3H, rotamer), 1.06 (dd, J=15, 6.6 Hz, 3H, rotamer). HRMS m/z (M+H)$^+$ calcd: 708.3195, obsd: 708.3201.

Example 502

Preparation of N-cyclopropyl-2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

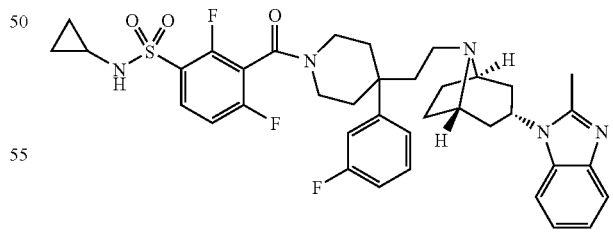

N-Cyclopropyl-2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (40 mg, 53%) was obtained as solid from 2,6-difluoro-3-(chlorosulfonyl)benzoic acid (52 mg, 0.2 mmol), cyclopropyl amine (14 μL, 0.2 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihychloride (52 mg, 0.1 mmol) following the procedure outlined in example 473. $^1$H NMR (400 MHz, CDCl$_3$), δ 7.98-7.96 (m, 1H), 7.65 (d, J=8.8 Hz, 1H), 7.38-7.33 (m, 1H), 7.31-7.26 (m, 1H), 7.19-7.12 (m, 2H), 7.10-7.06 (m, 2H), 7.04-6.94 (m, 2H), 5.55 (s, 1/2H, rotamer), 5.49 (s, 1/2H, rotamer), 4.64-4.58 (m, 1H), 4.27-4.22 (m, 1H), 3.42-3.35 (m, 2H), 3.25-3.19 (m, 3H), 2.57 (s, 3/2H, rotamer), 2.56 (s, 3/2H, rotamer), 2.41-2.14 (m, 5H), 2.03-1.77 (m, 10H0, 1.64 (J=7.9 Hz, 2H), 0.78-0.73 (m, 1H), 0.66-0.54 (m, 3H). HRMS m/z (M+H)$^+$ calcd: 706.3038, obsd: 706.3044.

Example 503

Preparation of 3-fluoro-4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

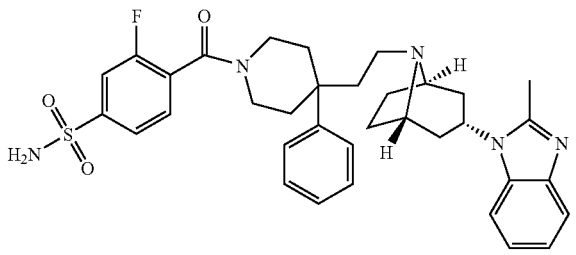

3-Fluoro-4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide (41 mg, 77%) was obtained as solid from 4-(aminosulfonyl)-2-fluorobenzoic acid (22 mg, 0.1 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 5. $^1$H NMR (400 MHz, CDCl$_3$) δ 7.68 (d, J=7.9 Hz, 1H), 7.63-7.60 (m, 2H), 7.40-7.36 (m, 2H), 7.29-7.23 (m, 5H), 7.18-7.12 (m, 2H), 6.18 (br, 2H), 4.61 (t, J=9 Hz, H), 4.21-4.18 (m, 1H), 3.36-3.18 (m, 5H), 2.49 (s, 3H), 2.39-2.19 (m, 4H), 1.96-1.81 (m, 10H), 1.62 (d, J=7.9 Hz, 2H). HRMS m/z (M+H)$^+$ calcd: 630.2914, obsd: 630.2907.

Example 504

Preparation of 3-chloro-4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

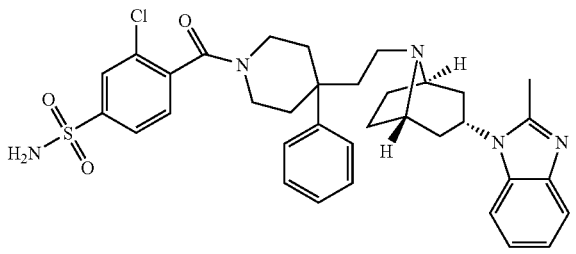

3-Chloro-4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide (27 mg, 42%) was obtained as solid from 4-(amino sulfonyl)-2-chlorobenzoic acid (24 mg, 0.1 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 5. $^1$H NMR (400 MHz, CDCl$_3$), δ 7.95 (s, 1/2H, rotamer), 7.91 (s, 1/2H, rotamer), 7.81-7.76 (m, 1H), 7.64-7.62 (m, 1H), 7.41-7.36 (m, 2H), 7.30-7.23 (m, 5H), 7.19-7.09 (m, 2H), 6.05 (br, 2H), 4.62 (br, 1H), 4.26-4.17 (m, 1H), 3.48-3.07 (m, 5H), 2.50 (s, 3/2H, rotamer), 2.49 (s, 3/2H, rotamer), 2.37-2.08 (m, 4H), 1.94-1.71 (m, 10H), 1.62 (d, 2H). HRMS m/z (M+H)$^+$ calcd: 646.2619, obsd: 646.2626.

Example 505

Preparation of 3,4-difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

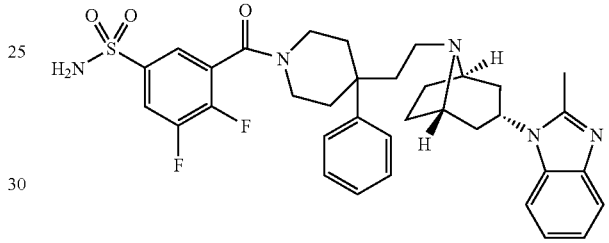

3,4-Difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (26 mg, 40%) was obtained from 5-(aminosulfonyl)-2,3-difluorobenzoic acid (0.15 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. $^1$H NMR (400 MHz, CDCl$_3$) δ 7.70-7.65 (m, 2H), 7.47-7.37 (m, 3H), 7.29-7.25 (m 4H), 7.20-7.13 (m, 2H), 4.84 (br, 1H), 4.14-4.11 (m, 1H), 3.65-3.20 (m, 6H), 2.57 (s, 3H), 2.53-2.48 (m, 2H), 2.30-2.11 (m, 3H), 1.97-1.71 (m, 11H). HRMS m/z (M+H)$^+$ calcd: 648.2820, obsd: 648.2828.

Example 506

Preparation of 3,4-difluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

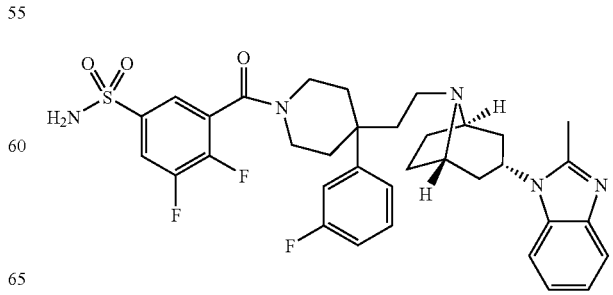

3,4-Difluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (20 mg, 30%) was obtained from 5-(aminosulfonyl)-2,3-difluorobenzoic acid (0.15 mmol), 1-((1R,5S)-8-{2-[4-(3-fluorophenyl)piperidin-4-yl]ethyl}-8-azabicyclo[3.2.1]oct-3-yl)-2-methyl-1H-benzimidazoledihydrochloride (52 mg, 0.1 mmol) and HATU (38 mg, 0.1 mmol) following the procedure outlined in example 5. $^1$H NMR (400 MHz, CDCl$_3$) δ 7.69-7.62 (m, 2H), 7.46-7.42 (m, 1H), 7.39-7.33 (m, 1H), 7.30-7.26 (m, 1H), 7.21-7.13 (m, 2H), 7.06 (d, J=7.9 Hz), 7.00-6.95 (m, 2H), 5.86 (br, 2H), 4.66-4.61 (m, 1H), 4.14-4.09 (m, 1H), 3.51 (br, 1H), 3.29 (br, 4H), 2.54 (s, 3H), 2.49-2.13 (m, 5H), 1.95-1.83 (m, 9H), 1.67-1.65 (m, 2H). HRMS m/z (M+H)$^+$ calcd: 666.2726, obsd: 666.2719.

Example 507

Preparation of 2,3-Difluoro-N-methyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

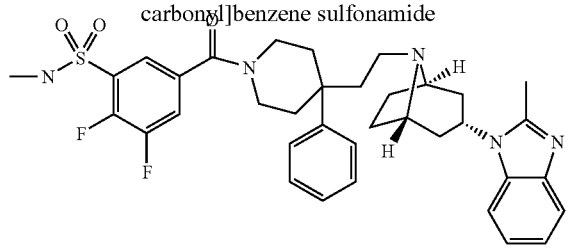

2,3-Difluoro-N-methyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (31 mg, 47%) was obtained as solid from 3-(chlorosulfonyl)-4,5-difluorobenzoic acid (52 mg, 0.2 mmol), methylamine (110 μL, 2.0 M in THF), 2-methyl-1-{(1R,5S)-8-[2-(4-phenylpiperidin-4-yl)ethyl]-8-azabicyclo[3.2.1]oct-3-yl}-1H-benzimidazole dihydro chloride (51 mg, 0.1 mmol) and HATU (38 mg, 0.1 mmol) following the procedure outlined in example 473. $^1$H NMR (400 MHz, CDCl$_3$) δ 7.68-7.64 (m, 2H), 7.50-7.45 (m, 1H), 7.41-7.37 (m, 2H), 7.30-7.24 (m 4H), 7.19-7.12 (m, 2H), 5.26 (br, 1H), 4.66-4.6- (m, 1H), 4.17 (br, 1H), 3.51 (br, 1H), 3.27 (br, 4H), 2.75 (d, J=2.3 Hz, 3H), 2.57 (s, 3H), 2.42-2.34 (m, 3H), 2.20 (br, 1H), 2.01-1.75 (m, 10H), 1.63 (d, J=7.90 Hz, 2 H). HRMS m/z (M+H)$^+$ calcd: 662.2976, obsd: 672.2985.

Example 508

Preparation of 2,3-difluoro-N-isopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

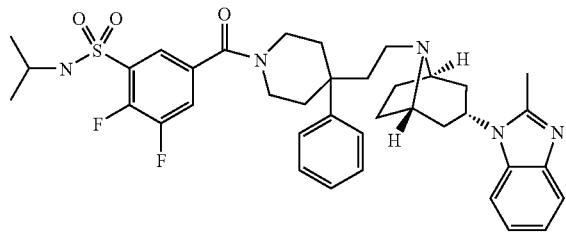

2,3-Difluoro-N-isopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene-sulfonamide (25 mg, 36%) was obtained as solid from 3-(chlorosulfonyl)-4,5-difluorobenzoic acid (52 mg, 0.2 mmol), isopropylamine (19 μL, 0.2 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. $^1$H NMR (400 MHz, CDCl$_3$) δ 7.69-7.65 (m, 2H), 7.50-7.45 (m, 1H), 7.41-7.37 (m, 2H), 7.30-7.24 (m 4H), 7.19-7.12 (m, 2H), 4.90 (d, J=7.7 Hz, 1H), 4.65 (m, 1H), 4.18 (br, 1H), 3.61-3.51 (m, 2H), 3.26 (br, 4H), 2.57 (s, 3H), 2.43-2.35 (m, 3H), 2.201-2.19 (m, 1H), 1.94-1.85 (m, 10H), 1.63 (d, J=7.90 Hz, 2H), 1.14 (d, J=6.6 Hz, 6H). HRMS m/z (M+H)$^+$ calcd: 690.3289, obsd: 690.3309.

Example 509

Preparation of N-cyclopropyl-2,3-difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

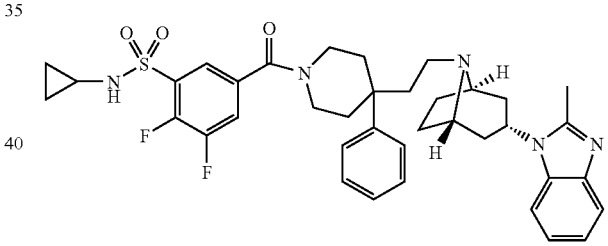

N-Cyclopropyl-2,3-difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide (29 mg, 42%) was obtained as solid from 3-(chlorosulfonyl)-4,5-difluorobenzoic acid (52 mg, 0.2 mmol), isopropylamine (15 μL, 0.2 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. $^1$H NMR (400 MHz, CDCl$_3$) δ 7.72-7.71 (m, 1H), 7.66-7.64 (m, 1H), 7.53-7.48 (m, 1H), 7.41-7.37 (m, 2H), 7.30-7.24 (m 4H), 7.19-7.12 (m, 2H), 5.61 (s, 1H), 4.67-4.57 (m, 1H), 4.18 (br, 1H), 3.51 (br, 1H), 3.27 (br, 4H), 2.57 (s, 3H), 2.42-2.28 (m, 4H), 2.221-2.20 (m, 1H), 1.94-1.76 (m, 10H), 1.65-1.60 (m, 2H), 0.71-0.61 (m, 4H). HRMS m/z (M+H)$^+$ calcd: 688.3133, obsd: 688.3123.

Example 510

Preparation of N-cyclopentyl-2,3-difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

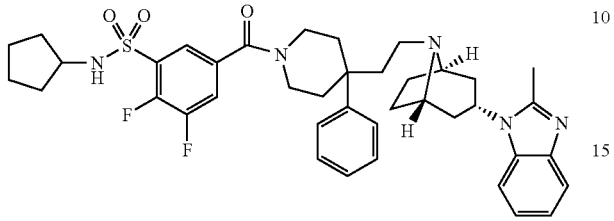

N-Cyclopentyl-2,3-difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide (29 mg, 40%) was obtained as solid from 3-(chlorosulfonyl)-4,5-difluorobenzoic acid (52 mg, 0.2 mmol), isopentylamine (22 μL, 0.2 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. $^1$H NMR (400 MHz, CDCl$_3$) δ 7.69-7.65 (m, 2H), 7.50-7.46 (m, 1H), 7.41-7.37 (m, 2H), 7.30-7.24 (m 4H), 7.19-7.12 (m, 2H), 5.01 (d, J=7.3 Hz, 1H), 4.68-4.64 (m, 1H), 4.18 (br, 1H), 3.69-3.64 (m, 1H), 3.51 (br, 1H), 3.29 (br, 4H), 2.57 (s, 3H), 2.44-2.36 (m, 3H), 2.20-2.18 (m, 1H), 1.97-1.70 (m, 12H), 1.69-1.60 (m, 4H), 1.57-1.47 (m, 2H), 1.45-1.24 (m, 2H). HRMS m/z (M+H)$^+$ calcd: 716.3446, obsd: 716.3456.

Example 511

Preparation of 4-fluoro-N-methyl-2-(methylamino)-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

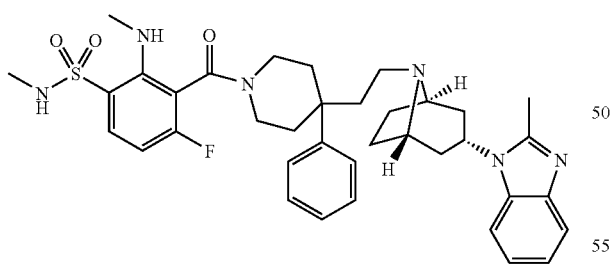

4-Fluoro-N-methyl-2-(methylamino)-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide (20 mg, 30%) was obtained as solid from 6-fluoro-2-(methylamino)-3-[(methyl amino)sulfonyl]benzoic acid (205 mg, 0.8 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. $^1$H NMR (400 MHz, CDCl$_3$) δ 7.79-7.74 (m, 1H), 7.66-7.64 (m, 1H), 7.41-7.34 (m, 2H), 7.30-7.21 (m 4H), 7.19-7.04 (m, 3H), 6.95-6.40 (m, 1H), 6.29-6.18 (m, 1H), 5.07-4.93 (m, 1H), 4.64 (br, 1H), 4.37-4.08 (m, 1H), 3.57-3.34 (m, 1H), 3.39-3.12 (m, 4H), 3.00 (d, J=5.4 Hz, 3/2H, rotamer), 2.75 (d, J=5.2 Hz, 3/2H, rotamer), 2.58-2.56 (m, 3H), 2.41-2.07 (m, 4H), 1.93-1.68 (m, 12H), 1.63-1.61 (m, 2H). HRMS m/z (M+H)$^+$ calcd: 673.3336, obsd: 673.3345.

Example 512

Preparation of 2,4-dichloro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene-sulfonamide

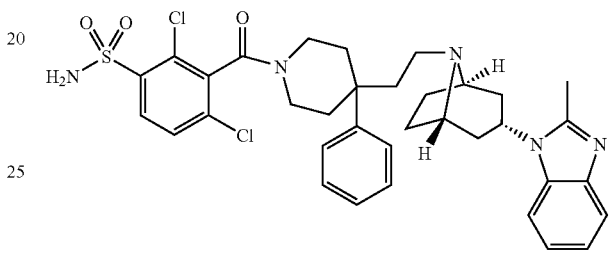

2,4-Dichloro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (36 mg, 53%) was obtained as solid from 3-(aminosulfonyl)-2,6-dichlorobenzoic acid (51 mg, 0.15 mmol), 2-methyl-1{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473.

$^1$H NMR (400 MHz, CDCl$_3$) δ 7.99-7.94 (d, J=8.4 Hz, 1H), 7.63-7.61 (d, J=7.2 Hz, 1H), 7.43-7.36 (m, 3H), 7.29-7.26 (m, 4H), 7.18-7.08 (m, 2H), 5.96 (br, 2H), 4.63 (br, 1H), 4.29-4.24 (m, 1H), 3.40-3.12 (m, 5H), 2.53 (s, 3H), 2.48-2.36 (m, 3H), 2.24-2.21 (m, 1H), 1.99-1.84 (m, 9H), 1.64-1.61 (m, 2H). HRMS m/z (M+H)$^+$ calcd: 680.2229, obsd: 680.2228.

Example 513

Preparation of 2,4-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

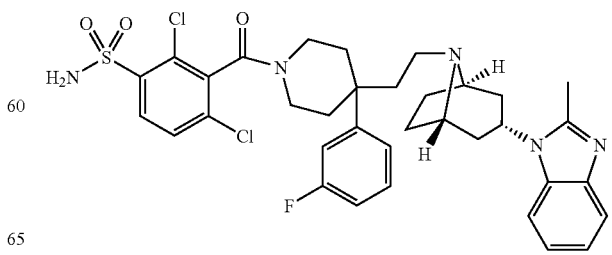

2,4-Dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzene sulfonamide (30 mg, 43%) was obtained as solid from 3-(aminosulfonyl)-2,6-dichlorobenzoic acid (51 mg, 0.15 mmol), 2-methyl-1-{(1R,5S)-8-[2-(4-(3-fluorophenyl) piperidin-4-yl)ethyl]-8-azabicyclo[3.2.1]oct-3-yl}-1H-benzimidazole dihydrochloride (52 mg, 0.1 mmol) and HATU (38 mg, 0.1 mmol) following the procedure outlined in example 473. ¹H NMR (400 MHz, CDCl₃) δ 8.01-7.99 (m, 1H), 7.64-7.62 (m, 1H), 7.45-7.35 (m, 2H), 7.34-7.28 (m, 1H), 7.22-7.12 (m, 2H), 7.08-7.06 (m, 1H), 6.99-6.95 (m, 2H), 5.79 (br, 2H), 4.65-4.55 (m, 1H), 4.27-4.23 (m, 1H), 3.43-3.12 (m, 5H), 2.54 (s, 3H), 2.41-2.37 (m, 4H), 2.19-2.16 (m, 1H), 1.94-1.83 (m, 9H), 1.66-1.65 (m, 2H). HRMS m/z (M+H)⁺ calcd: 698.2135, obsd: 698.2141.

Example 514

Preparation of 2,4-dichloro-N-methyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

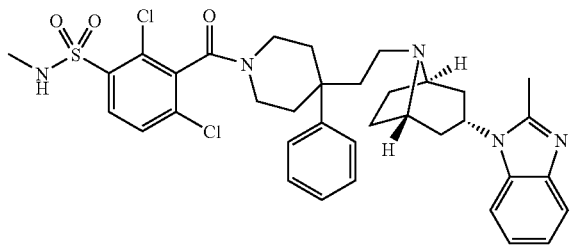

2,4-Dichloro-N-methyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (33 mg, 48%) was obtained as solid from 2,6-dichloro-3-(chlorosulfonyl)benzoic acid (58 mg, 0.20 mmol), methylamine (120 µL, 2.0 M in THF), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. ¹H NMR (400 MHz, CDCl₃) δ 8.06-8.03 (m, 1H), 7.66-7.64 (m, 1H), 7.52-7.44 (m, 1H), 7.41-7.37 (m, 2H), 7.30-7.24 (m, 4H), 7.19-7.12 (m, 2H), 5.31-5.13 (m, 1H), 4.64 (br, 1H), 4.34-4.25 (m, 1H), 3.43-3.12 (m, 5H), 2.68-2.63 (m, 3H), 2.57-2.55 (m, 3H), 2.39-2.34 (m, 3H), 2.26-2.20 (m, 1H), 1.99-1.82 (m, 10H), 1.63-1.62 (m, 2H). HRMS m/z (M+H)⁺ calcd: 694.2385, obsd: 694.2391.

Example 515

Preparation of 2,4-dichloro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide

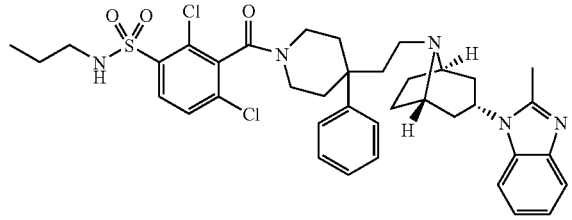

2,4-Dichloro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide (19 mg, 26%) was obtained as solid from 2,6-dichloro-3-(chlorosulfonyl)benzoic acid (58 mg, 0.20 mmol), propylamine (20 µL, 0.24 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. ¹H NMR (400 MHz, CDCl₃) δ 8.06-8.04 (m, 1H), 7.65 (d, 1H), 7.52-7.41 (m, 1H), 7.39-7.32 (m, 2H), 7.29-7.21 (m, 4H), 7.19-7.12 (m, 2H), 5.29-4.98 (m, 1H), 4.63 (br, 1H), 4.33-4.27 (m, 1H), 3.42-3.12 (m, 5H), 3.04-2.88 (m, 2H), 2.86-2.77 (m, 1H), 2.58-2.56 (m, 3H), 2.40-2.37 (m, 3H), 2.26-2.19 (m, 1H), 1.93-1.63 (m, 14H), 1.57-1.51 (m, 2H), 0.92-0.85 (m, 3H). HRMS m/z (M+H)⁺ calcd: 722.2698, obsd: 722.2686.

Example 516

Preparation of 2,4-dichloro-N-isopropyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

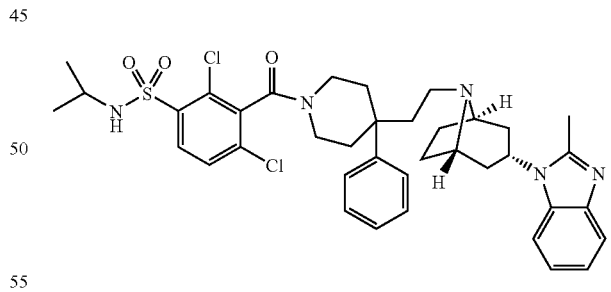

2,4-Dichloro-N-isopropyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (20 mg, 28%) was obtained as solid from 2,6-dichloro-3-(chlorosulfonyl)benzoic acid (58 mg, 0.20 mmol), isopropylamine (20.5 µL, 0.24 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. ¹H NMR (400 MHz, CDCl₃) δ 8.08-8.05 (m, 1H), 7.66-7.65 (m, 1H), 7.51-7.44 (m, 1H), 7.41-

7.37 (m, 2H), 7.30-7.25 (m, 4H), 7.20-7.12 (m, 2H), 4.95-4.83 (m, 1H), 4.64-4.62 (m, 1H), 4.32-4.27 (m, 1H), 3.49-3.34 (m, 2H), 3.27-3.24 (m, 3H), 3.19-3.14 (m, 1H), 2.57-2.56 (m, 3H), 2.40-2.37 (m, 3H), 2.26-2.18 (m, 1H), 1.96-1.82 (m, 10H), 1.64-1.62 (m, 2H), 1.21-1.02 (m, 6H). HRMS m/z (M+H)+ calcd: 722.2698, obsd: 722.2702.

Example 517

Preparation of 2,4-dichloro-N-cyclopropyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

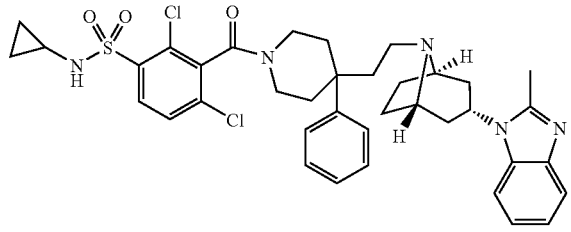

2,4-Dichloro-N-cyclopropyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (35 mg, 49%) was obtained as solid from 2,6-dichloro-3-(chlorosulfonyl)benzoic acid (58 mg, 0.20 mmol), cyclopropylamine (17 μL, 0.24 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. 1H NMR (400 MHz, CDCl3) δ 8.12-8.09 (m, 1H), 7.66-7.65 (m, 1H), 7.54-7.46 (m, 1H), 7.41-7.37 (m, 2H), 7.30-7.25 (m, 4H), 7.19-7.12 (m, 2H), 5.67-5.54 (m, 1H), 4.64 (br, 1H), 4.33-4.27 (m, 1H), 3.43-3.12 (m, 5H), 2.58-2.56 (m, 3H), 2.40-2.37 (m, 3H), 2.26-2.19 (m, 2H), 2.04-1.82 (m, 10H), 1.64-1.63 (m, 2H), 0.85-0.76 (m, 1H), 0.67-0.54 (m, 3H). HRMS m/z (M+H)+ calcd: 720.2542, obsd: 720.2558.

Example 518

Preparation of 2,4-dichloro-N-cyclopentyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

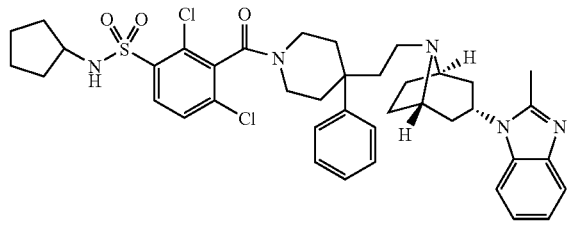

2,4-Dichloro-N-cyclopentyl-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide (28 mg, 37%) was obtained as solid from 2,6-dichloro-3-(chlorosulfonyl)benzoic acid (58 mg, 0.20 mmol), cyclopentylamine (20 μL, 0.24 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. 1H NMR (400 MHz, CDCl3) δ 8.08-8.06 (m, 1H), 7.67-7.65 (m, 1H), 7.52-7.44 (m, 1H), 7.41-7.34 (m, 2H), 7.29-7.25 (m, 4H), 7.19-7.12 (m, 2H), 5.09-4.96 (m, 1H), 4.62 (br, 1H), 4.31-4.28 (m, 1H), 3.60-3.50 (m, 1H), 3.42-3.11 (m, 5H), 2.58-2.53 (m, 3H), 2.40-2.37 (m, 4H), 2.25-2.18 (m, 1H), 1.99-1.75 (m, 11H), 1.73-1.49 (m, 8H). HRMS m/z (M+H)+ calcd: 748.2855, obsd: 748.2863.

Example 519

Preparation of 2-chloro-N-methoxy-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

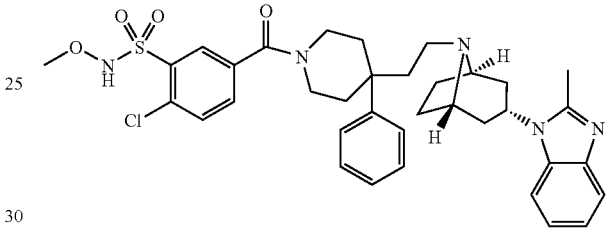

2-Chloro-N-methoxy-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (17 mg, 25%) was obtained as solid from 4-chloro-3-(chlorosulfonyl)benzoic acid (50 mg, 0.2 mmol), methoxyamine hydrochloride (21 mg, 0.20 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. 1H NMR (400 MHz, CDCl3) δ 8.14 (d, J=2.0 Hz, 1H), 8.09 (br, 1, H), 7.67-7.57 (m, 3H), 7.41-7.37 (m, 2H), 7.30-7.24 (m, 4H), 7.19-7.09 (m, 2H), 4.67 (br, 1H), 4.21-4.19 (m, 1H), 3.77 (s, 3H), 3.53-3.50 (m, 1H), 3.35-3.28 (m, 4H), 2.57 (s, 3H), 2.39 (br, 3H), 2.20-2.17 (m, 1H), 1.95-1.77 (m, 10H), 1.66-1.64 (m, 2H). HRMS m/z (M+H)+ calcd: 676.2724, obsd: 676.2727.

Example 520

Preparation of 2-chloro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzenesulfonamide

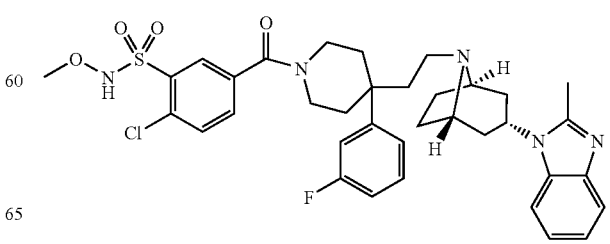

2-Chloro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzenesulfonamide (10 mg, 14%) was obtained as solid from 4-chloro-3-(chloro sulfonyl)benzoic acid (50 mg, 0.2 mmol), methoxyamine hydrochloride (21 mg, 0.20 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 473. $^1$H NMR (400 MHz, CDCl$_3$) δ 8.14 (d, J=1.6 Hz, 1H), 7.92 (br, 1, H), 7.71-7.59 (m, 3H), 7.38 (q, J=7.7 Hz, 1H), 7.30-7.26 (m, 1H), 7.20-7.13 (m, 2H), 7.08 (d, J=8.1 Hz, 1H), 7.01-6.96 (m, 2H), 4.67 (br, 1H), 4.14-4.11 (m, 1H), 3.78 (s, 3H), 3.59 (br, 1H), 3.54-3.31 (br, 4H), 2.59 (s, 3H), 2.44 (br, 2H), 2.28 (br, 2H), 2.11 (br, 2H), 1.97-1.65 (m, 10H). HRMS m/z (M+H)$^+$ calcd: 694.2630, obsd: 694.2630.

Example 521

Preparation of 2-chloro-N-ethoxy-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene lfonamide

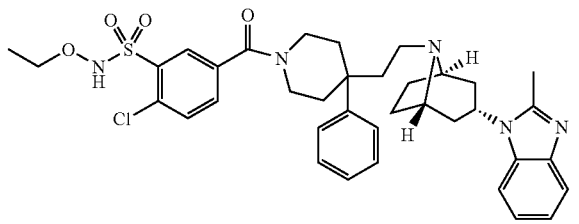

2-Chloro-N-ethoxy-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene-sulfonamide (6 mg, 8%) was obtained as solid from 4-chloro-3-(chlorosulfonyl)benzoic acid (50 mg, 0.2 mmol), ethoxyamine hydrochloride (29 mg, 0.20 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. $^1$H NMR (400 MHz, CDCl$_3$) δ 8.12 (s, 1H), 7.80 (s, 1H), 7.67-7.59 (m, 3H), 7.41-7.38 (m, 2H), 7.30-7.26 (m, 3H), 7.20-7.12 (m, 2H), 4.69 (br, 1H), 4.21 (br, 1H), 4.03 (q, J=7.0 Hz, 2H), 3.51 (br, 1H), 3.29 (br, 4H), 2.58 (s, 3H), 2.42-2.39 (m, 3H), 2.16 (br, 1H), 1.94 (br, 7H), 1.69 (br, 5H), 1.16 (t, J=7.0 Hz, 3H). HRMS m/z (M+H)$^+$ calcd: 690.2881, obsd: 690.2878.

Example 522

Preparation of 2-chloro-N-ethoxy-5-[(4-(3-fluoro phenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

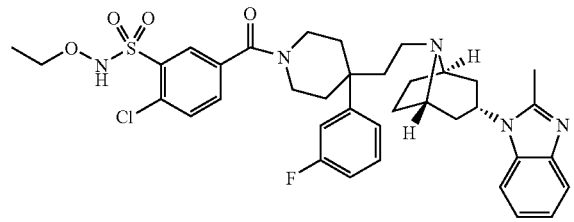

2-Chloro-N-ethoxy-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl) carbonyl]benzene-sulfonamide (12 mg, 17%) was obtained as solid from 4-chloro-3-(chlorosulfonyl)benzoic acid (50 mg, 0.2 mmol), ethoxyamine hydrochloride (29 mg, 0.20 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 473. $^1$H NMR (400 MHz, CDCl$_3$) δ 8.13 (d, J=1.8 Hz, 1H), 7.82 (br, 1, H), 7.67-7.59 (m, 3H), 7.37 (q, J=7.8 Hz, 1H), 7.29 (d, J=7.7 Hz, 1H), 7.20-7.13 (m, 2H), 7.08 (d, J=8.1 Hz, 1H), 7.01-6.96 (m, 2H), 4.81 (br, 1H), 4.17 (br, 1H), 4.04 (q, J=7.1 Hz, 2H), 3.53 (br, 1H), 3.39-3.31 (br, 4H), 2.59 (s, 3H), 2.43 (br, 2H), 2.29 (br, 1H), 2.10 (br, 2H), 1.97-1.93 (m, 8H), 1.71 (br, 4H), 1.16 (t, J=7.0 Hz, 3H). HRMS m/z (M+H)$^+$ calcd: 708.2787, obsd: 708.2797.

Example 523

Preparation of 4-chloro-N-methoxy-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene-sulfonamide

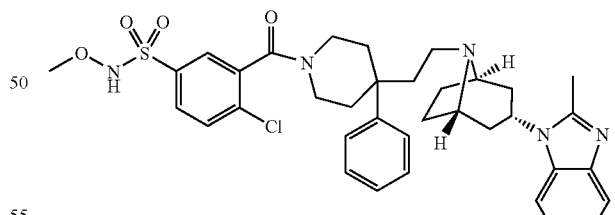

4-Chloro-N-methoxy-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide (2 mg) was obtained as solid from 2-chloro-5-(chlorosulfonyl)benzoic acid (50 mg, 0.2 mmol), methoxyamine hydrochloride (21 mg, 0.20 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. $^1$H NMR (400 MHz, CDCl$_3$) δ 7.90-7.85 (m, 2H), 7.66

(d, J=7.5 Hz, 1H), 7.57 (m, 1H), 7.42-7.33 (m, 2H), 7.30-7.26 (m, 4H), 7.20-7.12 (m, 3H), 4.70 (br, 1H), 4.30-4.22 (m, 1H), 3.80 (d, J=7.1 Hz, 3H), 3.42-3.09 (m, 7H), 2.56 (s, 3H), 2.43-2.08 (m, 4H), 1.95-1.90 (m, 8H), 1.89-1.75 (m, 3H). HRMS m/z (M+H)+ calcd: 676.2724, obsd: 676.2722.

Example 524

Preparation of 4-chloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzenesulfonamide

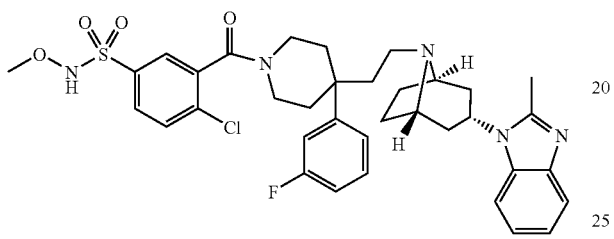

4-Chloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxy benzenesulfonamide (3.9 mg) was obtained as solid from 2-chloro-5-(chlorosulfonyl)benzoic acid (50 mg, 0.2 mmol), ethoxyamine hydrochloride (29 mg, 0.20 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 473. 1H NMR (400 MHz, CDCl3) δ 7.89-7.85 (m, 2H), 7.66 (d, J=7.7 Hz, 1H), 7.61-7.55 (m, 1H), 7.38-7.36 (m, 1H), 7.31-7.29 (m, 1H), 7.21-7.14 (m, 3H), 7.10-7.05 (m, 1H), 6.99-6.97 (m, 2H), 4.68-4.63 (m, 1H), 4.27-4.23 (m, 1H), 3.80 (d, J=4 Hz, 3H), 3.43-3.20 (m, 5H), 3.18-3.09 (m, 1H), 2.56 (s, 3H), 2.43-2.30 (m, 4H), 2.16-2.13 (m, 1H), 1.96-1.89 (m, 10H). HRMS m/z (M+H)+ calcd: 694.2630, obsd: 694.2625.

Example 525

Preparation of 4-chloro-N-ethoxy-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene-sulfonamide

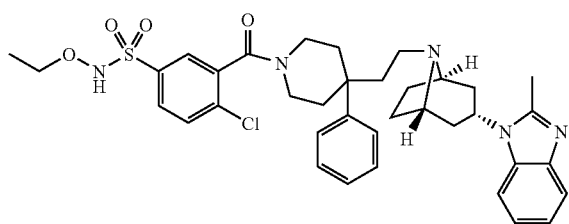

4-Chloro-N-ethoxy-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene-sulfonamide (3.1 mg) was obtained as solid from 2-chloro-5-(chlorosulfonyl)benzoic acid (50 mg, 0.2 mmol), ethoxyamine hydrochloride (29 mg, 0.20 mmol), 2-methyl-1-{(1R,5S)-8-[2-(4-phenylpiperidin-4-yl)ethyl]-8-azabicyclo[3.2.1]oct-3-yl}-1H-benzimidazole dihydrochloride (51 mg, 0.1 mmol) and HATU (38 mg, 0.1 mmol) following the procedure outlined in example 473. 1H NMR (400 MHz, CDCl3) δ 7.90-7.84 (m, 1H), 7.65 (d, J=7.5 Hz, 1H), 7.60-7.53 (m, 1H), 7.41-7.32 (m, 2H), 7.30-7.26 (m, 5H), 7.19-7.14 (m, 3H), 4.65 (br, 1H), 4.30-4.22 (m, 1H), 4.06-4.02 (m, 2H), 3.33-3.25 (m, 5H), 2.55 (s, 3H), 2.38 (br, 3H), 2.11-2.08 (m, 1H), 1.99-1.89 (m, 9H), 1.87-1.64 (m, 2H), 1.22-1.15 (m, 3H). HRMS m/z (M+H)+ calcd: 690.2881, obsd: 690.2880.

Example 526

Preparation of 3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethylbenzene sulfonamide

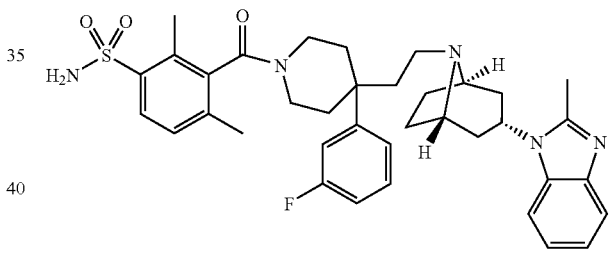

3-[(4-(3-Fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethylbenzene sulfonamide (25 mg, 38%) was obtained as solid from 3-(aminosulfonyl)-2,6-dimethylbenzoic acid (23 mg, 0.1 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 5. 1H NMR (400 MHz, CDCl3) δ 7.89 (d, J=8.2 Hz, 1H), 7.64 (d, J=7.2 Hz, 1H), 7.36 (q, J=7.9 HZ, 1H), 7.29 (d, J=7.4 Hz, 1H), 7.19-7.10 (m, 3H), 7.05 (d, J=7.9 HZ, 1H), 6.99-6.95 (m, 2H), 5.20 (br, 2H), 4.61-4.56 (m, 1H), 4.27-4.23 (m, 1H), 3.46-3.41 (m, 1H), 3.23 (br, 3H), 3.10-3.05 (m, 1H), 2.60 (s, 3/2H, rotamer), 2.53 (s, 3H), 2.41 (s, 3/2H, rotamer), 2.37 (s, 3/2H, rotamer), 2.33-2.29 (m, 2H), 2.19 (s, 3/2H, rotamer), 2.11-2.08 (m, 1H), 1.94-1.82 (m, 10H), 1.74-1.62 (m, 3H). HRMS m/z (M+H)+ calcd: 658.3227, obsd: 658.3223.

Example 527

Preparation of 3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N,2,4-trimethyl benzenesulfonamide

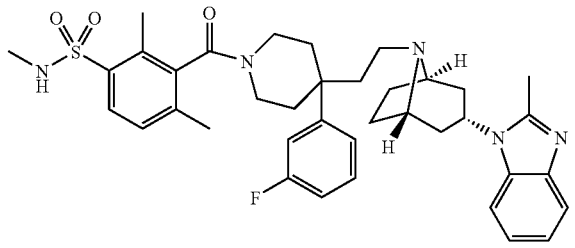

3-[(4-(3-Fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-2,4-trimethyl benzenesulfonamide (10 mg, 15%) was obtained as solid from 3-(chlorosulfonyl)-2,6-dimethylbenzoic acid (50 mg, 0.2 mmol), methylamine (120 µL, 2.0 M in THF), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 473. $^1$H NMR (400 MHz, CDCl$_3$) δ 7.91-7.88 (m, 1H), 7.66 (d, J=7.7 Hz, 1H), 7.36 (q, J=7.7 HZ, 1H), 7.29 (d, J=7.5 Hz, 1H), 7.22-7.14 (m, 3H), 7.05 (d, J=7.9 HZ, 1H), 6.99-6.95 (m, 2H), 4.63-4.52 (m, 2H), 4.33-4.29 (m, 1H), 3.43-3.34 (m, 1H), 3.25 (br, 3H), 3.05 (q, J=10.6 Hz, 1H), 2.64-2.55 (m, 8H), 2.42-4.21 (m, 7H), 2.08 (br, 1H), 1.95-1.88 (m, 6H), 1.84-1.63 (m, 6H). HRMS m/z (M+H)$^+$ calcd: 672.3384, obsd: 672.3400.

Example 528

Preparation of N-ethyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethylbenzenesulfonamide

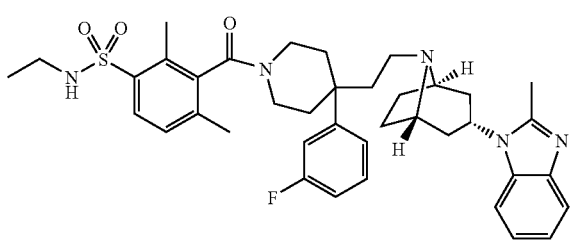

N-Ethyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethyl benzenesulfonamide (9.2 mg, 14%) was obtained as solid from 3-(chlorosulfonyl)-2,6-dimethylbenzoic acid (50 mg, 0.2 mmol), ethylamine (120 µL, 2.0 M in THF), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 473. $^1$H NMR (400 MHz, CDCl$_3$) δ 7.89 (d, J=8.0 Hz, 1H), 7.66 (d, J=7.3 Hz, 1H), 7.36 (q, J=7.7 Hz, 1H), 7.30 (d, J=8.1 Hz, 1H), 7.21-7.13 (m, 3H), 7.06 (d, J=7.9 HZ, 1H), 6.99-6.95 (m, 2H), 4.63-4.59 (m, 1H), 4.51-4.49 (m, 1H), 4.33-4.29 (m, 1H), 3.40-3.34 (m, 1H), 3.25-3.21 (m, 3H), 3.11-3.05 (m, 1H), 2.94-2.87 (m, 1H), 2.62 (s, 3H), 2.57 (s, 3H), 2.55-2.30 (m, 3H), 2.20 (s, 3H), 2.09-2.06 (m, 1H), 1.95-1.88 (m, 6H), 1.84-1.63 (m, 6H), 1.12 (t, J=7.2 Hz, 3H). HRMS m/z (M+H)$^+$ calcd: 686.3540, obsd: 686.3522.

Example 529

Preparation of 3-[(4-(3-fluorophenyl-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethyl-N-propylbenzenesulfonamide

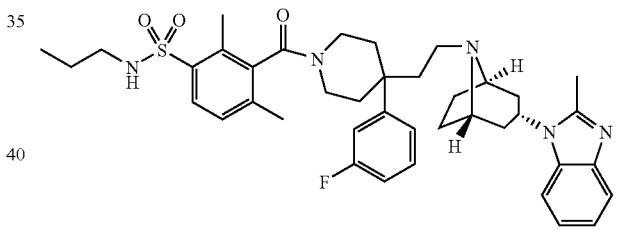

3-[(4-(3-Fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethyl-N-propylbenzenesulfonamide (8 mg, 12%) was obtained as solid from 3-(chlorosulfonyl)-2,6-dimethylbenzoic acid (50 mg, 0.2 mmol), propylamine (18 µL, 0.22 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 473. $^1$H NMR (400 MHz, CDCl$_3$) δ 7.91-7.88 (m, 1H), 7.66 (d, J=7.7 Hz, 1H), 7.36 (q, J=7.6 HZ, 1H), 7.33-7.31 (m, 1H), 7.21-7.13 (m, 3H), 7.06 (d, J=7.3 HZ, 1H), 6.99-6.95 (m, 2H), 4.63-4.59 (m, 1H), 4.53-4.42 (m, 1H), 4.33-4.24 (m, 1H), 3.43-3.34 (m, 1H), 3.25-3.21 (m, 3H), 3.09-2.88 (m, 2H), 2.84-2.76 (m, 1H), 2.62-2.56 (m, 6H), 2.42-2.20 (m, 6H), 2.08-2.06 (m, 1H), 1.95-1.88 (m, 6H), 1.84-1.63 (m, 6H), 1.53-1.46 (m, 2H), 0.90-0.84 (m, 3H). HRMS m/z (M+H)$^+$ calcd: 700.3697, obsd: 700.3696.

Example 530

Preparation of 3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-isopropyl-2,4-dimethylbenzenesulfonamide

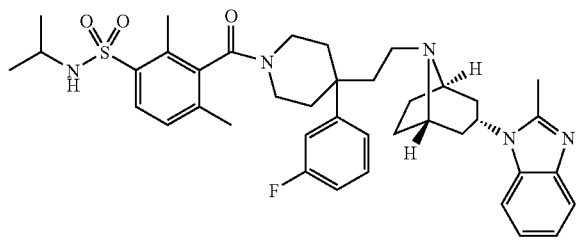

3-[(4-(3-Fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-isopropyl-2,4-dimethylbenzenesulfonamide (8 mg, 12%) was obtained as solid from 3-(chlorosulfonyl)-2,6-dimethylbenzoic acid (50 mg, 0.2 mmol), isopropylamine (19 µL, 0.22 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 473. $^1$H NMR (400 MHz, CDCl$_3$) δ 7.94-7.92 (m, 1H), 7.66 (d, J=7.1 Hz, 1H), 7.36 (q, J=7.7 HZ, 1H), 7.30-7.29 (m, 1H), 7.21-7.14 (m, 3H), 7.06 (d, J=7.9 HZ, 1H), 6.99-6.95 (m, 2H), 4.64-4.60 (m, 1H), 4.34-4.24 (m, 2H), 3.46-3.35 (m, 2H), 3.25-3.20 (m, 3H), 3.06-2.95 (m, 1H), 2.61 (s, 3H), 2.58 (s, 3H), 2.44-2.30 (m, 3H), 2.20 (s, 3H), 2.08-2.06 (m, 1H), 1.95-1.86 (m, 6H), 1.85-1.64 (m, 6H), 1.19-1.15 (m, 3H), 1.05-1.01 (m, 3H). HRMS m/z (M+H)$^+$ calcd: 700.3697, obsd: 700.3711.

Example 531

Preparation of N-cyclopropyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethylbenzenesulfonamide

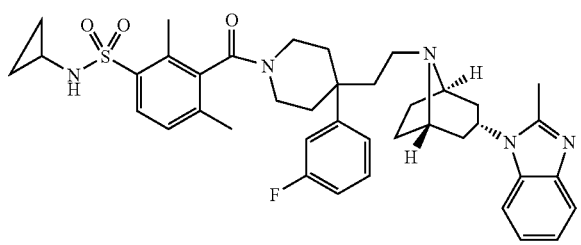

N-Cyclopropyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethylbenzenesulfonamide (12 mg, 17%) was obtained as solid from 3-(chlorosulfonyl)-2,6-dimethylbenzoic acid (50 mg, 0.2 mmol), cyclopropylamine (15 µL, 0.22 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 473. $^1$H NMR (400 MHz, CDCl$_3$) δ 7.96 (d, J=8.0 Hz, 1H), 7.66 (d, J=8.0 Hz, 1H), 7.38-7.34 (m, 1H), 7.31-7.29 (m, 1H), 7.21-7.13 (m, 3H), 7.06 (d, J=8.0 Hz, 1H), 6.99-6.95 (m, 2H), 5.29-5.14 (m, 1H), 4.61 (br, 1H), 4.32-4.29 (m, 1H), 3.60-3.37 (m, 2H), 3.24-3.20 (m, 3H), 3.06-3.01 (m, 2H), 2.60-2.57 (m, 6H), 2.40-2.30 (m, 3H), 2.21 (s, 3H), 2.08-2.06 (m, 1H), 1.94-1.81 (m, 9H), 1.69-1.63 (m, 3H), 0.60-0.53 (m, 4H). HRMS m/z (M+H)$^+$ calcd: 698.3540, obsd: 698.3567.

Example 532

Preparation of N-cyclopentyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethylbenzenesulfonamide

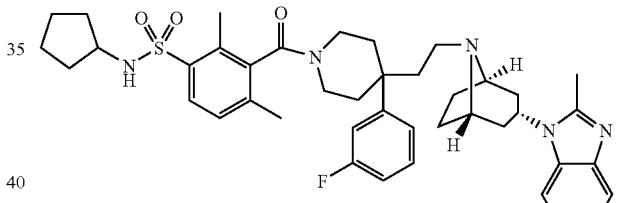

N-Cyclopentyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-2,4-dimethylbenzenesulfonamide (24 mg, 33%) was obtained as solid from 3-[(cyclopentyl amino)sulfonyl]-2,6-dimethyl benzoic acid (30 mg, 0.1 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (52 mg, 0.1 mmol) and HATU (38 mg, 0.1 mmol) following the procedure outlined in example 5. $^1$H NMR (400 MHz, CDCl$_3$) δ 7.93-7.91 (m, 1H), 7.67-7.64 (m, 1H), 7.36 (q, J=8.0 Hz, 1H), 7.30-7.28 (m, 1H), 7.21-7.12 (m, 3H), 7.07-7.05 (m, 1H), 6.99-6.95 (m, 2H), 4.63-4.53 (m, 2H), 4.31-4.28 (m, 1H), 3.59-3.50 (m, 1H), 3.44-3.34 (m, 1H), 3.24 (br, 3H), 3.08-3.00 (m, 1H), 2.61 (s, 3/2H, rotamer), 2.57 (s, 3/2H, rotamer), 2.56 (s, 3/2H, rotamer), 2.41 (s, 3/2H, rotamer), 2.39 (s, 3/2H, rotamer), 2.36-2.34 (m, 3H), 2.20 (s, 3/2H, rotamer), 2.08 (br, 1H), 1.95-1.76 (m, 10H), 1.69-1.56 (m, 5H), 1.52-1.45 (m, 3H), 1.32-1.27 (m, 1H). HRMS m/z (M+H)$^+$ calcd: 726.3853, obsd: 726.3824.

Example 533

Preparation of 4-hydroxy-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

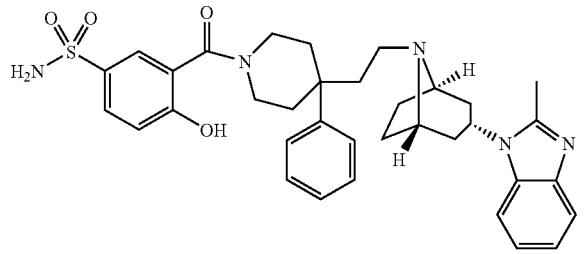

4-Hydroxy-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide (20 mg) was obtained as solid from 5-(aminosulfonyl)-2-hydroxybenzoic acid (43 mg, 0.2 mmol), 2-methyl-1-{(1R,5S)-8-[2-(4-phenylpiperidin-4-yl)ethyl]-8-aza bicyclo[3.2.1]oct-3-yl}-1H-benzimidazole (100 mg, 0.2 mmol) and HATU (76 mg, 0.2 mmol) following the procedure outlined in example 5. $^1$H NMR (400 MHz, DMSO-d$_6$) δ 10.66 (s, 1H), 7.74 (s, 1H), 7.65 (dd, J=2.4, 8.2 Hz, 1H), 7.54 (d, J=2.2 Hz, 1H), 7.49-7.47 (m, 1H), 7.38 (br, 5H), 7.22-7.10 (m, 5H), 6.96 (d, 8.6 Hz, 1H), 4.48 (br, 1H), 3.90 (br, 1H), 3.24 (br, 1H), 3.09-3.03 (m, 4H), 2.47-2.45 (m, 6H), 2.09 (br, 5H), 1.81 (br, 6H), 1.57 (br, 1H). HRMS m/z (M+H)$^+$ calcd: 628.2958, obsd: 628.2958.

Example 534

Preparation of 6-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1,2-benzisothiazol-3(2H)-one 1,1-dioxide

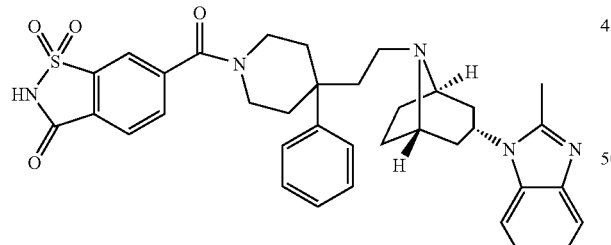

6-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]-1,2-benzisothiazol-3(2H)-one 1,1-dioxide (78 mg, 61%) was obtained as solid from 3-oxo-2,3-dihydro-1,2-benzisothiazole-6-carboxylic acid 1,1-dioxide (46 mg, 0.2 mmol), 2-methyl-1-{(1R,5S)-8-[2-(4-phenylpiperidin-4-yl)ethyl]-8-azabicyclo[3.2.1]oct-3-yl}-1H-benzimidazole (100 mg, 0.2 mmol) and HATU (76 mg, 0.2 mmol) following the procedure outlined in example 5. $^1$H NMR (400 MHz, DMSO-d$_6$) δ 7.63-7.61 (m, 2H), 7.57-7.54 (m, 1H), 7.50-7.47 (m, 1H), 7.44-7.33 (m, 5H), 7.25-7.20 (m, 1H), 7.15-7.07 (m, 3, H), 4.69-4.63 (m, 1H), 3.93 (br, 1H), 3.47 (br, 3H), 3.39-3.30 (m, 1H), 2.48 (s, 3H), 2.43-2.38 (m, 4H), 2.27-2.20 (m, 4H), 1.97-1.78 (m, 7H), 1.78-1.66 (m, 2H). HRMS m/z (M+H)$^+$ calcd: 638.2801, obsd: 638.2796.

Synthesis of Amides Via EDCI Coupling—Method P

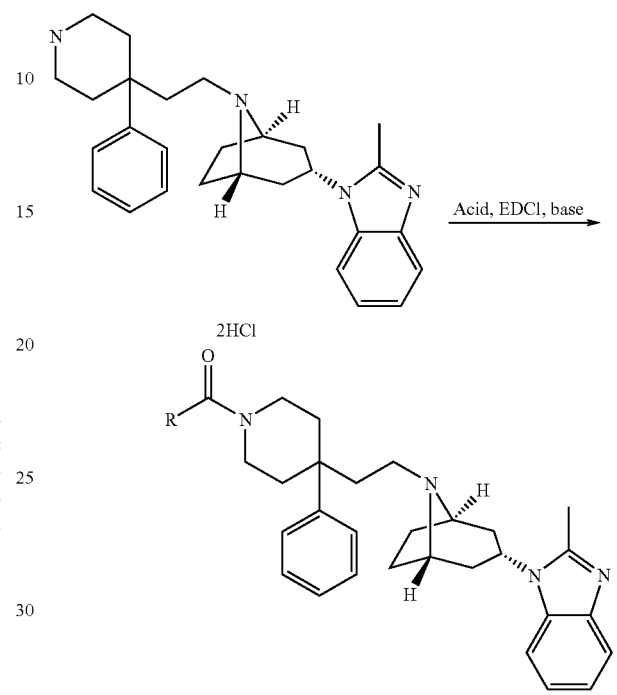

Synthesis of Amides Via HATU-Mediated Coupling—Method A

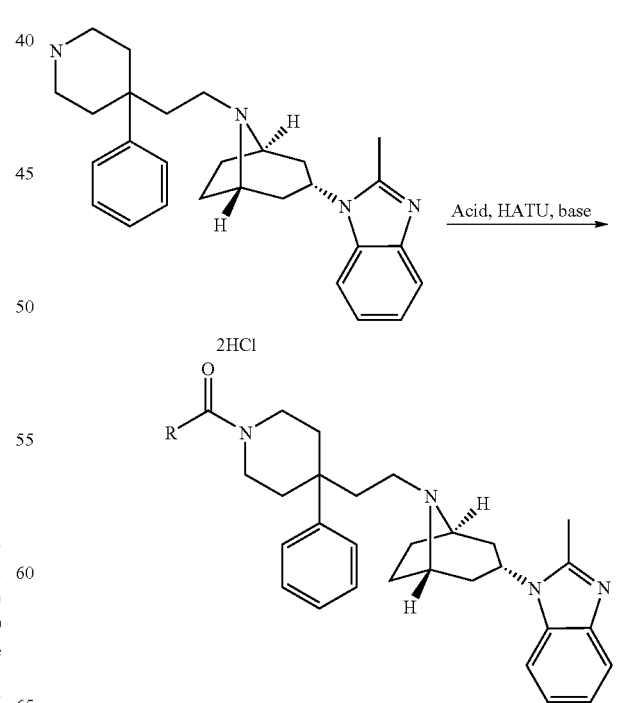

415
Synthesis of Amides Via Anhydride—Method B
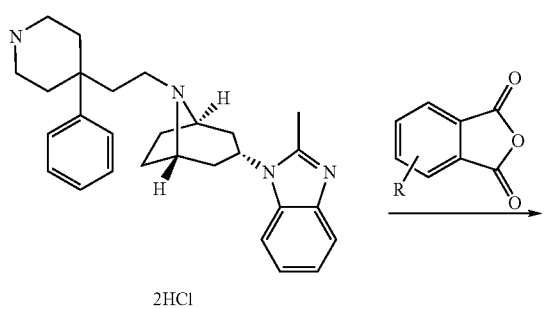
416
Synthesis of Amides Via Isatoic Anhydride Opening—Method U
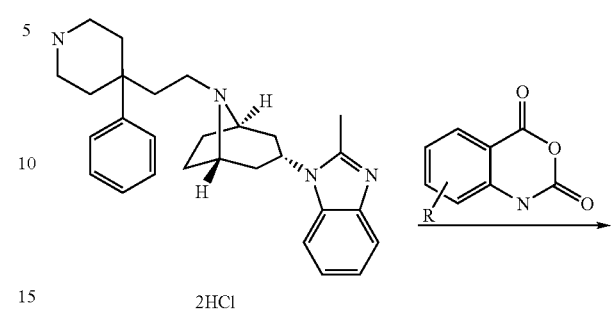
The following table includes compounds of the present invention that were prepared by the methods depicted above.
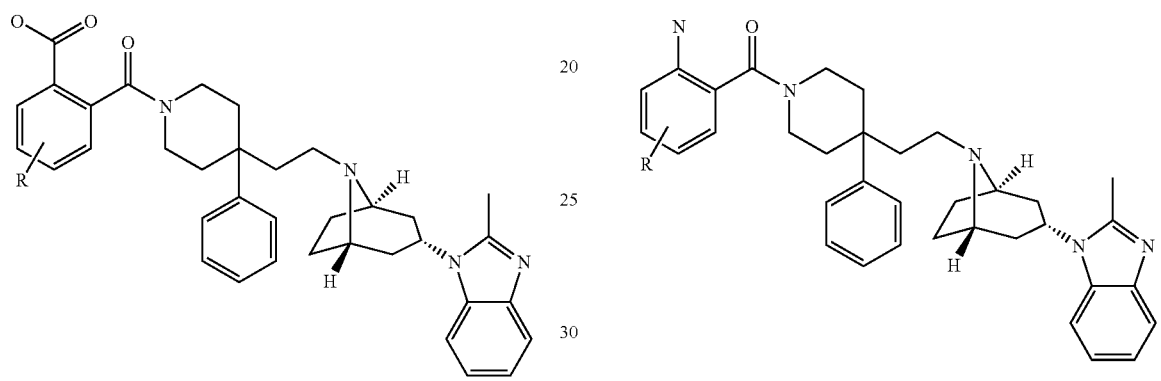
| Example | R | ES-LCMS | Ion | Method | Notes |
|---|---|---|---|---|---|
| 535 | (2,6-dimethyl-4-(pyridin-4-yl)phenyl)carbonyl pivaloyl group | 637 | M + H | P | 1 |

-continued
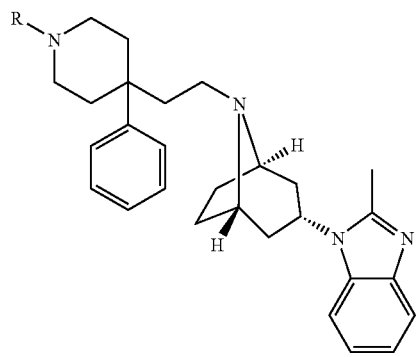
| Example | R | ES-LCMS | Ion | Method | Notes |
|---|---|---|---|---|---|
| 536 | 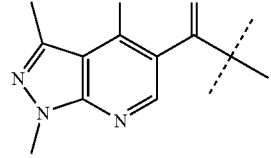 | 635 | M + H | A | |
| 537 | 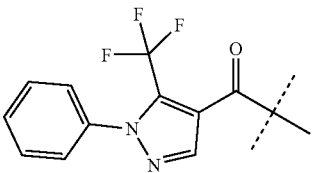 | 666 | M + H | A | |
| 538 | 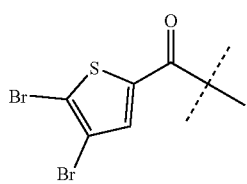 | 694 | M + H | A | |
| 539 | 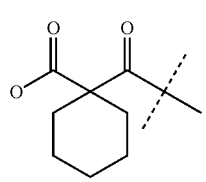 | 582 | M + H | A | 2 |
| 540 | 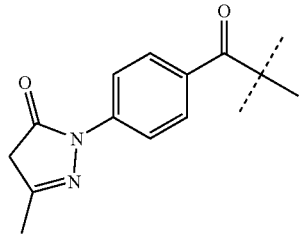 | 628 | M + H | A | |
| 541 | 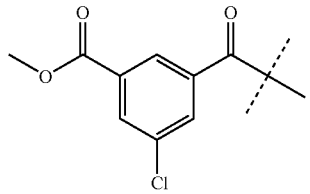 | 628 | M + H | A | 3 |

-continued
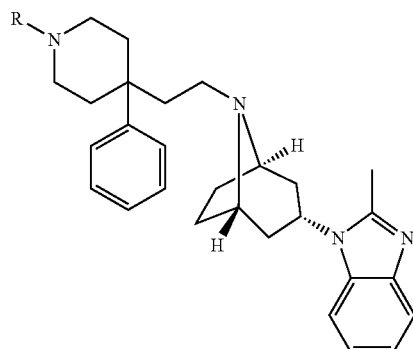
| Example | R | ES-LCMS | Ion | Method | Notes |
|---|---|---|---|---|---|
| 542 | | 746 | M + H | A | 3 |
| 543 | | 668 | M + H | A | 3 |
| 544 | | 615 | M + H | U | |
| 545 | | 685 | M + H | A | 4 |
| 546 | | 633 | M + H | A | 5 |

-continued
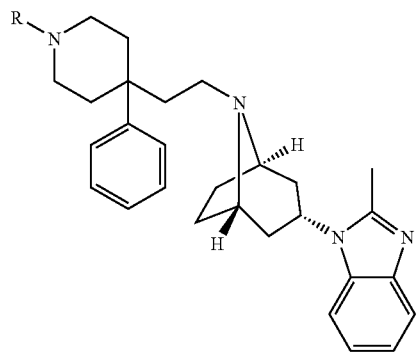
| Example | R | ES-LCMS | Ion | Method | Notes |
|---|---|---|---|---|---|
| 547 | 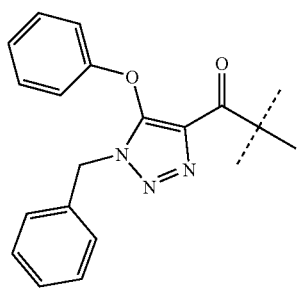 | 705 | M + H | A | 5 |
| 548 | 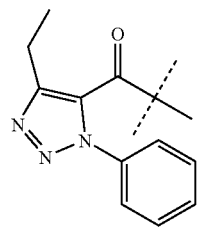 | 627 | M + H | A | 5 |
| 549 | 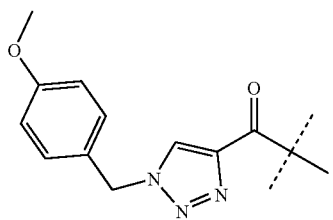 | 643 | M + H | A | 5 |
| 550 | 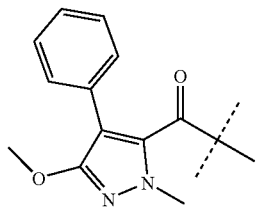 | 642 | M + H | A | 6 |

-continued
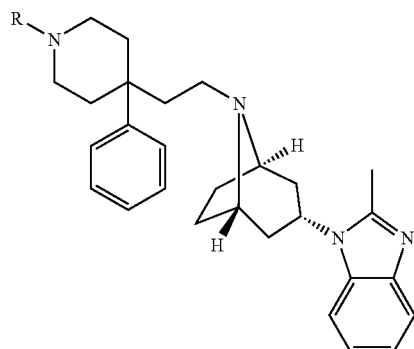
| Example | R | ES-LCMS | Ion | Method | Notes |
|---|---|---|---|---|---|
| 551 | 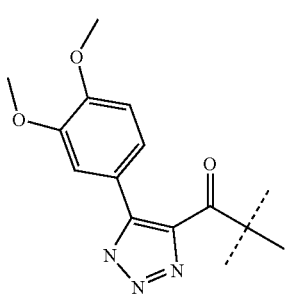 | 659 | M + H | A | 5 |
| 552 | 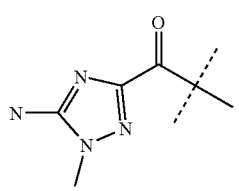 | 552 | M + H | A | 7 |
| 553 | 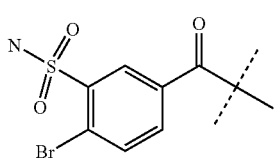 | 689 | M + H | A | 8 |
| 554 | 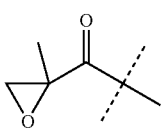 | 512 | M + H | A | |
| 555 | 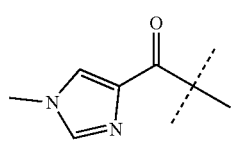 | 536 | M + H | A | |
| 556 | 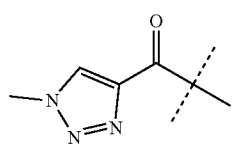 | 537 | M + H | A | 9 |

-continued
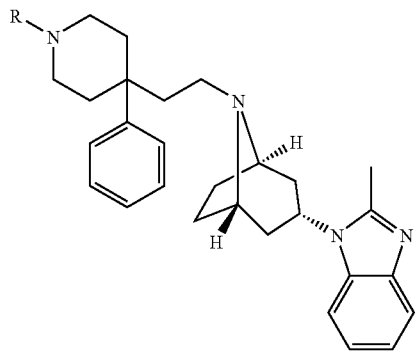
| Example | R | ES-LCMS | Ion | Method | Notes |
|---|---|---|---|---|---|
| 557 | | 599 | M + H | A | 9 |
| 558 | | 628 | M + H | A | 6 |
| 559 | | 628 | M + H | A | 10 |
| 560 | | 628 | M + H | A | 5 |
| 561 | | 553 | M + H | A | 11 |
| 562 | | 661 | M + H | A | 8 |

-continued
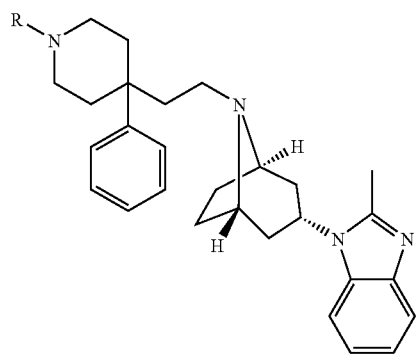
| Example | R | ES-LCMS | Ion | Method | Notes |
|---|---|---|---|---|---|
| 563 | 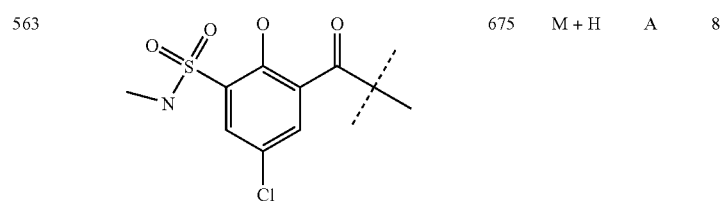 | 675 | M + H | A | 8 |
| 564 | 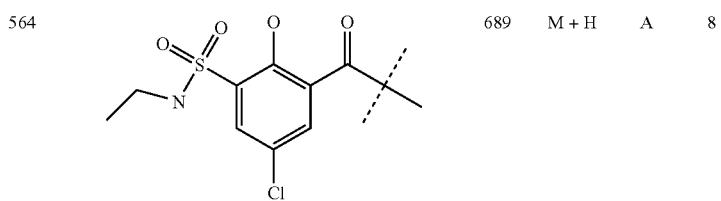 | 689 | M + H | A | 8 |
| 565 | 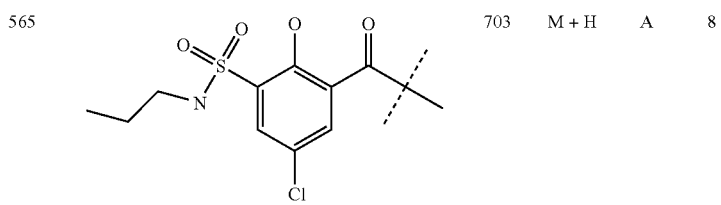 | 703 | M + H | A | 8 |
| 566 | 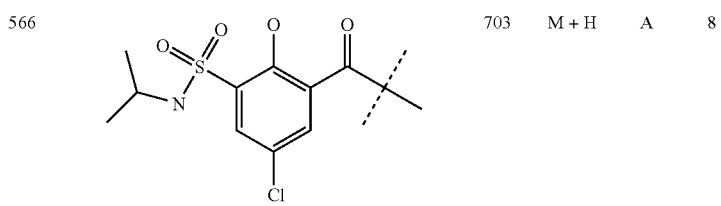 | 703 | M + H | A | 8 |
| 567 | 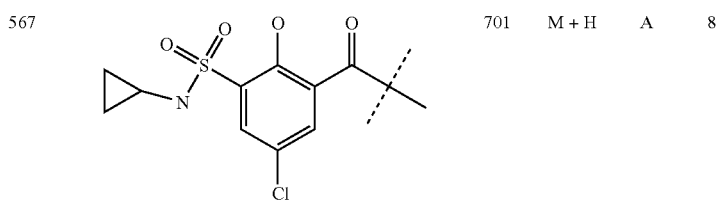 | 701 | M + H | A | 8 |

-continued

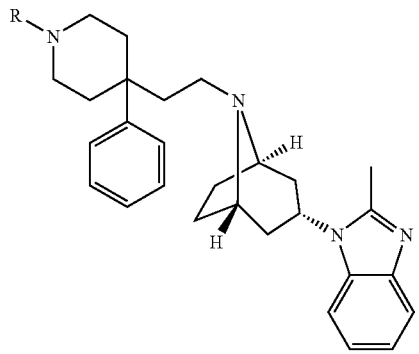

| Example | R | ES-LCMS | Ion | Method | Notes |
|---|---|---|---|---|---|
| 568 | (structure) | 641 | M + H | A | 8 |
| 569 | (structure) | 683 | M + H | A | 8 |
| 570 | (structure) | 866 | M + H | A | 8 |

Notes:
1. Compound was synthesized according to WO 00/66558, Schering Corporation, 2000.
2. Compound was synthesized according to procedure outlined for example 572.
3. Compound was synthesized according to the literature procedure described by M. H. Chen et al., Org. Prep. Proced. Int., 2000, v32, pp. 381-384.
4. Compound was synthesized according to the literature procedure described in J. Heterocycl. Chem. 26(5), 1461-8 (1989).
5. Compound was synthesized according to the literature procedure described in J. Chem. Res. Synop. 12, 400-1 (1984).
6. Compound was synthesized according to the literature procedure described in Chem. Ber., 109(1), 268-73 (1976).
7. Compound was synthesized according to the procedure described in EP 0016565A1, 1980.
8. Compound was synthesized according to procedure outlined for example 572.
9. Compound was synthesized according to the literature procedure described in J. Org. Chem., 41(6), 1041-51 (1976).
10. Compound was synthesized according to the literature procedure described in J. Med. Chem., 33(2), 781-9 (1990).
11. Compound was synthesized according to the literature procedure described in Bioorganic & Medicinal Chemistry Letters, 9(18), 2679-2684 (1999).

Example 571

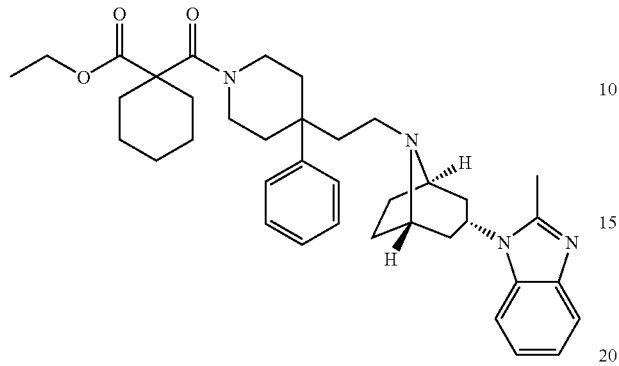

Ethyl 1-[(4-{2-[(1R,5S)-3-(2-methyl-1H-benzimidazol-1-yl)-8-azabicyclo[3.2.1]oct-8-yl]ethyl}-4-phenyl piperidin-1-yl)carbonyl]cyclohexanecarboxylate was synthesized via EDCI-HOBt acylation method P. $^1$H NMR (300 MHz, CDCl$_3$) δ 7.66 (d, 1H), 7.43-7.12 (m, 8H), 4.61 (m, 1H), 4.22-4.09 (m, 2H), 3.65 (m, 1H), 3.33-3.05 (m, 4H), 2.88 (m, 1H), 2.58 (s, 3H), 2.46-2.11 (m, 4H), 2.05 (s, 1H), 2.00-1.83 (m, 12H), 1.63-1.52 (m, 6H), 1.50-1.37 (m, 2H), 1.07-1.32 (m, 4H). HRMS C$_{38}$H$_{50}$N$_4$O$_3$ m/z 611.3961 (M+H)$_{Cal}$, 611.3973 (M+H)$_{Obs}$.

Example 572

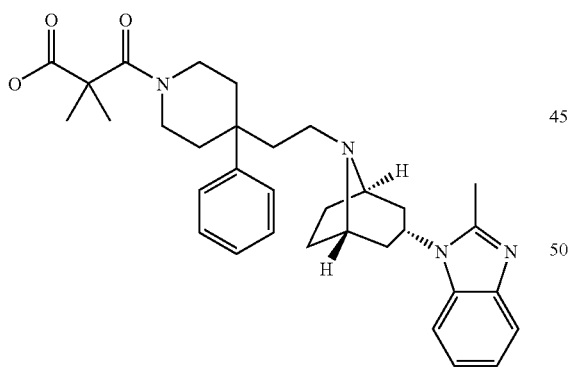

2,2-Dimethyl-3-(4-{2-[(1R,5S)-3-(2-methyl-1H-benzimidazol-1-yl)-8-azabicyclo[3.2.1]oct-8-yl]ethyl}-4-phenylpiperidin-1-yl)-3-oxopropanoic acid was prepared by treating title compound from example 628 with NaOH. $^1$H NMR (300 MHz, CDCl$_3$) δ 7.75 (d, 1H), 7.43-7.12 (m, 8H), 4.68 (m, 1H), 4.07 (m, 1H), 3.69 (m, 1H), 3.30-3.14 (m, 2H), 2.70-2.58 (m, 3H), 2.20 (m, 2H), 2.05-1.73 (m, 7H), 1.50-1.07 (m, 12H), 1.02-0.74 (m, 3H). HRMS C$_{33}$H$_{42}$N$_4$O$_3$ m/z 543.3335 (M+H)$_{Cal}$. 543.3337 (M+H)$_{Obs}$.

Example 573

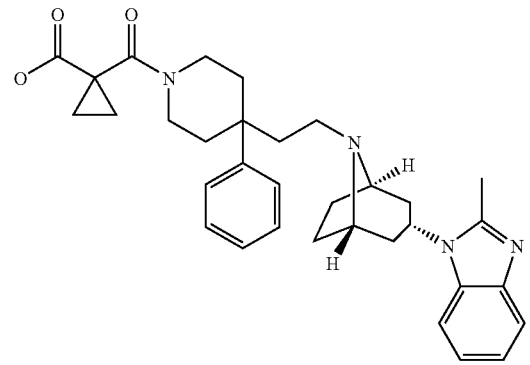

1-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]cyclopropanecarboxylic acid was prepared by treating title compound from example 573 with NaOH. $^1$H NMR (300 MHz, CDCl$_3$) δ 7.66 (d, 1H), 7.40-7.10 (m, 8H), 4.62 (m, 1H), 4.14 (m, 1H), 3.25 (m, 2H), 3.08 (m, 2H), 2.58 (s, 3H), 2.43-2.19 (m, 3H), 2.05-1.78 (m, 8H), 1.27 (s, 6H) 0.92-0.78 (m, 2H). HRMS C$_{33}$H$_{40}$N$_4$O$_3$ m/z 541.3179 (M+H)$_{Cal}$, 541.3163 (M+H)$_{Obs}$.

Example 574

2-Methyl-1-[(1R,5S)-8-(2-{1-[(5-methylpyrazin-2-yl)carbonyl]-4-phenylpiperidin-4-yl}ethyl)-8-azabicyclo[3.2.1]oct-3-yl]-1H-benzimidazole

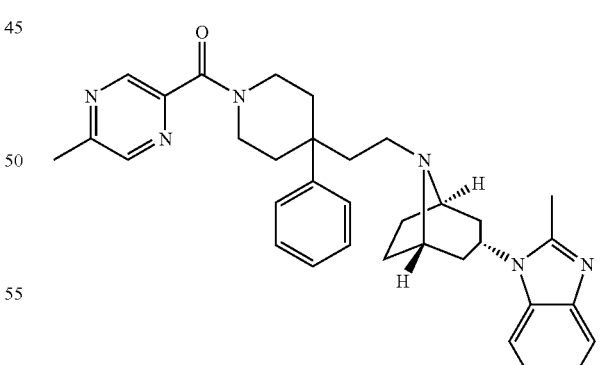

Method A (HATU). $^1$H NMR (300 MHz, CDCl$_3$) δ 8.78 (s, 1H), 8.41 (s, 1H), 7.67 (d, 1H), 7.45-7.09 (m, 8H), 4.61 (m, 1H), 4.25 (m, 1H), 3.75 (m, 1H), 3.42-3.19 (m, 4H), 2.62 (s, 3H), 2.57 (s, 3H), 2.40-2.19 (m, 4H), 2.00-1.79 (m, 10H), 1.63 (m, 2H). ES-LCMS m/z 548 (M+H).

Example 575

2-Methyl-1-[(1R,5S)-8-(2-{1-[(1-oxidopyridin-3-yl)carbonyl]-4-phenylpiperidin-4-yl}ethyl)-8-azabicyclo[3.2.1]oct-3-yl]-1H-benzimidazole

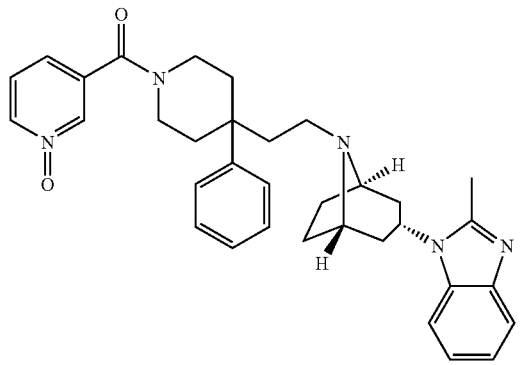

Method A (HATU). ¹H NMR (300 MHz, CDCl₃) δ 8.23 (d, 1H), 7.68 (d, 1H), 7.45-7.10 (m, 11H), 4.61 (m, 1H), 4.24 (m, 1H), 3.53 (m, 1H), 3.30-3.18 (m, 4H), 2.58 (s, 3H), 2.40-2.29 (m, 3H), 2.01-1.80 (m, 9H), 1.65 (m, 4H). ES-LCMS m/z 549 (M+H).

Example 576

1-[(1R,5S)-8-(2-{1-[(1,5-dimethyl-1H-pyrazol-3-yl)carbonyl]-4-phenylpiperidin-4-yl}ethyl)-8-azabicyclo[3.2.1]oct-3-yl]-2-methyl-1H-benzimidazole

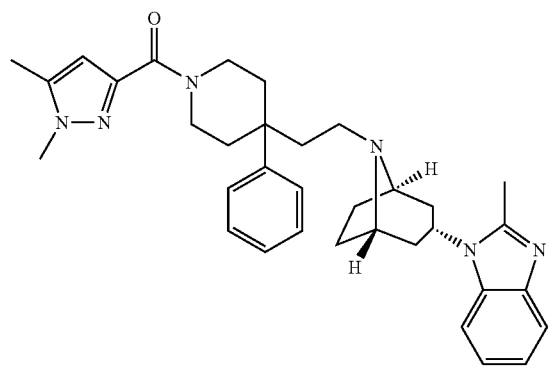

Method A (HATU). ¹H NMR (300 MHz, CDCl₃) δ 7.68 (d, 1H), 7.45-7.10 (m, 8H), 6.36 (s, 1H), 4.63 (m, 1H), 4.30-4.10 (m, 2H), 3.79 (s, 3H), 3.62 (m, 1H), 3.40-3.21 (m, 3H), 2.57 (s, 3H), 2.45-2.20 (m, 7H), 2.02-1.78 (m, 10H), 1.64-1.57 (m, 2H). ES-LCMS m/z 550 (M+H).

Example 577

1-[(1R,5S)-8-(2-{1-[(5-chlorothien-2-yl)carbonyl]-4-phenylpiperidin-4-yl}ethyl)-8-azabicyclo[3.2.1]oct-3-yl]-2-methyl-1H-benzimidazole

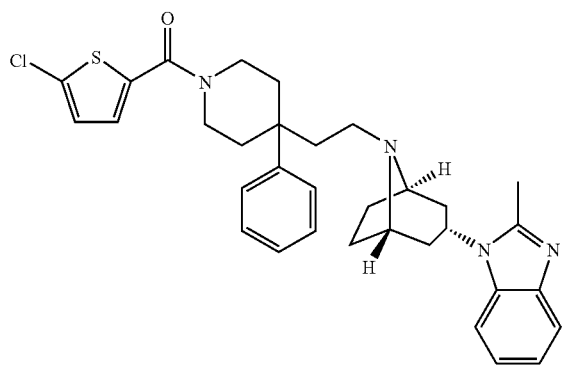

Method A (HATU). ¹H NMR (300 MHz, CDCl₃) δ 7.68 (d, 1H), 7.45-7.01 (m, 9H), 6.86 (d, 1H), 4.61 (m, 1H), 4.15-3.97 (m, 2H), 3.41 (m, 2H), 3.25 (m, 2H), 2.57 (s, 3H), 2.45-2.25 (m, 4H), 2.00-1.77 (m, 10H), 1.61-1.58 (m, 2H). ES-LCMS m/z 572 (M+H).

Example 578

5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1H-1,2,3-benzotriazole

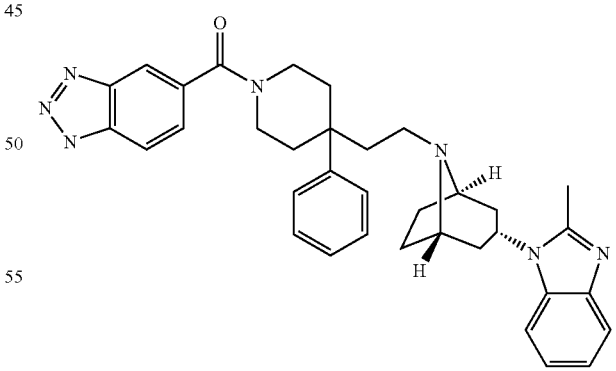

Method A (HATU). ¹H NMR (300 MHz, CDCl₃) δ 7.94 (s, 1H), 7.84 (d, 1H), 7.69 (d, 1H), 7.48-7.14 (m, 10H), 4.64 (m, 1H), 4.27 (m, 1H), 3.61 (m, 1H), 3.49-3.22 (m, 4H), 2.54 (s, 3H), 2.45-2.30 (m, 3H), 2.22 (m, 1H), 2.05-1.73 (m, 10H), 1.68-1.57 (m, 2H). ES-LCMS m/z 573 (M+H).

Example 579

1-[(1R,5S)-8-(2-{1-[(2-chloro-6-methylpyridin-3-yl)carbonyl]-4-phenylpiperidin-4-yl}ethyl)-8-azabicyclo[3.2.1]oct-3-yl]-2-methyl-1H-benzimidazole

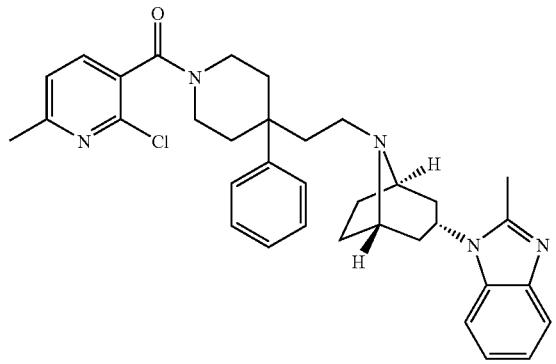

Method A (HATU). $^1$H NMR (300 MHz, CDCl$_3$) δ 7.70-7.55 (m, 1H), 7.47-7.08 (m, 10H), 4.61 (m, 1H), 4.23 (m, 1H), 3.49-3.17 (m, 5H), 2.57 (s, 6H), 2.45-2.29 (m, 3H), 2.13 (m, 1H), 2.02-1.78 (m, 10H), 1.68-1.56 (m, 2H). ES-LCMS m/z 581 (M+H)

Example 580

6-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1,3-benzothiazole

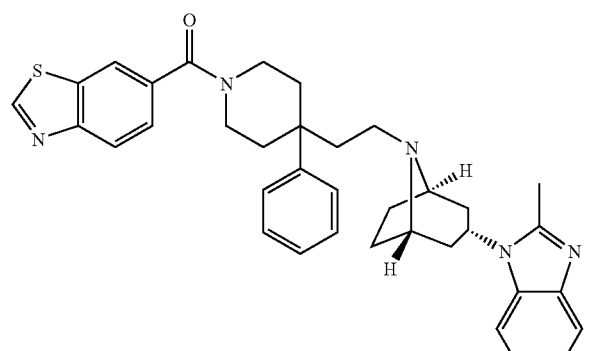

Method A (HATU). $^1$H NMR (300 MHz, CDCl$_3$) δ 9.08 (s, 1H), 8.20 (d, 1H), 8.03 (s, 1H), 7.69 (d, 1H), 7.55 (d, 1H), 7.41-7.09 (m, 8H), 4.61 (m, 1H), 4.23 (m, 1H), 3.62 (m, 1H), 3.48-3.17 (m, 4H), 2.55 (s, 3H), 2.45-2.28 (m, 3H), 2.25-2.09 (m, 2H), 2.01-1.78 (m, 9H), 1.63 (d, 2H). ES-LCMS m/z 589 (M+H).

Example 581 methyl 6-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]nicotinate

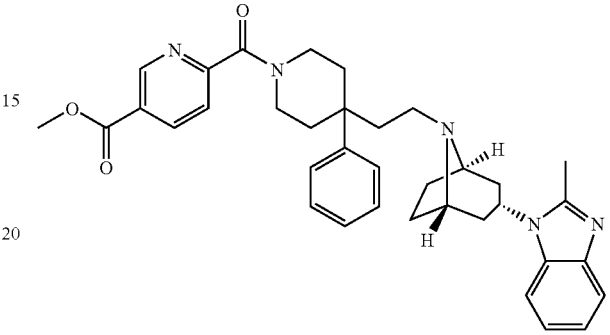

Method A (HATU). $^1$H NMR (300 MHz, CDCl$_3$) δ 9.19 (s, 1H), 8.38 (d, 1H), 7.65 (d, 1H), 7.45-7.09 (m, 8H), 4.61 (m, 1H), 4.21 (m, 1H), 3.98 (s, 3H), 3.64 (m, 1H), 3.48-3.21 (m, 4H), 2.57 (s, 3H), 2.48-2.29 (m, 3H), 2.25-2.15 (m, 1H), 2.02-1.79 (m, 10H), 1.62-1.55 (m, 2H). ES-LCMS m/z 591 (M+H).

Example 582

1-[(1R,5S)-8-(2-{1-[(4,5-dichloroisothiazol-3-yl)carbonyl]-4-phenylpiperidin-4-yl}ethyl)-8-azabicyclo[3.2.1]oct-3-yl]-2-methyl-1H-benzimidazole

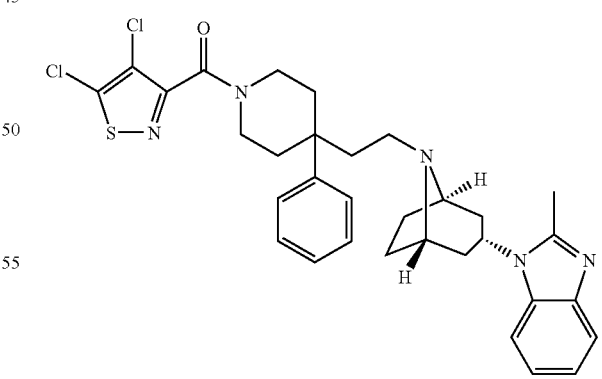

Method A (HATU). $^1$H NMR (300 MHz, CDCl$_3$) δ 7.68 (d, 1H), 7.43-7.09 (m, 8H), 4.65 (m, 1H), 4.30-4.13 (m, 1H), 3.60-3.17 (m, 5H), 2.58 (s, 3H), 2.46-2.19 (m, 4H), 2.05-1.81 (m, 10H), 1.69-1.59 (m, 2H). ES-LCMS m/z 607 (M+H).

Example 583

1-[(1R,5S)-8-(2-{1-[(2,4-dimethyl-1,3-thiazol-5-yl)carbonyl]-4-phenylpiperidin-4-yl}ethyl)-8-azabicyclo[3.2.1]oct-3-yl]-2-methyl-1H-benzimidazole

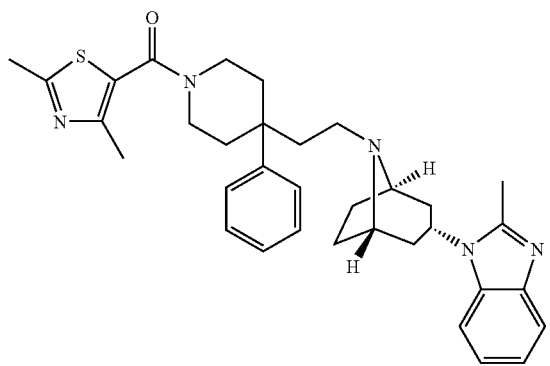

Method A (HATU). $^1$H NMR (300 MHz, CDCl$_3$) δ 7.65 (d, 1H), 7.46-7.18 (m, 8H), 4.61 (m, 1H), 3.98 (m, 1H), 3.42-3.19 (m, 4H), 2.67 (s, 3H), 2.56 (s, 3H), 2.41-2.19 (m, 7H), 2.05-1.75 (m, 10H), 1.70-1.55 (m, 2H). ES-LCMS m/z 567 (M+H).

Example 584

1-((1R,5S)-8-{2-[1-(2,5-dimethyl-3-furoyl)-4-phenylpiperidin-4-yl]ethyl}-8-azabicyclo[3.2.1]oct-3-yl)-2-methyl-1H-benzimidazole

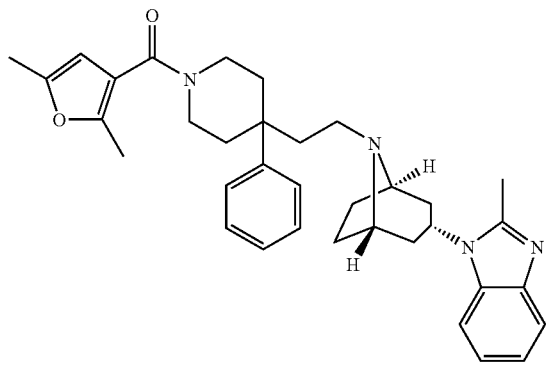

Method A (HATU). $^1$H NMR (300 MHz, CDCl$_3$) δ 7.68 (d, 1H), 7.42-7.11 (m, 8H), 5.91 (s, 1H), 4.61 (m, 1H), 4.06 (m, 1H), 3.76 (m, 1H), 3.40-3.18 (m, 4H), 2.57 (s, 3H), 2.44-2.33 (m, 4H), 2.31 (s, 3H), 2.24 (s, 3H), 2.00-1.72 (m, 10H), 1.62-1.53 (m, 2H). ES-LCMS m/z 550 (M+H).

Example 585

2-methyl-1-((1R,5S)-8-{2-[4-phenyl-1-(thien-2-ylacetyl)piperidin-4-yl]ethyl}-8-azabicyclo[3.2.1]oct-3-yl)-1H-bnzimidazole

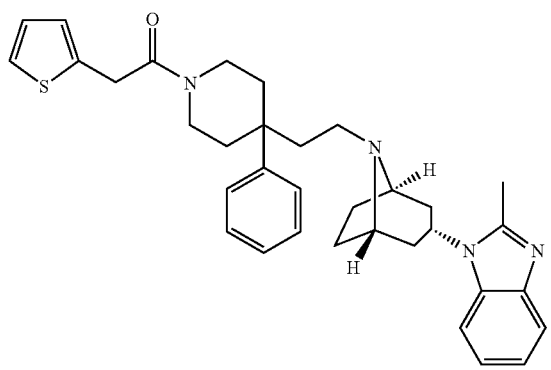

Method A (HATU). $^1$H NMR (300 MHz, CDCl$_3$) δ 7.71 (d, 1H), 7.43-7.09 (m, 9H), 7.01-6.83 (m, 2H), 4.75 (m, 1H), 4.10-3.97 (m, 1H), 3.90 (s, 2H), 3.84 (s, 1H), 3.75-3.59 (m, 4H), 2.54 (s, 3H), 2.52-2.36 (m, 1H), 2.25-1.57 (m, 14H). ES-LCMS m/z 552 (M+H).

Example 586

2-methyl-1-((1R,5S)-8-{2-[1-(3-methyl-2-furoyl)-4-phenylpiperidin-4-yl]ethyl}-8-azabicyclo[3.2.1]oct-3-yl)-1H-benzimidazole

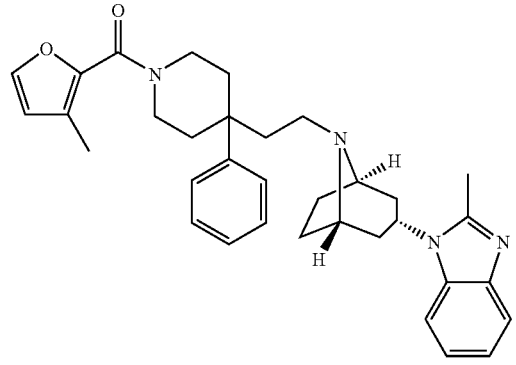

Method A (HATU). $^1$H NMR (300 MHz, CDCl$_3$) δ 7.66 (d, 1H), 7.43-7.09 (m, 9H), 6.32 (s, 1H), 4.63 (m, 1H), 3.98 (m, 1H), 3.48-3.20 (m, 4H), 2.58 (s, 3H), 2.48-2.20 (m, 7H), 2.02-1.78 (m, 10H), 1.70-1.55 (m, 2H). ES-LCMS m/z 536 (M+H).

Example 587

1-((1R,5S)-8-{2-[1-(4,5-dimethyl-2-furoyl)-4-phenylpiperidin-4-yl]ethyl}-8-azabicyclo[3.2.1]oct-3-yl)-2-methyl-1H-benzimidazole

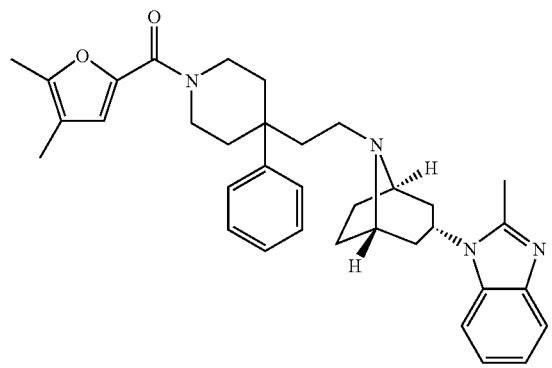

Method A (HATU). $^1$H NMR (300 MHz, CDCl$_3$) δ 7.68 (d, 1H), 7.44-7.13 (m, 8H), 6.73 (s, 1H), 4.64 (m, 1H), 4.20-4.07 (m, 2H), 3.55-3.21 (m, 4H), 2.58 (s, 3H), 2.48-2.21 (m, 7H), 2.03-1.80 (m, 13H), 1.70-1.59 (m, 2H). ES-LCMS m/z 550 (M+H).

Example 588

1-[(1R,5S)-8-(2-{1-[(1-tert-butyl-3-methyl-1H-pyrazol-5-yl)carbonyl]-4-phenylpiperidin-4-yl}ethyl)-8-azabicyclo[3.2.1]oct-3-yl]-2-methyl-1H-benzimidazole

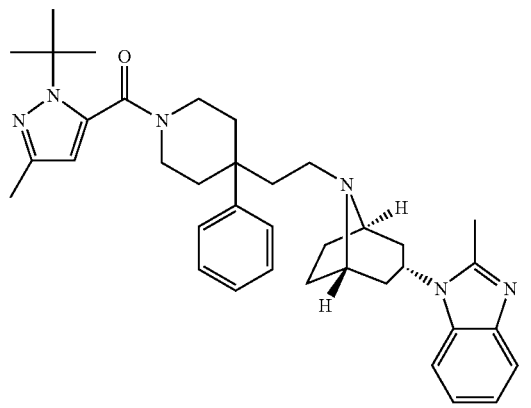

Method A (HATU). $^1$H NMR (300 MHz, CDCl$_3$) δ 7.66 (d, 1H), 7.46-7.13 (m, 8H), 5.95 (s, 1H), 4.63 (m, 1H), 4.20-4.13 (m, 1H), 3.62-3.48 (m, 1H), 3.41-3.13 (m, 4H), 2.58 (s, 3H), 2.48-2.28 (m, 3H), 2.26 (s, 1H), 2.24-2.10 (m, 1H), 2.00-1.65 (m, 12H), 1.59 (s, 10H). ES-LCMS m/z 592 (M+H).

Example 589

2-methyl-1-((1R,5S)-8-{2-[1-(1-oxidoisonicotinoyl)-4-phenylpiperidin-4-yl]ethyl}-8-azabicyclo[3.2.1]oct-3-yl)-1H-benzimidazole

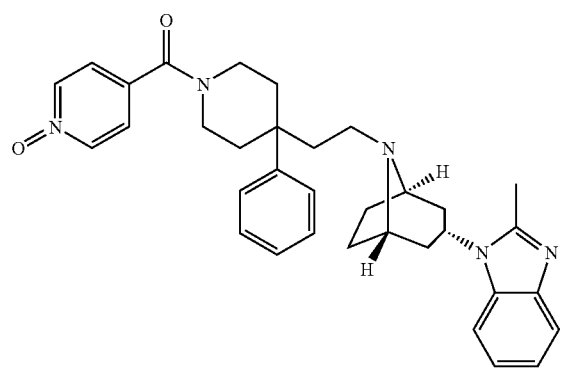

Method A (HATU). $^1$H NMR (300 MHz, CDCl$_3$) δ 8.25 (d, 2H), 8.18 (d, 1H), 7.42-7.12 (m, 10H), 4.63 (m, 1H), 3.39-3.20 (m, 4H), 2.58 (s, 3H), 2.41-2.30 (m, 3H), 1.97-1.77 (m, 10H), 1.68-1.49 (m, 5H). ES-LCMS m/z 549 (M+H).

Example 590

2-methyl-1-[(1R,5S)-8-(2-{1-[(5-methylthien-2-yl)carbonyl]-4-phenylpiperidin-4-yl}ethyl)-8-azabicyclo[3.2.1]oct-3-yl]-1H-benzimidazole

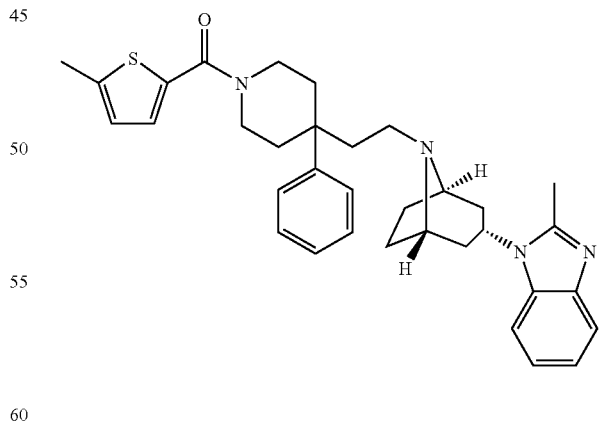

Method A (HATU). $^1$H NMR (300 MHz, CDCl$_3$) δ 7.68 (d, 1H), 7.45-7.06 (m, 9H), 6.69 (m, 1H), 4.64 (m, 1H), 4.19-4.00 (m, 2H), 3.44 (m, 2H), 3.30 (m, 2H), 2.58 (s, 3H), 2.51 (s, 3H), 2.48-2.23 (m, 4H), 2.04-1.81 (m, 10H), 1.70-1.60 (m, 2H). ES-LCMS m/z 552 (M+H).

Example 591

1-((1R,5S)-8-{2-[1-(5-bromo-2-furoyl)-4-phenylpiperidin-yl]ethyl}-8-azabicyclo[3.2.1]oct-3-yl)-2-methyl-1H-benzimidazole

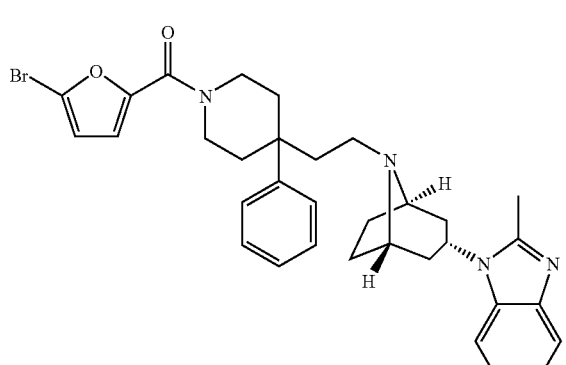

Method A (HATU). $^1$H NMR (300 MHz, CDCl$_3$) δ 7.69 (d, 1H), 7.47-7.13 (m, 8H), 6.96 (d, 1H), 6.43 (d, 1H), 4.66 (m, 1H), 4.20-4.07 (m, 2H), 3.52-3.22 (m, 4H), 2.59 (s, 3H), 2.49-2.24 (m, 4H), 2.04-1.81 (m, 10H), 1.70-1.60 (m, 2H). ES-LCMS m/z 600 (M+H).

Example 592

1-[(1R,5S)-8-(2-{1-[(5-bromothien-2-yl)carbonyl]-4-phenylpiperidin-4-yl}ethyl)-8-azabicyclo[3.2.1]oct-3-yl]-2-methyl-1H-benzimidazole

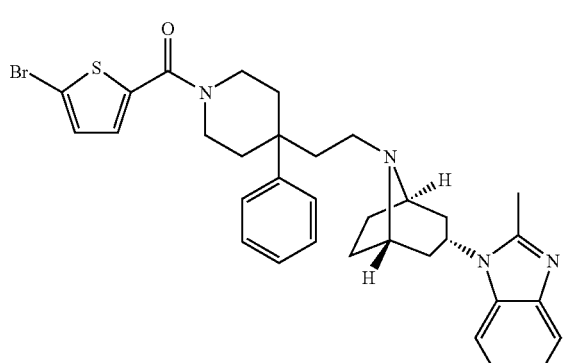

Method A (HATU). $^1$H NMR (300 MHz, CDCl$_3$) δ 7.66 (d, 1H), 7.48-7.13 (m, 9H), 7.07-6.95 (m, 1H), 4.64 (m, 1H), 4.10-3.94 (m, 2H), 3.53-3.21 (m, 4H), 2.58 (s, 3H), 2.46-2.25 (m, 4H), 2.04-1.79 (m, 10H), 1.71-1.57 (m, 2H). ES-LCMS m/z 616 (M+H).

Example 593

2-methyl-1-{(1R,5S)-8-[2-(4-phenyl-1-{4-[(trifluoromethyl)thio]benzoyl}piperidin-4-yl)ethyl]-8-azabicyclo[3.2.1]oct-3-yl}-1H-benzimidazole

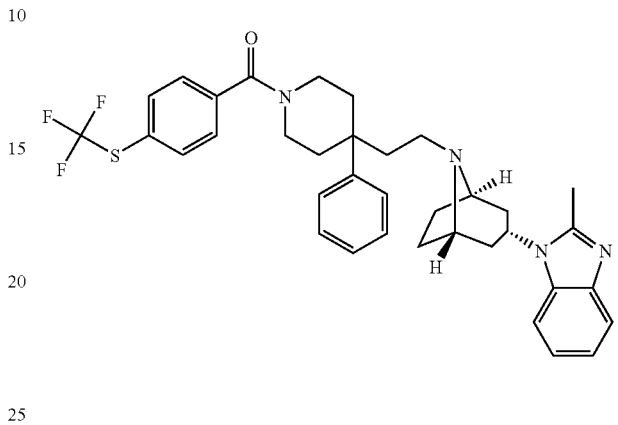

Method A (HATU). $^1$H NMR (300 MHz, CDCl$_3$) δ 7.80-7.62 (m, 3H), 7.50-7.11 (m, 11H), 4.63 (m, 1H), 4.25-4.13 (m, 1H), 3.60-3.17 (m, 4H), 2.57 (s, 1H), 2.44-2.29 (m, 3H), 2.20-2.08 (m, 1H), 2.02-1.70 (m, 10H), 1.62-1.57 (m, 2H). ES-LCMS m/z 632 (M+H).

Example 594

2-methyl-1-[(1R,5S)-8-(2-{1-[(5-methyl-3-phenylisoxazol-4-yl)carbonyl]-4-phenylpiperidin-4-yl}ethyl)-8-azabicyclo[3.2.1]oct-3-yl]-1H-benzimidazole

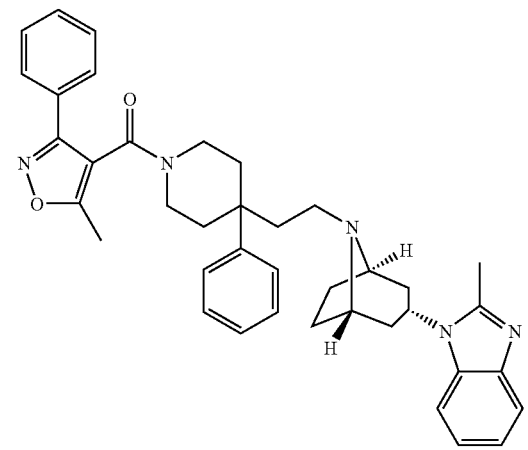

Method A (HATU). $^1$H NMR (300 MHz, CDCl$_3$) δ 7.74-7.65 (m, 2H), 7.51-7.14 (m, 12H), 4.59 (m, 1H), 4.18 (m, 1H), 3.38-3.17 (m, 4H), 2.57 (s, 3H), 2.48 (s, 3H), 2.44-2.17 (m, 4H), 2.01-1.54 (m, 12H). ES-LCMS m/z 613 (M+H).

Example 595

1-[(1R,5S)-8-(2-{1-[(2,6-dichloropyridin-3-yl)carbonyl]-4-phenylpiperidin-4-yl}ethyl)-8-azabicyclo[3.2.1]oct-3-yl]-2-methyl-1H-benzimidazole

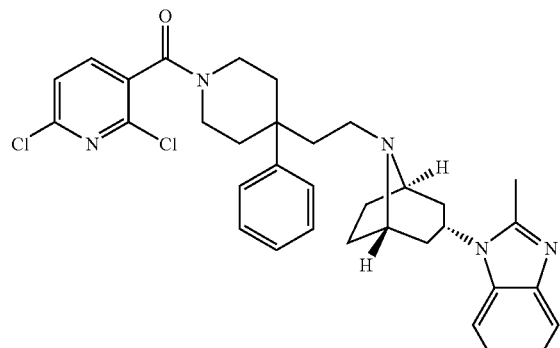

Method A (HATU). $^1$H NMR (300 MHz, CDCl$_3$) δ 7.74-7.60 (m, 2H), 7.54-7.05 (m, 9H), 4.61 (m, 1H), 4.23 (m, 1H), 3.45-3.02 (m, 5H), 2.56 (s, 3H), 2.47-2.09 (m, 4H), 2.00-1.75 (m, 8H), 1.70-1.53 (m, 2H), 1.28-1.20 (m, 2H). ES-LCMS m/z 601 (M+H).

Example 596

N-{4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}thiourea

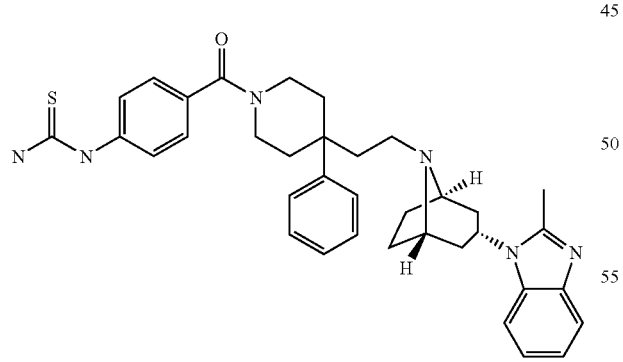

Method A (HATU). $^1$H NMR (300 MHz, CDCl$_3$) δ 8.95 (s, 1H), 7.67 (d, 1H), 7.45-7.06 (m, 10H), 6.35 (s, 1H), 4.61 (m, 1H), 4.20-4.09 (m, 1H), 3.71-3.51 (m, 1H), 3.48-3.16 (m, 4H), 2.56 (s, 3H), 2.46-2.13 (m, 4H), 2.04-1.55 (m, 13H), 1.27 (s, 2H). ES-LCMS m/z 606 (M+H).

Example 597 methyl 3-fluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzoate

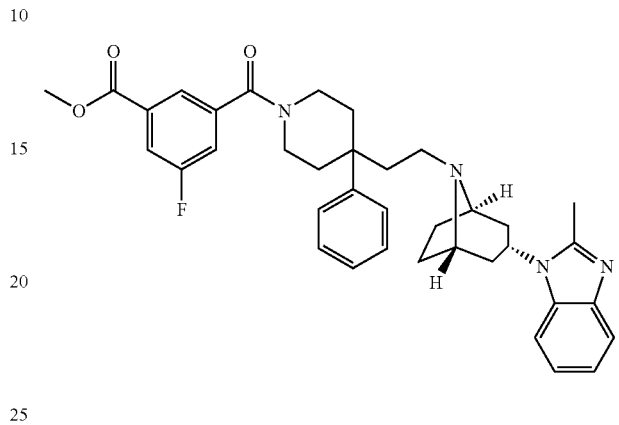

Method A (HATU). $^1$H NMR (300 MHz, CDCl$_3$) δ 7.85-7.63 (m, 2H), 7.42-7.09 (m, 10H), 4.62 (m, 1H), 4.30-4.15 (m, 1H), 3.94 (s, 3H), 3.62-3.19 (m, 5H), 2.57 (s, 3H), 2.46-2.12 (m, 4H), 2.00-1.75 (m, 10H), 1.73-1.55 (m, 2H). ES-LCMS m/z 608 (M+H).

Example 598

1-[(1R,5S)-8-(2-{1-[(2,4-dimethylpyridin-3-yl)carbonyl]-4-phenylpiperidin-4-yl}ethyl)-8-azabicyclo[3.2.1]oct-3-yl]-2-methyl-1H-benzimidazole

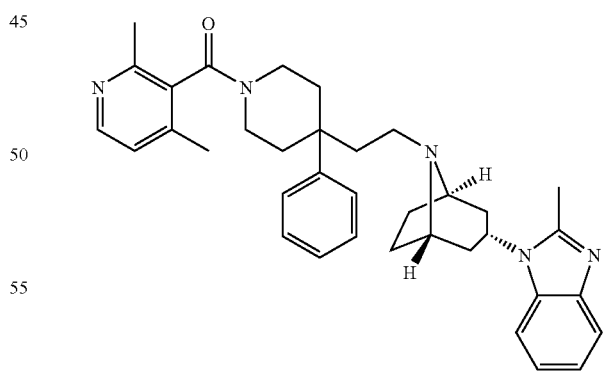

Method A (HATU). $^1$H NMR (300 MHz, CDCl$_3$) δ 8.36 (d, 1H), 7.65 (d, 1H), 7.44-7.23 (m, 8H), 7.05-6.93 (m, 1H), 4.61 (m, 1H), 4.36-4.25 (m, 1H), 3.50-3.03 (m, 7H), 2.56 (m, 4H), 2.37 (m, 4H), 2.15 (s, 3H), 1.97-1.54 (m, 12H). ES-LCMS m/z 561 (M+H).

Example 599 methyl 2,5-dimethyl-4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzoate

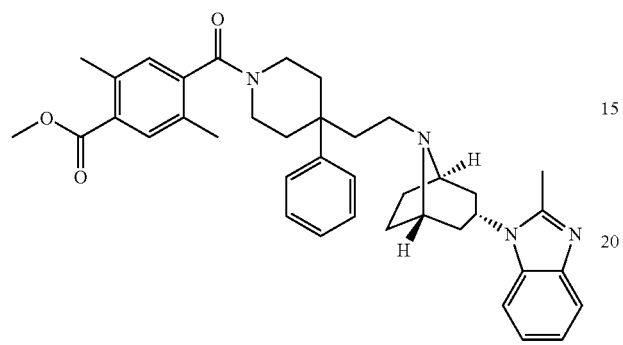

Method A (HATU). $^1$H NMR (300 MHz, CDCl$_3$) δ 7.83-7.60 (m, 2H), 7.50-7.08 (m, 9H), 4.62 (m, 1H), 4.30-4.11 (m, 1H), 3.91 (s, 2H), 3.42-3.08 (m, 6H), 2.94 (s, 3H), 2.81 (s, 3H), 2.57 (s, 3H), 2.40-2.14 (m, 4H), 2.05-1.75 (m, 10H), 2.20-1.57 (m, 2H). ES-LCMS m/z 618 (M+H).

Example 600

1-((1R,5S)-8-{2-[1-(3,5-dichloro-1-oxidoisonicotinoyl)-4-phenylpiperidin-4-yl]ethyl}-8-azabicyclo[3.2.1]oct-3-yl)-2-methyl-1H-benzimidazole

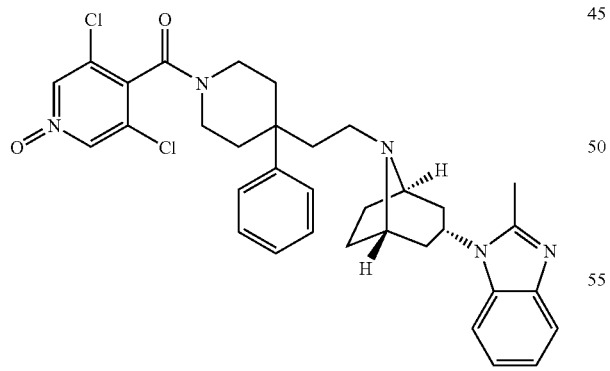

Method A (HATU). $^1$H NMR (300 MHz, CDCl$_3$) δ 8.23-8.10 (m, 1H), 7.70-7.61 (m, 1H), 7.45-7.08 (m, 9H), 4.61 (m, 1H), 4.35-4.24 (m, 1H), 2.58 (s, 3H), 2.48-2.22 (m, 4H), 2.04-1.77 (m, 10H), 1.70-1.57 (m, 2H). ES-LCMS m/z 617 (M+H).

Example 601

N-{2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}methanesulfonamide

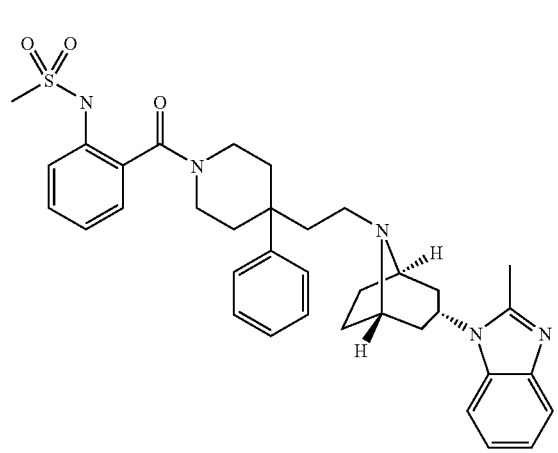

Method A (HATU). $^1$H NMR (300 MHz, methanol-d$_4$) δ 7.90-7.75 (m, 2H), 7.71-7.41 (m, 10H), 7.36-7.24 (m, 1H), 5.31 (m, 1H), 4.25-4.04 (m, 3H), 3.62-3.53 (m, 1H), 3.51-3.26 (m, 8H), 3.04-2.90 (m, 1H), 2.84 (s, 3H), 2.78-2.69 (m, 1H), 2.52-2.13 (m, 10H), 2.10-1.82 (m, 2H). ES-LCMS m/z 625 (M+H).

Example 602

4-chloro-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]aniline

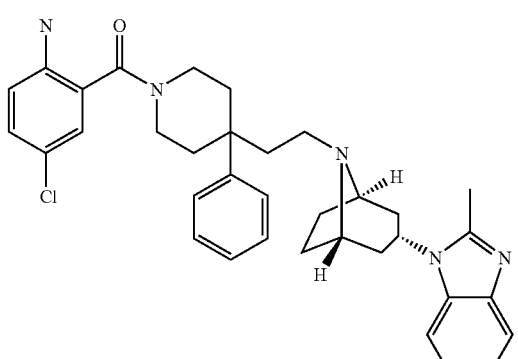

Method B (Anhydride). $^1$H NMR (300 MHz, methanol-d$_4$) δ 7.81-7.73 (m, 2H), 7.63-7.57 (m, 2H), 7.46 (s, 1H), 7.31 (m, 1H), 7.20-7.03 (m, 2H), 6.79 (d, 1H), 5.27 (m, 1H), 4.11-4.03 (m, 2H), 3.30 (m, 6H), 2.97-2.86 (m, 2H), 2.82 (s, 3H), 2.77-2.70 (m, 2H), 2.45-2.11 (m, 10H), 1.95-1.83 (m, 2H). ES-LCMS m/z 581 (M+H).

Example 603

4-bromo-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]aniline

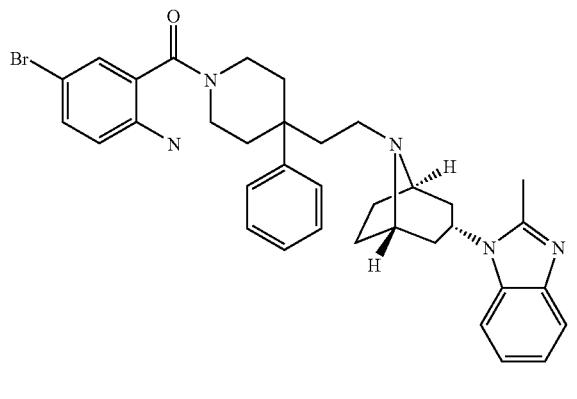

Method B (Anhydride). $^1$H NMR (300 MHz, methanol-d$_4$) δ 8.08-7.93 (m, 2H), 7.85-7.72 (m, 2H), 7.64-7.55 (m, 2H), 7.50-7.42 (m, 4H), 7.34-7.27 (m, 1H), 6.80 (d, 1H), 5.31 (m, 1H), 4.14-4.00 (m, 1H), 3.38-3.27 (m, 6H), 2.98-2.87 (m, 2H), 2.86 (s, 3H), 2.83-2.71 (m, 2H), 2.44-2.14 (m, 10H), 2.00-1.85 (m, 2H). ES-LCMS m/z 625 (M+H).

Example 604

1-[(1R,5S)-8-(2-{1-[(5-ethyl-1-phenyl-1H-1,2,3-triazol-4-yl)carbonyl]-4-phenylpiperidin-4-yl}ethyl)-8-azabicyclo[3.2.1]oct-3-yl]-2-methyl-1H-benzimidazole

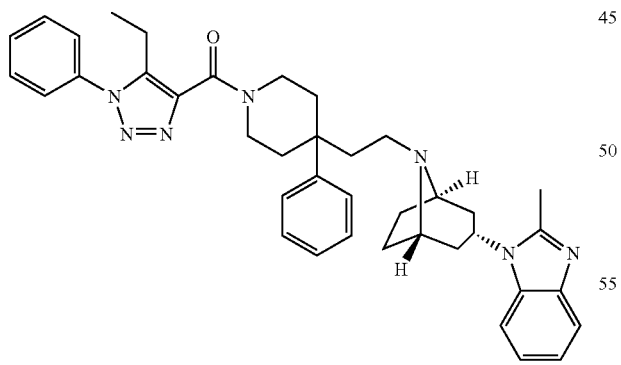

Method A (HATU). Acid precursor synthesized according to procedure outlined in *J. Chem. Res. Synop.*, 12, 400-1 (1984). $^1$H NMR (300 MHz, CDCl$_3$) δ 7.70-7.54 (m, 4H), 7.50-7.13 (m, 10H), 4.64 (m, 1H), 4.40-4.35 (m, 1H), 4.28-4.15 (m, 1H), 3.82-3.65 (m, 1H), 3.48-3.22 (m, 4H), 3.00-2.85 (m, 2H), 2.46-2.30 (m, 4H), 2.04-1.78 (m, 13H), 1.68-1.57 (m, 2H), 1.18-1.05 (m, 3H). ES-LCMS m/z 627 (M+H).

Example 605

4-({5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1H-1,2,3-triazol-4-yl}oxy)phenol

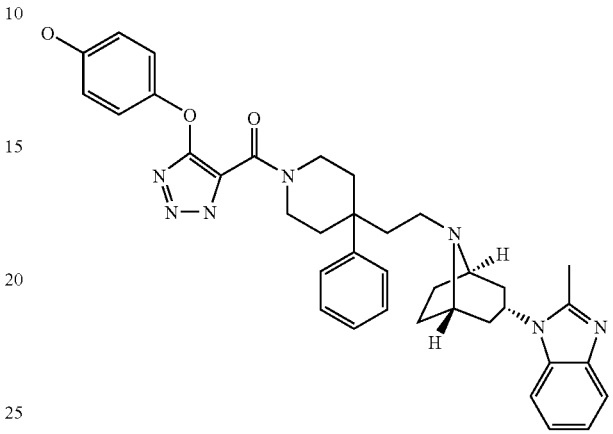

Method A (HATU). Acid precursor synthesized according to procedure outlined in *J. Chem. Res. Synop.*, 12, 400-1 (1984). $^1$H NMR (400 MHz, CDCl$_3$) δ 7.66 (d, 1H), 7.58-7.11 (m, 10H), 6.92-6.88 (m, 1H), 6.75-6.69 (m, 1H), 4.76 (m, 1H), 4.20-3.95 (m, 2H), 3.52-3.21 (m, 4H), 2.52-2.29 (m, 6H), 2.19-1.55 (m, 12H), 1.25 (s, 2H). ES-LCMS m/z 631 (M+H).

Example 606

2-methyl-1-[(1R,5S)-8-(2-{1-[(1-methyl-1H-1,2,3-triazol-5-yl)carbonyl]-4-phenylpiperidin-4-yl}ethyl)-8-azabicyclo[3.2.1]oct-3-yl]-1H-benzimidazole

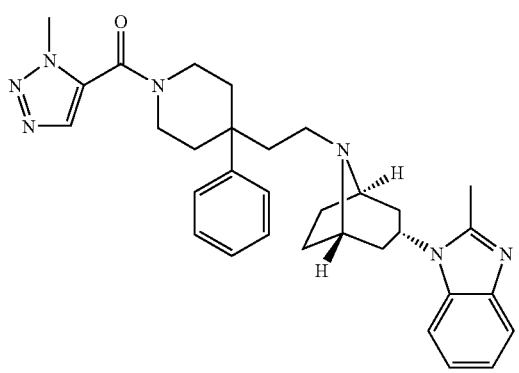

Method A (HATU). Acid precursor synthesized according to procedure outlined in *J. Org. Chem.* 41(6), 1041-51 (1976). $^1$H NMR (300 MHz, CDCl$_3$) δ 7.75-7.62 (m, 2H), 7.46-7.11 (m, 8H), 4.67-4.53 (m, 1H), 4.16 (s, 3H), 3.85-3.71 (m, 1H), 3.46-3.18 (m, H), 2.45-2.22 (m, 4H), 1.98-1.58 (m, 16H). ES-LCMS m/z 537 (M+H).

Example 607

(1R,5S)-8-{2-[1-(2,2-dimethylpropanoyl)-4-phenylpiperidin-4-yl]ethyl}-3-(3-isopropyl-5-methyl-4H-1,2,4-triazol-4-yl)-8-azabicyclo[3.2.1]octane

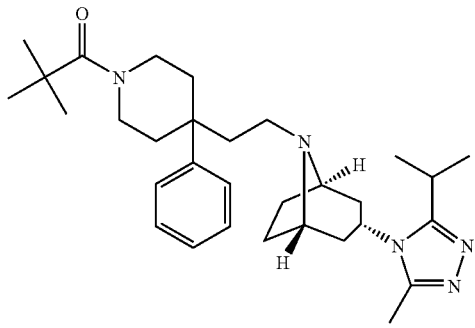

Method A (HATU). Amine portion synthesized according to the procedure described in WO01109106A2, Pfizer Corp. $^1$H NMR (300 MHz, CDCl$_3$) δ 7.44-7.20 (m, 5H), 4.53 (m, 1H), 3.96-3.88 (m, 2H), 3.35-2.89 (m, 8H), 2.44 (s, 3H), 2.22-2.15 (m, 2H), 2.01-1.71 (m, 8H), 1.59-1.49 (m, 4H), 1.36 (d, 5H), 1.29 (s, 9H). ES-LCMS m/z 505 (M+H).

Example 608

2-bromo-N-ethyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

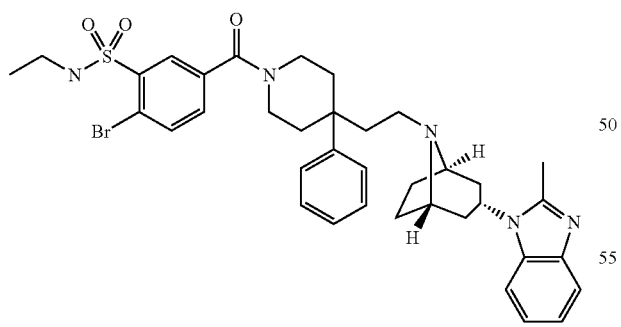

Method A (HATU). $^1$H NMR (300 MHz, CDCl$_3$) δ 8.14 (s, 1H), 7.80 (d, 1H), 7.68 (d, 1H), 7.48-7.15 (m, 9H), 5.19 (m, 1H), 4.63 (m, 1H), 4.24 (m, 1H), 3.57-3.49 (m, 1H), 3.38-3.19 (m, 4H), 3.04-2.95 (m, 2H), 2.58 (s, 3H), 2.44-2.33 (m, 3H), 2.22-2.17 (m, 1H), 1.95-1.75 (m, 10H), 1.61 (m, 2H), 1.12 (m, 3H). ES-LCMS m/z 717 (M+H).

Example 609

2-bromo-5-[(4-{2-[(1R,5S)-3-(2-methyl-1H-benzimidazol-1-yl)-8-azabicyclo[3.2.1]oct-8-yl]ethyl}-4-phenyl piperidin-1-yl)carbonyl]-N-propylbenzenesulfonamide

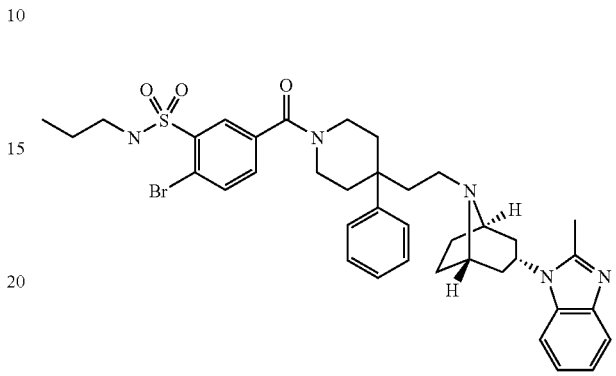

Method A (HATU). $^1$H NMR (300 MHz, CDCl$_3$) δ 8.14 (s, 1H), 7.80 (d, 1H), 7.68 (d, 1H), 7.48-7.15 (m, 9H), 5.22 (m, 1H), 4.62 (m, 1H), 4.26 (m, 1H), 3.49 (m, 2H), 3.35-3.25 (m, 4H), 2.92-2.85 (m, 2H), 2.58 (s, 3H), 2.44-2.33 (m, 3H), 2.21-2.17 (m, 1H), 1.95-1.75 (m, 10H), 1.61 (m, 2H), 1.52 (m, 2H), 0.89 (m, 3H). ES-LCMS m/z 731 (M+H).

Example 610

2-bromo-N-cyclopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

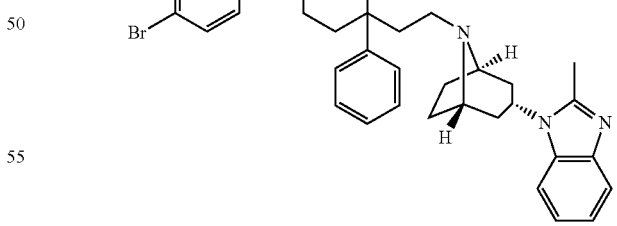

Method A (HATU). $^1$H NMR (300 MHz, CDCl$_3$) δ 8.19 (s, 1H), 7.79 (d, 1H), 7.68 (d, 1H), 7.51-7.16 (m, 9H), 5.68 (m, 1H), 4.66 (m, 1H), 4.20 (m, 1H), 4.26 (m, 1H), 3.54-3.27 (m, 5H), 2.58 (s, 3H), 2.41-2.36 (m, 3H), 2.17 (m, 2H), 1.95-1.75 (m, 10H), 1.64 (m, 2H), 0.68 (m, 4H). ES-LCMS m/z 729 (M+H).

Example 611

2-methyl-1-[(1R,5S)-8-(2-{4-phenyl-1-[(1-phenyl-1H-1,2,3-triazol-5-yl)carbonyl]piperidin-4-yl}ethyl)-8-azabicyclo[3.2.1]oct-3-yl]-1H-benzimidazole

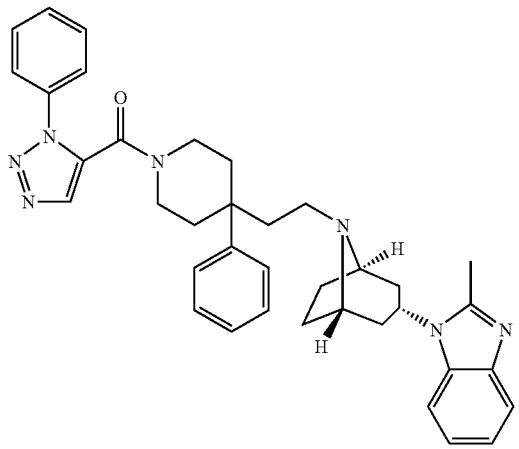

Method A (HATU). $^1$H NMR (300 MHz, CDCl$_3$) δ 7.84 (s, 1H), 7.70-7.48 (m, 5H), 7.43-7.11 (m, 8H), 4.58 (m, 1H), 4.20-4.10 (m, 1H), 3.22 (m, 4H), 3.01 (m, 1H), 2.40-2.23 (m, 3H), 1.96-1.60 (m, 15H), 1.26 (m, 2H). ES-LCMS m/z 599 (M+H).

Example 612

2-methyl-1-((1R,5S)-8-{2-[4-phenyl-1-(1H-1,2,3-triazol-5-ylcarbonyl)piperidin-4-yl]ethyl}-8-azabicyclo[3.2.1]oct-3-yl)-1H-benzimidazole

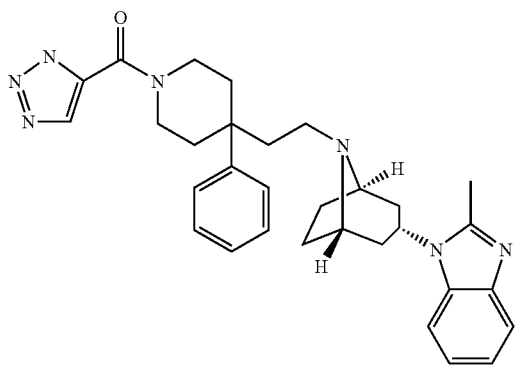

Method A (HATU). $^1$H NMR (300 MHz, CDCl$_3$) δ 8.13 (s, 1H), 7.70 (d, 1H), 7.40-7.15 (m, 8H), 4.67 (m, 1H), 4.40 (m, 1H), 4.19 (m, 1H), 3.72 (m, 1H), 3.44-3.26 (m, 1H), 2.49-2.21 (m, 8H), 2.01-1.85 (m, 10H), 1.66 (m, 2H), 1.26 (s, 1H). ES-LCMS m/z 523 (M+H).

Example 613

2-methyl-1-[(1R,5S)-8-(2-{4-phenyl-1-[(3-phenyloxiran-2-yl)carbonyl]piperidin-4-yl}ethyl)-8-azabicyclo[3.2.1]oct-3-yl]-1H-benzimidazole

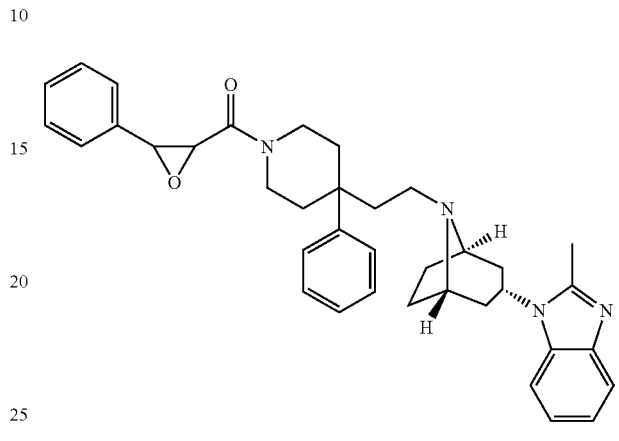

Method A (HATU). $^1$H NMR (300 MHz, CDCl$_3$) δ 7.66 (m, 1H), 7.38-7.16 (m, 13H), 4.59 (m, 1H), 4.08 (m, 1H), 3.62 (m, 1H), 3.24 (m, 2H), 2.59 (s, 3H), 2.55 (m, 1H), 2.34 (m, 2H), 1.93-1.82 (m, 5H), 1.70-1.52 (m, 10H), 1.25 (s, 2H). ES-LCMS m/z 574 (M+H).

Example 614

N-ethyl-2,4-difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

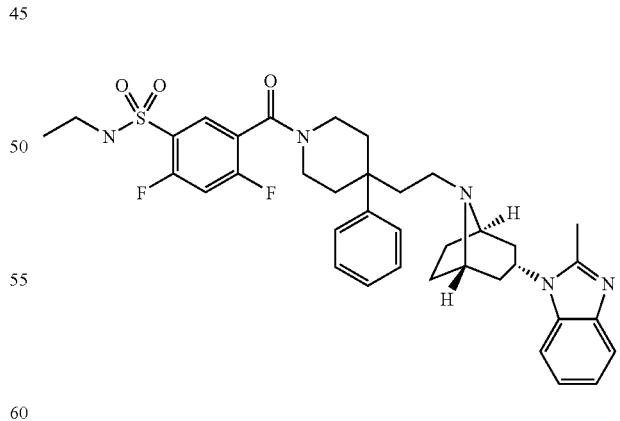

Method A (HATU). $^1$H NMR (300 MHz, methanol-d$_4$) δ 7.60-7.37 (m, 7H), 7.22 (m, 3H), 6.59 (d, 1H), 4.79 (m, 1H), 3.63 (m, 1H), 3.44 (m, 2H), 3.24 (m, 2H), 2.96 (m, 2H), 2.55 (s, 3H), 2.50-2.33 (m, 2H), 2.12-1.90 (m, 10H), 1.79 (m, 2H), 1.20 (m, 3H), 1.07 (m, 3H). ES-LCMS m/z 675 (M+H).

Example 615

2-methoxy-N-methyl-5-[(4-{2-[(1R,5S)-3-(2-methyl-1H-benzimidazol-1-yl-8-azabicyclo[3.2.1]oct-8-yl]ethyl}-4-phenylpiperdin-1-yl)carbonyl]benzenesulfonamide

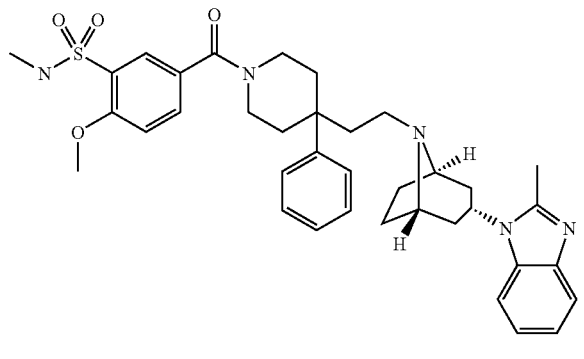

Method A (HATU). $^1$H NMR (300 MHz, methanol-d$_4$) δ 7.90 (d, 1H), 7.69 (d, 1H), 7.56 (d, 1H), 7.48-7.37 (m, 5H), 7.32-7.19 (m, 4H), 4.78 (m, 1H), 4.03 (s, 3H), 3.39-3.31 (m, 4H), 2.55 (d, 6H), 2.45 (m, 2H), 2.29 (m, 2H), 2.11-1.82 (m, 10H), 1.73 (m, 2H), 1.30 (s, 3H). ES-LCMS m/z 655 (M+H).

Example 616

N-ethyl-2-methoxy-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

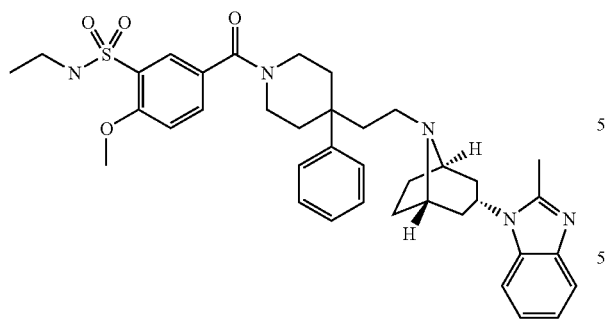

Method A (HATU). $^1$H NMR (300 MHz, methanol-d$_4$) δ 7.91 (s, 1H), 7.68 (m, 1H), 7.52 (m, 1H), 7.48-7.36 (m, 5H), 7.32-7.19 (m, 4H), 4.76 (m, 1H), 4.03 (s, 3H), 3.39-3.31 (m, 4H), 2.94 (m, 2H), 2.55 (s, 3H), 2.48-2.39 (m, 4H), 2.09-1.88 (m, 10H), 1.71 (m, 2H), 1.30 (s, 3H), 1.05 (m, 3H). ES-LCMS m/z 669 (M+H).

Example 617

N-isopropyl-2-methoxy-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide

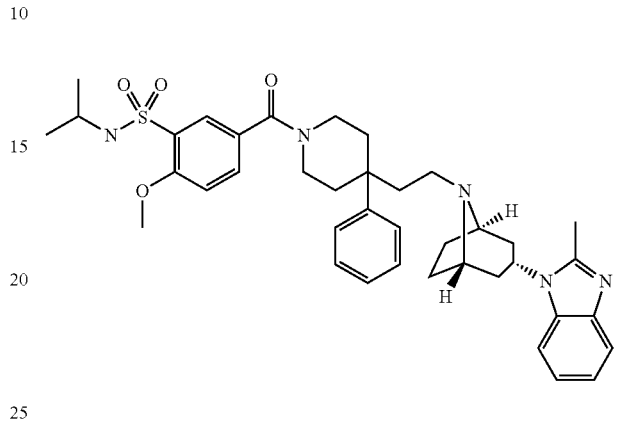

Method A (HATU). $^1$H NMR (300 MHz, methanol-d$_4$) δ 7.92 (d, 1H), 7.70 (m, 1H), 7.52 (m, 1H), 7.43-7.36 (m, 5H), 7.32-7.13 (m, 4H), 4.75 (m, 1H), 4.12 (m, 1H), 4.03 (s, 3H), 3.66 (m, 1H), 3.40-3.31 (m, 6H), 2.54 (s, 3H), 2.48-2.36 (m, 4H), 2.04-1.90 (m, 10H), 1.70 (m, 2H), 1.06 (d, 6H). ES-LCMS m/z 683 (M+H).

Example 618

N-cyclopropyl-2-methoxy-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide

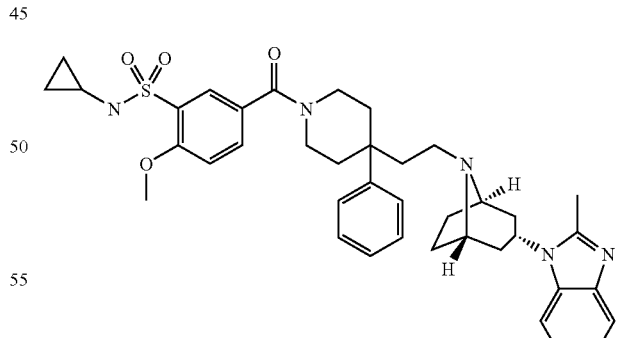

Method A (HATU). $^1$H NMR (300 MHz, methanol-d$_4$) δ 7.95 (m, 1H), 7.73 (m, 1H), 7.52 (m, 1H), 7.48-7.39 (m, 5H), 7.30-7.15 (m, 4H), 4.76 (m, 1H), 4.17 (m, 1H), 4.03 (s, 3H), 3.69 (m, 1H), 3.40-3.31 (m, 6H), 2.54 (s, 3H), 2.48-2.36 (m, 4H), 2.21-1.90 (m, 10H), 1.71 (m, 2H), 0.55 (m, 4H). ES-LCMS m/z 681 (M+H).

Example 619

2-chloro-5-[(4-{2-[(1R,5S)-3-(2-methyl-1H-benz-imidazol-1-yl)-8-azabicyclo[3.2.1]oct-8-yl]ethyl}-4-phenylpiperidin-1-yl)carbonyl]aniline

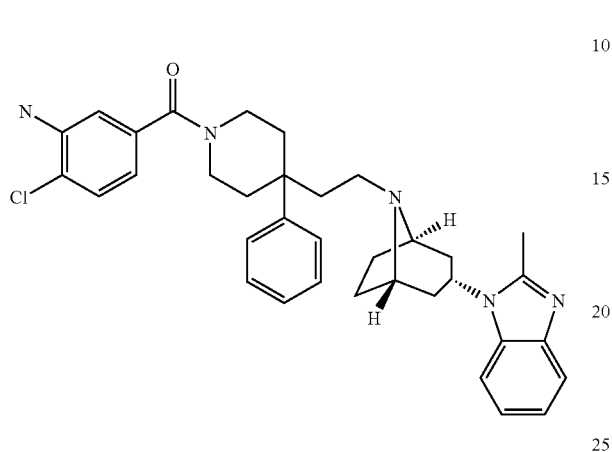

Method A (HATU). $^1$H NMR (300 MHz, methanol-$d_4$) δ 7.53 (m, 1H), 7.41 (m, 5H), 7.27-7.17 (m, 4H), 6.82 (s, 1H), 6.62 (d, 1H), 4.74 (m, 1H), 4.70 (m, 1H), 3.66 (m, 1H), 3.36-3.24 (m, 6H), 2.52 (s, 3H), 2.45-2.40 (m, 2H), 2.22 (m, 1H), 2.02-1.83 (m, 10H), 1.70 (m, 2H). ES-LCMS m/z 581 (M+H).

Example 620

N-{2-chloro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}methane sulfonamide

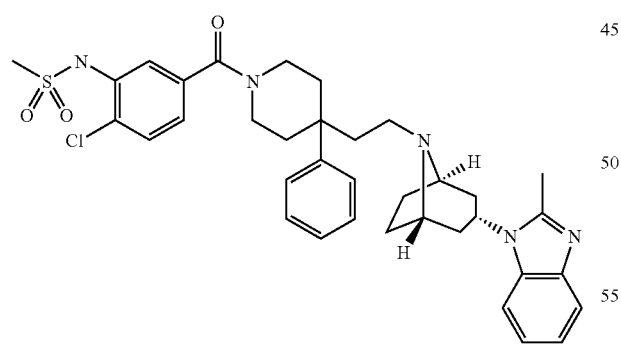

Method A (HATU). Intermediate 4-chloro-3-[(methylsulfonyl)amino]benzoic acid was synthesized in same fashion as described in example 639 from precursor example 619. $^1$H NMR (300 MHz, methanol-$d_4$) δ 7.72-7.68 (m, 2H), 7.53 (m, 2H), 7.41 (m, 5H), 7.27-7.17 (m, 3H), 4.73 (m, 1H), 4.14 (m, 1H), 3.53 (m, 7H), 3.30 (m, 2H), 2.51 (s, 3H), 2.45-2.29 (m, 4H), 2.01-1.89 (m, 10H), 1.69 (m, 2H). ES-LCMS m/z 659 (M+H).

Example 621

1-((1R,5S)-8-{2-[1-(2,6-dimethoxybenzoyl)-4-phenylpiperidin-4-yl]ethyl}-8-azabicyclo[3.2.1]oct-3-yl)-2-methyl-1H-benzimidazole

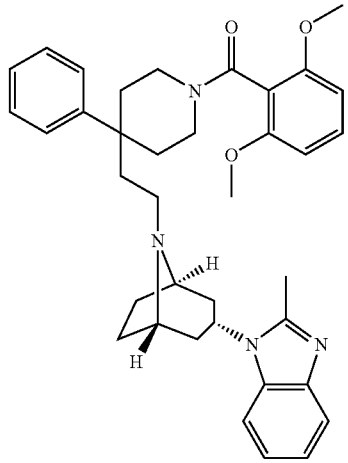

Acylation via EDCI-HOBt Method P using 2,6-dimethoxybenzoic acid (Aldrich) on 0.21 mmol scale yielded 50 mg (40%) product. $^1$H NMR (300 MHz, CDCl$_3$) δ 7.68 (d, 1H), 7.42-7.15 (m, 9H), 6.68-6.47 (m, 2H), 4.67 (m, 1H), 4.23 (m, 1H), 3.85 (s, 3H), 3.72 (s, 3H), 3.47-3.35 (m, 4H), 3.15-3.04 (m, 1H), 2.55 (s, 3H), 2.48-2.25 (m, 3H), 2.20-2.07 (m, 1H), 2.03-1.72 (m, 10H), 1.65 (m, 2H). HRMS C$_{37}$H$_{44}$N$_4$O$_3$ m/z 593.3492 (M+H)$_{Cal.}$, 593.3478 (M+H)$_{Obs}$.

Example 622

1-((1R,5S)-8-{2-[1-(2,6-dimethylbenzoyl)-4-phenylpiperidin-4-yl]ethyl}-8-azabicyclo[3.2.1]oct-3-yl)-2-methyl-1H-benzimidazole

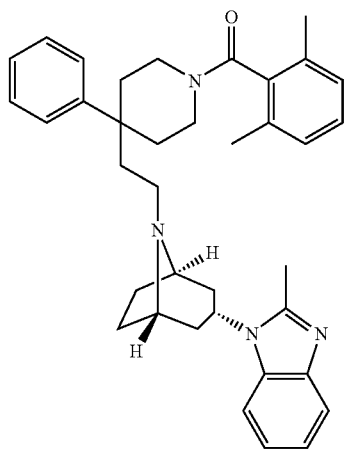

Acylation via EDCI-HOBt Method P using 2,6-dimethylbenzoic acid (Aldrich) on 0.14 mmol scale yielded 53 mg (67%) product. $^1$H NMR (300 MHz, CDCl$_3$) δ 7.87 (m, 1H), 7.51-6.97 (m, 11H), 5.51 (m, 2H), 4.22 (m, 1H), 4.05-3.88 (m, 2H), 3.50 (m, 1H), 3.28 (m, 1H), 3.09 (m, 3H), 2.82 (s, 3H), 2.62 (m, 1H), 2.30 (s, 6H), 2.20-2.02 (m, 10H), 1.88 (m, 1H), 1.71 (m, 1H). HRMS $C_{37}H_{44}N_4O$ m/z 561.3593 (M+H)$_{Cal}$, 561.3585 (M+H)$_{Obs}$.

Example 623

3-chloro-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]aniline

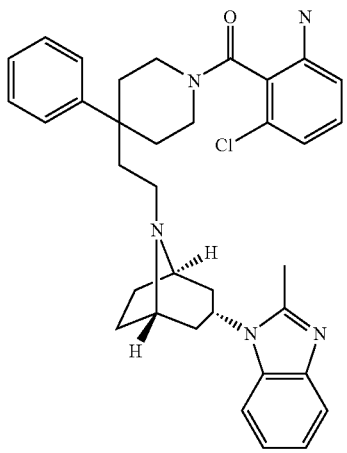

Acylation via EDCI-HOBt Method P using 2-amino-6-chlorobenzoic acid (Aldrich) on 0.14 mmol scale yielded 41 mg (50%) product. $^1$H NMR (300 MHz, CDCl$_3$) δ 7.92 (m, 1H), 7.58-7.25 (m, 8H), 7.07 (m, 1H), 6.80-6.55 (m, 2H), 5.50 (m, 1H), 4.26 (m, 5H), 3.99 (m, 3H), 3.50-3.29 (m, 2H), 3.25-3.09 (m, 1H), 2.99 (m, 2H), 2.83 (s, 3H), 2.20-2.58 (m, 2H), 2.42-2.02 (m, 9H). HRMS $C_{35}H_{40}ClN_5O$ m/z 582.3000 (M+H)$_{Cal}$, 582.3002 (M+H)$_{Obs}$.

Example 624

1-[(1R,5S)-8-(2-{1-[(4,6-dimethylpyrimidin-5-yl)carbonyl]-4-phenylpiperidin-4-yl}ethyl)-8-azabicyclo[3.2.1]oct-3-yl]-2-methyl-1H-benzimidazole

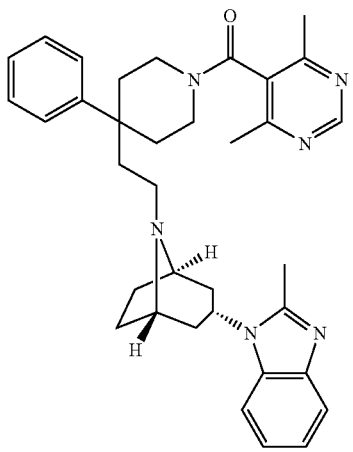

4,6-Dimethylpyrimidine-5-carboxylic acid was synthesized according to the procedure outlined in WO 00/66558, Schering Corporation, 2000, pages 67-69. Overall yield was 12% (3 steps).

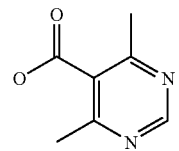

Acylation via EDCI-HOBt Method P using 4,6-dimethylpyrimidine-5-carboxylic acid on 0.16 mmol scale yielded 46 mg (51%) of the product. $^1$H NMR (300 MHz, CDCl$_3$) δ 8.92 (s, 1H), 7.55 (m, 1H), 7.43 (m, 5H), 7.20 (m, 3H), 4.88 (s, 1H), 4.74 (m, 1H), 4.27 (m, 1H), 3.51-3.07 (m, 5H), 2.54 (s, 6H), 2.50-2.20 (m, 7H), 2.05-1.84 (m, 9H), 1.69 (m, 2H). HRMS $C_{35}H_{42}N_6O$ m/z 563.3498 (M+H)$_{Cal}$, 563.3483 (M+H)$_{Obs}$.

Example 625

N-((1R,5S)-8-{2-[1-(3,5-dichloroisonicotinoyl)-4-phenylpiperidin-4-yl]ethyl}-8-azabicyclo[3.2.1]oct-3-yl)-N-[(2Z,4Z)-hexa-2,4-dienyl]ethanimidamide

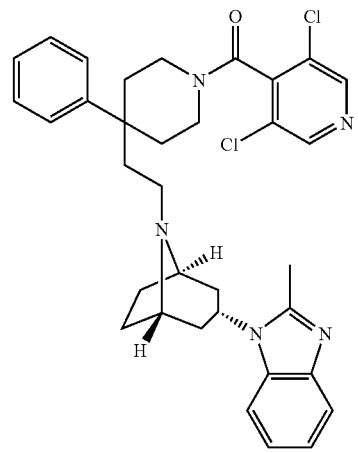

Acylation via EDCI-HOBt Method P using 4,6-dichloroisonicotinic acid (TCI America) on 0.16 mmol scale yielded 53 mg (55%) of the product. $^1$H NMR (300 MHz, CDCl$_3$) δ 8.66 (s, 1H), 8.61 (s, 1H), 7.54 (d, 1H), 7.42 (m, 5H), 7.30-7.1 (m, 3H), 4.75 (m, 1H), 4.26 (m, 1H), 3.48-3.30 (m, 5H), 3.19 (m, 1H), 2.54 (s, 3H), 2.45-2.26 (m, 4H), 2.10-1.84 (m, 10H), 1.71 (m, 2H). HRMS $C_{34}H_{37}Cl_2N_5O$ m/z 602.2453 (M+H)$_{Cal}$, 602.2476 (M+H)$_{Obs}$.

Example 626

3-methyl-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]aniline

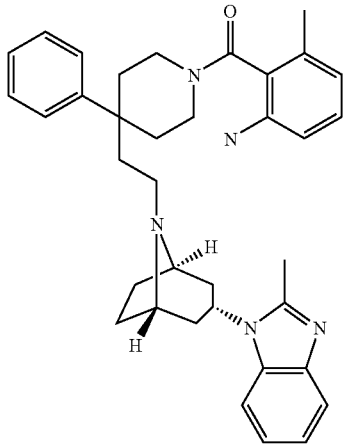

Acylation via EDCI-HOBt Method P using 2-amino-6-methylbenzoic acid (Aldrich) on 0.16 mmol scale yielded 39 mg (43%) of the product. $^1$H NMR (300 MHz, CDCl$_3$) δ 7.55 (m, 1H), 7.42 (m, 5H), 7.20 (m, 3H), 7.03 (m, 1H), 6.70-6.53 (m, 2H), 4.88 (s, 3H), 4.74 (m, 1H), 4.20 (m, 1H), 3.55-3.26 (m, 3H), 2.27 (m, 2H), 2.10-1.84 (m, 10H), 1.71 (m, 2H), 1.30 (s, 1H). HRMS C$_{36}$H$_{43}$N$_5$O m/z 562.3546 (M+H)$_{Cal}$, 562.3544 (M+H)$_{Obs}$.

Example 627 ethyl 2-ethyl-2-[(4-{2-[(1R,5S)-3-(2-methyl-1H-benzimidazol-1-yl)-8-azabicyclo[3.2.1]oct-8-yl]ethyl}-4-phenylpiperdin-1-yl)carbonyl]butonate

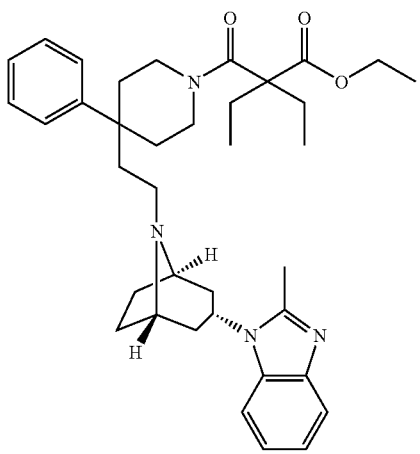

Preparation of 2-(ethoxycarbonyl)-2-ethylbutanoic acid

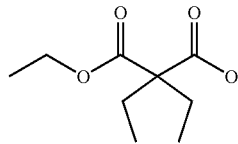

A solution of diethyl-malonic acid diethyl ester (3.0 g, 13.89 mmol) and potassium hydroxide (0.778 g, 13.89 mmol) in ethanol (50 ml) was stirred at room temperature for 18 hrs. The solvent was evaporated off and the residue was dissolved in water (20 ml) and extracted with dichloromethane (20 ml). This organic layer was discarded. The aqueous layer was then acidified with concentrated HCl and extracted with dichloromethane (3×20 ml). The combined organic layers were dried over magnesium sulfate and concentrated to give a colorless oil (1.9 g, 72%). $^1$H NMR (300 MHz, methanol-d$_4$) δ 4.17 (m, 2H), 1.89 (m, 4H), 1.25 (m, 3H), 0.83 (m, 6H). ES-LCMS m/z 188 (M+H).

Preparation of ethyl 2-ethyl-2-[(4-{2-[(1R,5S)-3-(2-methyl-1H-benzimidazol-1-yl)-8-azabicyclo[3.2.1]oct-8-yl]ethyl}-4-phenylpiperdin-1-yl)carbonyl]butonate (Example 627)

Acylation via EDCI-HOBt Method P using 2-(ethoxycarbonyl)-2-ethylbutanoic acid on 0.21 mmol scale yielded 115 mg (91%) of colorless oil. $^1$H NMR (300 MHz, CDCl$_3$) δ 7.88 (d, 1H), 7.67 (m, 2H), 7.40-7.18 (m, 6H), 4.87 (m, 1H), 4.75-4.40 (m, 2H), 4.22 (m, 3H), 3.41 (m, 2H), 3.12 (m, 2H), 2.55 (s, 3H), 2.45 (m, 1H), 2.20-1.61 (m, 16H), 1.44 (s, 1H), 1.21 (m, 3H), 0.92-0.70 (m, 6H). HRMS C$_{37}$H$_{50}$N$_4$O$_3$ m/z 599.3961 (M+H)$_{Cal}$, 599.3981 (M+H)$_{Obs}$.

Example 628 ethyl 2,2-dimethyl-3-(4-{2-[(1R,5S)-3-(2-methyl-1H-benzimidazol-1-yl)-8-azabicyclo[3.2.1]oct-8-yl]ethyl}-4-phenylpiperidin-1-yl)-3-oxopropanoate

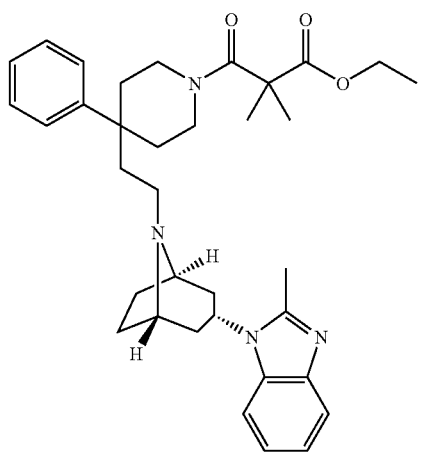

3-Ethoxy-2,2-dimethyl-3-oxopropanoic acid was prepared as in the case of diethyl dimethylmalonate on 15.96 mmol scale to give product as a colorless oil (1.8 g, 70%). ¹H NMR (300 MHz, methanol-d₄) δ 4.17 (m, 2H), 1.43 (s, 6H), 1.25 (m, 3H). ES-LCMS m/z 160 (M+H).

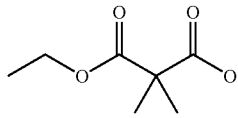

The compound in example 628 was prepared via acylation (EDCI-HOBt Method P) using 3-ethoxy-2,2-dimethyl-3-oxopropanoic acid on 0.21 mmol scale, yielding 98 mg (82%) of the product as a colorless oil. ¹H NMR (300 MHz, CDCl₃) δ 7.69 (d, 1H), 7.38 (m, 2H), 7.28 (m, 4H), 7.17 (m, 2H), 4.69 (m, 1H), 4.17 (m, 2H), 3.30 (m, 2H), 3.08 (m, 1H), 2.58 (s, 3H), 2.39 (m, 2H), 2.20 (m, 2H), 1.97-1.60 (m, 12H), 1.50-1.37 (m, 4H), 1.30-1.18 (m, 5H), 0.87 (m, 2H). HRMS C₃₅H₄₆N₄O₃ m/z 571.3648 (M+H)$_{Cal}$, 571.3646 (M+H)$_{Obs}$.

Example 629 ethyl 1-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]cyclopropanecarboxylate

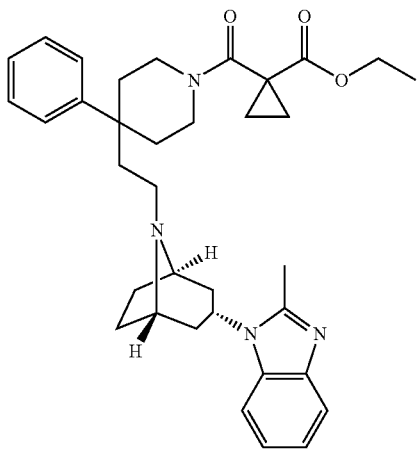

1-(Ethoxycarbonyl)cyclopropanecarboxylic acid was prepared as described in case of diethyl 1,1-cyclopropanedicarboxylate on 16.13 mmol scale to give product as a colorless oil (2.1 g, 82%). ¹H NMR (300 MHz, methanol-d₄) δ 3.95 (m, 2H), 1.43 (s, 4H), 0.98 (m, 3H). ES-LCMS m/z 158 (M+H).

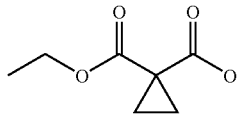

The compound in example 629 was prepared by acylation via EDCI-HOBt Method P using 1-(ethoxy carbonyl)cyclopropanecarboxylic acid on 0.21 mmol scale, yielding 82 mg (68%) product as a colorless oil. ¹H NMR (300 MHz, CDCl₃) δ 7.67 (m, 1H), 7.45-7.10 (m, 8H), 4.62 (m, 1H), 4.15 (m, 2H), 3.69 (m, 1H), 3.26 (m, 4H), 2.58 (s, 3H), 2.44-2.15 (m, 5H), 1.97-1.76 (m, 10H), 1.63 (m, 2H), 1.45 (m, 3H), 1.35-1.16 (m, 5H). HRMS C₃₅H₄₄N₄O₃ m/z 569.3492 (M+H)$_{Cal}$, 569.3503 (M+H)$_{Obs}$.

Example 630

2-methyl-1-((1R,5S)-8-{2-[4-phenyl-1-(pyrazin-2-ylcarbonyl)piperidin-4-yl]ethyl}-8-azabicyclo[3.2.1]oct-3-yl)-1H-benzimidazole

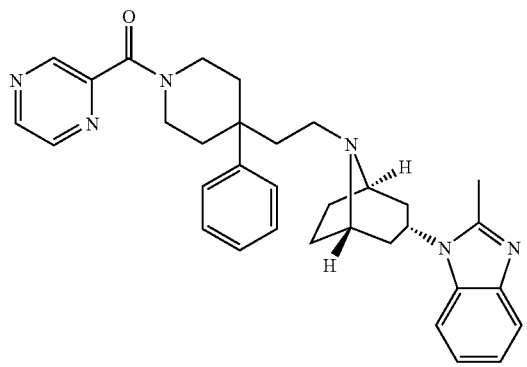

The title compound was obtained by method A (HATU) using 2-pyrazinecarboxylic acid on 0.16 mmol scale. ¹H NMR (300 MHz, CDCl₃) δ 8.89 (s, 1H), 8.59 (dd, 2H), 7.67 (m, 1H), 7.45-7.10 (m, 8H), 4.61 (m, 1H), 4.32-4.05 (m, 1H), 3.71 (m, 1H), 3.44-3.21 (m, 4H), 2.56 (s, 3H), 2.42-2.22 (m, 4H), 2.00-1.79 (m, 10H), 1.63 (m, 2H). ES-LCMS m/z 534 (M+H).

Example 631

2-methyl-1-[(1R,5S)-8-(2-{1-[(1-methyl-1H-pyrrol-2-yl)carbonyl]-4-phenylpiperidin-4-yl}ethyl)-8-azabicyclo[3.2.1]oct-3-yl]-1H-benzimidazole

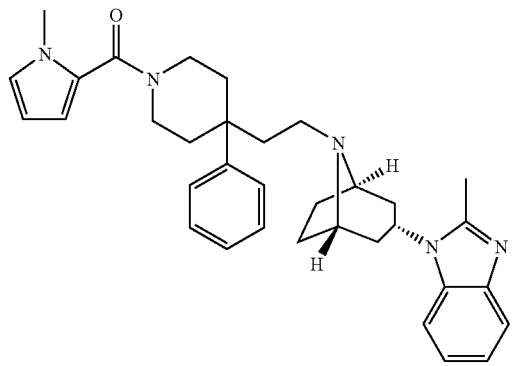

The title compound in example 631 was synthesized using method A (HATU) with 1-methyl-1H-pyrrole-2-carboxylic acid on 0.16 mmol scale. ¹H NMR (300 MHz, CDCl₃) δ 7.65 (d, 1H), 7.45-7.12 (m, 8H), 6.68 (s, 1H), 6.30 (d, 1H), 6.08 (m, 1H), 4.62 (m, 1H), 4.04 (m, 2H), 3.76 (s, 3H), 3.44 (m, 2H), 3.26 (m, 2H), 2.57 (s, 3H), 2.44-2.18 (m, 4H), 2.03-1.78 (m, 10H), 1.63 (m, 2H). ES-LCMS m/z 535 (M+H).

Example 632

2-methyl-1-((1R,5S)-8-{2-[4-phenyl-1-(1,2,3-thiadiazol-4-ylcarbonyl)piperidin-4-yl]ethyl}-8-azabicyclo[3.2.1]oct-3-yl)-1H-benzimidazole

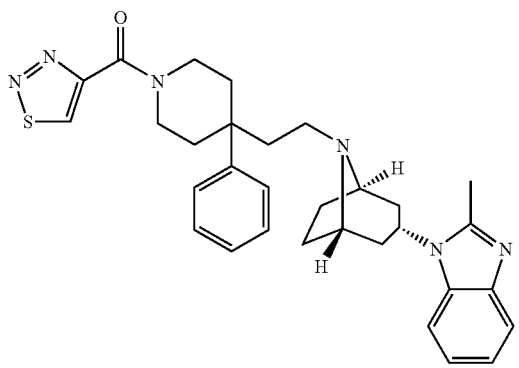

The title compound in example 632 was synthesized using method A (HATU) utilizing 1,2,3-thiadiazole-4-carboxylic acid on 0.16 mmol scale. $^1$H NMR (300 MHz, CDCl$_3$) δ 8.97 (m, 1H), 7.72-7.51 (m, 1H), 7.45-7.00 (m, 8H), 5.25 (m, 2H), 4.55 (m, 1H), 4.21 (m, 2H), 3.68-3.09 (m, 4H), 2.60-2.20 (m, 5H), 2.02-1.72 (m, 10H), 1.53 (m, 2H). ES-LCMS m/z 540 (M+H).

Example 633

2-methyl-1-[(1R,5S)-8-(2-{1-[(2-methylpyridin-3-yl)carbonyl]-4-phenylpiperidin-4-yl}ethyl)-8-azabicyclo[3.2.1]oct-3-yl]-1H-benzimidazole

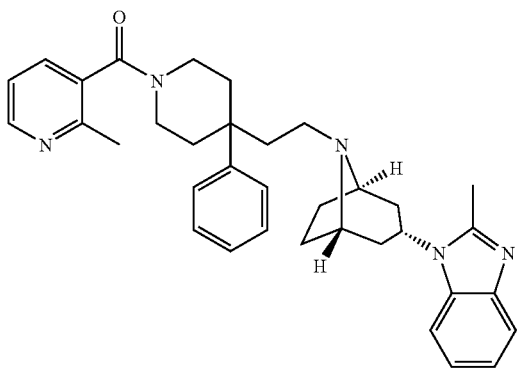

The title compound in example 633 was synthesized using method A (HATU) utilizing 2-methylnicotinic acid on 0.16 mmol scale. $^1$H NMR (300 MHz, CDCl$_3$) δ 8.54 (d, 1H), 7.65 (m, 1H), 7.45-7.08 (m, 10H), 4.61 (m, 1H), 4.28 (m, 1H), 3.45-3.07 (m, 5H), 2.65-2.48 (m, 4H), 2.43-2.30 (m, 5H), 2.22-2.03 (m, 2H), 1.97-1.77 (m, 8H), 1.63 (m, 2H). ES-LCMS m/z 547 (M+H).

Example 634

2-methyl-1-[(1R,5S)-8-(2-{1-[(6-methylpyridin-2-yl)carbonyl]-4-phenylpiperidin-4-yl}ethyl)-8-azabicyclo[3.2.1]oct-3-yl]-1H-benzimidazole

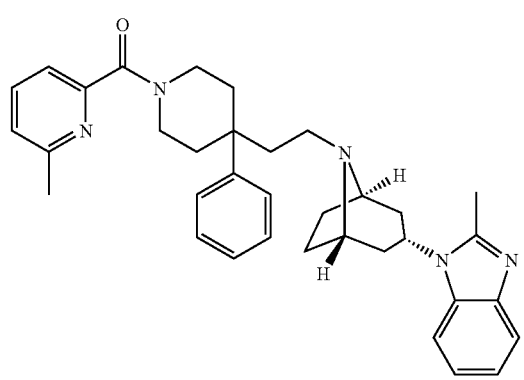

The title compound in example 634 was synthesized using method A (HATU) utilizing 6-methylpyridine-2-carboxylic acid on 0.16 mmol scale. $^1$H NMR (300 MHz, CDCl$_3$) δ 7.66 (m, 2H), 7.45-7.09 (m, 10H), 4.62 (m, 1H), 4.22 (m, 1H), 3.65 (m, 1H), 3.50-3.20 (m, 4H), 2.56 (m, 6H), 2.36 (m, 3H), 2.17 (m, 1H), 2.0-1.80 (m, 10H), 1.63 (m, 2H). ES-LCMS m/z 547 (M+H).

Example 635

1-[(1R,5S)-8-(2-{1-[(2-fluoropyridin-3-yl)carbonyl]-4-phenylpiperidin-4-yl}ethyl)-8-azabicyclo[3.2.1]oct-3-yl]-2-methyl-1H-benzimidazole

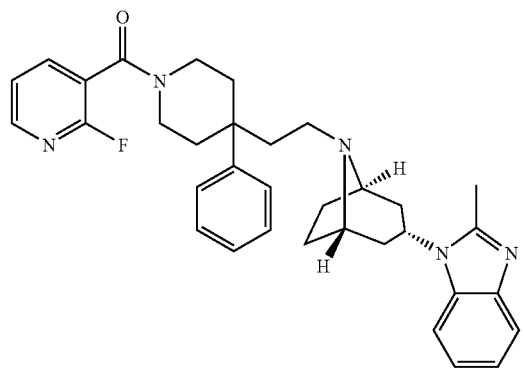

The title compound in example 635 was synthesized using method A (HATU) utilizing 2-fluoronicotinic acid on 0.16 mmol scale. $^1$H NMR (300 MHz, CDCl$_3$) δ 8.28 (d, 1H), 7.84 (m, 1H), 7.68 (m, 1H), 7.45-7.20 (m, 9H), 4.61 (m, 1H), 4.27

(m, 1H), 3.45-3.15 (m, 5H), 2.56 (s, 3H), 2.35 (m, 3H), 2.20 (m, 1H), 1.98-1.73 (m, 10H), 1.67-1.55 (m, 2H). ES-LCMS m/z 551 (M+H).

Example 636

1-[(1R,5S)-8-(2-{1-[(4-bromo-1-ethyl-3-methyl-1H-pyrazol-5-yl)carbonyl]-4-phenylpiperidin-4-yl}ethyl)-8-azabicyclo[3.2.1]oct-3-yl]-2-methyl-1H-benzimidazole

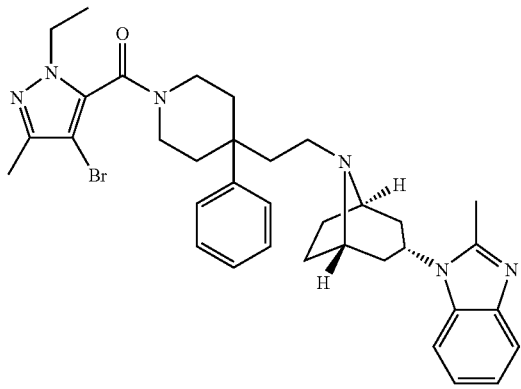

The title compound in example 636 was synthesized using method A (HATU) utilizing 4-bromo-1-ethyl-3-methyl-1H-pyrazole-5-carboxylic acid on 0.16 mmol scale. $^1$H NMR (300 MHz, CDCl$_3$) δ 7.66 (d, 1H), 7.50-7.05 (m, 8H), 4.64 (m, 1H), 4.30-2.86 (m, 2H), 3.55 (m, 1H), 3.40-3.28 (m, 4H), 2.58 (s, 3H), 2.37 (m, 3H), 2.25 (m, 3H), 2.12-1.78 (m, 10H), 1.65 (m, 2H), 1.46 (m, 2H), 1.33 (m, 3H). ES-LCMS m/z 642 (M+H).

Example 637

2-methyl-1-((1R,5S)-8-{2-[4-phenyl-1-(thien-3-yl-carbonyl)piperidin-4-yl]ethyl}-8-azabicyclo[3.2.1]oct-3-yl)-1H-benzimidazole

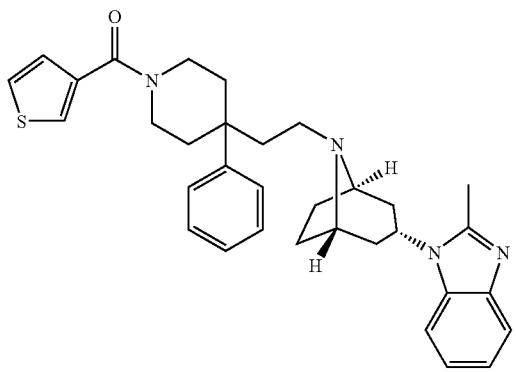

The title compound in example 637 was synthesized using method A (HATU) utilizing thiophene-3-carboxylic acid on 0.16 mmol scale. $^1$H NMR (300 MHz, CDCl$_3$) δ 7.66 (d, 1H), 7.54-7.20 (m, 11H), 4.62 (m, 1H), 4.15 (m, 1H), 3.74 (m, 1H), 3.42-3.20 (m, 4H), 2.57 (s, 3H), 2.45-2.12 (m, 4H), 2.05-1.25 (m, 10H), 1.64 (m, 2H). ES-LCMS m/z 538 (M+H).

Example 638

1-[(1R,5S)-8-(2-{1-[(3-bromothien-2-yl)carbonyl]-4-phenylpiperidin-4-yl}ethyl)-8-azabicyclo[3.2.1]oct-3-yl]-2-methyl-1H-benzimidazole

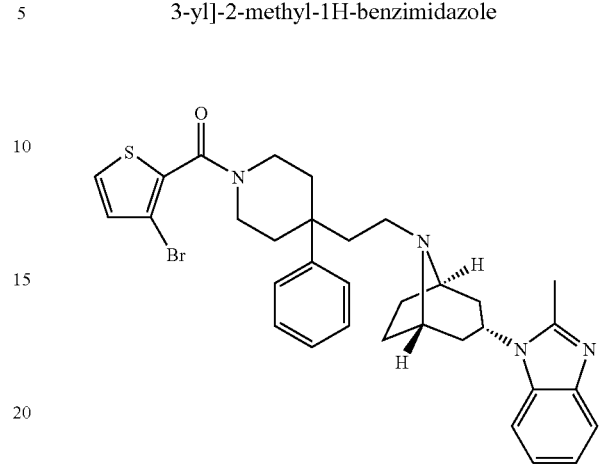

The title compound in example 638 was synthesized using method A (HATU) utilizing 3-bromothiophene-2-carboxylic acid on 0.16 mmol scale. $^1$H NMR (300 MHz, CDCl$_3$) δ 7.68 (d, 1H), 7.45-7.10 (m, 9H), 6.97 (d, 1H), 4.63 (m, 1H), 4.15 (m, 1H), 3.63 (m, 1H), 3.37-3.28 (m, 4H), 2.57 (s, 3H), 2.48-2.22 (m, 4H), 2.05-1.80 (m, 10H), 1.65 (m, 2H). ES-LCMS m/z 616 (M+H).

Example 639

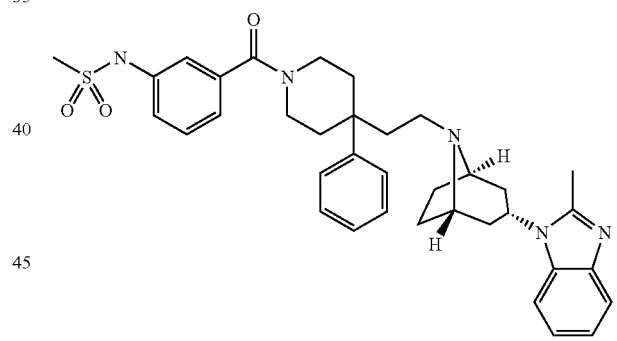

N-{3-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]phenyl}methane sulfonamide was synthesized as in the following scheme.

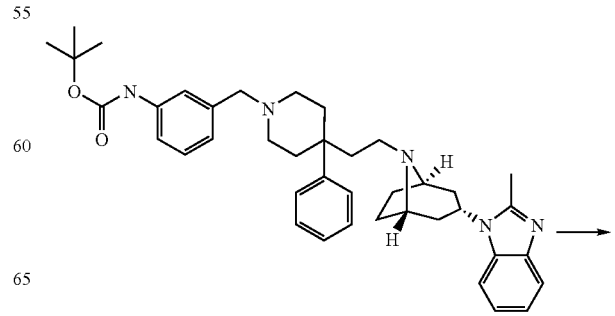

-continued

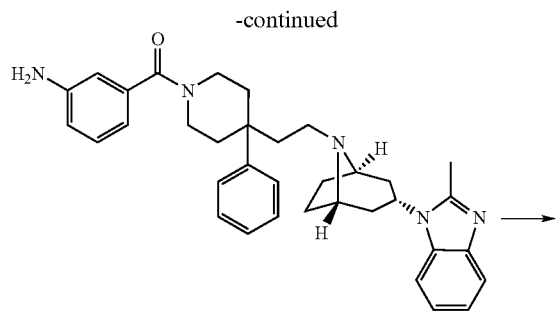

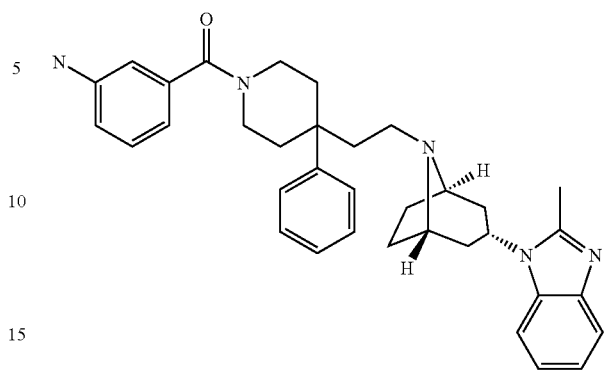

N-{3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}methane sulfonamide was synthesized by dissolving the amine precursor (60 mg, 0.11 mmol) in 3 ml dichloromethane cooled to 0° C., followed by addition of 2 eq of Hunig base and methane sulfonyl chloride (12 mg, 0.11 mmol) and stirring overnight at room temperature. The solution was then diluted with DCM and washed with $Na_2CO_3$, dried organic layer with $MgSO_4$ and rotovapped to dryness. Purified by reverse phase chromatography on C18 using Acetonitrile:water 10:90 to 90:10. Removal of solvent gave 38 mg (56%) of the product. $^1$H NMR (300 MHz, methanol-$d_4$) δ 7.83 (m, 2H), 7.68-7.43 (m, 9H), 7.33 (m, 1H), 5.34 (m, 1H), 4.21-4.11 (m, 3H), 3.63 (m, 1H), 3.46 (s, 3H), 3.38-3.27 (m, 4H), 2.97 (m, 2H), 2.85 (s, 3H), 2.79 (m, 2H), 2.46 (m, 3H), 2.29-2.19 (m, 7H), 1.99-1.87 (m, 2H). ES-LCMS m/z 625 (M+H).

example 639 tert-butyl 3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenylcarbamate was prepared by Method A (HATU) using 3-[(tert-butoxycarbonyl)amino] benzoic acid on 1.64 mmol scale. Purification by reverse phase chromatography on C18 using Acetonitrile:water 10:90 to 90:10 and removal of solvent gave 635 mg of product (60%). ES-LCMS m/z 647 (M+H).

Example 640

N-{4-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]phenyl}methane sulfonamide was synthesized similarly to the title compound in example 639.

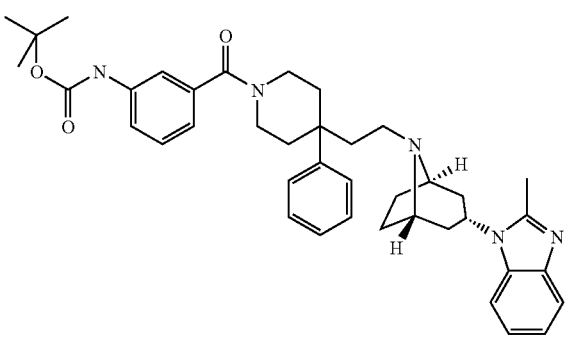

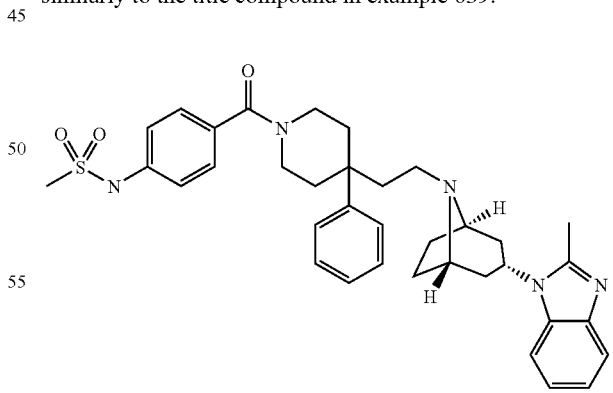

3-[(4-{2-[(1R,5S)-3-(2-methyl-1H-benzimidazol-1-yl)-8-azabicyclo[3.2.1]oct-8-yl]ethyl}-4-phenylpiperidin-1-yl) carbonyl]phenylamine was obtained by dissolving of Boc-derivative coupling product in 20 ml dichloromethane and treatment with 2 ml of trifluoroacetic acid at room temperature for 2 hrs. Removal of solvent gave product in quantitative yield. ES-LCMS m/z 547 (M+H).

Tert-butyl 4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenylcarbamate was prepared as described in example 639 using 4-[(tert-butoxycarbonyl) amino]benzoic acid to give 545 mg (53%) of product. ES-LCMS m/z 647 (M+H).

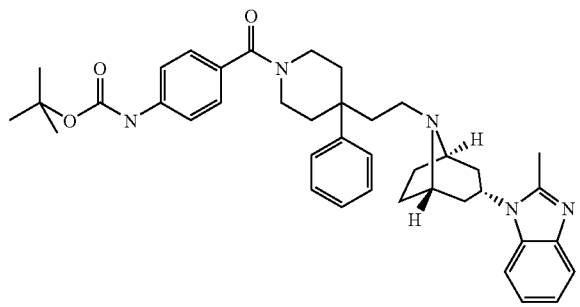

4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenylamine was prepared as in example 639. ES-LCMS m/z 547 (M+H).

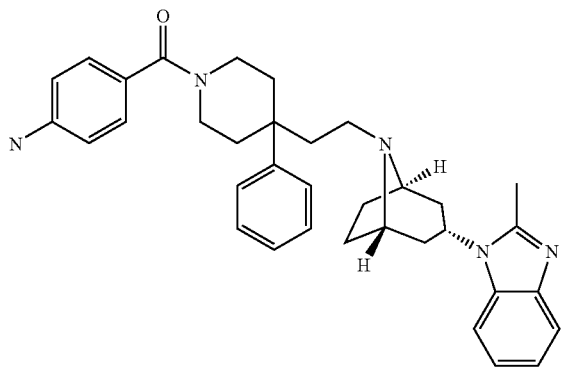

The title compound in example 640 (N-{4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}methanesulfonamide) was prepared as described for example 639 to give 28 mg (40%) of the title product of example 640. $^1$H NMR (300 MHz, methanol-$d_4$) δ 7.85 (m, 2H), 7.66-7.41 (m, 10H), 7.33 (m, 1H), 5.39 (m, 1H), 4.21-4.09 (m, 3H), 3.63 (m, 1H), 3.46 (s, 6H), 2.97-2.92 (m, 2H), 2.85 (s, 3H), 2.73 (m, 2H), 2.46-2.37 (m, 3H), 2.24 (m, 7H), 1.97-1.90 (m, 2H). ES-LCMS m/z 625 (M+H).

Example 641

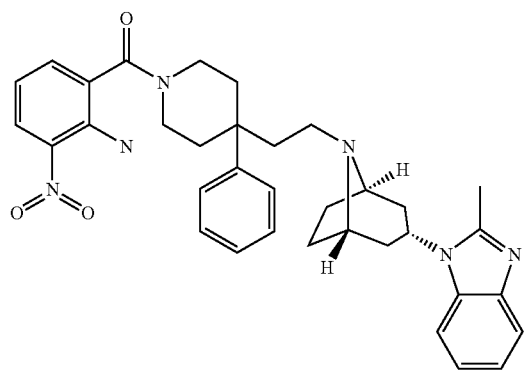

2-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]-6-nitrophenylamine was synthesized by method B (Anhydride) using 4-nitroisatoic anhydride on 0.16 mmol scale. $^1$H NMR (300 MHz, methanol-$d_4$) δ 7.80 (m, 1H), 7.60 (m, 3H), 7.46 (m, 5H), 7.31-7.25 (m, 2H), 5.31 (m, 1H), 4.20-4.10 (m, 2H), 3.52 (m, 1H), 3.35-3.22 (m, 3H), 2.94 (m, 2H), 2.82 (s, 3H), 2.75 (m, 2H), 2.40 (m, 3H), 2.20 (m, 7H), 1.93-1.86 (m, 2H). ES-LCMS m/z 592 (M+H).

Example 642

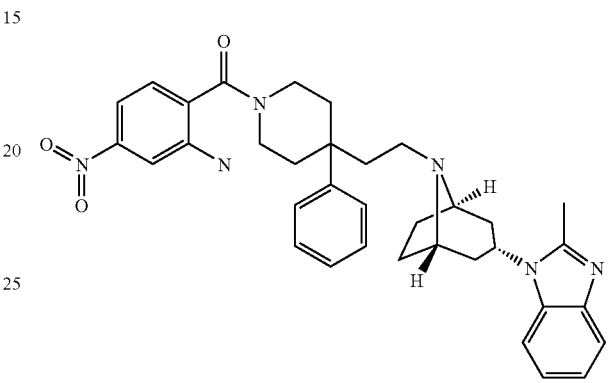

2-[(4-{2-[(1R,5S)-3-(2-Methyl-1H-benzimidazol-1-yl)-8-azabicyclo[3.2.1]oct-8-yl]ethyl}-4-phenylpiperidin-1-yl)carbonyl]-5-nitrophenylamine was synthesized by method B (Anhydride) using 5-nitroisatoic anhydride on 0.16 mmol scale. $^1$H NMR (300 MHz, methanol-$d_4$) δ 8.00 (d, 2H), 7.78 (m, 2H), 7.60 (m, 2H), 7.45 (m, 4H), 7.31 (m, 1H) 6.79 (d, 1H), 5.30 (m, 1H), 4.10 (m, 2H), 3.40-3.22 (m, 4H), 2.94 (m, 2H), 2.81 (m, 3H), 2.75 (m, 2H), 2.45-2.14 (m, 10H), 1.92-1.90 (m, 2H). ES-LCMS m/z 592 (M+H).

Example 643

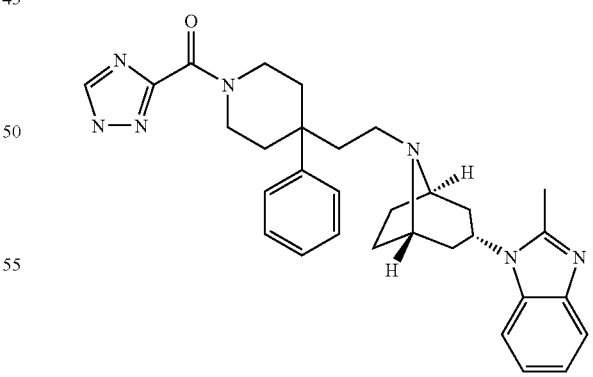

2-Methyl-1-((1R,5S)-8-{2-[4-phenyl-1-(1H-1,2,4-triazol-3-ylcarbonyl)piperidin-4-yl]ethyl}-8-azabicyclo[3.2.1]oct-3-yl)-1H-benzimidazole was synthesized by method A (HATU) using 1H-1,2,4-triazole-3-carboxylic acid on 0.16 mmol scale. $^1$H NMR (300 MHz, CDCl$_3$) δ 8.09 (s, 1H), 7.68 (m, 1H), 7.45-7.11 (m, 8H), 4.93 (m, 1H), 4.64 (m, 1H), 4.21

(m, 1H), 3.83 (m, 1H), 3.37-3.25 (m, 2H), 2.37 (m, 3H), 2.05-1.81 (m, 7H), 1.78-1.55 (m, 11H). ES-LCMS m/z 523 (M+H).

Example 644

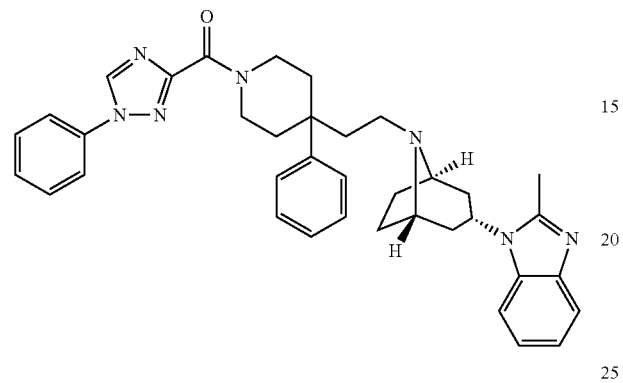

2-Methyl-1-[(1R,5S)-8-(2-{4-phenyl-1-[(1-phenyl-1H-1,2,4-triazol-3-yl)carbonyl]piperidin-4-yl}ethyl)-8-azabicyclo[3.2.1]oct-3-yl]-1H-benzimidazole was synthesized by method A (HATU) using 1-phenyl-1H-1,2,4-triazole-3-carboxylic acid on 0.16 mmol scale. $^1$H NMR (300 MHz, CDCl$_3$) δ 7.75-7.61 (m, 2H), 7.57-7.10 (m, 12H), 4.63 (m, 1H), 4.31 (m, 1H), 4.06 (m, 1H), 3.55-3.38 (m, 2H), 3.25 (m, 2H), 2.37 (m, 4H), 2.04-1.61 (m, 14H), 1.26 (m, 2H). ES-LCMS m/z 599 (M+H).

Example 645

2-Bromo-N-methyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide was obtained by method A (HATU) using acid 38 on 0.09 mmol scale. $^1$H NMR (300 MHz, CDCl$_3$) δ 8.14 (s, 1H), 7.79 (d, 1H), 7.66 (d, 1H), 7.52-7.08 (m, 9H), 5.47 (m, 1H), 4.62 (m, 1H), 4.25 (m, 1H), 3.50 (m, 1H), 3.26 (m, 4H), 2.57 (s, 3H), 2.39 (m, 3H), 2.18 (m, 1H), 2.04-1.58 (m, 12H), 1.27 (s, 3H). ES-LCMS m/z 703 (M+H).

Example 646

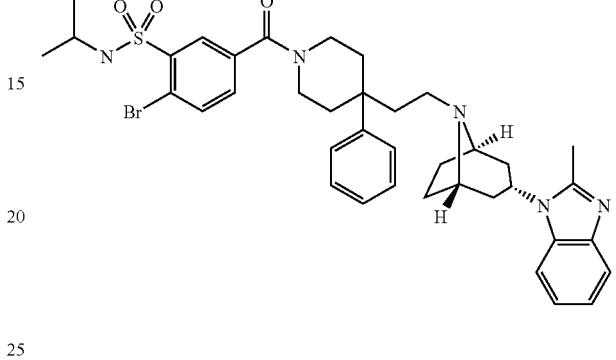

2-Bromo-N-isopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide was obtained by method A (HATU) using Acid 41 on 0.09 mmol scale. $^1$H NMR (300 MHz, CDCl$_3$) δ 8.16 (s, 1H), 7.80 (d, 1H), 7.65 (d, 1H), 7.50-7.08 (m, 9H), 5.09 (m, 1H), 4.63 (m, 1H), 4.23 (m, 1H), 3.46 (m, 1H), 3.26 (m, 4H), 2.58 (s, 3H), 2.36 (m, 3H), 2.18 (m, 1H), 2.00-1.75 (m, 10H), 1.65-1.58 (m, 2H), 1.12 (m, 6H). ES-LCMS m/z 731 (M+H).

Example 647

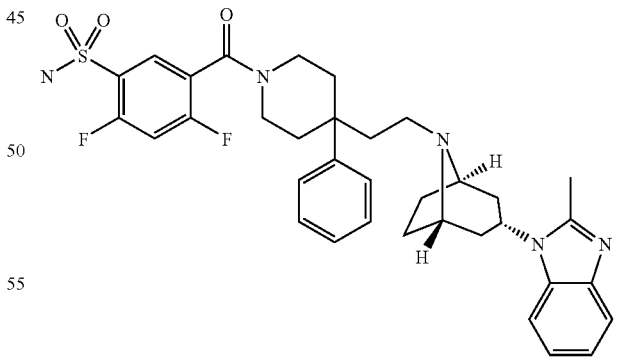

2,4-Difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide was obtained by method A (HATU) using Acid 31 on 0.14 mmol scale. $^1$H NMR (300 MHz, CDCl$_3$) δ 7.40 (m, 2H), 7.30-7.10

(m, 9H), 4.84 (m, 1H), 4.24 (m, 1H), 3.40 (m, 2H), 2.98 (s, 3H), 2.30 (m, 5H), 2.15-1.72 (m, 12H). ES-LCMS m/z 647 (M+H).

Example 648

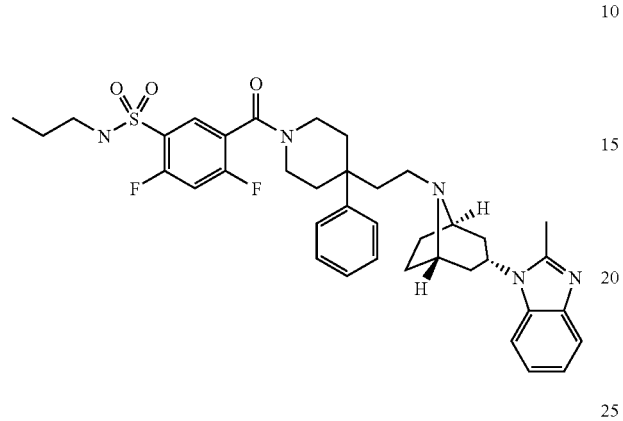

2,4-Difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide was obtained by method A (HATU) using Acid 34 on 0.14 mmol scale. $^1$H NMR (300 MHz, CDCl$_3$) δ 7.56 (m, 1H), 7.45-7.15 (m, 10H), 4.74 (m, 1H), 4.23 (m, 1H), 3.50-3.16 (m, 6H), 2.94 (m, 2H), 2.55 (s, 3H), 2.43 (m, 4H), 2.12-1.86 (m, 10H), 1.74 (m, 2H), 1.51 (m, 2H), 0.89 (m, 3H). ES-LCMS m/z 689 (M+H).

Example 649

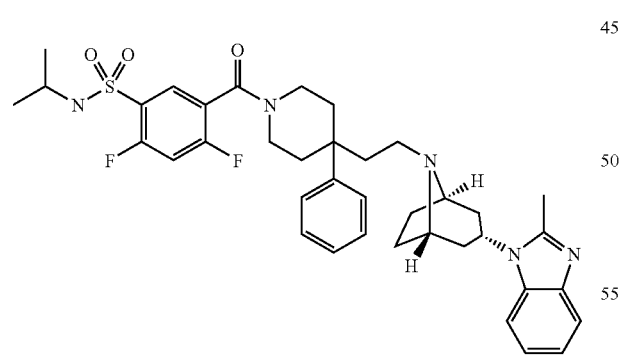

2,4-Difluoro-N-isopropyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzenesulfonamide was obtained by method A (HATU) using Acid 35 on 0.14 mmol scale. $^1$H NMR (300 MHz, CDCl$_3$) δ 7.68 (m, 1H), 7.45-7.15 (m, 9H), 7.00 (m, 1H), 4.83 (m, 1H), 4.62 (m, 1H), 4.28 (m, 1H), 3.60-3.18 (m, 6H), 2.58 (s, 3H), 2.44-2.15 (m, 4H), 2.00-1.76 (m, 10H), 1.62 (m, 2H), 1.13 (m, 6H). ES-LCMS m/z 689 (M+H).

Example 650

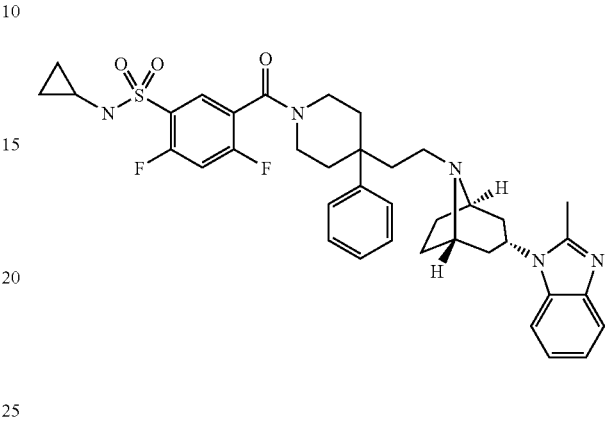

N-Cyclopropyl-2,4-difluoro-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzene sulfonamide was obtained by Method A (HATU) using Acid 36 on 0.14 mmol scale. $^1$H NMR (300 MHz, CDCl$_3$) δ 7.67 (m, 1H), 7.45-7.22 (m, 8H), 7.10 (m, 2H), 4.61 (m, 1H), 4.24 (m, 1H), 3.36-3.24 (m, 5H), 2.57 (s, 3H), 2.29 (m, 5H), 1.95-1.60 (m, 10H), 1.62 (m, 2H), 1.25 (s, 4H). ES-LCMS m/z 687 (M+H).

Example 651

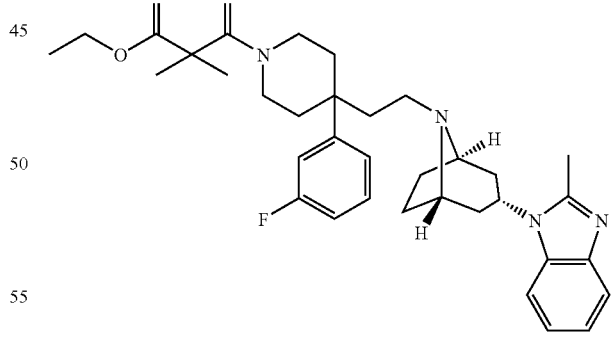

Ethyl 3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropanoate was obtained by Method A (HATU) using 3-ethoxy-2,2-dimethyl-3-oxopropanoic acid on 0.21 mmol scale. $^1$H NMR (300 MHz, methanol-d$_4$) δ 7.55 (m, 1H), 7.43 (m, 2H), 7.19 (m, 4H), 7.00 (m, 1H), 4.72 (m, 1H), 4.19 (m, 2H), 3.32 (m, 4H), 2.56 (s, 3H), 2.41 (m, 2H), 2.20 (m, 2H), 2.08-1.79 (m, 10H), 1.69 (m, 2H), 1.40 (s, 5H), 1.25 (m, 6H). ES-LCMS m/z 588 (M+H).

Example 652

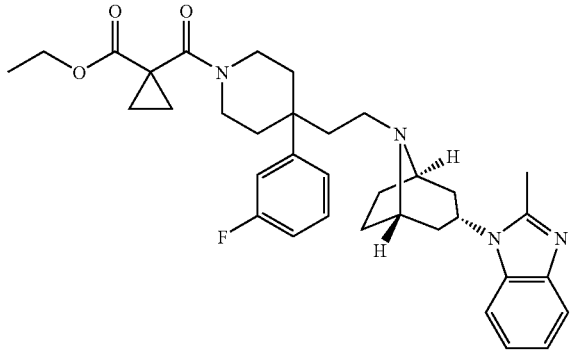

Ethyl 1-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]cyclopropane carboxylate was obtained by Method A (HATU) using 1-(ethoxycarbonyl)cyclopropanecarboxylic acid on 0.21 mmol scale. $^1$H NMR (300 MHz, methanol-$d_4$) δ 7.55 (m, 1H), 7.44 (m, 2H), 7.19 (m, 4H), 7.00 (m, 1H), 4.75 (m, 1H), 4.16 (m, 2H), 4.00 (m, 1H), 3.83 (m, 1H), 3.32 (m, 3H), 2.56 (s, 3H), 2.46 (m, 2H), 2.29 (m, 2H), 2.10-1.83 (m, 10H), 1.69 (m, 2H), 1.47 (s, 2H), 1.27 (m, 6H). ES-LCMS m/z 586 (M+H).

Example 653

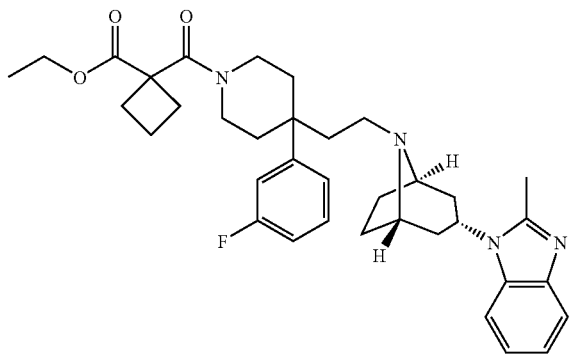

Ethyl 1-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]cyclobutane carboxylate was obtained by Method A (HATU) using 1-(ethoxycarbonyl)cyclobutanecarboxylic acid on 0.21 mmol scale. $^1$H NMR (300 MHz, methanol-$d_4$) δ 7.55 (m, 1H), 7.40 (m, 2H), 7.20 (m, 4H), 7.00 (m, 1H), 4.74 (m, 1H), 4.19 (m, 2H), 3.95 (m, 1H), 3.32 (m, 5H), 3.04 (m, 1H), 2.56 (s, 3H), 2.44 (m, 4H), 2.05-1.78 (m, 10H), 1.70 (m, 2H), 1.27 (m, 6H). ES-LCMS m/z 600 (M+H).

Example 653B

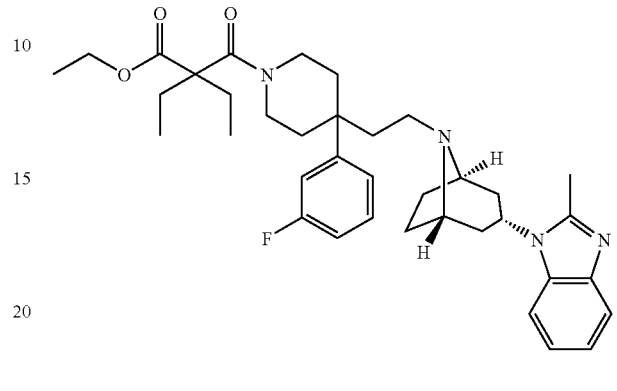

Ethyl 2-ethyl-2-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]butanoate was obtained by Method A (HATU) using 2-(ethoxycarbonyl)-2-ethylbutanoic acid on 0.21 mmol scale. $^1$H NMR (300 MHz, CDCl$_3$) δ 7.70 (d, 1H), 7.33 (m, 3H), 7.07 (m, 4H), 4.64 (m, 1H), 4.18 (m, 2H), 3.50 (m, 1H), 3.24 (m, 4H), 2.57 (s, 3H), 2.38 (m, 2H), 2.14 (m, 2H), 1.94-1.69 (m, 10H), 1.62 (m, 2H), 1.24 (m, 7H), 0.77 (m, 5H). ES-LCMS m/z 616 (M+H).

Example 654

2-Chloro-5-[(4-(3-chlorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

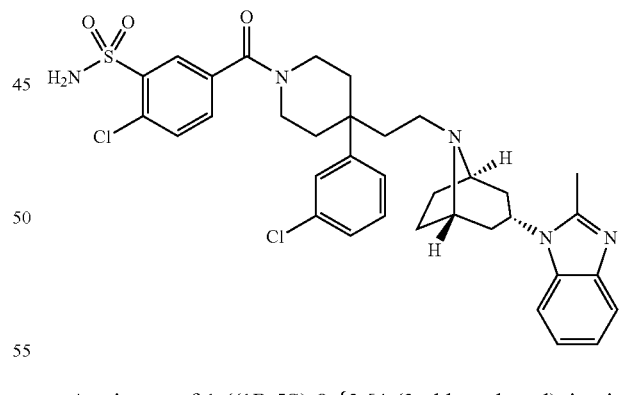

A mixture of 1-((1R,5S)-8-{2-[4-(3-chlorophenyl)piperidin-4-yl]ethyl}-8-azabicyclo[3.2.1]oct-3-yl)-2-methyl-1H-benzimidazole dihydrochloride (0.15 g, 0.32 mmol), 4-chloro-3-sulfamoylbenzoic acid (0.076 g, 0.32 mmol) and triethylamine (0.14 mL, 1 mmol) in dimethylformamide (1 mL) was treated with O-(7-azabenzotriazol-1-yl)-1,1,3,3-tetramethyluronium hexafluorophosphate (0.133 g, 0.35 mmol) and the resulting mixture was stirred for 1 h at rt. The mixture was diluted with water and the resulting precipitate was collected, washed with saturated sodium bicarbonate and water, dried and purified by chromatography on silica gel eluting with a 120:15:1 to 60:15:1 gradient of chloroform:methanol: ammonium hydroxide to give 2-chloro-5-[(4-(3-chlorophenyl)-4-{2-[(1R,5S)-3-(2-methyl-1H-benzimidazol-1-yl)-8-azabicyclo[3.2.1]oct-8-yl]ethyl}piperidin-1-yl)carbonyl] benzenesulfonamide as a white solid (0.052 g, 24%). $^1$H NMR (400 MHz, CD$_3$OD$_3$) δ 8.09 (s, 1H), 7.90 (s, 1H), 7.69 (m, 1H), 7.62 (m, 1H), 7.53 (m, 1H), 7.38-7.46 (m, 3H), 7.27-7.38 (m, 1H), 7.17-7.20 (m, 2H), 4.74 (m, 1H), 4.11 (m, 1H), 3.58 (m, 2H), 3.40 (m, 2H), 3.16-3.22 (m, 1H), 2.54 (s, 3H), 2.41-2.49 (m, 2H), 2.33-2.38 (m, 1H), 2.20-2.26 (m, 1H), 1.94-2.12 (m, 10H), 1.68-1.74 (m, 2H). HRMS C$_{35}$H$_{39}$Cl$_2$N$_5$O$_3$S m/z 680.2229 (M+H)$_{Cal.}$, 680.2239 (M+H)$_{Obs.}$.

Example 655

1-((1R,5S)-8-{2-[1-(2,2-Dimethylpropanoyl)-4-(2-methylphenyl)piperidin-4-yl]ethyl}-8-azabicyclo [3.2.1]oct-3-yl)-2-methyl-1H-benzimidazole

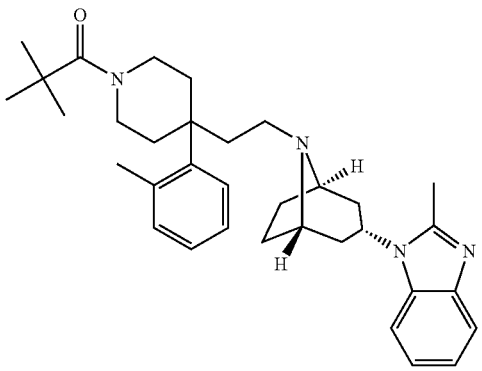

Tert-butyl 4-(1-cyano-2-ethoxy-2-oxoethyl)-4-(2-methylphenyl)piperidine-1-carboxylate. Using the same procedure as in Example 16b 1-bromo-2-methylbenzene (5.1 g, 30 mmol) was used in place of 1-chloro-3-iodobenzene to give tert-butyl 4-(1-cyano-2-ethoxy-2-oxoethyl)-4-(2-methylphenyl)piperidine-1-carboxylate as an oil that was used without further purification.

[1-(tert-Butoxycarbonyl)-4-(2-methylphenyl)piperidin-4-yl](cyano)acetic Acid. tert-Butyl 4-(1-cyano-2-ethoxy-2-oxoethyl)-4-(2-methylphenyl)piperidine-1-carboxylate was hydrolysed using the same procedure as in Example 16c to give [1-(tert-butoxycarbonyl)-4-(2-methylphenyl) piperidin-4-yl](cyano)acetic acid as an amber foam that was used without further purification.

tert-Butyl 4-(Cyanomethyl)-4-(2-methylphenyl) piperidine-1-carboxylate. [1-(tert-Butoxycarbonyl)-4-(2-methylphenyl)piperidin-4-yl](cyano)acetic acid was subjected to the same decarboxylation conditions used in Example 16d and purified by chromatography on silica gel eluting with a 1:9 to 1:1 ethyl acetate:hexane gradient to give tert-butyl 4-(cyanomethyl)-4-(2-methylphenyl)piperidine-1-carboxylate as a solid (2.4 g, 76% overall yield). $^1$H NMR (400 MHz, CDCl$_3$) δ 7.33 (m, 1H), 7.19 (m, 3H), 3.72 (m, 2H), 3.15 (m, 2H), 2.76 (s, 2H), 2.50-2.55 (m, 2H), 2.48 (s, 3H), 1.93 (m, 2H), 1.44 (s, 9H). ES-LCMS m/z 337 (M+23).

tert-Butyl 4-(2-methylphenyl)-4-(2-oxoethyl)piperidine-1-carboxylate. Using the same procedure as in Example 16e using tert-butyl 4-(cyanomethyl)-4-(2-methylphenyl) piperidine-1-carboxylate (2.4 g, 7.5 mmol) gave tert-butyl 4-(2-methylphenyl)-4-(2-oxoethyl)piperidine-1-carboxylate as a foam (1.6 g, 69%). $^1$H NMR (400 MHz, CDCl$_3$) δ 9.32 (t, 1H), 7.31 (m, 1H), 7.18 (m, 3H), 3.51-3.58 (m, 2H), 3.37-3.44 (m, 2H), 2.83 (s, 2H), 2.53 (s, 3H), 2.33 (m, 2H), 1.96 (m, 2H), 1.44 (s, 9H). ES-LCMS m/z 340 (M+23).

tert-Butyl 4-{2-[3-(2-Methyl-1H-benzimidazol-1-yl)-8-azabicyclo[3.2.1]oct-8-yl]ethyl}-4-(2-methylphenyl)piperidine-1-carboxylate. Using the same procedure as in Example 16f using tert-butyl 4-(2-methylphenyl)-4-(2-oxoethyl)piperidine-1-carboxylate (1.6 g, 5 mmol) gave tert-butyl 4-{2-[3-(2-methyl-1H-benzimidazol-1-yl)-8-azabicyclo[3.2.1] oct-8-yl]ethyl}-4-(2-methylphenyl)piperidine-1-carboxylate as a solid (2.5 g, 94%). $^1$H NMR (400 MHz, CDCl$_3$) δ 7.67 (m, 1H), 7.13-7.32 (m, 7H), 4.63 (m, 1H), 3.61 (m, 2H), 3.28 (m, 4H), 2.88 (m, 2H), 2.59 (s, 3H), 2.54 (s, 3H), 2.34-2.40 (m, 4H), 1.82-1.96 (m, 8H), 1.63 (m, 2H), 1.44 (s, 9H). ES-LCMS m/z 543 (M+1).

2-Methyl-1-(8-{2-[4-(2-methylphenyl) piperidin-4-yl] ethyl}-8-azabicyclo[3.2.1]oct-3-yl)-1H-benzimidazole Dihydrochloride. Using the same procedure as in Example 16g using tert-butyl 4-{2-[3-(2-methyl-1H-benzimidazol-1-yl)-8-azabicyclo[3.2.1]oct-8-yl]ethyl}-4-(2-methylphenyl) piperidine-1-carboxylate (2.5 g, 4.6 mmol) gave 2-methyl-1-(8-{2-[4-(2-methylphenyl)piperidin-4-yl]ethyl}-8-azabicyclo[3.2.1]oct-3-yl)-1H-benzimidazole dihydrochloride as a solid (2.2 g, 100%). $^1$H NMR (400 MHz, DMSO-d$_6$) δ 11.28 (s, 1H), 9.02 (m, 2H), 7.89 (m, 1H), 7.80 (m, 1H), 7.55 (m, 2H), 7.20 (m, 4H), 6.05 (m, 1H), 4.11 (m, 2H), 3.26 (m, 2H), 3.05 (m, 1H), 2.88 (s, 4H), 2.81 (m, 3H), 2.53 (s, 3H), 2.33 (m, 2H), 2.13-2.23 (m, 8H), 2.08 (m, 2H). ES-LCMS m/z 443 (M+1).

1-((1R,5S)-8-{2-[1-(2,2-Dimethylpropanoyl)-4-(2-methylphenyl)piperidin-4-yl]ethyl}-8-azabicyclo[3.2.1]oct-3-yl)-2-methyl-1H-benzimidazole (example 655). A mixture of 2-methyl-1-(8-{2-[4-(2-methylphenyl)piperidin-4-yl] ethyl}-8-azabicyclo[3.2.1]oct-3-yl)-1H-benzimidazole dihydrochloride (0.15 g, 0.31 mmol), triethylamine (0.087 mL, 0.62 mmol) and trimethylacetyl chloride (0.043 mL, 0.34 mmol) in dichloromethane (3 mL) was stirred at rt for 1 h. The reaction mixture was diluted with dichloromethane, washed with saturated sodium bicarbonate solution, dried, concentrated and purified by chromatography on silica gel eluting with 33:1 dichloromethane:methanol to give 1-((1R,5S)-8-{2-[1-(2,2-dimethylpropanoyl)-4-(2-methylphenyl)piperidin-4-yl]ethyl}-8-azabicyclo[3.2.1]oct-3-yl)-2-methyl-1H-benzimidazole as a white solid (0.073 g, 45%). $^1$H NMR (400 MHz, CDCl$_3$) δ 7.67 (m, 1H), 7.13-7.31 (m, 7H), 4.62 (m, 1H), 3.86 (m, 2H), 3.48 (m, 2H), 3.24 (m, 2H), 2.56 (m, 6H), 2.34 (m, 4H), 10.93 (m, 8H), 1.60 (m, 4H), 1.27 (s, 9H). HRMS C$_{34}$H$_{46}$N$_4$O m/z 527.3750 (M+H)$_{Cal.}$, 527.3749 (M+H)$_{Obs.}$.

Example 656

2-Chloro-5-{[4-{2-[(1R,5S)-3-(2-methyl-1H-benzimidazol-1-yl)-8-azabicyclo[3.2.1]oct-8-yl]ethyl}-4-(2-methylphenyl)piperidin-1-yl]carbonyl}benzenesulfonamide

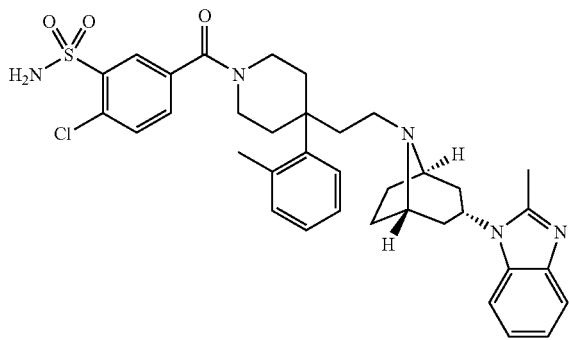

A mixture of 2-methyl-1-(8-{2-[4-(2-methylphenyl)piperidin-4-yl]ethyl}-8-azabicyclo[3.2.1]oct-3-yl)-1H-benzimidazole dihydrochloride (0.30 g, 0.63 mmol), 4-chloro-3-sulfamoylbenzoic acid (0.15 g, 0.63 mmol) and triethylamine (0.3 mL, 2 mmol) in dimethylformamide (2 mL) was treated with O-(7-azabenzotriazol-1-yl)-1,1,3,3-tetramethyluronium hexafluorophosphate (0.26 g, 0.69 mmol) and the resulting mixture was stirred for 1 h at rt. The mixture was diluted with water and the resulting precipitate was collected, washed with saturated sodium bicarbonate solution and water, dried and purified by chromatography on silica gel eluting with a gradient of 310:15:1 to 200:15:1 of chloroform:methanol:ammonium hydroxide to give 2-chloro-5-{[4-{2-[(1R,5S)-3-(2-methyl-1H-benzimidazol-1-yl)-8-azabicyclo[3.2.1]oct-8-yl]ethyl}-4-(2-methylphenyl)piperidin-1-yl]carbonyl}benzenesulfonamide as a white solid (0.089 g, 21%). $^1$H NMR (400 MHz, CD$_3$OD) δ 8.08 (s, 1H), 7.68 (m, 1H), 7.60 (m, 1H), 7.52 (m, 1H), 7.41 (m, 1H), 7.33 (m, 1H), 7.13-7.21 (m, 5H), 4.75 (m, 1H), 4.08 (m, 1H), 3.49-3.58 (m, 2H), 3.31 (m, 5H), 2.55 (m, 7H), 2.46 (m, 3H), 1.90-2.09 (m, 10H), 1.65 (m, 2H). HRMS C$_{36}$H$_{42}$ClN$_5$O$_3$S m/z 660.2775 (M+H)$_{Cal.}$, 660.2764 (M+H)$_{Obs.}$.

Example 657

Methyl 3-{[4-{2-[(1R,5S)-3-(2-Methyl-1H-benzimidazol-1-yl)-8-azabicyclo[3.2.1]oct-8-yl]ethyl}-4-(2-methylphenyl)piperidin-1-yl]carbonyl}benzoate

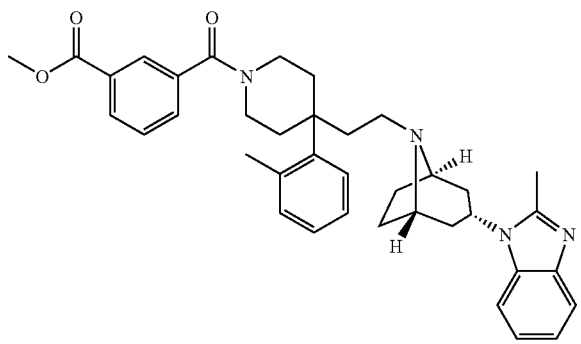

A mixture of 2-methyl-1-(8-{2-[4-(2-methyl phenyl)piperidin-4-yl]ethyl}-8-azabicyclo[3.2.1]oct-3-yl)-1H-benzimidazole dihydrochloride (0.40 g, 0.84 mmol), monomethyl isophthalate (0.15 g, 0.84 mmol) and triethylamine (0.4 mL, 2.9 mmol) in dimethylformamide (3 mL) was treated with O-(7-azabenzotriazol-1-yl)-1,1,3,3-tetramethyluronium hexafluorophosphate (0.35 g, 0.92 mmol) and stirred at rt for 1 h. The mixture was diluted with water and the resultant precipitate was collected, washed with water, dried and purified by chromatography on silica gel eluting with 1:33 methanol:dichloromethane to give methyl 3-{[4-{2-[(1R,5S)-3-(2-methyl-1H-benzimidazol-1-yl)-8-azabicyclo[3.2.1]oct-8-yl]ethyl}-4-(2-methylphenyl)piperidin-1-yl]carbonyl}benzoate as a glass (0.240 g, 47%). $^1$H NMR (400 MHz, CDCl$_3$) δ 8.08 (m, 2H), 7.67 (m, 2H), 7.59 (m, 1H), 7.49 (t, 1H), 7.13-7.29 (m, 6H), 4.62 (m, 1H), 4.11 (m, 1H), 3.93 (s, 3H), 3.56 (m, 2H), 3.26 (m, 2H), 2.54 (m, 5H), 2.36 (m, 4H), 1.95 (m, 10H), 1.64 (m, 4H). HRMS C$_{38}$H$_{44}$N$_4$O$_3$ m/z 605.3492 (M+H)$_{Cal.}$ 605.3497 (M+H)$_{Obs.}$.

Example 658

3-{[4-{2-[(1R,5S)-3-(2-Methyl-1H-benzimidazol-1-yl)-8-azabicyclo[3.2.1]oct-8-yl]ethyl}-4-(2-methylphenyl)piperidin-1-yl]carbonyl}benzoic Acid

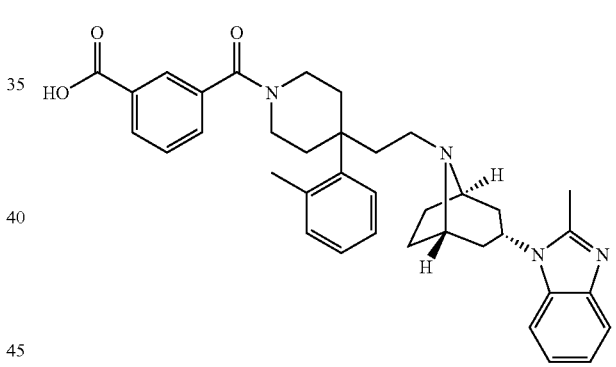

A solution of methyl 3-{[4-{2-[(1R,5S)-3-(2-methyl-1H-benzimidazol-1-yl)-8-azabicyclo[3.2.1]oct-8-yl]ethyl}-4-(2-methylphenyl)piperidin-1-yl]carbonyl}benzoate (0.15 g, 0.29 mmol) in methanol (1 mL) was treated with 2N sodium hydroxide solution (1.5 mL) and let stir at rt for 4 h. The mixture was concentrated to remove methanol and acidified by adding 1N hydrochloric acid. The resulting precipitate was collected, washed with water and dried to give 3-{[4-{2-[(1R,5S)-3-(2-methyl-1H-benzimidazol-1-yl)-8-azabicyclo[3.2.1]oct-8-yl]ethyl}-4-(2-methylphenyl)piperidin-1-yl]carbonyl}benzoic acid as a pale pink solid (0.04 g, 31%). $^1$H NMR (400 MHz, CD$_3$OD) δ 8.11 (m, 1H), 8.02 (s, 1H), 7.54 (m, 3H), 7.48 (m, 1H), 7.34 (m, 1H), 7.17-7.28 (m, 5H), 5.08 (m, 1H), 4.07 (m, 1H), 3.87 (m, 2H), 3.54 (m, 2H), 3.30 (m, 1H), 2.71 (m, 2H), 2.39-2.55 (m, 10H), 2.22-2.30 (m, 6H), 2.09 (m, 3H), 1.92 (m, 1H). HRMS C$_{37}$H$_{42}$N$_4$O$_3$ m/z 591.3335 (M+H)$_{Cal.}$, 591.3350 (M+H)$_{Obs.}$.

Example 659

1-((1R,5S)-8-{2-[4-(1,3-Benzodioxol-5-yl)-1-(2,2-dimethylpropanoyl)piperidin-4-yl]ethyl}-8-azabicyclo[3.2.1]oct-3-yl)-2-methyl-1H-benzimidazole

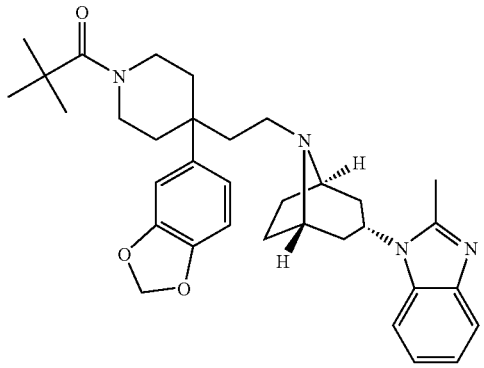

tert-Butyl 4-(1,3-benzodioxol-5-yl)-4-(1-cyano-2-ethoxy-2-oxoethyl)piperidine-1-carboxylate. Using the same procedure as in Example 16b 4-bromo-1,2-(methylenedioxy)benzene (10.2 g, 51 mmol) was used in place of 1-chloro-3-iodobenzene and purified by chromatography on silica gel eluting with a 1:9 to 1:2 ethyl acetate:hexane gradient to give tert-butyl 4-(1,3-benzodioxol-5-yl)-4-(1-cyano-2-ethoxy-2-oxoethyl)piperidine-1-carboxylate as a foam (4.6 g, 65%). $^1$H NMR (400 MHz, CDCl$_3$) δ 6.80 (m, 3H), 5.96 (s, 2H), 4.01 (m, 2H), 3.90 (m, 2H), 3.53 (s, 1H), 2.88 (m, 2H), 2.41-2.51 (m, 2H), 1.94-2.02 (m, 2H), 1.43 (s, 9H), 1.08 (t, 3H). ES-LCMS m/z 415 (M−1).

[4-(1,3-Benzodioxol-5-yl)-1-(tert-butoxycarbonyl)piperidin-4-yl](cyano)acetic Acid. tert-Butyl 4-(1,3-benzodioxol-5-yl)-4-(1-cyano-2-ethoxy-2-oxoethyl)piperidine-1-carboxylate (4.6 g, 11 mmol) was hydrolysed using the same procedure as in Example 16c to give [4-(1,3-benzodioxol-5-yl)-1-(tert-butoxycarbonyl)piperidin-4-yl](cyano)acetic acid as an amber foam (4.2 g, 100%). $^1$H NMR (400 MHz, CDCl$_3$) δ 6.82 (m, 3H), 5.97 (s, 2H), 3.88 (m, 2H), 3.55 (s, 1H), 2.88 (m, 2H), 2.48 (m, 2H), 1.89-2.03 (m, 2H), 1.41 (s, 9H). ES-LCMS m/z 387 (M−1).

tert-Butyl 4-(1,3-Benzodioxol-5-yl)-4-(cyano methyl)piperidine-1-carboxylate. [4-(1,3-Benzodioxol-5-yl)-1-(tert-butoxycarbonyl)piperidin-4-yl](cyano) acetic acid (4.2 g, 11 mmol) was subjected to the same decarboxylation conditions used in Example 16d and purified by chromatography on silica gel eluting with a 1:9 to 1:2 ethyl acetate:hexane gradient to give tert-butyl 4-(1,3-benzodioxol-5-yl)-4-(cyanomethyl) piperidine-1-carboxylate as a foam (2.9 g, 80%). $^1$H NMR (400 MHz, CDCl$_3$) δ 6.82 (m, 3H), 5.97 (s, 2H), 3.74 (m, 2H), 3.07 (m, 2H), 2.50 (s, 2H), 2.21 (m, 2H), 1.76-1.83 (m, 2H), 1.43 (s, 9H). ES-LCMS m/z 245 (M−99).

tert-Butyl 4-(1,3-benzodioxol-5-yl)-4-(2-oxoethyl)piperidine-1-carboxylate. Using the same procedure as in Example 16e tert-butyl 4-(1,3-benzodioxol-5-yl)-4-(cyanomethyl)piperidine-1-carboxylate (2.9 g, 8.6 mmol) gave tert-butyl 4-(1,3-benzodioxol-5-yl)-4-(2-oxoethyl)piperidine-1-carboxylate (2.0 g, 69%). $^1$H NMR (400 MHz, CDCl$_3$) δ 9.39 (t, 1H), 6.79-6.84 (m, 3H), 5.96 (s, 2H), 3.57-3.63 (m, 2H), 3.21-3.27 (m, 2H), 2.58 (s, 2H), 2.10-2.16 (m, 2H), 1.77-1.84 (m, 2H), 1.43 (s, 9H).

tert-Butyl 4-(1,3-benzodioxol-5-yl)-4-{2-[3-(2-methyl-1H-benzimidazol-1-yl)-8-azabicyclo[3.2.1]oct-8-yl]ethyl}piperidine-1-carboxylate. Using the same procedure as in Example 16f tert-butyl 4-(1,3-benzodioxol-5-yl)-4-(2-oxoethyl)piperidine-1-carboxylate (2.0 g, 5.8 mmol) gave tert-butyl 4-(1,3-benzodioxol-5-yl)-4-{2-[3-(2-methyl-1H-benzimidazol-1-yl)-8-azabicyclo[3.2.1]oct-8-yl]ethyl}piperidine-1-carboxylate after chromatography on silica gel eluting with a dichloromethane to 1:9 methanol:dichloromethane gradient as a foam (2.4 g, 73%). $^1$H NMR (400 MHz, CDCl$_3$) δ 7.66 (m, 1H), 7.28 (m, 1H), 7.12-7.20 (m, 2H), 6.79 (m, 2H), 6.72 (m, 1H), 5.96 (s, 2H), 4.64 (m, 2H), 3.63 (m, 2H), 3.30 (m, 2H), 3.19 (m, 4H), 2.60 (s, 3H), 2.43 (m, 2H), 1.71-2.08 (m, 11H), 1.44 (s, 9H). ES-LCMS m/z 573 (M+1).

1-(8-{2-[4-(1,3-Benzodioxol-5-yl)piperidin-4-yl]ethyl}-8-azabicyclo[3.2.1]oct-3-yl)-2-methyl-1H-benzimidazole dihydrochloride. Using the same procedure as in Example 16g tert-butyl 4-(1,3-benzo-dioxol-5-yl)-4-{2-[3-(2-methyl-1H-benzimidazol-1-yl)-8-azabicyclo[3.2.1]oct-8-yl]ethyl}piperidine-1-carboxylate (2.4 g, 4.2 mmol) gave 1-(8-{2-[4-(1,3-benzodioxol-5-yl)piperidin-4-yl]ethyl}-8-azabicyclo[3.2.1]oct-3-yl)-2-methyl-1H-benzimidazole dihydro-chloride as a solid (2.1 g, 100%). $^1$H NMR (400 MHz, DMSO-d$_6$) δ 11.22 (s, 1H), 9.06-9.13 (m, 2H), 7.88 (m, 1H), 7.80 (m, 1H), 7.56 (m, 2H), 7.02 (s, 1H), 6.91 (m, 1H), 6.82 (m, 1H), 6.02 (s, 2H), 4.07 (m, 2H), 3.19 (m, 2H), 2.88 (s, 3H), 2.78-2.83 (m, 4H), 2.52 (m, 2H), 1.95-2.26 (m, 11H). ES-LCMS m/z 473 (M+1).

Title compound in example 659. A mixture of 1-(8-{2-[4-(1,3-benzodioxol-5-yl)piperidin-4-yl]ethyl}-8-azabicyclo[3.2.1]oct-3-yl)-2-methyl-1H-benzimidazole dihydrochloride (0.2 g, 0.39 mmol), triethylamine (0.11 mL, 0.78 mmol) and trimethylacetyl chloride (0.053 mL, 0.43 mmol) in dichloromethane (4 mL) was stirred at rt for 1 h before the reaction mixture was quenched with saturated sodium bicarbonate solution. The organic layer was separated, dried and concentrated to give 1-((1R,5S)-8-{2-[4-(1,3-benzodioxol-5-yl)-1-(2,2-dimethylpropanoyl)piperidin-4-yl]ethyl}-8-azabicyclo[3.2.1]oct-3-yl)-2-methyl-1H-benzimidazole as a foam (0.18 g, 82%). $^1$H NMR (400 MHz, CDCl$_3$) δ 7.81 (m, 1H), 7.29 (m, 3H), 6.83 (m, 2H), 6.75 (m, 1H), 6.21 (m, 1H), 6.00 (s, 2H), 3.95 (m, 2H), 3.84 (m, 2H), 3.38 (m, 2H), 2.98 (m, 2H), 2.86 (s, 3H), 2.56 (m, 2H), 2.31 (m, 4H), 2.07-2.21 (m, 4H), 1.82 (m, 4H), 1.26 (s, 9H). HRMS C$_{34}$H$_{44}$N$_4$O$_3$ m/z 557.3492 (M+H)$_{Cal}$, 557.3495 (M+H)$_{Obs}$.

Example 660

5-[(4-(1,3-Benzodioxol-5-yl)-4-{2-[(1R,5S)-3-(2-methyl-1H-benzimidazol-1-yl)-8-azabicyclo[3.2.1]oct-8-yl]ethyl}piperidin-1-yl)carbonyl]-2-chlorobenzene sulfonamide

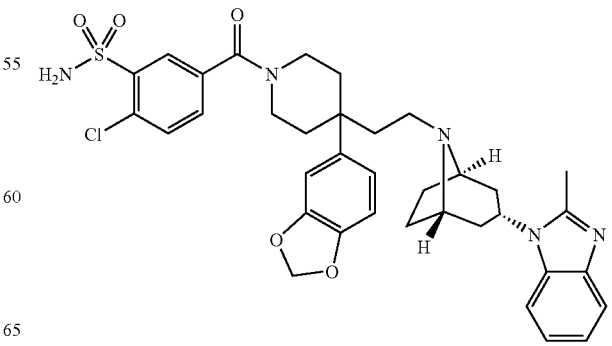

A mixture of 1-(8-{2-[4-(1,3-benzodioxol-5-yl)piperidin-4-yl]ethyl}-8-azabicyclo[3.2.1]oct-3-yl)-2-methyl-1H-benzimidazole dihydrochloride (0.40 g, 0.78 mmol), triethylamine (0.35 mL, 2.5 mmol) and 4-chloro-3-sulfamoylbenzoic acid (184 mg, 0.78 mmol) in dimethylformamide (2.5 mL) was treated with O-(7-azabenzotriazol-1-yl)-1,1,3,3-tetramethyluronium hexafluorophosphate (327 mg, 0.86 mmol) and the resulting mixture was stirred for 1 h at rt. The mixture was diluted with water and the resulting precipitate was collected, washed with saturated sodium bicarbonate solution and water, dried and purified by chromatography on silica gel eluting with a chloroform:methanol:ammonium hydroxide 400:15:1 to 200:15:1 gradient to give 5-[(4-(1,3-benzodioxol-5-yl)-4-{2-[(1R,5S)-3-(2-methyl-1H-benzimidazol-1-yl)-8-azabicyclo[3.2.1]oct-8-yl]ethyl}piperidin-1-yl) carbonyl]-2-chlorobenzenesulfonamide as a solid (0.09 g, 17%). $^1$H NMR (400 MHz, CD$_3$OD) δ 8.08 (s, 1H), 7.67 (m, 1H), 7.59 (m, 1H), 7.51 (m, 1H), 7.41 (m, 1H), 7.17 (m, 2H), 6.94 (s, 1H), 6.81-6.86 (m, 2H), 5.93 (s, 2H), 4.74 (m, 1H), 4.11 (m, 1H), 3.52 (m, 1H), 3.30 (m, 4H), 2.52 (s, 3H), 2.44 (m, 2H), 2.39 (m, 1H), 2.18 (m, 1H), 1.80-2.04 (m, 12H), 1.70 (m, 2H). HRMS C$_{36}$H$_{40}$ClN$_5$O$_5$ m/z 690.2517 (M+H)$_{Cal.}$, 690.2538 (M+H)$_{Obs.}$.

Example 661

1-[(1R,5S)-8-(2-{1-Benzyl-4-[3-(trifluoromethyl)phenyl]piperidin-4-yl}ethyl)-8-azabicyclo[3.2.1]oct-3-yl]-2-methyl-1H-benzimidazole

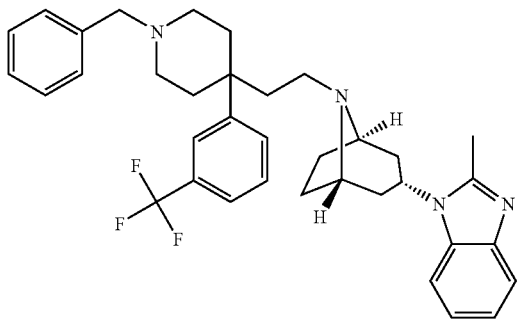

The following compounds were prepared according to the procedures in Example 16.

Ethyl (1-Benzylpiperidin-4-ylidene)(cyano)acetate. Using the same procedure as in Example 16a 1-benzylpiperidin-4-one (47.3 g, 0.25 mol) was used in place of tert-butyl 4-oxo-1-piperidine carboxylate to give ethyl (1-benzylpiperidin-4-ylidene)(cyano)acetate as a solid (72.2 g, 100%). $^1$H NMR (400 MHz, CDCl$_3$) δ 7.25-7.35 (m, 5H), 4.26 (q, 2H), 3.54 (s, 2H), 3.14 (m, 2H), 2.78 (m, 2H), 2.64 (m, 2H), 2.59 (m, 2H), 1.33 (t, 3H). ES-LCMS m/z 283 (M−1).

Ethyl {1-Benzyl-4-[3-(trifluoromethyl)phenyl]piperidin-4-yl}(cyano)acetate. Using the same procedure as in Example 16b 3-bromobenzotrifluoride (20.2 g, 0.09 mol) was used in place of 1-chloro-3-iodobenzene to give ethyl {1-benzyl-4-[3-(trifluoro methyl)phenyl]piperidin-4-yl}(cyano)acetate as a solid (5.6 g, 37%). $^1$H NMR (400 MHz, CDCl$_3$) δ 7.51-7.63 (m, 4H), 7.22-7.35 (m, 5H), 3.92 (m, 2H), 3.69 (s, 1H), 3.40 (s, 2H), 2.67 (m, 2H), 2.51 (m, 2H), 2.18-2.29 (m, 4H), 0.99 (t, 3H). ES-LCMS m/z 431 (M+1).

{1-Benzyl-4-[3-(trifluoromethyl)phenyl]piperidin-4-yl}(cyano)acetic Acid. Ethyl{1-benzyl-4-[3-(trifluoromethyl)phenyl]piperidin-4-yl}(cyano) acetate (5.6 g, 0.013 mol) was hydrolysed using the same procedure as in Example 16c to give an amber foam (5.2 g, 100%) that was used without further purification.

{1-Benzyl-4-[3-(trifluoromethyl)phenyl]piperidin-4-yl}acetonitrile. {1-Benzyl-4-[3-(trifluoromethyl)phenyl]piperidin-4-yl}(cyano)acetic acid (5.2 g, 0.013 mol) was subjected to the same decarboxylation conditions used in Example 16d and purified by column chromatography on silica gel eluting with 1:1 hexane:ethyl acetate to give {1-benzyl-4-[3-(trifluoromethyl)phenyl]piperidin-4-yl}acetonitrile as a solid (2.9 g, 63%). $^1$H NMR (400 MHz, CDCl$_3$) δ 7.51-7.58 (m, 4H), 7.25-7.36 (m, 5H), 3.49 (s, 2H), 2.60 (m, 4H), 2.35 (m, 4H), 2.10 (s, 2H). ES-LCMS m/z 359 (M+1).

{1-Benzyl-4-[3-(trifluoromethyl)phenyl]piperidin-4-yl}acetaldehyde. Using the same procedure as in Example 16e {1-benzyl-4-[3-(trifluoromethyl) phenyl]piperidin-4-yl}acetonitrile (2.4 g, 6.7 mmol) gave {1-benzyl-4-[3-(trifluoromethyl)phenyl]piperidin-4-yl}acetaldehyde as a tan foam (2.0 g, 83%). $^1$H NMR (400 MHz, CDCl$_3$) δ 9.38 (t, 1H), 7.48-7.60 (m, 4H), 7.25-7.32 (m, 5H), 3.45 (s, 2H), 2.70 (s, 2H), 2.56 (m, 2H), 2.38 (m, 2H), 2.25 (m, 2H), 2.01 (m, 2H). ES-LCMS m/z 360 (M−1).

Title compound in example 661: 1-[(1R,5S)-8-(2-{1-Benzyl-4-[3-(trifluoromethyl)phenyl]piperidin-4-yl}ethyl)-8-azabicyclo[3.2.1]oct-3-yl]-2-methyl-1H-benzimidazole. Using the same procedure as in Example 16f {1-benzyl-4-[3-(trifluoromethyl)phenyl]piperidin-4-yl}acetaldehyde (0.23 g, 0.64 mmol) was used in place of tert-butyl 4-(3-chlorophenyl)-4-(2-oxoethyl) piperidine-1-carboxylate to give 1-[(1R,5S)-8-(2-{1-benzyl-4-[3-(trifluoromethyl)phenyl]piperidin-4-yl}ethyl)-8-azabicyclo[3.2.1]oct-3-yl]-2-methyl-1H-benzimidazole as a glass (0.10 g, 27%). $^1$H NMR (400 MHz, CDCl$_3$) δ 7.67 (m, 1H), 7.55 (s, 1H), 7.49 (s, 3H), 7.26-7.33 (m, 6H), 7.12-7.20 (m, 2H), 4.63 (m, 1H), 3.53 (m, 2H), 3.25 (m, 2H), 2.72 (m, 2H), 2.56 (s, 3H), 2.38 (m, 4H), 2.24 (m, 2H), 1.84-1.94 (m, 10H), 1.63 (m, 2H). HRMS C$_{36}$H$_{41}$F$_3$N$_4$ m/z 587.3362 (M+H)$_{Cal.}$, 587.3375 (M+H)$_{Obs.}$.

Example 662

1-[(1R,5S)-8-(2-{1-(2,2-Dimethylpropanoyl)-4-[3-(trifluoromethyl)phenyl]piperidin-4-yl}ethyl)-8-azabicyclo[3.2.1]oct-3-yl]-2-methyl-1H-benzimidazole

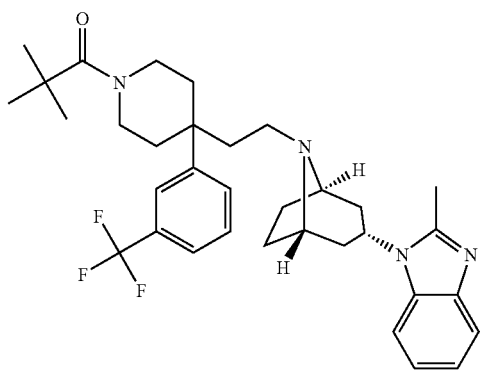

2-Methyl-1-[8-(2-{4-[3-(trifluoromethyl) phenyl]piperidin-4-yl}ethyl)-8-azabicyclo[3.2.1]oct-3-yl]-1H-benzimidazole dihydrochloride. A mixture of 1-[(1R,5S)-8-(2-{1-benzyl-4-[3-(trifluoromethyl)phenyl]piperidin-4-yl}ethyl)-

8-azabicyclo[3.2.1]oct-3-yl]-2-methyl-1H-benzimidazole (0.2 g, 0.34 mmol), 1N hydrochloric acid (0.34 mL) and 10% Palladium on carbon (50 mg) in methanol (10 mL) was hydrogenated overnight at rt and atmospheric pressure. The mixture was filtered through celite and concentrated to give 2-methyl-1-[8-(2-{4-[3-(trifluoromethyl)phenyl]piperidin-4-yl}ethyl)-8-azabicyclo[3.2.1]oct-3-yl]-1H-benzimidazole dihydrochloride as a solid (0.15 g, 89%) that was used without further purification.

Title compound in example 662: 1-[(1R,5S)-8-(2-{1-(2,2-Dimethylpropanoyl)-4-[3-(trifluoromethyl) phenyl]piperidin-4-yl}ethyl)-8-azabicyclo[3.2.1]oct-3-yl]-2-methyl-1H-benzimidazole. A mixture of 2-methyl-1-[8-(2-{4-[3-(trifluoromethyl)phenyl]piperidin-4-yl}ethyl)-8-azabicyclo[3.2.1]oct-3-yl]-1H-benzimidazole dihydrochloride (0.05 g, 0.1 mmol), triethylamine (0.028 mL, 0.2 mmol) and trimethylacetyl chloride (0.014 mL, 0.11 mmol) in dichloromethane (1 mL) was stirred 1 h at rt before the reaction mixture was quenched with saturated sodium bicarbonate solution. The organic layer was separated, dried, concentrated and purified by chromatography on silica gel eluting with 1:33 methanol:dichloromethane to give 1-[(1R,5S)-8-(2-{1-(2,2-dimethylpropanoyl)-4-[3-(trifluoro methyl)phenyl]piperidin-4-yl}ethyl)-8-azabicyclo[3.2.1]oct-3-yl]-2-methyl-1H-benzimidazole as a glass (0.025 g, 43%). $^1$H NMR (400 MHz, CDCl$_3$) δ 7.68 (m, 1H), 7.54 (m, 4H), 7.13-7.21 (m, 3H), 4.62 (m, 1H), 3.95 (m, 2H), 3.25-3.37 (m, 3H), 2.61 (s, 3H), 2.40 (m, 2H), 2.18 (m, 3H), 1.88 (m, 10H), 1.64 (m, 2H), 1.27 (s, 9H). HRMS C$_{34}$H$_{43}$F$_3$ON$_4$ m/z 581.3467 (M+H)$_{Cal.}$, 581.3476 (M+H)$_{Obs.}$.

Example 663

2-Chloro-5-({4-{2-[(1R,5S)-3-(2-methyl-1H-benzimidazol-1-yl)-8-azabicyclo[3.2.1]oct-8-yl]ethyl}-4-[3-(tri-fluoromethyl)phenyl]piperidin-1-yl}carbonyl) benzene-sulfonamide

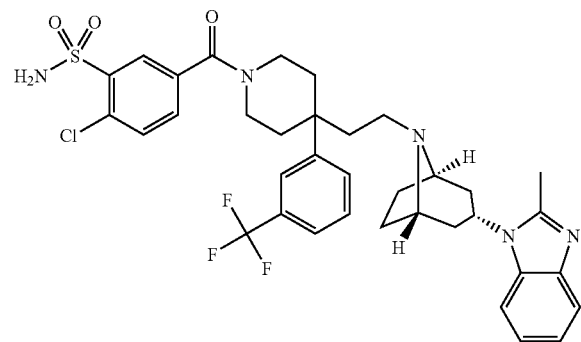

A mixture of 2-methyl-1-[8-(2-{4-[3-(trifluoromethyl) phenyl]piperidin-4-yl}ethyl)-8-azabicyclo[3.2.1]oct-3-yl]-1H-benzimidazole dihydrochloride (0.1 g, 0.2 mmol), triethylamine (0.056 mL, 0.4 mmol) and 3-(aminosulfonyl)-4-chlorobenzoyl chloride (0.056 g, 0.22 mmol) in dichloromethane (2 mL) was stirred at rt for 1.5 h. The reaction mixture was diluted with dichloromethane, washed with saturated sodium bicarbonate solution, dried, concentrated and purified by three successive chromatographies on silica gel eluting with mixtures of methanol in dichloromethane to give 2-chloro-5-({4-{2-[(1R,5S)-3-(2-methyl-1H-benzimidazol-1-yl)-8-azabicyclo[3.2.1]oct-8-yl]ethyl}-4-[3-(trifluoromethyl)phenyl]piperidin-1-yl}carbonyl)benzenesulfonamide as a wax (0.002 g, 2%). $^1$H NMR (400 MHz, CD$_3$OD$_3$) δ 7.79-7.94 (m, 2H), 7.57-7.71 (m, 5H), 7.40-7.54 (m, 2H), 7.15-7.21 (m, 2H), 4.73 (m, 1H), 4.15 (m, 1H), 3.39-3.55 (m, 4H), 3.16-3.22 (m, 1H), 2.52 (s, 3H), 2.34-2.50 (m, 3H), 2.22-2.32 (m, 1H), 1.94-2.12 (m, 10H), 1.68-1.74 (m, 2H). HRMS C$_{36}$H$_{39}$ClF$_3$N$_5$O$_3$S m/z 714.2492 (M+H)$_{Cal.}$, 714.2496 (M+H)$_{Obs.}$.

Example 664

1-((1R,5S)-8-{2-[4-(3-Chloro-5-fluorophenyl)-1-(2,2-dimethylpropanoyl)piperidin-4-yl]ethyl}-8-azabicyclo[3.2.1]oct-3-yl)-2-methyl-1H-benzimidazole

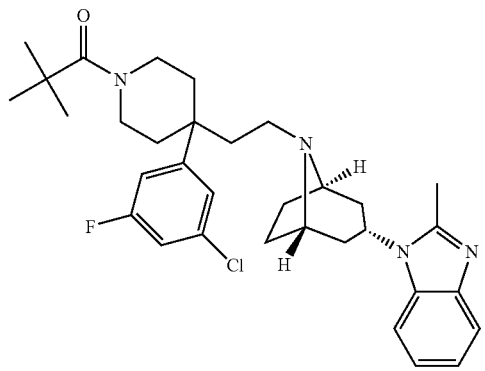

tert-Butyl 4-(3-chloro-5-fluorophenyl)-4-(1-cyano-2-ethoxy-2-oxoethyl)piperidine-1-carboxylate. Using the same procedure as in Example 16b 1-bromo-3-chloro-5-fluorobenzene (10.7 g, 51 mmol) was used in place of 1-chloro-3-iodobenzene to give tert-butyl 4-(3-chloro-5-fluorophenyl)-4-(1-cyano-2-ethoxy-2-oxoethyl)piperidine-1-carboxylate as an amber foam that was used without further purification.

[1-(tert-Butoxycarbonyl)-4-(3-chloro-5-fluorophenyl)piperidin-4-yl](cyano)acetic Acid. tert-Butyl 4-(3-chloro-5-fluorophenyl)-4-(1-cyano-2-ethoxy-2-oxoethyl)piperidine-1-carboxylate was hydrolysed using the same procedure as in Example 16c to give [1-(tert-butoxycarbonyl)-4-(3-chloro-5-fluorophenyl) piperidin-4-yl](cyano)acetic acid as an amber foam that was used without further purification.

tert-Butyl 4-(3-chloro-fluorophenyl)-4-(cyanomethyl)piperidine-1-carboxylate. [1-(tert-Butoxycarbonyl)-4-(3-chloro-5-fluorophenyl)piperidin-4-yl](cyano)acetic acid was subjected to the same decarboxylation conditions used in Example 16d and purified by chromatography on silica gel eluting with 1:4 ethyl acetate:hexane to give tert-butyl 4-(3-chloro-5-fluorophenyl)-4-(cyanomethyl)piperidine-1-carboxylate as a solid (2.3 g, 38% overall). $^1$H NMR (400 MHz, CDCl$_3$) δ 7.13 (s, 1H), 7.05 (m, 1H), 6.98 (m, 1H), 3.71 (m, 2H), 3.11 (m, 2H), 2.55 (s, 2H), 2.20 (m, 2H), 1.86 (m, 2H), 1.43 (s, 9H). ES-LCMS m/z 253 (M−99).

tert-Butyl 4-(3-chloro-5-fluorophenyl)-4-(2-oxoethyl)piperidine-1-carboxylate. Using the same procedure as in Example 16e tert-butyl 4-(3-chloro-5-fluorophenyl)-4-(cyanomethyl)piperidine-1-carboxylate (2.3 g, 6.5 mmol) gave tert-butyl 4-(3-chloro-5-fluorophenyl)-4-(2-oxoethyl)piperidine-1-carboxylate as an amber foam (1.5 g, 65%). $^1$H NMR (400 MHz, CDCl$_3$) δ 9.43 (t, 1H), 7.12 (s, 1H), 6.95-7.01 (m, 2H), 3.55-3.62 (m, 2H), 3.24-3.30 (m, 2H), 2.63 (s, 2H), 2.04-2.17 (m, 2H), 1.80-1.91 (m, 2H), 1.42 (s, 9H). ES-LCMS m/z 354 (M−1).

tert-Butyl 4-(3-chloro-5-fluorophenyl)-4-(2-[3-(2-methyl-1H-benzimidazol-1-yl)-8-azabicyclo[3.2.1]oct-8-yl]ethyl)piperidine-1-carboxylate. Using the same procedure as in Example 16f tert-butyl 4-(3-chloro-5-fluorophenyl)-4-(2-oxoethyl)piperidine-1-carboxylate (1.5 g, 4.2 mmol) gave tert-butyl 4-(3-chloro-5-fluorophenyl)-4-{2-[3-(2-methyl-1H-benzimidazol-1-yl)-8-azabicyclo[3.2.1]oct-8-yl]ethyl}piperidine-1-carboxylate as a solid (1.7 g, 71%). $^1$H NMR (400 MHz, CDCl$_3$) δ 7.66 (m, 1H), 7.29 (m, 1H), 7.17 (m, 2H), 7.08 (s, 1H), 6.98 (m, 1H), 6.91 (m, 1H), 4.66 (m, 2H), 3.83 (m, 2H), 3.62 (m, 2H), 3.25 (4H), 3.01 (m, 1H), 2.60 (s, 3H), 2.44 (m, 2H), 2.02 (m, 4H), 1.71-1.86 (m, 6H), 1.43 (s, 9H). ES-LCMS m/z 581 (M+1).

1-((1R,5S)-8-{2-[4-(3-Chloro-5-fluorophenyl) piperidin-4-yl]ethyl}-8-azabicyclo[3.2.1]oct-3-yl)-2-methyl-1H-benzimidazole dihydrochloride. Using the same procedure as in Example 16g tert-butyl 4-(3-chloro-5-fluorophenyl)-4-{2-[3-(2-methyl-1H-benzimidazol-1-yl)-8-azabicyclo[3.2.1]oct-8-yl]ethyl}piperidine-1-carboxylate (1.7 g, 2.9 mmol) gave 1-((1R,5S)-8-{2-[4-(3-chloro-5-fluorophenyl)piperidin-4-yl]ethyl}-8-azabicyclo[3.2.1]oct-3-yl)-2-methyl-1H-benzimidazole dihydrochloride as a solid (1.5 g, 100%). $^1$H NMR (400 MHz, DMSO-d$_6$) δ 11.26 (s, 1H), 9.14 (s, 2H), 7.89 (m, 1H), 7.80 (m, 1H), 7.55 (m, 2H), 7.37 (m, 1H), 7.30 (m, 2H), 6.03 (m, 1H), 4.11 (m, 2H), 3.22 (m, 2H), 3.11 (m, 1H), 2.88 (s, 3H), 2.75-2.90 (m, 4H), 2.30 (m, 2H), 2.10-2.25 (m, 8H), 2.08 (m, 2H). ES-LCMS m/z 481 (M+1).

1-((1R,5S)-8-{2-[4-(3-Chloro-5-fluorophenyl)-1-(2,2-dimethylpropanoyl)piperidin-4-yl]ethyl}-8-azabicyclo[3.2.1]oct-3-yl)-2-methyl-1H-benzimidazole (example 664). A mixture of 1-((1R,5S)-8-{2-[4-(3-chloro-5-fluorophenyl)piperidin-4-yl]ethyl}-8-azabicyclo[3.2.1]oct-3-yl)-2-methyl-1H-benzimidazole dihydrochloride (0.2 g, 0.39 mmol), triethylamine (0.11 mL, 0.78 mmol) and trimethylacetyl chloride (0.053 mL, 0.43 mmol) in dichloromethane (4 mL) was stirred at rt for 1 h before the reaction mixture was quenched with saturated sodium bicarbonate solution. The organic layer was separated, dried, concentrated and purified by two successive chromatographies on silica gel using a dichloromethane to methanol:dichloromethane 1:20 gradient to give 1-((1R,5S)-8-{2-[4-(3-chloro-5-fluorophenyl)-1-(2,2-dimethylpropanoyl)piperidin-4-yl]ethyl}-8-azabicyclo[3.2.1]oct-3-yl)-2-methyl-1H-benzimidazole as a glass (0.06 g, 27%). $^1$H NMR (400 MHz, CDCl$_3$) δ 7.67 (m, 1H), 7.29 (m, 1H), 7.17 (m, 2H), 7.09 (m, 1H), 7.00 (m, 1H), 6.93 (m, 1H), 4.72 (m, 1H), 3.90 (m, 2H), 3.37 (m; 4H), 2.61 (s, 3H), 2.47 (m, 2H), 1.89-2.11 (m, 8H), 1.78 (m, 6H), 1.27 (s, 9H). HRMS C$_{33}$H$_{42}$ClFN$_4$O m/z 565.3109 (M+H)$_{Cal}$, 565.3095 (M+H)$_{Obs}$.

Example 665

2-Chloro-5-[(4-(3-chloro-5-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzene sulfonamide

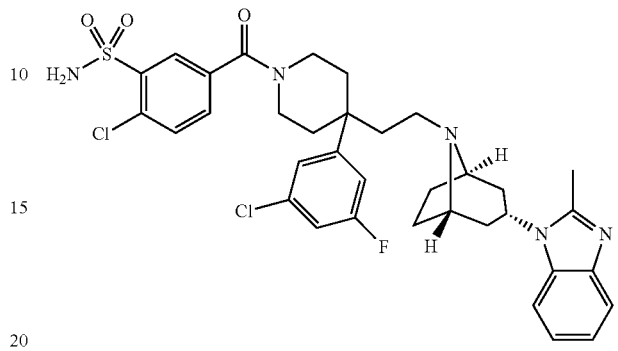

A mixture of 1-((1R,5S)-8-{2-[4-(3-chloro-5-fluorophenyl)piperidin-4-yl]ethyl}-8-azabicyclo[3.2.1]oct-3-yl)-2-methyl-1H-benzimidazole dihydrochloride (0.40 g, 0.78 mmol), triethylamine (0.35 mL, 2.5 mmol) and 4-chloro-3-sulfamoylbenzoic acid (184 mg, 0.78 mmol) in dimethylformamide (2.5 mL) was treated with O-(7-azabenzotriazol-1-yl)-1,1,3,3-tetramethyluronium hexafluorophosphate (327 mg, 0.86 mmol) and the resulting mixture was stirred for 1 h at rt. The mixture was diluted with water and the resulting precipitate was collected, washed with saturated sodium bicarbonate solution and water, dried and purified by chromatography on silica gel eluting with a gradient of chloroform:methanol:ammonium hydroxide 400:15:1 to 200:15:1 to give 2-chloro-5-[(4-(3-chloro-5-fluoro phenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzene-sulfonamide as a solid (0.20 g, 36%). $^1$H NMR (400 MHz, CD$_3$OD) δ 8.09 (s, 1H), 7.67 (m, 1H), 7.60 (m, 1H), 7.51 (m, 1H), 7.42 (m, 1H) 7.30 (s, 1H), 7.10-7.21 (m, 4H), 4.72 (m, 1H), 4.06 (m, 1H), 3.57 (m, 1H), 3.47 (m, 1H), 3.30 (m, 3H), 2.52 (s, 3H), 2.40-2.48 (m, 4H), 2.27 (m, 1H), 2.14 (m, 1H), 1.83-2.04 (m, 10H), 1.70 (m, 2H). HRMS C$_{35}$H$_{38}$Cl$_2$FN$_5$O$_3$S m/z 698.2134 (M+H)$_{Cal}$, 698.2161 (M+H)$_{Obs}$.

Example 666

1-((1R,5S)-8-{2-[1-(2,2-Dimethylpropanoyl)-4-(3-ethoxyphenyl)piperidin-4-yl]ethyl}-8-azabicyclo[3.2.1]oct-3-yl)-2-methyl-1H-benzimidazole

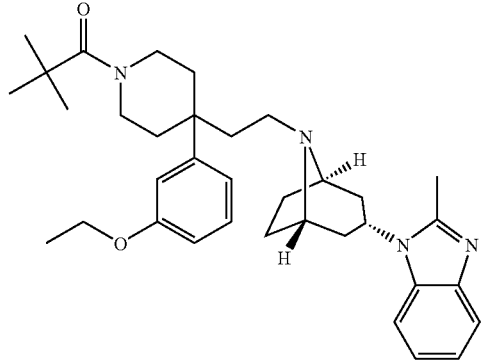

tert-Butyl 4-(1-cyano-2-ethoxy-2-oxoethyl)-4-(3-ethoxyphenyl)piperidine-1-carboxylate. Using the same procedure as in Example 16b 3-bromophenetole (10.2 g, 51 mmol) was used in place of 1-chloro-3-iodobenzene and purified by chromatography on silica gel eluting with a 1:9 to 1:2 ethyl acetate:hexane gradient to give tert-butyl 4-(1-cyano-2-ethoxy-2-oxoethyl)-4-(3-ethoxyphenyl)piperidine-1-carboxylate as an oil (5.4 g, 77%). $^1$H NMR (400 MHz, CDCl$_3$) δ 7.29 (m, 1H), 6.81-6.91 (m, 3H), 3.90-4.04 (m, 4H), 3.55 (s, 1H), 2.86 (m, 2H), 2.54 (m, 2H), 1.95-2.05 (m, 4H), 1.43 (s, 9H), 1.40 (t, 3H), 1.04 (t, 3H). ES-LCMS m/z 317 (M−99).

[1-(tert-Butoxycarbonyl)-4-(3-ethoxyphenyl)piperidin-4-yl](cyano)acetic Acid. tert-Butyl 4-(1-cyano-2-ethoxy-2-oxoethyl)-4-(3-ethoxy phenyl)piperidine-1-carboxylate was hydrolysed using the same procedure as in Example 16c to give [1-(tert-butoxycarbonyl)-4-(3-ethoxyphenyl)piperidin-4-yl](cyano)acetic acid as a pale yellow foam that was used without further purification.

tert-Butyl 4-(cyanomethyl)-4-(3-ethoxyphenyl) piperidine-1-carboxylate. [1-(tert-Butoxycarbonyl-4-(3-ethoxyphenyl)piperidin-4-yl](cyano)acetic acid was subjected to the same decarboxylation conditions used in Example 16d and purified by chromatography on silica gel eluting with a 1:9 to 1:2 ethyl acetate:hexane gradient to give tert-butyl 4-(cyanomethyl)-4-(3-ethoxyphenyl)piperidine-1-carboxylate as a solid (3.1 g, 72%). $^1$H NMR (400 MHz, CDCl$_3$) δ 7.31 (m, 1H), 6.80-6.94 (m, 3H), 4.04 (m, 2H), 3.74-3.80 (m, 2H), 3.06 (m, 2H), 2.53 (s, 2H), 2.30 (m, 2H), 1.83 (m, 2H), 1.43 (s, 9H), 1.40 (t, 3H). ES-LCMS m/z 245 (M−99).

tert-Butyl 4-(3-ethoxyphenyl)-4-(2-oxoethyl) piperidine-1-carboxylate. Using the same procedure as in Example 16e tert-butyl 4-(cyanomethyl)-4-(3-ethoxyphenyl)piperidine-1-carboxylate (3.1 g, 9 mmol) gave tert-butyl 4-(3-ethoxyphenyl)-4-(2-oxoethyl) piperidine-1-carboxylate as a solid (2.1 g, 68%). $^1$H NMR (400 MHz, CDCl$_3$) δ 9.37 (t, 1H), 7.30 (m, 1H), 6.89-6.92 (m, 2H), 6.76 (m, 1H), 4.02 (m, 2H), 3.59-3.65 (m, 2H), 3.19-3.26 (m, 2H), 2.60 (s, 2H), 2.17-2.22 (m, 2H), 1.85 (m, 2H), 1.43 (s, 9H), 1.40 (m, 3H).

tert-Butyl 4-(3-ethoxyphenyl)-4-{2-[3-(2-methyl-1H-benzimidazol-1-yl)-8-azabicyclo[3.2.1]oct-8-yl]ethyl}piperidine-1-carboxylate. Using the same procedure as in Example 16f tert-butyl 4-(3-ethoxy phenyl)-4-(2-oxoethyl)piperidine-1-carboxylate (2.1 g, 6 mmol) gave tert-butyl 4-(3-ethoxyphenyl)-4-{2-[3-(2-methyl-1H-benzimidazol-1-yl)-8-azabicyclo[3.2.1]oct-8-yl]ethyl}piperidine-1-carboxylate after chromatography on silica gel eluting with a dichloromethane to 1:9 methanol:dichloromethane gradient as a solid (3.0 g, 88%). $^1$H NMR (400 MHz. CDCl$_3$) δ 7.66 (m, 1H), 7.26 (m, 2H), 7.13-7.19 (m, 2H), 6.85 (m, 2H), 6.75 (m, 1H), 4.66 (m, 2H), 4.03 (m, 2H), 3.65 (m, 2H), 3.30 (m, 2H), 3.17 (m, 4H), 2.60 (s, 3H), 2.40 (m, 2H), 1.65-2.16 (m, 11H), 1.43 (s, 9H), 1.40 (m, 3H). ES-LCMS m/z 573 (M+1).

1-(8-{2-[4-(3-Ethoxyphenyl)piperidin-4-yl]ethyl}-8-azabicyclo[3.2.1]oct-3-yl)-2-methyl-1H-benzimidazole dihydrochloride. Using the same procedure as in Example 16g tert-butyl 4-(3-ethoxy phenyl)-4-{2-[3-(2-methyl-1H-benzimidazol-1-yl)-8-azabicyclo[3.2.1]oct-8-yl]ethyl}piperidine-1-carboxylate (3.0 g, 5.2 mmol) gave 1-(8-{2-[4-(3-ethoxyphenyl)piperidin-4-yl]ethyl}-8-azabicyclo[3.2.1]oct-3-yl)-2-methyl-1H-benzimidazole dihydrochloride as a solid (2.6 g, 100%). $^1$H NMR (400 MHz, DMSO-d$_6$) δ 11.21 (s, 1H), 9.04 (s, 2H), 7.88 (m, 1H), 7.80 (m, 1H), 7.55 (m, 2H), 7.31 (m, 1H), 6.83-6.94 (m, 3H), 6.02 (m, 1H), 4.07 (m, 2H), 3.21 (m, 2H), 2.88 (s, 3H), 2.75-2.83 (m, 4H), 2.52 (m, 2H), 2.18-2.34 (m, 8H), 2.08 (m, 4H), 1.33 (t, 3H). ES-LCMS m/z 473 (M+1).

1-((1R,5S)-8-{2-[1-(2,2-Dimethylpropanoyl)-4-(3-ethoxyphenyl)piperidin-4-yl]ethyl}-8-azabicyclo[3.2.1]oct-3-yl)-2-methyl-1H-benzimidazole (example 666). A mixture of 1-(8-{2-[4-(3-ethoxyphenyl) piperidin-4-yl]ethyl}-8-azabicyclo[3.2.1]oct-3-yl)-2-methyl-1H-benzimidazole dihydrochloride (0.2 g, 0.39 mmol), triethylamine (0.11 mL, 0.78 mmol) and trimethylacetyl chloride (0.053 mL, 0.43 mmol) in dichloromethane (4 mL) was stirred at rt for 1 h before the reaction mixture was quenched with saturated sodium bicarbonate solution. The organic layer was separated, dried, concentrated and purified by chromatography on silica gel eluting with a dichloromethane to 1:9 methanol:dichloromethane gradient to give 1-((1R,5S)-8-{2-[1-(2,2-dimethylpropanoyl)-4-(3-ethoxyphenyl) piperidin-4-yl]ethyl}-8-azabicyclo[3.2.1]oct-3-yl)-2-methyl-1H-benzimidazole as a foam (0.14 g, 65%). $^1$H NMR (400 MHz, CDCl$_3$) δ 7.65 (m, 1H), 7.28 (m, 2H), 7.16 (m, 2H), 6.86 (m, 2H), 6.76 (m, 1H), 4.63 (m, 1H), 4.04 (m, 2H), 3.94 (m, 2H), 3.29 (m, 4H), 2.59 (s, 3H), 2.40 (m, 2H), 2.19 (m, 2H), 1.66-1.95 (m, 12H), 1.43 (t, 3H), 1.26 (s, 9H). HRMS C$_{35}$H$_{48}$N$_4$O$_2$ m/z 557.3856 (M+H)$_{Cal.}$, 557.3840 (M+H)$_{Obs.}$.

Example 667

2-Chloro-5-[(4-(3-ethoxyphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

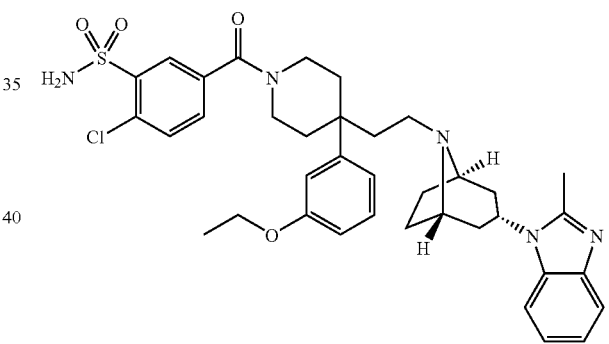

A mixture of 1-(8-{2-[4-(3-ethoxyphenyl) piperidin-4-yl]ethyl}-8-azabicyclo[3.2.1]oct-3-yl)-2-methyl-1H-benzimidazole dihydrochloride (0.40 g, 0.78 mmol), triethylamine (0.35 mL, 2.5 mmol) and 4-chloro-3-sulfamoylbenzoic acid (184 mg, 0.78 mmol) in dimethylformamide (2.5 mL) was treated with O-(7-azabenzotriazol-1-yl)-1,1,3,3-tetramethyluronium hexafluorophosphate (327 mg, 0.86 mmol) and the resulting mixture was stirred for 1 h at rt. The mixture was diluted with water and the resulting precipitate was collected, washed with saturated sodium bicarbonate solution and water, dried and purified by chromatography on silica gel eluting with a chloroform:methanol:ammonium hydroxide 400:15:1 to 200:15:1 gradient to give 2-chloro-5-[(4-(3-ethoxy phenyl)-4-{2-[(1R,5S)-3-(2-methyl-1H-benzimidazol-1-yl)-8-azabicyclo[3.2.1]oct-8-yl]ethyl}piperidin-1-yl) carbonyl]benzenesulfonamide as a solid (0.34 g, 62%). $^1$H NMR (400 MHz, CD$_3$OD) δ 8.08 (s, 1H), 7.67 (m, 1H), 7.59 (m, 1H), 7.51 (m, 1H), 7.41 (m, 1H), 7.29 (m, 1H), 7.17 (m, 2H), 6.93-6.98 (m, 2H), 6.81 (m, 1H), 4.74 (m, 1H), 4.17 (m, 1H), 4.04 (m, 2H), 3.54 (m, 1H), 3.30 (m, 4H), 2.52 (s, 3H), 2.40-2.48 (m, 4H), 2.27 (m, 1H), 2.14 (m, 1H), 1.83-2.04 (m, 10H), 1.70 (m, 2H), 1.40 (t, 3H). HRMS C$_{37}$H$_{44}$ClN$_5$O$_4$S m/z 690.2881 (M+H)$_{Cal.}$, 690.2901 (M+H)$_{Obs.}$.

Example 668

3-(1-(2,2-Dimethylpropanoyl)-4-{2-[(1R,5S)-3-(2-methyl-1H-benzimidazol-1-yl)-8-azabicyclo[3.2.1]oct-8-yl]ethyl}piperidin-4-yl)phenol

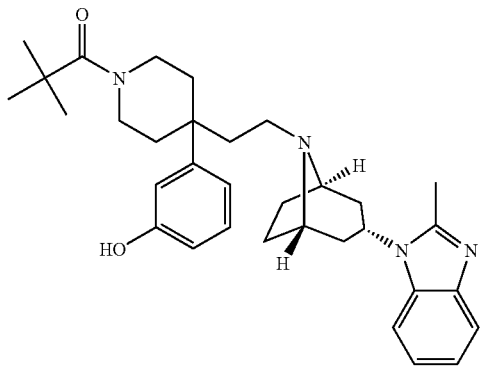

tert-Butyl 4-(cyanomethyl)-4-(3-methoxyphenyl)piperidine-1-carboxylate was prepared using the same procedures used in Example 16a-d using 1-bromo-3-methoxybenzene in the place of 1-chloro-3-iodobenzene in Example 16b.

tert-Butyl 4-(3-methoxyphenyl)-4-(2-oxoethyl)piperidine-1-carboxylate. Using the same procedure as in Example 16e tert-butyl 4-(cyanomethyl)-4-(3-methoxyphenyl)piperidine-1-carboxylate (1.2 g, 3.8 mmol) gave tert-butyl 4-(3-methoxyphenyl)-4-(2-oxoethyl)piperidine-1-carboxylate as a foam (0.9 g, 69%). $^1$H NMR (400 MHz, CDCl$_3$) δ 9.38 (t, 1H), 7.30 (m, 1H), 6.88-6.95 (m, 2H), 6.78 (m, 1H), 3.80 (s, 3H), 3.60 (m, 2H), 3.21-3.27 (m, 2H), 2.61 (s, 2H), 2.21 (m, 2H), 1.83 (m, 2H), 1.43 (s, 9H).

tert-Butyl 4-(3-methoxyphenyl)-4-{2-[3-(2-methyl-1H-benzimidazol-1-yl)-8-azabicyclo[3.2.1]oct-8-yl]ethyl}piperidine-1-carboxylate. Using the same procedure as in Example 16f tert-butyl 4-(3-methoxy phenyl)-4-(2-oxoethyl)piperidine-1-carboxylate (0.9 g, 2.5 mmol) gave tert-butyl 4-(3-methoxyphenyl)-4-{2-[3-(2-methyl-1H-benzimidazol-1-yl)-8-azabicyclo[3.2.1]oct-8-yl]ethyl}piperidine-1-carboxylate as a foam (1.2 g, 85%). $^1$H NMR (400 MHz, CDCl$_3$) δ 7.66 (m, 1H), 7.28 (m, 2H), 7.16 (m, 2H), 6.88 (m, 2H), 6.76 (m, 1H), 4.62 (m, 1H), 3.82 (s, 3H), 3.65 (m, 2H), 3.16-3.26 (m, 4H), 3.08 (m, 1H), 2.58 (s, 3H), 2.37 (m, 2H), 2.13 (m, 2H), 1.83-1.97 (m, 6H), 1.78 (m, 3H), 1.61 (m, 2H), 1.43 (s, 9H).

3-(4-{2-[3-(2-Methyl-1H-benzimidazol-1-yl)-8-azabicyclo[3.2.1]oct-8-yl]ethyl}piperidin-4-yl)phenol Hydrobromide. A mixture of tert-butyl 4-(3-methoxy phenyl)-4-{2-[3-(2-methyl-1H-benzimidazol-1-yl)-8-azabicyclo[3.2.1]oct-8-yl]ethyl}piperidine-1-carboxylate (235 mg, 0.42 mmol) and 48% hydrobromic acid was heated at 100° C. for 6 h. The mixture was concentrated and used without further purification.

3-(1-(2,2-Dimethylpropanoyl)-4-{2-[(1R,5S)-3-(2-methyl-1H-benzimidazol-1-yl)-8-azabicyclo[3.2.1]oct-8-yl]ethyl}piperidin-4-yl)phenol (example 668). A mixture of 3-(4-{2-[3-(2-methyl-1H-benzimidazol-1-yl)-8-azabicyclo[3.2.1]oct-8-yl]ethyl}piperidin-4-yl)phenol hydrobromide (0.22 g, 0.42 mmol), triethylamine (0.117 mL, 0.84 mmol) and trimethylacetyl chloride (0.057 mL, 0.462 mmol) in dichloromethane (2 mL) was stirred at rt for 3 h. The reaction mixture was diluted with dichloromethane, washed with saturated sodium bicarbonate solution, dried, concentrated and purified by chromatography on silica gel eluting with 33:1 dichloromethane:methanol to give 3-(1-(2,2-dimethyl propanoyl)-4-{2-[(1R,5S)-3-(2-methyl-1H-benzimidazol-1-yl)-8-azabicyclo[3.2.1]oct-8-yl]ethyl}piperidin-4-yl)phenol as a white solid (0.070 g, 32%). $^1$H NMR (400 MHz, DMSO-d$_6$) δ 9.25 (s, 1H), 7.47 (m, 1H), 7.34 (m, 1H), 7.05-7.15 (m, 3H), 6.77 (m, 1H), 6.73 (s, 1H), 6.59 (m, 1H), 4.51 (m, 1H), 3.74 (m, 2H), 3.24 (m, 4H), 2.47 (s, 3H), 2.36 (m, 2H), 1.97 (m, 2H), 1.86 (m, 4H), 1.75 (m, 6H), 1.58 (m, 2H), 1.15 (s, 9H). HRMS C$_{33}$H$_{44}$N$_4$O$_2$ m/z 529.3543 (M+H)$_{Cal.}$, 529-3542 (M+H)$_{Obs.}$.

Example 669

2-Chloro-5-[(4-(3-hydroxyphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

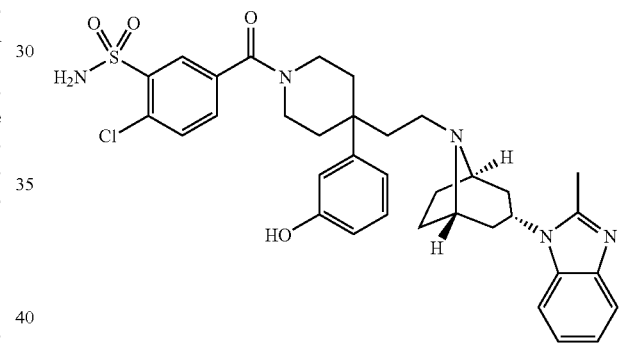

A mixture of 3-(4-{2-[3-(2-methyl-1H-benzimidazol-1-yl)-8-azabicyclo[3.2.1]oct-8-yl]ethyl}piperidin-4-yl)phenol hydrobromide (0.25 g, 0.48 mmol), triethylamine (0.212 mL, 1.5 mmol) and 4-chloro-3-sulfamoylbenzoic acid (0.113 g, 0.48 mmol) in dimethylformamide (1.5 mL) was treated with O-(7-azabenzotriazol-1-yl)-1,1,3,3-tetramethyluronium hexafluorophosphate (0.2 g, 0.53 mmol) and the resulting mixture was stirred for 1 h at rt. The mixture was diluted with water and the resulting precipitate was collected, washed with saturated sodium bicarbonate solution and water, dried and purified by column chromatography on silica gel eluting with 200:15:1 chloroform:methanol:ammonium hydroxide to give 2-chloro-5-[(4-(3-hydroxyphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide as a pink solid (0.022 g, 7%). $^1$H NMR (400 MHz, CD$_3$OD) δ 8.08 (s, 1H), 7.67 (m, 1H), 7.60 (m, 1H), 7.51 (m, 1H), 7.41 (m, 1H), 7.18 (m, 3H), 6.84 (m, 2H), 6.67 (m, 1H), 4.74 (m, 1H), 4.15 (m, 1H), 3.54 (m, 1H), 3.32 (m, 7H), 2.52 (s, 3H), 2.34-2.50 (m, 3H), 2.20-2.30 (m, 1H), 1.78-2.10 (m, 10H), 1.65-1.72 (m, 2H). HRMS C$_{35}$H$_{40}$ClN$_5$O$_4$S m/z 662.2568 (M+H)$_{Cal.}$, 662.2571 (M+H)$_{Obs.}$.

Example 670

1-((1R,5S)-8-{2-[4-(4-Chloro-3-fluorophenyl)-1-(2,2-dimethylpropanoyl)piperidin-4-yl]ethyl}-8-azabicyclo[3.2.1]oct-3-yl)-2-methyl-1H-benzimidazole

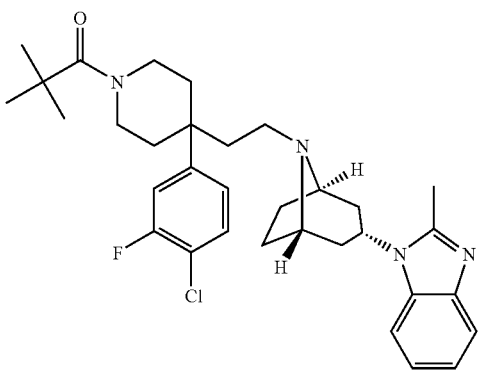

tert-Butyl 4-(4-chloro-3-fluorophenyl)-4-(1-cyano-2-ethoxy-2-oxoethyl)piperidine-1-carboxylate. Using the same procedure as in Example 16b 1-bromo-4-chloro-5-fluorobenzene (10.7 g, 51 mmol) was used in place of 1-chloro-3-iodobenzene to give tert-butyl 4-(4-chloro-3-fluorophenyl)-4-(1-cyano-2-ethoxy-2-oxoethyl)piperidine-1-carboxylate as an amber foam that was used without further purification.

[1-(tert-Butoxycarbonyl)-4-(4-chloro-3-fluorophenyl)piperidin-4-yl](cyano)acetic Acid. tert-Butyl-4-(4-chloro-3-fluorophenyl)-4-(1-cyano-2-ethoxy-2-oxoethyl)piperidine-1-carboxylate was hydrolysed using the same procedure as in Example 16c to give [1-(tert-butoxycarbonyl)-4-(4-chloro-3-fluorophenyl) piperidin-4-yl](cyano)acetic acid as an amber solid that was used without further purification.

tert-Butyl 4-(4-chloro-3-fluorophenyl)-4-(cyanomethyl)piperidine-1-carboxylate. [1-(tert-Butoxycarbonyl)-4-(4-chloro-3-fluorophenyl)piperidin-4-yl](cyano)acetic acid was subjected to the same decarboxylation conditions used in Example 16d and chromatographed on silica gel eluting with a gradient of ethyl acetate:hexane 1:20 to 1:1 to give tert-butyl 4-(4-chloro-3-fluorophenyl)-4-(cyanomethyl)piperidine-1-carboxylate as a solid (2.3 g, 38% overall). $^1$H NMR (400 MHz, CDCl$_3$) δ 7.44 (m, 1H), 7.09-7.16 (m, 2H), 3.69-3.75 (m, 2H), 3.09 (m, 2H), 2.54 (s, 2H), 2.20-2.25 (m, 2H), 1.85 (m, 2H), 1.43 (s, 9H). ES-LCMS m/z 253 (M−99).

tert-Butyl 4-(4-chloro-3-fluorophenyl)-4-(2-oxoethyl)piperidine-1-carboxylate. Using the same procedure as in Example 16e tert-butyl 4-(4-chloro-3-fluorophenyl)-4-(cyanomethyl)piperidine-1-carboxylate (2.3 g, 6.5 mmol) gave tert-butyl 4-(4-chloro-3-fluorophenyl)-4-(2-oxoethyl)piperidine-1-carboxylate as an amber foam (1.5 g, 65%). $^1$H NMR (400 MHz, CDCl$_3$) δ 9.43 (t, 1H), 7.40 (m, 1H), 7.07-7.16 (m, 2H), 3.57-3.63 (m, 2H), 3.22-3.29 (m, 2H), 2.66 (s, 2H), 2.11-2.17 (m, 2H), 1.86 (m, 2H), 1.43 (s, 9H). ES-LCMS m/z 354 (M−1).

tert-Butyl 4-(4-chloro-3-fluorophenyl)-4-{2-[3-(2-methyl-1H-benzimidazol-1-yl)-8-azabicyclo[3.2.1]oct-8-yl]ethyl}piperidine-1-carboxylate. Using the same procedure as in Example 16f tert-butyl 4-(4-chloro-3-fluorophenyl)-4-(2-oxoethyl)piperidine-1-carboxylate (1.5 g, 4.2 mmol) gave tert-butyl 4-(4-chloro-3-fluorophenyl)-4-{2-[3-(2-methyl-1H-benzimidazol-1-yl)-8-azabicyclo[3.2.1]oct-8-yl]ethyl}piperidine-1-carboxylate as a solid (1.4 g, 59%). $^1$H NMR (400 MHz, CDCl$_3$) δ 7.66 (m, 1H), 7.38 (m, 1H), 7.28 (m, 1H), 7.17 (m, 2H), 7.02-7.09 (m, 2H), 4.66 (m, 2H), 3.83 (m, 2H), 3.62 (m, 2H), 3.23 (m, 4H), 3.01 (m, 1H), 2.60 (s, 3H), 2.43 (m, 2H), 1.65-2.01 (m, 10H), 1.43 (s, 9H). ES-LCMS m/z 581 (M+1).

1-(8-{2-[4-(4-Chloro-3-fluorophenyl) piperidin-4-yl]ethyl}-8-azabicyclo[3.2.1]oct-3-yl)-2-methyl-1H-benzimidazole dihydrochloride. Using the same procedure as in Example 16g tert-butyl 4-(4-chloro-3-fluorophenyl)-4-{2-[3-(2-methyl-1H-benzimidazol-1-yl)-8-azabicyclo[3.2.1]oct-8-yl]ethyl}piperidine-1-carboxylate (1.4 g, 2.4 mmol) gave 1-(8-{2-[4-(4-chloro-3-fluorophenyl)piperidin-4-yl]ethyl}-8-azabicyclo[3.2.1]oct-3-yl)-2-methyl-1H-benzimidazole dihydrochloride as a solid (1.4 g, 93%). $^1$H NMR (400 MHz, DMSO-d$_6$) δ 11.22 (s, 1H), 9.03 (s, 2H), 7.88 (m, 1H), 7.80 (m, 1H), 7.46-7.62 (m, 4H), 7.26 (m, 1H), 6.03 (m, 1H), 4.08 (m, 2H), 3.23 (m, 2H), 3.11 (m, 1H), 2.87 (s, 3H), 2.75-2.90 (m, 4H), 2.30 (m, 2H), 2.10-2.25 (m, 8H), 2.08 (m, 2H). ES-LCMS m/z 481 (M+1).

1-((1R,5S)-8-{2-[4-(4-Chloro-3-fluorophenyl)-1-(2,2-dimethylpropanoyl)piperidin-4-yl]ethyl}-8-azabicyclo[3.2.1]oct-3-yl)-2-methyl-1H-benzimidazole (example 670). A mixture of 1-(8-{2-[4-(4-chloro-3-fluorophenyl)piperidin-4-yl]ethyl}-8-azabicyclo[3.2.1]oct-3-yl)-2-methyl-1H-benzimidazole dihydrochloride (0.20 g, 0.39 mmol), triethylamine (0.11 mL, 0.78 mmol) and trimethylacetyl chloride (0.053 mL, 0.43 mmol) in dichloromethane (4 mL) was stirred at rt for 1 h before the reaction mixture was quenched with saturated sodium bicarbonate solution. The organic layer was separated, dried, concentrated and purified by chromatography on silica gel eluting with a dichloromethane to 1:9 methanol:dichloromethane gradient to give 1-((1R,5S)-8-{2-[4-(4-chloro-3-fluorophenyl)-1-(2,2-dimethylpropanoyl)piperidin-4-yl]ethyl}-8-azabicyclo[3.2.1]oct-3-yl)-2-methyl-1H-benzimidazole as a white foam (0.11 g, 51%). $^1$H NMR (400 MHz, CDCl$_3$) δ 7.67 (m, 1H), 7.40 (m, 1H), 7.29 (m, 1H), 7.03-7.19 (m, 4H), 4.72 (m, 1H), 3.90 (m, 2H), 3.33 (m, 4H), 2.59 (s, 3H), 2.42 (m, 2H), 1.78-2.13 (m, 14H), 1.27 (s, 9H). HRMS C$_{33}$H$_{42}$ClFN$_4$O m/z 565.3109 (M+H)$_{Cal}$, 565.3134 (M+H)$_{Obs}$.

Example 671

2-Chloro-5-[(4-(4-chloro-3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzene sulfonamide

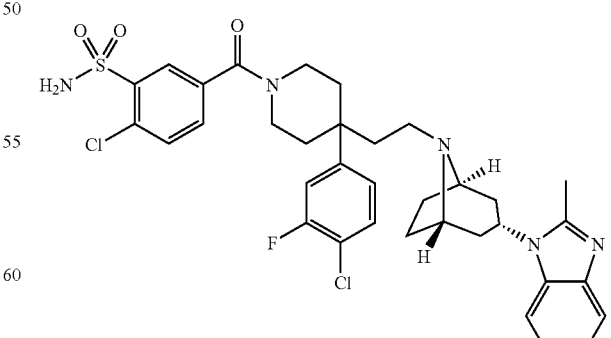

A mixture of 1-(8-{2-[4-(4-chloro-3-fluoro phenyl)piperidin-4-yl]ethyl}-8-azabicyclo[3.2.1]oct-3-yl)-2-methyl-1H-benzimidazole dihydrochloride (0.40 g, 0.78 mmol), triethylamine (0.35 mL, 2.5 mmol) and 4-chloro-3-sulfamoylbenzoic acid (184 mg, 0.78 mmol) in dimethylformamide (2.5 mL) was treated with O-(7-azabenzotriazol-1-yl)-1,1,3,3-tetramethyluronium hexafluorophosphate (327 mg, 0.86 mmol) and the resulting mixture was stirred for 1 h at rt. The mixture was diluted with water and the resulting precipitate was collected, washed with saturated sodium bicarbonate solution, with water, dried and purified by chromatography on silica gel eluting with a 400:15:1 to 200:15:1 gradient of chloroform:methanol:ammonium hydroxide to give 2-chloro-5-[(4-(4-chloro-3-fluoro phenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide as a solid (0.24 g, 43%). $^1$H NMR (400 MHz, CD$_3$OD) δ 8.09 (s, 1H), 7.68 (m, 1H), 7.61 (m, 1H), 7.34-7.54 (m, 4H), 7.17-7.26 (m, 3H), 4.73 (m, 1H), 4.09 (m, 1H), 3.59 (m, 1H), 3.43 (m, 1H), 3.30 (m, 3H), 2.53 (s, 3H), 2.40-2.48 (m, 4H), 2.28 (m, 1H), 2.16 (m, 1H), 1.83-2.04 (m, 10H), 1.70 (m, 2H). HRMS C$_{35}$H$_{38}$Cl$_2$FN$_5$O$_3$S m/z 698.2135 (M+H)$_{Cal.}$, 698.2142 (M+H)$_{Obs.}$.

Example 672

2-Methyl-1-((1R,5S)-8-{2-[4-phenyl-1-(tetrahydrofuran-2-ylcarbonyl)piperidin-4-yl]ethyl}-8-azabicyclo[3.2.1]oct-3-yl)-1H-benzimidazole

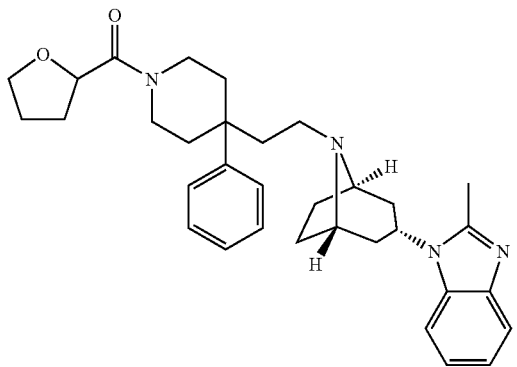

A mixture of 2-methyl-1-{8-[2-(4-phenylpiperidin-4-yl)ethyl]-8-azabicyclo[3.2.1]oct-3-yl}-}-1H-benzimidazole dihydrochloride (75 mg, 0.16 mmol), tetrahydro-2-furoic acid (18 mg, 0.16 mmol) and triethylamine (48 mg, 0.48 mmol) in dimethylformamide (0.5 mL) was treated with O-(7-azabenzotriazol-1-yl)-1,1,3,3-tetramethyluronium hexafluorophosphate (68 mg, 0.18 mmol) and the resulting mixture was stirred at rt for 1 h. The reaction mixture was diluted with water and the resulting precipitate was collected, washed with water and dried. The precipitate was triturated with a mixture of dichloromethane, methanol and hexane to give 2-methyl-1-((1R,5S)-8-{2-[4-phenyl-1-(tetrahydrofuran-2-ylcarbonyl)piperidin-4-yl]ethyl}-8-azabicyclo[3.2.1]oct-3-yl)-1H-benzimidazole as an off-white solid (0.017 g, 20%). $^1$H NMR (400 MHz, DMSO-d$_6$) δ 7.61-7.66 (m, 2H), 7.41 (m, 5H), 7.27-7.35 (m, 2H), 4.94 (m, 1H), 4.64 (m, 1H), 4.03 (m, 2H), 3.68-3.77 (m, 5H), 2.98-3.25 (m, 2H), 2.62-2.70 (m, 7H), 2.09-2.24 (m, 7H), 1.88-2.06 (m, 4H), 1.68-1.84 (m, 4H). HRMS C$_{33}$H$_{42}$N$_4$O$_2$ m/z 527.3386 (M+H)$_{Cal.}$, 527.3380 (M+H)$_{Obs.}$.

Example 673

2-Methyl-1-((1R,5S)-8-{2-[4-phenyl-1-(tetrahydrofuran-3-ylcarbonyl)piperidin-4-yl]ethyl}-8-azabicyclo[3.2.1]oct-3-yl)-1H-benzimidazole

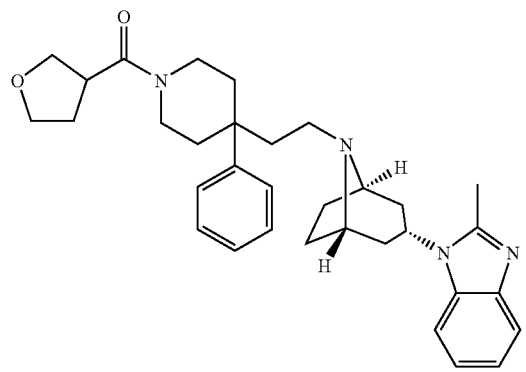

A mixture of 2-methyl-1-{8-[2-(4-phenyl piperidin-4-yl)ethyl]-8-azabicyclo[3.2.1]oct-3-yl}-1H-benzimidazole dihydrochloride (75 mg, 0.16 mmol), tetrahydro-3-furoic acid (18 mg, 0.16 mmol) and triethylamine (48 mg, 0.48 mmol) in dimethylformamide (0.5 mL) was treated with O-(7-azabenzotriazol-1-yl)-1,1,3,3-tetramethyluronium hexafluorophosphate (68 mg, 0.18 mmol) and the resulting mixture was stirred at rt for 1 h. The reaction mixture was diluted with water and extracted with dichloromethane. The residue from the dichloromethane layer was purified by chromatography on silica gel eluting with 1:20 methanol:dichloromethane to give 2-methyl-1-((1R,5S)-8-{2-[4-phenyl-1-(tetrahydrofuran-3-ylcarbonyl)piperidin-4-yl]ethyl}-8-azabicyclo[3.2.1]oct-3-yl)-1H-benzimidazole as a clear oil (0.019 g, 23%). $^1$H NMR (400 MHz, DMSO-d$_6$) δ 7.46 (m, 1H), 7.36 (m, 5H), 7.21 (m, 1H), 7.09 (m, 2H), 4.49 (m, 1H), 3.58-3.87 (m, 7H), 3.12-3.35 (m, 6H), 2.28-2.39 (m, 2H), 1.89-2.12 (m, 5H), 1.58-1.86 (m, 10H), 1.53-1.60 (m, 2H). HRMS C$_{33}$H$_{42}$N$_4$O$_2$ m/z 527.3386 (M+H)$_{Cal.}$, 527.3397 (M+H)$_{Obs.}$.

Example 674

1-((1R,5S)-8-{2-[1-(1-Benzofuran-2-ylcarbonyl)-4-phenylpiperidin-4-yl]ethyl}-8-azabicyclo[3.2.1]oct-3-yl)-2-methyl-1H-benzimidazole

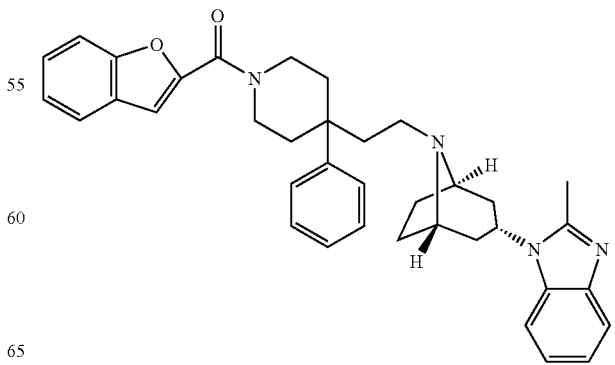

A mixture of 2-methyl-1-{8-[2-(4-phenyl piperidin-4-yl)ethyl]-8-azabicyclo[3.2.1]oct-3-yl}-1H-benzimidazole dihydrochloride (100 mg, 0.22 mmol), 2-benzofurancarboxylic acid (36 mg, 0.22 mmol) and triethylamine (66 mg, 0.66 mmol) in dimethylformamide (0.75 mL) was treated with O-(7-azabenzotriazol-1-yl)-1,1,3,3-tetramethyluronium hexafluorophosphate (92 mg, 0.24 mmol) and the resulting mixture was stirred at rt for 1 h. The reaction mixture was diluted with water and the resulting precipitate was collected, washed with water and dried. The precipitate was purified by chromatography on silica gel eluting with 1:20 methanol:dichloromethane to give 1-((1R,5S)-8-{2-[1-(1-benzofuran-2-ylcarbonyl)-4-phenylpiperidin-4-yl]ethyl}-8-azabicyclo[3.2.1]oct-3-yl)-2-methyl-1H-benzimidazole as a clear oil (0.075 g, 60%). $^1$H NMR (400 MHz, CDCl$_3$) δ 7.66 (m, 2H), 7.52 (m, 1H), 7.26-7.44 (m, 9H), 7.16 (m, 2H), 4.61 (m, 1H), 4.16 (m, 2H), 3.40-3.57 (m, 2H), 3.26 (m, 1H), 2.57 (m, 3H), 2.34 (m, 4H), 1.94 (m, 9H), 1.62 (m, 4H). HRMS C$_{37}$H$_{40}$N$_4$O$_2$ m/z 573.3229 (M+H)$_{Cal.}$, 573.3238 (M+H)$_{Obs.}$.

Example 675

(3R,3aS,6aR)-Hexahydrofuro[2,3-b]furan-3-yl 4-{2-[(1R,5S)-3-(2-methyl-1H-benzimidazol-1-yl)-8-azabicyclo[3.2.1]oct-8-yl]ethyl}-4-phenylpiperidine-1-carboxylate

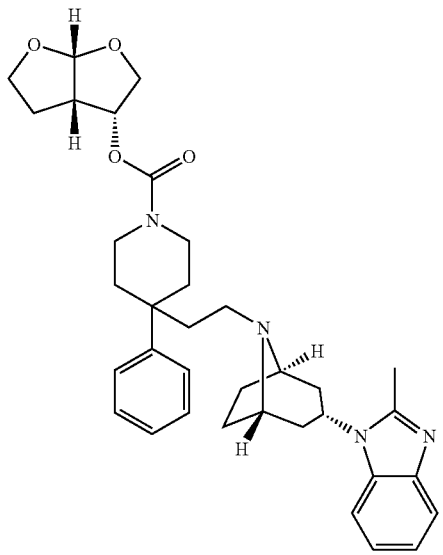

A mixture of 2-methyl-1-{8-[2-(4-phenyl piperidin-4-yl)ethyl]-8-azabicyclo[3.2.1]oct-3-yl}-1H-benzimidazole dihydrochloride (100 mg, 0.22 mmol), (3R,3aS,6aR)hexahydrofuro[2,3-b]furan-3-yl 4-nitrophenyl carbonate (78 mg, 0.26 mmol) and N,N-diisopropylethylamine (0.15 mL, 0.88 mmol) in acetonitrile (3 mL) was stirred at rt for 16 h. The reaction mixture was concentrated and the residue in dichloromethane was washed with saturated sodium carbonate solution, dried, concentrated and chromatographed on silica gel eluting with 1:40 methanol:dichloromethane to give (3R,3aS,6aR)-hexahydrofuro[2,3-b]furan-3-yl 4-{2-[(1R,5S)-3-(2-methyl-1H-benzimidazol-1-yl)-8-azabicyclo[3.2.1]oct-8-yl]ethyl}-4-phenylpiperidine-1-carboxylate as a clear glass (0.064 g, 50%). $^1$H NMR (400 MHz, CDCl$_3$) δ 7.38 (m, 2H), 7.29 (m, 5H), 7.16 (m, 2H), 5.71 (m, 1H), 5.18 (m, 1H), 4.59 (m, 1H), 3.75-4.04 (m, 7H), 3.22 (m, 3H), 3.05 (m, 1H), 2.58 (m, 3H), 2.19-2.36 (m, 4H), 1.80-1.92 (m, 9H), 1.61 (m, 5H). HRMS C$_{35}$H$_{44}$N$_4$O$_4$ m/z 585.3441 (M+H)$_{Cal.}$, 585.3440 (M+H)$_{Obs.}$.

Example 676

2-[(4-{2-[3-(2-Methyl-1H-benzimidazol-1-yl)-8-azabicyclo[3.2.1]oct-8-yl]ethyl}-4-phenylpiperidin-1-yl)carbonyl]benzenesulfonamide

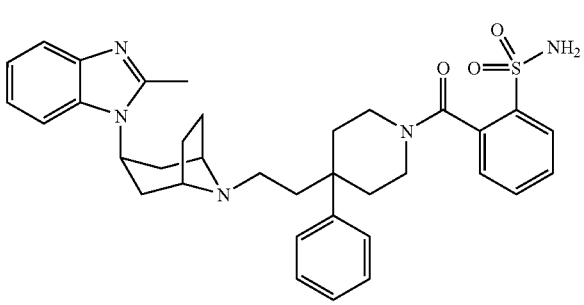

Example 676 was prepared as outlined below.

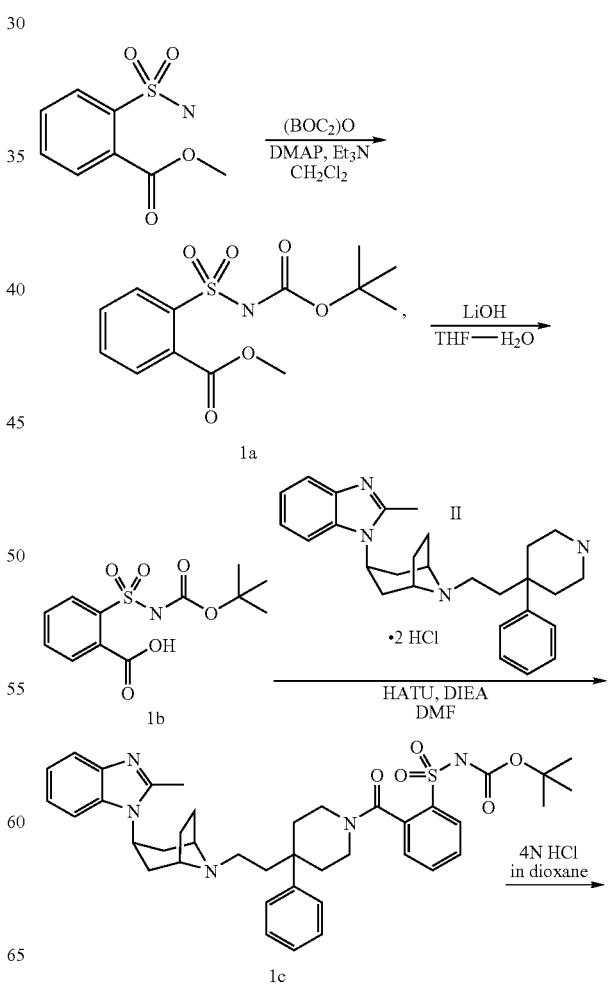

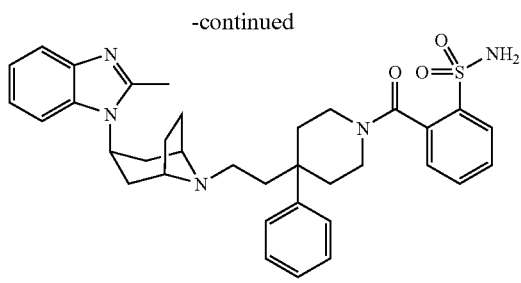

example 676

Methyl 2-{[(tert-butoxycarbonyl)amino]sulfonyl}benzoate 1a. A mixture of methyl 2-(aminosulfonyl)benzoate (500 mg, 2.3 mmol, 1 eq.), triethylamine (320 µL, 2.3 mmol, 1 eq.), 4-(dimethylamino)pyridine (281 mg, 2.3 mmol, 1 eq.) and di(tert-butyl) dicarbonate (1.0 g, 4.6 mmol, 2 eq.) in dichloromethane (20 mL) was stirred at RT for 2 h. The reaction was concentrated and the residue partitioned between dichloromethane and saturated ammonia chloride. The organic layer was dried and concentrated, and the residue purified by column chromatography on silica gel eluting with 1:1 hexane:ethyl acetate to afford methyl 2-{[(tert-butoxycarbonyl)amino]sulfonyl}benzoate (1a) as a white solid (326 mg, 45% yield). $^1$H NMR (300 MHz, DMSO) δ 11.71 (s, 1H), 8.00 (m, 1H), 7.75 (m, 2H), 7.67 (m, 1H), 3.83 (s, 3H), 1.27 (s, 9H). ES-LCMS m/z 314.16 (M−H).

2-{[(tert-butoxycarbonyl)amino]sulfonyl}benzoic acid 1b. A mixture of methyl 2-{[(tert-butoxycarbonyl)amino]sulfonyl}benzoate 1a (400 mg, 1.3 mmol, 1 equiv) and lithium hydroxide (1.6 g, 39 mmol, 30 equiv) in tetrahydrofuran (10 mL) and water (2.5 mL) was stirred at RT for 18 h. The reaction was partially concentrated, acidified with 1N HCl and the product extracted into ethyl acetate. The organic layer was dried and concentrated to afford 2-{[(tert-butoxycarbonyl)amino]sulfonyl}benzoic acid (1b) as a white solid (200 mg, 51% yield). $^1$H NMR (300 MHz, DMSO) δ 7.94 (m, 1H), 7.71 (m, 3H), 1.26 (s, 9H). ES-LCMS m/z 300.08 (M−H).

tert-Butyl {2-[(4-{2-[3-(2-methyl-1H-benzimidazol-1-yl)-8-azabicyclo[3.2.1]oct-8-yl]ethyl}-4-phenylpiperidin-1-yl)carbonyl]phenyl}sulfonyl carbamate, 1c. To a solution of endo 2-methyl-1-{8-[2-(4-phenylpiperidin-4-yl)ethyl]-8-azabicyclo[3.2.1]oct-3-yl}-1H-benzimidazole dihydrochloride II (238 mg, 0.47 mmol, 1 eq.) in dimethylformamide (14 mL) was added 2-{[(tert-butoxycarbonyl)amino]sulfonyl}benzoic acid 1b (140 mg, 0.47 mmol, 1 eq.) and N,N-diisopropylethyl amine (0.3 mL, 1.41 mmol, 3 eq.). After stirring at RT for several minutes, O-(7-azabenzotriazol-1-yl)-N,N,N',N'-tetramethyluroniumhexafluorophosphate (179 mg, 1.41 mmol, 1 eq.) was added and the reaction was stirred for 2 h. The mixture was partitioned between dichloromethane and water. The organic layer was dried and concentrated to provide crude tert-butyl {2-[(4-{2-[3-(2-methyl-1H-benzimidazol-1-yl)-8-azabicyclo[3.2.1]oct-8-yl]ethyl}-4-phenylpiperidin-1-yl)carbonyl]phenyl}sulfonylcarbamate 1c. The crude product was used without further purification.

2-[(4-{2-[3-(2-Methyl-1H-benzimidazol-1-yl)-8-azabicyclo[3.2.1]oct-8-yl]ethyl}-4-phenylpiperidin-1-yl)carbonyl]benzenesulfonamide (example 676). A mixture of crude tert-butyl {2-[(4-{2-[3-(2-methyl-1H-benzimidazol-1-yl)-8-azabicyclo[3.2.1]oct-8-yl]ethyl}-4-phenylpiperidin-1-yl)carbonyl]phenyl}sulfonyl carbamate 1c and 4N HCl in dioxane (3 mL) was stirred at RT for 2 h. The reaction mixture was partitioned between dichloromethane and saturated aqueous sodium bicarbonate. The organic layer was dried and concentrated and the residue was purified by prep. HPLC (Method Y) to provide 2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide 1 as a white solid (45 mg, 16% yield). $^1$H NMR (300 MHz, DMSO) δ 8.05 (m, 1H), 7.63 (m, 3H), 7.39-7.15 (m, 9H), 5.61 (m, 2H), 4.60 (m, 1H), 4.38 (m, 1H), 3.43-3.04 (m, 5H), 2.54 (s, 3H), 2.35-2.17 (m, 4H), 2.13-1.40 (m, 12H). ES-LCMS m/z 612.25 (M+H). Analytical HPLC (Method W) Rt 7.59 (95.89%).

Example 677

4-Chloro-N-methyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide

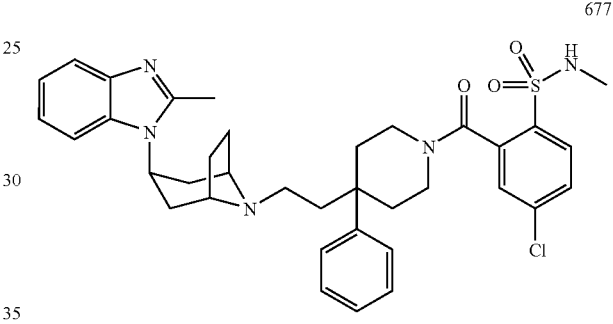

Example 677 was prepared as outlined below.

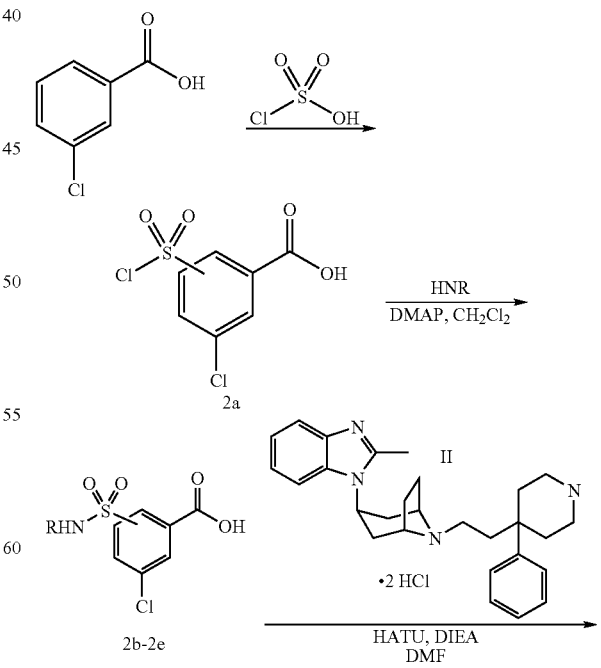

R = methyl, cyclopropyl, isopropyl, propyl

-continued

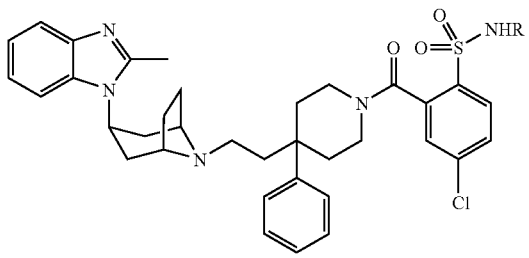

example 677: R = methyl; GW 854583X
example 678: R = cyclopropyl; GW 854584X
example 679: R = isopropyl; GW 854585X
example 680: R = propyl; GW 854586X A Mixture of 3-chloro-4-(chlorosulfonyl) benzoic acid and 5-chloro-2-(chlorosulfonyl)benzoic acid, 2a

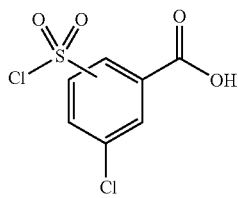

2a

3-Chlorobenzoic acid (7.0 g, 44.7 mmol, 1 equiv) was added at 0° C. to chlorosulfonic acid (40 mL). The reaction mixture was heated to 120° C. for 72 h, cooled to RT and poured slowly over ice. The product was extracted into diethyl ether, dried and concentrated to provide a 4:1 mixture of regioisomers, 5-chloro-4-(chlorosulfonyl)benzoic acid and 3-chloro-2-(chlorosulfonyl)benzoic acid 2a as a brown solid (5.26 g, 46% yield). $^1$H NMR (300 MHz, DMSO) δ 8.07 (m, 1H), 7.96 (m, 1H), 7.79 (m, 3H), 7.59 (m, 1H). ES-LCMS m/z 234.85 (M−2H) for $C_7H_5ClO_5S$.

A Mixture of 5-chloro-2-[(methylamino) sulfonyl]benzoic acid and 3-chloro-4-[(methylamino) sulfonyl]benzoic acid, 2b

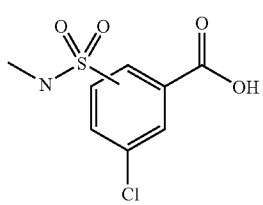

2b

To a solution of 3-chloro-4-(chlorosulfonyl)benzoic acid and 5-chloro-2-(chlorosulfonyl)benzoic acid 2a (0.5 g, 1.96 mmol, 1 eq.) in dichloromethane (10 mL) was added 4-(dimethylamino)pyridine (24 mg, 0.196 mmol, 0.1 eq.) and 2M methyl amine in THF (2.94 mL, 5.88 mmol, 3 eq.). The reaction mixture was stirred at RT for 18 h then concentrated to dryness. The residue was acidified with 1N HCl and the product was extracted into dichloromethane. The organic layer was concentrated, the residue taken up in water and acidified with 1N HCl. The product was extracted into dichloromethane, dried and concentrated to provide a crude mixture of 5-chloro-2-[(methylamino)sulfonyl]benzoic acid and 3-chloro-4-[(methylamino)sulfonyl]benzoic acid 2b. The residue was carried on without further purification. ES-LCMS m/z 248.01 (M−H).

4-Chloro-N-methyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide (example 677). The title compound was prepared from a mixture of 5-chloro-2-[(methylamino)sulfonyl]benzoic acid and 3-chloro-4-[(methylamino)sulfonyl]benzoic acid 2b and endo 2-methyl-1-{8-[2-(4-phenylpiperidin-4-yl)ethyl]-8-azabicyclo[3.2.1]oct-3-yl}-1H-benzimidazole dihydrochloride II following the general procedure for tert-butyl {2-[(4-{2-[3-(2-methyl-1H-benzimidazol-1-yl)-8-azabicyclo[3.2.1]oct-8-yl]ethyl}-4-phenyl piperidin-1-yl)carbonyl]phenyl}sulfonylcarbamate 1c. The desired regioisomer was purified by column chromatography on silica gel eluting with 10% methanol in ethyl acetate to afford 4-chloro-N-methyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzene sulfonamide 2 as a white solid (15 mg, 8% yield). $^1$H NMR (400 MHz, CDCl$_3$) δ 8.12 (d, 1H, J=7.9 Hz), 7.65 (m, 1H), 7.53 (m, 1H), 7.39 (m, 3H), 7.27 (m, 4H), 7.19-7.12 (m, 2H), 5.12 (q, 1H, J=5.2 Hz), 4.60 (m, 1H), 4.20 (m, 1H), 3.48-3.20 (m, 5H), 2.64 (d, 3H, J=5.3 Hz), 2.56 (s, 3H), 2.40-2.33 (m, 3H), 2.18 (m, 1H), 1.93-1.62 (m, 12H). ES-LCMS m/z 662.30 (M+2H). Analytical HPLC (Method Y) Rt 4.16 (90.0%).

Example 678

4-Chloro-N-cyclopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide

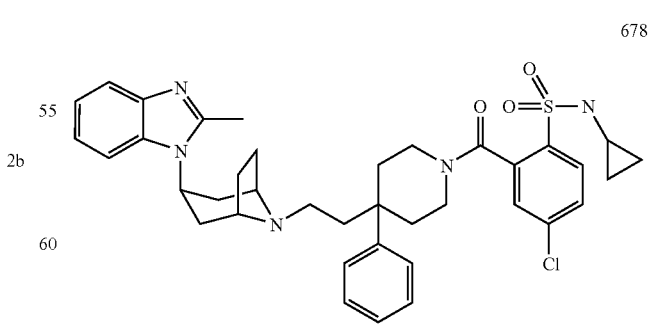

678

503

A Mixture of 5-chloro-2-[(cyclopropylamino)
sulfonyl]benzoic acid and 3-chloro-4-[(cyclopropyl
amino)sulfonyl]benzoic acid, 2c

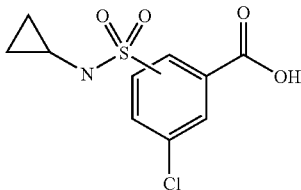

The mixture was prepared from a mixture of 3-chloro-4-(chlorosulfonyl)benzoic acid and 5-chloro-2-(chloro sulfonyl)benzoic acid 2a and cyclopropyl amine following the general procedure for 5-chloro-2-[(methyl amino)sulfonyl] benzoic acid and 3-chloro-4-[(methyl amino)sulfonyl]benzoic acid 2b. The crude reaction mixture was carried on without further purification.

ES-LCMS m/z 274 (M–H).

4-Chloro-N-cyclopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzene sulfonamide (example 678). The title compound was prepared from a mixture of 5-chloro-2-[(cyclopropyl amino)sulfonyl]benzoic acid and 3-chloro-4-[(cyclo propylamino)sulfonyl]benzoic acid 2c and endo 2-methyl-1-{8-[2-(4-phenylpiperidin-4-yl)ethyl]-8-azabicyclo[3.2.1]oct-3-yl}-1H-benzimidazole dihydrochloride II following the general procedure for tert-butyl {2-[(4-{2-[3-(2-methyl-1H-benzimidazol-1-yl)-8-azabicyclo[3.2.1]oct-8-yl]ethyl}-4-phenyl piperidin-1-yl)carbonyl]phenyl}sulfonylcarbamate 1c. The desired regioisomer was purified by column chromatography on silica gel eluting with 10% methanol in ethyl acetate to afford 4-chloro-N-cyclopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzene sulfonamide 3 as a white solid (15 mg, 11% yield). $^1$H NMR (400 MHz, CDCl$_3$) δ 8.18 (d, 1H, J=8.1 Hz), 7.65 (m, 1H), 7.54 (m, 1H), 7.41-7.12 (m, 9H), 5.48 (s, 1H), 4.60 (m, 1H), 4.20 (m, 1H), 3.45-3.23 (m, 6H), 2.56 (s, 3H), 2.40-2.33 (m, 3H), 2.20-2.17 (m, 1H), 1.97-1.58 (m, 10H), 0.70-0.56 (m, 4H). ES-LCMS m/z 688.35 (M+2H). Analytical HPLC (Method Y) Rt 3.34 (89.34%).

Example 679

4-Chloro-N-isopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide

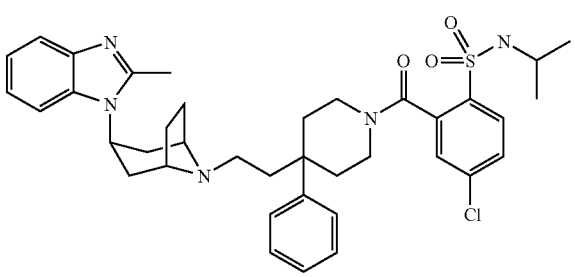

504

A Mixture of 5-chloro-2-[(isopropylamino)
sulfonyl]benzoic acid and 3-chloro-4-[(isopropyl
amino)sulfonyl]benzoic acid, 2d

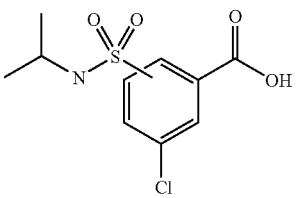

The mixture was prepared from a mixture of 3-chloro-4-(chlorosulfonyl)benzoic acid and 5-chloro-2-(chloro sulfonyl)benzoic acid 2a and isopropyl amine following the general procedure for 5-chloro-2-[(methylamino) sulfonyl] benzoic acid and 3-chloro-4-[(methylamino) sulfonyl] benzoic acid 2b. The crude reaction mixture was carried on without further purification. ES-LCMS m/z 276 (M–H).

4-Chloro-N-isopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzene sulfonamide (example 679). The title compound was prepared from a mixture of 5-chloro-2-[(isopropylamino) sulfonyl]benzoic acid and 3-chloro-4-[(isopropyl amino)sulfonyl]benzoic acid 2d and endo 2-methyl-1-{8-[2-(4-phenylpiperidin-4-yl)ethyl]-8-azabicyclo[3.2.1]oct-3-yl}-1H-benzimidazole dihydrochloride II following the general procedure for tert-butyl {2-[(4-{2-[3-(2-methyl-1H-benzimidazol-1-yl)-8-azabicyclo[3.2.1]oct-8-yl]ethyl}-4-phenyl piperidin-1-yl)carbonyl]phenyl}sulfonylcarbamate 1c. The desired regioisomer was purified by column chromatography on silica gel eluting with 10% methanol in ethyl acetate to afford 4-chloro-N-isopropyl-2-[(4-{2-[3-(2-methyl-1H-benzimidazol-1-yl)-8-azabicyclo[3.2.1]oct-8-yl]ethyl}-4-phenyl piperidin-1-yl)carbonyl]benzenesulfonamide 4 as a white solid (30 mg, 22% yield). $^1$H NMR (400 MHz, CDCl$_3$) δ 8.13 (d, 1H, J=8.0 Hz), 7.65 (d, 1H, J=7.3 Hz), 7.52 (m, 1H), 7.40-7.11 (m, 9H), 4.99 (d, 1H, J=7.32 Hz), 4.60 (m, 1H), 4.20 (m, 1H), 3.49-3.22 (m, 6H), 2.56 (s, 3H), 2.40-2.32 (m, 3H), 2.18 (m, 1H), 1.98-1.66 (m, 1H), 1.62 (m, 2H), 1.10 (d, 6H, J=6.59 Hz). ES-LCMS m/z 690.45 (M+2H). Analytical HPLC (Method Y) Rt 5.03 (88.43%).

Example 680

4-Chloro-2-[(4-{2-[3-(2-methyl-1H-benzimidazol-1-yl)-8-azabicyclo[3.2.1]oct-8-yl]ethyl}-4-phenylpiperidin-1-yl)carbonyl]-N-propylbenzenesulfonamide

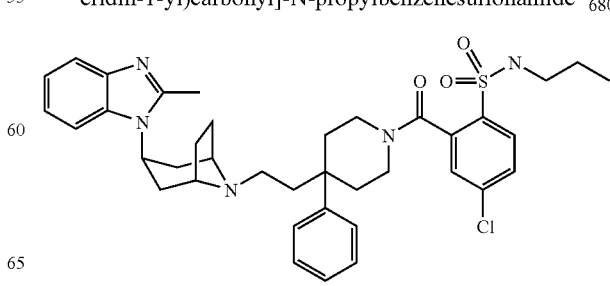

A mixture of 5-chloro-2-[(propylamino) sulfonyl]benzoic acid and 3-chloro-4-[(propylamino) sulfonyl]benzoic acid, 2e

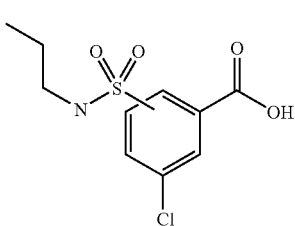

The mixture was prepared from a mixture of 3-chloro-4-(chlorosulfonyl)benzoic acid and 5-chloro-2-(chloro sulfonyl)benzoic acid 2a and propyl amine following the general procedure for 5-chloro-2-[(methylamino) sulfonyl]benzoic acid and 3-chloro-4-[(methylamino) sulfonyl]benzoic acid 2b. The crude reaction mixture was carried on without further purification. ES-LCMS m/z 276 (M–H).

4-Chloro-2-[(4-{2-[3-(2-methyl-1H-benzimidazol-1-yl)-8-azabicyclo[3.2.1]oct-8-yl]ethyl}-4-phenylpiperidin-1-yl) carbonyl]-N-propylbenzene sulfonamide (example 680). The title compound was prepared from a mixture of 5-chloro-2-[(propylamino) sulfonyl]benzoic acid and 3-chloro-4-[(propylamino) sulfonyl]benzoic acid 2e and endo 2-methyl-1-(8-[2-(4-phenylpiperidin-4-yl)ethyl]-8-azabicyclo[3.2.1]oct-3-yl)-1H-benzimidazole dihydrochloride II following the general procedure for tert-butyl {2-[(4-{2-[3-(2-methyl-1H-benzimidazol-1-yl)-8-azabicyclo[3.2.1]oct-8-yl]ethyl}-4-phenylpiperidin-1-yl)carbonyl]phenyl}sulfonylcarbamate 1c. The desired regioisomer was purified by column chromatography on silica gel eluting with 10% methanol in ethyl acetate to afford 4-chloro-2-[(4-{2-[3-(2-methyl-1H-benzimidazol-1-yl)-8-aza bicyclo[3.2.1]oct-8-yl]ethyl}-4-phenylpiperidin-1-yl)carbonyl]-N-propylbenzenesulfonamide 5 as a white solid (15 mg, 11% yield). $^1$H NMR (400 MHz, CDCl$_3$) δ (8.12, 1H, J=8.0 Hz), 7.65 (m, 1H), 7.52 (m, 1H), 7.41-7.12 (m, 9H), 5.10 (t, 1H, J=6.0 Hz), 4.59 (m, 1H), 4.20 (m, 1H), 3.48-3.19 (m, 6H), 2.89 (q, 1H, J=6.6 Hz), 2.56 (s, 3H), 2.55-2.32 (m, 3H), 2.17 (m, 1H), 1.93-1.64 (m, 10H), 1.61 (m, 1H), 1.50 (m, 2H), 0.882 (t, 3H, J=7.3 Hz). ES-LCMS m/z 690.33 (M+2H). Analytical HPLC (Method Y) Rt 5.39 (93.34%).

Example 681

4-Fluoro-2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide

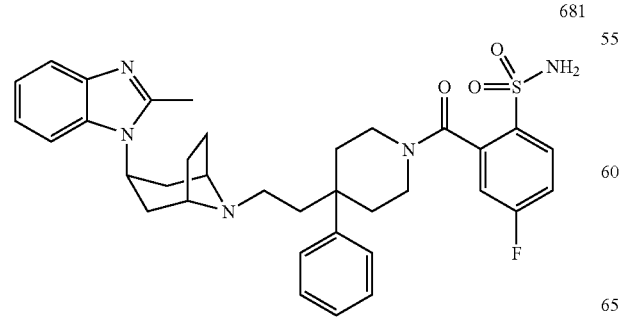

Example 681 was prepared as outlined below.

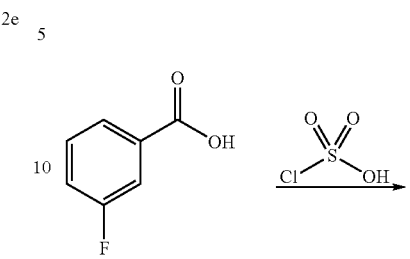

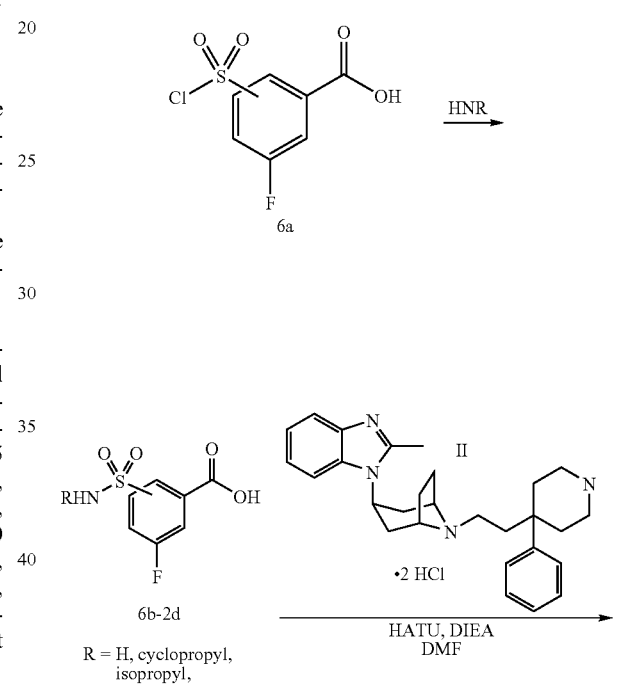

R = H, cyclopropyl, isopropyl,

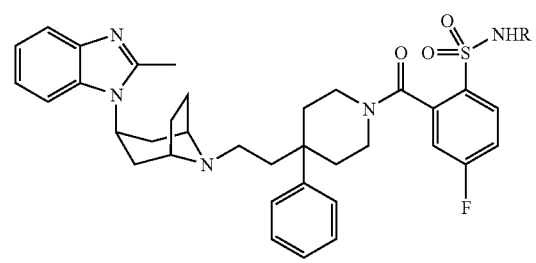

example 681: R = H
example 682: R = cyclopropyl
example 683: R = isopropyl

A mixture of 2-(chlorosulfonyl)-5-fluorobenzoic acid and 4-(chlorosulfonyl)-3-fluorobenzoic acid, 6a

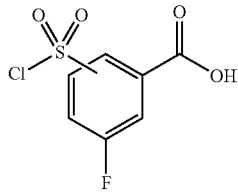

6a

3-Fluorobenzoic acid (7.0 g, 50 mmol, 1 equiv) was added at 0° C. to chlorosulfonic acid (40 mL). The reaction mixture was heated to 130° C. for 6 h, cooled to RT and poured slowly over ice. The product was extracted into diethyl ether, dried and concentrated to provide a 4:1 mixture of regioisomers, 2-(chloro sulfonyl)-5-fluorobenzoic acid and 4-(chlorosulfonyl)-3-fluorobenzoic acid 6b, as a brown solid (5.26 g, 46% yield). $^1$H NMR (400 MHz, CDCl$_3$) δ.8.14 (ddd, 1H, J=8.0 Hz, 2.4 Hz, 1.3 Hz), 8.05-8.01 (m, 2H), 7.98 (ddd, 1H, J=6.8 Hz, 2.4 Hz, 1.6 Hz), 7.79 (dd, 1H, J=6.8, 2.4 Hz), 7.71 (td, 1H, J=8.1, 2.4 Hz). ES-LCMS m/z 237.13 (M–H) for C$_7$H$_5$FO$_5$S.

A Mixture of 2-(aminosulfonyl)-5-fluoro benzoic acid and 4-(aminosulfonyl)-3-fluorobenzoic acid, 6b

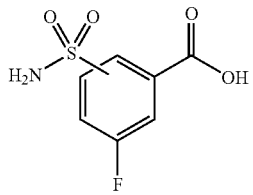

6b

Liquid ammonia was condensed at −78° C. into a reaction vessel containing a mixture of 2-(chlorosulfonyl)-5-fluorobenzoic acid and 4-(chlorosulfonyl)-3-fluoro benzoic acid 6a (100 mg, 0.419 mmol, 1 eq.). The reaction mixture was allowed to evaporate slowly upon warming to RT over 18 h. The crude residue contained a mixture of 2-(aminosulfonyl)-5-fluorobenzoic acid and 4-(aminosulfonyl)-3-fluorobenzoic acid and was used without further purification. ES-LCMS m/z 218 (M–H).

4-Fluoro-2-[(4-{2-[3-(2-methyl-1H-benzimidazol-1-yl)-8-azabicyclo[3.2.1]oct-8-yl]ethyl}-4-phenylpiperidin-1-yl) carbonyl]benzenesulfonamide (example 681). The title compound was prepared from a mixture of 2-(aminosulfonyl)-5-fluorobenzoic acid and 4-(aminosulfonyl)-3-fluorobenzoic acid 6b and endo 2-methyl-1-{8-[2-(4-phenylpiperidin-4-yl) ethyl]-8-aza bicyclo[3.2.1]oct-3-yl}-1H-benzimidazole dihydro-chloride II following the general procedure for tert-butyl {2-[(4-{2-[3-(2-methyl-1H-benzimidazol-1-yl)-8-azabicyclo[3.2.1]oct-8-yl]ethyl}-4-phenylpiperidin-1-yl) carbonyl]phenyl}sulfonylcarbamate 1c. The desired regioisomer was purified by column chromatography on silica gel eluting with 20% methanol in ethyl acetate to afford 4-fluoro-2-[(4-{2-[3-(2-methyl-1H-benzimidazol-1-yl)-8-azabicyclo[3.2.1]oct-8-yl]ethyl}-4-phenylpiperidin-1-yl) carbonyl]benzenesulfonamide 6 as a white solid (9.8 mg, 20% yield). $^1$H NMR (400 MHz, CDCl$_3$) δ 7.90 (t, 1H. J=7.7 Hz), 7.64 (m, 1H), 7.39 (m, 2H), 7.30-7.12 (m, 8H), 5.69 (broad s, 2H), 4.59 (m, 1H), 4.20 (m, 1H), 3.48-3.19 (m, 5H), 2.52 (s, 3H), 2.40-2.32 (m, 3H), 2.18 (m, 1H), 2.04-1.70 (m, 10H), 1.62 (m, 2H). ES-LCMS m/z 630.19 (M+H). Analytical HPLC (Method Y) Rt 4.16 (90.0%).

Example 682

N-Cyclopropyl-4-fluoro-2-[(4-{2-[3-(2-methyl-1H-benzimidazol-1-yl)-8-azabicyclo[3.2.1]oct-8-yl]ethyl}-4-phenylpiperidin-1-yl)carbonyl]benzene sulfonamide was synthesized analogously to example 861.

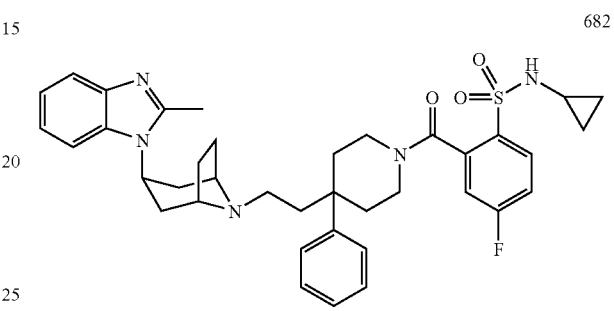

682

A mixture of 2-[(cyclopropylamino)sulfonyl]-5-fluorobenzoic acid and 4-[(cyclopropylamino) sulfonyl]-3-fluorobenzoic acid, 6c

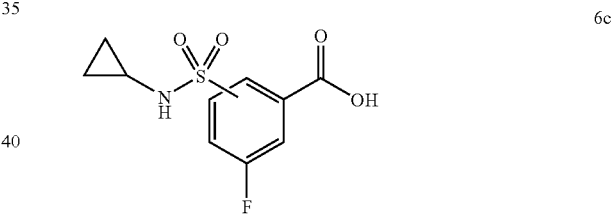

6c

The mixture was prepared from a mixture of 2-(chloro sulfonyl)-5-fluorobenzoic acid and 4-(chlorosulfonyl)-3-fluorobenzoic acid 6a and cyclopropyl amine following the general procedure for 5-chloro-2-[(methylamino) sulfonyl] benzoic acid and 3-chloro-4-[(methylamino) sulfonyl]benzoic acid 2b. The crude reaction mixture was carried on without further purification. ES-LCMS m/z 258 (M–H).

The title compound in example 682 was prepared from a mixture of 2-[(cyclopropylamino) sulfonyl]-5-fluorobenzoic acid and 4-[(cyclopropyl amino)sulfonyl]-3-fluorobenzoic acid 6c and endo 2-methyl-1-{8-[2-(4-phenylpiperidin-4-yl) ethyl]-8-azabicyclo[3.2.1]oct-3-yl}-1H-benzimidazole dihydrochloride II following the general procedure for tert-butyl {2-[(4-{2-[3-(2-methyl-1H-benzimidazol-1-yl)-8-azabicyclo[3.2.1]oct-8-yl]ethyl}-4-phenyl piperidin-1-yl) carbonyl]phenyl}sulfonylcarbamate 1c. The desired regioisomer was purified by column chromatography on silica gel eluting with 10% methanol in ethyl acetate to afford N-cyclopropyl-4-fluoro-2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide 7 as a white solid (40 mg, 20% yield). $^1$H NMR (400 MHz, CDCl$_3$) δ 7.97 (t, 1H, J=7.4 Hz), 7.65 (m, 1H), 7.38 (m, 2H, 7.29-7.12 (m, 8H), 5.87 (s, 1H), 4.59 (m, 1H), 4.19 (m, 2H), 3.50-3.10 (m, 5H), 2.55 (s, 3H), 2.39-2.16 (m, 5H), 1.92-1.73 (m, 10H), 1.60 (m, 2H), 0.70-0.50 (m, 4H). ES-LCMS m/z 670.18 (M+H). Analytical HPLC (Method Y) Rt 4.35 (94.82%).

Example 683

4-Fluoro-N-isopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide

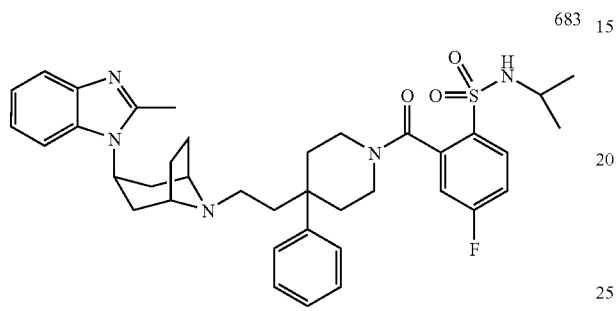

683

Example 683 was prepared analogously to example 681.

A mixture of 5-fluoro-2-[(isopropylamino)sulfonyl]benzoic acid and 4-fluoro-3-[(isopropylamino)sulfonyl]benzoic acid, 6d.

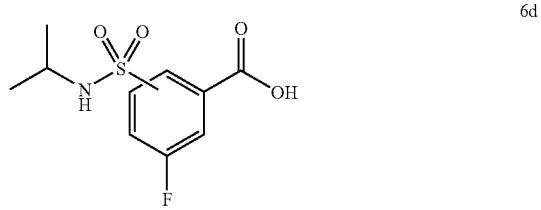

6d

The mixture was prepared from a mixture of 2-(chlorosulfonyl)-5-fluorobenzoic acid and 4-(chlorosulfonyl)-3-fluorobenzoic acid 6a and isopropyl amine following the general procedure for 5-chloro-2-[(methylamino) sulfonyl]benzoic acid and 3-chloro-4-[(methylamino) sulfonyl]benzoic acid 2b. The crude reaction mixture was carried on without further purification. ES-LCMS m/z 260 (M−H).

Title compound in example 683 was prepared from a mixture of 5-fluoro-2-[(isopropylamino)sulfonyl]benzoic acid and 4-fluoro-3-[(isopropylamino)sulfonyl]benzoic acid 6d and endo 2-methyl-1-{8-[2-(4-phenyl piperidin-4-yl)ethyl]-8-azabicyclo[3.2.1]oct-3-yl}-1H-benzimidazole dihydrochloride II following the general procedure for tert-butyl {2-[(4-{2-[3-(2-methyl-1H-benzimidazol-1-yl)-8-azabicyclo[3.2.1]oct-8-yl]ethyl}-4-phenylpiperidin-1-yl)carbonyl]phenyl}sulfonyl carbamate 1c. The desired regioisomer was purified by column chromatography on silica gel eluting with 10% methanol in ethyl acetate to afford 4-fluoro-N-isopropyl-2-[(4-{2-[3-(2-methyl-1H-benzimidazol-1-yl)-8-azabicyclo[3.2.1]oct-8-yl]ethyl}-4-phenylpiperidin-1-yl)carbonyl]benzenesulfonamide 8 as a white solid (45 mg, 25% yield). $^1$H NMR (400 MHz, CDCl$_3$) δ 7.92 (t, 1H, J=7.5 Hz), 7.65 (m, 1H), 7.38 (m, 2H), 7.29-7.11 (m, 8H), 5.14 (d, 1H, J=7.5 Hz), 4.59 (m, 1H), 4.18 (m, 1H), 3.54-3.18 (m, 6H), 2.55 (s, 3H), 2.39-2.18 (m, 4H), 1.91-1.81 (m, 10H), 1.61 (m, 2H), 1.15 (m, 6H). ES-LCMS m/z 672.22 (M+H). Analytical HPLC (Method Y) Rt 4.30 (100.0%).

Example 684

1-((1R,5S)-8-{2-[1-(2,2-dimethylpropanoyl)-4-(3-methoxyphenyl)piperidin-4-yl]ethyl}-8-azabicyclo[3.2.1]oct-3-yl)-2-methyl-1H-benzimidazole

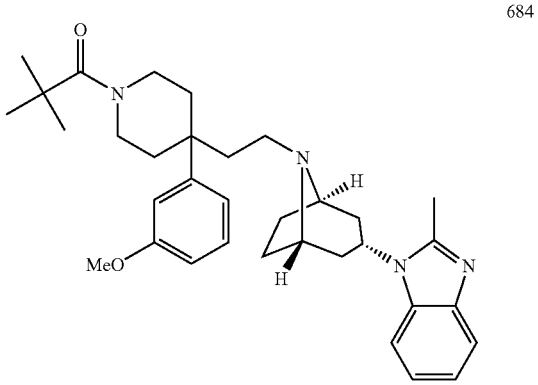

684

This compound was prepared from 3-methoxyphenylmagnesium bromide and 16a employing methods similar to those described in example 16. $^1$H NMR (400 MHz, DMSO-d$_6$) δ 7.47 (d, 1H, J=7 Hz), 7.34 (d, 1H, J=8 Hz), 7.27 (t, 1H, J=8 Hz), 7.11 (t, 1H, J=7 Hz), 7.08 (t, 1H, J=7 Hz), 6.94 (d, 1H, J=8 Hz), 6.88 (s, 1H), 6.79 (d, 1H, J=8 Hz), 4.51 (m, 1H), 3.75 (m, 2H), 3.74 (s, 3H), 3.23 (m, 4H), 2.50 (s, 3H, obscured by solvent peak), 2.34 (br dd, 2H, J=22, 9 Hz), 2.02 (m, 2H), 1.85 (m, 4H), 1.75 (m, 6H), 1.58 (d, 2H, J=8 Hz), 1.16 (s, 9H). HRMS C$_{34}$H$_{46}$N$_4$O$_2$ m/z 547.3186 (M+H)$_{Cal.}$, 543.3699 (M+H)$_{Obs.}$ 543.3708.

Example 685

1-((1R,5S)-8-{2-[1-(2,2-dimethylpropanoyl)-4-(4-trifluoromethylphenyl)piperidin-4-yl]ethyl}-8-azabicyclo[3.2.1]oct-3-yl)-2-methyl-1H-benzimidazole

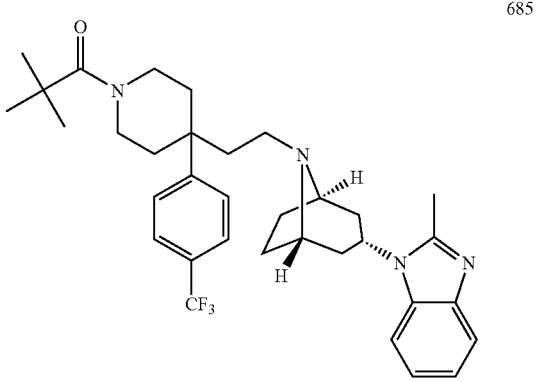

685

This compound was prepared from 4-trifluoro methylphenylmagnesium bromide and 16a employing methods similar to those described in example 16. $^1$H NMR (400 MHz, DMSO-d$_6$) δ 7.70 (d, 2H, J=8 Hz), 7.62 (d, 2H, J=8 Hz), 7.47

(d, 1H, J=7 Hz), 7.34 (d, 1H, J=7 Hz), 7.10 (t, 1H, J=7 Hz), 7.07 (t, 1H, J=7 Hz), 4.49 (m, 1H), 3.76 (m, 2H), 3.23 (m, 4H), 2.50 (s, 3H, obscured by solvent peak), 2.34 (br. dd, 2H, J=22, 9 Hz), 2.07 (m, 2H), 1.90-1.70 (m, 10H), 1.57 (d, 2H, J=7 Hz), 1.16 (s, 9H). HRMS $C_{34}H_{43}F_3N_4O$ m/z 581.3467 $(M+H)_{Cal.}$, 581.3474 $(M+H)_{Obs.}$

Example 686

2-Chloro-5-({4-{2-[(1R,5S)-3-(2-methyl-1H-benzimidazol-1-yl)-8-azabicyclo[3.2.1]oct-8-yl]ethyl}-4-[4-(trifluoromethyl)phenyl]piperidin-1-yl}carbonyl)benzene sulfonamide

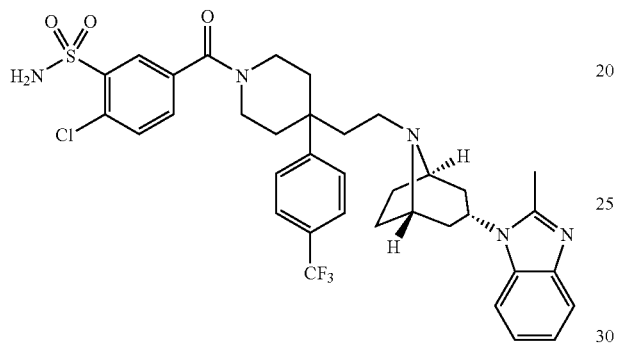

686

This compound was prepared from 4-trifluoro-methylphenylmagnesium bromide and 16a employing methods similar to those described in example 16. $^1$H NMR (400 MHz, CD$_3$OD) δ 7.95-7.78 (m, 2H), 7.71 (d, 2H, J=8 Hz), 7.67 (m, 1H), 7.64 (d, 2H, J=8 Hz), 7.52 (br.d, 1H, J=7 Hz), 7.42 (br. d, 1H, J=7 Hz), 7.20 (t, 1H, J=7 Hz), 7.17 (t, 1H, J=7 Hz), 4.74 (m, 1H), 4.19 (m, 1H), 3.40 (m, 4H), 3.18 (m, 1H), 2.52 (s, 3H), 2.43 (m, 3H), 2.25 (m, 1H), 1.99 (m, 10H), 1.71 (d, 2H, J=7 Hz). HRMS $C_{36}H_{39}ClF_3N_5O_3S$ m/z 714.2492 $(M+H)_{Cal.}$, 714.2492 $(M+H)_{Obs.}$

Example 687

2-Chloro-5-({4-{2-[(1R,5S)-3-(2-methyl-1H-benzimidazol-1-yl)-8-azabicyclo[3.2.1]oct-8-yl]ethyl}-4-[4-(methyl sulfonyl)phenyl]piperidin-1-yl}carbonyl)benzene sulfonamide

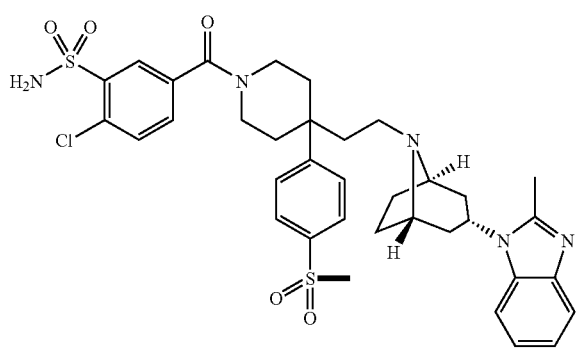

687

This compound was prepared from 4-(methyl thio)phenylmagnesium bromide and 16a employing methods similar to those described in example 16. The 4-(methylthio)phenyl intermediate corresponding to 16d was oxidized to the methylsulfonyl derivative with MCPBA and converted to compound 687 by methods similar to those outlined in example 16. $^1$H NMR (400 MHz, CD$_3$OD) δ 8.02 (d, 2H, J=6 Hz), 7.93 (m, 1H), 7.92 (m, 1H), 7.75 (d, 2H, J=6 Hz), 7.70 (m, 1H), 7.58 (d, 1H, J=7 Hz), 7.50 (d, 1H, J=7 Hz), 7.28 (m, 2H), 4.24 (m, 1H), 3.79 (m, 2H), 3.40 (m, 4H), 3.18 (m, 1H), 3.15 (s, 3H), 2.59 (s, 3H), 2.47 (m, 2H), 2.35 (m, 1H), 2.25-2.00 (m, 12H). HRMS $C_{36}H_{42}ClN_5O_5S_2$ m/z 724.2394 $(M+H)_{Cal.}$, 724.2372 $(M+H)_{Obs.}$

Example 688

1-[(1R,5S)-8-(2-{1-(2,2-Dimethylpropanoyl)-4-[4-(methylsulfonyl)phenyl]piperidin-4-yl}ethyl)-8-azabicyclo[3.2.1]oct-3-yl]-2-methyl-1H-benzimidazole

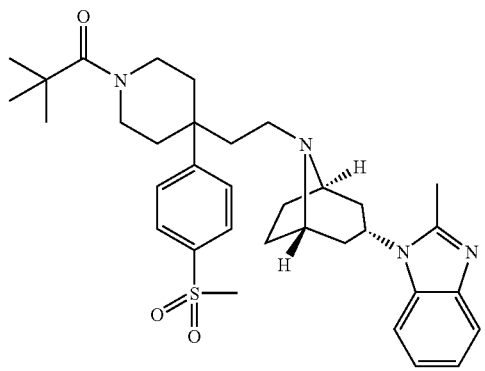

688

This compound was prepared from 4-(methyl thio)phenylmagnesium bromide and 16a employing methods similar to those described in example 16. The 4-(methylthio)phenyl intermediate corresponding to 16d was oxidized to the methylsulfonyl derivative with MCPBA and converted by methods similar to those outlined in example 16. $^1$H NMR (400 MHz, DMSO-d$_6$) δ 7.90 (d, 2H, J=8 Hz), 7.68 (d, 2H, J=8 Hz), 7.48 (d, 1H, J=6 Hz), 7.35 (d, 1H, J=7 Hz), 7.10 (m, 2H), 4.50 (m, 1H), 3.75 (m, 2H), 3.27 (m, 4H), 3.20 (s, 3H), 2.50 (s, 3H, obscured by solvent peak), 2.35 (dd, 1H, J=19, 10 Hz), 2.08 (m, 2H), 1.85 (m, 9H), 1.76 (m, 2H), 1.59 (m, 2H), 1.17 (s, 9H). HRMS $C_{34}H_{46}N_4O_3S$ m/z 591.3369 $(M+H)_{Cal.}$, 591.3397 $(M+H)_{Obs.}$

Example 689

2-Chloro-5-[(4-(3-isopropylphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

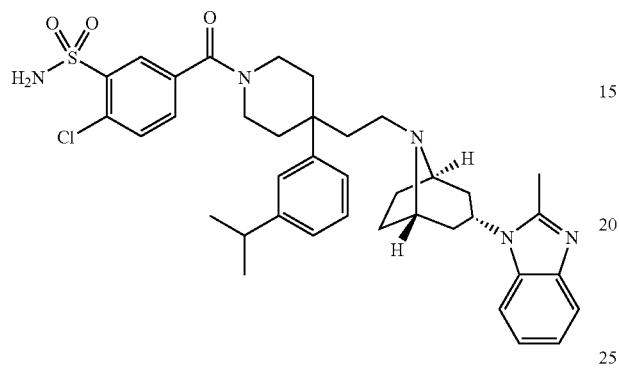

689

This compound was prepared from 3-isopropyl phenylmagnesium bromide and 16a employing methods similar to those described in example 16. $^1$H NMR (400 MHz, DMSO-$d_6$) δ 7.93 (s, 1H), 7.68 (d, 1H, J=8 Hz), 7.63 (br, 2H), 7.61 (d, 1H, J=8 Hz), 7.48 (d, 1H, J=7 Hz), 7.34 (d, 1H, J=7 Hz), 7.27 (t, 1H, J=8 Hz), 7.23 (s, 1H), 7.18 (d, 1H, J=7 Hz), 7.09 (m, 3H), 4.49 (m, 1H), 3.89 (m, 1H), 3.50-3.30 (m, 2H), 3.20 (m, 4H), 2.89 (m, 1H, J=7 Hz), 2.43 (s, 3H), 2.35 (br.dd, 2H, J=22, 10 Hz), 2.17 (m, 1H), 2.07 (m, 1H), 1.90-1.70 (m, 9H), 1.56 (br.d, 2H, J=8 Hz), 1.20 (d, 6H, J=7 Hz). HRMS $C_{38}H_{46}ClN_5O_3S$ m/z 688.3088 (M+H)$_{Cal.}$, 688.3075 (M+H)$_{Obs.}$.

Example 690

Methyl 3-[(4-(3-isopropylphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzoate

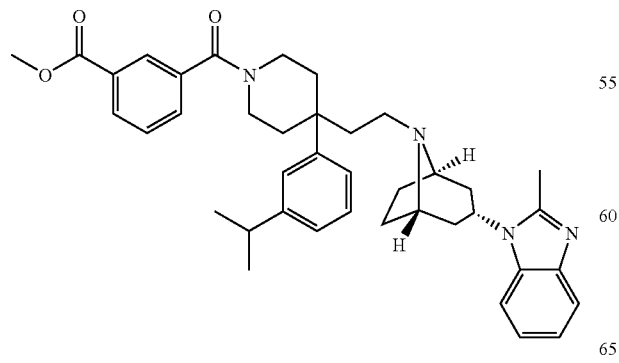

690

This compound was prepared from 3-isopropyl phenylmagnesium bromide and 16a employing methods similar to those described in example 16. $^1$H NMR (400 MHz, DMSO-$d_6$) δ 8.01 (d, 1H, J=7 Hz), 7.91 (s, 1H), 7.67 (d, 1H, J=8 Hz), 7.58 (t, 1H, J=8 Hz), 7.48 (d, 1H, J=7 Hz), 7.34 (d, 1H, J=7 Hz), 7.27 (t, 1H, J=8 Hz), 7.23 (s, 1H), 7.23 (d, 1H, J=8 Hz), 7.09 (m, 3H), 4.49 (m, 1H), 3.89 (m, 1H), 3.84 (s, 3H), 3.43 (m, 1H), 3.37 (m, 1H), 3.21 (m, 3H), 2.89 (m, 1H, J=7 Hz), 2.41 (s, 3H), 2.35 (m, 2H), 2.16 (m, 1H), 2.07 (m, 1H), 1.90-1.70 (m, 10H), 1.59 (br. d, 2H, J=8 Hz), 1.22 (d, 6H, J=8 Hz). HRMS $C_{40}H_{48}N_4O_3$ m/z 633.3805 (M+H)$_{Cal.}$, 633.3787 (M+H)$_{Obs.}$.

Example 691

3-[(4-(3-Isopropylphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzoic acid

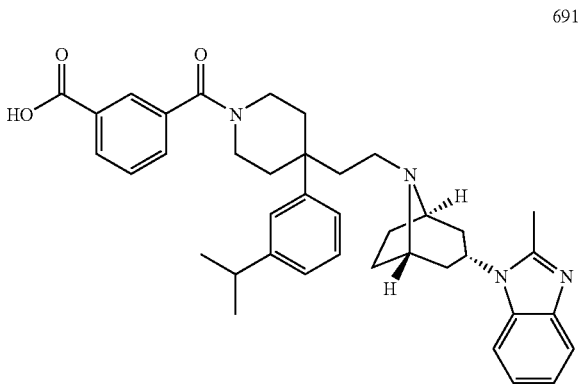

691

This compound was prepared by hydrolysis of the title compound in example 690 with lithium hydroxide employing methods familiar to those skilled in the art. $^1$H NMR (400 MHz, DMSO-$d_6$) δ 13.1 (br, 1H), 7.99 (d, 1H, J=8 Hz), 7.89 (s, 1H), 7.63 (d, 1H, J=8 Hz), 7.56 (t, 1H, J=7 Hz), 7.49 (d, 1H, J=7 Hz), 7.38 (br, 1H), 7.25 (m, 2H), 7.19 (d, 1H, J=8 Hz), 7.11 (m, 3H), 4.51 (br, 1H), 3.91 (br, 1H), 3.45 (m, 1H), 3.40-3.20 (m, 4H), 2.89 (m, 1H, J=7 Hz), 2.45 (s, 3H), 2.40-1.60 (m, 16H), 1.20 (d, 6H, J=7 Hz). HRMS $C_{39}H_{46}N_4O_3$ m/z 619.3684 (M+H)$_{Cal.}$, 619.3643 (M+H)$_{Obs.}$.

Example 692

(3S)-Tetrahydrofuran-3-yl 4-{2-[(1R,5S)-3-(2-methyl-1H-benzimidazol-1-yl)-8-azabicyclo[3.2.1]oct-8-yl]ethyl}-4-phenylpiperidine-1-carboxylate

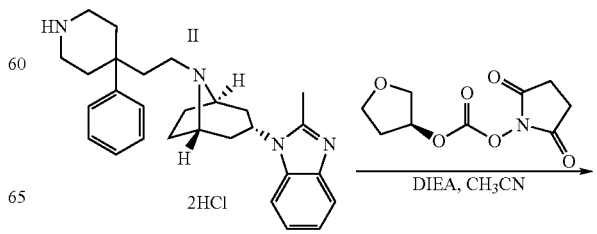

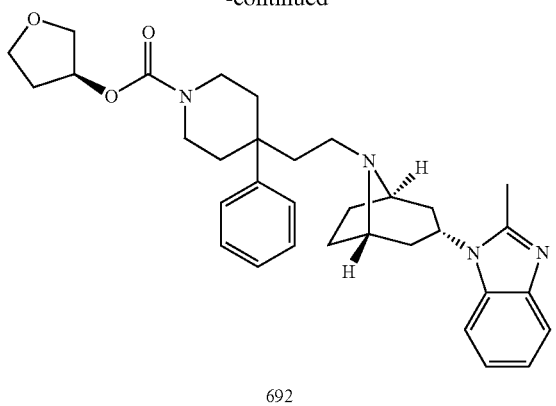

692

A solution of 1-({[(3S)-tetrahydrofuran-3-yloxy] carbonyl}oxy)pyrrolidine-2,5-dione (U.S. Pat. No. 6,344,465) (55 mg, 0.24 mmol), amine dihydrochloride II (100 mg, 0.199 mmol) and N,N-diisopropylethylamine (0.14 mL, 0.80 mmol) in acetonitrile (3 mL) was stirred overnight at rt. The solvent was removed at reduced pressure and the remaining material was dissolved in dichloromethane, washed with saturated sodium bicarbonate solution and dried over magnesium sulfate. Filtration and evaporation of the dichloromethane solution provided the crude product which was purified by chromatography on silica gel eluting with 5% methanol/dichloromethane. Title compound in example 692 was obtained as a white hygroscopic powder (70 mg, 65%). $^1$H NMR (400 MHz, CDCl$_3$) δ 7.66 (d, 1H, J=8 Hz), 7.37 (m, 2H), 7.30-7.20 (m, 4H), 7.16 (m, 2H), 5.25 (m, 1H), 4.61 (m, 1H), 3.85 (m, 4H), 3.73 (m, 2H), 3.22 (m, 4H), 2.58 (br s, 3H), 2.36 (m, 2H), 2.17 (m, 3H), 2.05-1.70 (m, 13H). HRMS C$_{33}$H$_{42}$N$_4$O$_3$ m/z 543.3335 (M+H)$_{Cal.}$, 543.3331 (M+H)$_{Obs.}$.

Example 693

1-{8-[2-(4-(3-fluorophenyl)-1-{[3-(trifluoromethyl) pyridin-2-yl]carbonyl}piperidin-4-yl)ethyl]-8-azabicyclo[3.2.1]oct-3-yl}-2-methyl-1H-benzimidazole

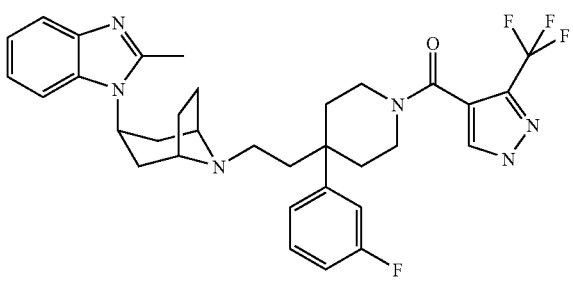

693

3-(Trifluoromethyl)-1H-pyrazole-4-carboxylic acid, 1a. A mixture of ethyl 3-(trifluoromethyl)-1H-pyrazole-4-carboxylate (100 mg, 0.48 mmol, 1 eq.), ethanol (5 mL) and 5N NaOH (5 mL) was heated to reflux for 72 h. The reaction was cooled to RT, acidified to pH 2 with 5 N HCl and the product extracted into ethyl acetate. The organic layers were dried over sodium sulfate, filtered and concentrated to provide 3-(trifluoromethyl) H-pyrazole-4-carboxylic acid (1a) as a white solid (80 mg, 93% yield). $^1$H NMR (400 MHz, DMSO-d6) δ 13.95 (broad s, 1H), 8.49 (s, 1H), 3.50 (broad s, 1H). ES-LCMS m/z 181.16 (M+H).

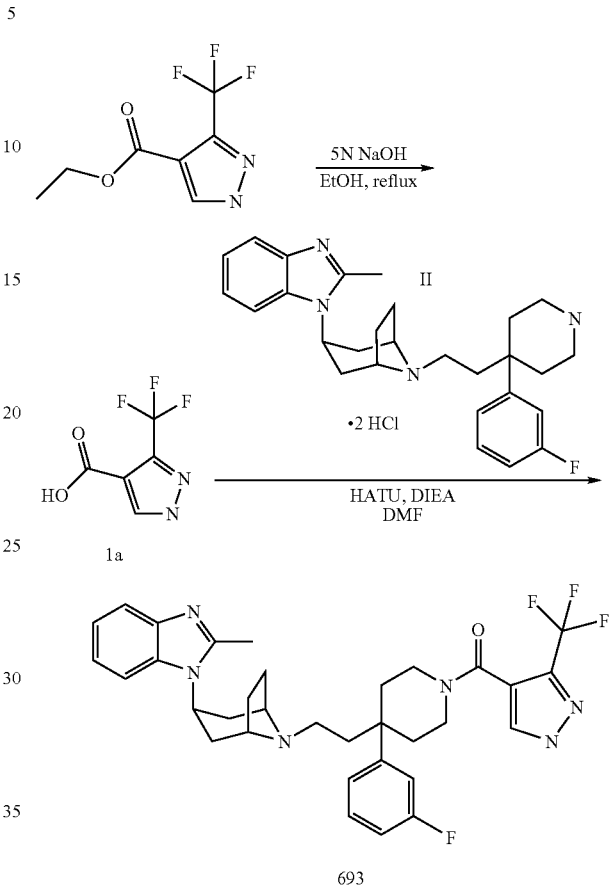

1-{8-[2-(4-(3-fluorophenyl)-1-{[3-(trifluoro methyl)pyridin-2-yl]carbonyl}piperidin-4-yl)ethyl]-8-azabicyclo[3.2.1] oct-3-yl}-2-methyl-1H-benzimidazole (example 693). To a solution of 1-(8-{2-[4-(3-fluoro phenyl)piperidin-4-yl] ethyl}-8-azabicyclo[3.2.1]oct-3-yl)-2-methyl-1H-benzimidazole dihydrochloride II (130 mg, 0.25 mmol, 1 eq.) in dimethylformamide (4 mL) was added 3-(trifluoromethyl)-1H-pyrazole-4-carboxylic acid, 1a, (50 mg, 0.27 mmol, 1 eq.) and N,N-diisopropylethyl amine (180 μL, 1.0 mmol, 4 eq.). After stirring at RT for several min, O-(7-azabenzotriazol-1-yl)-N,N,N',N'-tetramethyl-uroniumhexafluorophosphate (95 mg, 0.25 mmol, 1 eq.) was added and the reaction was stirred for 2 h. The mixture was partitioned between dichloromethane and satd. aq. NaHCO$_3$. The organic layer was dried and concentrated and the residue was purified by prep. HPLC (Method Y) to provide 1-{8-[2-(4-(3-fluorophenyl)-1-{[3-(trifluoromethyl)pyridin-2-yl]carbonyl}piperidin-4-yl) ethyl]-8-azabicyclo[3.2.1]oct-3-yl}-2-methyl-1H-benzimidazole 1 as a white solid (30 mg, 20% yield).

$^1$H NMR (300 MHz, DMSO-d6) δ 7.65 (m, 2H), 7.32 (m, 2H), 7.16 (m, 2H), 7.07 (m, 1H), 6.97 (m, 2H), 4.62 (m, 1H), 4.18 (m, 1H), 3.50 (m, 1H), 3.27 (m, 4H), 2.52 (m, 3H), 2.45-2.09 (m, 4H), 2.04-1.47 (m, 12H). ES-LCMS m/z 609.39 (M+H). Analytical HPLC (Method W) Rt 2.79 (95.89%).

Example 694

1-((1R,5S)-8-{2-[1-(2,2-dimethylpropanoyl)-4-(4-fluorophenyl)piperidin-4-yl]ethyl}-8-azabicyclo[3.2.1]oct-3-yl)-2-methyl-1H-benzimidazole

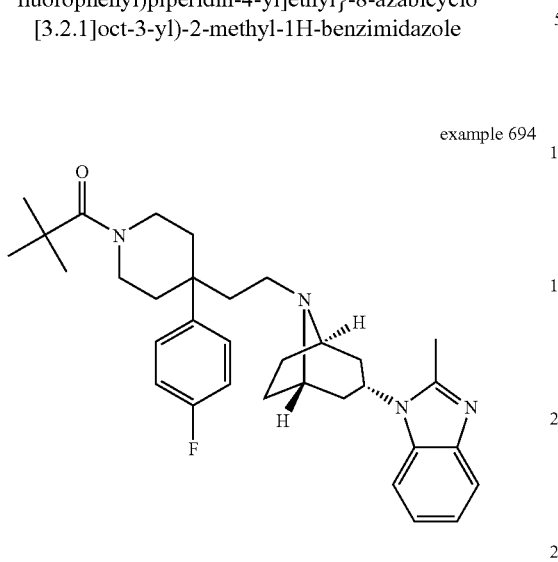

example 694

The title compound was prepared according to procedures analogous to those described for example 16. $^1$H NMR (300 MHz, CDCl$_3$) δ 7.68 (d, 1H, J=2.3 Hz), 7.66 (d, 1H, J=2.2 Hz), 7.32-7.25 (m, 2H), 7.18-7.15 (m, 2H), 7.09-7.04 (m, 2H), 4.68-4.55 (m, 1H), 3.95-3.90 (m, 2H), 3.41-3.20 (m, 4H), 2.57 (s, 3H), 2.43-2.33 (m, 2H), 2.19-2.14 (m, 2H), 1.95-1.62 (m, 12H), 1.26 (s, 9H). LRMS (ES, +ve ion) m/z 531.2 (M+H).

Example 695

1-((1R,5S)-8-{2-[4-(3,4-dichlorophenyl)-1-(2,2-dimethylpropanoyl)piperidin-4-yl]ethyl}-8-azabicyclo[3.2.1]oct-3-yl)-2-methyl-1H-benzimidazole

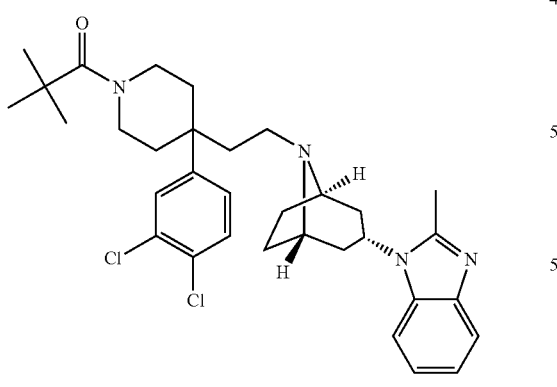

Example 695

The title compound was prepared according to procedures analogous to those described for example 16. $^1$H NMR (300 MHz, CDCl$_3$) δ 7.66 (d, 1H, J=6.9 Hz), 7.45 (d, 1H, J=8.3 Hz), 7.39 (br. s, 1H), 7.32-7.27 (m, 1H), 7.20-7.14 (br. m, 3H), 4.62 (app quint, 1H, J=9.2 Hz), 3.97-3.87 (m, 2H), 3.41-3.25 (m, 4H), 2.58 (s, 3H), 2.44-2.34 (m, 2H), 2.16-2.10 (m, 2H), 1.97-1.65 (m, 12H), 1.27 (s, 9H). LRMS (ES, +ve ion) m/z 581.0 (M+), 583.3 (M+2, $^{37}$Cl).

Example 696

1-((1R,5S)-8-{2-[1-benzoyl-4-(3,4-dichlorophenyl)piperidin-4-yl]ethyl}-8-azabicyclo[3.2.1]oct-3-yl)-2-methyl-1H-benzimidazole

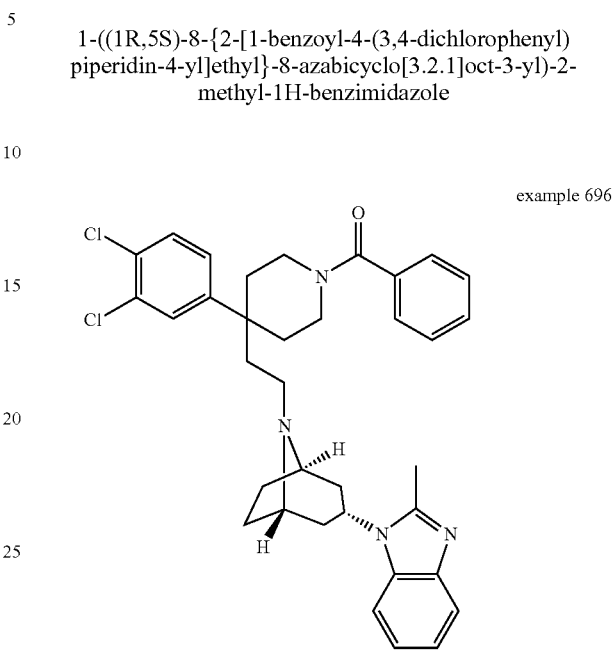

example 696

The title compound was prepared according to procedures analogous to those described for example 16. $^1$H NMR (300 MHz, CDCl$_3$) δ 7.66 (d, 1H, J=7.2 Hz), 7.44 (app t) overlapping 7.39 (br s, 8H total), 7.32-7.25 (m) overlapping 7.26 (s, CHCl$_3$, 2H total), 7.18-7.14 (m, 2H), 4.60 (app quint, 1H, J=8.8 Hz), 4.13 (br s, 1H), 3.57, 3.40, 3.27 (three overlapping br s, 6H total), 2.55 (s, 3H), 2.44-2.34 (m, 2H), 2.21-1.66 (m, 17H). FAB HRMS (calcd for MH$^+$, C$_{35}$H$_{38}$Cl$_2$N$_4$O) 601.2501; Found 601.2501.

Example 697

1-((1R,5S)-8-{2-[1-benzoyl-4-(3-chlorophenyl)piperidin-4-yl]ethyl}-8-azabicyclo[3.2.1]oct-3-yl)-2-methyl-1H-benzimidazole

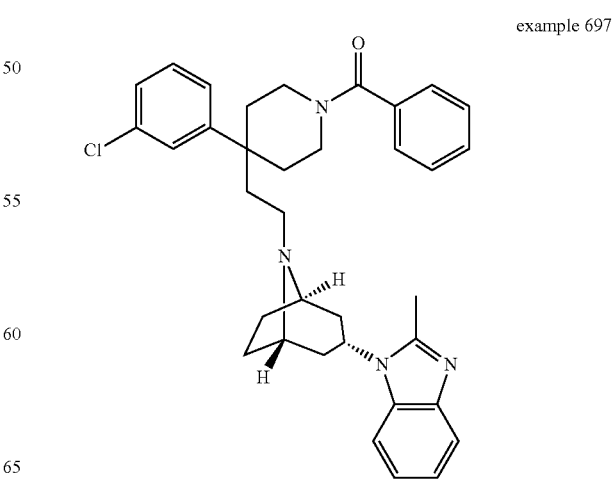

example 697

The title compound was prepared according to procedures analogous to those described for example 16. ¹H NMR (300 MHz, CDCl₃) δ 7.66 (d, 1H, J=6.9 Hz), 7.42-7.14 (m, 12H), 4.60 (app quint, 1H, J=9.1 Hz), 4.13 (br s, 1H), 3.56, 3.42 and 3.27 (three overlapping br s, 6H total), 2.55 (s, 3H), 2.44-1.63 (m, 17H). FAB HRMS (calcd for MH⁺, $C_{35}H_{39}ClN_4O$) 567.2891; Found 567.2885.

Example 698

1-((1R,5S)-8-{2-[1-(2,2-dimethylpropanoyl)-4-(3-fluorophenyl)piperidin-4-yl]ethyl}-8-azabicyclo[3.2.1]oct-3-yl)-2-methyl-1H-benzimidazole

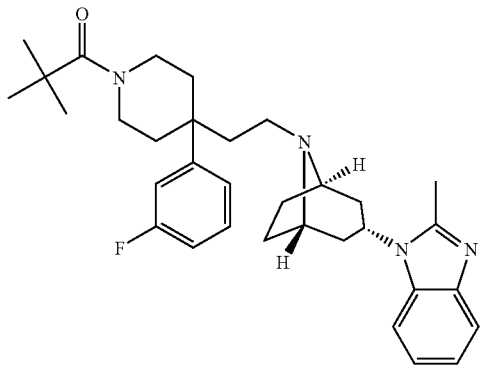

Example 698

The title compound was prepared according to procedures analogous to those described for example 16. ¹H NMR (300 MHz, CDCl₃) δ 7.66 (d, 1H, J=7.2 Hz), 7.38-7.29 (m, 2H), 7.20-6.92 (m, 5H), 4.61 (app quint, 1H, J=8.7 Hz), 3.96 and 3.91 (two overlapping br s, 2H total), 3.42-3.25 (m, 4H), 2.58 (s, 3H), 2.43-2.33 (m, 2H), 2.19-2.12 (m, 2H), 1.96-1.62 (m, 12H), 1.28 (s, 9H). LRMS (ES, +ve ion) m/z 531.3 (M+H).

Example 699

1-((1R,5S)-8-{2-[1-(2,2-dimethylpropanoyl)-4-thien-2-ylpiperidin-4-yl]ethyl}-8-azabicyclo[3.2.1]oct-3-yl)-2-methyl-1H-benzimidazole

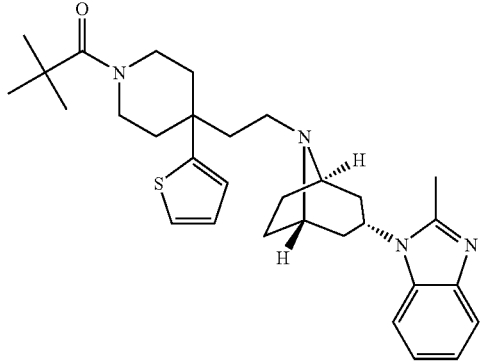

Example 699

The title compound was prepared according to procedures analogous to those described for example 16. ¹H NMR (300 MHz, CDCl₃) δ 7.66 (d, 1H, J=6.6 Hz), 7.33-7.15 (m, 4H), 6.99 (app t, 1H, J=4.3 Hz), 6.83 (d, 1H, J=3.3 Hz), 4.64 (app quint, 1H, J=9.0 Hz), 4.09 and 4.04 (two overlapping br s, 2H total), 3.33-3.20 (m, 4H), 2.58 (s, 3H), 2.45-2.34 (m, 2H), 2.20-1.64 (m, 14H), 1.28 (s, 9H). LRMS (ES, +ve ion) m/z 518.4 (M+).

Example 700

2-chloro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

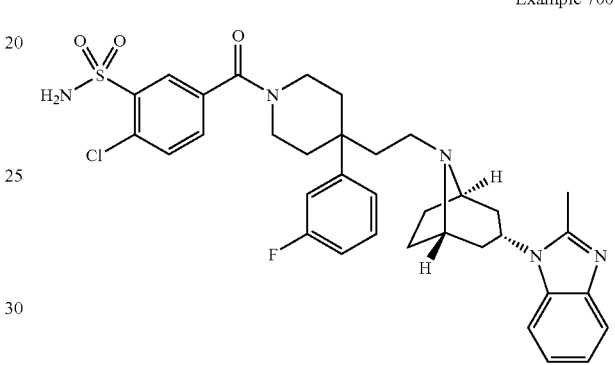

Example 700

The title compound was prepared according to procedures analogous to those described for example 16. ¹H NMR (300 MHz, CD₃OD) δ 7.93 (app d, 2H, J=9.6 Hz), 7.78-7.64 (m, 1H), 7.53-7.39 (m, 3H), 7.24-7.15 (m, 4H), 6.99 (app t, 1H, J=8.0 Hz), 4.73 (app quint, 1H, J=9.6 Hz), 4.20-4.15 (br m, 1H), 3.48-3.29 (m) overlapping 3.30 (s, MeOH, 6H total), 3.22-3.14 (m, 1H), 2.52 (s, 3H), 2.48-2.34 (m, 3H), 2.10-1.88 (m, 11H), NH₂ (not observed).

Example 701

1-((1R,5S)-8-{2-[1-(2,2-dimethylpropanoyl)-4-(3-ethylphenyl)piperidin-4-yl]ethyl}-8-azabicyclo[3.2.1]oct-3-yl)-2-methyl-1H-benzimidazole

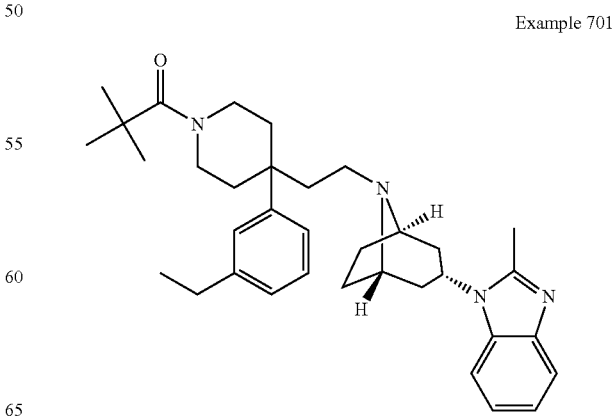

Example 701

The title compound was prepared according to procedures analogous to those described for example 16. ¹H NMR (300 MHz, CDCl₃) δ 7.69 (d, 1H, J=7.2 Hz), 7.33-7.08 (m, 7H), 4.68 (app quint, 1H, J=8.8 Hz), 3.98-3.93 (br m, 2H), 3.63 (br m, 2H), 3.36-3.29 (m, 4H), 2.68 (q, 2H, J=7.5 Hz), 2.59 (s, 3H), 2.47-2.37 (m, 2H), 2.26-2.20 (m, 2H), 2.01-1.66 (m, 10H), 1.29 (s) overlapping 1.26 (t, J=7.7 Hz, 12H total). LRMS (ES, +ve ion) m/z 541.4 (M+H).

Example 702

1-((1R,5S)-8-{2-[1-(2,2-dimethylpropanoyl)-4-(4-ethylphenyl)piperidin-4-yl]ethyl}-8-azabicyclo[3.2.1]oct-3-yl)-2-methyl-1H-benzimidazole Example 702

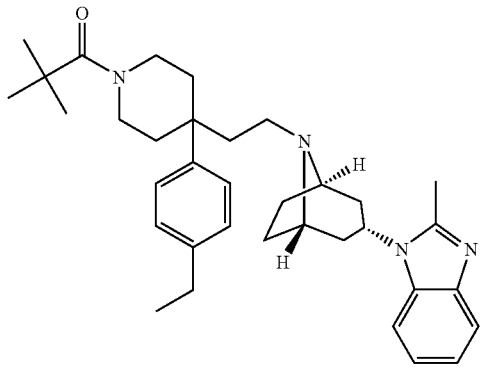

The title compound was prepared according to procedures analogous to those described for example 16. ¹H NMR (300 MHz, CDCl₃) δ 7.70-7.67 (m, 1H), 7.33-7.28 (m, 1H), 7.22-7.13 (m, 6H), 4.65 (app quint, 1H, J=8.9 Hz), 4.00-3.93 (m, 2H), 3.34-3.26 (m, 4H), 2.66 (q, 2H, J=7.5 Hz), 2.59 (s, 3H), 2.45-2.34 (m, 2H), 2.25-2.19 (m, 2H), 1.96-1.62 (m, 12H), 1.28 (s) overlapping 1.26 (t, J=7.7 Hz, 12H total). LRMS (ES, +ve ion) m/z 541.4 (M+H).

Example 703

Endo 1-((1R,5S)-8-{2-[4-(3-chloro-4-fluorophenyl)-1-(2,2-dimethylpropanoyl)piperidin-4-yl]ethyl}-8-azabicyclo[3.2.1]oct-3-yl)-2-methyl-1H-benzimidazole was synthesized according to the procedures described in example 16 with a 3-chloro-4-fluoro instead of a 3-chloro substitution in the phenyl ring.

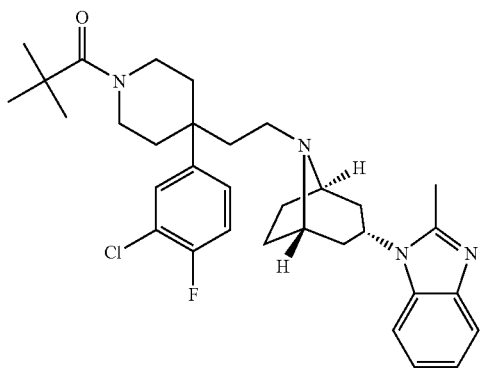

Tert-butyl 4-(3-chloro-4-fluorophenyl)-4-(1-cyano-2-ethoxy-2-oxoethyl)piperidine-1-carboxylate was prepared and used without further purification as described in example 16b from 1-fluoro-2-chloro-4-bromobenzene (10 g, 47.74 mmol) using tetrahydrofuran instead of diethyl ether as a solvent to afford an oil (6.76 g, 100%). ES-LCMS m/z 423 (M−H)⁺.

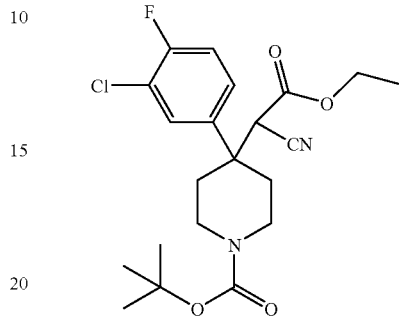

[1-(Tert-butoxycarbonyl)-4-(3-chloro-4-fluorophenyl)piperidin-4-yl](cyano)acetic acid was prepared and used without further purification as described in example 16c (6.76 g, 15.9 mmol) to afford an oil (6.31 g, 100%).

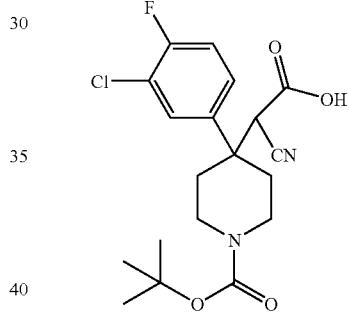

Tert-butyl endo 4-(3-chloro-4-fluorophenyl)-4-(cyanomethyl)piperidine-1-carboxylate was prepared as described in example 16d (6.31 g, 15.9 mmol), purified by column chromatography on silica gel, eluting with a gradient of 5-40% ethyl acetate in hexane to afford a beige solid (2.86 g, 51%). ¹H NMR (300 MHz, CDCl₃) δ 7.41 (dd, 1H, J=2.3, 2.5 Hz) 7.30-7.21 (m, 2H), 3.76-3.72 (m, 2H), 3.13 (br t, 2H, J=10.4 Hz), 2.57 (s, 2H), 2.29-2.24 (br m, 2H), 1.93-1.84 (m, 2H), 1.46 (s, 9H). ES-LCMS m/z 253 (M-BOC+H)⁺.

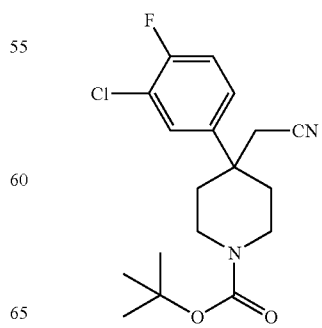

Tert-butyl 4-(3-chloro-4-fluorophenyl)-4-(2-oxoethyl)piperidine-1-carboxylate was prepared as described in example 16e from the product obtained in previous step (2.86 g, 8.106 mmol) to afford tert-butyl 4-(3-chloro-4-fluorophenyl)-4-(2-oxoethyl)piperidine-1-carboxylate as an oil (2.20 g, 76.2%). $^1$H-NMR (300 MHz, CDCl$_3$) δ 9.45 (t, 1H, J=2.6 Hz), 7.40 (dd, 1H, J=2.4 Hz), 7.28-7.20 (m, 2H), 3.66-3.60 (m, 2H), 3.33-3.25 (m, 2H), 2.68 (s, 2H), 2.24-2.17 (br m, 2H), 1.95-1.82 (m, 2H), 1.45 (s, 9H).

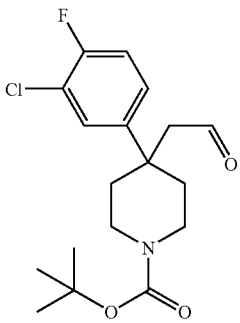

Tert-butyl 4-(3-chloro-4-fluorophenyl)-4-{2-[(1R,5S)-3-(2-methyl-1H-benzimidazol-1-yl)-8-azabicyclo[3.2.1]oct-8-yl]ethyl}piperidine-1-carboxylate was prepared as described in example 16f from the product obtained in previous step (2.20 g, 6.183 mmol) and purified by column chromatography on silica gel, eluting with a gradient of 2-7% methanol in dichloromethane to afford a rigid foam (1.35 g, 61.2%). $^1$H-NMR (300 MHz, CDCl$_3$) δ 7.70 (dd, 1H, J=2, 2.7 Hz), 7.35-7.31 (m, 2H), 7.23-7.11 (m, 4H), 4.72-4.63 (m, 1H), 3.90-3.81 (m, 2H), 3.68-3.63 (br m, 2H), 3.38-3.19 (m, 4H), 3.15-3.00 (m, 1H), 2.61 (s, 3H), 2.55-2.40 (m, 2H), 2.10-1.65 (m, 11H), 1.45 (s, 9H). ES-LCMS m/z 581 (M+H)$^+$.

Endo 1-((1R,5S)-8-{2-[4-(3-chloro-4-fluoro phenyl)piperidin-4-yl]ethyl}-8-azabicyclo[3.2.1]oct-3-yl)-2-methyl-1H-benzimidazole dihydrochloride was prepared and used without additional purification as described in example 16g from the product obtained in previous step (1.35 g, 2.26 mmol) to afford a rigid foam (1.28 g, 100%). ES-LCMS m/z 481 (M+H)$^+$.

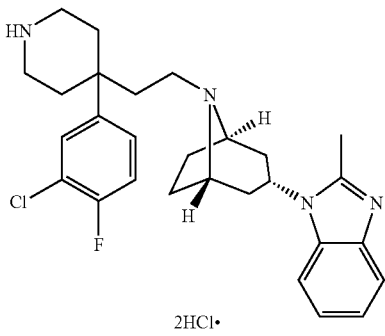

2HCl•

Endo 1-((1R,5S)-8-{2-[4-(3-chloro-4-fluoro phenyl)-1-(2,2-dimethylpropanoyl)piperidin-4-yl]ethyl}-8-azabicyclo[3.2.1]oct-3-yl)-2-methyl-1H-benzimidazole (example 703). Title compound in example 703 was prepared as described in example 16 from endo 1-((1R,5S)-8-{2-[4-(3-chloro-4-fluorophenyl)piperidin-4-yl]ethyl}-8-azabicyclo[3.2.1]oct-3-yl)-2-methyl-1H-benzimidazole dihydrochloride (100 mg, 0.18 mmol), using 3 equivalents of triethylamine and then purified by column chromatography on silica gel, eluting with a gradient of 2-5% methanol in dichloromethane to afford endo 1-((1R,5S)-8-{2-[4-(3-chloro-4-fluorophenyl)-1-(2,2-dimethylpropanoyl)piperidin-4-yl]ethyl}-8-azabicyclo[3.2.1]oct-3-yl)-2-methyl-1H-benzimidazole as a rigid foam (40 mg, 39.2%). $^1$H-NMR (300 MHz, CDCl$_3$) δ 7.69 (d, 1H, J=6.9 Hz), 7.37-7.31 (m, 2H), 7.18-7.14 (m, 4H), 4.75-4.59 (m, 1H), 3.96-3.90 (m, 2H), 3.40-3.32 (m, 4H), 2.60 (s, 3H), 2.47-2.37 (m, 2H), 2.19-2.16 (m, 2H), 2.12-1.79 (m, 8H), 1.70-1.65 (m, 4H), 1.30 (s, 9H). HRMS m/z (M+H) 565.3109 Cal., 565.3104 Obs.

Example 704

Endo 2-chloro-5-[(4-(3-chloro-4-fluoro phenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide was prepared from endo 1-((1R,5S)-8-{2-[4-(3-chloro-4-fluorophenyl)piperidin-4-yl]ethyl}-8-azabicyclo[3.2.1]oct-3-yl)-2-methyl-1H-benzimidazole dihydrochloride (200 mg, 0.36 mmol) as described in Example 719, purified by column chromatography on silica gel, eluting with a gradient of 0-5% methanol in dichloromethane to afford the title compound as an off white solid (37 mg, 14.6%). $^1$H-NMR (300 MHz, CDCl$_3$) δ 8.14 (s, 1H), 7.69-7.54 (m, 3H), 7.35-7.29 (m, 2H), 7.20-7.15 (m, 4H), 5.41 (br s, 2H), 4.66-4.60 (m, 1H), 4.18-4.10 (m, 1H), 3.51-3.29 (m, 4H), 2.58 (s, 3H), 2.48-2.37 (m, 2H), 2.03-1.67 (m, 15H). HRMS m/z (M+H)$^+$ 698.2135 Cal., 698.2132 Obs.

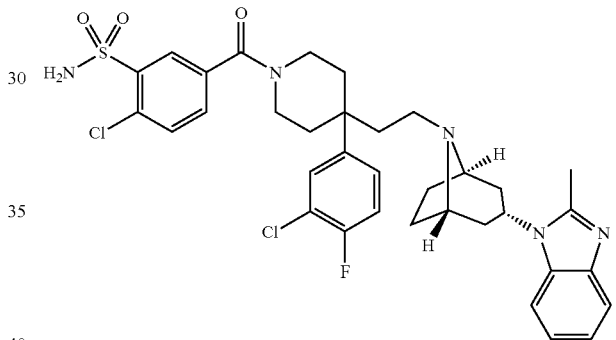

Example 705

Endo 1-[(1R,5S)-8-(2-{1-(2,2-dimethyl propanoyl)-4-[4-(methylthio)phenyl]piperidin-4-yl}ethyl)-8-azabicyclo[3.2.1]oct-3-yl]-2-methyl-1H-benzimidazole was synthesized according to the methods outlined in example 16 with a 4-methylthio instead of a 3-chloro substitution in the phenyl ring.

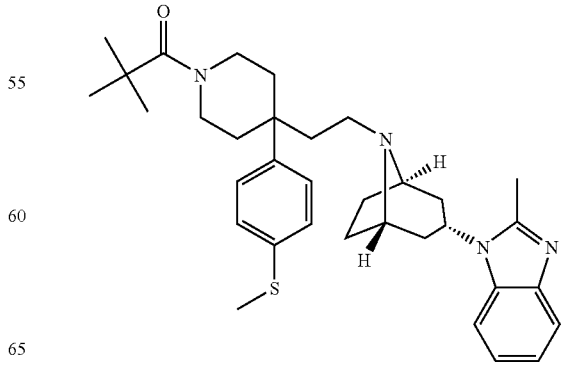

525

Tert-butyl endo 4-{2-[(1R,5S)-3-(2-methyl-1H-benzimidazol-1-yl)-8-azabicyclo[3.2.1]oct-8-yl]ethyl}-4-[4-(methylthio)phenyl]piperidine-1-carboxylate was prepared as described in example 16f (1.15 g, 3.29 mmol scale) and purified by column chromatography on silica gel, eluting with a gradient of 2.5-5% methanol in dichloromethane to afford an oil (1.39 g, 73.5%). $^1$H NMR (300 MHz, CDCl$_3$) δ 7.70 (d, 1H, J=7 Hz), 7.33-7.15 (m, 7H), 4.78-4.65 (m, 1H), 3.75-3.62 (br m, 2H), 3.38-3.31 (br m, 2H), 3.23-3.15 (m, 2H), 2.60 (s, 3H), 2.51 (s, 3H), 2.48-2.39 (m, 4H), 2.21-2.15 (m, 2H), 1.99-1.66 (m, 10H), 1.46 (s, 9H). ES-LCMS m/z 575 (M+H)$^+$.

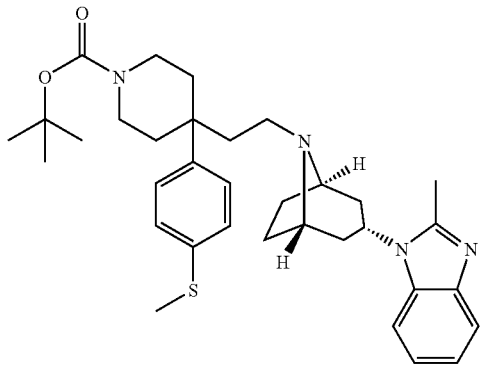

Endo 2-methyl-1-[(1R,5S)-8-(2-{4-[4-(methyl thio)phenyl]piperidin-4-yl}ethyl)-8-azabicyclo[3.2.1]oct-3-yl]-1H-benzimidazole dihydrochloride was prepared and used without further purification as described in example 16g from product from previous step (1.39 g, 2.418 mmol) to afford off white solid (1.03 g, 78%). ES-LCMS m/z 475 (M+H)$^+$.

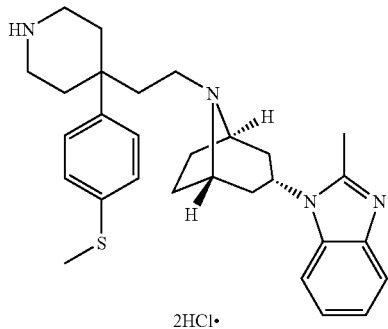

2HCl·

526

Example 705

The title compound in example 705 endo 1-[(1R,5S)-8-(2-{1-(2,2-dimethylpropanoyl)-4-[4-(methyl thio)phenyl]piperidin-4-yl}ethyl)-8-azabicyclo[3.2.1]oct-3-yl]-2-methyl-1H-benzimidazole was prepared as described in example 16 from the product obtained in previous step (100 mg, 0.183 mmol), using 3 equivalents of triethylamine and purified by column chromatography on silica gel, eluting with a gradient of 1-10% methanol in dichloromethane to afford beige solid (100.8 mg, 98.8%). $^1$H-NMR (300 MHz, CDCl$_3$) δ 7.69 (d, 1H, J=7.1 Hz), 7.34-7.18 (m, 7H), 4.71-4.57 (m, 1H), 3.99-3.94 (m, 2H), 3.32-3.25 (m, 4H), 2.59 (s, 3H), 2.52 (s, 3H), 2.45-2.35 (m, 2H), 2.28-2.12 (m, 2H), 1.97-1.89 (m, 5H), 1.83-1.75 (m, 4H), 1.68-1.60 (m, 2H), 1.35 (s, 9H). HRMS m/z (M+H) 559.3471 Cal., 559.3480 Obs.

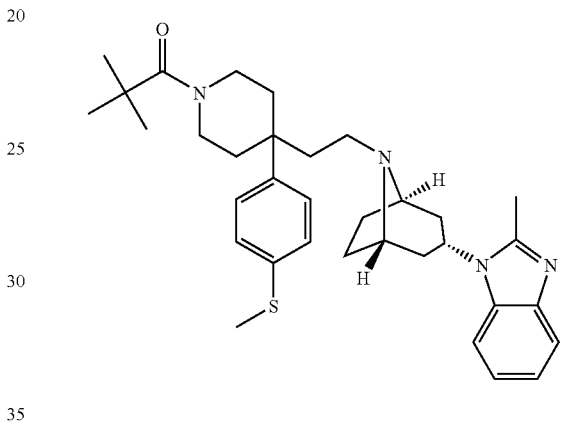

Example 706

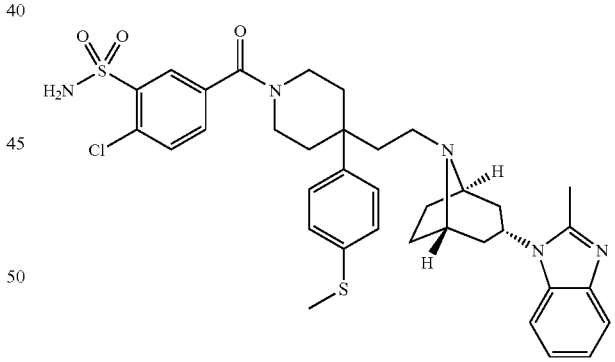

Endo 2-chloro-5-({4-{2-[(1R,5S)-3-(2-methyl-1H-benzimidazol-1-yl)-8-azabicyclo[3.2.1]oct-8-yl]ethyl}-4-[4-(methylthio)phenyl]piperidin-1-yl}carbonyl) benzenesulfonamide was prepared from endo 2-methyl-1-[(1R,5S)-8-(2-{4-[4-(methylthio)phenyl]piperidin-4-yl}ethyl)-8-azabicyclo[3.2.1]oct-3-yl]-1H-benzimidazole dihydrochloride (200 mg, 0.365 mmol) as described in Example 719 and purified by Plate Purification Method A to afford thick oil (61.4 mg, 24.3%). $^1$H-NMR (300 MHz, CDCl$_3$) δ 8.41 (s, 1H), 7.70 (d, 1H, J=7.1 Hz), 7.61-7.53 (m, 2H), 7.31-7.17 (m, 7H), 4.93-4.86 (m, 1H), 4.19-4.15 (m, 1H), 3.57-3.44 (m, 4H), 3.37-3.27 (m, 2H), 2.59 (s, 3H), 2.52

(s, 3H), 2.46-2.00 (m, 8H), 1.96-1.78 (m, 7H). HRMS m/z (M+H)+ 692.2496 Cal., 692.2498 Obs.

Example 707

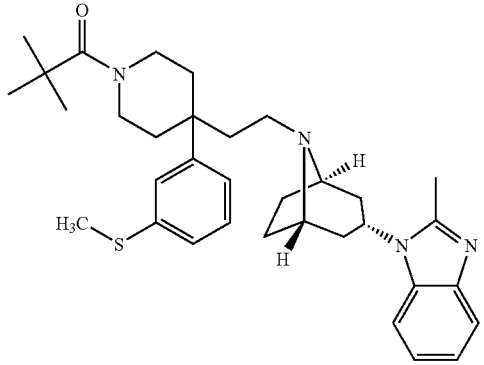

Endo 1-[(1R,5S)-8-(2-{1-(2,2-dimethyl-propanoyl)-4-[3-(methylthio)phenyl]piperidin-4-yl}ethyl)-8-azabicyclo[3.2.1]oct-3-yl]-2-methyl-1H-benzimidazole was synthesized according to the methods described in example 16 with a 3-methylthio instead of a 3-chloro substitution in the phenyl ring.

Tert-butyl 4-[3-(methylthio)phenyl]-4-(2-oxoethyl)piperidine-1-carboxylate was prepared and used without further purification as described in example 16e from respective intermediate described in example 720 (2.11 g, 6.09 mmol) to afford tert-butyl 4-[3-(methylthio)phenyl]-4-(2-oxoethyl)piperidine-1-carboxylate as an oil (1.14 g, 53.5%). ¹H-NMR (300 MHz, CDCl₃) δ 9.41 (t, 1H, J=3 Hz), 7.36-7.26 (m, 1H), 7.17-7.04 (m, 3H), 3.66-3.61 (br m, 2H), 3.32-3.24 (m, 2H), 2.66 (s, 2H), 2.51 (s, 3H), 2.27-2.21 (br m, 2H), 1.91-1.82 (m, 2H), 1.46 (s, 9H).

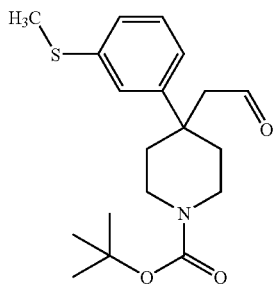

Tert-butyl endo 4-{2-[(1R,5S)-3-(2-methyl-1H-benzimidazol-1-yl)-8-azabicyclo[3.2.1]oct-8-yl]ethyl}-4-[3-(methylthio)phenyl]piperidine-1-carboxylate was prepared as described in example 16f from the product obtained in previous step (1.14 g, 3.26 mmol) and purified by column chromatography on silica gel, eluting with a gradient of 0-5% methanol in dichloromethane to afford a rigid foam (0.70 g, 37.3%). ¹H-NMR (300 MHz, CDCl₃) δ 7.70 (d, 1H, J=7 Hz), 7.34-7.08 (m, 7H), 4.70-4.65 (m, 1H), 3.75-3.65 (br m, 2H), 3.35-3.21 (m, 4H), 2.61 (s, 3H), 2.52 (s, 3H), 2.49-2.41 (m, 2H), 2.24-2.18 (m, 2H), 1.99-1.66 (m, 12H), 1.47 (s, 9H). ES-LCMS m/z 575 (M+H)+.

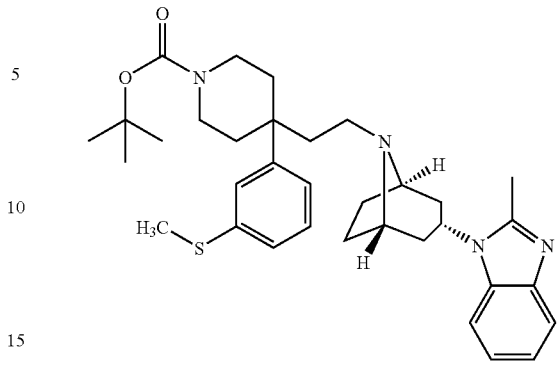

Endo 2-methyl-1-[(1R,5S)-8-(2-{4-[3-(methylthio)phenyl]piperidin-4-yl}ethyl)-8-azabicyclo[3.2.1]oct-3-yl]-1H-benzimidazole dihydrochloride was prepared and used without purification as described in example 16g from the product obtained in previous step (0.70 g, 1.217 mmol) to afford off white solid (0.353 g, 100%).

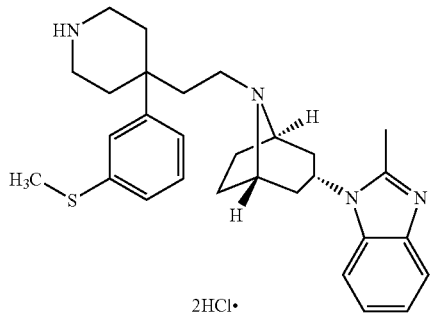

2HCl•

Endo 1-[(1R,5S)-8-(2-{1-(2,2-dimethyl propanoyl)-4-[3-(methylthio)phenyl]piperidin-4-yl}ethyl)-8-azabicyclo[3.2.1]oct-3-yl]-2-methyl-1H-benzimidazole was prepared as described in example 16 from the product obtained in previous step (100 mg, 0.1826 mmol), using 3 equivalents of triethylamine and purified by column chromatography on silica gel, eluting with a gradient of 0-5% methanol in dichloromethane to afford colorless oil (64 mg, 63%). ¹H NMR (300 MHz, CDCl₃) δ 7.69 (d, 1H, J=6.9 Hz), 7.36-7.09 (m, 7H), 4.68-4.60 (m, 1H), 3.98-3.93 (br m, 2H), 3.36-3.29 (m, 4H), 2.60 (s, 3H), 2.53 (s, 3H), 2.46-2.35 (m, 2H), 2.33-2.18 (m, 2H), 1.97-1.60 (m, 12H), 1.29 (s, 9H). HRMS m/z (M+H) 559.3471 Cal., 559.3464 Obs.

example 707

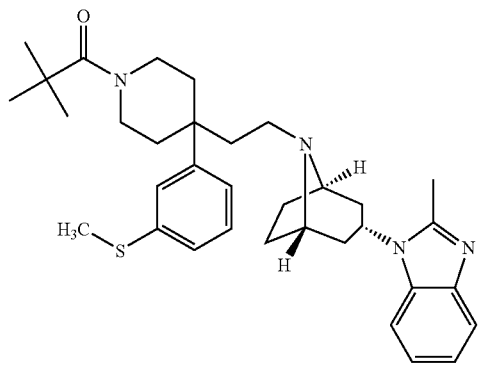

Example 708 endo 2-chloro-5-({4-{2-[(1R,5S)-3-(2-methyl-1H-benzimidazol-1-yl)-8-azabicyclo[3.2.1]oct-8-yl]ethyl}-4-[3-(methylthio)phenyl]piperidin-1-yl}carbonyl)benzene sulfonamide

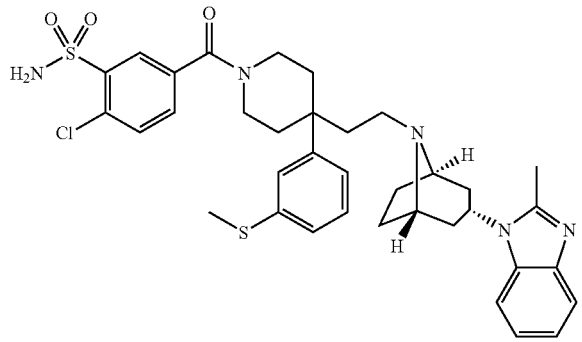

The title compound was prepared as described in Example 719 from dihydrochloride intermediate described in example 707 (200 mg, 0.365 mmol) and purified by column chromatography on silica gel, eluting with a gradient of 3.75-7.50% methanol in dichloromethane with 0.25% ammonium hydroxide to afford white solid (110 mg, 44%). $^1$H-NMR (300 MHz, CDCl$_3$) δ 8.13 (s, 1H), 7.67 (d, 1H, J=6.9 Hz), 7.62-7.52 (m, 2H), 7.37-7.32 (m, 2H), 7.28-7.15 (m, 4H), 7.08 (d, 1H, J=7.6 Hz), 5.44 (br s, 2H), 4.71-4.60 (m, 1H), 4.25-4.18 (br m, 1H), 3.58-3.50 (br m, 1H), 3.40-3.27 (br m, 4H), 2.57 (s, 3H), 2.52 (s, 3H), 2.46-2.36 (m, 3H), 2.25-2.16 (br m, 1H), 2.06-1.62 (m, 12H). HRMS m/z (M+H)$^+$ 692.2496 Cal., 692.2520 Obs.

Example 709 endo 1-((1R,5S)-8-{2-[1-(2,2-dimethylpropanoyl)-4-(4-methylphenyl)piperidin-4-yl]ethyl}-8-azabicyclo[3.2.1]oct-3-yl)-2-methyl-1H-benzimidazole

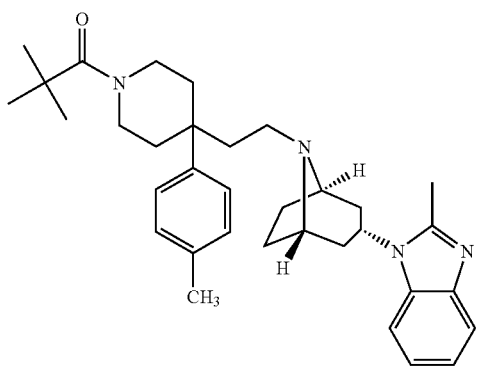

The title compound was synthesized according to the methods described in example 16 with a 4-methyl instead of a 3-chloro substitution in the phenyl ring.

Tert-butyl 4-(1-cyano-2-ethoxy-2-oxoethyl)-4-(4-methylphenyl)piperidine-1-carboxylate

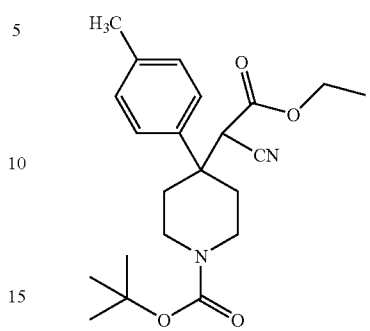

This intermediate was prepared as described in example 16b from 4-bromotoluene (11.97 g, 70 mmol) and using tetrahydrofuran instead of ether as a solvent zand purified by column chromatography on silica gel, eluting with 9:1-6:1 hexane-ethyl acetate to afford oily product (5.32 g, 81%). $^1$H-NMR (300 MHz, CDCl$_3$) δ 7.28-7.20 (m, 4H), 4.03-3.92 (m, 4H), 3.57 (s, 1H), 2.93-2.84 (m, 2H), 2.63-2.51 (br m, 2H), 2.36 (s, 3H), 1.45 (s, 9H), 1.05 (t, 3H, J=7.1 Hz). ES-LCMS m/z 287 (M-BOC+H)$^+$.

[1-(tert-butoxycarbonyl)-4-(4-methylphenyl)piperidin-4-yl](cyano)acetic acid

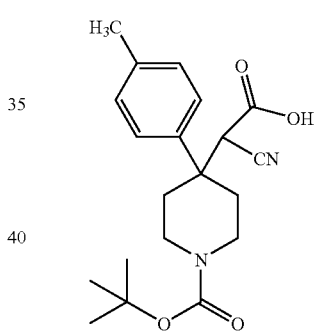

This intermediate was prepared and used without purification as described in example 16c from the product obtained in previous step (5.32 g, 13.76 mmol) to afford rigid foam (4.93 g, 100%). ES-LCMS m/z 259 (M-BOC+H).

Tert-butyl 4-(cyanomethyl)-4-(4-methylphenyl)piperidine-1-carboxylate

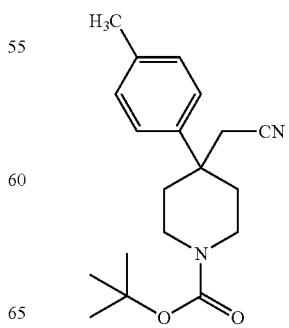

This intermediate was prepared as described in example 16d from the product obtained in previous step (4.93 g, 13.76 mmol) to afford a thick oil (3.51 g, 81%). $^1$H-NMR (300 MHz, CDCl$_3$) δ 7.28-7.21 (m, 4H), 3.80-3.72 (m, 2H), 3.10-3.03 (m, 2H), 2.54 (s, 2H), 2.37 (s, 3H) 2.35-2.31 (m, 2H), 1.89-1.80 (m, 2H), 1.46 (s, 9H). ES-LCMS m/z 215 (M-BOC+H)$^+$.

Tert-butyl 4-(4-methylphenyl)-4-(2-oxoethyl)piperidine-1-carboxylate

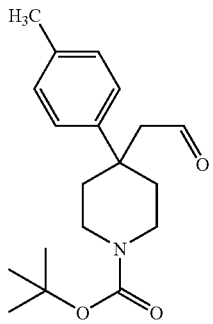

This intermediate was prepared as described in example 16e from the product obtained in previous step (1.55 g, 4.93 mmol) to afford an oil (1.28 g, 82%). $^1$H NMR (300 MHz, CDCl$_3$) δ 9.40 (t, 1H, J=2.9 Hz), 7.28-7.11 (m, 4H), 3.72-3.62 (m, 2H), 3.29-3.20 (m, 2H), 2.63 (s, 2H), 2.54 (s, 3H), 2.36-2.21 (m, 2H), 1.89-1.80 (m, 2H), 1.46 (s, 9H). ES-LCMS m/z 218 (M-BOC+H)$^+$.

Tert-butyl endo 4-{2-[(1R,5S)-3-(2-methyl-1H-benzimidazol-1-yl)-8-azabicyclo[3.2.1]oct-8-yl]ethyl}-4-(4-methylphenyl)piperidine-1-carboxylate

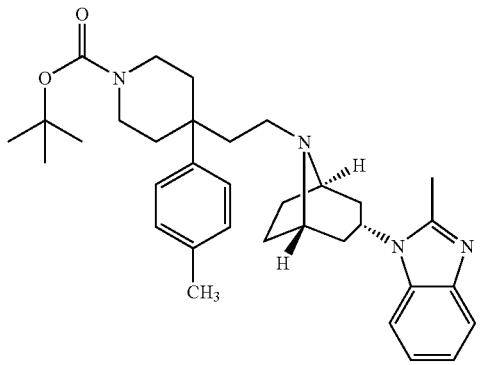

This intermediate was prepared as described in example 16f from the product obtained in previous step (0.60 g, 1.89 mmol) and purified by column chromatography on silica gel, eluting with a gradient of 2-5% methanol in dichloromethane to afford a rigid foam (0.61 g, 59%). $^1$H-NMR (300 MHz, CDCl$_3$) δ 7.70 (d, 1H, J=7.1 Hz), 7.33-7.12 (m, 7H), 4.71-4.65 (m, 1H), 3.75-3.62 (m, 2H), 3.40-3.19 (m, 4H), 2.60 (s, 3H), 2.48-2.25 (m, 2H), 2.36 (s, 3H), 2.22-2.09 (m, 2H), 2.05-1.60 (m, 12H), 1.45 (s, 9H). ES-LCMS m/z 543 (M+H)$^+$.

Endo 2-methyl-1-((1R,5S)-8-{2-[4-(4-methyl phenyl)piperidin-4-yl]ethyl}-8-azabicyclo[3.2.1]oct-3-yl)-1H-benzimidazole dihydrochloride

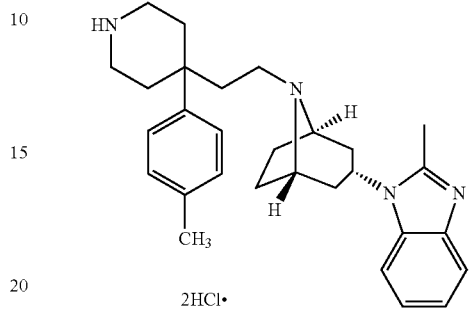

2HCl·

This intermediate was prepared and used without purification, as described in example 16g from the product obtained in previous step (0.61 g, 1.124 mmol) to afford a white solid (0.579 g, 100%).

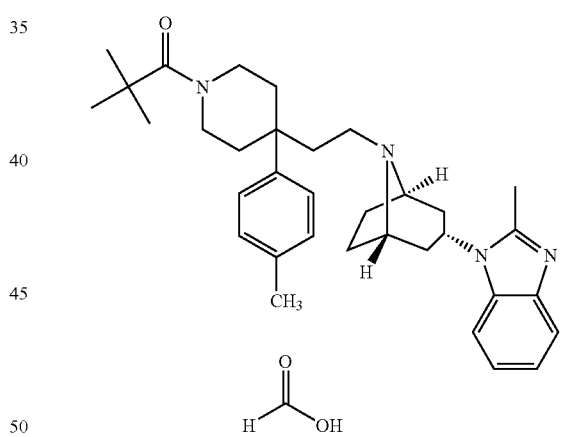

The 1:1 formic acid salt of the title compound from example 709 endo 1-((1R,5S)-8-{2-[1-(2,2-dimethylpropanoyl)-4-(4-methylphenyl)piperidin-4-yl]ethyl}-8-azabicyclo[3.2.1]oct-3-yl)-2-methyl-1H-benzimidazole was prepared as described in example 16 from the product obtained in previous step (100 mg, 0.194 mmol), using 3.2 equivalents of triethylamine and purified by Plate Purification Method A to afford a rigid foam (26.65 mg, 26%). $^1$H-NMR (300 MHz, CDCl$_3$) δ 8.44 (s, 1H), 7.71 (d, J=7.2 Hz, 1H), 7.30-7.16 (m, 7H), 6.20-5.80 (br s, 1H), 4.94-4.88 (m, 1H), 3.98-3.93 (m, 2H), 3.51-3.43 (m, 2H), 3.33-3.20 (m, 2H), 2.64-2.53 (m, 5H), 2.37 (s, 3H), 2.27-1.72 (m, 14H), 1.28 (s, 9H). HRMS m/z (M+H) 527.3750 Cal., 527.3745 Obs.

Example 710

Formic Acid Salt (1:1) of endo methyl 3-{[4-{2-[(1R,5S)-3-(2-methyl-1H-benzimidazol-1-yl)-8-azabicyclo[3.2.1]oct-8-yl]ethyl}-4-(4-methylphenyl)piperidin-1-yl]carbonyl}benzoate To a solution of the dihydrochloride intermediate obtained in Example

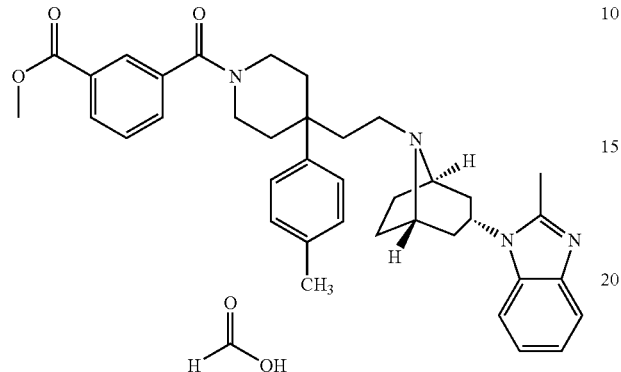

709 (250 mg, 0.485 mmol) in N,N-dimethylformamide (1 ml) was added methylhydrogen isophthalate (87.4 mg, 0.485 mmol), N,N-diisopropylethylamine (0.27 ml, 1.55 mmol) and O-(7-azabenzotriazol-1-yl)-1,1,3,3-tetramethyluronium haxafluorophosphate (184.3 mg, 0.485 mmol). The reaction mixture was stirred at room temperature for 4 h. Quenched by addition of a saturated solution of sodium bicarbonate and extracted with ethyl acetate (3×5 ml). The organic layer was washed with brine and concentrated. The product was purified by column chromatography on silica gel, eluting with a gradient of 2.5-5% methanol in dichloromethane. Further purification was accomplished by Plate Purification Method A to afford a solid product (72.2 mg, 23%).

$^1$H NMR (300 MHz, CDCl$_3$) δ 8.43 (br s, 1H), 8.12-8.05 (m, 2H), 7.71 (d, 1H, J=7.3 Hz), 7.61-7.59 (m, 1H), 7.50 (t, 1H, J=7.6 Hz), 7.30-7.23 (m, 7H), 4.96-4.83 (m, 1H), 4.30-4.17 (m, 1H), 3.94 (s, 3H), 3.89-3.80 (m, 4H), 3.43-3.27 (m, 3H), 2.64-2.52 (m, 2H), 2.59 (s, 3H), 2.38 (s, 3H), 2.35-1.92 (m, 12H). HRMS m/z (M+H)$^+$ 605.3492 Cal., 605.3479 Obs.

Example 711 endo 3-{[4-{2-[(1R,5S)-3-(2-methyl-1H-benzimidazol-1-yl)-8-azabicyclo[3.2.1]oct-8-yl]ethyl}-4-(4-methylphenyl)piperidin-1-yl]carbonyl}benzoic acid

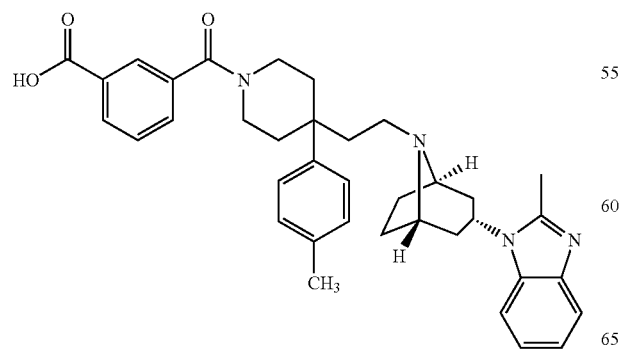

The title compound was prepared as described in example 718 from the product obtained in example 710 (43 mg, 0.0673 mmol) to afford a white solid (35.5 mg, 89.3%). $^1$H-NMR (300 MHz, MeOD) δ 8.15-8.11 (m, 1H), 8.05 (s, 1H), 7.60-7.50 (m, 4H), 7.38-7.19 (m, 6H), 5.23-5.13 (m, 1H), 4.23-4.10 (br m, 2H), 3.61-3.57 (br m, 1H), 3.40-3.28 (m, 4H), 2.80-2.60 (m, 4H), 2.59 (s, 3H), 2.42-2.15 (m, 9H), 2.38 (s, 3H), 2.05-1.75 (m, 2H). HRMS m/z (M+H)$^+$ 591.3335 Cal., 591.3363 Obs.

Example 712 endo 1-((1R,5S)-8-{2-[1-(2,2-dimethylpropanoyl)-4-(4-isopropylphenyl)piperidin-4-yl]ethyl}-8-azabicyclo[3.2.1]oct-3-yl)-2-methyl-1H-benzimidazole

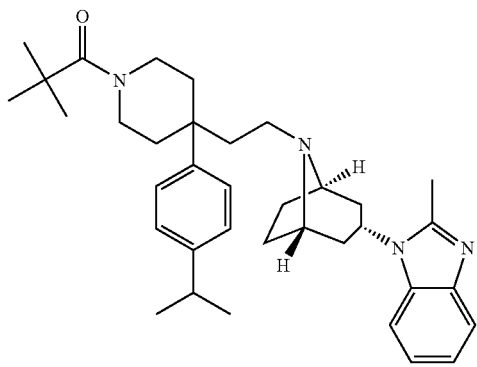

The title compound was synthesized according to the methods outlined in example 16 with a 4-isopropyl instead of a 3-chloro substitution in the phenyl ring.

Tert-butyl 4-(1-cyano-2-ethoxy-2-oxoethyl)-4-(4-isopropylphenyl)piperidine-1-carboxylate

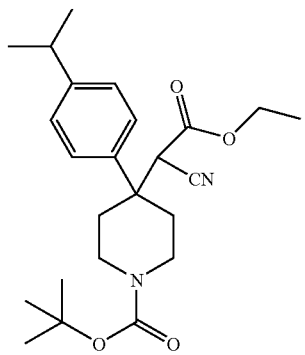

This intermediate was prepared and used without further purification as described in example 16b from 1-bromo-4-isopropylbenzene (10.25 g, 51.48 mmol) and purified by column chromatography on silica gel, eluting with a gradient of 9:1-6:1 hexane-ethyl acetate to afford 3.98 g of oil product (56% yield). ES-LCMS m/z 413 (M+Na)$^+$.

[1-(Tert-butoxycarbonyl)-4-(4-isopropylphenyl)piperidin-4-yl](cyano)acetic acid

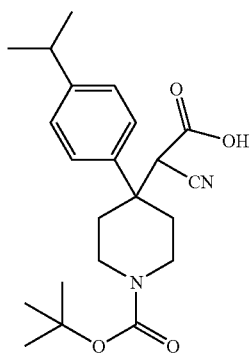

This intermediate was prepared and used without further purification as described in example 16c from the product obtained in previous step (3.98 g, 9.60 mmol) using isopropanol instead of ethanol to afford 3.71 g of oil (100%). ES-LCMS m/z 409 (M+Na)$^+$.

Tert-butyl 4-(cyanomethyl)-4-(4-isopropyl phenyl) piperidine-1-carboxylate

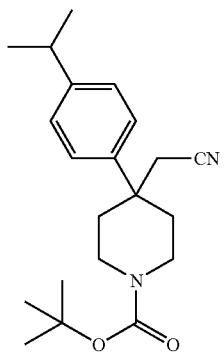

This intermediate was prepared as described in example 16d from the product from previous step (3.71 g, 9.60 mmol) and purified by column chromatography on silica gel, eluting with a gradient of 10-20% ethyl acetate in hexane to afford an oil which solidified upon standing (2.62 g, 78%). $^1$H-NMR (300 MHz, CDCl$_3$) δ 7.26-7.29 (m, 4H), 3.80-3.72 (m, 2H), 3.17-3.05 (m, 2H), 2.94-2.90 (m, 1H), 2.54 (s, 2H), 2.46-2.32 (m, 2H), 1.91-1.81 (m, 2H), 1.46 (s, 9H), 1.28 (s, 3H), 1.26 (s, 3H).

Tert-butyl 4-(4-isopropylphenyl)-4-(2-oxoethyl)piperidine-1-carboxylate

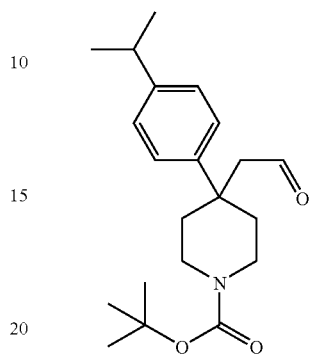

This intermediate was prepared as described in example 16e from the product obtained in previous step (2.62 g, 7.65 mmol) to afford 1.53 g of an oil (58%). $^1$H-NMR (300 MHz, CDCl$_3$) δ 9.40 (t, 1H, J=2.9 Hz), 7.30-7.20 (m, 4H) 3.66-3.61 (br m, 2H), 3.35-3.22 (m, 2H), 2.96-2.87 (m, 1H), 2.64 (d, 2H, J=2.9 Hz), 2.26-2.21 (br m, 2H), 1.90-1.81 (m, 2H), 1.46 (s, 9H) 1.27 (s, 3H), 1.25 (s, 3H). ES-LCMS m/z 368 (M+Na)$^+$.

tert-butyl endo 4-(4-isopropylphenyl)-4-{2-[(1R,5S)-3-(2-methyl-1H-benzimidazol-1-yl)-8-azabicyclo[3.2.1]oct-8-yl]ethyl}piperidine-1-carboxylate. This intermediate was prepared as described in example 16f from the product obtained in previous step (0.30 g, 0.868 mmol) and purified by column chromatography on silica gel, eluting with a gradient of 2-4% methanol in dichloromethane to afford a rigid foam (0.23 g, 60%). $^1$H-NMR (300 MHz, CDCl$_3$) δ 7.69 (d, 1H, J=7 Hz), 7.33-7.19 (m, 7H), 4.75-4.65 (m, 1H), 3.84-3.65 (m, 2H), 3.39-3.22 (m, 4H), 2.96-2.85 (m, 1H), 2.60 (s, 3H), 2.47-2.37 (m, 2H), 2.16-2.09 (m, 2H), 2.05-1.87 (m, 10H), 1.85-1.80 (m, 2H), 1.45 (s, 9H), 1.29 (s, 3H), 1.27 (s, 3H). ES-LCMS m/z 571 (M+H)$^+$.

Endo 1-((1R,5S)-8-{2-[4-(4-isopropylphenyl) piperidin-4-yl]ethyl}-8-azabicyclo[3.2.1]oct-3-yl)-2-methyl-1H-benzimidazole dihydrochloride.

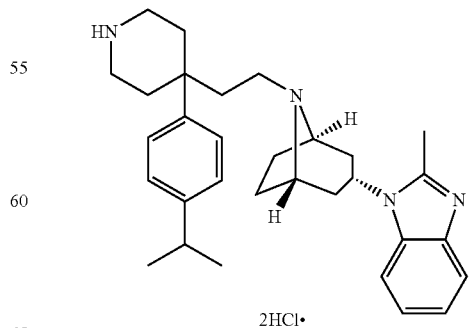

This intermediate was prepared and used without further purification as described in example 16g from the product obtained in previous step (0.23 g, 0.403 mmol) to afford 0.219 g of a white solid (100%). ES-LCMS m/z 443 (M+H)⁺.

Endo 1-((1R,5S)-8-{2-[1-(2,2-dimethyl propanoyl)-4-(4-isopropylphenyl)piperidin-4-yl]ethyl}-8-azabicyclo[3.2.1]oct-3-yl)-2-methyl-1H-benzimidazole (example 712). The title compound was prepared as described in example 16 from the dihydrochloride intermediate from example 711 (70 mg, 0.1287 mmol), using 3.2 equivalents of triethylamine and purified by column chromatography on silica gel, eluting with a gradient of 24% methanol in dichloromethane with 0.1% ammonium hydroxide to afford 49.7 mg of colorless oil. (70%). ¹H-NMR (300 MHz, CDCl₃) δ 7.68 (d, 1H, J=7.0 Hz), 7.33-7.16 (m, 7H), 4.78-4.60 (m, 1H), 3.98-3.93 (m, 2H), 3.36-3.20 (m, 4H), 2.97-2.88 (m, 1H), 2.59 (s, 3H), 2.45-2.35 (m, 2H), 2.24-2.19 (m, 2H), 1.96-1.73 (m, 10H), 1.66-1.64 (m, 2H), 1.29 (s, 9H), 1.28 (s, 3H), 1.26 (s, 3H). HRMS m/z (M+H) 555.4063 Cal., 555.4072 Obs.

Example 713 endo methyl 3-[(4-(4-isopropylphenyl)-4-{2-[(1R, 5S)-3-(2-methyl-1H-benzimidazol-1-yl)-8-azabicyclo[3.2.1]oct-8-yl]ethyl}piperidin-1-yl)carbonyl]benzoate

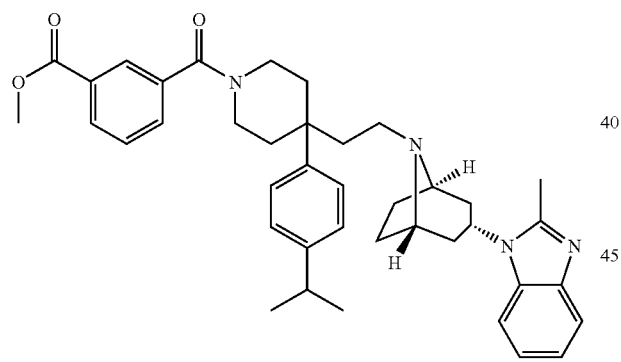

The title compound was prepared as described in example 719 from the dihydrochloride described in example 711 (70 mg, 0.1287 mmol) and methylhydrogen isophthalate (23.2 mg, 0.1287 mmol) and purified by column chromatography on silica gel, eluting with a gradient of 2.5-5% methanol in dichloromethane to afford a beige solid (46 mg, 56.4%). ¹H-NMR (300 MHz, CDCl₃) δ 8.11-8.03 (m, 2H), 7.70 (d, 1H, J=7 Hz), 7.62-7.57 (m, 1H), 7.53-7.48 (m, 1H), 7.33-7.15 (m, 7H), 4.71-4.60 (m, 1H), 4.30-4.20 (br s, 1H), 3.94 (s, 3H), 3.45-3.20 (m, 4H), 2.98-2.89 (m, 1H), 2.57 (s, 3H), 2.45-2.19 (m, 4H), 1.97-1.59 (m, 13H), 1.30 (s, 3H), 1.28 (s, 3H). HRMS m/z (M+H)⁺ 633.3804 Cal., 633.3801 Obs.

Example 714 endo 3-[(4-(4-isopropylphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzoic acid

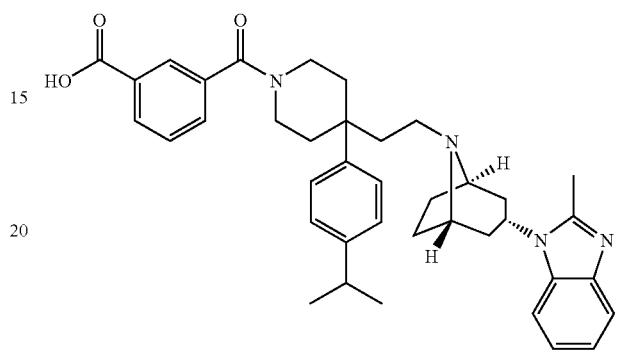

The title compound was prepared as described in example 718 from title compound in example 713 (31 mg, 0.049 mmol) and purified by Plate Purification Method A to afford white solid (10.4 mg, 34.3%). ¹H-NMR (300 MHz, MeOH-d₄) δ 8.31 (s, 1H), 8.14 (t, 1H, J=3.3 Hz), 8.05 (s, 1H), 7.59-7.56 (m, 3H), 7.49 (d, 1H, J=6.7 Hz), 7.37-7.22 (m, 5H), 5.19-5.12 (m, 1H), 4.19-4.15 (br m, 2H), 3.89-3.82 (br m, 2H), 3.59-3.54 (m, 1H), 3.39-3.27 (m, 4H), 2.99-2.88 (m, 1H), 2.77-2.67 (br m, 2H), 2.59-2.45 (m, 2H), 2.56 (s, 3H), 2.37-1.80 (m, 10H), 1.27 (s, 3H), 1.25 (s, 3H). HRMS m/z (M+H)⁺ 619.3648 Cal., 619.3647 Obs.

Example 715 endo 2-chloro-5-[(4-(4-isopropylphenyl)-4-{2-[(1R, 5S)-3-(2-methyl-1H-benzimidazol-1-yl)-8-azabicyclo[3.2.1]oct-8-yl]ethyl}piperidin-1-yl)carbonyl]benzene sulfonamide

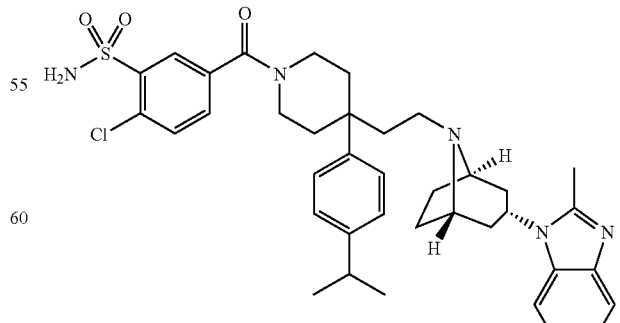

The title compound was prepared as described in Example 719 from dihydrochloride intermediate described in example 711 (100 mg, 0.184 mmol) and purified by column chromatography on silica gel, eluting with a gradient of 24% methanol in dichloromethane with 1% ammonium hydroxide to afford an off white solid (43.2 mg, 34%). $^1$H-NMR (300 MHz, CDCl$_3$) δ 8.13 (s, 1H), 7.67 (d, 1H, J=7 Hz), 7.61-7.52 (m, 3H), 7.33-7.13 (m, 6H), 5.42 (br s, 2H), 4.67-4.61 (m, 1H), 4.24-4.18 (br m, 1H), 3.55-3.42 (br m, 1H), 3.38-3.20 (br m, 4H), 3.00-2.91 (m, 1H), 2.57 (s, 3H), 2.45-2.35 (m, 4H), 2.27-2.21 (br m, 1H), 1.98-1.70 (m, 11H), 1.28 (s, 3H), 1.26 (s, 3H). HRMS m/z (M+H)$^+$ 688.3088 Cal., 688.3079 Obs.

Example 716 endo 1-((1R,5S)-8-{2-[1-(2,2-dimethylpropanoyl)-4-(3-methylphenyl)piperidin-4-yl]ethyl}-8-azabicyclo[3.2.1]oct-3-yl)-2-methyl-1H-benzimidazole

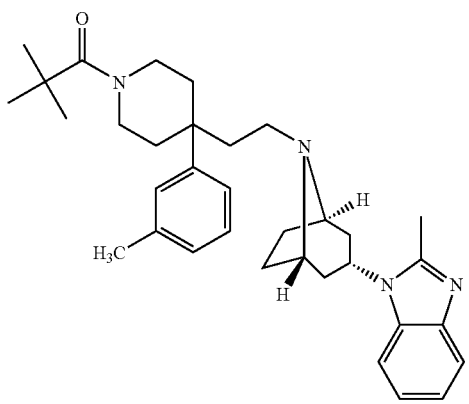

The title compound was synthesized according to the methods outlined in example 16 with a 3-methyl instead of a 3-chloro substitution in the phenyl ring.

Tert-butyl 4-(1-cyano-2-ethoxy-2-oxoethyl)-4-(3-methylphenyl)piperidine-1-carboxylate

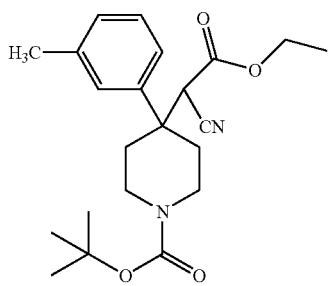

This intermediate was prepared and used without further purification as described in example 16b from 3-bromotoluene (11.97 g, 70 mmol) to afford 6.13 g of an oil (93.4%). ES-LCMS m/z 287 (M-BOC+H)$^+$.

[1-(Tert-butoxycarbonyl)-4-(3-methylphenyl)piperidin-4-yl](cyano)acetic acid

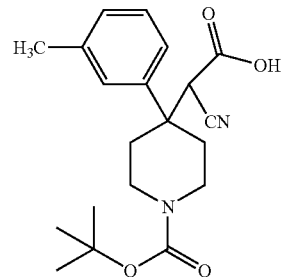

This intermediate was prepared as described in example 16c from the product obtained in previous step (6.13 g, 15.86 mmol) and was used without further purification to afford 5.68 g of an oil (100%). ES-LCMS m/z 259 (M-BOC+H)$^+$.

Tert-butyl 4-(cyanomethyl)-4-(3-methylphenyl) piperidine-1-carboxylate

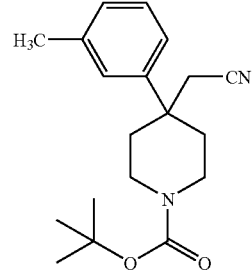

This intermediate was prepared as described in example 16d from the product obtained in previous step (5.68 g, 15.86 mmol) to afford 2.66 g of an oil (2.66 g, 53.3%). $^1$H NMR (300 MHz, CDCl$_3$) δ 7.34-7.28 (m, 1H), 7.18-7.12 (m, 3H) 3.82-3.72 (m, 2H), 3.13-3.04 (m, 2H), 2.55 (s, 2H), 2.39 (s, 3H) 2.37-2.31 (m, 2H), 1.91-1.82 (m, 2H), 1.46 (s, 9H). ES-LCMS m/z 215 (M-BOC+H)$^+$.

Tert-butyl 4-(3-methylphenyl)-4-(2-oxoethyl)piperidine-1-carboxylate

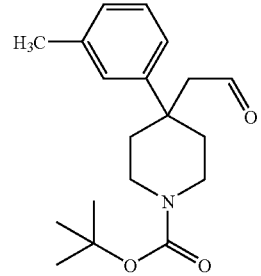

This intermediate was prepared as described in example 16e from the product described in previous step (2.66 g, 8.46 mmol) to afford 2.24 g of an oil (83%). $^1$H-NMR (300 MHz, CDCl$_3$) δ 9.39 (t, 1H, J=2.9 Hz), 7.31-7.28 (m, 1H), 7.20-7.07 (m, 3H), 3.68-3.60 (m, 2H), 3.31-3.22 (m, 2H), 2.64 (s, 2H), 2.38 (s, 3H), 2.27-2.21 (m, 2H), 1.90-1.81 (m, 2H), 1.46 (s, 9H).

Tert-butyl endo-4-{2-[(1R,5S)-3-(2-methyl-1H-benzimidazol-1-yl)-8-azabicyclo[3.2.1]oct-8-yl]ethyl}-4-(3-methylphenyl)piperidine-1-carboxylate.

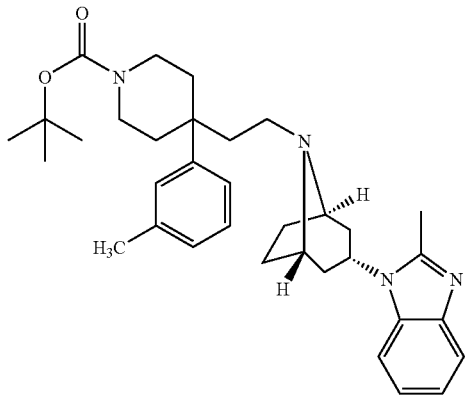

This intermediate was prepared as described in example 16f from the product obtained in previous step (0.60 g, 1.89 mmol) and purified by column chromatography on silica gel, eluting with 5% methanol in dichloromethane to afford 0.58 g of a rigid foam (0.58 g, 57%). $^1$H-NMR (300 MHz, CDCl$_3$) δ 7.70-7.68 (d, 1H, J=7 Hz), 7.34-7.04 (m, 7H), 4.73-4.63 (m, 1H), 3.70-3.66 (m, 2H), 3.30-3.21 (m, 4H), 2.60 (s, 3H), 2.46-2.32 (m, 2H), 2.39 (s, 3H), 2.18-2.09 (m, 2H), 2.00-1.90 (m, 6H), 1.85-1.75 (m, 4H), 1.73-1.60 (m, 2H), 1.44 (s, 9H). ES-LCMS m/z 543 (M+H)$^+$.

Endo 2-methyl-1-((1R,5S)-8-{2-[4-(3-methylphenyl)piperidin-4-yl]ethyl}-8-azabicyclo[3.2.1]oct-3-yl)-1H-benzimidazole dihydrochloride

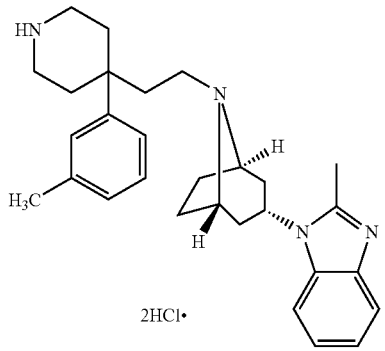

This intermediate was prepared and used without further purification as described in example 16g from the product obtained in previous step (0.58 g, 1.068 mmol) to afford 0.55 g of a white solid (100%). ES-LCMS m/z 443 (M+H)$^+$.

Example 716 endo 1-((1R,5S)-8-{2-[1-(2,2-dimethylpropanoyl)-4-(3-methylphenyl)piperidin-4-yl]ethyl}-8-azabicyclo[3.2.1]oct-3-yl)-2-methyl-1H-benzimidazole

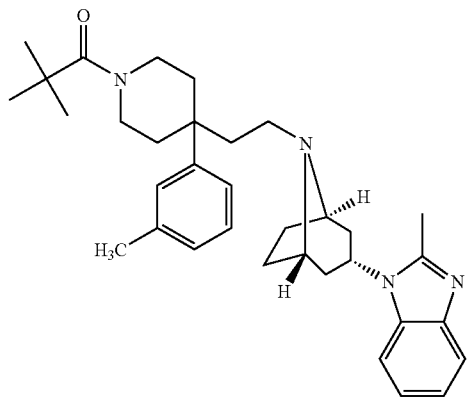

The title compound was prepared as described in example 16 from the product obtained in previous step (100 mg, 0.194 mmol), using 3.2 equivalents of triethylamine to afford 33 mg of a colorless oil (32%). $^1$H NMR (300 MHz, CDCl$_3$) δ 7.69 (d, 1H, J=7.1 Hz), 7.33-7.06 (m, 7H), 4.70-4.50 (m, 1H), 3.99-3.94 (m, 2H), 3.36-3.20 (m, 4H), 2.60 (s, 3H), 2.50-2.35 (m, 2H), 2.40 (s, 3H), 2.24-2.20 (m, 2H), 1.96-1.60 (m, 12H), 1.30 (s, 9H). HRMS m/z (M+H)$^+$ 527.3750 Cal., 527.3769 Obs.

Example 717 endo methyl 3-{[4-{2-[(1R,5S)-3-(2-methyl-1H-benzimidazol-1-yl)-8-azabicyclo[3.2.1]oct-8-yl]ethyl}-4-(3-methylphenyl)piperidin-1-yl]carbonyl}benzoate hydrochloride

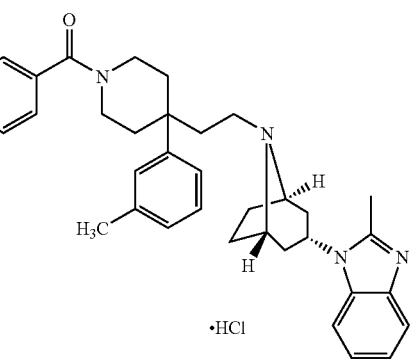

To a solution of methyl hydrogen isophthalate (70 mg, 0.3879 mmol) in dichloromethane (4 ml) was added 1-[3-(dimethylamino)propyl]-3-ethylcarbodiimide hydrochloride (74.36 mg, 0.3879 mmol), 1-hydroxybenzo-triazole (52.42 mg, 0.3879 mmol), endo 2-methyl-1-{8-[2-(4-phenylpiperidin-4-yl)ethyl]-8-azabicyclo[3.2.1]oct-3-yl}-1H-benzimidazole dihydrochloride II (200 mg, 0.3879 mmol) and N,N-diisopropylethylamine (0.225 ml, 1.29 mmol). After stirring at room temperature overnight, 10% citric acid (5 ml) was added to the mixture and extracted with dichloromethane (2×10 ml). The combined organic phase was washed with water (10 ml) and dried over anhydrous sodium sulfate.

After evaporation of the solvent the product was purified by column chromatography on silica gel, eluting with 2% methanol in dichloromethane and then treated with 4M HCl-dioxane solution (1.2 ml) to afford endo methyl 3-{[4-{2-[(1R,5S)-3-(2-methyl-1H-benzimidazol-1-yl)-8-azabicyclo[3.2.1]oct-8-yl]ethyl}-4-(3-methylphenyl)piperidin-1-yl]carbonyl}benzoate hydrochloride as a rigid white foam (94 mg, 38%). $^1$H NMR (300 MHz, CDCl$_3$) δ 12.19 (br s, 1H), 8.11-8.03 (m, 2H), 7.70-7.48 (m, 3H), 7.31-7.11 (m, 7H), 4.69-4.60 (m, 1H), 4.21-4.19 (m, 1H), 3.94 (s, 3H), 3.61-3.29 (m, 3H), 2.58 (s, 3H), 2.43-2.25 (m, 4H), 2.39 (s, 3H), 2.18-2.15 (m, 2H), 1.96-1.76 (m, 10H), 1.67-1.60 (m, 2H). HRMS m/z (M+H)$^+$ 605.3524 Cal., 605.3484 Obs.

Example 718 endo 3-{[4-{2-[(1R,5S)-3-(2-methyl-1H-benzimidazol-1-yl)-8-azabicyclo[3.2.1]oct-8-yl]ethyl}-4-(3-methylphenyl)piperidin-1-yl]carbonyl}benzoic acid

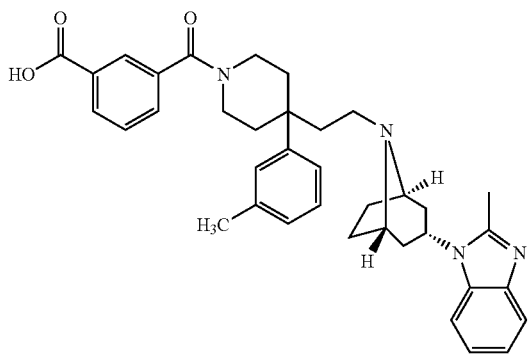

To a solution of the compound obtained in Example 717 (51 mg, 0.0795 mmol) in a 1:1 mixture of diethyl ether-methanol (2 ml), was added a 2M solution of sodium hydroxide (0.3 ml). The reaction mixture was heated at 50° C. for 30 minutes and allowed to cool to room temperature. A solution of 1N hydrochloric acid was added to adjust pH to 5 and the resulting mixture was extracted with dichloromethane (3×5 ml). After drying over sodium sulfate, the solution was concentrated to afford 42.5 mg of a rigid white foam (90.4%). $^1$H-NMR (300 MHz, MeOH-d$_4$) δ 8.12-8.08 (m, 1H), 8.01 (s, 1H), 7.57-7.44 (m, 4H), 7.36-7.15 (m, 5H), 7.10 (d, 1H, J=7.1 Hz), 5.00-4.82 (m, 1H), 4.19-4.15 (m, 1H), 3.58-3.49 (m, 3H), 3.43-3.33 (m, 3H), 2.61-2.40 (m, 2H), 2.55 (s, 3H), 2.38 (s, 3H), 2.27-2.17 (m, 2H), 2.15-1.95 (m, 10H), 1.90-1.78 (m, 2H). HRMS m/z (M+H)$^+$ 591.3313 Cal., 591.3345 Obs.

Example 719 endo 2-chloro-5-{[4-{2-[(1R,5S)-3-(2-methyl-1H-benzimidazol-1-yl)-8-azabicyclo[3.2.1]oct-8-yl]ethyl}-4-(3-methylphenyl)piperidin-1-yl]carbonyl}benzene sulfonamide

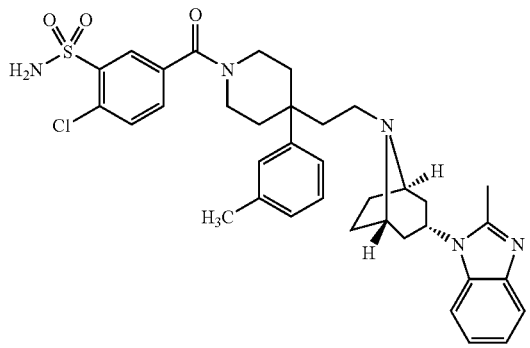

To a solution of endo 2-methyl-1-{8-[2-(4-phenylpiperidin-4-yl)ethyl]-8-azabicyclo[3.2.1]oct-3-yl}-1H-benzimidazole dihydrochloride (200 mg, 0.3879 mmol) in N,N-dimethylformamide (1.5 ml) was added 4-chloro-3-sulfamoylbenzoic acid (91.4 mg, 0.3879 mmol), triethylamine (0.163 ml, 1.1637 mmol) and O-(7-azabenzotriazol-1-yl)-1,1,3,3-tetramethyluronium haxafluorophosphate (162.2 mg, 0.4267). The reaction mixture was stirred at room temperature for 2 h. Water was added until a precipitate formed, after filtration the resulting solid was washed with saturated sodium bicarbonate solution (10 ml) and water (10 ml). The product was purified by column chromatography on silica gel, eluting with 5% methanol in dichloromethane with 0.5% ammonium hydroxide to afford endo 2-chloro-5-{[4-{2-[(1R,5S)-3-(2-methyl-1H-benzimidazol-1-yl)-8-azabicyclo[3.2.1]oct-8-yl]ethyl}-4-(3-methylphenyl) piperidin-1-yl]carbonyl}benzenesulfonamide as a white solid (115 mg, 45%). $^1$H-NMR (300 MHz, CDCl$_3$) δ 7.92-7.83 (m, 1H), 7.74-7.66 (m, 1H), 7.57-7.49 (m, 1H), 7.33-7.07 (m, 8H), 5.44 (br s, 2H), 4.69-4.62 (m, 1H), 4.35-4.23 (m, 1H), 3.42-3.16 (m, 6H), 2.55 (s, 3H), 2.45-2.30 (m, 2H), 2.35 (s, 3H), 2.28-2.18 (m, 1H), 2.05-1.60 (m, 12H). HRMS m/z (M+H)$^+$ 660.2775 Cal., 660.2772 Obs.

Example 720 endo 1-[(1R,5S)-8-(2-{1-(2,2-dimethylpropanoyl)-4-[3-(methylsulfonyl)phenyl]piperidin-4-yl}ethyl)-8-azabicyclo[3.2.1]oct-3-yl]-2-methyl-1H-benzimidazole

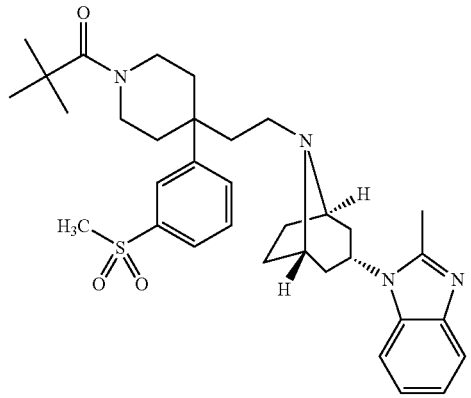

Title compound in example 720 was synthesized according to the methods outlined in example 16 with a 3-methylsulfonyl instead of a 3-chloro substitution in the phenyl ring.

Tert-butyl 4-(1-cyano-2-ethoxy-2-oxoethyl)-4-[3-(methylthio)phenyl]piperidine-1-carboxylate

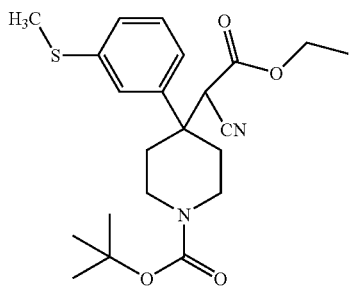

This intermediate was prepared as described in example 16b from 3-bromothioanisole (4.56 g, 22.45 mmol) and using tetrahydrofuran instead of diethyl ether as a solvent and purified by column chromatography on silica gel, eluting with a gradient of 9:1-6:1 hexane-ethyl acetate to afford tert-butyl 4-(1-cyano-2-ethoxy-2-oxoethyl)-4-[3-(methylthio)phenyl]piperidine-1-carboxylate as an oil (1.61 g, 71%). $^1$H NMR (300 MHz, CDCl$_3$) δ 7.37-7.14 (m, 4H), 4.01-3.82 (m, 4H), 3.59 (s, 1H), 2.95-2.87 (m, 2H), 2.62-2.50 (m, 2H), 2.51 (s, 3H) 2.17-1.97 (m, 2H), 1.46 (m, 9H). ES-LCMS m/z 417 (M−H)$^−$.

{1-(tert-butoxycarbonyl)-4-[3-(methylthio) phenyl]piperidin-4-yl}(cyano)acetic acid

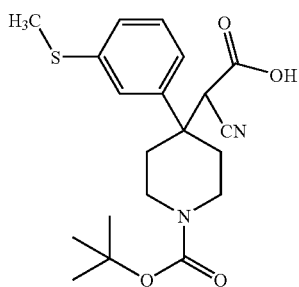

This intermediate was prepared and used without further purification as described in example 16c from the product obtained in previous step (1.61 g, 3.846 mmol) to afford 1.50 g of an oil (100%).

Tert-butyl 4-(cyanomethyl)-4-[3-(methylthio)phenyl]piperidine-1-carboxylate

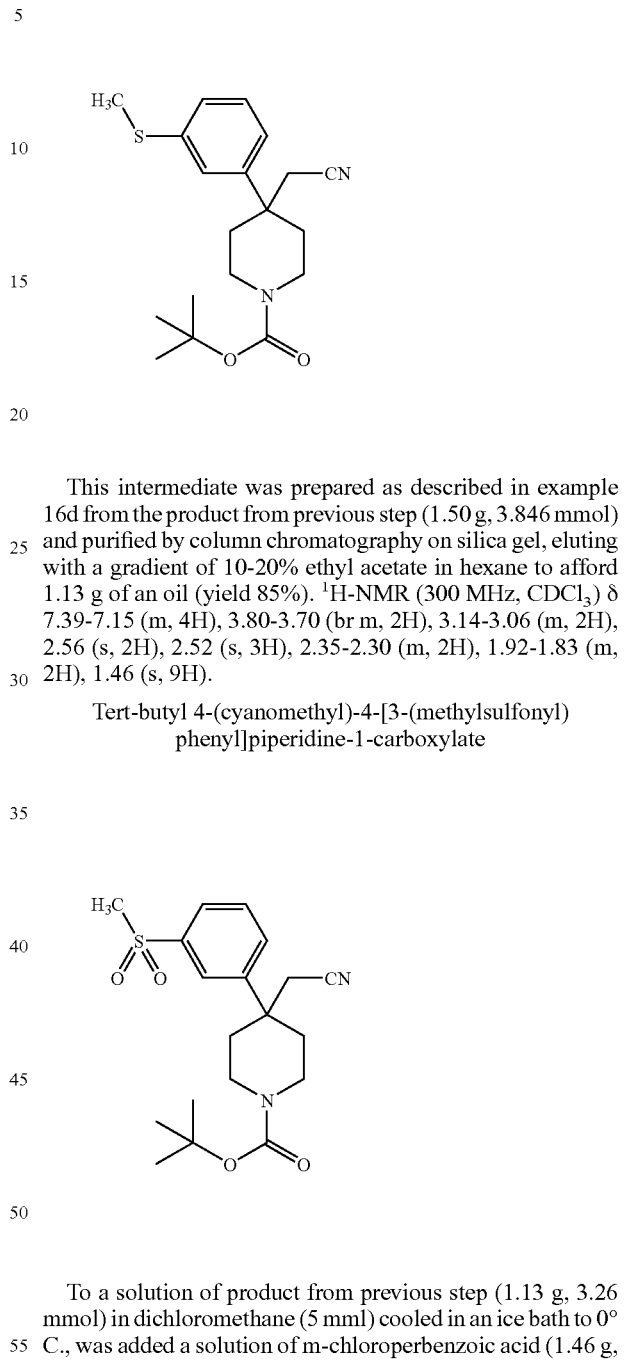

This intermediate was prepared as described in example 16d from the product from previous step (1.50 g, 3.846 mmol) and purified by column chromatography on silica gel, eluting with a gradient of 10-20% ethyl acetate in hexane to afford 1.13 g of an oil (yield 85%). $^1$H-NMR (300 MHz, CDCl$_3$) δ 7.39-7.15 (m, 4H), 3.80-3.70 (br m, 2H), 3.14-3.06 (m, 2H), 2.56 (s, 2H), 2.52 (s, 3H), 2.35-2.30 (m, 2H), 1.92-1.83 (m, 2H), 1.46 (s, 9H).

Tert-butyl 4-(cyanomethyl)-4-[3-(methylsulfonyl)phenyl]piperidine-1-carboxylate

To a solution of product from previous step (1.13 g, 3.26 mmol) in dichloromethane (5 mml) cooled in an ice bath to 0° C., was added a solution of m-chloroperbenzoic acid (1.46 g, 8.48 mmol) in dichloromethane (15 ml) dropwise. The mixture was stirred at 0° C. for 1 h and a 5% solution of sodium thiosulfate in saturated sodium bicarbonate (50 ml) was then added. The resulting mixture was allowed to stir at room temperature for 30 minutes and extracted with dichloromethane (50 ml). The combined organic phase was washed with 1N NaOH (2×30 ml), water (2×20 ml), dried over anhydrous sodium sulfate and concentrated the solvent to afford tert-butyl 4-(cyanomethyl)-4-[3-(methylsulfonyl)phenyl]piperidine-1-carboxylate as a rigid foam (1.05 g, 85%). AP-LCMS m/z 279 (M-BOC+H)$^+$. This material was used without further purification.

547

Tert-butyl 4-[3-(methylsulfonyl)phenyl]-4-(2-oxoethyl)piperidine-1-carboxyla

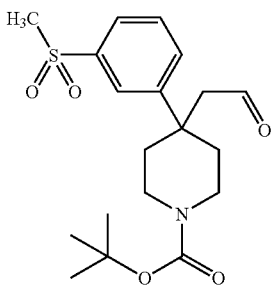

This intermediate was prepared as described in example 16e from the product obtained in previous step (1.05 g, 2.774 mmol) to afford 0.69 g of a rigid foam (yield 65%), which was used further without additional purification. AP-LCMS m/z 282 (M-BOC+H)$^+$.

Tert-butyl endo 4-{2-[(1R,5S)-3-(2-methyl-1H-benzimidazol-1-yl)-8-azabicyclo[3.2.1]oct-8-yl]ethyl}-4-[3-(methylsulfonyl)phenyl]piperidine-1-carboxylate

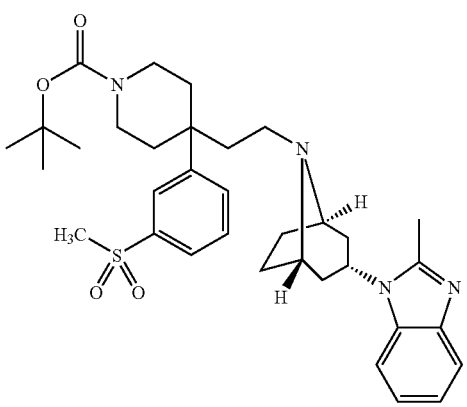

This intermediate was prepared as described in example 16f from the product obtained in previous step (0.69 g, 1.808 mmol) and purified by column chromatography on silica gel, eluting with 5% methanol in dichloromethane to afford 0.37 g of an oil (yield 34%). $^1$H-NMR (300 MHz, CDCl$_3$) δ 7.94 (s, 1H), 7.90-7.83 (m, 1H), 7.70-7.61 (m, 3H), 7.34-7.28 (m, 1H), 7.19-7.14 (m, 2H), 4.68-4.61 (m, 1H), 3.70-3.64 (m, 2H), 3.32-3.21 (m, 4H), 3.10 (s, 3H), 2.61 (s, 3H), 2.50-2.38 (m, 2H), 2.25-2.17 (m, 2H), 2.05-1.78 (m, 8H), 1.70-1.57 (m, 4H), 1.45 (s, 9H). ES-LCMS m/z 607 (M+H)$^+$.

548

Tert-butyl endo 4-{2-[(1R,5S)-3-(2-methyl-1H-benzimidazol-1-yl)-8-azabicyclo[3.2.1]oct-8-yl]ethyl}-4-[3-(methylsulfonyl)phenyl]piperidine-1-carboxylate dihydrochloride

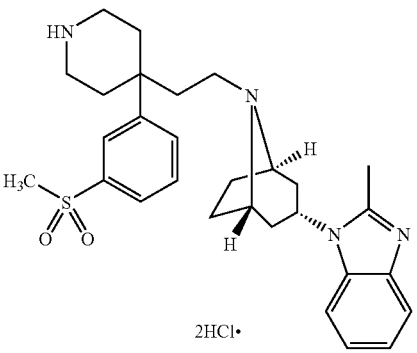

This intermediate was prepared as described in example 16g from the product from previous step (0.37 g, 0.6097 mmol) to afford the dihydrochloride as white solid (0.353 g, 100%). ES-LCMS m/z 507 (M+H)$^+$. This material was used without further purification.

Endo 1-[(1R,5S)-8-(2-{1-(2,2-dimethylpropanoyl)-4-[3-(methylsulfonyl)phenyl]piperidin-4-yl}ethyl)-8-azabicyclo[3.2.1]oct-3-yl]-2-methyl-1H-benzimidazole

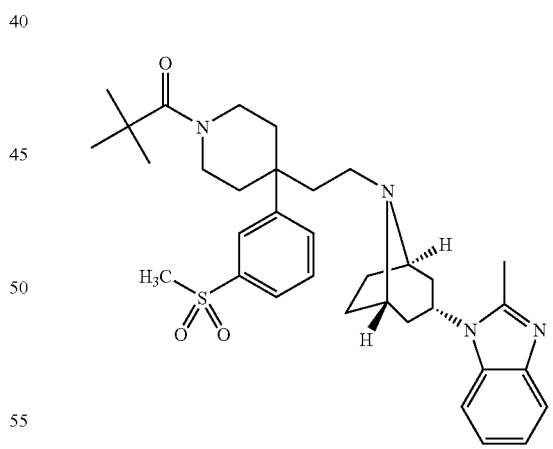

The title compound in example 720 was prepared as described in example 16 from the product obtained in previous step (100 mg, 0.1725 mmol), using 3.2 equivalents of triethylamine to afford 65.4 mg of a colorless oil (yield 64%). $^1$H-NMR (300 MHz, CDCl$_3$) δ 7.94 (s, 1H), 7.88-7.83 (m, 1H), 7.70-7.60 (m, 3H), 7.33-7.28 (m, 1H), 7.20-7.14 (m, 2H), 4.71-4.58 (m, 1H), 3.94-3.88 (m, 2H), 3.51-3.40 (m, 2H), 3.28-3.20 (m, 1H), 3.11 (s, 3H), 2.61 (s, 3H), 2.47-2.37

(m, 2H), 2.30-2.18 (m, 2H), 2.05-1.90 (m, 10H), 1.75-1.58 (m, 3H), 1.41 (s, 9H). HRMS m/z (M+H) 591.3369 Cal., 591.3369 Obs.

Example 721

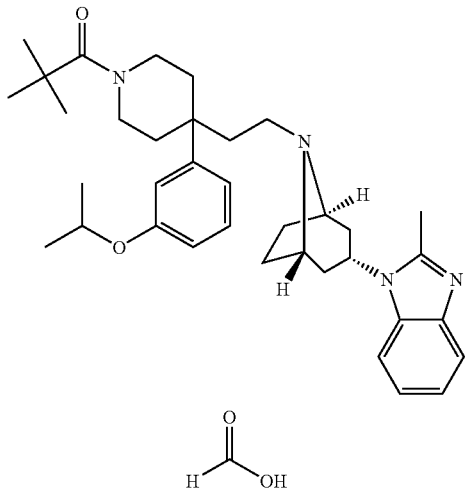

Formic acid salt of endo1-((1R,5S)-8-{2-[1-(2,2-dimethylpropanoyl)-4-(3-isopropoxyphenyl) piperidin-4-yl]ethyl}-8-azabicyclo[3.2.1]oct-3-yl)-2-methyl-1H-benzimidazole (1:1) was synthesized according to the methods outlined in example 16 with a 3-isopropoxy instead of a 3-chloro substitution in the phenyl ring.

Tert-butyl 4-(1-cyano-2-ethoxy-2-oxoethyl)-4-(3-isopropoxyphenyl)piperidine-1-carboxylate

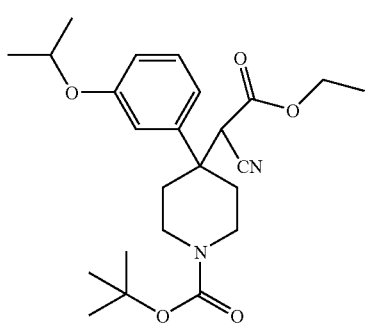

This intermediate was prepared as described in example 16b from 1-bromo-3-isopropoxybenzene (10 g, 46.5 mmol) using tetrahydrofuran instead of diethyl ether as a solvent and purified by column chromatography on silica gel, eluting with a gradient of 9:1-6:1 ethyl acetate in hexane to afford 4.68 g of an oil (yield 70%). ES-LCMS m/z 453 (M+Na)$^+$. This material was used without further purification.

[1-(Tert-butoxycarbonyl)-4-(3-isopropoxyphenyl) piperidin-4-yl](cyano)acetic acid

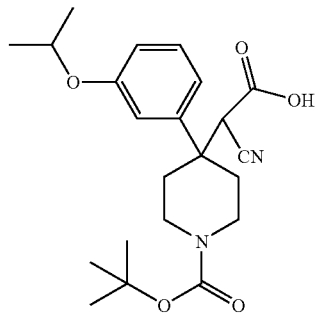

This intermediate was prepared and used without further purification as described in example 16c from the product obtained in previous step (4.68 g, 10.87 mmol) to afford 4.37 g of an oil (yield 100%). ES-LCMS m/z 303 (M-BOC+H)$^+$.

Tert-butyl 4-(cyanomethyl)-4-(3-isopropoxyphenyl) piperidine-1-carboxylate

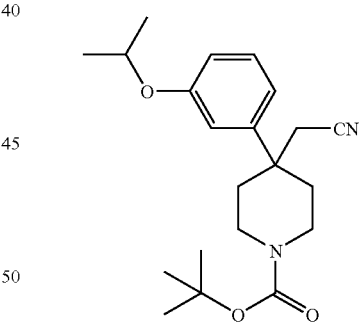

This intermediate was prepared as described in example 16d from the product obtained in previous step (4.37 g, 10.87 mmol) and purified by column chromatography on silica gel, eluting with a gradient of 10-20% ethyl acetate in hexane to afford 2.45 g of an oil (yield 62.5%). $^1$H-NMR (300 MHz, CDCl$_3$) δ 7.32 (t, 1H, J=8 Hz), 6.93 (d, 1H, J=7.9 Hz), 6.89 (s, 1H), 6.83 (d, 1H, J=5.9 Hz), 4.61-4.53 (m, 1H), 3.81-3.72 (br m, 2H), 3.12-3.04 (m, 2H), 2.54 (s, 2H), 2.34-2.29 (m, 2H), 1.89-1.80 (m, 2H), 1.46 (s, 9H), 1.37 (s, 3H), 1.35 (s, 3H). ES-LCMS m/z 259 (M-BOC+H)$^+$.

551

Tert-butyl 4-(3-isopropoxyphenyl)-4-(2-oxoethyl)piperidine-1-carboxylate

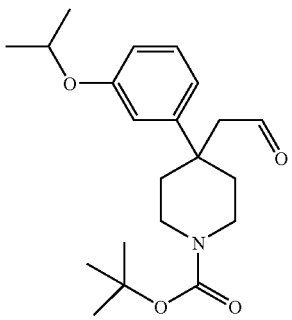

This intermediate was prepared and used without further purification as described in example 16e from the product obtained in previous step (2.45 g, 6.834 mmol) to afford 1.96 g of an oil (yield 79.3%).

Tert-butyl endo 4-(3-isopropoxyphenyl)-4-{2-[(1R,5S)-3-(2-methyl-1H-benzimidazol-1-yl)-8-azabicyclo[3.2.1]oct-8-yl]ethyl}piperidine-1-carboxylate.

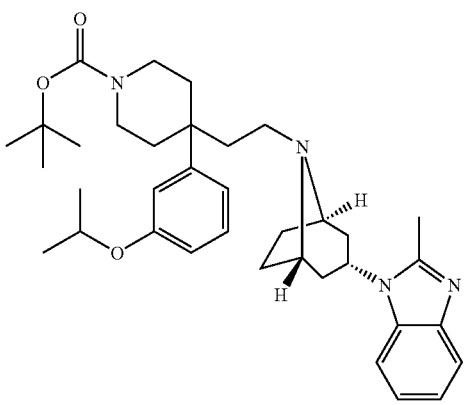

This intermediate was prepared as described in example 16f from the product obtained in previous step (1.96 g, 5.422 mmol) and purified by column chromatography on silica gel, eluting with a gradient of 0-10% methanol in dichloromethane to afford 1.42 g of a rigid foam (yield 46.4%). $^1$H-NMR (300 MHz, CDCl$_3$) δ 7.70 (d, 1H, J=7.2 Hz), 7.30-7.15 (m, 3H), 6.93-6.70 (m, 4H), 4.74-4.61 (br m, 1H), 4.59-4.53 (m, 1H), 3.68-3.64 (br m, 2H), 3.35-3.00 (m, 4H), 2.61 (s, 3H), 2.57-2.41 (m, 2H), 2.20-2.15 (m, 2H), 2.05-1.60 (m, 12H), 1.46 (s, 9H), 1.37 (s, 3H), 1.35 (s, 9H).

552

Endo 1-((1R,5S)-8-{2-[4-(3-isopropoxyphenyl) piperidin-4-yl]ethyl}-8-azabicyclo[3.2.1]oct-3-yl)-2-methyl-1H-benzimidazole dihydrochloride

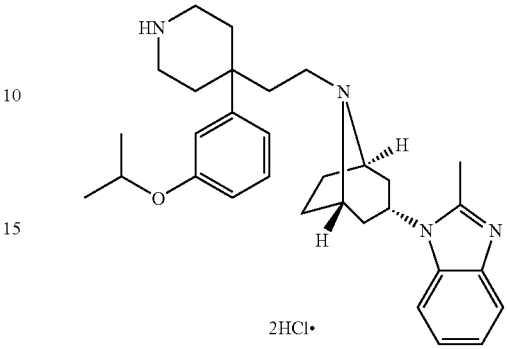

This intermediate was prepared and used without purification as described in example 16g from the product obtained in previous step (1.42 g, 2.42 mmol) to afford 1.32 g of a rigid foam (yield 97.5%). ES-LCMS m/z 487 (M+H)$^+$.

Formic acid salt of endo 1-((1R,5S)-8-{2-[1-(2,2-dimethylpropanoyl)-4-(3-isopropoxyphenyl) piperidin-4-yl]ethyl}-8-azabicyclo[3.2.1]oct-3-yl)-2-methyl-1H-benzimidazole.

The title compound in example 721 was prepared as described in example 16 from the product obtained in previous step (100 mg, 0.179 mmol), using 3 equivalents of triethylamine and purified by Plate Purification Method A to afford 21.2 mg of a colorless oil (yield 21%). $^1$H-NMR (300 MHz, CDCl$_3$) δ 8.46 (s, 1H), 7.70 (d, 1H, J=7.2 Hz), 7.32-7.15 (m, 4H), 6.93-6.78 (m, 3H), 4.85-4.76 (m, 1H), 4.62-4.54 (m, 1H), 3.98-3.93 (br m, 2H), 3.46-3.40 (br m, 2H), 3.36-3.28 (m, 2H), 2.60 (s, 3H), 2.57-2.46 (m, 2H), 2.21-1.73 (m, 14H), 1.39 (s, 3H), 1.37 (s, 3H), 1.30 (s, 9H). HRMS m/z (M+H) 571.4012 Cal., 571.4014 Obs.

Example 722

Formic Acid Salt (1:1) of endo 2-chloro-5-[(4-(3-isopropoxyphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

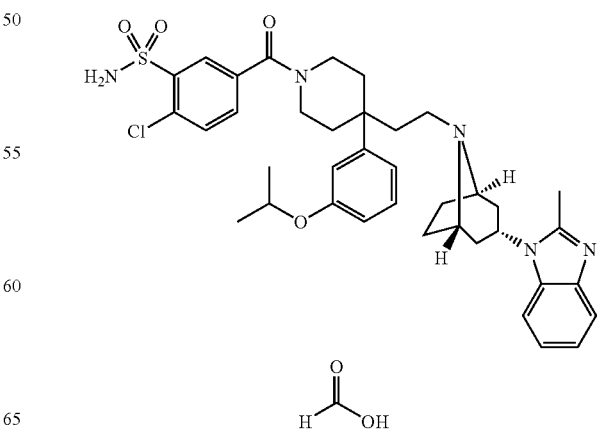

The title compound in example 722 was prepared as described in Example 719 from dihydrochloride described in example 721 (200 mg, 0.357 mmol) and purified by Plate Purification Method A to afford a 1:1 salt of a formic acid and endo 2-chloro-5-[(4-(3-isopropoxyphenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide as an off-white solid (34 mg, 13%). $^1$H-NMR (300 MHz, CDCl$_3$) δ 8.41 (br s, 1H), 8.13 (s, 1H), 7.70 (d, 1H, J=7.2 Hz), 7.62-7.53 (m, 1H), 7.59 (s, 1H), 7.34-7.24 (m, 2H), 7.20-7.15 (m, 2H), 6.87-6.80 (m, 3H), 4.83-4.77 (m, 1H), 4.65-4.52 (m, 1H), 4.22-4.19 (br m, 1H), 3.50-3.27 (m, 4H), 2.59 (s, 3H), 2.56-2.46 (m, 2H), 2.20-1.83 (m, 15H), 1.80-1.75 (m, 2H), 1.37 (s, 3H), 1.35 (s, 3H). HRMS m/z (M+H)$^+$ 704.3037 Cal., 704.3055 Obs.

Example 723 endo 3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzonitrile

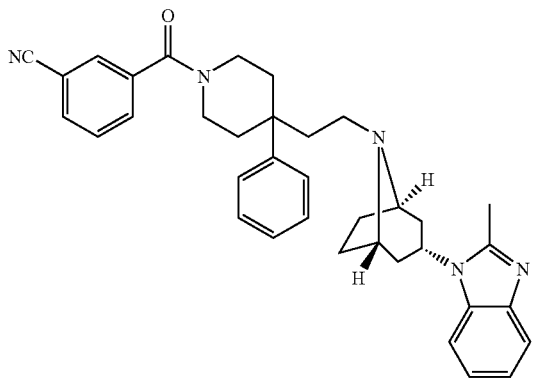

To a solution of 1,1'-carbonyldiimidazole (68.1 mg, 0.42 mmol) and 3-cyanobenzoic acid (51.5 mg, 0.35 mmol) in dichloromethane (6 ml) was added endo 2-methyl-1-{8-[2-(4-phenylpiperidin-4-yl)ethyl]-8-azabicyclo[3.2.1]oct-3-yl}-1H-benzimidazole II and converted to the free base (0.15 g, 0.35 mmol). The mixture was stirred at room temperature for 4 h and water (5 ml) was then added. The resultant mixture was extracted with dichloromethane (3×5 ml) and washed with saturated sodium bicarbonate (1×5 ml) and brine (1×5 ml). After drying over sodium sulfate, the solution was concentrated and purified by column chromatography on silica gel, eluting with 5% methanol in dichloro-methane to afford 70 mg of a colorless oil (yield 36%). $^1$H NMR (300 MHz, CDCl$_3$) δ 7.74-7.22 (m, 11H), 7.20-7.13 (m, 2H), 4.69-4.55 (m, 1H), 4.30-4.20 (br m, 1H), 3.40-3.19 (m, 4H), 2.58 (s, 3H), 2.44-2.37 (m, 3H), 2.34-2.06 (br m, 1H), 1.96-1.84 (m, 11H), 1.65-1.60 (m, 2H). HRMS m/z (M+H) 558.3166 Cal., 558.3252 Obs.

Example 724 endo 2-methyl-1-[(1R,5S)-8-(2-{4-phenyl-1-[3-(2H-tetraazol-5-yl)benzoyl]piperidin-4-yl}ethyl)-azabicyclo[3.2.1]oct-3-yl]-1H-benzimidazole

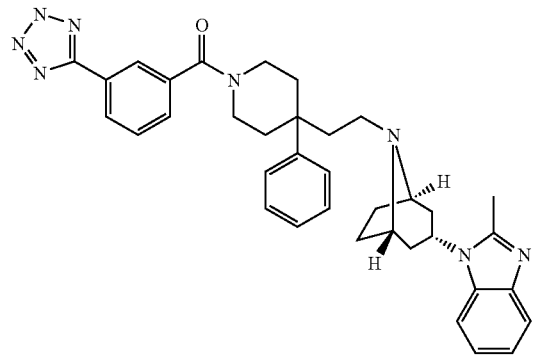

To a solution of title compound from example 723 (40 mg, 0.0717 mmol) in toluene (4 ml)) was added trimethylsilylazide (24.77 mg, 0.215 mmol) and dibutyltin oxide (16.18 mg, 0.065 mmol), the mixture was heated to reflux for 15 h, diluted with dichloromethane (20 ml), dried over sodium sulfate and concentrated. The crude product was purified by column chromatography on silica gel, eluting with a gradient of 5-20% methanol in dichloromethane to afford endo 2-methyl-1-[(1R,5S)-8-(2-{4-phenyl-1-[3-(2H-tetraazol-5-yl)benzoyl]piperidin-4-yl}ethyl)-8-azabicyclo[3.2.1]oct-3-yl]-1H-benzimidazole as a solid (36 mg, 84%). $^1$H-NMR (300 MHz, MeOD) δ 8.18 (d, 1H, J=7.8 Hz), 8.11 (s, 1H), 7.61-7.55 (m, 2H), 7.50-7.42 (m, 6H), 7.33-7.22 (m, 3H), 5.01-4.82 (m, 1H), 4.35-4.20 (br m, 1H), 3.85-3.80 (br m, 2H), 3.70-3.65 (br m, 1H), 3.32-3.27 (m, 2H), 2.73-2.63 (m, 2H), 2.57 (s, 3H), 2.53-2.50 (m, 1H), 2.48-2.37 (m, 1H), 2.31-1.86 (m, 12H). HRMS m/z (M+H) 601.3211 Cal., 601.387 Obs.

Example 725 endo N'-hydroxy-3-[(4-{2-[(1R,5S)-3-(2-methyl-1H-benzimidazol-1-yl)-8-azabicyclo[3.2.1]oct-8-yl]ethyl}-4-phenylpiperidin-yl)carbonyl]benzenecarboximidamide

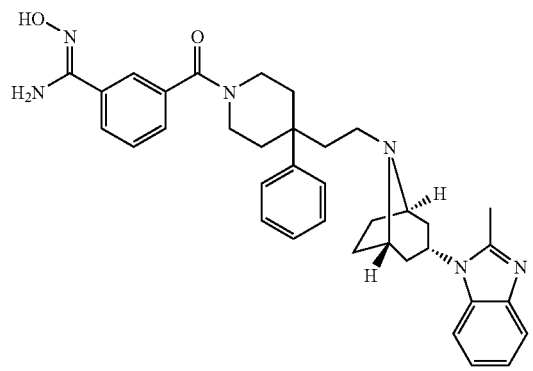

To a suspension of hydroxylamine hydrochloride (1.706 g, 24.55 mmol) in a 9:1 mixture of methanol-water (8 ml) was added triethylamine (3.42 ml, 24.55 mmol), followed by the title compound from example 723 (2.74 g, 4.91 mmol). After heating to reflux for 1 h, a solid which precipitated was collected by filtration to afford endo N'-hydroxy-3-[(4-{2-[(1R,5S)-3-(2-methyl-1H-benzimidazol-1-yl)-8-azabicyclo[3.2.1]oct-8-yl]ethyl}-4-phenylpiperidin-yl)carbonyl]benzenecarboximidamide (1.49 g, 51.3%). $^1$H NMR (300 MHz, DMSO-$d_6$) δ 9.71 (s, 1H), 7.75 (d, 1H, J=7.6 Hz), 7.66 (s, 1H), 7.51-7.35 (m, 8H), 7.26-7.21 (m, 1H), 7.15-7.07 (m, 2H), 5.88 (s, 2H), 4.57-4.51 (br m, 1H), 3.91-3.83 (br m, 1H), 3.50-3.40 (m, 2H), 3.26-3.16 (br m, 3H), 2.44 (s, 3H), 2.38-2.32 (m, 2H), 2.13-2.09 (br m, 2H), 1.85-1.73 (m, 10H), 1.61-1.58 (br m, 2H). HRMS m/z (M+H) 591.3448 Cal., 591.3458 Obs.

Example 726 endo 2-methyl-1-[(1R,5S)-8-(2-{1-[3-(2-oxido-3H-1,2,3,5-oxathiadiazol-4-yl)benzoyl]-4-phenylpiperidin-4-yl}ethyl)-8-azabicyclo[3.2.1]oct-3-yl]-1H-benzimidazole

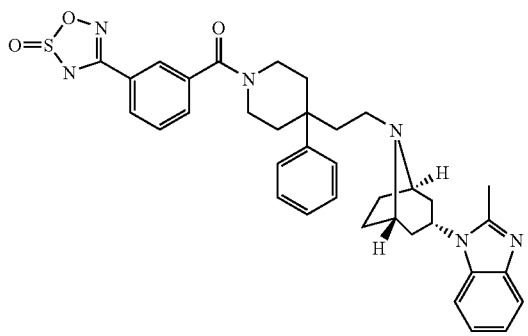

The title compound was prepared (based on procedure from Yasuhisa Kohara, Keiji Kubo, Eiko Imamiya, Takeo Wada, Yoshiyuki Inada and Takehiko Naka, "Synthesis and Angiotensin II Receptor Antagonistic Activities of Benzimidazole Derivatives Bearing Acidic Heterocycles as Novel Tetrazole Bioisosteres." *J. Med. Chem.*, 39, 5228-5235 (1996)) from the product obtained in example 725 (200 mg, 0.339 mmol) and purified by column chromatography on silica gel, eluting with a gradient of 2.5-15% methanol in dichloromethane to afford endo 2-methyl-1-[(1R,5S)-8-(2-{1-[3-(2-oxido-3H-1,2,3,5-oxathiadiazol-4-yl)benzoyl]-4-phenylpiperidin-4-yl}ethyl)-8-azabicyclo[3.2.1]oct-3-yl]-1H-benzimidazole as a white solid (41 mg, 19%). $^1$H-NMR (300 MHz, MeOH-d4) δ 8.02 (d, 1H, J=7.3 Hz), 7.96 (s, 1H), 7.60-7.43 (m, 8H), 7.34-7.23 (m, 3H), 4.98-4.89 (m, 1H), 4.30-4.24 (br m, 1H), 3.87-3.84 (br m, 2H), 3.71-3.63 (br m, 1H), 3.36-3.25 (m, 3H), 2.73-2.40 (m, 5H), 2.61 (s, 3H), 2.31-1.92 (m, 9H). HRMS m/z (M+H) 637.2961 Cal., 637.2974 Obs.

Example 727 endo 3-{3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}-1,2,4-thiadiazol-5(4H)-one

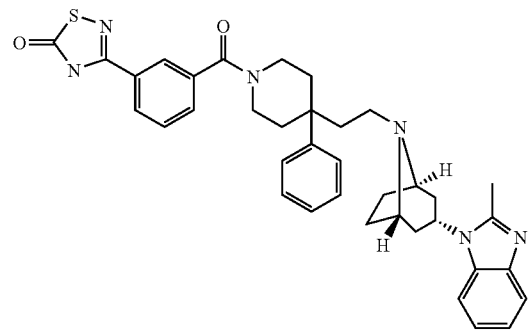

The title compound in example 727 was prepared (based on procedure from Yasuhisa Kohara, Keiji Kubo, Eiko Imamiya, Takeo Wada, Yoshiyuki Inada and Takehiko Naka, "Synthesis and Angiotensin II Receptor Antagonistic Activities of Benzimidazole Derivatives Bearing Acidic Heterocycles as Novel Tetrazole Bioisosteres." *J. Med. Chem.*, 39, 5228-5235 (1996)) from the product obtained in example 725 (300 mg, 0.5078 mmol) and purified by column chromatography on silica gel, eluting with a gradient of 5-10% methanol in dichloromethane to afford endo 3-{3-[(4-(2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl)-1,2,4-thiadiazol-5(4H)-one as a thick oil (57 mg, 17.7%). $^1$H-NMR (300 MHz, MeOH-$d_4$) δ 8.06 (d, 1H, J=7.6 Hz), 8.00 (s, 1H), 7.82 (br s, 2H), 7.61-7.54 (m, 3H), 7.51-7.46 (m, 3H), 7.30-7.21 (m, 3H), 4.89-4.80 (m, 1H), 4.30-4.18 (br m, 1H), 3.75-3.52 (br m, 3H), 3.36-3.32 (m, 3H), 2.58-2.45 (m, 1H), 2.55 (s, 3H), 2.40-1.81 (m, 14H). HRMS m/z (M+H)$^+$ 633.3011 Cal., 633.3013 Obs.

Example 728 endo 3-{3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}-1,2,4-oxadiazole-5(4H)-thione

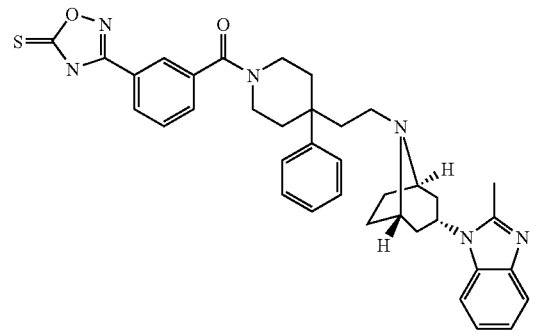

The title compound was prepared (based on procedure from Yasuhisa Kohara, Keiji Kubo, Eiko Imamiya, Takeo Wada, Yoshiyuki Inada and Takehiko Naka, "Synthesis and Angiotensin II Receptor Antagonistic Activities of Benzimidazole Derivatives Bearing Acidic Heterocycles as Novel Tetrazole Bioisosteres." *J. Med. Chem.*, 39, 5228-5235 (1996)) from the product obtained in example 725 (300 mg, 0.5078 mmol) and purified by column chromatography on silica gel, eluting with a gradient of 5-10% methanol in dichloromethane to afford endo 3-{3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}-1,2,4-oxadiazole-5(4H)-thione as a white solid (32 mg, 10%). $^1$H-NMR (300 MHz, MeOH-$d_4$) δ 8.03 (d, 1H, J=7.6 Hz), 7.96 (s, 1H), 7.59-7.42 (m, 8H), 7.39-7.20 (m, 3H), 4.97-4.88 (m, 1H), 4.25-4.18 (br m, 1H), 3.73-3.25 (br m, 6H), 2.68-2.60 (m, 1H), 2.57 (s, 3H), 2.57-1.83 (m, 914H). HRMS m/z (M+H)$^+$ 633.3011 Cal., 633.2999 Obs.

Example 729 exo 1-{(1R,5S)-8-[2-(1-benzoyl-4-phenylpiperidin-4-yl)ethyl]-8-azabicyclo[3.2.1]oct-3-yl}-5-fluoro-2-methyl-1H-benzimidazole

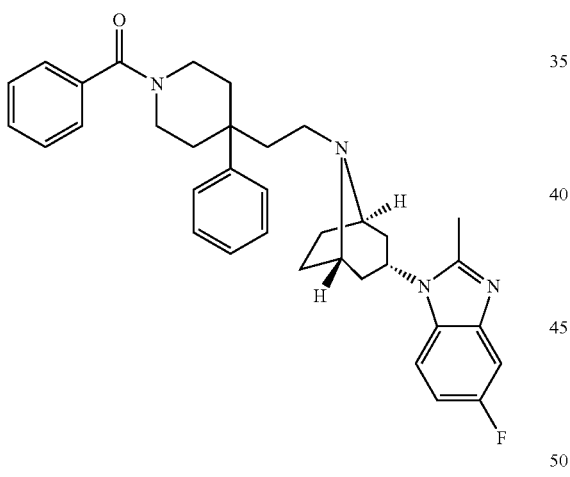

The title compound was prepared from exo 5-fluoro-2-methyl-1-{(1R,5S)-8-[2-(4-phenylpiperidin-4-yl)ethyl]-8-azabicyclo[3.2.1]oct-3-yl}-1H-benzimidazole (200 mg, 0.448 mmol), which was obtained using analogous chemistry to that described in the synthesis of exo1-(8-azabicyclo[3.2.1]oct-3-yl)-2-methyl-1H-benzimidazole as described elsewhere in this application, and benzoyl chloride (75.6 mg, 0.54 mmol). Products were purified by Plate Purification Method A to afford exo 1-{(1R,5S)-8-[2-(1-benzoyl-4-phenylpiperidin-4-yl)ethyl]-8-azabicyclo[3.2.1]oct-3-yl}-5-fluoro-2-methyl-1H-benzimidazole as an oil (1 mg, 0.4%). ES-LC/MS (CLND) m/z 551 (M+H)$^+$.

Example 730 exo 1-{(1R,5S)-8-[2-(1-benzoyl-4-phenylpiperidin-4-yl)ethyl]-8-azabicyclo[3.2.1]oct-3-yl}-5-fluoro-1H-benzimidazole

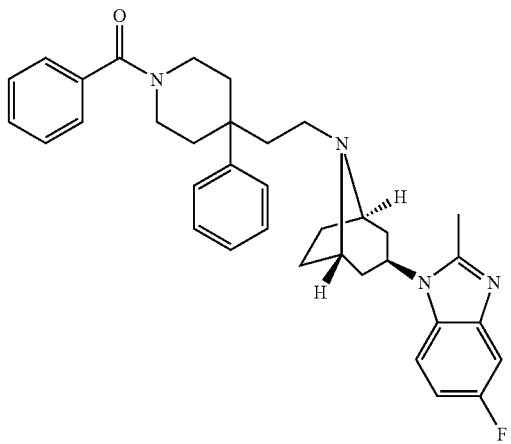

The title compound was prepared as described in example 729 from exo 5-fluoro-1-{(1R,5S)-8-[2-(4-phenylpiperidin-4-yl)ethyl]-8-azabicyclo[3.2.1]oct-3-yl}-1H-benzimidazole (100 mg, 0.231 mmol), which was obtained using analogous chemistry to that described in the synthesis of exo1-(8-azabicyclo[3.2.1]oct-3-yl)-2-methyl-1H-benzimidazole as described elsewhere in this application, and benzoyl chloride (35.7 mg, 0.254 mmol) and purified by Plate Purification Method A to afford exo 1-{(1R,5S)-8-[2-(1-benzoyl-4-phenylpiperidin-4-yl)ethyl]-8-azabicyclo[3.2.1]oct-3-yl}-5-fluoro-1H-benzimidazole as an oil (1 mg, 0.8%). ES-LCMS (CLND) m/z 537 (M+H)$^+$.

Example 731 exo 1-{(1R,5S)-8-[2-(1-benzoyl-4-phenylpiperidin-4-yl)ethyl]-8-azabicyclo[3.2.1]oct-3-yl}-2-methyl-5-(methylsulfonyl)-1H-benzimidazole

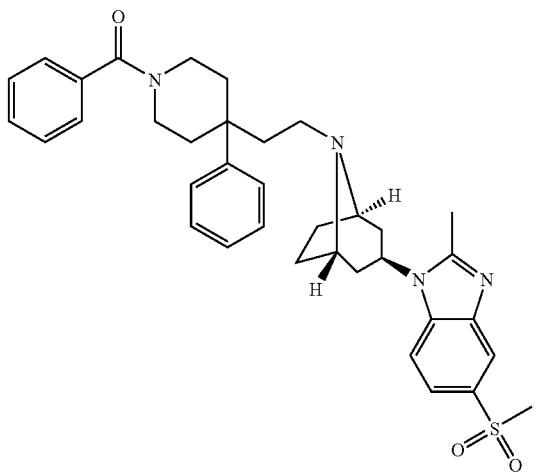

The title compound was prepared from exo 2-methyl-5-(methylsulfonyl)-1-{(1R,5S)-8-[2-(4-phenylpiperidin-4-yl)ethyl]-8-azabicyclo[3.2.1]oct-3-yl}-1H-benzimidazole (100 mg, 0.197 mmol), which was obtained using analogous chemistry to that described in the synthesis of exo-1-(8-azabicyclo[3.2.1]oct-3-yl)-2-methyl-1H-benzimidazole as described elsewhere in this application, and benzoyl chloride (41.5 mg, 0.296 mmol), purified by Plate Purification Method A to afford exo 1-{(1R,5S)-8-[2-(1-benzoyl-4-phenyl piperidin-4-yl)ethyl]-8-azabicyclo[3.2.1]oct-3-yl}-2-methyl-5-(methylsulfonyl) H-benzimidazole as an oil (1 mg, 0.8%). ES-LCMS (CLND) m/z 611 (M+H)+.

Example 732 exo 1-((1R,5S)-8-{2-[1-(cyclopentylcarbonyl)-4-phenylpiperidin-4-yl]ethyl}-8-azabicyclo[3.2.1]oct-3-yl)-2-methyl-5-(methylsulfonyl)-1H-benzimidazle

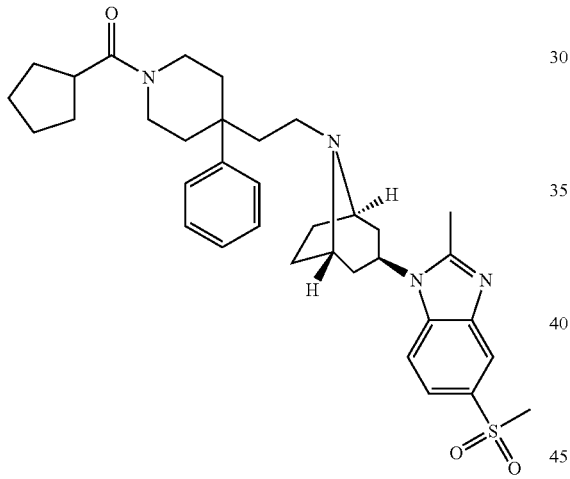

The title compound was prepared from exo 2-methyl-5-(methylsulfonyl)-1-{(1R,5S)-8-[2-(4-phenylpiperidin-4-yl)ethyl]-8-azabicyclo[3.2.1]oct-3-yl}-1H-benzimidazole (100 mg, 0.197 mmol), which was obtained using analogous chemistry to that described in the synthesis of exo-1-(8-azabicyclo[3.2.1]oct-3-yl)-2-methyl-1H-benzimidazole as described elsewhere in this application, and cyclopentane carbonyl chloride (39.2 mg, 0.296 mmol) and purified by Plate Purification Method A to afford exo 1-((1R,5S)-8-{2-[1-(cyclopentyl carbonyl)-4-phenylpiperidin-4-yl]ethyl}-8-azabicyclo[3.2.1]oct-3-yl)-2-methyl-5-(methylsulfonyl)-1H-benzimidazole as an oil (0.9 mg, 0.75%). ES-LCMS (CLND) m/z 603 (M+H)+.

Example 733 exo 1-{(1R,5S)-8-[2-(1-benzoyl-4-phenylpiperidin-4-yl)ethyl]-8-azabicyclo[3.2.1]oct-3-yl}-5-(trifluoromethyl)-1H-benzimidazole

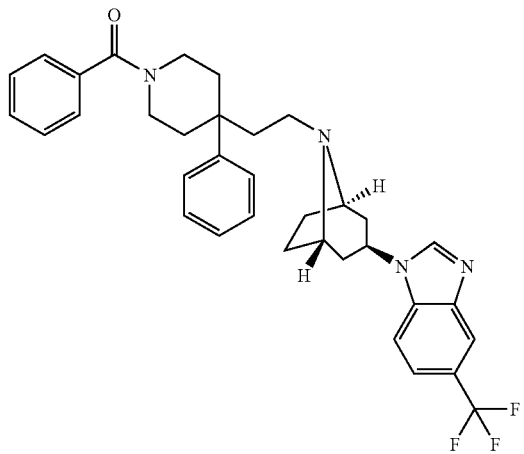

The title compound was prepared from exo 1-{(1R,5S)-8-[2-(4-phenylpiperidin-4-yl)ethyl]-8-azabicyclo[3.2.1]oct-3-yl}-5-(trifluoromethyl)-1H-benzimidazole (110 mg, 0.228 mmol), which was obtained using analogous chemistry to that described in the synthesis of exo 1-(8-azabicyclo[3.2.1]oct-3-yl)-2-methyl-1H-benzimidazole as described elsewhere in this application, and benzoyl chloride (48.1 mg, 0.342 mmol). The crude was purified by Plate Purification Method A to afford exo 1-{(1R,5S)-8-[2-(1-benzoyl-4-phenylpiperidin-4-yl)ethyl]-8-azabicyclo[3.2.1]oct-3-yl}-5-(trifluoromethyl)-1H-benzimidazole as an oil (3.4 mg, 2.5%). ES-LCMS (CLND) m/z 587 (M+H)+.

Example 734 exo 1-((1R,5S)-8-{2-[1-(cyclopentylcarbonyl-4-phenylpiperidin-4-yl]ethyl}-8-azabicyclo[3.2.1]oct-3-yl)-5-(trifluoromethyl)-1H-benzimidazole

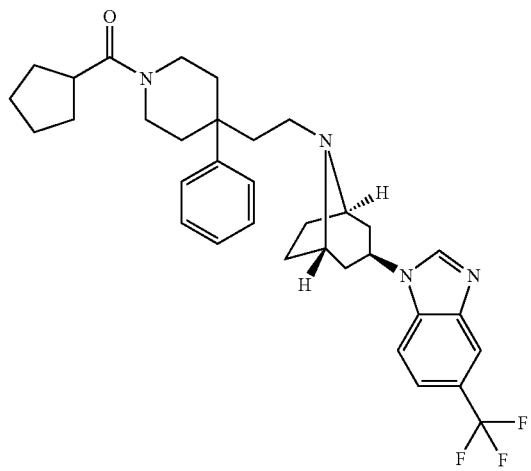

The title compound was prepared from exo 1-{(1R,5S)-8-[2-(4-phenylpiperidin-4-yl)ethyl]-8-azabicyclo[3.2.1]oct-3-yl}-5-(trifluoromethyl)-1H-benzimidazole (110 mg, 0.228 mmol), which was obtained using analogous chemistry to that described in the synthesis of exo 1-(8-azabicyclo[3.2.1]oct-3-yl)-2-methyl-1H-benzimidazole as described elsewhere in this application, and cyclopentane carbonyl chloride (48.1 mg, 0.342 mmol). The crude was purified by Plate Purification Method A to afford exo 1-((1R,5S)-8-{2-[1-(cyclopentylcarbonyl)-4-phenylpiperidin-4-yl]ethyl}-8-azabicyclo[3.2.1]oct-3-yl)-5-(trifluoromethyl)-1H-benzimidazole as an oil (4.8 mg, 3.6%). ES-LCMS (CLND) m/z 579 (M+H)$^+$.

Examples 735-737 were synthesized by deprotecting the Boc-protected intermediate depicted below and acylation via CDI method, described in example 723.

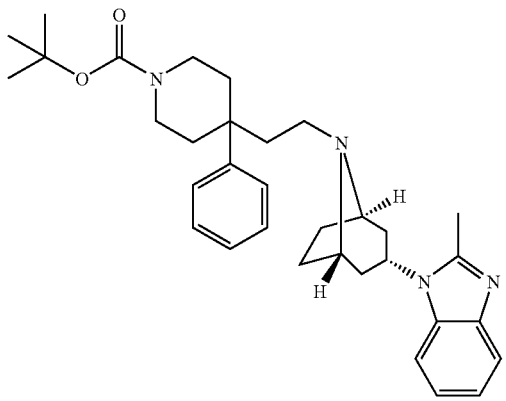

Example 735 endo 1-((1R,5S)-8-{2-[1-(cyclopropylcarbonyl)-4-phenylpiperidin-4-yl]ethyl}-8-azabicyclo[3.2.1]oct-3-yl)-2-methyl-1H-benzimidazole

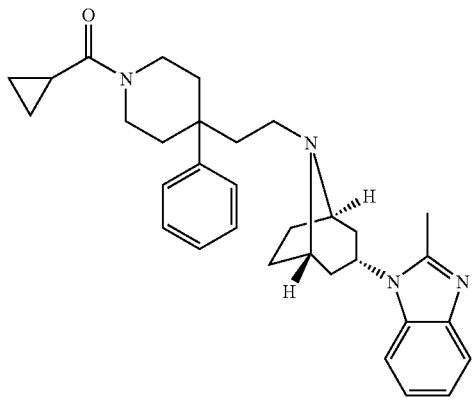

The title compound was prepared as described in example 723 from cyclopropane carboxylic acid (9.3 mg, 0.108 mmol) and purified by column chromatography on silica gel, eluting with a gradient of 2-10% methanol in dichloromethane to afford endo 1-((1R,5S)-8-{2-[1-(cyclopropylcarbonyl)-4-phenylpiperidin-4-yl]ethyl}-8-azabicyclo[3.2.1]oct-3-yl)-2-methyl-1H-benzimidazole as a colorless oil (41 mg, 77%). $^1$H-NMR (300 MHz, DMSO-d$_6$) δ 7.50 (dd, 1H, J=2.8, 2.1 Hz), 7.43-7.35 (m, 4H), 7.25-7.02 (m, 4H), 4.57-4.49 (m, 1H), 3.86-3.76 (m, 2H), 3.38-3.17 (m, 6H), 2.49 (s, 3H), 2.42-2.31 (m, 2H), 2.31-1.77 (m, 10H), 1.65-1.58 (m, 2H), 0.80-0.62 (m, 5H). HRMS m/z (M+H) 497.3280 Cal., 497.3274 Obs.

Example 736 endo 1-((1R,5S)-8-{2-[1-(1H-imidazol-1-ylcarbonyl)-4-phenylpiperidin-4-yl]ethyl}-8-azabicyclo[3.2.1]oct-3-yl)-2-methyl-1H-benzimidazole

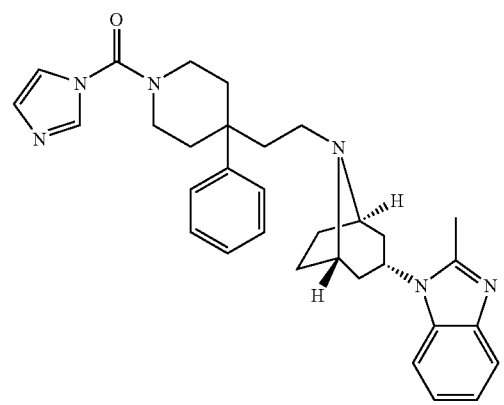

The title compound was prepared as described in example 723 from 2-thiophene carboxylic acid (13.84 mg, 0.108 mmol). The reaction mixture was stirred at room temperature overnight. The crude product was purified by column chromatography on silica gel, eluting with a gradient of 2-10% methanol in dichloromethene to afford endo 1-((1R,5S)-8-{2-[1-(1H-imidazol-1-ylcarbonyl)-4-phenylpiperidin-4-yl]ethyl}-8-azabicyclo[3.2.1]oct-3-yl)-2-methyl-1H-benzimidazole as a colorless oil (28.6 mg, 49.4%). $^1$H-NMR (300 MHz, CDCl$_3$) δ 7.86 (s, 1H), 7.71-7.67 (m, 1H), 7.45-7.39 (m, 2H), 7.33-7.24 (m, 4H), 7.22-7.11 (m, 4H), 4.67-4.62 (m, 1H), 3.91-3.80 (m, 2H), 3.40-3.22 (m, 4H), 2.60 (s, 3H), 2.50-2.34 (m, 4H), 2.10-1.96 (m, 10H), 1.69-1.63 (m, 2H). HRMS m/z (M+H) 523.3185 Cal., 523.3190 Obs.

Example 737 endo 4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzonitrile

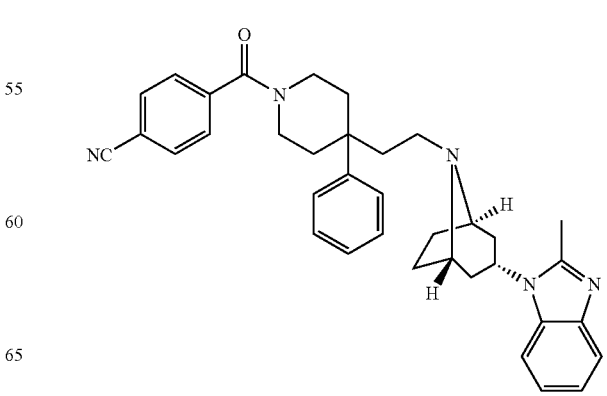

The title compound was prepared as described in example 723 from 4-cyanobenzoic acid (47.53 mg, 0.322 mmol). The reaction mixture was stirred at room temperature overnight. The crude was purified by column chromatography on silica gel, eluting with 3% methanol in dichloromethene to afford endo 4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzonitrile as a colorless oil (58 mg, 32%). $^1$H-NMR (300 MHz, CDCl$_3$) δ 7.74-7.67 (m, 3H), 7.51-7.26 (m, 8H), 7.22-7.13 (m, 2H), 4.65-4.59 (m, 1H), 4.25-4.20 (br m, 1H), 3.55-3.25 (m, 4H), 2.58 (s, 3H), 2.45-2.33 (br m, 3H), 2.21-2.17 (br m, 1H), 1.96-1.80 (m, 11H), 1.76-1.62 (m, 2H). HRMS m/z (M+H) 558.3318 Cal., 558.3237 Obs.

Example 738 endo 2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzonitrile

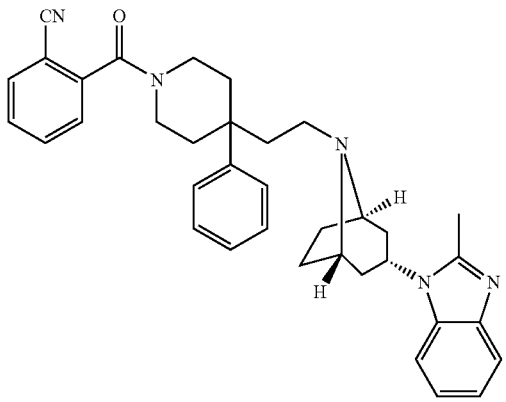

The title compound was prepared as described in example 710 by coupling 2-carboxybenzonitrile (36.5 mg, 0.247 mmol) via HATU (method M) and purified by column chromatography on silica gel, eluting with 5% methanol in dichloromethane to afford endo 2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzonitrile as a rigid foam (66 mg, 48%). $^1$H NMR (300 MHz, CDCl$_3$) δ 7.75-7.65 (m, 3H), 7.56-7.15 (m, 10H), 4.69-4.63 (m, 1H), 4.32-4.27 (br m, 1H), 3.45-3.35 (m, 4H), 2.58 (s, 3H), 2.46-2.38 (m, 3H), 2.20-2.19 (br m, 2H), 2.17-1.82 (m, 10H), 1.75-1.62 (m, 2H). HRMS m/z (M+H) 558.3233 Cal., 558.3226 Obs.

Example 739 endo 2-methyl-1-((1R,5S)-8-{2-[4-phenyl-1-(thien-2-ylcarbonyl)piperidin-4-yl]ethyl}-8-azabicyclo[3.2.1]oct-3-yl)-1H-benzimidazole

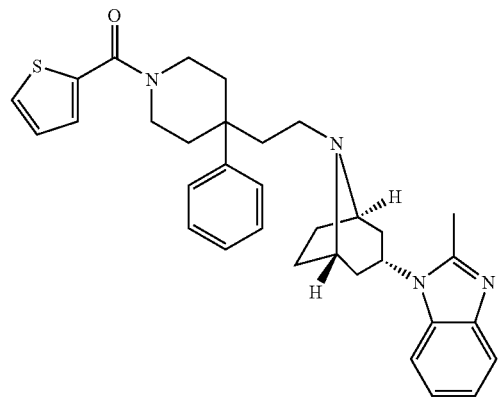

The title compound was prepared from 2-thiophene carboxylic acid (24 mg, 0.186 mmol) using EDCI-HOBT (method P) and purified by column chromatography on silica gel, eluting with 5% methanol in dichloromethane to afford endo 2-methyl-1-((1R,5S)-8-{2-[4-phenyl-1-(thien-2-ylcarbonyl)piperidin-4-yl]ethyl}-8-azabicyclo[3.2.1]oct-3-yl)-1H-benzimidazole as a colorless oil (14 mg, 14%). $^1$H-NMR (300 MHz, CDCl$_3$) δ 7.68-7.67 (d, 1H, J=6.9 Hz), 7.46-7.15 (m, 10H), 7.13-7.04 (m, 1H), 4.66-4.60 (m, 1H), 4.16-4.00 (br m, 2H), 3.50-3.40 (m, 2H), 3.30-3.25 (br m, 2H), 2.58 (s, 3H), 2.42-2.28 (m, 4H), 2.11-1.98 (m, 10H), 1.72-1.63 (m, 2H). HRMS m/z (M+H) 539.2845 Cal., 539.2859 Obs.

Example 740 endo 1-cyclopropyl-2-[1-(8-{2-[1-(cyclopropylcarbonyl)-phenylpiperidine-4-yl]ethyl}-8-azabicyclo[3.2.1]oct-3-yl)-1H-benzimidazol-2-yl]ethanone

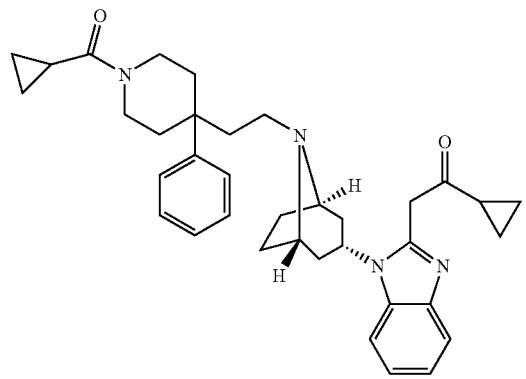

The title compound was prepared as described in Example 3, from cyclopropane carbonyl chloride (12.36 mg, 0.118 mmol), via acid chloride Method Q, to afford endo 1-cyclopropyl-2-[1-(8-{2-[1-(cyclopropylcarbonyl)-4-phenylpiperidine-4-yl]ethyl}-8-azabicyclo[3.2.1]oct-3-yl)-1H-benzimidazol-2-yl]ethanone as an off-white foam (26 mg, 43%).

¹H-NMR (300 MHz, CDCl₃) δ 7.76-7.72 (m, 1H), 7.40-7.34 (m, 5H), 7.33-7.18 (m, 3H), 4.56-4.54 (m, 1H), 4.23-4.19 (m, 2H), 4.15-3.94 (m, 2H), 3.48-3.40 (m, 1H), 3.38-3.26 (m, 3H), 2.42-2.13 (m, 5H), 1.94-1.74 (m, 11H), 1.70-1.62 (m, 2H), 1.13-1.03 (m, 2H), 1.02-0.95 (m, 4H), 0.88-0.75 (m, 2H). HRMS m/z (M+H) 565.3543 Cal., 565.3541 Obs.

Synthesis of Carbamates

Examples 741-743

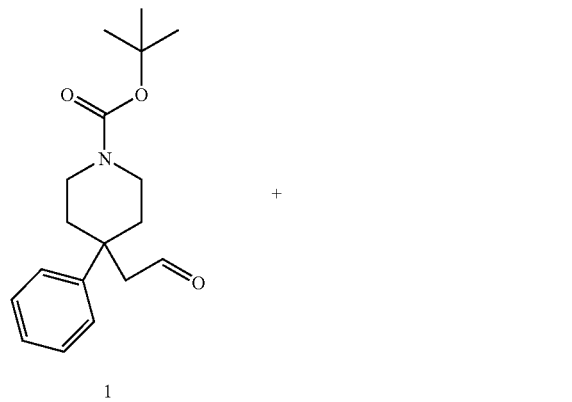

1

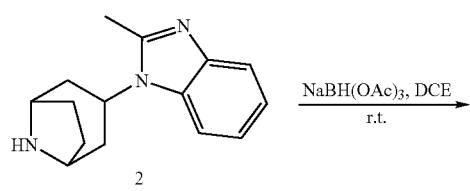

2

NaBH(OAc)₃, DCE
r.t.

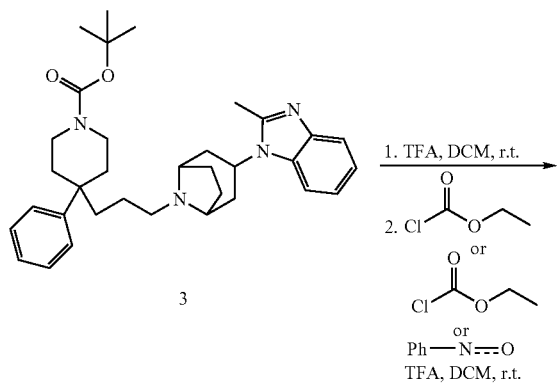

3

1. TFA, DCM, r.t.

2. Cl–C(=O)–O–Et or Cl–C(=O)–O–Et or Ph—N═O
TFA, DCM, r.t.

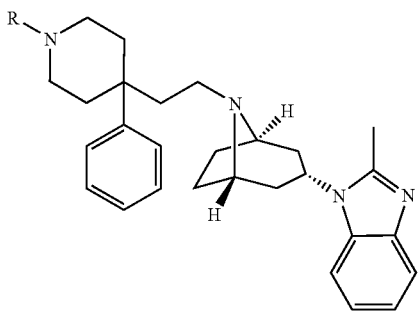

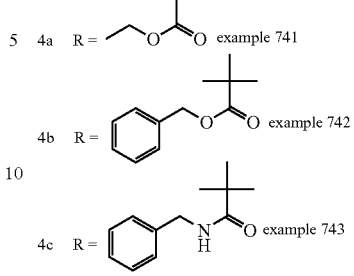

4a  R = –CH₂–O–C(=O)–C(CH₃)₃   example 741
4b  R = –CH₂–Ph–CH₂–O–C(=O)    example 742
4c  R = –CH₂–Ph–CH₂–NH–C(=O)   example 743

Synthesis of 3 of the Above Scheme:

To a solution of 1 (0.3 g, 1 mmol) in dichloroethane (15 mL), amine 2 (0.032 g, 0.148 mmol) was added NaBH(OAc)₃ (0.424 g, 2 mmol). The mixture was stirred at r.t. overnight, and then quenched with saturated sodium bicarbonate solution, extracted with methylene chloride, dried over sodium sulfate, filtered and concentrated. Purification by chromatotron with 5% MeOH and 0.5% ammonium hydroxide in methylene chloride gave 0.267 g as white solid. ¹H NMR (400 MHz, CDCl₃, ppm) δ 7.62-7.59 (1H, m), 7.36-7.28 (5H, m), 7.20-7.18 (1H, m), 7.14-7.10 (2H, m), 4.43-4.34 (1H, m), 3.68-3.60 (2H, broad), 3.24 (2H, broad s), 3.18 (2H, td, J=9.3 Hz, 2.5 Hz), 2.48 (3H, s), 2.39 (2H, broad t, J=11.9 Hz), 2.20-2.18 (4H, broad), 1.88-1.74 (6H, broad m), 2.10-1.97 (3H, m), 1.79-1.65 (6H, m), 1.55 (2H, d, J=8.1 Hz), 1.47 (2H, dd, J=5.2 Hz, 3.5 Hz), 1.40 (9H, s). ¹³C NMR (400 MHz, CDCl₃, ppm) δ 155.20, 151.20, 144.83, 143.19, 133.75, 128.82, 126.82, 126.37, 121.96, 121.69, 119.42, 111.49, 79.53, 58.71, 48.38, 46.41, 41.38, 40.66, 39.43, 35.75, 34.42, 28.69, 26.88, 14.96. LRMS: calcd. for C₃₄H₄₅Cl₂N₄O₂ (M+H)⁺ 611.3.

Synthesis of 4a-4c of the Above Scheme:

Deprotection of Boc with 25% TFA in dichloromethane at r.t. was followed by quenching with saturated sodium bicarbonate solution and extracted with ethyl acetate. The organic layer was dried, filtered and concentrated. 1 eq. of chloroformates or phenyl isocyanate and 3 eq. triethyl amine were used at r.t. until the reactions were complete by LC-MS. The final products were purified by PHPLC.

Example 741

1.7 mg. HRMS: calcd. for C₃₁H₄₁N₄O₂ (M+H)⁺ 501.3230, found: 501.3205.

Example 742

1.3 mg. HRMS: calcd. for C₃₆H₄₃N₄O₂ (M+H)⁺ 548.3389, found: 548.3405.

Example 743

1.0 mg. HRMS: calcd. for C₃₅H₄₂N₅O (M+H)⁺ 563.3386, found: 563.3379.

The Synthesis of Analogues with C3-Linker Dichloro Analogues

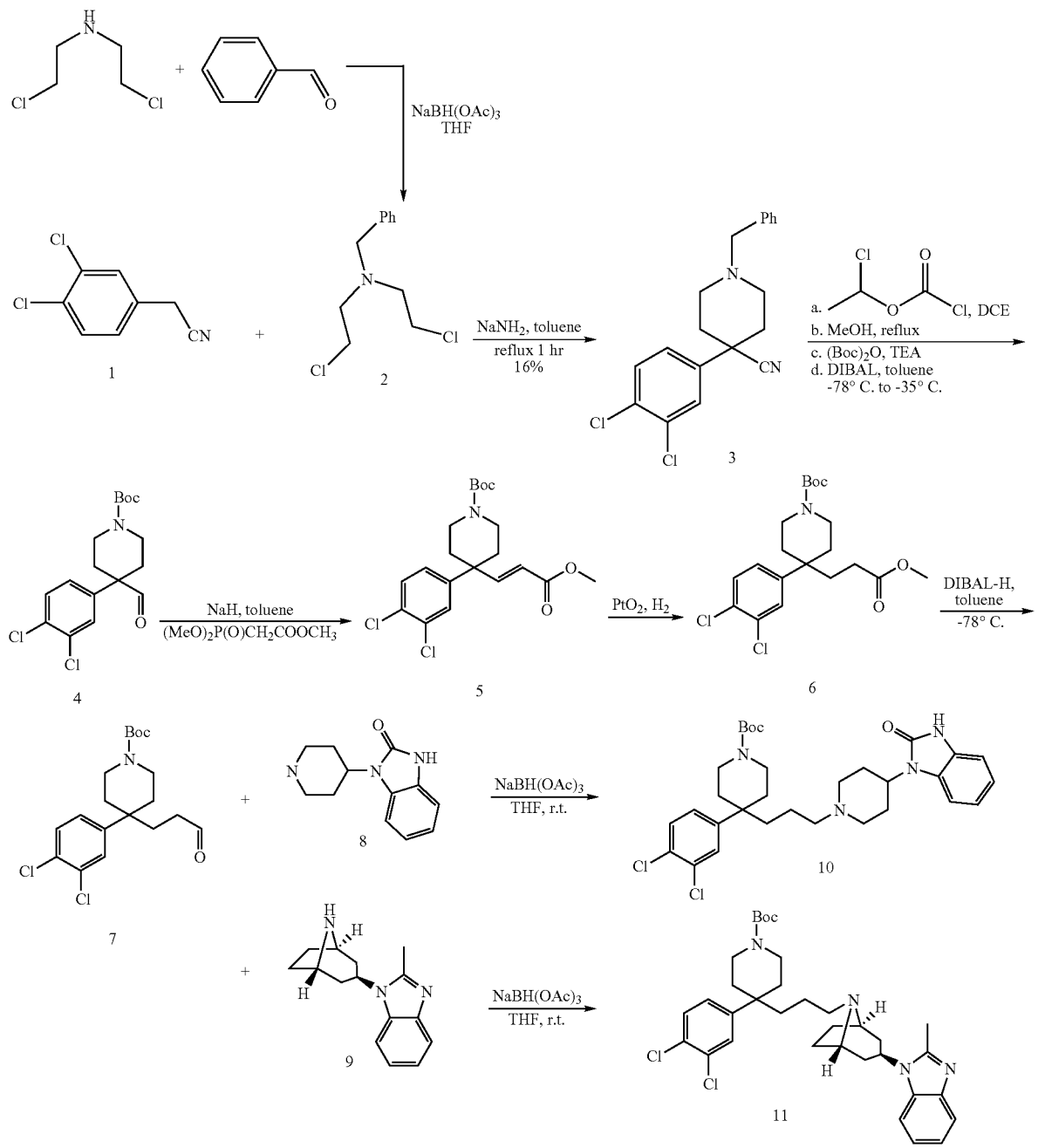

Synthesis of 2 of the Above Scheme:

To a suspension of bis(2-chloroethyl)amine hydrochloride (22.48 g, 125.9 mmol) in dichloroethane (300 mL), benzaldehyde (14.1 mL, 138.5 mmol), triethyl amine (43.8 mL, 314.9 mmol) and NaBH(OAc)$_3$ were added sequentially. The cloudy content was stirred at r.t. overnight. It was then quenched with saturated sodium bicarbonate solution, extracted with ethyl acetate. The organic layer was dried over sodium sulfate, filtered and concentrated to give 35.7 g product as oil. $^1$H NMR (400 MHz, CDCl$_3$) δ[ppm]: 7.33-7.31 (5H, m), 3.73 (2H, s), 3.49 (4H, t, J=7.1 Hz), 2.92 (4H, t, J=7.2 Hz). $^{13}$CNMR (400 MHz, CDCl$_3$) δ[ppm]: 139.06, 128.83, 128.69, 127.87, 127.62, 127.24, 59.43, 56.59, 42.43.

Synthesis of 3 of the Above Scheme:

To a solution of 1 (1.18 g, 6.32 mmol) in toluene (50 mL), NaNH$_2$ (1.48 g, 50% in toluene, 18.96 mmol) was added at r.t. (the content turned red upon the addition of sodium amide). The mixture was then heated to reflux for 1 hour. The reaction was quenched with HCl (0.1N, 50 mL). The content pH was adjusted to ~11 with NaOH (50% aqueous solution). The organic layer was separated. The aqueous layer was extracted twice with ethyl acetate. The combined organic layer was dried (Na$_2$SO$_4$), filtered and concentrated. The residue was purified by flash column chromatography with hexane/ethyl acetate (8/1 to 4/1) afforded 0.38 g product as red oil (17%). $^1$H NMR (400 MHz, CDCl$_3$) δ[ppm]: 7.58 (1H, d, J=2 Hz), 7.49 (1H, d, J=14.1 Hz), 7.45-7.28 (6H, m), 3.59 (2H, s), 2.99 (2H, d, J=11.8 Hz), 2.51-2.48 (2H, broad m), 2.07-2.05 (4H, broad). $^{13}$CNMR (400 MHz, CDCl$_3$) δ[ppm]: 140.75, 138.18, 133.49, 131.16, 129.29, 128.62, 128.47, 128.15, 127.54, 125.40, 121.47, 63.07, 50.75, 42.62, 36.78. LRMS: calcd. for C$_{19}$H$_{18}$Cl$_2$N$_2$ (M$^+$) 344.1, found 344.3.

Synthesis of 4 of the Above Scheme:

To a solution of 3 (3.28 g, 9.53 mmol) in dichloroethane (200 mL), 1-chloroethyl chloroformate (1.54 mL, 14.30 mmol) was added at 0° C. and stirred for 15 mins. It was then heated to reflux for 1 hr. After cooling to the r.t., the dichloroethane was removed under reduced pressure. The residue was dissolved in methanol and heated to reflux for 20 mins (reaction was complete by GC-MS). The methanol was removed under reduced pressure. After redissolving the residue in THF (150 mL), (Boc)$_2$O (3.12 g, 14.3 mmol) and triethyl amine (4.0 mL, 28.60 mmol) were added. The content was stirred at r.t. overnight. Ethyl acetate was added. The organic layer was washed with saturated sodium bicarbonate solution, dried (Na$_2$SO$_4$), filtered and concentrated. Flash column chromatography with hexane/EtOAc (8/1 to 6/1) afforded 0.677 g product as yellow solid (20% yield) and another impure fraction (0.894 g, ~85% purity). $^1$H NMR (400 MHz, CDCl$_3$) δ[ppm]: 7.50 (1H, d, J=2.2 Hz), 7.43 (1H, d, J=8.7 Hz), 7.27 (1H, dd, J=8.6 Hz, 2.2 Hz), 4.24 (2H, broad s), 3.12 (2H, broad s), 2.03-1.98 (2H, m), 1.88-1.80 (2H, m), 1.43 (9H, s). $^{13}$CNMR (400 MHz, CDCl$_3$) δ[ppm]: 154.45, 140.09, 133.57, 132.87, 131.28, 128.01, 125.31, 120.68, 80.51, 42.72, 41.31, 36.30, 28.59. LRMS: calcd. for C$_{17}$H$_{20}$Cl$_2$N$_2$O$_2$ (M$^+$) 354.1 found 354.2.

To a solution of the product from the last step (0.677 g, 1.91 mmol) in toluene (30 mL), DIBAL-H (5.7 mL, 1M in toluene) was added at −78° C. The content was warmed to −35° C. over 3.5 hrs period. The reaction was completed (monitored by GC-MS) and then quenched with saturated ammonium chloride solution (30 mL). The content was extracted with ethyl acetate (GC-MS indicated that incomplete quenching might lead to the cleavage of Boc protecting group. MeOH might be a better choice of quenching reagent). So the content was retreated with (Boc)$_2$O (2 eq.) and triethyl amine (2 eq.) for 2 hrs. The organic layer was washed with NaOH (0.1N), separated, dried (Na$_2$SO$_4$), filtered and concentrated. Flash column chromatography with hexane/ethyl acetate (8/1) afforded 0.14 g (21% yield). $^1$H NMR (400 MHz, CDCl$_3$) δ[ppm]: 9.38 (1H, s), 7.40 (1H, d, J=17.4 Hz), 7.36 (1H, d, J=2.2 Hz), 7.10 (1H, J=2.1 Hz), 3.86 (2H, broad s), 3.08 (2H, broad), 2.34 (2H, d, J=13.7 Hz), 1.92 (2H, broad), 1.44 (9H, s). LRMS calcd. for C$_{12}$H$_{13}$Cl$_2$NO (M-Boc+H)$^+$ 257.0, found 257.1.

Synthesis of 5 of the Above Scheme:

To a suspension of NaH (0.025 g, 60% in mineral oil, 0.627 mmol) in toluene, trimethyl phosphonoacetate (0.1 mL, 0.627 mmol) was added. The content was stirred at r.t. for 1 hr before 4 (0.14 g, 0.392 mmol) in toluene (2 mL) was added (in case of a large scale reaction, an ice bath is necessary to control the reaction). The content was stirred at r.t. overnight during which it turned cloudy. The reaction was quenched with water. The content was extracted with ethyl acetate. The combined organic layer was dried (Na$_2$SO$_4$), filtered and concentrated. $^1$H NMR (400 MHz, CDCl$_3$) δ[ppm]: (crude) 7.40 (1H, d, J=8.6 Hz), 7.33 (1H, J=2 Hz), 7.10 (1H, dd, J=8.4 Hz, 2.0 Hz), 6.90 (1H, J=16.1 Hz), 5.67 (1H, J=16.1 Hz), 3.71 (3H, s), 3.52-3.36 (4H, m), 2.08-1.96 (4H, m), 1.44 (9H, s).

Synthesis of 6 of the Above Scheme:

To a solution of the residue in EtOH (15 mL), PtO$_2$ was added. The content was stirred under 1 atm H$_2$ for 3 hrs (the reaction was complete by GC-MS). The content was filtered through celite and concentrated. Flash column chromatography with hexane/ethyl acetate (4/1) afforded 0.123 g (76% yield) product as oil. $^1$H NMR (400 MHz, CDCl$_3$) δ[ppm]: 7.42 (1H, d, J=8.4 Hz), 7.32 (1H, J=2.1 Hz), 7.10 (1H, dd, J=8.6 Hz, 2.2 Hz), 3.64 (2H, broad), 3.57 (3H, s), 3.11 (2H, t, J=10 Hz), 2.07-1.89 (6H, m), 1.72-1.67 (2H, m), 1.43 (9H, s).

Synthesis of 7 of the Above Scheme:

DIBAL-H (0.593 mL, 1M in toluene, 0.593 mmol) was cooled to −78° C. and added into a solution of 6 (0.123 g, 0.296 mmol) in toluene (15 mL) (also cooled to −78° C. with a dry ice-acetone bath, necessary to prevent overreduction) dropwise (to keep the internal temperature as low as possible). The content was stirred at −78° C. for 2.5 hrs and the reaction was quenched with a cooled MeOH (−78° C.) dropwise (the addition needs to be slow to keep the internal temperature low and prevent overreduction). After the addition completed, the content was warmed to r.t. and filtered through celite. The filtrate was washed with brine. The aquous layer was extracted with ethyl acetate. The combined organic layer was dried with Na$_2$SO$_4$, filtered and concentrated. $^1$H NMR (400 MHz, CDCl$_3$) δ[ppm]: 9.59 (1H, s), 7.41 (1H, d, J=8.4 Hz), 7.37 (1H, d, J=3.8 Hz), 7.31 (1H, dd, J=8.3 Hz, 2.2 Hz), 3.66-3.63 (2H, m), 3.12-3.06 (2H, m), 2.13-2.02 (4H, m), 1.89-1.85 (2H, m), 1.77-1.64 (2H, m), 1.44 (9H, s).

Synthesis of 10 of the Above Scheme:

To a solution of 7 (½ the residue from the last step, ~0.148 mmol) in THF (15 mL), amine 8 (0.032 g, 0.148 mmol) was added. The content was stirred at r.t. for 10 mins before NaBH(OAc)$_3$ (0.094 g, 0.444 mmol) was added. It was stirred at r.t. overnight, and then quenched with saturated sodium bicarbonate solution, extracted with methylene chloride, dried over sodium sulfate, filtered and concentrated. Prep. TLC purification with 5% MeOH and 0.5% ammonium hydroxide in methylene chloride gave 9 mg product. $^1$H NMR (400 MHz, CDCl$_3$) δ[ppm]: 9.13 (1H, s), 7.40 (1H, d, J=8.5 Hz), 7.34 (1H, d, J=1.9 Hz), 7.07 (1H, dd, J=8.4 Hz, 1.9 Hz), 4.32 (1H, broad s), 3.63 (2H, m), 3.12 (2H, broad t, J=10.2 Hz), 2.92 (2H, broad s), 2.42 (1H, broad s), 2.22 (2H, broad s), 2.10-1.97 (3H, m), 1.79-1.65 (6H, m), 1.58 (2H, broad s), 1.43 (9H, s), 1.12-1.08 (2H, broad). HRMS: calcd. for C$_{31}$H$_{41}$Cl$_2$N$_4$O$_3$ (M+H)$^+$ 587.2556, found 587.2565.

Synthesis of 11 of the Above Scheme:

Following the route described towards 10, 43 mg of product 11 was synthesized. $^1$H NMR (400 MHz, CDCl$_3$) δ[ppm]: 7.66-7.63 (1H, m), 7.56 (1H, broad s), 7.40-7.36 (2H, m), 7.20-7.13 (3H, m), 4.52-4.43 (1H, m), 3.63 (2H, m), 3.26 (2H, broad s), 3.18 (2H, td, J=9.2 Hz, 2.8 Hz), 2.58-2.48 (5H, broad), 2.33-2.28 (2H, m), 2.07-2.00 (4H, m), 1.76-1.60 (8H, m), 1.44 (9H, s), 1.19 (2H, broad s). LRMS: calcd. for C$_{34}$H$_{45}$Cl$_2$N$_4$O$_2$ (M+H)$^+$ 611.3, found 611.0.

The Synthesis of Analogues with C3-Linker-Unsubstituted Scaffold

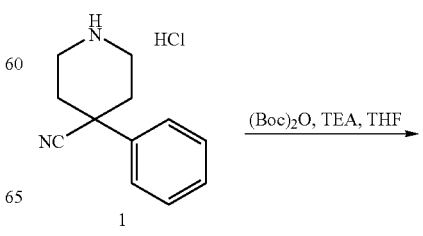

1

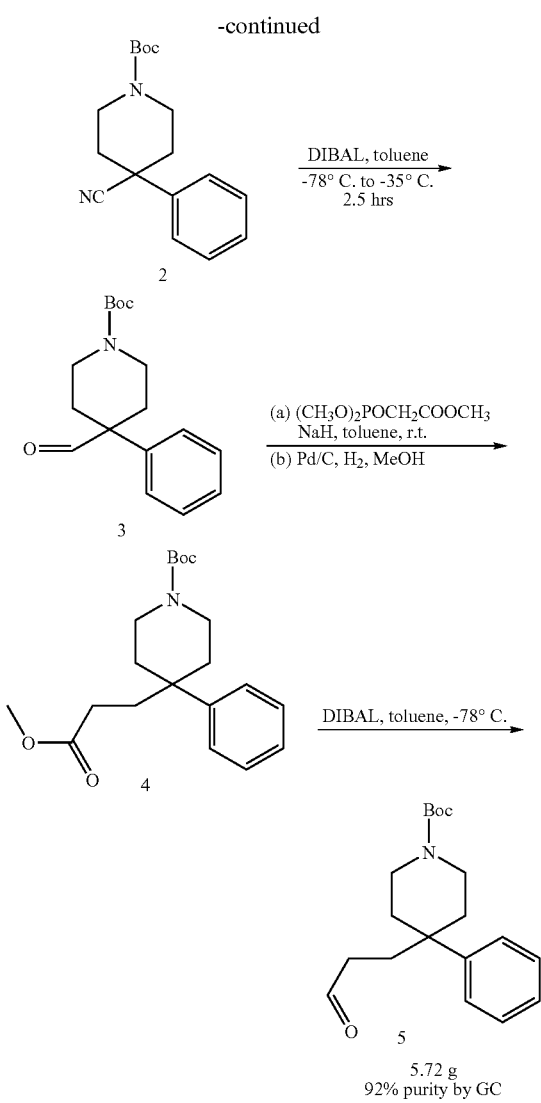

Synthesis of 2 of the Above Scheme:

To a suspension of 1 (22 g, 98.8 mmol) in THF (300 mL), TEA (45 mL, 326 mmol) and (Boc)$_2$O (24 g, 110 mmol) were added and the content was stirred at r.t. overnight, followed by addition of HCl (250 mL, 0.1 N) and the mixture was extracted with ethyl acetate. The organic layer was combined, dried over Na$_2$SO$_4$, filtered and concentrated to give 26.2 g product as white crystalline solid (93% yield). $^1$H NMR (400 MHz, CDCl$_3$) δ[ppm]: 7.46-7.25 (5H, m), 4.26 (2H, brs), 3.18 (2H, brs), 2.07 (2H, d, J=13.5 Hz), 1.93 (3H, t, J=9.4 Hz), 1.47 (9H, s). $^{13}$CNMR (400 MHz, CDCl$_3$) δ[ppm]: 154.67, 139.88, 129.54, 129.38, 128.57, 125.77, 121.60, 80.39, 43.20, 41.52, 36.48, 28.65. LRMS: m/z calcd. for C$_{17}$H$_{22}$N$_2$O$_2$ (M$^+$) 286.17, found 286.2.

Synthesis of 3 of the Above Scheme:

DIBAL-H (60 mL, 1M in hexane, 60 mmol) was added to a solution of 2 (8.0 g, 28.0 mmol) in toluene (200 mL) at −78° C. with a dry-ice acetone bath. The content was warmed to −35° C. over about 2 hrs and stirred at −35° C. for another hour. The reaction was quenched with saturated ammonium chloride (100 mL), filtered through celite. The organic layer was separated, dried (Na$_2$SO$_4$), filtered and concentrated to afford 6.95 g product as light yellow oil (86% yield). $^1$H NMR (400 MHz, CDCl$_3$) δ[ppm]: 9.40 (1H, s), 7.45-7.25 (5H, m), 3.85 (2H, brs), 3.10 (2H, br), 2.36 (2H, d, J=13.6 Hz), 1.98 (2H, br), 1.44 (9H, s). $^{13}$CNMR (400 MHz, CDCl$_3$) δ[ppm]: 201.18, 154.96, 138.34, 129.40, 128.02, 127.16, 79.93, 53.26, 40.88, 30.77, 28.64. LRMS: m/z calcd. for C$_{17}$H$_{23}$NO$_3$ 289.2, found 289.2 (M$^+$).

Synthesis of 4 of the Above Scheme:

To a suspension of NaH (1.15 g, 60% in mineral oil, 28.86 mmol) in toluene (100 mL) at 0° C., trimethyl phosphonoacetate (4.28 mL, 26.45 mmol) was added dropwise and the content was warmed up to r.t. and stirred for 50 mins. A solution of 3 (6.95 g, 24.05 mmol) in toluene (50 mL) was next added and the mixture stirred at r.t. overnight. Following addition of water, the organic layer was separated, dried (Na$_2$SO$_4$), filtered and concentrated to give 8.26 g product as colorless oil (>90% purity by GC-MS analysis). LRMS: m/z calcd. for C$_{20}$H$_{27}$NO$_4$ 345.19, found 345.3 (M+). The oil from the last step was dissolved in MeOH (200 mL). Pd/C (1 g, 5%) was added. The content was stirred under 1 atm H$_2$ for 2.5 hrs and then filtered through celite. The solvent was removed under reduced pressure. The residue was purified by flash column chromatography with hexane/ethyl acetate (2/1) to give 6.5 g product as colorless oil (78% yield over two steps). $^1$H NMR (400 MHz, CDCl$_3$) δ[ppm]: 7.47-7.18 (5H, m), 3.70-3.64 (2H, m), 3.54 (3H, s), 3.12 (2H, m), 2.16-2.12 (2H, m), 1.98-1.87 (4H, m), 1.71-1.64 (2H, m), 1.43 (9H, s). LRMS: m/z calcd. for C$_{20}$H$_{29}$NO$_4$ 347.2, found 347.3 (M$^+$).

Synthesis of 5 of the Above Scheme:

DIBAL-H (38 mL, 1M in toluene, 38 mmol) was cooled to −78° C. and added into a solution of 4 (6.5 g, 18.73 mmol) in toluene (80 mL) (also cooled to −78° C. with a dry ice-acetone bath to prevent overreduction) dropwise (to keep the internal temperature as low as possible). The content was stirred at −78° C. for 2.5 hrs and the reaction was quenched with a cooled MeOH (−78° C.) dropwise (the addition needs to be slow to keep the internal temperature low and prevent overreduction). After the addition completed, the content was warmed to r.t. and filtered through celite. The filtrate was washed with brine. The aquous layer was extracted with ethyl acetate. The combined organic layer was dried with Na$_2$SO$_4$, filtered and concentrated to give 5.72 g product as light green oil (92% purity by GC-MS analysis). $^1$H NMR (400 MHz, CDCl$_3$) δ[ppm]: 9.53 (1H, s), 7.46-7.25 (5H, m), 3.73-3.67 (2H, m), 3.10-3.05 (2H, m), 2.17-2.09 (4H, m), 1.90-1.86 (2H, t, J=8.0 Hz), 1.71-1.64 (2H, m), 1.43 (9H, s). LRMS: m/z calcd. for C$_{19}$H$_{27}$NO$_3$ 317.2, found 317.3 (M+).

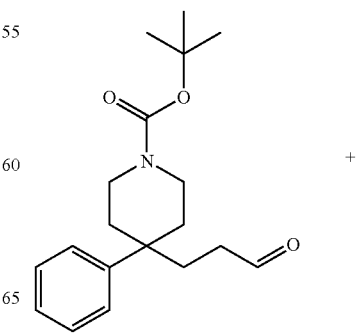

-continued

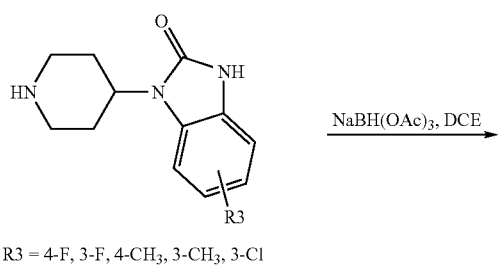

R3 = 4-F, 3-F, 4-CH₃, 3-CH₃, 3-Cl

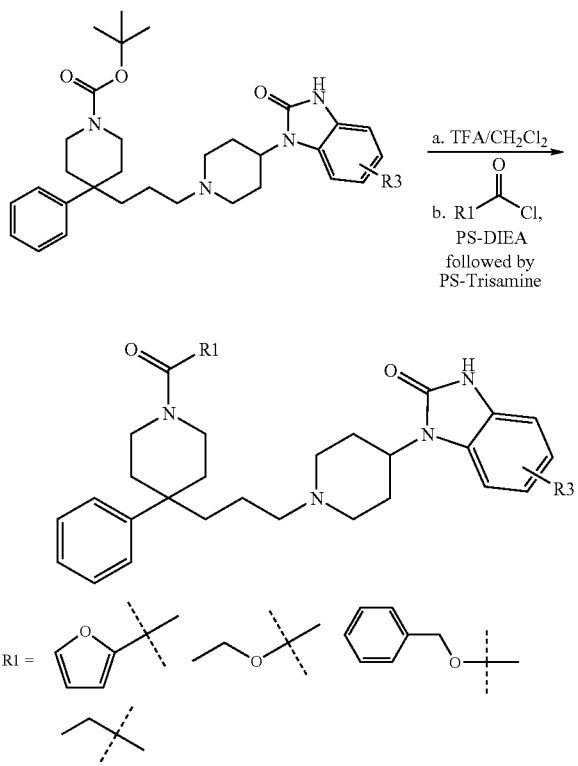

FlexChem Robins Block (24 glass tubes setting) was used for this parallel synthesis. To each glass tube, N₂ was flushed to remove air. Then amines (0.92 eq.), NaBH(OAc)₃ (2 eq.), DCE (1 mL), and aldehyde (1 eq) in THF (1 mL) were added sequentially. The block was sealed and rotated at r.t. overnight. The content was drained through a 24 wells filter plate overnight and the filtrate was collect in the same 24 tubes setting. TFA (1 mL) was added to each tube. The block was sealed and shaken for 80 min. The reaction was complete as evident by LC-MS. The gasket was removed and the solvent and TFA were removed under reduced pressure. Saturated sodium bicarbonate was added to each tube followed by DCM. The organic layer was pipeted out to another 24 tubes block. Acid chlorides or chloroformates (2.7 eq) and PS-DIEA (2.7 eq) were added. The block was sealed and rotated overnight. It was cooled in a freezer for 20 mins before the gasket was removed. PS-Trisamine (2.7 eq) was added and the block was sealed and rotated at r.t. for 4 hrs. The content was filtered, concentrated and the residue was purified with Preparative HPLC. All the compounds were obtained as formic acid salt.

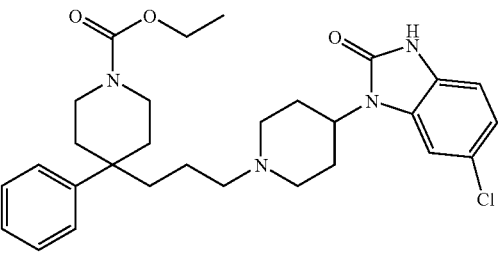

Example 744

2.7 mg product. $^1$H NMR (400 MHz, CDCl$_3$) δ[ppm]: 11.00 (1H, s), 7.82 (1H, s), 7.41-7.34 (5H, m), 7.24-7.20 (2H, m), 6.98-6.93 (3H, m), 6.61-6.59 (1H, m), 4.10-4.02 (1H, m), 3.93-3.88 (2H, m), 2.79 (2H, broad d, J=15.4 Hz), 2.26-2.16 (9H, m), 1.92 (2H, broad t, J=11.5 Hz), 1.76 (2H, broad t, J=10.1 Hz), 10.64-10.55 (4H, m), 1.08-1.02 (2H, broad). HRMS: C$_{29}$H$_{37}$ClN$_4$O$_3$ calcd. for (M+H)$^+$ 547.2476, found 547.2480.

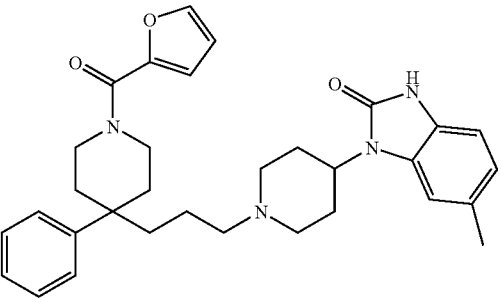

Example 745

6.7 mg product. $^1$H NMR (400 MHz, CDCl$_3$) δ[ppm]: 10.67 (1H, s), 7.79 (1H, s), 7.39-7.33 (5H, m), 7.21-7.18 (1H, t, J=6.7 Hz), 6.97-6.92 (2H, m), 6.78 (2H, dd, J=29.1 Hz, 7.9 Hz), 6.59-6.58 (1H, m), 4.06-4.00 (1H, m), 3.90-3.87 (2H, m), 2.79 (2H, broad d, J=10.5 Hz), 2.28 (3H, s), 2.25-2.15 (6H, m), 1.90 (2H, broad t, J=11 Hz), 1.68-1.63 (2H, m), 1.57-1.48 (4H, m), 1.02 (2H, broad s). HRMS: C$_{32}$H$_{38}$N$_4$O$_3$ calcd. for (M+H)$^+$ 527.3022, found 527.3013.

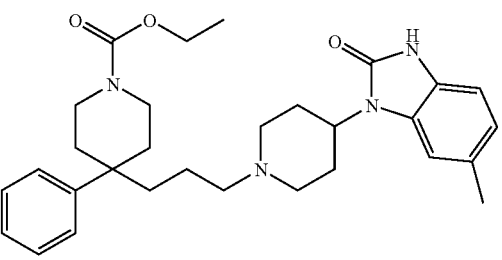

Example 746

9.6 mg product. $^1$H NMR (400 MHz, CDCl$_3$) δ[ppm]: 10.67 (1H, s), 7.34-7.32 (5H, m), 7.19-7.17 (1H, m), 6.96

(1H, s), 6.77 (2H, dd, J=28.8 Hz, 7.7 Hz), 4.02-3.96 (3H, m), 3.06 (2H, m), 2.77 (2H, broad d, J=10.7 Hz), 2.28 (3H, s), 2.24-2.04 (6H, m), 1.88 (2H, broad d, J=11.2 Hz), 1.68-1.63 (2H, m), 1.57-1.51 (4H, m), 1.14 (3H, t, J=7.1 Hz), 1.04 (2H, m). HRMS: C$_{30}$H$_{40}$N$_4$O$_3$ calcd. for (M+H)$^+$ 505.3179, found 505.152.

Example 747

5.3 mg product. $^1$H NMR (400 MHz, CDCl$_3$) δ[ppm]: 10.68 (1H, s), 7.39-7.30 (10H, m), 7.23-7.19 (1H, m), 6.98 (1H, s), 6.79 (2H, dd, J=22.4 Hz, 8.9 Hz), 5.06 (2H, s), 4.09-4.01 (1H, m), 3.61 (2H, m), 3.12 (2H, broad s), 2.79 (2H, broad d, J=11.8 Hz), 2.31 (3H, s), 2.28-2.09 (6H, m), 1.91 (2H, t, J=11.3 Hz), 1.70 (2H, t, J=9.9 Hz), 1.60-1.50 (4H, m), 1.07-1.02 (2H, m). HRMS: C$_{35}$H$_{42}$N$_4$O$_3$ calcd. for (M+H)$^+$ 567.3335, found 567.3334.

Example 748

6.9 mg product. $^1$H NMR (400 MHz, CDCl$_3$) δ[ppm]: 10.67 (1H, s), 7.36-7.31 (5H, m), 6.97 (1H, s), 6.78 (2H, dd, J=28.2 Hz, 7.7 Hz), 4.03-4.00 (1H, broad s), 3.78-3.74 (1H, broad), 3.57-3.53 (1H, broad), 3.15-3.10 (1H, m), 3.04-2.99 (1H, m), 2.76 (1H, m), 2.29 (3H, s), 2.27-2.04 (9H, m), 1.85 (1H, broad s), 1.72-1.54 (6H, m), 1.08 (3H, broad s), 0.94 (3H, t, J=7.5 Hz). HRMS: C$_{30}$H$_{40}$N$_4$O$_3$ calcd. for (M+H)$^+$ 489.3229, found 489.3212.

Synthesis of C2-Scaffold, BBN Method

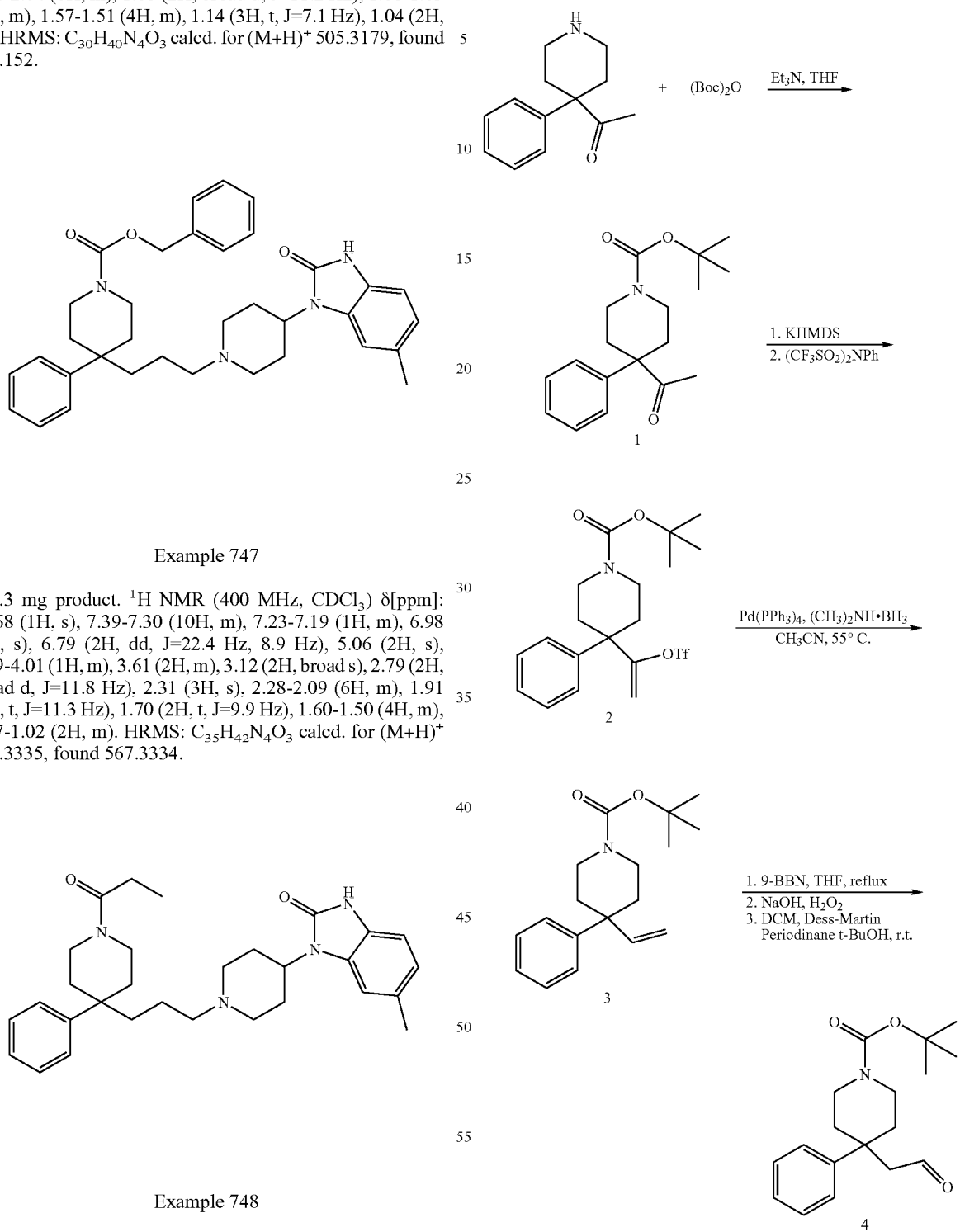

Synthesis of 1 of the BBN Method:

$^1$H NMR (400 MHz, CDCl$_3$) δ[ppm]: 7.37-7.34 (2H, m), 7.28-7.25 (3H, m), 3.77-3.73 (2H, m), 3.19-3.13 (2H, m), 2.37-2.33 (2H, m), 1.99-1.93 (2H, m), 1.90 (3H, s), 1.43 (9H, s).

Synthesis of 2 of the BBN Method:

To a solution of 1 (2.926 g, 9.66 mmol) in toluene (40 mL) at −78° C., KHMDS (0.5 M in toluene, 21.2 mL) was added dropwise. The content was stirred at −78° C. for 10 mins and the dry ice-acetone bath was removed. The stirring was continued for another 15 mins and the content was cooled back to −78° C. (CF$_3$SO$_2$)$_2$NPh (4.14 g, 11.6 mmol) in toluene (30 mL) was added. The resulting light brown content was stirred overnight during which it was warmed to r.t. After work-up with water and ethyl acetate, the residue was purified by flash column chromatography with hexane/EtOAc (20/1 to 10/1) to give 3.20 g product (yield 76%). $^1$H NMR (400 MHz, CDCl$_3$) δ[ppm]: 7.46-7.44 (2H, m), 7.40-7.36 (2H, m), 7.30-7.26 (1H, m), 5.41 (1H, d, J=5.0 Hz), 5.32 (1H, d, J=4.8 Hz), 3.62-3.56 (2H, m), 3.34 (2H, broad s), 2.30-2.24 (2H, m), 2.14-2.08 (2H, m), 1.43 (9H, s). $^{13}$C NMR (400 MHz, d$_6$-acetone) δ[ppm]: 205.32, 160.71, 154.36, 140.30, 128.95, 127.60, 127.41, 103.26, 46.17, 40.65, 39.69, 33.04, 27.94.

Synthesis of 3 of the BBN Method:

A suspension of K$_2$CO$_3$ (0.105 g, 0.76 mmol) and (CH$_3$)$_2$NH.BH$_3$ (0.04 g, 0.76 mmol) in CH$_3$CN (1 mL) in a pressure tube was stirred at r.t. for 10 min. A solution of 2 (0.33 g, 0.76 mmol) in CH$_3$CN (4 mL) was added under nitrogen atmosphere, followed with Pd(PPh$_3$)$_4$. The tube was sealed. The content was stirred at 65° C. overnight. After cooling to r.t., the content was filtered and concentrated. The residue was purified by fish column chromatography with hexane/EtOAc (20/1) to give 0.14 g product (64% yield). $^1$H NMR (400 MHz, d$_6$-acetone) δ[ppm]: 7.36-7.29 (4H, m), 7.20-7.16 (1H, m), 5.85 (1H, dd, J=10.8 Hz, 17.7 Hz), 5.11 (1H, d, J=10.9 Hz), 4.95 (1H, d, J=17.6 Hz), 3.50-3.44 (2H, m), 3.41-3.33 (2H, m), 2.07-2.01 (2H, m), 1.96-1.91 (2H, m), 1.43 (9H, s). $^{13}$CNMR (400 MHz, d$_6$-acetone) δ[ppm]: 205.39, 154.55, 145.93, 145.84, 128.67, 126.88, 114.46, 113.49, 78.67, 43.48, 40.70, 34.98, 28.05. Elemental Analysis: calcd. for C$_{18}$H$_{15}$NO$_2$ C, 75.22%; H, 8.77%; N, 4.87%; found C, 75.16%; H, 8.81%; N, 4.87%. IR is also available.

Synthesis of 4 of the BBN Method:

To a solution of 3 (0.267 g, 0.93 mmol) in THF (20 mL) at r.t., 9-BBN (2.8 mL, 0.5 M in THF) was added. The content was heated to reflux overnight. The content was cooled to rt. Sodium hydroxide (0.5 mL, 6.0 M in H$_2$O) was added, followed with hydrogen peroxide (30% in H$_2$O, 1 mL). The mixture was stirred at r.t. for 4 hrs, diluted with EtOAc, washed with brine. The organic layer was separated, dried over Na$_2$SO$_4$, filtered and concentrated. The residue was purified with chromatotron (1/1 hexane/EtOAc) to give 0.28 g (99% yield) alcohol. $^1$H NMR (400 MHz, d$_6$-acetone) δ[ppm]: 7.29-7.21 (4H, m), 7.16-7.13 (1H, m), 3.61-3.55 (2H, m), 3.26 (2H, t, J=7.3 Hz), 3.08-3.02 (2H, m), 2.10-2.07 (3H, m), 1.78 (2H, t, J=7.4 Hz), 1.71-1.64 (2H, m), 1.37 (9H, s).

To a suspension of Dess-Matin periodinane in dichloromethane (15 mL) at r.t., t-BuOH was added and the content was stirred for 10 mins. A solution of the alcohol in dichloromethane was added dropwise at r.t. and stirred for 15 mins. The content was diluted with Et2O, washed with 1.3 N NaOH, dried over Na2SO4, filtered, and concentrated. The residue was purified by flash column chromatography with hexane/EtOAc (3/1) to give 0.2 g product as oil (72% yield).

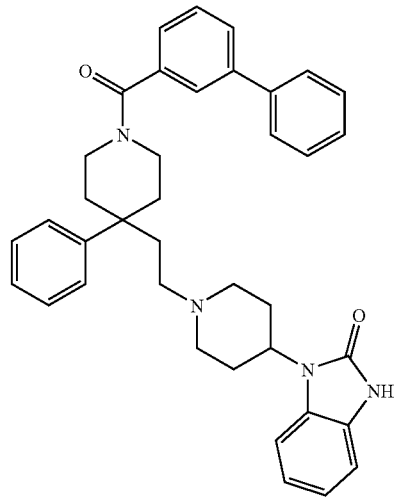

Example 749

HRMS calc. for C$_{38}$H$_{41}$N$_4$O$_2$ (M+H)$^+$ 585.3230, found 585.3201.

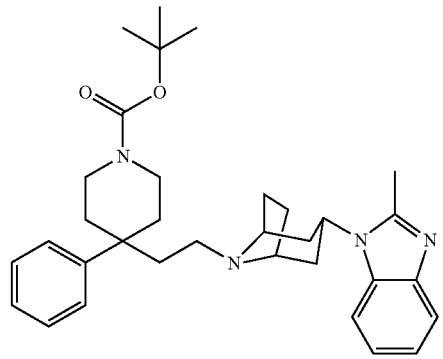

Example 750

HRMS calc. for C$_{32}$H$_{37}$N$_4$O$_2$ (M+H)$^+$ 509.2917, found 509.2948. $^1$H NMR (400 MHz, CDCl$_3$) δ[ppm]: 7.92 (1H, s), 7.85 (1H, broad s), 7.71-7.23 (6H, m), 4.57-4.42 (1H, m), 3.71-3.63 (4H, m), 3.23-3.17 (2H, m), 2.85-2.76 (2H, m), 2.59 (3H, s), 2.46-2.45 (2H, m), 2.07-1.98 (4H, m), 1.90-1.87 (2H, m), 1.80-1.70 (6H, m), 1.42 (9H, s). MS calcd for C$_{33}$H$_{45}$N$_4$O$_2$ (M+H)$^+$ 529, found 529.

Example 707

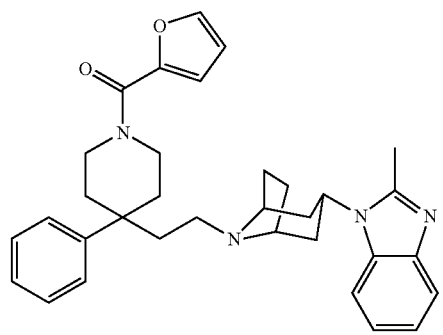

$^1$H NMR (400 MHz, CDCl$_3$) δ[ppm]: 7.90 (1H, s), 7.51 (1H, s), 7.46-7.35 (7H, m), 6.99-6.94 (1H, m), 6.46 (1H, s), 4.49-4.43 (1H, m), 4.14-4.11 (2H, m), 3.48 (2H, s), 3.28 (2H, s), 2.56 (3H, s), 2.40-2.34 (4H, m), 2.19 (2H, broad s), 1.93-1.85 (5H, m), 1.63-1.57 (5H, m). MS calcd. for C$_{33}$H$_{39}$N$_4$O$_2$ (M+H)$^+$ 523, found 523.

O-Linked Piperidines were Synthesized According to the Scheme Depicted Below.

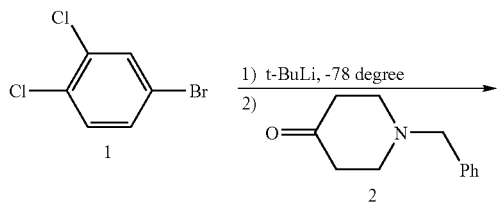
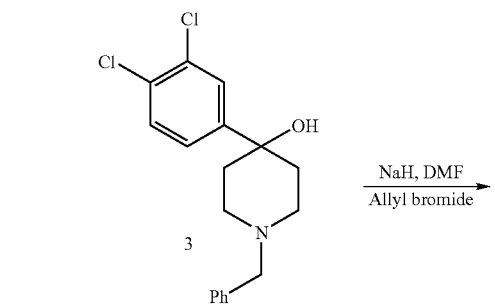
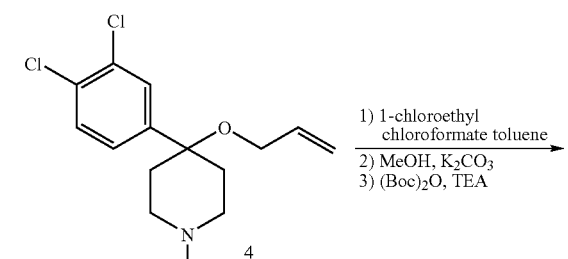
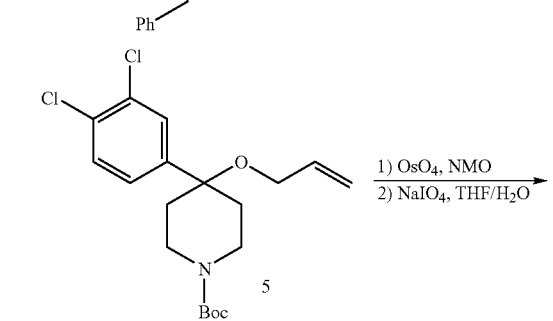
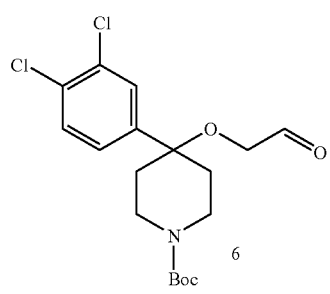
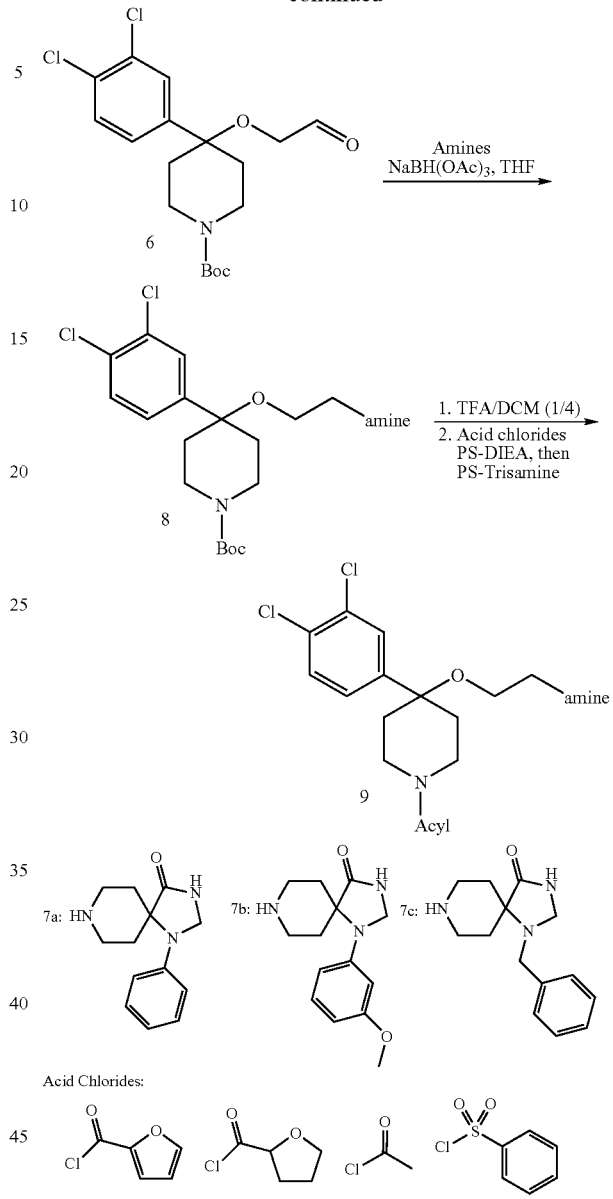

Synthesis of 3 in the Scheme for O-Linked Piperidines:

t-BuLi (31.2 mL, 1.7 M in pentane, 53.1 mmol) was added to Et$_2$O at −78° C., followed by 1-bromo-3,4-dichlorobenzene (3.4 mL, 26.6 mmol) dropwise. The content was stirred at −78° C. for another 5 mins before 2 (4.92 mL, 26.6 mmol) was added. It was stirred and gradually warmed up to r.t. overnight. Water was added. The mixture was extracted with ethyl acetate. The combined organic layer was dried over sodium sulfate, filtered and concentrated to afford 9 g product as light brown oil (100% yield). $^1$H NMR (400 MHz, CDCl$_3$) δ[ppm]: 7.62 (1H, d, J=2.2 Hz), 7.39 (1H, d, J=8.4 Hz), 7.36-7.30 (5H, m), 7.28-7.24 (1H, m), 3.58 (2H, s), 2.79 (2H, d, J=11.4 Hz), 2.44 (2H, t, J=6.8 Hz), 2.11 (2H, td, J=113.4 Hz, 3.5 Hz), 1.76 (1H, s), 1.68 (2H, dd, J=13.9 Hz, 2.2 Hz).

Synthesis of 4 in the Scheme for O-Linked Piperidines:

To a solution of 3 (9.0 g, 26.87 mmol) in DMF, NaH (2.15 g, 60% in mineral oil, 53.73 mmol) and allyl bromide (2.8 mL, 32.24 mmol) were added. The content was stirred at r.t. overnight. The reaction was quenched with water, extracted with ethyl acetate, dried over sodium sulfate, filtered and concentrated. The residue was purified by flash column chromatography with hexane/ethyl acetate (3/1) to give 7.47 g (74%) product as yellow oil. $^1$H NMR (400 MHz, CDCl$_3$) δ[ppm]: 7.49 (1H, d, J=2.0 Hz), 7.40 (1H, d, J=8.4 Hz), 7.35-7.27 (5H, m), 7.27-7.23 (1H, m), 5.91-5.82 (1H, m), 5.28 (1H, dd, J=17.2 Hz, 1.6 Hz), 3.58-3.55 (4H, m), 2.74 (2H, d, J=111.0 Hz), 2.50-2.43 (2H, m), 1.98 (4H, d, J=3.3). LRMS: calcd. for $C_{21}H_{24}Cl_2NO$ (M+H)$^+$ 376, found 376.

Synthesis of 5 in the Scheme for O-Linked Piperidines:

A solution of 4 (7.47 g, 199.92 mmol) in dichloroethane (120 mL) was cooled to 0° C., 1-chloroethyl chloroformate (4.22 mL, 39.16 mmol) was added dropwise. The content was stirred at 0° C. for 15 mins and then heated to reflux for 1 hr. The solvent was removed under reduced pressure. The residue was redissolved in MeOH and the content was refluxed for 1 hr. After cooling to r.t., water and ethyl acetate were added (saw precipitate). The content was filtered to give crystalline pale-white solid. To a suspension of the solid in THF (150 mL), triethyl amine (8.35 mL, 60 mmol) and (Boc)$_2$O were added. The content was stirred at r.t overnight. Water (100 mL) and brine (100 mL) were added. The mixture was extracted with ethyl acetate. The combined organic layer was washed with 0.1 N NaOH (2×), dried over sodium sulfate, filtered and concentrated. Flash column chromatography with hexane/ethyl acetate (9/1) gave 3.19 g product as colorless oil (42% yield). $^1$H NMR (400 MHz, CDCl$_3$) δ[ppm]: 7.45 (1H, d, J=2.0 Hz), 7.42 (1H, d, J=8.4 Hz), 7.22 (1H, dd, J=8.4 Hz, 2.2 Hz), 5.90-5.80 (1H, m), 5.27 (1H, dd, J=17.2 Hz, 1.6 Hz), 5.14 (1H, dd, J=10.5 Hz, 1.3 Hz), 3.99 (2H, d, J=13.0 Hz), 3.58 (2H, d, J=5.1 Hz), 3.18 (2H, d, J=9.2 Hz), 1.98 (2H, d, J=12.7 Hz), 1.80 (2H, td, J=13.2 Hz, 5.6 Hz), 1.46 (9H, s). LRMS: calcd. for $C_{19}H_{26}Cl_2NO_3$ (M+H)$^+$ 386, found 386.

Synthesis of 6 in the Scheme for O-Linked Piperidines:

To a solution of 5 (3.19 g, 8.29 mmol) in acetone (80 mL), t-BuOH (20 mL) and water (20 mL) were added, followed by OsO$_4$ (2.5% in t-BuOH, 5.2 mL, 0.42 mmol). The content was stirred at r.t for 5 mins and then NMO (1.94 g, 16.6 mmol) was added. It was stirred for another 2 hrs at r.t. The reaction was quenched with saturated NaHSO$_3$ (100 mL), extracted with ethyl acetate, dried over sodium sulfate, filtered and concentrated to give 3.5 g colorless oil. To a solution of the oil in THF (100 mL), water (25 mL) was added, followed by NaIO$_4$ (4.44 g, 20.73 mmol). The content was stirred at r.t for 4 hrs. Water (100 mL) was added. The mixture was extracted with ethyl acetate. The organic layer was washed with 1:1 water:brine, dried over sodium sulfate, filtered and concentrated to give 2.66 g product (83% yield). $^1$H NMR (400 MHz, CDCl$_3$) δ[ppm]: 9.66 (1H, s), 7.46-7.43 (2H, m), 7.24-7.22 (2H, m), 4.00 (2H, broad d, J=10.6 Hz), 3.69 (2H, s), 3.22 (2H, broad d, J=11.7 Hz), 2.03-2.00 (2H, m), 1.90-1.83 (2H, m), 1.46 (9H, s).

Synthesis of 8a in the Scheme for O-Linked Piperidines:

To a solution of 6 (0.885 g, 2.29 mmol) in THF (10 mL), amine 7a (0.792 g, 3.44 mmol) was added. The content was stirred at r.t. for 5 mins and then NaBH(OAc)$_3$ (1.214 g, 5.73 mmol) was added. The content was stirred at r.t. overnight. The reaction was quenched with saturated sodium bicarbonate solution, extracted with ethyl acetate, dried over sodium sulfate, filtered and concentrated. Chromatograph purification with 5% MeOH+0.5% ammonium hydroxide in methylene chloride gave 0.62 g product as white solid. $^1$H NMR (400 MHz, CDCl$_3$) δ[ppm]: 7.89 (1H, s), 7.45-7.39 (2H, m), 7.26 (3H, broad s), 6.90-6.84 (3H, m), 4.72 (2H, s), 4.09-3.95 (2H, broad), 3.19 (4H, broad s), 2.87-2.63 (8H, m), 2.00-1.96 (2H, m), 1.77-1.67 (4H, m), 1.45 (9H, s). LRMS: calcd. for $C_{31}H_{41}Cl_2N_4O_4$ 603, found 603.

Synthesis of 8b in the Scheme for O-Linked Piperidines:

0.48 g product as white solid. $^1$H NMR (400 MHz, CDCl$_3$) δ[ppm]: 7.45-7.41 (2H, m), 7.29 (1H, d, J=7.5 Hz), 7.19-7.17 (1H, broad), 6.59-6.57 (1H, broad), 6.43-6.38 (2H, m), 6.25 (1H, s), 4.70 (2H, s), 4.02-3.93 (2H, broad), 3.78 (3H, s), 3.18 (4H, broad s), 2.85-2.62 (8H, m), 2.04-1.97 (2H, broad), 1.78-1.66 (4H, m), 1.46 (9H, s). LRMS: calcd. for $C_{32}H_{43}Cl_2N_4O_5$ 633, found 633.

Synthesis of 8c in the Scheme for O-Linked Piperidines:

0.56 g product as white solid. $^1$H NMR (400 MHz, CDCl$_3$) δ[ppm]: 7.44 (1H, d, J=1.6 Hz), 7.36 (1H, d, J=8.5 Hz), 7.32-7.28 (4H, m), 7.22-7.17 (2H, m), 4.37 (2H, s), 3.96 (2H, broad s), 3.28 (2H, s), 3.10 (4H, broad), 2.76 (2H, d, J=11.2 Hz), 2.47 (2H, t, J=5.7 Hz), 2.04-1.91 (4H, m), 1.88-1.74 (4H, m), 1.45 (9H, s). LRMS: calcd. for $C_{32}H_{43}Cl_2N_4O_4$ 617, found 617.

Parallel Synthesis Using Robins Block 8a-8c were deprotected with TFA (1 mL) in dichloromethane (4 mL) at r.t for 20 min. Saturated sodium bicarbonate solution was added. The mixture was extracted with ethyl acetate. The organic layer was dried over sodium sulfate, filtered and concentrated. The residue was dissolved in dichloromethane (4 mL) and added to Robins block (1 mL/each tube). To each tube were added PS-DIEA (3 eq) and acid chloride (1.5 eq.). The block was sealed and rotated overnight. It was cooled in a freezer for 15 mins and opened. PS-Trisamine (3 eq.) was added. The block was sealed and rotated for 4 hrs. The content in each tube was poured into a 24-wells filtering block and drained overnight. The solvent was removed under reduced pressure and the residue was purified by preparative HPLC to give the desired product.

Example 752

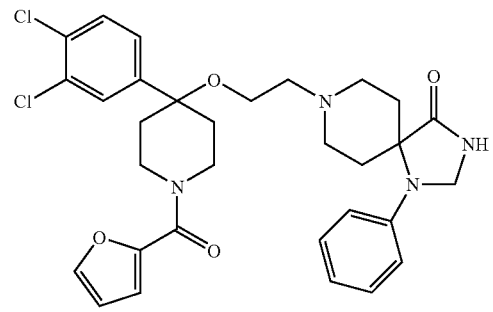

¹H NMR (400 MHz, CD₃OD) δ[ppm]: 8.47 (1H, s), 7.67 (2H, d, J=2.2 Hz), 7.45 (1H, dd, J=8.4 Hz, 2.0 Hz), 7.26 (2H, t, J=8.2 Hz), 7.02-6.99 (3H, m), 6.89 (1H, t, J=7.4 Hz), 6.57 (1H, dd, J=3.5 Hz, 1.8 Hz), 4.72 (2H, s), 4.39 (2H, broad s), 3.75 (2H, td, J=12.6 Hz, 2.8 Hz), 3.44-3.29 (6H, m), 3.22 (2H, t, J=5.0 Hz), 2.79 (2H, td, J=14.5 Hz, 4.8 Hz), 2.24 (2H, d, J=13.5 Hz), 2.01-1.94 (4H, m). HRMS calcd. for $C_{31}H_{35}Cl_2N_4O_4$ (M+H)⁺ 597.2035, found 597.2045.

Example 753

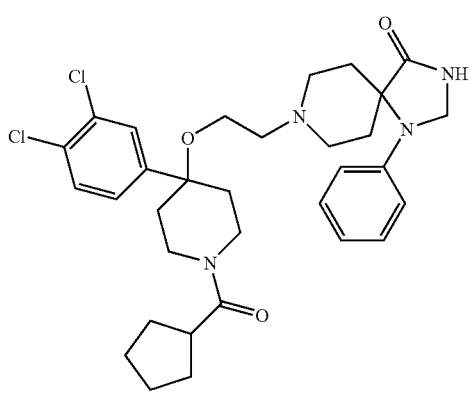

¹H NMR (400 MHz, CD₃OD) δ[ppm]: 8.55 (1H, s), 7.69 (1H, d, J=1.8 Hz), 7.58 (1H, dd, J=5.7 Hz, 1.8 Hz), 7.47 (1H, d, J=8.4 Hz), 7.30 (2H, t, J=8.0 Hz), 7.04 (2H, d, J=8.2 Hz), 6.92 (1H, t, J=8.2 Hz), 4.74 (2H, s), 4.45 (1H, broad d, J=12.2), 3.98 (1H, t, J=113.5 Hz), 3.72 (2H, t, J=12.1 Hz), 3.58 (1H, t, J=8.2 Hz), 3.43-3.32 (6H, m), 3.21 (2H, broad s), 3.16-3.08 (1H, m), 2.81 (2H, broad t, J=10.6 Hz), 2.32-2.15 (3H, m), 2.03-1.30 (10H, m). HRMS calcd. for $C_{32}H_{41}Cl_2N_4O_3$ (M+H)⁺ 599.2555, found 599.2520.

Example 754

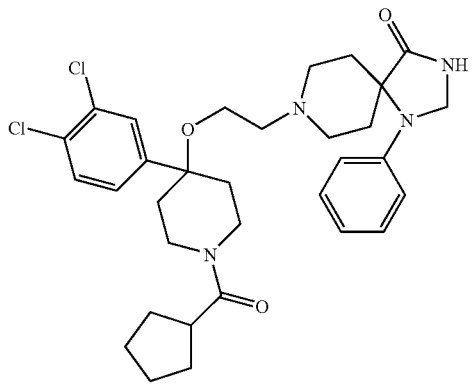

HRMS calcd. for $C_{28}H_{35}Cl_2N_4O_3$ (M+H)⁺ 545.2084, found 545.2062. Elemental Analysis: calcd. for $C_{29}H_{37}Cl_2N_4O_5$ (formic acid salt) C, 58.88%; H, 6.13%; N, 9.47%; found C, 58.19%; H, 6.13%; N, 9.27%.

Example 755

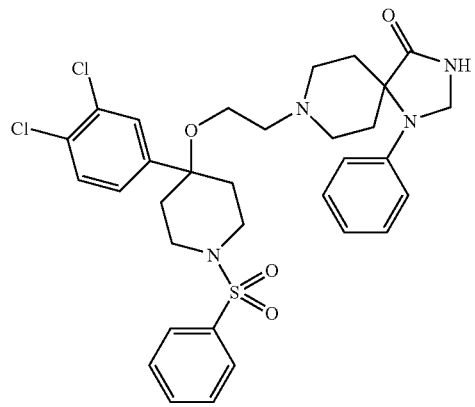

¹HNMR (400 MHz, CD₃OD) δ[ppm]: 8.48 (1H, broad s), 7.86-7.79 (2H, m), 7.62-7.51 (5H, m), 7.41-7.32 (3H, m), 7.06-6.95 (3H, m), 4.76 (2H, s), 3.76 (2H, d, J=19.6 Hz), 3.51-2.99 (8H, m), 2.71 (2H, t, J=111.2 Hz), 2.58 (2H, td, J=14.5 Hz, 0.6 Hz), 2.20 (2H, t, J=13.5 Hz), 2.02 (2H, td, J=12.6 Hz, 4.1 Hz), 1.75 (2H, d, J=14.6 Hz). HRMS cacld for $C_{32}H_{37}Cl_2N_4O_4S$ (M+H)⁺ 643.1912, found 643.1926. Elemental Analysis for $C_{33}H_{38}Cl_2N_4O_4S$ (formic acid salt) calcd. C, 57.47%; H, 5.55%; N, 8.12%; found C, 56.94%; H, 5.68%; N, 8.04%.

Example 756

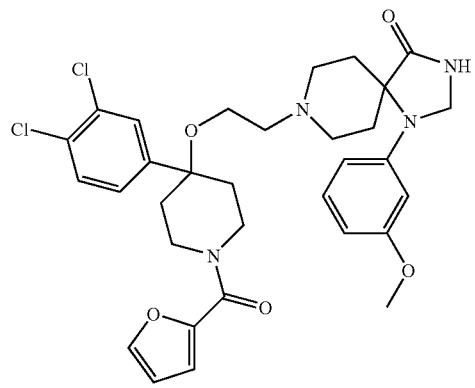

¹HNMR (400 MHz, CD₃OD) δ[ppm]: 8.51 (1H, broad s), 7.70 (1H, s), 7.59 (1H, d, J=8.5 Hz), 7.84 (1H, dd, J=6.5 Hz, 1.8 Hz), 7.21 (1H, t, J=8.1 Hz), 1.05 (1H, d, J=3.5 Hz), 6.68 (2H, dd, 8.3 Hz, 1.4 Hz), 6.61 (1H, dd, J=3.3 Hz, 1.7 Hz), 6.54-6.49 (3H, m), 4.72 (2H, s), 4.43 (2H, broad d, J=11.8 Hz), 3.85-3.75 (5H, m), 3.46-3.27 (8H, m), 2.85 (2H, td, J=14.5 Hz, 3.5 Hz), 2.28 (2h, d, J=13.5 Hz), 2.06-1.95 (4H, m). HRMS calcd. for $C_{32}H_{37}Cl_2N_4O_5$ (M+H)⁺, 627.2141 found 627.2128. Elemental Analysis for $C_{33}H_{38}Cl_2N_4O_7$

Example 757

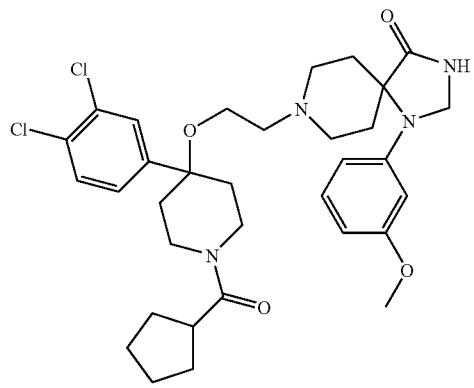

¹HNMR (400 MHz, CD₃OD) δ[ppm]: 8.51 (1H, broad s), 7.69 (1H, d, J=1.8 Hz), 7.58 (1H, d, J=8.4 Hz), 7.47 (1H, dd, J=8.4 Hz, 1.8 Hz), 7.22 (1H, t, J=8.1 Hz), 6.67 (1H, broad d, J=8.1 Hz), 6.55-6.50 (4H, m), 4.73 (2H, s), 4.45 (1H, d, J=12.8 Hz), 4.00 (1H, d, J=14.4 Hz), 3.79-3.62 (5H, m), 3.55 (1H, t, J=7.1 Hz), 3.45-3.32 (6H, m), 3.22-3.11 (4H, m), 2.80 (2H, td, J=14.3 Hz, 3.5 Hz), 2.22 (2H, broad d, J=11.6 Hz), 1.99-1.62 (10H, m). HRMS calcd. for $C_{33}H_{43}Cl_2N_4O_4$ (M+H)⁺ 629.2661, found 629.2664.

Example 758

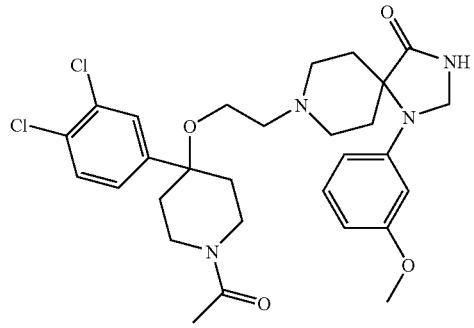

¹HNMR (400 MHz, CD₃OD) δ[ppm]: 8.50 (1H, broad s), 7.69 (1H, d, J=1.8 Hz), 7.58 (1H, d, J=8.5 Hz), 7.47 (1H, dd, J=8.4 Hz, 1.8 Hz), 7.22 (1H, t, J=8.1 Hz), 6.68 (1H, dd, J=8.3 Hz, 1.6 Hz), 6.55-6.50 (4H, m), 4.73 (2H, s), 4.43 (1H, d, J=13.1 Hz), 3.86-3.74 (6H, m), 3.59 (1H, t, J=10.9 Hz), 3.44-3.32 (4H, m), 3.23 (2H, s), 3.12 (1H, t, J=9.4 Hz), 2.85-2.77 (2H, m), 2.25-2.25-2.17 (5H, m), 2.04-1.75 (4H, m). HRMS calcd. for $C_{29}H_{37}Cl_2N_4O_4$ (M+H)⁺ 575.2192, found 575.2190. Elemental Analysis calcd. for $C_{30}H_{39}Cl_2N_4O_6$ (formic acid salt) C, 57.97%; H, 6.16%; N, 9.01%; found C, 57.83%; H, 6.31%; N, 8.94%.

Example 759

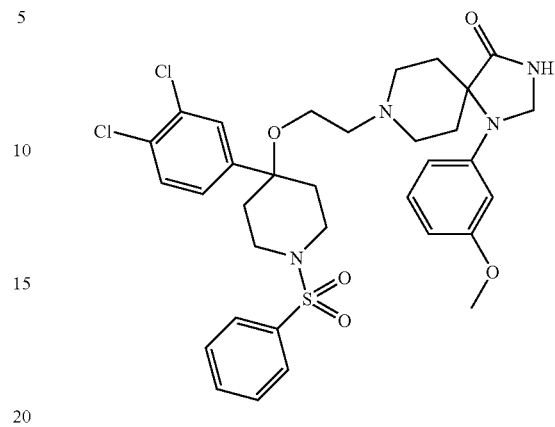

¹HNMR (400 MHz, CD₃OD) δ[ppm]: 8.47 (1H, broad s), 7.82-7.78 (2H, m), 7.61 (1H, d, J=1.8 Hz), 7.57-7.52 (4H, m), 7.40 (1H, dd, J=8.4 Hz, 1.8 Hz), 7.26 (1H, t, J=8.3 Hz), 6.64 (1H, dd, J=8.3 Hz, 1.8 Hz), 6.58 (1H, broad d, J=8.2 Hz), 6.50 (1H, s), 4.74 (2H, s), 3.82 (3H, s), 3.72 (2H, d, J=11.8 Hz), 3.41-3.35 (2H, m), 3.25 (2H, t, J=4.7 Hz), 3.04 (2H, broad d, J=11.0 Hz), 2.91 (2H, broad s), 2.71 (2H, t, J=10.7 Hz), 2.54 (2H, td, J=14.3 Hz, 4.8 Hz), 2.22 (2H, d, J=13.4 Hz), 2.00 (2H, td, J=12.7 Hz, 3.1 Hz), 1.73 (2H, d, J=14.3 Hz). HRMS: calcd. for $C_{33}H_{39}Cl_2N_4O_4S$ (M+H)⁺ 673.2018, found 673.2002.

Example 760

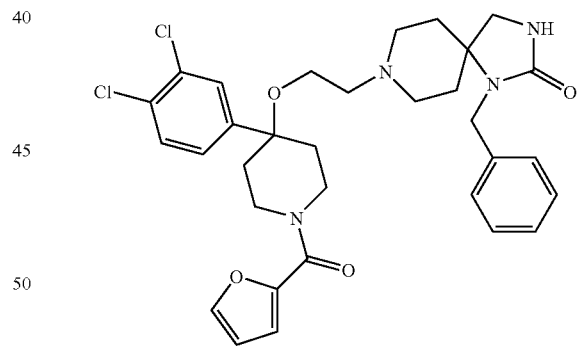

¹HNMR (400 MHz, CD₃OD) δ[ppm]: 8.43 (1H, broad s), 7.70 (1H, s), 7.65 (1H, d, J=1.6 Hz), 7.55 (1H, d, J=14.7 Hz), 7.41 (1H, dd, J=8.4 Hz, 1.8 Hz), 7.36-7.29 (4H, m), 7.26-7.22 (1H, m), 7.05 (1H, d, J=3.3 Hz), 6.62-6.59 (1H, m), 4.45-4.41 (4H, m), 3.40 (2H, s), 3.33-3.27 (4H, m), 3.05 (2H, d, J=12.1 Hz), 2.80 (2H, t, J=4.8 Hz), 2.40 (2H, t, J=12.5 Hz), 2.22 (2H, d, J=113.5 Hz), 2.05-1.94 (4H, m), 1.60 (2H, d, J=13.1 Hz). HRMS: calcd. for $C_{32}H_{37}Cl_2N_4O_4$ (M+H)⁺ 611.2192, found 611.2205. Elemental Analysis: calcd. for $C_{33}H_{39}Cl_2N_4O_6$ (formic acid salt) C, 60.27%; H, 5.82%; N, 8.52%; found C, 61.08%; H, 5.91%; N, 8.44%.

Example 761
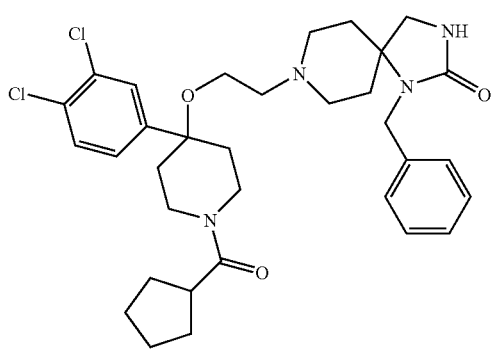
¹HNMR (400 MHz, CD₃OD) δ[ppm]: 7.59 (1H, d, J=2.0 Hz), 7.46 (1H, d, J=8.4 Hz), 7.37-7.27 (5H, m), 7.23-7.20 (1H, m), 4.44-4.37 (3H, m), 3.97 (1H, d, J=12.8 Hz), 3.54-3.45 (2H, m), 3.34 (2H, s), 3.23-3.18 (2H, m), 3.11-3.00 (1H, m), 2.86 (2H, broad d, J=11.4 Hz), 2.60 (2H, t, J=115.5 Hz), 2.17-2.11 (4H, m), 1.95-1.49 (14H, m). HRMS: calcd. for $C_{33}H_{43}Cl_2N_4O_3$ (M+H)⁺ 613.2712, found 613.2723.
Example 762
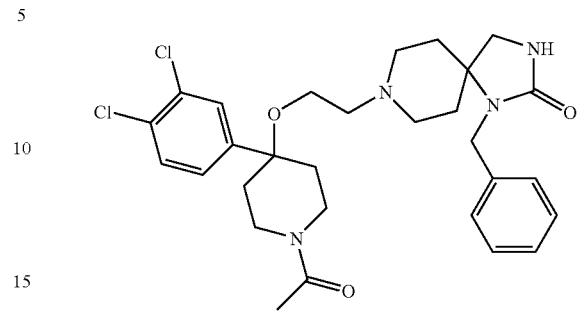
¹HNMR (400 MHz, CD₃OD) δ[ppm]: 8.38 (1H, broad), 7.63 (1H, d, J=1.7 Hz), 7.51 (1H, d, J=8.4 Hz), 7.41-7.25 (6H, m), 4.52-4.41 (3H, m), 3.80 (2H, t, J=11.8 Hz), 3.53 (1H, t, J=13.2 hz), 3.38 (2H, d, J=10.1 Hz), 3.26 (2H, broad s), 3.09-2.95 (4H, m), 2.83-2.67 (2H, m), 2.45-2.30 (2H, m), 2.17-1.81 (8H, m), 1.58-1.51 (2H, m). HRMS cacld for $C_{29}H_{37}Cl_2N_4O_3$ (M+H)⁺ 559.2243, found 559.2240.
Examples 763-774 were synthesized analogously to example 16 and 703.
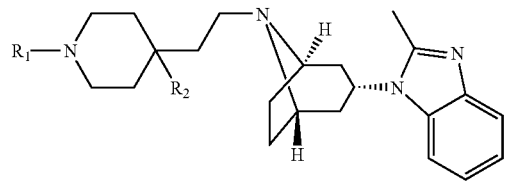
| Example | R¹ | R² | ESI-MS m/z (M + H) |
|---|---|---|---|
| 763 | 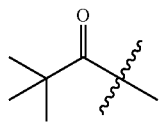 | 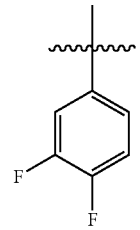 | 549 |
| 764 | 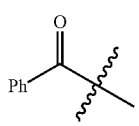 | 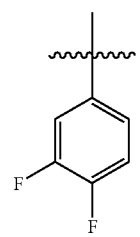 | 569 |

-continued
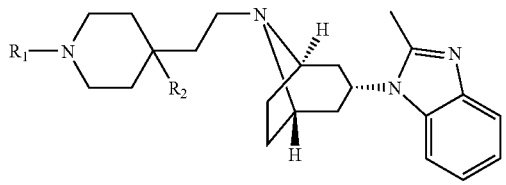
| | R¹ | R² | ESI-MS m/z (M + H) |
|---|---|---|---|
| 765 | PhC(O)- (α-methyl) | 3-MeO-phenyl | 563 |
| 766 | 3-MeO-C₆H₄-C(O)- (α-methyl) | 3,4-diF-phenyl | 627 |
| 767 | 3-HO-C₆H₄-C(O)- (α-methyl) | 3,4-diF-phenyl | 613 |
| Example # | | | |
|---|---|---|---|
| 768 | 3-(5-oxo-4,5-dihydro-1,2,4-oxadiazol-3-yl)phenyl-C(O)- (α-methyl) | phenyl | 617 |
| 769 | t-Bu-C(O)- (α-methyl) | 4-MeO-phenyl | 543 |

-continued
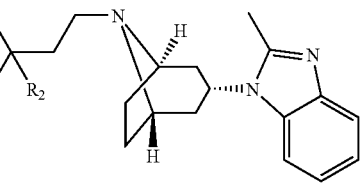
| | R¹ | R² | ESI-MS m/z (M + H) |
|---|---|---|---|
| 770 | 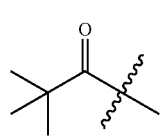 | 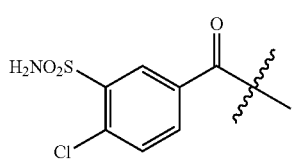 | 548 |
| 771 | 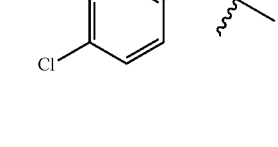 |  | 716 |
| 772 | 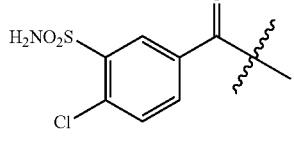 | | 665 |
| 773 | | | 645 |
| 774 | | | 681 |

The following compounds were synthesized using chemistry described elsewhere in this application.

Example 775 tert-butyl 4-{3-[4-(2-oxo-2,3-dihydro-1H-benzimidazol-1-yl)piperidin-1-yl]propyl}-4-phenylpiperidine-1-carboxylate

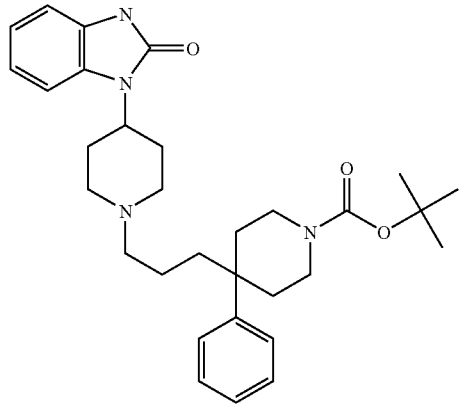

$^1$H NMR (400 MHz, CDCl$_3$) δ 10.43 (m, 1H), 7.32-6.98 (m, 10H), 4.28 (m, 1H), 3.65 (m, 2H), 3.09 (m, 2H), 2.87-2.84 (m, 2H), 2.37 (m, 2H), 2.18 (m, 4H), 1.95 (m, 1H), 1.70 (m, 4H), 1.54 (m, 2H), 1.41 (s, 9H), 1.14-1.00 (m, 2H). MS (electrospray +) 519.27 (M+1).

Example 776 tert-butyl 4-{2-[(1R,5S)-3-(2-methyl-1H-benzimidazol-1-yl)-8-azabicyclo[3.2.1]oct-8-yl]ethyl}-4-phenylpiperidine-1-carboxylate

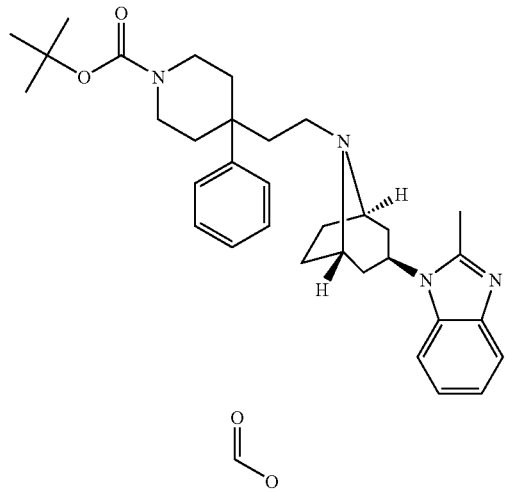

$^1$H NMR (300 MHz, methanol-d$_4$) δ 7.76 (m, 1H), 7.59-7.38 (m, 5H), 7.39-7.13 (m, 3H), 4.80-4.63 (m, 1H), 3.95 (m, 2H), 3.81-3.63 (m, 2H), 3.20-3.09 (m, 2H), 2.80-2.55 (m, 7H), 2.28-2.20 (m, 2H), 2.13-1.92 (m, 8H), 1.90-1.75 (m, 2H), 1.47 (s, 9H). MS (electrospray +) 529.60 (M+1).

Example 777

1-((1R,5S)-8-{2-[1-(cyclopentylcarbonyl)-4-phenylpiperidin-4-yl]ethyl}-8-azabicyclo[3.2.1]oct-3-yl)-2-methyl-1H-benzimidazole

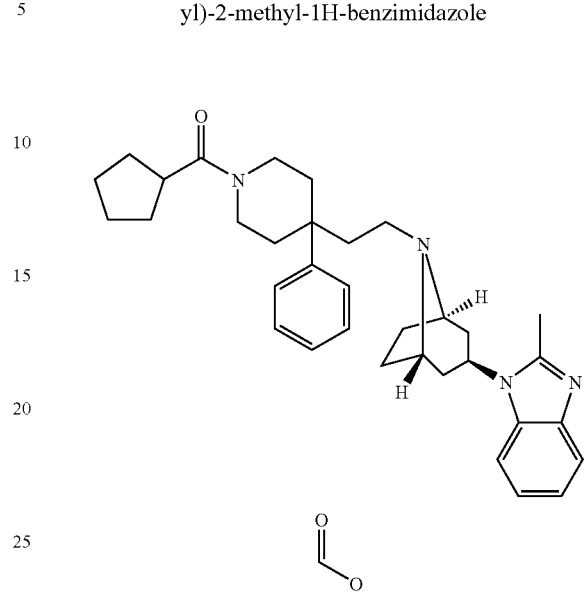

$^1$H NMR (300 MHz, methanol-d$_4$) δ 7.65 (m, 1H), 7.48-7.32 (m, 5H), 7.26-7.06 (m, 3H), 4.65 (m, 1H), 4.04-3.71 (m, 4H), 3.20 (m, 1H), 3.09-2.94 (m, 2H), 2.71-2.46 (m, 7H), 2.32-2.16 (m, 2H), 2.10-1.86 (m, 8H), 1.83-1.47 (m, 10H). HR MS (M+H) calc: 525.3593, found 525.3595, delta 0.2 mmu.

Example 778

1-{(1R,5S)-8-[2-(1-benzoyl-4-phenylpiperidin-4-yl)ethyl]-8-azabicyclo[3.2.1]oct-3-yl}-2-methyl-1H-benzimidazole

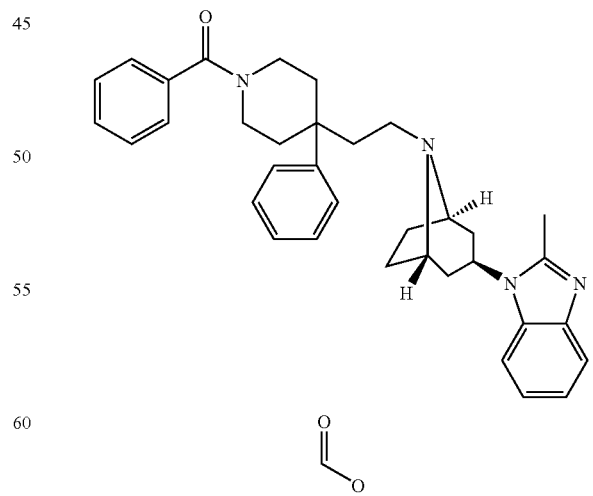

$^1$H NMR (300 MHz, methanol-d$_4$) δ 7.80 (m, 1H), 7.62-7.17 (m, 13H), 4.74 (m, 1H), 4.30-4.13 (m, 1H), 4.02 (m, 2H), 3.71-3.55 (m, 1H), 3.32 (s, 2H), 2.84-2.71 (m, 4H), 2.65 (s, 3H), 2.45 (m, 1H), 2.29-1.81 (m, 11H). HRMS (M+H) calc: 533.3280, found 533.3267, delta 1.3 mmu.

Example 779

1-benzoyl-4-phenyl-4-{2-[4-(3-phenylpropyl)piperidin-1-yl]ethyl}piperidine

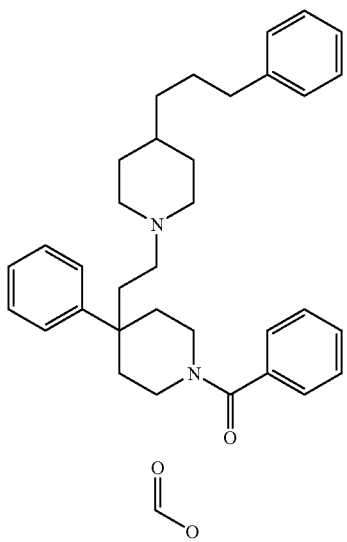

$^1$H NMR (300 MHz, methanol-$d_4$) δ 7.45-7.33 (m, 9H), 7.29-7.17 (m, 3H), 7.14-7.05 (m, 3H), 4.15 (m, 1H), 3.55 (m, 1H), 3.30-3.15 (m, 4H), 2.58-2.33 (m, 7H), 2.26-2.18 (m, 1H), 2.00-1.73 (m, 6H), 1.59 (m, 2H), 1.41 (m, 1H), 1.29-1.15 (m, 4H). HRMS (M+H) calc: 495.3375, found 495.3376, delta 0.1 mmu.

Example 780

1-benzoyl-4-{2-[4-(3-benzyl-1,2,4-oxadiazol-5-yl)piperidin-1-yl]ethyl}-4-phenylpiperidine

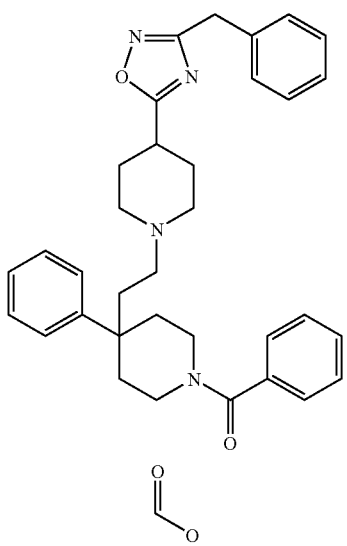

$^1$H NMR (300 MHz, methanol-$d_4$) δ 7.45-7.39 (m, 9H), 7.29-7.18 (m, 6H), 4.14 (m, 1H), 4.01 (s, 2H), 3.58 (m, 1H), 3.30-3.16 (m, 3H), 3.02-2.86 (m, 3H), 2.38 (m, 1H), 2.20 (m, 4H), 2.06-1.98 (m, 2H), 1.91-1.74 (m, 6H). HRMS (M+H) calc: 535.3073, found 535.3098, delta 2.5 mmu.

Example 781

1-(1-{2-[1-(cyclopentylcarbonyl)-4-phenylpiperidin-4-yl]ethyl}piperidin-4-yl)-2-methyl-1H-benzimidazole

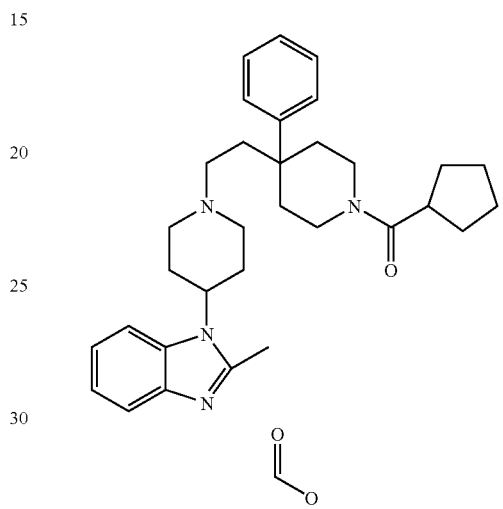

$^1$H NMR (400 MHz, methanol-$d_4$) δ 7.65 (m, 1H), 7.52-7.44 (m, 2H), 7.39-7.30 (m, 5H), 7.24-7.14 (m, 1H), 4.89 (m, 1H), 4.02-3.91 (m, 1H), 3.81-3.75 (m, 1H), 3.62-3.53 (m, 2H), 3.13-3.02 (m, 3H), 3.00-2.73 (m, 8H), 2.26-2.09 (m, 6H), 1.84-1.49 (m, 10H), 1.24-1.13 (m, 1H). HRMS (M+H) calc: 499.3435, found 499.3434, delta 0.1 mmu.

Example 782

1-{1-[2-(1-benzoyl-4-phenylpiperidin-4-yl)ethyl]piperidin-4-yl}-2-methyl-1H-benzimidazole

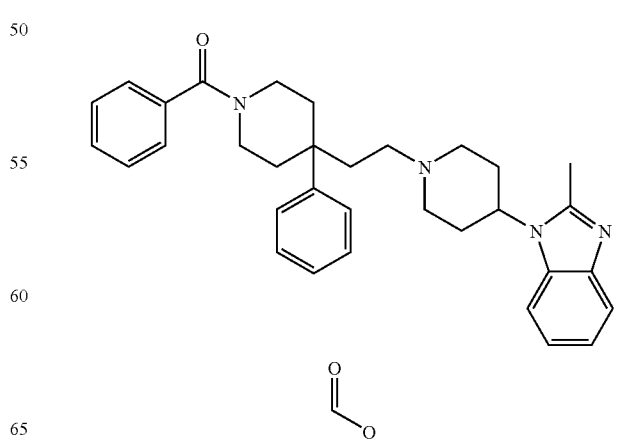

¹H NMR (400 MHz, methanol-d₄) δ 7.63 (m, 1H), 7.51-7.45 (m, 3H), 7.40-7.32 (m, 6H), 7.24-7.16 (m, 2H), 6.91 (s, 1H), 6.70 (s, 1H), 4.89 (m, 1H), 4.89 (m, 1H), 4.10 (m, 1H), 3.80 (m, 1H), 3.60 (m, 2H), 3.37-3.24 (m, 3H), 3.10 (m, 3H), 2.95-2.86 (m, 2H), 2.77 (m, 2H), 2.31 (m, 2H), 2.22-2.13 (m, 4H), 1.92-1.87 (m, 2H), 1.23-1.18 (m, 1H). HRMS (M+H) calc: 507.3126, found 507.3115, delta 1.1 mmu.

Example 783

1-(1-{2-[1-(2-furoyl)-4-phenylpiperidin-4-yl]ethyl}piperidin-4-yl)-2-methyl-1H-benzimidazole

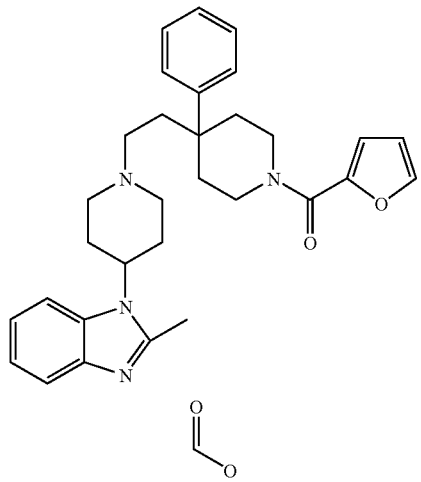

¹H NMR (400 MHz, methanol-d₄) δ 8.22 (m, 1H), 7.67 (m, 1H), 7.58 (s, 1H), 7.60-7.48 (m, 2H), 7.42-7.31 (m, 4H), 7.22 (m, 1H), 6.91 (m, 1H), 6.49 (s, 1H), 4.89 (m, 1H), 4.06 (m, 2H), 3.68-3.56 (m, 2H), 3.08 (m, 2H), 3.00-2.75 (m, 7H), 2.56 (s, 3H), 2.32-2.18 (m, 5H), 1.88 (m, 2H). MS (electrospray +) 523.42 (M+1).

Example 784

1-(1-{2-[1-(isoxazol-5-ylcarbonyl)-4-phenylpiperidin-4-yl]ethyl}piperidin-4-yl)-2-methyl-1H-benzimidazole

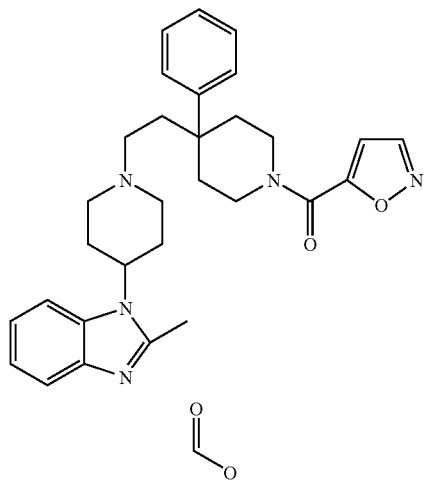

¹H NMR (400 MHz, methanol-d₄) δ 7.64 (m, 1H), 7.46 (m, 2H), 7.41-7.27 (m, 7H), 7.24-7.10 (m, 1H), 4.88 (m, 1H), 4.07 (m, 2H), 3.61-3.49 (m, 1H), 3.20 (s, 2H), 3.11-3.00 (m, 2H), 2.93-2.84 (m, 2H), 2.79-2.71 (m, 4H), 2.30 (m, 1H), 2.21-2.09 (m, 4H), 1.92-1.75 (m, 2H), 1.21 (m, 1H). HRMS (M+H) calc: 498.2869, found 498.2845, delta 2.4 mmu.

Example 785 tert-butyl 4-{2-[(1R,5S)-3-(2-methyl-1H-benzimidazol-1-yl)-8-azabicyclo[3.2.1]oct-8-yl]ethyl}-4-phenylpiperidine-1-carboxylate

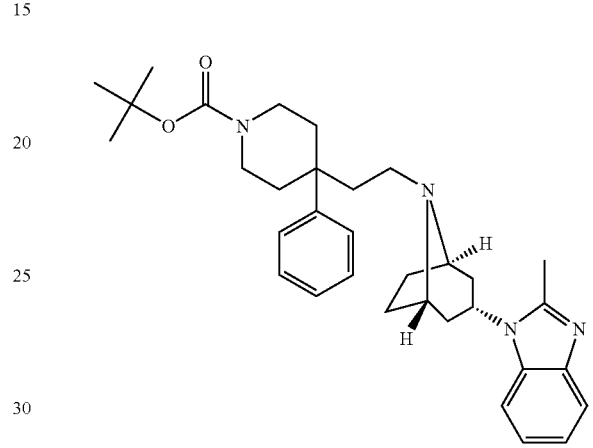

¹H NMR (400 MHz, CDCl₃) δ 7.22 (m, 1H), 6.91-6.68 (m, 8H), 4.15 (m, 1H), 3.23-3.18 (m, 2H), 2.82-2.67 (m, 4H), 2.12 (s, 3H), 1.97-1.87 (m, 2H), 1.76-1.64 (m, 2H), 1.51-1.29 (m, 10H), 1.17-1.13 (m, 2H), 1.00 (s, 9H). MS (electrospray +) 529.61 (M+1).

Example 786

1-[(1R,5S)-8-(2-{1-[(3-chlorothien-2-yl)carbonyl]-4-phenylpiperidin-4-yl}ethyl)-8-azabicyclo[3.2.1]oct-3-yl]-2-methyl-1H-benzimidazole

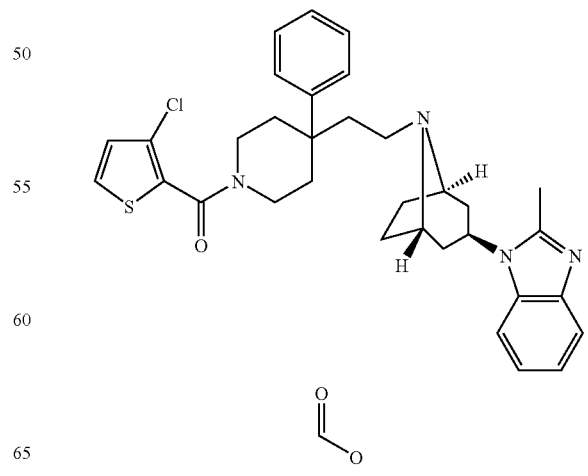

¹H NMR (400 MHz, methanol-d₄) δ 7.66 (m, 1H), 7.56-7.43 (m, 5H), 7.34-7.23 (m, 3H), 7.01 (m, 2H), 4.72 (m, 1H), 4.10 (m, 2H), 3.41-3.28 (m, 4H), 2.90 (m, 2H), 2.79 (m, 2H), 2.68 (s, 3H), 2.41-1.94 (m, 12H). HRMS (M+H) calc: 573.2455, found 573.2452, delta 0.3 mmu.

Example 787

(1R,5S)-8-{2-[1-(2-furoyl)-4-phenylpiperidin-4-yl]ethyl}-3-phenyl-8-azabicyclo[3.2.1]octane

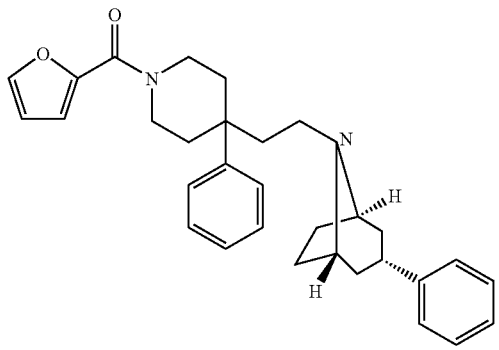

¹H NMR (400 MHz, CDCl₃) δ 7.38 (s, 1H), 7.31-7.00 (m, 10H), 6.86 (m, 1H), 6.38 (m, 1H), 3.98 (m, 1H), 3.48-3.27 (m, 2H), 3.12 (m, 2H), 2.96-2.86 (m, 1H), 2.38-2.15 (m, 4H), 1.98 (m, 3H), 1.86-1.76 (m, 4H), 1.60-1.50 (m, 4H), 1.29 (m, 2H). HRMS (M+H) calc: 469.2855, found 469.2858, delta 0.3 mmu.

Example 788

(1R,5S)-8-[2-(1-benzoyl-4-phenylpiperidin-4-yl)ethyl]-3-phenyl-8-azabicyclo[3.2.1]octane

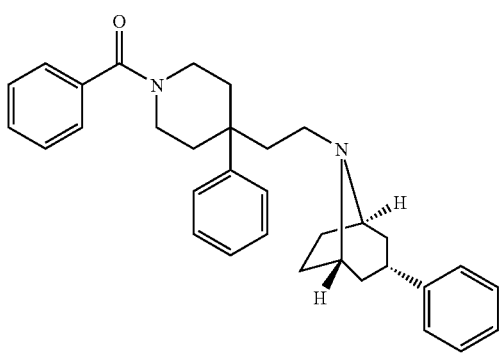

¹H NMR (400 MHz, CDCl₃) δ 7.44-7.26 (m, 13H), 7.15 (m, 2H), 4.16-4.12 (m, 1H), 3.58 (m, 1H), 3.45 (m, 1H), 3.32-3.16 (m, 3H), 3.01 (m, 1H), 2.41-2.26 (m, 3H), 2.16-1.86 (m, 5H), 1.78-1.63 (m, 5H), 1.38-1.24 (m, 3H). HRMS (M+H) calc: 479.3062, found 479.3057, delta 0.6 mmu.

Example 789

1-[(1R,5S)-8-(2-{1-[(2,4-dimethyl-1-oxidopyridin-3-yl)carbonyl]-4-phenylpiperidin-4-yl}ethyl)-8-azabicyclo[3.2.1]oct-3-yl]-2-methyl-1H-benzimidazole

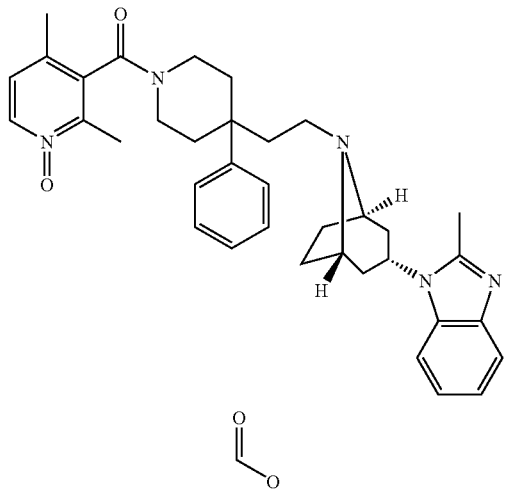

¹H NMR (500 MHz, DMSO-d₆) δ 8.18 (m, 1H), 7.49 (m, 1H), 7.37 (m, 5H), 7.26-7.08 (m, 4H), 4.51 (m, 1H), 4.02-3.89 (m, 2H), 3.60-3.44 (m, 2H), 3.35-3.21 (m, 4H), 3.02 (m, 1H), 2.54-2.38 (m, 4H), 2.38-2.28 (m, 3H), 2.25-2.09 (m, 3H), 2.03 (m, 2H), 1.87-1.70 (m, 8H), 1.58 (m, 2H). HRMS (M+H) calc: 578.3495, found 578.3519, delta 2.4 mmu.

Example 790

(1R,5S)-3-(1,3-benzodioxol-5-yl)-8-[2-(1-benzoyl-4-phenylpiperidin-4-yl)ethyl]-8-azabicyclo[3.2.1]octane

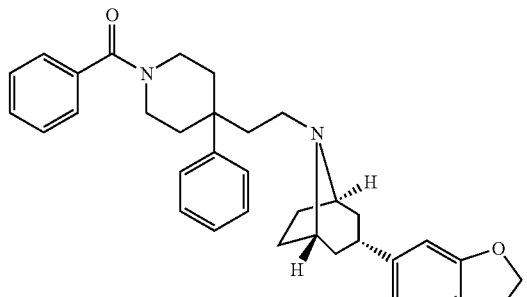

¹H NMR (400 MHz, CDCl₃) δ 73.7-7.12 (m, 9H), 6.67-6.63 (m, 2H), 5.83 (s, 2H), 4.04 (m, 1H), 3.61-3.10 (m, 5H), 2.89 (m, 1H), 2.41-2.17 (m, 3H), 2.10-1.82 (m, 6H), 1.71 (m, 1H), 1.64-1.46 (m, 4H), 1.36-1.28 (m, 2H), 1.19 (m, 2H). HRMS (M+H) calc: 523.2961, found 523.2957, delta 0.4 mmu.

Example 791

6-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-2H-1,2,4-benzothiadiazin-3(4H)-one 1,1-dioxide

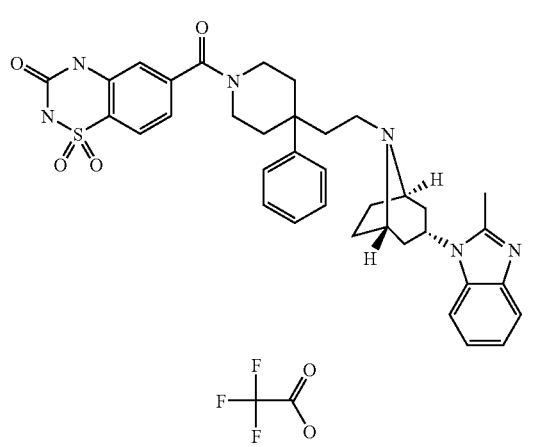

¹H NMR (500 MHz, DMSO-d₆) δ 11.17 (s, 1H), 7.84-7.69 (m, 3H), 7.65-7.56 (m, 1H), 7.51-7.36 (m, 6H), 7.3-7.17 (m, 2H), 5.15 (m, 1H), 4.34-3.84 (m, 5H), 3.27 (m, 2H), 2.81-2.71 (m, 5H), 2.62 (m, 2H), 2.54-2.50 (m, 2H), 2.25-2.11 (m, 8H), 1.86 (m, 2H). MS (electrospray +) 653.18 (M+1).

Example 792

2-{(1R,5S)-8-[2-(1-benzoyl-4-phenylpiperidin-4-yl)ethyl]-8-azabicyclo[3.2.1]oct-3-yl}-1H-isoindole-1,3(2H)-dione

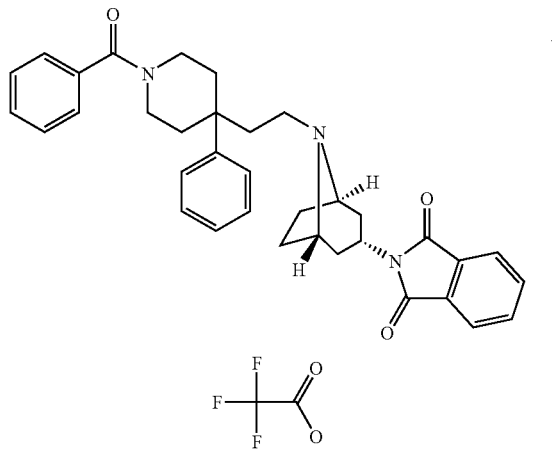

¹H NMR (500 MHz, DMSO-d₆) δ 7.80 (s, 4H), 7.43-7.33 (m, 9H), 7.21 (m, 1H), 4.31 (m, 1H), 4.07 (m, 1H), 3.88 (m, 1H), 3.13 (m, 3H), 2.50 (s, 2H), 2.18-1.98 (m, 4H), 1.80-1.66 (m, 9H), 1.42-1.36 (m, 2H). HRMS (M+H) calc: 548.2913, found 548.2900, delta 1.3 mmu.

Example 793 methyl 3,3-dimethyl-4-(4-{2-[(1R,5S)-3-(2-methyl-1H-benzimidazol-1-yl)-8-azabicyclo[3.2.1]oct-8-yl]ethyl}-4-phenylpiperidin-1-yl)-4-oxobutanoate

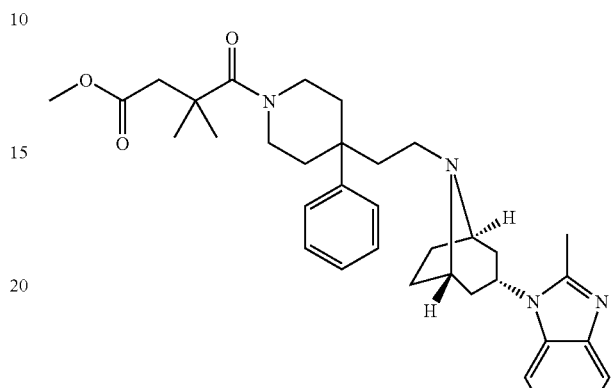

¹H NMR (400 MHz, CDCl₃) δ 7.61 (m, 1H), 7.32-7.05 (m, 8H), 4.62-4.52 (m, 1H), 4.10-3.99 (m, 1H), 3.89-3.82 (m, 2H), 3.59 (m, 4H), 2.51 (m, 5H), 2.31 (m, 2H), 2.17 (m, 1H), 1.91-1.70 (m, 9H), 1.54 (m, 2H), 1.18 (m, 6H). HRMS (M+H) calc: 571.3646, found 571.3666, delta 1.8 mmu.

Example 794 tert-butyl 4-{2-[(1R,5S)-3-(1H-1,2,3-benzotriazol-1-yl)-8-azabicyclo[3.2.1]oct-8-yl]ethyl}-4-phenylpiperidine-1-carboxylate

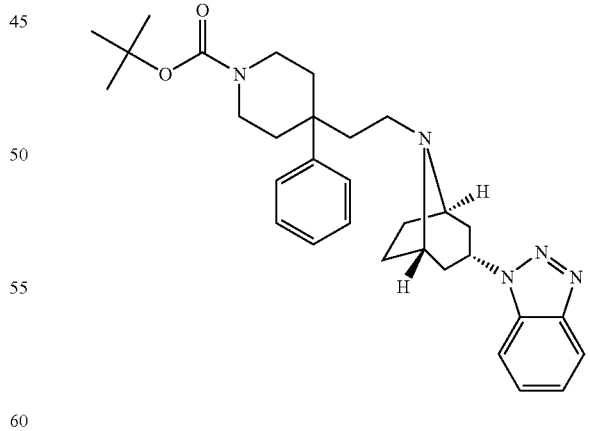

¹H NMR (300 MHz, CDCl₃) δ 7.95 (m, 1H), 7.43-7.08 (m, 8H), 4.78 (m, 1H), 3.62-3.57 (m, 2H), 3.17-3.08 (m, 4H), 2.46-2.34 (m, 2H), 2.27-2.18 (m, 2H), 2.12-1.92 (m, 4H), 1.81-1.54 (m, 8H), 1.38 (s, 9H). HRMS (M+H) calc: 516.3339, found 516.3336, delta 0.2 mmu.

Example 795

1-((1R,5S)-8-{2-[1-(cyclopropylcarbonyl)-4-phenylpiperidin-4-yl]ethyl}-8-azabicyclo[3.2.1]oct-3-yl)-2-methyl-1H-benzimidazole

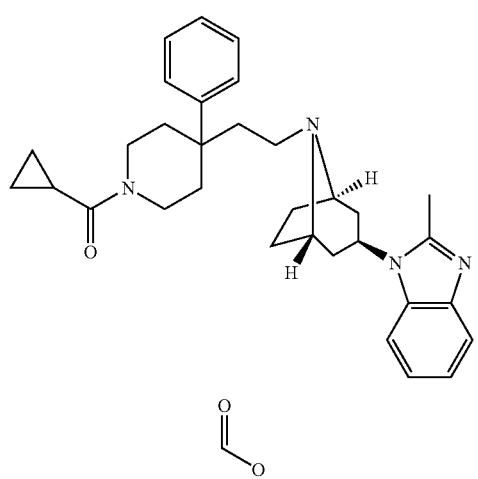

¹H NMR (400 MHz, methanol-d₄) δ 7.92 (m, 1H), 7.55-7.39 (m, 5H), 7.31-7.16 (m, 3H), 4.71 (m, 1H), 4.09-3.95 (m, 4H), 3.52-3.39 (m, 1H), 3.29-3.07 (m, 2H), 2.88-2.74 (m, 4H), 2.65 (s, 3H), 2.39-1.73 (m, 12H), 0.83-0.74 (m, 4H). HRMS (M+H) calc: 497.3280, found 497.3286, delta 0.6 mmu.

Example 796

1-((1R,5S)-8-{2-[1-(cyclobutylcarbonyl)-4-phenylpiperidin-4-yl]ethyl}-8-azabicyclo[3.2.1]oct-3-yl)-2-methyl-1H-benzimidazole

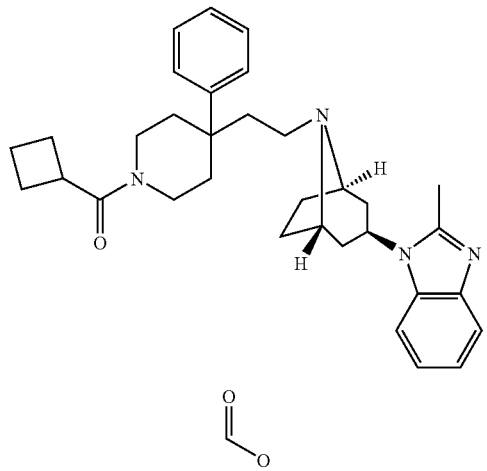

¹H NMR (400 MHz, methanol-d₄) δ 8.28 (s, 1H), 7.50-7.38 (m, 5H), 7.29-7.13 (m, 3H), 4.69 (m, 1H), 4.10-3.93 (m, 3H), 3.62-3.57 (m, 1H), 3.37-3.04 (m, 4H), 2.86-2.66 (m, 4H), 2.60 (s, 3H), 2.26-1.89 (m, 14H), 1.77-1.70 (m, 3H). HRMS (M+H) calc: 511.3437, found 511.3434, delta 0.6 mmu.

Example 797

2-methyl-1-((1R,5S)-8-{2-[4-phenyl-1-(thien-2-ylcarbonyl)piperidin-4-yl]ethyl}-8-azabicyclo[3.2.1]oct-3-yl)-1H-benzimidazole

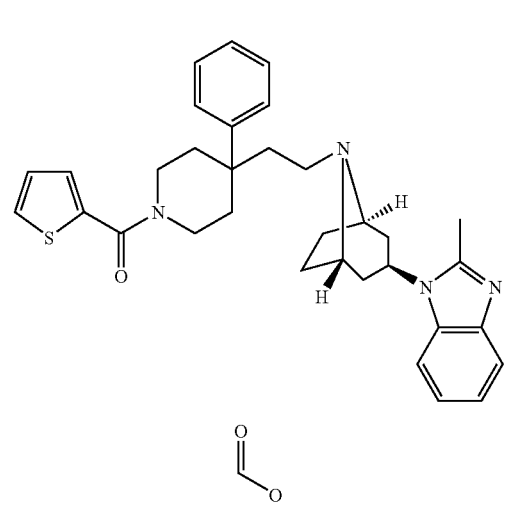

¹H NMR (300 MHz, methanol-d₄) δ 7.96 (m, 1H), 7.62-7.59 (m, 1H), 7.52-7.17 (m, 9H), 7.10 (m, 1H), 4.73 (m, 1H), 4.06 (m, 4H), 3.49-3.36 (m, 2H), 2.90-2.73 (m, 4H), 2.64 (s, 3H), 2.38-1.91 (m, 12H). HRMS (M+H) calc: 539.2845, found 539.2854, delta 0.9 mmu.

Example 798

1-((1R,5S)-8-{2-[1-(2,2-dimethylpropanoyl)-4-phenylpiperidin-4-yl]ethyl}-8-azabicyclo[3.2.1]oct-3-yl)-2-methyl-1H-benzimidazole

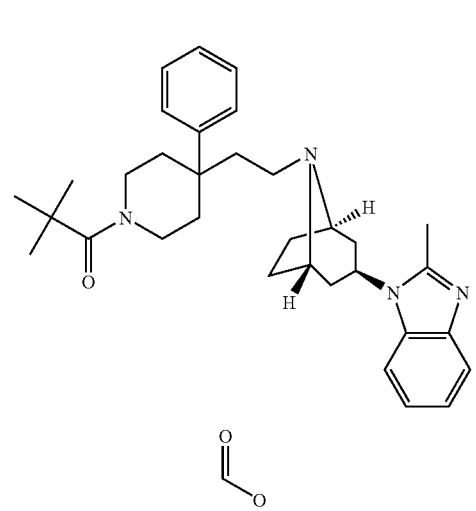

¹H NMR (400 MHz, methanol-d₄) δ 7.84 (m, 1H), 7.56-7.40 (m, 5H), 7.32-7.26 (m, 1H), 7.20 (m, 2H), 4.73 (m, 1H), 4.03 (m, 3H), 3.30-3.20 (m, 3H), 2.85-2.74 (m, 4H), 2.64 (s, 3H), 2.32-2.29 (m, 2H), 2.20-2.11 (m, 4H), 2.03 (m, 4H), 1.87-1.82 (m, 3H), 1.27 (s, 9H). HRMS (M+H) calc: 513.3593, found 513.3607, delta 1.3 mmu.

Example 799

2-methyl-1-[(1R,5S)-8-(2-{1-[(3-methylthien-2-yl}carbonyl]-4-phenylpiperidin-4-yl}ethyl)-8-azabicyclo[3.2.1]oct-3-yl]-1H-benzimidazole

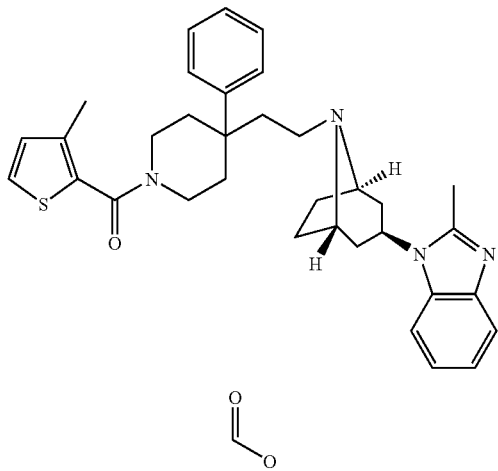

MS (electrospray +) 553 (M+1).

Example 800

2-methyl-1-[(1R,5S)-8-(2-{1-[(4-methyl-1,2,3-thiadiazol-5-yl)carbonyl]-4-phenylpiperidin-4-yl}ethyl)-8-azabicyclo[3.2.1]oct-3-yl]-1H-benzimidazole

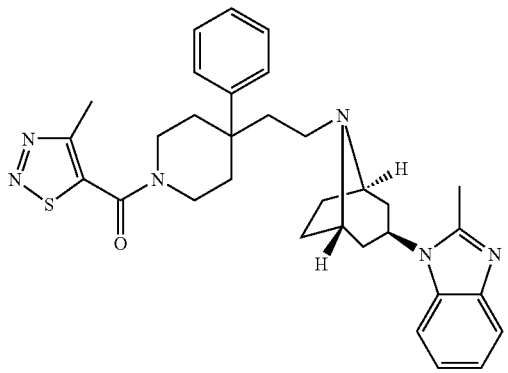

MS (electrospray +) 555 (M+1).

Example 802

Preparation of 2-chloro-4-fluoro-5-[(methylamino)sulfonyl]benzoic acid

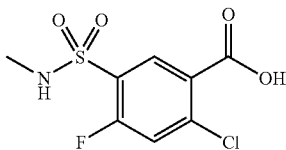

20.02 g (73.4 mmol) of 2-chloro-3-chlorosulfonyl-4-fluorobenzoic acid was added as a solid to a cooled solution of 10.5 mL of methylamine (40% aqueous solution, 293.6 mmol) in 400 mL of water. Reaction was monitored by LC/MS and complete after one hour. The reaction was acidified to pH=1 with concentrated HCl, and solid precipitated out. Product was obtained by filtration. 17.54 g obtained as a pale tan solid (89% yield). $^1$H NMR (300 MHz, DMSO-$d_6$) δ13.83-14.01 (br, 1H), 8.21-8.26 (d, 1H, J=9.11 Hz), 7.98-8.03 (q, 1H, J=4.82), 7.88-7.92 (d, 1H, J=9.11 Hz), 2.55-2.56 (d, 3H, J=4.82 Hz).

Preparation of 4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methylbenzenesulfonamide

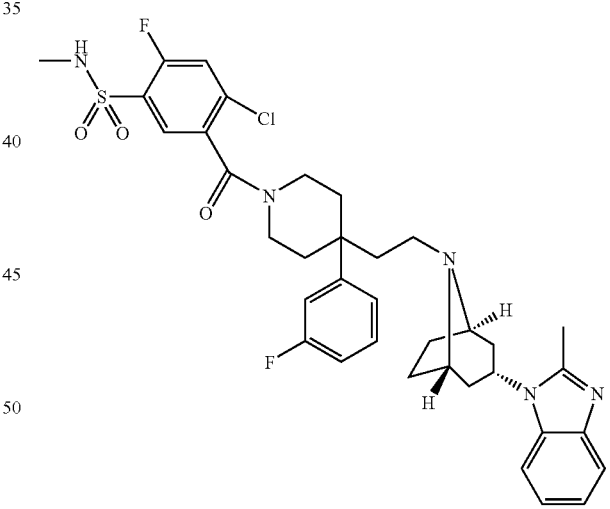

5.36 g (12.0 mmol) 1-((1R,5S)-8-{2-[4-(3-fluorophenyl)piperidin-4-yl]ethyl}-8-azabicyclo[3.2.1]oct-3-yl)-2-methyl-1H-benzimidazole, 3.20 g (12.0 mmol) 2-chloro-4-fluoro-5-[(methylamino)sulfonyl]benzoic acid were combined following the general procedure in Example 5. 3.97 g recovered (47.6% yield). $^1$H NMR (300 MHz, DMSO-$d_6$) δ 7.96-8.05 (br, 1H), 7.75-7.94 (m, 2 H), 7.38-7.56 (m, 3H), 7.24-7.30 (m, 2H), 7.07-7.18 (m, 3H), 4.48-4.60 (m, 1H), 3.91-4.03 (m, 1H), 3.23-3.49 (m, 6H), 3.04-3.13 (m, 1H), 2.52-2.60 (m, 4H), 2.33-2.44 (m, 2H), 2.12-2.32 (br, 2H), 2.01-2.09 (m, 2H), 1.76-1.95 (m, 8H), 1.60-1.66 (m, 2H). LC/MS m/z (M+H): 696

607

Preparation of (1R,5S)-8-{2-[1-{2-chloro-4-fluoro-5-[(methylamino)sulfonyl]benzoyl}-4-(3-fluorophenyl)piperidin-4-yl]ethyl}-3-(2-methyl-1H-benzimidazol-1-yl)-8-azoniabicyclo[3.2.1]octane, toluenesulfonic acid salt

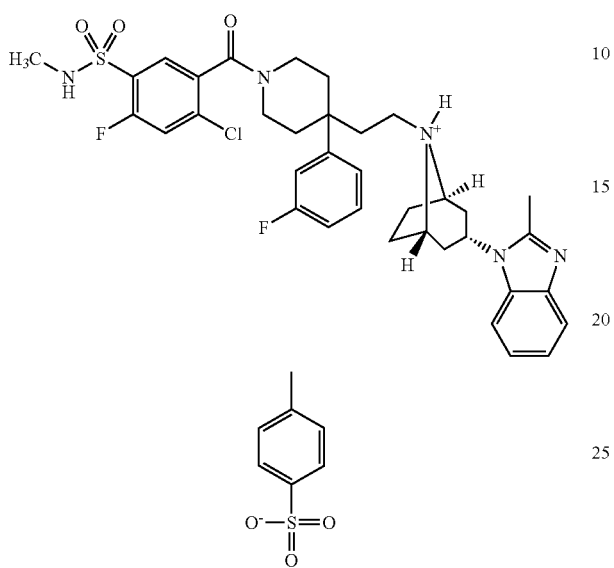

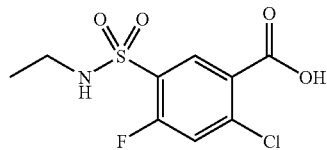

The reaction vessel was charged with (1R,5S)-8-{2-[1-{2-chloro-4-fluoro-5-[(methylamino)sulfonyl]benzoyl}-4-(3-fluorophenyl)piperidin-4-yl]ethyl}-3-(2-methyl-1H-benzimidazol-1-yl)-8-azoniabicyclo[3.2.1]octane (5.0 g) and tetrahydrofuran (65 ml, 13 volumes). The mixture was stirred and heated to 50° C. A solution of toluenesulfonic acid monohydrate (1.4 g, 1 M in tetrahydrofuran, 1 equivalent) was added to the hot mixture. After cooling, the solid was collected by filtration, washed with tetrahydrofuran (2×2.5 volumes) and dried in vacuo. Yield 93%.

Example 803

Preparation of 2-chloro-5-[(ethylamino)sulfonyl]-4-fluorobenzoic acid

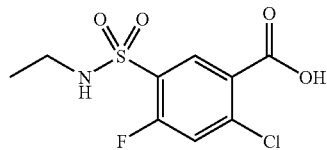

1.023 g (3.6 mmol) 3-chlorosulfonyl-4-fluorobenzoic acid was added to 5.49 mL (10.98 mmol) ethylamine in THF. THF was evaporated off at the completion of the reaction. Diluted with dichloromethane and extracted with 6N NaOH. Combined aqueous layers were then acidified to pH=1 with 6N HCl. Product creashes out and is collected by filtration and rinsed with water. Crude product was used in subsequent step without further purification.

$^1$H NMR (300 MHz, DMSO-d$_6$) δ 8.13-8.16 (d, 1H, J=7.96 Hz), 8.07-8.11 (t, 1H, J=9.79 Hz), 7.79-7.82 (d, 1H, J=9.79 Hz), 2.86-2.95 (m, 2H), 0.96-1.01 (t, 3H, J=7.34 Hz).

608

Preparation of 4-chloro-N-ethyl-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

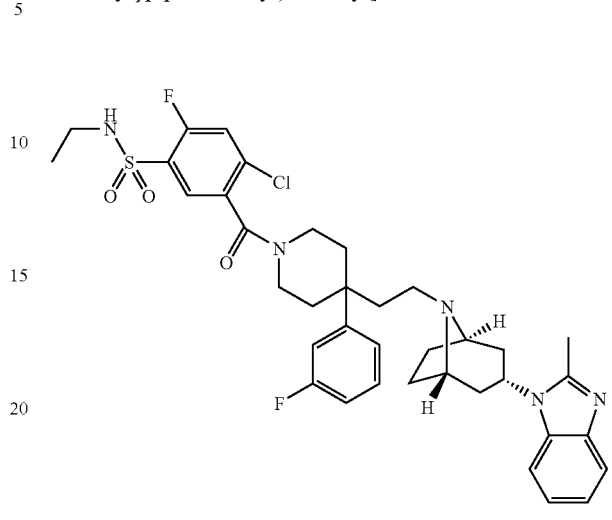

0.103 g (0.23 mmol) 1-((1R,5S)-8-{2-[4-(3-fluorophenyl)piperidin-4-yl]ethyl}-8-azabicyclo[3.2.1]oct-3-yl)-2-methyl-1H-benzimidazole and 0.129 g (0.46 mmol) 2-chloro-5-[(ethylamino)sulfonyl]-4-fluorobenzoic acid were combined following the HATU general procedure in Example 5. This compound was purified by flash chromatography on a 0-100% gradient of 1N methanolic ammonia in ethyl acetate in ethyl acetate. 0.76 g obtained (44% yield). $^1$H NMR (300 MHz, DMSO-d$_6$) δ 8.04-8.14 (m, 1H), 7.86-7.89 (d, 1H J=9.83 Hz), 7.72-7.79 (m, 3H), 7.41-7.51 (m, 3. H), 7.21-7.26 (m, 2H), 7.09-7.15 (m, 1H), 5.00-5.11 (m, 1H), 4.03-4.14 (m, 2H), 3.87-3.99 (m, 1H), 3.19-3.38 (m, 2H), 2.96-3.05 (m, 1H), 2.85-2.94 (m, 3H), 2.69-2.80 (m, 4H), 2.51-2.64 (m, 2H), 1.93-2.26 (m, 11H), 1.73-1.88 (m, 2H), 0.94-1.12 (m, 3H). LC/MS m/z (M+H): 710.

Example 804

Preparation of 2-chloro-4-fluoro-5-{[(2,2,2-trifluoroethyl)amino]sulfonyl}benzoic acid

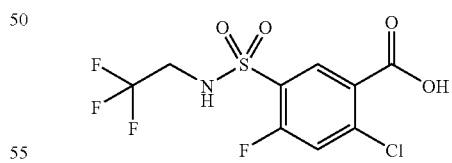

4.997 g (18.3 mmol) 3-chlorosulfonyl-4-fluorobenzoic acid, 2.90 g (27.5 mmol) NaHCO$_3$ were dissolved in 50 mL water. 1.45 mL (18.3 mmol) trifluoroethylamine was added dropwise to solution. Solution was acidified to pH=1 with concentrated HCl and product was extracted into ethyl acetate. Dried over MgSO$_4$ and concentrated. 5.27 g recovered (83% yield). Crude product was used in subsequent step without further purification. $^1$H NMR (300 MHz, DMSO-d$_6$) δ 9.22-9.37 (dt, 1H, J=6.44, 30.24 Hz), 7.80-7.92 (dd, 1H, J=9.91, 25.78 Hz), 4.04-4.16 (m, 1H), 3.77-3.90 (m, 1H).

Preparation of 4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-(2,2,2-trifluoroethyl)benzenesulfonamide

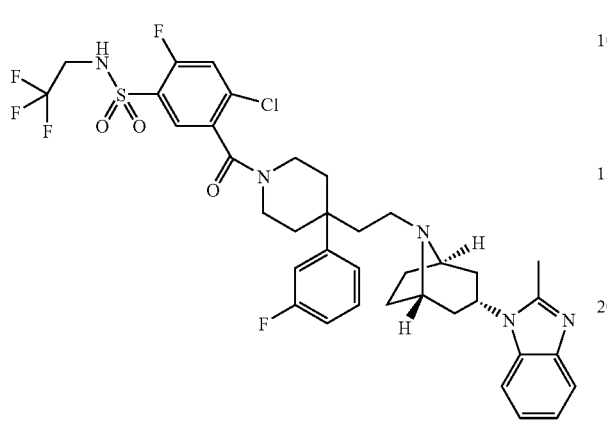

8.792 g (19.7 mmol) 1-((1R,5S)-8-{2-[4-(3-fluorophenyl)piperidin-4-yl]ethyl}-8-azabicyclo[3.2.1]oct-3-yl)-2-methyl-1H-benzimidazole and 6.59 g (19.7 mmol) 2-chloro-5-[(2,2,2-trifluoroethylamino)sulfonyl]-4-fluorobenzoic acid were combined following the HATU general procedure in Example 5. This compound was purified by flash chromatography on a 0-100% gradient of 1N methanolic ammonia in ethyl acetate in ethyl acetate. 6.31 g obtained (42% yield). $^1$H NMR (300 MHz, DMSO-$d_6$) δ 9.18-9.25 (br, 1H), 7.75-7.94 (m, 2H), 7.35-7.52 (m, 3H), 7.22-7.28 (m, 2H), 7.04-7.15 (m, 3H), 4.45-4.56 (m, 1H), 3.80-4.00 (m, 3H), 3.20-3.43 (m, 6H), 2.99-3.07 (m, 1H), 2.48-2.52 (m, 3H), 2.32-2.41 (m, 2H), 1.97-2.29 (br, 2H), 1.74-1.91 (m, 8H), 1.59-1.64 (m, 2H).

Preparation of 4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-propylbenzenesulfonamide

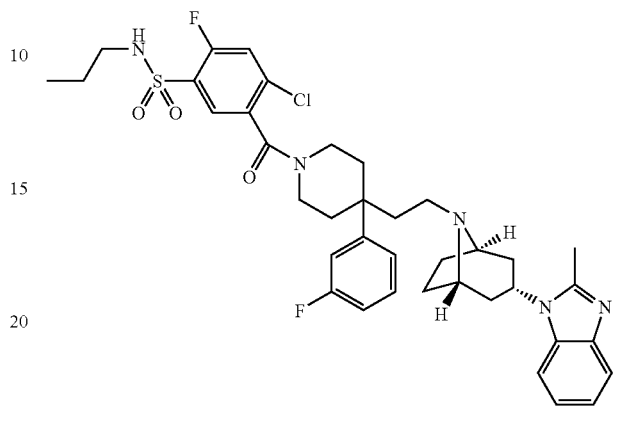

0.366 g (0.82 mmol) 1-((1R,5S)-8-{2-[4-(3-fluorophenyl)piperidinyl]ethyl}-8-azabicyclo[3.2.1]oct-3-yl)-2-methyl-1H-benzimidazole and 0.363 g (1.23 mmol) 2-chloro-4-fluoro-5-[(propylamino)sulfonyl]benzoic acid were combined following the HATU general procedure in Example 5. This compound was purified by flash chromatography on a 0-100% gradient of 90:5:5 acetonitrile: ammonium hydroxide: water in acetonitrile. 0.24 g obtained (40% yield). $^1$H NMR (300 MHz, DMSO-$d_6$) δ 8.04-8.15 (br, 1H), 7.69-7.90 (m, 2H), 7.32-7.52 (m, 3H), 7.19-7.26 (m, 2H), 7.01-7.15 (m, 3H), 4.41-4.56 (m, 1H), 3.86-3.98 (m, 1H), 3.19-3.43 (m, 6H), 2.97-3.08 (m, 1H), 2.77-2.88 (m, 2H), 2.44 (s, 3H), 2.28-2.41 (m, 2H), 1.96-2.17 (m, 2H), 1.71-1.92 (m, 9H), 1.56-1.64 (m, 2H), 1.31-1.42 (m, 2H), 0.73-0.81 (m, 3H).

Example 805

Preparation of 2-chloro-4-fluoro-5-[(propylamino)sulfonyl]benzoic acid

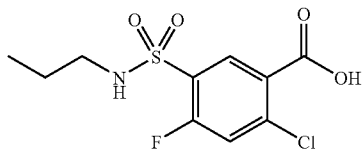

2.512 g (9.2 mmol) 3-chlorosulfonyl-4-fluorobenzoic acid was added to 2.27 mL (27.6 mmol) propylamine following the general procedure in for 2-chloro-5-[(ethylamino)sulfonyl]-4-fluorobenzoic acid. Crude product was used in subsequent step without further purification. $^1$H NMR (300 MHz, DMSO-$d_6$) δ 8.19-8.22 (d, 1H, J=7.84 Hz), 8.12-8.16 (t, 1H, J=11.59 Hz), 7.85-7.88 (d, 1H, J=9.90 Hz), 2.80-2.87 (q, 2H, J=6.82), 1.33-1.45 (m, 2H), 0.77-0.82 (t, 3H, J=7.51 Hz).

Example 806

Preparation of 2-chloro-4-fluoro-5-[(isopropylamino)sulfonzoic acid

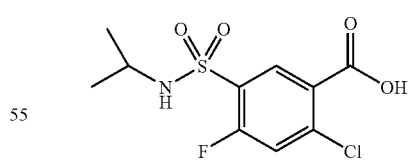

1.002 g (3.6 mmol) 3-chlorosulfonyl-4-fluorobenzoic acid was added to 0.94 mL (10.9 mmol) isopropylamine following the general procedure in for 2-chloro-5-[(ethylamino)sulfonyl]-4-fluorobenzoic acid. Crude product was used in subsequent step without further purification $^1$H NMR (300 MHz, DMSO-$d_6$) δ 8.20-8.23 (d, 1H, J=8.28 Hz), 8.12-8.17 (t, 1H, J=7.30 Hz), 7.83-7.87 (d, 1H, J=10.23 Hz), 3.30-3.43 (m, 1H), 0.98-1.01 (d, 6H, J=6.34 Hz).

611

Preparation of 4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-isopropylbenzenesulfonamide

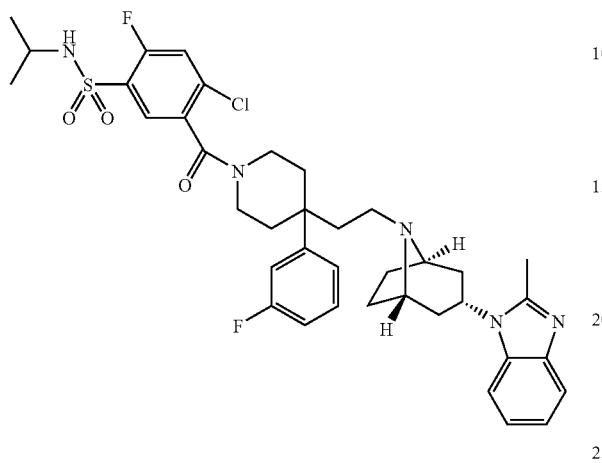

0.290 g (0.65 mmol) 1-((1R,5S)-8-{2-[4-(3-fluorophenyl)piperidin-4-yl]ethyl}-8-azabicyclo[3.2.1]oct-3-yl)-2-methyl-1H-benzimidazole and 0.288 g (0.975 mmol) 2-chloro-4-fluoro-5-[(isopropylamino)sulfonyl]benzoic acid were combined following the HATU general procedure in Example 5. This compound was purified by reverse phase chromatography on a 0-100% gradient of 0.1% TFA in water in acetonitrile. 0.196 g obtained (42% yield). $^1$H NMR (300 MHz, DMSO-$d_6$) δ 8.09-8.19 (m, 1H), 7.76-7.99 (m, 2H), 7.38-7.55 (m, 4H), 7.25-7.31 (m, 1H), 7.07-7.20 (m, 3H), 4.52-4.62 (m, 1H), 3.92-4.01 (m, 1H), 3.29-3.43 (m, 6H), 3.01-3.11 (m, 1H), 2.76 (s, 1H), 2.47-2.51 (m, 2H), 2.36-2.45 (m, 1H), 1.78-2.04 (m, 12H), 1.25-1.32 (m, 3H), 0.99-1.07 (m, 6H).

612

Preparation of 4-chloro-N-cyclopropyl-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

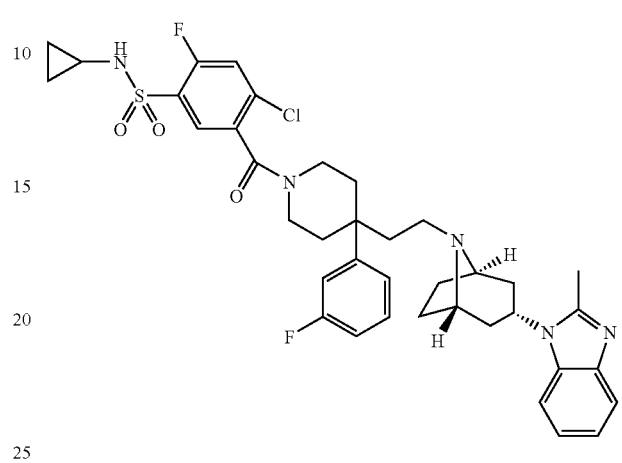

0.335 g (0.75 mmol) 1-((1R,5S)-8-{2-[4-(3-fluorophenyl)piperidin-4-yl]ethyl}-8-azabicyclo[3.2.1]oct-3-yl)-2-methyl-1H-benzimidazole and 0.242 g (0.83 mmol) 2-chloro-4-fluoro-5-[(cyclopropylamino)sulfonyl]benzoic acid were combined following the HATU general procedure in Example 5. This compound was purified by reverse phase chromatography on a 0-100% gradient of 0.1% TFA in water in acetonitrile. 0.231 g obtained (43% yield). $^1$H NMR (300 MHz, DMSO-$d_6$) δ 8.38-8.47 (br, 1H), 7.72-7.92 (m, 2H), 7.33-7.51 (m, 3H), 7.20-7.28 (m, 2H), 7.01-7.16 (m, 3H), 4.45-4.57 (m, 1H), 4.06-4.12 (m, 1H), 3.87-3.98 (m, 1H), 3.21-3.42 (m, 6H), 2.97-3.10 (m, 1H), 2.44 (s, 3H), 2.23-2.42 (m, 2H), 1.95-2.17 (m, 2H), 1.72-1.92 (m, 8H), 1.55-1.65 (m, 2H), 0.34-0.53 (m, 4H).

Example 807

Preparation of 2-chloro-5-[(cyclopropylamino)sulfonyl]-4-fluorobenzoic acid

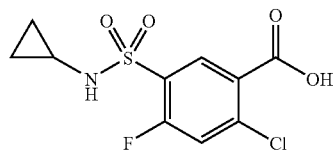

1.005 g (3.6 mmol) 3-chlorosulfonyl-4-fluorobenzoic acid was added to 0.76 mL (10.9 mmol) cyclopropylamine following the general procedure in for 2-chloro-5-[(ethylamino)sulfonyl]-4-fluorobenzoic acid. Crude product was used in subsequent step without further purification $^1$H NMR (300 MHz, DMSO-$d_6$) δ 8.46-8.48 (d, 1H, J=2.83 Hz), 8.22-8.26 (d, 1H, J=7.69 Hz), 7.86-7.90 (d, 1H, J=9.70), 2.23-2.32 (m, 1H), 0.46-0.56 (m, 2H), 0.36-0.44 (m, 2H).

Example 808

Preparation of 2-chloro-5-[(cyclopentylamino)sulfonyl]-4-fluorobenzoic acid

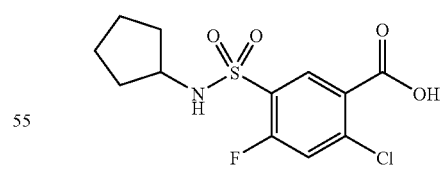

1.01 g (3.7 mmol) 3-chlorosulfonyl-4-fluorobenzoic acid was added to 1.08 mL (10.9 mmol) cyclopentylamine following the general procedure in for 2-chloro-5-[(ethylamino)sulfonyl]-4-fluorobenzoic acid. Crude product was used in subsequent step without further purification $^1$H NMR (300 MHz, DMSO-$d_6$) δ 8.21-8.24 (m, 2H), 7.84-7.88 (d, 1H, J=10.14 Hz), 48-3.59 (m, 1H), 1.48-1.70 (m, 4H), 1.28-1.46 (m, 4H).

613

Preparation of 4-chloro-N-cyclopentyl-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

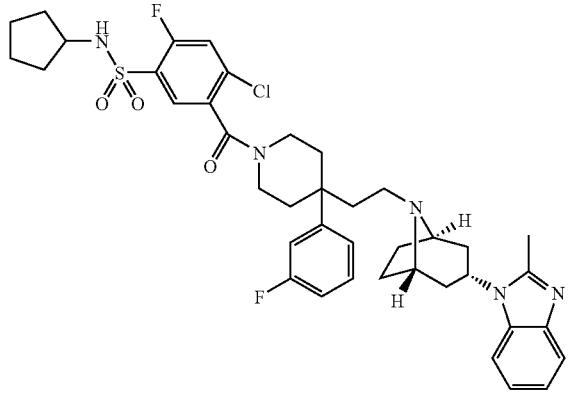

0.103 g (0.23 mmol) 1-((1R,5S)-8-{2-[4-(3-fluorophenyl)piperidin-4-yl]ethyl}-8-azabicyclo[3.2.1]oct-3-yl)-2-methyl-1H-benzimidazole and 0.148 g (0.46 mmol) 2-chloro-4-fluoro-5-[(cyclopentylamino)sulfonyl]benzoic acid were combined following the HATU general procedure in Example 5. This compound was purified by reverse phase chromatography on a 0-100% gradient of 0.1% TFA in water in acetonitrile. 0.068 g obtained (40% yield). $^1$H NMR (300 MHz, DMSO-d$_6$) δ 9.32-9.49 (br, 1H), 8.13-8.25 (m, 2H), 7.73-7.91 (m, 3H), 7.39-7.56 (m, 2H), 7.08-7.30 (m, 3H), 5.00-5.15 (m, 1H), 4.03-4.16 (m, 2H), 3.83-4.02 (m, 1H), 3.35-3.58 (m, 2H), 3.19-3.33 (m, 2H), 3.16 (s, 1H), 2.94-3.08 (m, 2H), 2.67-2.80 (m, 6H), 2.54-2.65 (m, 1H), 2.02-2.26 (m, 8H), 1.72-2.01 (m, 2H), 1.47-1.67 (m, 4H), 1.26-1.44 (m, 4H)

(Alkyl- or alkoxy-amino)benzoic Acids listed below were prepared using the following scheme

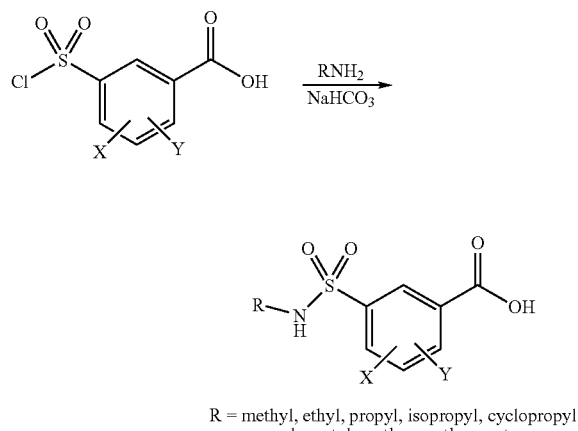

R = methyl, ethyl, propyl, isopropyl, cyclopropyl cyclopentyl, methoxy, ethoxy, etc.

X, Y = Cl, F,

614

Preparation of 2-Chloro-4-Fluoro-5-[(Methylamino)sulfonyl]benzoic Acid

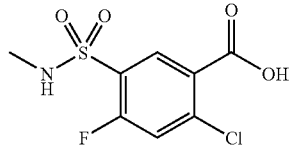

At 0° C., to a stirred ice-water suspension (~200 mL) of 2-chloro-5-(chlorosulfonyl)-4-fluorobenzoic acid was slowly added a precooled 40% methylamine (13 mL). The reaction mixture was then stirred for 2 hours before being acidified to pH~2. The desired product was precipitated and filtered out. After being dried overnight, the pure 2-chloro-4-fluoro-5-[(methylamino)sulfonyl]benzoic acid was obtained as white solid (9.8 g, 100%).

The corresponding substituted aminosulfonyl benzoic acids used in this patent were prepared in the similar methods as described above.

Example 809

Preparation of 2,4-Difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzenesulfonamide

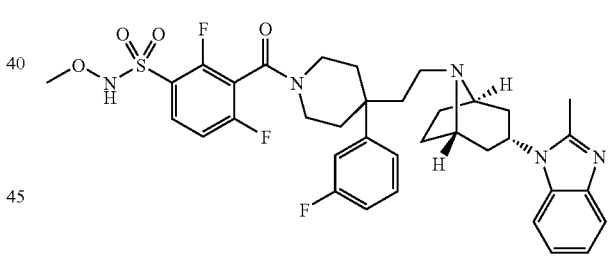

2,4-Difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzenesulfonamide (11 mg, 17%) was obtained as solid from 3-(chlorosulfonyl)-2,6-difluorobenzoic acid (105 mg, 0.4 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole (52 mg, 0.1 mmol) and methoxyamine hydrochloride (33 mg, 0.4 mmol) following the coupling procedure in example 473. $^1$H NMR (400 MHz, CD$_3$OD), δ 8.04 (q, J=3.3 Hz, 1H), 7.97 (s, 2H), 7.53 (d, J=9.6 Hz, 1H), 7.45-7.40 (m, 2H), 7.36-7.16 (m, 4, H), 7.01 (t, J=6.8 Hz, 1H), 4.80-4.71 (m, 1H), 4.20-4.19 (br, 1H), 3.74 (d, J=10.1 Hz, 3H), 3.57-3.42 (m, 4H), 3.30-3.27 (m, 1H), 2.54 (s, 3H), 2.51-2.25 (m, 4H), 2.09-1.93 (m, 10H), 1.75 (d, J=7.6 Hz, 2H). HRMS m/z (M+H)$^+$ calcd: 696.2831, obsd: 696.2831.

Example 810

Preparation of 2-(4-fluorophenyl)-2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-N-methylacetamide

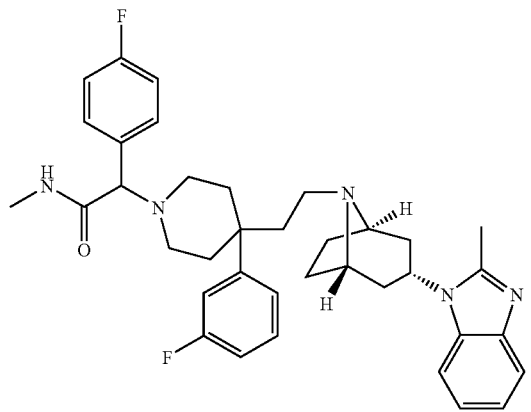

(4-Fluorophenyl)(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetic acid (prepared from 1-((1R,5S)-8-{2-[4-(3-fluorophenyl)piperidin-4-yl]ethyl}-8-azabicyclo[3.2.1]oct-3-yl)-2-methyl-1H-benzimidazole and 4-fluorophenylboronic acid following the procedure outlined in example 412. (19 mg, 0.032 mmol) was coupled with methylamine (16 μL, 2M in THF) under promotion of HATU (12 mg, 0.032 mmol) The title compound was obtained as solid (12 mg, 60%) after purification by flash chromatography, eluting with a gradient of 0-10% methanol in ethyl acetate. $^1$H NMR (400 MHz, CDCl3) δ 7.66 (d, J=7.1 Hz, 1H), 7.32-7.24 (m, 4H), 7.19-7.12 (m, 2H), 7.03-6.89 (m, 6H), 4.59 (br, 1H), 3.75 (s, 1H), 3.22 (br, 2H), 2.84 (d, J=4.9 Hz, 3H), 2.55 (s, 3H), 2.52-2.47 (m, 1H), 2.40-2.09 (m, 6H), 1.93-1.87 (m, 7H), 1.78-1.61 (m, 6H). HRMS m/z (M+H)$^+$ calcd 612.3514, obsd 612.3530.

Example 811

Preparation of 2,4-difluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzenesulfonamide

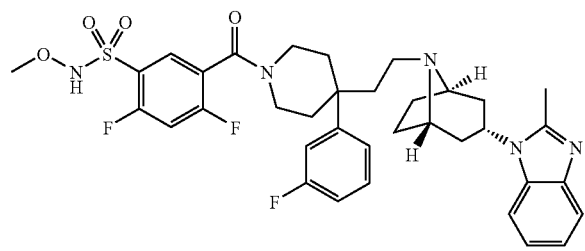

2,4-Difluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzene sulfonamide (119 mg, 43%) was obtained as solid from 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (244 mg. 0.4 mmol) and 2,4-difluoro-5-[(methoxyamino)sulfonyl]benzoic acid (266 mg, 1 mmol) and HATU (152 mg, 0.4 mmol), following the coupling procedure in example 5. $^1$H NMR (400 MHz, CDCl3) δ 7.66 (d, J=7.3 Hz, 1H), 7.40-7.34 (m, 1H), 7.0 (d, J=7.3 Hz, 1H), 7.21-7.14 (m, 2H), 7.04-6.96 (m, 5H), 4.65-4.60 (m, 1H), 4.23-4.20 (m, 1H), 3.80 (s, 3H), 3.34-3.24 (m, 6H), 2.58 (s, 3H), 2.45-2.37 (m, 2H), 2.34-2.14 (m, 2H), 2.07-1.77 (m, 12H). HRMS m/z (M+H)$^+$ calcd 696.2831, obsd 696.2812.

Example 812

Preparation of 4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzenesulfonamide

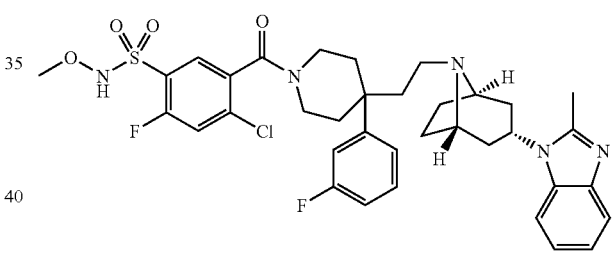

4-Chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methoxybenzenesulfonamide (170 mg, 60%) was obtained as solid from 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (244 mg. 0.4 mmol) and 2-chloro-4-fluoro-5-[(methoxyamino)sulfonyl]benzoic acid (283 mg, 1 mmol) and HATU (152 mg, 0.4 mmol), following the procedures outlined in example 5. $^1$H NMR (400 MHz, CDCl3) δ 7.91 (d, J=7.2 Hz, 1/2H, rotamer), 7.76 (d, J=7.1 Hz, 1/2H, rotamer), 7.63 (d, J=7.5 Hz, 1H), 7.38-7.28 (m, 3H), 7.18-7.12 (m, 2H), 7.08-7.04 (m, 1H), 6.98-6.94 (m, 2H), 4.62-4.57 (m, 1H), 4.26-4.17 (m, 1H), 3.78 (d, J=9.9 Hz, 3H), 3.42-3.10 (m, 6H), 2.55 (s, 3/2H, rotamer), 2.54 (s, 3/2H, rotamer), 2.42-2.32 (m, 3H), 2.14-2.07 (m, 1H), 1.94-1.70 (m, 10H), 1.64-1.63 (m, 2H). HRMS m/z (M+H)$^+$ calcd 712.2536, obsd 712.2546.

Example 813

Preparation of 2,4-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-propylbenzenesulfonamide

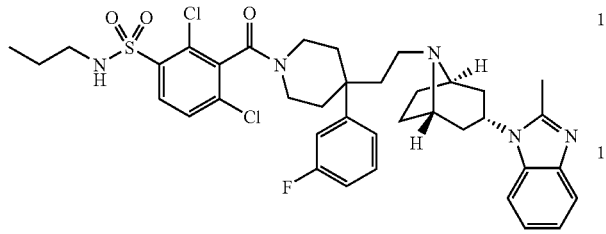

2,4-Dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-propylbenzenesulfonamide (11 mg, 15%) was obtained as solid from 2,6-dichloro-3-(chlorosulfonyl)benzoic acid (58 mg, 0.2 mmol), propyl amine (20 µL, 0.2 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (61 mg, 0.1 mmol) following the procedure outlined in example 473. $^1$H NMR (400 MHz, CD$_2$Cl$_2$), δ 8.06=8.01 (m, 1H), 7.59-7.48 (m, 2H), 7.42-7.34 (m, 2H), 7.20-7.16 (m, 3H), 7.14-6.96 (m, 2H), 4.68 (br, 1H), 4.23-4.20 (m, 1H), 3.47-3.13 (m, 6H), 2.96-2.82 (m, 4), 2.53 (s, 3/2H), 2.41 (s, 3/2H), 2.36-2.16 (m, 5H), 1.98-1.84 (m, 7 h), 1.68-1.61 (m, 2H), 1.52-1.44 (m, 2H), 0.90-0.86 (m, 3H). HRMS m/z (M+H)$^+$ calcd: 740.2604, obsd: 740.2589.

Example 814

Preparation of 2,4-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-isopropylbenzenesulfonamide

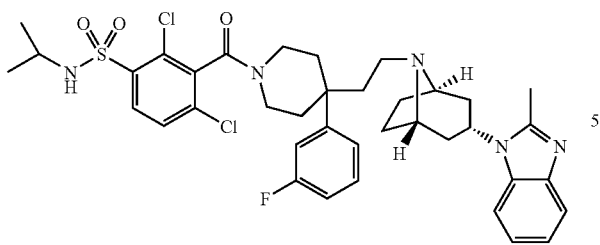

2,4-Dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-isopropylbenzene sulfonamide (13.5 mg, 18%) was obtained as solid from 2,6-dichloro-3-(chlorosulfonyl)benzoic acid (58 mg, 0.2 mmol), isopropyl amine (20 µL, 0.2 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (61 mg, 0.1 mmol) following the procedure outlined in example 473. $^1$H NMR (400 MHz, CD$_2$Cl$_2$), δ 8.07 (d, J=8.6 Hz, 1H), 7.58-7.50 (m, 2H), 7.42-7.35 (m, 2H), 7.21-7.12 (m, 2H), 7.06-6.95 (m, 3H), 4.70-4.65 (m, 1H), 4.23-4.19 (m, 1H), 3.47-3.27 (m, 5H), 3.22-3.14 (m, 2H), 2.53 (s, 3H), 2.46-2.32 (m, 3H), 2.16 (br, 1H), 1.98-1.83 (m, 11H), 1.68 (d, J=7.7 Hz, 2H), 1.25-1.03 (m, 6H). HRMS m/z (M+H)$^+$ calcd: 740.2604, obsd: 740.2590.

Example 815

Preparation of 2,4-dichloro-N-cyclopropyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

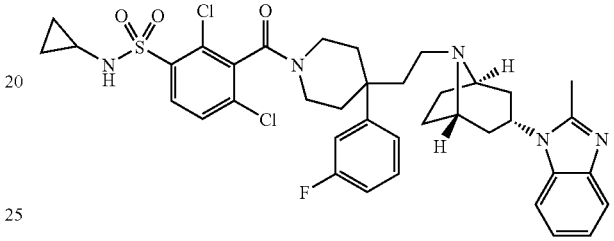

2,4-Dichloro-N-cyclopropyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzene sulfonamide (12 mg, 15%) was obtained as solid from 2,6-dichloro-3-(chlorosulfonyl)benzoic acid (58 mg, 0.2 mmol), cyclopropyl amine (17 µL, 0.2 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (61 mg, 0.1 mmol) following the procedure outlined in example 473. $^1$H NMR (400 MHz, CD$_2$Cl$_2$), δ 8.10 (d, J=7.6 Hz, 1H), 7.59-7.52 (m, 2H), 7.42-7.36 (m, 2H), 7.19-7.12 (m, 3H), 7.07-6.97 (m, 2H), 4.67-4.63 (m, 1H), 4.24-4.20 (m, 1H), 3.49-3.14 (m, 6H), 2.53 (s, 3H), 2.44-2.33 (m, 3H), 2.12 (br, 1H), 1.96-1.85 (m, 11H), 1.67-1.65 (m, 2H), 0.74-0.67 (m, 1H), 0.61-0.51 (m, 3H). HRMS m/z (M+H)$^+$ calcd: 738.2448, obsd: 738.2433.

Example 816

Preparation of 2,4-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-(2,2,2-trifluoroethyl)benzenesulfonamide

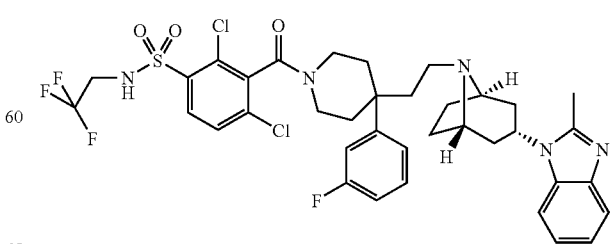

2,4-Dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-(2,2,2-trifluoroethyl) benzenesulfonamide (220 mg, 56%) was obtained as solid from 2,6-dichloro-3-(chlorosulfonyl)benzoic acid (290 mg, 1 mmol), 2,2,2-trifluroethylamine (160 μL, 2 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (305 mg, 0.5 mmol) following the procedure outlined in example 473. $^1$H NMR (400 MHz, CD$_2$Cl$_2$), δ 8.03 (d, J=8.4 Hz, 1H), 7.59-7.54 (m, 1H), 7.562-7.47 (m, 1H), 7.42-7.34 (m, 2H), 7.19-7.12 (m, 3H), 7.06-6.96 (m, 2H), 4.65-4.60 (m, 1H), 4.22-4.18 (m, 1H), 3.79-3.69 (m, 2H), 3.48-3.45 (m, 1H), 3.27-3.12 (m, 3H), 3.11-3.05 (m, 1H), 2.52 (s, 3H), 2.43-2.30 (m, 3H), 2.19-2.16 (m, 2H), 1.97-1.81 (m, 10H), 1.66-1.62 (m, 2H). HRMS m/z (M+H)$^+$ calcd: 780.2165, obsd: 780.2164.

Example 817

Preparation of 2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-(2,2,2-trifluoroethyl)benzenesulfonamide

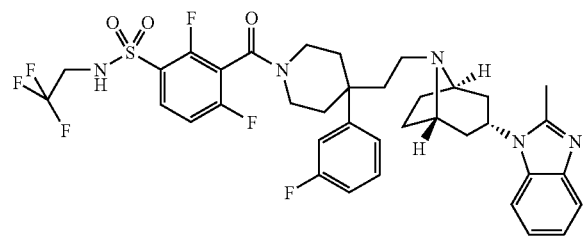

2,4-Difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-(2,2,2-trifluoroethyl) benzenesulfonamide (260 mg, 70%) was obtained as solid from 2,6-difluro-3-(chlorosulfonyl)benzoic acid (260 mg, 1 mmol), 2,2,2-trifluroethylamine (160 μL, 2 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (305 mg, 0.5 mmol) following the procedure outlined in example 473. $^1$H NMR (400 MHz, CD$_2$Cl$_2$), δ 7.98-7.92 (m, 1H), 7.60-7.58 (m, 1H), 7.41-7.32 (m, 2H), 7.22-7.20 (m, 2H), 7.16-6.98 (m, 4H), 4.69-4.67 (m, 1H), 4.18 (br, 1H), 3.80-3.62 (m, 1H0, 3.45-3.39 (m, 3H), 3.25-3.20 (m, 1H), 2.55 (s, 3H), 2.40-2.42 (m, 2H), 2.42-2.40 (m, 1H), 2.32-1.83 (m, 212H), 1.73-1.38 (m, 2H). HRMS m/z (M+H)$^+$ calcd: 748.2756, obsd: 748.2759.

Example 818

Preparation of 2-chloro-N-ethoxy-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

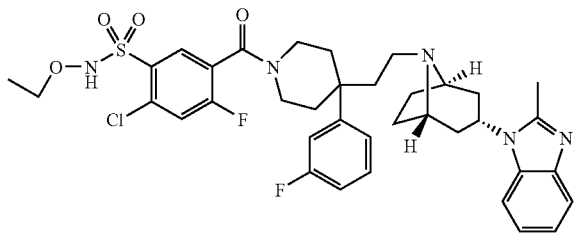

2-Chloro-N-ethoxy-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (60 mg, 16%) was obtained as solid from 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (305 mg. 0.5 mmol) and 2-fluoro-4-chloro-5-[(ethoxyamino)sulfonyl]benzoic acid (297 mg, 1 mmol) and HATU (190 mg, 0.5 mmol), following the procedures outlined in example 5. $^1$H NMR (400 MHz, CD2Cl2) δ 8.15 (br, 1H), 7.59-7.57 (m, 1H), 7.42-7.35 (m, 3H), 7.16-7.12 (m, 3H), 7.07-6.97 (m, 2H), 4.64-4.60 (m, 1H), 4.15-4.01 (m, 4H), 3.42-3.19 (m, 5H), 2.53 (s, 3H), 2.43-2.32 (m, 3H), 2.18-2.11 (m, 1H), 1.96-1.83 (m, 10H), 1.66-1.64 (m, 2H), 1.17 (t, J=6.9 Hz, 3H). HRMS m/z (M+H)$^+$ calcd 726.2692, obsd 726.2704.

Example 819

Preparation of 2,4-dichloro-N-ethoxy-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

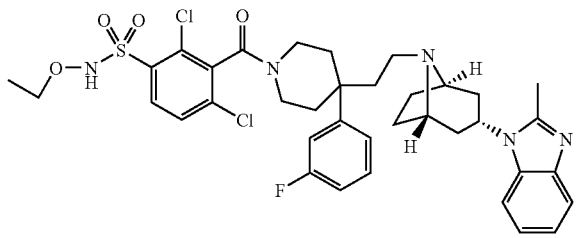

2,4-Dichloro-N-ethoxy-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (22.5 mg, 6%) was obtained as solid from 2,6-dichloro-3-(chlorosulfonyl)benzoic acid (290 mg, 1 mmol), ethoxyamine hydrochloride (195 mg, 2 mmol) and 1-((1R,5S)-8-{2-[4-(3-fluorophenyl)piperidinyl]ethyl}-8-azabicyclo[3.2.1]oct-3-yl)-2-methyl-1H-benzimidazole dihydrochloride (305 mg, 0.5 mmol) following the procedure outlined in example 473. $^1$H NMR (400 MHz, CD$_2$Cl$_2$), δ 8.10-8.08 (m, 1H), 7.60-7.55 (m, 2H), 7.40-7.35 (m, 2H), 7.18-7.12 (m, 3H), 7.07-6.96 (m, 2H), 4.65-4.60 (m, 2H), 4.23-4.20 (m, 1H), 4.06-4.00 (m, 2H), 3.34-3.12 (m, 6H), 2.54-2.53 (m, 2H), 2.44-2.44 (m, 4H), 2.20-2.03 (m, 2H), 1.97-1.84 (m, 12H), 1.65 (d, J=7.9 Hz, 2H), 1.18-1.14 (m, 3H). HRMS m/z (M+H)$^+$ calcd: 742.2397, obsd: 742.2424.

Example 820

Preparation of N-ethoxy-2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

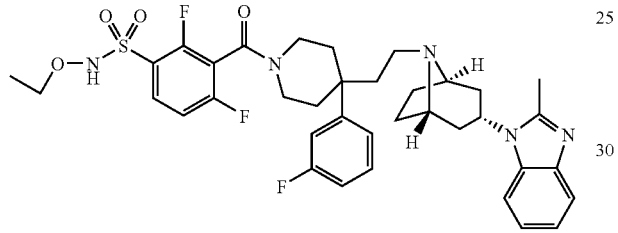

N-ethoxy-2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzene sulfonamide (27.9 mg, 8%) was obtained as solid from 2,6-difluoro-3-(chlorosulfonyl)benzoic acid (260 mg, 1 mmol), ethoxyamine hydrochloride (195 mg, 2 mmol) and 1-((1R,5S)-8-{2-[4-(3-fluorophenyl)piperidinyl]ethyl}-8-azabicyclo[3.2.1]oct-3-yl)-2-methyl-1H-benzimidazole dihydrochloride (305 mg, 0.5 mmol) following the procedure outlined in example 473. $^1$H NMR (400 MHz, CD$_2$Cl$_2$), δ 8.00-7.95 (m, 1H), 7.58-7.56 (m, 1H), 7.42-7.35 (m, 2H), 7.17-7.10 (m, 4H), 7.06-6.97 (m, 2H), 4.65-4.60 (m, 1H), 4.21-4.00 (m, 3H), 3.43-3.19 (m, 5H), 2.53 (s, 3H), 2.44-2.32 (m, 4H), 2.17-2.15 (m, 1H), 1.97-1.80 (m, 10H), 1.65 (d, J=7.8 Hz, 2H), 1.18-1.11 (m, 3H). HRMS m/z (M+H)$^+$ calcd: 710.2988, obsd: 710.2975.

Example 821

Preparation of N-ethoxy-2,4-difluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

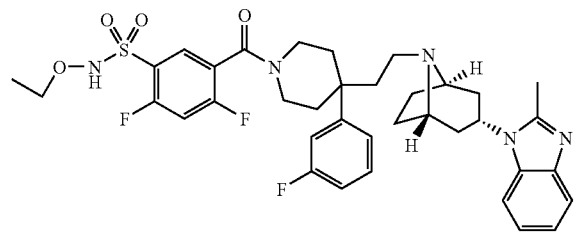

N-ethoxy-2,4-difluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzene sulfonamide (25 mg, 7%) was obtained as solid from 2,4-difluoro-3-(chlorosulfonyl)benzoic acid (260 mg, 1 mmol), ethoxyamine hydrochloride (195 mg, 2 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (305 mg, 0.5 mmol) following the procedure outlined in example 473. $^1$H NMR (400 MHz, CD$_2$Cl$_2$), δ 7.96 (br, 1H), 7.57-7.55 (m, 1H), 7.42-7.35 (m, 2H), 7.16-7.11 (m, 3H), 7.08-6.96 (m, 3H), 4.65-4.60 (m, 1H), 4.14-4.03 (m, 3H), 3.42-3.17 (m, 5H), 2.52 (s, 3H), 2.43-2.31 (m, 4), 2.13-2.09 (m, 1H), 1.98-1.80 (m, 10H), 1.65 (d, J=7.8 Hz, 2H), 1.18 (t, J=7.0 Hz, 3H). HRMS m/z (M+H)$^+$ calcd: 710.2988, obsd: 710.2975.

Example 822

Preparation of 1-((1R,5S)-8-{2-[1-{2,4-difluoro-5-[(4-methylpiperazin-1-yl)sulfonyl]benzoyl}-4-(3-fluorophenyl)piperidin-4-yl]ethyl}-8-azabicyclo[3.2.1]oct-3-yl)-2-methyl-1H-benzimidazole

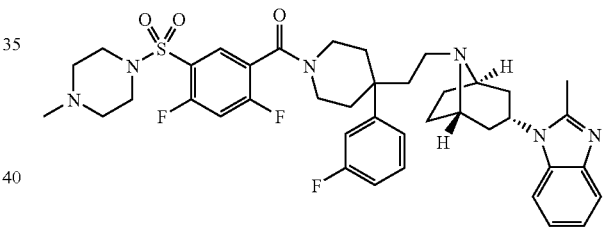

1-((1R,5S)-8-{2-[1-{2,4-difluoro-5-[(4-methylpiperazin-1-yl)sulfonyl]benzoyl}-4-(3-fluorophenyl)piperidin-4-yl]ethyl}-8-azabicyclo[3.2.1]oct-3-yl)-2-methyl-1H-benzimidazole (170 mg, 44%) was obtained as solid from 2-chloro-4-fluoro-5-[(4-methylpiperazin-1-yl)sulfonyl]benzoic acid (170 mg, 0.5 mmol), HATU (190 mg, 0.5 mmol) and 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (305 mg, 0.5 mmol) following the procedure outlined in example 5. $^1$H NMR (400 MHz, DMSO-d$_6$), δ 7.93-7.88 (m, 1H), 7.79-7.75 (m, 1H), 7.47 (d, J=8.4 Hz, 1H), 7.43-7.33 (m, 2H), 7.23-7.21 (m, 3H), 7.12-7.04 (m, 3H), 4.50-4.46 (m, 1H), 3.93-3.90 (m, 1H), 3.30 (br, 4H), 3.16-3.04 (m, 5H), 2.43 (s, 3H), 2.32 (br, 6H), 2.13-2.12 (m, 4H), 1.98-1.57 (m, 13H). HRMS m/z (M+H)$^+$ calcd: 765.3149, obsd: 765.3165.

| Example # | Structure | ¹H NMR (400 MHz, CDCl₃) | HRMS m/z (M + H)⁺ |
|---|---|---|---|
| 823 | | δ 7.66(d, J=7.1Hz, 1H), 7.33-7.24(m, 4H), 7.19-7.12(m, 2H), 7.04-6.89(m, 6H), 4.59(br, 1H), 3.73(s, 1H), 3.29-3.22(m, 4H), 2.55(s, 3H), 2.52-2.48(m, 1H), 2.40-2.10(m, 6H), 1.93-1.87(m, 8H), 1.79-1.61(m, 6H). 1.53-1.46(m, 2, H), 1.43-1.30(m, 2H), 0.92(t, J=7.3Hz, 3H) | Calcd 654.3983, obsd 654.3998. |
| 824 | | δ 8.06(d, J=8.4Hz, 1H), 7.57-7.50(m, 2H), 7.42-7.35(m, 2H), 7.20-7.12(m, 3H), 7.06-6.96(m, 2H), 470-4.65(m, 1H), 4.22-4.18(m, 1H), 3.58-3.12(m, 6H), 2.52(s, 3H), 2.46-2.36(m, 3H), 2.18(br, 2H), 1.96-1.83(m, 11H), 1.79-1.61(m, 6H), 1.47-1.38(m, 4H). | calcd: 766.2761, obsd 766.2776 |
| 825 | | δ 8.18(br, 1H), 7.59-7.57(m, 1H), 7.43-7.33(m, 6H), 7.29-7.25(m, 1H), 7.20-7.16(m, 2H), 4.67-4.62(m, 1H), 4.18-4.15(m, 1H), 3.78(s, 3H), 3.40-3.31(m, 4H), 3.18-3.15(m, 1H), 2.54(s, 3H), 2.46-2.34(m, 3H), 2.18-2.02(m, 1H) 1.99-1.84(m, 11H), 1.68-1.67(2H). | calcd 694.2630, obsd 694.2623. |
| 826 | | δ 8.21(d, J=10Hz, 2H), 7.66(d, J=10Hz, 1H), 7.50(s, 2H), 7.35-7.29(m, 2H), 7.20-7.13(m, 2H), 7.10-6.90(m, 3H), 4.60(br, 1H), 4.20(br, 1H), 3.55(br, 1H), 3.40-3.25(m, 4H), 3.18(s, 3H), 3.04(s, 3H), 2.57(s, 3H), 2.45-2.35(m, 2H), 2.30-2.21(m, 2H), 1.95-1.89(m, 12H), 1.65-1.63(m, 2H). | calcd: 765.3149, obsd 765.3165. |

Example 827

Preparation of 2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-5,6,7,8-tetrahydro-4(1H)-quinolinone

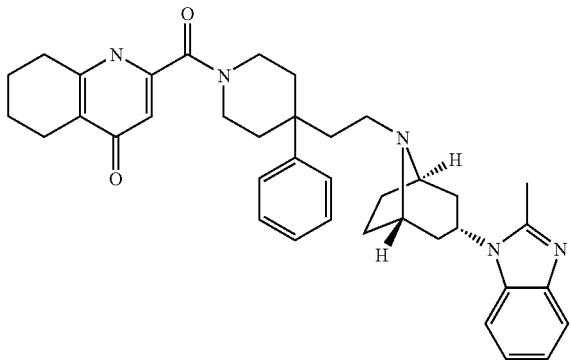

2-[(4-{2-[(1R,5S)-3-(2-methyl-1H-benzimidazol-1-yl)-8-azabicyclo[3.2.1]oct-8-yl]ethyl}-4-phenyl-1-piperidinyl)carbonyl]-5,6,7,8-tetrahydro-4(1H)-quinolinone (5.2 mg; 17% yield) was obtained as a solid from 4-oxo-1,4,5,6,7,8-hexahydro-2-quinolinecarboxylic acid (9.66 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M−H): 602.36.

Example 828

3-hydroxy-5-[(4-{2-[3-(2-methyl-1H-benzimidazol-1-yl)-8-azabicyclo[3.2.1]oct-8-yl]ethyl}-4-phenyl-1-piperidinyl)carbonyl]-2-pyrrolidinone

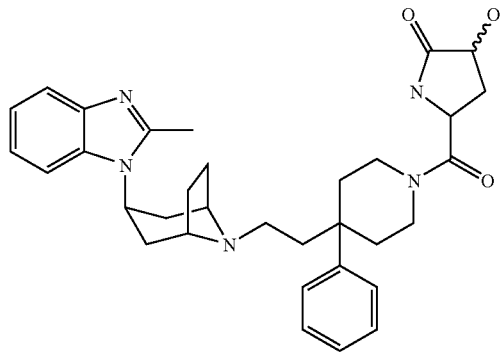

3-hydroxy-5-[(4-{2-[3-(2-methyl-1H-benzimidazol-1-yl)-8-azabicyclo[3.2.1]oct-8-yl]ethyl}-4-phenyl-1-piperidinyl)carbonyl]-2-pyrrolidinone (12.05 mg; 43% yield) was obtained as a solid from 4-hydroxy-5-oxoproline (7.25 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 556.22.

Example 829

N,N-dimethyl-4-[(4-{2-[3-(2-methyl-1H-benzimidazol-1-yl)-8-azabicyclo[3.2.1]oct-8-yl]ethyl}-4-phenyl-1-piperidinyl)carbonyl]-1,3-thiazol-2-amine

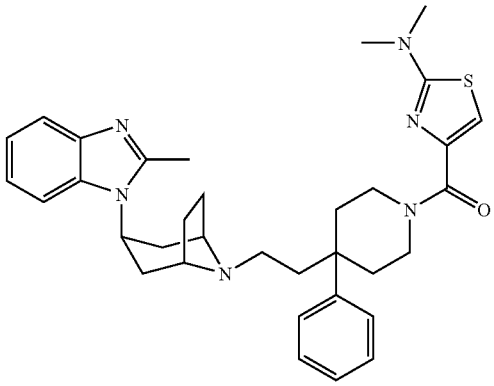

N,N-dimethyl-4-[(4-{2-[3-(2-methyl-1H-benzimidazol-1-yl)-8-azabicyclo[3.2.1]oct-8-yl]ethyl}-4-phenyl-1-piperidinyl)carbonyl]-1,3-thiazol-2-amine (14.49 mg; 50% yield) was obtained as a solid from 2-(dimethylamino)-1,3-thiazole-4-carboxylic acid hydrobromide (12.65 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 583.23.

Example 830

2-methyl-1-{8-[2-(1-{[1-methyl-4-(methyloxy)-1H-1,2,3-triazol-5-yl]carbonyl}-4-phenyl-4-piperidinyl)ethyl]-8-azabicyclo[3.2.1]oct-3-yl}-1H-benzimidazole

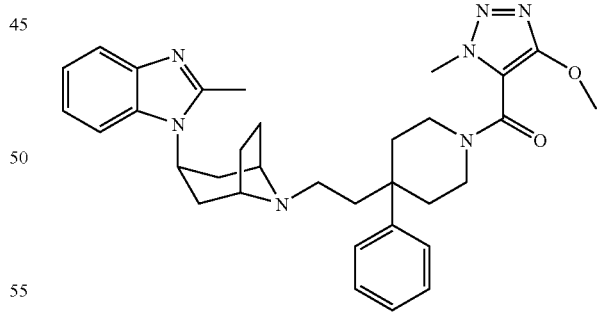

2-methyl-1-{8-[2-(1-{[1-methyl-4-(methyloxy)-1H-1,2,3-triazol-5-yl]carbonyl}-4-phenyl-4-piperidinyl)ethyl]-8-azabicyclo[3.2.1]oct-3-yl}-1H-benzimidazole (2.99 mg; 11% yield) was obtained as a solid from 1-methyl-4-(methyloxy)-1H-1,2,3-triazole-5-carboxylic acid (8.95 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 568.20.

Example 831

5-methyl-3-[(4-{2-[3-(2-methyl-1H-benzimidazol-1-yl)-8-azabicyclo[3.2.1]oct-8-yl]ethyl}-4-phenyl-1-piperidinyl)carbonyl]dihydro-2(3H)-furanone

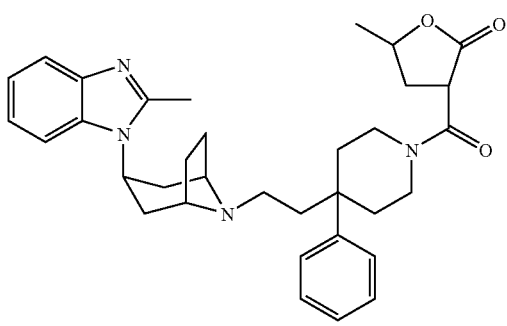

5-methyl-3-[(4-{2-[3-(2-methyl-1H-benzimidazol-1-yl)-8-azabicyclo[3.2.1]oct-8-yl]ethyl}-4-phenyl-1-piperidinyl)carbonyl]dihydro-2(3H)-furanone (10.39 mg; 36% yield) was obtained as a solid from 5-methyl-2-oxotetrahydro-3-furancarboxylic acid (7.90 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 569.25

Example 832

N-[2-methyl-3-(4-{2-[3-(2-methyl-1H-benzimidazol-1-yl)-8-azabicyclo[3.2.1]oct-8-yl]ethyl}-4-phenyl-1-piperidinyl)-3-oxopropyl]-1H-pyrrole-2-carboxamide

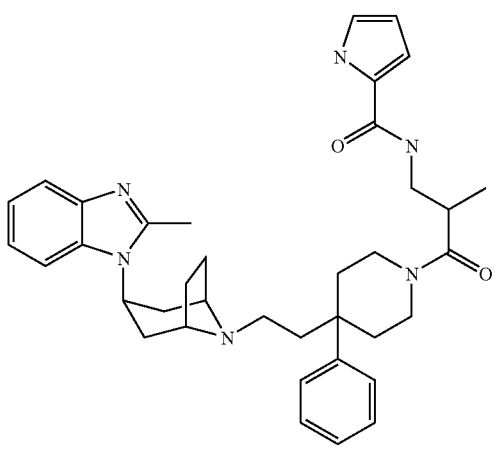

N-[2-methyl-3-(4-{2-[3-(2-methyl-1H-benzimidazol-1-yl)-8-azabicyclo[3.2.1]oct-8-yl]ethyl}-4-phenyl-1-piperidinyl)-3-oxopropyl]-1H-pyrrole-2-carboxamide (13.35 mg; 44% yield) was obtained as a solid from 2-methyl-3-[(1H-pyrrol-2-ylcarbonyl)amino]propanoic acid (7.90 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 607.26

Example 833

2-methyl-1-(8-{2-[4-phenyl-1-(1H-pyrrolo[2,3-b]pyridin-3-ylcarbonyl)-4-piperidinyl]ethyl}-8-azabicyclo[3.2.1]oct-3-yl)-1H-benzimidazole

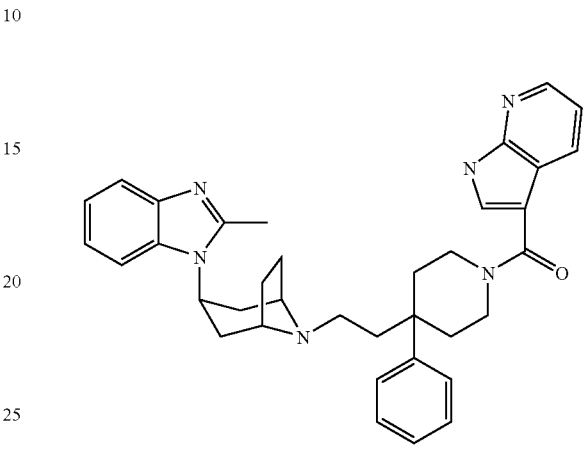

2-methyl-1-(8-{2-[4-phenyl-1-(1H-pyrrolo[2,3-b]pyridin-3-ylcarbonyl)-4-piperidinyl]ethyl}-8-azabicyclo[3.2.1]oct-3-yl)-1H-benzimidazole (9.29 mg; 32% yield) was obtained as a solid from 1H-pyrrolo[2,3-b]pyridine-3-carboxylic acid (8.10 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 573.21

Example 834

1-{8-[2-(1-{[2-(1H-imidazol-4-yl)cyclopropyl]carbonyl}-4-phenyl-4-piperidinyl)ethyl]-8-azabicyclo[3.2.1]oct-3-yl}-2-methyl-1H-benzimidazole

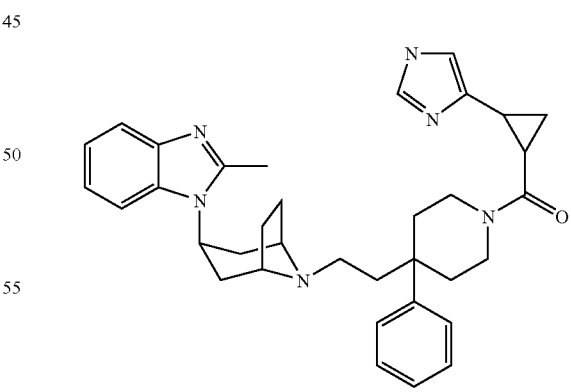

2-methyl-1-(8-{2-[4-phenyl-1-(1H-pyrrolo[2,3-b]pyridin-3-ylcarbonyl)-4-piperidinyl]ethyl}-8-azabicyclo[3.2.1]oct-3-yl)-1H-benzimidazole (12.60 mg; 45% yield) was obtained as a solid from 2-(1H-imidazol-4-yl)cyclopropanecarboxylic acid hydrochloride (9.43 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 563.24

Example 835

4,5-diethyl-2-[(4-{2-[3-(2-methyl-1H-benzimidazol-1-yl)-8-azabicyclo[3.2.1]oct-8-yl]ethyl}-4-phenyl-1-piperidinyl)carbonyl]phenol

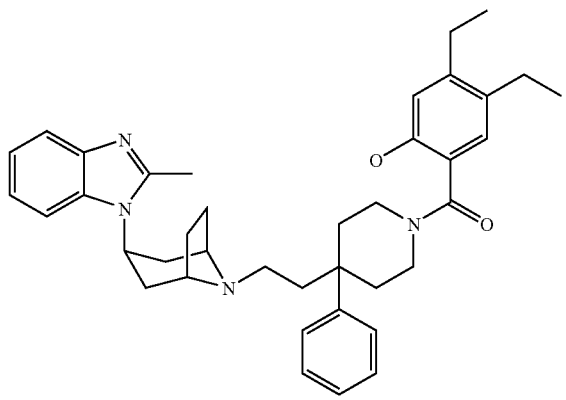

4,5-diethyl-2-[(4-{2-[3-(2-methyl-1H-benzimidazol-1-yl)-8-azabicyclo[3.2.1]oct-8-yl]ethyl}-4-phenyl-1-piperidinyl)carbonyl]phenol (6.39 mg; 21% yield) was obtained as a solid from 4,5-diethyl-2-hydroxybenzoic acid (9.71 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 605.27.

Example 836

1-[8-(2-{1-[(3,4-dichloro-2-furanyl)carbonyl]-4-phenyl-4-piperidinyl}ethyl)-8-azabicyclo[3.2.1]oct-3-yl]-2-methyl-1H-benzimidazole

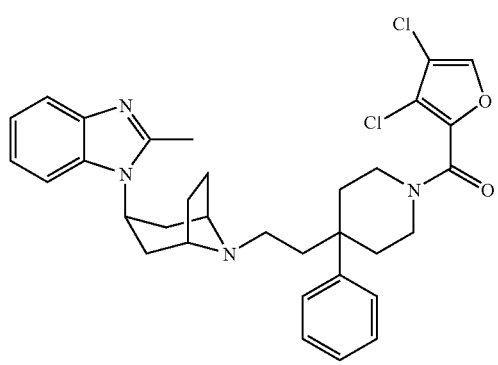

1-[8-(2-{1-[(3,4-dichloro-2-furanyl)carbonyl]-4-phenyl-4-piperidinyl}ethyl)-8-azabicyclo[3.2.1]oct-3-yl]-2-methyl-1H-benzimidazole (12.19 mg; 41% yield) was obtained as a solid from 3,4-dichloro-2-furancarboxylic acid (9.04 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 591.12.

Example 837

(2S,3S)—N,N,3-trimethyl-1-(4-{2-[3-(2-methyl-1H-benzimidazol-1-yl)-8-azabicyclo[3.2.1]oct-8-yl]ethyl}-4-phenyl-1-piperidinyl)-1-oxo-2-pentanamine

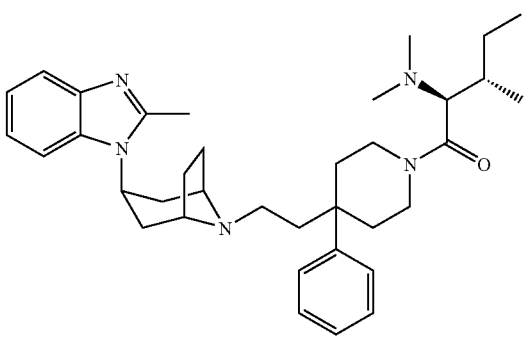

(2S,3S)—N,N,3-trimethyl-1-(4-{2-[3-(2-methyl-1H-benzimidazol-1-yl)-8-azabicyclo[3.2.1]oct-8-yl]ethyl}-4-phenyl-1-piperidinyl)-1-oxo-2-pentanamine (10.05 mg; 35% yield) was obtained as a solid from N,N-dimethyl-L-isoleucine (7.96 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride # (25 mg, 0.05 mmol) and HATU (19 mg, 0.05 mmol) following the procedure outlined in example 5. ES-LCMS m/z (M+H): 570.15.

Example 838

1-[8-(2-{1-[(2,6-difluoro-3-pyridinyl)carbonyl]-4-phenyl-4-piperidinyl}ethyl)-8-azabicyclo[3.2.1]oct-3-yl]-2-methyl-1H-benzimidazole

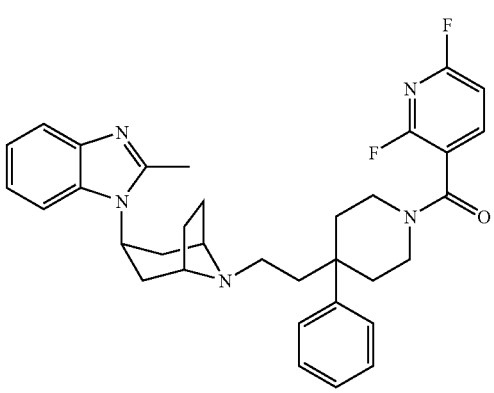

1-[8-(2-{1-[(2,6-difluoro-3-pyridinyl)carbonyl]-4-phenyl-4-piperidinyl}ethyl)-8-azabicyclo[3.2.1]oct-3-yl]-2-methyl-1H-benzimidazole (8.35 mg; 29% yield) was obtained as a solid from 2,6-difluoro-3-pyridinecarboxylic acid (7.95 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 570.19.

Example 839

1-(4-{2-[3-(2-methyl-1H-benzimidazol-1-yl)-8-azabicyclo[3.2.1]oct-8-yl]ethyl}-4-phenyl-1-piperidinyl)-1-oxo-2-(2-thienyl)-2-propanol

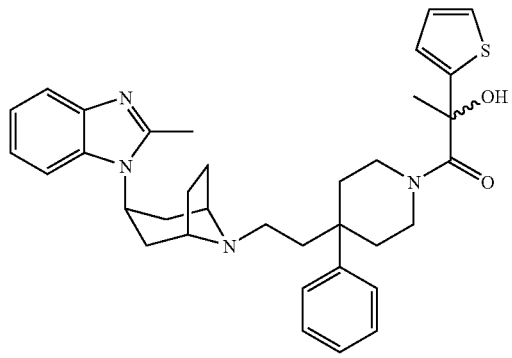

1-(4-{2-[3-(2-methyl-1H-benzimidazol-1-yl)-8-azabicyclo[3.2.1]oct-8-yl]ethyl}-4-phenyl-1-piperidinyl)-1-oxo-2-(2-thienyl)-2-propanol (4.95 mg; 17% yield) was obtained as a solid from 2-hydroxy-2-(2-thienyl)propanoic acid (8.60 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 583.17.

Example 840

2-methyl-1-{8-[2-(1-{[3-(1-methylethyl)-5-isoxazolyl]carbonyl}-4-phenyl-4-piperidinyl)ethyl]-8-azabicyclo[3.2.1]oct-3-yl}-1H-benzimidazole

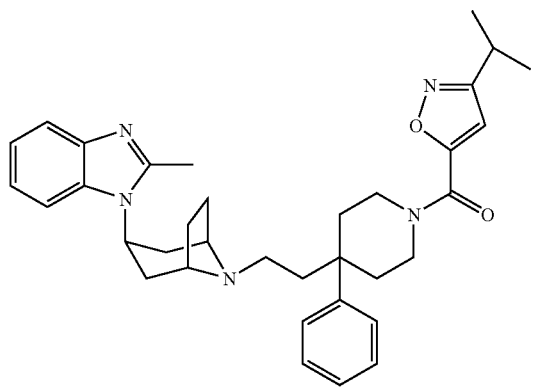

2-methyl-1-{8-[2-(1-{[3-(1-methylethyl)-5-isoxazolyl]carbonyl}-4-phenyl-4-piperidinyl)ethyl]-8-azabicyclo[3.2.1]oct-3-yl}-1H-benzimidazole (11.29 mg; 40% yield) was obtained as a solid from 3-(1-methylethyl)-5-isoxazolecarboxylic acid hydrochloride (8.86 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 566.27.

Example 841

2-methyl-1-[8-(2-{4-phenyl-1-[(4-phenyl-1H-1,2,3-triazol-5-yl)carbonyl]-4-piperidinyl}ethyl)-8-azabicyclo[3.2.1]oct-3-yl]-1H-benzimidazole

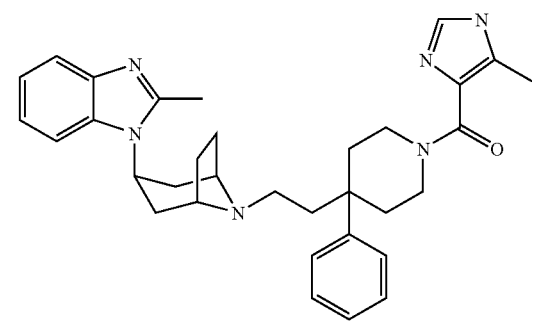

2-methyl-1-[8-(2-{4-phenyl-1-[(4-phenyl-1H-1,2,3-triazol-5-yl)carbonyl]-4-piperidinyl}ethyl)-8-azabicyclo[3.2.1]oct-3-yl]-1H-benzimidazole (10.29 mg; 34% yield) was obtained as a solid from 4-phenyl-1H-1,2,3-triazole-5-carboxylic acid hydrochloride (9.45 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 600.20.

Example 842

2-methyl-1-[8-(2-{1-[(4-methyl-1H-imidazol-5-yl)carbonyl]-4-phenyl-4-piperidinyl}ethyl)-8-azabicyclo[3.2.1]oct-3-yl]-1H-benzimidazole 2-methyl-1-[8-(2-{1-[(4-methyl-1H-imidazol-5-yl)carbonyl]-4-phenyl-4-piperidinyl}ethyl)-8-azabicyclo[3.2.1]oct-3-yl]-1H-benzimidazole (9.10 mg; 34% yield) was obtained as a solid from 4-methyl-1H-imidazole-5-carboxylic acid (6.30 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M−H): 535.52.

Example 843

1-{2-[(4-{2-[3-(2-methyl-1H-benzimidazol-1-yl)-8-azabicyclo[3.2.1]oct-8-yl]ethyl}-4-phenyl-1-piperidinyl)carbonyl]-3-pyridinyl}ethanone

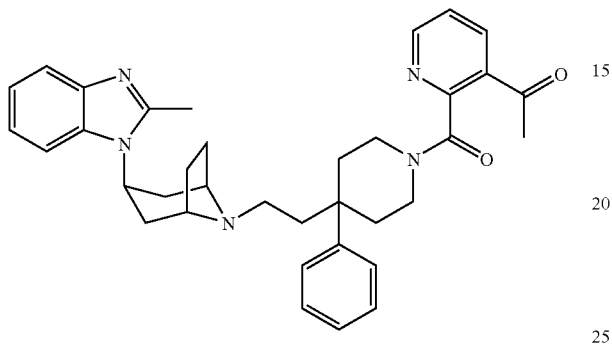

1-{2-[(4-{2-[3-(2-methyl-1H-benzimidazol-1-yl)-8-azabicyclo[3.2.1]oct-8-yl]ethyl}-4-phenyl-1-piperidinyl)carbonyl]-3-pyridinyl}ethanone (12.60 mg; 44% yield) was obtained as a solid from 3-acetyl-2-pyridinecarboxylic acid (9.35 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 576.24.

Example 844

5-[(4-{2-[3-(2-methyl-1H-benzimidazol-1-yl)-8-azabicyclo[3.2.1]oct-8-yl]ethyl}-4-phenyl-1-piperidinyl)carbonyl]-4-pyridazinol

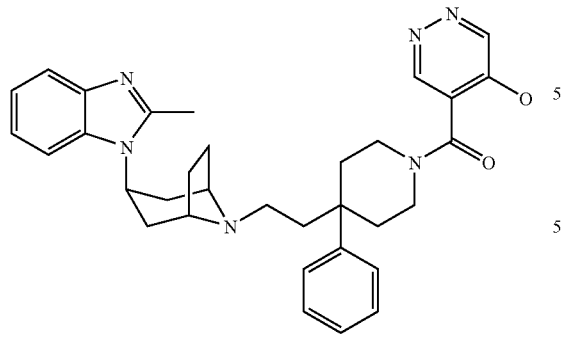

5-[(4-{2-[3-(2-methyl-1H-benzimidazol-1-yl)-8-azabicyclo[3.2.1]oct-8-yl]ethyl}-4-phenyl-1-piperidinyl)carbonyl]-4-pyridazinol (9.75 mg; 35% yield) was obtained as a solid from 5-hydroxy-4-pyridazinecarboxylic acid (7.00 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 551.24.

Example 845

2-methyl-1-{8-[2-(4-phenyl-1-{[3-(4-pyridinyl)-5-isoxazolyl]carbonyl}-4-piperidinyl)ethyl]-8-azabicyclo[3.2.1]oct-3-yl}-1H-benzimidazole

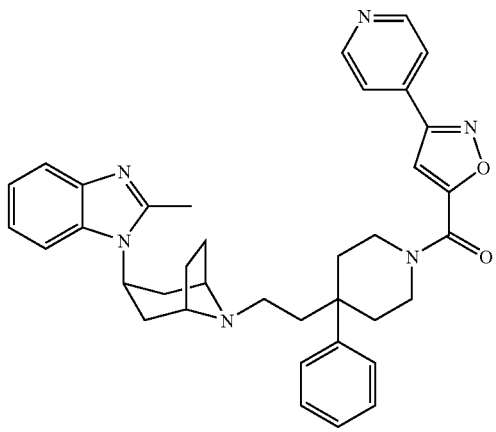

2-methyl-1-{8-[2-(4-phenyl-1-([3-(4-pyridinyl)-5-isoxazolyl]carbonyl}-4-piperidinyl)ethyl]-8-azabicyclo[3.2.1]oct-3-yl)-1H-benzimidazole (15.39 mg; 51% yield) was obtained as a solid from 3-(4-pyridinyl)-5-isoxazolecarboxylic acid (9.51 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 601.16.

Example 846

1-(8-{2-[1-(2,3-dihydro-1-benzofuran-3-ylcarbonyl)-4-phenyl-4-piperidinyl]ethyl}-8-azabicyclo[3.2.1]oct-3-yl)-2-methyl-1H-benzimidazole

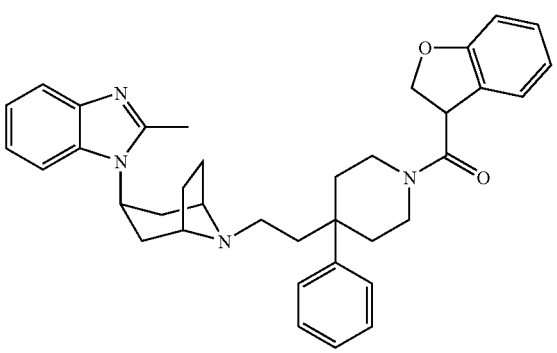

1-(8-{2-[1-(2,3-dihydro-1-benzofuran-3-ylcarbonyl)-4-phenyl-4-piperidinyl]ethyl}-8-azabicyclo[3.2.1]oct-3-yl)-2-methyl-1H-benzimidazole (17.9 mg; 62% yield) was obtained as a solid from 2,3-dihydro-1-benzofuran-3-carboxylic acid (8.20 mg, 0.05 mmol), 2-methyl-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 575.2.

Example 847

3-[(4-{2-[3-(2-methyl-1H-benzimidazol-1-yl)-8-azabicyclo[3.2.1]oct-8-yl]ethyl}-4-phenyl-1-piperidinyl)carbonyl]-2,3-dihydro-1H-pyrrolo[1,2-a]pyrrol-1-one

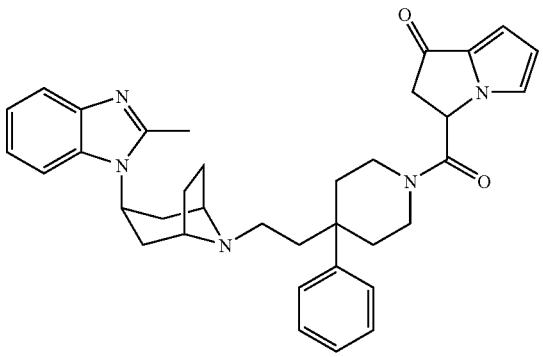

3-[(4-{2-[3-(2-methyl-1H-benzimidazol-1-yl)-8-azabicyclo[3.2.1]oct-8-yl]ethyl}-4-phenyl-1-piperidinyl)carbonyl]-2,3-dihydro-1H-pyrrolo[1,2-a]pyrrol-1-one (11.5 mg; 40% yield) was obtained as a solid from 1-oxo-2,3-dihydro-1H-pyrrolo[1,2-a]pyrrole-3-carboxylic acid (9.35 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 576.22.

Example 848

3-(4-{2-[3-(2-methyl-1H-benzimidazol-1-yl)-8-azabicyclo[3.2.1]oct-8-yl]ethyl}-4-phenyl-1-piperidinyl)-3-oxo-1-(4-pyridinyl)-1-propanol

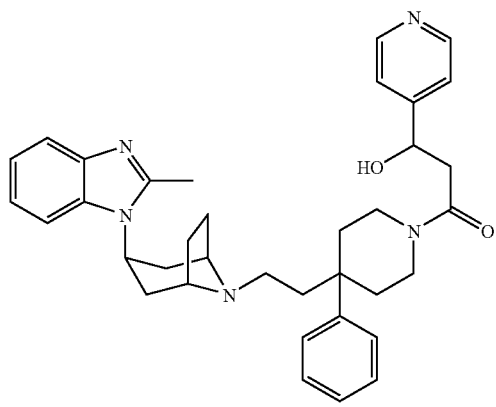

3-(4-{2-[3-(2-methyl-1H-benzimidazol-1-yl)-8-azabicyclo[3.2.1]oct-8-yl]ethyl}-4-phenyl-1-piperidinyl)-3-oxo-1-(4-pyridinyl)-1-propanol (18.59 mg; 64% yield) was obtained as a solid from 3-hydroxy-3-(4-pyridinyl)propanoic acid (8.35 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 578.22.

Example 849

2-methyl-1-{8-[2-(1-{[(2S)-1-methyl-2-phenylcyclopropyl]carbonyl}-4-phenyl-4-piperidinyl)ethyl]-8-azabicyclo[3.2.1]oct-3-yl}-1H-benzimidazole

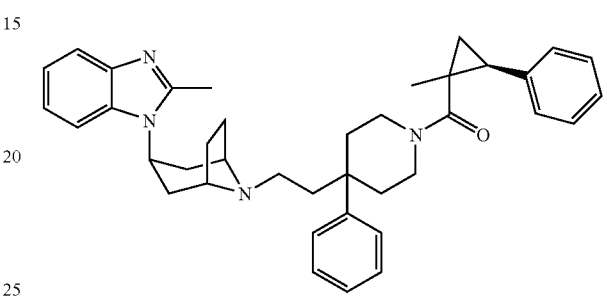

2-methyl-1-{8-[2-(1 {[(2S)-1-methyl-2-phenylcyclopropyl]carbonyl}-4-phenyl-4-piperidinyl)ethyl]-8-azabicyclo[3.2.1]oct-3-yl}-1H-benzimidazole (18.91 mg; 64% yield) was obtained as a solid from (2S)-1-methyl-2-phenylcyclopropanecarboxylic acid (8.81 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 587.26.

Example 850

4,6-dimethyl-3-[(4-{2-[3-(2-methyl-1H-benzimidazol-1-yl)-8-azabicyclo[3.2.1]oct-8-yl]ethyl}-4-phenyl-1-piperidinyl)carbonyl]-2(1H)-pyridinone

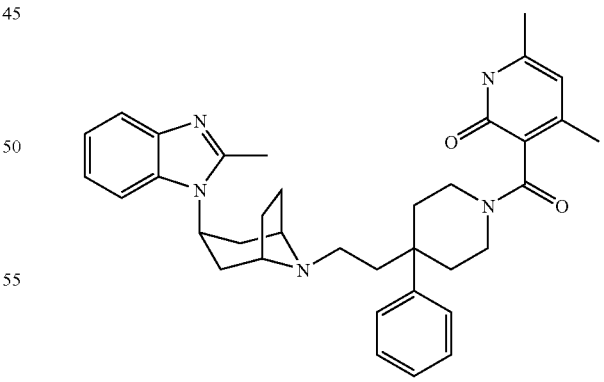

4,6-dimethyl-3-[(4-{2-[3-(2-methyl-1H-benzimidazol-1-yl)-8-azabicyclo[3.2.1]oct-8-yl]ethyl}-4-phenyl-1-piperidinyl)carbonyl]-2(1H)-pyridinone (17.84 mg; 62% yield) was obtained as a solid from 4,6-dimethyl-2-oxo-1,2-dihydro-3-pyridinecarboxylic acid (8.35 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 578.23.

Example 851

N-(hydroxymethyl)-5-[(4-{2-[3-(2-methyl-1H-benzimidazol-1-yl)-8-azabicyclo[3.2.1]oct-8-yl]ethyl}-4-phenyl-1-piperidinyl)carbonyl]-3-pyridinecarboxamide

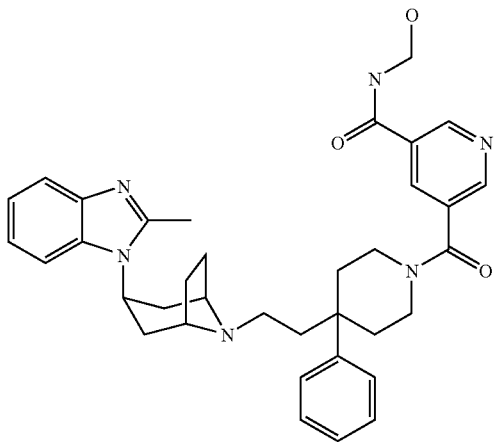

N-(hydroxymethyl)-5-[(4-{2-[3-(2-methyl-1H-benzimidazol-1-yl)-8-azabicyclo[3.2.1]oct-8-yl]ethyl}-4-phenyl-1-piperidinyl)carbonyl]-3-pyridinecarboxamide (5.55 mg; 18% yield) was obtained as a solid from 5-{[(hydroxymethyl)amino]carbonyl}-3-pyridinecarboxylic acid (10.90 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 601.2.

Example 852

1-(8-{2-[1-(1H-benzimidazol-5-ylacetyl)-4-phenyl-4-piperidinyl]ethyl}-8-azabicyclo[3.2.1]oct-3-yl)-2-methyl-1H-benzimidazole

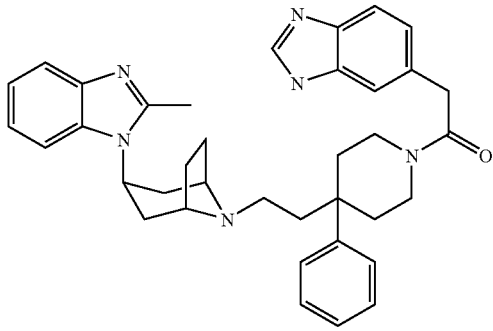

1-(8-{2-[1-(1H-benzimidazol-5-ylacetyl)-4-phenyl-4-piperidinyl]ethyl}-8-azabicyclo[3.2.1]oct-3-yl)-2-methyl-1H-benzimidazole (15.20 mg; 52% yield) was obtained as a solid from 1H-benzimidazol-5-ylacetic acid (10.63 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 587.18.

Example 853

6-chloro-4-[(4-{2-[3-(2-methyl-1H-benzimidazol-1-yl)-8-azabicyclo[3.2.1]oct-8-yl]ethyl}-4-phenyl-1-piperidinyl)carbonyl]-2(1H)-pyridinone

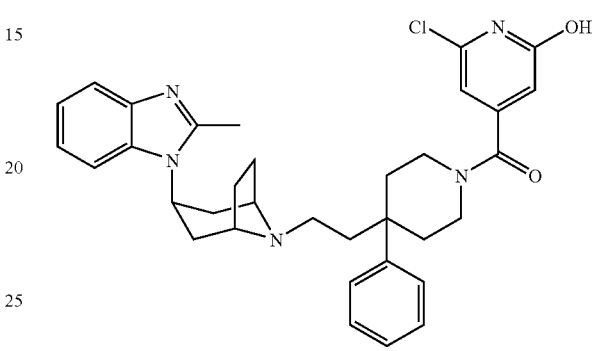

6-chloro-4-[(4-{2-[3-(2-methyl-1H-benzimidazol-1-yl)-8-azabicyclo[3.2.1]oct-8-yl]ethyl}-4-phenyl-1-piperidinyl)carbonyl]-2(1H)-pyridinone (7.69 mg; 26% yield) was obtained as a solid from 6-chloro-2-oxo-1,2-dihydro-4-pyridinecarboxylic acid (8.67 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 584.16.

Example 854

5-[(4-{2-[3-(2-methyl-1H-benzimidazol-1-yl)-8-azabicyclo[3.2.1]oct-8-yl]ethyl}-4-phenyl-1-piperidinyl)carbonyl]-5,6,7,8-tetrahydro-2-naphthalenol

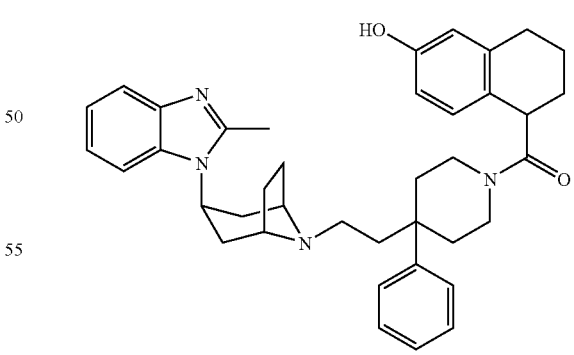

5-[(4-{2-[3-(2-methyl-1H-benzimidazol-1-yl)-8-azabicyclo[3.2.1]oct-8-yl]ethyl}-4-phenyl-1-piperidinyl)carbonyl]-5,6,7,8-tetrahydro-2-naphthalenol (18.15 mg; 60% yield) was obtained as a solid from 6-hydroxy-1,2,3,4-tetrahydro-1-naphthalenecarboxylic acid (9.61 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 603.24.

Example 855

2-[2-(4-{2-[3-(2-methyl-1H-benzimidazol-1-yl)-8-azabicyclo[3.2.1]oct-8-yl]ethyl}-4-phenyl-1-piperidinyl)-2-oxoethyl][1,2,4]triazolo[1,5-a]pyrimidine

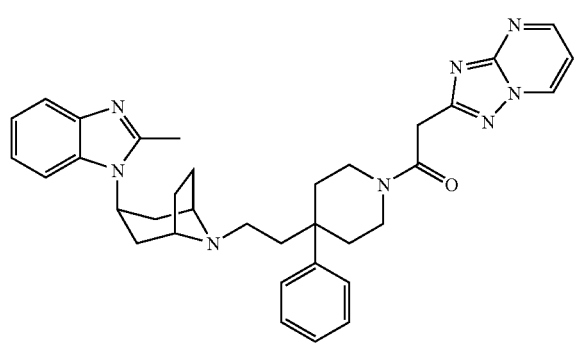

2-[2-(4-{2-[3-(2-methyl-1H-benzimidazol-1-yl)-8-azabicyclo[3.2.1]oct-8-yl]ethyl}-4-phenyl-1-piperidinyl)-2-oxoethyl][1,2,4]triazolo[1,5-a]pyrimidine (10.54 mg; 36% yield) was obtained as a solid from [1,2,4]triazolo[1,5-a]pyrimidin-2-ylacetic acid (8.90 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 589.22.

Example 856

3-{1-[(4-{2-[3-(2-methyl-1H-benzimidazol-1-yl)-8-azabicyclo[3.2.1]oct-8-yl]ethyl}-4-phenyl-1-piperidinyl)carbonyl]propyl}dihydro-2(3H) furanone

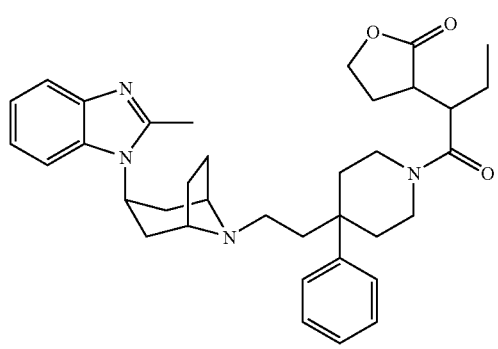

3-{1-[(4-{2-[3-(2-methyl-1H-benzimidazol-1-yl)-8-azabicyclo[3.2.1]oct-8-yl]ethyl}-4-phenyl-1-piperidinyl)carbonyl]propyl}dihydro-2(3H)-furanone (15.24 mg; 52% yield) was obtained as a solid from 2-(2-oxotetrahydro-3-furanyl)butanoic acid (8.60 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 583.26.

Example 857

1-[8-(2-{1-[(3-ethenyl-2-pyridinyl)carbonyl]-4-phenyl-4-piperidinyl}ethyl)-8-azabicyclo[3.2.1]oct-3-yl]-2-methyl-1H-benzimidazole

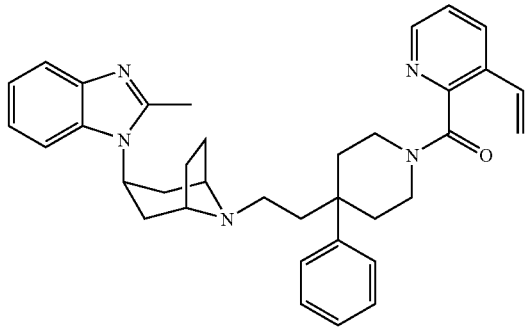

1-[8-(2-{1-[(3-ethenyl-2-pyridinyl)carbonyl]-4-phenyl-4-piperidinyl}ethyl)-8-azabicyclo[3.2.1]oct-3-yl]-2-methyl-1H-benzimidazole (5.05 mg; 18% yield) was obtained as a solid from 3-ethenyl-2-pyridinecarboxylic acid (7.54 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 560.22.

Example 858

5-[(4-{2-[3-(2-methyl-1H-benzimidazol-1-yl)-8-azabicyclo[3.2.1]oct-8-yl]ethyl}-4-phenyl-1-piperidinyl)carbonyl]-1,3-benzothiazole

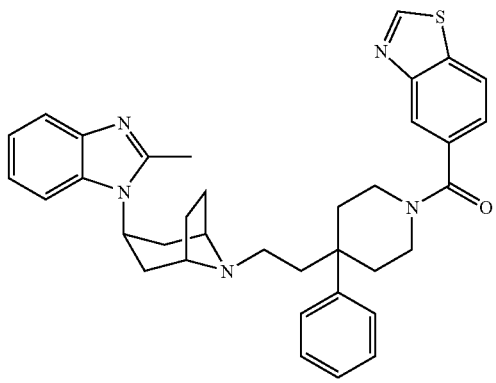

5-[(4-{2-[3-(2-methyl-1H-benzimidazol-1-yl)-8-azabicyclo[3.2.1]oct-8-yl]ethyl}-4-phenyl-1-piperidinyl)carbonyl]-1,3-benzothiazole (7.95 mg; 27% yield) was obtained as a solid from 1,3-benzothiazole-5-carboxylic acid (8.95 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 590.17.

Example 859

1-[8-(2-{1-[(1,1-dioxidotetrahydro-2-thienyl)carbonyl]-4-phenyl-4-piperidinyl}ethyl)-8-azabicyclo[3.2.1]oct-3-yl]-2-methyl-1H-benzimidazole

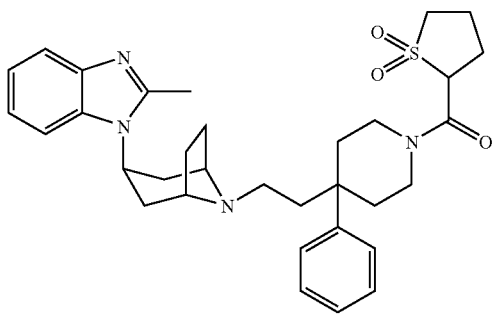

1-[8-(2-{1-[(1,1-dioxidotetrahydro-2-thienyl)carbonyl]-4-phenyl-4-piperidinyl}ethyl)-8-azabicyclo[3.2.1]oct-3-yl]-2-methyl-1H-benzimidazole (8.89 mg; 31% yield) was obtained as a solid from tetrahydro-2-thiophenecarboxylic acid 1,1-dioxide (8.20 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 575.16.

Example 860

2-methyl-7-[(4-{2-[3-(2-methyl-1H-benzimidazol-1-yl)-8-azabicyclo[3.2.1]oct-8-yl]ethyl}-4-phenyl-1-piperidinyl)carbonyl]furo[2,3-c]pyridine

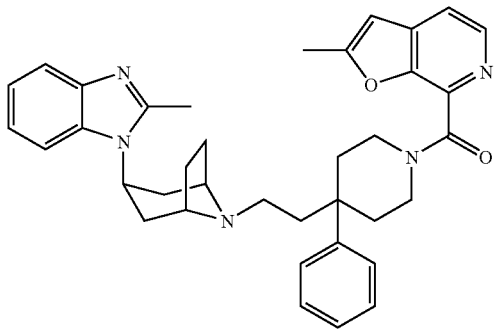

2-methyl-7-[(4-{2-[3-(2-methyl-1H-benzimidazol-1-yl)-8-azabicyclo[3.2.1]oct-8-yl]ethyl}-4-phenyl-1-piperidinyl)carbonyl]furo[2,3-c]pyridine (10.35 mg; 35% yield) was obtained as a solid from 2-methylfuro[2,3-c]pyridine-7-carboxylic acid (8.85 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 588.22.

Example 861

2-methyl-1-[8-(2-{1-[(1-oxidotetrahydro-2H-thiopyran-4-yl)carbonyl]-4-phenyl-4-piperidinyl}ethyl)-8-azabicyclo[3.2.1]oct-3-yl]-1H-benzimidazole

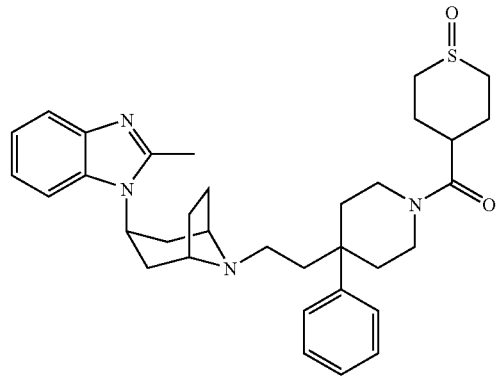

2-methyl-1-[8-(2-{1-[(1-oxidotetrahydro-2H-thiopyran-4-yl)carbonyl]-4-phenyl-4-piperidinyl}ethyl)-8-azabicyclo[3.2.1]oct-3-yl]-1H-benzimidazole (15.85 mg; 55% yield) was obtained as a solid from tetrahydro-2H-thiopyran-4-carboxylic acid 1-oxide (8.11 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 573.24.

Example 862

2-methyl-1-{8-[2-(1-{[2-(methyloxy)-1,3-thiazol-5-yl]carbonyl}-4-phenyl-4-piperidinyl)ethyl]-8-azabicyclo[3.2.1]oct-3-yl}-1H-benzimidazole

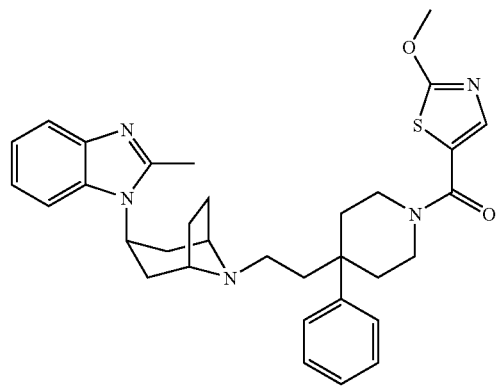

2-methyl-1-{8-[2-(1-{[2-(methyloxy)-1,3-thiazol-5-yl]carbonyl}-4-phenyl-4-piperidinyl)ethyl]-8-azabicyclo[3.2.1]oct-3-yl}-1H-benzimidazole (10.75 mg; 38% yield) was obtained as a solid from 2-(methyloxy)-1,3-thiazole-5-carboxylic acid (7.95 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 570.21.

Example 863

4-methyl-1-[(4-{2-[3-(2-methyl-1H-benzimidazol-1-yl)-8-azabicyclo[3.2.1]oct-8-yl]ethyl}-4-phenyl-1-piperidinyl)carbonyl]cyclohexanol

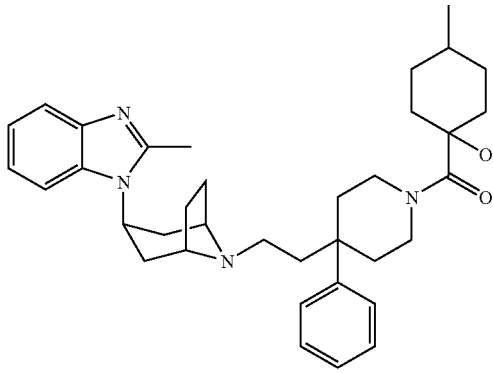

4-methyl-1-[(4-{2-[3-(2-methyl-1H-benzimidazol-1-yl)-8-azabicyclo[3.2.1]oct-8-yl]ethyl}-4-phenyl-1-piperidinyl)carbonyl]cyclohexanol (11.20 mg; 40% yield) was obtained as a solid from 1-hydroxy-4-methylcyclohexanecarboxylic acid (7.90 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 569.27.

Example 864

4-[(4-{2-[3-(2-methyl-1H-benzimidazol-1-yl)-8-azabicyclo[3.2.1]oct-8-yl]ethyl}-4-phenyl-1-piperidinyl)carbonyl]-2,1,3-benzoxadiazole

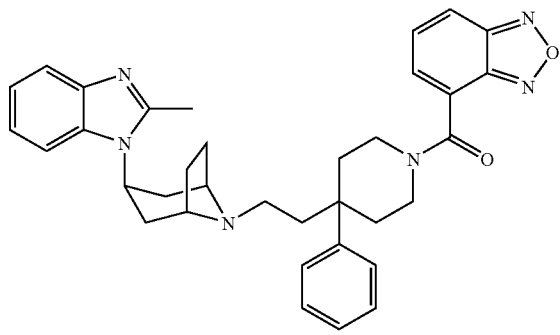

4-[(4-{2-[3-(2-methyl-1H-benzimidazol-1-yl)-8-azabicyclo[3.2.1]oct-8-yl]ethyl}-4-phenyl-1-piperidinyl)carbonyl]-2,1,3-benzoxadiazole (19.39 mg; 67% yield) was obtained as a solid from 2,1,3-benzoxadiazole-4-carboxylic acid (8.20 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 575.22.

Example 865

2-(4-{2-[3-(2-methyl-1H-benzimidazol-1-yl)-8-azabicyclo[3.2.1]oct-8-yl]ethyl}-4-phenyl-1-piperidinyl)-2-oxo-1-(3-pyridinyl)ethanol

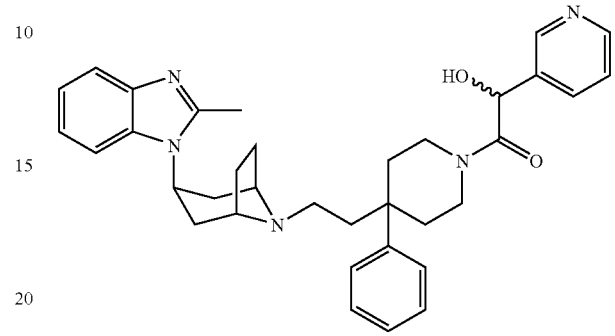

2-(4-{2-[3-(2-methyl-1H-benzimidazol-1-yl)-8-azabicyclo[3.2.1]oct-8-yl]ethyl}-4-phenyl-1-piperidinyl)-2-oxo-1-(3-pyridinyl)ethanol (15.04 mg; 54% yield) was obtained as a solid from hydroxy(3-pyridinyl)acetic acid (7.65 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 564.16.

Example 866

N-{2,2-dimethyl-3-[2-(4-{2-[3-(2-methyl-1H-benzimidazol-1-yl)-8-azabicyclo[3.2.1]oct-8-yl]ethyl}-4-phenyl-1-piperidinyl)-2-oxoethyl]cyclobutyl}acetamide

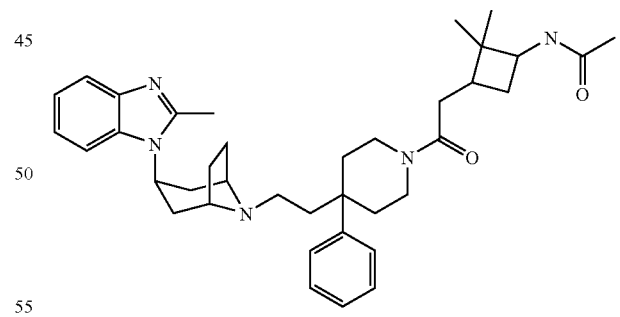

N-{2,2-dimethyl-3-[2-(4-{2-[3-(2-methyl-1H-benzimidazol-1-yl)-8-azabicyclo[3.2.1]oct-8-yl]ethyl}-4-phenyl-1-piperidinyl)-2-oxoethyl]cyclobutyl}acetamide (15.85 mg; 52% yield) was obtained as a solid from [3-(acetylamino)-2,2-dimethylcyclobutyl]acetic acid (9.96 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 610.30.

Example 867

2-methyl-1-[8-(2-{4-phenyl-1-[(4-phenyl-2-pyridinyl)carbonyl]-4-piperidinyl}ethyl)-8-azabicyclo[3.2.1]oct-3-yl]-1H-benzimidazole

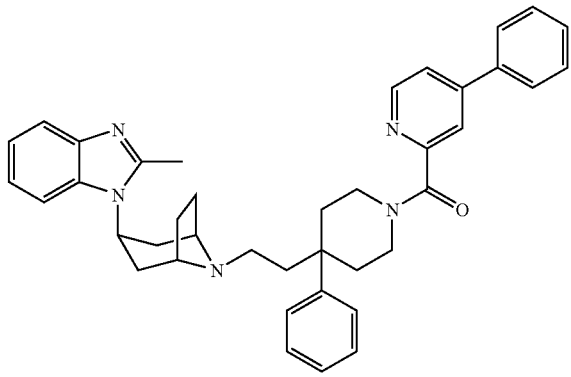

2-methyl-1-[8-(2-{4-phenyl-1-[(4-phenyl-2-pyridinyl)carbonyl]-4-piperidinyl}ethyl)-8-azabicyclo[3.2.1]oct-3-yl]-1H-benzimidazole (14.94 mg; 49% yield) was obtained as a solid from 4-phenyl-2-pyridinecarboxylic acid (9.96 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 610.20.

Example 868

1-{8-[2-(1-{[6-chloro-4-(methyloxy)-3-pyridinyl]carbonyl}-4-phenyl-4-piperidinyl)ethyl]-8-azabicyclo[3.2.1]oct-3-yl}-2-methyl-1H-benzimidazole

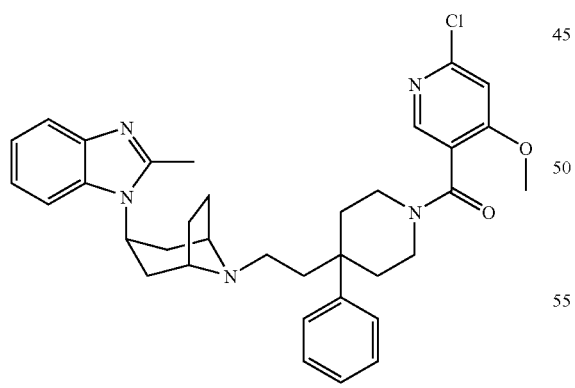

1-{8-[2-(1-{[6-chloro-4-(methyloxy)-3-pyridinyl]carbonyl}-4-phenyl-4-piperidinyl)ethyl]-8-azabicyclo[3.2.1]oct-3-yl}-2-methyl-1H-benzimidazole (17.05 mg; 57% yield) was obtained as a solid from 6-chloro-4-(methyloxy)-3-pyridinecarboxylic acid (9.37 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 598.19.

Example 869

8-[(4-{2-[3-(2-methyl-1H-benzimidazol-1-yl)-8-azabicyclo[3.2.1]oct-8-yl]ethyl}-4-phenyl-1-piperidinyl)carbonyl]-2H-chromen-2-one

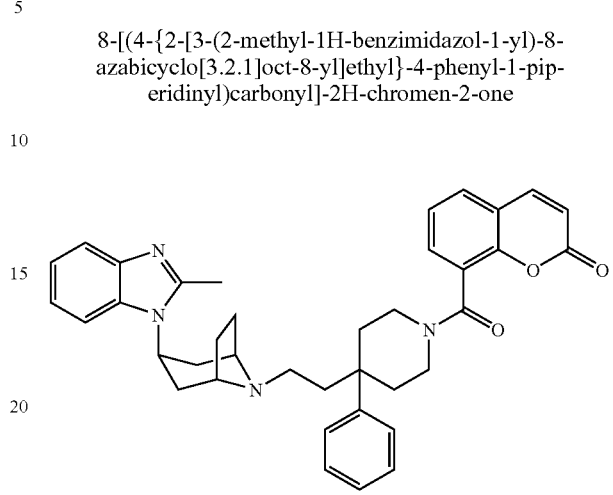

8-[(4-{2-[3-(2-methyl-1H-benzimidazol-1-yl)-8-azabicyclo[3.2.1]oct-8-yl]ethyl}-4-phenyl-1-piperidinyl)carbonyl]-2H-chromen-2-one (20.64 mg; 68% yield) was obtained as a solid from 2-oxo-2H-chromene-8-carboxylic acid (9.50 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 601.19.

Example 870

2-methyl-1-{8-[2-(4-phenyl-1-{[3-(2-pyridinyl)-5-isoxazolyl]carbonyl}-4-piperidinyl)ethyl]-8-azabicyclo[3.2.1]oct-3-yl}-1H-benzimidazole

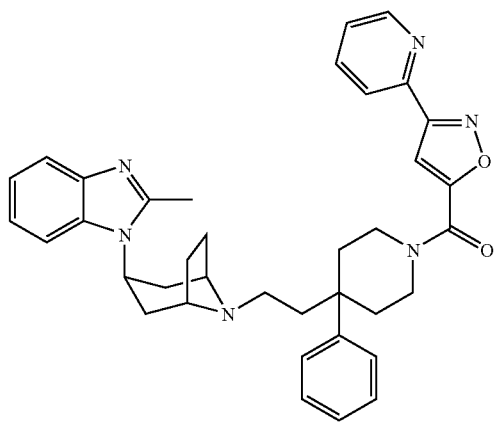

2-methyl-1 {8-[2-(4-phenyl-1-{[3-(2-pyridinyl)-5-isoxazolyl]carbonyl}-4-piperidinyl)ethyl]-8-azabicyclo[3.2.1]oct-3-yl}-1H-benzimidazole (13.15 mg; 44% yield) was obtained as a solid from 3-(2-pyridinyl)-5-isoxazolecarboxylic acid (9.50 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19

Example 871 methyl 2-[(4-{2-[3-(2-methyl-1H-benzimidazol-1-yl)-8-azabicyclo[3.2.1]oct-8-yl]ethyl}-4-phenyl-1-piperidinyl)carbonyl]-3-pyridinecarboxylate

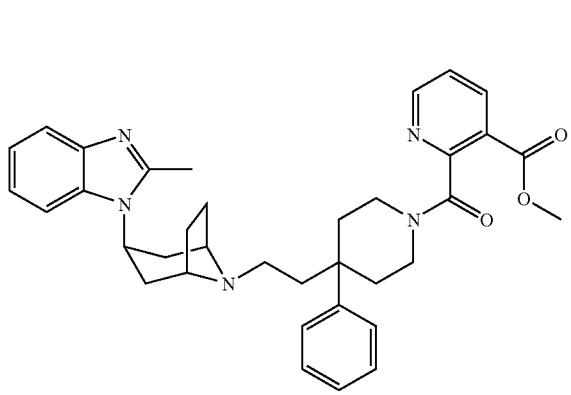

Methyl 2-[(4-{2-[3-(2-methyl-1H-benzimidazol-1-yl)-8-azabicyclo[3.2.1]oct-8-yl]ethyl}-4-phenyl-1-piperidinyl)carbonyl]-3-pyridinecarboxylate (8.45 mg; 28% yield) was obtained as a solid from 3-[(methyloxy)carbonyl]-2-pyridinecarboxylic acid (9.05 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 592.21.

Example 872

(1R)-2-(4-{2-[3-(2-methyl-1H-benzimidazol-1-yl)-8-azabicyclo[3.2.1]oct-8-yl]ethyl}-4-phenyl-1-piperidinyl)-1-(3-methylphenyl)-2-oxoethanol

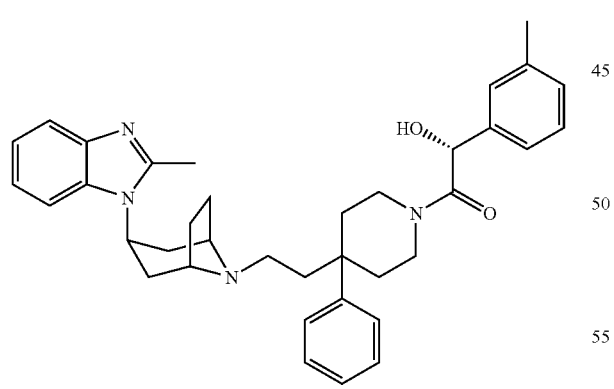

(1R)-2-(4-{2-[3-(2-methyl-1H-benzimidazol-1-yl)-8-azabicyclo[3.2.1]oct-8-yl]ethyl}-4-phenyl-1-piperidinyl)-1-(3-methylphenyl)-2-oxoethanol (11.85 mg; 41% yield) was obtained as a solid from (2R)-hydroxy(3-methylphenyl)ethanoic acid (8.30 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H): 577.24.

Example 873

2-methyl-1-[8-(2-{1-[(2-methyl-1-benzofuran-7-yl)carbonyl]-4-phenyl-4-piperidinyl}ethyl)-8-azabicyclo[3.2.1]oct-3-yl]-1H-benzimidazole

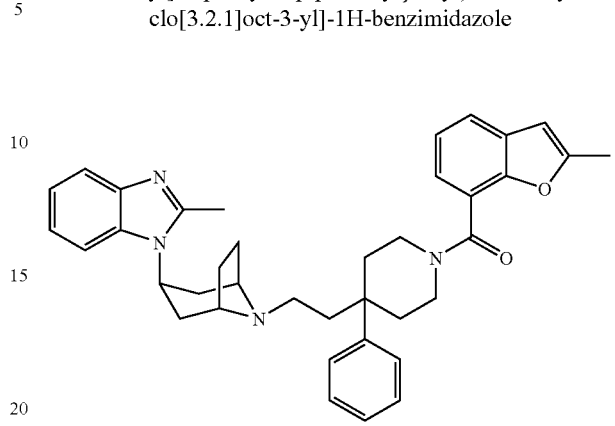

2-methyl-1-[8-(2-{1-[(2-methyl-1-benzofuran-7-yl)carbonyl]-4-phenyl-4-piperidinyl}ethyl)-8-azabicyclo[3.2.1]oct-3-yl]-1H-benzimidazole (12.30 mg; 42% yield) was obtained as a solid from 2-methyl-1-benzofuran-7-carboxylic acid (8.80 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H):587.22.

Example 874

2-methyl-1-{8-[2-(1-{[6-(methyloxy)-3-pyridinyl]carbonyl}-4-phenyl-4-piperidinyl)ethyl]-8-azabicyclo[3.2.1]oct-3-yl}-1H-benzimidazole

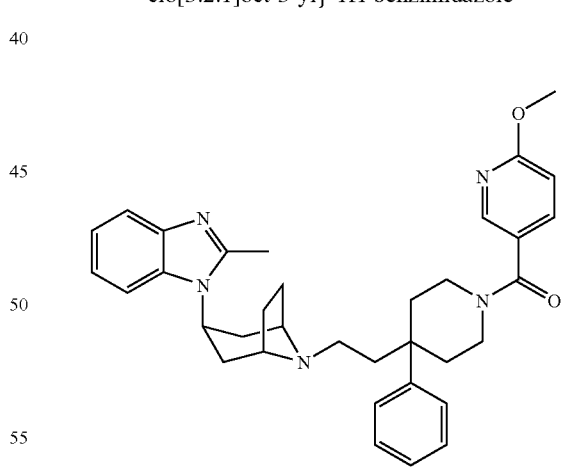

2-methyl-1-{8-[2-(1-{[6-(methyloxy)-3-pyridinyl]carbonyl}-4-phenyl-4-piperidinyl)ethyl]-8-azabicyclo[3.2.1]oct-3-yl}-1H-benzimidazole (13.0 mg; 43% yield) was obtained as a solid from 6-(methyloxy)-3-pyridinecarboxylic acid (9.37 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H):598.18.

Example 875

2-methyl-1-{8-[2-(4-phenyl-1-{[3-(trifluoromethyl)-2-pyridinyl]carbonyl}-4-piperidinyl)ethyl]-8-azabicyclo[3.2.1]oct-3-yl}-1H-benzimidazole

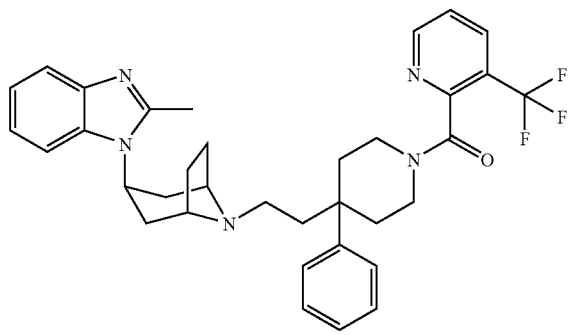

2-methyl-1-{8-[2-(4-phenyl-1-{[3-(trifluoromethyl)-2-pyridinyl]carbonyl}-4-piperidinyl)ethyl]-8-azabicyclo[3.2.1]oct-3-yl}-1H-benzimidazole (11.89 mg; 39% yield) was obtained as a solid from 3-(trifluoromethyl)-2-pyridinecarboxylic acid (9.56 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H):602.19.

Example 876

2-methyl-1-{8-[2-(4-phenyl-1-{[4-(trifluoromethyl)-1H-pyrazol-3-yl]carbonyl}-4-piperidinyl)ethyl]-8-azabicyclo[3.2.1]oct-3-yl}-1H-benzimidazole

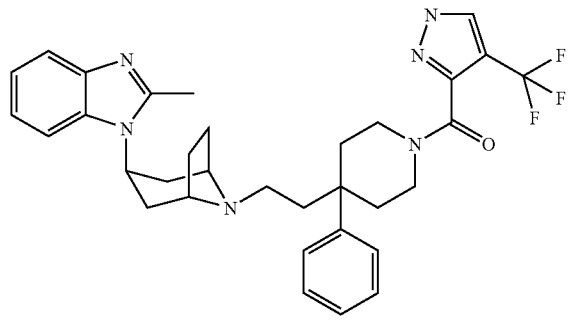

2-methyl-1-{8-[2-(4-phenyl-1-{[4-(trifluoromethyl)-1H-pyrazol-3-yl]carbonyl}-4-piperidinyl)ethyl]-8-azabicyclo[3.2.1]oct-3-yl}-1H-benzimidazole (3.94 mg; 13% yield) was obtained as a solid from 4-(trifluoromethyl)-1H-pyrazole-3-carboxylic acid (9.00 mg, 0.05 mmol), 2-methyl-1-{8-[2-(4-phenyl-4-piperidinyl)ethyl]-8-azabicyclo[3.2.1]oct-3-yl}-1H-benzimidazole hydrochloride (25 mg, 0.05 mmol) and HATU (19 mg, 0.05 mmol) following the procedure outlined in example 5. ES-LCMS m/z (M+H):591.19.

Example 877

5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-3H-1,2,3-benzoxathiazole 2,2-dioxide

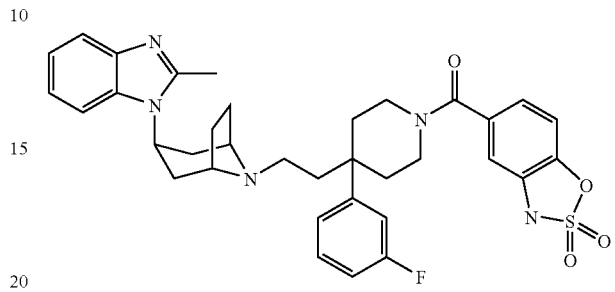

5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-3H-1,2,3-benzoxathiazole 2,2-dioxide (18 mg; 27% yield) was obtained as a solid from 3H-1,2,3-benzoxathiazole-5-carboxylic acid 2,2-dioxide (22 mg, 0.1 mmol), 1-(8-{2-[4-(3-fluorophenyl)-4-piperidinyl]ethyl}-8-azabicyclo[3.2.1]oct-3-yl)-2-methyl-1H-benzimidazole hydrochloride (50 mg, 0.1 mmol) and HATU (38 mg, 0.1 mmol) following the procedure outlined in example 5. ES-LCMS m/z (M+H): 644.29.

Example 878

1-(8-{2-[4-(3-fluorophenyl)-(1H-pyrazol-4-ylcarbonyl)-4-piperidinyl]ethyl}-8-azabicyclo[3.2.1]oct-3-yl)-2-methyl-1H-benzimidazole

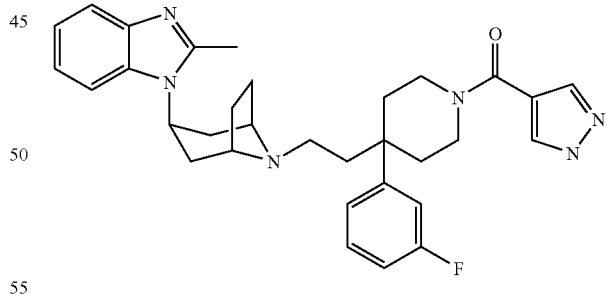

1-(8-{2-[4-(3-fluorophenyl)-1-(1H-pyrazol-4-ylcarbonyl)-4-piperidinyl]ethyl}-8-azabicyclo[3.2.1]oct-3-yl)-2-methyl-1H-benzimidazole (38 mg; 37% yield) was obtained as a solid from 1H-pyrazole-4-carboxylic acid (21 mg, 0.2 mmol), 1-(8-{2-[4-(3-fluorophenyl)-4-piperidinyl]ethyl}-8-azabicyclo[3.2.1]oct-3-yl)-2-methyl-1H-benzimidazole hydrochloride (100 mg, 0.2 mmol) and HATU (73 mg, 0.2 mmol) following the procedure outlined in example 5. ES-LCMS m/z (M+H): 541.20.

Example 879

1-{8-[2-(4-(3-fluorophenyl)-1-{[3-(methyloxy)-1H-pyrazol-4-yl]carbonyl}-4-piperidinyl)ethyl]-8-azabicyclo[3.2.1]oct-3-yl}-2-methyl-1H-benzimidazole

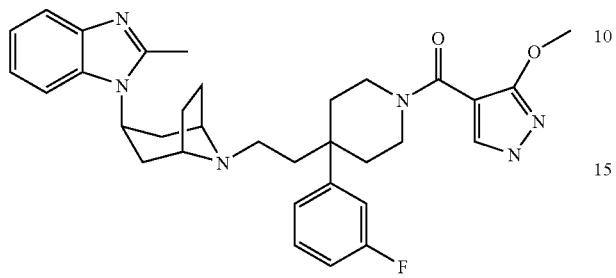

1-{8-[2-(4-(3-fluorophenyl)-1-{[3-(methyloxy)-1-(phenylmethyl)-1H-pyrazol-4-yl]carbonyl}-4-piperidinyl)ethyl]-8-azabicyclo[3.2.1]oct-3-yl}-2-methyl-1H-benzimidazole was obtained as a crude mixture from 3-(methyloxy)-1-(phenylmethyl)-1H-pyrazole-4-carboxylic acid (23 mg, 0.1 mmol), 1-(8-(2-[4-(3-fluorophenyl)-4-piperidinyl]ethyl)-8-azabicyclo[3.2.1]oct-3-yl)-2-methyl-1H-benzimidazole hydrochloride (50 mg, 0.1 mmol) and HATU (38 mg, 0.1 mmol) following the procedure outlined in example 5. ES-LCMS m/z (M+H): 661.46. The crude mixture was then treated with PdCl$_2$ (25 mg) under 50 psi H$_2$ to provide 1-{8-[2-(4-(3-fluorophenyl)-1-{[3-(methyloxy)-1H-pyrazol-4-yl]carbonyl}-4-piperidinyl)ethyl]-8-azabicyclo[3.2.1]oct-3-yl}-2-methyl-1H-benzimidazole as solid (30, 52%). ES-LCMS m/z (M+H): 571.24

Example 880

2,4-dichloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-N-methylbenzenesulfonamide

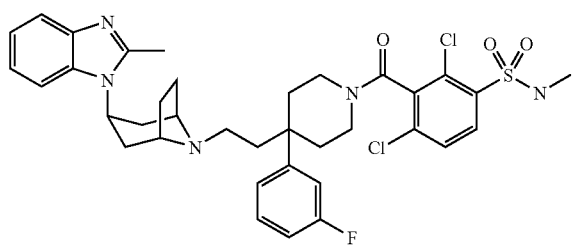

Example 880 was prepared according to figure below.

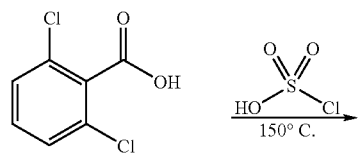

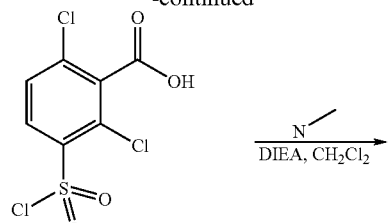

example 880-1a

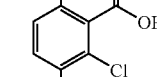

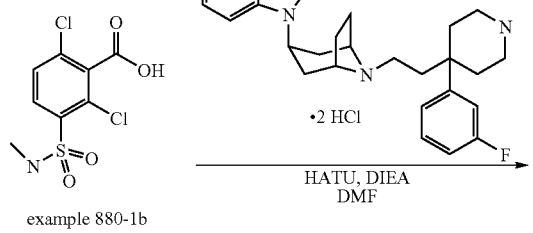

example 880-1b

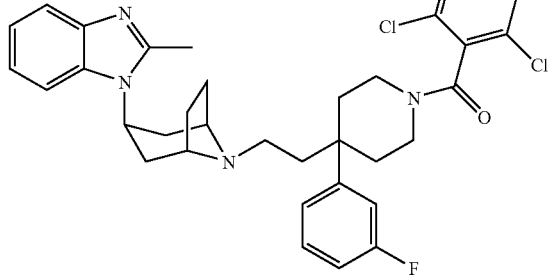

example 880

Synthesis of 880-1a 2,6-dichloro-3-(chlorosulfonyl)benzoic acid

Chlorosulfonic acid was slowly added to 2,6-dichlorobenzoic acid at RT under N$_2$. The reaction was heated to 150° C. for 3 h, then slowly poured over ice and the product extracted into Et$_2$O. The organic layer was dried over MgSO$_4$, filtered and concentrated to give 2,6-dichloro-3-(chlorosulfonyl)benzoic acid 880-1a as a brown solid (12.9 g, 85% yield).

$^1$H NMR (400 MHz, DMSO) δ 13.42 (broad s, 1H), 7.88 (d, J=8. Hz, 1H), 7.46 (d, J=8.4 Hz, 1H).

Synthesis of 880-1b 2,6-dichloro-3-[(methylamino)sulfonyl]benzoic acid

A mixture of 2,6-dichloro-3-(chlorosulfonyl)benzoic acid 880-1a (200 mg, 0.69 mmol, 1 equiv) and 4 mL CH$_2$Cl$_2$ was treated with diisopropylamine (248 μL, 1.38 mmol, 2 equiv) and 2M methyl amine (415 μL, 0.83 mmol, 1.2 equiv). The reaction was stirred at RT overnight, wherein the crude mixture contained 2,6-dichloro-3-[(methylamino)sulfonyl]benzoic acid 880-1 b. The mixture was carried directly into the following reaction. ES-LCMS m/z 284.0 (M−H)

Synthesis of 880

2,4-dichloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-N-methylbenzenesulfonamide

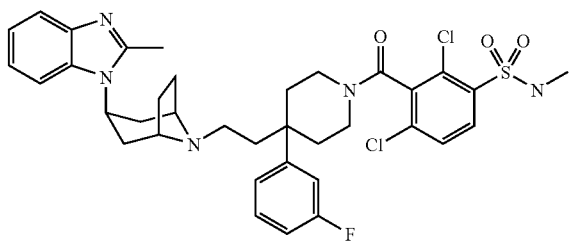

To a solution of 1-(8-{2-[4-(3-fluorophenyl)piperidin-4-yl]ethyl}-8-azabicyclo[3.2.1]oct-3-yl)-2-methyl-1H-benzimidazole dihydrochloride (100 mg, 0.16 mmol, 1 equiv) and N,N-diisopropylethyl amine (117 µL, 0.66 mmol, 4 equiv) in dimethylformamide (2 mL) was added the mixture of 2,6-dichloro-3-[(methylamino)sulfonyl]benzoic acid 880-1 b. After stirring at RT for several min, O-(7-azabenzotriazol-1-yl)-N,N,N',N'-tetramethyluroniumhexafluorophosphate (62 mg, 0.16 mmol, 1 equiv) was added and the reaction was stirred for 18 h. The mixture was partitioned between dichloromethane and satd. aq. NaHCO$_3$. The organic layer was dried and concentrated and the residue was purified by SiO$_2$ flash column chromatography (100% EtOAc→10% 2M NH$_3$ in MeOH in EtOAC) to provide 2,4-dichloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-N-methylbenzenesulfonamide (example 880) as a white solid (25 mg, 22% yield).

$^1$H NMR (300 MHz, CDCl$_3$) δ 8.05 (m, 1H), 7.65 (m, 1H), 7.49 (m, 1H), 7.39-7.29 (m, 3H), 7.19-6.95 (m, 5H), 5.34 (m, 1H), 4.60 (m, 1H), 4.27 (m, 1H), 3.48-3.12 (m, 6H), 2.66 (m, 3H), 2.56 (m, 3H), 2.42-2.27 (m, 3H), 2.22-1.76 (m, 7H), 1.64 (m, 2H), 1.42 (m, 2H). ES-LCMS m/z 712.2 (M+H).

Example 881

4-chloro-N-(1,1-dimethylethyl)-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide

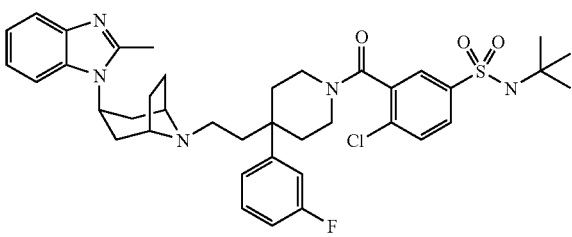

Example 881 was prepared according to figure below.

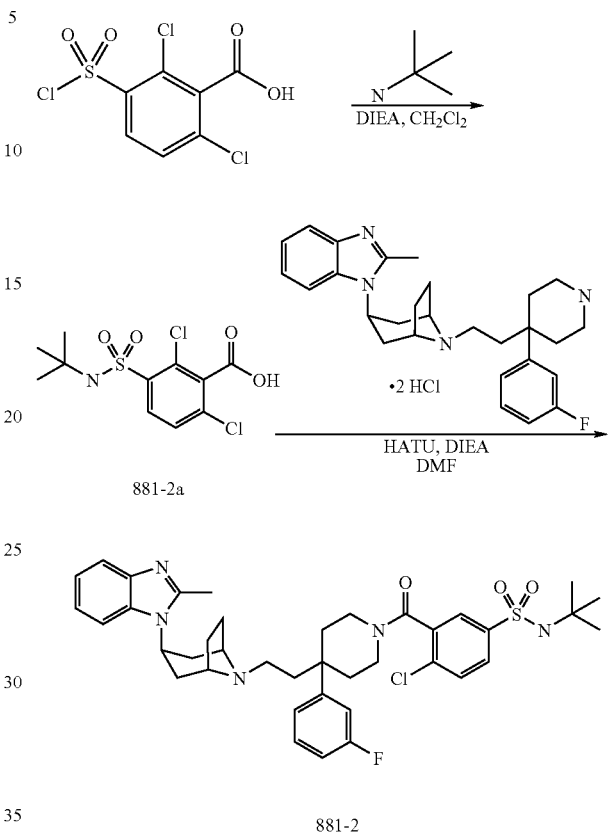

Synthesis of 881-2a 2-chloro-5-{[(1,1-dimethylethyl)amino]sulfonyl}benzoic acid Prepared from a mixture of 2-chloro-5-(chlorosulfonyl)benzoic acid (200 mg, 0.78 mmol, 1 equiv) tert-butyl amine (98 µL, 0.94 mmol, 1.2 equiv) and DIEA (248 µL, 1.38 mmol, 2 equiv) following the general procedure for 2,6-dichloro-3-[(methylamino)sulfonyl]benzoic acid 881-1b. The crude reaction mixture was carried on without further purification.
ES-LCMS m/z 315.2 (M+Na)

Synthesis of 881

4-chloro-N-(1,1-dimethylethyl)-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide

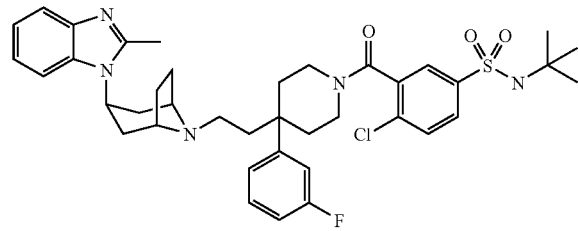

Prepared from a mixture of 2-chloro-5-{[(1,1-dimethylethyl)amino]sulfonyl}benzoic acid 2b, 1-(8-{2-[4-(3-fluorophenyl)-4-piperidinyl]ethyl}-8-azabicyclo[3.2.1]oct-3-yl)-2-methyl-1H-benzimidazole (100 mg, 0.16 mmol, 1 equiv), DIEA (117 μL, 0.66 mmol, 4 equiv) and HATU (62 mg, 0.16 mmol, 1 equiv) following the general procedure for 2,4-dichloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-N-methylbenzenesulfonamide example 880. The crude product was purified by column chromatography on silica gel eluting with 10% 2M NH$_3$ in methanol in ethyl acetate to afford 4-chloro-N-(1,1-dimethylethyl)-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide as a white solid (40.3 mg, 35% yield).

$^1$H NMR (300 MHz, CDCl$_3$) δ 7.89-7.80 (m, 1H), 7.71-7.64 (m, 1H), 7.55-7.48 (m, 1H), 7.38-7.26 (m, 3H), 7.19-6.94 (m, 6H), 4.92-4.54 (m, 2H), 4.23 (m, 1H), 3.47-3.04 (m, 6H), 2.56 (m, 3H), 2.54-1.34 (m, 14H), 1.24 (m, 9H). ES-LCMS m/z 720.2 (M+H).

Example 882

N-(1,1-dimethylethyl)-2,4-difluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide

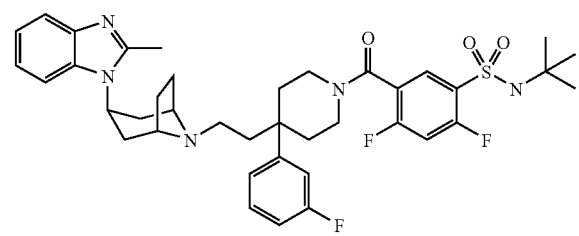

Prepared according to figure below.

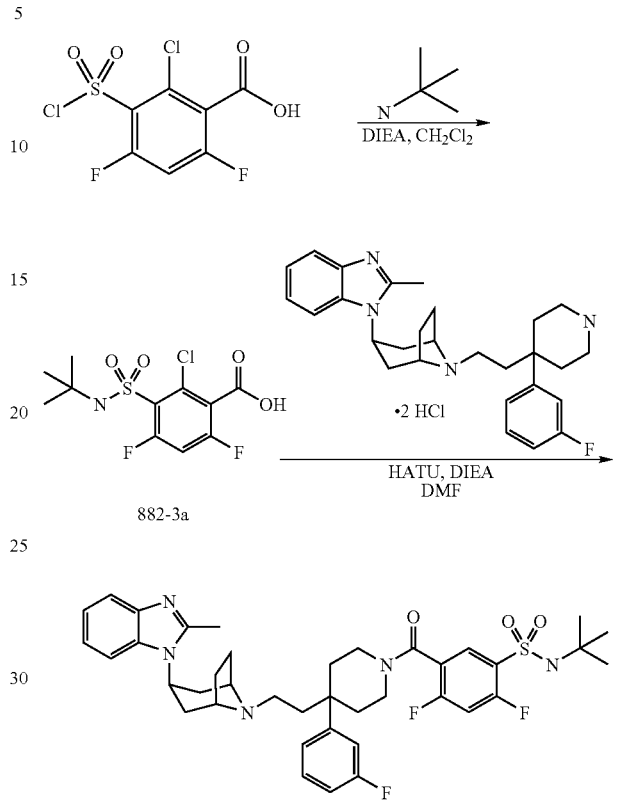

Synthesis of 882-3a

5-{[(1,1-dimethylethyl)amino]sulfonyl}-2,4-difluorobenzoic acid

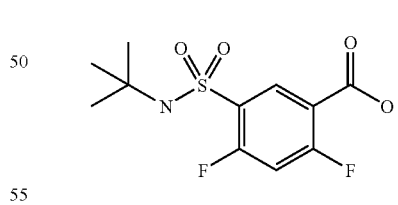

Prepared from a mixture of 5-(chlorosulfonyl)-2,4-difluorobenzoic acid (200 mg, 0.78 mmol, 1 equiv), tert-butyl amine (98 mL, 0.94 mmol, 1.2 equiv) and DIEA (280 μL, 1.56 mmol, 2 equiv) following the general procedure for 2,6-dichloro-3-[(methylamino)sulfonyl]benzoic acid 880-1b. The crude reaction mixture was carried on without further purification.

ES-LCMS m/z 292.3 (M−H)

Synthesis of 882

N-(1,1-dimethylethyl)-2,4-difluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide

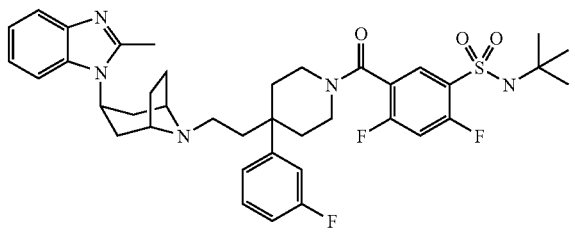

Prepared from a mixture of 5-{[(1,1-dimethylethyl)amino]sulfonyl}-2,4-difluorobenzoic acid 882-3b 1-(8-{2-[4-(3-fluorophenyl)-4-piperidinyl]ethyl}-8-azabicyclo[3.2.1]oct-3-yl)-2-methyl-1H-benzimidazole (100 mg, 0.16 mmol, 1 equiv), DIEA (117 μL, 0.66 mmol, 4 equiv) and HATU (62 mg, 0.16 mmol, 1 equiv) following the general procedure for 2,4-dichloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-N-methylbenzenesulfonamide 1. The crude product was purified by column chromatography on silica gel eluting with 10% 2M NH$_3$ in methanol in ethyl acetate to afford N-(1,1-dimethylethyl)-2,4-difluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide (example 882) as a white solid (46 mg, 40% yield).

$^1$HNMR (400 MHz, CDCl$_3$) δ 8.00 (m, 1H), 7.66 (m, 1H), 7.93-6.95 (m, 9H), 4.86 (m, 1H), 4.62 (m, 1H), 4.15 (m, 2H), 3.44-3.14 (m, 5H), 2.92 (m, 3H), 2.58-1.60 (m, 14H), 1.25 (m, 9H). HRMS m/z (M+H): Calcd for C$_{39}$H$_{46}$F$_3$N$_5$O$_3$S, 722.34; found 722.3352.

Example 883

4-chloro-N-(1,1-dimethylethyl)-2-fluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide

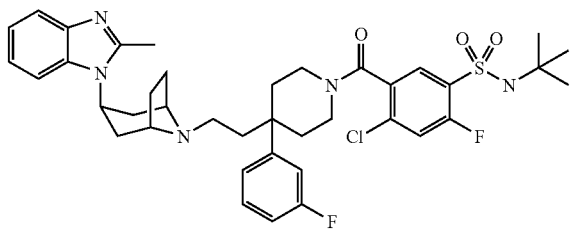

Prepared according to figure below

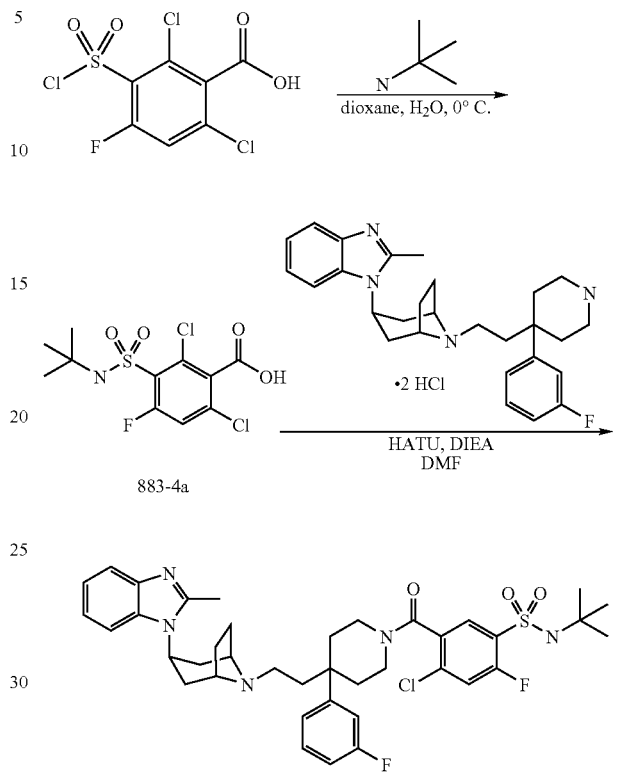

Synthesis of 883-4a 2-chloro-5-{[(1,1-dimethylethyl)amino]sulfonyl}-4-fluorobenzoic acid

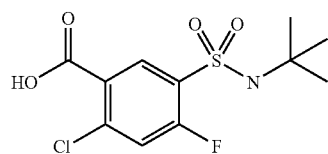

tert-Butyl amine (77 mL, 0.7 mol, 10 equiv) was added to 300 mL dioxane at 0° C. Ice chips were added to the flask for several minutes before the addition of 2-chloro-5-(chlorosulfonyl)-4-fluorobenzoic acid (20 g, 73.24 mmol, 1 equiv). Both the internal and external temperature of the reaction was maintained at or below 0° C. for 2 h. The reaction was then concentrated half-way and acidified to pH 2 with 1N HCl. The product was extracted into EtOAc. The organics were dried over Na$_2$SO$_4$, filtered and concentrated down to give 2-chloro-5-{[(1,1-dimethylethyl)amino]sulfonyl}-4-fluorobenzoic acid 883-4a as a brown solid (21 g; 92% yield).

$^1$H NMR (400 MHz, DMSO) δ 8.23 (d, J=7.8 Hz, 1H), 8.06 (broad s, 1H), 7.82 (d, J=9.8 Hz, 1H). ES-LCMS m/z 308.2 (M−H)

659

Synthesis of 883

4-chloro-N-(1,1-dimethylethyl)-2-fluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide

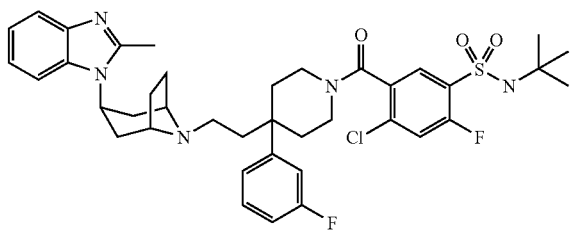

To a solution of 1-(8-{2-[4-(3-fluorophenyl-4-piperidinyl]ethyl}-8-azabicyclo[3.2.1]oct-3-yl)-2-methyl-1H-benzimidazole (32.0 g, 61.6 mmol, 1 equiv) in dimethylformamide (300 mL) was added 2-chloro-5-{[(1,1-dimethylethyl)amino]sulfonyl}-4-fluorobenzoic acid 883-4b (21 g, 67.8 mmol, 1.1 equiv) and N,N-diisopropylethyl amine (44 mL, 0.25 mol. 4 equiv). After stirring at RT for several min, O-(7-azabenzotriazol-1-yl)-N,N,N',N'-tetramethyluronium-hexafluorophosphate (23.4 g, 61.6 mmol, 1 equiv) was added and the reaction was stirred for 2 h. The mixture was partitioned between ethyl acetate and water. The organic layer was washed with satd. aq. NaHCO$_3$, H$_2$O and satd. aq. NaCl, then dried over Na$_2$SO$_4$, filtered and concentrated. The residue was taken up in 200 mL MeOH and stirred with Amberjet 4400 OH Basic Ion Exchanger (60 g) for 1 h. The mixture was filtered and concentrated and the residue was purified by silica gel flash column chromatography in 20% 2M NH$_3$ in MeOH in EtOAc to afford 4-chloro-N-(1,1-dimethylethyl)-2-fluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide (example 883) as a white solid (21 g; 46% yield).

$^1$H NMR (400 MHz, CDCl$_3$) δ 8.00 (m, 1H), 7.86-7.76 (m, 2H), 7.49 (m, 1H), 7.44-7.35 (m, 2H), 7.23 (m, 2H), 7.15-7.04 (m, 3H), 4.55-4.45 (m, 1H), 3.98-3.86 (m, 1H), 3.42-3.35 (m, 1H), 3.25 (m, 2H), 3.05-2.96 (m, 1H), 2.45 (m, 3H), 2.39-2.32 (m, 2H), 2.23-1.99 (m, 2H), 1.92-1.72 (m, 11H), 1.60 (m, 2H), 1.12 (m, 9H). HRMS m/z (M+H) Calcd for C$_{39}$H$_{46}$ClF$_2$N$_5$O$_3$S, 738.30; Found, 738.30.

Example 884

2,4-dichloro-N-(1,1-dimethylethyl)-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide

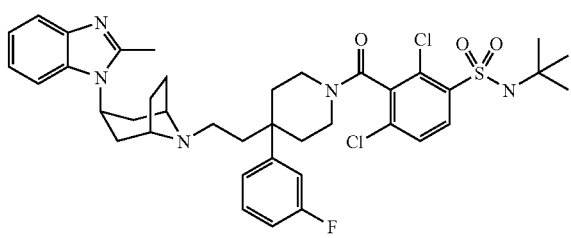

660

Example 884 was prepared according to figure below.

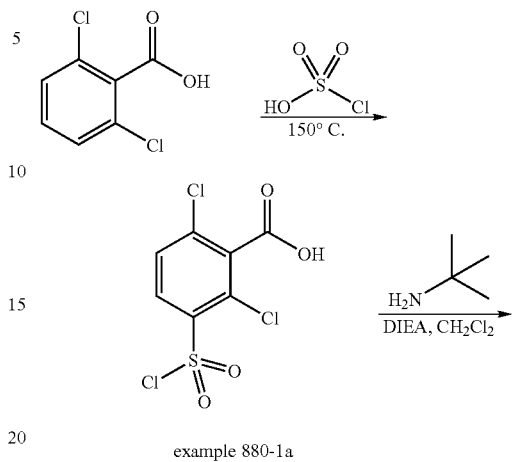

example 880-1a

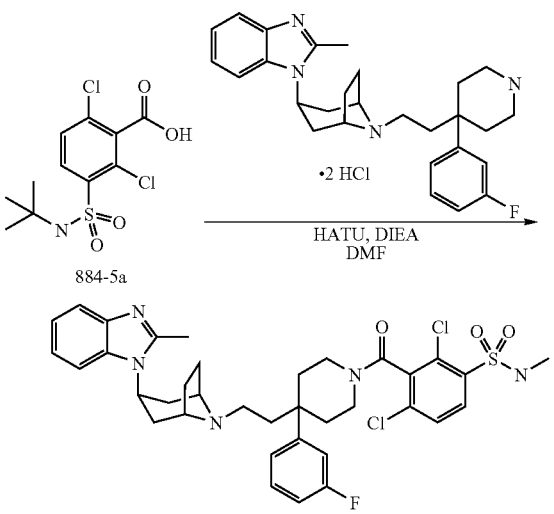

Synthesis of 884-5a 2,6-dichloro-3-{[(1,1-dimethylethyl)amino]sulfonyl}benzoic acid

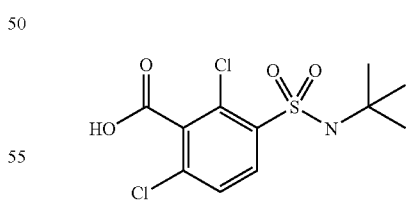

Prepared from a mixture of 2,6-dichloro-3-{[(1,1-dimethylethyl)amino]sulfonyl}benzoic acid 884-5a (200 mg, 0.69 mmol, 1 equiv), tert-butyl amine and DIEA (248 μL, 1.38 mmol, equiv) following the general procedure for 2,6-dichloro-3-[(methylamino)sulfonyl]benzoic acid 880-1b. The crude reaction mixture was carried on without further purification.

ES-LCMS m/z 327.4 (M+H)

Synthesis of 884

2,4-dichloro-N-(1,1-dimethylethyl)-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide

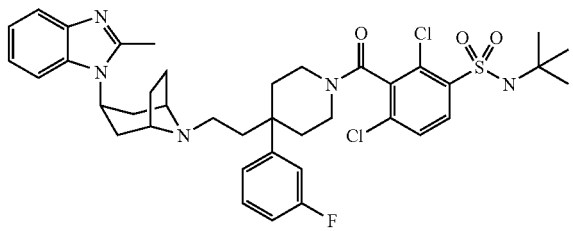

Prepared from a mixture of 2,6-dichloro-3-{[(1,1-dimethylethyl)amino]sulfonyl}benzoic acid 884-5a, 1-(8-{2-[4-(3-fluorophenyl)-4-piperidinyl]ethyl}-8-azabicyclo[3.2.1]oct-3-yl)-2-methyl-1H-benzimidazole (100 mg, 0.16 mmol, 1 equiv), DIEA (117 µL, 0.66 mmol, 4 equiv) and HATU (62 mg, 0.16 mmol, 1 equiv) following the general procedure for 2,4-dichloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-N-methylbenzenesulfonamide (example 880). The crude product was purified by column chromatography on silica gel eluting with 10% 2M NH₃ in methanol in ethyl acetate to afford 2,4-dichloro-N-(1,1-dimethylethyl)-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonamide 5 as a white solid (21 mg, 17% yield).

$^1$H NMR (400 MHz, CDCl$_3$) δ 8.08 (m, 1H), 7.66 (m, 1H), 7.47 (m, 1H), 7.39-7.26 (m, 3H), 7.20-6.95 (m, 5H), 4.98 (m, 1H), 4.61 (m, 1H), 4.27 (m, 1H), 3.71 (m, 1H), 3.51-3.07 (m, 7H), 2.57 (m, 3H), 2.47-1.37 (m, 11H), 1.23 (m, 9H). HRMS m/z (M+H) Calcd for C$_{39}$H$_{46}$Cl$_2$FN$_5$O$_3$S, 754.2761: Found, 754.2761.

Example 885

2,4-difluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfinic acid

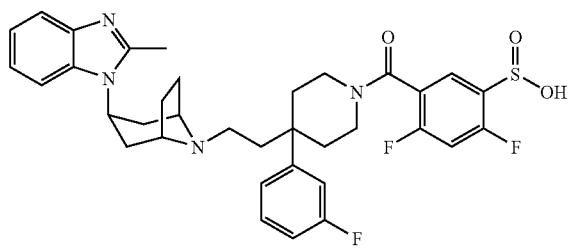

Example was prepared according the figure below.

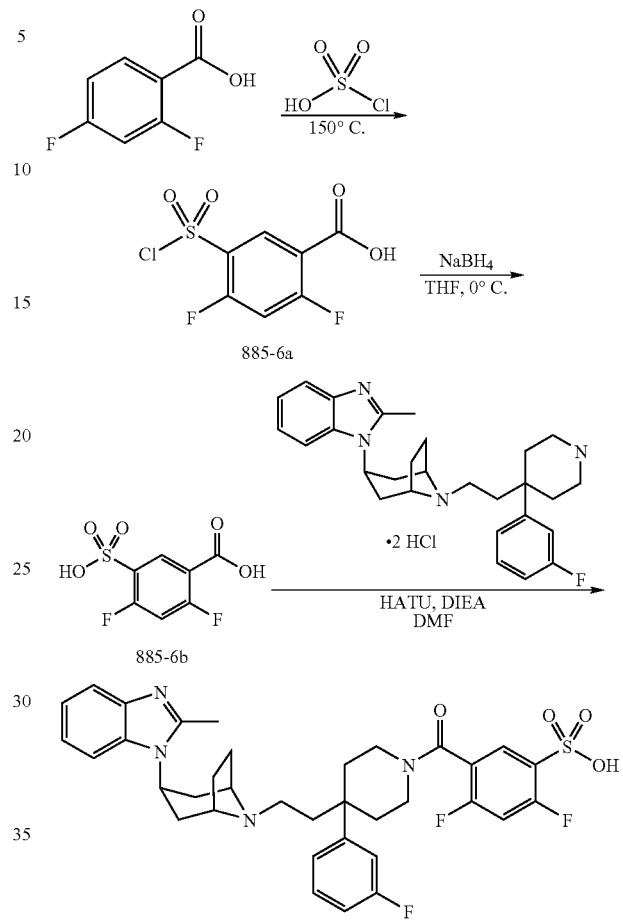

Synthesis of 885-6a 5-(chlorosulfonyl)-2,4-difluorobenzoic acid

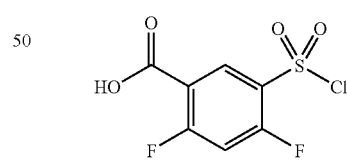

A mixture of chlorosulfonic acid (200 mL) and 2,4-difluorobenzoic acid (40 g, 253 mmol, 1 equiv) was heated to 155° C. for 3 h. The reaction was cooled to RT and poured slowly over ice. The product was extracted into ether and the organics dried over MgSO$_4$, filtered and concentrated to give 5-(chlorosulfonyl)-2,4-difluorobenzoic acid 6a as brown solid (61 g, 94% yield).

$^1$H NMR (400 MHz, CDCl$_3$) δ 8.98 (broad s, 1H), 8.72 (t, J=7.6 Hz, 1H), 7.21 (t, J=9.5 Hz, 1H). ES-LCMS m/z 255.3 (M−H)

Synthesis of 885-6b 2,4-difluoro-5-sulfobenzoic acid

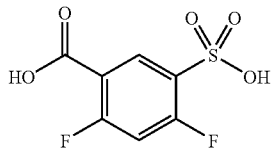

Sodium borohydride (0.59 g, 15.6 mmol, 8 equiv) was added portionwise to a solution of 5-(chlorosulfonyl)-2,4-difluorobenzoic acid 885-6a (0.5 g, 1.9 mmol, 1 equiv) in 10 mL THF at 0° C. The reaction was stirred at this temperature for 1 h and then concentrated down and the residue acidified to pH 2 with 5N HCl. The precipitate was removed by filtration and the liquid concentrated down to provide 2,4-difluoro-5-sulfobenzoic acid 885-6b as a white solid (433 mg, 100% yield)

$^1$H NMR (400 MHz, DMSO) δ 8.18 (t, J=8.0 Hz, 1H), 7.52 (t, J=10.2 Hz, 1H).

Synthesis of example 885

2,4-difluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonic acid

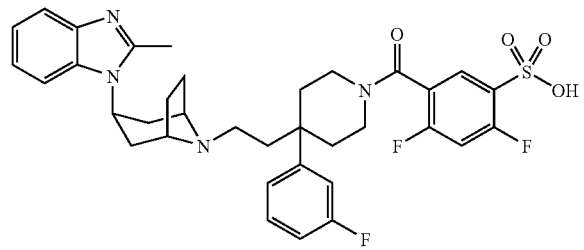

Prepared from a mixture of 2,4-difluoro-5-sulfobenzoic acid 885-6b (580 mg, 0.58 mmol, 2 equiv), 1-(8-{2-[4-(3-fluorophenyl)-4-piperidinyl]ethyl}-8-azabicyclo[3.2.1]oct-3-yl)-2-methyl-1H-benzimidazole (150 mg, 0.29 mmol, 1 equiv), DIEA (260 μL, 1.45 mmol, 5 equiv) and HATU (110 mg, 0.29 mmol, 1 equiv) following the general procedure for 2,4-dichloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-N-methylbenzenesulfonamide, example 880. The crude product was purified by prep HPLC (HPLC Method C) to afford 2,4-difluoro-5-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]benzenesulfonic acid (example 885) as a white solid (40 mg, 22% yield).

$^1$H NMR (400 MHz, CDCl$_3$) δ 7.64 (m, 1H), 7.53 (m, 1H), 7.47-7.40 (m, 2H), 7.27-7.03 (m, 6H), 4.88 (m, 1H), 3.88-3.05 (m, 4H), 2.64-2.34 (m, 14H, 2.22-1.80 (m, 8H). ES-LCMS m/z 651.3 (M+H).

HPLC Method C

Preparative High Pressure Liquid Chromatography data was acquired using a Waters LC-UV system. The system operates using a Waters Symmetry Shield RP18 3.9×150 mm, 5 μm column at 35 mL/minute. The mobile phase consists of Water (0.1% NH4OH) and MeOH. The gradient used starts a 0% MeOH: 90% Water (0.1% NH4OH) and moves to 90% MeOh: 10% Water (0.1% NH4OH) over 7 minutes. There is a one minute wash of the column using 100% MeOH for one minute, until eight minutes and then original conditions return at 8.1 minutes to 8.5

Example 886

4-fluoro-7-[(4-{2-[3-(2-methyl-1H-benzimidazol-1-yl)-8-azabicyclo[3.2.1]oct-8-yl]ethyl}-4-phenyl-1-piperidinyl)carbonyl]-1,3-benzoxazol-2(3H)-one

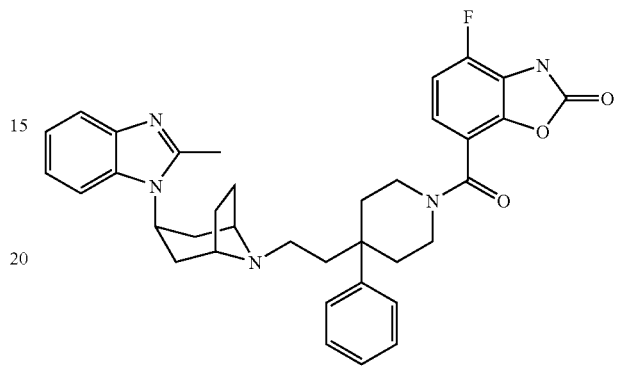

Prepared from a mixture of 4-fluoro-2-oxo-2,3-dihydro-1,3-benzoxazole-7-carboxylic acid (9.8 mg, 0.05 mmol, 1 equiv), endo 2-methyl-1-{8-[2-(4-phenylpiperidin-4-yl)ethyl]-8-azabicyclo[3.2.1]oct-3-yl}-1H-benzimidazole dihydrochloride (25 mg, 0.05 mmol, 1 equiv), DIEA (36 μL, 0.2 mmol, 4 equiv) and HATU (19 mg, 0.05 mmol, 1 equiv) following the general procedure for 2,4-dichloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]-N-methylbenzenesulfonamide (example 880). The crude product was purified by prep HPLC (HPLC Method C) to provide 4-fluoro-7-[(4-{2-[3-(2-methyl-1H-benzimidazol-1-yl)-8-azabicyclo[3.2.1]oct-8-yl]ethyl}-4-phenyl-1-piperidinyl)carbonyl]-1,3-benzoxazol-2(3H)-one as a white solid (5 mg, 17% yield).

NMR (400 MHz, CDCl$_3$) δ 7.51-7.34 (m, 1H), 7.26-7.22 (m, 1H), 7.16-7.07 (m, 4H), 4.53 (m, 1H), 3.94 (m, 1H), 3.5-3.1 (m, 6H), 2.54-2.05 (m, 12H), 1.96-1.59 (m, 6H). ES-LCMS m/z 608.17 (M+H).

Example 887

1-{1-(2,2-dimethylpropanoyl)-4-phenylpiperdin-4-yl]-2-[3-(2-methyl-1H-benzimidaol-1-yl)-8-azabicyclo[3.2.1]oct-8-yl]ethanol

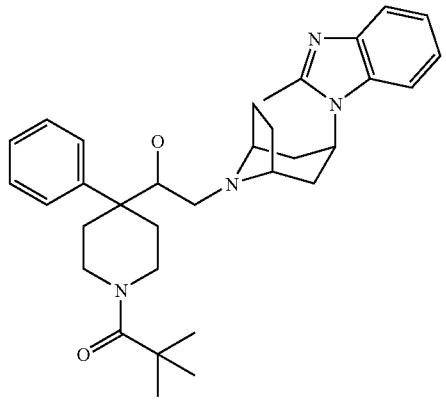

Synthesis of 2-bromo-1-[1-(2,2-dimethylpropanoyl)-4-phenylpiperdin-4-yl]ethanone

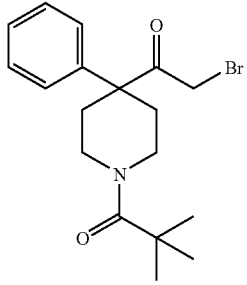

To a suspension of 4-acetyl-4-phenyl piperdine hydrochloride (20.8 mmol) in DCM (200 ml) was added TEA (541.1 mmol) and the mixture was stirred under an inert atmosphere for 10 minutes. Pivaloyl chloride (22.8 mmol) was added and the mixture was stirred until HPLC analysis indicated that the reaction was complete. Water and EtOAc were added. The ethyl acetate layer was separated and washed with satd. NaHCO$_3$, water, brine and dried (Na$_2$SO$_4$). Removal of solvent under vacuum gave the intermediate ketone, which was used directly in the next step. $^1$H NMR (400 MHz, DMSO d-6) 7.21-7.40 (m, 5H), 3.77-3.82 (dt, 2H), 3.14-3.21 (t, 2H), 2.45-2.51 (m, 2H), 2.31-2.41 (d, 2H), 1.20 (s, 2H), 1.14 (s, 9H). LCMS m/z (M+H) calcd: 287.48 obsd: 288.44. To a solution of 1-[1-(2,2-dimethylpropanoyl)-4-phenylpiperdin-4-yl]ethanone in MeOH (125 ml) at 0° C. Br$_2$ was added (24.5 mmol) dropwise over 10 minutes. The mixture was stirred 12 hrs. at room temperature under an inert atmosphere. H$_2$O (20 ml) was added and the resulting mixture was stirred for an additional 0.5 hr. Et$_2$O and water (250 ml 1:1) were added, the organic layer was washed with water, satd. K$_2$CO$_3$ solution, dried (Na$_2$SO$_4$) and the solvent was removed in-vacuo to give 2 as a lightly colored powder (7 g, 92%). HPLC: rt=5.26 min. This compound was used directly in the following step.

The synthesis of 1-{1-(2,2-dimethylpropanoyl)-4-phenylpiperdin-4-yl]-2-[3-(2-methyl-1H-benzimidaol-1-yl)-8-azabicyclo[3.2.1]oct-8-yl]ethanone

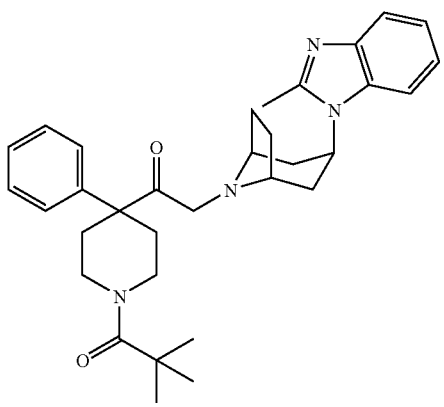

To the amine IV in scheme III (3 mmol) in Et$_2$O was added TEA (17.9 mmol) and the reaction mixture was stirred under inert atmosphere for 1 hr. Next, 2-bromo-1-[1-(2,2-dimethylpropanoyl)-4-phenylpiperdin-4-yl]ethanone (2.7 mmol) in Et$_2$O (20 ml) was added and the resulting mixture was stirred overnight. Benzene (50 ml) and TEA (14.3 mmol) were added to the reaction and the whole was heated to 90° C. overnight. The reaction was cooled to room temperature and concentrated in-vacuo. The crude material in DCM was washed with brine, and water and then dried (Na$_2$SO$_4$). Concentration under vacuum gave 1-{1-(2,2-dimethylpropanoyl)-4-phenylpiperdin-4-yl]-2-[3-(2-methyl-1H-benzimidaol-1-yl)-8-azabicyclo[3.2.1]oct-8-yl]ethanone, which was purified by silica gel chromatography (DCM: MeOH; 9.5:0.5) to give (400 mg, 30%) as a white powder. $^1$H NMR (400 MHz, CDCl3), 7.67 (d, 1H), 7.29-7.42 (m, 6H), 7.08-7.22 (m, 2H), 4.63-4.78 (m, 1H), 4.08-4.18 (m, 3H), 3.28-3.39 (m, 2H), 3.12-3.23 (m, 2H), 3.08-3.10 (s, 2H), 2.61 (s, 3H), 2.50 (m, 2H), 2.39-2.40 (m, 2H), 2.10 (s, 2H), 1.84-1.90 (m, 2H), 1.61 (s, 3H), 1.28 (s, 9H). LCMS m/z (M+H) calcd: 526.72, obsd: 527.45

The synthesis of 1-{1-(2,2-dimethylpropanoyl)-4-phenylpiperdin-4-yl]-2-[3-(2-methyl-1H-benzimidaol-1-yl)-8-azabicyclo[3.2.1]oct-8-yl]ethanol

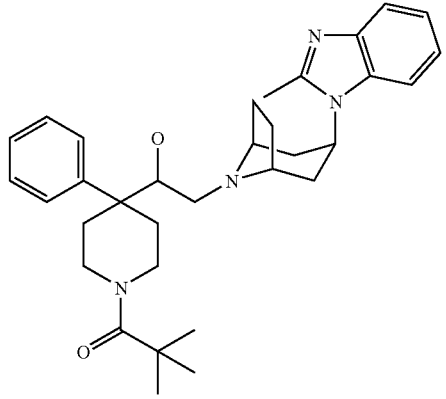

To a solution of 1-{1-(2,2-dimethylpropanoyl)-4-phenylpiperdin-4-yl]-2-[3-(2-methyl-1H-benzimidaol-1-yl)-8-azabicyclo[3.2.1]oct-8-yl]ethanone (30 mg) in MeOH (5 ml) was added NaBH$_4$ (0.9 mmol) and the reaction mixture was stirred overnight. Satd. NaHCO$_3$ was added and the product was extracted with DCM (3×). The organics were dried (Na$_2$SO$_4$). Removal of solvent under of vacuum gave the desired product 4 as a white solid. $^1$H NMR (CDCl$_3$) 7.64-7.70 (m, 11H), 7.35-7.41 (m, 4H), 7.29-7.30 (m, 1H), 7.11 (m, 2H), 4.49-4.62 (m, 1H), 4.22-4.30 (s, 2H), 3.50-3.60 (dd, 1H), 3.34 (t, 1H), 3.15 (t, 1H), 2.90-2.77 (q, 2H), 2.51 (s, 3H), 2.34-2.44 (m, 3H), 2.22 (d, 1H), 2.1 (dd, 1H), 1.94 (m, 4H), 1.90 (m, 1H), 1.71-1.80 (m, 3H), 1.25 (s, 9H). HPLC (3.483 min, 100%)

HPLC: ZORBAX (2.1×50 mm; 3.5 micron), T=40° C.; ACN/water+0.05% TFA; 0-to-95% over 8 min.

Example 888

3-(4-(3-isopropylphenyl)-4-{2-[3-(2-methyl-1H-benzimidazole-1-yl)-8-azabicyclo[3.2.1]oct-8-yl]ethyl}piperdin-1-yl)2,2-dimethyl-3-oxopropan-1-ol

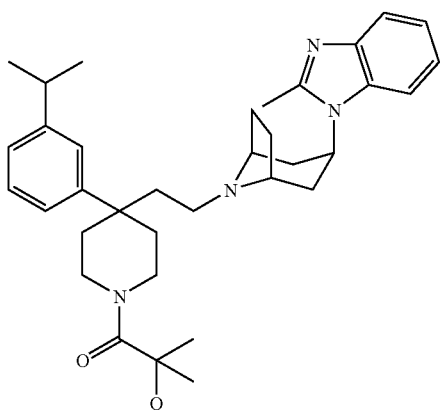

This compound was prepared from 3-isopropyl phenylmagnesium bromide and 16a according to the procedure described in example 16. To a solution of 3-hydroxy-2,2-dimethylpropanoic acid (0.14 mmol), DIEA (1.7 mmol) and HATU (0.14 mmol) in DMF was added 1-(8-{2-[4-(-3-isopropylphenyl)piperdin-4-yl]ethyl}-8-azabicyclo[3.2.1]oct-3-yl)-2-methyl-1H-benzimidazole hydrochloride (0.13 mmol) in the same solvent and stirring was continued overnight. The reaction mixture was diluted with EtOAc, and washed with NaHCO₃, water, and satd. brine and dried (Na₂SO₄). The solvent was removed in-vacuo and the crude material was purified by HPLC to 1 as a clear film. H NMR (400 MHz, CDCl3) 9.72 (s, 2H), 8.48 (s, 1H), 7.64 (d, 1H), 7.04-7.36 (m, 8H), 4.74 (t, 1H), 3.19-3.32 (m, 4H), 2.88-2.97 (m, 3H), 2.60 (s, 3H), 2.43-2.47 (d, 4H), 2.37 (s, 2H), 1.86-2.33 (m, 10H), 1.77 (d, 2H), 1.26-1.28 (d, 6H). LCMS m/z (M+H) calc: 556.79, obsd: 557.79.

Example 889

Preparation of 1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-cyclobutanecarboxylic acid

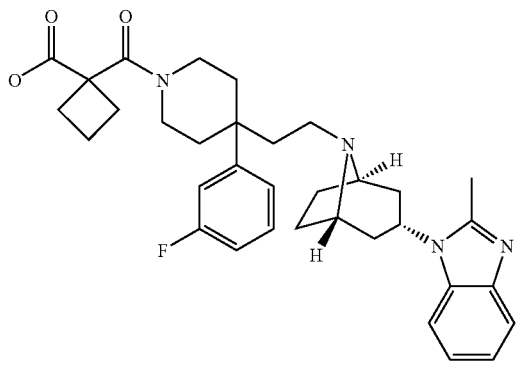

1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-cyclobutanecarboxylic acid was obtained from a solution of 1-(ethoxycarbonyl)cyclobutane carboxylic acid (0.031 g, 0.18 mmol), 1-(8-(2-[4-(-3-Fluoro-phenyl)-piperidin-4-yl]-ethyl)-8-aza-bicyclo[3.2.1]oct-3-yl)-2-methyl-1H-benzoimidazole dihydrochloride (0.075 g, 0.18 mmol), and HATU (0.067 g, 0.18 mmol) following the procedure outlined in example 5 to produce 1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-cyclobutanecarboxylic acid ethyl ester. The ester (0.100 g, 0.167 mmol), 5 N NaOH (10 ml) and ethanol (4 ml) was stirred at 90° C. for 3 hrs. The reaction was evaporated to dryness and residue was suspend in water (10 ml) and neutralized with 1N HCl. The aqueous layer was extracted with ethyl acetate (3×10 ml). The organic layer was dried using magnesium sulfate and concentrated down to form the title compound as a white solid (0.078 g, 81%). ¹H NMR (400 MHz, CDCl3), 7.70 (m, 1H), 7.32-7.16 (m, 4H), 7.04 (m, 1H), 6.97-6.92 (m, 2H), 4.74 (m, 1H), 4.24-3.99 (m, 4H), 3.44-3.40 (m, 1H), 3.30 (br, 2H), 3.19 (m, 1H), 3.10 (m, 1H), 2.77 (m, 1H), 2.59 (s, 3H), 2.44-2.28 (br, 4H) 2.10-2.00 (m, 4H), 1.91-1.78 (m, 8H), 1.66 (m, 2H). ES-LCMS m/z 573 (M+1).

Example 890

Preparation of N-[1-Ethyl-1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-2,2-dimethyl-propionamide

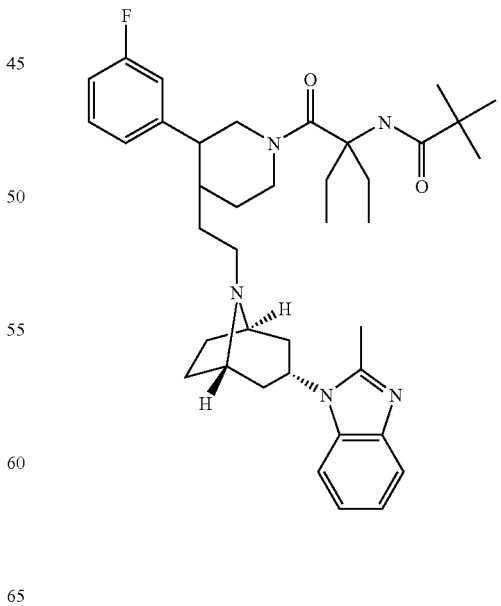

669

Prepared as outlined below.

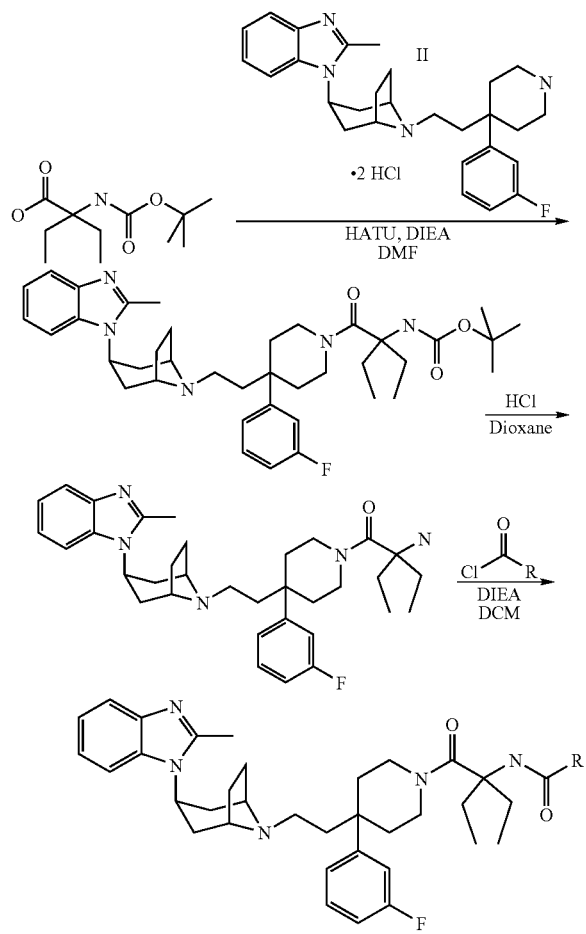

Example 890: R = t-butyl
Example 891: R = methyl

Preparation of [1-Ethyl-1-(4-(3-fluoro-phenyl)-4-{2-[3-(2-methyl-benzoimidazol 1-yl)-8-aza-bicyclo[3.2.1]oct-8-yl]-ethyl}piperidine-1-carbonyl)-propyl]-carbamic acid tert-butyl ester

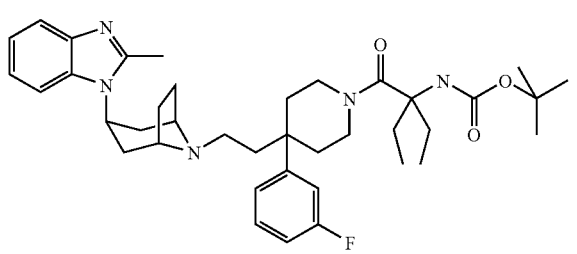

A mixture of 2-tert-Butoxycarbonylamino-2-ethyl-butyric acid (0.291 g, 1.35 mmol), 1-(8-{2-[4-(3-Fluoro-phenyl)piperidin-4-yl]-ethyl}-8-aza-bicyclo[3.2.1]oct-3-yl)-2-methyl-1H-enzoimidazole dihydrochloride (0.700 g, 1.35 mmol), and HATU (0.514 g, 1.35 mmol) following the procedure outlined in example 5. Obtained 0.712 g (80%) of an oil. ES-LCMS m/z 660 (M+1).

670

Preparation of 2-Amino-2-ethyl-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one

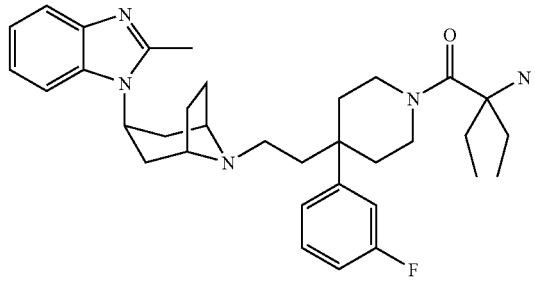

[1-Ethyl-1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-carbamic acid tert-butyl ester was treated with 4N HCl (20 ml) in dioxane and then solvent was removed in vacuo. Residue was dissolved in water neutralized and extracted with EtOAc×3 to yield 0.600 g (99%) of the deprotected amine product as an oil. ES-LCMS m/z 560 (M+1).

Preparation of Title Example 890:

A solution of 2-Amino-2-ethyl-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.100 g, 0.178 mmol), 2,2-Dimethyl-propionyl chloride (0.021 g, 0.178 mmol) and DIEA (0.069 g, 0.534 mmol) were stirred at room temperature in DCE (3 ml) for 2 hours. Solvent was removed and compound was purified by RP-HPLC to yield 0.065 g (57%). $^1$H NMR (400 MHz, CDCl3) 7.82 (s, 1H), 7.67 (m, 1H), 7.36 (m, 1H), 7.29 (m, 1H), 7.16 (m, 2H), 7.09 (m, 1H), 6.99 (m, 1H), 4.60 (m, 1H), 4.07 (br, 2H), 3.32-3.23 (m, 4H), 2.79 (m, 2H), 2.57 (s, 3H), 2.36 (m, 2H), 2.21 (m, 2H), 1.92 (m, 6H), 1.80 (m, 4H), 1.65 (m, 6H), 1.23 (s, 9H) 0.76 (br, 5H). ES-LCMS m/z 644 (M+1).

Example 891

Preparation of N-[1-Ethyl-1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide

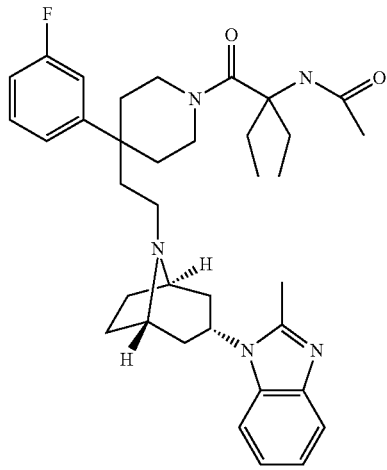

A solution of 2-Amino-2-ethyl-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.100 g, 0.178 mmol), acetyl chloride (0.014 g, 0.178 mmol) and DIEA (0.069 g, 0.534 mmol) were stirred at room temperature in DCM (3 ml) for 2 hours. Solvent was removed and compound was purified by RP-HPLC to yield 0.072 g (67%). $^1$H NMR (400 MHz, CDCl3) 7.67 (m, 1H), 7.40-7.29 (m, 2H), 7.18 (m, 2H), 7.09 (m, 1H), 6.99 (m, 2H), 4.60 (m, 1H) 4.04 (br, 2H), 3.32-3.23 (m, 4H), 2.74 (m, 2H), 2.57 (s, 3H), 2.36 (m, 2H), 2.20 (m, 2H), 2.01 (s, 3H), 1.92 (m, 6H), 1.82-1.63 9 (m, 10H), 0.78 (br, 5H). ES-LCMS m/z 602 (M+1).

Example 892

Preparation of 2,4-Difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-N-propyl-benzenesulfonamide

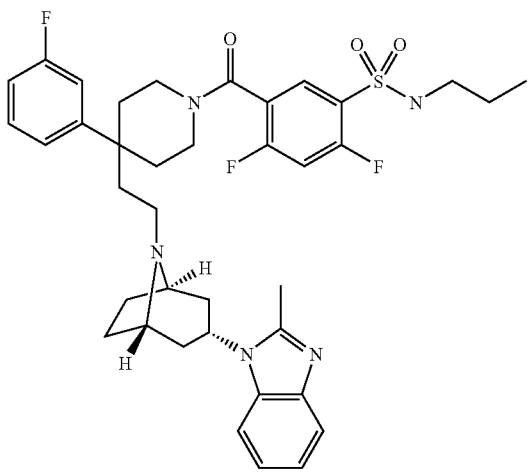

2,4-Difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-N-propyl-benzenesulfonamide (0.068 g, 53%) was obtained from a solution of 2,4-Difluoro-5-propylsulfamoyl-benzoic acid (ACID 34) (0.050 g, 0.18 mmol), 1-(8-{2-[4-(3-Fluoro-phenyl)-piperidin-4-yl]-ethyl}-8-aza-bicyclo[3.2.1]oct-3-yl)-2-methyl-1H-benzoimidazole dihydrochloride (0.075 g, 0.18 mmol), and HATU (0.067 g, 0.18 mmol) following the procedure outlined in example 5. 1H NMR (400 MHz, CDCl3) 7.63 (m, 1H), 7.36-7.28 (m, 3H), 7.15 (m, 2H), 7.08 (m, 1H), 6.96 (m, 3H), 4.60 (m, 1H), 4.22 (m, 1H), 3.37 (m, 2H), 3.23 (m, 3H), 2.98 (m, 2H) 2.56 (s, 3H), 2.38 (m, 3H), 2.12 (m, 1H), 1.93-1.82 (m, 11H), 1.62 (m, 2H), 1.51 (m, 2H), 0.89 (m, 3H). ES-LCMS m/z 708 (M+1).

Example 893

Preparation of 2,4-Difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-N-isopropyl-benzenesulfonamide

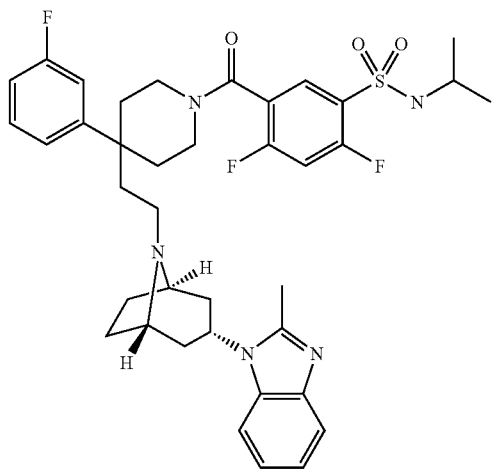

2,4-Difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-N-isopropyl-benzenesulfonamide (0.071 g, 55%) was obtained from a solution of 2,4-Difluoro-5-isopropylsulfamoyl-benzoic acid (ACID 35) (0.050 g, 0.18 mmol), 1-(8-{2-[4-(3-Fluoro-phenyl)-piperidinyl]-ethyl}-8-aza-bicyclo[3.2.1]oct-3-yl)-2-methyl-1H-enzoimidazole dihydrochloride (0.075 g, 0.18 mmol), and HATU (0.067 g, 0.18 mmol) following the procedure outlined in example 5. 1H NMR (400 MHz, CDCl3) 7.96 (m, 1H), 7.66 (m, 1H), 7.36-7.29 (m, 2H), 7.17 (m, 2H), 7.08 (m, 1H), 6.98 (m, 3H), 4.91 (m, 1H), 4.61 (m, 1H), 4.23 (m, 1H), 3.54 (m, 1H), 3.37 (m, 1H), 3.25 (m, 3H), 2.56 (s, 3H), 2.41-2.28 (m, 3H), 2.14 (m, 1H), 1.96-1.74 (m, 10H), 1.63 (m, 2H), 1.12 (m, 6H). ES-LCMS m/z 708 (M+1).

Example 894

Preparation of N-Cyclopropyl-2,4-difluoro-5-(4-(3-fluoro-Phenyl)-4-{2-[3-(2-methyl-benzoimidazol-1-yl)-8-aza-bicyclo[3.2.1]oct-8-yl]-ethyl}-piperidine-1-carbonyl)-benzenesulfonamide

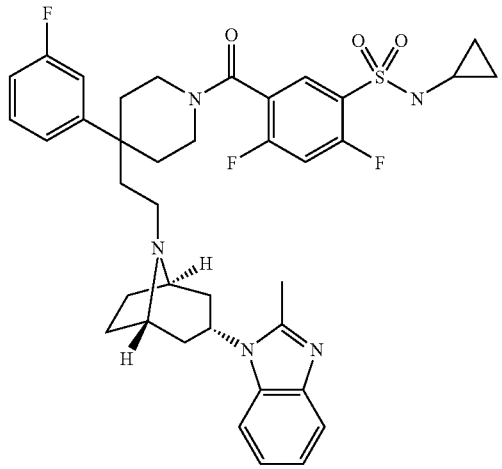

N-Cyclopropyl-2,4-difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-benzenesulfonamide (0.081 g, 64%) was obtained from a solution of 5-Cyclopropylsulfamoyl-2,4-difluoro-benzoic acid (ACID 36) (0.050 g, 0.18 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.075 g, 0.18 mmol), and HATU (0.067 g, 0.18 mmol) following the procedure outlined in example 5. 1H NMR (400 MHz, CDCl3) 8.01 (m, 1H), 7.66 (m, 1H), 7.37-7.29 (m, 2H), 7.16 (m, 2H), 7.08-6.90 (m, 4H), 5.47 (m, 1H), 4.64 (m, 1H), 4.24 (m, 1H), 3.37 (m, 2H), 3.27-3.17 (m, 3H), 2.57 (s, 3H), 2.42-2.29 (m, 4H), 2.13 (m, 1H), 1.94-1.78 (m, 10H), 1.65 (m, 2H), 0.65 (m, 4H). ES-LCMS m/z 706 (M+1).

Example 895

Preparation of 2,4-Difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-benzenesulfonamide

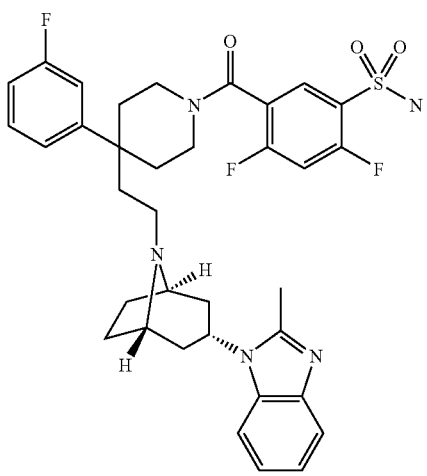

2,4-Difluoro-5-(4-(3-fluoro-phenyl)-4-(2-[3-(2-methyl-benzoimidazol-1-yl)-8-aza-bicyclo[3.2.1]oct-8-yl]-ethyl)piperidine-1-carbonyl)-benzenesulfonamide (0.059 g, 49%) was obtained from a solution of 2,4-Difluoro-5-sulfamoyl-benzoic acid (ACID 31) (0.043 g, 0.18 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.075 g, 0.18 mmol), and HATU (0.067 g, 0.18 mmol) following the procedure outlined in example 5. 1H NMR (400 MHz, CDCl3) 7.98 (m, 1H), 7.66 (m, 1H), 7.37-7.29 (m, 2H), 7.18-6.97 (m, 6H), 5.35 (m, 1H), 4.61 (m, 1H), 4.20 (m, 1H), 3.38 (m, 2H), 3.25 (m, 3H), 2.56 (s, 3H), 2.44-2.27 (m, 3H), 2.14 (m, 1H), 1.96-1.79 (m, 10H), 1.66 (m, 2H). ES-LCMS m/z 666 (M+1).

Example 896

Preparation of 2,4-Difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-N-methyl-benzenesulfonamide

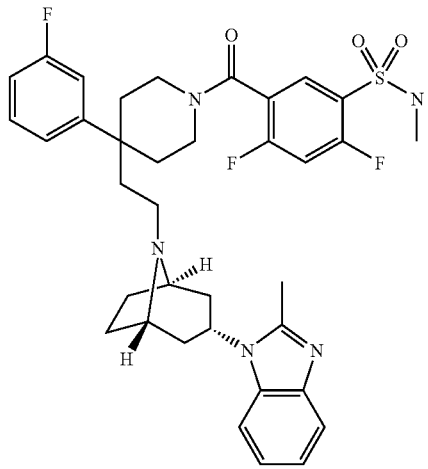

2,4-Difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-N-methyl-benzenesulfonamide (0.063 g, 51%) was obtained from a solution of 2,4-Difluoro-5-methylsulfamoyl-benzoic acid (ACID 32) (0.045 g, 0.18 mmol), 1-(8-{2-[4-(3-Fluoro-phenyl)-piperidin-4-yl]-ethyl}-8-aza-bicyclo[3.2.1]oct-3-yl)-2-methyl-1H-benzoimidazole dihydrochloride (0.075 g, 0.18 mmol), and HATU (0.067 g, 0.18 mmol) following the procedure outlined in example 5.1H NMR (400 MHz, CDCl3) 7.98 (m, 1H), 7.68 (m, 1H), 7.36 (m, 1H), 7.29 (m, 1H), 7.19 (m, 2H), 7.09 (m, 1H), 6.99 (m, 3H), 4.82 (m, 1H), 4.63 (m, 1H), 4.23 (m, 1H), 3.39 (m, 2H), 3.30 (m, 2H), 3.22 (m, 1H), 2.74 (s, 3H), 2.59 (s, 3H), 2.42 (m, 2H), 2.29 (m, 2H), 2.17 (m, 2H), 1.98-1.71 (m, 10H), 1.67 (m, 2H). ES-LCMS m/z 680 (M+1).

Example 897

Preparation of N-Ethyl-2,4-difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-benzenesulfonamide

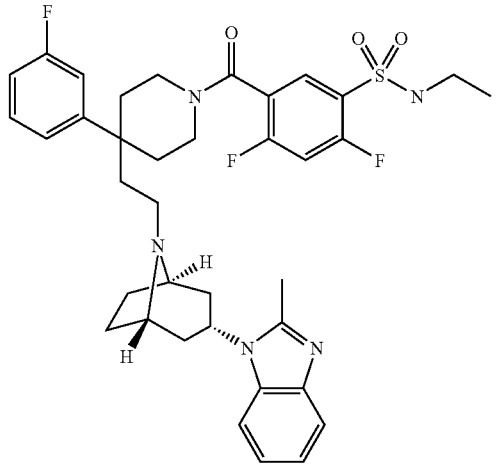

Preparation of N-Ethyl-2,4-difluoro-5-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-benzenesulfonamide (0.067 g, 54%) was obtained from a solution of 5-Ethylsulfamoyl-2,4-difluoro-benzoic acid (ACID 33) (0.047 g, 0.18 mmol), 1-(8-{2-[4-(3-Fluoro-phenyl)piperidin-4-yl]-ethyl}-8-aza-bicyclo[3.2.1]oct-3-yl)-2-methyl-1H-benzoimidazole dihydrochloride (0.075 g, 0.18 mmol), and HATU (0.067 g, 0.18 mmol) following the procedure outlined in example 5. 1H NMR (400 MHz, CDCl3) 7.98 (m, 1H), 7.68 (m, 1H), 7.39 (m, 1H), 7.31 (m, 1H), 7.18 (m, 2H), 7.09 (m, 1H), 6.98 (m, 3H), 4.81 (br, 2H), 4.20 (m, 1H), 3.38 (m, 4H), 3.21 (m, 1H), 3.16 (m, 2H), 2.61 (s, 3H), 2.44 (m, 2H), 2.31 (m, 1H), 2.19 (m, 1H), 2.02-1.61 (m, 12H), 1.16 (m, 3H). ES-LCMS m/z 694 (M+1).

Example 898

Preparation of [1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-carbamic acid tert-butyl ester

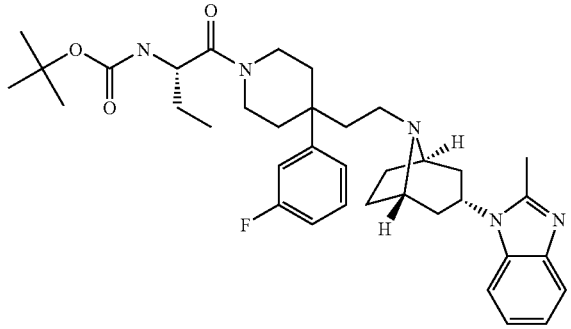

[1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-carbamic acid tert-butyl ester (0.580 g, 66%) was obtained as an oil from 2-tert-Butoxycarbonylamino-butyric acid (0.298 g, 1.40 mmol), 1-(8-{2-[4-(3-Fluoro-phenyl)-piperidin-4-yl]-ethyl}-8-aza-bicyclo[3.2.1]oct-3-yl)-2-methyl-1H-benzoimidazole dihydrochloride (0.725 g, 1.40 mmol) and HATU (0.590 g, 1.50 mmol) following the procedure outlined in example 5. ES-LCMS m/z 632 (M+1).

Example 899

Preparation of 2,2,2-Trifluoro-N-[1-(4-(3-fluoro-phenyl-4-{2-[3-(2-methyl-benzoimidazol-1-yl)-8-aza-bicyclo[3.2.1]oct-8-yl]-ethyl}-piperidine-1-carbonyl)-propyl]-acetamide

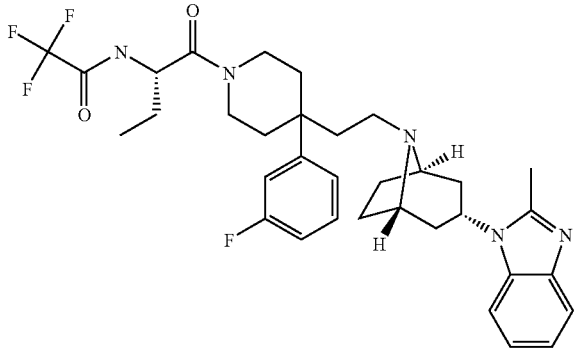

2,2,2-Trifluoro-N-[1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide was obtained from treating[1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-carbamic acid tert-butyl ester (0.580 g, 0.92 mmol) with HCl as outlined in the procedure for example 890 to form 2-Amino-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)butan-1-one (0.488 g, 99%). 2-Amino-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.049 g, 0.09 mmol, trifluoroaceticanhydirde (0.019 g, 0.09 mmol) and DIEA (0.034 g, 0.534 mmol) were reacted following the procedure outlined in example 890 to give the title compound, 2,2,2-Trifluoro-N-[1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide (0.034 g, 60%) as an oil. ES-LCMS m/z 628 (M+1).

Example 900

Preparation of 2-Chloro-N-[1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide

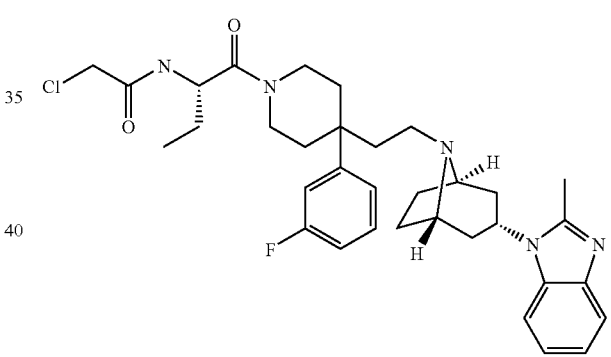

2-Chloro-N-[1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide was obtained from treating[1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-carbamic acid tert-butyl ester (0.580 g, 0.92 mmol) with HCl as outlined in the procedure for example 890 to form 2-Amino-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.488 g, 99%). 2-Amino-1-(4-(3-fluoro-phenyl)-4-{2-[3-(2-methyl-benzoimidazol-1-yl)-8-aza-bicyclo[3.2.1]oct-8-yl]-ethyl)piperidin-1-yl)-butan-1-one (0.049 g, 0.09 mmol, Chloro-acetyl chloride (0.010 g, 0.09 mmol) and DIEA (0.034 g, 0.534 mmol) were reacted following the procedure outlined in example 890 to give the title compound, 2-Chloro-N-[1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide (0.024 g, 44%) as an oil. ES-LCMS m/z 608 (M+1).

Example 901

Preparation of N-[1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-2,2-dimethyl-propionamide

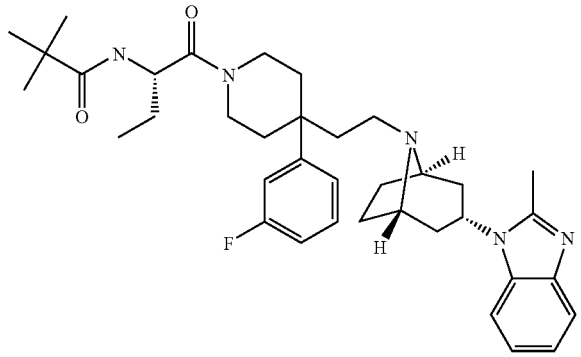

N-[1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-2,2-dimethyl-propionamide was obtained from treating[1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-carbamic acid tert-butyl ester (0.580 g, 0.92 mmol) with HCl as outlined in the procedure for example 890 to form 2-Amino-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.488 g, 99%). 2-Amino-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.049 g, 0.09 mmol, 2,2-Dimethyl-propionyl chloride (0.011 g, 0.09 mmol) and DIEA (0.034 g, 0.534 mmol) were reacted following the procedure outlined in example 890 to give the title compound, N-[1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-2,2-dimethyl-propionamide (0.030 g, 54%) as an oil. ES-LCMS m/z 616 (M+1).

Example 892

Preparation of 2,2-Dichloro-N-[1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide

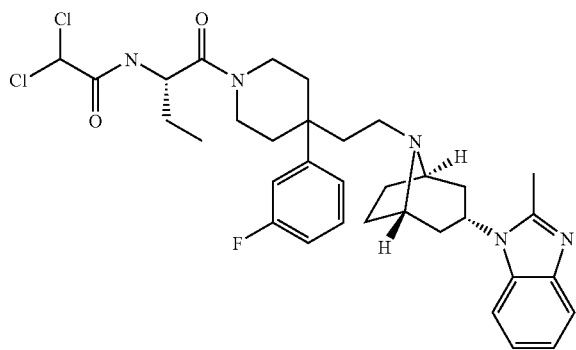

2,2-Dichloro-N-[1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide was obtained from treating[1-(4-(3-Fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-carbamic acid tert-butyl ester (0.580 g, 0.92 mmol) with HCl as outlined in the procedure for example 890 to form 2-Amino-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.488 g, 99%). 2-Amino-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.049 g, 0.09 mmol, Dichloro-acetyl chloride (0.013 g, 0.09 mmol) and DIEA (0.034 g, 0.534 mmol) were reacted following the procedure outlined in example 890 to give the title compound, 2,2-Dichloro-N-[1-(4-(3-fluoro-phenyl)-4-{2-[3-(2-methyl-benzoimidazol-1-yl)-8-aza-bicyclo[3.2.1]oct-8-yl]-ethyl}-piperidine-1-carbonyl)-propyl]-acetamide (0.039 g, 67%) as an oil. ES-LCMS m/z 642 (M+1).

Example 893

Preparation of [2-(4-(3-Fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-carbamic acid tert-butyl ester

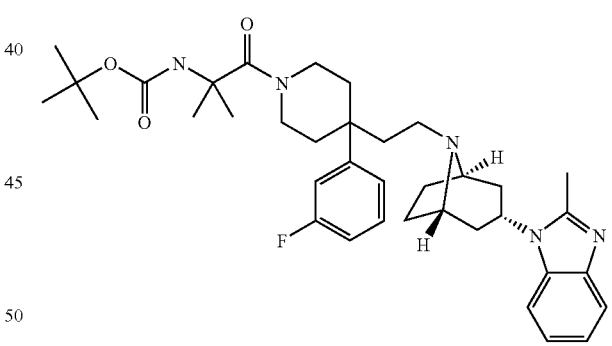

2-(4-(3-Fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-carbamic acid tert-butyl ester (0.610 g, 69%) was obtained as a oil from 2-tert-Butoxycarbonylamino-2-methyl-propionic acid (0.284 g, 1.40 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.725 g, 1.40 mmol) and HATU (0.590 g, 1.50 mmol) following the procedure outlined in example 5. ES-LCMS m/z 632 (M+1).

Example 904

Preparation of 2,2,2-Trifluoro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide

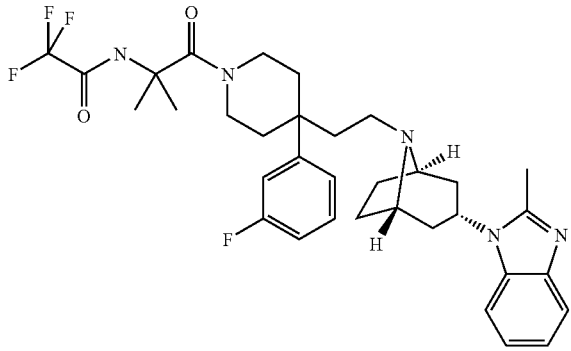

2,2,2-Trifluoro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide was obtained from treating 2-(4-(3-Fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-carbamic acid tert-butyl ester (0.610 g, 0.97 mmol) with HCl as outlined in the procedure in example 890 to form 2-Amino-1-(4-(3-fluoro-phenyl)-4-{2[3-(2-methyl-benzoimidazol-1-yl)-8-aza-bicyclo[3.2.1]oct-8-yl]-ethyl}-piperidin-1-yl)-2-methyl-propan-1-one (0.510 g, 99%). 2-Amino-1-(4-(3-fluoro-phenyl)-4-{2[3-(2-methyl-benzoimidazol-1-yl)-8-aza-bicyclo[3.2.1]oct-8-yl]-ethyl}-piperidin-1-yl)-2-methyl-propan-1-one (0.050 g, 0.09 mmol, trifluoroaceticanhydirde (0.019 g, 0.09 mmol) and DIEA (0.034 g, 0.534 mmol) were reacted following the procedure outlined in example 890 to give the title compound, 2,2,2-Trifluoro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide (0.024 g, 42%) as an oil. ES-LCMS m/z 628 (M+1).

Example 905

Preparation of 2,2-Dichloro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide


2,2-Dichloro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide was obtained from treating 2-(4-(3-Fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-carbamic acid tert-butyl ester (0.610 g, 0.97 mmol) with HCl as outlined in the procedure for example 890 to form 2-Amino-1-(4-(3-fluoro-phenyl)-4-{2[3-(2-methyl-benzoimidazol-1-yl)-8-aza-bicyclo[3.2.1]oct-8-yl]-ethyl}-piperidin-1-yl)-2-methyl-propan-1-one (0.510 g, 99%). 2-Amino-1-(4-(3-fluoro-phenyl)-4-{2[3-(2-methyl-benzoimidazol-1-yl)-8-aza-bicyclo[3.2.1]oct-8-yl]-ethyl}-piperidin-1-yl)-2-methyl-propan-1-one (0.050 g, 0.09 mmol), Dichloro-acetyl chloride (0.013 g, 0.09 mmol) and DIEA (0.034 g, 0.534 mmol) were reacted following the procedure outlined in example 890 to give the title compound, 2,2-Dichloro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide (0.028 g, 48%) as an oil. ES-LCMS m/z 642 (M+1).

Example 906

Preparation of 2-Chloro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide

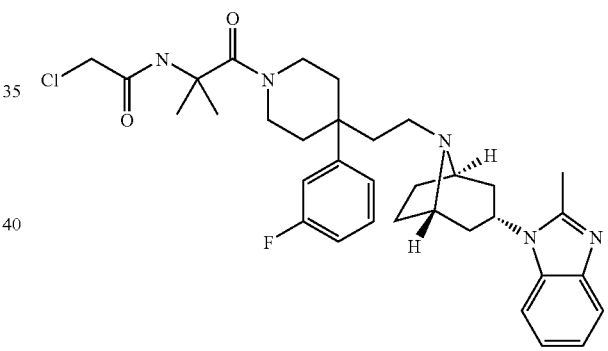

2-Chloro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide was obtained from treating 2-(4-(3-Fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-carbamic acid tert-butyl ester (0.610 g, 0.97 mmol) with HCl as outlined in the procedure for Example 890 to form 2-Amino-1-(4-(3-fluoro-phenyl)-4-{2[3-(2-methyl-benzoimidazol-1-yl)-8-aza-bicyclo[3.2.1]oct-8-yl]-ethyl}-piperidin-1-yl)-2-methyl-propan-1-one (0.510 g, 99%). 2-Amino-1-(4-(3-fluoro-phenyl)-4-{2[3-(2-methyl-benzoimidazol-1-yl)-8-aza-bicyclo[3.2.1]oct-8-yl]-ethyl}-piperidin-1-yl)-2-methyl-propan-1-one (0.050 g, 0.09 mmol, Chloro-acetyl chloride (0.010 g, 0.09 mmol) and DIEA (0.034 g, 0.534 mmol) were reacted following the procedure outlined in Example 890 to give the title compound, 2-Chloro-N-[2-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-1,1-dimethyl-2-oxo-ethyl]-acetamide (0.027 g, 49%) as an oil. ES-LCMS m/z 608 (M+1).

Example 907

Preparation of 1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2-methylpropyl}carbamate

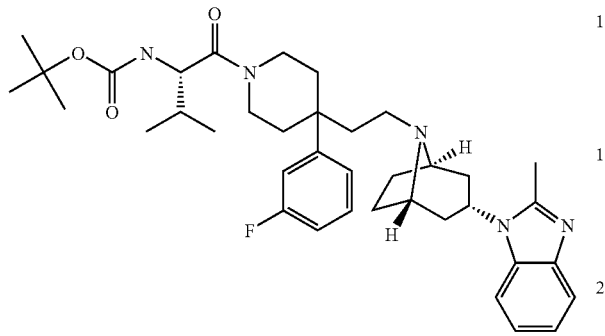

1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2-methylpropyl}carbamate (0.614 g, 68%) was obtained as a oil from N-{[(1,1-dimethylethyl)oxy]carbonyl}L-valine (0.303 g, 1.40 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.725 g, 1.40 mmol) and HATU (0.590 g, 1.50 mmol) following the procedure outlined in example 5. ES-LCMS m/z 648 (M+1).

Example 908A

Preparation of 2,2-dichloro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2-methylpropyl}acetamide

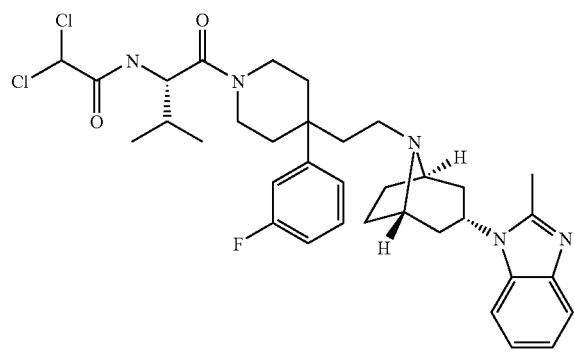

2,2-dichloro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2-methylpropyl}acetamide was obtained from treating 1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2-methylpropyl}carbamate (0.614 g, 0.95 mmol) with HCl as outlined in the procedure for Example 890 to form {(1S)-1-[(4-(3-fluorophenyl)-4-{2-[(1R,5S) 3-(2-methyl-1H-benzimidazol-1-yl)-8-azabicyclo[3.2.1]oct-8-yl]ethyl}-1-piperidinyl) carbonyl]-2-methylpropyl}amine (0.512 g, 99%). {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2-methylpropyl}amine (0.050 g, 0.09 mmol), Dichloro-acetyl chloride (0.013 g, 0.09 mmol) and DIEA (0.034 g, 0.534 mmol) were reacted following the procedure outlined in Example 890 to give the title compound, 2,2-dichloro-N-(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2-methylpropyl}acetamide (0.031 g, 53%) as an oil. ES-LCMS m/z 656 (M+1).

Example 908B

Preparation of 2-chloro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2-methylpropyl}acetamide

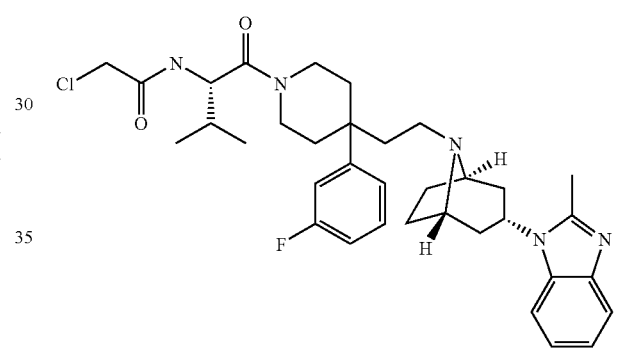

2-chloro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2-methylpropyl}acetamide was obtained from treating 1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2-methylpropyl}carbamate (0.614 g, 0.95 mmol) with HCl as outlined in the procedure for Example 890 to form {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2-methylpropyl}amine (0.512 g, 99%). {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2-methylpropyl}amine (0.050 g, 0.09 mmol), Chloro-acetyl chloride (0.011 g, 0.09 mmol) and DIEA (0.034 g, 0.534 mmol) were reacted following the procedure outlined in Example 890 to give the title compound, 2-chloro-N{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2-methylpropyl}acetamide (0.037 g, 66%) as an oil. ES-LCMS m/z 622 (M+1).

Example 909

Preparation of 1,1-dimethylethyl (2S)-2-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1-pyrrolidinecarboxylate

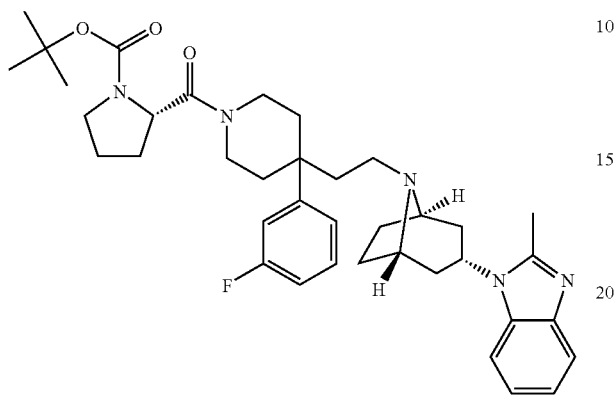

1,1-dimethylethyl (2S)-2-[(4-(3-fluorophenyl)-4-{2-[(1R, 5S)-3-(2-methyl-1H-benzimidazol-1-yl)-8-azabicyclo[3.2.1]oct-8-yl]ethyl}-1-piperidinyl)carbonyl]-1-pyrrolidinecarboxylate (0.645 g, 72%) was obtained as a oil from 1-{[(1,1-dimethylethyl)oxy]carbonyl}-L-proline (0.301 g, 1.4 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.725 g, 1.40 mmol) and HATU (0.590 g, 1.50 mmol) following the procedure outlined in example 5. ES-LCMS m/z 644 (M+1).

Example 910

Preparation of 1-[(1R,5S)-8-(2-{4-(3-fluorophenyl)-1-[1-(trifluoroacetyl)-L-prolyl]-4-piperidinyl}ethyl)-8-azabicyclo[3.2.1]oct-3-yl]-2-methyl-1H-benzimidazole

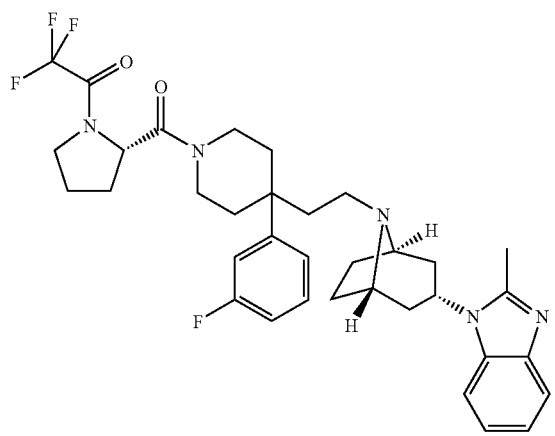

1-[(1R,5S)-8-(2-{4-(3-fluorophenyl)-1-[1-(trifluoroacetyl)-L-prolyl]-4-piperidinyl}ethyl)-8-azabicyclo[3.2.1]oct-3-yl]-2-methyl-1H-benzimidazole was obtained from treating 1,1-dimethylethyl (2S)-2-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1-pyrrolidinecarboxylate (0.645 g, 1.01 mmol) with HCl as outlined in the procedure for Example 890 to form 1-((1R,5S)-8-{2-[4-(3-fluorophenyl)-1-L-prolyl-4-piperidinyl]ethyl}-8-azabicyclo[3.2.1]oct-3-yl)-2-methyl-1H-benzimidazole (0.545 g, 99%). 1-((1R,5S)-8-{2-[4-(3-fluorophenyl)-1-L-prolyl-4-piperidinyl]ethyl}-8-azabicyclo[3.2.1]oct-3-yl)-2-methyl-1H-benzimidazole (0.050 g, 0.09 mmol), trifluoroaceticanhydirde (0.019 g, 0.09 mmol) and DIEA (0.034 g, 0.534 mmol) were reacted following the procedure outlined in Example 890 to give the title compound, 1-[(1R,5S)-8-(2-{4-(3-fluorophenyl)-1-[1-(trifluoroacetyl)-L-prolyl]-4-piperidinyl}ethyl)-8-azabicyclo[3.2.1]oct-3-yl]-2-methyl-1H-benzimidazole (0.021 g, 36%) as an oil. ES-LCMS m/z 640 (M+1).

Example 911

Preparation of 1-((1R,5S)-8-{2-[1-[1-(dichloroacetyl)-L-prolyl]-4-(3-fluorophenyl)-4-piperidinyl]ethyl}-8-azabicyclo[3.2.1]oct-3-yl)-2-methyl-1H-benzimidazole

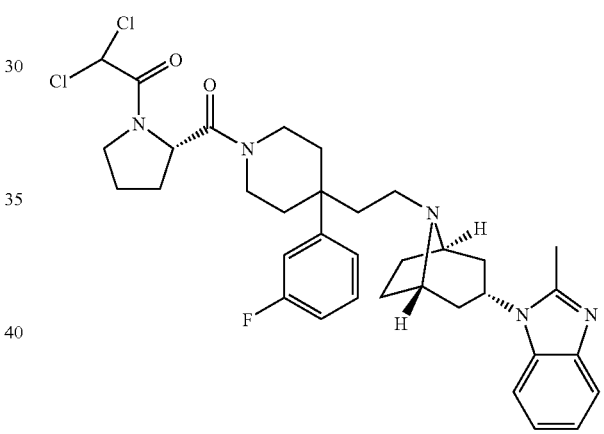

1-((1R,5S)-8-{2-[1-[1-(dichloroacetyl)-L-prolyl]-4-(3-fluorophenyl)-4-piperidinyl]ethyl}-8-azabicyclo[3.2.1]oct-3-yl)-2-methyl-1H-benzimidazole was obtained from treating 1,1-dimethylethyl (2S)-2-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1-pyrrolidinecarboxylate (0.645 g, 1.01 mmol) with HCl as outlined in the procedure for Example 890 to form 1-((1R,5S)-8-{2-[4-(3-fluorophenyl)-1-L-prolyl-4-piperidinyl]ethyl}-8-azabicyclo[3.2.1]oct-3-yl)-2-methyl-1H-benzimidazole (0.545 g, 99%). 1-((1R,5S)-8-{2-[4-(3-fluorophenyl)-1-L-prolyl-4-piperidinyl]ethyl}-8-azabicyclo[3.2.1]oct-3-yl)-2-methyl-1H-benzimidazole (0.050 g, 0.09 mmol), Dichloro-acetyl chloride (0.013 g, 0.09 mmol) and DIEA (0.034 g, 0.534 mmol) were reacted following the procedure outlined in Example 890 to give the title compound, 1-((1R,5S)-8-{2-[1-[1-(dichloroacetyl)-L-prolyl]-4-(3-fluorophenyl)-4-piperidinyl]ethyl}-8-azabicyclo[3.2.1]oct-3-yl)-2-methyl-1H-benzimidazole (0.029 g, 49%) as an oil. ES-LCMS m/z 654 (M+1).

Example 912

Preparation of 1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}carbamate

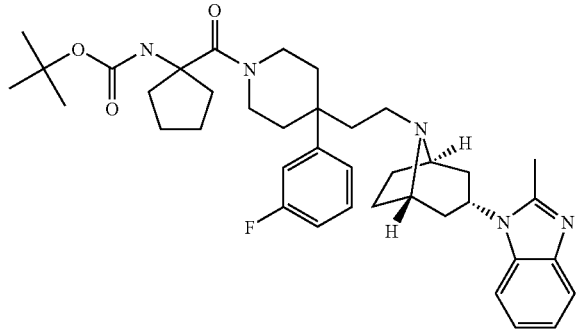

1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}carbamate (0.627 g, 68%) was obtained as a oil from 1-({[(1,1dimethylethyl)oxy]carbonyl}amino)cyclopentanecarboxylic acid (0.320 g, 1.4 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.725 g, 1.40 mmol) and HATU (0.590 g, 1.50 mmol) following the procedure outlined in example 5. ES-LCMS m/z 658 (M+1).

Example 913

Preparation of 2,2,2-trifluoro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}acetamide

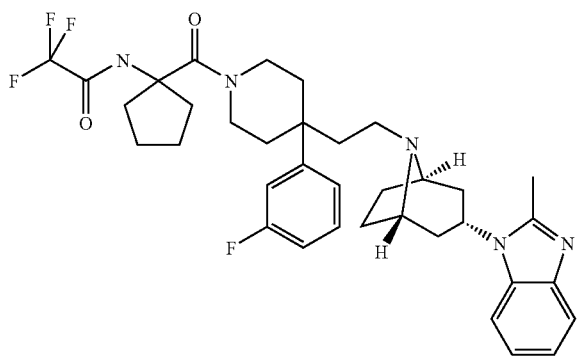

2,2,2-trifluoro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}acetamide was obtained from treating 1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}carbamate (0.627 g, 0.95 mmol) with HCl as outlined in the procedure for Example 890 to form 1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentanamine (0.528 g, 99%). 1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentanamine (0.050 g, 0.09 mmol), trifluoroacetic anhydride (0.019 g, 0.09 mmol) and DIEA (0.034 g, 0.534 mmol) were reacted following the procedure outlined in Example 890 to give the title compound, 2,2,2-trifluoro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}acetamide (0.027 g, 46%) as an oil. ES-LCMS m/z 654 (M+1).

Example 914

Preparation of N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}-2,2-dimethylpropanamide

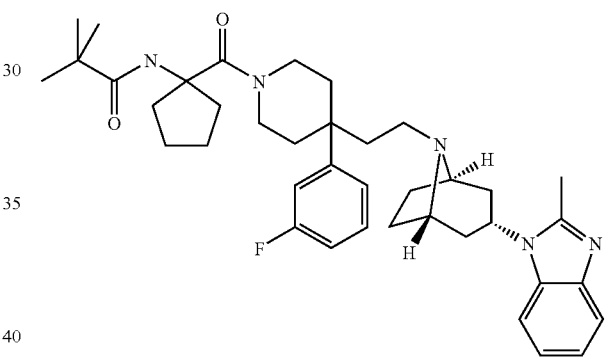

N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}-2,2-dimethylpropanamide was obtained from treating 1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}carbamate (0.627 g, 0.95 mmol) with HCl as outlined in the procedure for Example 890 to form 1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentanamine (0.528 g, 99%). 1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentanamine (0.050 g, 0.09 mmol), 2,2-Dimethyl-propionyl chloride (0.011 g, 0.09 mmol) and DIEA (0.034 g, 0.534 mmol) were reacted following the procedure outlined in Example 890 to give the title compound, N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopentyl}-2,2-dimethylpropanamide (0.031 g, 54%) as an oil. ES-LCMS m/z 642 (M+1).

Example 915

Preparation of 1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}carbamate

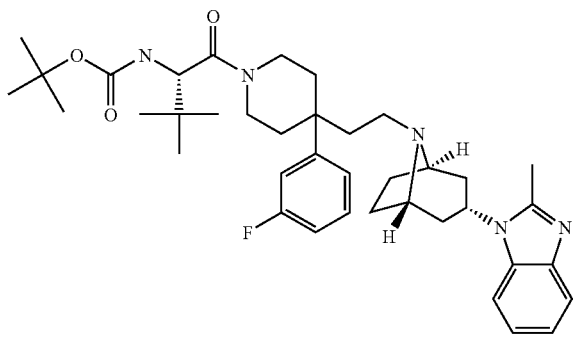

1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}carbamate (0.591 g, 64%) was obtained as a oil from N-{[(1,1-dimethylethyl)oxy]carbonyl}-3-methyl-L-valine (0.320 g, 1.4 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.725 g, 1.40 mmol) and HATU (0.590 g, 1.50 mmol) following the procedure outlined in example 5. ES-LCMS m/z 660 (M+1).

Example 916

Preparation of 2,2,2-trifluoro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2,2-dimethylpropyl}acetamide

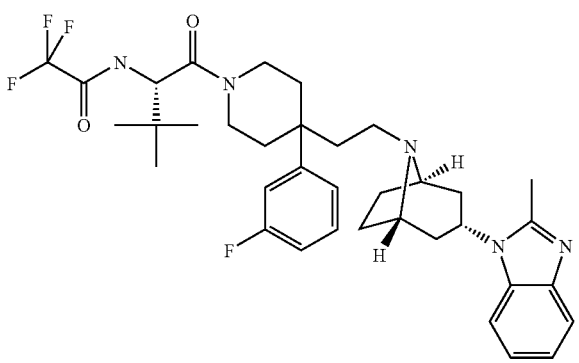

2,2,2-trifluoro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}acetamide was obtained from treating 1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}carbamate (0.591 g, 0.90 mmol) with HCl as outlined in the procedure for Example 890 to form (2S)-1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-3,3-dimethyl-1-oxo-2-butanamine (0.500 g, 99%). 2S)-1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-3,3-dimethyl-1-oxo-2-butanamine (0.050 g, 0.09 mmol), trifluoroaceticanhydirde (0.019 g, 0.09 mmol) and DIEA (0.034 g, 0.534 mmol) were reacted following the procedure outlined in Example 890 to give the title compound, 2,2,2-trifluoro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}acetamide (0.033 g, 56%) as an oil. ES-LCMS m/z 656 (M+1).

Example 917

Preparation of 2-chloro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2,2-dimethylpropyl}acetamide

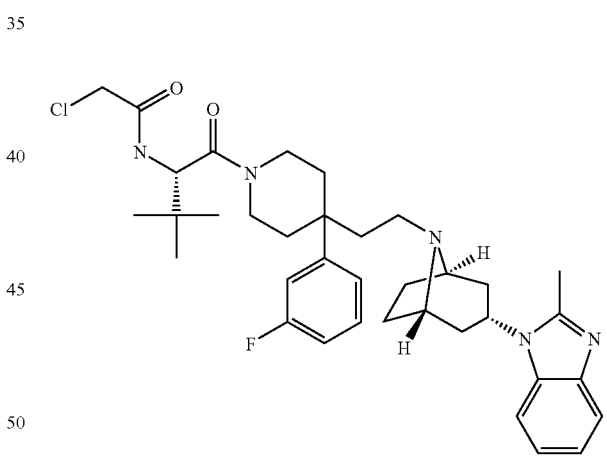

2-chloro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}acetamide was obtained from treating 1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl)-}-piperidinyl)carbonyl]-2,2-dimethylpropyl}carbamate (0.591 g, 0.90 mmol) with HCl as outlined in the procedure for Example 890 to form (2S)-1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-3,3-dimethyl-1-oxo-2-butanamine (0.500 g, 99%). 2S)

1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-3,3-dimethyl-1-oxo-2-butanamine (0.050 g, 0.09 mmol), Chloro-acetyl chloride (0.011 g, 0.09 mmol) and DIEA (0.034 g, 0.534 mmol) were reacted following the procedure outlined in Example 890 to give the title compound, 2-chloro-N-(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}acetamide (0.038 g, 66%) as an oil. ES-LCMS m/z 636 (M+1).

Example 918

Preparation of 2,2-dichloro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}acetamide

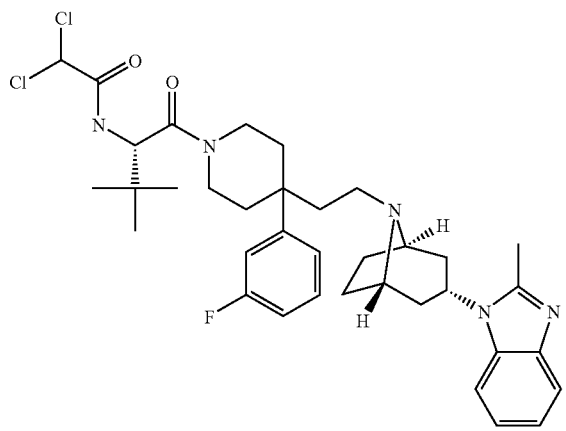

2,2-dichloro-N-{(1S)-1-[(4-(3-fluorophenyl-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}acetamide was obtained from treating 1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}carbamate, example 915, (0.591 g, 0.90 mmol) with HCl as outlined in the procedure for Example 890 to form (2S)-1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-3,3-dimethyl-1-oxo-2-butanamine (0.500 g, 99%). 2S)-1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-3,3-dimethyl-1-oxo-2-butanamine (0.050 g, 0.09 mmol), Dichloro-acetyl chloride (0.013 g, 0.09 mmol) and DIEA (0.034 g, 0.534 mmol) were reacted following the procedure outlined in Example 890 to give the title compound, 2-dichloro-N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-2,2-dimethylpropyl}acetamide (0.036 g, 60%) as an oil. ES-LCMS m/z 670 (M+1).

Example 919

Preparation of N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}-2,2-dimethylpropanamide

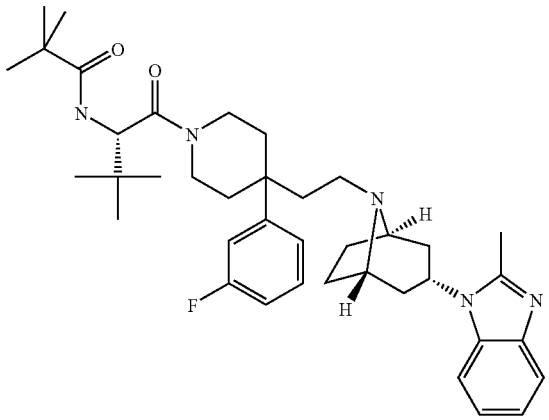

N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}-2,2-dimethylpropanamide was obtained from treating 1,1-dimethylethyl {(1S)-1-[(4-(3-fluorophenyl)-4-{2-[(1R,5S)-3-(2-methyl-1H-benzimidazol-1-yl)-8-azabicyclo[3.2.1]oct-8-yl]ethyl)-}-piperidinyl)carbonyl]-2,2-dimethylpropyl}carbamate, example 915, (0.591 g, 0.90 mmol) with HCl as outlined in the procedure for Example 890 to form (2S)-1-(4-(3-fluorophenyl-4-{2-[(1R,5S)-3-(2-methyl-1H-benzimidazol-1-yl)-8-azabicyclo[3.2.1]oct-8-yl]ethyl}-1-piperidinyl)-3,3-dimethyl-1-oxo-2-butanamine (0.500 g, 99%). 2S)-1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-3,3-dimethyl-1-oxo-2-butanamine (0.050 g, 0.09 mmol), 2,2-Dimethyl-propionyl chloride (0.011 g, 0.09 mmol) and DIEA (0.034 g, 0.534 mmol) were reacted following the procedure outlined in Example 890 to give the title compound, N-{(1S)-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2,2-dimethylpropyl}-2,2-dimethylpropanamide (0.032 g, 55%) as an oil. ES-LCMS m/z 644 (M+1).

Example 920

Preparation of 1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]cyclohexyl}carbamate

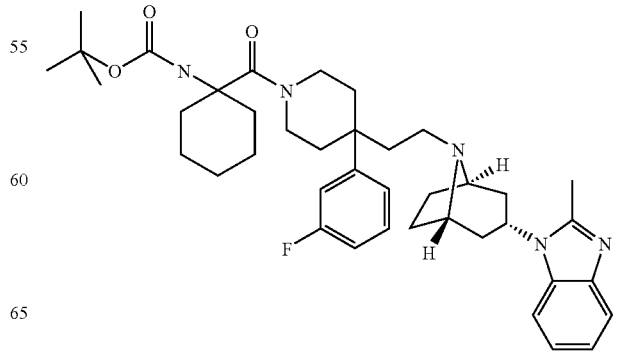

1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]cyclohexyl}carbamate (0.598 g, 64%) was obtained as a oil from 1-({[(1,1-dimethylethyl)oxy]carbonyl}amino)cyclohexanecarboxylic acid (0.320 g, 1.4 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.725 g, 1.40 mmol) and HATU (0.590 g, 1.50 mmol) following the procedure outlined in example 5. ES-LCMS m/z 672 (M+1).

Example 921

Preparation of 1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}carbamate

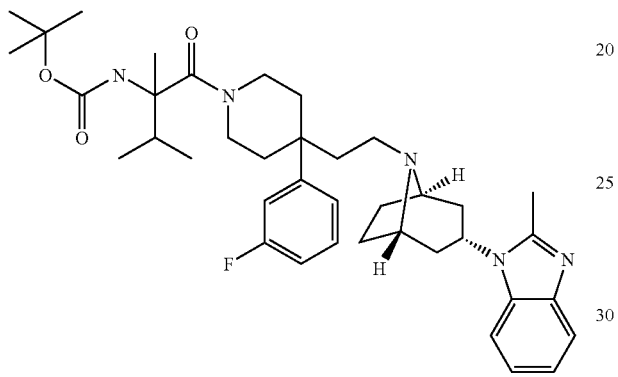

1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}carbamate (0.623 g, 67%) was obtained as a oil from N-{[(1,1-dimethylethyl)oxy]carbonyl}-3-methylisovaline (0.320 g, 1.4 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.725 g, 1.40 mmol) and HATU (0.590 g, 1.50 mmol) following the procedure outlined in example 5. ES-LCMS m/z 660 (M+1).

Example 922

Preparation of 2,2,2-trifluoro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}acetamide

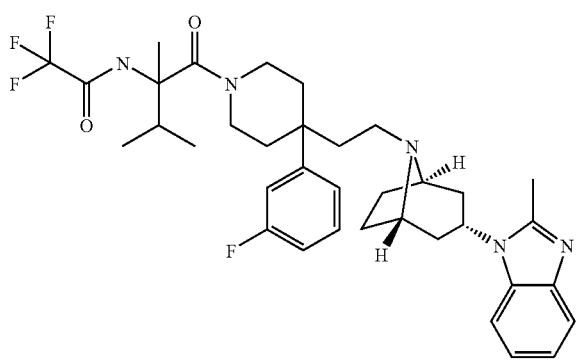

2,2,2-trifluoro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}acetamide was obtained from treating 1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}carbamate, example 915, (0.623 g, 0.94 mmol) with HCl as outlined in the procedure for Example 890 to form 1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,3-dimethyl-1-oxo-2-butanamine (0.524 g, 99%). 1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,3-dimethyl-1-oxo-2-butanamine (0.050 g, 0.09 mmol), trifluoroaceticanhydirde (0.019 g, 0.09 mmol) and DIEA (0.034 g, 0.534 mmol) were reacted following the procedure outlined in Example 890 to give the title compound, 2,2,2-trifluoro-N-({-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}acetamide (0.036 g, 61%) as an oil. ES-LCMS m/z 656 (M+1).

Example 923A

Preparation of 2-chloro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}acetamide

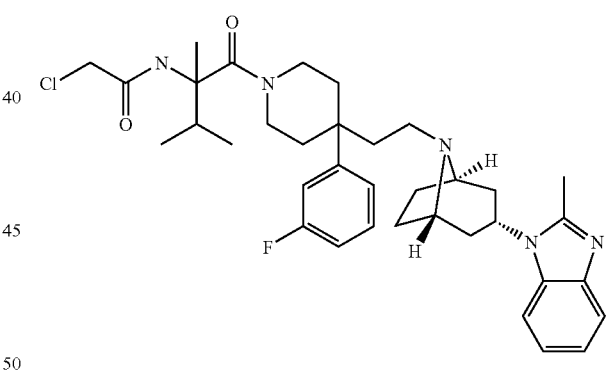

2-chloro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}acetamide was obtained from treating 1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}carbamate, example 915, (0.623 g, 0.94 mmol) with HCl as outlined in the procedure for Example 890 to form 1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,3-dimethyl-1-oxo-2-butanamine (0.524 g, 99%). 1-(4-(3-fluorophenyl)-4-{2-[(1R,5S)-3-(2-methyl- 1H-benzimidazol-1-yl)-8-azabicyclo[3.2.1]oct-8-yl]ethyl}-1-piperidinyl)-2,3-dimethyl-1-oxo-2-butanamine (0.050 g, 0.09 mmol), Chloro-acetyl chloride (0.011 g, 0.09 mmol) and DIEA (0.034 g, 0.534 mmol) were reacted following the procedure outlined in Example 890 to give the title compound, 2-chloro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}acetamide (0.030 g, 52%) as an oil. ES-LCMS m/z 636 (M+1).

Example 923B

Preparation of N-{1-[(4-(3-fluorophenyl)-4-{2-[(1R, 5S)-3-(2-methyl-1H-benzimidazol-1-yl)-8-azabicyclo[3.2.1]oct-8-yl]ethyl}-1-piperidinyl)carbonyl]-1,2-dimethylpropyl}-2,2-dimethylpropanamide

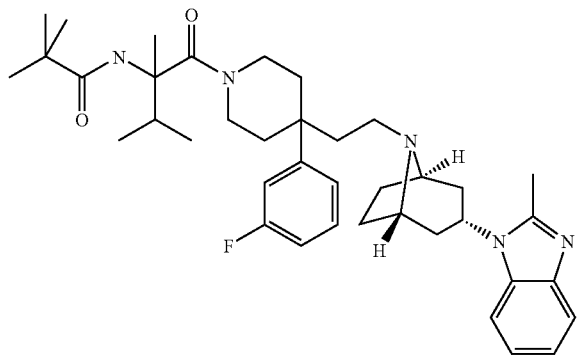

N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}-2,2-dimethylpropanamide was obtained from treating 1,1-dimethylethyl {1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}carbamate, example 915, (0.623 g, 0.94 mmol) with HCl as outlined in the procedure for Example 890 to form 1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,3-dimethyl-1-oxo-2-butanamine (0.524 g, 99%). 1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,3-dimethyl-1-oxo-2-butanamine (0.050 g, 0.09 mmol), 2,2-Dimethyl-propionyl chloride (0.011 g, 0.09 mmol) and DIEA (0.034 g, 0.534 mmol) were reacted following the procedure outlined in Example 890 to give the title compound, N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-1,2-dimethylpropyl}-2,2-dimethylpropanamide (0.039 g, 67%) as an oil. ES-LCMS m/z 643 (M+1).

Example 924

Preparation of 2,2-dichloro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}acetamide

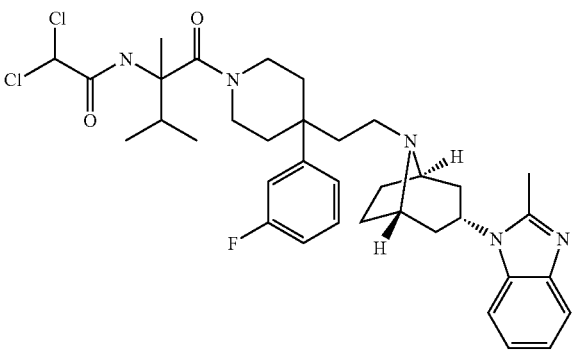

2,2-dichloro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}acetamide was obtained from treating 1,1-dimethylethyl {1-[(4-(3-fluorophenyl-4-{2-[(1R,5S)-3-(2-methyl-1H-benzimidazol-1-yl)-8-azabicyclo[3.2.1]oct-8-yl]ethyl}-1-piperidinyl)carbonyl]-1,2-dimethylpropyl}carbamate, example 915, (0.623 g, 0.94 mmol) with HCl as outlined in the procedure for Example 890 to form 1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,3-dimethyl-1-oxo-2-butanamine (0.524 g, 99%). 1-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,3-dimethyl-1-oxo-2-butanamine (0.050 g, 0.09 mmol), Dichloro-acetyl chloride (0.013 g, 0.09 mmol) and DIEA (0.034 g, 0.534 mmol) were reacted following the procedure outlined in Example 890 to give the title compound, 2,2-dichloro-N-{1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]-1,2-dimethylpropyl}acetamide (0.042 g, 69%) as an oil. ES-LCMS m/z 643 (M+1).

Example 925

Preparation of 3-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,2-dimethyl-3-oxopropanoic acid

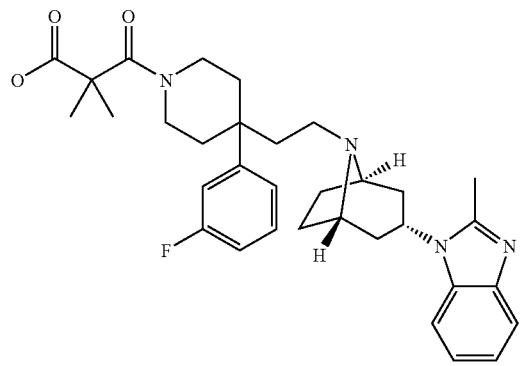

3-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,2-dimethyl-3-oxopropanoic acid was obtained from 3-Ethoxy-2,2-dimethyl-3-oxopropanoic acid, Example 628, (0.029 g, 0.18 mmol), 1-(8-(2-[4-(3-Fluoro-phenyl)-piperidin-4-yl]-ethyl)-8-aza-bicyclo[3.2.1]oct-3-yl)-2-methyl-1H-enzoimidazole dihydrochloride (0.075 g, 0.18 mmol), and HATU (0.067 g, 0.18 mmol) following the procedure outlined in example 5 to produce ethyl 3-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,2-dimethyl-3-oxopropanoate. Ethyl 3-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-2,2-dimethyl-3-oxopropanoate (0.100 g, 0.170 mmol), 5 N NaOH (10 ml) and ethanol (4 ml) was stirred at 90° C. for 3 hrs. The reaction was evaporated to dryness and residue was suspend in water (10 ml) and neutralized with 1N HCl. The aqueous layer was extracted with ethyl acetate (3×10 ml). The organic layer was dried using magnesium sulfate and concentrated down to form the title compound as a white solid (0.081 g, 85%). ES-LCMS m/z 561 (M+1).

Example 926

Preparation of 2,2,2-trichloro-N-{1-ethyl-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]propyl}acetamide

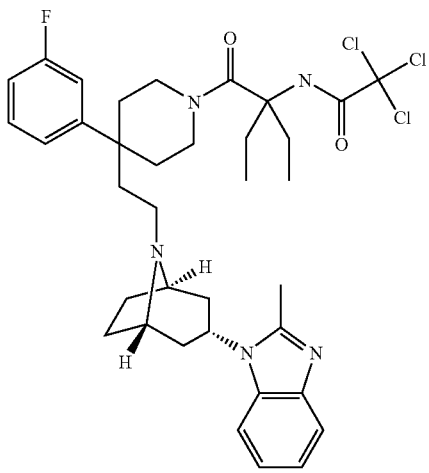

2-Amino-2-ethyl-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one (0.100 g, 0.178 mmol), trichloroacetyl chloride (0.032 g, 0.178 mmol) and DIEA (0.069 g, 0.534 mmol) as outlined in procedure for procedure for Example 890 to give title compound, 2,2,2-trichloro-N-{1-ethyl-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]propyl}acetamide (0.068 g, 54%). ES-LCMS m/z 706 (M+1).

Example 927

Preparation of N-{1-ethyl-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]propyl}-2,2,2-trifluoroacetamide

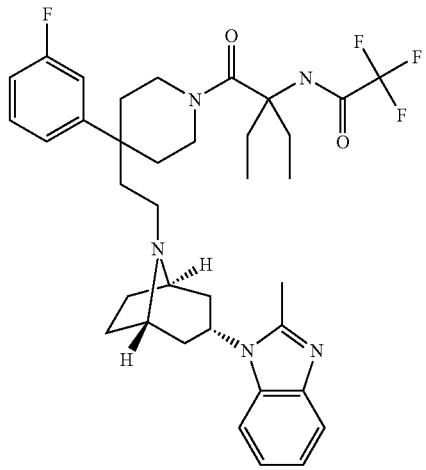

2-Amino-2-ethyl-1-(4-(3-fluoro-phenyl)-4-{2-[3-(2-methyl-benzoimidazol-1-yl)-8-aza-bicyclo[3.2.1]oct-8-yl]-ethyl}-piperidin-1-yl)-butan-1-one example 890 (0.100 g, 0.178 mmol), trifluoroacetic anhydride (0.038 g, 0.178 mmol) and DIEA (0.069 g, 0.534 mmol) as outlined in procedure for procedure for Example 890 to give title compound, N-{1-ethyl-1-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]propyl}-2,2,2-trifluoroacetamide (0.061 g, 52%). ES-LCMS m/z 656 (M+1).

Example 928

Preparation of [3-(1-(2,2-dimethylpropanoyl)-4-{2-[(1R,5S)-3-(2-methyl-1H-benzimidazol-1-yl)-8-azabicyclo[3.2.1]oct-8-yl]ethyl}-4-piperidinyl)phenyl]methanol

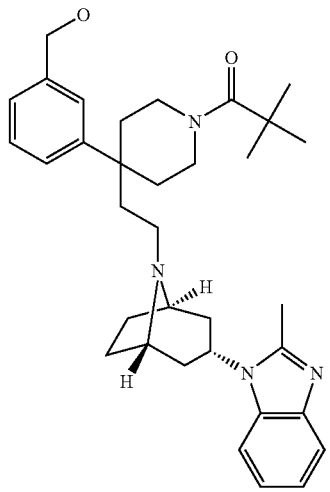

[3-(4-{2-[(1R,5S)-3-(2-methyl-1H-benzimidazol-1-yl)-8-azabicyclo[3.2.1]oct-8-yl]ethyl}-4-piperidinyl) phenyl]methanol dihydrochloride (0.100 g, 0.188 mmol), Dimethylpropionyl chloride (0.024 g, 0.188 mmol) and DIEA (0.069 g, 0.534 mmol) were stirred at room temperature in DCM (3 ml) for 2 hours. Solvent was removed and compound was purified by RP-HPLC to give the title compound, [3-(1-(2,2-dimethylpropanoyl)-4-{2-[(1R,5S)-3-(2-methyl-1H-benzimidazol-1-yl)-8-azabicyclo[3.2.1]oct-8-yl]ethyl}-4-piperidinyl)phenyl]methanol (0.069 g, 71%). ES-LCMS m/z 543 (M+1).

Example 929

Preparation of N-{2,5-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}-1,1,1-trifluoromethanesulfonamide

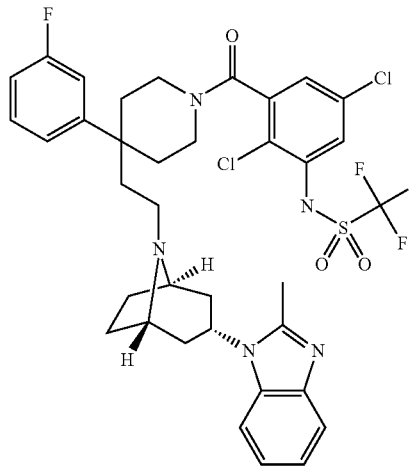

N-{2,5-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}-1,1,1-trifluoromethanesulfonamide was obtained through procedure outlined in scheme.

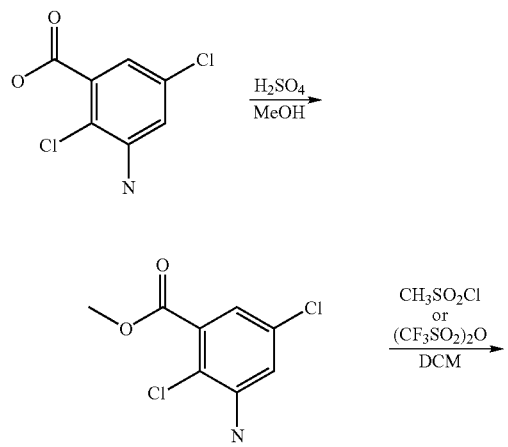

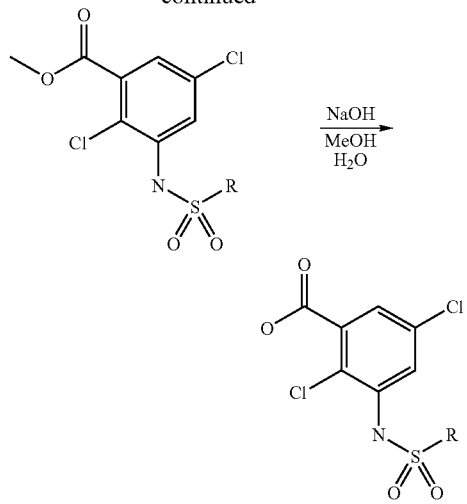

Preparation of methyl 3-amino-2,5-dichlorobenzoate

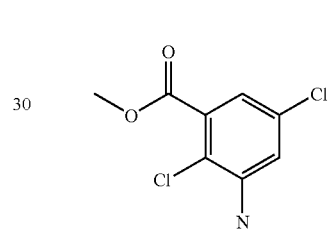

3-amino-2,5-dichlorobenzoic acid (5.00 g, 24.27 mmol) was stirred in methanol (30 ml) at room temperature. Sulfuric Acid (5 ml) was added dropwise. Reaction stirred for 3 hours and was then diluted with water (30 ml) and basified using sodium hydroxide. Mixture was extracted with ethyl acetate× 3. Solvent was removed to afford methyl 3-amino-2,5-dichlorobenzoate (4.20 g, 79%) as a solid.

Preparation of methyl 2,5-dichloro-3-{[(trifluoromethyl)sulfonyl]amino}benzoate

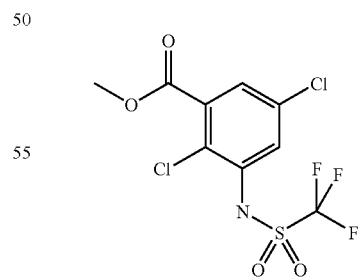

methyl 3-amino-2,5-dichlorobenzoate (2.10 g, 9.55 mmol), DIEA (3.0 ml) were stirred in DCM (40 ml) at 0° C. Triflic anhydride (3.90 g, 14.31 mmol) was added dropwise whike stirring at 0° C. After 2 hrs at 0° C., reaction was allowed to warm to room temperature while stirring overnight. Quenched rxn with saturated NH4Cl and washed with brine. Organic layer with dried to yield crude methyl 2,5-dichloro-3-{[(trifluoromethyl) sulfonyl]amino}benzoate (4.0 g) which will be carried on.

Preparation of 2,5-dichloro-3-{[(trifluoromethyl) sulfonyl]amino}benzoic acid hydrochloride

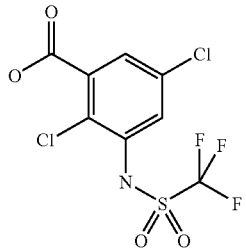

Crude methyl 2,5-dichloro-3-{[(trifluoromethyl) sulfonyl]amino}benzoate (4.0 g) was dissolved in methanol (30 ml) and 4N NaOH (30 ml) was added while stirring at room temperature for 18 hrs. Removed solvent and added 4N HCl (10 ml). Stirred at room temperature for 4 hours. Filtered off solid to give 2,5-dichloro-3-{[(trifluoromethyl) sulfonyl]amino}benzoic acid hydrochloride in quantitative yield.

Preparation of Example 929

N-{2,5-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}-1,1,1-trifluoromethanesulfonamide (0.140 g, 47%) was obtained as a oil from (0.320 g, 1.4 mmol), 2,5-dichloro-3-{[(trifluoromethyl) sulfonyl]amino}benzoic acid hydrochloride (0.157 g, 0.46 mmol), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.200 g, 0.39 mmol) and HATU (0.150 g, 0.46 mmol) following the procedure outlined in example 5. ES-LCMS m/z 766 (M+1).

Example 930

Preparation of N-{2,5-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}methanesulfonamide

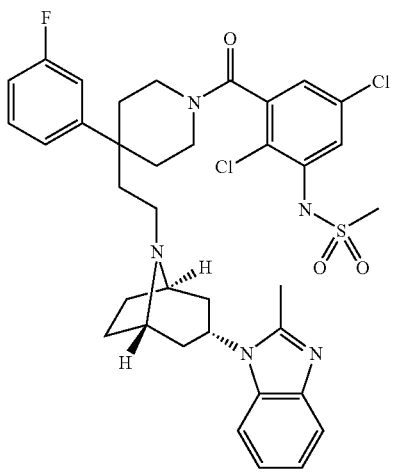

Preparation of methyl 2,5-dichloro-3-[(methylsulfonyl)amino]benzoate

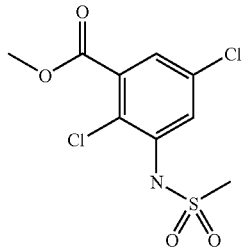

From common intermediate methyl 3-amino-2,5-dichlorobenzoate following the procedure outlined in scheme. Methyl 3-amino-2,5-dichlorobenzoate (2.10 g, 9.55 mmol), DIEA (3.0 ml) were stirred in DCM (40 ml) at 0° C. methanesulfonyl chloride (2.18 g, 19.08 mmol) was added dropwise whike stirring at 0° C. After 2 hrs at 0° C., reaction was allowed to warm to room temperature while stirring overnight. Quenched rxn with saturated NH4Cl and washed with brine. Organic layer with dried to yield crude methyl 2,5-dichloro-3-[(methylsulfonyl)amino]benzoate (3.10 g) which will be carried on. methyl 2,5-dichloro-3-[(methylsulfonyl)amino]benzoate (3.10 g) was treated with NaOH, methanol following procedure outlined in scheme to form 2,5-dichloro-3-[(methylsulfonyl)amino]benzoic acid hydrochloride (3.53 g).

Preparation of Example 930

N-{2,5-dichloro-3-[(4-(3-fluorophenyl)-4-{2-[(1R,5S)-3-(2-methyl-1H-benzimidazol-1-yl)-8-azabicyclo[3.2.1]oct-8-yl]ethyl}-1-Piperidinyl)carbonyl]phenyl}methanesulfonamide (0.127 g, 45%) was obtained as a oil from 2,5-dichloro-3-[(methylsulfonyl)amino]benzoic acid hydrochloride (0.132 g, 0.46 mmol), 1-(8-{2-[4-(3-Fluoro-phenyl)-piperidin-4-yl]-ethyl}-8-aza-bicyclo[3.2.1]oct-3-yl)-2-methyl-1H-benzoimidazole dihydrochloride (0.200 g, 0.39 mmol) and HATU (0.150 g, 0.46 mmol) following the procedure outlined in example 5. ES-LCMS m/z 712 (M+1).

Example 931

Preparation of 1,1,1-trifluoro-N-({4-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]phenyl}methyl)methanesulfonamide

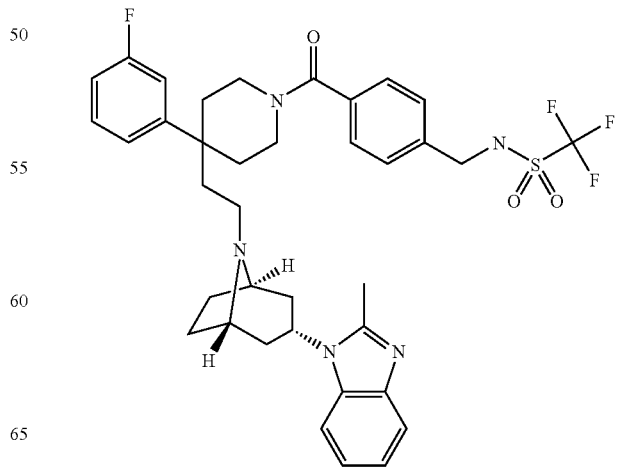

By the procedure outlined in example 929, starting from 4-(aminomethyl)benzoic acid (2.00 g, 13.24 mmol) was treated with sulfuric acid to form methyl 4-(aminomethyl)benzoate (1.20 g, 55%). Methyl 4-(aminomethyl)benzoate (0.600 g, 3.63 mmol) was treated with triflic anhydride (1.512 g, 4.92 mmol) in DCM (20 ml) to give crude methyl 4-({[(trifluoromethyl)sulfonyl]amino}methyl) benzoate (0.402 g, 37%). Methyl 4-({[(trifluoromethyl) sulfonyl] amino}methyl) benzoate (0.402 g, 1.35 mmol) was treated with NaOH and methanol to give 4-({[(trifluoromethyl)sulfonyl]amino}methyl)benzoic acid hydrochloride (0.380 g, 95%). The title compound, 1,1,1-trifluoro-N-({4-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl) carbonyl]phenyl}methyl) methanesulfonamide (0.145 g, 52%) was obtained as a oil from 4-({[(trifluoromethyl)sulfonyl]amino}methyl)benzoic acid hydrochloride (0.157 g, 0.461), 1-(8-{2-[4-(3-Fluoro-phenyl)-piperidin-4-yl]-ethyl}-8-aza-bicyclo[3.2.1]oct-3-yl)-2-methyl-1H-benzoimidazole dihydrochloride (0.200 g, 0.39 mmol) and HATU (0.150 g, 0.46 mmol) following the procedure outlined in example 5. ES-LCMS m/z 712 (M+1).

Example 932

Preparation of N-({4-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}methyl) methanesulfonamide

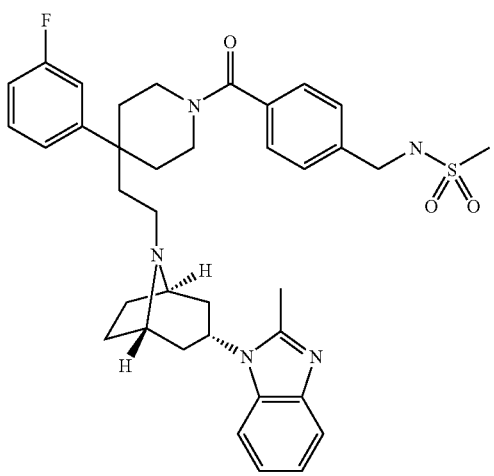

By the procedure outlined in scheme example 929, starting from 4-(aminomethyl)benzoic acid (2.00 g, 13.24 mmol) was treated with sulfuric acid to form methyl 4-(aminomethyl)benzoate (1.20 g, 55%). Methyl 4-(aminomethyl)benzoate (0.600 g, 3.63 mmol) was treated with methanesulfonyl chloride (0.832 g, 7.26 mmol)) in DCM (20 ml) to give crude methyl 4-{[(methylsulfonyl)amino]methyl}benzoate (0.398 g, 45%). Methyl 4-{[(methylsulfonyl)amino]methyl}benzoate (0.398 g, 1.63 mmol) was treated with NaOH and methanol to give 4-{[(methylsulfonyl)amino]methyl}benzoic acid hydrochloride (0.370 g, 98%). The title compound, N-({4-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}methyl) methanesulfonamide (0.128 g, 50%) was obtained as a oil from 4-{[(methylsulfonyl)amino]methyl}benzoic acid hydrochloride (0.132 g, 0.461), 1-(8-{2-[4-(3-Fluoro-phenyl)-piperidin-4-yl]-ethyl}-8-aza-bicyclo[3.2.1]oct-3-yl)-2-methyl-1H-enzoimidazole dihydrochloride (0.200 g, 0.39 mmol) and HATU (0.150 g, 0.46 mmol) following the procedure outlined in example 5. ES-LCMS m/z 658 (M+1).

Example 933

Preparation of 2-chloro-N-ethyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

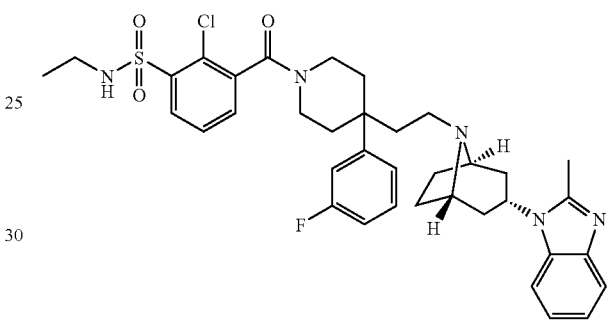

Preparation of 2-chloro-3-[(ethylamino)sulfonyl]benzoic acid. To a solution of methyl 2-chloro-3-(chlorosulfonyl)benzoate (608 mg, 2.26 mmol) and K$_2$CO$_3$ (770 mg, 5.6 mmol) in 10 mL benzene was added ethylamine (5.6 mL, 11.2 mmol). Purification of the product provided methyl 2-chloro-3-[(ethylamino)sulfonyl]benzoate (335 mg, 53%) as a solid. $^1$H NMR (400 MHz, CDCl$_3$), δ 8.24 (dd, 1H, J=8.0, 1.7 Hz), 7.90 (dd, 1H, J=7.8, 1.7 Hz), 7.47 (t, 1H, J=7.8 Hz), 5.14 (t, 1H, J=5.9 Hz), 3.94 (s, 3H), 2.98 (qd, 2H, J=7.3, 6.0 Hz), 1.09 (t, 3H, J=7.2 Hz); ESI-MS 278 (M+H), 300 (M+Na). Methyl 2-chloro-3-[(ethylamino)sulfonyl]benzoate was hydrolyzed using aqueous NaOH to provide 2-chloro-3-[(ethylamino)sulfonyl]benzoic acid as a solid, which was used without further purification. ESI-MS 264 (M+H), 286 (M+Na).

2-chloro-N-ethyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (282 mg, 83%) was obtained as a solid from 2-chloro-3-[(ethylamino)sulfonyl]benzoic acid (51 mg, 0.19 mmol), 1-(((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (117 mg, 0.19 mmol) and HATU (80 mg, 0.21 mmol) following the procedure outlined in example 5. $^1$H NMR (400 MHz, CDCl$_3$), δ 8.12 (m, 1H), 7.64 (m, 1H), 7.53-7.40 (m, 2H), 7.38-7.25 (m, 2H), 7.14 (m, 2H), 7.05 (m, 1H), 7.00-6.92 (m, 2H), 5.80-5.35 (m, 2H), 4.52 (m, 1H), 4.20 (m, 1H), 3.45-2.87 (m, 7H), 2.52 (m, 3H, rotamers), 2.40-1.60 (m, 15H), 1.1 (m, 3H); ESI-MS 692 (M+H).

Example 934

Preparation of 2-chloro-N-cyclopropyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide

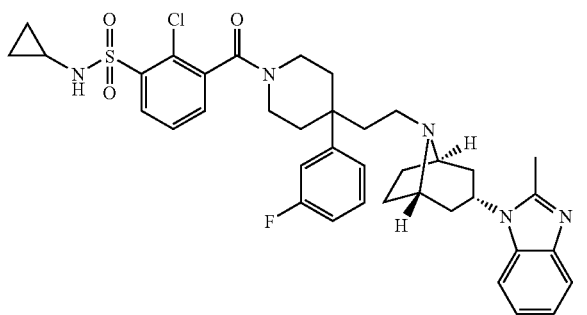

Preparation of 2-chloro-3-[(cyclopropylamino)sulfonyl]benzoic acid. To a solution of methyl 2-chloro-3-(chlorosulfonyl)benzoate (608 mg, 2.26 mmol) and $K_2CO_3$ (770 mg, 5.6 mmol) in 10 mL benzene was added cyclopropylamine (0.78 mL, 11.2 mmol). Purification of the product provided methyl 2-chloro-3-[(cyclopropylamino)sulfonyl]benzoate (355 mg, 54%) as a solid. $^1$H NMR (400 MHz, $CDCl_3$), δ 8.28 (dd, 1H, J=7.9, 1.7 Hz), 7.90 (dd, 1H, J=7.8, 1.7 Hz), 7.48 (t, 1H, J=7.8 Hz), 5.63 (s, 1H), 3.93 (s, 3H), 2.17 (m, 1H), 0.65-0.58 (m, 2H), 0.57-0.50 (m, 2H); ESI-MS 290 (M+H), 312 (M+Na). Methyl 2-chloro-3-[(cyclopropylamino)sulfonyl]benzoate was hydrolyzed using aqueous NaOH to provide 2-chloro-3-[(cyclopropylamino)sulfonyl]benzoic acid as a solid, which was used without further purification. ESI-MS 276 (M+H), 298 (M+Na).

2-chloro-N-cyclopropyl-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]benzenesulfonamide (288 mg, 91%) was obtained as a solid from 2-chloro-3-[(cyclopropylamino)sulfonyl]benzoic acid (41 mg, 0.15 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (90 mg, 0.15 mmol) and HATU (62 mg, 0.16 mmol) following the procedure outlined in example 5. $^1$H NMR (400 MHz, $CDCl_3$), δ 8.18 (m, 1H), 7.65 (m, 1H), 7.56-7.25 (m, 4H), 7.15 (m, 2H), 7.05 (m, 1H), 7.01-6.91 (m, 2H), 5.95-5.44 (m, 2H), 4.61 (m, 1H), 4.23 (m, 1H), 3.45-3.05 (m, 5H), 2.56 (s, 1.5H, rotamer), 2.54 (s, 1.5H, rotamer), 2.43-1.74 (m, 1H), 1.70-1.58 (m, 2H), 0.78 (m, 1H), 0.63-0.50 (m, 2H); ESI-MS 704 (M+H).

Example 935

Preparation of 1,1,1-trifluoro-N-[3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropyl]methanesulfonamide

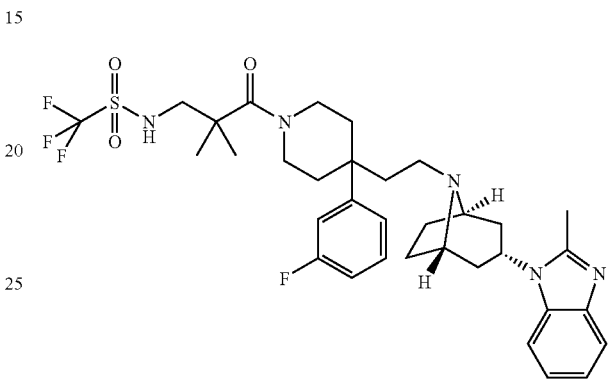

Preparation of 2,2-dimethyl-3-{[(trifluoromethyl)sulfonyl]amino}propanoic acid. To a −78° C. solution of methyl 3-amino-2,2-dimethylpropanoate (318 mg, 2.4 mmol) and $Et_3N$ (0.34 mL, 2.44 mmol) in 4 mL $CH_2Cl_2$ was added trifluoromethanesulfonic anhydride (0.81 mL, 4.84 mmol). The reaction was stirred for 4 h below −40° C. and quenched with saturated aqueous $NaHCO_3$. The crude methyl 2,2-dimethyl-3-{[(trifluoromethyl)sulfonyl]amino}propanoate was isolated and hydrolyzed using aqueous NaOH to provide 2,2-dimethyl-3-{[(trifluoromethyl)sulfonyl]amino}propanoic acid which was used without further purification.

1,1,1-trifluoro-N-[3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropyl]methanesulfonamide (41 mg, 44%) was obtained as a solid from 2,2-dimethyl-3-{[(trifluoromethyl)sulfonyl]amino}propanoic acid (100 mg, 0.40 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. $^1$H NMR (400 MHz, $CDCl_3$), δ7.71-7.67 (m, 1H), 7.41-7.21 (m, 4H), 7.07 (m, 1H), 7.02-6.94 (m, 2H), 4.84 (q, 1H, J=9.5 Hz), 3.94 (m, 2H), 3.45 (m, 2H), 3.21 (m, 5H) 262 (s, 3H), 2.54 (m, 2H), 2.20 (m, 2H), 2.14-1.95 (m, 6H), 1.87 (m, 2H), 1.81-1.71 (m, 4H), 1.33 (s, 6H); ESI-MS 678 (M+H).

Example 936

Preparation of N-{2-chloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}methanesulfonamide

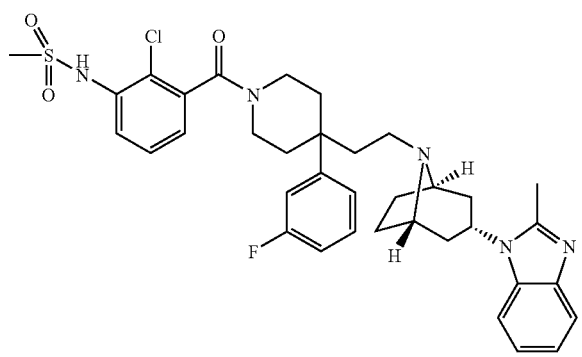

Preparation of 2-chloro-3-[(methylsulfonyl)amino]benzoic acid. To a solution of methyl 3-amino-2-chlorobenzoate (517 mg, 2.79 mmol) and pyridine (0.25 mL, 3.06 mmol) in 8 mL CH$_2$Cl$_2$ was added methanesulfonylchloride (0.24 mL, 3.06 mmol). After washing with 1M HCl, methyl 2-chloro-3-[(methylsulfonyl)amino]benzoate was isolated as a solid in quantitative yield. $^1$H NMR (400 MHz, CDCl$_3$), δ 7.77 (dd, 1H, J=8.2, 1.6 Hz), 7.61 (dd, 1H, J=7.9, 1.6 Hz), 7.33 (t, 1H, J=7.9 Hz), 7.16 (s, 1H), 3.91 (s, 3H), 2.99 (5, 3H); ESI-MS 262 (M–H). Methyl 2-chloro-3-[(methylsulfonyl)amino]benzoate was hydrolyzed using aqueous NaOH to provide 2-chloro-3-[(methylsulfonyl)amino]benzoic acid as a solid, which was used without further purification. ESI-MS 248 (M–H).

N-{2-chloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}methanesulfonamide (18 mg, 20%) was obtained as a solid from 2-chloro-3-[(methylsulfonyl)amino]benzoic acid (49 mg, 0.20 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. $^1$H NMR (400 MHz, CDCl$_3$), δ 7.72-7.63 (m, 2H), 7.41-7.25 (m, 4H), 7.16 (m, 2H), 7.07 (m, 1H), 7.02-6.93 (m, 2H), 4.62 (m, 1H), 4.22 (m, 1H), 3.48-3.09 (m, 5H), 3.07 (2, 1.5H, rotamer), 3.04 (s, 1.5H, rotamer), 2.58-2.53 (m, 3H, rotamers), 2.45-2.24 (m, 3H), 2.18-1.61 (m, 15H); ESI-MS 678 (M+H).

Example 937

Preparation of N-{4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}-1,1,1-trifluoromethanesulfonamide

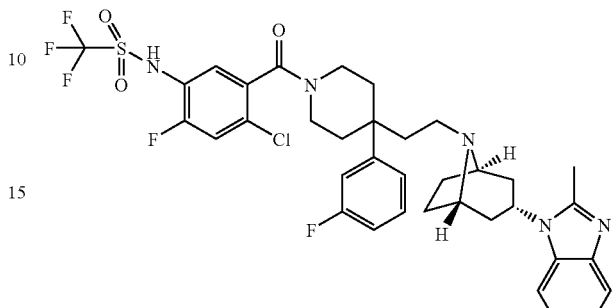

Preparation of 2-chloro-4-fluoro-5-{[(trifluoromethyl)sulfonyl]amino}benzoic acid. To a −78° C. solution of methyl 5-amino-2-chloro-4-fluorobenzoate (195 mg, 1.0 mmol) and Et$_3$N (0.13 mL, 1.0 mmol) in 2 mL CH$_2$Cl$_2$ was added trifluoromethanesulfonic anhydride (0.32 mL, 1.9 mmol). The reaction was stirred for 4 h below −40° C. and quenched with saturated aqueous NaHCO$_3$. The crude methyl 2-chloro-4-fluoro-5-{[(trifluoromethyl)sulfonyl]amino}benzoate (ESI-MS 336 (M+H)) was isolated and hydrolyzed using aqueous NaOH to provide 2-chloro-4-fluoro-5-{[(trifluoromethyl)sulfonyl]amino}benzoic acid (ESI-MS 320 (M–H)) which was used without further purification.

N-{4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}-1,1,1-trifluoromethanesulfonamide (27 mg, 26%) was obtained as a solid from 2-chloro-4-fluoro-5-{[(trifluoromethyl)sulfonyl]amino}benzoic acid (90 mg, 0.28 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. $^1$H NMR (400 MHz, CDCl$_3$), δ 7.68 (m, 1H), 7.58-7.46 (m, 1H), 7.38 (m, 1H), 7.31-7.19 (m, 3H), 7.14 (m, 1H), 7.08-6.93 (m, 3H), 5.06 (m, 1H), 4.12 (m, 1H), 3.89-3.63 (m, 2H), 3.48-3.08 (m, 4H), 2.77-2.33 (m, 7H), 2.30-1.76 (m, 12H); ESI-MS 750 (M+H).

Example 938

Preparation of N-{1-ethyl-1-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]propyl}methanesulfonamide

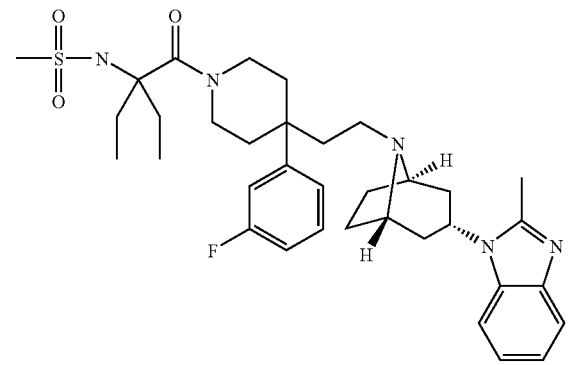

Preparation of 2-ethyl-2-[(methylsulfonyl)amino]butanoic acid. To a solution of 0° C. solution of diethylglycine (205 mg, 1.56 mmol) in 2 mL 1M NaOH was added methanesulfonyl chloride (0.14 mL, 1.81 mmol) with periodic stirring and addition of another 2 mL 1M NaOH. The reaction mixture was stirred for 1 h at 0° C., 4h at room temperature, and then acidified with 1M HCl and extracted into EtOAc to provide the crude 2-ethyl-2-[(methylsulfonyl)amino]butanoic acid (37 mg, 11%) as a solid, which was used without further purification. $^1$H NMR (400 MHz, CDCl$_3$), δ 5.19 (s, 1H), 3.06 (s, 3H), 2.14 (m, 2H), 1.92 (m, 2H), 0.96 (t, 6H, J=7.4 Hz).

N-{1-ethyl-1-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]propyl}methanesulfonamide (69 mg, 79%) was obtained as a solid from 2-ethyl-2-[(methylsulfonyl)amino]butanoic acid (37 mg, 0.18 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. $^1$H NMR (400 MHz, CDCl$_3$), δ 7.65-7.62 (m, 1H), 7.39-7.30 (m, 1H), 7.28 (m, 1H), 7.19-7.11 (m, 2H), 7.06 (m, 1H), 7.01-6.91 (m, 2H), 6.35 (s, 0.3H, rotamer), 6.28 (s, 0.7H, rotamer), 4.75 (br. s, 1H), 4.07-3.96 (m, 2H), 3.39-3.25 (m, 4H), 2.98 (s, 2H, rotamer), 2.97 (s, 1H, rotamer), 2.57 (s, 3H), 2.48-2.38 (m, 2H), 2.31 (m, 2H), 2.24-2.15 (m, 2H), 2.01-1.91 (m, 4H), 1.90-1.74 (m, 8H), 1.74-1.63 (m, 2H), 0.96-0.85 (m, 6H); ESI-MS 638 (M+H).

Example 939

Preparation of N-{4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}methanesulfonamide

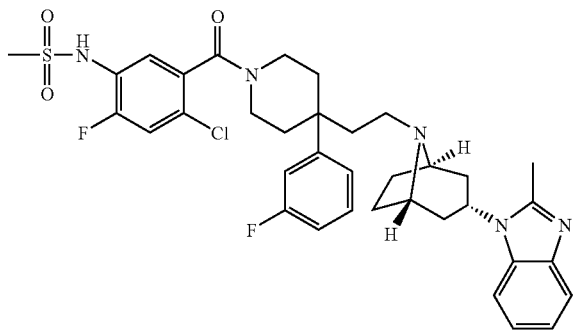

Preparation of 2-chloro-4-fluoro-5-[(methylsulfonyl)amino]benzoic acid. To a solution of methyl 5-amino-2-chloro-4-fluorobenzoate (152 mg, 0.75 mmol) and pyridine (0.07 mL, 0.82 mmol) in 3 mL CH$_2$Cl$_2$ was added methanesulfonyl chloride (0.06 mL, 0.82 mmol). After 3 days at room temperature, the reaction mixture was washed with saturated aqueous NaHCO$_3$ and filtered through a silica plug to provide methyl 2-chloro-4-fluoro-5-[(methylsulfonyl)amino]benzoate (96 mg, 44%) as a solid (ESI-MS 280 (M–H)), which was hydrolyzed using aqueous NaOH to provide 2-chloro-4-fluoro-5-[(methylsulfonyl)amino]benzoic acid (ESI-MS 266 (M–H)), which was used without further purification.

N-{4-chloro-2-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}methanesulfonamide (15.9 mg, 7%) was obtained as a solid from 2-chloro-4-fluoro-5-[(methylsulfonyl)amino]benzoic acid (91 mg, 0.34 mmol), 1-((1R,5S)-8-{2-4-(3-fluorophenyl)piperidin-4-yl]ethyl}-8-azabicyclo[3.2.1]oct-3-yl)-2-methyl-1H-benzimidazole dihydrochloride (210 mg, 0.34 mmol) and HATU (194 mg, 0.51 mmol) following the procedure outlined in example 5. $^1$H NMR (400 MHz, CDCl$_3$), δ 7.66 (m, 1H), 7.55 (m, 0.5H, rotamer), 7.42-7.32 (m, 1.5H, rotamer), 7.31-7.27 (m, 1H), 7.25-7.11 (m, 3H), 7.07 (m, 1H), 7.02-6.93 (m, 2H), 4.65 (br. s, 1H), 4.29-4.11 (m, 1H), 3.47-3.11 (m, 5H), 3.08 (s, 1.5H, rotamer), 3.05 (s, 1.5H, rotamer), 2.56 (s, 3H), 2.46-2.35 (m, 2H), 2.33-2.24 (m, 1H), 2.18-2.10 (m, 1H), 2.00-1.73 (m, 10H), 1.67 (m, 2H); ESI-MS 696 (M+H).

Example 940

Preparation of N-[3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropyl]propane-2-sulfonamide

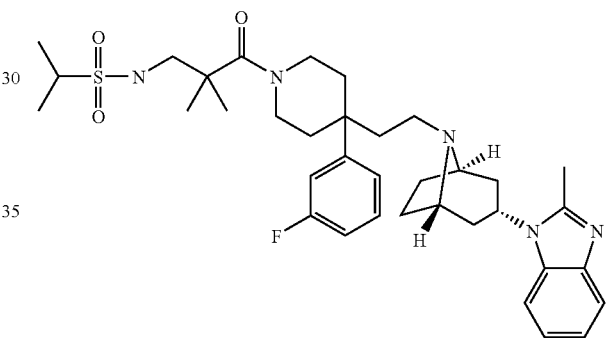

Preparation of 3-[(isopropylsulfonyl)amino]-2,2-dimethylpropanoic acid. To a solution of methyl 3-amino-2,2-dimethylpropanoate (200 mg, 1.53 mmol) and Et$_3$N (0.64 mL, 4.59 mmol) in 2 mL CH$_2$Cl$_2$ was added isopropylsulfonyl chloride (0.34 mL, 3.05 mmol). The reaction was stirred for 24 h, quenched by the addition of saturated aqueous NaHCO$_3$, extracted with CHCl$_3$, and chromatographed (1:1 hex:EtOAc) to provide methyl 3-[(isopropylsulfonyl)amino]-2,2-dimethylpropanoate (77 mg, 21%) as a solid. $^1$H NMR (400 MHz, CDCl$_3$), 4.78 (t, 1H, J=6.6 Hz), 3.68 (s, 3H), 3.20-3.11 (m, 3H), 1.36 (d, 6H, J=6.9 Hz), 1.23 (s, 6H). Methyl 3-[(isopropylsulfonyl)amino]-2,2-dimethylpropanoate was hydrolyzed using aqueous NaOH to provide 3-[(isopropylsulfonyl)amino]-2,2-dimethylpropanoic acid, which was used without further purification.

N-[3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropyl]propane-2-sulfonamide (130 mg, 74%) was obtained as a solid from 3-[(isopropylsulfonyl)amino]-2,2-dimethylpropanoic acid (60 mg, 0.27 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (164 mg, 0.27 mmol) and HATU (154 mg, 0.41 mmol) following the procedure outlined in example 5. $^1$H NMR (400 MHz, CDCl$_3$), δ 7.68-7.64 (m, 1H), 7.36 (m, 1H), 7.29 (m, 1H), 7.16 (m, 2H), 7.08 (m, 1H), 7.00 (m, 1H), 6.96 (m, 1H), 5.36 (t, 1H, J=6.6 Hz), 4.65 (br. s, 1H), 3.93 (m, 2H), 3.33-3.20 (m, 4H), 3.15 (m, 1H), 3.10 (m, 2H), 2.58 (s, 3H), 2.40 (m, 2H), 2.19 (m, 2H), 2.00-1.73 (m, 10H), 1.67 (m, 2H), 1.39 (s, 3H), 1.37 (s, 3H), 1.33 (5, 6H); ESI-MS 652 (M+H).

Example 941

Preparation of N-{2,4-difluoro-5-[(4-(3-fluorophenyl-4-{2-[(1R,5S)-3-(2-methyl-1H-benzimidazol-1-yl)-8-azabicyclo[3.2.1]oct-8-yl]ethyl}piperidin-1-yl)carbonyl]phenyl}methanesulfonamide

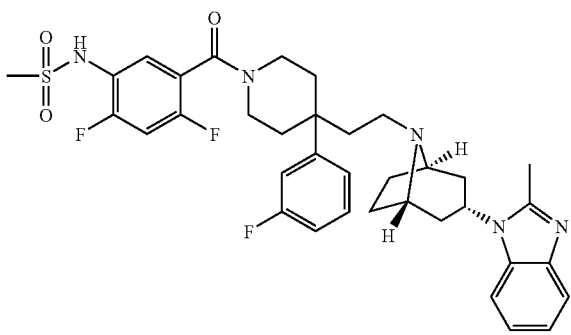

Preparation of 2,4-difluoro-5-[(methylsulfonyl)amino] benzoic acid. To a solution of methyl 5-amino-2,4-difluorobenzoate (252 mg, 1.35 mmol) and pyridine (0.13 mL, 1.61 mmol) in 5 mL CH$_2$Cl$_2$ was added methanesulfonyl chloride (0.12 mL, 1.48 mmol). After 24 h at room temperature, the reaction mixture was washed with saturated aqueous NaHCO$_3$ and extracted with CHCl$_3$ to provide crude methyl 2,4-difluoro-5-[(methylsulfonyl)amino]benzoate as a solid (ESI-MS 264 (M–H)), which was hydrolyzed using aqueous NaOH to provide 2,4-difluoro-5-[(methylsulfonyl)amino] benzoic acid (ESI-MS 250 (M–H)), which was used without further purification.

N-{2,4-difluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl] phenyl}methanesulfonamide (7.0 mg, 13%) was obtained as a solid from 2,4-difluoro-5-[(methylsulfonyl)amino]benzoic acid (20 mg, 0.08 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole d hydrochloride (48 mg, 0.08 mmol) and HATU (45 mg, 0.12 mmol) following the procedure outlined in example 5. $^1$H NMR (400 MHz, CDCl$_3$), δ 7.73-7.68 (m, 1H), 7.60 (5, 1H), 7.41 (m, 1H), 7.25-7.15 (m, 3H), 7.12-7.07 (m, 1H), 7.04-6.93 (m, 3H), 4.26-4.11 (m, 1H), 3.89-3.63 (m, 2H), 3.58-3.43 (m, 2H), 3.29-3.16 (m, 2H), 3.07 (5, 2H, rotamer), 3.02 (s, 1H, rotamer), 2.70 (5, 3H), 2.41-1.61 (m, 16H); ESI-MS 681 (M+H).

Example 942

Preparation of N-{2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl) carbonyl]phenyl}methanesulfonamide

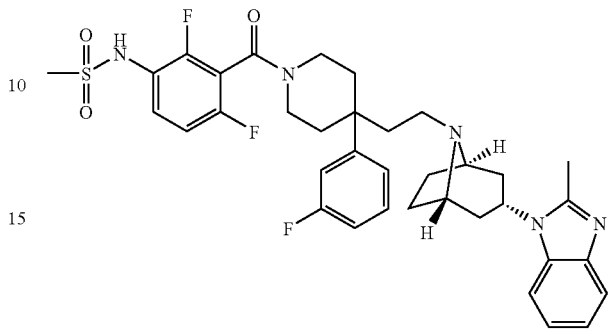

Preparation of 2,6-difluoro-3-[(methylsulfonyl)amino] benzoic acid. To a solution of methyl 3-amino-2,6-difluorobenzoate (530 mg, 2.83 mmol) and pyridine (0.28 mL, 3.40 mmol) in 10 mL CH$_2$Cl$_2$ was added methanesulfonyl chloride (0.24 mL, 3.11 mmol). After 24 h at room temperature, the reaction mixture was washed with saturated aqueous NaHCO$_3$ and extracted with CHCl$_3$ to provide crude methyl 2,6-difluoro-3-[(methylsulfonyl)amino]benzoate as a solid (ESI-MS 264 (M–H)), which was hydrolyzed using aqueous NaOH to provide 2,6-difluoro-3-[(methylsulfonyl)amino] benzoic acid (ESI-MS 250 (M–H)), which was used without further purification.

N-{2,4-difluoro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl] phenyl}methanesulfonamide (30.5 mg, 49%) was obtained as a solid from 2,6-difluoro-3-[(methylsulfonyl)amino]benzoic acid (26 mg, 0.10 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole d hydrochloride (56 mg, 0.09 mmol) and HATU (53 mg, 0.14 mmol) following the procedure outlined in example 5.
$^1$H NMR (400 MHz, CDCl$_3$), δ 7.79 (m, 1H), 7.55 (m, 1H), 7.42 (m, 1H), 7.34-7.23 (m, 3H), 7.13 (m, 1H), 7.05-6.94 (m, 3H), 6.02 (br. s, 1H), 4.13 (m, 1H), 3.98-3.80 (m, 2H), 3.59-3.43 (m, 2H), 3.23 (m, 1H), 3.08 (s, 3H), 2.97-3.85 (m, 2H), 2.82 (s, 3H), 2.61-2.46 (m, 2H), 2.39-1.86 (m, 12H); ESI-MS 681 (M+H).

Example 943

Preparation of N-{2-chloro-4-fluoro-5-[(4-(3-fluorophenyl)-4-{2-[(1R,5S)-3-(2-methyl-1H-benzimidazol-1-yl)-8-azabicyclo[3.2.1]oct-8-yl] ethyl}piperidin-1-yl)carbonyl] phenyl}methanesulfonamide

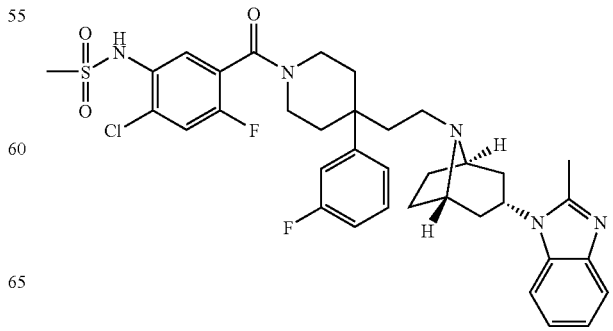

Preparation of 4-chloro-2-fluoro-5-[(methylsulfonyl)amino]benzoic acid. To a solution of methyl 5-amino-4-chloro-2-fluorobenzoate (248 mg, 1.22 mmol) and pyridine (0.12 mL, 1.46 mmol) in 5 mL CH$_2$Cl$_2$ was added methanesulfonyl chloride (0.10 mL, 1.34 mmol). After 5 days at room temperature, the reaction mixture was washed with saturated aqueous NaHCO$_3$ and extracted with CHCl$_3$ to provide crude methyl 4-chloro-2-fluoro-5-[(methylsulfonyl)amino]benzoate as a solid (ESI-MS 280 (M−H)), which was hydrolyzed using aqueous NaOH to provide 4-chloro-2-fluoro-5-[(methylsulfonyl)amino]benzoic acid (ESI-MS 266 (M−H)), which was used without further purification.

N-{2-chloro-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}methanesulfonamide (56 mg, 59%) was obtained as a solid from 4-chloro-2-fluoro-5-[(methylsulfonyl)amino]benzoic acid (43 mg, 0.16 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.13 mmol) and HATU (78 mg, 0.20 mmol) following the procedure outlined in example 5. $^1$H NMR (400 MHz, CDCl$_3$), δ 7.68-7.61 (m, 1H), 7.61 (br. s, 1H), 7.36 (m, 1H), 7.31-7.26 (m, 1H), 7.25-7.21 (m, 1H), 7.21-7.12 (m, 2H), 7.07 (m, 1H), 7.02-6.93 (m, 2H), 4.68 (br. s, 1H), 4.19 (m, 1H), 3.50-3.15 (m, 5H), 3.04 (s, 3H), 2.58 (s, 3H), 2.51-2.34 (m, 2H), 2.28 (m, 2H), 2.15 (m, 2H), 2.07-1.76 (m, 10H), 1.69 (m, 2H); ESI-MS 696 (M+H).

Example 944

Preparation of 1-[(1R,5S)-8-(2-{4-(3-fluorophenyl)-1-[3-(1H-1,2,4-triazol-1-yl)benzoyl]piperidin-4-yl}ethyl)-8-azabicyclo[3.2.1]oct-3-yl]-2-methyl-1H-benzimidazole

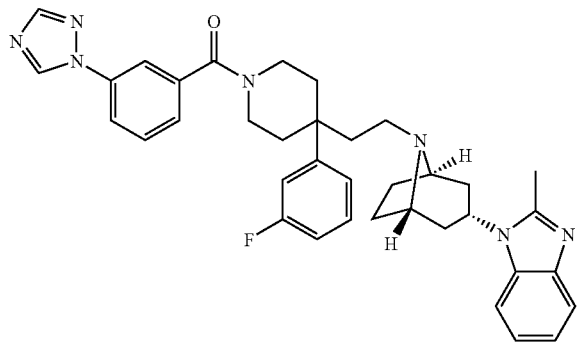

1-[(1R,5S)-8-(2-{4-(3-fluorophenyl)-1-[3-(1H-1,2,4-triazol-1-yl)benzoyl]piperidin-4-yl}ethyl)-8-azabicyclo[3.2.1]oct-3-yl]-2-methyl-1H-benzimidazole (89 mg, 47%) was obtained as a solid from 3-(1H-1,2,4-triazol-1-yl)benzoic acid (107 mg, 0.56 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (160 mg, 0.31 mmol) and HATU (176 mg, 0.46 mmol) following the procedure outlined in example 5. $^1$H NMR (400 MHz, CDCl$_3$), δ 8.58 (s, 1H), 8.11 (5, 1H), 7.77-7.72 (m, 2H), 7.67 (d, 1H, J=7.9 Hz), 7.56 (t, 1H, J=7.8 Hz), 7.43-7.24 (m, 3H), 7.17 (m, 2H), 7.09 (d, 1H, J=7.7 Hz), 7.04-6.94 (m, 2H), 4.61 (m, 1H), 4.19 (m, 1H), 3.60 (m, 1H), 3.47-3.17 (m, 3H), 2.56 (s, 3H), 2.43-2.26 (m, 3H), 2.13 (m, 1H), 2.02-1.55 (m, 12H); ESI-MS 618 (M+H).

Example 945

Preparation of 2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)propanoic acid

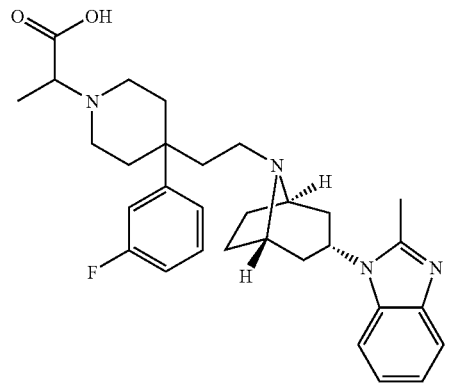

To a −78° C. solution of benzyl 2-hydroxypropanoate (250 mg, 1.39 mmol) and 4A molecular sieves in 2 mL CH$_2$Cl$_2$ was added trifluoromethanesulfonic anhydride (0.33 mL, 1.97 mmol). After stirring for 10 min at this temperature, 2,6-lutidine (0.31 mL, 2.62 mmol) was added. After 15 min, diisopropylethylamine (0.46 mL, 2.62 mmol) was added and after another 15 min, a solution of 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (400 mg, 0.66 mmol) in 3 mL CH$_2$Cl$_2$ was added. The reaction mixture was stirred at −78° C., then allowed to warm to room temperature overnight, washed with saturated aqueous NaHCO$_3$, and purified by chromatography (3% (2M NH$_3$/MeOH) in CHCl$_3$) to provide benzyl 2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)propanoate (146 mg, 37%) as a solid. $^1$H NMR (400 MHz, CDCl$_3$), δ 7.68 (m, 1H), 7.37-7.26 (m, 7H), 7.22-7.13 (m, 2H), 7.08 (m, 1H), 6.98 (m, 1H), 6.92 (m, 1H), 5.09 (s, 2H), 4.62 (m, 1H), 3.39-3.17 (m, 2H), 2.89-1.26 (m, 27H); ESI-MS 609 (M+H).

A solution of benzyl 2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)propanoate (136 mg, 0.223 mmol) in 8 mL MeOH was stirred for 3 h under an atmospheric pressure of hydrogen and in the presence of catalytic 5% Pd/C. Filtration and evaporation afforded 2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)propanoic acid (90.0 mg, 78%) as a solid. $^1$H NMR (400 MHz, CDCl$_3$), δ 7.69 (m, 1H), 7.40 (m, 1H), 7.26-7.12 (m, 4H), 7.09-6.95 (m, 2H), 5.37 (m, 1H), 3.85-3.55 (m, 5H), 2.81-1.77 (18H), 2.62 (s, 3H), 1.61-1.41 (3H); ESI-MS 517 (M−H).

Example 946

Preparation of 2-cyclohexyl-2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-N-methylacetamide

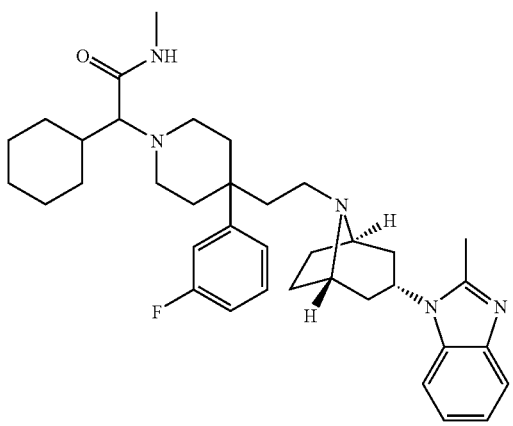

Preparation of cyclohexyl(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetic acid. To a −78° C. solution of benzyl cyclohexyl(hydroxy)acetate (61 mg, 0.25 mmol) and 4A molecular sieves in 1.2 mL $CH_2Cl_2$ was added trifluoromethanesulfonic anhydride (0.05 mL, 0.30 mmol). After stirring for 10 min at this temperature, 2,6-lutidine (0.06 mL, 0.49 mmol) was added. After 15 min, diisopropylethylamine (0.09 mL, 0.49 mmol) was added and after another 15 min, a solution of 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (153 mg, 0.30 mmol) in 1 mL $CH_2Cl_2$ was added. The reaction mixture was stirred at −78° C., then allowed to warm to room temperature overnight, washed with saturated aqueous $NaHCO_3$, and purified by preparatory TLC using 5% MeOH in $CHCl_3$ to afford benzyl cyclohexyl(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetate (33 mg, 20%) as an oil. $^1H$ NMR (400 MHz, $CDCl_3$), δ 7.68-7.64 (m, 1H), 7.33-7.23 (m, 7H), 7.20-7.12 (m, 2H), 7.05 (m, 1H), 6.97 (m, 1H), 6.89 (m, 1H), 5.05 ($AB_q$, 2H, J=12.3 Hz), 4.61 (m, 1H), 3.26-3.18 (m, 2H), 2.92 (d, 1H, J=10.4 Hz), 2.70 (m, 1H), 2.64-2.50 (m, 2H), 2.57 (s, 3H), 2.46-2.30 (m, 3H), 2.12-0.81 (m, 25H); ESI-MS 677 (M+H).

A solution of benzyl cyclohexyl(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetate (23.8 mg, 0.035 mmol) in 3 mL MeOH was stirred for 3 h under an atmospheric pressure of hydrogen and in the presence of catalytic 5% Pd/C. Filtration and evaporation afforded cyclohexyl(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetic acid (17.5 mg, 85%). ESI-MS 585 (M−H).

To a solution of cyclohexyl(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetic acid (22.0 mg, 0.037 mmol), methylamine (0.056 mL of a 2M solution in THF, 0.11 mmol), N-hydroxybenzotriazole (10.1 mg, 0.075 mmol) and N-methylmorpholine (0.10 mL, 0.094 mmol) in 1 mL DMF was added EDC (14 mg, 0.075 mmol). The reaction mixture was stirred for 24 h, then diluted with 4:1 EtOAc:hex and washed with saturated aqueous $NaHCO_3$, dried ($Na_2SO_4$) and chromatographed (5% (2M $NH_3$/MeOH) in $CHCl_3$) to provide 2-cyclohexyl-2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-N-methylacetamide (8.1 mg, 36%) as a solid. $^1H$ NMR (400 MHz, $CDCl_3$), δ 7.66 (m, 1H), 7.33-7.27 (m, 2H), 7.20-7.11 (m, 2H), 7.05 (m, 1H), 6.98 (m, 1H), 6.90 (m, 1H), 4.64 (m, 1H), 3.33-3.20 (m, 2H), 2.80 (d, 3H, J=4.9 Hz), 2.59 (s, 3H), 2.47-0.79 (m, 27H); ESI-MS 600 (M+H).

Example 947

Preparation of 2-cyclohexyl-2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetamide

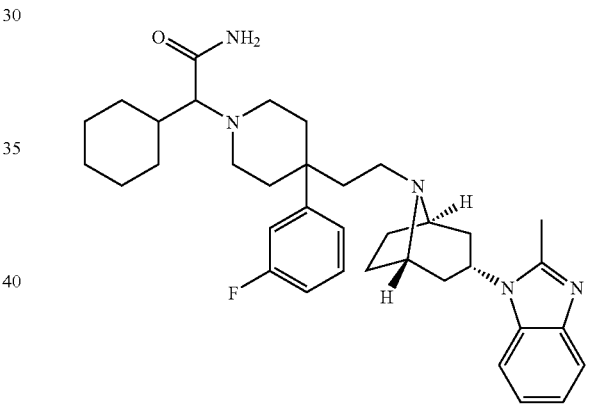

To a solution of cyclohexyl(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetic acid (22.0 mg, 0.037 mmol), hydroxylamine (0.2 mL of a 28% solution in water, 3.3 mmol), N-hydroxybenzotriazole (10.1 mg, 0.075 mmol) and N-methylmorpholine (0.10 mL, 0.094 mmol) in 1 mL DMF was added EDC (14 mg, 0.075 mmol). The reaction mixture was stirred for 24 h, then diluted with 4:1 EtOAc:hex and washed with saturated aqueous $NaHCO_3$, dried ($Na_2SO_4$) and chromatographed (5% (2M $NH_3$/MeOH) in $CHCl_3$) to provide 2-cyclohexyl-2-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)acetamide (7.7 mg, 35%) as a solid. $^1H$ NMR (400 MHz, $CDCl_3$), δ 7.66 (m, 1H), 7.34-7.27 (m, 2H), 7.20-7.12 (m, 2H), 7.06 (m, 1H), 6.99 (m, 1H), 6.90 (m, 1H), 4.61 (m, 1H), 3.27-3.19 (m, 2H), 2.73-2.62 (m, 2H), 2.58 (s, 3H), 2.47-0.78 (m, 27H); ESI-MS 589 (M+H).

Example 948

Preparation of 2-chloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methylbenzenesulfonamide

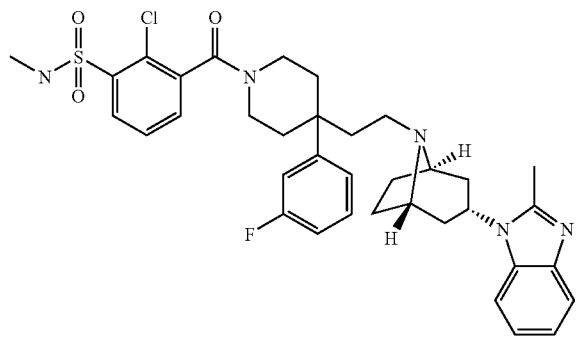

Preparation of 2-chloro-3-[(methylamino)sulfonyl]benzoic acid. To a solution of methyl 2-chloro-3-(chlorosulfonyl)benzoate (608 mg, 2.26 mmol) and $K_2CO_3$ (770 mg, 5.6 mmol) in 10 mL benzene was added a 2M solution of methylamine in THF (5.6 mL, 11.2 mmol). Purification of the product (2:1 hex:EtOAc) provided methyl 2-chloro-3-[(methylamino)sulfonyl]benzoate (430 mg, 72%) as a solid. $^1$H NMR (400 MHz, CDCl$_3$), δ 8.23 (dd, 1H, J=7.9, 1.7 Hz), 7.90 (dd, 1H, J=7.8, 1.7 Hz), 7.48 (t, 1H, J=7.9 Hz), 5.16 (q, 1H, J=5.2 Hz), 3.94 (s, 3H), 2.62 (d, 3H, J=5.3 Hz); ESI-MS 264 (M+H). Methyl 2-chloro-3-[(methylamino)sulfonyl]benzoate was hydrolyzed using aqueous NaOH to provide 2-chloro-3-[(methylamino)sulfonyl]benzoic acid as a solid, which was used without further purification. ESI-MS 250 (M+H), 272 (M+Na).

2-chloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-N-methylbenzenesulfonamide (87 mg, 62%) was obtained as a solid from 2-chloro-3-[(methylamino)sulfonyl]benzoic acid (52 mg, 0.21 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (127 mg, 0.21 mmol) and HATU (87 mg, 0.23 mmol) following the procedure outlined in example 5. $^1$H NMR (400 MHz, CDCl$_3$), δ 8.40 (m, 1H), 7.62 (m, 1H), 7.53-7.28 (m, 4H), 7.13 (m, 2H), 7.04 (m, 1H), 6.99-6.90 (m, 2H), 5.92-5.59 (m, 2H), 4.60 (m, 1H), 4.2 (m, 1H), 3.42-3.03 (m, 6H), 2.63-2.58 (m, 3H, rotamers), 2.54 (s, 1.5H, rotamer), 2.52 (5, 1.5H, rotamer), 2.41-2.23 (m, 3H), 2.17-1.58 (m, 11H); ESI-MS 678 (M+H).

Example 949

Preparation of 3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropan-1-ol

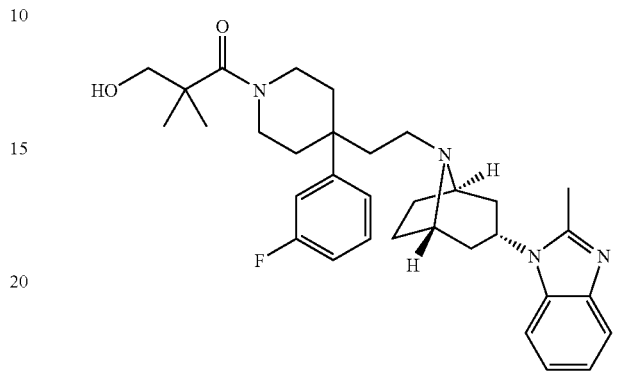

3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropan-1-ol (63 mg, 88%) was obtained as a solid from 3-hydroxy-2,2-dimethylpropanoic acid (23 mg, 0.20 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (80 mg, 0.13 mmol) and HATU (75 mg, 0.20 mmol) following the procedure outlined in example 5. $^1$H NMR (400 MHz, CDCl$_3$), δ 7.67-7.63 (m, 1H), 7.38-7.28 (m, 2H), 7.15 (m, 2H), 7.08 (m, 1H), 7.02-6.92 (m, 2H), 4.60 (m, 1H), 3.90 (m, 2H), 3.72 (m, 1H), 3.45 (m, 2H), 3.25 (m, 4H), 2.57 (s, 3H), 2.37 (m, 2H), 2.19 (m, 2H), 1.99-1.85 (m, 6H), 1.85-1.74 (m, 4H), 1.63 (m, 2H), 1.26 (s, 6H); ESI-MS 547 (M+H).

Example 950

Preparation of N-[3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropyl]methanesulfonamide

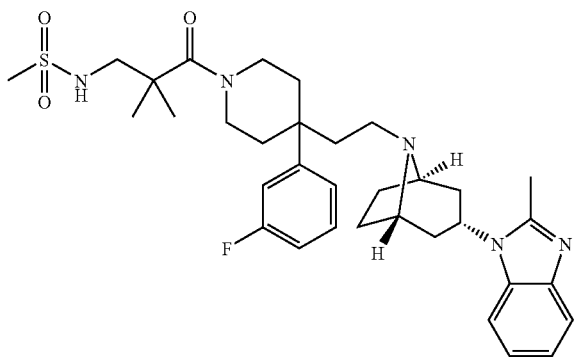

Preparation of 2,2-dimethyl-3-[(methylsulfonyl)amino]propanoic acid. To a solution of methyl 3-amino-2,2-dimethylpropanoate (249 mg, 1.90 mmol) and Et₃N (0.80 mL, 5.70 mmol) in 2 mL CH₂Cl₂ was added methanesulfonyl chloride (0.29 mL, 3.80 mmol). The reaction was stirred for 2 days, quenched by the addition of saturated aqueous NaHCO₃, extracted with CHCl₃, and chromatographed (1:1 hex:EtOAc) to provide methyl 2,2-dimethyl-3-[(methylsulfonyl)amino]propanoate (124 mg, 31%) as a clear oil. ¹H NMR (400 MHz, CDCl₃), 4.95 (t, 1H, J=6.8 Hz), 3.69 (s, 3H), 3.16 (d, 2H, J=6.8 Hz), 2.95 (s, 3H), 1.24 (s, 6H). Methyl 2,2-dimethyl-3-[(methylsulfonyl)amino]propanoate was hydrolyzed using aqueous NaOH to provide 2,2-dimethyl-3-[(methylsulfonyl)amino]propanoic acid, which was used without further purification. ¹H NMR (400 MHz, CDCl₃), δ 10.28 (br. s, 1H), 5.56 (br. s, 1H), 3.14 (s, 2H), 2.94 (s, 3H), 1.25 (5, 6H).

N-[3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropyl]methanesulfonamide (41 mg, 48%) was obtained as a solid from 2,2-dimethyl-3-[(methylsulfonyl)amino]propanoic acid (38 mg, 0.20 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. ¹H NMR (400 MHz, CDCl₃), δ 7.63 (m, 1H), 7.34 (m, 1H), 7.28 (m, 1H), 7.14 (m, 2H), 7.06 (m, 1H), 6.99 (m, 1H), 6.94 (m, 1H), 5.52 (t, 1H, J=6.8 Hz), 4.63 (m, 1H), 3.89 (m, 2H), 3.24 (m, 4H), 3.08 (d, 2H, J=6.8 Hz), 2.93 (s, 3H), 2.56 (s, 3H), 2.37 (m, 2H), 2.18 (m, 2H), 1.92 (m, 6H), 1.78 (m, 4H), 1.64 (m, 2H), 1.32 (s, 6H); ESI-MS 624 (M+H).

Example 951

Preparation of N-{2,6-dichloro-4-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl)}-1,1,1-trifluoromethanesulfonamide

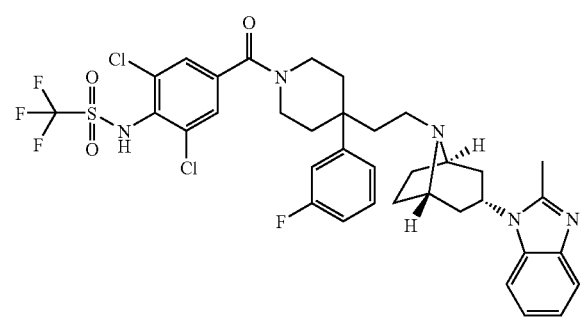

N-{2,6-dichloro-4-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}-1,1,1-trifluoromethanesulfonamide (63 mg, 60%) was obtained as an oil from 3,5-dichloro-4-{[(trifluoromethyl)sulfonyl]amino}benzoic acid (70 mg, 0.21 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. ¹H NMR (400 MHz, CDCl₃), δ 7.68-7.64 (m, 1H), 7.37-7.25 (m, 4H), 7.18 (m, 2H), 7.08 (m, 1H), 7.01-6.90 (m, 2H), 5.17 (m, 1H), 4.02 (m, 1H), 3.52 (m, 1H), 3.30 (m, 2H), 2.64 (5, 3H), 2.56 (m, 2H), 2.23-1.69 (m, 13H); ESI-MS 766 (M+H).

Example 952

Preparation of N-{2-chloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}-1,1,1-trifluoromethanesulfonamide

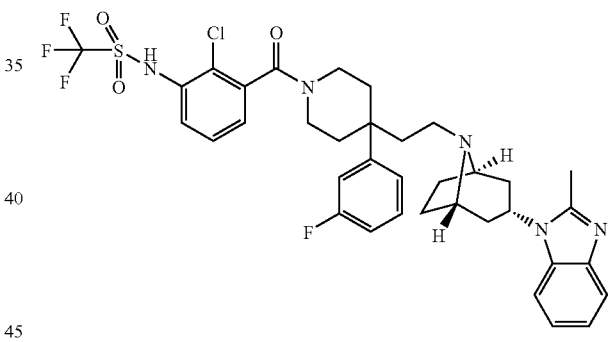

N-{2-chloro-3-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}-1,1,1-trifluoromethanesulfonamide (12 mg, 12%) was obtained as a solid from 2-chloro-3-{[(trifluoromethyl)sulfonyl]amino}benzoic acid (66 mg, 0.22 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. ¹H NMR (400 MHz, CDCl₃), δ 7.70-7.64 (m, 1H), 7.58 (m, 1H), 7.42-7.28 (m, 2H), 7.25-6.92 (m, 5H), 6.88-6.74 (m, 2H), 5.00-4.70 (m, 1H), 4.32-4.00 (m, 1H), 3.75-3.00 (m, 5H), 2.58 (s, 3H), 2.32-1.20 (m, 17H); ESI-MS 732 (M+H).

Example 953

Preparation of 1-((1R,5S)-8-{2-[1-(2-chloro-4-fluoro-5-nitrobenzoyl)-4-(3-fluorophenyl)piperidin-4-yl]ethyl}-8-azabicyclo[3.2.1]oct-3-yl)-2-methyl-1H-benzimidazole

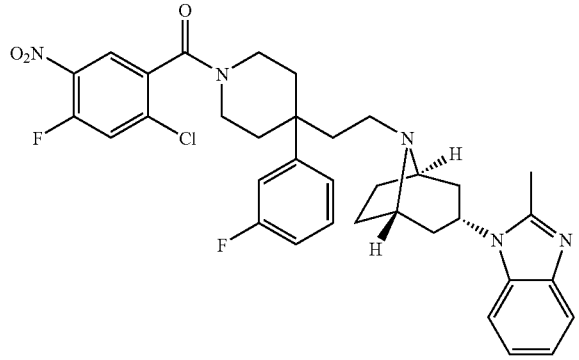

1-((1R,5S)-8-{2-[1-(2-chloro-4-fluoro-5-nitrobenzoyl)-4-(3-fluorophenyl)piperidin-4-yl]ethyl}-8-azabicyclo[3.2.1]oct-3-yl)-2-methyl-1H-benzimidazole (14 mg, 16%) was obtained as an oil from 2-chloro-4-fluoro-5-nitrobenzoic acid (39 mg, 0.18 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. $^1$H NMR (400 MHz, CDCl$_3$), δ 7.66 (m, 1H), 7.43-7.27 (m, 3H), 7.16 (m, 2H), 7.07 (m, 1H), 7.03-6.93 (m, 3H), 4.62 (m, 1H), 4.24 (m, 1H), 3.46-3.07 (m, 6H), 2.57 (s, 3H), 2.44-1.59 (m, 15H); ESI-MS 648 (M+H).

Example 954

Preparation of N-{2,6-dichloro-4-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}methanesulfonamide

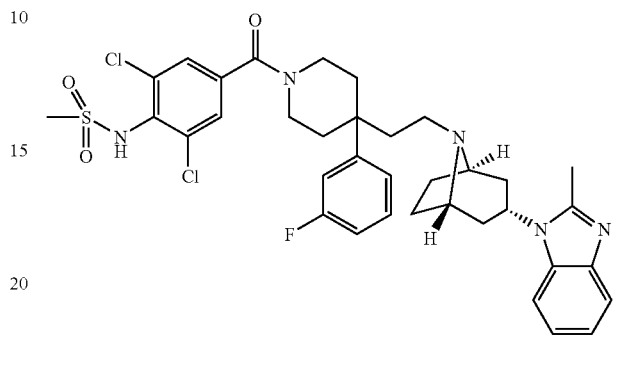

N-{2,6-dichloro-4-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]phenyl}methanesulfonamide (28 mg, 28%) was obtained as a solid from 3,5-dichloro-4-[(methylsulfonyl)amino]benzoic acid (59 mg, 0.21 mmol), 1-((1R,5S)-8-{2-[4-(3-fluorophenyl)piperidin-4-yl]ethyl}-8-azabicyclo[3.2.1]oct-3-yl)-2-methyl-1H-benzimidazole dihydrochloride (83 mg, 0.14 mmol) and HATU (75 mg, 0.20 mmol) following the procedure outlined in example 5. $^1$H NMR (400 MHz, CDCl$_3$), δ 7.62 (m, 1H), 7.37-7.22 (m, 3H), 7.13 (m, 2H), 7.05 (m, 1H), 7.01-6.88 (m, 3H), 4.58 (m, 1H), 4.12 (m, 1H), 3.55-3.22 (m, 5H), 3.21 (m, 3H, rotamers), 2.53 (m, 3H, rotamers), 2.41-1.56 (m, 15H); ESI-MS 712 (M+H)

Additional examples of a the formula below were generated by coupling acids listed in the table using method A in example 5.

| Example | % Yield | Acid | Method used | Observed mass (M + 1) |
|---|---|---|---|---|
| 958 | | 3-amino-1H-pyrazole-4-carboxylic acid | A | 556 |
| 959 | 47 | 3-chloro-5-methylisoxazole-4-carboxylic acid | A | 572 |
| 960 | 53 | 2-(hydroxymethyl)-1H-benzimidazole-6-carboxylic acid | A | 603 |

-continued
| Example | % Yield | Acid | Method used | Observed mass (M + 1) |
|---|---|---|---|---|
| 961 | 45 | 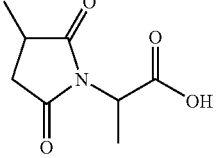 | A | 596 |
| 962 | 28 | 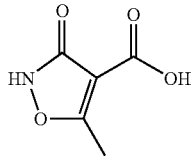 | A | 554 |
| 963 | 57 | 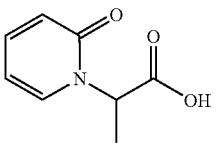 | A | 578 |
| 964 | 59 | 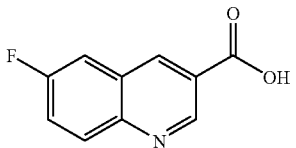 | A | 602 |
| 965 | 30 | 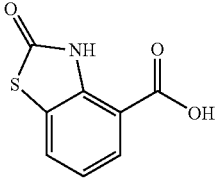 | A | 606 |
| 966 | 46 | 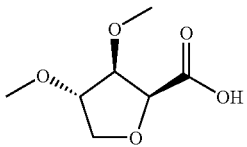 | A | 587 |
| 967 | 57 | 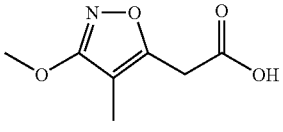 | A | 582 |
| 968 | 40 | 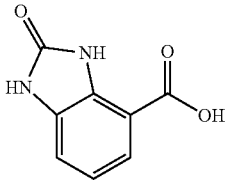 | A | 589 |
| 969 | 43 | 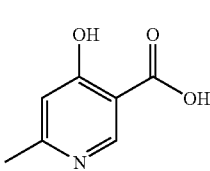 | A | 564 |

-continued

| Example | % Yield | Acid | Method used | Observed mass (M + 1) |
|---------|---------|------|-------------|------------------------|
| 970 | 40 | 4-(2-methoxyethoxy)benzoic acid | A | 607 |
| 971 | 44 | 1-(2-cyanoethyl)-5-oxopyrrolidine-3-carboxylic acid | A | 593 |
| 972 | 54 | 2-cyclohexyl-2-methylpropanoic acid | A | 581 |
| 973 | 54 | 2,4-dimethyloxazole-5-carboxylic acid | A | 552 |
| 974 | 42 | 5-oxo-5H-thiazolo[3,2-a]pyrimidine-6-carboxylic acid | A | 607 |
| 975 | 48 | 5-chloro-2-methylpyrimidine-4-carboxylic acid | A | 583 |
| 976 | 28 | oxazole-4-carboxylic acid | A | 524 |
| 977 | 54 | 2-(3-methoxy-2-oxopyridin-1(2H)-yl)propanoic acid | A | 608 |
| 978 | 45 | 2-propylthiazole-5-carboxylic acid | A | 582 |

-continued

| Example | % Yield | Acid | Method used | Observed mass (M + 1) |
|---------|---------|------|-------------|----------------------|
| 979 | 51 | pyrrole-2-carbonyl-NH-CH(CH₃)-CH₂-COOH | A | 607 |
| 980 | 47 | benzisoxazole-4-carboxylic acid | A | 574 |
| 981 | 31 | 2-oxo-1,2-dihydroquinoline-8-carboxylic acid | A | 600 |
| 982 | 31 | 2-acetamido-6-hydroxybenzoic acid | A | 606 |
| 983 | 16 | 3-cyanopyridine-2-carboxylic acid | A | 559 |
| 984 | 38 | 1-ethyl-5-methyl-1H-pyrazole-3-carboxylic acid | A | 565 |
| 985 | 42 | 2-(piperidin-1-yl)-2-oxoacetic acid | A | 568 |
| 986 | 21 | 2-(1H-1,2,3-triazol-1-yl)acetic acid | A | 538 |
| 987 | 34 | 5-(trifluoromethyl)picolinic acid | A | 602 |

-continued
| Example | % Yield | Acid | Method used | Observed mass (M + 1) |
|---|---|---|---|---|
| 988 | 40 | 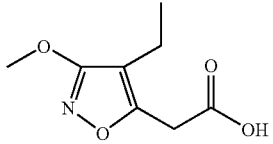 | A | 596 |
| 989 | 20 | 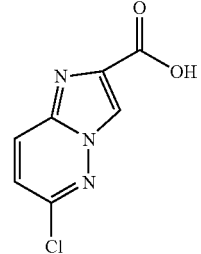 | A | 608 |
| 990 | 55 | 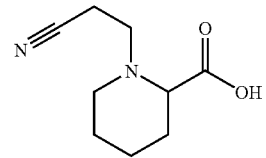 | A | 593 |
| 991 | 46 | 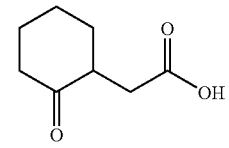 | A | 567 |
| 992 | 49 | 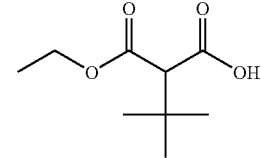 | A | 599 |
| 993 | 32 | 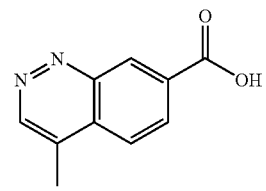 | A | 599 |
| 994 | 45 | 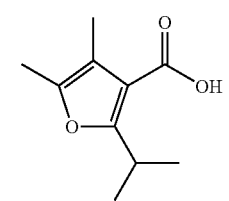 | A | 593 |

-continued
| Example | % Yield | Acid | Method used | Observed mass (M + 1) |
|---|---|---|---|---|
| 995 | 16 | 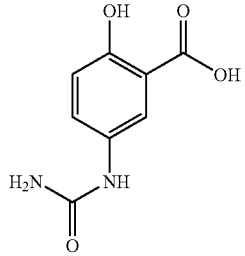 | A | 607 |
| 996 | 44 | 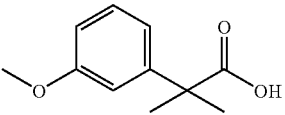 | A | 605 |
| 997 | 40 |  | A | 603 |
| 998 | 20 | 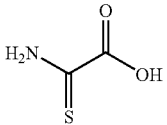 | A | 516 |
| 999 | 34 | 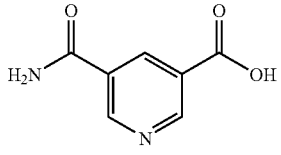 | A | 577 |
| 1000 | 33 | 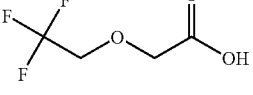 | A | 569 |
| 1001 | 29 | 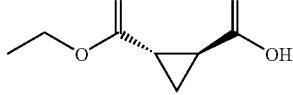 | A | 569 |
| 1002 | 45 | 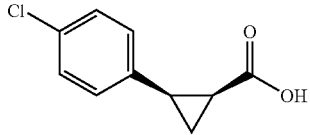 | A | 607 |
| 1003 | 43 | 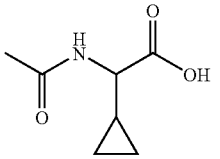 | A | 568 |

-continued

| Example | % Yield | Acid | Method used | Observed mass (M + 1) |
|---|---|---|---|---|
| 1004 | 45 | 1-hydroxycyclohexyl-butanoic acid | A | 597 |
| 1005 | 42 | trans-2-(4-methoxyphenyl)cyclopropanecarboxylic acid | A | 603 |
| 1006 | 16 | 2-(dimethylamino)-6-hydroxy-5-methylpyrimidine-4-carboxylic acid | A | 608 |
| 1007 | 18 | 3-methyl-2,4-dioxo-1,2,3,4-tetrahydropyrimidine-5-carboxylic acid | A | 581 |
| 1008 | 21 | 2-acetamido-2-methylbutanoic acid | A | 570 |
| 1009 | 34 | 2-acetylnicotinic acid | A | 576 |
| 1010 | 43 | 2-(2-oxooctahydro-1H-indol-7-yl)acetic acid | A | 608 |
| 1011 | | 2,2-dimethyl-3-oxo-3-(3-(trifluoromethyl)phenylsulfonamido)propanoic acid | A | 768 |

-continued

| Example | % Yield | Acid | Method used | Observed mass (M + 1) |
|---|---|---|---|---|
| 1012 | | ![phenylsulfonyl dimethylmalonic acid amide] | A | 700 |
| 1013 | | ![4-trifluoromethylphenylsulfonyl dimethylmalonic acid amide] | A | 768 |
| 1014 | | ![4-hydroxy-1,2,5-thiadiazole-3-carboxylic acid] | A | 575 |

Example 958

4-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-1H-pyrazol-3-amine Example 959

1-[(1R,5S)-8-(2-{1-[(3-chloro-5-methylisoxazol-4-yl)carbonyl]-4-phenylpiperidin-4-yl}ethyl)-8-azabicyclo[3.2.1]oct-3-yl]-2-methyl-1H-benzimidazole

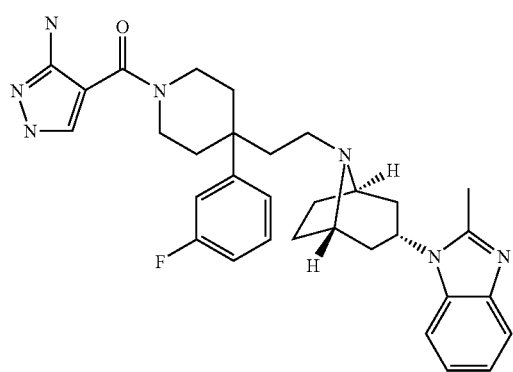

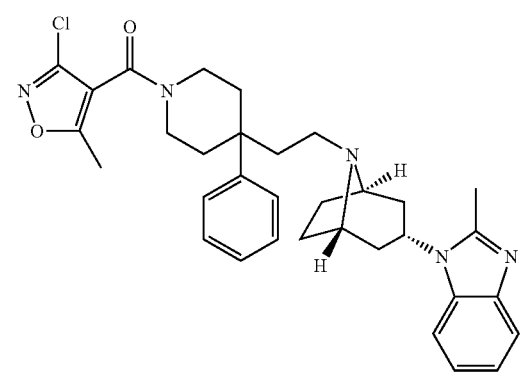

Example 960

{6-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1H-benzimidazol-2-yl}methanol

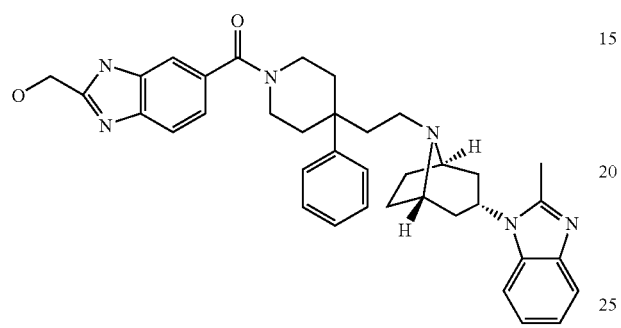

Example 961

3-methyl-1-[1-methyl-2-(4-{2-[(1R,5S)-3-(2-methyl-1H-benzimidazol-1-yl)-8-azabicyclo[3.2.1]oct-8-yl]ethyl}-4-phenylpiperidin-1-yl)-2-oxoethyl]pyrrolidine-2,5-dione

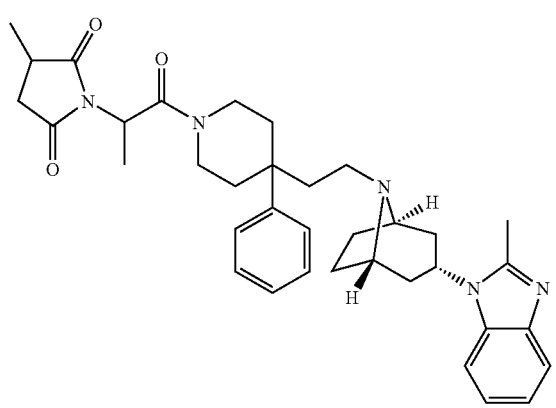

Example 962

5-methyl-4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]isoxazol-3(2H)-one

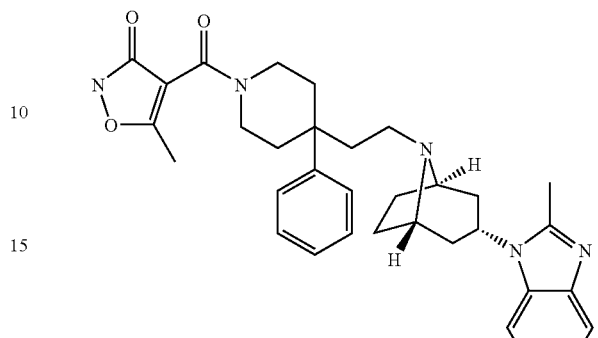

Example 963

1-[1-methyl-2-(4-{2-[(1R,5S)-3-(2-methyl-1H-benzimidazol-1-yl)-8-azabicyclo[3.2.1]oct-8-yl]ethyl}-4-phenylpiperidin-1-yl)-2-oxoethyl]pyridin-2(1H)-one

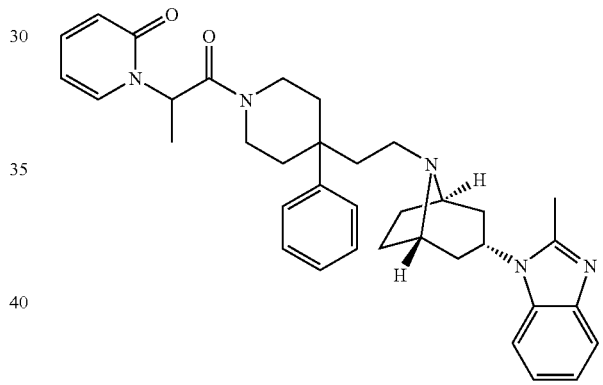

Example 964

6-fluoro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]quinoline

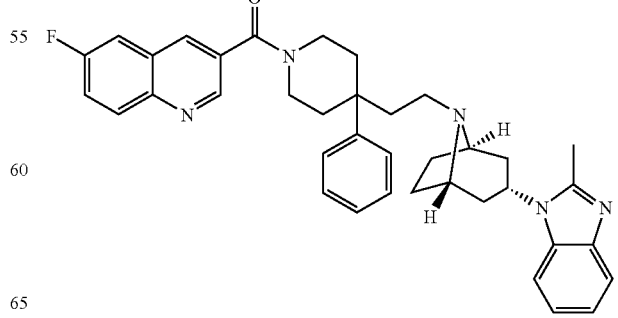

Example 965

4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbnyl]-1,3-benzothiazol-2(3H)-one

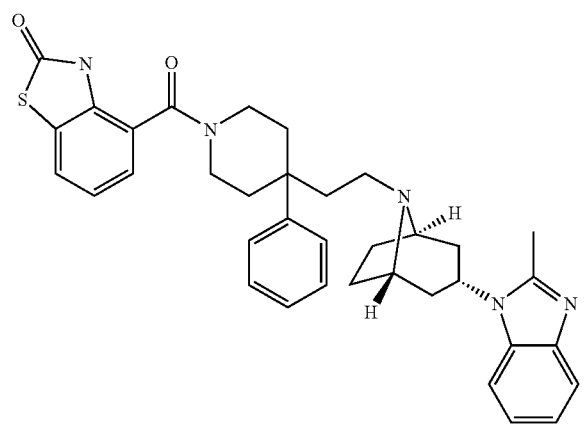

Example 966

1-((1R,5S)-8-{2-[1-((3S,4S)-3,4-dimethoxy-(2S)-tetrahydrofuran-2-carbonyl)-4-phenylpiperidin-4-yl]ethyl}-8-azabicyclo[3.2.1]oct-3-yl)-2-methyl-1H-benzimidazole

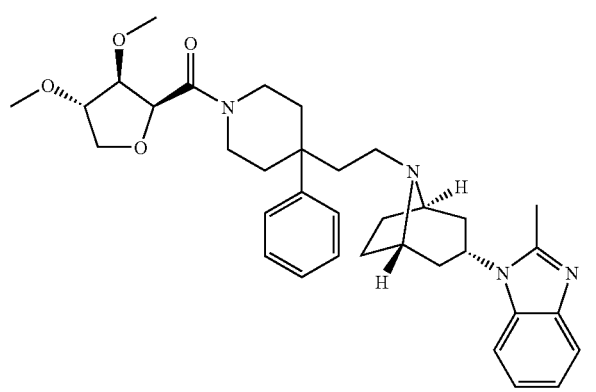

Example 967

1-[(1R,5S)-8-(2-{1-[(3-methoxy-4-methylisoxazol-5-yl)acetyl]-4-phenylpiperidin-4-yl}ethyl)-8-azabicyclo[3.2.1]oct-3-yl]-2-methyl-1H-benzimidazole

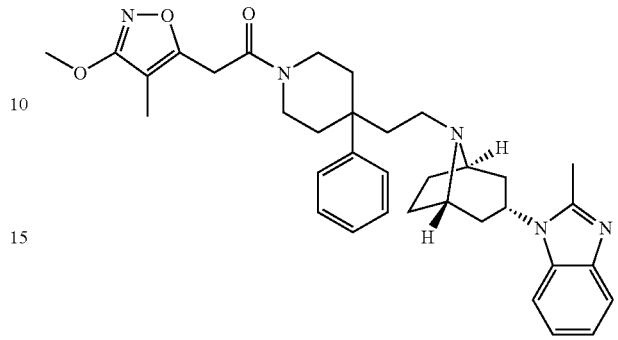

Example 968

4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1,3-dihydro-2H-benzimidazol-2-one

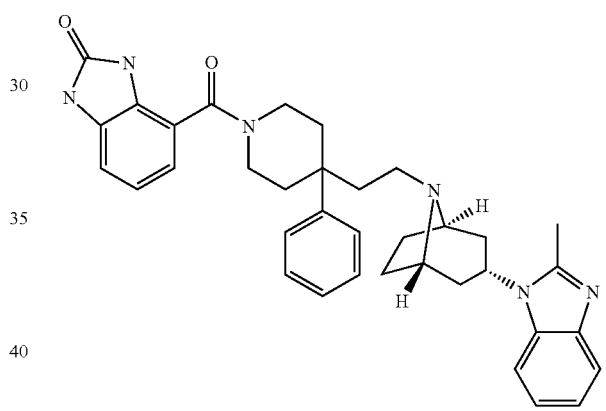

Example 969

2-methyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-4-ol

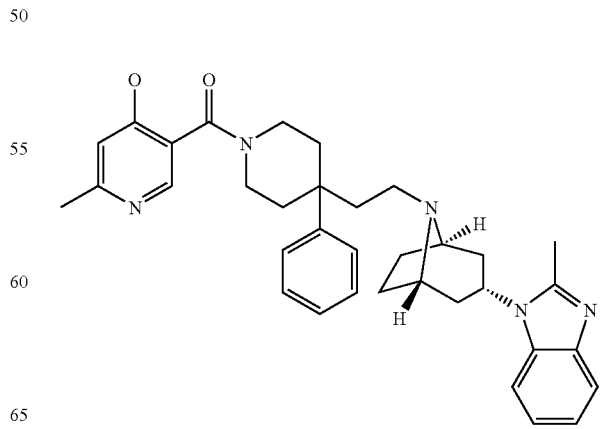

Example 970

1-[(1R,5S)-8-(2-{1-[4-(2-methoxyethoxy)benzoyl]-4-phenylpiperidin-4-yl}ethyl)-8-azabicyclo[3.2.1]oct-3-yl]-2-methyl-1H-benzimidazole

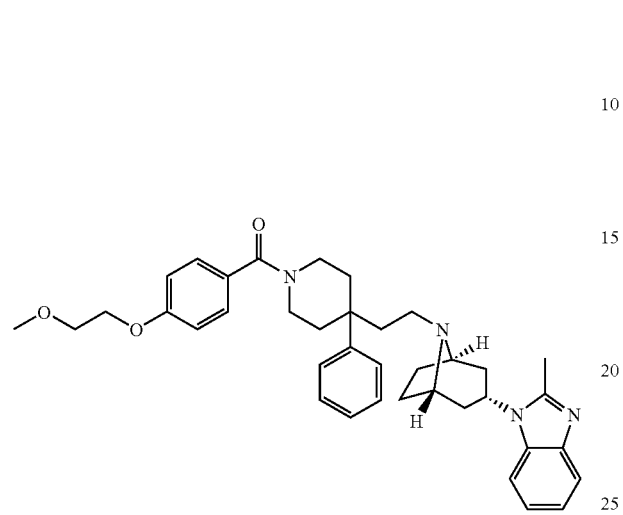

Example 971

3-{4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-2-oxopyrrolidin-1-yl}propanenitrile

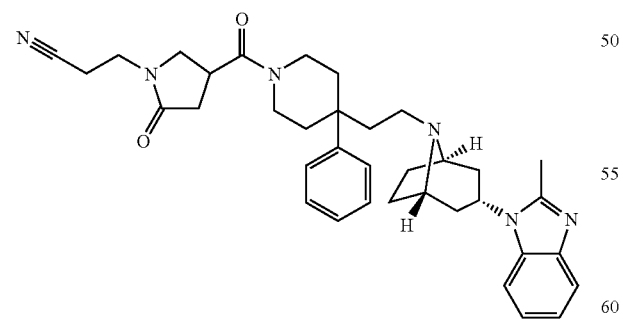

Example 972

1-((1R,5S)-8-{2-[1-(2-cyclohexyl-2-methylpropanoyl)-4-phenylpiperidin-4-yl]ethyl}-8-azabicyclo[3.2.1]oct-3-yl)-2-methyl-1H-benzimidazole

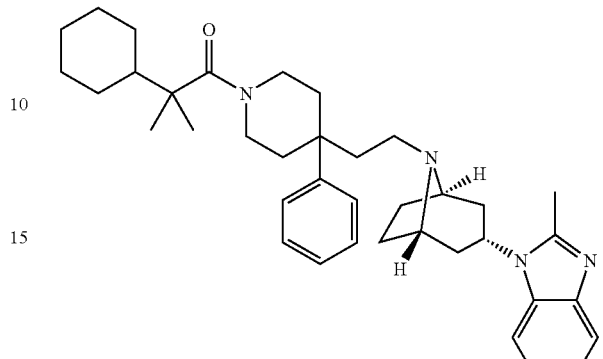

Example 973

1-[(1R,5S)-8-(2-{1-[(2,4-dimethyl-1,3-oxazol-5-yl)carbonyl]-4-phenylpiperidin-4-yl}ethyl)-8-azabicyclo[3.2.1]oct-3-yl]-2-methyl-1H-benzimidazole

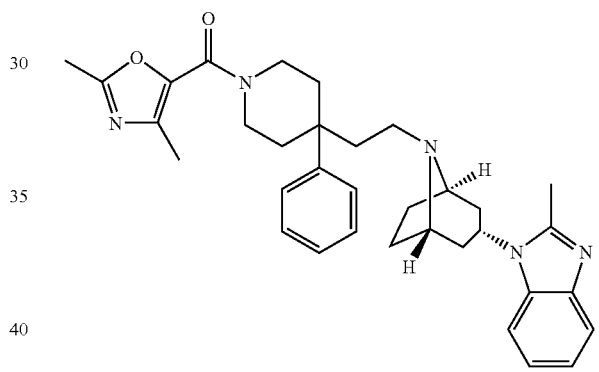

Example 974

6-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-5H-[1,3]thiazolo[3,2-a]pyrimidin-5-one

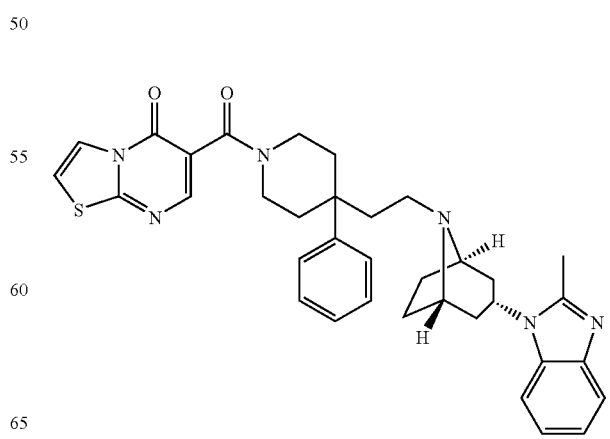

Example 975

1-[(1R,5S)-8-(2-{1-[(5-chloro-2-methylpyrimidin-4-yl)carbonyl]-4-phenylpiperidin-4-yl}ethyl)-8-azabicyclo[3.2.1]oct-3-yl]-2-methyl-1H-benzimidazole

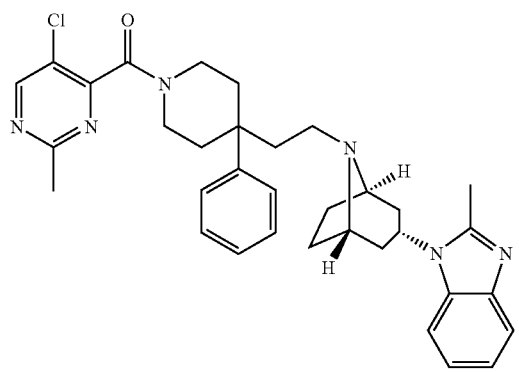

Example 976

2-methyl-1-((1R,5S)-8-{2-[1-(1,3-oxazol-4-ylcarbonyl)-4-phenylpiperidin-4-yl]ethyl}-8-azabicyclo[3.2.1]oct-3-yl)-1H-benzimidazole

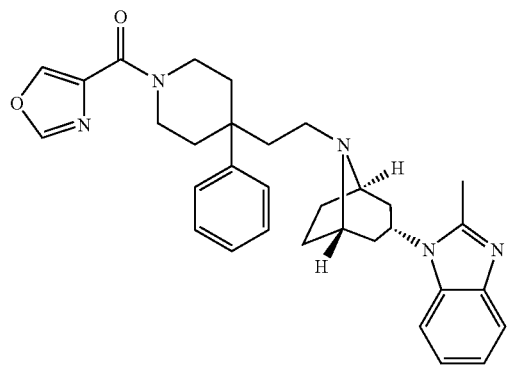

Example 977

3-methoxy-1-[1-methyl-2-(4-{2-[(1R,5S)-3-(2-methyl-1H-benzimidazol-1-yl)-8-azabicyclo[3.2.1]oct-8-yl]ethyl}-4-phenylpiperidin-1-yl)-2-oxoethyl]pyridin-2(1H)-one

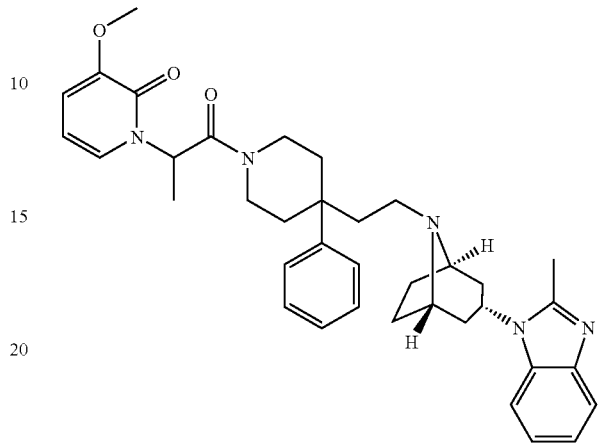

Example 978

2-methyl-1-[(1R,5S)-8-(2-{4-phenyl-1-[(2-propyl-1,3-thiazol-5-yl)carbonyl]piperidin-4-yl}ethyl)-8-azabicyclo[3.2.1]oct-3-yl]-1H-benzimidazole

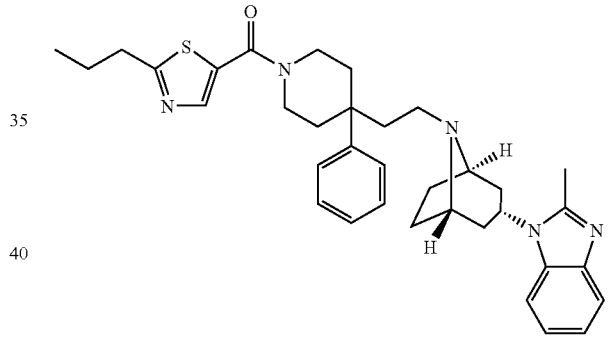

Example 979

N-[1-methyl-3-(4-{2-[(1R,5S)-3-(2-methyl-1H-benzimidazol-1-yl)-8-azabicyclo[3.2.1]oct-8-yl]ethyl}-4-phenylpiperidin-1-yl)-3-oxopropyl]-1H-pyrrole-2-carboxamide

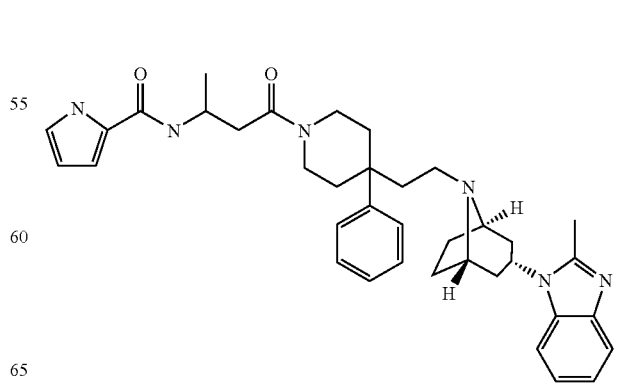

Example 980

4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-2,1-benzisoxazole

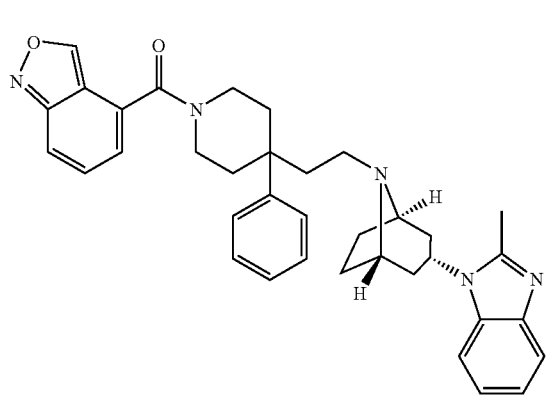

Example 981

8-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]quinolin-2(1H)-one

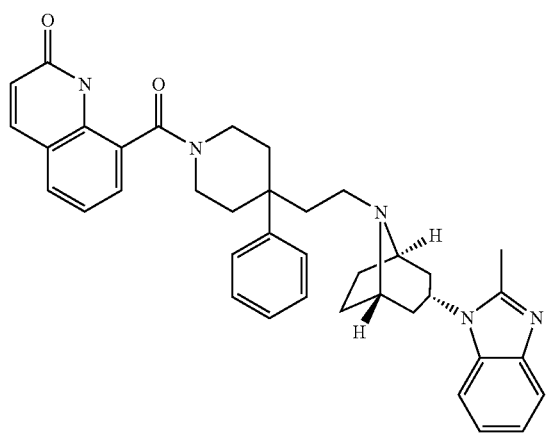

Example 982

N-{3-hydroxy-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}acetamide

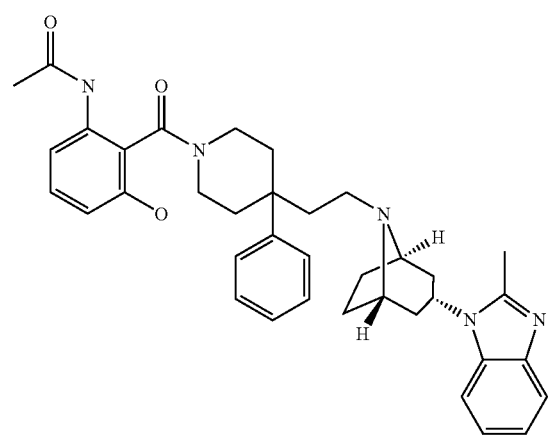

Example 983

2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]nicotinonitrile

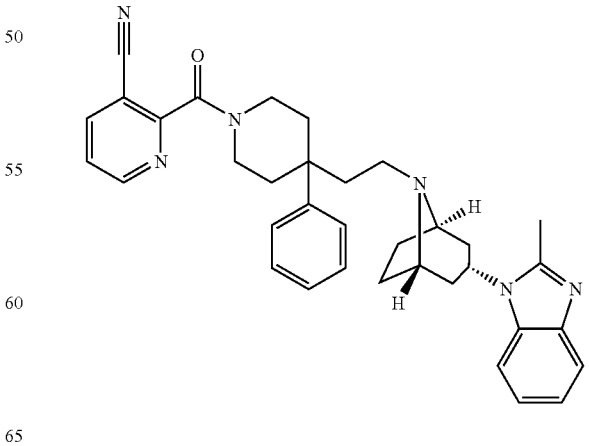

Example 984

1-[(1R,5S)-8-(2{-[(1-ethyl-5-methyl-1H-pyrazol-3-yl)carbonyl]-4-phenylpiperidin-4-yl}ethyl)-8-azabicyclo[3.2.1]oct-3-yl]-2-methyl-1H-benzimidazole

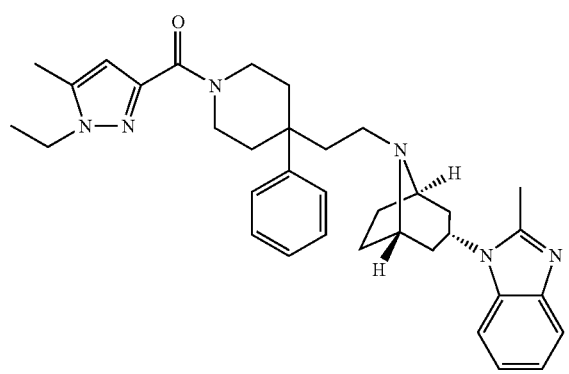

Example 985

2-methyl-1-[(1R,5S)-8-(2-{1-[oxo(piperidin-1-yl)acetyl]-4-phenylpiperidin-4-yl}ethyl)-8-azabicyclo[3.2.1]oct-3-yl]-1H-benzimidazole

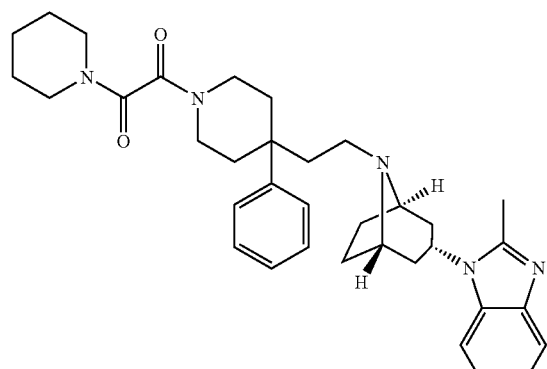

Example 986

2-methyl-1-((1R,5S)-8-{2-[4-phenyl-1-(2H-1,2,3-triazol-2-ylacetyl)piperidin-4-yl]ethyl}-8-azabicyclo[3.2.1]oct-3-yl)-1H-benzimidazole

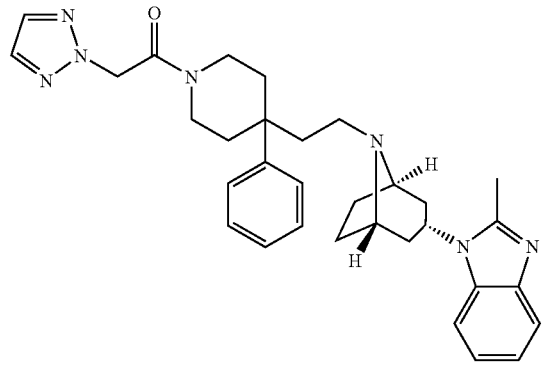

Example 987

2-methyl-1-{(1R,5S)-8-[2-(4-phenyl-1-{[5-(trifluoromethyl)pyridin-2-yl]carbonyl}piperidin-4-yl)ethyl]-8-azabicyclo[3.2.1]oct-3-yl}-1H-benzimidazole

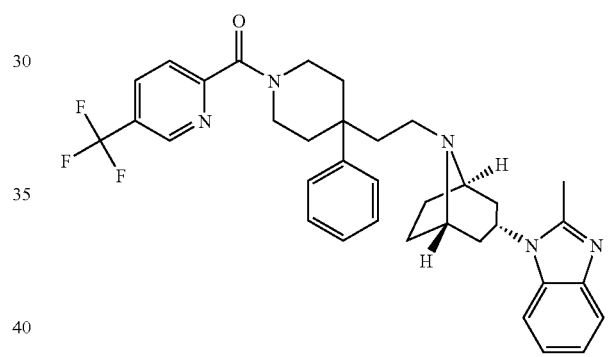

Example 988

1-[(1R,5S)-8-(2-{1-[(4-ethyl-3-methoxyisoxazol-5-yl)acetyl]-4-phenylpiperidin-4-yl}ethyl)-8-azabicyclo[3.2.1]oct-3-yl]-2-methyl-1H-benzimidazole

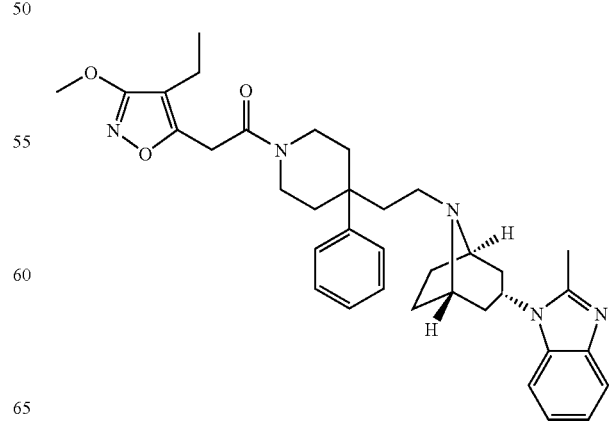

Example 989

6-chloro-2-[(4-{2-[(1R,5S)-3-(2-methyl-1H-benz-imidazol-1-yl)-8-azabicyclo[3.2.1]oct-8-yl]ethyl}-4-phenylpiperidin-1-yl)carbonyl]imidazo[1,2-b]pyridazine

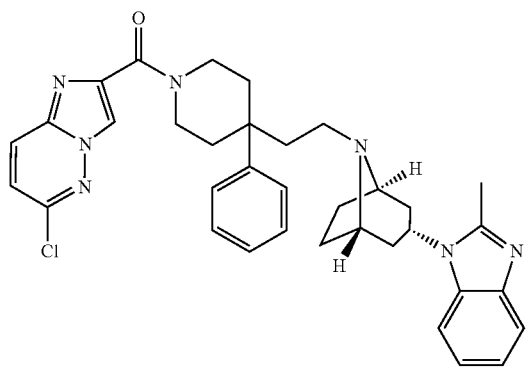

Example 990

3-{2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]piperidin-1-yl}propanenitrile

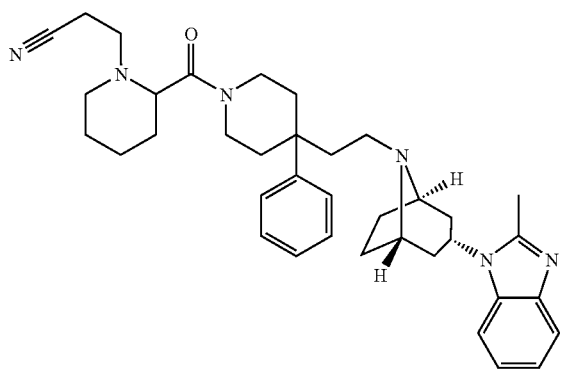

Example 991

2-[2-(4-{2-[(1R,5S)-3-(2-methyl-1H-benzimidazol-1-yl)-8-azabicyclo[3.2.1]oct-8-yl]ethyl}-4-phenylpiperidin-1-yl)-2-oxoethyl]cyclohexanone

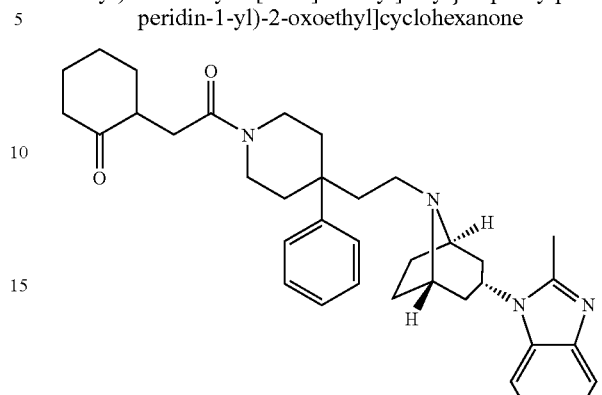

Example 992 ethyl 3,3-dimethyl-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]butanoate

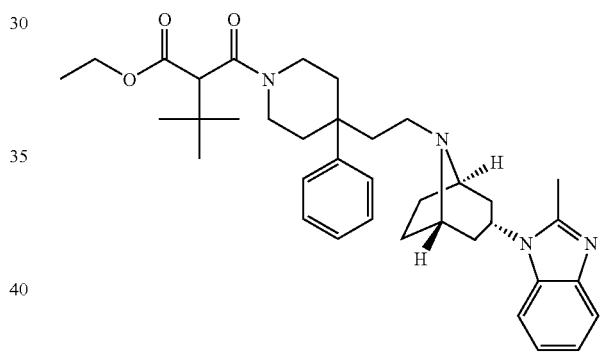

Example 993

4-methyl-7-[(4-{2-[(1R,5S)-3-(2-methyl-1H-benz-imidazol-1-yl)-8-azabicyclo[3.2.1]oct-8-yl]ethyl}-4-phenyl piperidin-1-yl)carbonyl]cinnoline

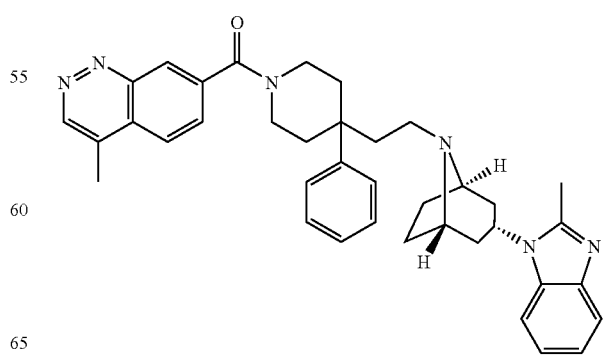

Example 994

1-((1R,5S)-8-{2-[1-(2-isopropyl-4,5-dimethyl-3-furoyl)-4-phenylpiperidin-4-yl]ethyl}-8-azabicyclo[3.2.1]oct-3-yl)-2-methyl-1H-benzimidazole

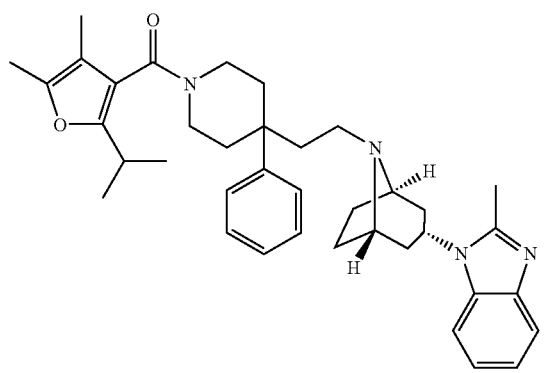

Example 995

N-{4-hydroxy-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]phenyl}urea

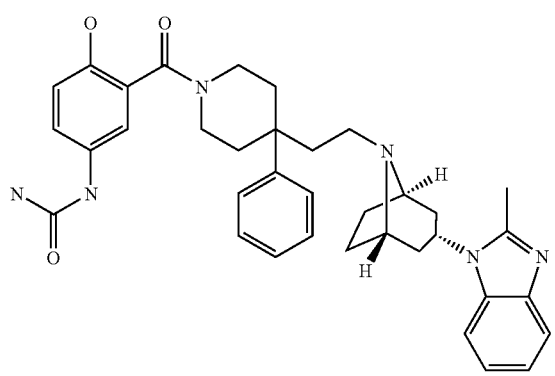

Example 996

1-[(1R,5S)-8-(2-{1-[2-(3-methoxyphenyl)-2-methylpropanoyl]-4-phenylpiperidin-4-yl}ethyl)-8-azabicyclo[3.2.1]oct-3-yl]-2-methyl-1H-benzimidazole

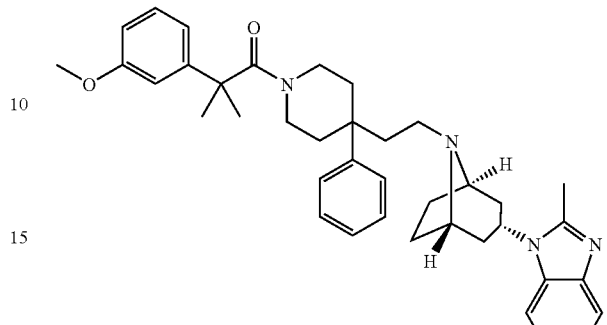

Example 997

1-methyl-4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1,3-dihydro-2H-benzimidazol-2-one

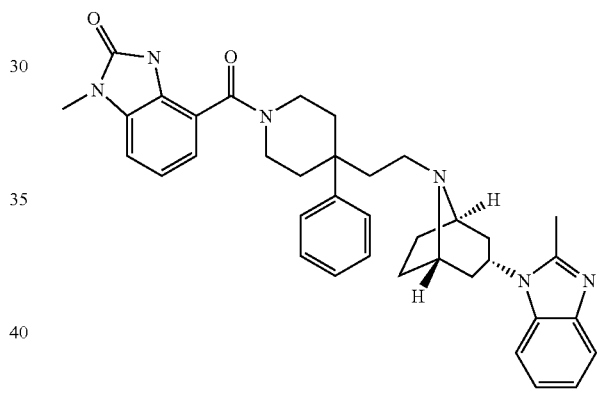

Example 998

2-(4-{2-[(1R,5S)-3-(2-methyl-1H-benzimidazol-1-yl)-8-azabicyclo[3.2.1]oct-8-yl]ethyl}-4-phenylpiperidin-1-yl)-2-oxoethanethioamide

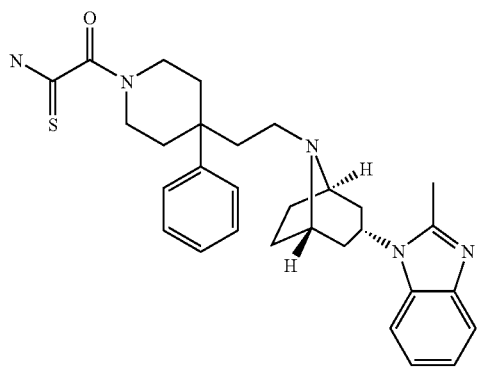

Example 999

5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]nicotinamide

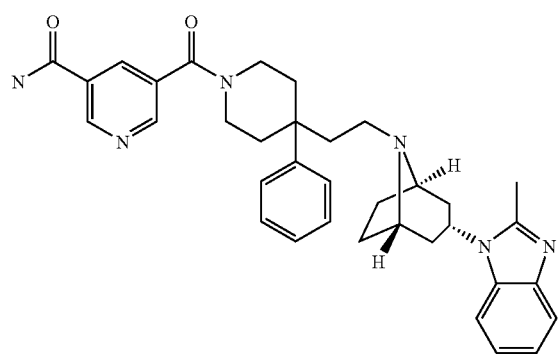

Example 1000

2-methyl-1-[(1R,5S)-8-(2-{4-phenyl-1-[(2,2,2-trifluoroethoxy)acetyl]piperidin-4-yl}ethyl)-8-azabicyclo[3.2.1]oct-3-yl]-1H-benzimidazole

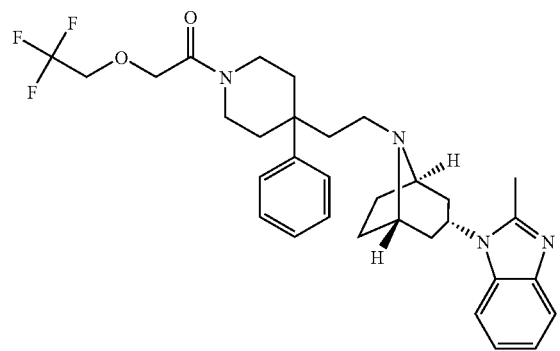

Example 1001 ethyl (1S,2S)-2-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]cyclopropanecarboxylate

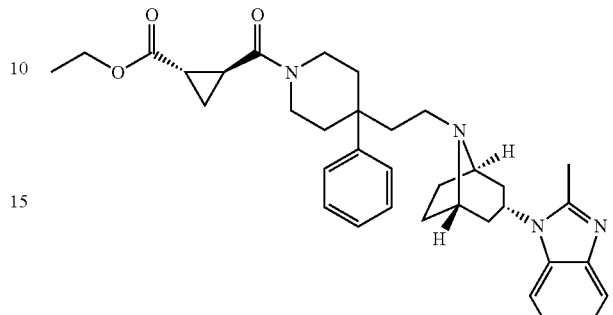

Example 1002

1-{(1R,5S)-8-[2-(1-{[(1S,2R)-2-(4-chlorophenyl)cyclopropyl]carbonyl}-4-phenylpiperidin-4-yl)ethyl]-8-azabicyclo[3.2.1]oct-3-yl}-2-methyl-1H-benzimidazole

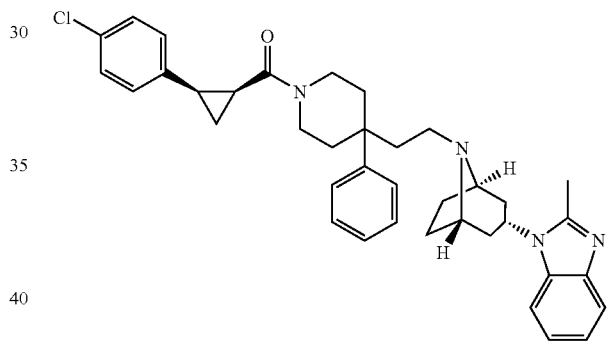

Example 1003

N-[1-cyclopropyl-2-(4-{2-[(1R,5S)-3-(2-methyl-1H-benzimidazol-1-yl)-8-azabicyclo[3.2.1]oct-8-yl]ethyl}-4-phenylpiperidin-1-yl)-2-oxoethyl]acetamide

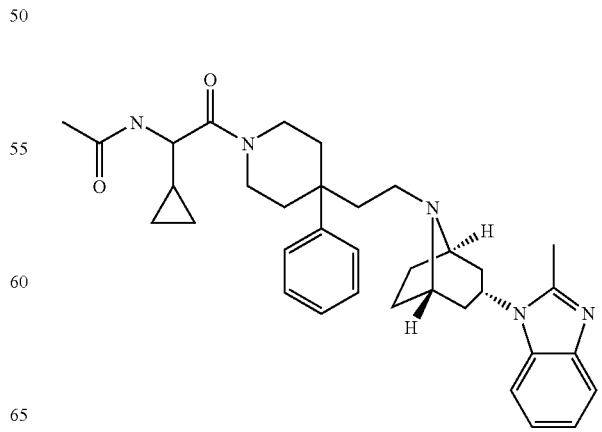

Example 1004

1-{1-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]propyl}cyclohexanol

Example 1006

2-(dimethylamino)-5-methyl-6-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyrimidin-4-ol

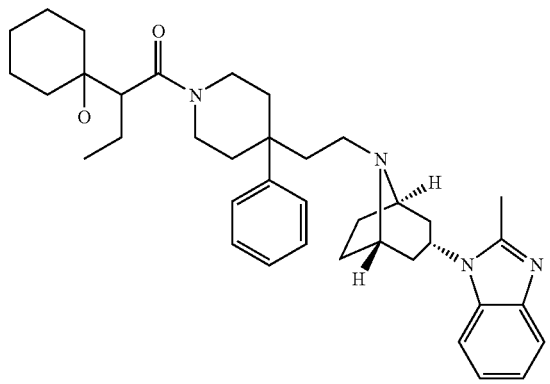

Example 1005

1-{(1R,5S)-8-[2-({[(1R,2R)-2-(4-methoxyphenyl)cyclopropyl]carbonyl}-4-phenylpiperidin-4-yl)ethyl]-8-azabicyclo[3.2.1]oct-3-yl}-2-methyl-1H-benzimidazole

Example 1007

3-methyl-5-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyrimidine-2,4(1H,3H)-dione

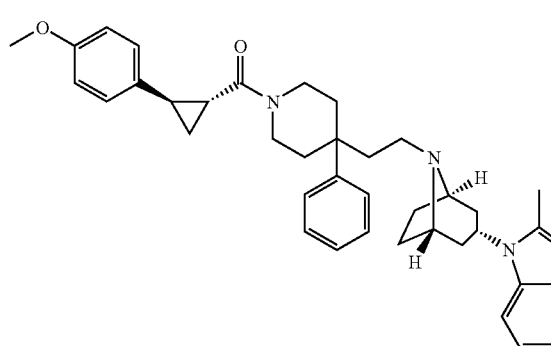

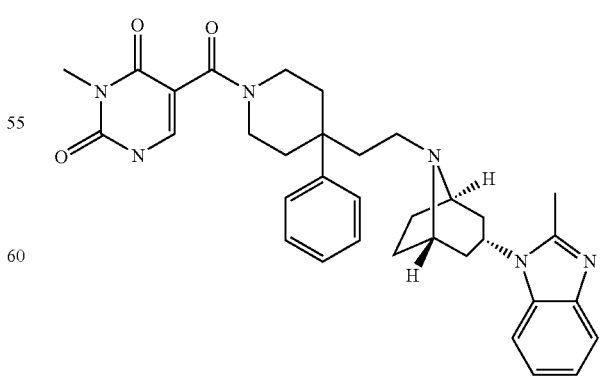

Example 1008

N-{1-methyl-1-[(4-{2-[(1R,5S)-3-(2-methyl-1H-benzimidazol-1-yl)-8-azabicyclo-[3.2.1]oct-8-yl]ethyl}-4-phenylpiperidin-1-yl)carbonyl]propyl}acetamide

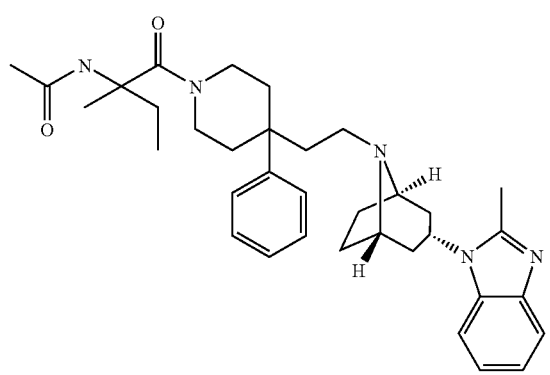

Example 1009

1-{3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]pyridin-2-yl}ethanone

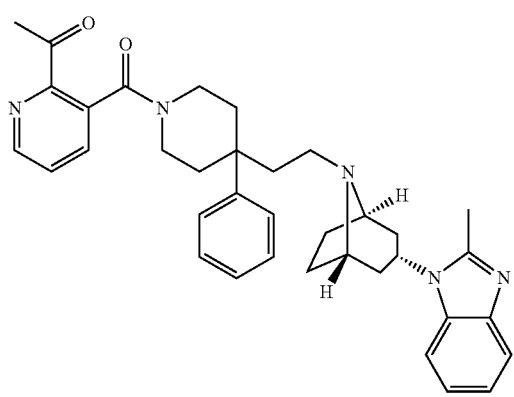

Example 1010

7-[2-(4-{2-[(1R,5S)-3-(2-methyl-1H-benzimidazol-1-yl)-8-azabicyclo[3.2.1]oct-8-yl]ethyl}-4-phenylpiperidin-1-yl)-2-oxoethyl]octahydro-2H-indol-2-one

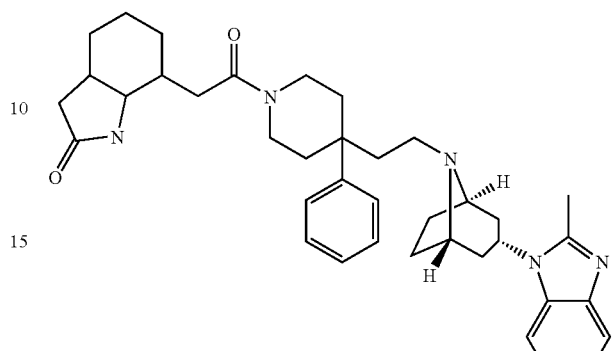

Example 1011

3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxo-N-{[3-(trifluoromethyl)phenyl]sulfonyl}propanamide

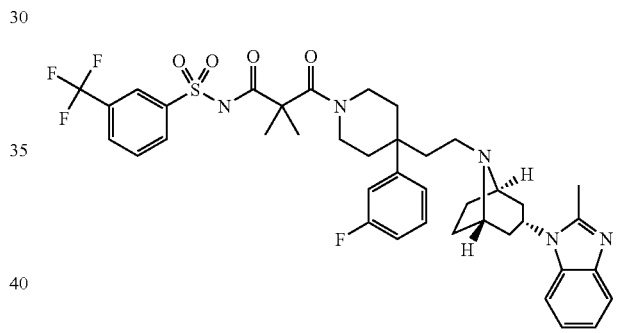

Synthesis of 2,2-dimethyl-3-oxo-3-({[3-(trifluoromethyl)phenyl]sulfonyl}amino)propanoic acid

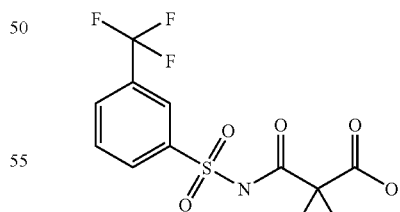

2,2-dimethyl-3-oxo-3-({[3-(trifluoromethyl)phenyl]sulfonyl}amino)propanoic acid was prepared in the same manner as 2,2-dimethyl-3-oxo-3-[(phenylsulfonyl)amino]propanoic acid starting from 3-(trifluoromethyl)benzenesulfonyl chloride.

$^1$HNMR (300 MHz, Chloroform-D1) δ ppm 1.4 (m, 6H) 5.1 (m, 1H) 7.9 (M, 1H) 8.1 (m, 1H) 8.2 (m, 1H) 8.3 (m, 1H) 10.0 (s, 1H), Electrospray LC-MS 362 (M+23)

Example 1012

3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxo-N-(phenylsulfonyl)propanamide

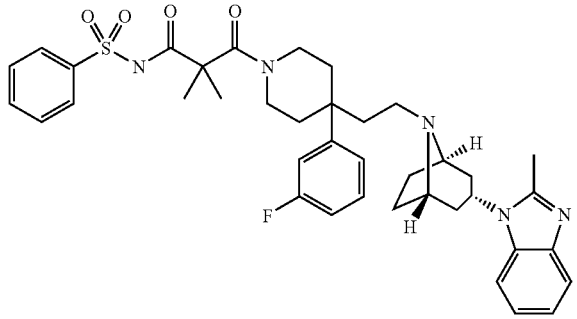

The synthesis of 2,2-dimethyl-3-oxo-3-[(phenylsulfonyl)amino]propanoic acid

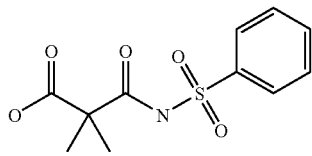

Benzenesulfonamide was made by adding benzenesulfonyl chloride to a solution of ammonia in tetrahydrofuran and evaporating to a solid. Benzenesulfonamide (87 mg, 0.50 mmole) was added to a shaken suspension of 3-ethoxy-2,2-dimethyl-3-oxopropanoic acid (100 mg, 0.62 mmole) reactivated on PS-DCC resin (1.62 g, 1.25 mmole) and 1.50 mmole of N,N-dimethylpyridin-4-amine in DCE. When reaction is complete the resin is filtered off and the organic layer washed with 1N HCl dried and evaporated. The resulting residue was dissolved in 6 ml of ethanol and 6 ml of 1N LiOH was added and heated to 40° C. The reaction was neutralized with 1N HCl and evaporated to afford 2,2-dimethyl-3-oxo-3-[(phenylsulfonyl)amino]propanoic acid as a crude product which was used with no further purification.

$^1$HNMR (300 MHz, Chloroform-D1) δ ppm 1.4 (m, 6H) 4.9 (s, 1H) 7.6 (m, 3H) 7.9 (m, 1H) 8.1 (m, 1H) 9.8 (s, 1H), Electrospray LC-MS 180 (M+23).

Example 1013

3-(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxo-N-{[4-(trifluoromethyl)phenyl]sulfonyl}propanamide

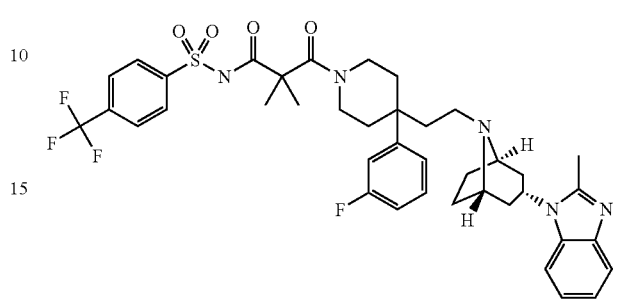

The synthesis of 2,2-dimethyl-3-oxo-3-({[4-(trifluoromethyl)phenyl]sulfonyl}amino)propanoic acid

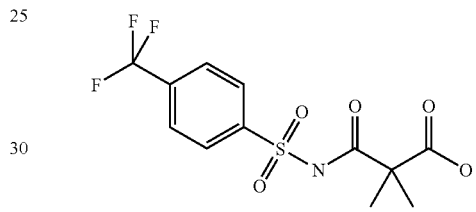

2,2-dimethyl-3-oxo-3-({[4-(trifluoromethyl)phenyl]sulfonyl}amino)propanoic acid was prepared in the same manner as 2,2-dimethyl-3-oxo-3-[(phenylsulfonyl)amino]propanoic acid starting from 4-(trifluoromethyl)benzenesulfonyl chloride.

$^1$HNMR (300 MHz, Chloroform-D1) δ ppm 1.4 (m, 6H) 5.1 (s, 1H) 7.8 (M, 2H) 8.1 (d, J=8.78 Hz, 1H) 8.2 (d, J=9.0 Hz, 1H) 9.9 (s, 1H)

Example 1014

4-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-1,2,5-thiadiazol-3-ol

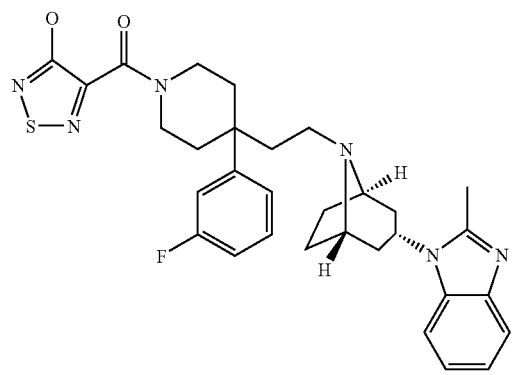

Example 1015

1-[(1R,5S)-8-(2-{1-[2-(1H-imidazol-4-yl)-2-methyl-propanoyl]-4-phenylpiperidin-4-yl}ethyl)-8-azabicyclo[3.2.1]oct-3-yl]-2-methyl-1H-benzimidazole

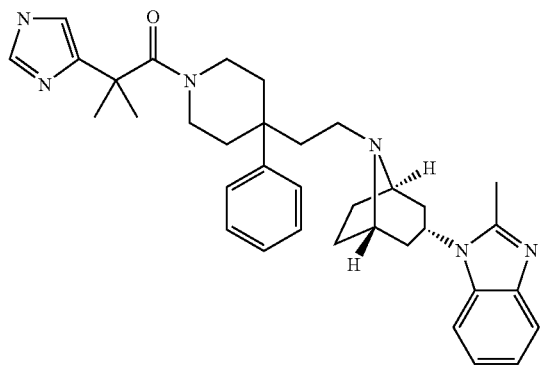

Using Method A (HATU) 2-(1H-imidazol-4-yl)-2-methyl-propanoic acid and endo 2-methyl-1-{8-[2-(4-phenylpiperidin-4-yl)ethyl]-8-azabicyclo[3.2.1]oct-3-yl}-1H-benzimidazole dihydrochloride were coupled to afford 1-[(1R,5S)-8-(2-{1-[2-(1H-imidazol-4-yl)-2-methylpropanoyl]-4-phenylpiperidin-4-yl}ethyl)-8-azabicyclo[3.2.1]oct-3-yl]-2-methyl-1H-benzimidazole 11.8 mg 42% yield.

1H NMR (400 MHz, DMSO-D6) d ppm 1.2 (m, 1H) 1.5 (m, 8H) 1.7 (m, 8H) 2.3 (m, 2H) 2.5 (m, 3H) 2.5 (m, 8H) 3.2 (m, 2H) 4.5 (m, 1H) 7.1 (m, 10H) 11.9 (m, 1H)

Electrospray LC-MS 565 (M+H)

Example 1016

4-methyl-8-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]quinoline

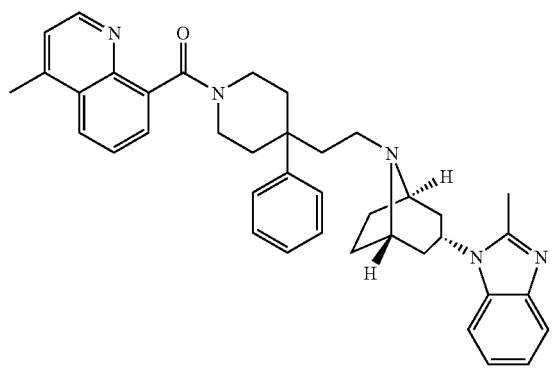

Using Method A (HATU) 4-methylquinoline-8-carboxylic acid and endo 2-methyl-1-{8-[2-(4-phenylpiperidin-4-yl)ethyl]-8-azabicyclo[3.2.1]oct-3-yl}-1H-benzimidazole dihydrochloride were coupled to afford 4-methyl-8-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]quinoline 14.8 mg 49% yield.

1H NMR (400 MHz, DMSO-D6) d ppm 1.7 (m, 10H) 2.1 (m, 2H) 2.3 (m, 6H) 2.7 (m, 3H) 2.9 (m, 1H) 3.2 (m, 4H) 3.6 (m, 1H) 4.0 (m, 1H) 4.5 (m, 1H) 7.1 (m, 2H) 7.2 (m, J=2.9 Hz, 1H) 7.4 (m, 6H) 7.5 (m, J=5.4 Hz, 1H) 7.6 (m, 2H) 8.2 (m, J=5.7, 2.1 Hz, 1H) 8.7 (m, 1H)

Electrospray LC-MS 598 (M+H)

Example 1017

4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1,3-benzoxazol-2(3H)-one

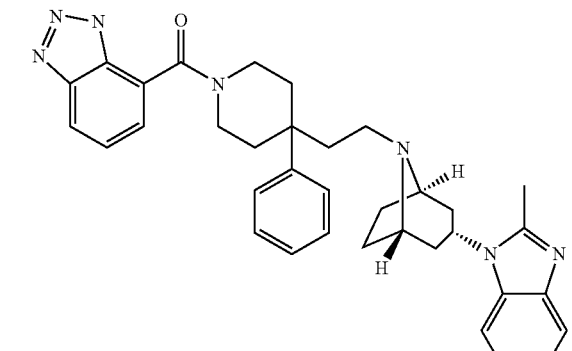

Using Method A (HATU) 2-oxo-2,3-dihydro-1,3-benzoxazole-4-carboxylic acid and endo 2-methyl-1-{8-[2-(4-phenylpiperidin-4-yl)ethyl]-8-azabicyclo[3.2.1]oct-3-yl}-1H-benzimidazole dihydrochloride were coupled to afford 4-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1,3-benzoxazol-2(3H)-one 8.7 mg 30% yield.

1H NMR (400 MHz, DMSO-D6) d ppm 1.6 (m, 2H) 1.8 (m, 9H) 2.4 (m, 2H) 2.4 (m, 3H) 2.5 (m, 7H) 3.2 (m, 3H) 4.5 (m, 1H) 7.2 (m, 5H) 7.4 (m, 6H) 7.5 (m, 1H)

Electrospray LC-MS 590 (M+H)

Example 1018

7-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1H-1,2,3-benzotriazole Using Method A (HATU) 1H-1,2,3-benzotriazole-7-carboxylic acid and endo 2-methyl-1-{8-[2-(4-phenylpiperidin- 4-yl)ethyl]-8-azabicyclo[3.2.1]oct-3-yl}-1H-benzimidazole dihydrochloride were coupled to afford 7-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]-1H-1,2,3-benzotriazole 9.9 mg 34% yield.

1H NMR (400 MHz, DMSO-D6) d ppm 1.6 (m, 1H) 1.8 (m, 8H) 2.4 (m, 4H) 2.5 (m, 8H) 3.2 (m, 3H) 4.0 (m, 1H) 4.5 (m, 1H) 7.1 (m, 2H) 7.2 (m, 1H) 7.4 (m, 8H) 8.0 (m, 1H)

Electrospray LC-MS 574 (M+H)

Example 1019

6-fluoro-7-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-1H-1,2,3-benzotriazole

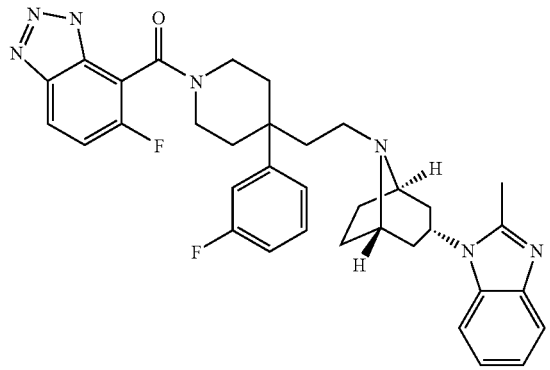

Using Method A (HATU) 6-fluoro-1H-1,2,3-benzotriazole-7-carboxylic acid and endo-1-(8-{2-[4-(3-fluorophenyl)piperidin-4-yl]ethyl}-8-azabicyclo[3.2.1]oct-3-yl)-2-methyl-1H-benzimidazole dihydrochloride were coupled to afford 6-fluoro-7-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-1H-1,2,3-benzotriazole 83.9 mg 62% yield.

1H NMR (400 MHz, METHANOL-D4) d ppm 1.7 (m, 1H) 2.0 (m, 4H) 2.4 (m, 4H) 2.8 (m, 3H) 3.4 (m, 13H) 4.7 (m, 1H) 7.2 (m, 10H) 7.9 (m, 1H)

Electrospray LC-MS 610 (M+H)

Preparation of the ethyl 6-fluoro-1H-1,2,3-benzotriazole-7-carboxylate

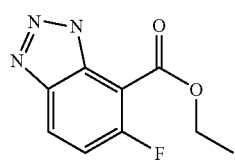

ethyl 2,3-diamino-6-fluorobenzoate (1.00 g, 5.04 mmole) in 50 ml of water and 10 ml acetic acid was cooled to −10° C. To this solution was added dropwise sodium nitrite (348 mg, 5.04 mmole) in 30 ml of water. After the addition the reaction was warmed to 0° C. for 30 min, then to room temperature for 1 hr, and finally 50° C. for 1 hr. The reaction was filtered after stirring over night and washed with water. The dark brownish purple solid was dissolved in ethylacetate dried over magnesium sulfate and evaporated to afford ethyl 6-fluoro-1H-1,2,3-benzotriazole-7-carboxylate (920 mg, 87% yield) 1H NMR (400 MHz, METHANOL-D4) δ ppm 1.3 (t, J=7.1 Hz, 3H) 4.4 (q, J=7.0 Hz, 2H) 7.2 (dd, J=11.2, 9.0 Hz, 1H) 8.1 (dd, J=9.1, 4.1 Hz, 1H).

Preparation of the 6-fluoro-1H-1,2,3-benzotriazole-7-carboxylic acid

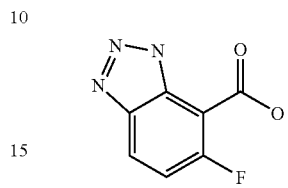

ethyl 6-fluoro-1H-1,2,3-benzotriazole-7-carboxylate (920 mg) was heated in 6N HCl until all of the starting material disappeared. Evaporation of the HCl afforded 718 mg of a brownish solid.

¹H NMR (300 MHz, DMSO-D6) δ ppm 7.4 (dd, J=11.2, 9.0 Hz, 1H) 8.3 (dd, J=9.1, 4.1 Hz, 1H).

Example 1020

5-fluoro-4-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-1,3-benzoxazol-2(3H)-one

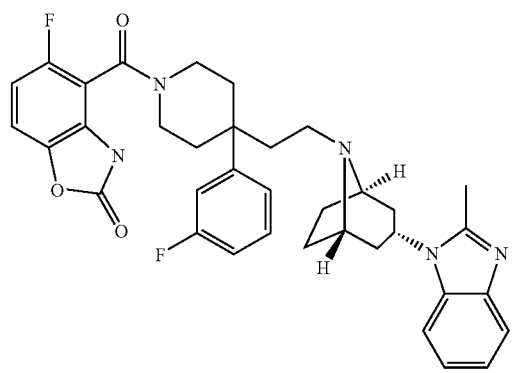

Using Method A (HATU) 5-fluoro-2-oxo-2,3-dihydro-1,3-benzoxazole-4-carboxylic acid and endo-1-(8-{2-[4-(3-flourophenyl) piperidin-4-yl]ethyl}-8-azabicyclo[3.2.1]oct-3-yl)-2-methyl-1H-benzimidazole dihydrochloride were coupled to afford 5-fluoro-4-[(4-(3-fluorophenyl)-4-{2-[(1R,5S)-3-(2-methyl-1H-benzimidazol-1-yl)-8-azabicyclo[3.2.1]oct-8-yl]ethyl}piperidin-1-yl)carbonyl]-1,3-benzoxazol-2(3H)-one. 1H NMR (300 MHz, METHANOL-D4) d ppm 1.4 (d, J=6.5 Hz, 1H) 1.8 (m, 3H) 2.0 (m, 8H) 2.2 (m, 3H) 2.5 (m, 3H) 3.0 (m, 3H) 3.5 (m, 4H) 4.2 (m, 1H) 7.0 (m, 2H) 7.3 (m, 7H) 7.6 (m, 1H) 8.0 (m, 1H)

Electrospray LC-MS 626 (M+H)

Preparation of 2-amino-6-fluoro-3-hydroxybenzoic acid

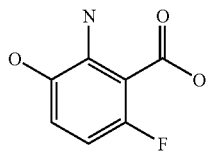

2-amino-6-fluorobenzoic acid (5.00 g, 32.2 mmole) was dissolved in 30 ml of 2N sodium hydroxide. To this was added dropwise a solution of sodium persulfate (7.67 g, 32.2 mmole) in 80 ml of water. After stirring over night the resulting black solution was extracted with 2 L of ether and 1 L of ethylacetate. Evaporation of the water gave a black solid that was used with no purification.

1H NMR (400 MHz, DMSO-D6) δ ppm 6.2 (dd, J=11.5, 8.6 Hz, 1H) 6.7 (dd, J=8.6, 4.9 Hz, 1H)
LC-MS

5-fluoro-2-oxo-2,3-dihydro-1,3-benzoxazole-4-carboxylic acid

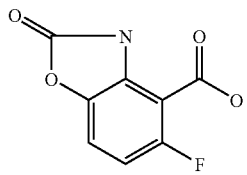

To a THF solution of 2-amino-6-fluoro-3-hydroxybenzoic acid (520 mg, 3.04 mmole) and n,n-diisopropylethylamine (942 mg, 7.29 mmole) was added bis(trichloromethyl) carbonate (1.08 g, 3.64 mmole) and stirred. Removal of solvent under vacuum afforded a residue, which was run on reversephase flash chromatography 10 to 90% acetonitrile water (0.01% TFA). The resulting fractions were evaporated.

APCI LC-MS 196 (M−H) 198 (M+H)

Examples below were synthesized as follows.

Method AA. Synthesis of Functionalized Carboxamide Carboxylic Acids Via Amination of Cyclic Anhydrides (Acids 69-79 and 97-153).

1 mmol of anhydride was treated with 10 mmol of either a 0.5M solution of NH3 in Dioxane or a 2M solution of either methylamine, ethylamine, isopropylamine or cyclopropylamine in THF at 40° C. in a sealed tube for 72 h. The reaction mixtures were concentrated to remove solvent and excess amine to give the crude carboxamide carboxylic acid as the salt of the corresponding amine. Crude materials were used without further purification or characterization in the subsequent coupling reaction to generate final compounds.

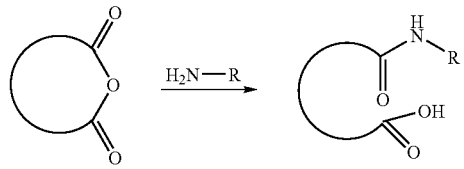

Method BB. Synthesis of Benzimidazole Carboxylic Acids (Acids 65-68, 88, and 89)

Step 1: 50 mmol of an appropriately substituted 2-amino-3-nitrobenzoic acid ester in 250 mL of EtOH/EtOAc (1:1) was treated with 980 mg of 10% Pd/C and H2(g) (1 atm) at ambient temperature for 16 h. The catalyst was filtered off and the filtrate concentrated to give the corresponding dianiline as a crystalline solid in quantitative yield. The crude material was carried on to either step 2A or 2B without further purification.

Step 2A: 5.6 mmol of the dianiline was treated with 15 mL of either triethyl orthoacetate or triethyl orthoformate at 120° C. for 16 h. The reaction mixture was concentrated to dryness to give the corresponding benzimidazole as a crystalline solid that was carried on to step 3 without further purification.

Step 2B: Alternatively, 6.0 mmol of dianiline was treated with 6.3 mmol BrCN in 15 mL CH3OH at reflux for 3 h. The reaction mixture was cooled to ambient temperature and precipitate was filtered off to give the corresponding 2-aminobenzimidazole.

Step 3: Benzimidazoles obtained from steps 2A and 2B were treated with 6N HCl at 80° C. for 8 h. The reaction mixtures were concentrated to dryness to give the benzimidazole carboxylic acids which were used without purification in coupling reactions to yield final compounds.

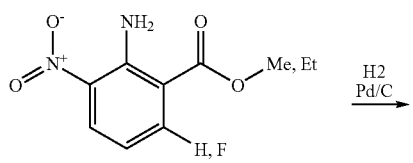

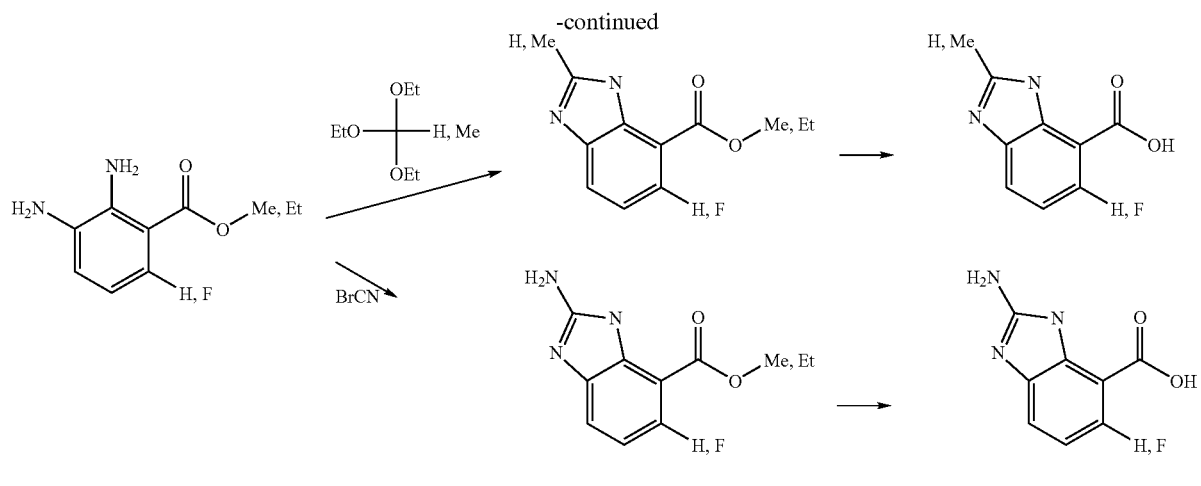

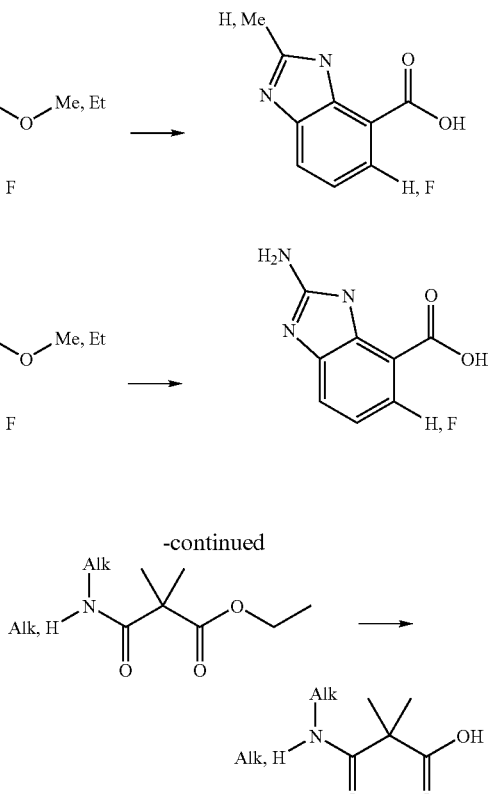

Method CC. Synthesis of Carboxamide Carboxylic Acids by Amination of Dimethyl Malonate (Acids 90-96).

Step 1: Diethyl dimethylpropanedioate (10 g, 53 mmol) in 170 mL EtOH was treated with 3.00 g (53 mmol) KOH at ambient temperature for 4 days. The reaction mixture was concentrated to dryness and partitioned between EtOAc and water. The aqueous phase was isolated, combined with fresh EtOAc and the pH adj to 2 with 6N HCl. The organic phase was isolated and the aqueous portion extracted twice with EtOAc. The organic phases were combined, dried over MgSO4, filtered and concentrated to give 6.56 g (41 mmol) 3-(ethyloxy)-2,2-dimethyl-3-oxopropanoic acid as a clear oil. 1H NMR (300 MHz, CDCl3) d 4.20 (q, J=7.1 Hz, 2H), 1.46 (s, 6H), 1.26 (t, J=7.1 Hz, 3H).

Step 2: 400 mg (2.50 mmol)) 3-(ethyloxy)-2,2-dimethyl-3-oxopropanoic acid dissolved in 4 mL THF was treated with 1,1'-carbonyldiimidazole (405 mg, 2.50 mmol) at ambient temperature until CO$_2$ evolution ceased (~20 min). To this solution was added 7.50 mmol (3 eq) of either ammonia, methylamine, ethylamine, 2-amino-2-methyl-1-propanol, cyclopropylamine, isopropylamine, 2-propen-1-ylamine, or N,N-dimethylamine. The reaction mixtures were shaken gently at ambient temperature for 16 h, concentrated to dryness, partitioned between DCE (8 mL) and 0.5N HCl (10 mL), shaken vigorously, organic phases isolated, dried over MgSO4 filtered and concentrated to dryness. Identity of these carboxamide ester intermediates was confirmed by 1H NMR.

Step 3: The carboxamide esters so obtained were treated with 2.5 mL (2.5 mmol) of 1N LiOH in 2.5 mL EtOH at ambient temperature for 16 h. The reaction mixtures were concentrated to dryness and used in coupling reactions without further purification or characterization.

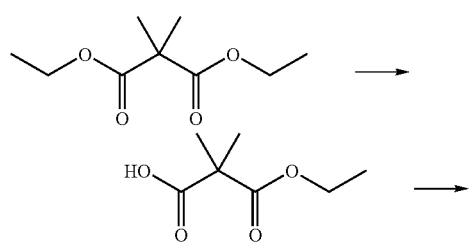

Method DD: Synthesis of Carboxamide Carboxylic Acids from Iodobenzoic Acids or Ester Carboxylic Acids (Acids 80-86) as Exemplified by Synthesis of 3-[({[2,4-bis(methyloxy)phenyl]methyl}amino)carbonyl]-4-chlorobenzoic acid (Acid 84).

Step 1: 2-Chloro-5-iodobenzoic acid (2 g, 7.08 mmol) in 25 mL THF was treated with 1,1'-carbonyldiimidazole (1.15 g, 7.08 mmol) at ambient temperature until CO$_2$ evolution ceased (~20 min). 2,4-Dimethoxybenzylamine (1.18 g, 7.08 mmol) was added and stirred at ambient temperature for 16 h. The reaction mixture was concentrated to dryness, partitioned between EtOAc and saturated NaHCO3, the organic phase isolated, dried over MgSO4, filtered and concentrated to give N-{[2,4-bis(methyloxy)phenyl]methyl}-2-chloro-5-iodobenzamide (3.00 g, 6.95 mmol) as a pale yellow oil that crystallized on standing. 1H NMR (300 MHz, CDCl3) d 7.95 (d, J=2.2 Hz, 1H), 7.62 (dd, J=8.5, 2.2 Hz, 1H), 7.25 (m, 1H), 7.10 (m, 1H), 6.63 (m, 1H), 6.45 (m, 2H), 4.55 (d, J=5.7 Hz, 2H), 3.83 (s, 3H), 3.80 (s, 3H). LCMS ES+ 431.82, 433.77 (M+H).

Step 2: N-{[2,4-bis(methyloxy)phenyl]methyl}-2-chloro-5-iodobenzamide (2.78 g, 6.44 mmol) dissolved in 100 mL CH$_3$OH with dicyclohexylamine (3.85 mL, 19 mmol) was treated with POPd2 catalyst (AC2000) under an atmosphere of CO(g) at 1 atm pressure and ambient temperature for 3 days. The catalyst was filtered off and the filtrate concentrated to a small volume, cooled in ice bath, and the resultant precipitate filtered off. A second crop was obtained from the mother liquor and the two batches were combined to give methyl 3-[({[2,4-bis(methyloxy)phenyl]methyl}amino)carbonyl]-4-chlorobenzoate (2.26 g, 6.21 mmol) as a white crystalline solid. 1H NMR (300 MHz, DMSO-D6) d 8.82 (m, 1H), 7.96 (dd, J=8.3, 2.2 Hz, 1H), 7.91 (m, 1H), 7.65 (d, J=8.3

Hz, 1H), 7.19 (d, J=8.2 Hz, 1H), 6.56 (d, J=2.5 Hz, 1H), 6.51 (dd, J=8.3, 2.5 Hz, 1H), 4.34 (d, J=5.9 Hz, 2H), 3.86 (s, 3H), 3.79 (s, 3H), 3.74 (s, 3H). LCMS ES+ 363.99, 365.97 (M+H).

Step 3: Methyl 3-[({[2,4-bis(methyloxy)phenyl]methyl}amino)carbonyl]-4-chlorobenzoate (600 mg, 1.65 mmol) dissolved in 17 mL CH₃OH was treated with 16.5 mL 1N LiOH at ambient temperature for 16 h. The reaction mixture was concentrated to dryness, partitioned between EtOAc and water, the aqueous phase isolated and the pH adjusted to 2 with 6N HCl. The resultant precipitate was cooled in an ice bath with stirring, filtered, and washed with water to give 3-[({[2,4-bis(methyloxy)phenyl]methyl}amino)carbonyl]-4-chlorobenzoic acid (533 mg, 1.52 mmol) as a white crystalline solid. 1H NMR (300 MHz, DMSO-D6) d ppm 8.96 (m, 1H), 8.29 (d, J=2.2 Hz, 1H), 8.00 (dd, J=8.4, 2.3 Hz, 1H), 7.65 (d, J=8.3 Hz, 1H), 7.09 (d, J=8.3 Hz, 1H), 6.55 (d, J=2.3 Hz, 1H), 6.50 (dd, J=8.3, 2.3 Hz, 1H), 4.35 (d, J=5.6 Hz, 1H), 3.79 (s, 3H), 3.73 (s, 3H). LCMS ES+ 349.88, 351.91 (M+H).

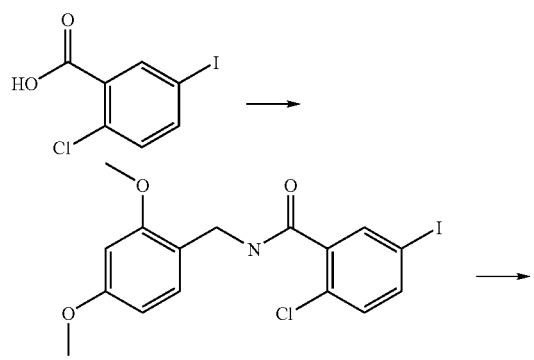

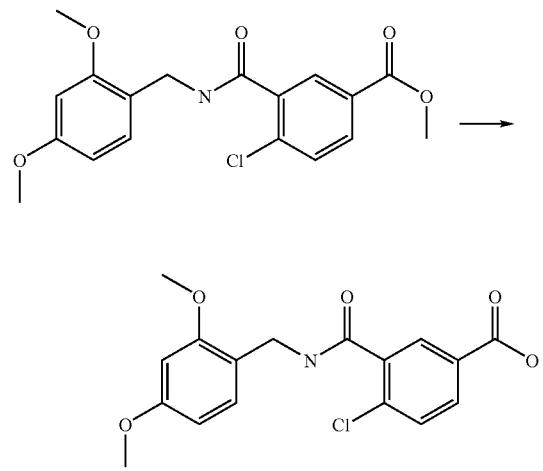

Acids 80-83 were synthesized in an analogous fashion from the appropriately substituted iodobenzoic acid and the appropriate amine.

Acids 85, 86, and 154 were synthesized from diethyl dimethylpropanedioate, diethyl diethylpropanedioate, or diethyl 1,1-cyclobutanedicarboxylate, respectively, and 2,4-Dimethoxybenzylamine using Method CC, step 1 and Method DD steps 1 and 3.

The table below lists acids 55-154, their properties, method of their synthesis as well as yields.

| Acid # | Structure | Yield | ES-LCMS | Ion | Method |
|---|---|---|---|---|---|
| Acid 55 | 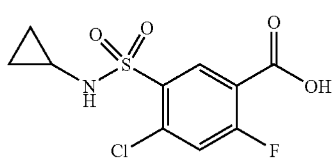 | | 293.94 | (M + H) | H |
| Acid 56 | 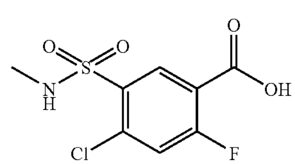 | 75 | 267.95 | (M + H) | H |
| Acid 57 | 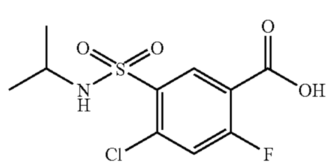 | 57 | 317.96 | (M + Na) | H |
| Acid 58 | 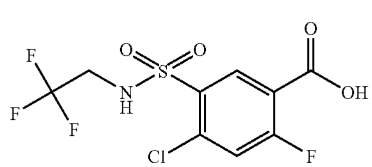 | 85 | 357.92 | (M + Na) | H |

-continued

| Acid # | Structure | Yield | ES-LCMS | Ion | Method |
|---|---|---|---|---|---|
| Acid 59 | 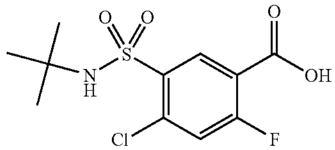 | 23 | 332 | (M + Na) | H |
| Acid 60 | 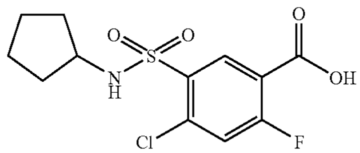 | 77 | 343.97 | (M + Na) | H |
| Acid 61 | 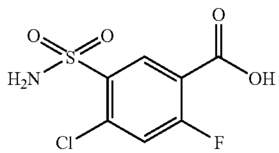 | 55 | 275.87 | (M + Na) | H |
| Acid 62 | 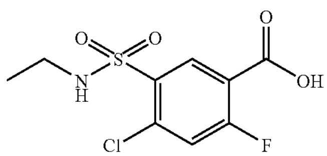 | | 282.08 | (M + H) | H |
| Acid 63 | 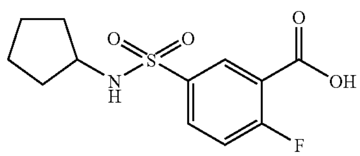 | | 310.01 | (M + Na) | H |
| Acid 64 | 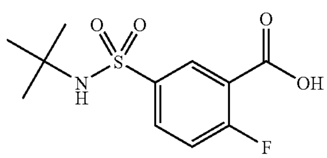 | | 298.1 | (M + Na) | H |
| Acid 65 | 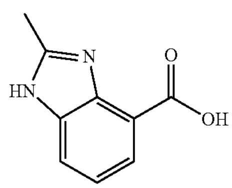 | | | | BB |
| Acid 66 | 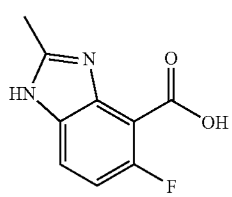 | | | | BB |
| Acid 67 | 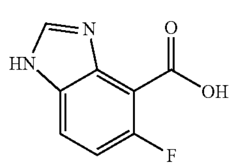 | | | | BB |

-continued

| Acid # | Structure | Yield | ES-LCMS | Ion | Method |
|---|---|---|---|---|---|
| Acid 68 | 2-amino-5-fluoro-1H-benzimidazole-4-carboxylic acid | | | | BB |
| Acid 69 | 2-carbamoylcyclopropane-1-carboxylic acid | | | | AA |
| Acid 70 | 2-carbamoylcyclopent-1-ene-1-carboxylic acid | | | | AA |
| Acid 71 | 4-carbamoyl-3,3-dimethylbutanoic acid (H₂N-C(O)-CH₂-C(CH₃)₂-CH₂-COOH) | | | | AA |
| Acid 72 | 3-carbamoylpyrazine-2-carboxylic acid | | | | AA |
| Acid 73 | 2-carbamoylcyclobutane-1-carboxylic acid | | | | AA |
| Acid 74 | 2-(methylcarbamoyl)cyclopropane-1-carboxylic acid | | | | AA |
| Acid 75 | 5-(cyclopropylamino)-2,2-dimethyl-5-oxopentanoic acid | | | | AA |
| Acid 76 | 4-(cyclopropylamino)-2,2-dimethyl-4-oxobutanoic acid | | | | AA |
| Acid 77 | 2-(cyclopropylcarbamoyl)cyclopropane-1-carboxylic acid | | | | AA |

-continued

| Acid # | Structure | Yield | ES-LCMS | Ion | Method |
|---|---|---|---|---|---|
| Acid 78 | 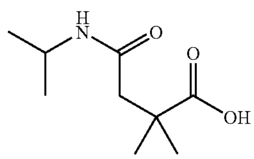 | | | | AA |
| Acid 79 | 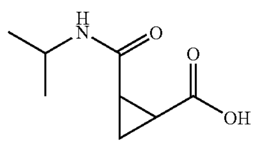 | | | | AA |
| glax | 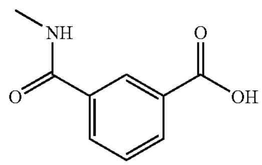 | | | | |
| Acid 80 | | 68 | 239.9 | (M + H) | DD |
| Acid 81 | | 73 | 241.91 | (M + H) | DD |
| Acid 80 | | 68 | 239.9 | (M + H) | DD |
| Acid 81 | | 73 | 241.91 | (M + H) | DD |
| commercial | 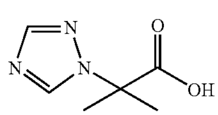 | | | | |
| Acid 80 | | 68 | 239.9 | (M + H) | DD |

-continued

| Acid # | Structure | Yield | ES-LCMS | Ion | Method |
|---|---|---|---|---|---|
| Acid 81 | 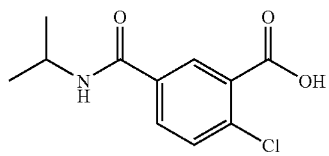 | 73 | 241.91 | (M + H) | DD |
| Acid 82 | 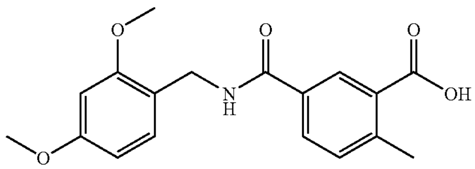 | 54 | 329.95 | (M + H) | DD |
| Acid 83 | 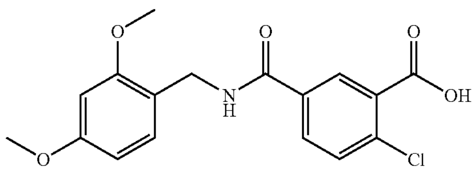 | 94 | 349.89, 351.91 | (M + H) | DD |
| Acid 84 | 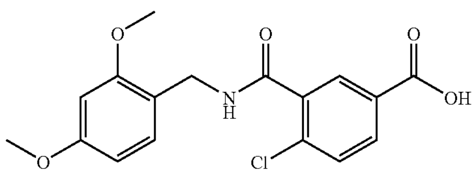 | 92 | 349.88, 351.91 | (M + H) | DD |
| Acid 85 | 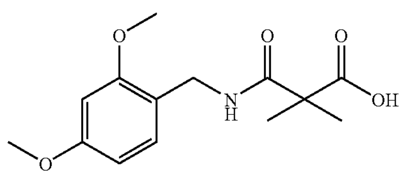 | 100 | 304 | (M + Na) | DD |
| Acid 86 | 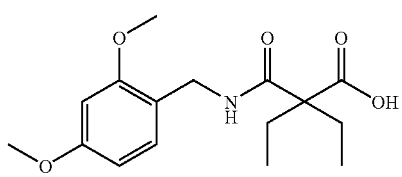 | 82 | 331.98 | (M + Na) | DD |
| commercial | 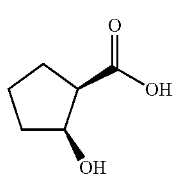 | | | | |
| glax | 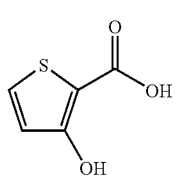 | | | | |
| Acid 87 | 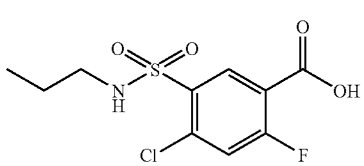 | 75 | 318.03 | (M + Na) | H |

-continued

| Acid # | Structure | Yield | ES-LCMS | Ion | Method |
|---|---|---|---|---|---|
| Acid 88 | 1H-benzimidazole-4-carboxylic acid | | | | BB |
| Acid 89 | 2-amino-1H-benzimidazole-4-carboxylic acid | | | | BB |
| Acid 90 | 2,2-dimethyl-3-(methylamino)-3-oxopropanoic acid | | | | CC |
| Acid 91 | 3-(ethylamino)-2,2-dimethyl-3-oxopropanoic acid | | | | CC |
| Acid 92 | 3-[(2-hydroxy-2-methylpropyl)amino]-2,2-dimethyl-3-oxopropanoic acid | | | | CC |
| Acid 93 | 3-(cyclopropylamino)-2,2-dimethyl-3-oxopropanoic acid | | | | CC |
| Acid 94 | 3-(dimethylamino)-2,2-dimethyl-3-oxopropanoic acid | | | | CC |
| Acid 95 | 3-(allylamino)-2,2-dimethyl-3-oxopropanoic acid | | | | CC |
| Acid 96 | 3-(isopropylamino)-2,2-dimethyl-3-oxopropanoic acid | | | | CC |
| Acid 97 | 4-amino-2,2-dimethyl-4-oxobutanoic acid | | | | AA |
| Acid 98 | 6-carbamoylcyclohex-3-ene-1-carboxylic acid | | | | AA |

-continued

| Acid # | Structure | Yield | ES-LCMS | Ion | Method |
|---|---|---|---|---|---|
| Acid 99 | 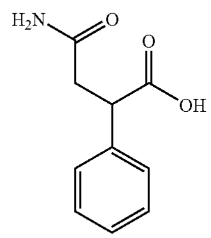 | | | | AA |
| Acid 100 | 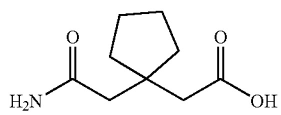 | | | | AA |
| Acid 101 | 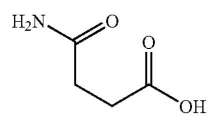 | | | | AA |
| Acid 102 | 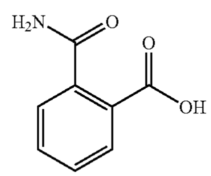 | | | | AA |
| Acid 103 | 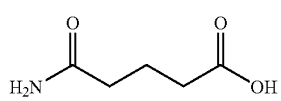 | | | | AA |
| Acid 104 | 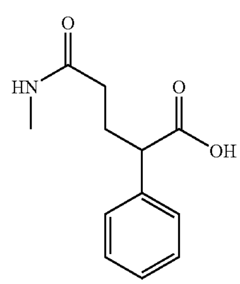 | | | | AA |
| Acid 105 | 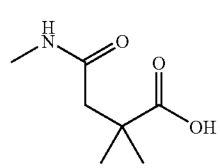 | | | | AA |
| Acid 106 | 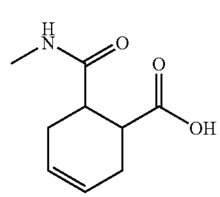 | | | | AA |

-continued

| Acid # | Structure | Yield | ES-LCMS | Ion | Method |
|---|---|---|---|---|---|
| Acid 107 | 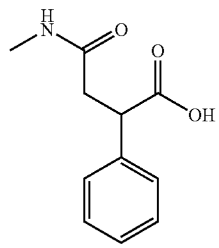 | | | | AA |
| Acid 108 | 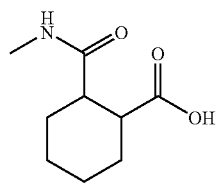 | | | | AA |
| Acid 109 | 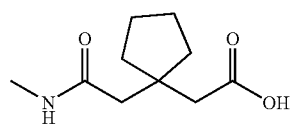 | | | | AA |
| Acid 110 | 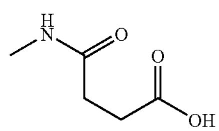 | | | | AA |
| Acid 111 | 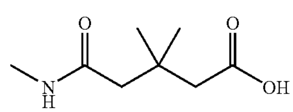 | | | | AA |
| Acid 112 | 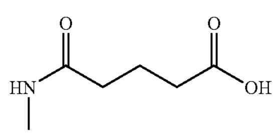 | | | | AA |
| Acid 113 | 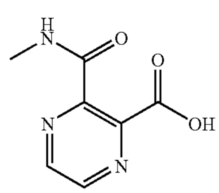 | | | | AA |
| Acid 114 | 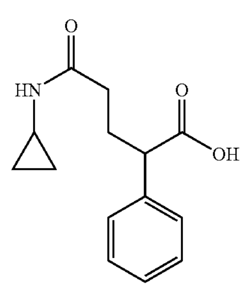 | | | | AA |

-continued

| Acid # | Structure | Yield | ES-LCMS | Ion | Method |
|---|---|---|---|---|---|
| Acid 115 | 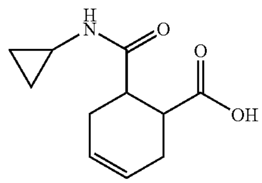 | | | | AA |
| Acid 116 | 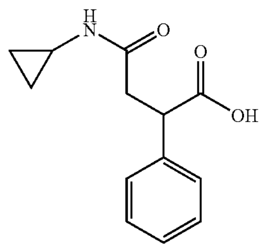 | | | | AA |
| Acid 117 | 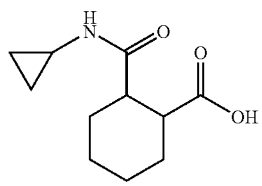 | | | | AA |
| Acid 118 | 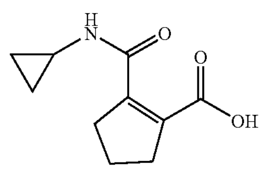 | | | | AA |
| Acid 119 | 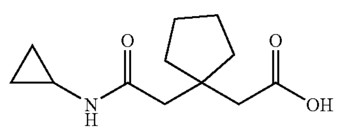 | | | | AA |
| Acid 120 | 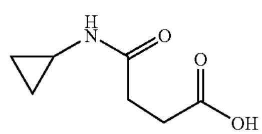 | | | | AA |
| Acid 121 | 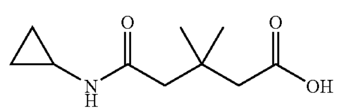 | | | | AA |
| Acid 122 | 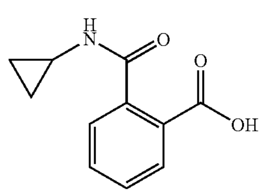 | | | | AA |
| Acid 123 | 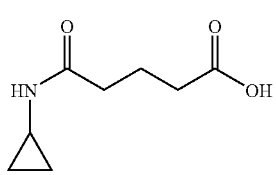 | | | | AA |

-continued

| Acid # | Structure | Yield | ES-LCMS | Ion | Method |
|---|---|---|---|---|---|
| Acid 124 | 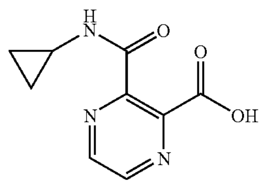 | | | | AA |
| Acid 125 | 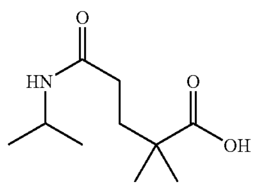 | | | | AA |
| Acid 126 | 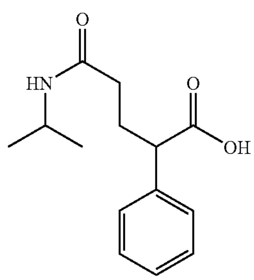 | | | | AA |
| Acid 127 | 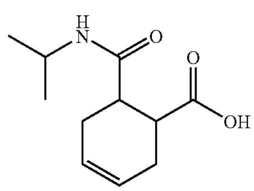 | | | | AA |
| Acid 128 | 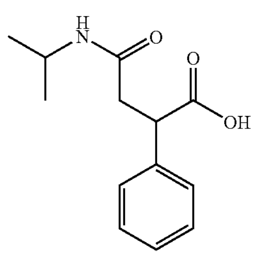 | | | | AA |
| Acid 129 | 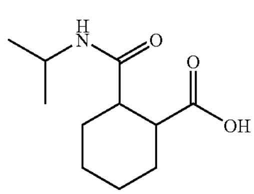 | | | | AA |
| Acid 130 | 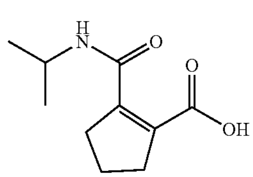 | | | | AA |

-continued
| Acid # | Structure | Yield | ES-LCMS | Ion | Method |
|---|---|---|---|---|---|
| Acid 131 | 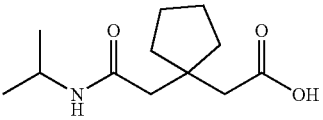 | | | | AA |
| Acid 132 | 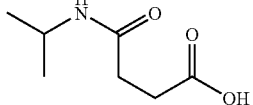 | | | | AA |
| Acid 133 | 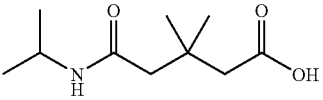 | | | | AA |
| Acid 134 | 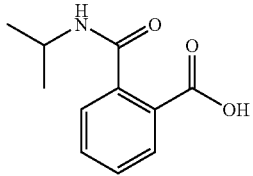 | | | | AA |
| Acid 135 | 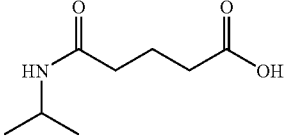 | | | | AA |
| Acid 136 | 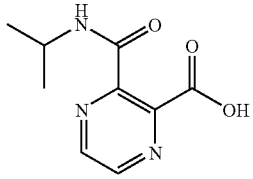 | | | | AA |
| Acid 137 | 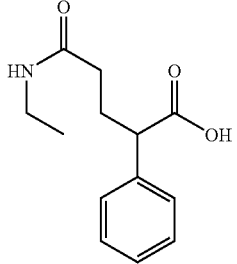 | | | | AA |
| Acid 138 | 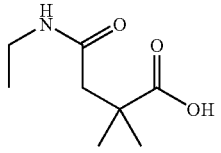 | | | | AA |
| Acid 139 | 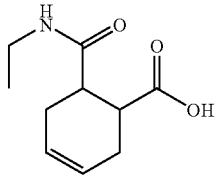 | | | | AA |

-continued

| Acid # | Structure | Yield | ES-LCMS | Ion | Method |
|--------|-----------|-------|---------|-----|--------|
| Acid 140 | 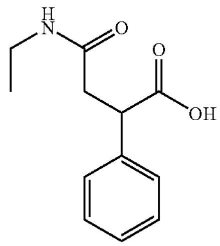 | | | | AA |
| Acid 141 | 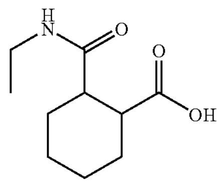 | | | | AA |
| Acid 142 | 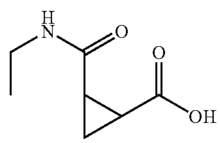 | | | | AA |
| Acid 143 | 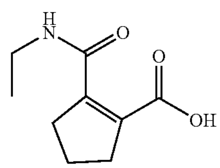 | | | | AA |
| Acid 144 | 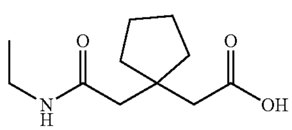 | | | | AA |
| Acid 145 | 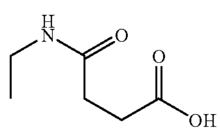 | | | | AA |
| Acid 146 | 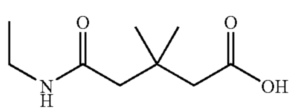 | | | | AA |
| Acid 147 | 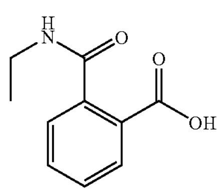 | | | | AA |
| Acid 148 | 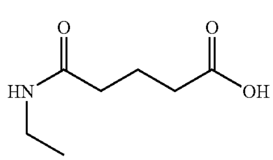 | | | | AA |

| Acid # | Structure | Yield | ES-LCMS | Ion | Method |
|---|---|---|---|---|---|
| Acid 149 | (N-ethylcarbamoyl pyrazine-2-carboxylic acid) | | | | AA |
| Acid 150 | (2-(ethylcarbamoyl)cyclobutane-1-carboxylic acid) | | | | AA |
| Acid 151 | (4-amino-4-oxobut-2-enoic acid) | | | | AA |
| Acid 152 | (2-(ethylcarbamoyl)-3,4,5,6-tetrafluorobenzoic acid) | | | | AA |
| Acid 153 | (6-(ethylcarbamoyl)-3,4-dimethylcyclohex-3-ene-1-carboxylic acid) | | | | AA |
| glax | (4-hydroxy-7-(trifluoromethyl)quinoline-3-carboxylic acid) | | | | |
| glax | (4-hydroxy-7-(trifluoromethyl)quinoline-3-carboxylic acid) | | | | |
| glax | (2,4-dioxo-1,2,3,4-tetrahydropyrimidine-5-carboxylic acid) | | | | |

| Acid # | Structure | Yield | ES-LCMS | Ion | Method |
|---|---|---|---|---|---|
| glax | ![structure] | | | | |
| glax | ![structure] | | | | |
| glax | ![structure] | | | | |
| glax | ![structure] | | | | |
| glax | ![structure] | | | | |
| glax | ![structure] | | | | |
| glax | ![structure] | | | | |
| glax | ![structure] | | | | |

-continued
| Acid # | Structure | Yield | ES-LCMS | Ion | Method |
|---|---|---|---|---|---|
| glax | 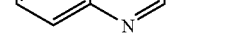 | | | | |
| glax | 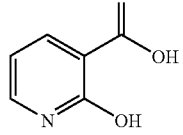 | | | | |
| glax | 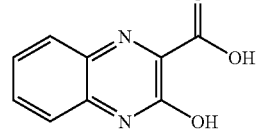 | | | | |
| glax | 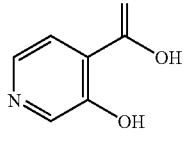 | | | | |
| glax | 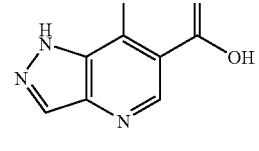 | | | | |
| glax | 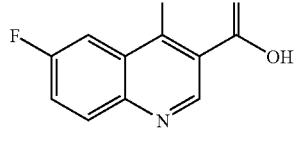 | | | | |
| glax | 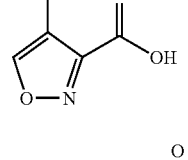 | | | | |
| glax | 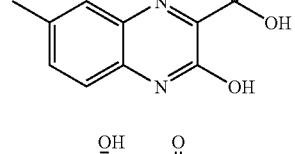 | | | | |
| glax | 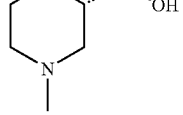 | | | | |

-continued
| Acid # | Structure | Yield | ES-LCMS | Ion | Method |
|---|---|---|---|---|---|
| glax | 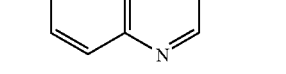 | | | | |
| glax | 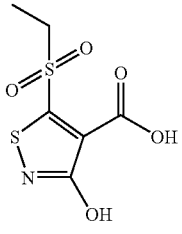 | | | | |
| glax | 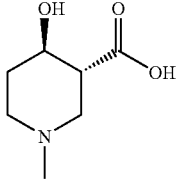 | | | | |
| glax | 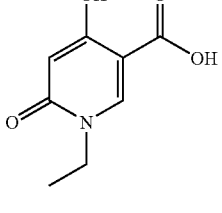 | | | | |
| glax | 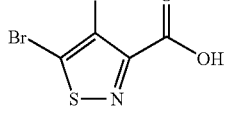 | | | | |
| Acid 154 | 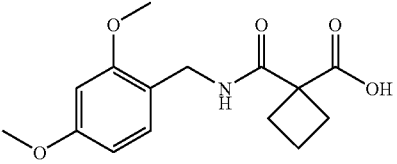 | 83 | 315.94 | (M + Na) | DD |

The following examples were prepared using acids described elsewhere in this invention

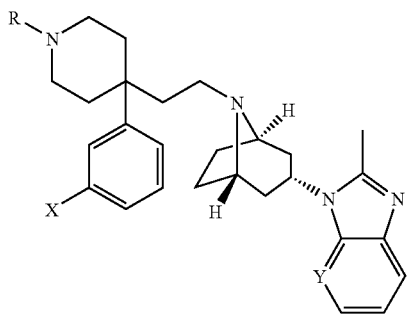

| Example | Acid # or source | R | X | Y | % Yield | LCMS ES | Ion | Method |
|---|---|---|---|---|---|---|---|---|
| 1021 | Acid 83 | H₂N-C(=O)-C₆H₃(Cl)-C(=O)CH₃ | H | C | 36 | 610.18 | (M + H) | F |
| 1022 | Acid 82 | H₂N-C(=O)-C₆H₃(CH₃)-C(=O)CH₃ | CH₃ | C | 52 | 604.24 | (M + H) | F |
| 1023 | Acid 83 | H₂N-C(=O)-C₆H₃(Cl)-C(=O)CH₃ | CH₃ | C | 52 | 624.22 | (M + H) | F |
| 1024 | Acid 85 | H₂N-C(=O)-C(CH₃)₂-C(=O)CH₃ | CH₃ | C | 38 | 556.27 | (M + H) | F |
| 1025 | Acid 55 | cyclopropyl-NH-SO₂-C₆H₂(Cl)(F)-C(=O)CH₃ | F | C | 42 | 722.36 | (M + H) | A |
| 1026 | Acid 56 | CH₃-NH-SO₂-C₆H₂(Cl)(F)-C(=O)CH₃ | F | C | 36 | 696.18 | (M + H) | A |
| 1027 | Acid 57 | iPr-NH-SO₂-C₆H₂(Cl)(F)-C(=O)CH₃ | F | C | 52 | 724.38 | (M + H) | A |

-continued

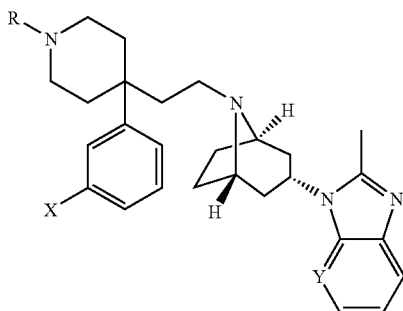

| Example | Acid # or source | R | X | Y | % Yield | LCMS ES | Ion | Method |
|---|---|---|---|---|---|---|---|---|
| 1028 | Acid 58 | (2,2,2-trifluoroethyl)sulfamoyl-chloro-fluoro-acetophenone | F | C | 56 | 764.33 | (M + H) | A |
| 1029 | Acid 59 | tert-butylsulfamoyl-chloro-fluoro-acetophenone | F | C | 32 | 738.37 | (M + H) | A |
| 1030 | Acid 60 | cyclopentylsulfamoyl-chloro-fluoro-acetophenone | F | C | 50 | 750.23 | (M + H) | A |
| 1031 | Acid 61 | sulfamoyl-chloro-fluoro-acetophenone | F | C | 49 | 682.32 | (M + H) | A |
| 1032 | Acid 62 | ethylsulfamoyl-chloro-fluoro-acetophenone | F | C | 54 | 710.34 | (M + H) | A |
| 1033 | Acid 63 | cyclopentylsulfamoyl-fluoro-acetophenone | F | C | 26 | 716.42 | (M + H) | A |
| 1034 | Acid 64 | tert-butylsulfamoyl-fluoro-acetophenone | F | C | 29 | 704.42 | (M + H) | A |

-continued

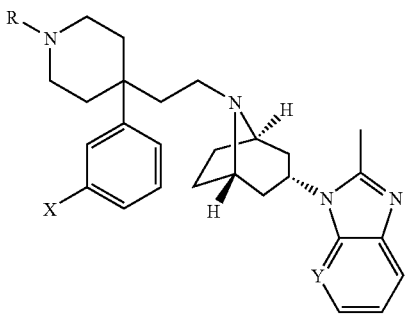

| Example | Acid # or source | R | X | Y | % Yield | LCMS ES | Ion | Method |
|---|---|---|---|---|---|---|---|---|
| 1035 | Acid 65 | 2-methyl-1H-benzimidazol-4-yl methyl ketone | F | C | 28 | 605.35 | (M + H) | A |
| 1036 | Acid 66 | 2-methyl-5-fluoro-1H-benzimidazol-4-yl methyl ketone | F | C | 48 | 623.32 | (M + H) | A |
| 1037 | Acid 67 | 5-fluoro-1H-benzimidazol-4-yl methyl ketone | F | C | 46 | 609.28 | (M + H) | A |
| 1038 | Acid 68 | 2-amino-5-fluoro-1H-benzimidazol-4-yl methyl ketone | F | C | 13 | 624.34 | (M + H) | A |
| 1039 | Acid 69 | 2-acetylcyclopropane-1-carboxamide | F | C | 44 | 558.38 | (M + H) | A |
| 1040 | Acid 70 | 2-acetylcyclopent-1-ene-1-carboxamide | F | C | 57 | 584.39 | (M + H) | A |
| 1041 | Acid 71 | 3,3-dimethyl-5-oxohexanamide | F | C | 58 | 588.45 | (M + H) | A |

-continued

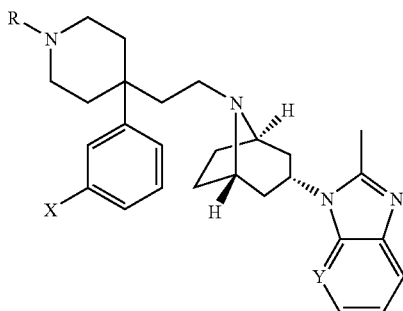

| Example | Acid # or source | R | X | Y | % Yield | LCMS ES | Ion | Method |
|---|---|---|---|---|---|---|---|---|
| 1042 | Acid 72 | (pyrazine carboxamide acetyl) | F | C | 52 | 596.35 | (M + H) | A |
| 1043 | Acid 73 | (cyclobutane carboxamide acetyl) | F | C | 23 | 572.34 | (M + H) | A |
| 1044 | Acid 74 | (N-methyl cyclopropane carboxamide acetyl) | F | C | 41 | 572.35 | (M + H) | A |
| 1045 | Acid 75 | (N-cyclopropyl amide, gem-dimethyl ketone) | F | C | 29 | 628.39 | (M + H) | A |
| 1046 | Acid 76 | (N-cyclopropyl amide, gem-dimethyl ketone) | F | C | 43 | 614.42 | (M + H) | A |
| 1047 | Acid 77 | (N-cyclopropyl cyclopropane carboxamide acetyl) | F | C | 64 | 598.42 | (M + H) | A |
| 1048 | Acid 78 | (N-isopropyl amide, gem-dimethyl ketone) | F | C | 27 | 616.5 | (M + H) | A |

-continued

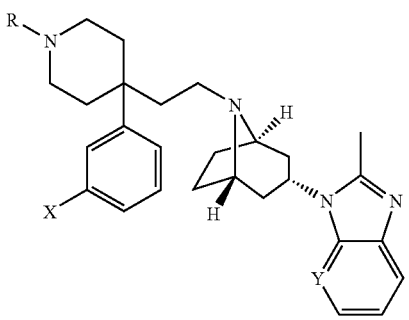

| Example | Acid # or source | R | X | Y | % Yield | LCMS ES | Ion | Method |
|---|---|---|---|---|---|---|---|---|
| 1049 | Acid 79 | *N-isopropyl, acetyl cyclopropane carboxamide* | F | C | 39 | 600.45 | (M + H) | A |
| 1050 | glax | *N-methyl 3-acetylbenzamide* | F | C | 37 | 608.4 | (M + H) | A |
| 1051 | Acid 86 | *2-acetyl-2-ethylbutanamide* | F | C | 37 | 588.4 | (M + H) | A |
| 1052 | Acid 80 | *N-cyclopropyl 3-acetyl-4-chlorobenzamide* | H | C | 48 | 650.19 | (M + H) | A |
| 1053 | Acid 81 | *N-isopropyl 3-acetyl-4-chlorobenzamide* | H | C | 39 | 652.22 | (M + H) | A |
| 1054 | Acid 80 | *N-cyclopropyl 3-acetyl-4-chlorobenzamide* | F | C | 56 | 668.22 | (M + H) | A |
| 1055 | Acid 81 | *N-isopropyl 3-acetyl-4-chlorobenzamide* | F | C | 43 | 670.21 | (M + H) | A |

-continued
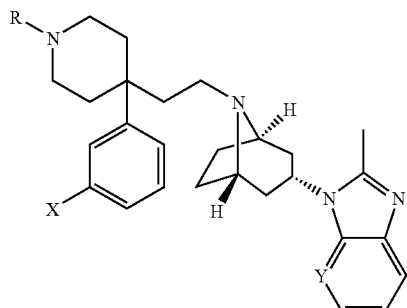
| Example | Acid # or source | R | X | Y | % Yield | LCMS ES | Ion | Method |
|---|---|---|---|---|---|---|---|---|
| 1056 | commercial | [1,2,4-triazol-1-yl-C(CH3)2-C(O)-] | F | C | 39 | 584.24 | (M + H) | A |
| 1057 | Acid 80 | [cyclopropyl-NH-C(O)-phenyl(4-Cl)-C(O)-] | CH3 | C | 41 | 664.25 | (M + H) | A |
| 1058 | Acid 81 | [iPr-NH-C(O)-phenyl(4-Cl)-C(O)-] | CH3 | C | 41 | 666.26 | (M + H) | A |
| 1059 | Acid 82 | [2,4-dimethoxybenzyl-NH-C(O)-phenyl(4-CH3)-C(O)-] | F | C | 45 | 758.33 | (M + H) | A |
| 1060 | Acid 83 | [2,4-dimethoxybenzyl-NH-C(O)-phenyl(4-Cl)-C(O)-] | F | C | 36 | 778.29 | (M + H) | A |
| 1061 | Acid 84 | [2,4-dimethoxybenzyl-NH-C(O)-phenyl(2-Cl)-C(O)-] | F | C | 66 | 778.29 | (M + H) | A |
| 1062 | Acid 85 | [2,4-dimethoxybenzyl-NH-C(O)-C(CH3)2-C(O)-] | F | C | 41 | 710.28 | (M + H) | A |

-continued
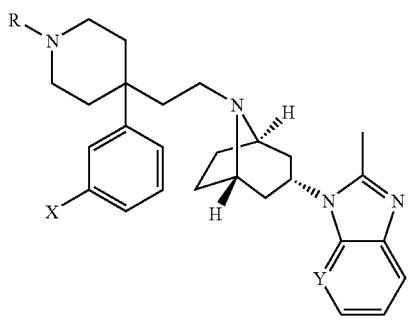
| Example | Acid # or source | R | X | Y | % Yield | LCMS ES | Ion | Method |
|---|---|---|---|---|---|---|---|---|
| 1063 | Acid 86 | (2,4-dimethoxybenzyl NH-C(=O)-C(Et)₂-C(=O)-CH₃) | F | C | 56 | 738.33 | (M + H) | A |
| 1064 | Acid 82 | (H₂N-C(=O)-phenyl-CH₃ with acetyl) | H | C | 39 | 590.25 | (M + H) | F |
| 1065 | Acid 84 | (H₂N-C(=O)-phenyl-Cl with acetyl) | H | C | 13 | 610.18 | (M + H) | F |
| 1066 | Acid 82 | (H₂N-C(=O)-phenyl-CH₃ with acetyl) | F | C | 48 | 608.24 | (M + H) | F |
| 1067 | Acid 83 | (H₂N-C(=O)-phenyl-Cl with acetyl) | F | C | 53 | 628.18 | (M + H) | F |
| 1068 | Acid 84 | (H₂N-C(=O)-phenyl-Cl with acetyl) | F | C | 47 | 628.17 | (M + H) | F |
| 1069 | Acid 154 | (H₂N-C(=O)-cyclobutyl-acetyl) | F | C | 46 | 572.27 | (M + H) | F |

-continued

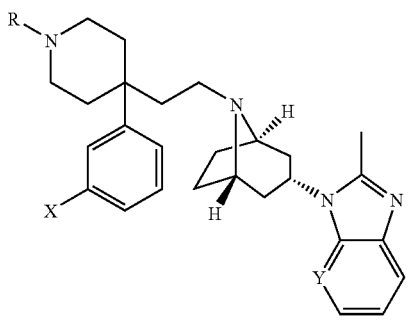

| Example | Acid # or source | R | X | Y | % Yield | LCMS ES | Ion | Method |
|---|---|---|---|---|---|---|---|---|
| 1070 | Acid 85 | H₂N-C(O)-C(CH₃)₂-C(O)-CH₃ | F | C | 33 | 560.26 | (M + H) | F |
| 1071 | Acid 84 | 2-chloro-5-acetyl-benzamide | CH₃ | C | 23 | 624.24 | (M + H) | F |
| 1072 | Acid 154 | 1-acetyl-cyclobutane-1-carboxamide | CH₃ | C | 34 | 568.28 | (M + H) | F |
| 1073 | Acid 85 | H₂N-C(O)-C(CH₃)₂-C(O)-CH₃ | H | C | 18 | 542.29 | (M + H) | F |
| 1075 | commercial | 2-hydroxy-cyclopentyl methyl ketone | F | C | 49 | 559.14 | (M + H) | A |
| 1076 | glax | 2-acetyl-3-hydroxy-thiophene | F | C | 39 | 573.05 | (M + H) | A |
| 1077 | Acid 87 | propyl-sulfonamide-chloro-fluoro-acetophenone | F | C | 52 | 724.38 | (M + H) | A |

-continued

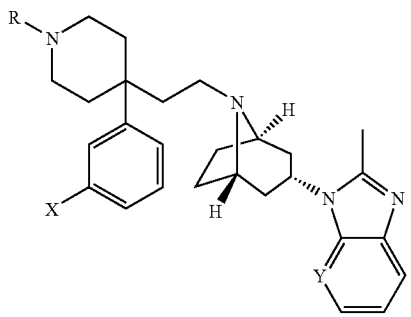

| Example | Acid # or source | R | X | Y | % Yield | LCMS ES | Ion | Method |
|---|---|---|---|---|---|---|---|---|
| 1078 | Acid 88 | (1H-benzimidazol-4-yl)acetyl | F | C | 27 | 591.27 | (M + H) | A |
| 1079 | Acid 89 | (2-amino-1H-benzimidazol-4-yl)acetyl | F | C | 22 | 606.35 | (M + H) | A |
| 1080 | Acid 90 | N-methyl 2,2-dimethyl-3-oxobutanamide | F | C | 24 | 574.35 | (M + H) | A |
| 1081 | Acid 91 | N-ethyl 2,2-dimethyl-3-oxobutanamide | F | C | 34 | 588.36 | (M + H) | A |
| 1082 | Acid 92 | N-(2-hydroxy-2-methylpropyl) 2,2-dimethyl-3-oxobutanamide | F | C | 23 | 632.47 | (M + H) | A |
| 1083 | Acid 93 | N-cyclopropyl 2,2-dimethyl-3-oxobutanamide | F | C | 33 | 598.79 | (M − 1) | A |
| 1084 | Acid 94 | N,N-dimethyl 2,2-dimethyl-3-oxobutanamide | F | C | 18 | 588.33 | (M + H) | A |
| 1085 | Acid 95 | N-allyl 2,2-dimethyl-3-oxobutanamide | F | C | 41 | 600.37 | (M + H) | A |

-continued
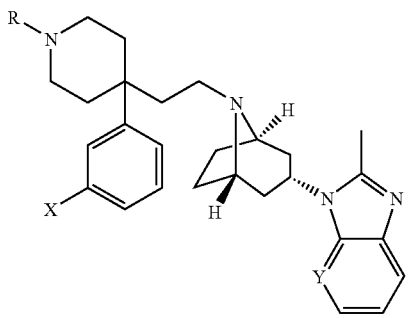
| Example | Acid # or source | R | X | Y | % Yield | LCMS ES | Ion | Method |
|---|---|---|---|---|---|---|---|---|
| 1086 | Acid 96 | | F | C | 45 | 602.4 | (M + H) | A |
| 1087 | Acid 97 | | F | C | 33 | 574.36 | (M + H) | A |
| 1088 | Acid 98 | | F | C | 32 | 598.39 | (M + H) | A |
| 1089 | Acid 99 | | F | C | 49 | 622.42 | (M + H) | A |
| 1090 | Acid 100 | | F | C | 55 | 614.44 | (M + H) | A |
| 1091 | Acid 101 | | F | C | 50 | 546.36 | (M + H) | A |
| 1092 | Acid 102 | | F | C | 15 | 594.37 | (M + H) | A |
| 1093 | Acid 103 | | F | C | 54 | 560.41 | (M + H) | A |

-continued
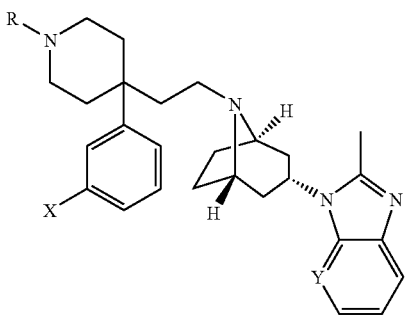
| Example | Acid # or source | R | X | Y | % Yield | LCMS ES | Ion | Method |
|---|---|---|---|---|---|---|---|---|
| 1094 | Acid 104 | | F | C | 27 | 650.43 | (M + H) | A |
| 1095 | Acid 105 | | F | C | 40 | 610.32 | (M + H) | A |
| 1096 | Acid 106 | | F | C | 42 | 612.35 | (M + H) | A |
| 1097 | Acid 107 | | F | C | 27 | 636.39 | (M + H) | A |
| 1098 | Acid 108 | | F | C | 31 | 614.39 | (M + H) | A |

-continued
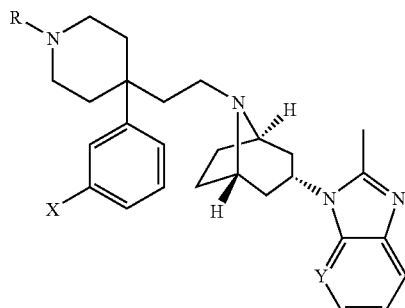
| Example | Acid # or source | R | X | Y | % Yield | LCMS ES | Ion | Method |
|---|---|---|---|---|---|---|---|---|
| 1099 | Acid 109 | (methylamide-cyclopentane-acetone) | F | C | 31 | 628.44 | (M + H) | A |
| 1100 | Acid 110 | (methylamide-ketone) | F | C | 34 | 560.37 | (M + H) | A |
| 1101 | Acid 111 | (methylamide-dimethyl-ketone) | F | C | 40 | 602.38 | (M + H) | A |
| 1102 | Acid 112 | (methylamide-ketone) | F | C | 39 | 574.4 | (M + H) | A |
| 1103 | Acid 113 | (methylamide-acetylpyrazine) | F | C | 34 | 610.35 | (M + H) | A |
| 1104 | Acid 114 | (cyclopropylamide-phenyl-ketone) | F | C | 20 | 676.4 | (M + H) | A |
| 1105 | Acid 115 | (cyclopropylamide-cyclohexene-acetyl) | F | C | 31 | 638.38 | (M + H) | A |

-continued

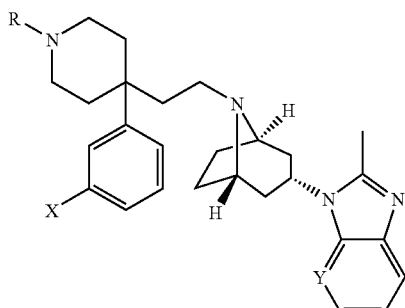

| Example | Acid # or source | R | X | Y | % Yield | LCMS ES | Ion | Method |
|---|---|---|---|---|---|---|---|---|
| 1106 | Acid 116 | *cyclopropyl-NH-C(O)-CH2-CH(Ph)-C(O)-CH3* | F | C | 27 | 662.42 | (M + H) | A |
| 1107 | Acid 117 | *cyclopropyl-NH-C(O)-(2-acetylcyclohexyl)* | F | C | 25 | 640.49 | (M + H) | A |
| 1108 | Acid 118 | *cyclopropyl-NH-C(O)-(2-acetylcyclopentenyl)* | F | C | 37 | 624.44 | (M + H) | A |
| 1109 | Acid 119 | *cyclopropyl-NH-C(O)-CH2-C(cyclopentyl)(CH2-C(O)CH3)* | F | C | 19 | 654.44 | (M + H) | A |
| 1110 | Acid 120 | *cyclopropyl-NH-C(O)-CH2-CH2-C(O)-CH3* | F | C | 53 | 586.41 | (M + H) | A |
| 1111 | Acid 121 | *cyclopropyl-NH-C(O)-CH2-C(CH3)2-CH2-C(O)-CH3* | F | C | 29 | 628.44 | (M + H) | A |
| 1112 | Acid 122 | *cyclopropyl-NH-C(O)-(2-acetylphenyl)* | F | C | 41 | 634.42 | (M + H) | A |

-continued
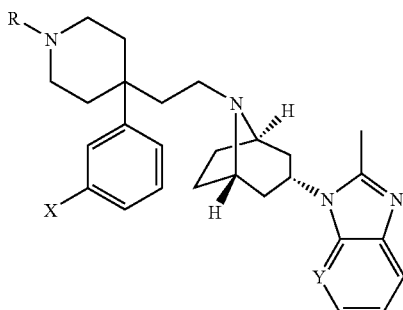
| Example | Acid # or source | R | X | Y | % Yield | LCMS ES | Ion | Method |
|---|---|---|---|---|---|---|---|---|
| 1113 | Acid 123 | *cyclopropyl-NH-C(=O)-CH2CH2CH2-C(=O)-CH3* | F | C | 47 | 600.45 | (M + H) | A |
| 1114 | Acid 124 | *cyclopropyl-NH-C(=O)-(3-acetylpyrazin-2-yl)* | F | C | 31 | 636.36 | (M + H) | A |
| 1115 | Acid 125 | *iPr-NH-C(=O)-CH2CH2-C(CH3)2-C(=O)-CH3* | F | C | 21 | 630.43 | (M + H) | A |
| 1116 | Acid 126 | *iPr-NH-C(=O)-CH2CH2-CH(Ph)-C(=O)-CH3* | F | C | 24 | 678.51 | (M + H) | A |
| 1117 | Acid 127 | *iPr-NH-C(=O)-(2-acetyl-4-cyclohexenyl)* | F | C | 38 | 640.51 | (M + H) | A |

-continued

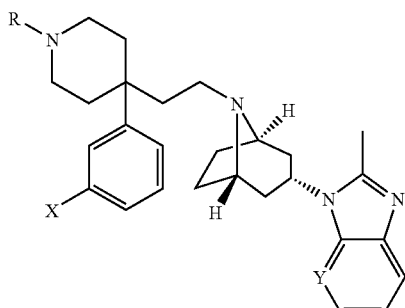

| Example | Acid # or source | R | X | Y | % Yield | LCMS ES | Ion | Method |
|---|---|---|---|---|---|---|---|---|
| 1118 | Acid 128 | *isopropyl-NH-C(O)-CH2-CH(Ph)-C(O)-CH3* | F | C | 33 | 664.5 | (M + H) | A |
| 1119 | Acid 129 | *isopropyl-NH-C(O)-(2-acetylcyclohexyl)* | F | C | 35 | 642.51 | (M + H) | A |
| 1120 | Acid 130 | *isopropyl-NH-C(O)-(2-acetylcyclopentenyl)* | F | C | 38 | 626.47 | (M + H) | A |
| 1121 | Acid 131 | *isopropyl-NH-C(O)-CH2-C(cyclopentyl)-CH2-C(O)-CH3* | F | C | 15 | 656.49 | (M + H) | A |
| 1122 | Acid 132 | *isopropyl-NH-C(O)-CH2-CH2-C(O)-CH3* | F | C | 34 | 588.45 | (M + H) | A |
| 1123 | Acid 133 | *isopropyl-NH-C(O)-CH2-C(CH3)2-CH2-C(O)-CH3* | F | C | 36 | 630.51 | (M + H) | A |
| 1124 | Acid 134 | *isopropyl-NH-C(O)-(2-acetylphenyl)* | F | C | 33 | 636.45 | (M + H) | A |

-continued

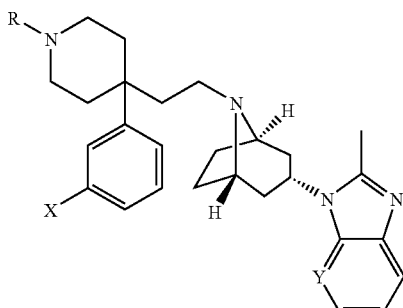

| Example | Acid # or source | R | X | Y | % Yield | LCMS ES | Ion | Method |
|---|---|---|---|---|---|---|---|---|
| 1125 | Acid 135 | *structure: N-isopropyl amide with 4-oxopentyl chain* | F | C | 34 | 602.48 | (M + H) | A |
| 1126 | Acid 136 | *structure: N-isopropyl 3-acetylpyrazine-2-carboxamide* | F | C | 29 | 638.43 | (M + H) | A |
| 1127 | Acid 137 | *structure: N-ethyl amide with 4-oxo-3-phenylpentyl chain* | F | C | 20 | 664.52 | (M + H) | A |
| 1128 | Acid 138 | *structure: N-ethyl 3,3-dimethyl-4-oxopentanamide* | F | C | 25 | 602.45 | (M + H) | A |
| 1129 | Acid 139 | *structure: N-ethyl 2-acetylcyclohex-3-enecarboxamide* | F | C | 26 | 626.45 | (M + H) | A |

-continued
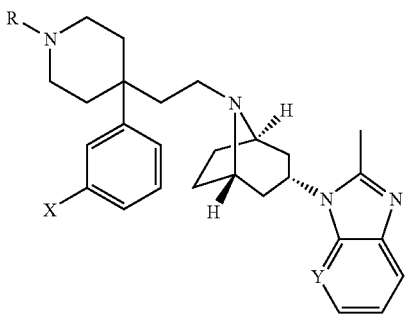
| Example | Acid # or source | R | X | Y | % Yield | LCMS ES | Ion | Method |
|---|---|---|---|---|---|---|---|---|
| 1130 | Acid 140 | | F | C | 31 | 650.51 | (M + H) | A |
| 1131 | Acid 141 | | F | C | 25 | 628.52 | (M + H) | A |
| 1132 | Acid 142 | | F | C | 44 | 586.42 | (M + H) | A |
| 1133 | Acid 143 | | F | C | 34 | 612.49 | (M + H) | A |
| 1134 | Acid 144 | | F | C | 18 | 640.49 | (M + H) | A |
| 1135 | Acid 145 | | F | C | 41 | 574.43 | (M + H) | A |
| 1136 | Acid 146 | | F | C | 23 | 616.48 | (M + H) | A |

-continued
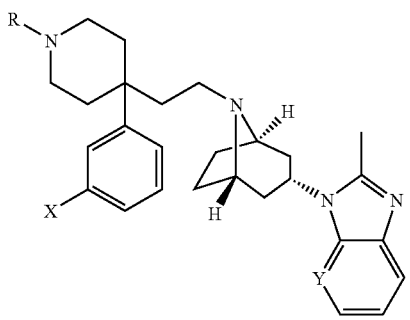
| Example | Acid # or source | R | X | Y | % Yield | LCMS ES | Ion | Method |
|---|---|---|---|---|---|---|---|---|
| 1137 | Acid 147 | (ethylcarbamoyl-acetylphenyl) | F | C | 25 | 622.44 | (M + H) | A |
| 1138 | Acid 148 | (N-ethyl 5-oxohexanamide) | F | C | 37 | 588.45 | (M + H) | A |
| 1139 | Acid 149 | (N-ethyl acetylpyrazine carboxamide) | F | C | 35 | 624.44 | (M + H) | A |
| 1140 | Acid 150 | (N-ethyl acetylcyclobutane carboxamide) | F | C | 35 | 600.46 | (M + H) | A |
| 1141 | Acid 151 | (amide oxopentenamide) | F | C | 33 | 544.35 | (M + H) | A |
| 1142 | Acid 152 | (N-ethyl tetrafluoro acetylbenzamide) | F | C | 15 | 694.34 | (M + H) | A |

-continued
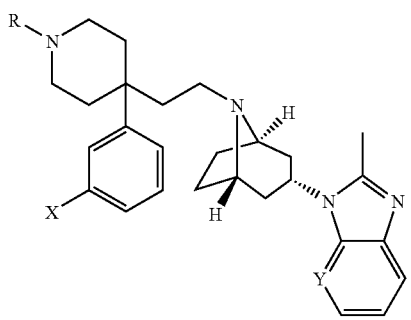
| Example | Acid # or source | R | X | Y | % Yield | LCMS ES | Ion | Method |
|---|---|---|---|---|---|---|---|---|
| 1143 | Acid 153 | (N-ethyl carboxamide acetyl dimethyl cyclohexene) | F | C | 14 | 654.43 | (M + H) | A |
| 1144 | glax | (4-hydroxy-3-acetyl-7-trifluoromethyl quinoline) | F | C | 52 | 686.4 | (M + H) | A |
| 1145 | glax | (5-acetyl uracil) | F | C | 18 | 585.34 | (M + H) | A |
| 1146 | glax | (4-(imidazol-1-ylmethyl)acetophenone) | F | C | 29 | 631.37 | (M + H) | A |
| 1147 | glax | (1-methyl-4-(2-oxopropyl)imidazole) | F | C | 30 | 569.35 | (M + H) | A |

-continued
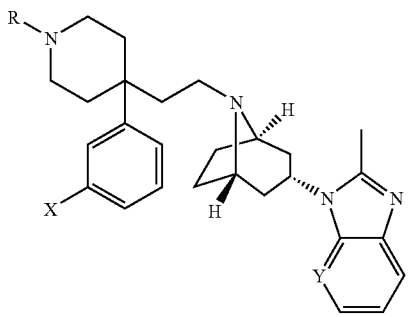
| Example | Acid # or source | R | X | Y | % Yield | LCMS ES | Ion | Method |
|---|---|---|---|---|---|---|---|---|
| 1148 | glax | (3-acetylphenyl)acetamide-N-phenyl | F | C | 30 | 684.4 | (M + H) | A |
| 1149 | glax | 3-acetyl-2,2,3-trimethyl-N-phenylcyclopentanecarboxamide | F | C | 12 | 704.44 | (M + H) | A |
| 1150 | glax | 2-acetyl-4-hydroxy-5-oxopyrrolidine | F | C | 11 | 574.41 | (M + H) | A |
| 1151 | glax | 5-acetyl-4-hydroxy-2-mercaptopyrimidine | F | C | 45 | 601.36 | (M + H) | A |
| 1152 | glax | 4-acetyl-6-methyl-3(2H)-pyridazinone | F | C | 65 | 583.38 | (M + H) | A |
| 1153 | glax | 3-acetyl-4-hydroxyquinoline | F | C | 47 | 618.41 | (M + H) | A |

-continued
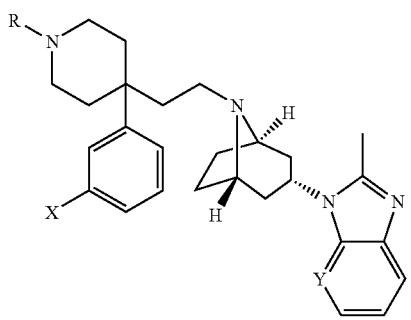
| Example | Acid # or source | R | X | Y | % Yield | LCMS ES | Ion | Method |
|---|---|---|---|---|---|---|---|---|
| 1154 | glax | (4-hydroxy-1,6-naphthyridin-3-yl acetyl) | F | C | 17 | 619.39 | (M + H) | A |
| 1155 | glax | (3-acetyl-2-hydroxypyridine) | F | C | 54 | 568.38 | (M + H) | A |
| 1156 | glax | (3-acetyl-2-hydroxyquinoxaline) | F | C | 63 | 619.4 | (M + H) | A |
| 1157 | glax | (4-acetyl-3-hydroxypyridine) | F | C | 44 | 568.37 | (M + H) | A |
| 1158 | glax | (6-acetyl-5-hydroxy-1H-pyrazolo[4,3-b]pyridine) | F | C | 15 | 608.43 | (M + H) | A |
| 1159 | glax | (3-acetyl-6-fluoro-4-hydroxyquinoline) | F | C | 38 | 636.4 | (M + H) | A |
| 1160 | glax | (3-acetyl-4-hydroxyisoxazole) | F | C | 13 | 558.36 | (M + H) | A |

-continued
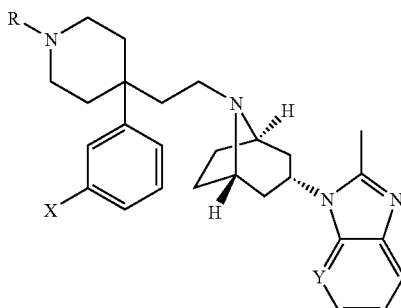
| Example | Acid # or source | R | X | Y | % Yield | LCMS ES | Ion | Method |
|---|---|---|---|---|---|---|---|---|
| 1161 | glax | (3-hydroxy-7-methyl-quinoxalin-2-yl)methanone | F | C | 76 | 633.43 | (M + H) | A |
| 1162 | glax | (4-hydroxy-1-methyl-piperidin-3-yl)methanone | F | C | 47 | 588.45 | (M + H) | A |
| 1163 | glax | (4-hydroxy-6-oxo-5,6-dihydro-[1,5]naphthyridin-3-yl)methanone | F | C | 12 | 635.45 | (M + H) | A |
| 1164 | glax | (5-ethanesulfonyl-3-hydroxy-isothiazol-4-yl)methanone | F | C | 23 | 666.36 | (M + H) | A |
| 1165 | glax | (4-hydroxy-1-methyl-piperidin-3-yl)methanone | F | C | 70 | 588.45 | (M + H) | |

-continued

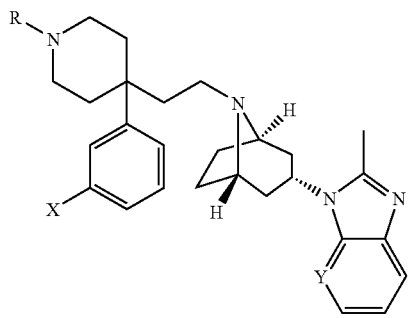

| Example | Acid # or source | R | X | Y | % Yield | LCMS ES | Ion | Method | |
|---|---|---|---|---|---|---|---|---|---|
| 1166 | glax | (4-hydroxy-1-ethyl-2-oxo-pyridin-5-yl)C(O)CH3 | F | C | 41 | 612.41 | (M + H) | A | A |
| 1167 | glax | (3-bromo-4-hydroxy-isothiazol-5-yl)C(O)CH3 | F | C | 20 | 652.26 | (M + H) | A | |

Example 1021

Example 1022

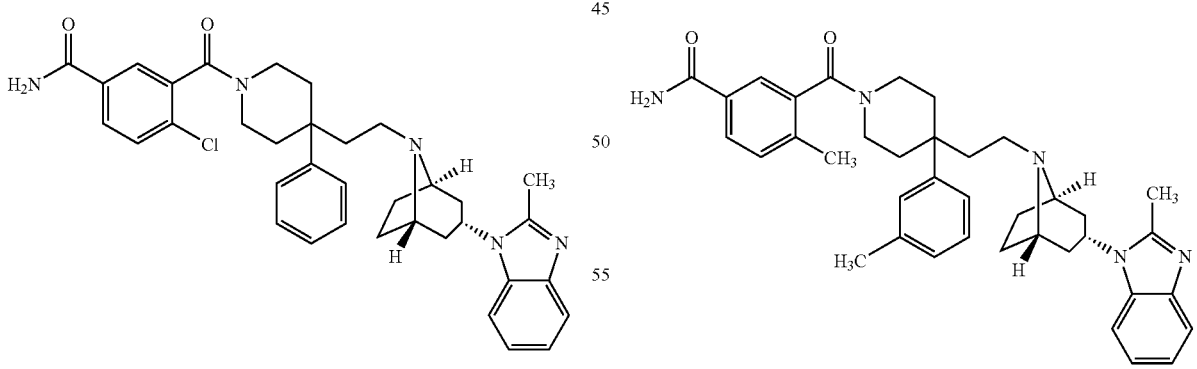

4-chloro-3-[(4-{2-[(1R,5S)-3-(2-methyl-1H-benzimidazol-1-yl)-8-azabicyclo[3.2.1]oct-8-yl]ethyl}-4-phenylpiperidin-1-yl)carbonyl]benzamide. $^1$H NMR (300 MHz, CD$_3$OD) δ 7.96-7.07 (m, 12H), 4.75 (m, 1H), 4.21 (m, 1H), 3.90-3.10 (m, 6H), 2.53 (s, 3H), 2.50-1.68 (m, 15H).

4-methyl-3-{[4-(2-[(1R,5S)-3-(2-methyl-1H-benzimidazol-1-yl)-8-azabicyclo[3.2.1]oct-8-yl]ethyl}-4-(3-methylphenyl)-1-piperidinyl]carbonyl}benzamide. $^1$H NMR (300 MHz, CD$_3$OD) δ 7.96-7.07 (m, 11H), 4.75 (m, 1H), 4.31-4.15

(m, 1H), 3.91-3.10 (m, 6H), 2.53 (s, 3H), 2.50-1.68 (m, 15H), 2.43 (s, 1.5H), 2.38 (s, 3H), 2.25 (s, 1.5H).

Example 1023

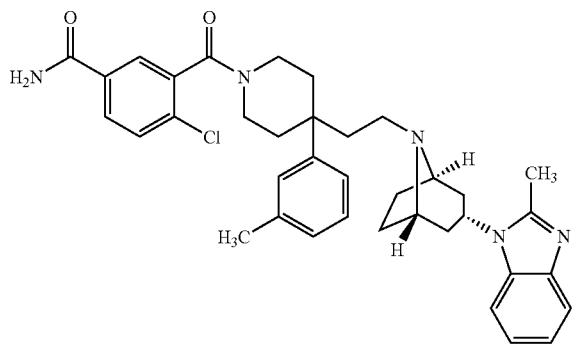

4-chloro-3-{[4-{2-[(1R,5S)-3-(2-methyl-1H-benzimidazol-1-yl)-8-azabicyclo[3.2.1]oct-8-yl]ethyl}-4-(3-methylphenyl)-1-piperidinyl]carbonyl}benzamide. $^1$H NMR (300 MHz, CD$_3$OD) δ 7.96-7.07 (m, 11H), 4.75 (m, 1H), 4.22 (m, 1H), 3.80-3.16 (m, 6H), 2.53 (s, 3H), 2.50-1.68 (m, 15H), 2.38 (s, 3H).

Example 1024

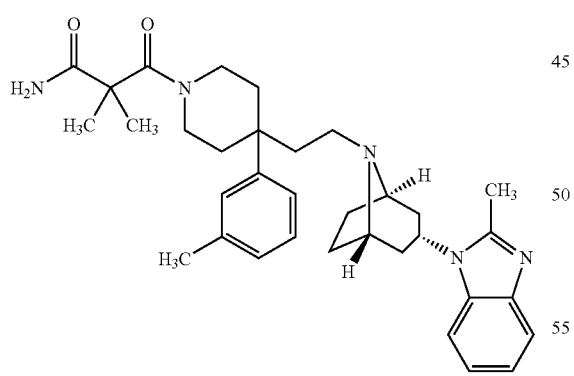

2,2-dimethyl-3-[4-{2-[(1R,5S)-3-(2-methyl-1H-benzimidazol-1-yl)-8-azabicyclo[3.2.1]oct-8-yl]ethyl}-4-(3-methylphenyl)-1-piperidinyl]-3-oxopropanamide. $^1$H NMR (300 MHz, CD$_3$OD) δ 7.55-7.06 (m, 8H), 4.77 (m, 1H), 4.02 (m, 1H), 3.89-3.17 (m, 6H), 2.67-1.68 (m, 21H), 2.56 (s, 3H), 2.37 (s, 3H).

Example 1025

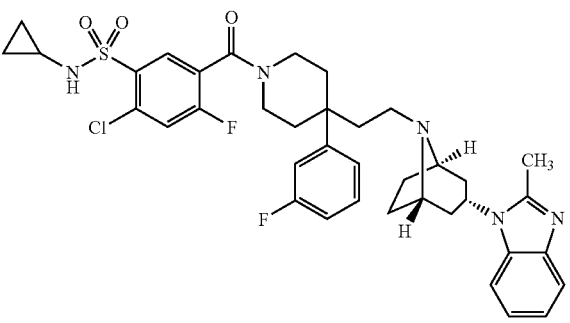

2-chloro-N-cyclopropyl-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]benzenesulfonamide. $^1$H NMR (300 MHz, CD$_3$OD) δ ppm 8.18 (m, 1H), 7.67 (d, J=8.8 Hz, 1H), 7.58 (m, 1H), 7.47 (m, 2H), 7.30 (s, 1H), 7.29-7.20 (m, 3H), 1.05 (m, 1H), 4.79 (m, 1H), 4.21 (m, 1H), 3.60-3.25 (m, 8H), 2.59 (s, 3H), 2.52-1.70 (m, 15H), 0.56 (m, 4H).

Example 1026

2-chloro-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-N-methylbenzenesulfonamide. $^1$H NMR (300 MHz, CD$_3$OD) δ ppm 8.09 (m, 1H), 7.60 (d, J=8.8 Hz, 1H), 7.53 (m, 1H), 7.40 (m, 2H), 7.25-7.16 (m, 4H), 7.00 (m, 1H), 4.75 (m, 1H), 4.16 (m, 1H), 3.53-3.18 (m, 8H), 2.55 (d, J=9.3 Hz, 3H), 2.52-1.70 (m, 16H).

Example 1027

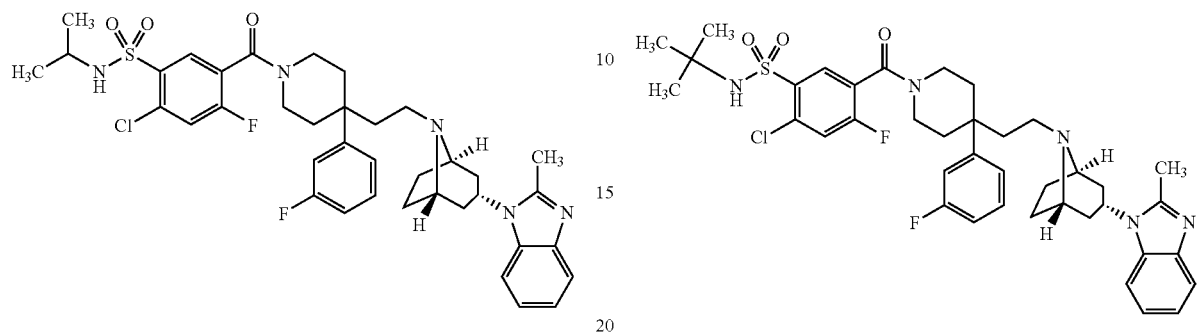

2-chloro-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-N-(1-methylethyl)benzenesulfonamide. $^1$H NMR (300 MHz, CD$_3$OD) δ ppm 8.11 (m, 1H), 7.60 (d, J=8.8 Hz, 1H), 7.53 (m, 1H), 7.40 (m, 2H), 7.25-7.16 (m, 4H), 7.00 (m, 1H), 4.74 (m, 1H), 4.17 (m, 1H), 3.53-3.18 (m, 8H), 2.53 (s, 3H), 2.52-1.70 (m, 14H), 1.07 (d, J=6.5 Hz, 6H).

Example 1028

2-chloro-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-N (2,2,2-trifluoroethyl)benzenesulfonamide. $^1$H NMR (300 MHz, CD$_3$OD) δ ppm 8.10 (m, 1H), 7.60 (d, J=8.8 Hz, 1H), 7.51 (m, 1H), 7.40 (m, 2H), 7.25-7.16 (m, 4H), 7.00 (m, 1H), 4.73 (m, 1H), 4.16 (m, 1H), 3.77 (q, J=9.4 Hz, 2H), 3.53-3.18 (m, 8H), 2.53 (s, 3H), 2.52-1.68 (m, 13H).

Example 1029

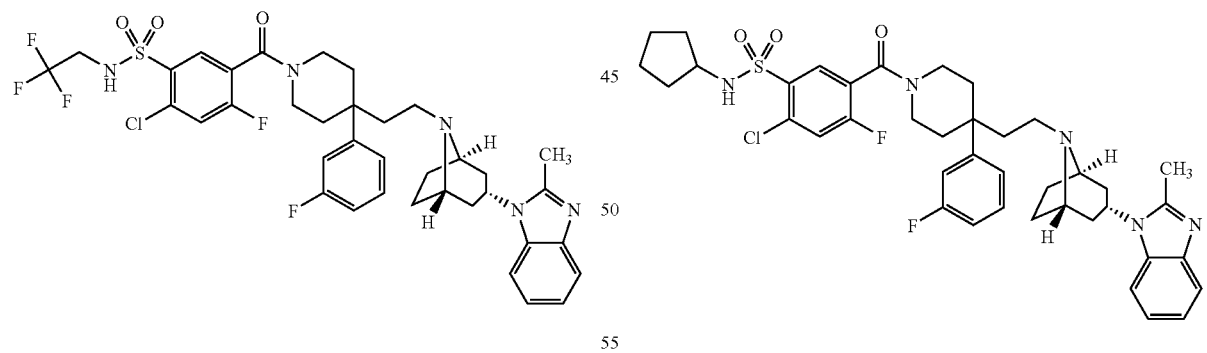

2-chloro-N-(1,1-dimethylethyl)-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]benzenesulfonamide. $^1$H NMR (300 MHz, CD$_3$OD) δ ppm 8.10 (m, 1H), 7.58 (d, J=8.8 Hz, 1H), 7.51 (m, 1H), 7.40 (m, 2H), 7.25-7.16 (m, 4H), 7.00 (m, 1H), 4.74 (m, 1H), 4.17 (m, 1H), 3.53-3.18 (m, 8H), 2.53 (s, 3H), 2.52-1.69 (m, 13H), 1.20 (s, 9H).

Example 1030

2-chloro-N-cyclopentyl-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]benzenesulfonamide. $^1$H NMR (300 MHz, CD$_3$OD) δ ppm 8.11 (m, 1H), 7.60 (d, J=8.8 Hz, 1H), 7.51 (m, 1H), 7.40 (m, 2H), 7.25-7.16 (m, 4H), 7.00 (m, 1H), 4.72 (m, 1H), 4.16 (m, 1H), 3.57-3.18 (m, 8H), 2.53 (s, 3H), 2.52-1.39 (m, 22H).

Example 1031

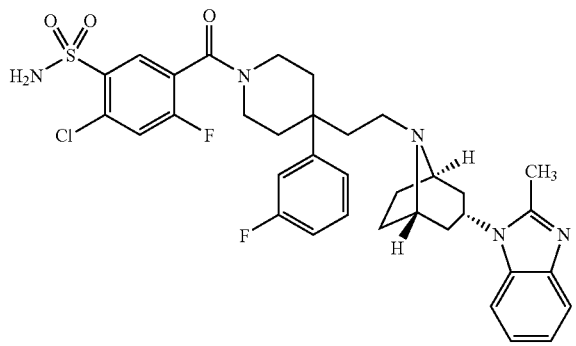

2-chloro-4-fluoro-5-[(4-(3-fluorophenyl)-4-{2-[(1R,5S)-3-(2-methyl-1H-benzimidazol-1-yl)-8-aza bicyclo[3.2.1]oct-8-yl]ethyl}-1-piperidinyl)carbonyl]benzenesulfonamide. $^1$H NMR (300 MHz, CD$_3$OD) δ ppm 8.10 (m, 1H), 7.58 (d, J=9.0 Hz, 1H), 7.51 (m, 1H), 7.40 (m, 2H), 7.25-7.16 (m, 4H), 7.00 (m, 1H), 4.73 (m, 1H), 4.16 (m, 1H), 3.52-3.19 (m, 8H), 2.53 (s, 3H), 2.52-1.69 (m, 13H).

Example 1032

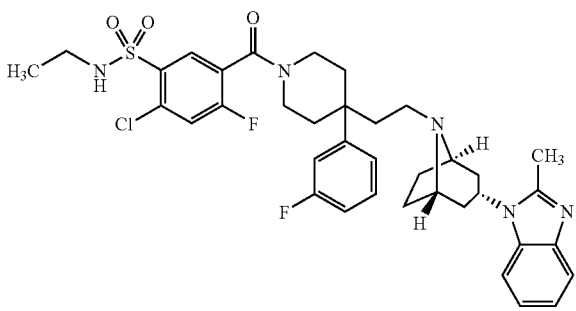

2-chloro-N-ethyl-4-fluoro-5-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]benzenesulfonamide. $^1$H NMR (300 MHz, CD$_3$OD) δ ppm 8.09 (m, 1H), 7.59 (d, J=9.1 Hz, 1H), 7.51 (m, 1H), 7.40 (m, 2H), 7.25-7.16 (m, 4H), 7.00 (m, 1H), 4.74 (m, 1H), 4.16 (m, 1H), 3.52-3.19 (m, 8H), 2.97 (q, J=7.2 Hz, 2H), 2.53 (s, 3H), 2.52-1.69 (m, 13H), 1.06 (t, J=7.2 Hz, 3H).

Example 1033

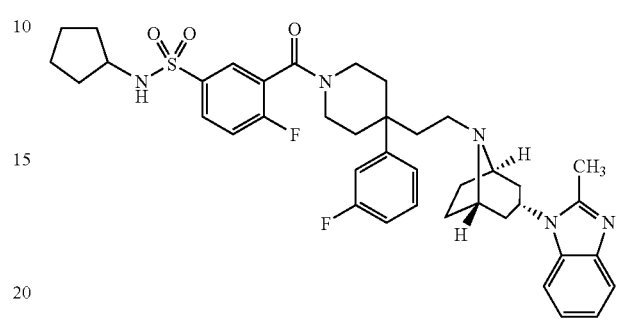

N-cyclopentyl-4-fluoro-3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]benzenesulfonamide. $^1$H NMR (300 MHz, CD$_3$OD) δ ppm 7.98 (m, 1H), 7.88 (m, 1H), 7.53 (m, 1H), 7.41 (m, 3H), 7.25-7.16 (m, 4H), 7.00 (m, 1H), 4.73 (m, 1H), 4.17 (m, 1H), 3.60-3.18 (m, 8H), 2.52 (s, 3H), 2.52-1.34 (m, 22H).

Example 1034

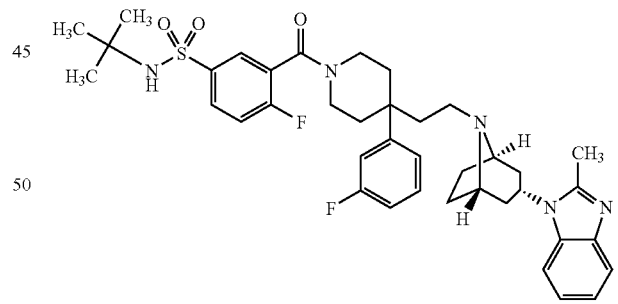

N-(1,1-dimethylethyl)-4-fluoro-3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]benzenesulfonamide. $^1$H NMR (300 MHz, CD$_3$OD) δ ppm 8.01 (m, 1H), 7.89 (m, 1H), 7.52 (m, 1H), 7.40 (m, 3H), 7.25-7.16 (m, 4H), 7.00 (m, 1H), 4.74 (m, 1H), 4.17 (m, 1H), 3.52-3.17 (m, 8H), 2.53 (s, 3H), 2.52-1.68 (m, 13H), 1.19 (s, 9H).

Example 1035

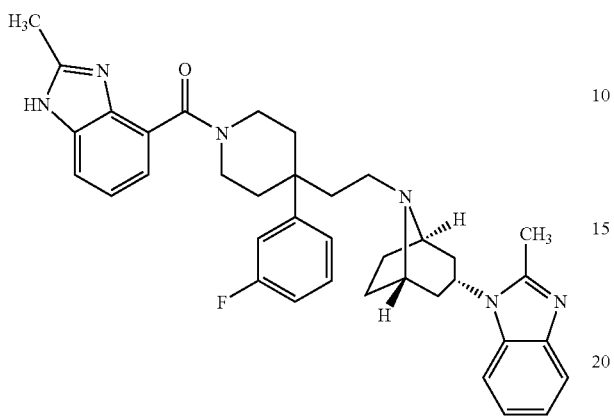

1-[(1R,5S)-8-(2-{4-(3-fluorophenyl)-1-[(2-methyl-1H-benzimidazol-4-yl)carbonyl]-4-piperidinyl}ethyl)-8-azabicyclo[3.2.1]oct-3-yl]-2-methyl-1H-benzimidazole. $^1$H NMR (300 MHz, CD$_3$OD) δ ppm 8.01-6.94 (m, 11H), 4.90-4.72 (m, 1H), 3.97 (m, 1H), 3.70-3.16 (m, 8H), 2.65 (s, 3H), 2.55 (s, 3H), 2.46-1.38 (m, 14H).

Example 1039

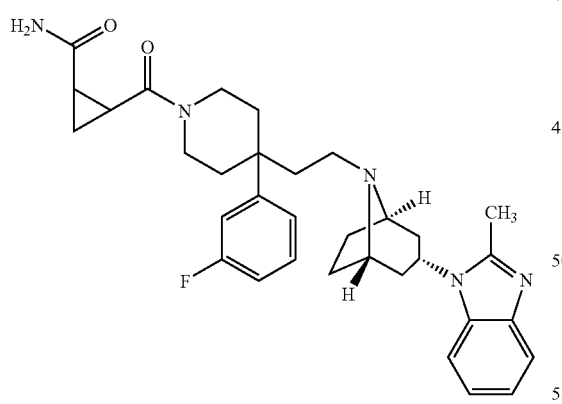

2-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclopropanecarboxamide. $^1$H NMR (300 M Hz, CD$_3$OD) δ ppm 7.53 (m, 1H), 7.41 (m, 2H), 7.25-7.14 (m, 4H), 6.98 (m, 1H), 4.74 (m, 1H), 4.11-3.79 (m, 2H), 3.52-3.29 (m, 7H), 3.08 (m, 1H), 2.55 (s, 3H), 2.52-1.17 (m, 16H).

Example 1040

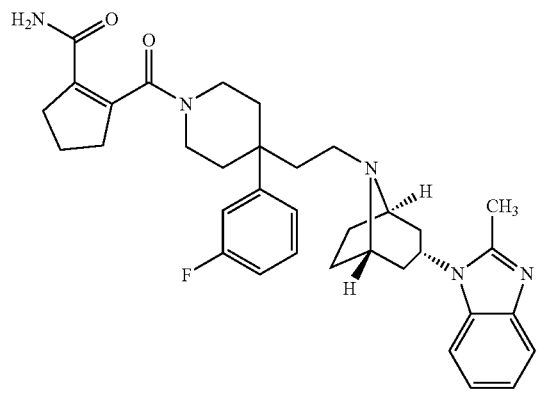

2-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-1-cyclopentene-1-carboxamide. $^1$H NMR (300 MHz, CD$_3$OD) δ ppm 7.53 (m, 1H), 7.41 (m, 2H), 1.25-7.14 (m, 4H), 6.97 (m, 1H), 4.74 (m, 1H), 4.0 (m, 1H), 3.55 (m, 1H), 3.35-3.20 (m, 5H), 3.00 (m, 1H), 2.54 (s, 3H), 2.80-1.17 (m, 20H).

Example 1041

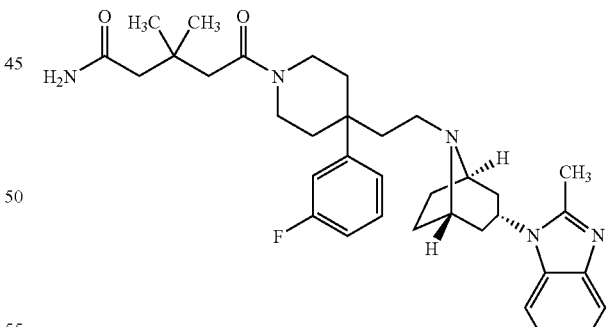

5-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-3,3-dimethyl-5-oxopentanamide. $^1$H NMR (300 MHz, CD$_3$OD) δ ppm 7.50 (m, 1H), 7.40 (m, 2H), 7.25-7.16 (m, 4H), 6.98 (m, 1H), 4.74 (m, 1H), 4.00 (m, 1H), 3.83 (m, 1H), 3.42-1.68 (m, 24H), 2.55 (s, 3H), 1.10 (d, J=3.8 Hz, 6H).

Example 1042

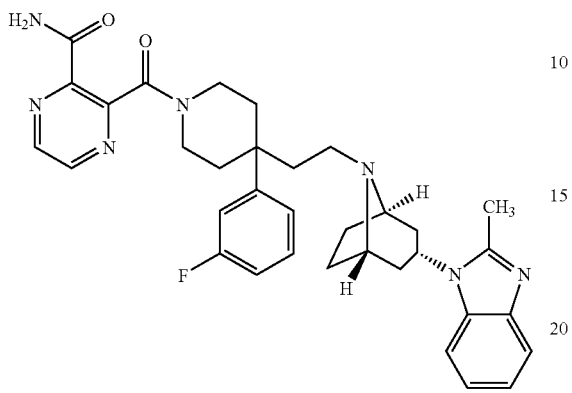

3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-2-pyrazinecarboxamide. $^1$H NMR (300 MHz, CD$_3$OD) δ ppm 8.78 (d, J=2.5 Hz, 1H), 8.73 (d, J=2.5 Hz, 1H), 7.52 (m, 1H), 7.40 (m, 2H), 7.25-7.16 (m, 4H), 6.98 (m, 1H), 4.74 (m, 1H), 4.15 (m, 1H), 3.46-1.68 (m, 21H), 2.52 (s, 3H).

Example 1043

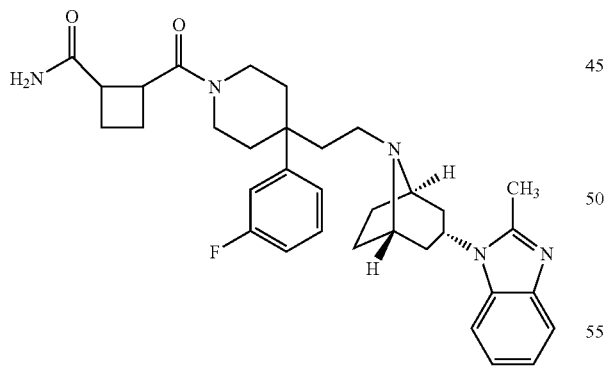

2-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]cyclobutanecarboxamide. $^1$H NMR (300 M Hz, CD$_3$OD) δ ppm 7.52 (m, 1H), 7.40 (m, 2H), 7.25-7.16 (m, 4H), 6.97 (m, 1H), 4.73 (m, 1H), 4.15-1.68 (m, 28H), 2.55 (s, 3H).

Example 1045

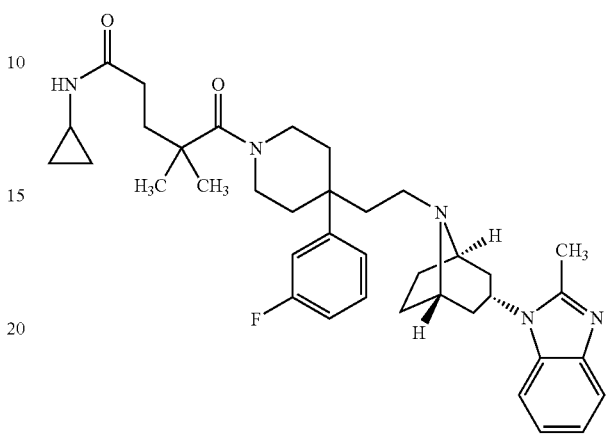

N-cyclopropyl-5-(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)-4,4-dimethyl-5-oxopentanamide. $^1$H NMR (300 MHz, CD$_3$OD) δ ppm 7.52 (m, 1H), 7.40 (m, 2H), 7.25-7.12 (m, 4H), 6.96 (m, 1H), 4.75 (m, 1H), 3.98 (m, 1H), 3.36-1.68 (m, 28H), 2.55 (s, 3H).

Example 1050

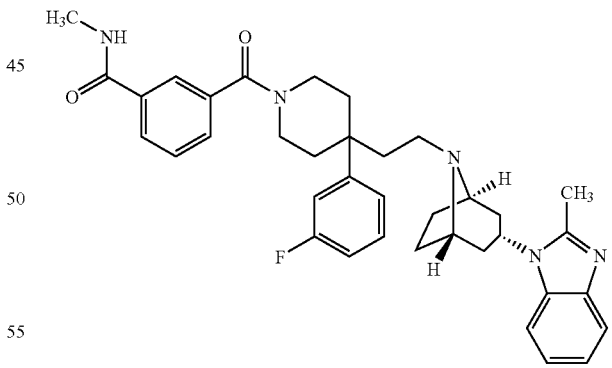

3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-N-methylbenzamide. $^1$H NMR (300 MHz, CD$_3$OD) δ ppm 7.85 (m, 1H), 7.84 (m, 1H), 7.55 (m, 3H), 7.40 (m, 2H), 7.26-7.16 (m, 4H), 7.00 (m, 1H), 4.73 (m, 1H), 4.13 (m, 1H), 3.58 (m, 1H), 3.46-1.68 (m, 20H), 2.91 (s, 3H), 2.51 (s, 3H).

Example 1051

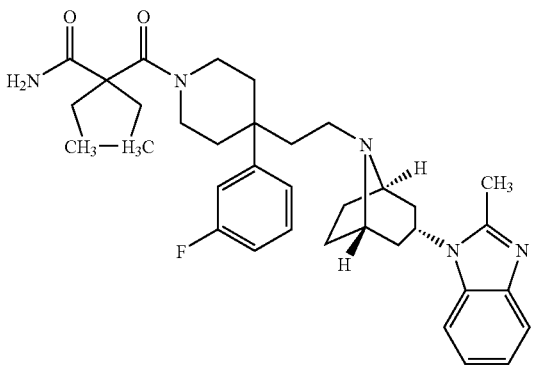

2-ethyl-2-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]butanamide. $^1$H NMR (300 MHz, CD$_3$OD) δ 7.52 (m, 1H), 7.41 (m, 2H), 7.26-7.16 (m, 4H), 6.98 (m, 1H), 4.74 (m, 1H), 3.97 (m, 1H), 3.67 (m, 1H), 3.34-3.21 (m, 5H), 2.55 (s, 3H), 2.41 (m, 2H), 2.22 (m, 2H), 2.03-1.69 (m, 15H), 0.80 (m, 6H).

Example 1168

Preparation of 1-(4-(1,3-benzodioxol-5-yl)-4-{2-[(1R,5S)-3-(2-methyl-1H-benzimidazol-1-yl)-8-azabicyclo[3.2.1]oct-8-yl]ethyl}piperidin-1-yl)-2-methyl-1-oxopropan-2-ol

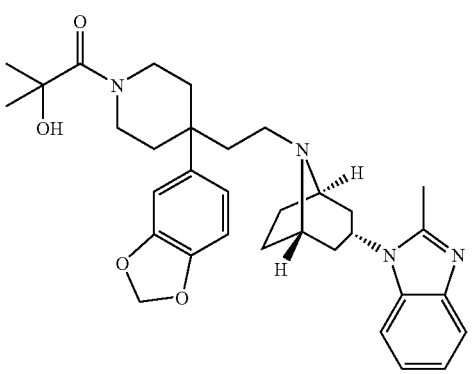

A mixture of 1-(8-{2-[4-(1,3-benzodioxol-5-yl)piperidin-4-yl]ethyl}-8-azabicyclo[3.2.1]oct-3-yl)-2-methyl-1H-benzimidazole dihydrochloride (0.20 g, 0.39 mmol), triethylamine (0.17 mL, 1.25 mmol) and 2-hydroxyisobutyric acid (41 mg, 0.39 mmol) in dimethylformamide (1.25 mL) was treated with O-(7-azabenzotriazol-1-yl)-1,1,3,3-tetramethyluronium hexafluorophosphate (163 mg, 0.43 mmol) and the resulting mixture was stirred for 1 h at rt. The mixture was diluted with water and the resulting precipitate was collected, washed with saturated sodium bicarbonate solution, with water, dried and purified by chromatography on silica gel eluting with a dichloromethane to methanol-dichloromethane 1:19 gradient to give 1-(4-(1,3-benzodioxol-5-yl)-4-{2-[(1R,5S)-3-(2-methyl-1H-benzimidazol-1-yl)-8-azabicyclo[3.2.1]oct-8-yl]ethyl}piperidin-1-yl)-2-methyl-1-oxopropan-2-ol as a solid (0.10 g, 44%). HRMS C$_{33}$H$_{42}$N$_4$O$_4$ m/z 559.3284 (M+H)$_{Cal.}$ 559.3276 (M+H)$_{Obs.}$.

Example 1169

Preparation of 1-((1R,5S)-8-{2-[4-(1,3-benzodioxol-5-yl)-1-isobutyrylpiperidin-4-yl]ethyl}-8-azabicyclo[3.2.1]oct-3-yl)-2-methyl-1H-benzimidazole

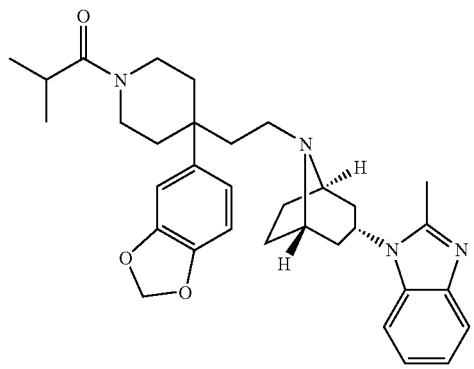

A mixture of 1-(8-{2-[4-(1,3-benzodioxol-5-yl)piperidin-4-yl]ethyl}-8-azabicyclo[3.2.1]oct-3-yl)-2-methyl-1H-benzimidazole dihydrochloride (0.20 g, 0.39 mmol), triethylamine (0.17 mL, 1.25 mmol) and isobutyric acid (34 mg, 0.39 mmol) in dimethylformamide (1.25 mL) was treated with O-(7-azabenzotriazol-1-yl)-1,1,3,3-tetramethyluronium hexafluorophosphate (163 mg, 0.43 mmol) and the resulting mixture was stirred for 1 h at rt. The mixture was diluted with water and the resulting precipitate was collected, washed with saturated sodium bicarbonate solution, with water and dried to give 1-((1R,5S)-8-{2-[4-(1,3-benzodioxol-5-yl)-1-isobutyrylpiperidin-4-yl]ethyl}-8-azabicyclo[3.2.1]oct-3-yl)-2-methyl-1H-benzimidazole as a solid (0.15 g, 72%). HRMS C$_{33}$H$_{42}$N$_4$O$_3$ m/z 543.3335 (M+H)$_{Cal.}$ 543.3322 (M+H)$_{Obs.}$.

Example 1170

Preparation of 3-(4-(1,3-benzodioxol-5-yl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropan-1-ol

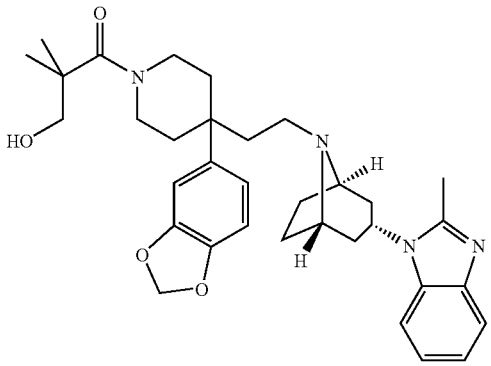

A mixture of 1-(8-{2-[4-(1,3-benzodioxol-5-yl)piperidin-4-yl]ethyl}-8-azabicyclo[3.2.1]oct-3-yl)-2-methyl-1H-benzimidazole dihydrochloride (0.20 g, 0.39 mmol), triethylamine (0.17 mL, 1.25 mmol) and 2,2-dimethyl-3-hydroxypropionic acid (46 mg, 0.39 mmol) in dimethylformamide (1.25 mL) was treated with O-(7-azabenzotriazol-1-yl)-1,1,3,3-tetramethyluronium hexafluorophosphate (163 mg, 0.43 mmol) and the resulting mixture was stirred for 1 h at rt. The mixture was diluted with water and the resulting gummy precipitate was dissolved in dichloromethane, washed with saturated sodium bicarbonate solution, with water, dried and purified by chromatography on silica gel eluting with a dichloromethane to methanol-dichloromethane 1:9 gradient to give 3-(4-(1,3-benzodioxol-5-yl)-4-{2-[(1R,5S)-3-(2-methyl-1H-benzimidazol-1-yl)-8-azabicyclo[3.2.1]oct-8-yl]ethyl}piperidin-1-yl)-2,2-dimethyl-3-oxopropan-1-ol as a solid (0.13 g, 59%). $^1$H NMR (400 MHz, CDCl$_3$) δ 7.66 (m, 1H), 7.29 (m, 1H), 7.15 (m, 2H), 6.80 (m, 2H), 6.73 (m, 1H), 5.97 (s, 2H), 4.62 (m, 1H), 3.92 (m, 2H), 3.75 (m, 1H), 3.46 (s, 2H), 3.26 (m, 4H), 2.57 (s, 3H), 2.38 (m, 2H), 2.14 (m, 2H), 1.91-2.00 (m, 6H), 1.70-1.78 (m, 4H), 1.64 (m, 2H), 1.25 (s, 6H). HRMS C$_{34}$H$_{44}$N$_4$O$_4$ m/z 573.3441 (M+H)$_{Cal.}$ 573.3428 (M+H)$_{Obs.}$

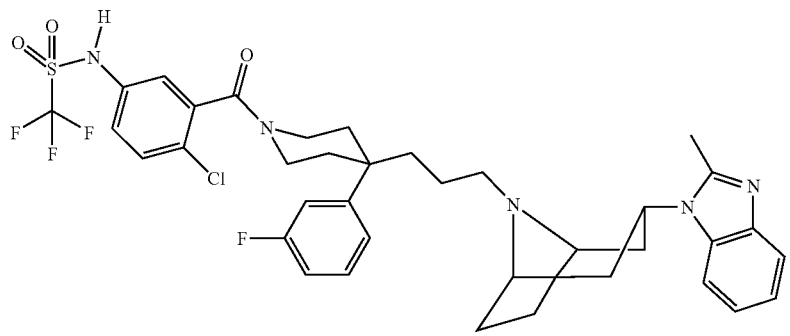

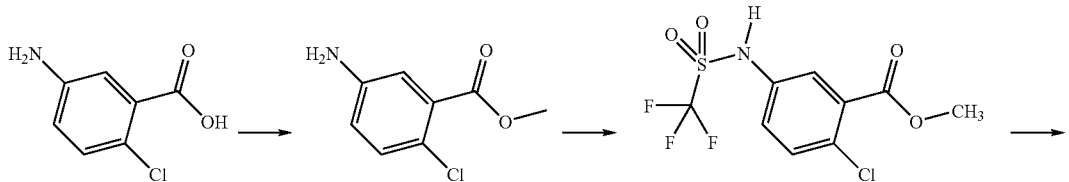

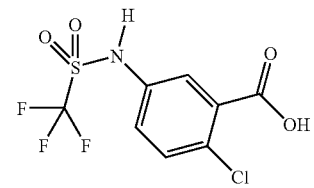

Example 1171

N-{4-chloro-3-[(4-(3-fluorophenyl)-4-{2-[3-(2-methyl-1H-benzimidazol-1-yl)-8-azabicyclo[3.2.1]oct-8-yl]ethyl}piperidin-1-yl)carbonyl]phenyl}-1,1,1-trifluoromethanesulfonamide a) Preparation of methyl 5-amino-2-chlorobenzoate

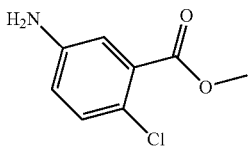

To a solution of 5-amino-2-chlorobenzoic acid (6.0 g, 35 mmol) in anhydrous methanol (100 ml) was added dropwise thionyl chloride (15 ml) with stirring under a nitrogen atmosphere. After stirring for 3 hours the volatiles were removed by spin evaporation in vacuo and the residue was dissolved in ethyl acetate and washed with saturated aqueous sodium bicarbonate and then water. The organic layer was concentrated by spin evaporation in vacuo with the addition of dichloromethane (3 times) to give methyl 5-amino-2-chlorobenzoate as a white solid (6.2 g, 95%). $^1$H-NMR (400 MHz, DMSO-$d_6$): δ 7.20-7.14 (m, 1H), 7.13-7.02 (m, 1H), 6.73-6.67 (m. 1H), 3.89 (s, 3H). ES-LCMS m/z 186 (M+H).

b) Preparation of methyl 2-chloro-5-{[(trifluoromethyl)sulfonyl]amino}benzoate

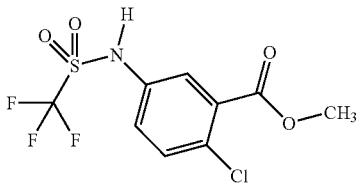

Triflic anhydride (1.53 g, 5.39 mmol) was added dropwise to a solution of methyl 5-amino-2-chlorobenzoate (2.0 g, 10.8 mmol) in dichloromethane (35 ml) at 0° C. while stirring under a nitrogen atmosphere. After warming to room temperature over 1 hour, the thick slurry was diluted with additional dichloromethane (200 ml) and washed with aqueous 1 N hydrochloric acid and then water. The dichloromethane layer was dried with MgSO$_4$ and the volatiles were removed by spin evaporation in vacuo to give methyl 2-chloro-5-{[(trifluoromethyl)sulfonyl]amino}benzoate as a tan oil (1.7 g, 100%). $^1$H-NMR (400 MHz, DMSO-$d_6$): δ 9.43 (s, 1H), 7.55-7.18 (m, 5H), 3.92-3.82 (m, 2H), 3.31-3.18 (m, 2H), 2.40-1.92 (m, 4H), and 1.38 (s, 9H). ES-LCMS m/z 317 (M+H).

c) Preparation of 2-chloro-5-{[(trifluoromethyl)sulfonyl]amino}benzoic acid

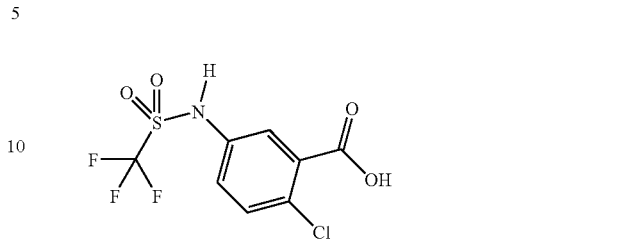

A solution of methyl 2-chloro-5-{[(trifluoromethyl)sulfonyl]amino}benzoate (1.0 g, 3.15 mmol), sodium hydroxide (378 mg, 9.44 mmol), methanol (6 ml) and water (6 ml) was stirred for 1 hour. Removal of the volatiles by spin evaporation in vacuo gave a residue that was dissolved in 1 N aqueous hydrochloric acid. The aqueous solution was extracted with ethyl acetate (3 times) and the organic layers were combined, washed with water, and concentrated by spin evaporation in vacuo to give 2-chloro-5-{[(trifluoromethyl)sulfonyl]amino}benzoic acid as a crystalline solid (0.78 g, 82%). $^1$H-NMR (400 MHz, DMSO-$d_6$): δ 7.63-7.60 (m, 1H), 7.59-7.54 (m, 1H), 7.40-7.35 (m, 1H). ES-LCMS m/z 304 (M+H).

d) Preparation of N-{4-chloro-3-[(4-(3-fluorophenyl)-4-{2-[3-(2-methyl-1H-benzimidazol-1-yl)-8-azabicyclo[3.2.1]oct-8-yl]ethyl}piperidin-1-yl)carbonyl]phenyl}-1,1,1-trifluoromethanesulfonamide

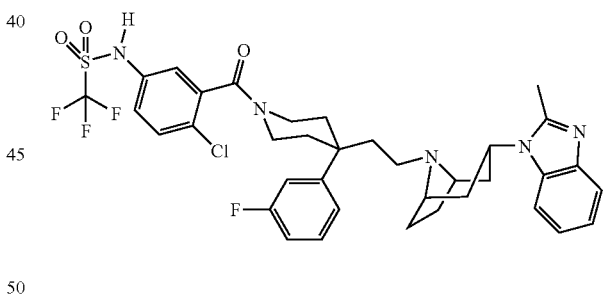

N-{4-Chloro-3-[(4-(3-fluorophenyl)-4-{2-[3-(2-methyl-1H-benzimidazol-1-yl)-8-azabicyclo[3.2.1]oct-8-yl]ethyl}piperidin-1-yl)carbonyl]phenyl}-1,1,1-trifluoromethanesulfonamide (43 mg, 23%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol), 2-chloro-5-{[(trifluoromethyl)sulfonyl]amino}benzoic acid (82 mg. 270 mmol), HATU (140 mg, 389 mmol), and DIEA (95 mg, 738 mmol) following the procedure outlined in example 5. $^1$H-NMR (400 MHz, DMSO-$d_6$): 8.6 (bs, 1H), 7.56-7.38 (m, 3H), 7.32-7.06 (m, 6H), 6.96-6.77 (m, 2H), 4.90-4.76 (bs, 1H), 4.04-3.82 (m, 3H), 3.40-3.15 (m, 5H+H$_2$O), 3.07-2.94 (m, 1H), 2.64-2.36 (m, 2H+DMSO), 2.23-1.68 (m, 14H). ES-LCMS m/z 732 (M+H).

Example 1172

1,1,1-Trifluoro-N-{3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide

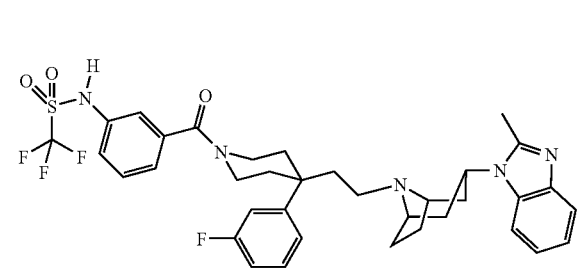

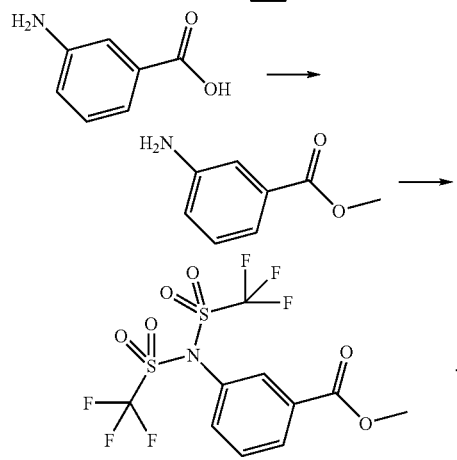

a) Preparation of methyl 3-amino-benzoate

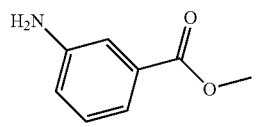

To a solution of 3-amino-benzoic acid (10.0 g, 72 mmol) in anhydrous methanol (100 ml) was added dropwise acetyl chloride (15 ml) with stirring under a nitrogen atmosphere. After stirring for 3 hours the volatiles were removed by spin evaporation in vacuo and the residue was dissolved in ethyl acetate and washed with saturated aqueous sodium bicarbonate and then water. The organic layer was concentrated by spin evaporation in vacuo with the addition of dichloromethane (3 times) give methyl 5-amino-2-chlorobenzoate as a white solid. (9.8 g, 89%). $^1$H-NMR (400 MHz, DMSO-$d_6$. δ 7.92-7.78 (m, 2H), 7.50-7.44 (m, 1H), 7.4-7.36 (m, 1H), 3.94 (s, 3H) ES-LCMS m/z 152 (M+H).

b) Preparation of methyl 3-{bis[(trifluoromethyl)sulfonyl]amino}benzoate

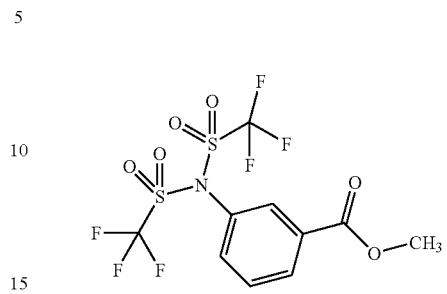

Triflic anhydride (3.73 g, 13.2 mmol) was added dropwise to a solution of methyl 3-amino-benzoate (2.0 g, 13.2 mmol) and DIEA (2.3 ml) in dichloromethane (50 ml) at 0° C. while stirring under a nitrogen atmosphere. After warming to room temperature over 1 hour, the thick slurry was diluted with additional dichloromethane (200 ml) and washed with aqueous 1 N hydrochloric acid and the water. The dichloromethane layer was dried with MgSO$_4$ and the volatiles were removed by spin evaporation in vacuo to give methyl 3-bis[(trifluoromethyl)sulfonyl]amino}benzoate as a tan oil (5.4 g, 100%). $^1$H-NMR (400 MHz, DMSO-$d_6$): δ 7.73-7.65 (m, 2H), 7.55-7.50 (m, 1H), 7.44-7.36 (m, 1H), 3.95 (s, 3H). ES-LCMS m/z 416 (M+H).

c) Preparation of 3-{[(trifluoromethyl)sulfonyl]amino}benzoic acid

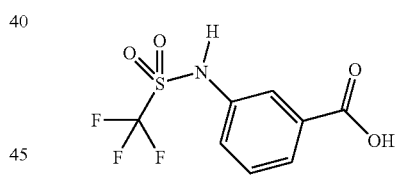

A solution of methyl 3-{bis[(trifluoromethyl)sulfonyl]amino}benzoate (5.4 g, 13.0 mmol), sodium hydroxide (3.12 g, 78.0 mmol), methanol (125 ml) and water (125 ml) was stirred for 2 hours. The solution from concentration to 75 ml by spin evaporation in vacuo and dilution with 100 ml water was extracted with ethyl acetate. The aqueous layer was acidified with 12 N hydrochloric acid and again extracted with ethyl acetate. The organic layer was washed with water and concentrated by spin evaporation in vacuo, with the addition of dichloromethane (3 times) to give a residue that was dissolved in 1 N aqueous hydrochloric acid. The aqueous solution was extracted with ethyl acetate (3 times) and the organic layers were combined, washed with water, and concentrated by spin evaporation in vacuo to 3-{[(trifluoromethyl)sulfonyl]amino}benzoic acid as a solid (2.3 g, 66%). $^1$H-NMR (400 MHz, DMSO-$d_6$): ): δ 7.83-7.78 (m, 2H), 7.55-7.50 (m, 1H), 7.50-7.46 (m, 1H). ES-LCMS m/z 269 (M+H).

d) Preparation of 1,1,1-trifluoro-N-{3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide

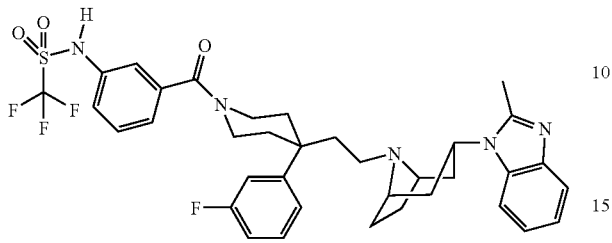

1,1,1-Trifluoro-N-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide (72 mg, 100%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol), 3-{[(trifluoromethyl)sulfonyl]amino}benzoic acid (73 mg. 270 mmol), HATU (140 mg, 369 mmol), and DIEA (95 mg, 738 mmol) following the procedure outlined in example 5. $^1$H-NMR (400 MHz, DMSO-$d_6$): δ 8.83-8.68 (bs, 1H), 7.58-7.49 (m, 1H), 7.59-7.49 (m, 2H), 7.49-7.38 (m, 2H), 7.21-7.05 (m, 4H), 7.02-6.91 (m, 2H), 6.79-6.67 (m, 1H), 5.03-4.76 (m, 1H), 4.13-3.96 (m, 3H), 3.57-3.01 (m, 6H), 2.54-2.39 (M, 5H), 2.24-1.97 (m, 8H), 1.97-1.68 (m, 3H), 1.31-1.14 (m, 2H). ES-LCMS m/z 698 (M+H).

Example 1173

N-{3-[(4-(3-Fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide a) Preparation of 3-[(methylsulfonyl)aino]benzoic acid

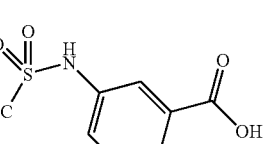

To a solution of methyl 3-amino-benzoate (2.0 g, 13.2 mmol) and pyridine (2.30 g, 29.1 mmol) in dichloromethane (50 ml) at −10° C. under a nitrogen atmosphere was slowly added methanesulfonyl chloride (2.25 ml, 29.1 mmol) by syringe. After 2 hours, water was added and the volatiles were removed by spin evaporation in vacuo. A solution of the residue and sodium hydroxide (3.175 g, 79.4 mmol) in methanol (50 ml) and water (50 ml) was stirred for 18 hours. The residue after removal of the volatiles by spin evaporation in vacuo was dissolved in 1 N hydrochloric acid and extracted with ethyl acetate. The organic layer was washed with water and the volatiles were removed by spin evaporation in vacuo to give 3-[(methylsulfonyl)amino]benzoic acid as an oil. (1.32 g, 46%). $^1$H-NMR (400 MHz, DMSO-$d_6$): δ 7.83-7.78 (m, 2H), 7.55-7.50 (m, 1H), 7.50-7.46 (m, 1H), 3×80 (s, 3H). ES-LCMS m/z 216 (M+H).

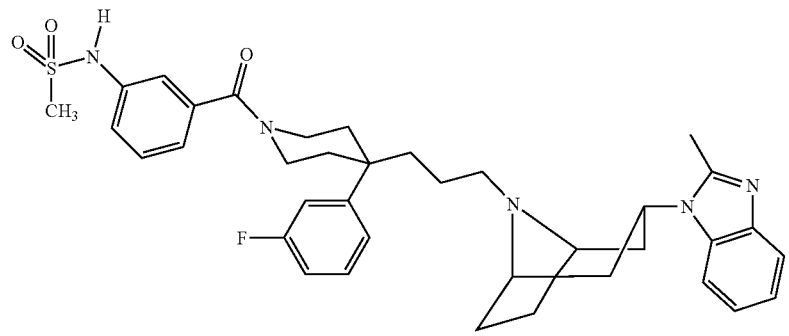

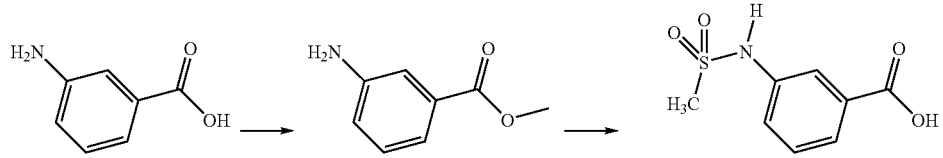

b) Preparation of N-{3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide

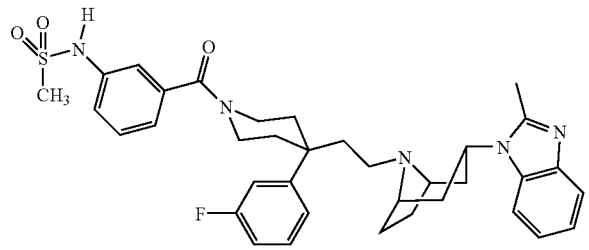

N-{3-[(4-(3-Fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide (72 mg, 100%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol 3-[(methylsulfonyl)amino]benzoic acid (73 mg. 270 mmol), HATU (140 mg, 369 mmol), and DIEA (95 mg, 738 mmol) following the procedure outlined in example 5. $^1$H-NMR (400 MHz, DMSO-d$_6$): δ 9.90 (bs 1H), 7.49-7.49 (m, 1H), 7.44-7.31 (m, 3H), 7.27-7.20 (m, 3H), 7.19-7.15 (m, 1H), 7.14-7.00 (m, 4H), 4.55-4.39 (m, 1H), 3.91-3.79 (m, 1H), 3.53-3.40 (m, 1H), 3.40-3.09 (m, 2H), 3.03-2.96 (m, 3H), 2.51-2.45 (m, 5H), 2.44-2.40 (m, 3H), 2.40-2.30 (m, 2H), 2.17-1.96 (m, 2H), 1.91-1.70 (m, 4H), 1.64-1.52 (m, 2H), 1.25-1.10 (m, 1H). ES-LCMS m/z 644 (M+H).

Example 1174

N-{3-Chloro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide a) Preparation of methyl 4-amino-2-chlorobenzoate

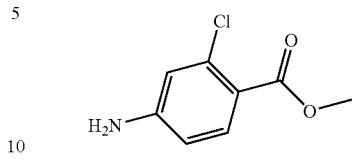

Methyl 4-amino-2-chlorobenzoate (5.1 g, 94%) was obtained as solid from 4-amino-2-chlorobenzic acid (5.0 g, 29.1 mmol)) following the procedure outlined for methyl 5-amino-2-chlorobenzoate. $^1$H-NMR (400 MHz, DMSO-d6): δ 7.64-7.57 (m, 1H), 6.65-6.57 (m, 1H), 6.51-6.39 (m, 1H), 6.16 (bs, 2H), 3.71 (s, 3H). ES-LCMS m/z 186 (M+H).

b) Preparation of 2-chloro-4-[(methylsulfonyl)amino]benzoic acid

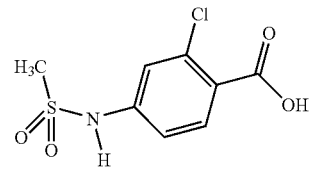

2-Chloro-4-[(methylsulfonyl)amino]benzoic acid (5.1 g, 94%) was obtained as an oil from methyl 4-amino-2-chlorobenzoate (5.0 g, 29.1 mmol)) following the procedure outlined for 3-[(methylsulfonyl)amino]benzoic acid. $^1$H-NMR (400 MHz, DMSO-d$_6$): δ 13.11 (bs, 1H), 10.29 (bs, 1H), 7.83-7.80 (m, 1H), 7.24-7.22 (m, 1H), 7.21-7.18 (m, 1H), 3.11 (s, 3H). ES-LCMS m/z 250 (M+H).

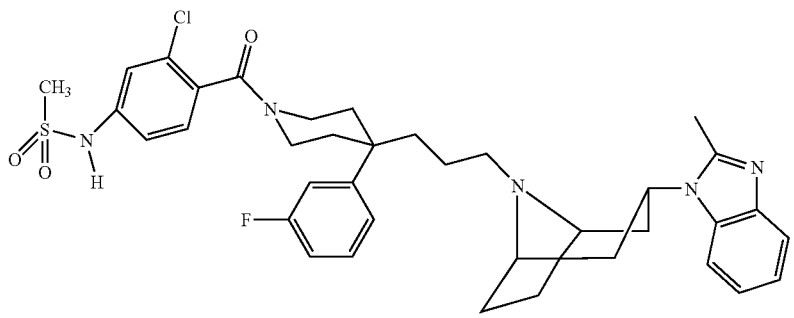

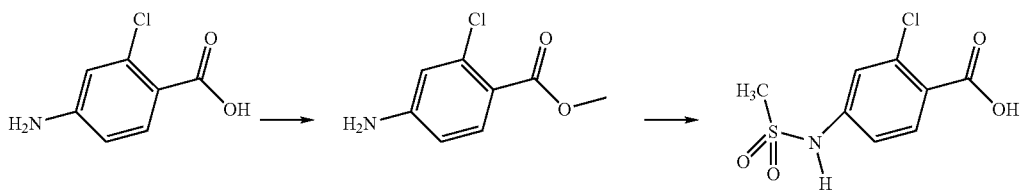

c) Preparation of N-{3-chloro-4-[(4-(3-fluorophenyl)-4-(2-[3-(2-methyl-1H-benzimidazol-1-yl)-8-azabicyclo[3.2.1]oct-8-yl]ethyl)-1-piperidinyl)carbonyl]phenyl}methanesulfonamide

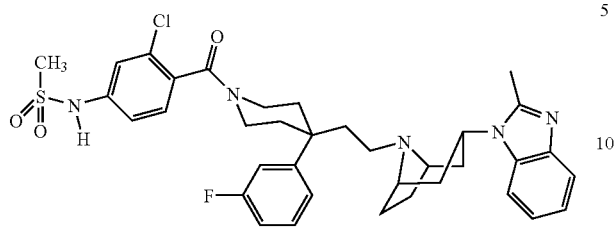

N-{3-Chloro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide (29 mg, 17.4%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol), 2-chloro-4-[(methylsulfonyl)amino]benzoic acid (68 mg. 0.270 mmol), HATU (140 mg, 369 mmol), and DIEA (95 mg, 738 mmol) following the procedure outlined in example 5. $^1$H-NMR (400 MHz, DMSO-$d_6$): δ 7.55-7.44)m, 1H0, 7.44-7.27 (m, 3H), 7.27-6.98 (m, 8H), 4.56-4.42 (m, 1H), 3.97-3.82 (m, 1H), 3.39-3.17 (m, 3H), 3.10-2.93 (m, 5H), 2.44-2.40 (m, 3H), 2.39-2.29 (m, 2H), 2.19-2.02 (m, 3H), 1.93-1.69 (m, 6H), 1.62-1.54 (m, 2H), 1.24-1.07 (m, 2H), 0.98-0.91 (m, 1H). ES-LCMS m/z 678 (M+H).

Example 1175

N-{4-chloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide a) Preparation of 2-chloro-5-[(methylsulfonyl)amino]benzoic acid

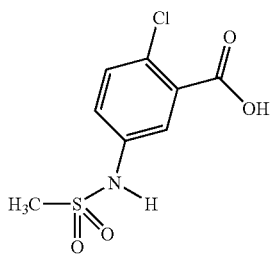

2-Chloro-5-[(methylsulfonyl)amino]benzoic acid (1.83 g, 68%) was obtained as an oil from methyl 5-amino-2-chlorobenzoate (2.0 g, 10.8 mmol)) following the procedure outlined for 2-chloro-4-[(methylsulfonyl)amino]benzoic acid. $^1$H-NMR (400 MHz, DMSO-$d_6$): δ 13.46 (bs, 1H), 10.05 (s, 1H), 7.62-7.55 (m, 1H), 7.50-7.45 (m, 1H), 7.37-7.30 (m, 1H), 3.02 (s, 3H). ES-LCMS m/z 249 (M+H).

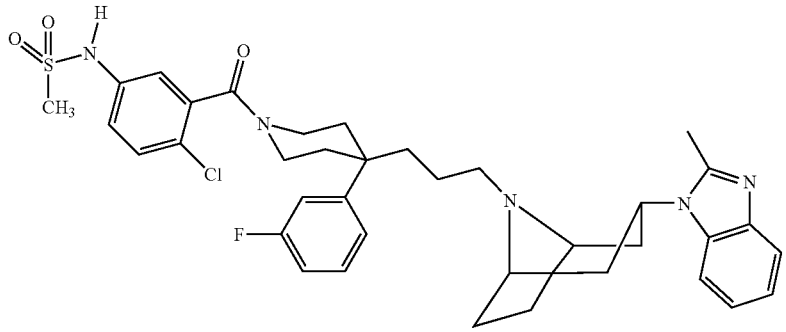

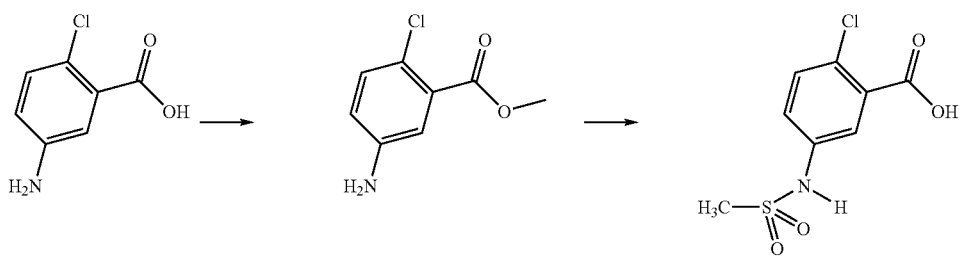

b) Preparation of N-{4-chloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide

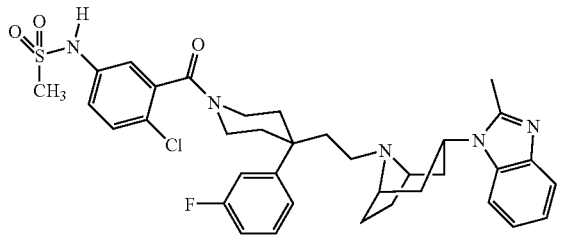

N-{4-Chloro-3-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide (103 mg, 61.6%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol 2-chloro-5-[(methylsulfonyl)amino]benzoic acid (68 mg. 0.270 mmol), HATU (140 mg, 369 mmol), and DIEA (95 mg, 738 mmol) following the procedure outlined in example 5. $^1$H-NMR (400 MHz, DMSO-d$_6$): δ 10.00 (bs, 1H), 7.57-7.47 (m, 2H), 7.45-7.34 (m, 2H), 7.28-7.21 (m, 3H), 7.18-7.02 (m, 4H), 4.57-4.43 (m, 1H), 3.98-3.83 (m, 1H), 3.45-3.21 (m, 8H), 3.11-2.99 (m, 4H), 2.46-2.41 (m, 3H), 2.41-2.30 (m, 2H), 2.21-2.02 (m, 2H), 1.99-1.72 (m, 6H), 1.65-1.56 (m, 2H). ES-LCMS m/z 678 (M+H).

Example 1176

N-{3-Fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide a) Preparation of methyl 4-amino-2-fluorobenzoate

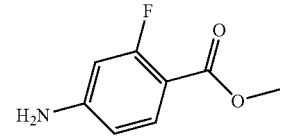

Methyl 4-amino-2-fluorobenzoate (1.98 g, 98%) was obtained as solid from 4-amino-2-fluorobenzic acid (2.0 g, 12.90 mmol)) following the procedure outlined for methyl 5-amino-2-chlorobenzoate. $^1$H-NMR (400 MHz, DMSO-d$_6$): δ 7.61-7.58 (m, 1H), 6.42-6.37 (m, 1H), 6.32-6.25 (m, 3H), 3.72 (s, 3H). ES-LCMS m/z 170 (M+H).

b) Preparation of 2-fluoro-4-[(methylsulfonyl)amino]benzoic acid

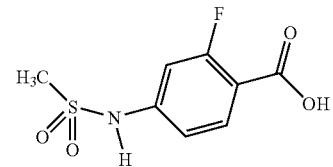

2-Fluoro-4-[(methylsulfonyl)amino]benzoic acid (5.1 g, 94%) was obtained as an oil from methyl 4-amino-2-fluorobenzoate (5.0 g, 29.1 mmol)) following the procedure outlined in example 3-[(methylsulfonyl)amino]benzoic acid. $^1$H-NMR (400 MHz, DMSO-d$_6$): δ 7.69-7.59 (m, 1H), 6.45-6.40 (m, 1H), 6.40-6.32 (m, 3H), 3.72 (s, 3H). ES-LCMS m/z 234 (M+H).

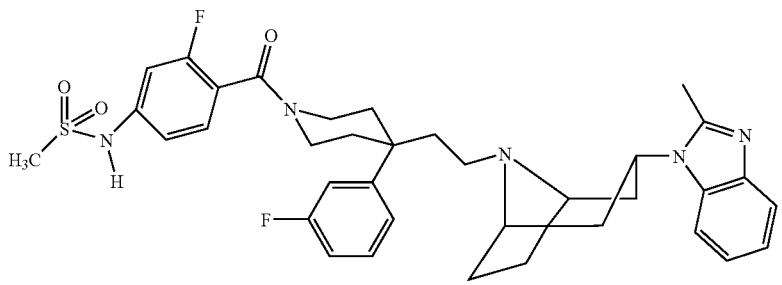

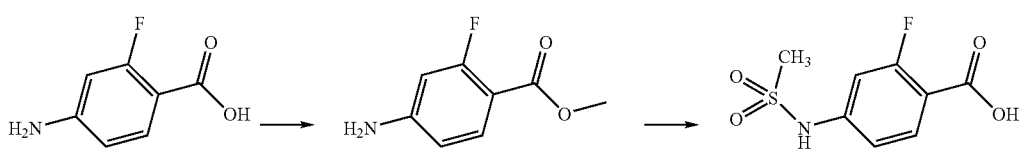

c) Preparation of N-{3-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide

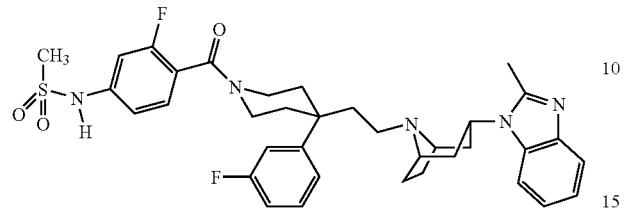

N-{3-Fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide (26 mg, 15%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol), 2-chloro-4-[(methylsulfonyl)amino]benzoic acid (U20375/163/1) (68 mg. 0.270 mmol), HATU (140 mg, 369 mmol), and DIEA (95 mg, 738 mmol) following the procedure outlined in example 5. $^1$H-NMR (400 MHz, DMSO-$d_6$): δ 7.49-7.45 (m, 1H), 7.43-7.28 (m, 3H), 7.25-7.01 (m, 8H), 4.54-4.42 (m, 1H), 3.95-3.83 (m, 1H), 3.38-3.196 (m, 5H+H2O), 3.08-2.97 (m, 4H), 2.51-2.40 (m, 2H), 2.39-2.29 (m, 2H), 2.18-2.01 (m, 3H), 1.91-1.70 (m, 6H), 1.62-1.55 (m, 2H), 1.23-1.10 (m, 2H), 0.98-0.92 (m, 1H). ES-LCMS m/z 662 (M+H).

Example 1177

N-{3-Chloro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}-1,1,1-trifluoromethanesulfonamide

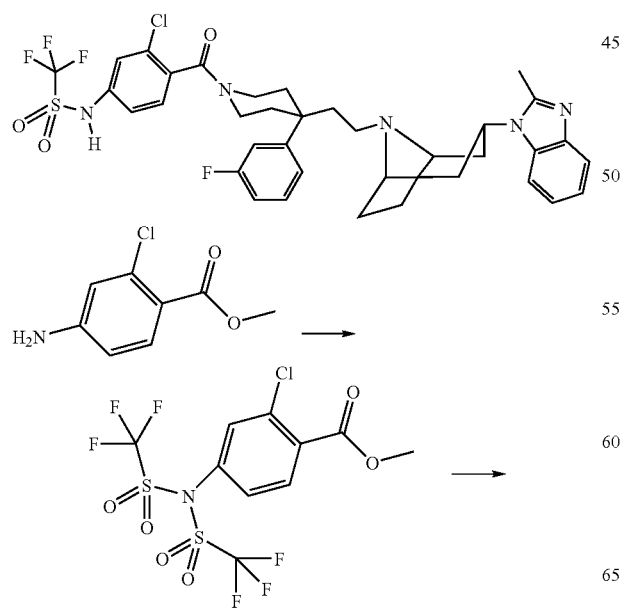

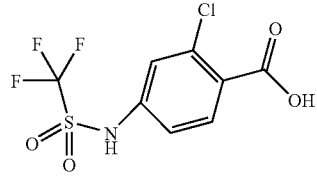

b) Preparation of methyl 4-{bis[(trifluoromethyl)sulfonyl]amino}-2-chlorobenzoate

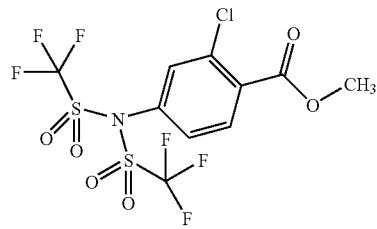

Triflic anhydride (3.73 g, 13.2 mmol) was added dropwise to a solution of methyl 4-amino-2-chlorobenzoate (2.45 g, 13.2 mmol) and ethyl[bis(1-methylethyl)]amine (2.3 ml) in dichloromethane (50 ml) at 0° C. while stirring under a nitrogen atmosphere. After warming to room temperature over 1 hour, the thick slurry was diluted with additional dichloromethane (200 ml) and washed with aqueous 1 N hydrochloric acid and the water. The dichloromethane layer was dried with MgSO$_4$ and the volatiles were removed by spin evaporation in vacuo to give methyl 4-{bis[(trifluoromethyl)sulfonyl]amino}-2-chlorobenzoate as a tan oil (5.9 g, 100%). ES-LCMS m/z 450 (M+H).

c) Preparation of 2-chloro-4-{[(trifluoromethyl)sulfonyl]amino}benzoic acid

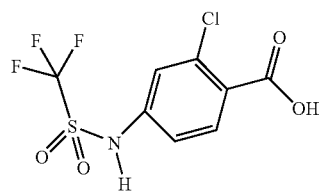

A solution of methyl 4-{bis[(trifluoromethyl)sulfonyl]amino}-2-chlorobenzoate (5.9 g, 13.1 mmol), sodium hydroxide (3.12 g, 78.0 mmol), methanol (125 ml) and water (125 ml) was stirred for 2 hours. The solution from concentration to 75 ml by spin evaporation in vacuo and dilution with 100 ml water was extracted with ethyl acetate. The aqueous layer was acidified with 12 N hydrochloric acid and again extracted with ethyl acetate. The organic layer was washed with water and concentrated by spin evaporation in vacuo, with the addition of dichloromethane (3 times) to give a residue that was dissolved in 1 N aqueous hydrochloric acid. The aqueous solution was extracted with ethyl acetate (3 times) and the organic layers were combined, washed with water, and concentrated by spin evaporation in vacuo 2-chloro-4-{[(trifluoromethyl)sulfonyl]amino}benzoic acid as a solid (3.6 g, 61%). ES-LCMS m/z 304 (M+H).

d) Preparation of N-{3-chloro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}-1,1,1-trifluoromethanesulfonamide

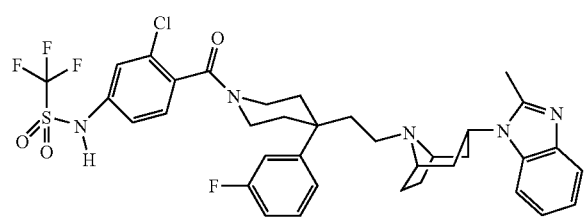

N-{3-chloro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}-1,1,1-trifluoromethanesulfonamide (35 mg, 19%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol), 2-chloro-4-{[(trifluoromethyl)sulfonyl]amino}benzoic (82 mg. 270 mmol), HATU (140 mg, 369 mmol), and DIEA (95 mg, 738 mmol) following the procedure outlined in example 5. ES-LCMS m/z 732 (M+H).

Example 1178

1,1,1-Trifluoro-N-{2-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide a) Preparation of Methyl 4-amino-3-fluorobenzoate

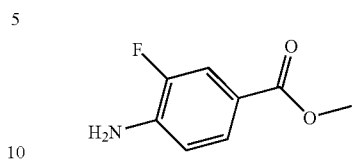

Methyl 4-amino-3-fluorobenzoate (1.01 g, 92%) was obtained as solid from 4-amino-3-fluorobenzic acid (1.0 g, 6.4 mmol) following the procedure outlined in example 1171. ES-LCMS m/z 170 (M+H).

b) Preparation of 3-fluoro-4-{[(trifluoromethyl)sulfonyl]amino}benzoic acid

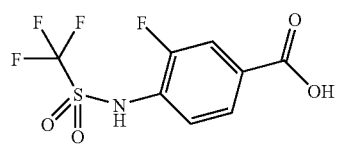

3-Fluoro-4-{[(trifluoromethyl)sulfonyl]amino}benzoic acid (0.892 g, 97%) was obtained as an oil from methyl 4-amino-3-fluorobenzoate (1.80 g, 6.39 mmol)) following the procedure outlined in example 1174. ES-LCMS m/z 288 (M+H).

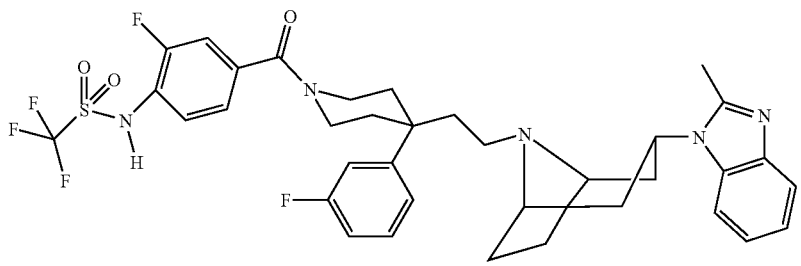

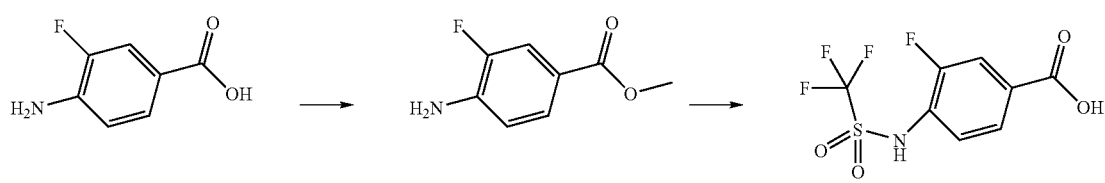

c) Preparation of 1,1,1-trifluoro-N-{2-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide

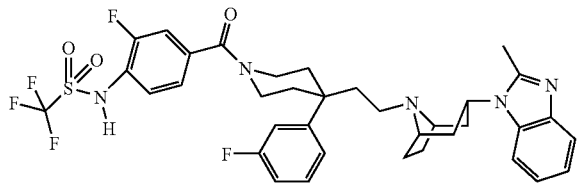

1,1,1-Trifluoro-N-{2-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide (85 mg, 48%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol), 3-fluoro-4-{[(trifluoromethyl)sulfonyl]amino}benzoic acid (78 mg. 270 mmol), HATU (140 mg, 369 mmol), and DIEA (95 mg, 738 mmol) following the procedure outlined in example 5. ES-LCMS m/z 716 (M+H).

Example 1179

1,1,1-Trifluoro-N-{3-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide a) Preparation of methyl 4-amino-2-fluorobenzoate

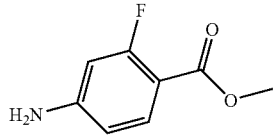

Methyl 4-amino-2-fluorobenzoate (1.85 g, 84%) was obtained as solid from 4-amino-2-fluorobenzic acid (2.0 g, 12.90 mmol)) following the procedure outlined in example 1171. ES-LCMS m/z 170 (M+H).

b) Preparation of 2-fluoro-4-{[(trifluoromethyl)sulfonyl]amino}benzoic acid

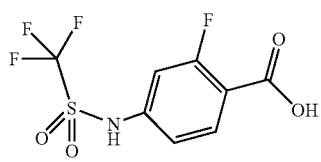

2-Fluoro-4-{[(trifluoromethyl)sulfonyl]amino}benzoic acid (1.32 g, 74%) was obtained as an oil from methyl 4-amino-2-fluorobenzoate (1.05 g, 6.2 mmol)) following the procedure outlined in example 1174. ES-LCMS m/z 288 (M+H).

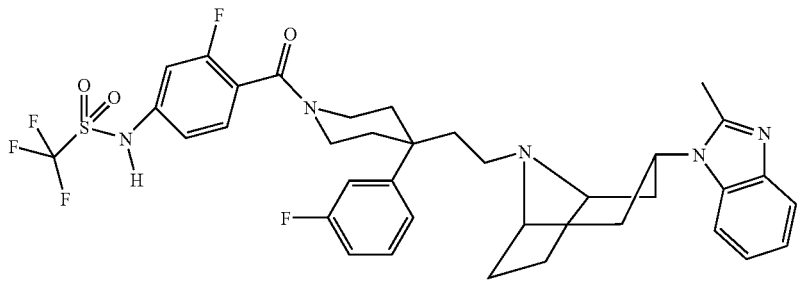

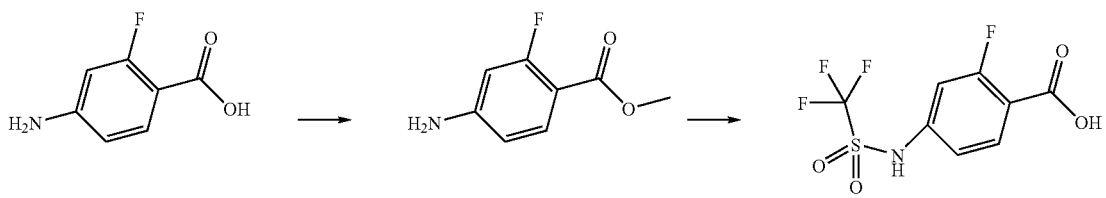

c) Preparation of 1,1,1-trifluoro-N-{3-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide

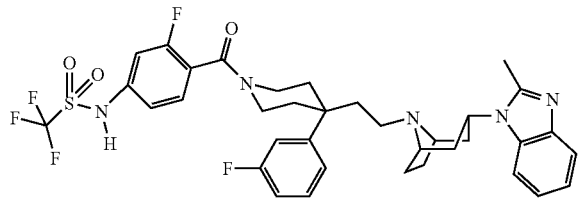

1,1,1-Trifluoro-N-{3-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide (85 mg, 48%) was obtained as a solid from 1-(8-{2-[4-(3-fluorophenyl)-4-piperidinyl]ethyl)-8-azabicyclo[3.2.1]oct-3-yl)-2-methyl-1H-benzimidazole (150 mg, 246 mmol), 2-fluoro-4-{[(trifluoromethyl)sulfonyl]amino}benzoic acid (78 mg. 270 mmol), HATU (140 mg, 369 mmol), and DIEA (95 mg, 738 mmol) following the procedure outlined in example 5. ES-LCMS m/z 716 (M+H).

Example 1180

N-{2-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide a) Preparation of methyl 4-amino-3-fluorobenzoate

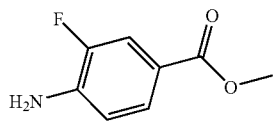

Methyl 4-amino-3-fluorobenzoate (0.98 g, 90.0%) was obtained as solid from 4-amino-3-fluorobenzic acid (1.0 g, 6.45 mmol)) following the procedure outlined in example 1171. ES-LCMS m/z 170 (M+H).

b) Preparation of 3-fluoro-4-[(methylsulfonyl)amino]benzoic acid

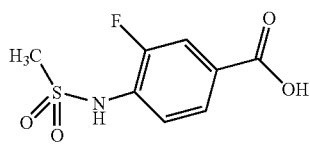

3-Fluoro-4-[(methylsulfonyl)amino]benzoic acid (490 mg, 66%) was obtained as an oil from methyl 4-amino-3-fluorobenzoate (0.54 g, 3.19 mmol) following the procedure outlined in example 1174. ES-LCMS m/z 234 (M+H).

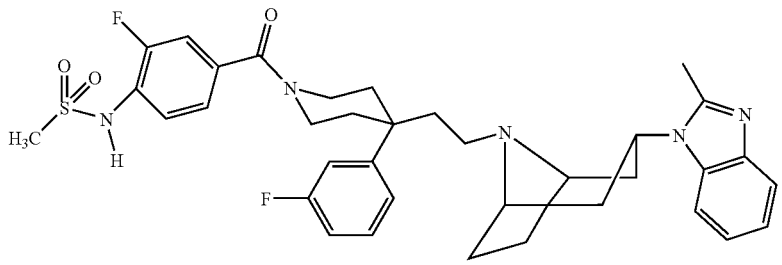

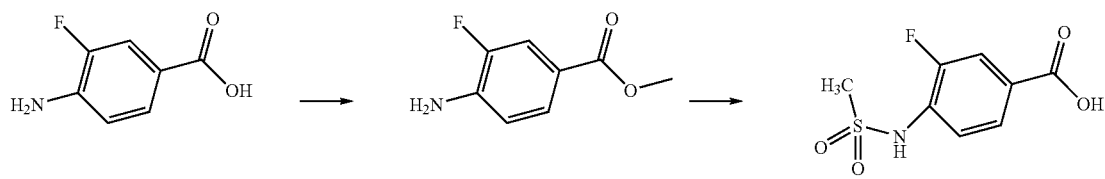

c) Preparation of N-{2-fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide

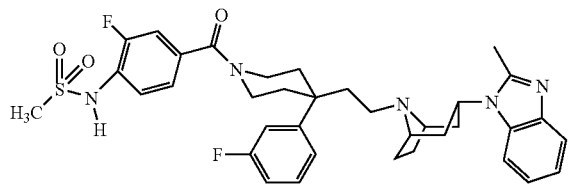

N-{2-Fluoro-4-[(4-(3-fluorophenyl)-4-{2-[3-(2-methyl-1H-benzimidazol-1-yl)-8-azabicyclo[3.2.1]oct-8-yl]ethyl}-1-piperidinyl)carbonyl]phenyl}methanesulfonamide (92 mg, 52%) was obtained as a solid from 1-(8-{2-[4-(3-fluorophenyl)-4-piperidinyl]ethyl}-8-azabicyclo[3.2.1]oct-3-yl)-2-methyl-1H-benzimidazole (150 mg, 246 mmol), 3-fluoro-4-[(methylsulfonyl)amino]benzoic acid (U20375/147/1) (78 mg. 270 mmol), HATU (140 mg, 369 mmol), and DIEA (95 mg, 738 mmol) following the procedure outlined in example 5. ES-LCMS m/z 662 (M+H).

Example 1181

N-{4-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}methanesulfonamide

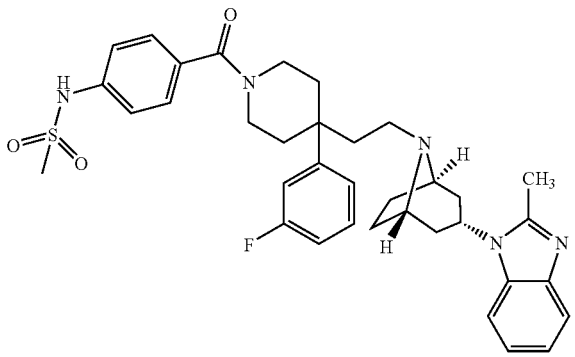

The synthesis of 4-[(methylsulfonyl)amino]benzoic acid

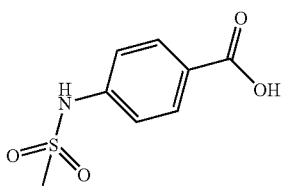

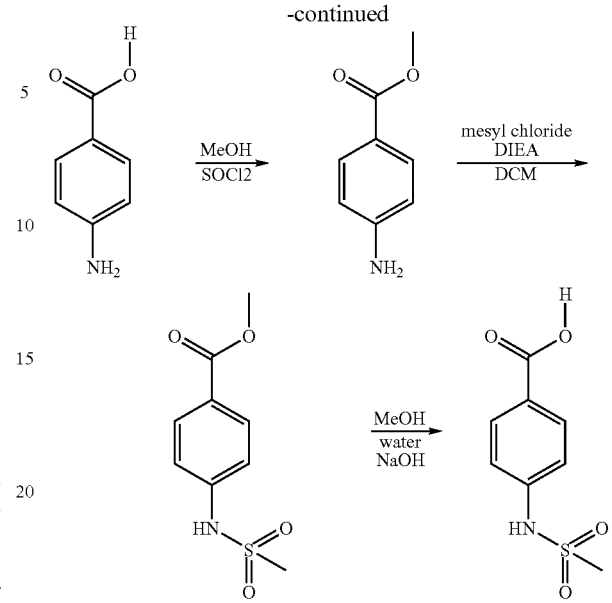

2.1 g (15.6 mmol) of 4-aminobenzoic acid was dissolved in anhydrous MeOH, added 14.47 g (123.3 mmol) of thionyl chloride dropwise under N2 while stirring at rt. After dtiring for four hours, solvents were removed and redissolved in 100 mL EtOAc and 40 mL of saturated NaHCO3 aq, stirred 30 min, separated and washed with 3×20 mL water. Organics were dried yielding 2.17 g (yield 92.1%) of methyl 4-aminobenzoate. $^1$H NMR (300 MHz, CDCl3): 7.88 (2H, d, J=8.6 Hz), 6.66 (2H, d, J=8.6 Hz), 4.19 (2H, broad s), 3.88 (3H, s). $^{13}$C NMR (300 MHz, CDCl3): 167.8 (C=O), 151.4 (Cq), 131.9 (2×CH), 120.0 (Cq), 113.8 (2×CH), 50.9 (CH3).

1.13 g (7.48 mmol) of methyl 4-aminobenzoate was dissolved in 20 mL of anhydrous DCM and 1.97 g (17.19 mmol) of mesyl chloride was added at 4 deg C., followed by the 2.22 g (17.19 mmol) of the diethylisopropylamine. Reaction was carried out overnight at room temperature resulting methyl 4-[(methylsulfonyl)amino]benzoate, which was used in the next step without additional purification.

3.6 g (90 mmol) of NaOH was added to the solution of methyl 4-[(methylsulfonyl)amino]benzoate in 40 mL methanol and 20 mL water and stirred overnight at room temperature. Solvents were then removed and the product purified by ethyl acetate extraction from 1N aqueous hydrochloric acid, providing 1.2 g (yield 74.6%) of the 4-[(methylsulfonyl)amino]benzoic acid. 1H NMR in d-chloroform: 8.03 (2H, d, J=8.7 Hz), 7.34 (2H, d, J=8.7 Hz), 3.09 (3H, s). $^{13}$C NMR in d-chloroform: 131.2, 117.9, 38.6.

The synthesis of N-{4-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}methanesulfonamide 270 mg (0.61 mmol) of 1-((1R,5S)-8-{2-[4-(3-fluorophenyl)-4-piperidinyl]ethyl}-8-azabicyclo[3.2.1]oct-3-yl)-2-methyl-1H-benzimidazole dihydrochloride salt trihydrate was dissolved in the dichloromethane, and added 195 mg (0.91 mmol) of the 4-[(methylsulfonyl)amino]benzoic acid, 440 mg (0.91 mmol) of HATU and 391 mg (3.03 mmol) of the diethylisopropylamine an the reaction carried out as described in example 5, resulting in title N-{4-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]phenyl}methanesulfonamide, yield 32% after HPLC purification.

1H NMR ($d_4$-methanol, 400 MHz): 7.53 (1H, m), 7.40 (4H, m), 7.31 (2H, d, J=7.7 Hz), 7.22 (4H), 6.99 (1H, m), 4.74 (1H, m), 4.09 (1H, broad s), 3.68 (1H, broad s), 3.39 (4H, m), 3.03 (4H, m), 2.52 (s, 3H), 2.45 (2H, m), 2.32 (1H, broad s), 2.23 (1H, broad s), 1.95 (10H, m), 1.71 (1H, m)

Example 1074

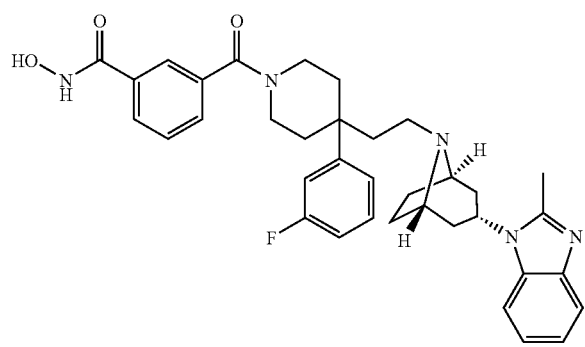

3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-N-hydroxybenzamide Example 1074 was prepared according to scheme below.

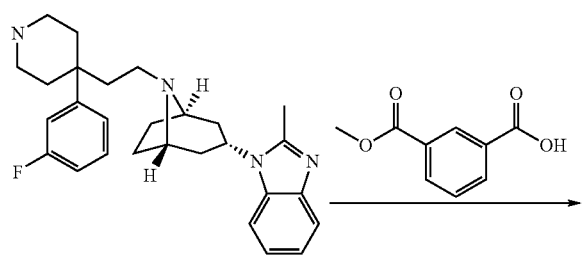

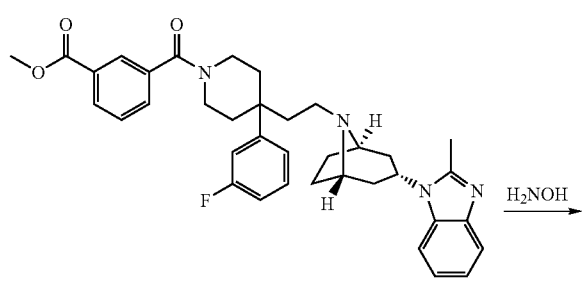

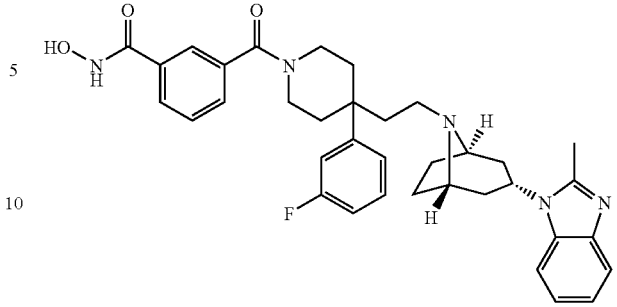

1-((1R,5S)-8-{2-[4-(3-fluorophenyl)-4-piperidinyl]ethyl}-8-azabicyclo[3.2.1]oct-3-yl)-2-methyl-1H-benzimidazole (500 mg, 0.962 mmol) was combined with 3-[(methyloxy)carbonyl]benzoic acid (173 mg, 0.962 mmol) and DIPEA (373 mg, 2.88 mmol) in 8 mL DMF and treated with HATU (366 mg, 0.962 mmol) at ambient temperature for 16 h. The reaction mixture was treated with satd. NaHCO$_3$ which yielded a solid precipitate that was filtered off, washed with water and dried to give methyl 3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]benzoate (395 mg, 0.649 mmol, 67%) as a white solid. ES-LCMS m/z 609.1 (M+H).

Hydroxylamine.HCl (26 mg, 0.360 mmol) dissolved in 5 mL EtOH was cooled in an ice bath and treated with 0.5M NaOCH$_3$ (1.92 mL, 0.96 mmol) for 15 min with stirring. Methyl 3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]benzoate (183 mg, 0.300 mmol) was added to the reaction mixture and allowed to stir 16 h at ambient temperature. The reaction mixture was concentrated to dryness and purified by RP-HPLC on a C-18 column eluted with 0→50% CH$_3$CN in H$_2$O with 0.1% formic acid buffer. The appropriate fractions were combined and concentrated to give 3-[(4-(3-fluorophenyl)-4-{2-[(1R,5S)-3-(2-methyl-1H-benzimidazol-1-yl)-8-azabicyclo[3.2.1]oct-8-yl]ethyl}-1-piperidinyl)carbonyl]-N-hydroxybenzamide (20 mg, 0.032 mmol, 9%) as a clear glass. ES-LCMS m/z 610.14 (M+H), 608.21 (M−1).

CC-Chemokine Receptor-5 Binding by Scintillation Proximity Assay

The compounds of this invention were evaluated as antagonists of CCR5 by high-throughput screening using scintillation proximity assay (SPA) binding that measures inhibition of binding of $^{125}$I-MIP1□ to the human CCR5 chemokine receptor.

Human CCR5 receptors were expressed in Chinese Hamster Ovary (CHO) cells. Cells were grown in suspension and 50 to 80 ml CCR5 cell pellets were prepared.

Membranes were prepared according to the following procedure: 1) weighed pellet; 2) prepared an ice-cold 50 mM HEPES buffer, containing 0.0025 mg/ml Pefabloc, 0.0001 mg/ml Pepstatin A, 0.0001 mg/ml Leupeptin, 0.0001 mg/ml Aprotinin (protease inhibitor cocktail), pH 7.4; 3) homogenized pellet in 5 volumes of HEPES buffer; 4) homogenized again with a glass homogenizer for 10 to 20 strokes; 5) centrifuged homogenate at 18,000 rpm in a F28/36 rotor using a Sorvall RC26 PIUS refrigerated Centrifuge for 30 minutes; 6) discarded supernatant and resuspended pellet in 3 volumes of HEPES buffer; 7) homogenized and centrifuged again using steps 4-6 for two more times; 8) re-weighed pellet and homogenize in three times weight-to-volume of HEPES buffer; 9) placed aliquot 0.5 to 1.5 ml of the membrane preparation into small vials and stored at −80° C.; 10) determined the protein concentration of the membrane preparation using the Bio-Rad or BCA method; and 11) characterized the membrane homogenate for the assay conditions including protein concentration, optimal protein-to-bead ratio in SPA, and saturation curve to determine $K_d$ and $B_{max}$ (number of binding sites) in SPA.

The saturation curve binding experiment was performed by adding varying amounts of [$^{125}$I]MIP1α (0-8.5 nM) to membranes and beads in concentrations chosen from the optimal protein/bead ratio. The data was analyzed using a non-linear curve-fitting program. The $K_d$ and $B_{max}$ were derived from the curve.

Bacitracin 50 mg/ml was dissolved in deionized water, brought to a boil for 5 minutes (to destroy protease activity) and cooled. One milliliter aliquots were prepared and stored at −80° C.

Protease inhibitor cocktail was prepared by dissolving 25 mg/ml of Pefabloc, 1 mg/ml of Leupeptin, 1 mg/ml of Aprotinin and 1 mg/ml of Pepstatin A in 100% DMSO. The cocktail could be aliquoted and stored frozen at −20° C. until needed.

Any reagent bottles and reservoirs that come in contact with the radioligand were treated with Sigmacote to reduce sticking. Containers were rinsed with undiluted Sigmacote and with deionized water for several times and allowed to air dry before using.

Color quench assay was performed with a [$^{125}$I]SPA PVT color quench kit (Cat. No. RPAQ 4030, Amersham Ltd.). A color quench curve was generated for each Packard TopCount and was stored in each counting protocol specific for the assay. This was done to prevent colored compounds from quenching the scintillation counts.

Compounds of this invention were prepared for SPA according to the following protocol. Compounds for a single concentration determination (one shots) were delivered in 96 well Packard Optiplates containing 1 μl of compound in 100% DMSO in columns A1-H10 (80 compounds/plate). Column A11 to H11 was used for total binding (Bo: zero standard—bound radioactive counts in the absence of added inhibitor or test compound) (vehicle-5 μl of the appropriate DMSO concentration) and column A12 to D12 was used for determination of nonspecific binding (NSB). No further preparation was required. Compounds for concentration-response curves (10 points) were delivered in 96-Packard Optiplates containing 1 μl of compound in 100% DMSO in columns A1-H10. A 10-point concentration-response curve was desired for each compound with a starting high concentration of 30 μM (in the assay final). Column A11 to H11 was used for total binding (Bo) (vehicle-5 μl of the appropriate DMSO concentration) and column A12 to D12 was used for determination of nonspecific binding. No further preparation was required.

Assay buffer was prepared by mixing 50 mM HEPES buffer (pH 7.4), 1 mM CaCl$_2$, 5 mM MgCl$_2$ which could be made ahead as a 100× stock, 1% BSA (bovine serum albumin), 0.5 mg/ml Bacitracin, and protease inhibitor cocktail (100 uL/100 ml). DMSO was added to equal a final concentration of 2% per well (includes compound % DMSO) if needed.

[$^{125}$I]MIP1α radioligand dilutions was prepared in containers treated with Sigmacote. Each 50 μCi vial was reconstituted with 0.5 ml of deionized water and stored at 4° C. The specific activity was 2,000 Ci/mmol. 50 μL (~60,000 cpm; 0.17 nM) of [$^{125}$I]MIP1α was added to each assay well.

Zero standard (Bo) was prepared by making a 20% DMSO solution and adding 5 μl of 20% DMSO solution to each well in columns A11-H11. This gave a final 2% DMSO concentration for the well when added to the 1% in the assay buffer.

A stock dilution of MIP1α at 100 uM was made using deionized water and aliquoted and frozen. The MIP-1α stock solution was diluted to a concentration of 2 μM in the same 20% DMSO solution used above. 5 μl of the resultant solution was added to the wells in column A12 to D12 to give a final assay concentration of 100 nM. This procedure was conducted in a Sigmacote-treated container.

The final assay concentration for the membrane was 15 μg per well. SPA beads were prepared by adding 5 ml of assay buffer to a 500 mg vial. The final concentration of SPA beads in the assay was 0.25 mg/well. Membranes and beads were premixed as a 1:1 (membrane:bead) mixture and maintained at mixture at 4° C. with constant stirring. 50 μl of the mixture was added to each assay well. After all reagents had been added to the plates (total assay volume 100 μl), plates were shaken for 4 hours at room temperature. After 4 hours, the plates were placed on the TopCount in a count the plates on the TopCount for 30 sec per well using an appropriate program (i.e., one with a quench curve established for the conditions of the assay).

Data reduction was performed using the Microsoft Excel Addins Robofit or Robosage. For single concentration assays (one shots), the result of each test well was expressed as % inhibition using the following formula: 100*(1−(U1−C2)/(C1−C2)), where U1 was the unknown sample in cpm observed in a particular well, C1 was the average of column 12 cpm observed in the absence of any added inhibitor, and C2 was the average of column 11 cpm observed in the presence of 1 uM of MIP1α. For concentration-response assays, the result of each test well was expressed as % B/Bo (% total specific binding) using the following formula: 100*(U1−C2)/C1−C2). Curves were generated by plotting the % B/Bo versus the concentration and the IC$_{50}$ was derived using the equation y=Vmax*(1−(x^n/(k^n+x^n))).

For controls and standards, each plate contained 12 wells of total binding (column A11-H11). The cpm/well were averaged and used in data reduction as value C1. Each plate also contained 4 wells of non-specific binding (wells A12-D12). The counts of these wells were averaged and used in data reduction as value C2. A standards plate was included in each experiment. This plate contained a 14-point concentration-response curve (in triplicate) for the standard compound MIP1α at a starting concentration of 1 μM. The average historical pK$_i$ obtained with MIP1α was 7.6.

The relevant biological response field for a single concentration (one shots) was % inhibition. Inhibition values of >40 or >50% were considered positive responses. The relevant biological response field for a concentration-response experiment was pK$_i$.

HOS Assay (Also Referred to as HOS-LTR-Luciferase Assay)

HOS-CD4.CCR5-LTR-Luciferase (Bioresource Registration # 21164): Human Osteosarcoma cell line was engineered to overexpress human CD4 and human CCR5 (AIDS Repository cat# 3318) stably transfected with HIV-1-LTR-Luciferase reporter.

Growth and Maintenance of the HOS-CD4.CCR5-LTR-Luciferase cell line: The cells were propagated in DMEM containing 2% FBS. Cells were split by standard trypsinization when confluency reached 80% (roughly every 2 to 3 days).

Titering of virus stocks: HIV-1 virus stocks were titered in the assay system in order to obtain an estimate of the number of infectious particles per unit volume (described as RLU/ml). Virus stocks were diluted into DMEM containing 2% FBS and assayed as described in the "procedure" section below.

Procedure: Black-walled 96-well tissue culture plates were seeded with HOS-CD4.CCR5-LTR-Luciferase @0.6 to 1.2× $10^3$ cells per well in 50 μl DMEM containing 2% FBS and placed in a humidified incubator @37° C., 5% $CO_2$ overnight. The following day, test compounds were titrated 4-fold at 2× the final concentration in DMEM 2% FBS+0.2% DMSO. 50 μl of titrated compound was transferred to the HOS cells and the plates were placed in a humidified incubator at 37° C., 5% $CO_2$ for 1 hr. An additional 60 μl of 2× titrated compound was transferred to a clear-walled 96-well tissue culture plate and 60 μl of HIV (diluted to appropriate m.o.i.) was added to each well and thoroughly mixed. 100 μl of the HIV/compound mixture was transferred to the black-walled plates containing 100 μl of cells/compound. The plates were placed in a humidified incubator at 37° C., 5% $CO_2$ for 72 hr. Following the 72 hour incubation, 150 μl of supernatant was removed and 50 μl of reconstituted LUCITE (kit reagent) was added to each well. Each plate was sealed and read in a Topcount (Packard) luminometer at 1 s/well.

Data Reduction: Relative Light Units (RLU) were expressed as % control (RLU at drug concentration/RLU no drug)*100=% Control. $IC_{50}$ values were determined by any one of the following four nonlinear regression models:

$$y=V\max*(1-(x^n/(K^n+x^n)))+Y2;$$

$$y=V\max*(1-(x^n/(K^n+x^n)));$$

$$y=V\max*(1-(x/(K+x)))+Y2;$$

$$y=V\max*(1-(x/(K+x)));$$

where K is $IC_{50}$, Y2 is baseline, and N is Hill Coefficient.

Each of the compounds of the present invention provides a $pIC_{50}$ value of at least 5 when tested in each of the above-described assays.

Test compounds are employed in free or salt form.

While we have hereinbefore presented a number of embodiments of this invention, it is apparent that our basic construction can be altered to provide other embodiments which utilize the compounds and methods of this invention. Therefore, it will be appreciated that the scope of the invention is to be defined by the appended claims rather than by the specific embodiments which have been represented by way of example.

What is claimed is:

1. A compound selected from the group consisting of (a)

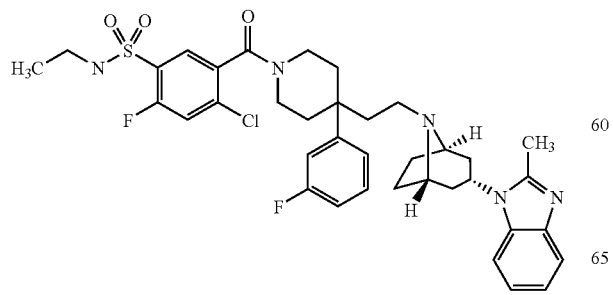

-continued (b)

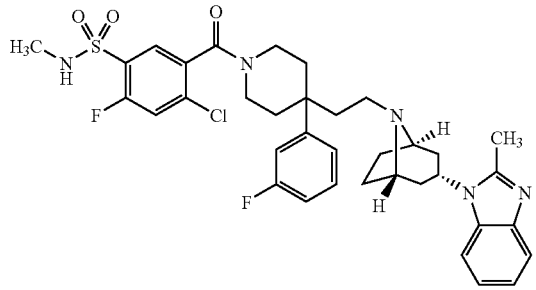

(c)

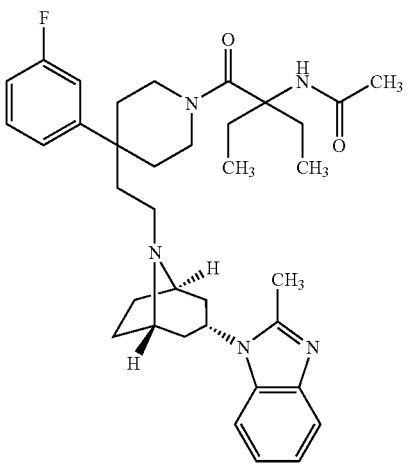

(d)

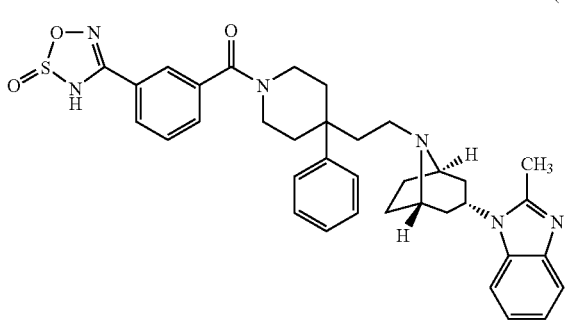

(e)

-continued
(f)
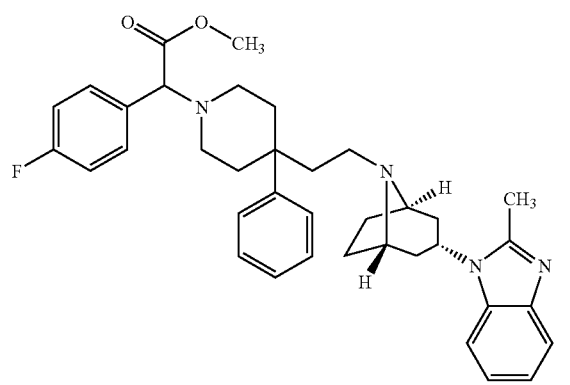
(g)
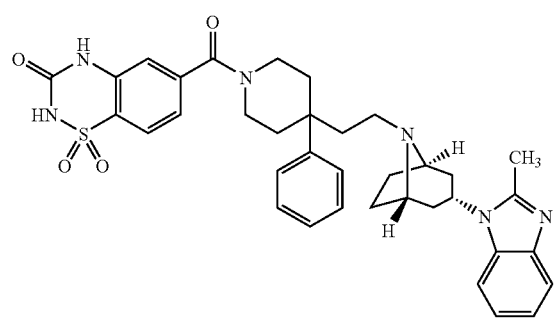
(h)
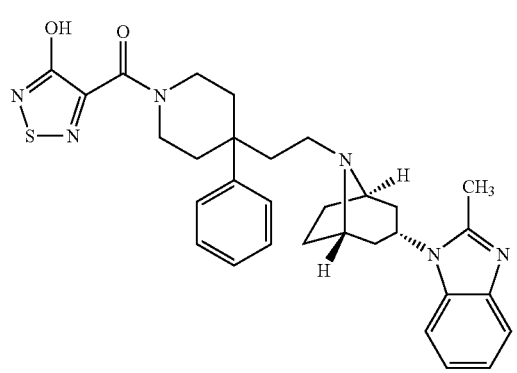
(i)
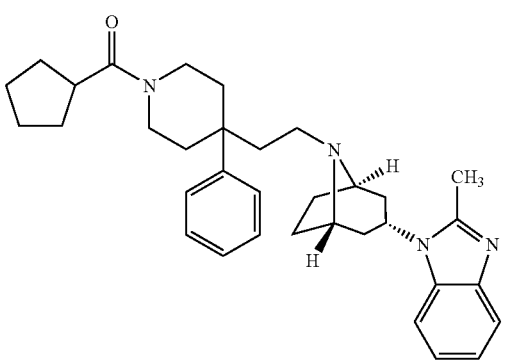
-continued
(j)
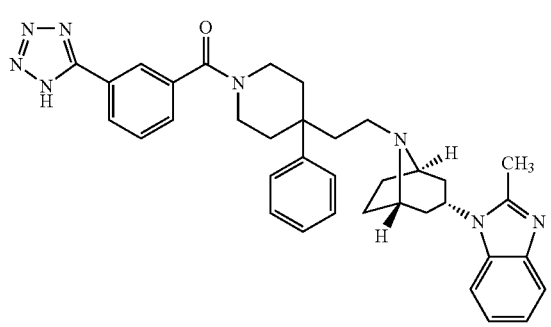
(k)
(l)
(m)

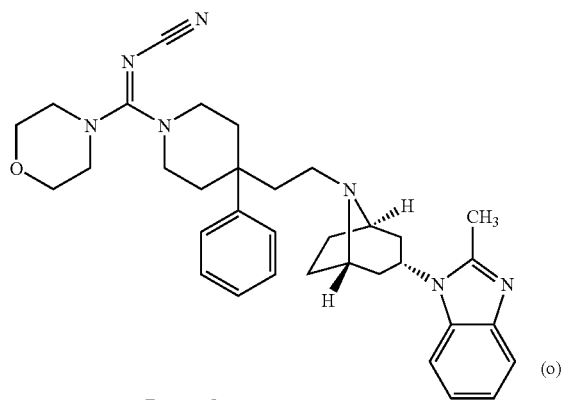
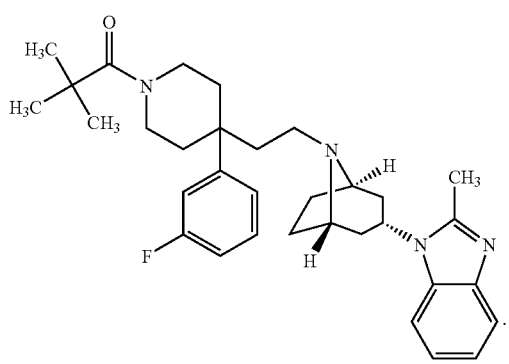
2. A composition comprising a compound according to claim 1 and a pharmaceutically acceptable carrier, adjuvant, or vehicle.
3. The composition according to claim 2 in the form of a tablet or capsule.
4. The composition according to claim 2 in the form of a liquid.
\* \* \* \* \*